US012486269B2

(12) United States Patent
Lei et al.

(10) Patent No.: US 12,486,269 B2
(45) Date of Patent: Dec. 2, 2025

(54) COMPOUNDS AND COMPOSITIONS FOR TREATING CONDITIONS ASSOCIATED WITH CALCITONIN RECEPTOR AND/OR AMYLIN RECEPTOR ACTIVITY

(71) Applicant: Aconcagua Bio, Inc., South San Francisco, CA (US)

(72) Inventors: Hui Lei, Shanghai (CN); Cui Li, Shanghai (CN); Chunliang Lu, Shanghai (CN); Ding Xue, Shanghai (CN); Haizhen Zhang, Shanghai (CN); Zhuming Zhang, Shanghai (CN); Jian Liu, New York, NY (US); Zhe Nie, New York, NY (US); Anatoly Ruvinsky, New York, NY (US); Eric Therrien, New York, NY (US); Evelyne Houang, New York, NY (US)

(73) Assignee: Aconcagua Bio, Inc., South San Francisco, CA (US)

( * ) Notice: Subject to any disclaimer, the term of this patent is extended or adjusted under 35 U.S.C. 154(b) by 0 days.

(21) Appl. No.: 19/074,260

(22) Filed: Mar. 7, 2025

(65) Prior Publication Data

US 2025/0257067 A1 Aug. 14, 2025

Related U.S. Application Data

(63) Continuation of application No. PCT/US2025/015122, filed on Feb. 7, 2025.

(30) Foreign Application Priority Data

Feb. 8, 2024 (WO) ................ PCT/CN2024/076922
Jun. 6, 2024 (WO) ................ PCT/CN2024/097824
Nov. 21, 2024 (WO) ................ PCT/CN2024/133596
Dec. 24, 2024 (WO) ................ PCT/CN2024/141875

(51) Int. Cl.

| | |
|---|---|
| ***C07D 471/14*** | (2006.01) |
| ***A61K 31/4365*** | (2006.01) |
| ***A61K 31/437*** | (2006.01) |
| ***A61K 31/444*** | (2006.01) |
| ***A61K 31/4709*** | (2006.01) |
| ***A61K 31/4725*** | (2006.01) |
| ***A61K 31/4985*** | (2006.01) |
| ***A61K 31/519*** | (2006.01) |
| ***A61K 31/5383*** | (2006.01) |
| ***C07D 495/04*** | (2006.01) |
| ***C07D 495/10*** | (2006.01) |
| ***C07D 513/14*** | (2006.01) |
| ***C07D 519/00*** | (2006.01) |

(52) U.S. Cl.

CPC ........ *C07D 471/14* (2013.01); *A61K 31/4365* (2013.01); *A61K 31/437* (2013.01); *A61K 31/444* (2013.01); *A61K 31/4709* (2013.01); *A61K 31/4725* (2013.01); *A61K 31/4985* (2013.01); *A61K 31/519* (2013.01); *A61K 31/5383* (2013.01); *C07D 495/04* (2013.01); *C07D 495/10* (2013.01); *C07D 513/14* (2013.01); *C07D 519/00* (2013.01)

(58) Field of Classification Search

None

See application file for complete search history.

(56) References Cited

U.S. PATENT DOCUMENTS

| | | | |
|---|---|---|---|
| 7,396,936 | B1 | 7/2008 | Pryor et al. |
| 2025/0042916 | A1 | 2/2025 | Lei et al. |
| 2025/0051355 | A1 | 2/2025 | Lei et al. |

FOREIGN PATENT DOCUMENTS

| | | | |
|---|---|---|---|
| WO | WO 97/014681 | A1 | 4/1997 |
| WO | WO 03/076440 | A1 | 9/2003 |
| WO | WO 2005/025504 | A2 | 3/2005 |
| WO | WO 2006/004188 | A1 | 1/2006 |
| WO | WO 2010/039913 | A1 | 4/2010 |
| WO | WO 2010/039922 | A1 | 4/2010 |
| WO | WO 2016/055790 | A1 | 4/2016 |
| WO | WO 2025/015268 | | 1/2025 |
| WO | WO 2025/015269 | | 1/2025 |

OTHER PUBLICATIONS

Boccia et al. "Amylin brain circitry", Peptides, 132: 170366 (Jul. 2020), 10 pages.

Cao et al. "Structure-based insight into development of selective and non-selective amylin and calcitonin receptor agonists", Nature Chemical Biology, Aug. 3, 2023, 20(2): 162-169.

Kruse et al. "Development of Cagrilintide, a Long-Acting Amylin Analogue", Journal of Medicinal Chemistry, 2021, vol. 64, Issue 15, pp. 11183-11194.

Larsen et al. "The Calcitonin Receptor Plays a Major Role in Glucose Regulation as a Function of Dual Amylin and Calcitonin Receptor Agonist Therapy" J Pharmacol Exp Ther., Jul. 2020; 374(1): 74-83.

Larsen et al. "Does receptor balance matter?—Comparing the efficacies of the dual amylin and calcitonin receptor agonists cagrilintide and KBP-336 on metabolic parameters in preclinical models" Biomedicine & Pharmacotherapy, 2022, 156, 113842, 13 pages.

Mathiesen et al. "Amylin and Calcitonin: Potential Therapeutic Strategies to Reduce Body Weight and Liver Fat", Frontiers in Endocrinology, Jan. 2011, vol. 11, Article 617400, 11 pages.

Naot et al. "The Activity of Peptides of the Calcitonin Family in Bone", Physiological Reviews, vol. 99, Issue 1, pp. 781-805.

Srinivasan et al. "Calcitonin: A useful old friend", J Musculoskelet Neuronal Interact, 2020; 20(4): 600-609.

(Continued)

*Primary Examiner* — Leslie A. Royds Draper

(74) *Attorney, Agent, or Firm* — Sheppard Mullin Richter & Hampton LLP

(57) ABSTRACT

The present disclosure provides compounds for modulating calcitonin receptor and/or amylin receptor activity, as well as pharmaceutical compositions comprising the compounds disclosed herein. Also provided are methods for treating a calcitonin receptor and/or amylin receptor associated disease or disorder.

26 Claims, No Drawings

(56) References Cited

OTHER PUBLICATIONS

Wells et al. "Does salmon calcitonin cause cancer? A review and meta-analysis", Osteoporos Int. (2016) vol. 27, pp. 13-19.
International Search Report and Written Opinion dated May 13, 2025 for PCT International Patent Application No. PCT/US2025/015122, 22 pages.
Bandhari, et al., "Solid-Phase Synthesis of Pyrrolo [3,4-b] pyridines and related Pyridine-Fused Heterocycles," Synthesis, No. 11, 1, Jan. 1, 1999, pp. 1951-1960.
Chiou et al., "Studies on the acetylation of 3,6-diamino-1 H-pyrazolo [3,4-b] pyridine-5-carbonitrile derivatives," Journal of Heterocyclic Chemisty, vol. 47, No. 4, Jul. 1, 2010, pp. 861-872.
Gámez-Montaño, et al., "Multicomponent domino process to oxa-bridged polyheterocycles and pyrrolopyridines, structural diversity derived from work-up procedure," Tetrahedron, vol. 58, Jun. 6, 2002, pp. 6351-6358.
Gámez-Montaño, et al., "Rapid access to tetracyclic ring system of lennoxamine type natural product by combined use of a novel three-component reaction and Pummerer cyclization," Chemical Communications, No. 20, 24, Sep. 29, 2002, pp. 2448-2449.
Hendrikse Erica R. et al. "Identification of Small-Molecule Positive Modulators of Calcitonin-like Receptor-Based Receptors", ACS Pharmacology & Translational Science, vol. 3, No. 2, Mar. 12, 2020, pp. 305-320.
Hill, "A Multicomponent Approach to a Highly Substituted 1H-Pyrazolo [3,4-b] pyridines,", Synthesis, vol. 48, No. 14, May 17, 2016, pp. 2201-2204.
Singh et al., "Molecular modelling study to discover novel JAK2 signaling pathway inhibitor," Journal of Biomolecular Structure & Dynamics, vol. 41, No. 12, Jul. 15, 2022, pp. 5827-5838.
Vilches-Herrera et al., "One-Pot, Three-Component Synthesis of 7-Azaindole Derivatives from N-Substituted 2-Amino-4-cyanopyrroles, various Aldehydes, and Active Methylene Compounds," ACS Combinational Science, vol. 14, No. 7, Jun. 5, 2012, pp. 434-441.
Xia, et al., "Catalytic Ugi-Type Condensation of α-Isocyanoacetamide and Chiral Cyclic Imine: Access to Asymmetric Construction of Several Heterocycles," The Journal of Organic Chemistry, vol. 78, No. 7, Feb. 26, 2013, pp. 3120-3131.

COMPOUNDS AND COMPOSITIONS FOR TREATING CONDITIONS ASSOCIATED WITH CALCITONIN RECEPTOR AND/OR AMYLIN RECEPTOR ACTIVITY

CROSS REFERENCE TO RELATED APPLICATIONS

The application is a continuation of International Patent Application No. PCT/US2025/015122, filed Feb. 7, 2025, which claims the benefit of International Patent Application Number PCT/CN2024/076922, filed on Feb. 8, 2024, International Patent Application Number PCT/CN2024/097824, filed on Jun. 6, 2024, International Patent Application Number PCT/CN2024/133596, filed on Nov. 21, 2024, and International Patent Application Number PCT/CN2024/141875, filed Dec. 24, 2024, each of which is incorporated herein by reference in its entirety.

FIELD

The present disclosure provides compounds for modulating calcitonin receptor and/or amylin receptor activity, as well as pharmaceutical compositions comprising the compounds disclosed herein. Also provided are methods for treating calcitonin receptor and/or amylin receptor associated diseases, disorders, and conditions.

BACKGROUND

Calcitonin and amylin are hormones that interact with receptors within the same family to exert their effects on the human organism. Calcitonin, derived from thyroid C cells, is known for its inhibitory effect on osteoclasts. Calcitonin of mammalian origin promotes insulin sensitivity, while the more potent calcitonin extracted from salmon additionally inhibits gastric emptying, promotes gallbladder relaxation, increases energy expenditure and induces satiety as well as weight loss. Studies have also indicated that oral salmon calcitonin (sCT) exerts an insulin-sensitizing effect to improve glucose metabolism in obesity and type 2 diabetes. European Journal of Pharmacology, 2024, 737(7): 91-96.

Amylin receptors (AMYRs) are G protein-coupled receptors (GPCRs), which respond to the peptide hormones amylin and calcitonin. Amylin receptors are heterodimers comprising the calcitonin receptor, which is a G protein-coupled receptor, and one of three receptor-modifying proteins. Amylin, formed primarily in pancreatic islet β cells, is cosecreted with insulin in response to caloric intake. Patients with type 1 diabetes have lower baseline amylin serum concentrations, and amylin response to caloric intake is absent. Patients with type 2 diabetes requiring insulin also have a diminished amylin response to caloric intake, potentially related to the degree of β-cell impairment. Key physiologic functions of amylin in maintaining glucose homeostasis include suppressing glucagon release in response to caloric intake, delaying the rate of gastric emptying, and stimulating the satiety center in the brain to limit caloric intake.

The synthetic amylin analogue pramlintide is an approved treatment for diabetes mellitus as an adjunctive therapy to mealtime insulin which promotes better glycemic control and small but significant weight loss. AM833 (cagrilintide), an investigational novel long-acting acylated amylin analogue, acts as a non-selective amylin receptor agonist. This amylin receptor agonist can serve as an attractive novel treatment for obesity, resulting in reduction of food intake and significant weight loss in a dose-dependent manner. *J Obes Metab Syndr.* 2021; 30(4): 320-325.

Accordingly, modulators of the amylin and/or calcitonin receptor could be useful in treating various metabolic disorders, as well as inducing weight loss.

SUMMARY

The present disclosure provides small molecule calcitonin and/or amylin receptor modulators (e.g., amylin-receptor agonists), as well as pharmaceutical compositions comprising the compounds disclosed herein. Also provided are methods for treating calcitonin receptor and/or amylin receptor associated diseases or disorders. It has been shown that calcitonin receptor activation is important for blood glucose regulation in diabetes; this is in addition to the known metabolic beneficial role of amylin receptor activation. Journal of Pharmacology and Experimental Therapeutics, 2020, 374 (1) 74-83.

This disclosure also provides pharmaceutical compositions comprising one or more compounds as disclosed herein, or a stereoisomer or mixture of stereoisomers thereof, or pharmaceutically acceptable salt thereof, and a pharmaceutically acceptable excipient.

Also provided herein are pharmaceutical compositions comprising one or more compounds as disclosed herein, or a stereoisomer or mixture of stereoisomers thereof, or pharmaceutically acceptable salt thereof, and a pharmaceutically acceptable excipient.

Also provided herein are methods for treating or preventing a calcitonin receptor and/or an amylin receptor associated disease or disorder in a subject in need thereof, the method comprising administering to a subject in need thereof a therapeutically effective amount of a compound disclosed herein (e.g., a compound of Formula I or subformula thereof, or a pharmaceutically acceptable salt, stereoisomer, mixture of stereoisomers, or solvate thereof), or a pharmaceutical composition thereof. In some embodiments, the method further comprises administering to the subject, a therapeutically effective amount of one or more additional therapy or therapeutic agent to the patient, such as, but not limited to, an antidiabetic agent, an anti-obesity agent, a weight loss agent, a GLP-1 receptor agonist, an anti-emetic agent, an agent to treat non-alcoholic steatohepatitis (NASH), gastric electrical stimulation, dietary monitoring, physical activity, or a combination thereof.

In some embodiments, the calcitonin receptor and/or amylin receptor associated disease or disorder is a bone disorder, a metabolic disorder, pain, a neurodegenerative disease or disorder, a cardiovascular disease, or other disease or disorder.

In some embodiments, the calcitonin receptor and/or amylin receptor associated disease or disorder is a bone disorder, including, but not limited to, osteoporosis, Paget's disease, hypercalcemia, Sudeck's atrophy, polystatic fibrous dysplasia, intersemocostoclavicular ossification, osteogenesis imperfecta, osteopenia, periodontal disease or defect, osteolytic bone disease, metastatic bone disorder, or bone loss resulting from a malignancy, autoimmune arthritides, a breakage or fracture, or immobility or disuse.

In some embodiments, the calcitonin receptor and/or amylin receptor associated disease or disorder is pain, including, but not limited to, osteopathic pain, phantom limb pain, general pain, hyperalgesia, or pain associated with diabetic neuropathy.

In some embodiments, the calcitonin receptor and/or amylin receptor associated disease or disorder is a neurodegenerative disease or disorder, including, but not limited to, Alzheimer's disease.

In some embodiments, the calcitonin receptor and/or amylin receptor associated disease or disorder is a metabolic disorder, including, but not limited to, non-alcoholic fatty liver disease (NAFLD), non-alcoholic steatohepatitis (NASH), insulin dependent diabetes, non-insulin dependent diabetes, impaired glucose tolerance, obesity, syndrome X, or other diabetic complication.

In some embodiments, the calcitonin receptor and/or amylin receptor associated disease or disorder is include primary or secondary hyperthyroidism, endocrine disorder, conditions associated with inhibiting gastric secretion, gastrointestinal disorders, renal osteodystrophy, or male infertility.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, $-C(O)NH_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., $-(CH_2)_3CH_3$), sec-butyl (i.e., $-CH(CH_3)CH_2CH_3$), isobutyl (i.e., $-CH_2CH(CH_3)_2$), and tert-butyl (i.e., $-C(CH_3)_3$), and "propyl" includes n-propyl (i.e., $-(CH_2)_2CH_3$), and isopropyl (i.e., $-CH(CH_3)_2$).

"Alkenyl" refers to an alkyl group containing at least one (e.g., 1-3, or 1) carbon-carbon double bond and having from 2 to 20 carbon atoms (i.e., $C_{2-20}$ alkenyl), 2 to 12 carbon atoms (i.e., $C_{2-12}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include, e.g., ethenyl, propenyl, butadienyl (including 1,2-butadienyl, and 1,3-butadienyl).

"Alkynyl" refers to an alkyl group containing at least one (e.g., 1-3, or 1) carbon-carbon triple bond and having from 2 to 20 carbon atoms (i.e., $C_{2-20}$ alkynyl), 2 to 12 carbon atoms (i.e., $C_{2-12}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy, and 1,2-dimethylbutoxy.

"Alkoxyalkyl" refers to an alkyl group as defined above, wherein a hydrogen atom is replaced by an alkoxy group as defined herein.

"Haloalkyl" refers to an unbranched or branched alkyl group as defined above, wherein one or more (e.g., 1 to 6 or 1 to 3) hydrogen atoms are replaced by an independently selected halo group. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Haloalkoxy" refers to an alkoxy group as defined above, wherein one or more (e.g., 1 to 6, or 1 to 3) hydrogen atoms are replaced by an independently selected halo group.

"Haloalkoxyalkyl" refers to an alkyl group as defined above, wherein a hydrogen atom is replaced by a haloalkoxy group as defined herein.

"Hydroxyalkyl" refers to an alkyl group as defined above, wherein one or more (e.g., 1 to 6, or 1 to 3) hydrogen atoms are replaced by a hydroxy group.

"Cyanoalkyl" refers to an alkyl group as defined above, wherein one, or one or more (e.g., 1 to 6, or 1 to 3) hydrogen atoms are replaced by cyano.

"Alkylthio" refers to the group "alkyl-S—".

"Acyl" refers to a group $-C(O)R$, wherein R is hydrogen, alkyl, cycloalkyl, heterocyclyl, aryl, heteroalkyl, or heteroaryl; each of which may be optionally substituted, as defined herein. Examples of acyl include formyl, acetyl, cyclohexylcarbonyl, cyclohexylmethyl-carbonyl, and benzoyl.

"Amido" refers to both a "C-amido" group which refers to the group —C(O)$NR^yR^z$ and an "N-amido" group which refers to the group —$NR^y$C(O)$R^z$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to the group —$NR^yR^z$ wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Amidino" refers to —C($NR^y$)($NR^z_2$), wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl, and anthryl. Aryl, however, does not encompass or overlap in any way with heteroaryl defined below. If one or more aryl groups are fused with a heteroaryl, the resulting ring system is heteroaryl regardless of point of attachment. If one or more aryl groups are fused with a heterocyclyl, the resulting ring system is heterocyclyl regardless of point of attachment. If one or more aryl groups are fused with a cycloalkyl, the resulting ring system is cycloalkyl regardless of point of attachment.

"Carbamoyl" refers to both an "O-carbamoyl" group which refers to the group —O—C(O)$NR^yR^z$ and an "N-carbamoyl" group which refers to the group —$NR^y$C(O)O$R^z$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Carboxyl ester" or "ester" refer to both —OC(O)$R^x$ and —C(O)O$R^x$, wherein $R^x$ is alkyl, alkenyl, alkynyl, cycloalkyl, heterocyclyl, aryl, heteroalkyl, or heteroaryl; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_{3-20}$ cycloalkyl), 3 to 14 ring carbon atoms (i.e., $C_{3-12}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl, and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl, and the like. Further, the term cycloalkyl is intended to encompass any non-aromatic ring which may be fused to an aryl ring, regardless of the attachment to the remainder of the molecule (e.g., 2,3-dihydro-1H-indenyl). Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to an alkyl group as defined above, wherein a hydrogen atom is replaced by a cycloalkyl group as defined herein.

"Imino" refers to a group —C($NR^y$)$R^z$, wherein $R^y$ and $R^z$ are each independently hydrogen, alkyl, alkenyl, alkynyl, cycloalkyl, heterocyclyl, aryl, heteroalkyl, or heteroaryl; each of which may be optionally substituted, as defined herein.

"Imido" refers to a group —C(O)$NR^y$C(O)$R^z$ or —N(C(O)$R^y$)C(O)$R^z$, wherein $R^y$ and $R^z$ are each independently hydrogen, alkyl, alkenyl, alkynyl, cycloalkyl, heterocyclyl, aryl, heteroalkyl, or heteroaryl; each of which may be optionally substituted, as defined herein, or $R^y$ and $R^z$ are taken together to form a heterocyclyl which may be optionally substituted, as defined herein.

"Halogen" or "halo" refers to atoms occupying group VIIA of the periodic table, such as fluoro, chloro, bromo, or iodo.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —$S(O)_2$—, and the like, where R is H, alkyl, aryl, cycloalkyl, heteroalkyl, heteroaryl or heterocyclyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroalkylene" refers to a divalent heteroalkyl group. "Heteroalkylene" groups must have at least one carbon and at least one heteroatomic group within the chain. The term "heteroalkylene" includes unbranched or branched saturated chain having carbon and heteroatoms. By way of example, 1, 2, or 3 carbon atoms may be independently replaced with the same or different heteroatomic group. Heteroatomic groups include, but are not limited to, —$NR^y$—, —O—, —S—, —S(O)—, —$S(O)_2$—, and the like, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkylene groups include, e.g., —$CH_2OCH_2$—, —CH($CH_3$)$OCH_2$—, —$CH_2CH_2OCH_2$—, —$OCH_2$—, —CH($CH_3$)O—, —$CH_2CH_2O$—, —$CH_2CH_2OCH_2CH_2OCH_2$—, —$CH_2CH_2OCH_2CH_2O$—, —$CH_2SCH_2$—, —CH($CH_3$)$SCH_2$—, —$CH_2CH_2SCH_2$—, —$CH_2CH_2SCH_2CH_2SCH_2$—, —$SCH_2$—, —CH($CH_3$)S—, —$CH_2CH_2S$—, —$CH_2CH_2SCH_2CH_2S$—, —$CH_2S(O)_2CH_2$—, —CH($CH_3$)$S(O)_2CH_2$—, —$CH_2CH_2S(O)_2CH_2$—, —$CH_2CH_2S(O)_2CH_2CH_2OCH_2$—, —$CH_2NR^yCH_2$—, —CH($CH_3$)$NR^yCH_2$—, —$CH_2CH_2NR^yCH_2$—, —$CH_2CH_2NR^yCH_2CH_2NR^yCH_2$—, etc., where $R^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkylene includes 1 to 10 carbon atoms, 1 to 8 carbon atoms, or 1 to 4 carbon atoms; and 1 to 3 heteroatoms, 1 to 2 heteroatoms, or 1 heteroatom. As used herein, the term "heteroalkylene" does not include groups such as amides or other functional groups having an oxo present on one or more carbon atoms.

"Heteroaryl" refers to an aromatic group having a single ring or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl, benzotriazolyl, benzo[4,6]imidazo[1,2-a]pyridyl, carbazolyl, cinnolinyl, dibenzofuranyl, dibenzothienyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, thienyl, triazolyl, tetrazolyl, and triazinyl. Examples of the fused-heteroaryl rings include, but are not limited to, benzo[d]thiazolyl, quinolinyl, isoquinolinyl, benzo[b]thienyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or partially unsaturated cyclic alkyl group, with one or more ring heteroatoms independently selected from nitrogen, oxygen, and sulfur. The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro, and may comprise one or more (e.g., 1 to 3) oxo (=O) (e.g., —C(O)—, —S(O)—, $—S(O)_2—$, or —P(O)—) or N-oxide ($—O^-$) moieties. Any non-aromatic ring or fused ring system containing at least one heteroatom and one non-aromatic ring is considered a heterocyclyl, regardless of the attachment to the remainder of the molecule. For example, fused ring systems such as 6,7-dihydro-5H-cyclopenta[b]pyridinyl, decahydroquinazolinyl, 1,2,3,4-tetrahydroquinazolinyl, and 5,6,7,8-tetrahydroquinazolinyl are heterocyclyl, regardless of the attachment (i.e., can be bound through a carbon atom or a heteroatom). Further, the term heterocyclyl is intended to encompass any non-aromatic ring containing at least one heteroatom, which ring may be fused to a cycloalkyl, an aryl, or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur, or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiomorpholinyl, thiamorpholinyl, 1-oxo-thiomorpholinyl, and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as oxabicyclo[2.2.2]octanyl, 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Sulfonyl" refers to the group $—S(O)_2R^y$, where $R^y$ is hydrogen, alkyl, alkenyl, alkynyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl, and toluenesulfonyl.

"Sulfinyl" refers to the group $—S(O)R^y$, where $R^y$ is hydrogen, alkyl, alkenyl, alkynyl, cycloalkyl, heterocyclyl, aryl, heteroalkyl, or heteroaryl; each of which may be optionally substituted, as defined herein.

The terms "optional" or "optionally" means that the subsequently described event or circumstance may or may not occur, and that the description includes instances where said event or circumstance occurs and instances in which it does not. Also, the term "optionally substituted" refers to any one or more (e.g., 1 to 5, or 1 to 3) hydrogen atoms on the designated atom or group may or may not be replaced by a moiety other than hydrogen.

As used herein, the term "compound," is meant to include any or all stereoisomers, geometric isomers, tautomers, and isotopically enriched analogs (e.g., deuterated analogs) of the structures depicted. Compounds herein identified by name or structure as one particular tautomeric form are intended to include other tautomeric forms unless otherwise specified.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^{3}H$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life, reduced dosage requirements, and/or an improvement in therapeutic index. An $^{18}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, aluminum, ammonium, calcium, and magnesium salts. Salts derived from organic bases include, but are not limited to, salts of $NH_3$, or primary, secondary, tertiary amines, such as salts derived from a N-containing heterocycle, a N-containing heteroaryl, or derived from an amine of formula $N(R^{N})_3$ (e.g., $HN^{+}(R^{N})_3$ or $(alkyl)N^{+}(R^{N})_3$) where each $R^{N}$ is independently hydrogen, alkyl, alkenyl, alkynyl, haloalkyl, cycloalkyl, heterocyclyl, aryl, or heteroaryl, wherein each is optionally substituted, such as by one or more (e.g., 1-5 or 1-3) substituents (e.g., halo, cyano, hydroxy, amino, alkyl, alkenyl, alkynyl, haloalkyl, alkoxy, or haloalkoxy). Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, acyl, alkenyl, alkoxy, alkoxyalkyl, alkyl, alkylthio, alkynyl, amidino, amido, amino, aryl, azido, carbamoyl, carboxyl, carboxyl ester, cyano, cyanoalkyl, cycloalkyl, cycloalkylalkyl, guanidino, halo, haloalkoxy, haloalkoxyalkyl, haloalkyl, heteroalkyl, heteroaryl, heterocyclyl, hydrazino, hydroxy, hydroxyalkyl, imido, imino, nitro, oxo, sulfinyl, sulfonic acid, sulfonyl, thiocyanate, thiol, thione, or combinations thereof.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxy, halo, alkoxy, cycloalkyl, heterocyclyl, aryl, and heteroaryl. In other embodiments, the one or more substituents may be further substituted with halo, alkyl, haloalkyl, hydroxy, alkoxy, cycloalkyl, heterocyclyl, aryl, or heteroaryl, each of which is substituted. In other embodiments, the substituents may be further substituted with halo, alkyl, haloalkyl, alkoxy, hydroxy, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

The term "pharmaceutically acceptable" as used herein indicates that the compound, or salt or composition thereof is compatible chemically and/or toxicologically with the other ingredients comprising a formulation and/or the subject being treated therewith.

The term "administration" or "administering" refers to a method of giving a dosage of a compound or pharmaceutical composition to a vertebrate or invertebrate, including a mammal, a bird, a fish, or an amphibian. The method of administration can vary depending on various factors, e.g., the components of the pharmaceutical composition, the site of the disease, and the severity of the disease.

The terms "effective amount" or "effective dosage" or "pharmaceutically effective amount" or "therapeutically effective amount," as used herein, refer to a sufficient amount of a chemical entity (e.g., a compound of Formula I, or a pharmaceutically acceptable salt, stereoisomer, mixture of stereoisomers, or solvate thereof) being administered which will relieve to some extent one or more of the symptoms of the disease or condition being treated, and can include curing the disease. "Curing" means that the symptoms of active disease are eliminated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study. In some embodiments, a "therapeutically effective amount" of a compound as provided herein refers to an amount of the compound that is effective as a monotherapy or combination therapy.

The term "excipient" or "pharmaceutically acceptable excipient" means a pharmaceutically-acceptable material, composition, or vehicle, such as a liquid or solid filler, diluent, carrier, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009.

The term "pharmaceutical composition" refers to a mixture of a compound of Formula I, or a pharmaceutically acceptable salt, stereoisomer, mixture of stereoisomers, or solvate thereof as provided herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to, rectal, oral, intravenous, aerosol, parenteral, ophthalmic, pulmonary, and topical administration.

The term "calcitonin receptor and/or amylin receptor associated disease or disorder" as used herein is meant to include, without limitation, those diseases, disorders, or conditions in which activation of at least one calcitonin receptor (CTR) and/or amylin receptor (AMY) by calcitonin and/or amylin contributes to the symptomology or progression of the disease or disorder. These diseases or disorders may arise from one or more of a genetic, iatrogenic, immunological, infectious, metabolic, oncological, toxic, surgical, and/or traumatic etiology.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "preventing", as used herein, is the prevention of the onset, recurrence or spread, in whole or in part, of the disease or condition as described herein, or a symptom thereof.

The terms "subject," "patient," or "individual," as used herein, are used interchangeably and refers to any animal, including mammals such as mice, rats, other rodents, rabbits, dogs, cats, swine, cattle, sheep, horses, primates, and humans. In some embodiments, the term refers to a subject, particularly a mammalian subject, for whom diagnosis, prognosis, or therapy is desired or needed. In some embodiments, the subject is a human. In some embodiments, the subject has experienced and/or exhibited at least one symptom of the disease, disorder, or condition to be treated and/or prevented.

The terms "treatment regimen" and "dosing regimen" are used interchangeably to refer to the dose and timing of administration of each therapeutic agent in a combination.

The term "pharmaceutical combination," as used herein, refers to a pharmaceutical treatment resulting from the mixing or combining of more than one active ingredient and includes both fixed and non-fixed combinations of the active ingredients.

The term "combination therapy" as used herein refers to a dosing regimen of two different therapeutically active agents (i.e., the components or combination partners of the combination), wherein the therapeutically active agents are administered together or separately in a manner prescribed by a medical care taker or according to a regulatory agency as defined herein.

The term "modulate," "modulating," or "modulation," as used herein, refers to a regulation or an adjustment (e.g., increase or decrease) and can include, for example agonism, partial agonism or antagonism.

Compounds

Provided herein are compounds that are amylin modulators. In some embodiments, provided is a compound of Formula I:

I

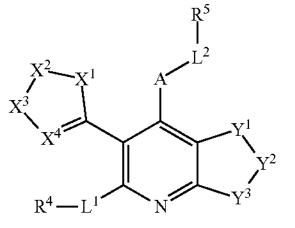

or a pharmaceutically acceptable salt, stereoisomer, mixture of stereoisomers, or solvate thereof, wherein $X^1$, $X^2$, $X^3$, $X^4$, A, $Y^1$, $Y^2$, $Y^3$, $L^1$, $L^2$, $R^4$, and $R^5$, are each independently as defined herein.

In some embodiments, provided is a compound of Formula I:

I

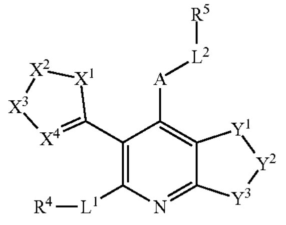

or a pharmaceutically acceptable salt, stereoisomer, mixture of stereoisomers, or solvate thereof, wherein:

A is $C_{1-6}$ alkylene, $C_{2-6}$ alkenylene, $C_{2-6}$ alkynylene, $C_{3-10}$ cycloalkylene, heterocyclylene, arylene, or heteroarylene; wherein the $C_{1-6}$ alkylene, $C_{2-6}$ alkenylene, $C_{2-6}$ alkynylene, $C_{3-10}$ cycloalkylene, heterocyclylene, arylene, or heteroaryl of A is independently optionally substituted with one to five $Z^A$;

$X^1$ is O, S, NH, $NR^A$, CH, or $CR^B$;

one of $X^2$ and $X^3$ is C(O); and the other of $X^2$ and $X^3$ is O, S, NH, $NR^A$, CH, or $CR^B$;

$X^4$ is N, CH, or $CR^B$;

provided that at least one of $X^1$, $X^2$, $X^3$, and $X^4$ is a heteroatom;

each $R^A$ is independently selected from cyano, $C_{1-3}$ alkyl, and $C_{1-3}$ haloalkyl; wherein each $C_{1-3}$ alkyl of $R^A$ is independently optionally substituted with $—NH_2$, $—NHC_{1-3}$ alkyl, $—N(C_{1-3}\ alkyl)_2$, hydroxy, or $C_{1-3}$ alkoxy;

each $R^B$ is independently selected from halo, hydroxy, $—NH_2$, cyano, $C_{1-3}$ alkyl, $C_{1-3}$ haloalkyl, $C_{1-3}$ alkoxy, and $C_{1-3}$ haloalkoxy; wherein each $C_{1-3}$ alkyl of $R^B$ is independently optionally substituted with $—NH_2$, $—NHC_{1-3}$ alkyl, $—N(C_{1-3}\ alkyl)_2$, hydroxy, or $C_{1-3}$ alkoxy;

$Y^1$ is —C(O)—, —C(S)—, $—S(O)_2—$, $—S(O)(NR^6)—$, or $—P(O)(R^7)—$;

$Y^2$ is —O—, —S—, $—NR^2—$, or $—C(R^2)_2—$; wherein the bond between $Y^1$ and $Y^2$ is a single bond; and $Y^3$ is $—NR^2—$, —O—, —S—, $—C(R^3)_2—$, $—NR^8—C(R^3)_2—$, $—O—C(R^3)_2—$, $—S—C(R^3)_2—$, $—C(R^{3a})_2—C(R^{3a})_2—$, $—C(R^{3a})_2—C(R^{3a})_2—C(R^{3a})_2—$, or $—CR^3{=}CR^3—$; or $Y^1$ is —C(O)—, —C(S)—, $—S(O)_2—$, $—S(O)(NR^6)—$, or $—P(O)(R^7)—$;

$Y^2$ is —N— or $—CR^2—$, and $Y^3$ is —N— or $—CR^3—$; wherein the bond between $Y^2$ and $Y^3$ is a double bond; or $Y^1$ is —N— or $—CR^1—$;

$Y^2$ is —N— or $—CR^2—$; wherein the bond between $Y^1$ and $Y^2$ is a double bond; and $Y^3$ is $—NR^8—$, —O—, or —S—;

provided that the ring comprising $Y^1$, $Y^2$, and $Y^3$ contains at least one heteroatom;

$L^1$ is $C_{1-3}$ alkylene, $C_{2-3}$ alkenylene, $C_{2-3}$ alkynylene, $C_{1-3}$ heteroalkylene, $C_{3-6}$ cycloalkylene, or 4-6 membered heterocyclylene; wherein the $C_{1-3}$ alkylene, $C_{2-3}$ alkenylene, $C_{2-3}$ alkynylene, $C_{1-3}$ heteroalkylene, $C_{3-6}$ cycloalkylene, or 4-6 membered heterocyclylene of $L^1$ is independently optionally substituted with one to five substituents independently selected from halo, oxo, hydroxy, cyano, $C_{1-3}$ alkyl, $C_{1-3}$ haloalkyl, $C_{1-3}$ alkoxy, and $C_{1-3}$ haloalkoxy;

$L^2$ is a bond, —O—, —S—, —$NR^2$a—, —C(O)—, —C(O)O—, —OC(O)—, —OC(O)O—, —C(O)$NR^2$a—, —$NR^{2a}$C(O)—, —OC(O)$NR^2$a—, —$NR^{2a}$C(O)O—, —$NR^{2a}$C(O)$NR^2$b—, —S(O)—, —$S(O)_2$—, —S(O)$NR^{2a}$—, —$S(O)_2NR^{2a}$—, —$NR^{2a}$S(O)—, —$NR^{2a}S(O)_2$—, —$NR^{2a}$S(O)$NR^{2b}$—, —$NR^{2a}S(O)_2$ $NR^{2b}$—, $C_{1-6}$ alkylene, $C_{2-6}$ alkenylene, $C_{2-6}$ alkynylene, $C_{1-6}$ heteroalkylene, $C_{3-6}$ cycloalkylene, 4-6 membered heterocyclylene, or 5 membered heteroarylene; wherein the $C_{1-3}$ alkylene, $C_{2-3}$ alkenylene, $C_{2-3}$ alkynylene, $C_{1-3}$ heteroalkylene, $C_{3-6}$ cycloalkylene, 4-6 membered heterocyclylene, or 5 membered heteroarylene of $L^2$ is independently optionally substituted with one to five substituents independently selected from halo, oxo, hydroxy, cyano, —$NH_2$, —$NHC_{1-3}$ alkyl, —N($C_{1-3}$ alkyl)$_2$, $C_{1-3}$ alkyl, $C_{1-3}$ haloalkyl, $C_{1-3}$ alkoxy, and $C_{1-3}$ haloalkoxy;

$R^1$ is hydrogen, halo, hydroxy, cyano, $C_{1-3}$ alkyl, $C_{2-3}$ alkenyl, $C_{2-3}$ alkynyl, $C_{1-3}$ haloalkyl, $C_{1-3}$ alkoxy, or $C_{1-3}$ haloalkoxy;

each $R^2$ is independently hydrogen, $C_{1-3}$ alkyl, $C_{2-3}$ alkenyl, $C_{2-3}$ alkynyl, $C_{1-3}$ haloalkyl, $C_{3-6}$ cycloalkyl, phenyl, 4 to 6-membered heterocyclyl, or 5 to 6-membered heteroaryl; wherein each $C_{1-3}$ alkyl, $C_{2-3}$ alkenyl, $C_{2-3}$ alkynyl, $C_{1-3}$ haloalkyl, $C_{3-6}$ cycloalkyl, phenyl, 4 to 6-membered heterocyclyl, or 5 to 6-membered heteroaryl of $R^2$ is independently optionally substituted with one to five substituents independently selected from halo, hydroxy, cyano, $C_{1-3}$ alkyl, $C_{2-3}$ alkenyl, $C_{2-3}$ alkynyl, $C_{1-3}$ haloalkyl, $C_{1-3}$ alkoxy, or $C_{1-3}$ haloalkoxy;

or $R^2$ and any one or two of $R^1$, $R^3$, $R^{3a}$, $R^6$, $R^7$, and $R^8$, together with the atoms to which they are attached, form a $C_{3-10}$ cycloalkyl, heterocyclyl, or heteroaryl; wherein the $C_{3-10}$ cycloalkyl, heterocyclyl, or heteroaryl is optionally substituted with one to five $Z^2$;

each $R^{2a}$ and $R^{2b}$ is independently hydrogen, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $R^{2a}$ and $R^{2b}$ is independently optionally substituted with one to five $Z^2$a;

or $R^{2a}$ and $R^{2b}$ are taken together with the atoms to which they are attached to form heterocyclyl independently optionally substituted by one to five $Z^2$a;

each $R^3$ is independently hydrogen, hydroxy, —$NR^{3b}R^{3c}$, $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ haloalkyl, $C_{1-6}$ haloalkoxy, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ haloalkyl, $C_{1-6}$ haloalkoxy, $C_{3-10}$ cycloalkyl, heterocyclyl, aryl, or heteroaryl of $R^3$ is independently optionally substituted with one to five $Z^3$;

or two $R^3$, together with the atom(s) to which they are attached, form a $C_{3-10}$ cycloalkyl, heterocyclyl, aryl, or heteroaryl; wherein the $C_{3-10}$ cycloalkyl, heterocyclyl, aryl, or heteroaryl is optionally substituted with one to five $Z^3$;

or two $R^3$, together with the carbon atom to which both are attached, form an oxo;

each $R^{3a}$ is independently hydrogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-10}$ cycloalkyl, heterocyclyl, aryl, or heteroaryl of $R^{3a}$ is independently optionally substituted with one to five $Z^{3a}$;

or two $R^{3a}$, together with the atom(s) to which they are attached, form a $C_{3-10}$ cycloalkyl, heterocyclyl, or heteroaryl; wherein the $C_{3-10}$ cycloalkyl, heterocyclyl, or heteroaryl is optionally substituted with one to five $Z^{3a}$;

or two $R^{3a}$, together with the carbon atom to which both are attached, form an oxo;

$R^{3b}$ and $R^{3c}$ are each independently hydrogen, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $R^{3b}$ and $R^{3c}$ is independently optionally substituted with one to five substituents independently selected from halo, hydroxy, cyano, $C_{1-3}$ alkyl, $C_{1-3}$ haloalkyl, $C_{1-3}$ alkoxy, and $C_{1-3}$ haloalkoxy;

or $R^{3b}$ and $R^{3c}$ are taken together with the nitrogen atom to which they are attached to form a heterocyclyl optionally substituted with one to five $Z^{3b}$;

$R^4$ is $C_{1-6}$ alkyl, $C_{3-10}$ cycloalkyl, heterocyclyl, aryl, or heteroaryl; wherein the $C_{1-6}$ alkyl, $C_{3-10}$ cycloalkyl, heterocyclyl, aryl, or heteroaryl of $R^4$ is independently optionally substituted with one to five $Z^4$;

$R^5$ is hydrogen, halo, hydroxy, amino, cyano, $C_{1-6}$ alkyl, $C_{1-6}$ alkoxy, $C_{1-6}$ haloalkyl, $C_{3-10}$ cycloalkyl, heterocyclyl, aryl, or heteroaryl; wherein the $C_{1-6}$ alkyl, $C_{1-6}$ alkoxy, $C_{1-6}$ haloalkyl, $C_{3-10}$ cycloalkyl, heterocyclyl, aryl, or heteroaryl of $R^5$ is independently optionally substituted with one to five $Z^5$;

$R^6$ is hydrogen, $C_{1-3}$ alkyl, $C_{1-3}$ haloalkyl, $C_{3-6}$ cycloalkyl, or 4 to 6-membered heterocyclyl; wherein the $C_{1-3}$ alkyl, $C_{1-3}$ haloalkyl, $C_{3-6}$ cycloalkyl, or 4 to 6-membered heterocyclyl is optionally substituted with one to five substituents independently selected from halo, oxo, hydroxy, cyano, $C_{1-3}$ alkyl, $C_{1-3}$ haloalkyl, $C_{1-3}$ alkoxy, and $C_{1-3}$ haloalkoxy;

$R^7$ is hydroxy, $C_{1-3}$ alkoxy, $C_{1-3}$ haloalkoxy, $C_{1-3}$ alkyl, or $C_{1-3}$ haloalkyl;

$R^8$ is hydrogen, —$S(O)_2$—$C_{1-3}$ alkyl, —$S(O)_2$—$C_{1-3}$ haloalkyl, $C_{1-3}$ alkyl, $C_{1-3}$ haloalkyl $C_{3-6}$ cycloalkyl, or 4 to 6-membered heterocyclyl; wherein the —$S(O)_2$—$C_{1-3}$ alkyl, —$S(O)_2$—$C_{1-3}$ haloalkyl, $C_{1-3}$ alkyl, $C_{1-3}$ haloalkyl $C_{3-6}$ cycloalkyl, or 4 to 6-membered heterocyclyl of $R^8$ is optionally substituted with one to five substituents independently selected from halo, oxo, hydroxy, cyano, $C_{1-3}$ alkyl, $C_{1-3}$ haloalkyl, $C_{1-3}$ alkoxy, and $C_{1-3}$ haloalkoxy;

each $Z^A$, $Z^2$, $Z^{2a}$, $Z^3$, $Z^{3a}$, $Z^{3b}$, $Z^4$, and $Z^5$; is independently halo, cyano, nitro, oxo, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, heteroaryl, -L-H, -L-$C_{1-6}$ alkyl, -L-$C_{2-6}$ alkenyl, -L-$C_{2-6}$ alkynyl, -L-$C_{1-6}$ haloalkyl, -L-$C_{3-10}$ cycloalkyl, -L-heterocyclyl, -L-aryl, or -L-heteroaryl; wherein each $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $Z^A$, $Z^2$, $Z^{2a}$, $Z^3$, $Z^{3b}$, $Z^4$, and $Z^5$ are each independently optionally substituted with one to five $Z^{1a}$;

each L is independently —O—, —S—, —$NR^{20}$—, —C(O)—, —C(O)O—, —OC(O)—, —OC(O)O—, —C(O)$NR^{20}$—, —$NR^{20}$C(O)—, —OC(O)$NR^{20}$—, —$NR^{20}$C(O)O—, —$NR^{20}$C(O)$NR^{21}$—, —S(O)—, —$S(O)_2$—, —S(O)$NR^{20}$—, —$S(O)_2NR^{20}$—, —$NR^{20}$S(O)—, —$NR^{20}S(O)_2$—, —$NR^{20}$S(O) $NR^{21}$—, or —$NR^{20}S(O)_2NR^{21}$—;

each $R^{20}$ and $R^{21}$ is independently hydrogen, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $R^{20}$ and $R^{21}$ is independently optionally substituted with one to five $Z^{1a}$; or an $R^{20}$ and $R^{21}$ are taken together with the atoms to which they are attached to form heterocyclyl independently optionally substituted by one to five $Z^{1a}$; and each $Z^{1a}$ is independently halo, hydroxy, cyano, nitro, oxo, —SH, —$NH_2$, —NH—$C_{1-6}$ alkyl, —N($C_{1-6}$ alkyl)$_2$, —S—$C_{1-6}$ alkyl, $C_{1-6}$ alkoxy, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl; wherein each —NH—$C_{1-6}$ alkyl, —N($C_{1-6}$ alkyl)$_2$, —S—$C_{1-6}$ alkyl, $C_{1-6}$ alkoxy, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $Z^{1a}$ is independently optionally substituted with one to five substituents independently selected from $C_{1-6}$ alkyl, oxo, halo, hydroxy, and cyano.

In some embodiments, provided is a compound of Formula I:

I

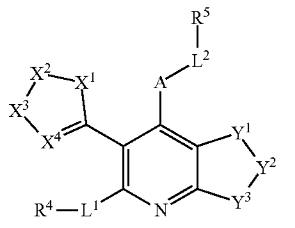

or a pharmaceutically acceptable salt, stereoisomer, mixture of stereoisomers, or solvate thereof, wherein:

A is $C_{1-6}$ alkylene, $C_{2-6}$ alkenylene, $C_{2-6}$ alkynylene, $C_{3-10}$ cycloalkylene, heterocyclylene, arylene, or heteroarylene; wherein the $C_{1-6}$ alkylene, $C_{2-6}$ alkenylene, $C_{2-6}$ alkynylene, $C_{3-10}$ cycloalkylene, heterocyclylene, arylene, or heteroaryl of A is independently optionally substituted with one to five $Z^A$;

$X^1$ is O, S, NH, $NR^A$, CH, or $CR^B$;

one of $X^2$ and $X^3$ is C(O); and the other of $X^2$ and $X^3$ is O, S, NH, $NR^A$, CH, or $CR^B$;

$X^4$ is N, CH, or $CR^B$;

provided that at least one of $X^1$, $X^2$, $X^3$, and $X^4$ is a heteroatom;

each $R^A$ is independently selected from cyano, $C_{1-3}$ alkyl, and $C_{1-3}$ haloalkyl; wherein each $C_{1-3}$ alkyl of $R^A$ is independently optionally substituted with —$NH_2$, —$NHC_{1-3}$ alkyl, —N($C_{1-3}$ alkyl)$_2$, hydroxy, or $C_{1-3}$ alkoxy;

each $R^B$ is independently selected from halo, hydroxy, cyano, $C_{1-3}$ alkyl, $C_{1-3}$ haloalkyl, $C_{1-3}$ alkoxy, and $C_{1-3}$ haloalkoxy; wherein each $C_{1-3}$ alkyl of $R^B$ is independently optionally substituted with —$NH_2$, —$NHC_{1-3}$ alkyl, —N($C_{1-3}$ alkyl)$_2$, hydroxy, or $C_{1-3}$ alkoxy;

$Y^1$ is —C(O)—, —C(S)—, —S(O)$_2$—, —S(O)($NR^6$)—, or —P(O)($R^7$)—;

$Y^2$ is —O—, —S—, —$NR^2$— or —C($R^2$)$_2$—; wherein the bond between $Y^1$ and $Y^2$ is a single bond; and $Y^3$ is —$NR^8$—, —O—, —S—, —C($R^3$)$_2$—, —$NR^8$—C($R^3$)$_2$—, —O—C($R^3$)$_2$—, —S—C($R^3$)$_2$—, —C($R^{3a}$)$_2$—C($R^{3a}$)$_2$—, —C($R^{3a}$)$_2$—C($R^{3a}$)$_2$—C($R^{3a}$)$_2$—, or —$CR^3$=$CR^3$—; or $Y^1$ is —C(O)—, —C(S)—, —S(O)$_2$—, —S(O)($NR^6$)—, or —P(O)($R^7$)—;

$Y^2$ is —N— or —$CR^2$—, and $Y^3$ is —N— or —$CR^3$—; wherein the bond between $Y^2$ and $Y^3$ is a double bond; or $Y^1$ is —N— or —$CR^1$—;

$Y^2$ is —N— or —$CR^2$—; wherein the bond between $Y^1$ and $Y^2$ is a double bond; and $Y^3$ is —$NR^8$—, —O—, or —S—;

provided that the ring comprising $Y^1$, $Y^2$, and $Y^3$ contains at least one heteroatom;

$L^1$ is $C_{1-3}$ alkylene, $C_{2-3}$ alkenylene, $C_{2-3}$ alkynylene, $C_{1-3}$ heteroalkylene, $C_{3-6}$ cycloalkylene, or 4-6 membered heterocyclylene; wherein the $C_{1-3}$ alkylene, $C_{2-3}$ alkenylene, $C_{2-3}$ alkynylene, $C_{1-3}$ heteroalkylene, $C_{3-6}$ cycloalkylene, or 4-6 membered heterocyclylene of $L^1$ is independently optionally substituted with one to five substituents independently selected from halo, oxo, hydroxy, cyano, $C_{1-3}$ alkyl, $C_{1-3}$ haloalkyl, $C_{1-3}$ alkoxy, and $C_{1-3}$ haloalkoxy;

$L^2$ is a bond, —O—, —S—, —$NR^{2a}$—, —C(O)—, —C(O)O—, —OC(O)—, —OC(O)O—, —C(O)$NR^{2a}$—, —$NR^{2a}$C(O)—, —OC(O)$NR^{2a}$—, —$NR^{2a}$C(O)O—, —$NR^{2a}$C(O)$NR^{2b}$—, —S(O)—, —S(O)$_2$—, —S(O)$NR^{2a}$—, —S(O)$_2NR^{2a}$—, —$NR^{2a}$S(O)—, —$NR^{2a}$S(O)$_2$—, —$NR^{2a}$S(O)$NR^{2b}$—, —$NR^{2a}$S(O)$_2NR^{2b}$—, $C_{1-6}$ alkylene, $C_{2-6}$ alkenylene, $C_{2-6}$ alkynylene, $C_{1-6}$ heteroalkylene, $C_{3-6}$ cycloalkylene, 4-6 membered heterocyclylene, or 5 membered heteroarylene; wherein the $C_{1-3}$ alkylene, $C_{2-3}$ alkenylene, $C_{2-3}$ alkynylene, $C_{1-3}$ heteroalkylene, $C_{3-6}$ cycloalkylene, 4-6 membered heterocyclylene, or 5 membered heteroarylene of $L^2$ is independently optionally substituted with one to five substituents independently selected from halo, oxo, hydroxy, cyano, —$NH_2$, —$NHC_{1-3}$ alkyl, —N($C_{1-3}$ alkyl)$_2$, $C_{1-3}$ alkyl, $C_{1-3}$ haloalkyl, $C_{1-3}$ alkoxy, and $C_{1-3}$ haloalkoxy;

$R^1$ is hydrogen, halo, hydroxy, cyano, $C_{1-3}$ alkyl, $C_{2-3}$ alkenyl, $C_{2-3}$ alkynyl, $C_{1-3}$ haloalkyl, $C_{1-3}$ alkoxy, or $C_{1-3}$ haloalkoxy;

each $R^2$ is independently hydrogen, $C_{1-3}$ alkyl, $C_{2-3}$ alkenyl, $C_{2-3}$ alkynyl, $C_{1-3}$ haloalkyl, $C_{3-6}$ cycloalkyl, phenyl, 4 to 6-membered heterocyclyl, or 5 to 6-membered heteroaryl; wherein each $C_{1-3}$ alkyl, $C_{2-3}$ alkenyl, $C_{2-3}$ alkynyl, $C_{1-3}$ haloalkyl, $C_{3-6}$ cycloalkyl, phenyl, 4 to 6-membered heterocyclyl, or 5 to 6-membered heteroaryl of $R^2$ is independently optionally substituted with one to five substituents independently selected from halo, hydroxy, cyano, $C_{1-3}$ alkyl, $C_{2-3}$ alkenyl, $C_{2-3}$ alkynyl, $C_{1-3}$ haloalkyl, $C_{1-3}$ alkoxy, or $C_{1-3}$ haloalkoxy;

or $R^2$ and any one of $R^1$, $R^3$, $R^{3a}$, $R^6$, $R^7$, and $R^8$, together with the atoms to which they are attached, form a $C_{3-10}$ cycloalkyl, heterocyclyl, or heteroaryl; wherein the $C_{3-10}$ cycloalkyl, heterocyclyl, or heteroaryl is optionally substituted with one to five $Z^2$;

each $R^{2a}$ and $R^{2b}$ is independently hydrogen, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $R^{2a}$ and $R^{2b}$ is independently optionally substituted with one to five $Z^2$a;

or $R^{2a}$ and $R^{2b}$ are taken together with the atoms to which they are attached to form heterocyclyl independently optionally substituted by one to five $Z^2$a;

each $R^3$ is independently hydroxy, —$NR^{3b}R^{3c}$, $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ haloalkyl, $C_{1-6}$ haloalkoxy, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ haloalkyl, $C_{1-6}$ haloalkoxy, $C_{3-10}$ cycloalkyl, heterocyclyl, aryl, or heteroaryl of $R^3$ is independently optionally substituted with one to five $Z^3$;

or two $R^3$, together with the atom(s) to which they are attached, form a $C_{3-10}$ cycloalkyl, heterocyclyl, aryl, or heteroaryl; wherein the $C_{3-10}$ cycloalkyl, heterocyclyl, aryl, or heteroaryl is optionally substituted with one to five $Z^3$;

or two $R^3$, together with the carbon atom to which both are attached, form an oxo;

each $R^{3a}$ is independently hydrogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-10}$ cycloalkyl, heterocyclyl, aryl, or heteroaryl of $R^{3a}$ is independently optionally substituted with one to five $Z^{3a}$;

or two $R^{3a}$, together with the atom(s) to which they are attached, form a $C_{3-10}$ cycloalkyl, heterocyclyl, or heteroaryl; wherein the $C_{3-10}$ cycloalkyl, heterocyclyl, or heteroaryl is optionally substituted with one to five $Z^{3a}$;

or two $R^{3a}$, together with the carbon atom to which both are attached, form an oxo;

$R^{3b}$ and $R^{3c}$ are each independently hydrogen, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $R^{3b}$ and $R^{3c}$ is independently optionally substituted with one to five substituents independently selected from halo, hydroxy, cyano, $C_{1-3}$ alkyl, $C_{1-3}$ haloalkyl, $C_{1-3}$ alkoxy, and $C_{1-3}$ haloalkoxy;

or $R^{3b}$ and $R^{3c}$ are taken together with the nitrogen atom to which they are attached to form a heterocyclyl optionally substituted with one to five $Z^{3b}$;

$R^4$ is $C_{1-6}$ alkyl, $C_{3-10}$ cycloalkyl, heterocyclyl, aryl, or heteroaryl; wherein the $C_{1-6}$ alkyl, $C_{3-10}$ cycloalkyl, heterocyclyl, aryl, or heteroaryl of $R^4$ is independently optionally substituted with one to five $Z^4$;

$R^5$ is hydrogen, halo, hydroxy, amino, cyano, $C_{1-6}$ alkyl, $C_{1-6}$ alkoxy, $C_{1-6}$ haloalkyl, $C_{3-10}$ cycloalkyl, heterocyclyl, aryl, or heteroaryl; wherein the $C_{1-6}$ alkyl, $C_{1-6}$ alkoxy, $C_{1-6}$ haloalkyl, $C_{3-10}$ cycloalkyl, heterocyclyl, aryl, or heteroaryl of $R^5$ is independently optionally substituted with one to five $Z^5$;

$R^6$ is hydrogen, $C_{1-3}$ alkyl, $C_{1-3}$ haloalkyl, $C_{3-6}$ cycloalkyl, or 4 to 6-membered heterocyclyl; wherein the $C_{1-3}$ alkyl, $C_{1-3}$ haloalkyl, $C_{3-6}$ cycloalkyl, or 4 to 6-membered heterocyclyl is optionally substituted with one to five substituents independently selected from halo, oxo, hydroxy, cyano, $C_{1-3}$ alkyl, $C_{1-3}$ haloalkyl, $C_{1-3}$ alkoxy, and $C_{1-3}$ haloalkoxy;

$R^7$ is hydroxy, $C_{1-3}$ alkoxy, $C_{1-3}$ haloalkoxy, $C_{1-3}$ alkyl, or $C_{1-3}$ haloalkyl;

$R^8$ is hydrogen, —$S(O)_2$—$C_{1-3}$ alkyl, —$S(O)_2$—$C_{1-3}$ haloalkyl, $C_{1-3}$ alkyl, $C_{1-3}$ haloalkyl $C_{3-6}$ cycloalkyl, or 4 to 6-membered heterocyclyl; wherein the —$S(O)_2$—$C_{1-3}$ alkyl, —$S(O)_2$—$C_{1-3}$ haloalkyl, $C_{1-3}$ alkyl, $C_{1-3}$ haloalkyl $C_{3-6}$ cycloalkyl, or 4 to 6-membered heterocyclyl of $R^8$ is optionally substituted with one to five substituents independently selected from halo, oxo, hydroxy, cyano, $C_{1-3}$ alkyl, $C_{1-3}$ haloalkyl, $C_{1-3}$ alkoxy, and $C_{1-3}$ haloalkoxy;

each $Z^A$, $Z^2$, $Z^{2a}$, $Z^3$, $Z^{3a}$, $Z^{3b}$, $Z^4$, and $Z^5$; is independently halo, cyano, nitro, oxo, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, heteroaryl, -L-H, -L-$C_{1-6}$ alkyl, -L-$C_{2-6}$ alkenyl, -L-$C_{2-6}$ alkynyl, -L-$C_{1-6}$ haloalkyl, -L-$C_{3-10}$ cycloalkyl, -L-heterocyclyl, -L-aryl, or -L-heteroaryl; wherein each $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $Z^A$, $Z^2$, $Z^{2a}$, $Z^3$, $Z^{3a}$, $Z^{3b}$, $Z^4$, and $Z^5$ are each independently optionally substituted with one to five $Z^{1a}$;

each L is independently —O—, —S—, —$NR^{20}$—, —C(O)—, —C(O)O—, —OC(O)—, —OC(O)O—, —C(O)$NR^{20}$—, —$NR^{20}$C(O)—, —OC(O)$NR^{20}$—, —$NR^{20}$C(O)O—, —$NR^{20}$C(O)$NR^{21}$—, —S(O)—, —$S(O)_2$—, —S(O)$NR^{20}$—, —$S(O)_2NR^{20}$—, —$NR^{20}$S(O)—, —$NR^{20}S(O)_2$—, —$NR^{20}$S(O)$NR^{21}$—, or —$NR^{20}S(O)_2NR^{21}$—;

each $R^{20}$ and $R^{21}$ is independently hydrogen, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl; wherein each $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $R^{20}$ and $R^{21}$ is independently optionally substituted with one to five $Z^{1a}$; or an $R^{20}$ and $R^{21}$ are taken together with the atoms to which they are attached to form heterocyclyl independently optionally substituted by one to five $Z^{1a}$; and each $Z^{1a}$ is independently halo, hydroxy, cyano, nitro, oxo, —SH, —$NH_2$, —NH—$C_{1-6}$ alkyl, —N($C_{1-6}$ alkyl)$_2$, —S—$C_{1-6}$ alkyl, $C_{1-6}$ alkoxy, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl; wherein each —NH—$C_{1-6}$ alkyl, —N($C_{1-6}$ alkyl)$_2$, —S—$C_{1-6}$ alkyl, $C_{1-6}$ alkoxy, $C_{1-6}$ alkyl, $C_{2-6}$ alkenyl, $C_{2-6}$ alkynyl, $C_{1-6}$ haloalkyl, $C_{3-10}$ cycloalkyl, heterocyclyl, aryl, or heteroaryl of $Z^{1a}$ is independently optionally substituted with one to five substituents independently selected from $C_{1-6}$ alkyl, oxo, halo, hydroxy, and cyano.

In some embodiments, when A is $C_{1-6}$ alkylene; then $R^5$ is $C_{3-10}$ cycloalkyl, heterocyclyl, aryl, or heteroaryl; wherein the $C_{3-10}$ cycloalkyl, heterocyclyl, aryl, or heteroaryl is independently optionally substituted.

In some embodiments, $Y^1$ is —C(O)—, —$S(O)_2$—, —S(O)($NR^6$)—, or —P(O)($R^7$)—; $Y^2$ is —O—, —S—, —$NR^2$— or —C$(R^2)_2$—; and the bond between $Y^1$ and $Y^2$ is a single bond; and $Y^3$ is —$NR^8$—, —C$(R^3)_2$—, —C$(R^{3a})_2$—C$(R^{3a})_2$—, or —C$(R^{3a})_2$—C$(R^{3a})_2$—C$(R^{3a})_2$—.

In some embodiments, $Y^1$ is —C(O)—, —$S(O)_2$—, —S(O)($NR^6$)—, or —P(O)($R^7$)—; $Y^2$ is —O—, —S—, —$NR^2$—, or —C$(R^2)_2$—; and the bond between $Y^1$ and $Y^2$ is a single bond; and $Y^3$ is —$NR^8$—.

In some embodiments, $R^6$ is $C_{1-3}$ alkyl.

In some embodiments, $R^7$ is $C_{1-3}$ alkyl.

In some embodiments, $Y^1$ is —C(O)— or —$S(O)_2$—.

In some embodiments, $Y^1$ is —C(O)— or —$S(O)_2$—; and the bond between $Y^1$ and $Y^2$ is a single bond.

In some embodiments, $Y^1$ is —C(O)—.

In some embodiments, $Y^1$ is —C(O)—; and the bond between $Y^1$ and $Y^2$ is a single bond.

In some embodiments, $Y^1$ is —$S(O)_2$—; and the bond between $Y^1$ and $Y^2$ is a single bond.

In some embodiments, $Y^2$ is —$NR^2$— or —C$(R^2)_2$—; and the bond between $Y^1$ and $Y^2$ is a single bond.

In some embodiments, $Y^2$ is $—NR^2—$ or $—C(R^2)_2—$; and the bond between $Y^1$ and $Y^2$ is a single bond.

In some embodiments, $Y^2$ is $—NR_2—$.

In some embodiments, $Y^2$ is $—NR^2—$; and the bond between $Y^1$ and $Y^2$ is a single bond.

In some embodiments, $Y^1$ is $—C(O)—$; and $Y^2$ is $—NR^2—$; and the bond between $Y^1$ and $Y^2$ is a single bond.

In some embodiments, $Y^3$ is $—N—$ or $—C(R^3)_2—$.

In some embodiments, $Y^3$ is $—C(R^3)_2—$.

In some embodiments, $Y^1$ is $—C(O)—$ or $—S(O)_2—$; $Y^2$ is $—NR^2—$ or $—C(R^2)_2—$; and the bond between $Y^1$ and $Y^2$ is a single bond; and $Y^3$ is $—N—$ or $—C(R^3)_2—$.

In some embodiments, provided is a compound of Formula IA:

IA

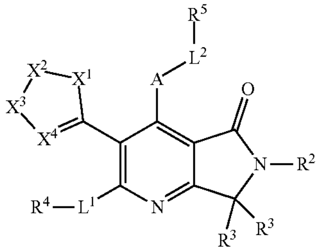

or a pharmaceutically acceptable salt, stereoisomer, mixture of stereoisomers, or solvate thereof, wherein each $X^1$, $X^2$, $X^3$, $X^4$, A, $L^1$, $L^2$, $R^2$, $R^3$, $R^4$, and $R^5$ are independently as defined herein.

In some embodiments, $R^2$ and $R^3$, together with the atoms to which they are attached, form a heterocyclyl optionally substituted with one to five $Z^2$.

In some embodiments, $R^2$ and $R^3$, together with the atoms to which they are attached, form an unsubstituted heterocyclyl.

In some embodiments, $R^2$ is hydrogen.

In some embodiments, each $R^3$ is independently hydrogen or $C_{1-3}$ alkyl.

In some embodiments, provided is a compound of Formula IB:

IB

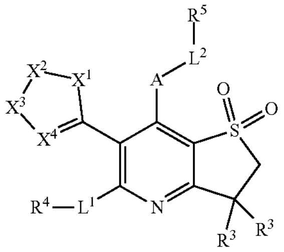

or a pharmaceutically acceptable salt, stereoisomer, mixture of stereoisomers, or solvate thereof, wherein each $X^1$, $X^2$, $X^3$, $X^4$, A, $L^1$, $L^2$, $R^3$, $R^4$, and $R^5$ are independently as defined herein.

In some embodiments, provided is a compound of Formula IC:

IC

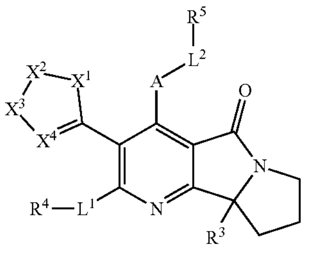

or a pharmaceutically acceptable salt, stereoisomer, mixture of stereoisomers, or solvate thereof, wherein each $X^1$, $X^2$, $X^3$, $X^4$, A, $L^1$, $L^2$, $R^3$, $R^4$, and $R^5$ are independently as defined herein.

In some embodiments, provided is a compound of Formula ID:

ID

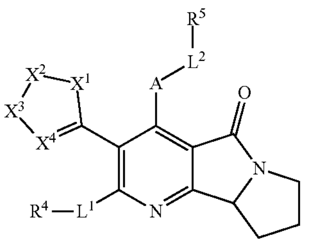

or a pharmaceutically acceptable salt, stereoisomer, mixture of stereoisomers, or solvate thereof, wherein each $X^1$, $X^2$, $X^3$, $X^4$, A, $L^1$, $L^2$, $R^4$, and $R^5$ are independently as defined herein.

In some embodiments, provided is a compound of Formula IE:

IE

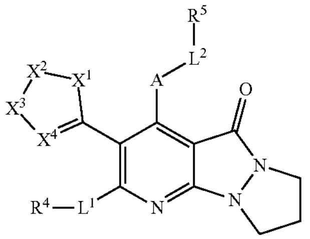

or a pharmaceutically acceptable salt, stereoisomer, mixture of stereoisomers, or solvate thereof, wherein each $X^1$, $X^2$, $X^3$, $X^4$, A, $L^1$, $L^2$, $R^4$, and $R^5$ are independently as defined herein.

In some embodiments, provided is a compound of Formula IF:

IF

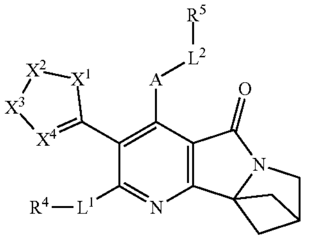

or a pharmaceutically acceptable salt, stereoisomer, mixture of stereoisomers, or solvate thereof, wherein each $X^1$, $X^2$, $X^3$, $X^4$, A, $L^1$, $L^2$, $R^4$, and $R^5$ are independently as defined herein.

In some embodiments, provided is a compound of Formula IG:

IG

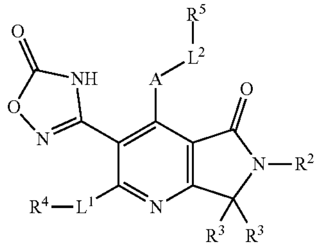

or a pharmaceutically acceptable salt, stereoisomer, mixture of stereoisomers, or solvate thereof, wherein each A, $L^1$, $L^2$, $R^2$, $R^3$, $R^4$, and $R^5$ are independently as defined herein.

In some embodiments, $R^2$ and $R^3$, together with the atoms to which they are attached, form a heterocyclyl optionally substituted with one to five $Z^2$.

In some embodiments, $R^2$ and $R^3$, together with the atoms to which they are attached, form an unsubstituted heterocyclyl.

In some embodiments, $R^2$ is hydrogen.

In some embodiments, each $R^3$ is independently hydrogen or $C_{1-3}$ alkyl.

In some embodiments, provided is a compound of Formula IH:

IH

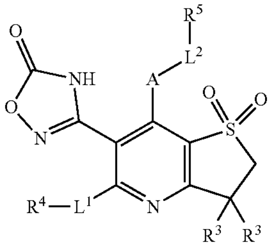

or a pharmaceutically acceptable salt, stereoisomer, mixture of stereoisomers, or solvate thereof, wherein each A, $L^1$, $L^2$, $R^3$, $R^4$, and $R^5$ are independently as defined herein.

In some embodiments, provided is a compound of Formula IJ:

IJ

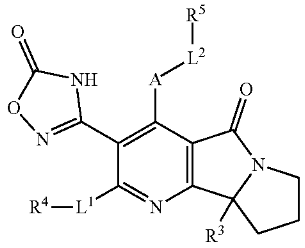

or a pharmaceutically acceptable salt, stereoisomer, mixture of stereoisomers, or solvate thereof, wherein each A, $L^1$, $L^2$, $R^3$, $R^4$, and $R^5$ are independently as defined herein.

In some embodiments, provided is a compound of Formula IK:

IK

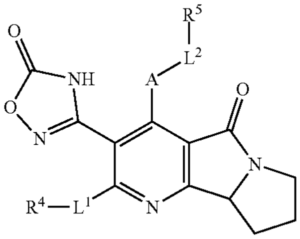

or a pharmaceutically acceptable salt, stereoisomer, mixture of stereoisomers, or solvate thereof, wherein each A, $L^1$, $L^2$, $R^4$, and $R^5$ are independently as defined herein.

In some embodiments, provided is a compound of Formula IL:

IL

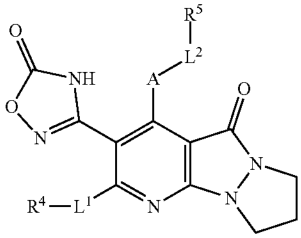

or a pharmaceutically acceptable salt, stereoisomer, mixture of stereoisomers, or solvate thereof, wherein each $X^1$, $X^2$, $X^3$, $X^4$, A, $L^1$, $L^2$, $R^4$, and $R^5$ are independently as defined herein.

In some embodiments, provided is a compound of Formula IM:

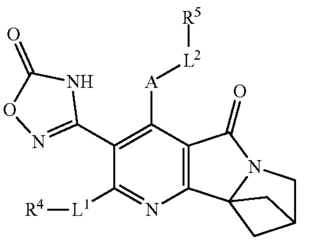

IM or a pharmaceutically acceptable salt, stereoisomer, mixture of stereoisomers, or solvate thereof, wherein each A, $L^1$, $L^2$, $R^4$, and $R^5$ are independently as defined herein.

In some embodiments, A is $C_{1-6}$ alkylene, $C_{3-10}$ cycloalkylene, heterocyclylene, arylene, or heteroarylene; wherein the $C_{1-6}$ alkylene, $C_{3-10}$ cycloalkylene, heterocyclylene, arylene, or heteroarylene of A is independently optionally substituted with one to five $Z^A$.

In some embodiments, A is $C_{1-6}$ alkylene, $C_{3-10}$ cycloalkylene, 3 to 10-membered heterocyclylene, $C_{6-10}$ arylene, or 5 to 10-membered heteroarylene; wherein each is independently optionally substituted with one to five $Z^A$.

In some embodiments, A is $C_{3-10}$ cycloalkylene, 3 to 10-membered heterocyclylene, $C_{6-10}$ arylene, or 5 to 10-membered heteroarylene; wherein each is independently optionally substituted with one to five $Z^A$.

In some embodiments, A is $C_{3-10}$ cycloalkylene or 3 to 10-membered heterocyclylene; wherein the cycloalkylene or heterocyclylene is optionally substituted with one to five $Z^A$.

In some embodiments, A is arylene or heteroarylene; wherein the arylene or heteroarylene is optionally substituted with one to five $Z^A$.

In some embodiments, A is arylene optionally substituted with one to five $Z^A$.

In some embodiments, A is heteroarylene optionally substituted with one to five $Z^A$.

In some embodiments, A is $C_{3-10}$ cycloalkylene optionally substituted with one to five $Z^A$.

In some embodiments, A is 3 to 10-membered heterocyclylene optionally substituted with one to five $Z^A$.

In some embodiments, A is unsubstituted $C_{3-10}$ cycloalkylene, unsubstituted 3 to 10-membered heterocyclylene, unsubstituted $C_{6-10}$ arylene, or unsubstituted 5 to 10-membered heteroarylene.

In some embodiments, A is unsubstituted arylene.

In some embodiments, A is unsubstituted heteroarylene.

In some embodiments, A is unsubstituted $C_{3-10}$ cycloalkylene.

In some embodiments, A is unsubstituted 3 to 10-membered heterocyclylene.

In some embodiments, A is methylene, ethylene, n-propylene,

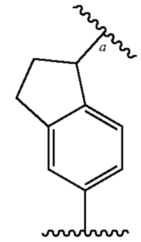 , 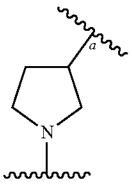 , 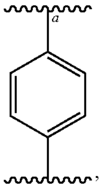 ,

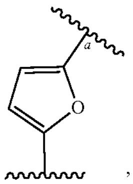 , 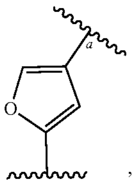 , 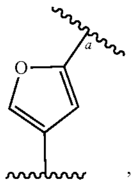 ,

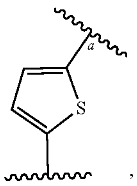 , 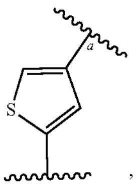 , 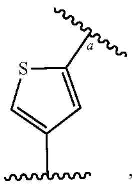 ,

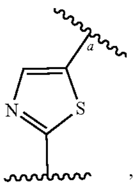 , 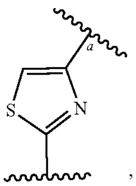 , 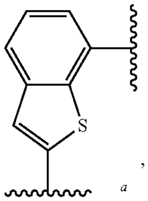 ,

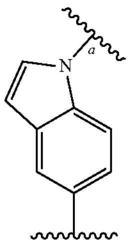 , 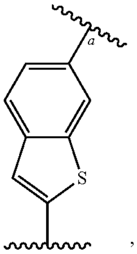 , 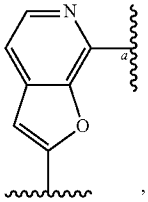 ,

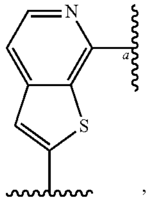 , 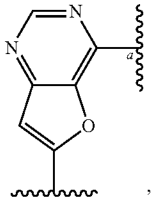 , 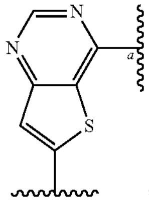 ,

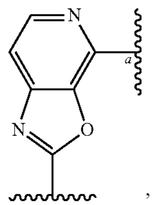 , 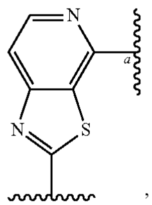 , 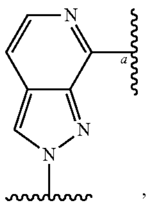 ,

-continued
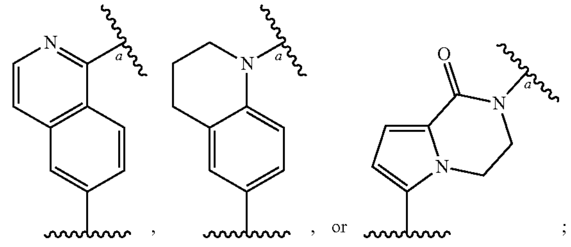
, , or ;
wherein bond a is bonded to $L^2$.
In some embodiments, A is
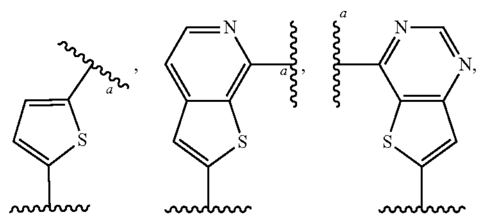
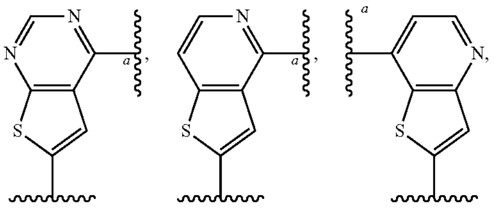
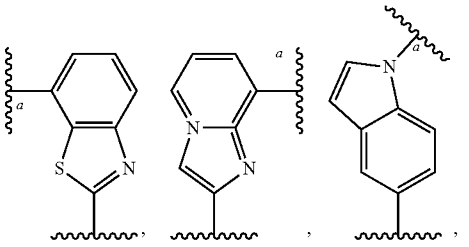
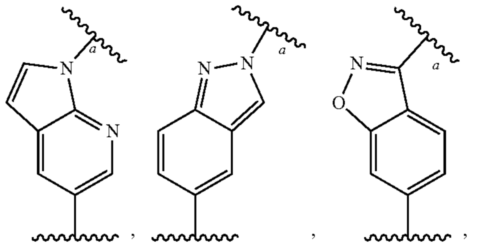
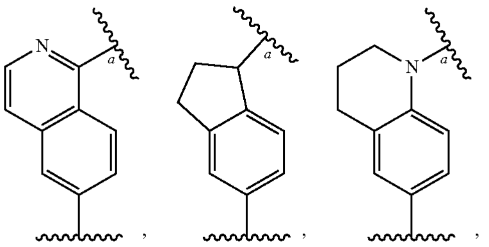
-continued
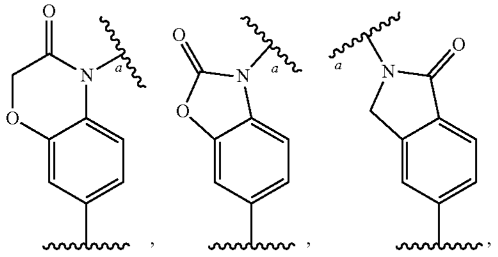
, , , or
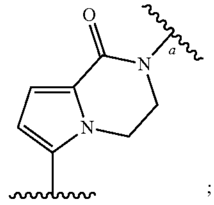
;
wherein each is independently optionally substituted with one to five $Z^4$; and wherein bond a is bonded to $L^2$.
In some embodiments, A is
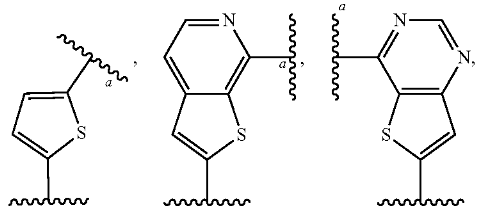
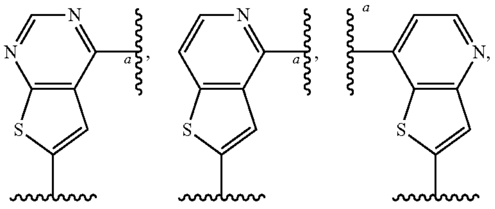
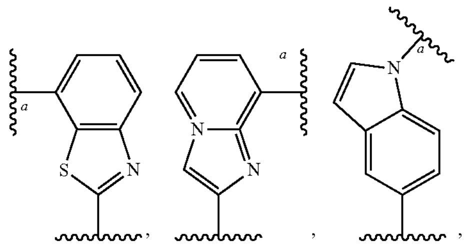
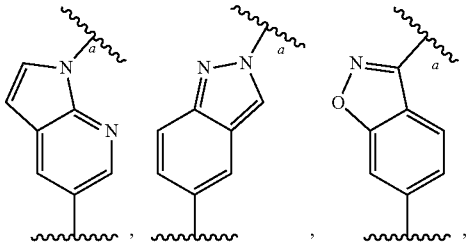

-continued

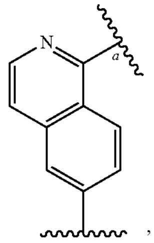 , 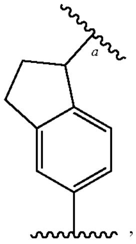 , 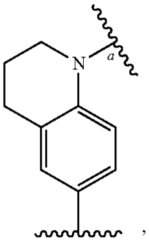 ,

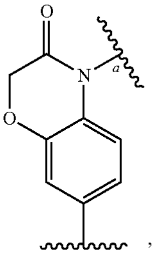 , 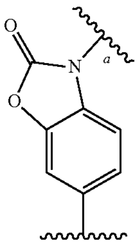 , 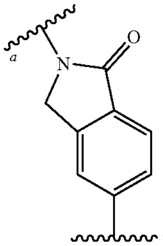 , or

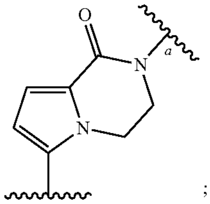 ;

wherein each is independently optionally substituted with one to three substituents independently selected from halo, $C_{1-6}$ alkyl and $C_{1-6}$ haloalkyl; and wherein bond a is bonded to $L^2$.

In some embodiments, A is

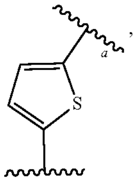 , 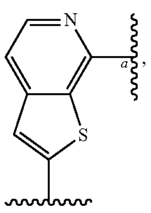 , 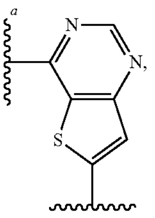

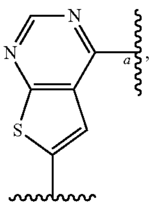 , 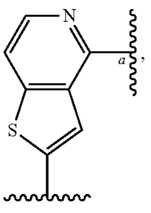 , 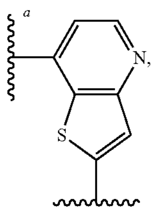

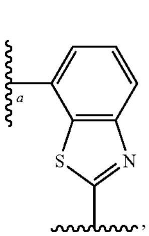 , 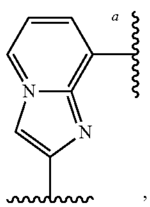 , 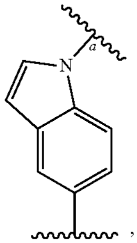 ,

-continued

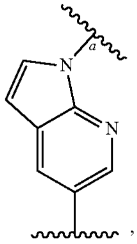 , 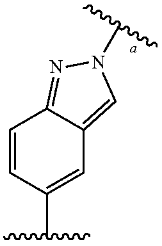 , 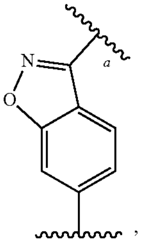 ,

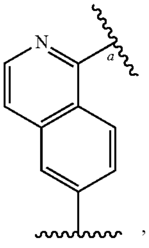 , 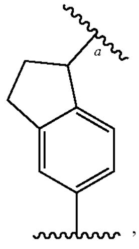 , 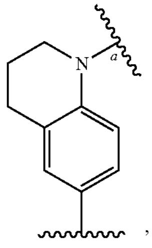 ,

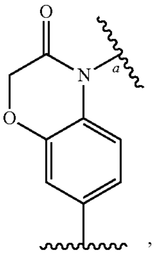 , 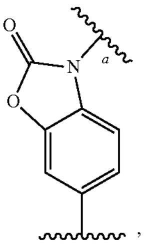 , 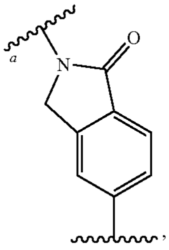 , or

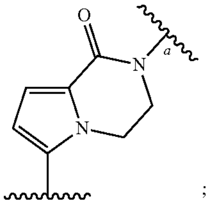 ;

wherein each is independently optionally substituted with one to three substituents independently selected from $C_{1-6}$ alkyl and $C_{1-6}$ haloalkyl; and wherein bond a is bonded to $L^2$.

In some embodiments, A is

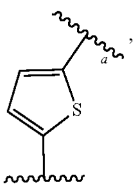 , 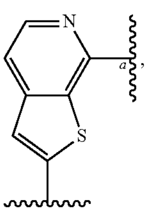 , 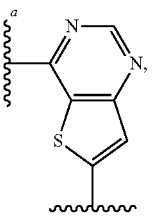

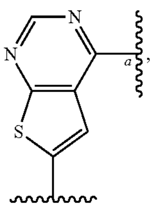 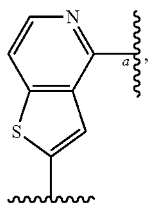 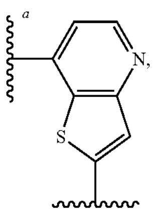

-continued
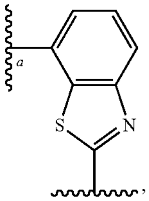, 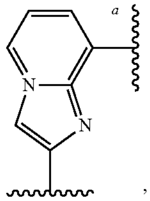, 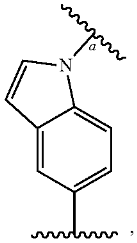, 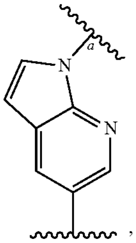, 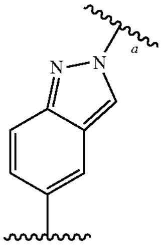, 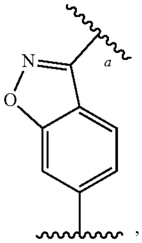, 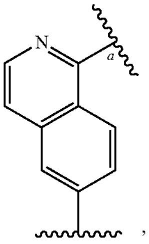, 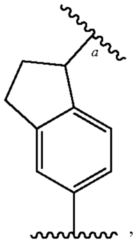, 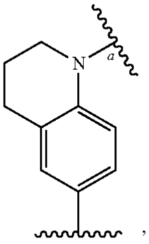, 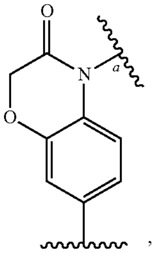, 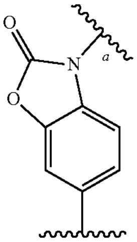, 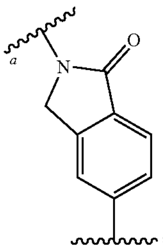, or 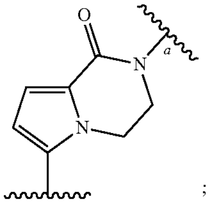;
wherein each is independently optionally substituted with one to three substituents independently selected from methyl, $CHF_2$, and $CF_3$; and wherein bond a is bonded to $L^2$.
In some embodiments, A is
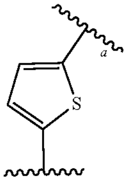, 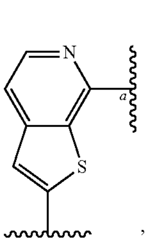, 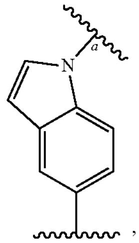,
-continued
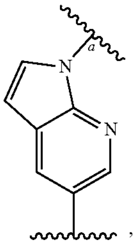, 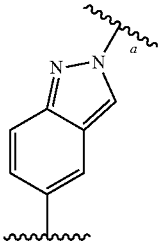, 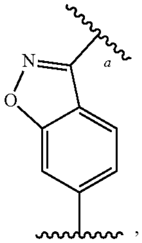, 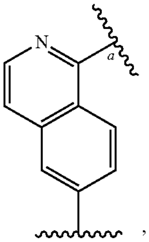, 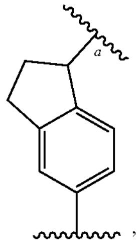, 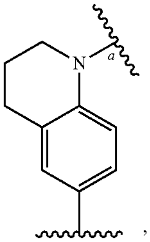, 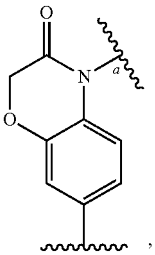, 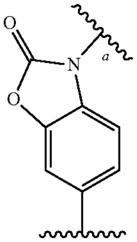, or 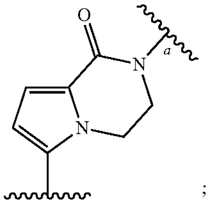;
and wherein bond a is bonded to $L^2$.
In some embodiments, A is
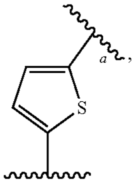, 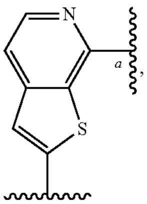, 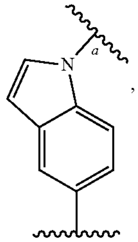, 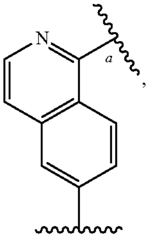, 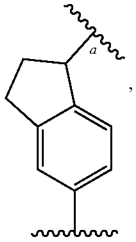, 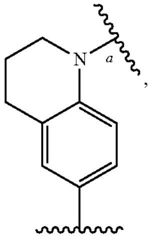, or -continued

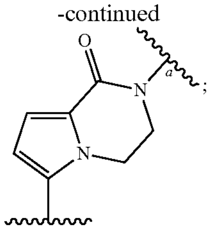

wherein bond a is bonded to $L^2$.

In some embodiments, A is

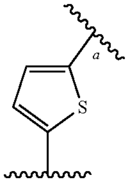 or 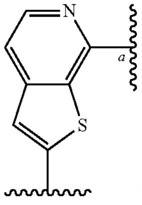 ;

wherein bond a is bonded to $L^2$.

In some embodiments, at least one of $X^1$, $X^2$, $X^3$, and $X^4$ is other than CH or $CR^B$.

In some embodiments, at least one of $X^1$, $X^2$, $X^3$, and $X^4$ is O, S, N, NH, or $NR^A$.

In some embodiments, $X^1$ is O, NH, or $NR^A$. In some embodiments, $X^1$ is O. In some embodiments, $X^1$ is NH or $NR^A$. In some embodiments, $X^1$ is NH. In some embodiments, $X^1$ is $NR^A$. In some embodiments, $R^A$ is methyl. In some embodiments, $X^1$ is O, NH, or $NCH_3$.

In some embodiments, $X^2$ is C(O). In some embodiments, the moiety

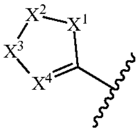 is 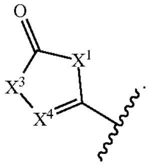.

In some embodiments, $X^3$ is O, NH, or $NR^A$. In some embodiments, $X^3$ is O. In some embodiments, $X^3$ is NH or $NR^A$. In some embodiments, $X^3$ is NH. In some embodiments, $X^3$ is $NR^A$. In some embodiments, $R^A$ is methyl.

In some embodiments, $X^3$ is C(O). In some embodiments, the moiety

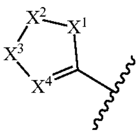 is 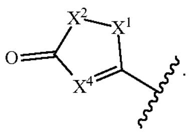.

In some embodiments, $X^2$ is O, NH, or $NR^A$. In some embodiments, $X^2$ is O. In some embodiments, $X^2$ is NH or $NR^A$. In some embodiments, $X^2$ is NH. In some embodiments, $X^2$ is $NR^A$. In some embodiments, $R^A$ is methyl.

In some embodiments, $X^4$ is N, CH, or $CR^B$. In some embodiments, $X^4$ is N or CH. In some embodiments, $X^4$ is N. In some embodiments, $X^4$ is CH.

In some embodiments, the moiety

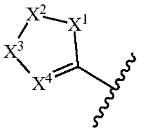 is 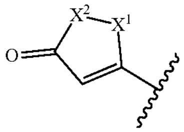 or 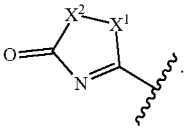.

In some embodiments, the moiety

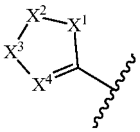 is 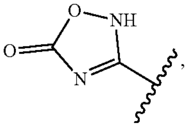, 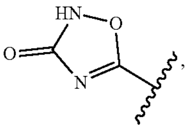, 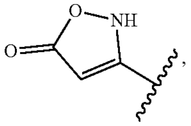, or 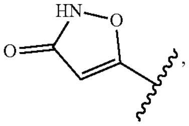, wherein each is optionally substituted with $R^B$.

In some embodiments, the moiety

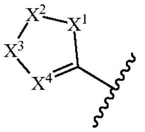 is 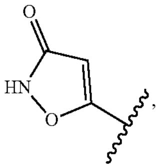, 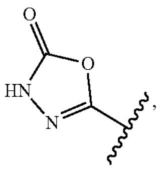, or 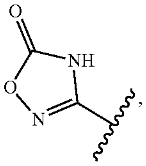, wherein each is optionally substituted with $R^B$.

In some embodiments, each $R^B$ is independently $C_{1-3}$ alkyl.

In some embodiments, the moiety

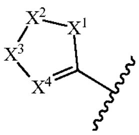 is 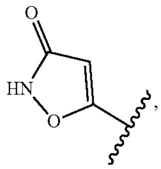, 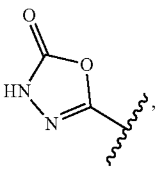, 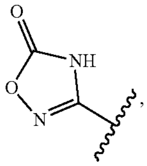, or 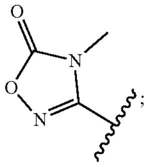;

In some embodiments, $L^1$ is $C_{1-3}$ alkylene or $C_{1-3}$ heteroalkylene; wherein each is optionally substituted with one to five independently selected halo. In some embodiments, $L^1$ is $C_{1-3}$ alkylene or $C_{1-3}$ heteroalkylene. In some embodiments, $L^1$ is $C_{1-3}$ alkylene.

In some embodiments, $R^4$ is $C_{1-6}$ alkyl optionally substituted with one to five $Z^4$.

In some embodiments, $R^4$ is aryl or heteroaryl; wherein the aryl or heteroaryl is optionally substituted with one to five $Z^4$.

In some embodiments, $R^4$ is $C_{3-10}$ cycloalkyl or aryl; wherein the $C_{3-10}$ cycloalkyl or heteroaryl is optionally substituted with one to five $Z^4$.

In some embodiments, $R^4$ is $C_{3-10}$ cycloalkyl or aryl; wherein the $C_{3-10}$ cycloalkyl or heteroaryl is optionally substituted with halo, $C_{1-6}$ alkyl, $C_{1-6}$ haloalkyl, or $C_{3-10}$ cycloalkyl.

In some embodiments, $R^4$ is cyclohexyl or phenyl; wherein the cyclohexyl or phenyl is optionally substituted with one to five $Z^4$.

In some embodiments, $R^4$ is cyclohexyl or phenyl; wherein the cyclohexyl or phenyl is independently optionally substituted with halo, $C_{1-6}$ alkyl, $C_{1-6}$ haloalkyl, or $C_{3-10}$ cycloalkyl.

In some embodiments, $R^4$ is $C_{3-10}$ cycloalkyl, heterocyclyl, aryl, or heteroaryl; wherein the $C_{1-6}$ alkyl, $C_{3-10}$ cycloalkyl, heterocyclyl, aryl, or heteroaryl of $R^4$ is independently optionally substituted with one to five $Z^4$.

In some embodiments, $R^4$ is $C_{3-10}$ cycloalkyl, heterocyclyl, aryl, or heteroaryl; wherein the $C_{1-6}$ alkyl, $C_{3-10}$ cycloalkyl, heterocyclyl, aryl, or heteroaryl of $R^4$ is independently optionally substituted with halo, $C_{1-6}$ alkyl, $C_{1-6}$ haloalkyl, or $C_{3-10}$ cycloalkyl.

In some embodiments, $R^4$ is $C_{3-10}$ cycloalkyl, heterocyclyl, aryl, or heteroaryl; wherein the $C_{1-6}$ alkyl, $C_{3-10}$ cycloalkyl, heterocyclyl, aryl, or heteroaryl of $R^4$ is independently optionally substituted with one to three substituents independently selected from halo, $C_{1-6}$ alkyl, $C_{1-6}$ haloalkyl, $C_{1-6}$ alkoxy, heteroaryl, and $C_{3-10}$ cycloalkyl.

In some embodiments, $R^4$ is phenyl,

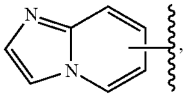, 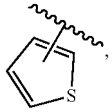, 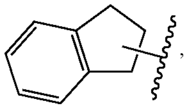, 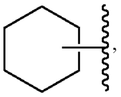, 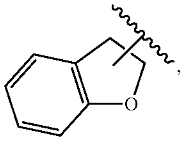, 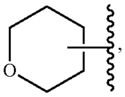, or 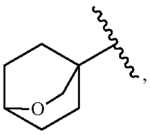, wherein each is independently optionally substituted with one to three $Z^4$.

In some embodiments, $R^4$ is phenyl

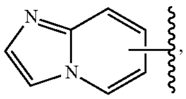, 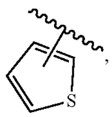, 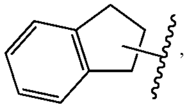,

-continued

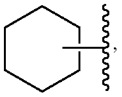, 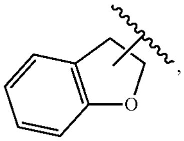, 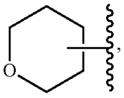, or 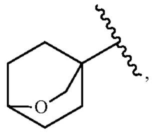, wherein each is independently optionally substituted with one to three substituents independently selected from halo, $C_{1-6}$ alkyl, $C_{1-6}$ haloalkyl, $C_{1-6}$ alkoxy, pyrazolyl, and $C_{3-6}$ cycloalkyl.

In some embodiments, $L^1$-$R^4$ is

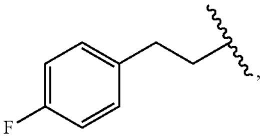, 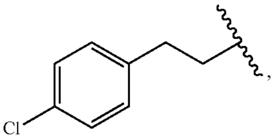,

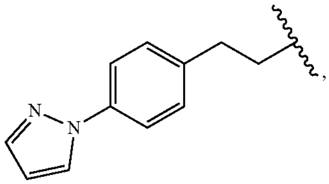,

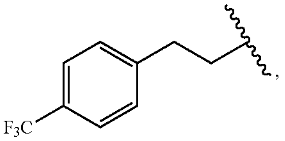,

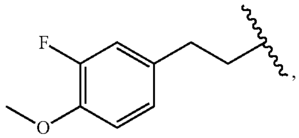,

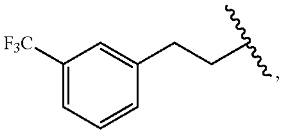, 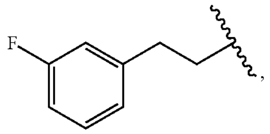,

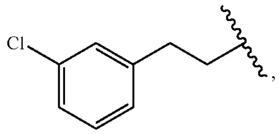,

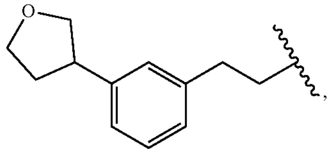, 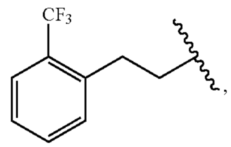,

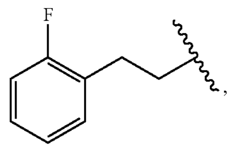, 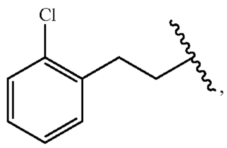,

-continued

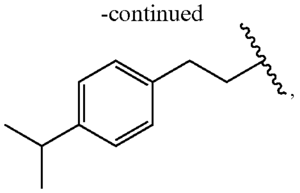,

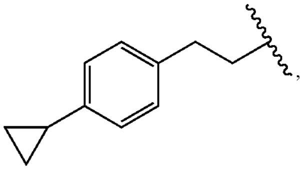,

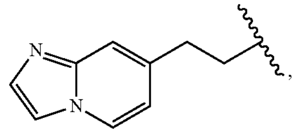, 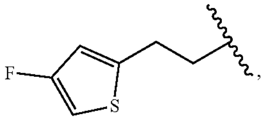,

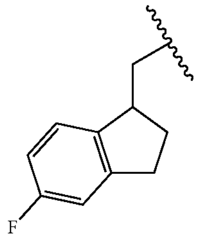, 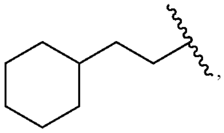,

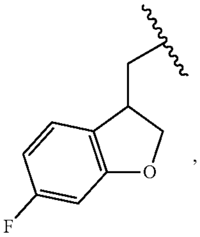, 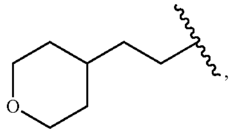, or

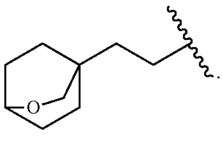.

In some embodiments, $L^2$ is a bond, —$NR^{2a}$—, —C(O)—, —C(O)$NR^{2a}$—, —$NR^{2a}$C(O)—, $C_{1-6}$ alkylene, $C_{2-6}$ alkenylene, $C_{2-6}$ alkynylene, $C_{1-6}$ heteroalkylene, 4-6 membered heterocyclylene, or 5 membered heteroarylene; wherein the $C_{1-6}$ alkylene, $C_{2-6}$ alkenylene, $C_{2-6}$ alkynylene, $C_{1-6}$ heteroalkylene, 4-6 membered heterocyclylene, or 5 membered heteroarylene is independently optionally substituted with one to five substituents independently selected from halo, oxo, hydroxy, cyano, $C_{1-3}$ alkyl, $C_{1-3}$ haloalkyl, $C_{1-3}$ alkoxy, and $C_{1-3}$ haloalkoxy.

In some embodiments, $L^2$ is a bond, —C(O)—, —$NR^{2a}$—, —C(O)$NR^{2a}$—, —$NR^{2a}$C(O)—, $C_{1-6}$ alkylene, $C_{1-6}$ heteroalkylene, 4-6 membered heterocyclylene, or 5 membered heteroarylene; wherein the $C_{1-6}$ alkylene, $C_{1-6}$ heteroalkylene, 4-6 membered heterocyclylene, or 5 membered heteroarylene is independently optionally substituted with one to five substituents independently selected from halo, oxo, hydroxy, cyano, $C_{1-3}$ alkyl, $C_{1-3}$ haloalkyl, $C_{1-3}$ alkoxy, and $C_{1-3}$ haloalkoxy.

In some embodiments, $L^2$ is a bond, —$NR^{2a}$—, —C(O)—, —C(O)$NR^{2a}$—, $C_{1-6}$ alkylene, $C_{1-6}$ heteroalkylene, or 4-6 membered heterocyclylene; wherein the $C_{1-6}$ alkylene or $C_{1-6}$ heteroalkylene is optionally substituted with one to three substituents independently selected from methyl and oxo.

In some embodiments, $L^2$ is a bond, —$NR^{2a}$—, —C(O)—, —C(O)$NR^{2a}$—, $C_{1-6}$ alkylene, $C_{1-6}$ heteroalkylene, or 4-6 membered heterocyclylene; wherein the $C_{1-6}$ alkylene or $C_{1-6}$ heteroalkylene is optionally substituted with methyl.

In some embodiments, $R^{2a}$ is hydrogen or methyl. In some embodiments, $R^{2a}$ is hydrogen.

In some embodiments, $L^2$ is a bond, —$NR^{2a}$—, —C(O)—, —C(O)$NR^{2a}$—, $C_{1-6}$ alkylene, $C_{1-6}$ heteroalkylene, or 4-6 membered heterocyclylene; wherein $R^{2a}$ is hydrogen or methyl; and wherein the $C_{1-6}$ alkylene or $C_{1-6}$ heteroalkylene is optionally substituted with methyl.

In some embodiments, $L^2$ is a bond, —$NR^{2a}$—, —C(O)—, —C(O)$NR^{2a}$—, $C_{1-6}$ alkylene, $C_{1-6}$ heteroalkylene, or 4-6 membered heterocyclylene; wherein $R^{2a}$ is hydrogen or methyl; and wherein the $C_{1-6}$ alkylene or $C_{1-6}$ heteroalkylene is optionally substituted with one to three substituents independently selected from methyl and oxo.

In some embodiments, $L^2$ is a bond, —NH—, —$NHCH_2$—, —NH—$CH(CH_3)$—, —$N(CH_3)$—$CH_2$—, —$OCH_2$—, —$CH_2$—, —$CH_2CH_2$—, —C(O)—, —C(O)NH—$CH_2$—, —C(O)$N(CH_3)$—$CH_2$—.

In some embodiments, $L^2$ is a bond, —NH—, —$NHCH_2$—, —NH—$CH(CH_3)$—, —$N(CH_3)$—$CH_2$—, —$OCH_2$—, —$CH_2$—, —$CH(CH_3)$—, —$CH_2CH_2$—, —C(O)—, —C(O)NH—$CH_2$—, —C(O)$N(CH_3)$—$CH_2$—.

In some embodiments, $R^5$ is hydrogen, halo, amino, cyano, $C_{1-6}$ alkyl, $C_{1-6}$ alkoxy, $C_{3-10}$ cycloalkyl, heterocyclyl, aryl, or heteroaryl; wherein the $C_{1-6}$ alkyl, $C_{1-6}$ alkoxy, $C_{3-10}$ cycloalkyl, heterocyclyl, aryl, or heteroaryl is independently optionally substituted with one to five $Z^5$.

In some embodiments, $R^5$ is $C_{3-10}$ cycloalkyl, heterocyclyl, aryl, or heteroaryl; wherein the cycloalkyl, heterocyclyl, aryl, or heteroaryl of $R^5$ is independently optionally substituted with one to five $Z^5$.

In some embodiments, $R^5$ is $C_{3-10}$ cycloalkyl, heterocyclyl, or aryl; wherein the cycloalkyl, heterocyclyl, or aryl of $R^5$ is independently optionally substituted with one to five $Z^5$.

In some embodiments, $R^5$ is $C_{1-6}$ alkyl optionally substituted with $C_{3-10}$ cycloalkyl, heterocyclyl, aryl, or heteroaryl; wherein the $C_{3-10}$ cycloalkyl, heterocyclyl, aryl, or heteroaryl is optionally substituted with one to five $Z^{1a}$.

In some embodiments, $R^5$ is $C_{1-6}$ alkyl, aryl, or heteroaryl; wherein the aryl or heteroaryl is optionally substituted with one to five $Z^5$.

In some embodiments, $R^5$ is aryl or heteroaryl; wherein the aryl or heteroaryl is optionally substituted with one to five $Z^5$.

In some embodiments, $R^5$ is hydrogen, halo, amino, cyano, $C_{1-6}$ alkyl, $C_{1-6}$ alkoxy, $C_{3-10}$ cycloalkyl, heterocyclyl, or aryl; wherein the $C_{1-6}$ alkyl, $C_{1-6}$ alkoxy, $C_{3-10}$ cycloalkyl, heterocyclyl, or aryl is independently optionally substituted with one to five $Z^5$.

In some embodiments, $R^5$ is $C_{3-10}$ cycloalkyl, heterocyclyl, aryl, or heteroaryl; wherein the cycloalkyl, heterocyclyl, aryl, or heteroaryl of $R^5$ is independently optionally substituted with one to five $Z^5$, and wherein at least one $Z^5$ group is fluorine.

In some embodiments, $R^5$ is

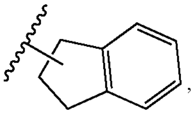, 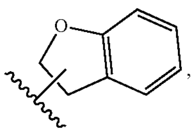,

-continued

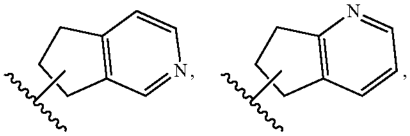

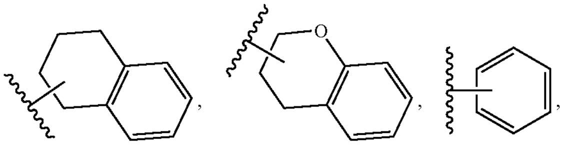

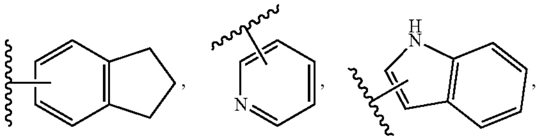

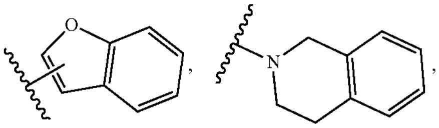

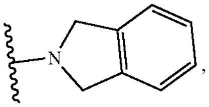

or

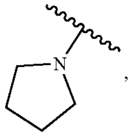

wherein each is independently optionally substituted with one to five $Z^5$.

In some embodiments, $R^5$ is

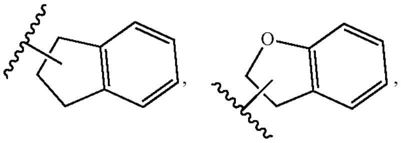

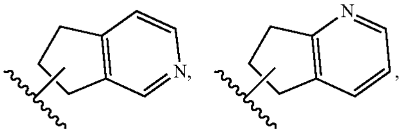

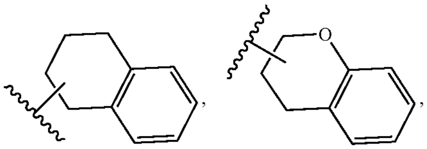

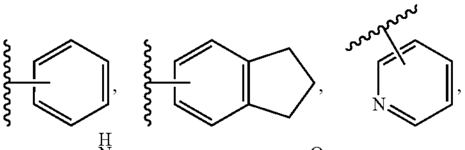

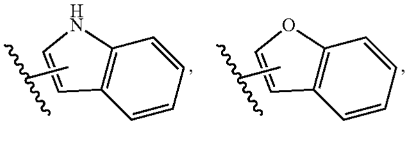

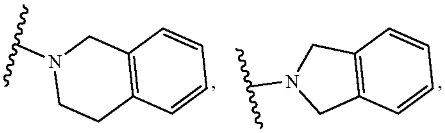

or

-continued

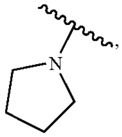

wherein each is independently optionally substituted with one to five substituents independently selected from halo, $C_{1-6}$ alkyl, $C_{1-6}$ alkoxy, $C_{1-6}$ haloalkoxy, $C_{1-6}$ haloalkyl, cyano, and halo substituted phenyl.

In some embodiments, $L^2$-$R^5$ is

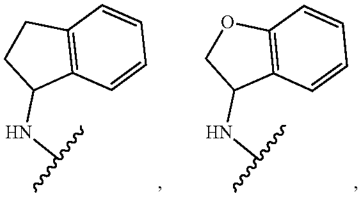

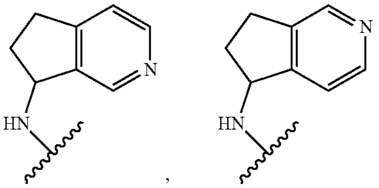

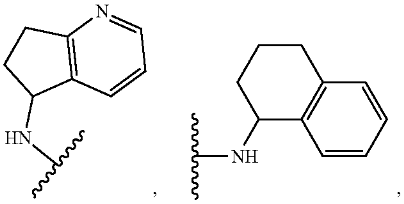

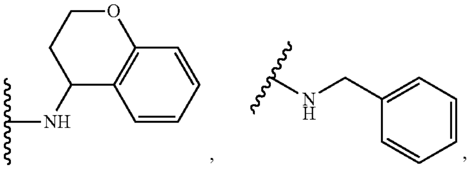

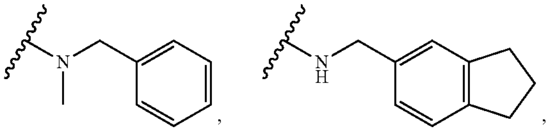

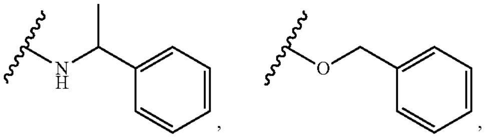

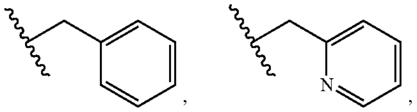

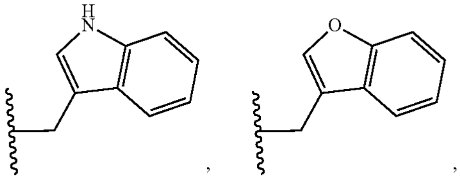

-continued

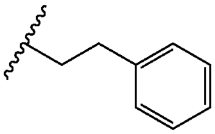,
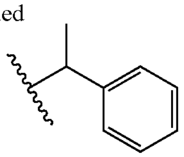,
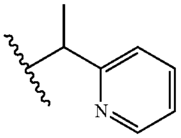,
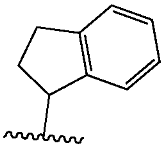,
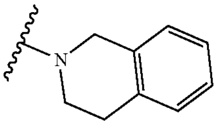,
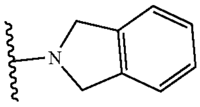,
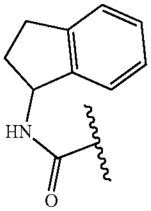,
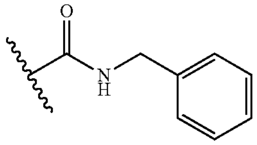, -continued

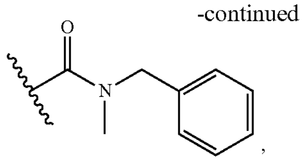,
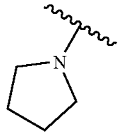, or
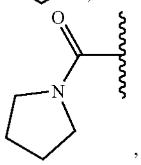, wherein the ring moiety of each is independently optionally substituted with one to five substituents independently selected from halo, $C_{1-6}$ alkyl, $C_{1-6}$ alkoxy, $C_{1-6}$ haloalkoxy, $C_{1-6}$ haloalkyl, cyano, and halo substituted phenyl.

In some embodiments, $R^6$ is $C_{1-3}$ alkyl or cyclopropyl. In some embodiments, $R^6$ is $C_{1-3}$ alkyl.

In some embodiments, $R^7$ is $C_{1-3}$ alkyl or cyclopropyl. In some embodiments, $R^7$ is $C_{1-3}$ alkyl.

In some embodiments, provided is compound selected from Table 1, or a pharmaceutically acceptable salt, stereoisomer, mixture of stereoisomers, or solvate thereof:

TABLE 1

| Compound No. | Structure |
|---|---|
| 101 | 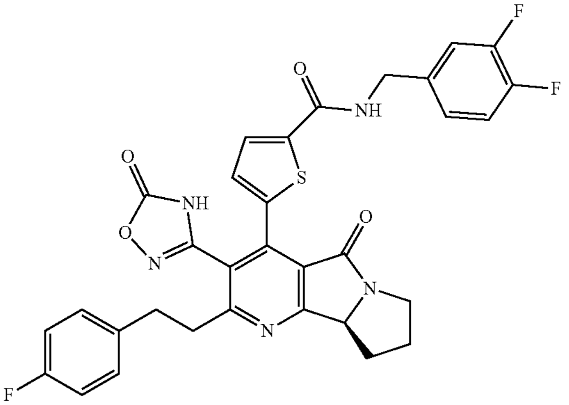 [SMILES: O=C(NCc1ccc(F)c(F)c1)c1ccc(-c2c3c(nc(CCc4ccc(F)cc4)c2-c2noc(=O)[nH]2)[C@@H]2CCCN2C3=O)s1] |
| 102 | 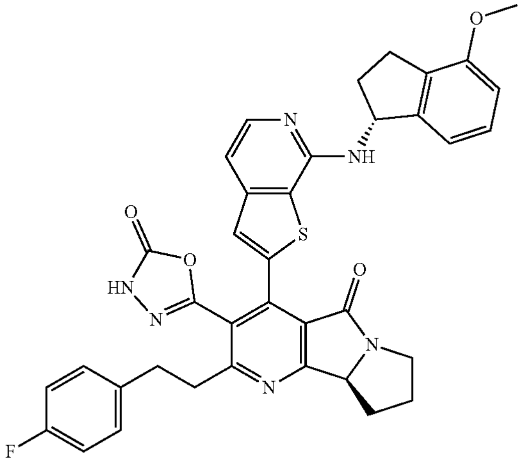 [SMILES: COc1cccc2c1CC[C@H]2Nc1nccc2cc(-c3c4c(nc(CCc5ccc(F)cc5)c3-c3n[nH]c(=O)o3)[C@@H]3CCCN3C4=O)sc12] |

TABLE 1-continued
| Compound No. | Structure |
| --- | --- |
| 103 | 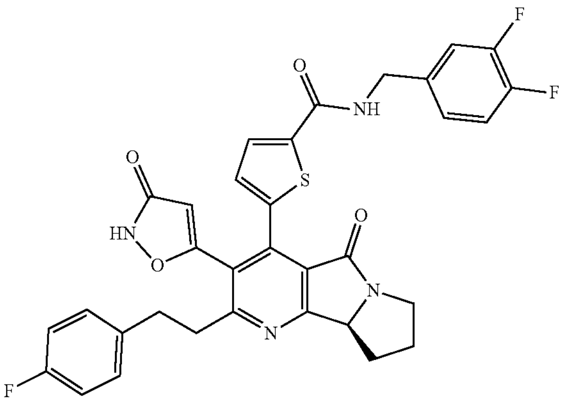 [SMILES: O=C(NCc1ccc(F)c(F)c1)c1ccc(-c2c3c(nc(CCc4ccc(F)cc4)c2-c2cc(=O)[nH]o2)[C@@H]2CCCN2C3=O)s1] |
| 104 | 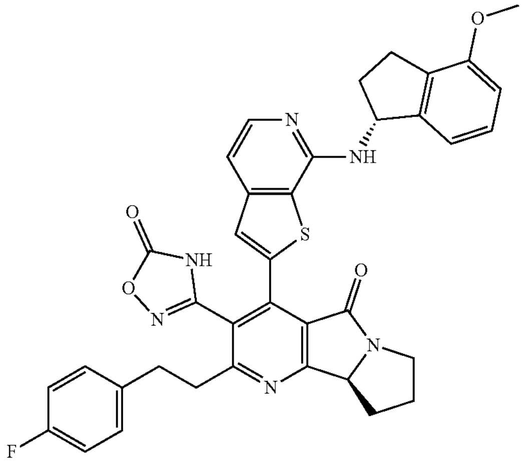 [SMILES: COc1cccc2c1CC[C@H]2Nc1nccc2cc(-c3c4c(nc(CCc5ccc(F)cc5)c3-c3noc(=O)[nH]3)[C@@H]3CCCN3C4=O)sc12] |
| 107 | 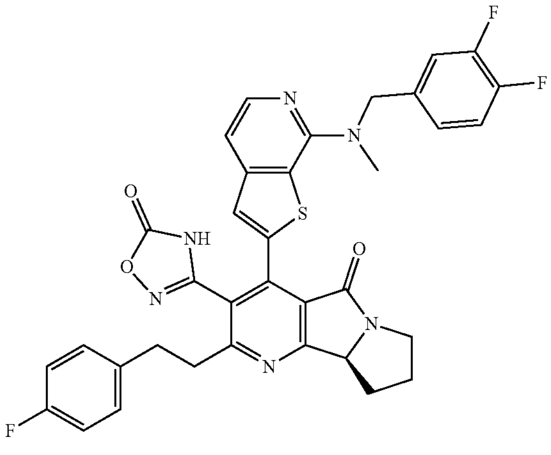 [SMILES: CN(Cc1ccc(F)c(F)c1)c1nccc2cc(-c3c4c(nc(CCc5ccc(F)cc5)c3-c3noc(=O)[nH]3)[C@@H]3CCCN3C4=O)sc12] |

TABLE 1-continued
| Compound No. | Structure |
| --- | --- |
| 108 | 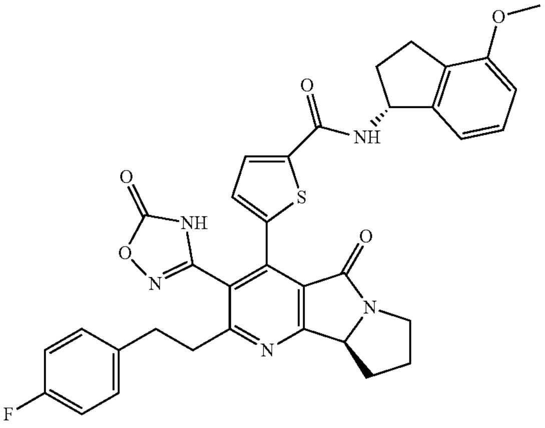 [SMILES: COc1cccc2c1CC[C@H]2NC(=O)c1ccc(-c2c3c(nc(CCc4ccc(F)cc4)c2-c2noc(=O)[nH]2)[C@@H]2CCCN2C3=O)s1] |
| 109 | 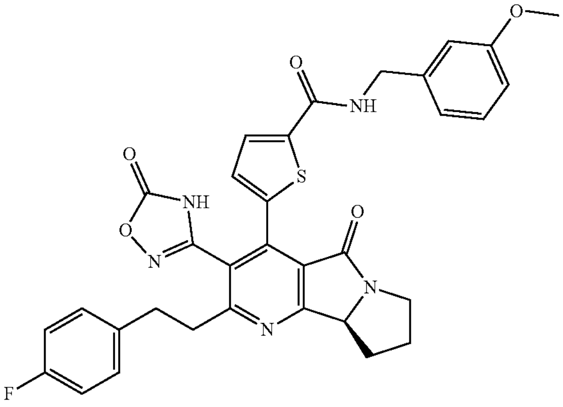 [SMILES: COc1cccc(CNC(=O)c2ccc(-c3c4c(nc(CCc5ccc(F)cc5)c3-c3noc(=O)[nH]3)[C@@H]3CCCN3C4=O)s2)c1] |
| 110 | 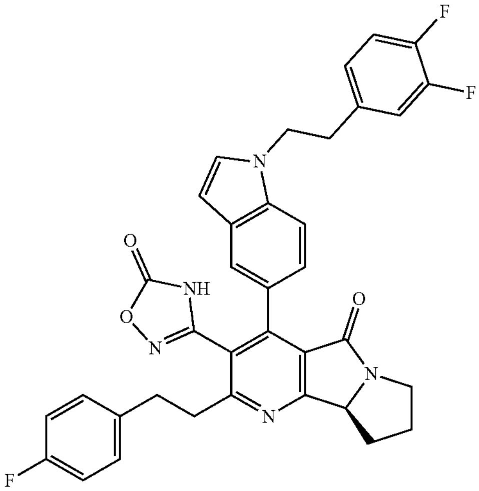 [SMILES: O=C1c2c(nc(CCc3ccc(F)cc3)c(-c3noc(=O)[nH]3)c2-c2ccc3c(ccn3CCc3ccc(F)c(F)c3)c2)[C@@H]2CCCN12] |

TABLE 1-continued
| Compound No. | Structure |
| --- | --- |
| 111 | 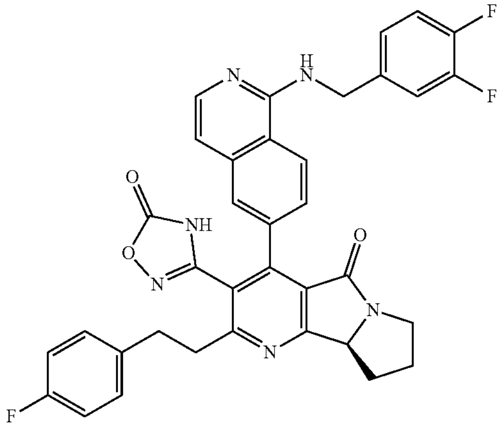 [SMILES: O=C1c2c(nc(CCc3ccc(F)cc3)c(-c3noc(=O)[nH]3)c2-c2ccc3c(NCc4ccc(F)c(F)c4)nccc3c2)[C@@H]2CCCN12] |
| 112 | 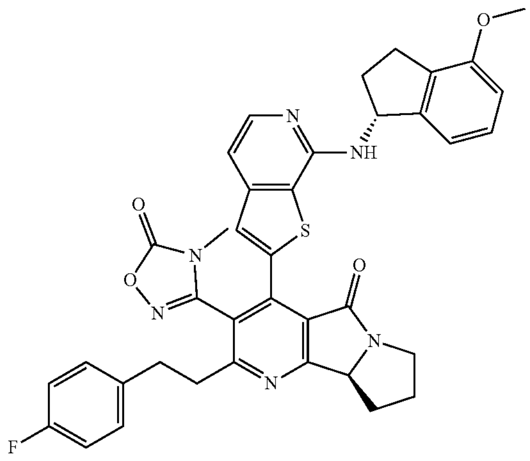 [SMILES: COc1cccc2c1CC[C@H]2Nc1nccc2cc(-c3c4c(nc(CCc5ccc(F)cc5)c3-c3noc(=O)n3C)[C@@H]3CCCN3C4=O)sc12] |
| 113 | 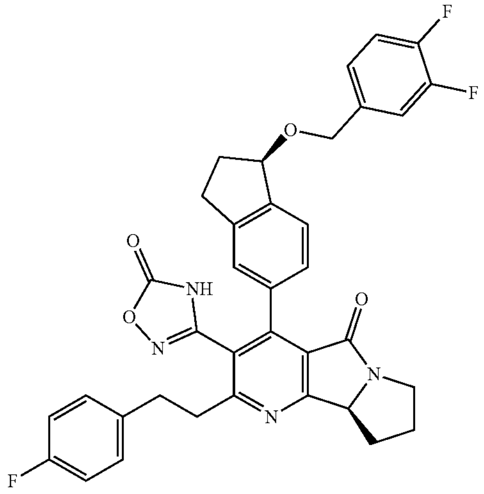 [SMILES: O=C1c2c(nc(CCc3ccc(F)cc3)c(-c3noc(=O)[nH]3)c2-c2ccc3c(c2)CC[C@H]3OCc2ccc(F)c(F)c2)[C@@H]2CCCN12] |

TABLE 1-continued
| Compound No. | Structure |
|---|---|
| 114 | 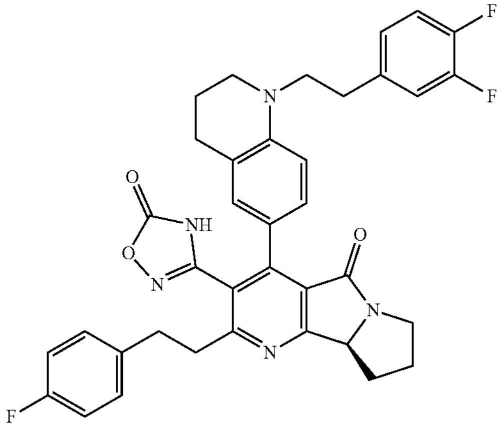 [SMILES: O=C1c2c(nc(CCc3ccc(F)cc3)c(-c3noc(=O)[nH]3)c2-c2ccc3c(c2)CCCN3CCc2ccc(F)c(F)c2)[C@@H]2CCCN12] |
| 115 | 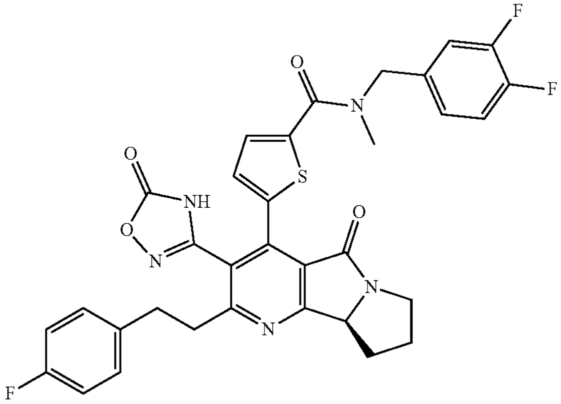 [SMILES: CN(Cc1ccc(F)c(F)c1)C(=O)c1ccc(-c2c3c(nc(CCc4ccc(F)cc4)c2-c2noc(=O)[nH]2)[C@@H]2CCCN2C3=O)s1] |
| 116 | 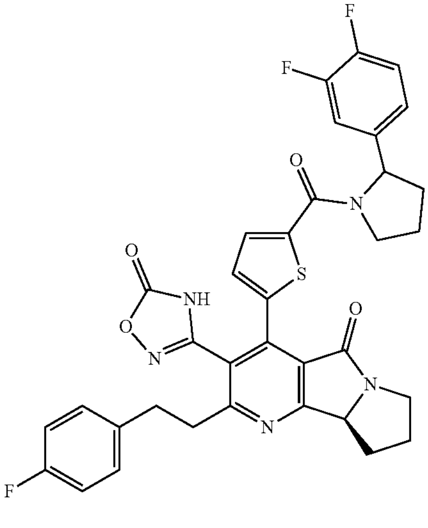 [SMILES: O=C(c1ccc(-c2c3c(nc(CCc4ccc(F)cc4)c2-c2noc(=O)[nH]2)[C@@H]2CCCN2C3=O)s1)N1CCCC1c1ccc(F)c(F)c1] |

TABLE 1-continued
| Compound No. | Structure |
| --- | --- |
| 117 | 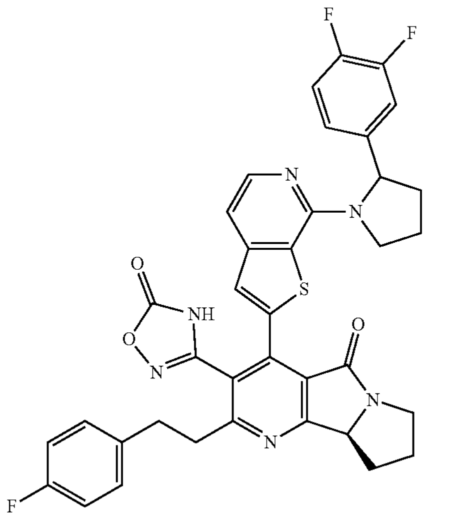 [SMILES: O=C1c2c(nc(CCc3ccc(F)cc3)c(-c3noc(=O)[nH]3)c2-c2cc3ccnc(N4CCCC4c4ccc(F)c(F)c4)c3s2)[C@@H]2CCCN12] |
| 118 | 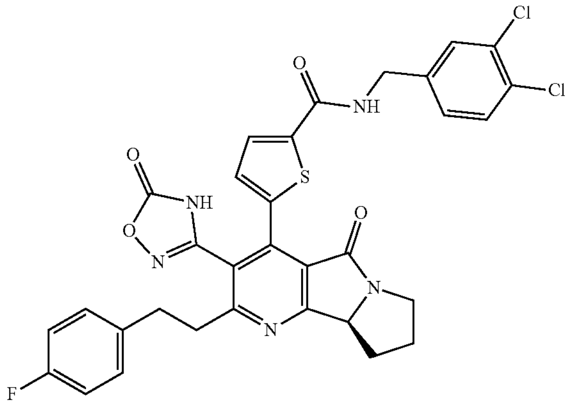 [SMILES: O=C(NCc1ccc(Cl)c(Cl)c1)c1ccc(-c2c3c(nc(CCc4ccc(F)cc4)c2-c2noc(=O)[nH]2)[C@@H]2CCCN2C3=O)s1] |
| 119 | 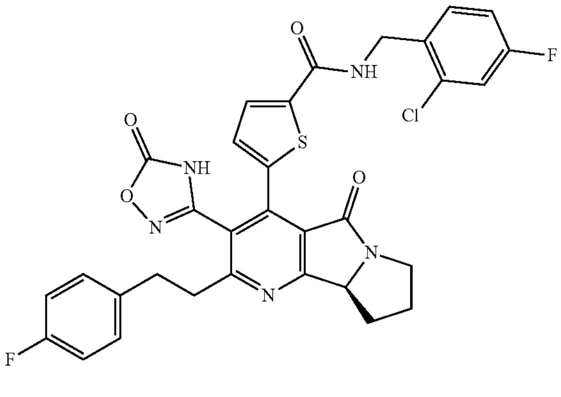 [SMILES: O=C(NCc1ccc(F)cc1Cl)c1ccc(-c2c3c(nc(CCc4ccc(F)cc4)c2-c2noc(=O)[nH]2)[C@@H]2CCCN2C3=O)s1] |

TABLE 1-continued
| Compound No. | Structure |
| --- | --- |
| 120 | 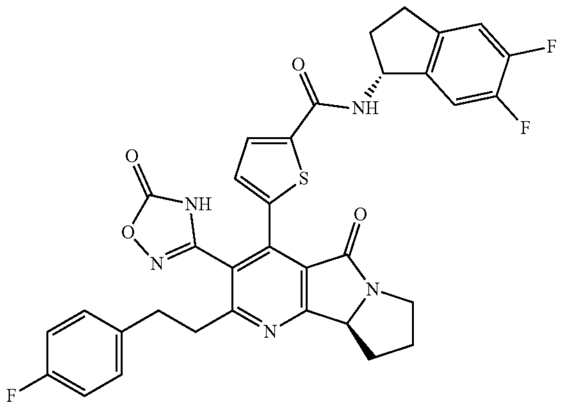 [SMILES: O=C(N[C@@H]1CCc2cc(F)c(F)cc21)c1ccc(-c2c3c(nc(CCc4ccc(F)cc4)c2-c2noc(=O)[nH]2)[C@@H]2CCCN2C3=O)s1] |
| 121 | 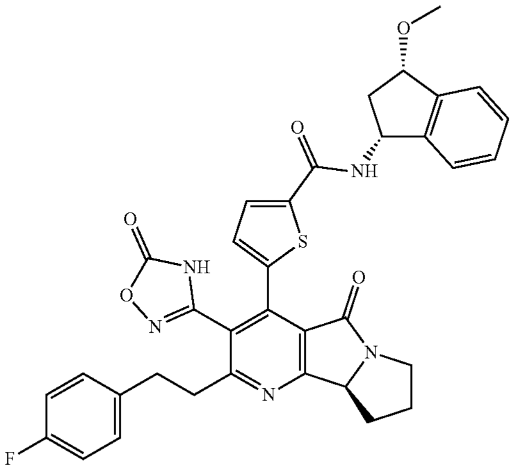 [SMILES: CO[C@H]1C[C@@H](NC(=O)c2ccc(-c3c4c(nc(CCc5ccc(F)cc5)c3-c3noc(=O)[nH]3)[C@@H]3CCCN3C4=O)s2)c2ccccc21] |
| 122 | 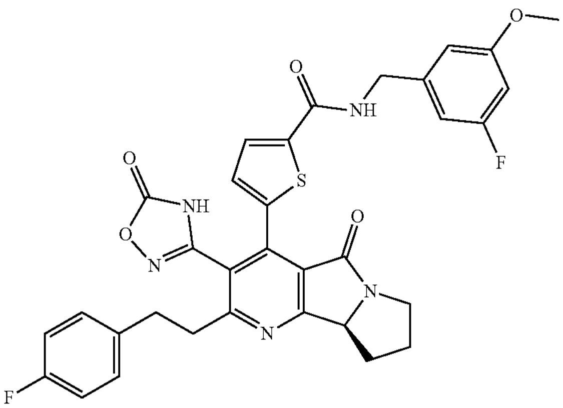 [SMILES: COc1cc(F)cc(CNC(=O)c2ccc(-c3c4c(nc(CCc5ccc(F)cc5)c3-c3noc(=O)[nH]3)[C@@H]3CCCN3C4=O)s2)c1] |

TABLE 1-continued
| Compound No. | Structure |
|---|---|
| 123 | 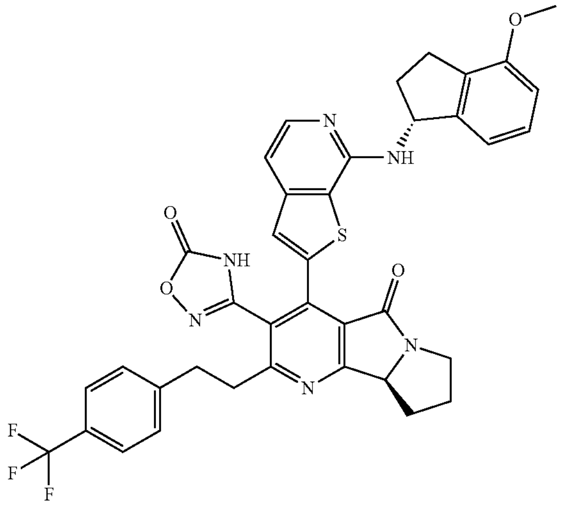 [SMILES: COc1cccc2c1CC[C@H]2Nc1nccc2cc(-c3c4c(nc(CCc5ccc(C(F)(F)F)cc5)c3-c3noc(=O)[nH]3)[C@@H]3CCCN3C4=O)sc12] |
| 124 | 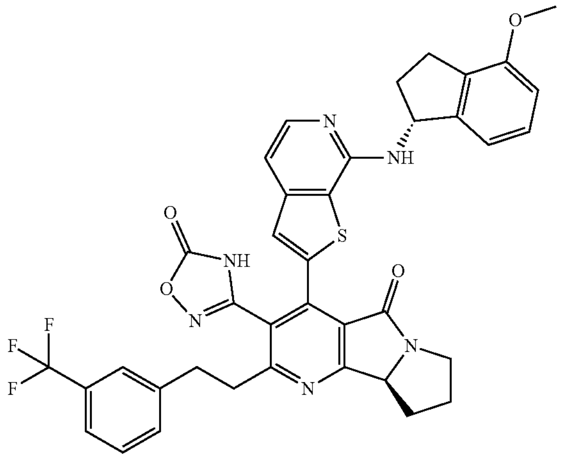 [SMILES: COc1cccc2c1CC[C@H]2Nc1nccc2cc(-c3c4c(nc(CCc5cccc(C(F)(F)F)c5)c3-c3noc(=O)[nH]3)[C@@H]3CCCN3C4=O)sc12] |
| 125 | 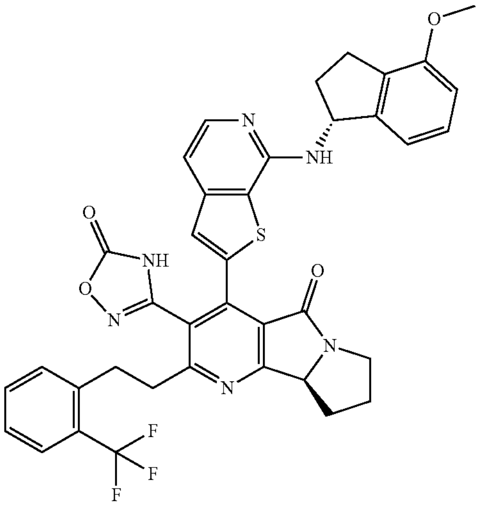 [SMILES: COc1cccc2c1CC[C@H]2Nc1nccc2cc(-c3c4c(nc(CCc5ccccc5C(F)(F)F)c3-c3noc(=O)[nH]3)[C@@H]3CCCN3C4=O)sc12] |

TABLE 1-continued
| Compound No. | Structure |
| --- | --- |
| 126 | 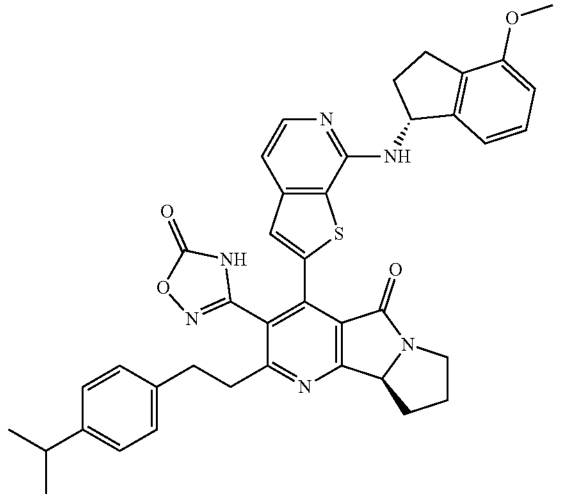 [SMILES: COc1cccc2c1CC[C@H]2Nc1nccc2cc(-c3c4c(nc(CCc5ccc(C(C)C)cc5)c3-c3noc(=O)[nH]3)[C@@H]3CCCN3C4=O)sc12] |
| 127 | 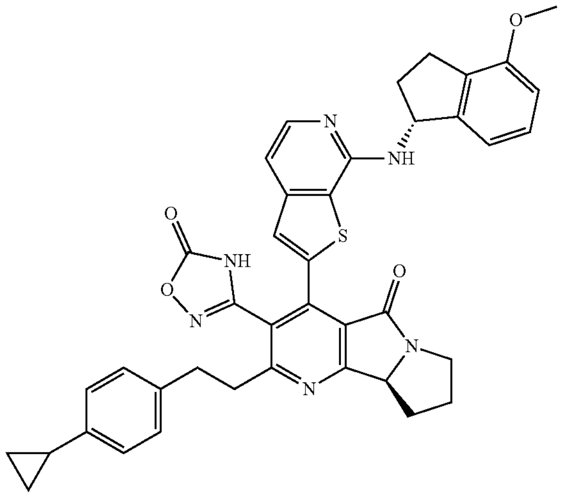 [SMILES: COc1cccc2c1CC[C@H]2Nc1nccc2cc(-c3c4c(nc(CCc5ccc(C6CC6)cc5)c3-c3noc(=O)[nH]3)[C@@H]3CCCN3C4=O)sc12] |
| 128 | 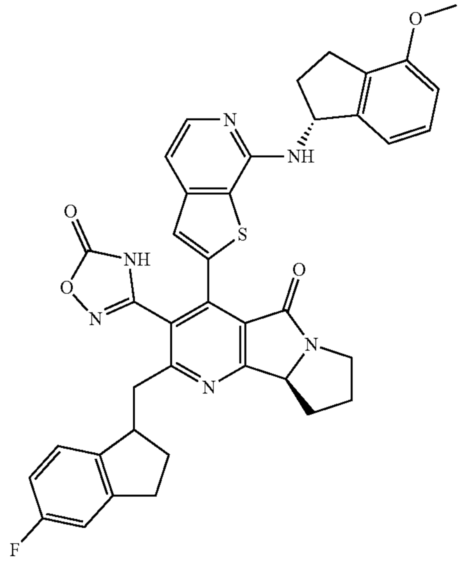 [SMILES: COc1cccc2c1CC[C@H]2Nc1nccc2cc(-c3c4c(nc(CC5CCc6cc(F)ccc65)c3-c3noc(=O)[nH]3)[C@@H]3CCCN3C4=O)sc12] |

TABLE 1-continued
| Compound No. | Structure |
| --- | --- |
| 129 | 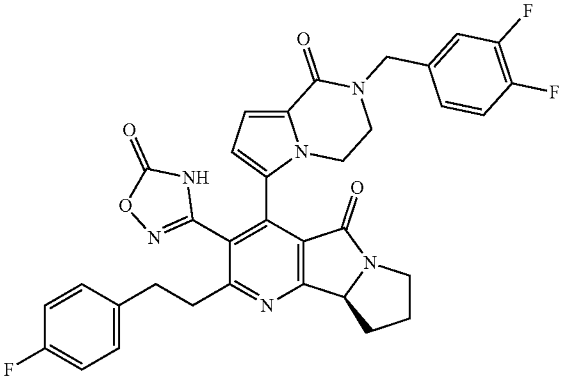 [SMILES: O=C1c2ccc(-c3c4c(nc(CCc5ccc(F)cc5)c3-c3noc(=O)[nH]3)[C@@H]3CCCN3C4=O)n2CCN1Cc1ccc(F)c(F)c1] |
| 130 | 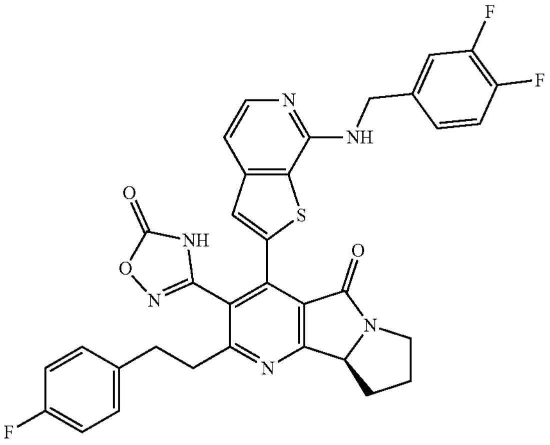 [SMILES: O=C1c2c(nc(CCc3ccc(F)cc3)c(-c3noc(=O)[nH]3)c2-c2cc3ccnc(NCc4ccc(F)c(F)c4)c3s2)[C@@H]2CCCN12] |
| 133 | 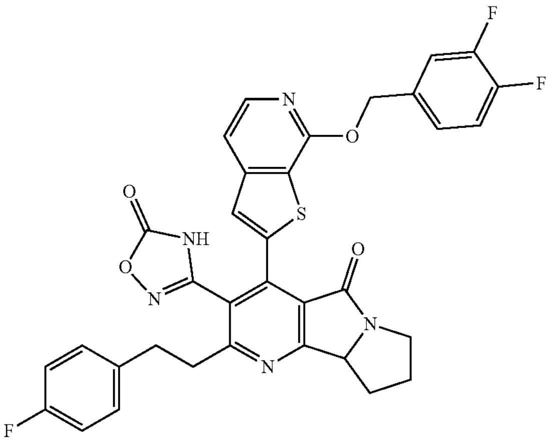 [SMILES: O=C1c2c(nc(CCc3ccc(F)cc3)c(-c3noc(=O)[nH]3)c2-c2cc3ccnc(OCc4ccc(F)c(F)c4)c3s2)C2CCCN12] |

TABLE 1-continued
| Compound No. | Structure |
| --- | --- |
| 137 | 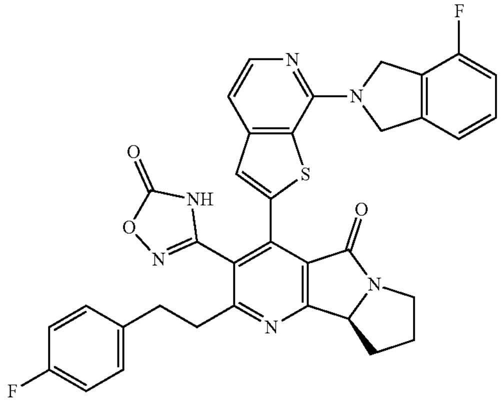 [SMILES: O=C1c2c(nc(CCc3ccc(F)cc3)c(-c3noc(=O)[nH]3)c2-c2cc3ccnc(N4Cc5cccc(F)c5C4)c3s2)[C@@H]2CCCN12] |
| 138 | 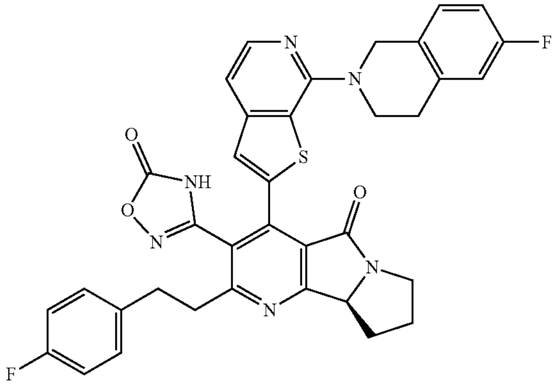 [SMILES: O=C1c2c(nc(CCc3ccc(F)cc3)c(-c3noc(=O)[nH]3)c2-c2cc3ccnc(N4CCc5cc(F)ccc5C4)c3s2)[C@@H]2CCCN12] |
| 139 | 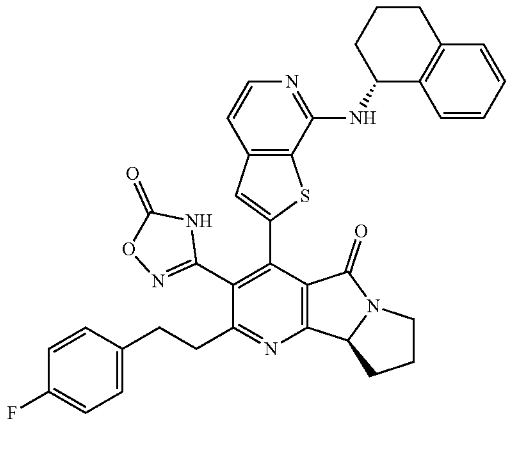 [SMILES: O=C1c2c(nc(CCc3ccc(F)cc3)c(-c3noc(=O)[nH]3)c2-c2cc3ccnc(N[C@@H]4CCCc5ccccc54)c3s2)[C@@H]2CCCN12] |

TABLE 1-continued
| Compound No. | Structure |
| --- | --- |
| 140 | 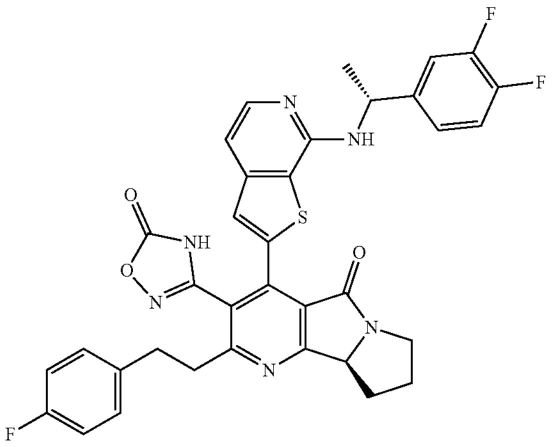 [SMILES: C[C@@H](Nc1nccc2cc(-c3c4c(nc(CCc5ccc(F)cc5)c3-c3noc(=O)[nH]3)[C@@H]3CCCN3C4=O)sc12)c1ccc(F)c(F)c1] |
| 141 | 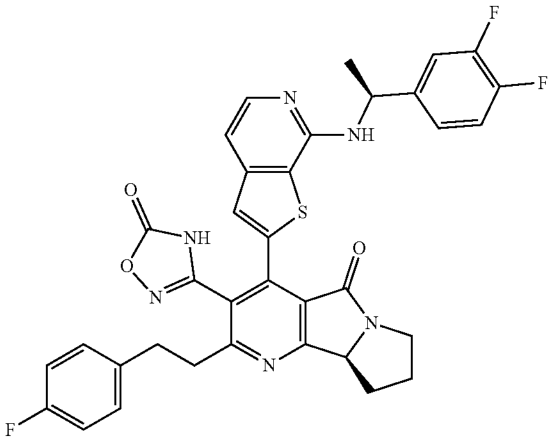 [SMILES: C[C@H](Nc1nccc2cc(-c3c4c(nc(CCc5ccc(F)cc5)c3-c3noc(=O)[nH]3)[C@@H]3CCCN3C4=O)sc12)c1ccc(F)c(F)c1] |
| 146 | 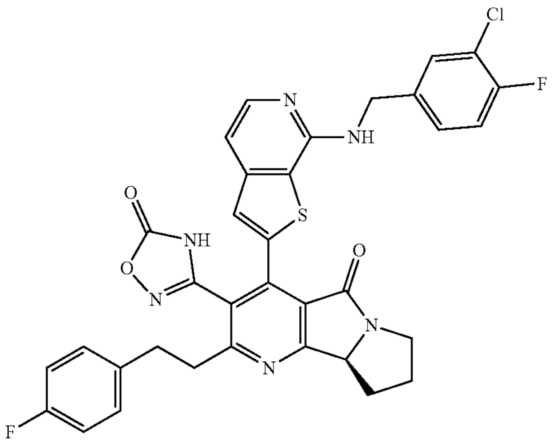 [SMILES: O=C1c2c(nc(CCc3ccc(F)cc3)c(-c3noc(=O)[nH]3)c2-c2cc3ccnc(NCc4ccc(F)c(Cl)c4)c3s2)[C@@H]2CCCN12] |

TABLE 1-continued
| Compound No. | Structure |
|---|---|
| 147 | 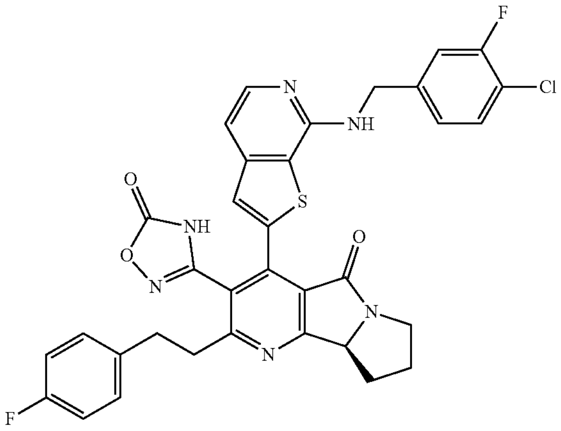 [SMILES: O=C1c2c(nc(CCc3ccc(F)cc3)c(-c3noc(=O)[nH]3)c2-c2cc3ccnc(NCc4ccc(Cl)c(F)c4)c3s2)[C@@H]2CCCN12] |
| 148 | 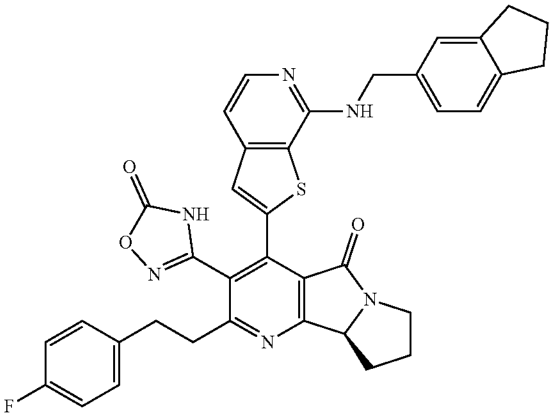 [SMILES: O=C1c2c(nc(CCc3ccc(F)cc3)c(-c3noc(=O)[nH]3)c2-c2cc3ccnc(NCc4ccc5c(c4)CCC5)c3s2)[C@@H]2CCCN12] |
| 149 | 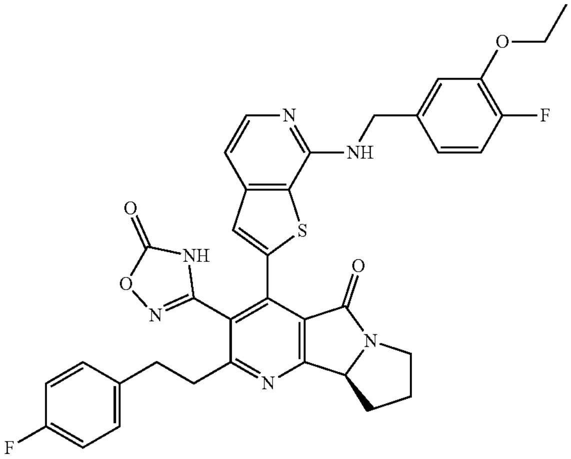 [SMILES: CCOc1cc(CNc2nccc3cc(-c4c5c(nc(CCc6ccc(F)cc6)c4-c4noc(=O)[nH]4)[C@@H]4CCCN4C5=O)sc23)ccc1F] |

TABLE 1-continued
| Compound No. | Structure |
| --- | --- |
| 150 | 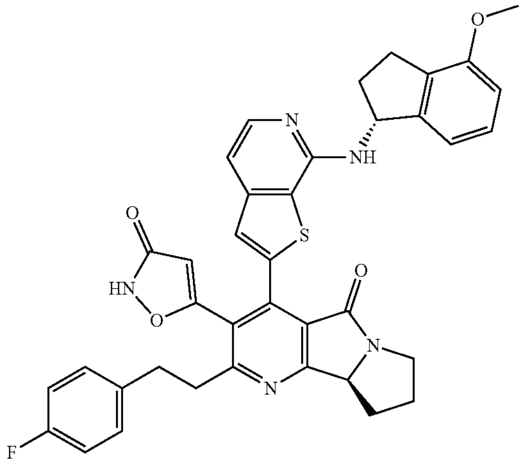 [SMILES: COc1cccc2c1CC[C@H]2Nc1nccc2cc(-c3c4c(nc(CCc5ccc(F)cc5)c3-c3cc(=O)[nH]o3)[C@@H]3CCCN3C4=O)sc12] |
| 151 | 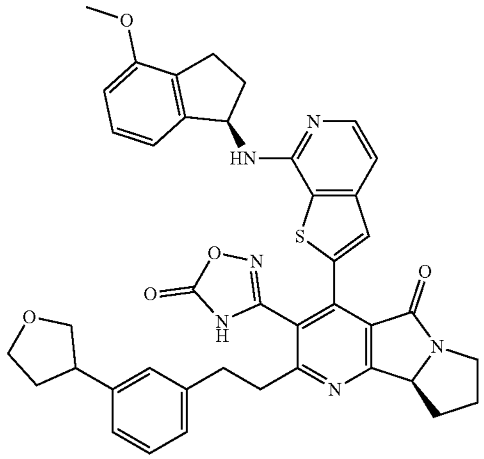 [SMILES: COc1cccc2c1CC[C@H]2Nc1nccc2cc(-c3c4c(nc(CCc5cccc(C6CCOC6)c5)c3-c3noc(=O)[nH]3)[C@@H]3CCCN3C4=O)sc12] |
| 152 | 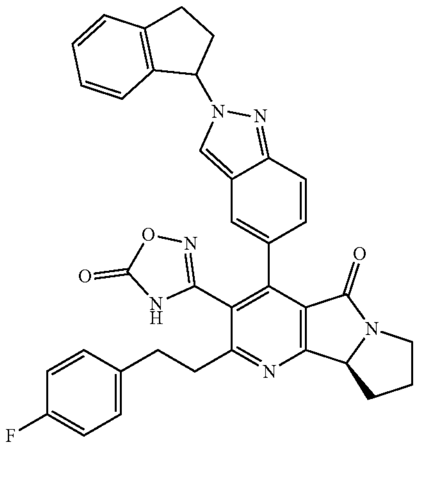 [SMILES: O=C1c2c(nc(CCc3ccc(F)cc3)c(-c3noc(=O)[nH]3)c2-c2ccc3nn(C4CCc5ccccc54)cc3c2)[C@@H]2CCCN12] |

TABLE 1-continued
| Compound No. | Structure |
|---|---|
| 153 | 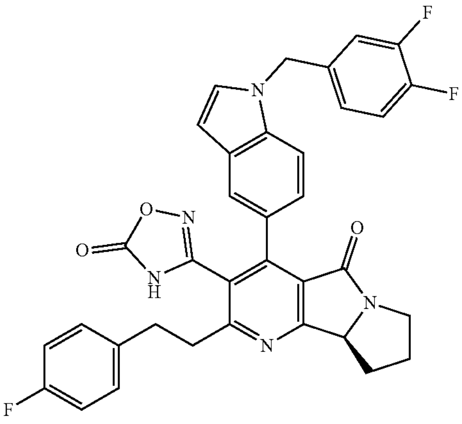 [SMILES: O=C1c2c(nc(CCc3ccc(F)cc3)c(-c3noc(=O)[nH]3)c2-c2ccc3c(ccn3Cc3ccc(F)c(F)c3)c2)[C@@H]2CCCN12] |
| 154 | 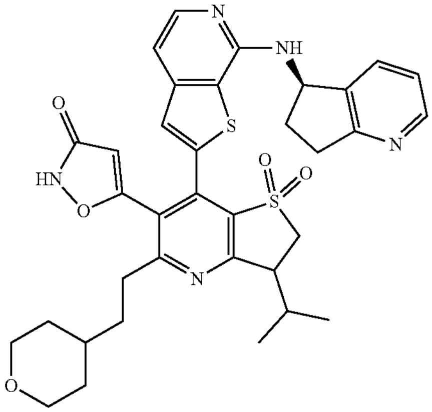 [SMILES: CC(C)C1CS(=O)(=O)c2c1nc(CCC1CCOCC1)c(-c1cc(=O)[nH]o1)c2-c1cc2ccnc(N[C@@H]3CCc4ncccc43)c2s1] |
| 155 | 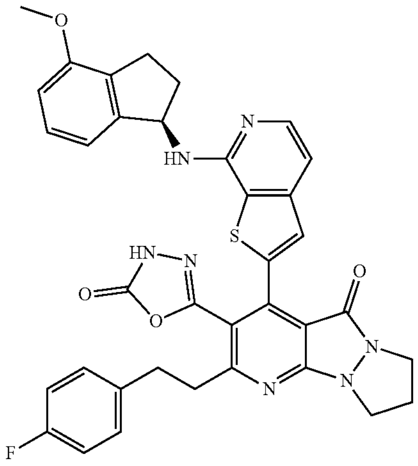 [SMILES: COc1cccc2c1CC[C@H]2Nc1nccc2cc(-c3c(-c4n[nH]c(=O)o4)c(CCc4ccc(F)cc4)nc4c3c(=O)n3n4CCC3)sc12] |

TABLE 1-continued
| Compound No. | Structure |
| --- | --- |
| 156 | 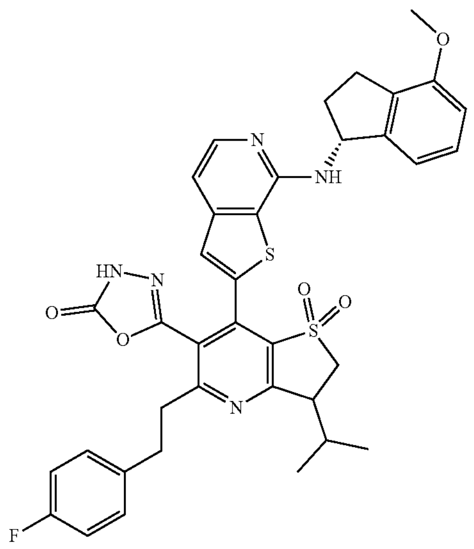 |
| 157 | 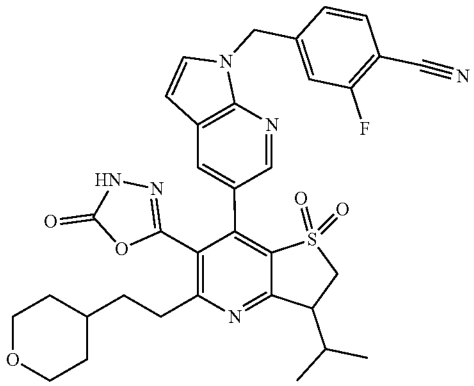 [SMILES: CC(C)C1CS(=O)(=O)c2c1nc(CCC1CCOCC1)c(-c1n[nH]c(=O)o1)c2-c1cnc2c(ccn2Cc2ccc(C#N)c(F)c2)c1] |
| 158 | 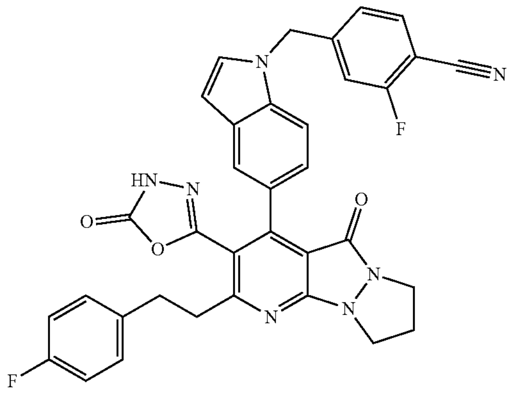 [SMILES: N#Cc1ccc(Cn2ccc3cc(-c4c(-c5n[nH]c(=O)o5)c(CCc5ccc(F)cc5)nc5c4c(=O)n4n5CCC4)ccc32)cc1F] |

TABLE 1-continued
| Compound No. | Structure |
| --- | --- |
| 159 | 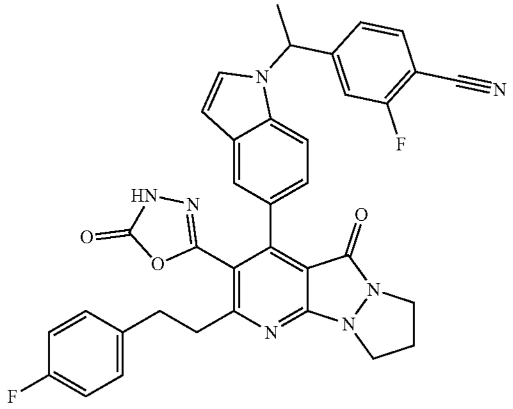 [SMILES: CC(c1ccc(C#N)c(F)c1)n1ccc2cc(-c3c(-c4n[nH]c(=O)o4)c(CCc4ccc(F)cc4)nc4c3c(=O)n3n4CCC3)ccc21] |
| 160 | 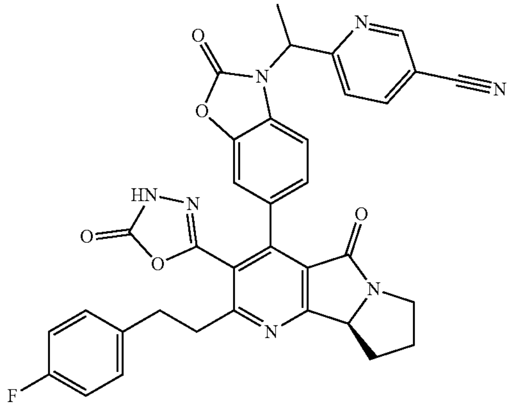 [SMILES: CC(c1ccc(C#N)cn1)n1c(=O)oc2cc(-c3c4c(nc(CCc5ccc(F)cc5)c3-c3n[nH]c(=O)o3)[C@@H]3CCCN3C4=O)ccc21] |
| 161 | 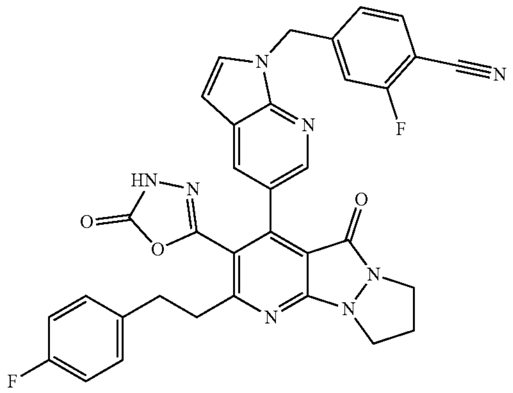 |
| 162 | 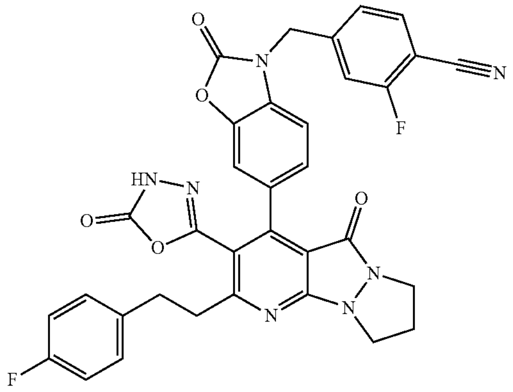 [SMILES: N#Cc1ccc(Cn2c(=O)oc3cc(-c4c(-c5n[nH]c(=O)o5)c(CCc5ccc(F)cc5)nc5c4c(=O)n4n5CCC4)ccc32)cc1F] |

TABLE 1-continued
| Compound No. | Structure |
| --- | --- |
| 163 | 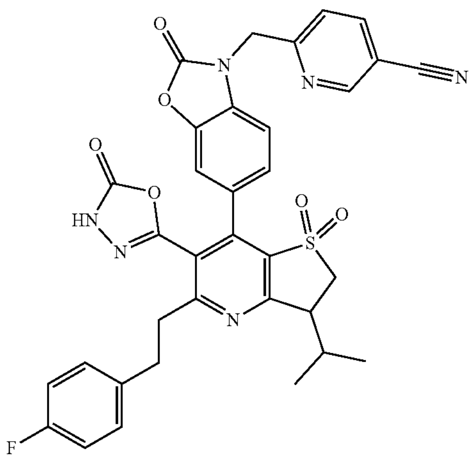 |
| 164 | 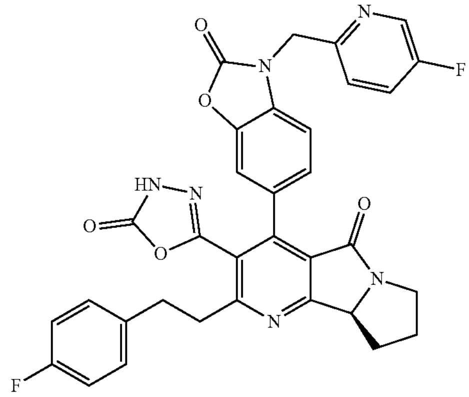 [SMILES: O=C1c2c(nc(CCc3ccc(F)cc3)c(-c3n[nH]c(=O)o3)c2-c2ccc3c(c2)oc(=O)n3Cc2ccc(F)cn2)[C@@H]2CCCN12] |
| 165 | 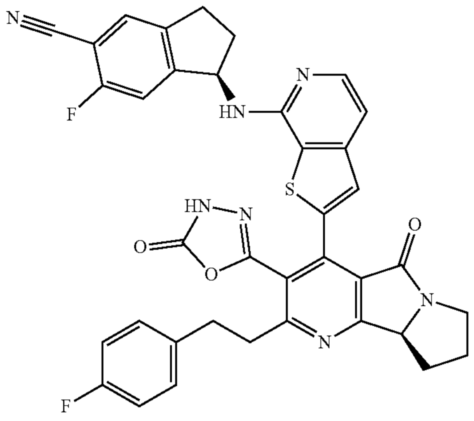 [SMILES: N#Cc1cc2c(cc1F)[C@H](Nc1nccc3cc(-c4c5c(nc(CCc6ccc(F)cc6)c4-c4n[nH]c(=O)o4)[C@@H]4CCCN4C5=O)sc13)CC2] |

TABLE 1-continued
| Compound No. | Structure |
|---|---|
| 166 | 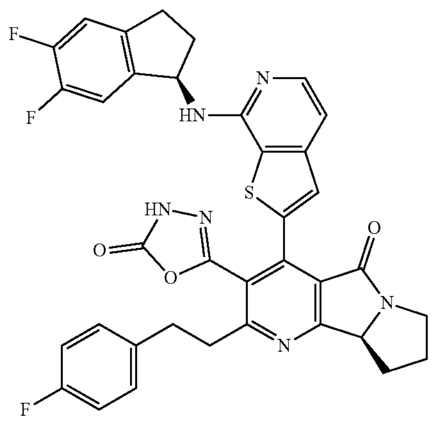 [SMILES: O=C1c2c(nc(CCc3ccc(F)cc3)c(-c3n[nH]c(=O)o3)c2-c2cc3ccnc(N[C@@H]4CCc5cc(F)c(F)cc54)c3s2)[C@@H]2CCCN12] |
| 167 | 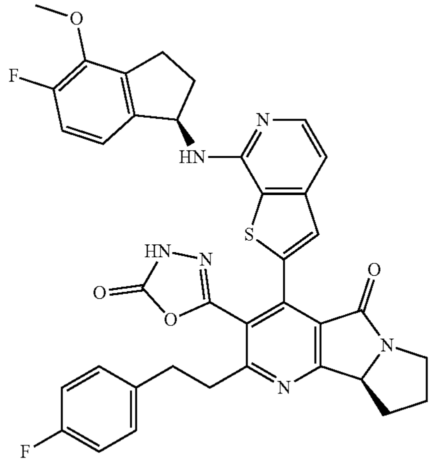 [SMILES: COc1c(F)ccc2c1CC[C@H]2Nc1nccc2cc(-c3c4c(nc(CCc5ccc(F)cc5)c3-c3n[nH]c(=O)o3)[C@@H]3CCCN3C4=O)sc12] |
| 168 | 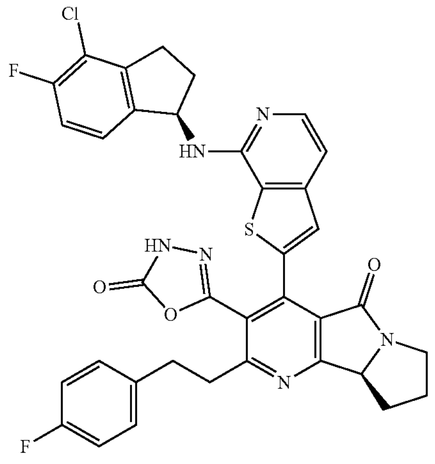 [SMILES: O=C1c2c(nc(CCc3ccc(F)cc3)c(-c3n[nH]c(=O)o3)c2-c2cc3ccnc(N[C@@H]4CCc5c4ccc(F)c5Cl)c3s2)[C@@H]2CCCN12] |

TABLE 1-continued
| Compound No. | Structure |
|---|---|
| 169 | 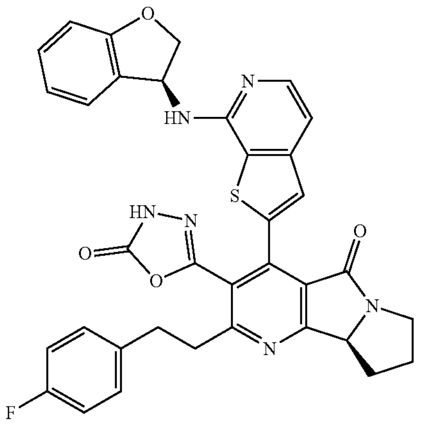 [SMILES: O=C1c2c(nc(CCc3ccc(F)cc3)c(-c3n[nH]c(=O)o3)c2-c2cc3ccnc(N[C@@H]4COc5ccccc54)c3s2)[C@@H]2CCCN12] |
| 170 | 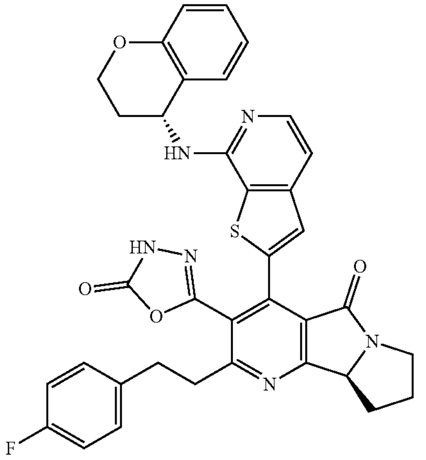 [SMILES: O=C1c2c(nc(CCc3ccc(F)cc3)c(-c3n[nH]c(=O)o3)c2-c2cc3ccnc(N[C@@H]4CCOc5ccccc54)c3s2)[C@@H]2CCCN12] |
| 171 | 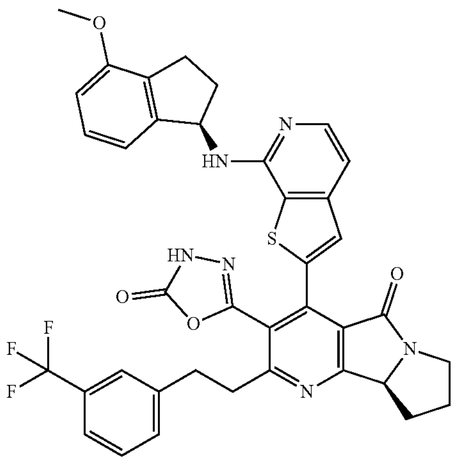 [SMILES: COc1cccc2c1CC[C@H]2Nc1nccc2cc(-c3c4c(nc(CCc5cccc(C(F)(F)F)c5)c3-c3n[nH]c(=O)o3)[C@@H]3CCCN3C4=O)sc12] |

TABLE 1-continued
| Compound No. | Structure |
|---|---|
| 172 | 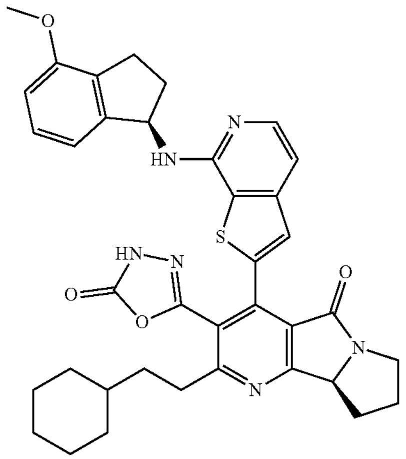 [SMILES: COc1cccc2c1CC[C@H]2Nc1nccc2cc(-c3c4c(nc(CCC5CCCCC5)c3-c3n[nH]c(=O)o3)[C@@H]3CCCN3C4=O)sc12] |
| 173 | 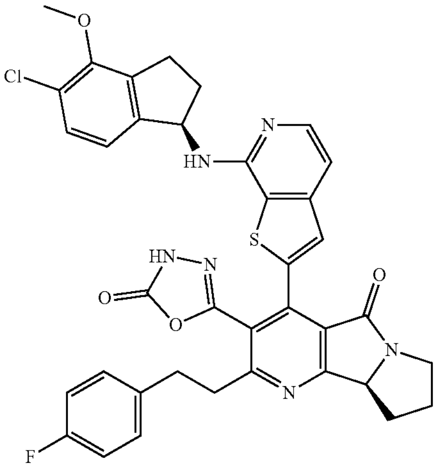 [SMILES: COc1c(Cl)ccc2c1CC[C@H]2Nc1nccc2cc(-c3c4c(nc(CCc5ccc(F)cc5)c3-c3n[nH]c(=O)o3)[C@@H]3CCCN3C4=O)sc12] |
| 174 | 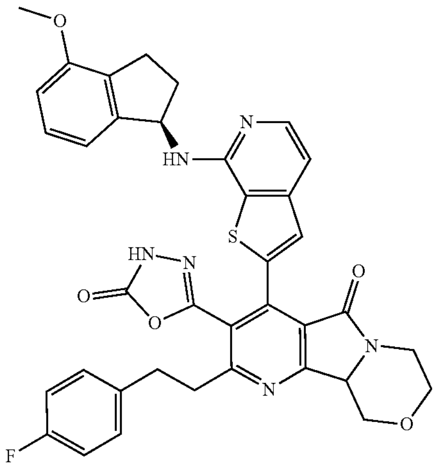 [SMILES: COc1cccc2c1CC[C@H]2Nc1nccc2cc(-c3c4c(nc(CCc5ccc(F)cc5)c3-c3n[nH]c(=O)o3)C3COCCN3C4=O)sc12] |

TABLE 1-continued
| Compound No. | Structure |
|---|---|
| 175 | 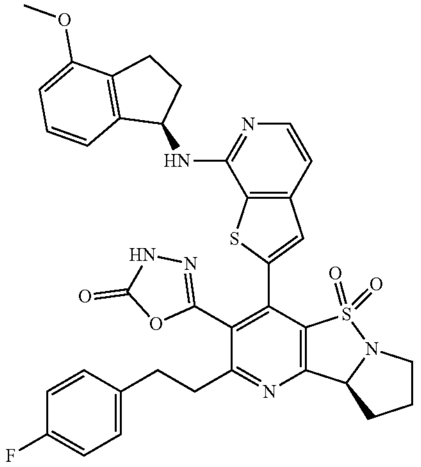 [SMILES: COc1cccc2c1CC[C@H]2Nc1nccc2cc(-c3c(-c4n[nH]c(=O)o4)c(CCc4ccc(F)cc4)nc4c3S(=O)(=O)N3CCC[C@@H]43)sc12] |
| 176 | 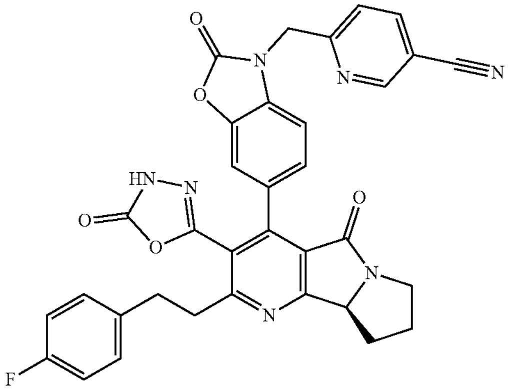 [SMILES: N#Cc1ccc(Cn2c(=O)oc3cc(-c4c5c(nc(CCc6ccc(F)cc6)c4-c4n[nH]c(=O)o4)[C@@H]4CCCN4C5=O)ccc32)nc1] |
| 177 | 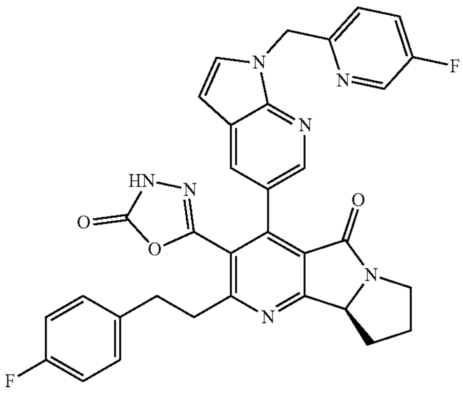 [SMILES: O=C1c2c(nc(CCc3ccc(F)cc3)c(-c3n[nH]c(=O)o3)c2-c2cnc3c(ccn3Cc3ccc(F)cn3)c2)[C@@H]2CCCN12] |

TABLE 1-continued
| Compound No. | Structure |
| --- | --- |
| 178 | 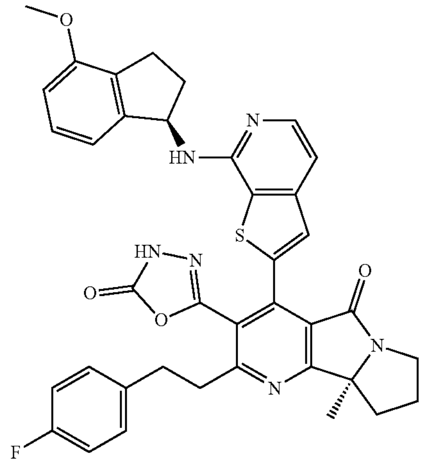 [SMILES: COc1cccc2c1CC[C@H]2Nc1nccc2cc(-c3c4c(nc(CCc5ccc(F)cc5)c3-c3n[nH]c(=O)o3)[C@]3(C)CCCN3C4=O)sc12] |
| 179 | 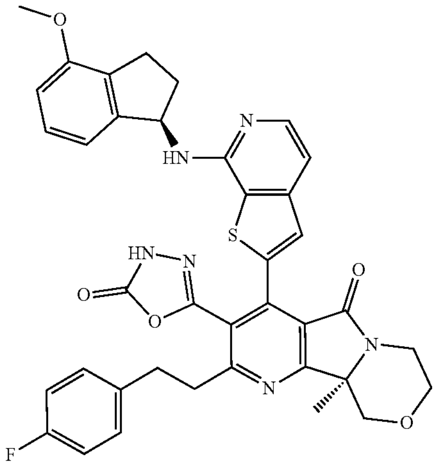 [SMILES: COc1cccc2c1CC[C@H]2Nc1nccc2cc(-c3c4c(nc(CCc5ccc(F)cc5)c3-c3n[nH]c(=O)o3)[C@]3(C)COCCN3C4=O)sc12] |
| 180 | 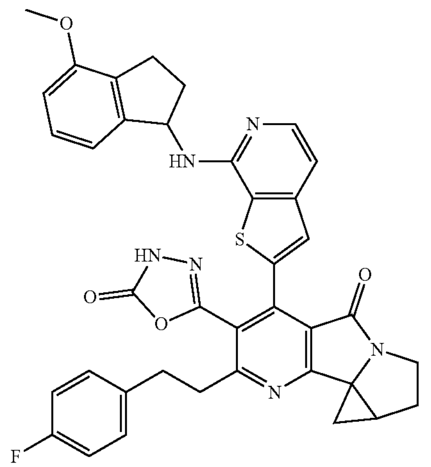 [SMILES: COc1cccc2c1CCC2Nc1nccc2cc(-c3c4c(nc(CCc5ccc(F)cc5)c3-c3n[nH]c(=O)o3)C35CC3CCN5C4=O)sc12] |

TABLE 1-continued
| Compound No. | Structure |
| --- | --- |
| 181 | 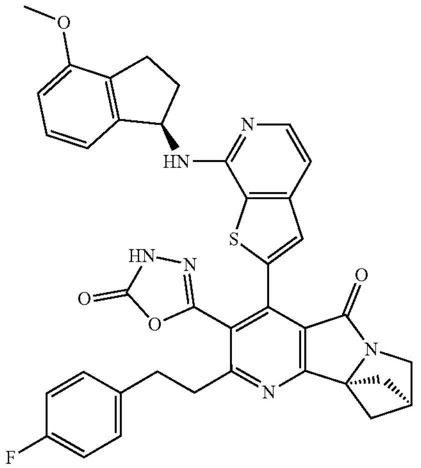 [SMILES: COc1cccc2c1CC[C@H]2Nc1nccc2cc(-c3c(-c4n[nH]c(=O)o4)c(CCc4ccc(F)cc4)nc4c3C(=O)N3C[C@H]5C[C@@]43C5)sc12] |
| 182 | 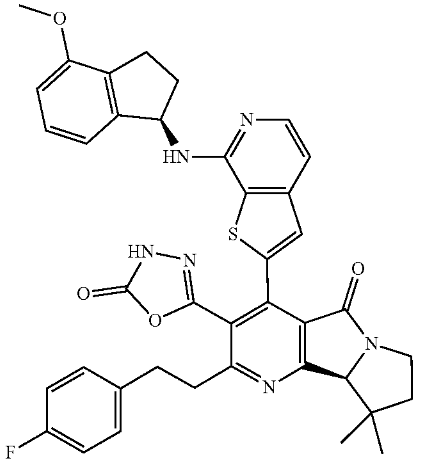 [SMILES: COc1cccc2c1CC[C@H]2Nc1nccc2cc(-c3c4c(nc(CCc5ccc(F)cc5)c3-c3n[nH]c(=O)o3)[C@H]3N(CCC3(C)C)C4=O)sc12] |
| 183 | 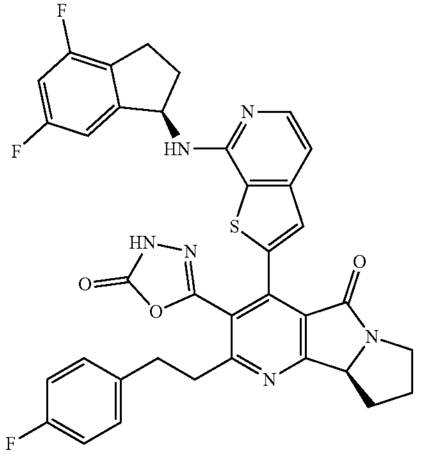 [SMILES: O=C1c2c(nc(CCc3ccc(F)cc3)c(-c3n[nH]c(=O)o3)c2-c2cc3ccnc(N[C@@H]4CCc5c(F)cc(F)cc54)c3s2)[C@@H]2CCCN12] |

TABLE 1-continued
| Compound No. | Structure |
|---|---|
| 184 | 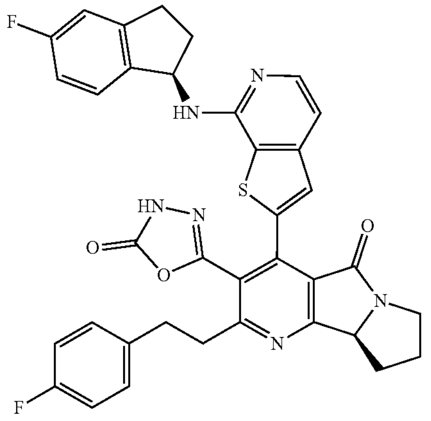 [SMILES: O=C1c2c(nc(CCc3ccc(F)cc3)c(-c3n[nH]c(=O)o3)c2-c2cc3ccnc(N[C@@H]4CCc5cc(F)ccc54)c3s2)[C@@H]2CCCN12] |
| 185 | 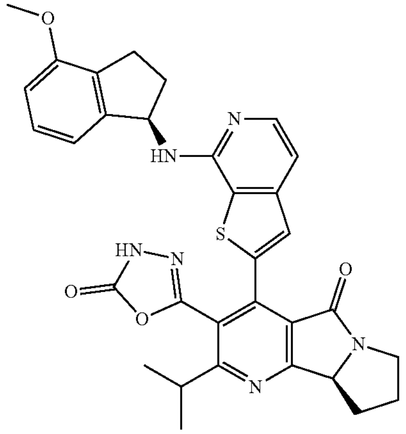 [SMILES: COc1cccc2c1CC[C@H]2Nc1nccc2cc(-c3c4c(nc(C(C)C)c3-c3n[nH]c(=O)o3)[C@@H]3CCCN3C4=O)sc12] |
| 186 | 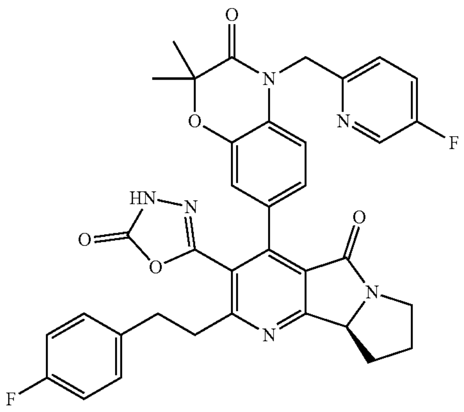 [SMILES: CC1(C)Oc2cc(-c3c4c(nc(CCc5ccc(F)cc5)c3-c3n[nH]c(=O)o3)[C@@H]3CCCN3C4=O)ccc2N(Cc2ccc(F)cn2)C1=O] |

TABLE 1-continued
| Compound No. | Structure |
| --- | --- |
| 187 | 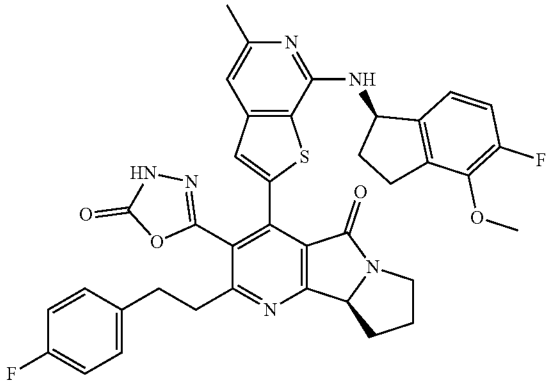 [SMILES: COc1c(F)ccc2c1CC[C@H]2Nc1nc(C)cc2cc(-c3c4c(nc(CCc5ccc(F)cc5)c3-c3n[nH]c(=O)o3)[C@@H]3CCCN3C4=O)sc12] |
| 188 | 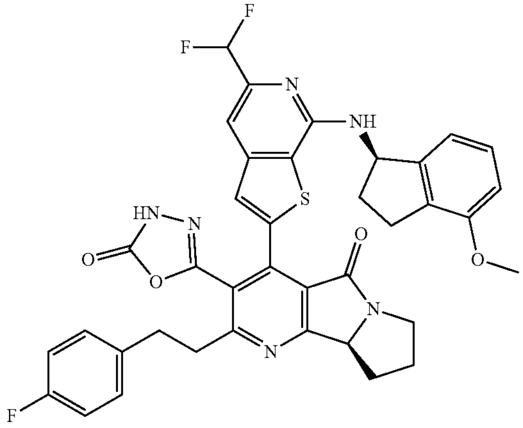 [SMILES: COc1cccc2c1CC[C@H]2Nc1nc(C(F)F)cc2cc(-c3c4c(nc(CCc5ccc(F)cc5)c3-c3n[nH]c(=O)o3)[C@@H]3CCCN3C4=O)sc12] |
| 189 | 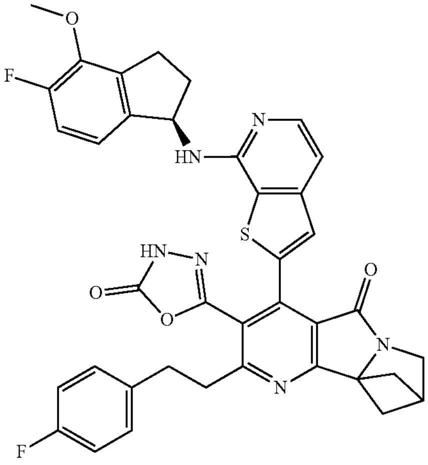 |

TABLE 1-continued
| Compound No. | Structure |
|---|---|
| 190 | 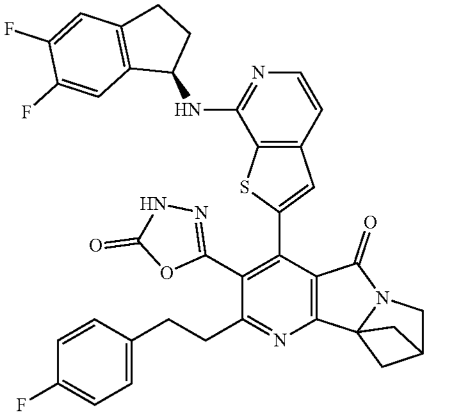 |
| 191 | 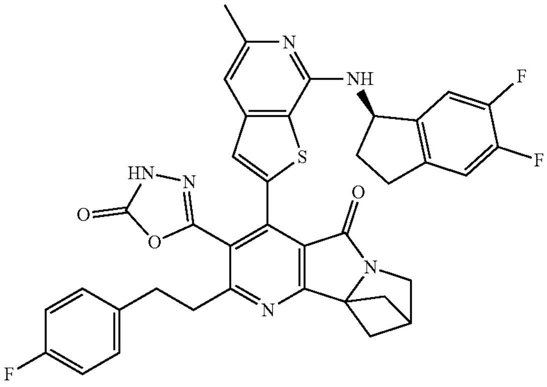 |
| 192 | 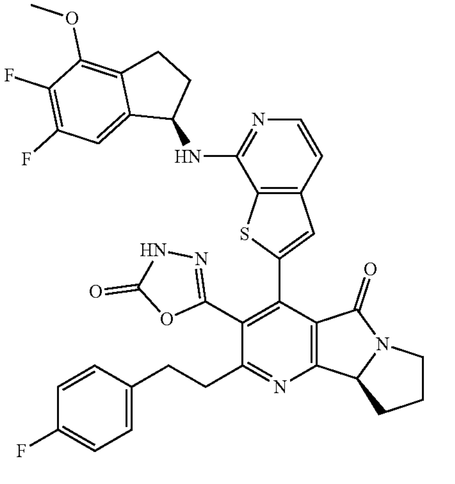 |

TABLE 1-continued
| Compound No. | Structure |
|---|---|
| 193 | 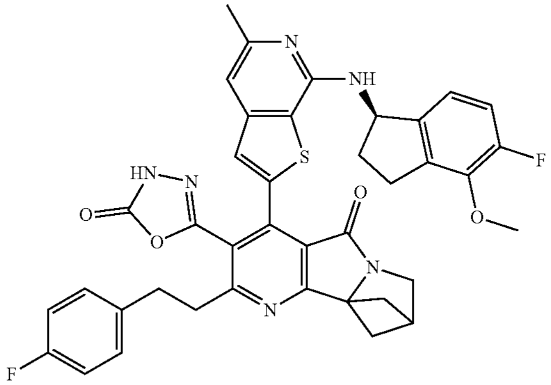 [SMILES: COc1c(F)ccc2c1CC[C@H]2Nc1nc(C)cc2cc(-c3c4c(nc(CCc5ccc(F)cc5)c3-c3n[nH]c(=O)o3)C35CC(CN3C4=O)C5)sc12] |
| 194 | 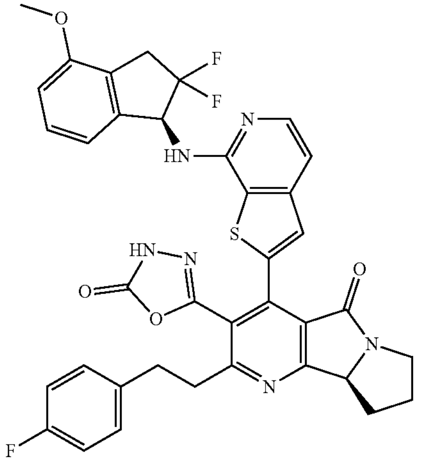 [SMILES: COc1cccc2c1CC(F)(F)[C@H]2Nc1nccc2cc(-c3c4c(nc(CCc5ccc(F)cc5)c3-c3n[nH]c(=O)o3)[C@@H]3CCCN3C4=O)sc12] |
| 195 | 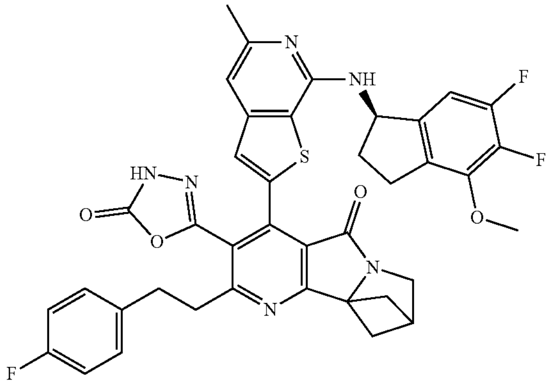 [SMILES: COc1c(F)c(F)cc2c1CC[C@H]2Nc1nc(C)cc2cc(-c3c4c(nc(CCc5ccc(F)cc5)c3-c3n[nH]c(=O)o3)C35CC(CN3C4=O)C5)sc12] |

TABLE 1-continued
| Compound No. | Structure |
|---|---|
| 196 | 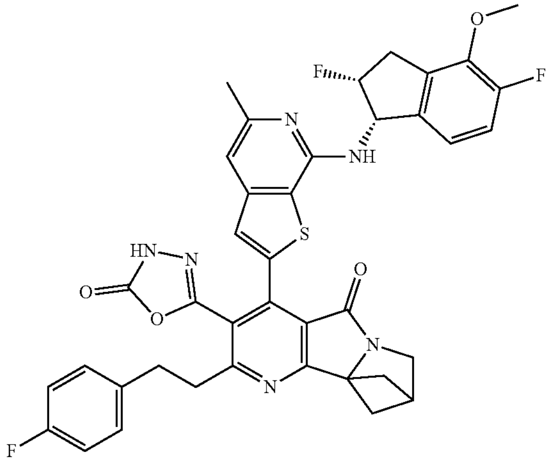 [SMILES: COc1c(F)ccc2c1C[C@@H](F)[C@H]2Nc1nc(C)cc2cc(-c3c4c(nc(CCc5ccc(F)cc5)c3-c3n[nH]c(=O)o3)C35CC(CN3C4=O)C5)sc12] |
| 197 | 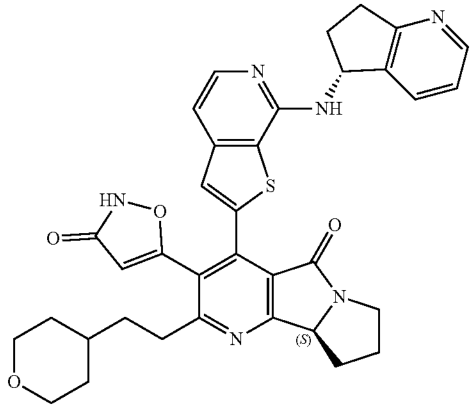 |
| 198 | 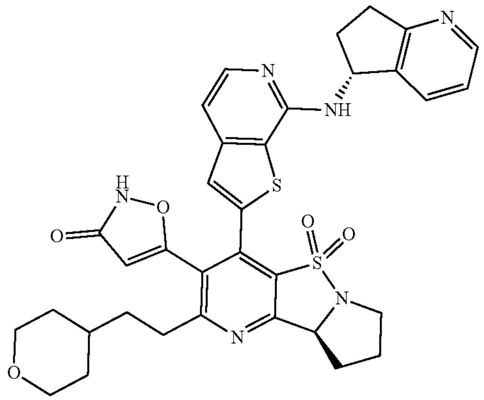 [SMILES: O=c1cc(-c2c(CCC3CCOCC3)nc3c(c2-c2cc4ccnc(N[C@@H]5CCc6ncccc65)c4s2)S(=O)(=O)N2CCC[C@@H]32)o[nH]1] |

TABLE 1-continued
| Compound No. | Structure |
|---|---|
| 199 | 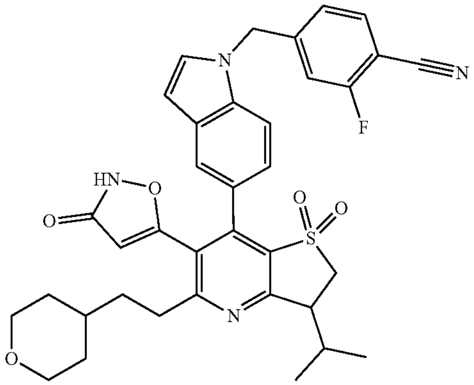 [SMILES: CC(C)C1CS(=O)(=O)c2c1nc(CCC1CCOCC1)c(-c1cc(=O)[nH]o1)c2-c1ccc2c(ccn2Cc2ccc(C#N)c(F)c2)c1] |
| 200 | 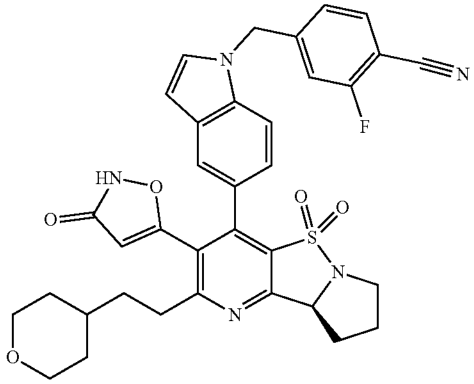 [SMILES: N#Cc1ccc(Cn2ccc3cc(-c4c(-c5cc(=O)[nH]o5)c(CCC5CCOCC5)nc5c4S(=O)(=O)N4CCC[C@@H]54)ccc32)cc1F] |
| 201 | 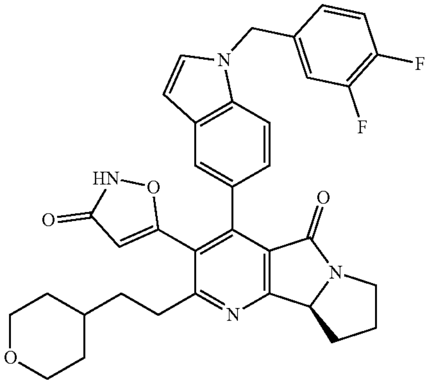 [SMILES: O=C1c2c(nc(CCC3CCOCC3)c(-c3cc(=O)[nH]o3)c2-c2ccc3c(ccn3Cc3ccc(F)c(F)c3)c2)[C@@H]2CCCN12] |
| 202 | 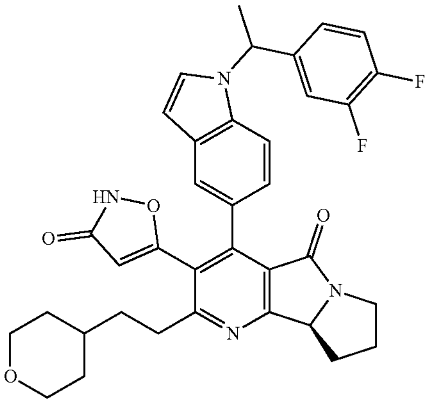 |

TABLE 1-continued
| Compound No. | Structure |
|---|---|
| 203 | 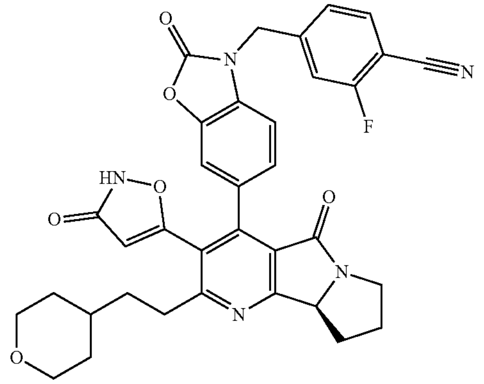 [SMILES: N#Cc1ccc(Cn2c(=O)oc3cc(-c4c5c(nc(CCC6CCOCC6)c4-c4cc(=O)[nH]o4)[C@@H]4CCCN4C5=O)ccc32)cc1F] |
| 204 | 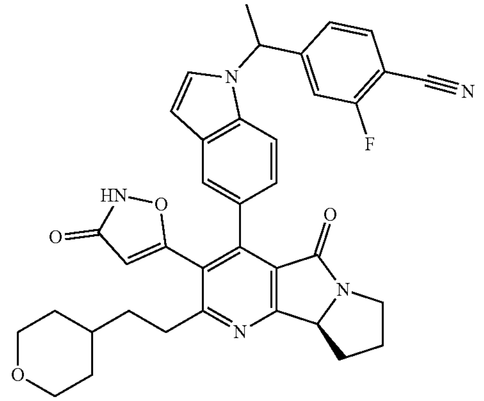 [SMILES: CC(c1ccc(C#N)c(F)c1)n1ccc2cc(-c3c4c(nc(CCC5CCOCC5)c3-c3cc(=O)[nH]o3)[C@@H]3CCCN3C4=O)ccc21] |
| 205 | 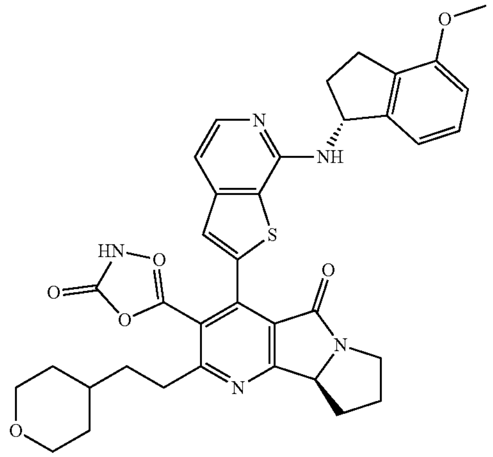 |

TABLE 1-continued
| Compound No. | Structure |
| --- | --- |
| 206 | 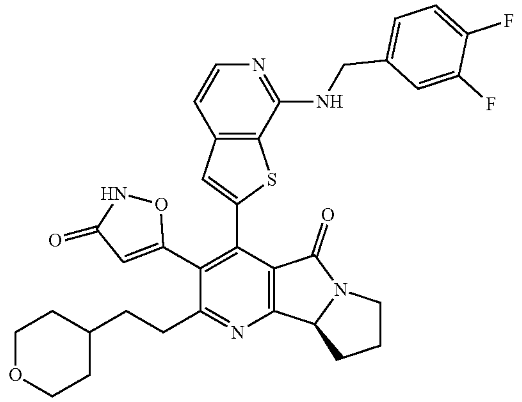 [SMILES: O=C1c2c(nc(CCC3CCOCC3)c(-c3cc(=O)[nH]o3)c2-c2cc3ccnc(NCc4ccc(F)c(F)c4)c3s2)[C@@H]2CCCN12] |
| 207 | 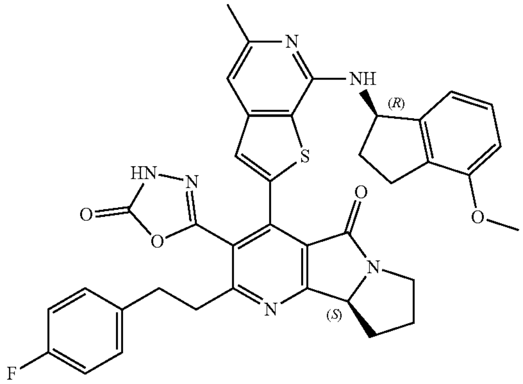 |
| 208 | 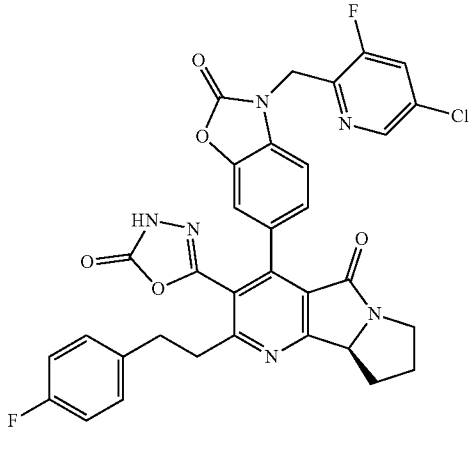 |

TABLE 1-continued
| Compound No. | Structure |
|---|---|
| 209 | 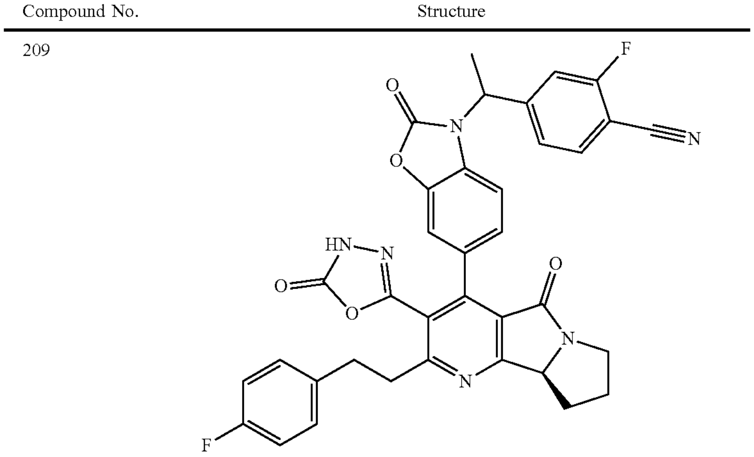 |
| 210 | 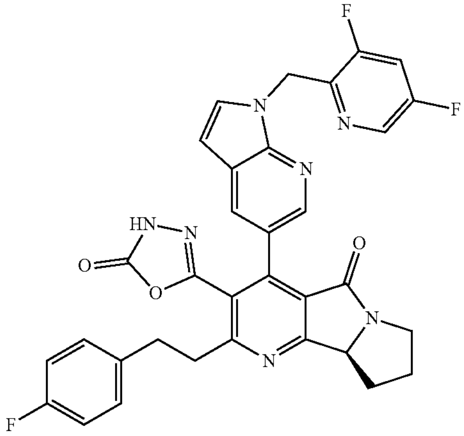 [SMILES: O=C1c2c(nc(CCc3ccc(F)cc3)c(-c3n[nH]c(=O)o3)c2-c2cnc3c(ccn3Cc3ncc(F)cc3F)c2)[C@@H]2CCCN12] |
| 211 | 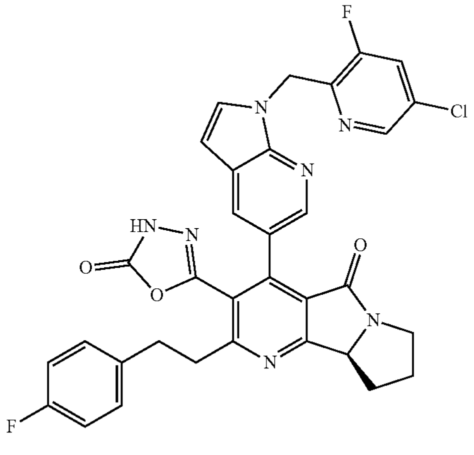 [SMILES: O=C1c2c(nc(CCc3ccc(F)cc3)c(-c3n[nH]c(=O)o3)c2-c2cnc3c(ccn3Cc3ncc(Cl)cc3F)c2)[C@@H]2CCCN12] |

TABLE 1-continued
| Compound No. | Structure |
| --- | --- |
| 212 | 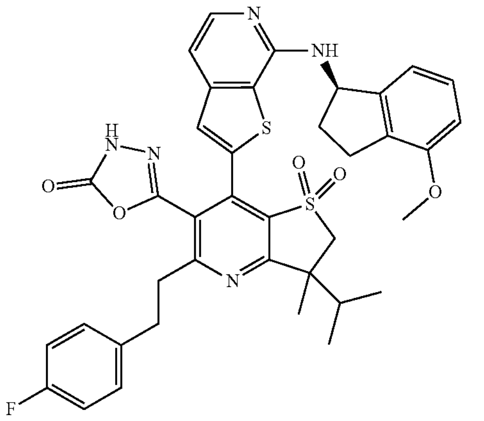 [SMILES: COc1cccc2c1CC[C@H]2Nc1nccc2cc(-c3c(-c4n[nH]c(=O)o4)c(CCc4ccc(F)cc4)nc4c3S(=O)(=O)CC4(C)C(C)C)sc12] |
| 213 | 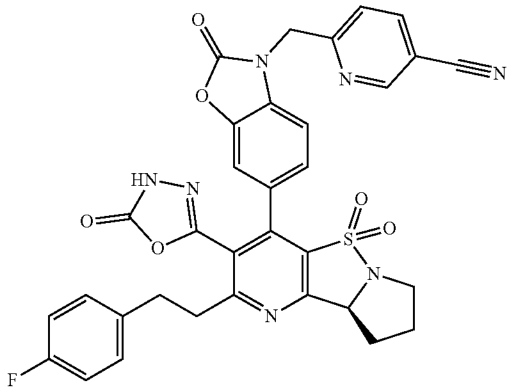 [SMILES: N#Cc1ccc(Cn2c(=O)oc3cc(-c4c(-c5n[nH]c(=O)o5)c(CCc5ccc(F)cc5)nc5c4S(=O)(=O)N4CCC[C@@H]54)ccc32)nc1] |
| 214 | 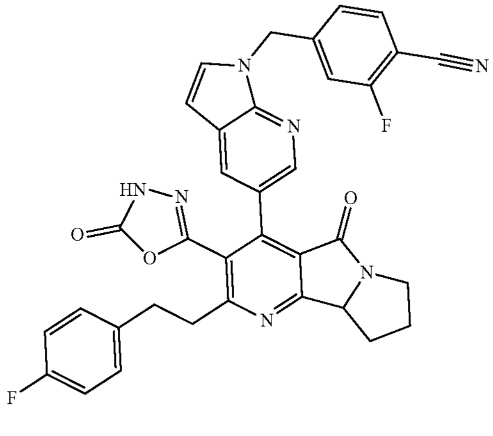 [SMILES: N#Cc1ccc(Cn2ccc3cc(-c4c5c(nc(CCc6ccc(F)cc6)c4-c4n[nH]c(=O)o4)C4CCCN4C5=O)cnc32)cc1F] |

TABLE 1-continued
| Compound No. | Structure |
| --- | --- |
| 215 | 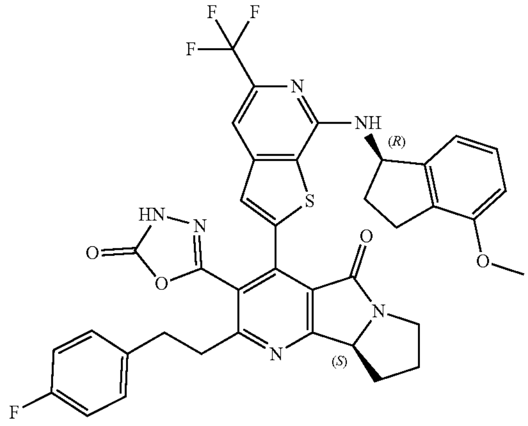 |
| 216 | 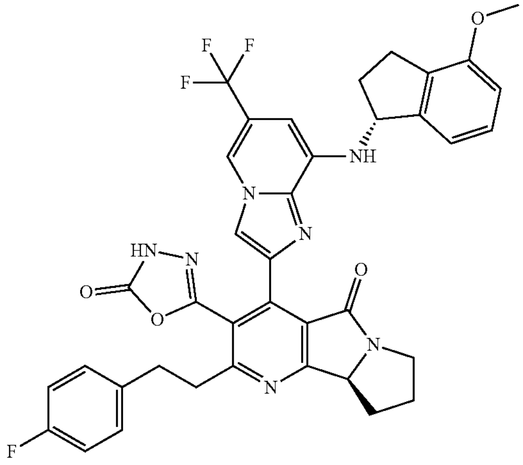 [SMILES: COc1cccc2c1CC[C@H]2Nc1cc(C(F)(F)F)cn2cc(-c3c4c(nc(CCc5ccc(F)cc5)c3-c3n[nH]c(=O)o3)[C@@H]3CCCN3C4=O)nc12] |
| 217 | 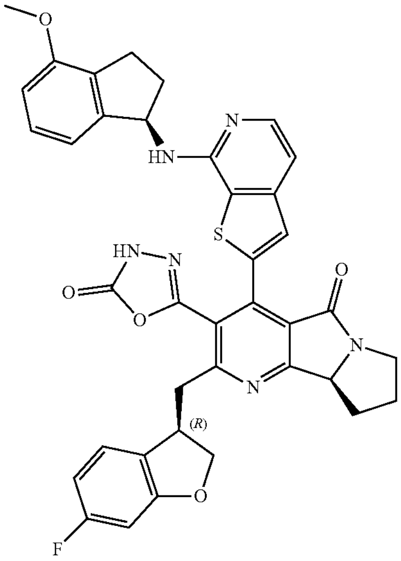 |

TABLE 1-continued
| Compound No. | Structure |
|---|---|
| 218 | 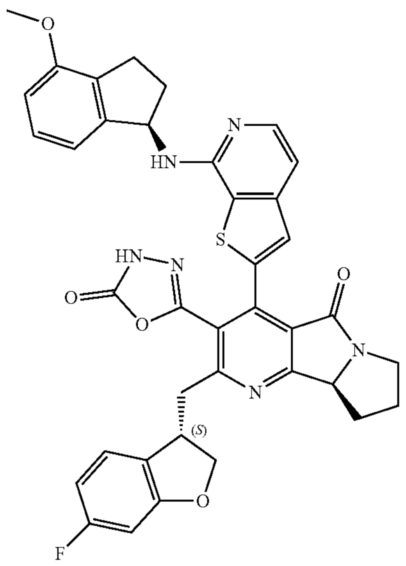 |
| 219 | 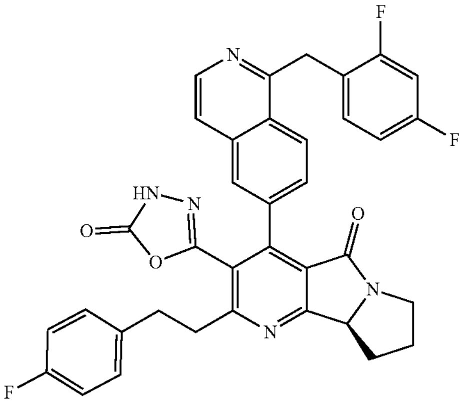 [SMILES: O=C1c2c(nc(CCc3ccc(F)cc3)c(-c3n[nH]c(=O)o3)c2-c2ccc3c(Cc4ccc(F)cc4F)nccc3c2)[C@@H]2CCCN12] |
| 220 | 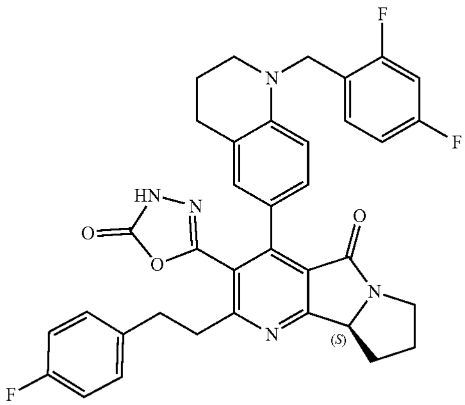 |

TABLE 1-continued
| Compound No. | Structure |
| --- | --- |
| 221 | 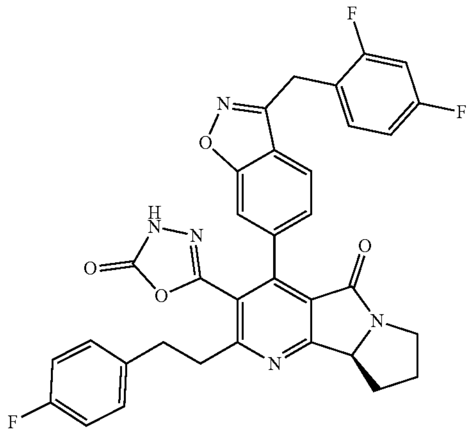 [SMILES: O=C1c2c(nc(CCc3ccc(F)cc3)c(-c3n[nH]c(=O)o3)c2-c2ccc3c(Cc4ccc(F)cc4F)noc3c2)[C@@H]2CCCN12] |
| 222 | 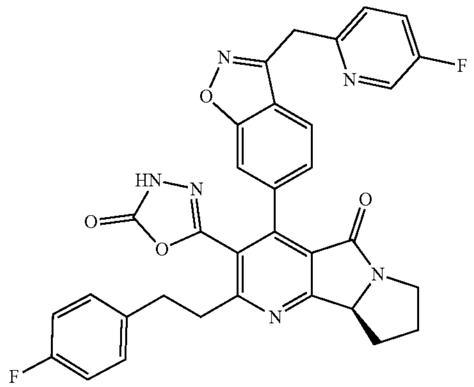 [SMILES: O=C1c2c(nc(CCc3ccc(F)cc3)c(-c3n[nH]c(=O)o3)c2-c2ccc3c(Cc4ccc(F)cn4)noc3c2)[C@@H]2CCCN12] |
| 223 | 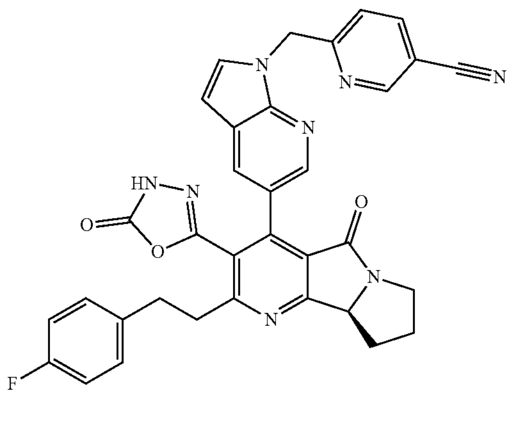 [SMILES: N#Cc1ccc(Cn2ccc3cc(-c4c5c(nc(CCc6ccc(F)cc6)c4-c4n[nH]c(=O)o4)[C@@H]4CCCN4C5=O)cnc32)nc1] |

TABLE 1-continued
| Compound No. | Structure |
|---|---|
| 224 | 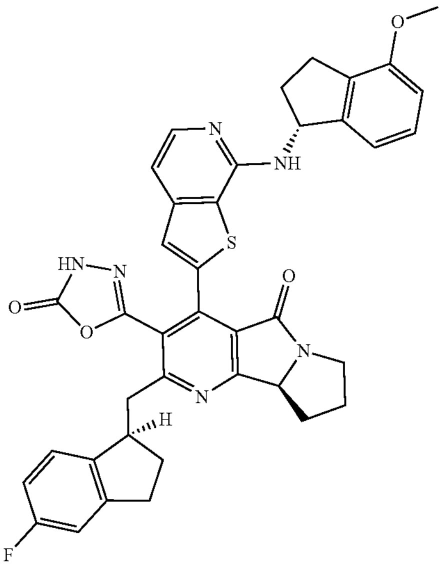 [SMILES: COc1cccc2c1CC[C@H]2Nc1nccc2cc(-c3c4c(nc(C[C@H]5CCc6cc(F)ccc65)c3-c3n[nH]c(=O)o3)[C@@H]3CCCN3C4=O)sc12] |
| 225 | 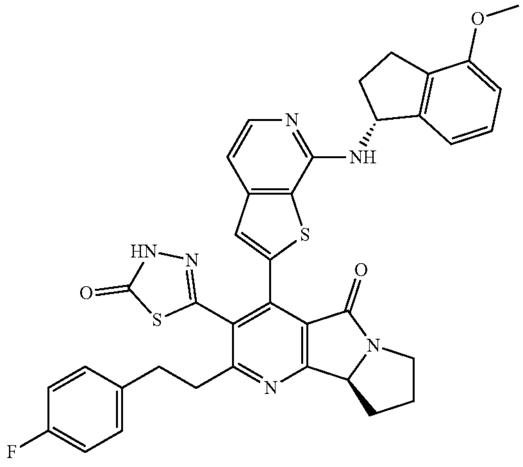 [SMILES: COc1cccc2c1CC[C@H]2Nc1nccc2cc(-c3c4c(nc(CCc5ccc(F)cc5)c3-c3n[nH]c(=O)s3)[C@@H]3CCCN3C4=O)sc12] |
| 226 | 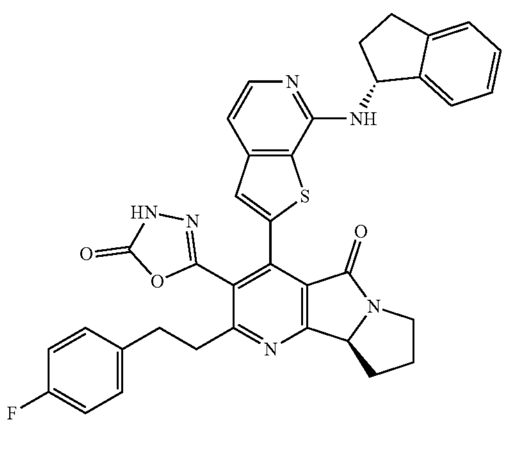 [SMILES: O=C1c2c(nc(CCc3ccc(F)cc3)c(-c3n[nH]c(=O)o3)c2-c2cc3ccnc(N[C@@H]4CCc5ccccc54)c3s2)[C@@H]2CCCN12] |

TABLE 1-continued
| Compound No. | Structure |
| --- | --- |
| 227 | 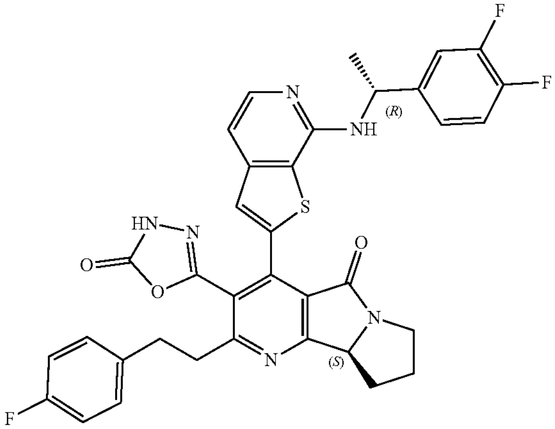 |
| 228 | 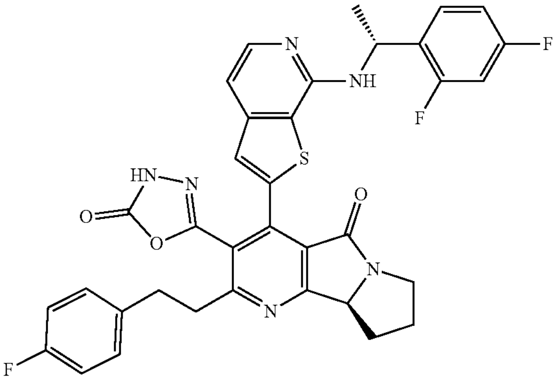 [SMILES: C[C@@H](Nc1nccc2cc(-c3c4c(nc(CCc5ccc(F)cc5)c3-c3n[nH]c(=O)o3)[C@@H]3CCCN3C4=O)sc12)c1ccc(F)cc1F] |
| 229 | 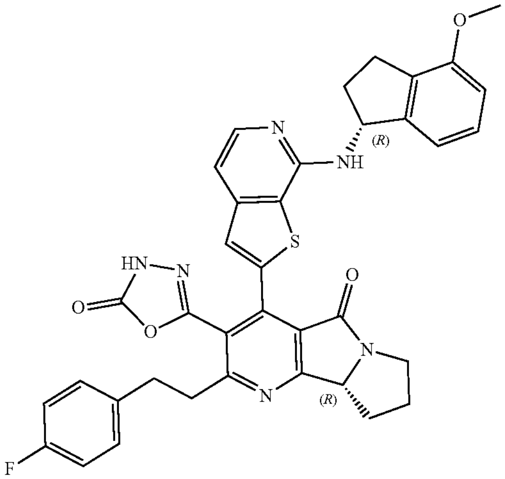 |

TABLE 1-continued
| Compound No. | Structure |
|---|---|
| 230 | 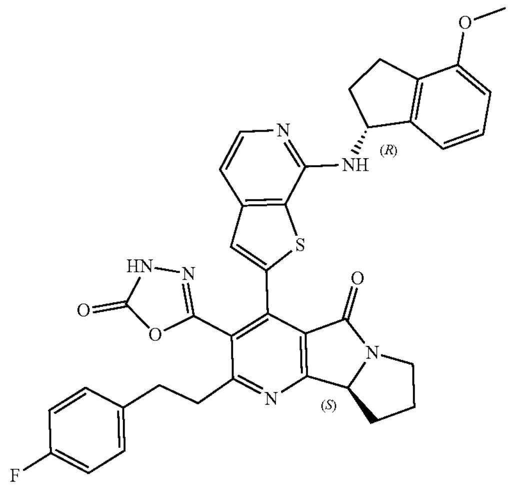 |
| 231 | 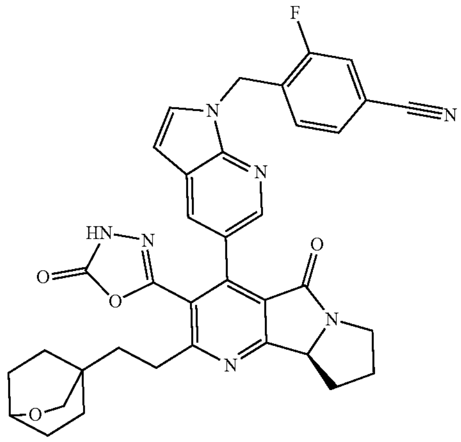 [SMILES: N#Cc1ccc(Cn2ccc3cc(-c4c5c(nc(CCC67CCC(CC6)OC7)c4-c4n[nH]c(=O)o4)[C@@H]4CCCN4C5=O)cnc32)c(F)c1] |
| 232 | 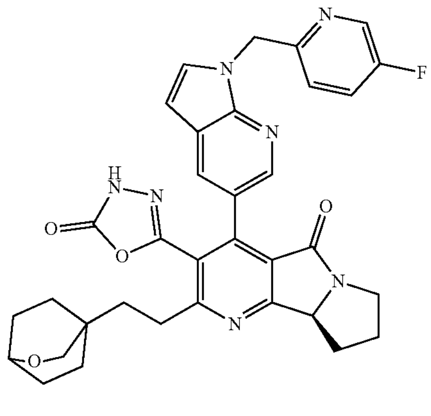 [SMILES: O=C1c2c(nc(CCC34CCC(CC3)OC4)c(-c3n[nH]c(=O)o3)c2-c2cnc3c(ccn3Cc3ccc(F)cn3)c2)[C@@H]2CCCN12] |

TABLE 1-continued
| Compound No. | Structure |
|---|---|
| 233 | 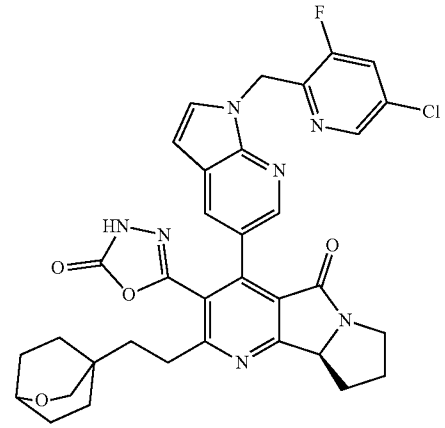 [SMILES: O=C1c2c(nc(CCC34CCC(CC3)OC4)c(-c3n[nH]c(=O)o3)c2-c2cnc3c(ccn3Cc3ncc(Cl)cc3F)c2)[C@@H]2CCCN12] |
| 234 | 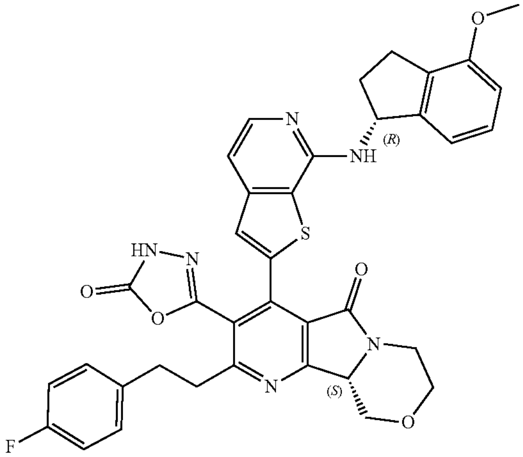 |
| 235 | 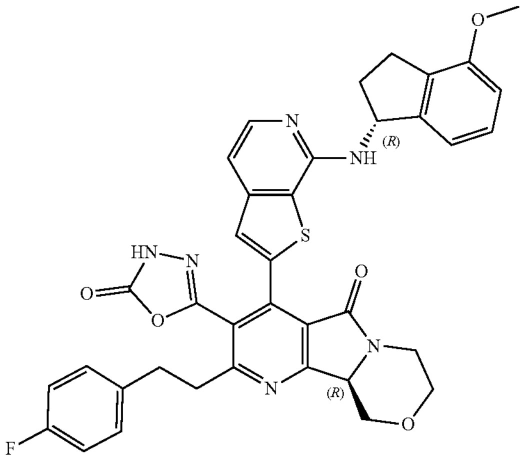 |

TABLE 1-continued
| Compound No. | Structure |
| --- | --- |
| 236 | 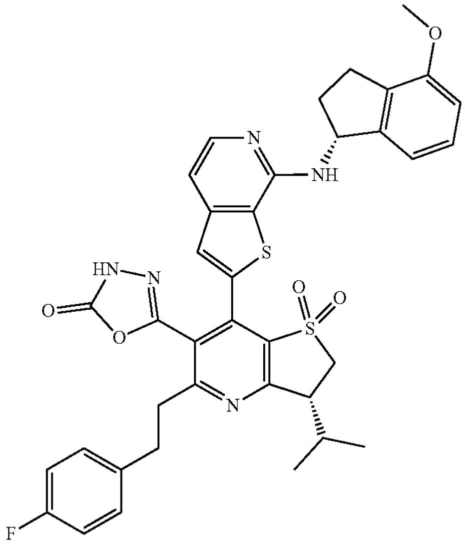 [SMILES: COc1cccc2c1CC[C@H]2Nc1nccc2cc(-c3c(-c4n[nH]c(=O)o4)c(CCc4ccc(F)cc4)nc4c3S(=O)(=O)C[C@@H]4C(C)C)sc12] |
| 237 | 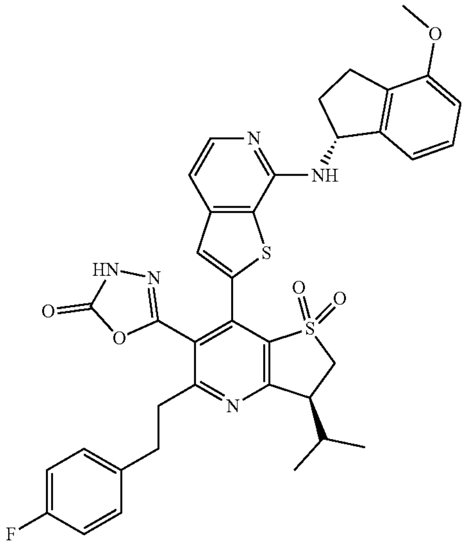 [SMILES: COc1cccc2c1CC[C@H]2Nc1nccc2cc(-c3c(-c4n[nH]c(=O)o4)c(CCc4ccc(F)cc4)nc4c3S(=O)(=O)C[C@H]4C(C)C)sc12] |
| 238 | 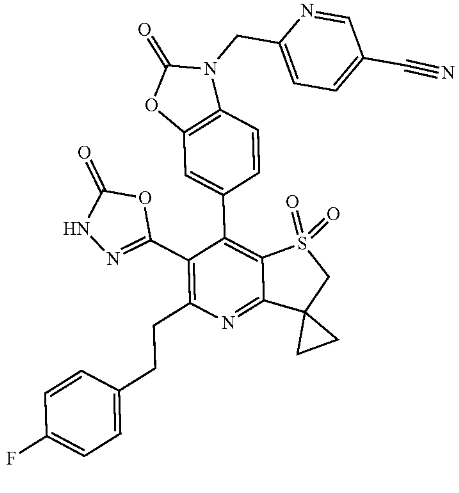 [SMILES: N#Cc1ccc(Cn2c(=O)oc3cc(-c4c(-c5n[nH]c(=O)o5)c(CCc5ccc(F)cc5)nc5c4S(=O)(=O)CC54CC4)ccc32)nc1] |

TABLE 1-continued
| Compound No. | Structure |
| --- | --- |
| 239 | 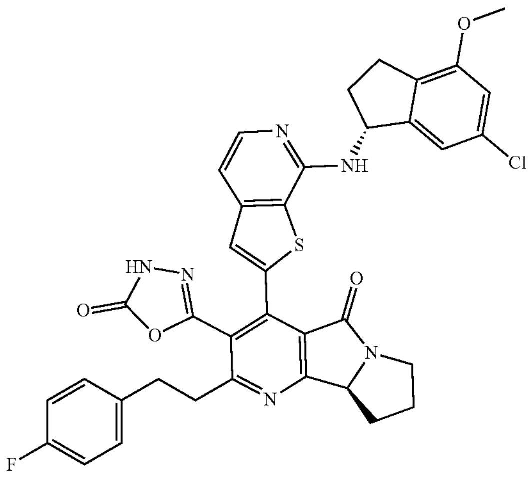 [SMILES: COc1cc(Cl)cc2c1CC[C@H]2Nc1nccc2cc(-c3c4c(nc(CCc5ccc(F)cc5)c3-c3n[nH]c(=O)o3)[C@@H]3CCCN3C4=O)sc12] |
| 240 | 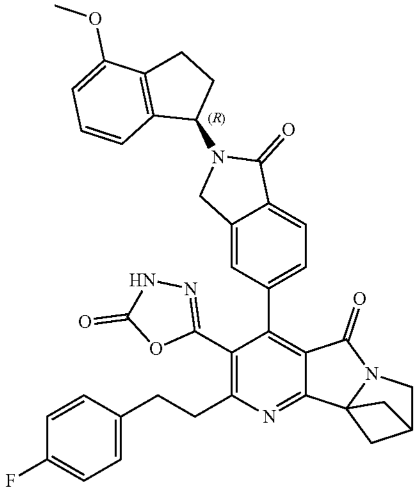 |
| 241 | 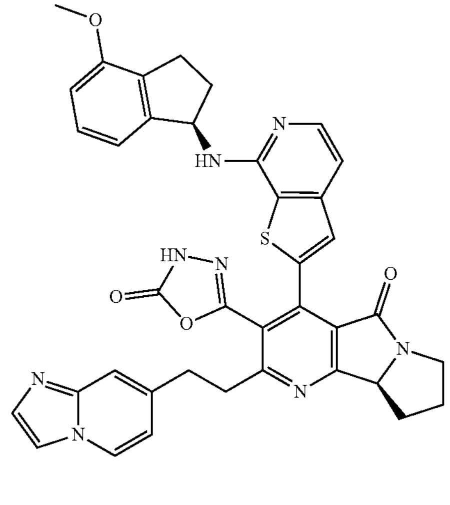 [SMILES: COc1cccc2c1CC[C@H]2Nc1nccc2cc(-c3c4c(nc(CCc5ccn6ccnc6c5)c3-c3n[nH]c(=O)o3)[C@@H]3CCCN3C4=O)sc12] |

TABLE 1-continued
| Compound No. | Structure |
|---|---|
| 242 | 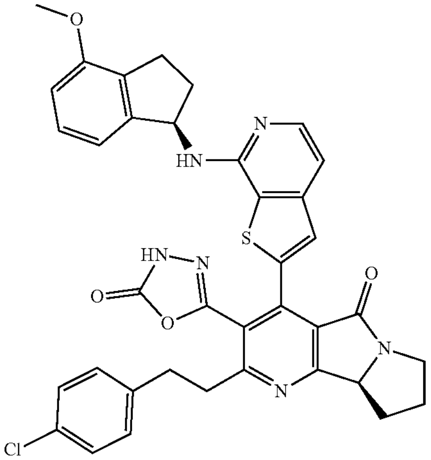 [SMILES: COc1cccc2c1CC[C@H]2Nc1nccc2cc(-c3c4c(nc(CCc5ccc(Cl)cc5)c3-c3n[nH]c(=O)o3)[C@@H]3CCCN3C4=O)sc12] |
| 243 | 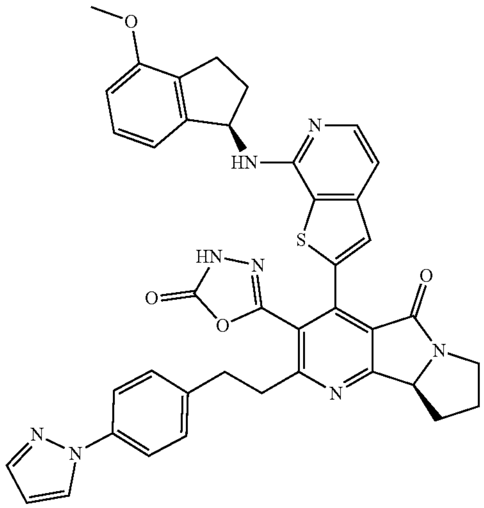 [SMILES: COc1cccc2c1CC[C@H]2Nc1nccc2cc(-c3c4c(nc(CCc5ccc(-n6cccn6)cc5)c3-c3n[nH]c(=O)o3)[C@@H]3CCCN3C4=O)sc12] |
| 244 | 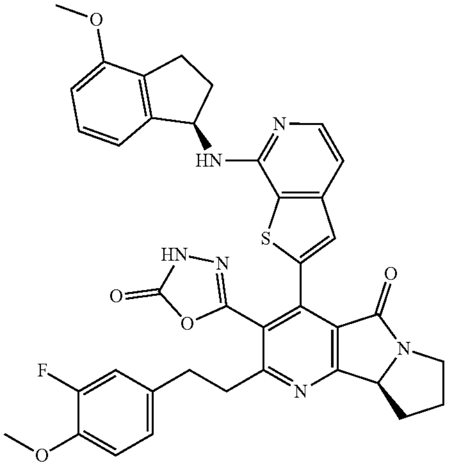 [SMILES: COc1ccc(CCc2nc3c(c(-c4cc5ccnc(N[C@@H]6CCc7c(OC)cccc76)c5s4)c2-c2n[nH]c(=O)o2)C(=O)N2CCC[C@@H]32)cc1F] |

TABLE 1-continued
| Compound No. | Structure |
| --- | --- |
| 245 | 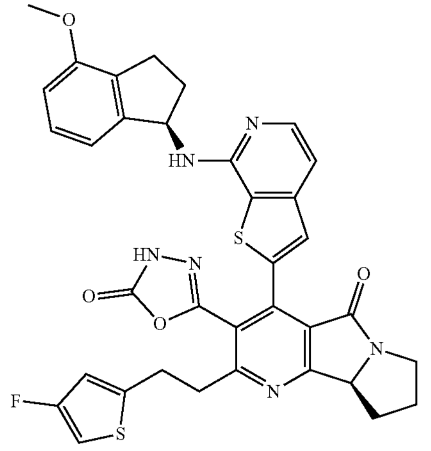 [SMILES: COc1cccc2c1CC[C@H]2Nc1nccc2cc(-c3c4c(nc(CCc5cc(F)cs5)c3-c3n[nH]c(=O)o3)[C@@H]3CCCN3C4=O)sc12] |
| 246 | 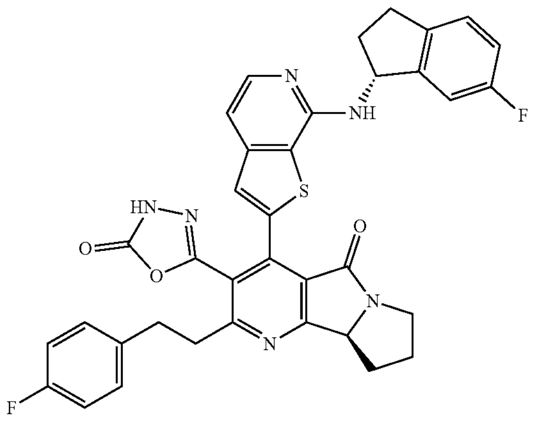 [SMILES: O=C1c2c(nc(CCc3ccc(F)cc3)c(-c3n[nH]c(=O)o3)c2-c2cc3ccnc(N[C@@H]4CCc5ccc(F)cc54)c3s2)[C@@H]2CCCN12] |
| 247 | 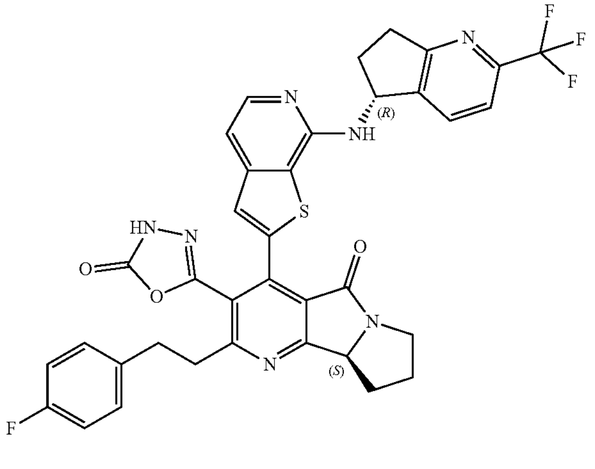 |

TABLE 1-continued
| Compound No. | Structure |
| --- | --- |
| 248 | 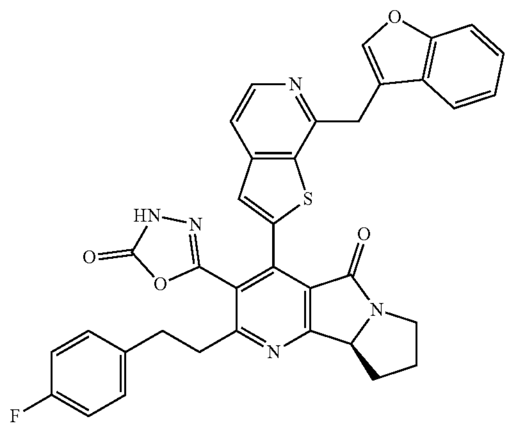 [SMILES: O=C1c2c(nc(CCc3ccc(F)cc3)c(-c3n[nH]c(=O)o3)c2-c2cc3ccnc(Cc4coc5ccccc45)c3s2)[C@@H]2CCCN12] |
| 249 | 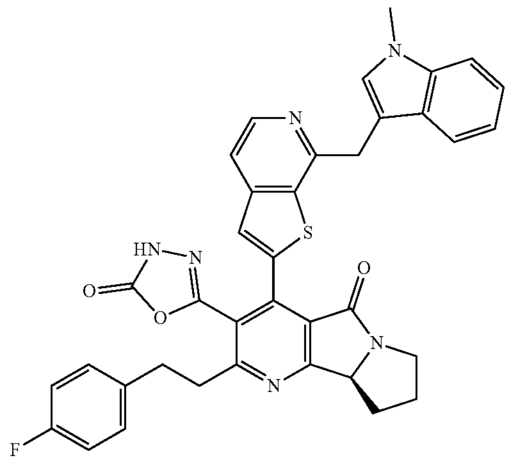 [SMILES: Cn1cc(Cc2nccc3cc(-c4c5c(nc(CCc6ccc(F)cc6)c4-c4n[nH]c(=O)o4)[C@@H]4CCCN4C5=O)sc23)c2ccccc21] |
| 250 | 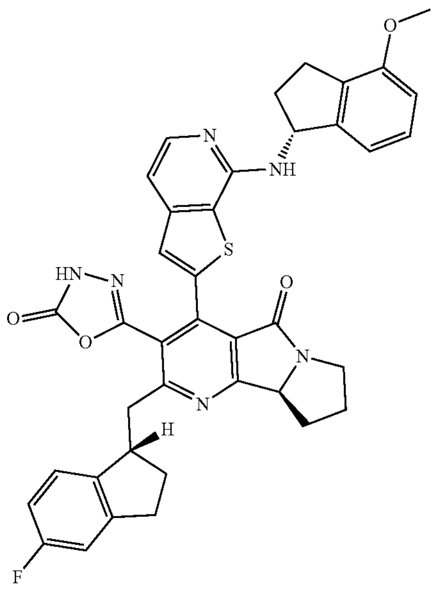 [SMILES: COc1cccc2c1CC[C@H]2Nc1nccc2cc(-c3c4c(nc(C[C@@H]5CCc6cc(F)ccc65)c3-c3n[nH]c(=O)o3)[C@@H]3CCCN3C4=O)sc12] |

TABLE 1-continued
| Compound No. | Structure |
| --- | --- |
| 251 | 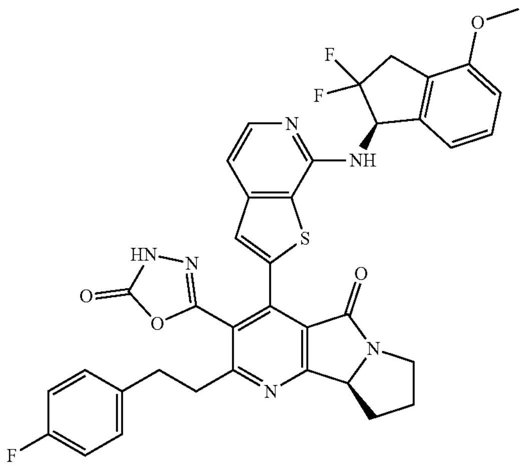 [SMILES: COc1cccc2c1CC(F)(F)[C@@H]2Nc1nccc2cc(-c3c4c(nc(CCc5ccc(F)cc5)c3-c3n[nH]c(=O)o3)[C@@H]3CCCN3C4=O)sc12] |
| 252 | 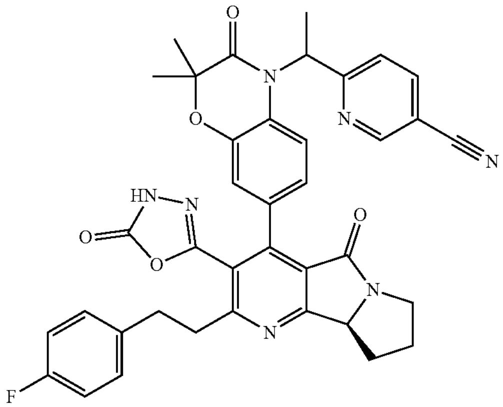 [SMILES: CC(c1ccc(C#N)cn1)N1C(=O)C(C)(C)Oc2cc(-c3c4c(nc(CCc5ccc(F)cc5)c3-c3n[nH]c(=O)o3)[C@@H]3CCCN3C4=O)ccc21] |
| 253 | 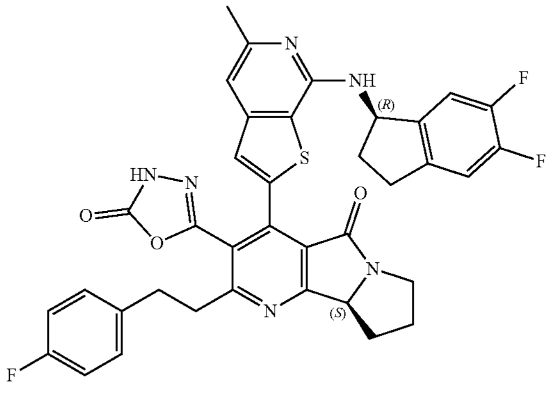 |

TABLE 1-continued
| Compound No. | Structure |
| --- | --- |
| 254 | 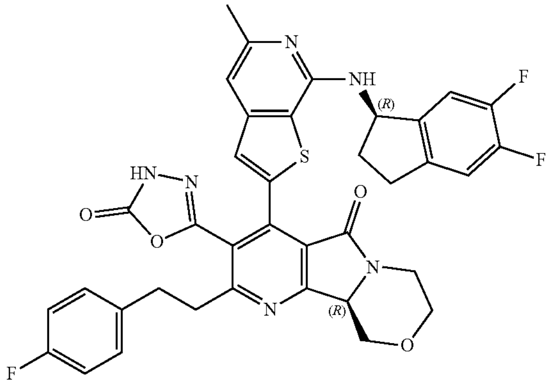 |
| 255 | 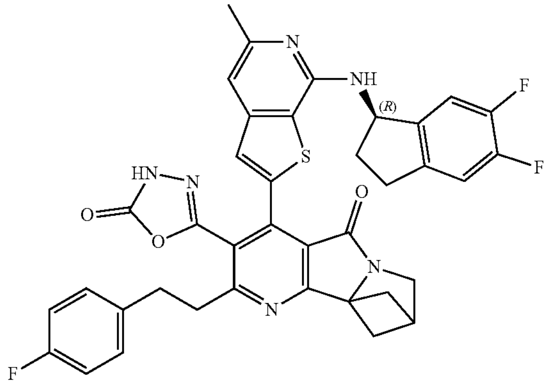 |
| 256 | 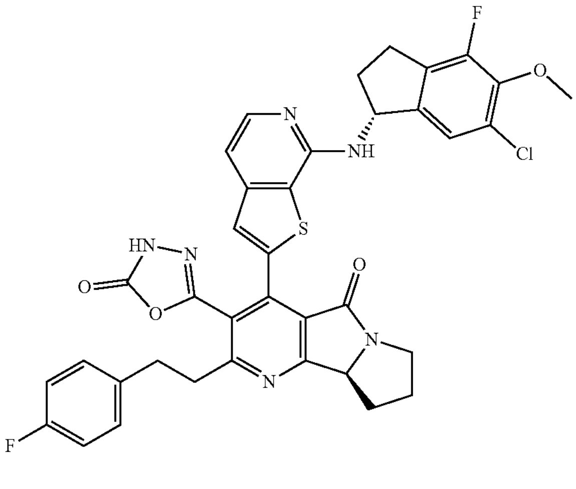 [SMILES: COc1c(Cl)cc2c(c1F)CC[C@H]2Nc1nccc2cc(-c3c4c(nc(CCc5ccc(F)cc5)c3-c3n[nH]c(=O)o3)[C@@H]3CCCN3C4=O)sc12] |

TABLE 1-continued
| Compound No. | Structure |
| --- | --- |
| 257 | 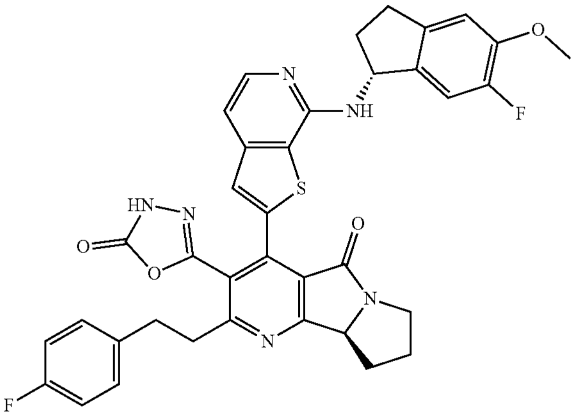 [SMILES: COc1cc2c(cc1F)[C@H](Nc1nccc3cc(-c4c5c(nc(CCc6ccc(F)cc6)c4-c4n[nH]c(=O)o4)[C@@H]4CCCN4C5=O)sc13)CC2] |
| 258 | 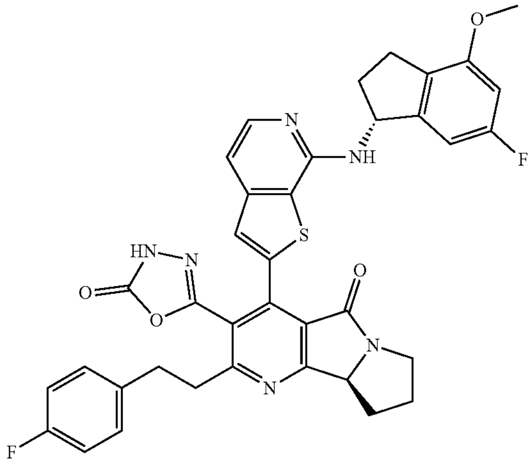 [SMILES: COc1cc(F)cc2c1CC[C@H]2Nc1nccc2cc(-c3c4c(nc(CCc5ccc(F)cc5)c3-c3n[nH]c(=O)o3)[C@@H]3CCCN3C4=O)sc12] |
| 259 | 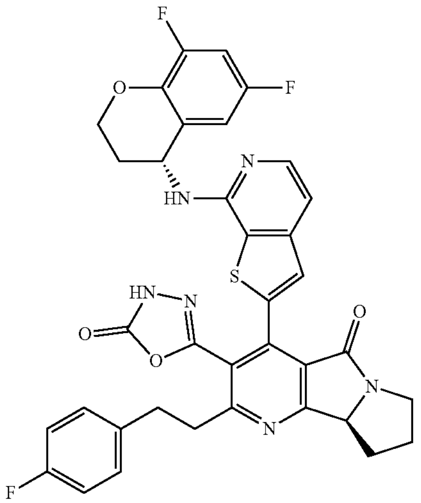 [SMILES: O=C1c2c(nc(CCc3ccc(F)cc3)c(-c3n[nH]c(=O)o3)c2-c2cc3ccnc(N[C@@H]4CCOc5c(F)cc(F)cc54)c3s2)[C@@H]2CCCN12] |

TABLE 1-continued
| Compound No. | Structure |
| --- | --- |
| 260 | 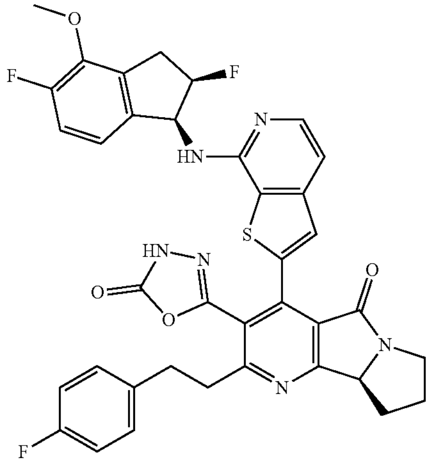 [SMILES: COc1c(F)ccc2c1C[C@@H](F)[C@H]2Nc1nccc2cc(-c3c4c(nc(CCc5ccc(F)cc5)c3-c3n[nH]c(=O)o3)[C@@H]3CCCN3C4=O)sc12] |
| 261 | 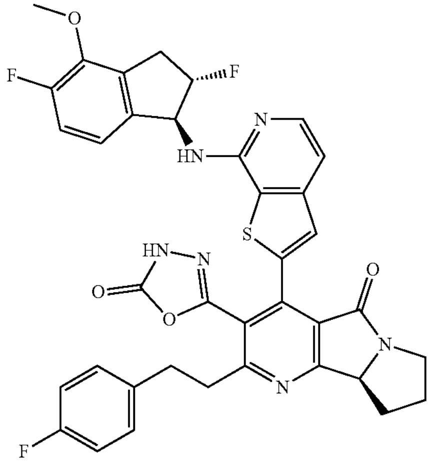 [SMILES: COc1c(F)ccc2c1C[C@H](F)[C@H]2Nc1nccc2cc(-c3c4c(nc(CCc5ccc(F)cc5)c3-c3n[nH]c(=O)o3)[C@@H]3CCCN3C4=O)sc12] |
| 262 | 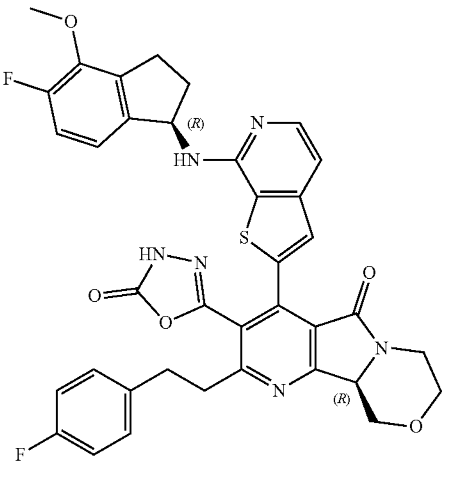 |

TABLE 1-continued
| Compound No. | Structure |
|---|---|
| 263 | 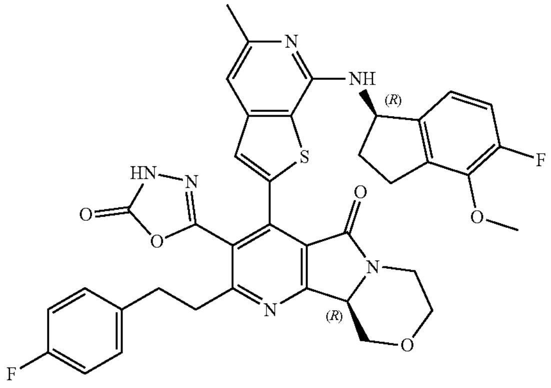 |
| 264 | 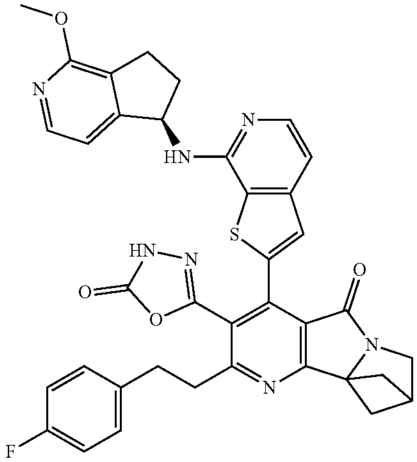 [SMILES: COc1nccc2c1CC[C@H]2Nc1nccc2cc(-c3c4c(nc(CCc5ccc(F)cc5)c3-c3n[nH]c(=O)o3)C35CC(CN3C4=O)C5)sc12] |
| 265 | 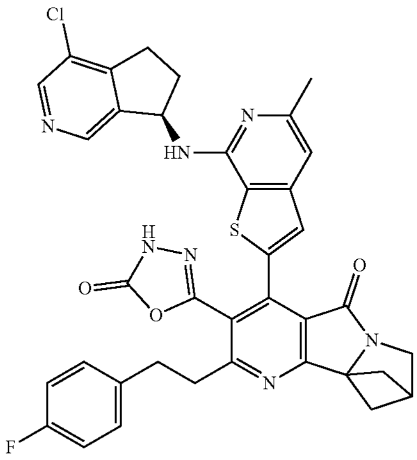 [SMILES: Cc1cc2cc(-c3c4c(nc(CCc5ccc(F)cc5)c3-c3n[nH]c(=O)o3)C35CC(CN3C4=O)C5)sc2c(N[C@@H]2CCc3c(Cl)cncc32)n1] |

TABLE 1-continued
| Compound No. | Structure |
| --- | --- |
| 266 | 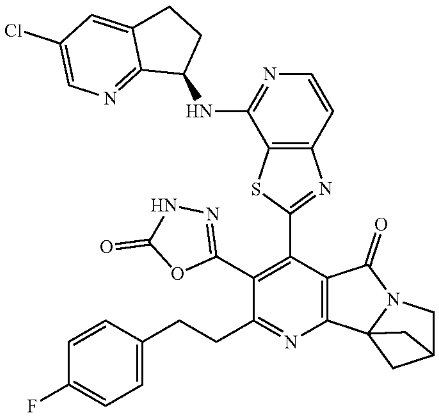 [SMILES: O=C1c2c(nc(CCc3ccc(F)cc3)c(-c3n[nH]c(=O)o3)c2-c2nc3ccnc(N[C@@H]4CCc5cc(Cl)cnc54)c3s2)C23CC(CN12)C3] |
| 267 | 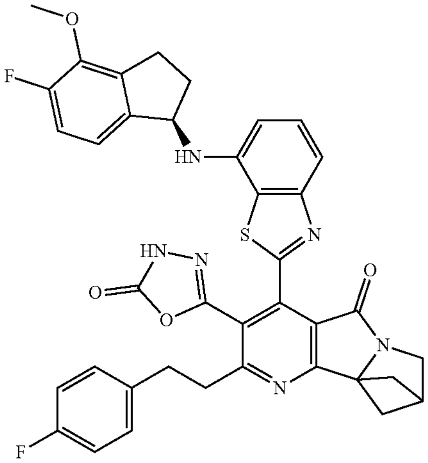 [SMILES: COc1c(F)ccc2c1CC[C@H]2Nc1cccc2nc(-c3c4c(nc(CCc5ccc(F)cc5)c3-c3n[nH]c(=O)o3)C35CC(CN3C4=O)C5)sc12] |
| 268 | 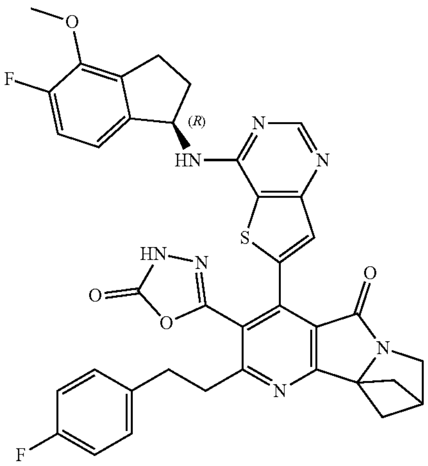 |

TABLE 1-continued
| Compound No. | Structure |
| --- | --- |
| 269 | 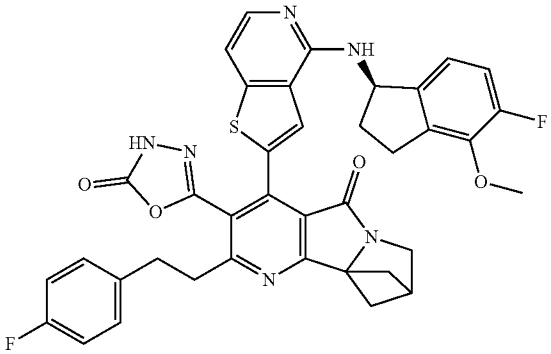 [SMILES: COc1c(F)ccc2c1CC[C@H]2Nc1nccc2sc(-c3c4c(nc(CCc5ccc(F)cc5)c3-c3n[nH]c(=O)o3)C35CC(CN3C4=O)C5)cc12] |
| 270 | 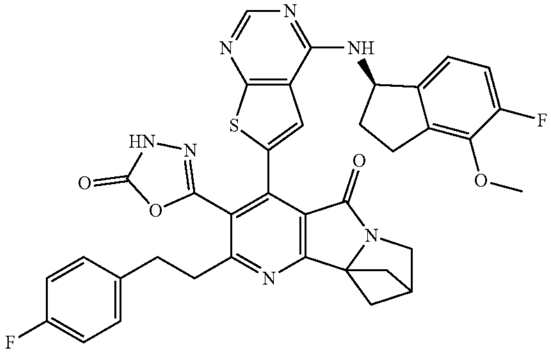 [SMILES: COc1c(F)ccc2c1CC[C@H]2Nc1ncnc2sc(-c3c4c(nc(CCc5ccc(F)cc5)c3-c3n[nH]c(=O)o3)C35CC(CN3C4=O)C5)cc12] |
| 271 | 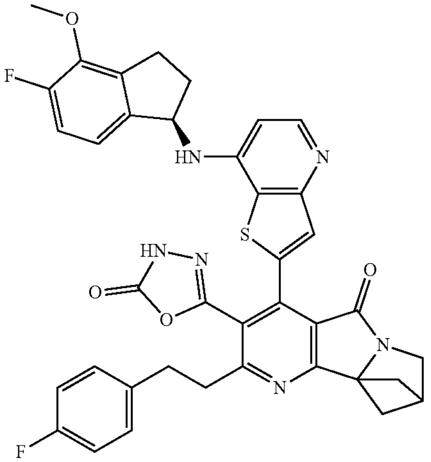 [SMILES: COc1c(F)ccc2c1CC[C@H]2Nc1ccnc2cc(-c3c4c(nc(CCc5ccc(F)cc5)c3-c3n[nH]c(=O)o3)C35CC(CN3C4=O)C5)sc12] |

TABLE 1-continued
| Compound No. | Structure |
|---|---|
| 272 | 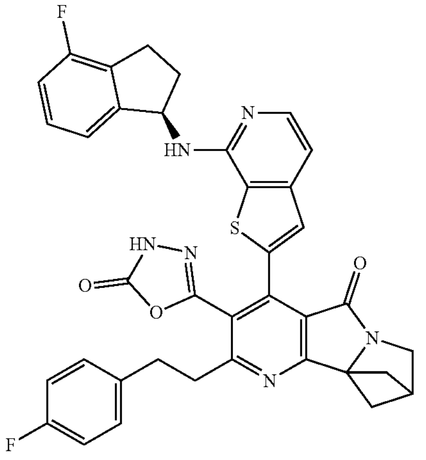 [SMILES: O=C1c2c(nc(CCc3ccc(F)cc3)c(-c3n[nH]c(=O)o3)c2-c2cc3ccnc(N[C@@H]4CCc5c(F)cccc54)c3s2)C23CC(CN12)C3] |
| 273 | 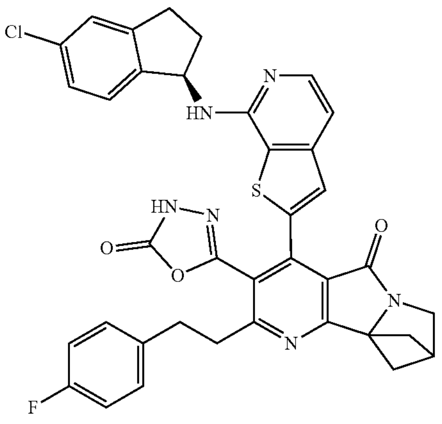 [SMILES: O=C1c2c(nc(CCc3ccc(F)cc3)c(-c3n[nH]c(=O)o3)c2-c2cc3ccnc(N[C@@H]4CCc5cc(Cl)ccc54)c3s2)C23CC(CN12)C3] |
| 274 | 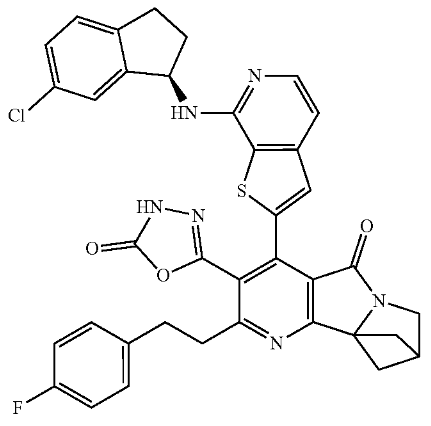 [SMILES: O=C1c2c(nc(CCc3ccc(F)cc3)c(-c3n[nH]c(=O)o3)c2-c2cc3ccnc(N[C@@H]4CCc5ccc(Cl)cc54)c3s2)C23CC(CN12)C3] |

TABLE 1-continued
| Compound No. | Structure |
|---|---|
| 275 | 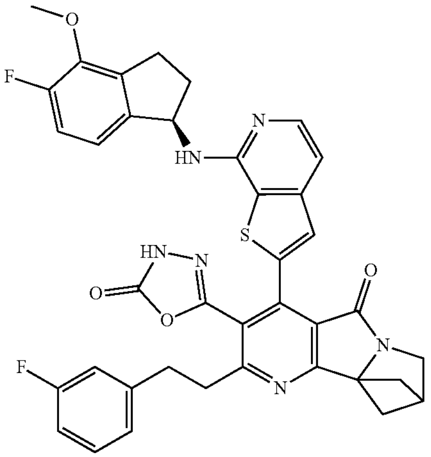 [SMILES: COc1c(F)ccc2c1CC[C@H]2Nc1nccc2cc(-c3c4c(nc(CCc5cccc(F)c5)c3-c3n[nH]c(=O)o3)C35CC(CN3C4=O)C5)sc12] |
| 276 | 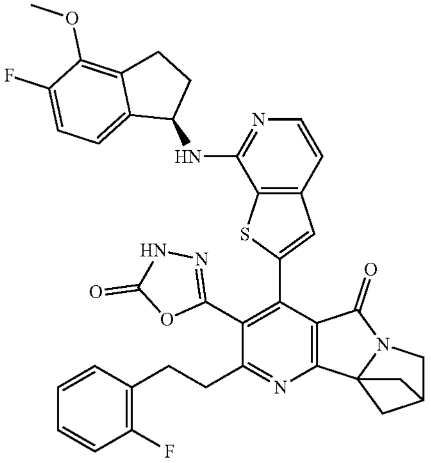 [SMILES: COc1c(F)ccc2c1CC[C@H]2Nc1nccc2cc(-c3c4c(nc(CCc5ccccc5F)c3-c3n[nH]c(=O)o3)C35CC(CN3C4=O)C5)sc12] |
| 277 | 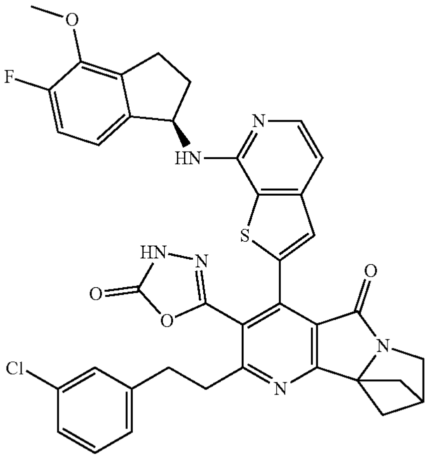 [SMILES: COc1c(F)ccc2c1CC[C@H]2Nc1nccc2cc(-c3c4c(nc(CCc5cccc(Cl)c5)c3-c3n[nH]c(=O)o3)C35CC(CN3C4=O)C5)sc12] |

TABLE 1-continued
| Compound No. | Structure |
|---|---|
| 278 | 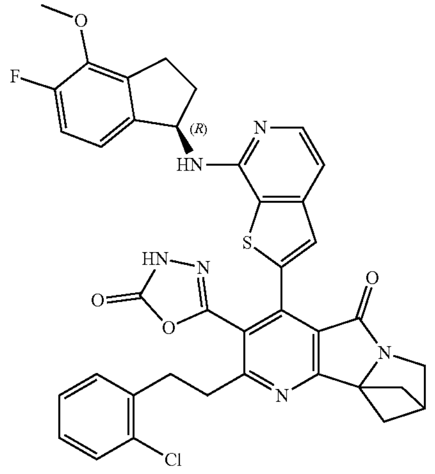 |
| 279 | 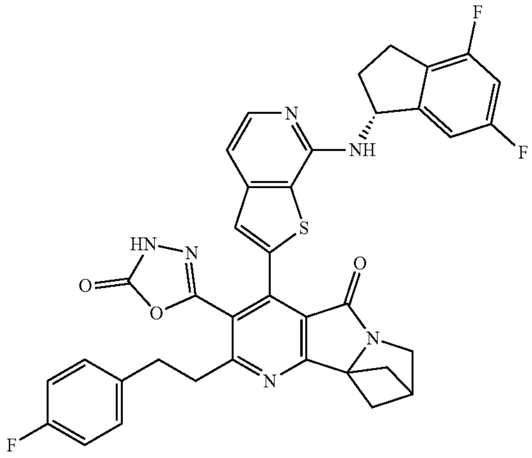 [SMILES: O=C1c2c(nc(CCc3ccc(F)cc3)c(-c3n[nH]c(=O)o3)c2-c2cc3ccnc(N[C@@H]4CCc5c(F)cc(F)cc54)c3s2)C23CC(CN12)C3] |
| 280 | 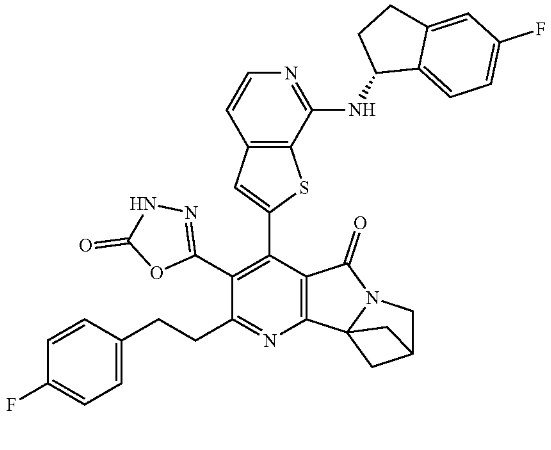 [SMILES: O=C1c2c(nc(CCc3ccc(F)cc3)c(-c3n[nH]c(=O)o3)c2-c2cc3ccnc(N[C@@H]4CCc5cc(F)ccc54)c3s2)C23CC(CN12)C3] |

TABLE 1-continued
| Compound No. | Structure |
|---|---|
| 281 | 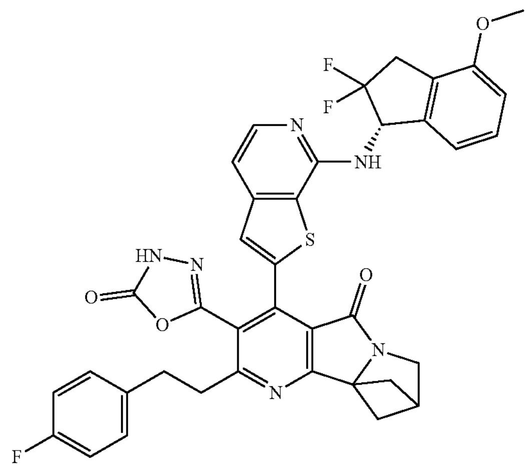 [SMILES: COc1cccc2c1CC(F)(F)[C@H]2Nc1nccc2cc(-c3c4c(nc(CCc5ccc(F)cc5)c3-c3n[nH]c(=O)o3)C35CC(CN3C4=O)C5)sc12] |
| 282 | 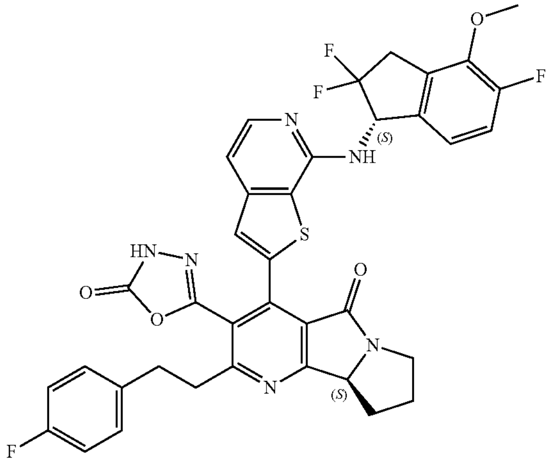 |
| 283 | 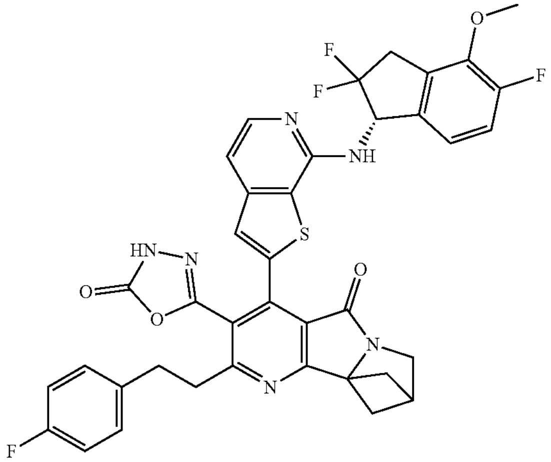 |

TABLE 1-continued
| Compound No. | Structure |
| --- | --- |
| 284 | 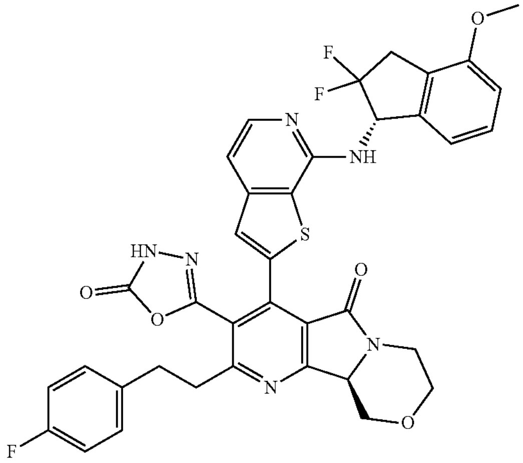 [SMILES: COc1cccc2c1CC(F)(F)[C@H]2Nc1nccc2cc(-c3c4c(nc(CCc5ccc(F)cc5)c3-c3n[nH]c(=O)o3)[C@@H]3COCCN3C4=O)sc12] |
| 285 | 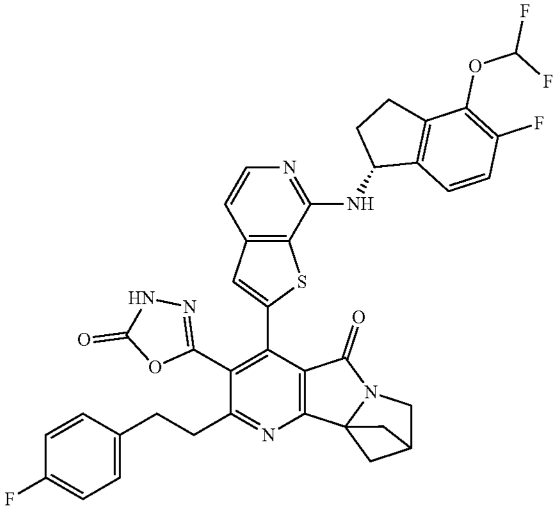 [SMILES: O=C1c2c(nc(CCc3ccc(F)cc3)c(-c3n[nH]c(=O)o3)c2-c2cc3ccnc(N[C@@H]4CCc5c4ccc(F)c5OC(F)F)c3s2)C23CC(CN12)C3] |
| 286 | 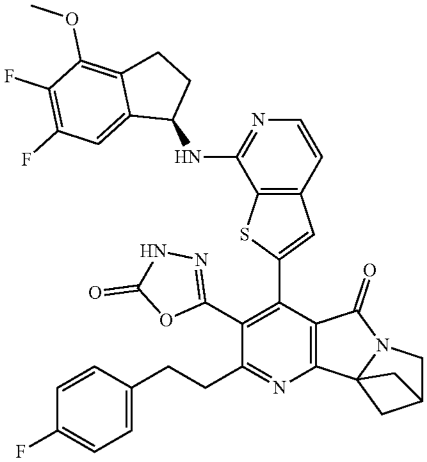 [SMILES: COc1c(F)c(F)cc2c1CC[C@H]2Nc1nccc2cc(-c3c4c(nc(CCc5ccc(F)cc5)c3-c3n[nH]c(=O)o3)C35CC(CN3C4=O)C5)sc12] |

TABLE 1-continued
| Compound No. | Structure |
| --- | --- |
| 287 | 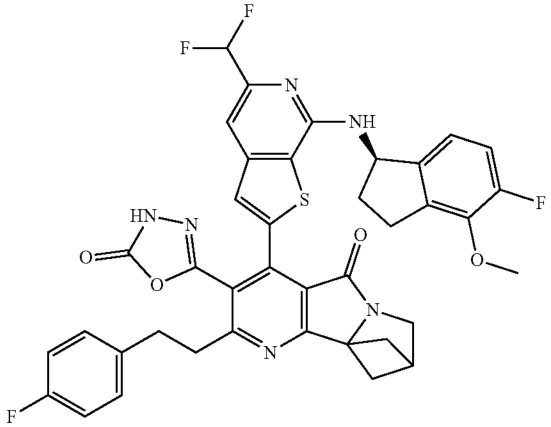 [SMILES: COc1c(F)ccc2c1CC[C@H]2Nc1nc(C(F)F)cc2cc(-c3c4c(nc(CCc5ccc(F)cc5)c3-c3n[nH]c(=O)o3)C35CC(CN3C4=O)C5)sc12] |
| 288 | 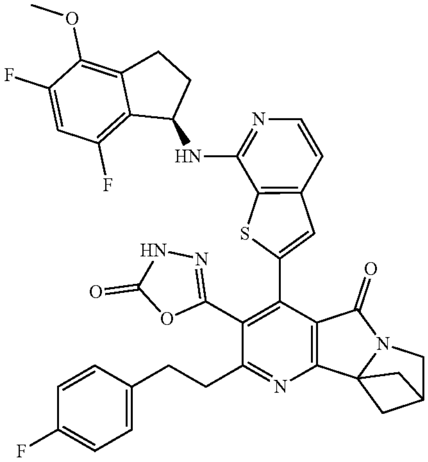 [SMILES: COc1c(F)cc(F)c2c1CC[C@H]2Nc1nccc2cc(-c3c4c(nc(CCc5ccc(F)cc5)c3-c3n[nH]c(=O)o3)C35CC(CN3C4=O)C5)sc12] |
| 289 | 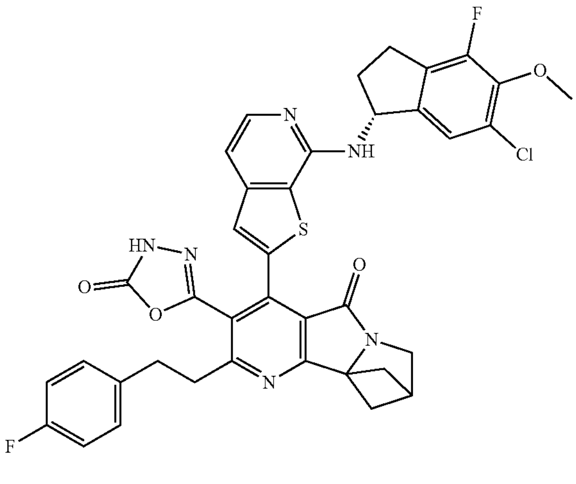 |

TABLE 1-continued
| Compound No. | Structure |
| --- | --- |
| 290 | 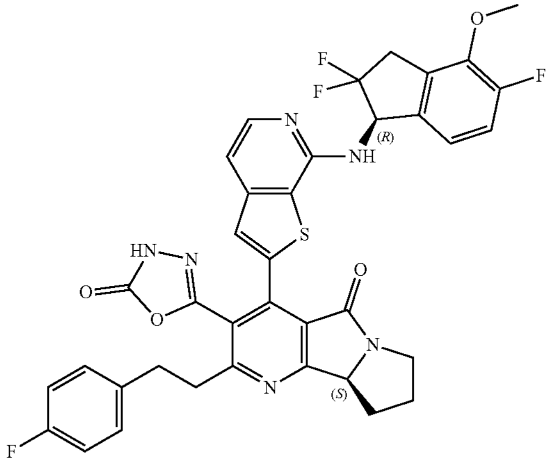 |
| 291 | 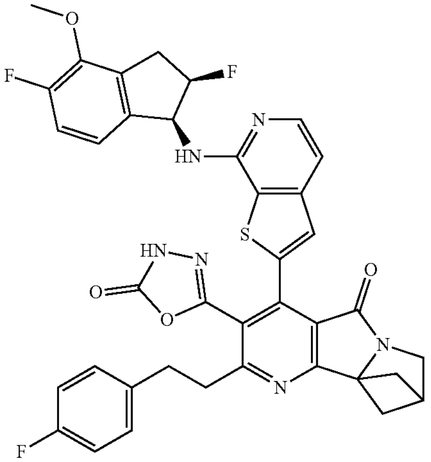 [SMILES: COc1c(F)ccc2c1C[C@@H](F)[C@H]2Nc1nccc2cc(-c3c4c(nc(CCc5ccc(F)cc5)c3-c3n[nH]c(=O)o3)C35CC(CN3C4=O)C5)sc12] |
| 292 | 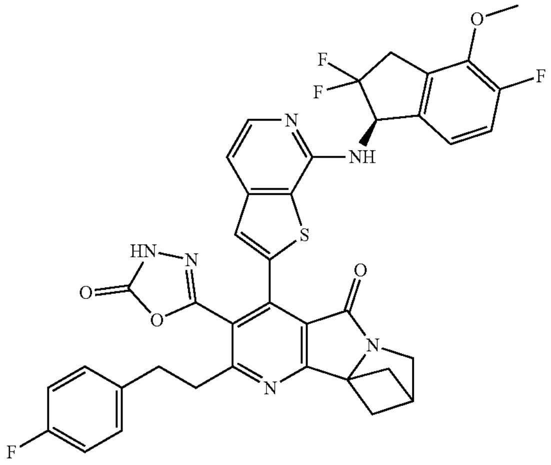 [SMILES: COc1c(F)ccc2c1CC(F)(F)[C@@H]2Nc1nccc2cc(-c3c4c(nc(CCc5ccc(F)cc5)c3-c3n[nH]c(=O)o3)C35CC(CN3C4=O)C5)sc12] |

TABLE 1-continued
| Compound No. | Structure |
|---|---|
| 293 | 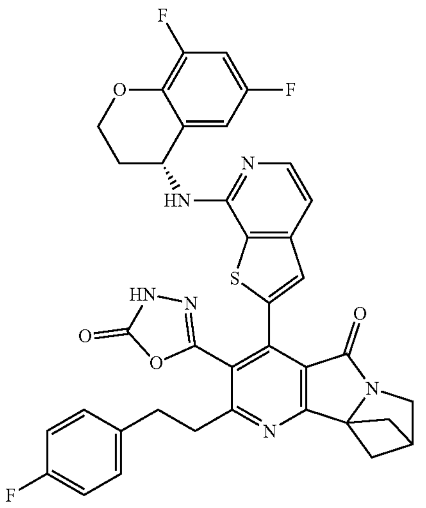 [SMILES: O=C1c2c(nc(CCc3ccc(F)cc3)c(-c3n[nH]c(=O)o3)c2-c2cc3ccnc(N[C@@H]4CCOc5c(F)cc(F)cc54)c3s2)C23CC(CN12)C3] |
| 294 | 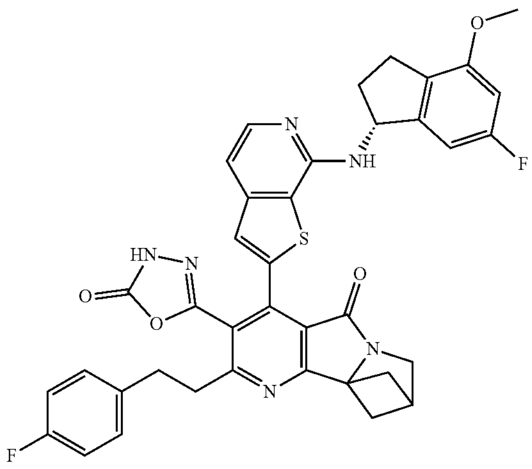 [SMILES: COc1cc(F)cc2c1CC[C@H]2Nc1nccc2cc(-c3c4c(nc(CCc5ccc(F)cc5)c3-c3n[nH]c(=O)o3)C35CC(CN3C4=O)C5)sc12] |
| 295 | 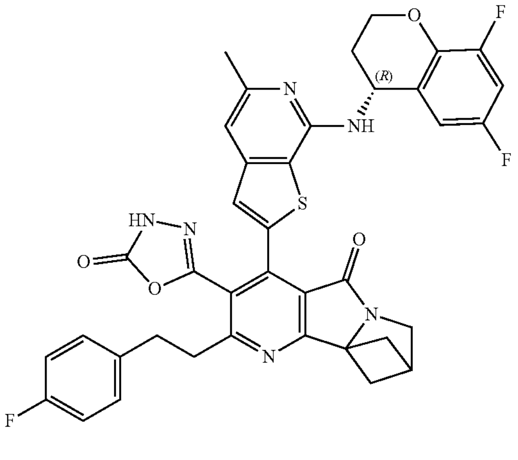 |

TABLE 1-continued
| Compound No. | Structure |
|---|---|
| 296 | 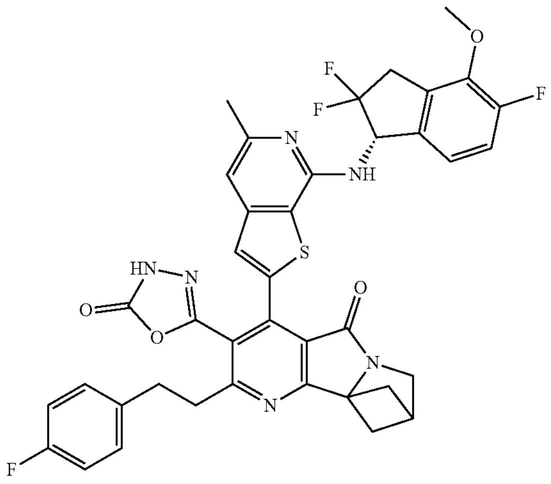 [SMILES: COc1c(F)ccc2c1CC(F)(F)[C@H]2Nc1nc(C)cc2cc(-c3c4c(nc(CCc5ccc(F)cc5)c3-c3n[nH]c(=O)o3)C35CC(CN3C4=O)C5)sc12] |
| 297 | 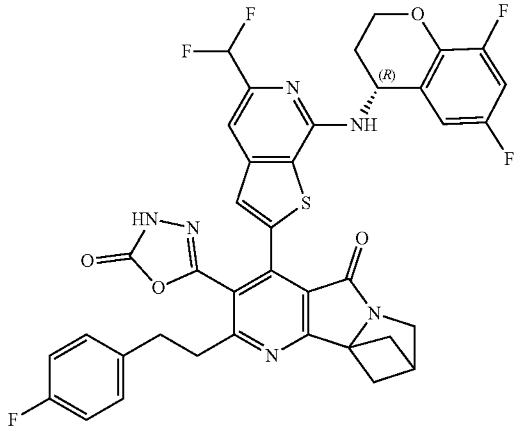 |
| 298 | 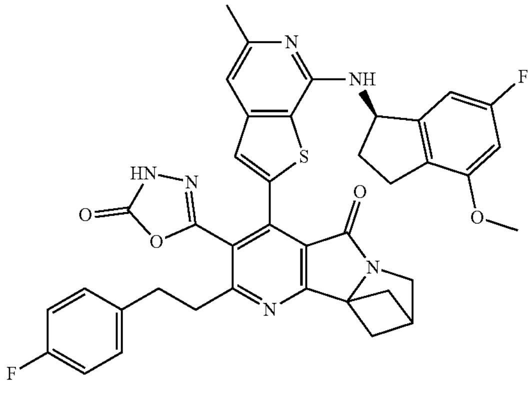 [SMILES: COc1cc(F)cc2c1CC[C@H]2Nc1nc(C)cc2cc(-c3c4c(nc(CCc5ccc(F)cc5)c3-c3n[nH]c(=O)o3)C35CC(CN3C4=O)C5)sc12] |

TABLE 1-continued
| Compound No. | Structure |
|---|---|
| 299 | 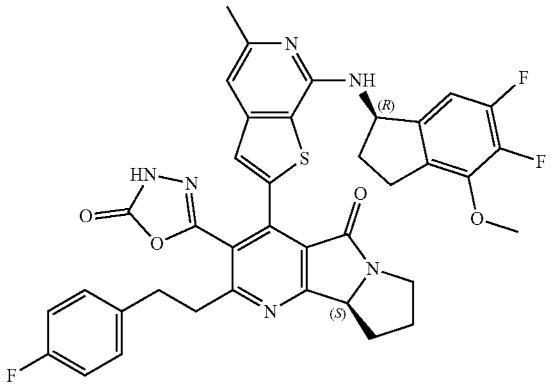 |
| 300 | 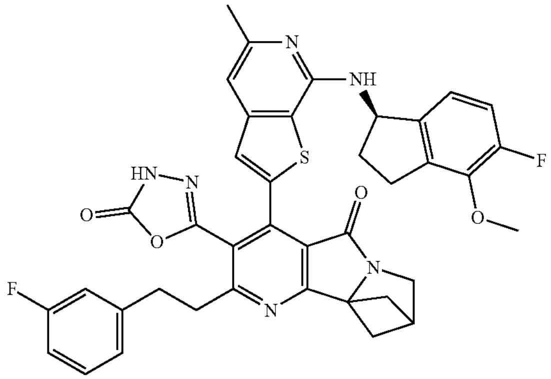 [SMILES: COc1c(F)ccc2c1CC[C@H]2Nc1nc(C)cc2cc(-c3c4c(nc(CCc5cccc(F)c5)c3-c3n[nH]c(=O)o3)C35CC(CN3C4=O)C5)sc12] |
| 301 | 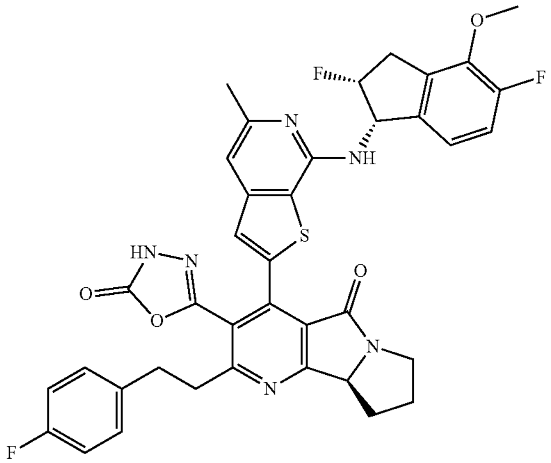 [SMILES: COc1c(F)ccc2c1C[C@@H](F)[C@H]2Nc1nc(C)cc2cc(-c3c4c(nc(CCc5ccc(F)cc5)c3-c3n[nH]c(=O)o3)[C@@H]3CCCN3C4=O)sc12] |

TABLE 1-continued

| Compound No. | Structure |
|---|---|
| 302 | 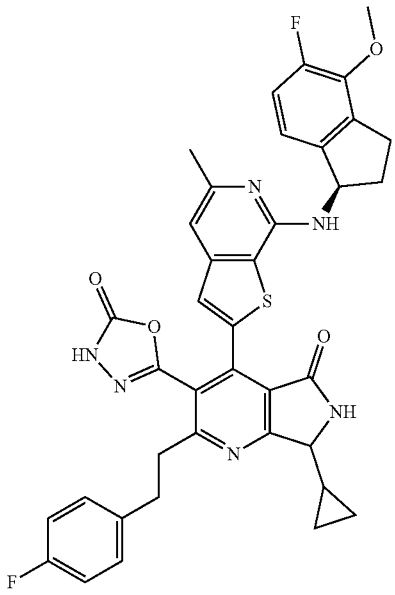 [SMILES: COc1c(F)ccc2c1CC[C@H]2Nc1nc(C)cc2cc(-c3c4c(nc(CCc5ccc(F)cc5)c3-c3n[nH]c(=O)o3)C(C3CC3)NC4=O)sc12] |
| 303 | 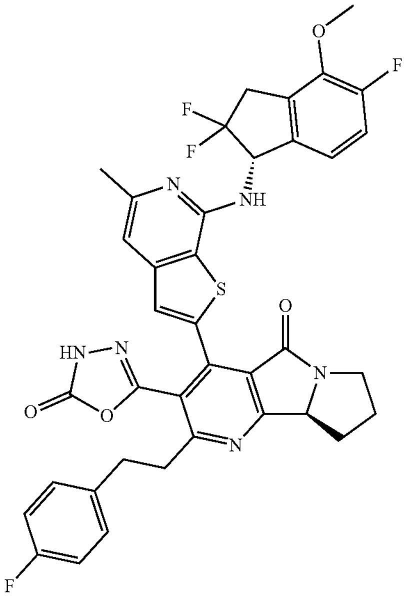 [SMILES: COc1c(F)ccc2c1CC(F)(F)[C@H]2Nc1nc(C)cc2cc(-c3c4c(nc(CCc5ccc(F)cc5)c3-c3n[nH]c(=O)o3)[C@@H]3CCCN3C4=O)sc12] |

The compounds of Formula I provided herein encompass stereochemical forms of the compounds, for example, optical isomers, such as enantiomers, diastereomers, as well as mixtures thereof, e.g., mixtures of enantiomers and/or diastereomers, including racemic mixtures, as well as equal or non-equal mixtures of individual enantiomers and/or diastereomers. All stereochemical forms are contemplated in this disclosure. Unless otherwise indicated, when a disclosed compound is named or depicted by a structure without specifying the stereochemistry and has one or more chiral centers, it is understood to represent all possible stereoisomers of the compound. Representative stereochemical forms are provided throughout the specification, including but not limited to those delineated in Table 2. In some embodiments, provided is compound selected from Table 2, or a pharmaceutically acceptable salt, stereoisomer, mixture of stereoisomers, or solvate thereof:

TABLE 2
| Structure |
|---|
| 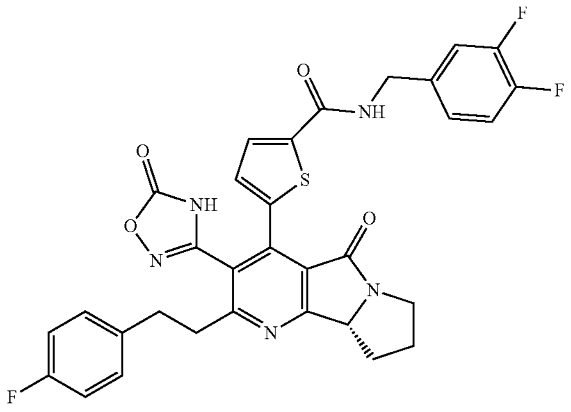 [SMILES: O=C(NCc1ccc(F)c(F)c1)c1ccc(-c2c3c(nc(CCc4ccc(F)cc4)c2-c2noc(=O)[nH]2)[C@H]2CCCN2C3=O)s1] |
| 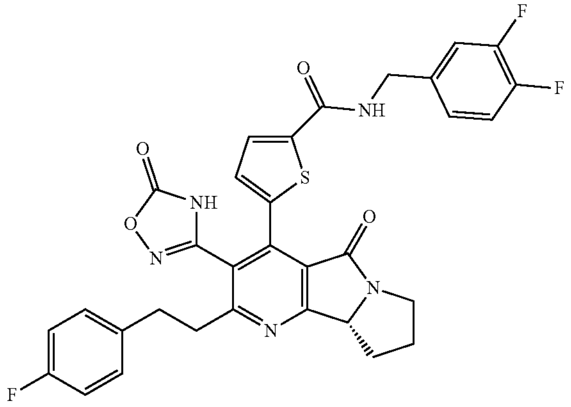 [SMILES: O=C(NCc1ccc(F)c(F)c1)c1ccc(-c2c3c(nc(CCc4ccc(F)cc4)c2-c2noc(=O)[nH]2)[C@H]2CCCN2C3=O)s1] |
| 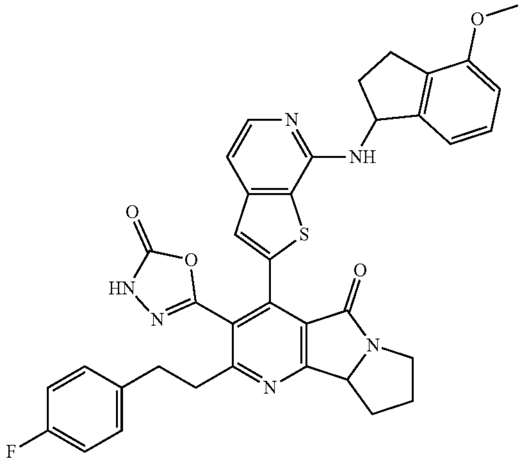 [SMILES: COc1cccc2c1CCC2Nc1nccc2cc(-c3c4c(nc(CCc5ccc(F)cc5)c3-c3n[nH]c(=O)o3)C3CCCN3C4=O)sc12] |
TABLE 2-continued
| Structure |
|---|
| 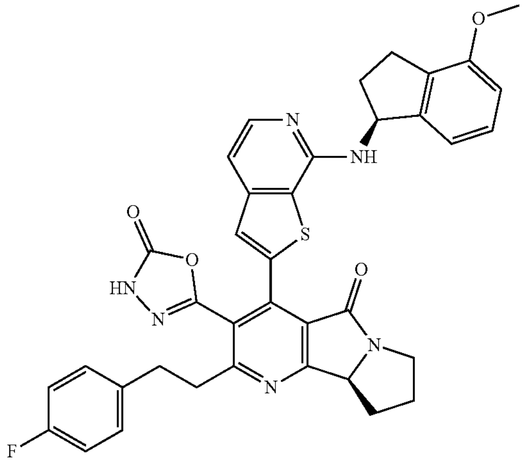 [SMILES: COc1cccc2c1CC[C@@H]2Nc1nccc2cc(-c3c4c(nc(CCc5ccc(F)cc5)c3-c3n[nH]c(=O)o3)[C@@H]3CCCN3C4=O)sc12] |
| 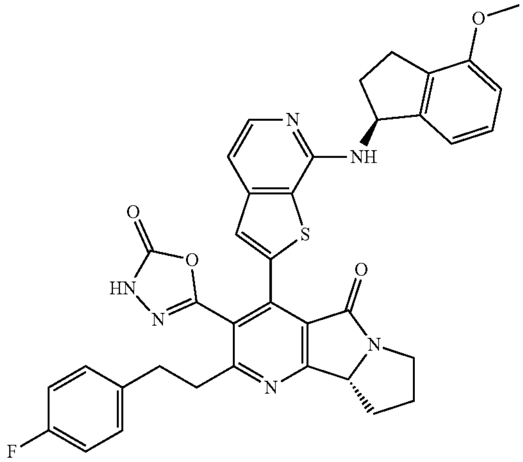 [SMILES: COc1cccc2c1CC[C@@H]2Nc1nccc2cc(-c3c4c(nc(CCc5ccc(F)cc5)c3-c3n[nH]c(=O)o3)[C@H]3CCCN3C4=O)sc12] |
| 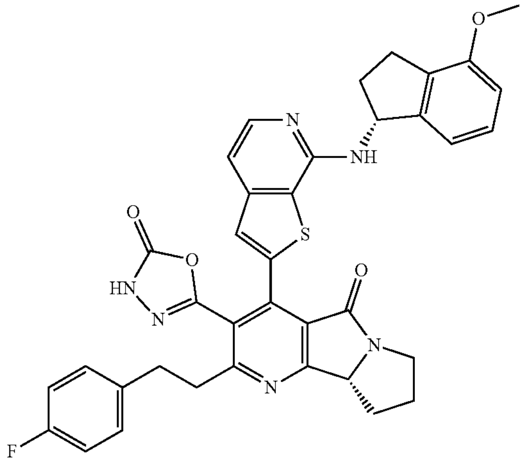 [SMILES: COc1cccc2c1CC[C@H]2Nc1nccc2cc(-c3c4c(nc(CCc5ccc(F)cc5)c3-c3n[nH]c(=O)o3)[C@H]3CCCN3C4=O)sc12] |

TABLE 2-continued
| Structure |
|---|
| 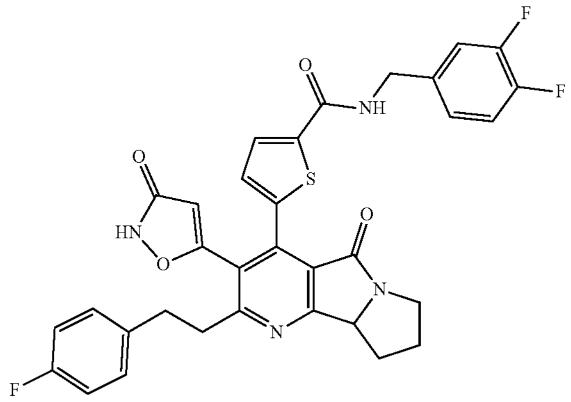 [SMILES: O=C(NCc1ccc(F)c(F)c1)c1ccc(-c2c3c(nc(CCc4ccc(F)cc4)c2-c2cc(=O)[nH]o2)C2CCCN2C3=O)s1] |
| 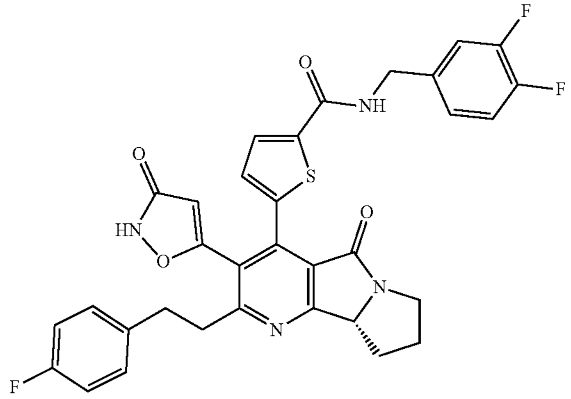 [SMILES: O=C(NCc1ccc(F)c(F)c1)c1ccc(-c2c3c(nc(CCc4ccc(F)cc4)c2-c2cc(=O)[nH]o2)[C@H]2CCCN2C3=O)s1] |
| 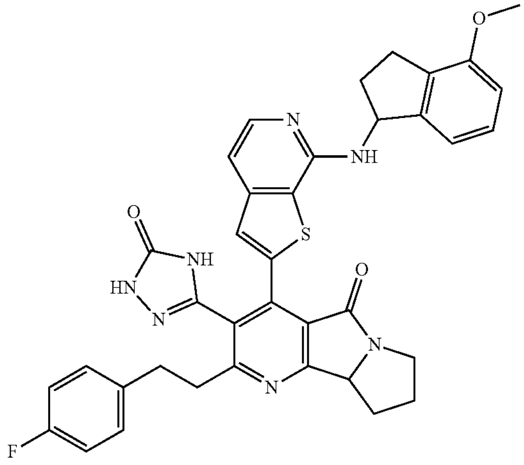 [SMILES: COc1cccc2c1CCC2Nc1nccc2cc(-c3c4c(nc(CCc5ccc(F)cc5)c3-c3n[nH]c(=O)[nH]3)C3CCCN3C4=O)sc12] |
TABLE 2-continued
| Structure |
|---|
| 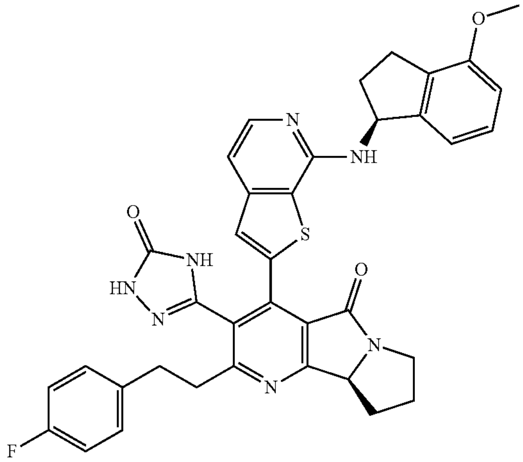 [SMILES: COc1cccc2c1CC[C@@H]2Nc1nccc2cc(-c3c4c(nc(CCc5ccc(F)cc5)c3-c3n[nH]c(=O)[nH]3)[C@@H]3CCCN3C4=O)sc12] |
| 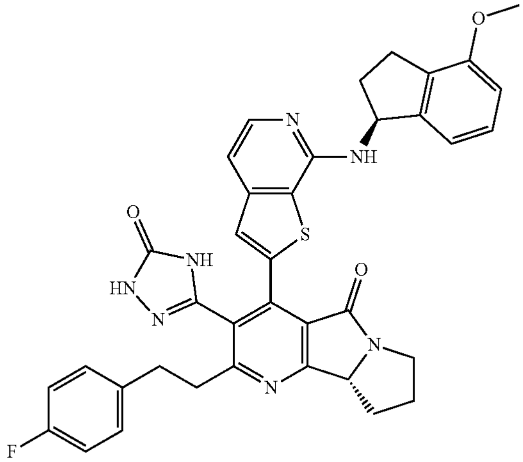 [SMILES: COc1cccc2c1CC[C@@H]2Nc1nccc2cc(-c3c4c(nc(CCc5ccc(F)cc5)c3-c3n[nH]c(=O)[nH]3)[C@H]3CCCN3C4=O)sc12] |
| 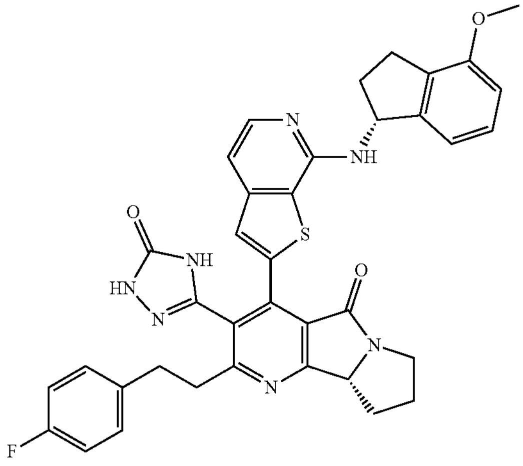 [SMILES: COc1cccc2c1CC[C@H]2Nc1nccc2cc(-c3c4c(nc(CCc5ccc(F)cc5)c3-c3n[nH]c(=O)[nH]3)[C@H]3CCCN3C4=O)sc12] |

TABLE 2-continued
| Structure |
| --- |
| 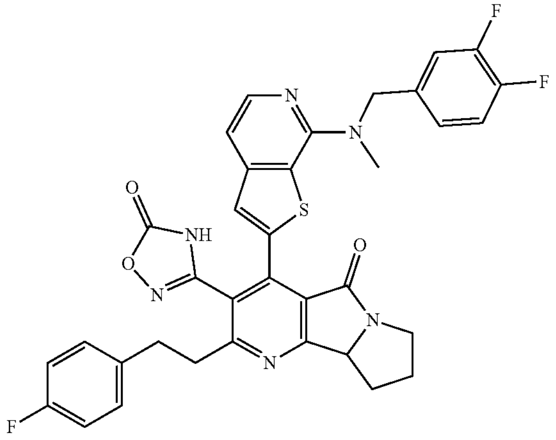 [SMILES: CN(Cc1ccc(F)c(F)c1)c1nccc2cc(-c3c4c(nc(CCc5ccc(F)cc5)c3-c3noc(=O)[nH]3)C3CCCN3C4=O)sc12] |
| 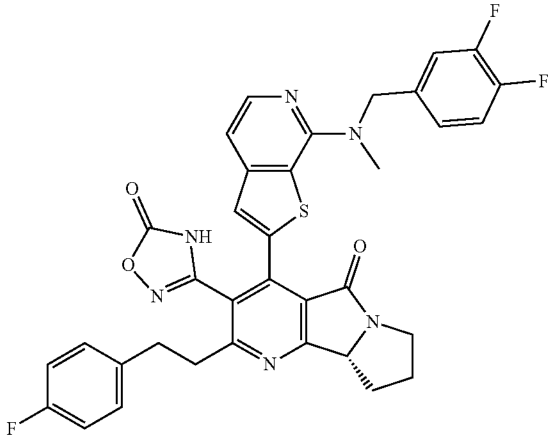 [SMILES: CN(Cc1ccc(F)c(F)c1)c1nccc2cc(-c3c4c(nc(CCc5ccc(F)cc5)c3-c3noc(=O)[nH]3)[C@H]3CCCN3C4=O)sc12] |
| 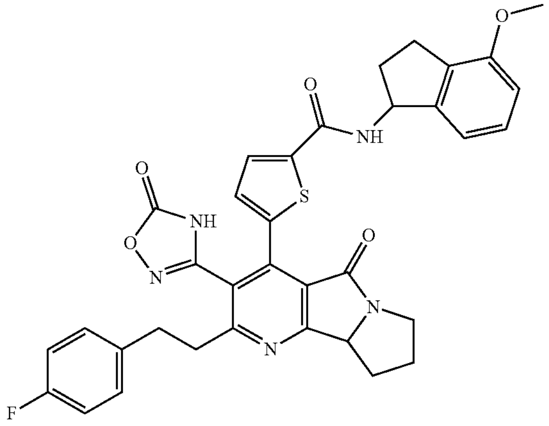 [SMILES: COc1cccc2c1CCC2NC(=O)c1ccc(-c2c3c(nc(CCc4ccc(F)cc4)c2-c2noc(=O)[nH]2)C2CCCN2C3=O)s1] |
TABLE 2-continued
| Structure |
| --- |
| 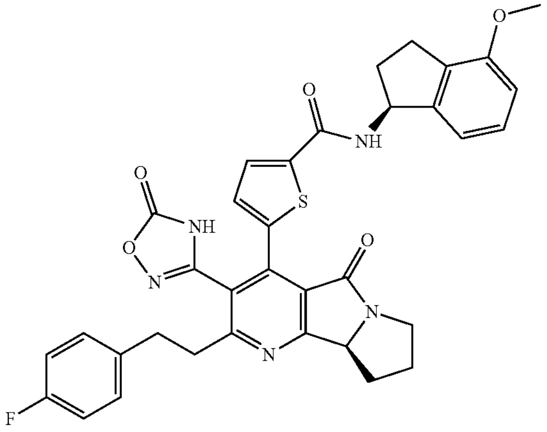 [SMILES: COc1cccc2c1CC[C@@H]2NC(=O)c1ccc(-c2c3c(nc(CCc4ccc(F)cc4)c2-c2noc(=O)[nH]2)[C@@H]2CCCN2C3=O)s1] |
| 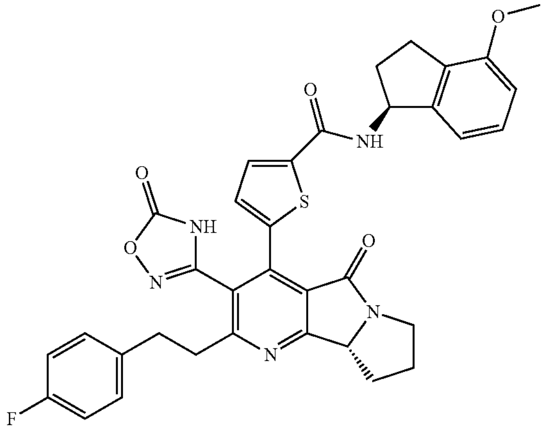 [SMILES: COc1cccc2c1CC[C@@H]2NC(=O)c1ccc(-c2c3c(nc(CCc4ccc(F)cc4)c2-c2noc(=O)[nH]2)[C@H]2CCCN2C3=O)s1] |
| 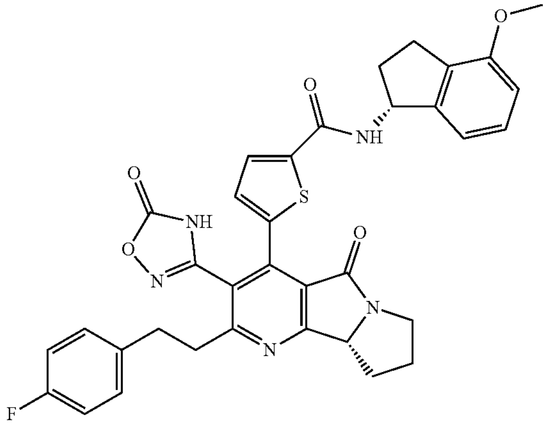 [SMILES: COc1cccc2c1CC[C@H]2NC(=O)c1ccc(-c2c3c(nc(CCc4ccc(F)cc4)c2-c2noc(=O)[nH]2)[C@H]2CCCN2C3=O)s1] |

TABLE 2-continued
| Structure |
| --- |
| 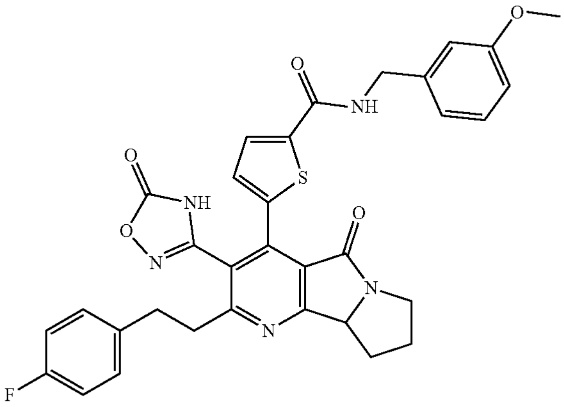 [SMILES: COc1cccc(CNC(=O)c2ccc(-c3c4c(nc(CCc5ccc(F)cc5)c3-c3noc(=O)[nH]3)C3CCCN3C4=O)s2)c1] |
| 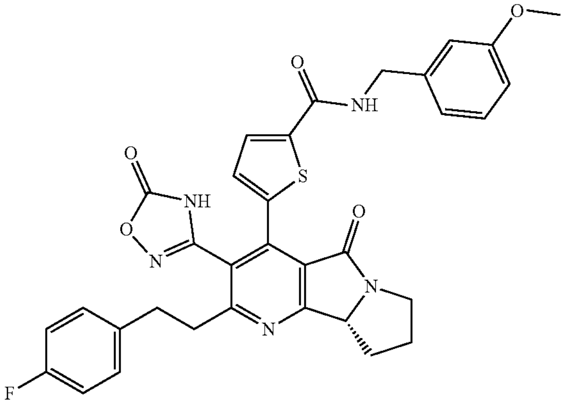 [SMILES: COc1cccc(CNC(=O)c2ccc(-c3c4c(nc(CCc5ccc(F)cc5)c3-c3noc(=O)[nH]3)[C@H]3CCCN3C4=O)s2)c1] |
| 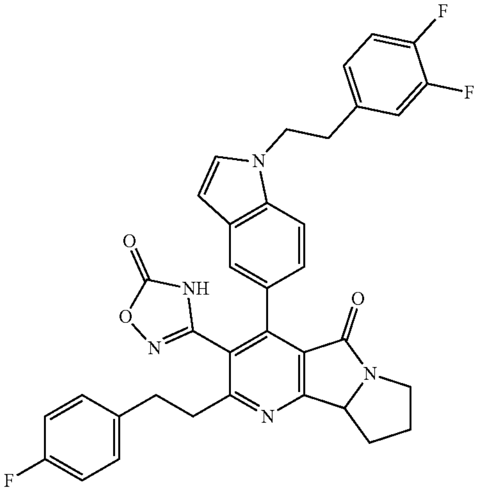 [SMILES: O=C1c2c(nc(CCc3ccc(F)cc3)c(-c3noc(=O)[nH]3)c2-c2ccc3c(ccn3CCc3ccc(F)c(F)c3)c2)C2CCCN12] |
TABLE 2-continued
| Structure |
| --- |
| 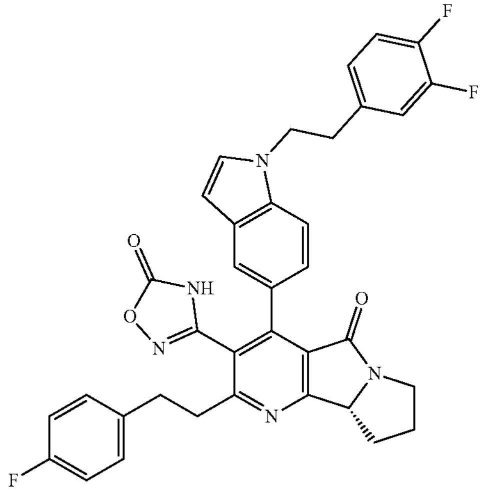 [SMILES: O=C1c2c(nc(CCc3ccc(F)cc3)c(-c3noc(=O)[nH]3)c2-c2ccc3c(ccn3CCc3ccc(F)c(F)c3)c2)[C@H]2CCCN12] |
| 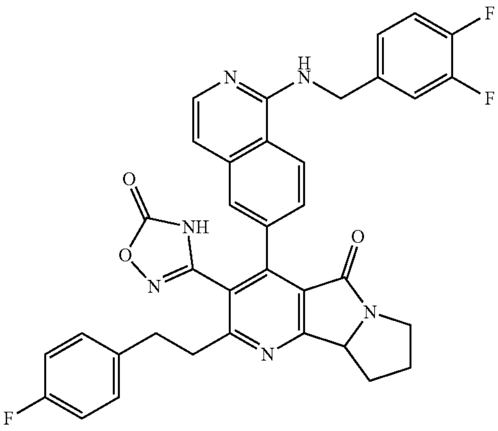 [SMILES: O=C1c2c(nc(CCc3ccc(F)cc3)c(-c3noc(=O)[nH]3)c2-c2ccc3c(NCc4ccc(F)c(F)c4)nccc3c2)C2CCCN12] |
| 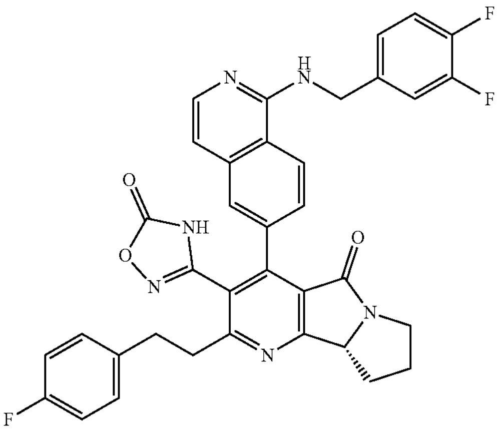 [SMILES: O=C1c2c(nc(CCc3ccc(F)cc3)c(-c3noc(=O)[nH]3)c2-c2ccc3c(NCc4ccc(F)c(F)c4)nccc3c2)[C@H]2CCCN12] |

TABLE 2-continued
| Structure |
| --- |
| 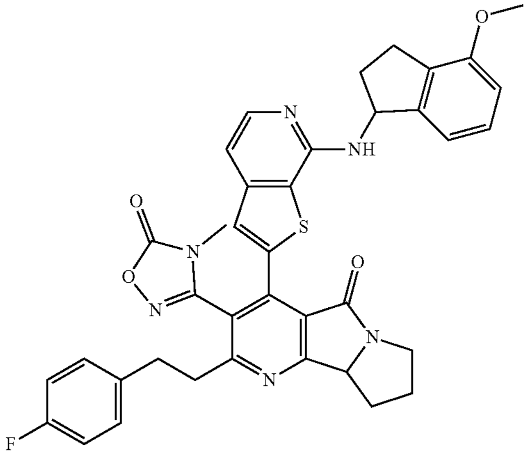 [SMILES: COc1cccc2c1CCC2Nc1nccc2cc(-c3c4c(nc(CCc5ccc(F)cc5)c3-c3noc(=O)n3C)C3CCCN3C4=O)sc12] |
| 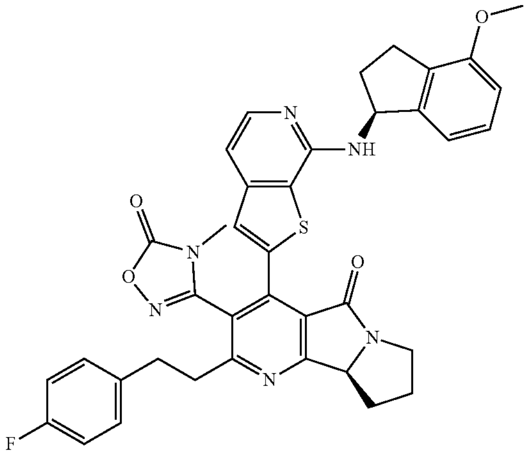 [SMILES: COc1cccc2c1CC[C@@H]2Nc1nccc2cc(-c3c4c(nc(CCc5ccc(F)cc5)c3-c3noc(=O)n3C)[C@@H]3CCCN3C4=O)sc12] |
| 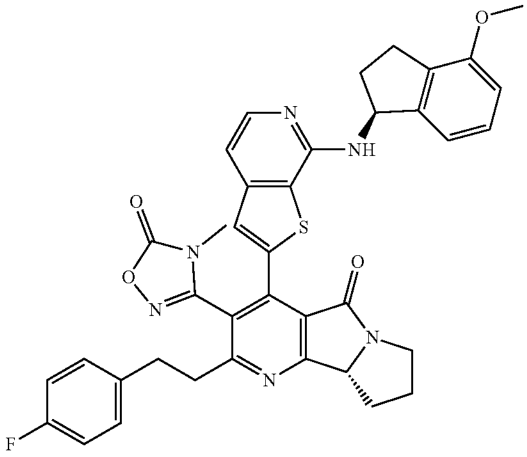 [SMILES: COc1cccc2c1CC[C@@H]2Nc1nccc2cc(-c3c4c(nc(CCc5ccc(F)cc5)c3-c3noc(=O)n3C)[C@H]3CCCN3C4=O)sc12] |
TABLE 2-continued
| Structure |
| --- |
| 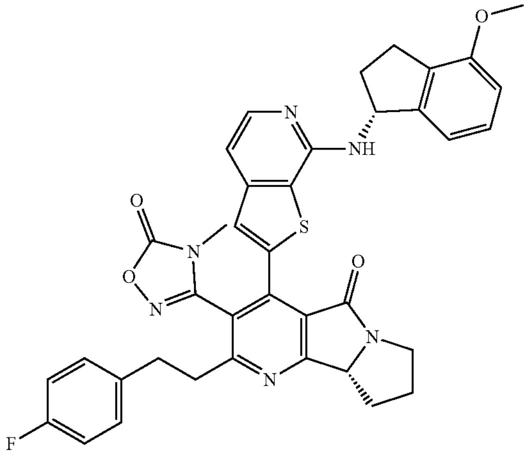 [SMILES: COc1cccc2c1CC[C@H]2Nc1nccc2cc(-c3c4c(nc(CCc5ccc(F)cc5)c3-c3noc(=O)n3C)[C@H]3CCCN3C4=O)sc12] |
| 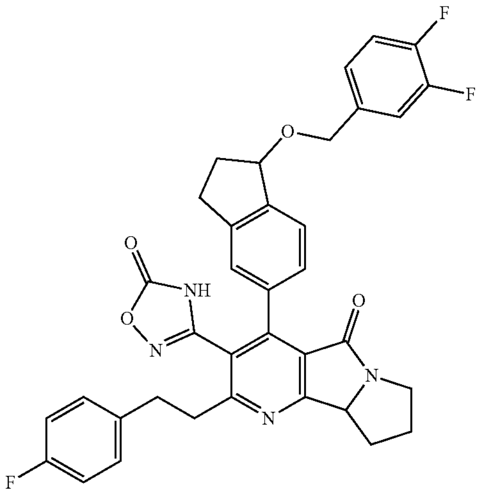 [SMILES: O=C1c2c(nc(CCc3ccc(F)cc3)c(-c3noc(=O)[nH]3)c2-c2ccc3c(c2)CCC3OCc2ccc(F)c(F)c2)C2CCCN12] |
| 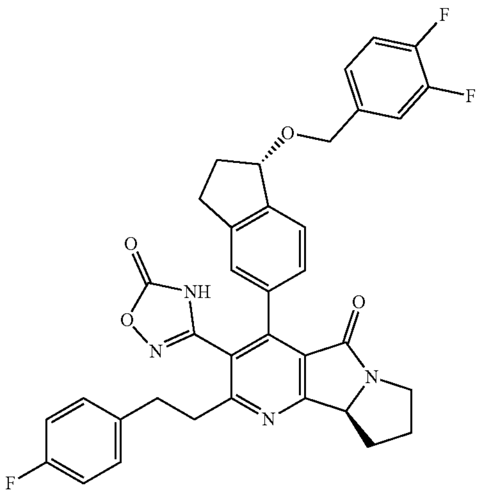 [SMILES: O=C1c2c(nc(CCc3ccc(F)cc3)c(-c3noc(=O)[nH]3)c2-c2ccc3c(c2)CC[C@@H]3OCc2ccc(F)c(F)c2)[C@@H]2CCCN12] |

TABLE 2-continued
| Structure |
| --- |
| 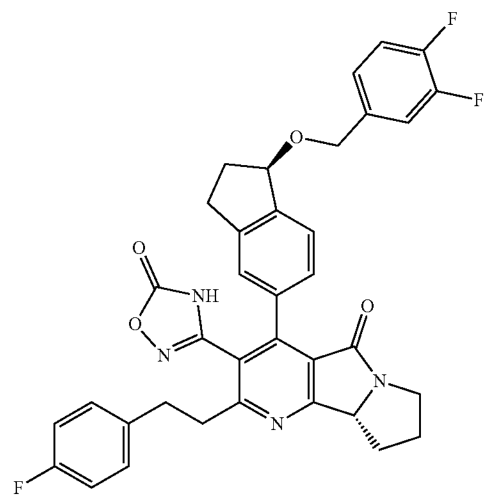 [SMILES: O=C1c2c(nc(CCc3ccc(F)cc3)c(-c3noc(=O)[nH]3)c2-c2ccc3c(c2)CC[C@H]3OCc2ccc(F)c(F)c2)[C@H]2CCCN12] |
| 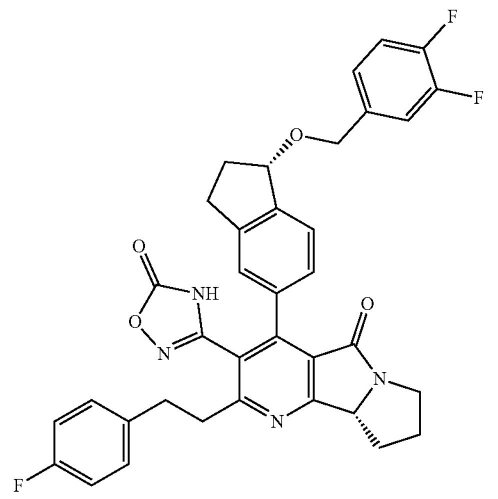 [SMILES: O=C1c2c(nc(CCc3ccc(F)cc3)c(-c3noc(=O)[nH]3)c2-c2ccc3c(c2)CC[C@@H]3OCc2ccc(F)c(F)c2)[C@H]2CCCN12] |
| 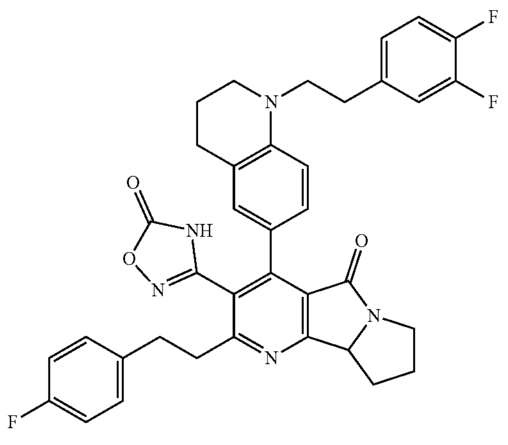 [SMILES: O=C1c2c(nc(CCc3ccc(F)cc3)c(-c3noc(=O)[nH]3)c2-c2ccc3c(c2)CCCN3CCc2ccc(F)c(F)c2)C2CCCN12] |
TABLE 2-continued
| Structure |
| --- |
| 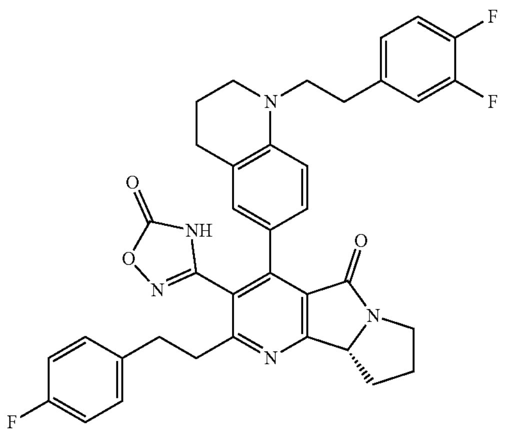 [SMILES: O=C1c2c(nc(CCc3ccc(F)cc3)c(-c3noc(=O)[nH]3)c2-c2ccc3c(c2)CCCN3CCc2ccc(F)c(F)c2)[C@H]2CCCN12] |
| 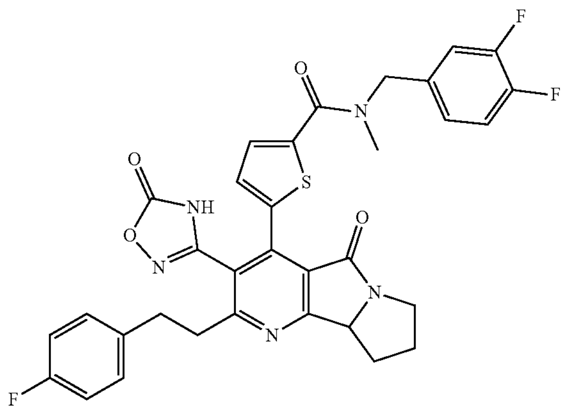 [SMILES: CN(Cc1ccc(F)c(F)c1)C(=O)c1ccc(-c2c3c(nc(CCc4ccc(F)cc4)c2-c2noc(=O)[nH]2)C2CCCN2C3=O)s1] |
| 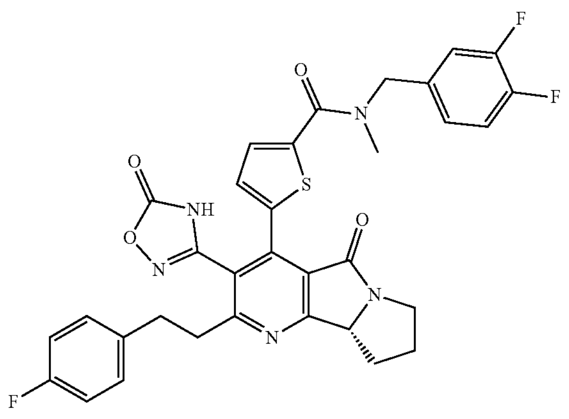 [SMILES: CN(Cc1ccc(F)c(F)c1)C(=O)c1ccc(-c2c3c(nc(CCc4ccc(F)cc4)c2-c2noc(=O)[nH]2)[C@H]2CCCN2C3=O)s1] |

TABLE 2-continued
| Structure |
| --- |
| 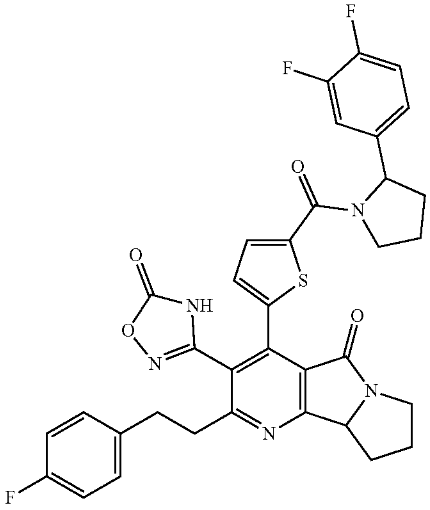 [SMILES: O=C(c1ccc(-c2c3c(nc(CCc4ccc(F)cc4)c2-c2noc(=O)[nH]2)C2CCCN2C3=O)s1)N1CCCC1c1ccc(F)c(F)c1] |
| 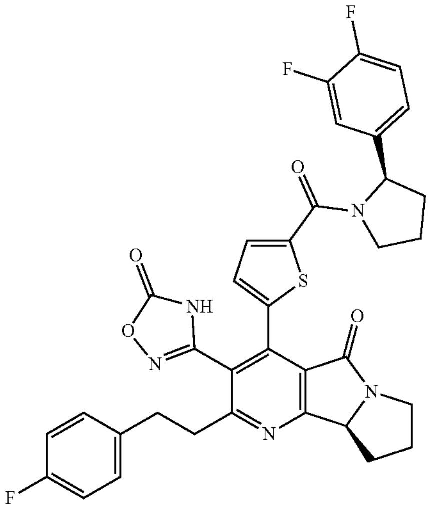 [SMILES: O=C(c1ccc(-c2c3c(nc(CCc4ccc(F)cc4)c2-c2noc(=O)[nH]2)[C@@H]2CCCN2C3=O)s1)N1CCC[C@@H]1c1ccc(F)c(F)c1] |
| 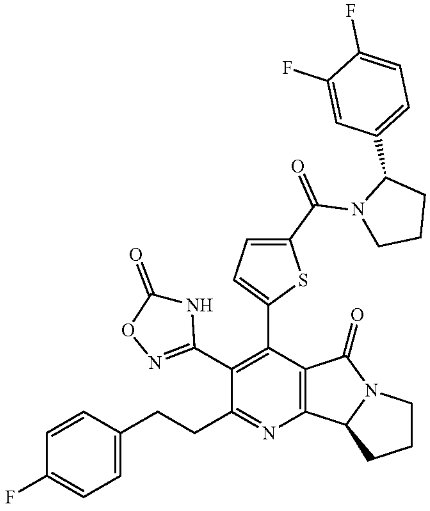 [SMILES: O=C(c1ccc(-c2c3c(nc(CCc4ccc(F)cc4)c2-c2noc(=O)[nH]2)[C@@H]2CCCN2C3=O)s1)N1CCC[C@H]1c1ccc(F)c(F)c1] |
TABLE 2-continued
| Structure |
| --- |
| 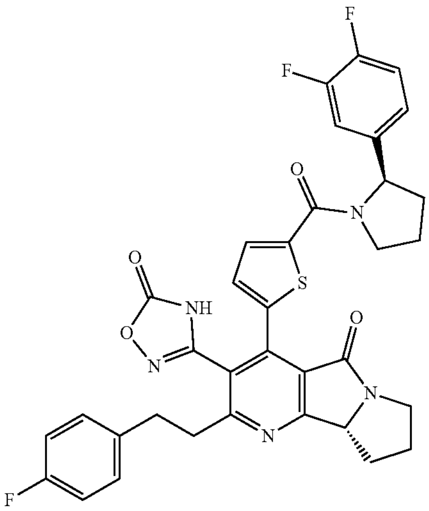 [SMILES: O=C(c1ccc(-c2c3c(nc(CCc4ccc(F)cc4)c2-c2noc(=O)[nH]2)[C@H]2CCCN2C3=O)s1)N1CCC[C@@H]1c1ccc(F)c(F)c1] |
| 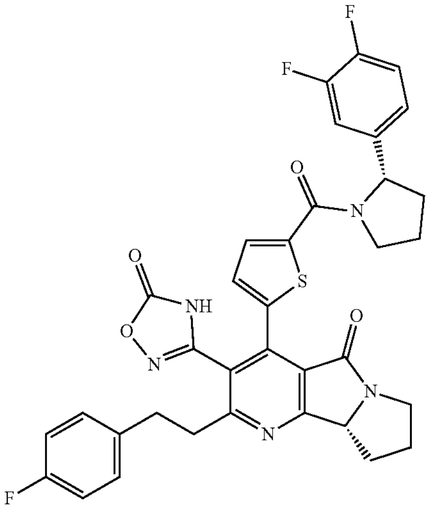 [SMILES: O=C1c2c(nc(CCc3ccc(F)cc3)c(-c3noc(=O)[nH]3)c2-c2ccc(C(=O)N3CCC[C@H]3c3ccc(F)c(F)c3)s2)[C@H]2CCCN12] |
| 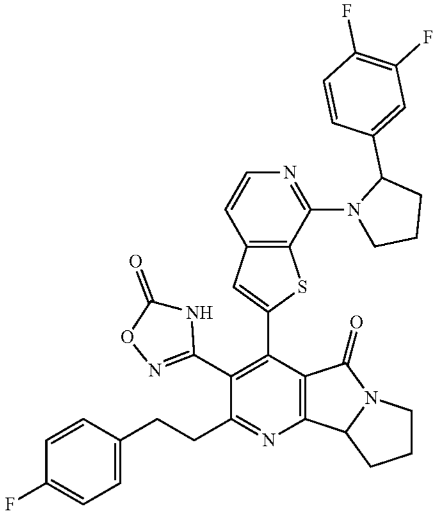 [SMILES: O=C1c2c(nc(CCc3ccc(F)cc3)c(-c3noc(=O)[nH]3)c2-c2cc3ccnc(N4CCCC4c4ccc(F)c(F)c4)c3s2)C2CCCN12] |

TABLE 2-continued
| Structure |
| --- |
| 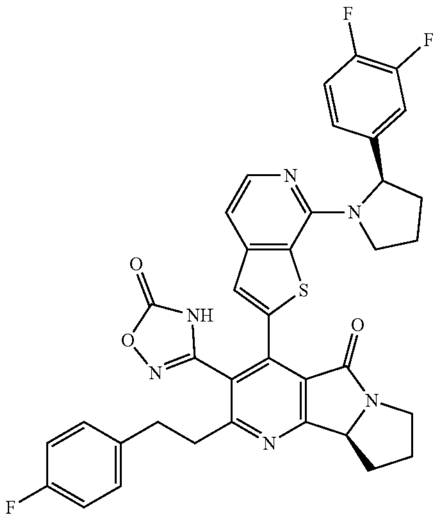 [SMILES: O=C1c2c(nc(CCc3ccc(F)cc3)c(-c3noc(=O)[nH]3)c2-c2cc3ccnc(N4CCC[C@@H]4c4ccc(F)c(F)c4)c3s2)[C@@H]2CCCN12] |
| 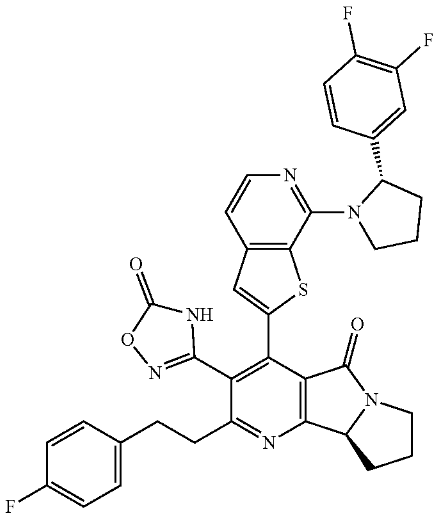 [SMILES: O=C1c2c(nc(CCc3ccc(F)cc3)c(-c3noc(=O)[nH]3)c2-c2cc3ccnc(N4CCC[C@H]4c4ccc(F)c(F)c4)c3s2)[C@@H]2CCCN12] |
| 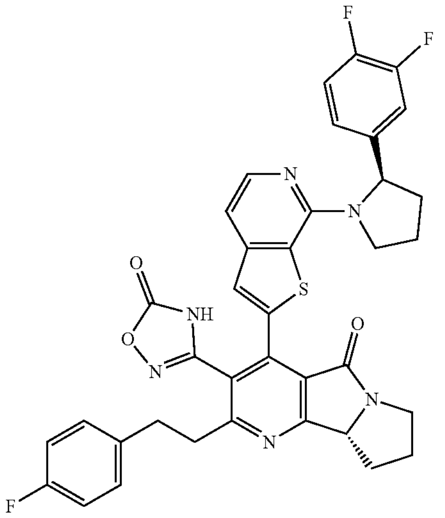 [SMILES: O=C1c2c(nc(CCc3ccc(F)cc3)c(-c3noc(=O)[nH]3)c2-c2cc3ccnc(N4CCC[C@@H]4c4ccc(F)c(F)c4)c3s2)[C@H]2CCCN12] |
TABLE 2-continued
| Structure |
| --- |
| 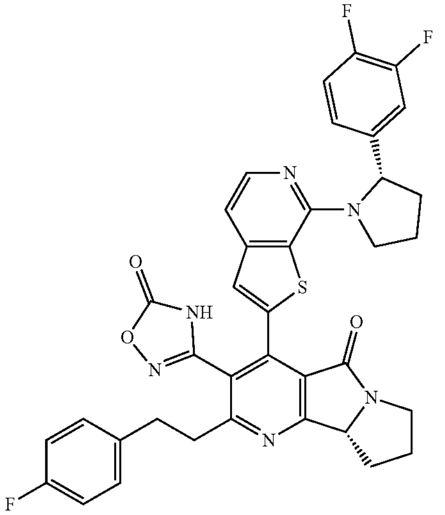 [SMILES: O=C1c2c(nc(CCc3ccc(F)cc3)c(-c3noc(=O)[nH]3)c2-c2cc3ccnc(N4CCC[C@H]4c4ccc(F)c(F)c4)c3s2)[C@H]2CCCN12] |
| 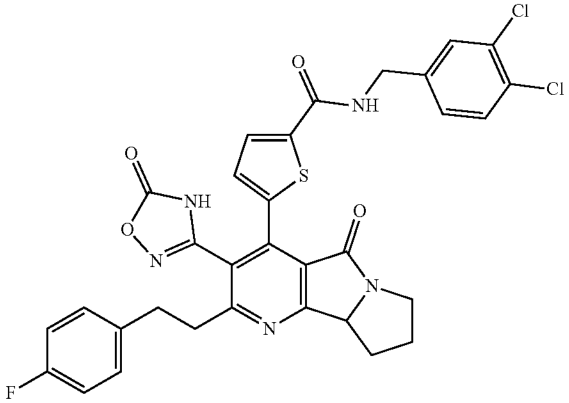 [SMILES: O=C(NCc1ccc(Cl)c(Cl)c1)c1ccc(-c2c3c(nc(CCc4ccc(F)cc4)c2-c2noc(=O)[nH]2)C2CCCN2C3=O)s1] |
| 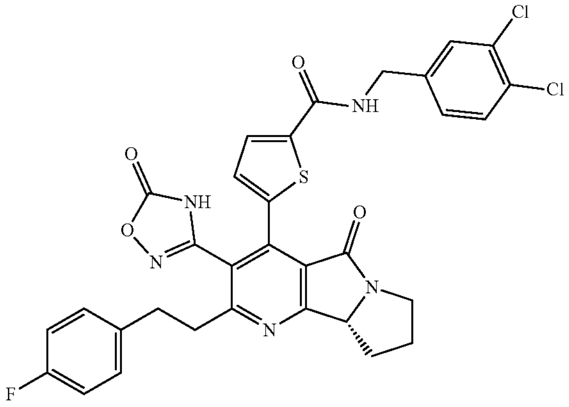

TABLE 2-continued
| Structure |
| --- |
| 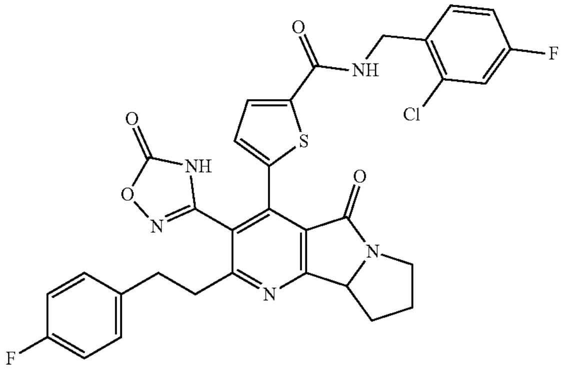 [SMILES: O=C(NCc1ccc(F)cc1Cl)c1ccc(-c2c3c(nc(CCc4ccc(F)cc4)c2-c2noc(=O)[nH]2)C2CCCN2C3=O)s1] |
| 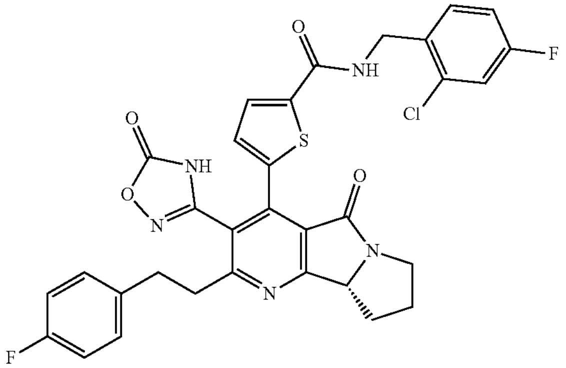 [SMILES: O=C(NCc1ccc(F)cc1Cl)c1ccc(-c2c3c(nc(CCc4ccc(F)cc4)c2-c2noc(=O)[nH]2)[C@H]2CCCN2C3=O)s1] |
| 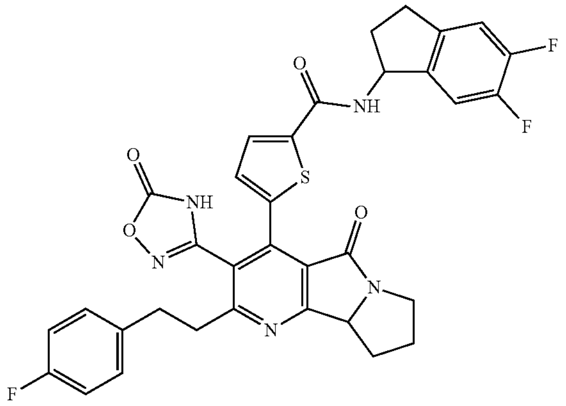 [SMILES: O=C(NC1CCc2cc(F)c(F)cc21)c1ccc(-c2c3c(nc(CCc4ccc(F)cc4)c2-c2noc(=O)[nH]2)C2CCCN2C3=O)s1] |
| 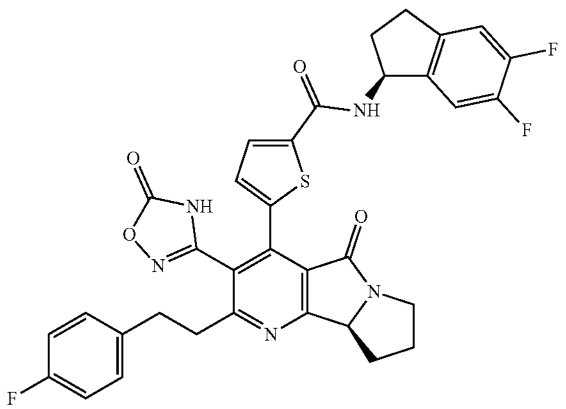 [SMILES: O=C(N[C@H]1CCc2cc(F)c(F)cc21)c1ccc(-c2c3c(nc(CCc4ccc(F)cc4)c2-c2noc(=O)[nH]2)[C@@H]2CCCN2C3=O)s1] |
TABLE 2-continued
| Structure |
| --- |
| 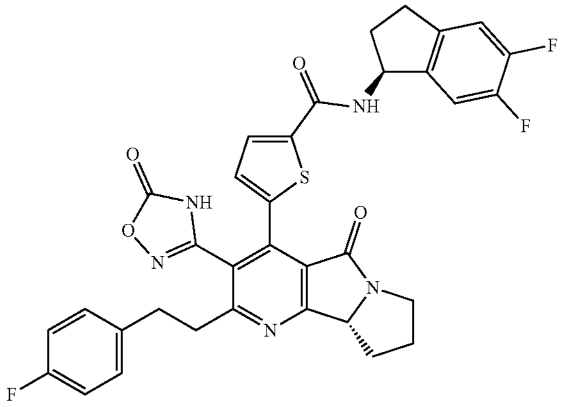 [SMILES: O=C(N[C@H]1CCc2cc(F)c(F)cc21)c1ccc(-c2c3c(nc(CCc4ccc(F)cc4)c2-c2noc(=O)[nH]2)[C@H]2CCCN2C3=O)s1] |
| 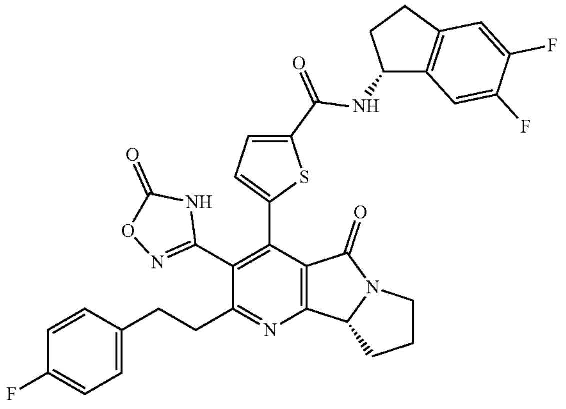 [SMILES: O=C(N[C@@H]1CCc2cc(F)c(F)cc21)c1ccc(-c2c3c(nc(CCc4ccc(F)cc4)c2-c2noc(=O)[nH]2)[C@H]2CCCN2C3=O)s1] |
| 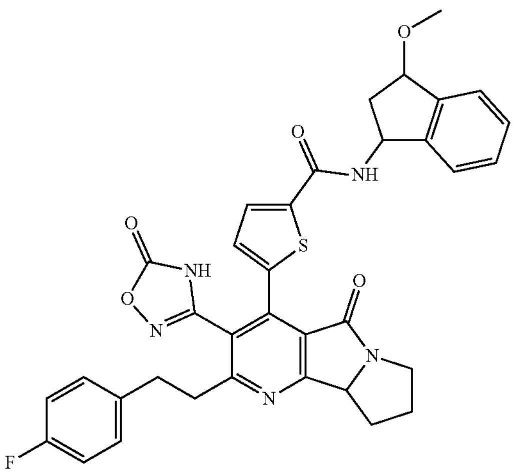 [SMILES: COC1CC(NC(=O)c2ccc(-c3c4c(nc(CCc5ccc(F)cc5)c3-c3noc(=O)[nH]3)C3CCCN3C4=O)s2)c2ccccc21] |

TABLE 2-continued
| Structure |
| --- |
| 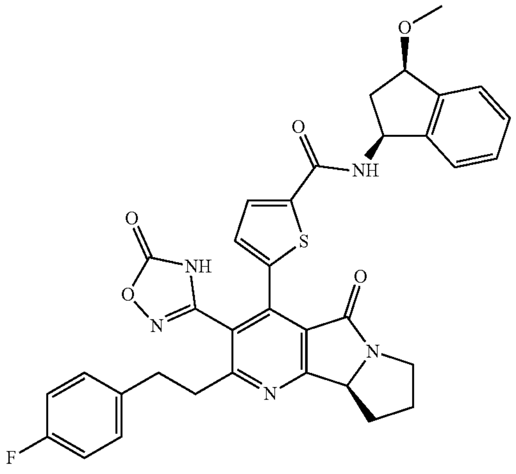 [SMILES: CO[C@@H]1C[C@H](NC(=O)c2ccc(-c3c4c(nc(CCc5ccc(F)cc5)c3-c3noc(=O)[nH]3)[C@@H]3CCCN3C4=O)s2)c2ccccc21] |
| 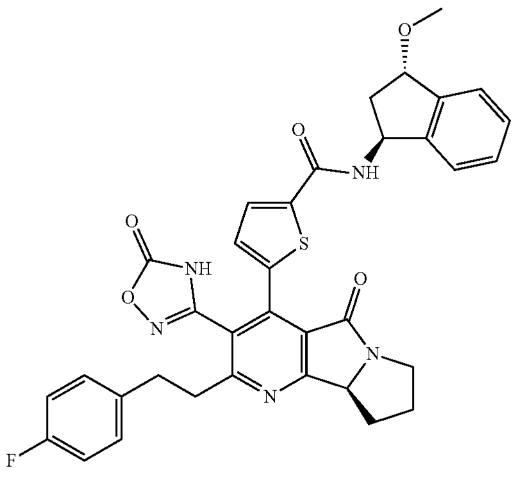 [SMILES: CO[C@H]1C[C@H](NC(=O)c2ccc(-c3c4c(nc(CCc5ccc(F)cc5)c3-c3noc(=O)[nH]3)[C@@H]3CCCN3C4=O)s2)c2ccccc21] |
| 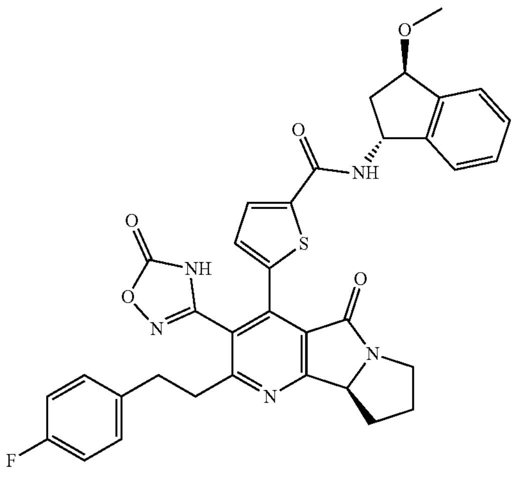 [SMILES: CO[C@@H]1C[C@@H](NC(=O)c2ccc(-c3c4c(nc(CCc5ccc(F)cc5)c3-c3noc(=O)[nH]3)[C@@H]3CCCN3C4=O)s2)c2ccccc21] |
TABLE 2-continued
| Structure |
| --- |
| 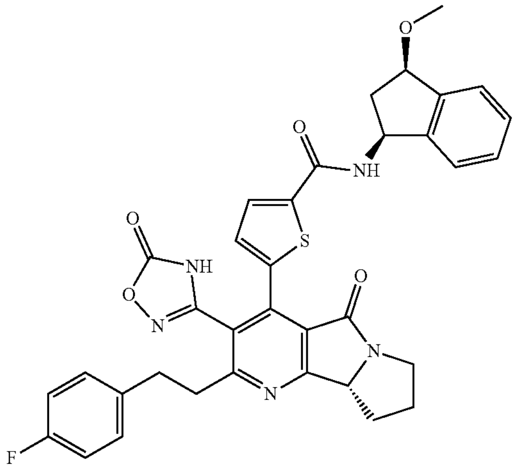 [SMILES: CO[C@@H]1C[C@H](NC(=O)c2ccc(-c3c4c(nc(CCc5ccc(F)cc5)c3-c3noc(=O)[nH]3)[C@H]3CCCN3C4=O)s2)c2ccccc21] |
| 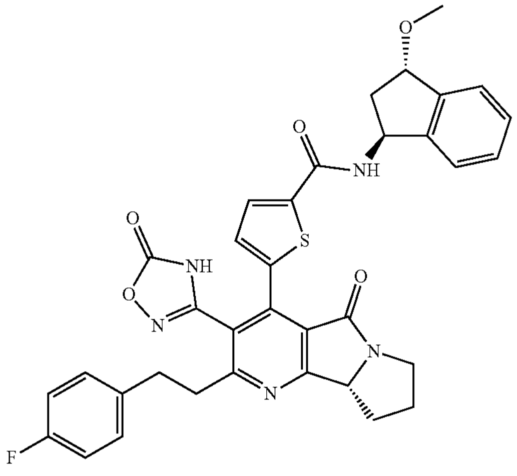 [SMILES: CO[C@H]1C[C@H](NC(=O)c2ccc(-c3c4c(nc(CCc5ccc(F)cc5)c3-c3noc(=O)[nH]3)[C@H]3CCCN3C4=O)s2)c2ccccc21] |
| 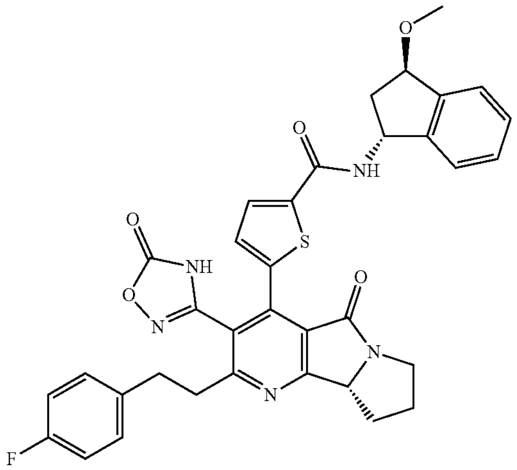 [SMILES: CO[C@@H]1C[C@@H](NC(=O)c2ccc(-c3c4c(nc(CCc5ccc(F)cc5)c3-c3noc(=O)[nH]3)[C@H]3CCCN3C4=O)s2)c2ccccc21]

TABLE 2-continued
| Structure |
| --- |
| 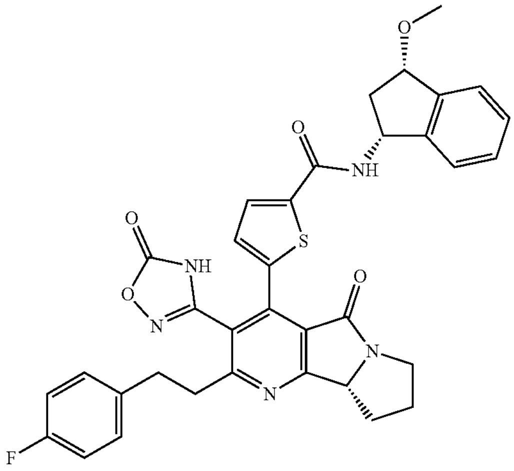 [SMILES: CO[C@H]1C[C@@H](NC(=O)c2ccc(-c3c4c(nc(CCc5ccc(F)cc5)c3-c3noc(=O)[nH]3)[C@H]3CCCN3C4=O)s2)c2ccccc21] |
| 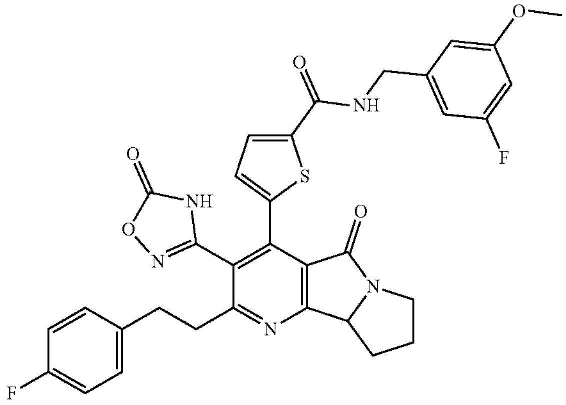 [SMILES: COc1cc(F)cc(CNC(=O)c2ccc(-c3c4c(nc(CCc5ccc(F)cc5)c3-c3noc(=O)[nH]3)C3CCCN3C4=O)s2)c1] |
| 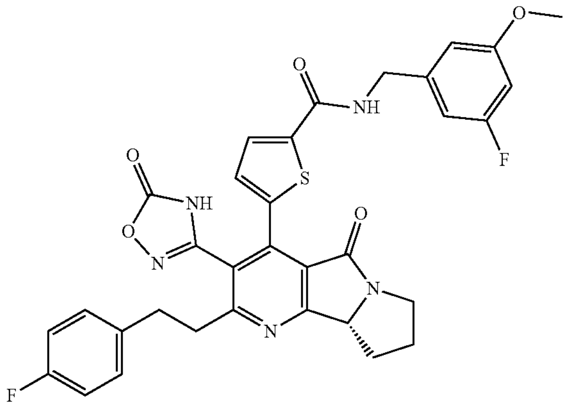 [SMILES: COc1cc(F)cc(CNC(=O)c2ccc(-c3c4c(nc(CCc5ccc(F)cc5)c3-c3noc(=O)[nH]3)[C@H]3CCCN3C4=O)s2)c1] |
TABLE 2-continued
| Structure |
| --- |
| 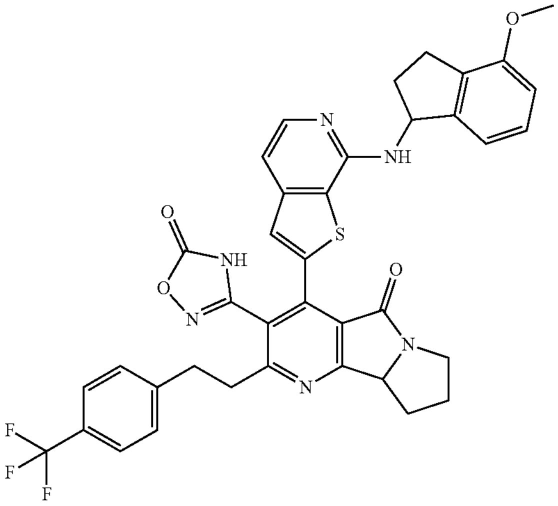 [SMILES: COc1cccc2c1CCC2Nc1nccc2cc(-c3c4c(nc(CCc5ccc(C(F)(F)F)cc5)c3-c3noc(=O)[nH]3)C3CCCN3C4=O)sc12] |
| 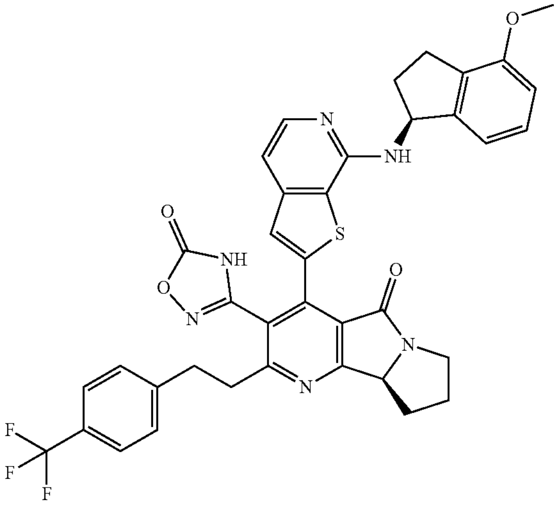 [SMILES: COc1cccc2c1CC[C@@H]2Nc1nccc2cc(-c3c4c(nc(CCc5ccc(C(F)(F)F)cc5)c3-c3noc(=O)[nH]3)[C@@H]3CCCN3C4=O)sc12] |
| 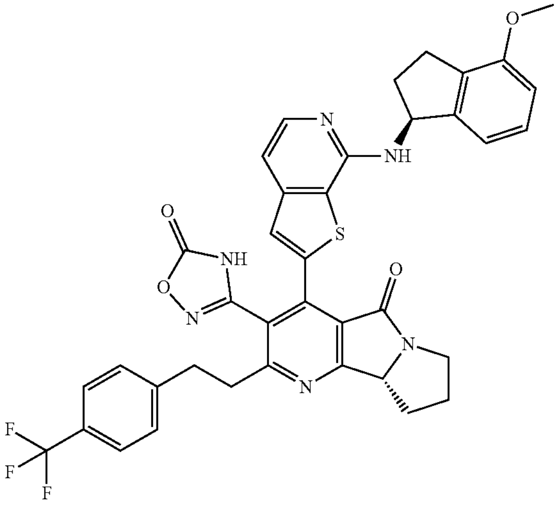 [SMILES: COc1cccc2c1CC[C@@H]2Nc1nccc2cc(-c3c4c(nc(CCc5ccc(C(F)(F)F)cc5)c3-c3noc(=O)[nH]3)[C@H]3CCCN3C4=O)sc12] |

TABLE 2-continued
| Structure |
| --- |
| 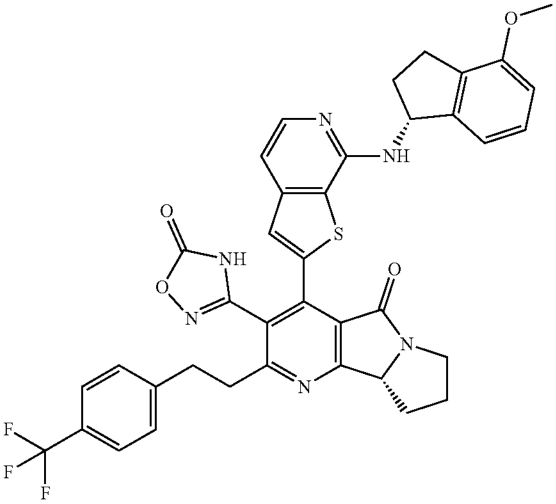 [SMILES: COc1cccc2c1CC[C@H]2Nc1nccc2cc(-c3c4c(nc(CCc5ccc(C(F)(F)F)cc5)c3-c3noc(=O)[nH]3)[C@H]3CCCN3C4=O)sc12] |
| 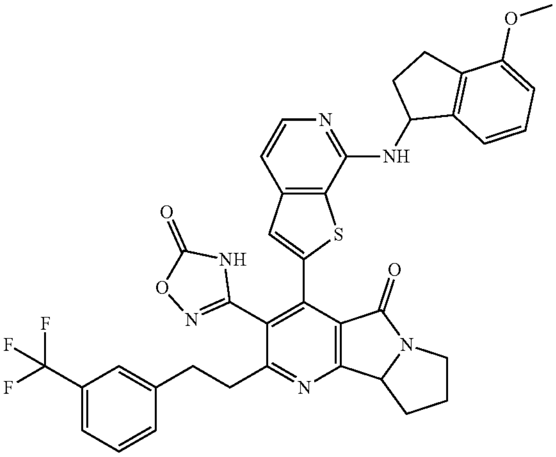 [SMILES: COc1cccc2c1CCC2Nc1nccc2cc(-c3c4c(nc(CCc5cccc(C(F)(F)F)c5)c3-c3noc(=O)[nH]3)C3CCCN3C4=O)sc12] |
| 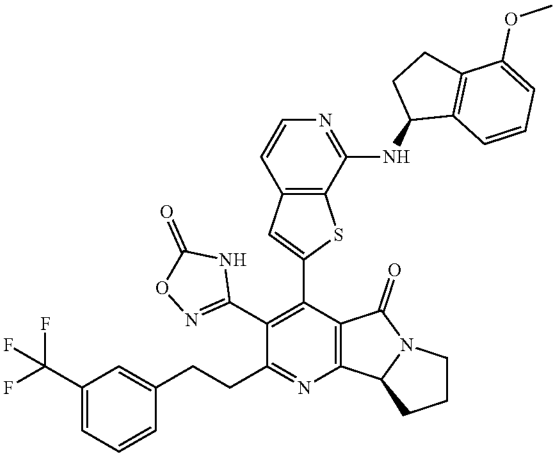 [SMILES: COc1cccc2c1CC[C@@H]2Nc1nccc2cc(-c3c4c(nc(CCc5cccc(C(F)(F)F)c5)c3-c3noc(=O)[nH]3)[C@@H]3CCCN3C4=O)sc12] |
TABLE 2-continued
| Structure |
| --- |
| 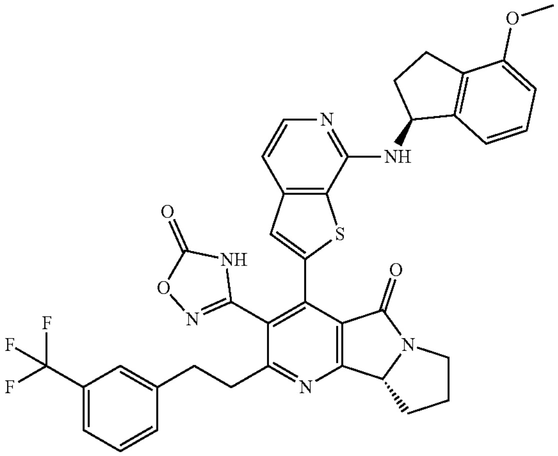 [SMILES: COc1cccc2c1CC[C@@H]2Nc1nccc2cc(-c3c4c(nc(CCc5cccc(C(F)(F)F)c5)c3-c3noc(=O)[nH]3)[C@H]3CCCN3C4=O)sc12] |
| 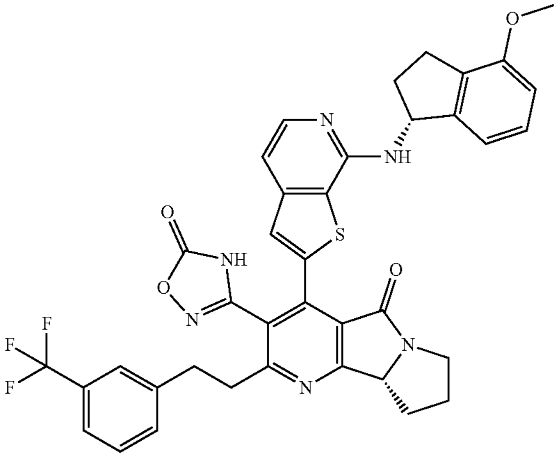 [SMILES: COc1cccc2c1CC[C@H]2Nc1nccc2cc(-c3c4c(nc(CCc5cccc(C(F)(F)F)c5)c3-c3noc(=O)[nH]3)[C@H]3CCCN3C4=O)sc12] |
| 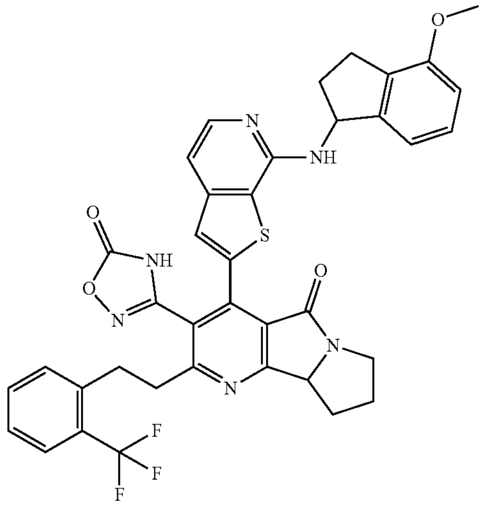 [SMILES: COc1cccc2c1CCC2Nc1nccc2cc(-c3c4c(nc(CCc5ccccc5C(F)(F)F)c3-c3noc(=O)[nH]3)C3CCCN3C4=O)sc12] |

| Structure |
|---|
| 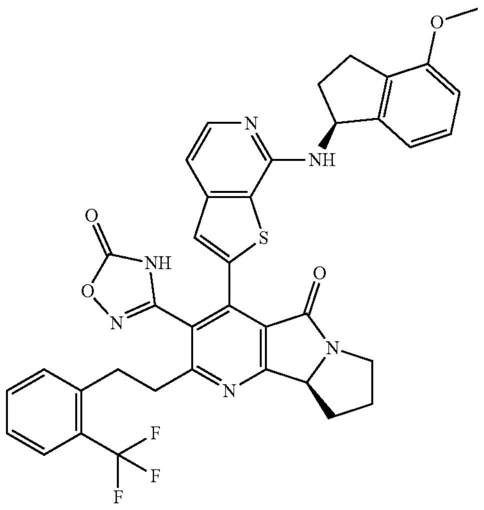 [SMILES: COc1cccc2c1CC[C@@H]2Nc1nccc2cc(-c3c4c(nc(CCc5ccccc5C(F)(F)F)c3-c3noc(=O)[nH]3)[C@@H]3CCCN3C4=O)sc12] |
| 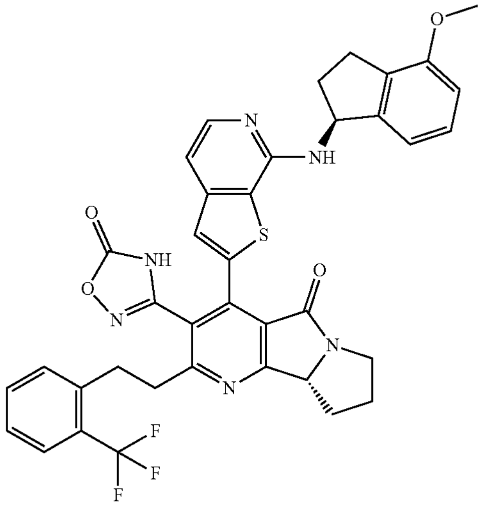 [SMILES: COc1cccc2c1CC[C@@H]2Nc1nccc2cc(-c3c4c(nc(CCc5ccccc5C(F)(F)F)c3-c3noc(=O)[nH]3)[C@H]3CCCN3C4=O)sc12] |
| 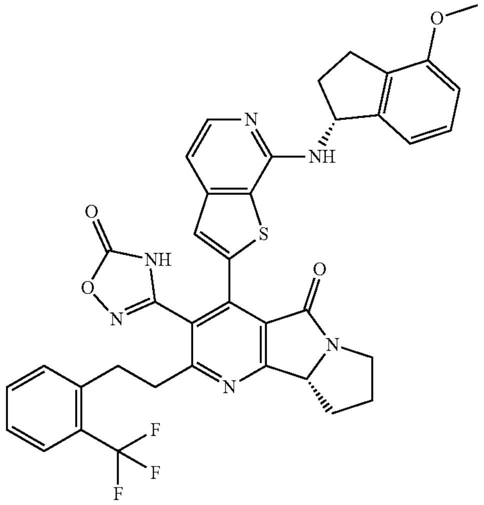 [SMILES: COc1cccc2c1CC[C@H]2Nc1nccc2cc(-c3c4c(nc(CCc5ccccc5C(F)(F)F)c3-c3noc(=O)[nH]3)[C@H]3CCCN3C4=O)sc12] |
| Structure |
|---|
| 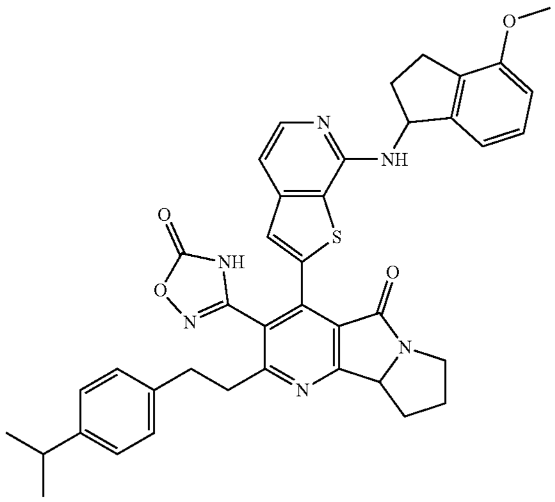 [SMILES: COc1cccc2c1CCC2Nc1nccc2cc(-c3c4c(nc(CCc5ccc(C(C)C)cc5)c3-c3noc(=O)[nH]3)C3CCCN3C4=O)sc12] |
| 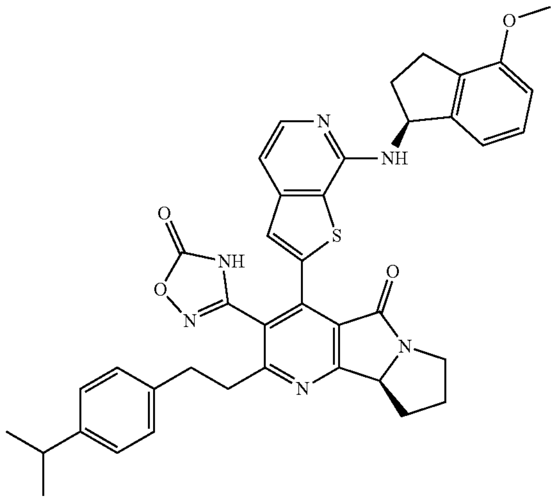 [SMILES: COc1cccc2c1CC[C@@H]2Nc1nccc2cc(-c3c4c(nc(CCc5ccc(C(C)C)cc5)c3-c3noc(=O)[nH]3)[C@@H]3CCCN3C4=O)sc12] |
| 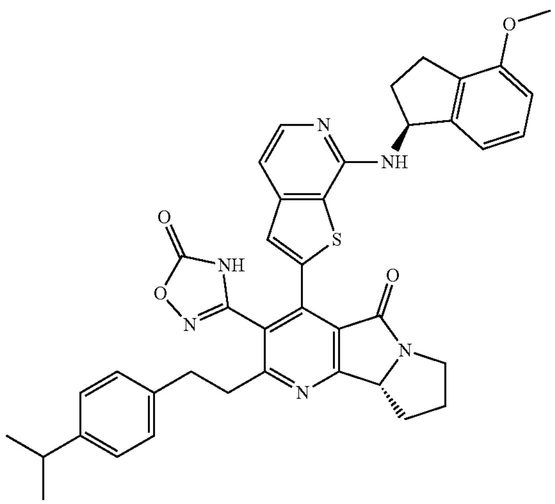 [SMILES: COc1cccc2c1CC[C@@H]2Nc1nccc2cc(-c3c4c(nc(CCc5ccc(C(C)C)cc5)c3-c3noc(=O)[nH]3)[C@H]3CCCN3C4=O)sc12] |

TABLE 2-continued
| Structure |
|---|
| 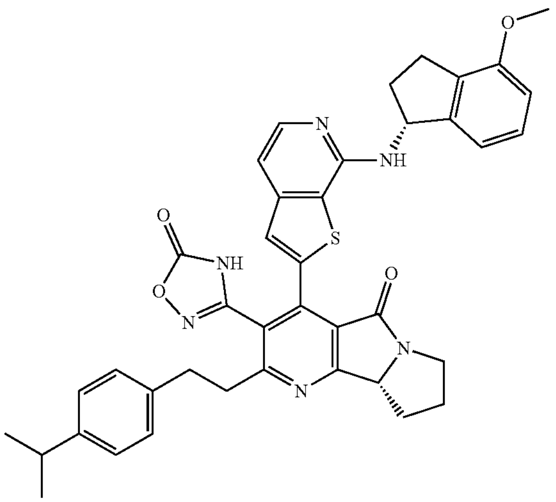 [SMILES: COc1cccc2c1CC[C@H]2Nc1nccc2cc(-c3c4c(nc(CCc5ccc(C(C)C)cc5)c3-c3noc(=O)[nH]3)[C@H]3CCCN3C4=O)sc12] |
| 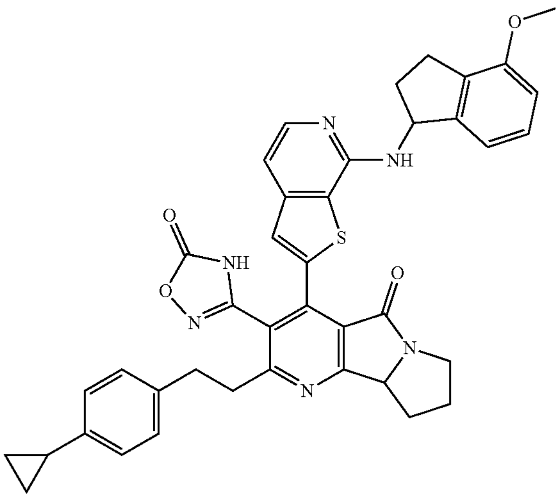 [SMILES: COc1cccc2c1CCC2Nc1nccc2cc(-c3c4c(nc(CCc5ccc(C6CC6)cc5)c3-c3noc(=O)[nH]3)C3CCCN3C4=O)sc12] |
| 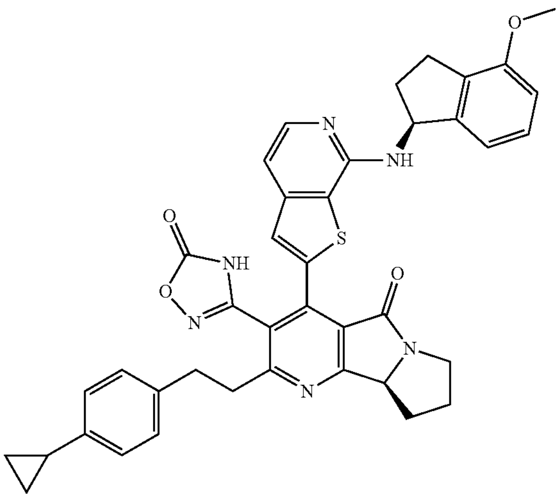 [SMILES: COc1cccc2c1CC[C@@H]2Nc1nccc2cc(-c3c4c(nc(CCc5ccc(C6CC6)cc5)c3-c3noc(=O)[nH]3)[C@@H]3CCCN3C4=O)sc12] |
TABLE 2-continued
| Structure |
|---|
| 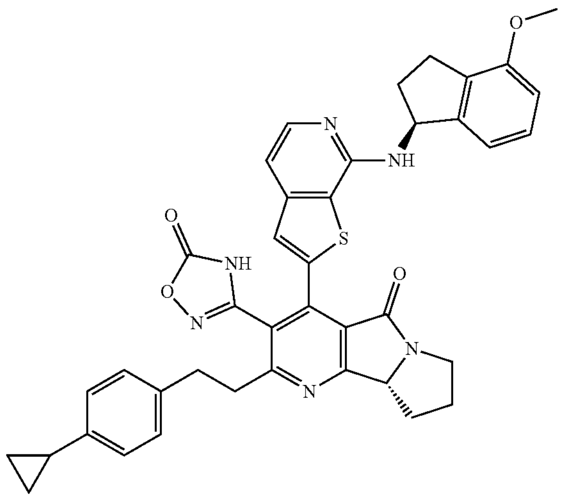 [SMILES: COc1cccc2c1CC[C@@H]2Nc1nccc2cc(-c3c4c(nc(CCc5ccc(C6CC6)cc5)c3-c3noc(=O)[nH]3)[C@H]3CCCN3C4=O)sc12] |
| 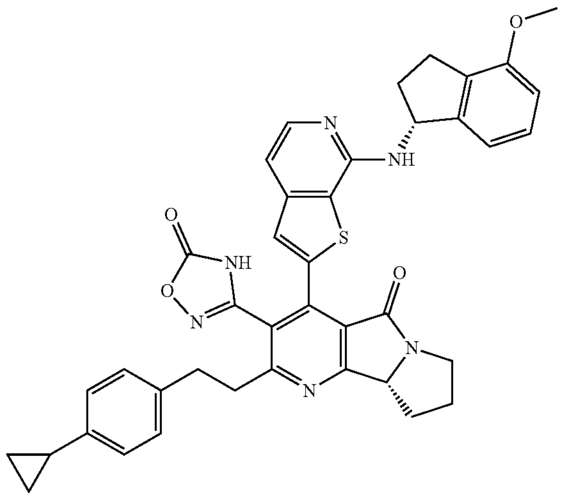 [SMILES: COc1cccc2c1CC[C@H]2Nc1nccc2cc(-c3c4c(nc(CCc5ccc(C6CC6)cc5)c3-c3noc(=O)[nH]3)[C@H]3CCCN3C4=O)sc12] |
| 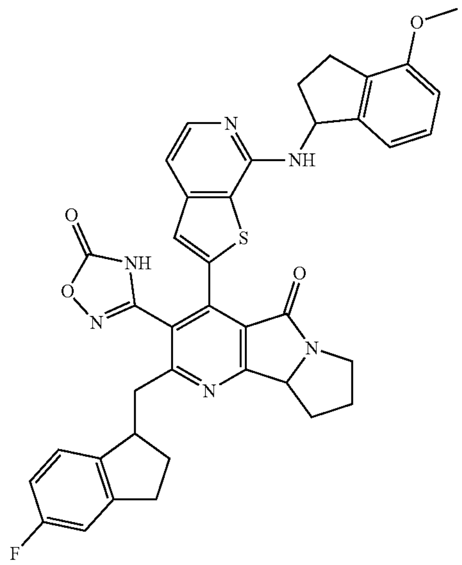 [SMILES: COc1cccc2c1CCC2Nc1nccc2cc(-c3c4c(nc(CC5CCc6cc(F)ccc65)c3-c3noc(=O)[nH]3)C3CCCN3C4=O)sc12]

TABLE 2-continued
| Structure |
| --- |
| 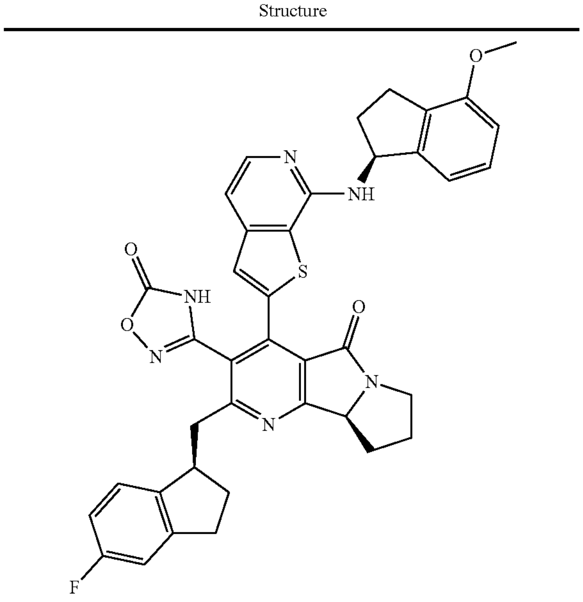 |
| 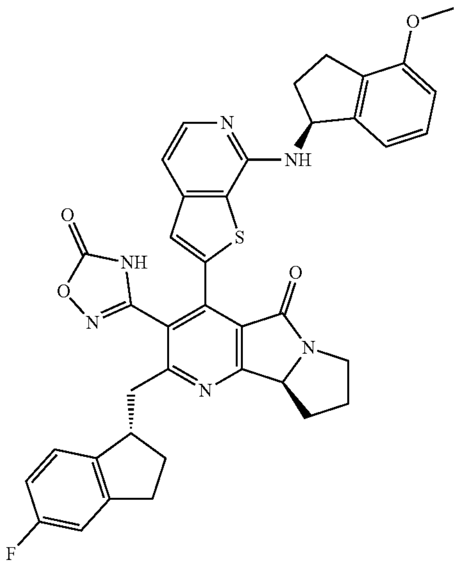 [SMILES: COc1cccc2c1CC[C@@H]2Nc1nccc2cc(-c3c4c(nc(C[C@@H]5CCc6cc(F)ccc65)c3-c3noc(=O)[nH]3)[C@@H]3CCCN3C4=O)sc12] |
TABLE 2-continued
| Structure |
| --- |
| 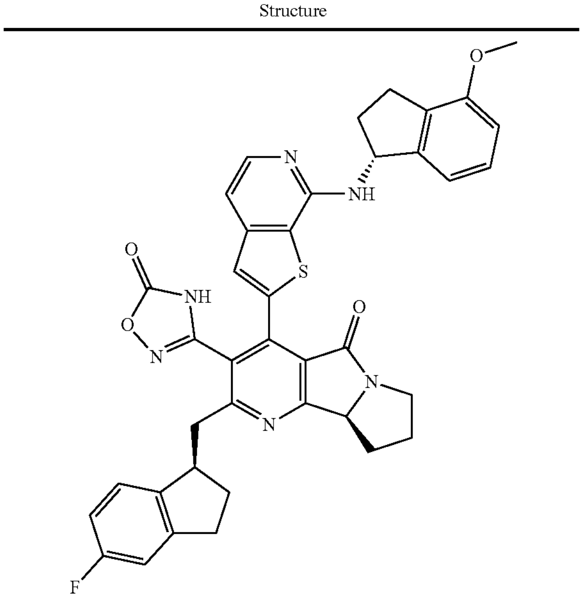 |
| 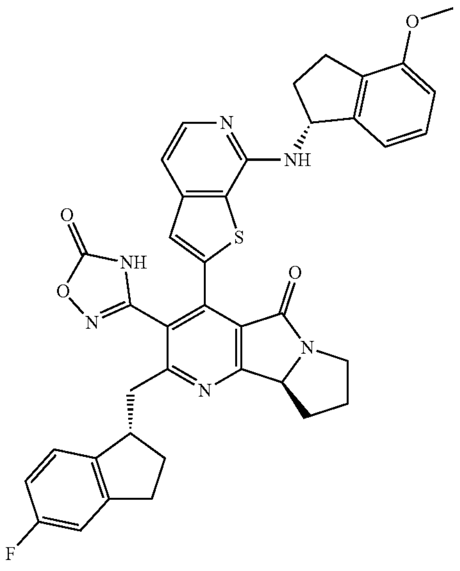 [SMILES: COc1cccc2c1CC[C@H]2Nc1nccc2cc(-c3c4c(nc(C[C@@H]5CCc6cc(F)ccc65)c3-c3noc(=O)[nH]3)[C@@H]3CCCN3C4=O)sc12]

TABLE 2-continued
| Structure |
| --- |
| 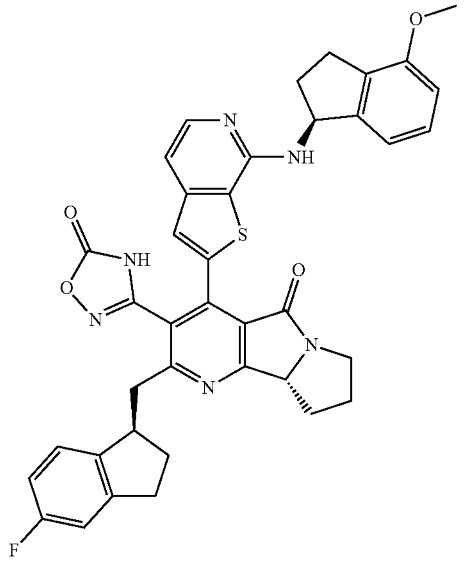 [SMILES: COc1cccc2c1CC[C@@H]2Nc1nccc2cc(-c3c4c(nc(C[C@H]5CCc6cc(F)ccc65)c3-c3noc(=O)[nH]3)[C@H]3CCCN3C4=O)sc12] |
| 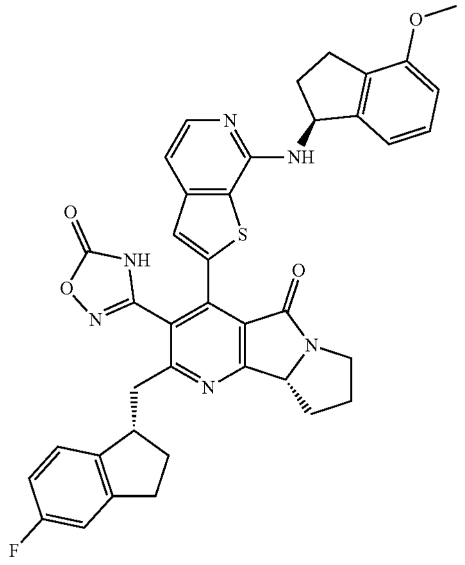 [SMILES: COc1cccc2c1CC[C@@H]2Nc1nccc2cc(-c3c4c(nc(C[C@@H]5CCc6cc(F)ccc65)c3-c3noc(=O)[nH]3)[C@H]3CCCN3C4=O)sc12] |
TABLE 2-continued
| Structure |
| --- |
| 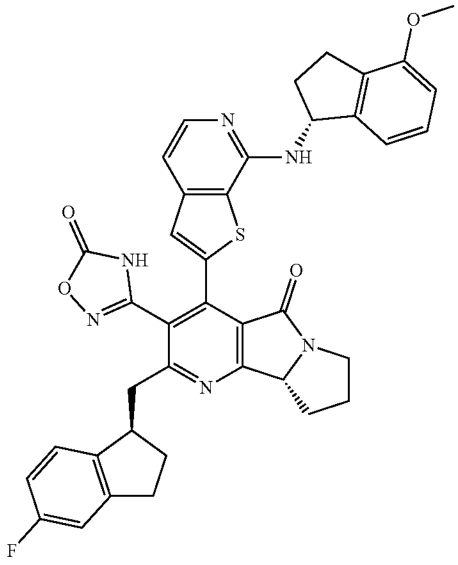 [SMILES: COc1cccc2c1CC[C@H]2Nc1nccc2cc(-c3c4c(nc(C[C@H]5CCc6cc(F)ccc65)c3-c3noc(=O)[nH]3)[C@H]3CCCN3C4=O)sc12] |
| 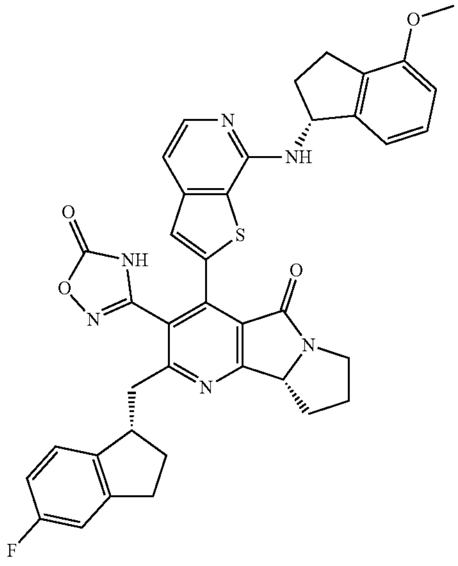 [SMILES: COc1cccc2c1CC[C@H]2Nc1nccc2cc(-c3c4c(nc(C[C@@H]5CCc6cc(F)ccc65)c3-c3noc(=O)[nH]3)[C@H]3CCCN3C4=O)sc12] |
| 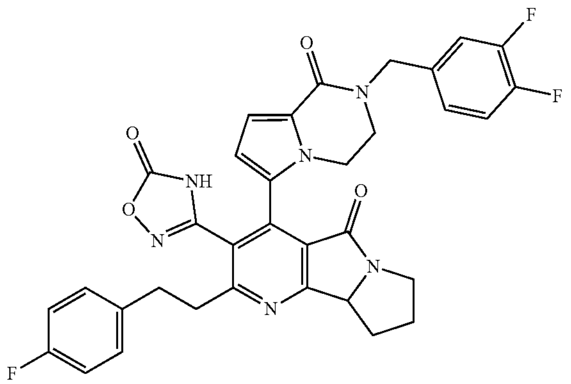 [SMILES: O=C1c2ccc(-c3c4c(nc(CCc5ccc(F)cc5)c3-c3noc(=O)[nH]3)C3CCCN3C4=O)n2CCN1Cc1ccc(F)c(F)c1] |

TABLE 2-continued
| Structure |
| --- |
| 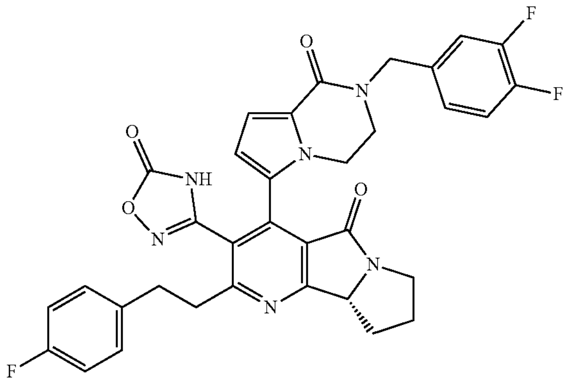 [SMILES: O=C1c2ccc(-c3c4c(nc(CCc5ccc(F)cc5)c3-c3noc(=O)[nH]3)[C@H]3CCCN3C4=O)n2CCN1Cc1ccc(F)c(F)c1] |
| 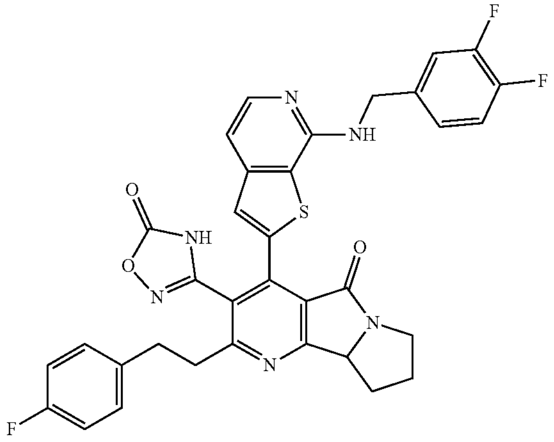 [SMILES: O=C1c2c(nc(CCc3ccc(F)cc3)c(-c3noc(=O)[nH]3)c2-c2cc3ccnc(NCc4ccc(F)c(F)c4)c3s2)[C@H]2CCCN12] |
| 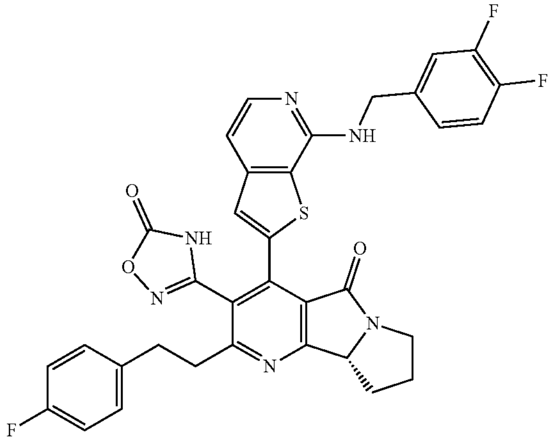 |
TABLE 2-continued
| Structure |
| --- |
| 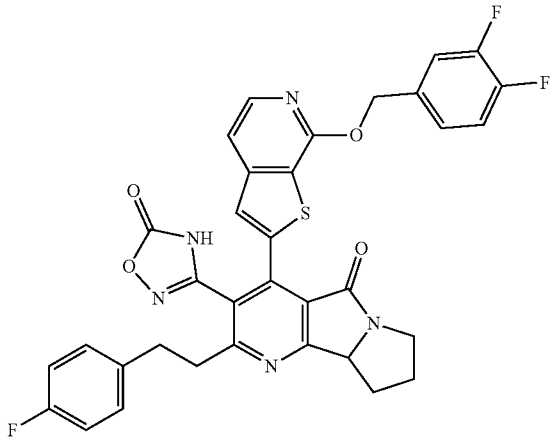 [SMILES: O=C1c2c(nc(CCc3ccc(F)cc3)c(-c3noc(=O)[nH]3)c2-c2cc3ccnc(OCc4ccc(F)c(F)c4)c3s2)C2CCCN12] |
| 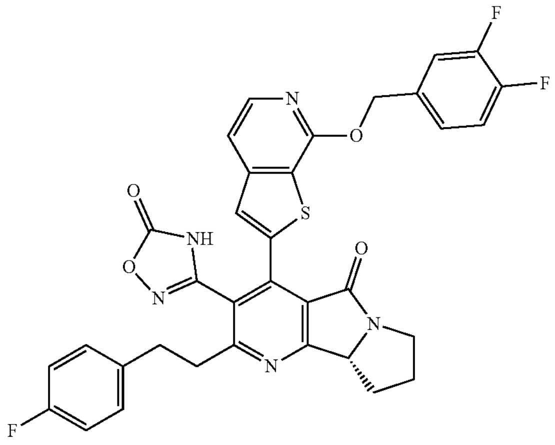 [SMILES: O=C1c2c(nc(CCc3ccc(F)cc3)c(-c3noc(=O)[nH]3)c2-c2cc3ccnc(OCc4ccc(F)c(F)c4)c3s2)[C@H]2CCCN12] |
| 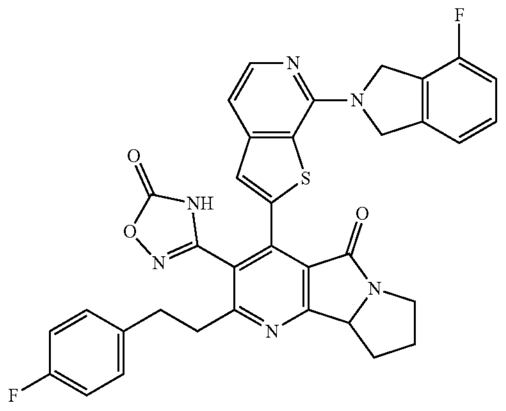 |

TABLE 2-continued
Structure
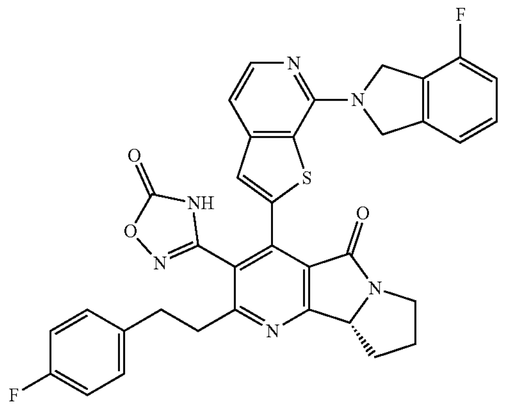 [SMILES: O=C1c2c(nc(CCc3ccc(F)cc3)c(-c3noc(=O)[nH]3)c2-c2cc3ccnc(N4Cc5cccc(F)c5C4)c3s2)C2CCCN12]
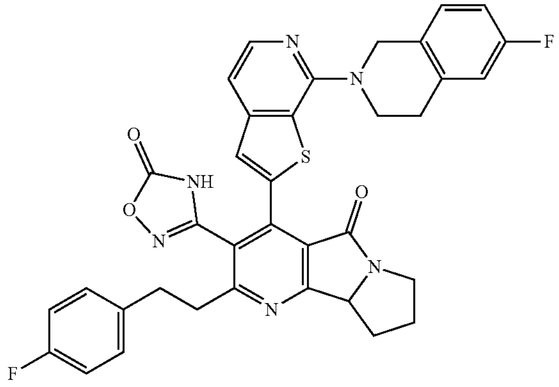 [SMILES: O=C1c2c(nc(CCc3ccc(F)cc3)c(-c3noc(=O)[nH]3)c2-c2cc3ccnc(N4CCc5cc(F)ccc5C4)c3s2)C2CCCN12]
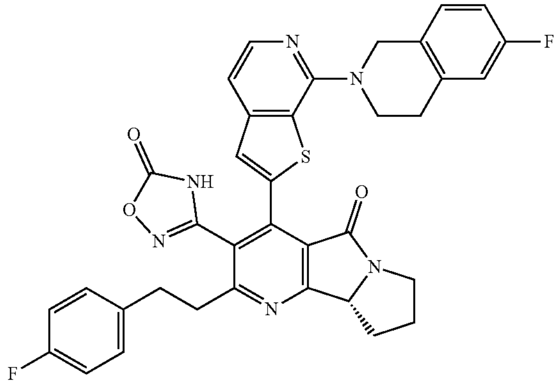 [SMILES: O=C1c2c(nc(CCc3ccc(F)cc3)c(-c3noc(=O)[nH]3)c2-c2cc3ccnc(N4CCc5cc(F)ccc5C4)c3s2)[C@H]2CCCN12]
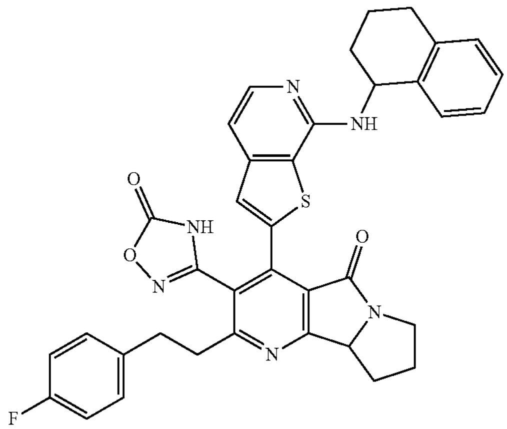 [SMILES: O=C1c2c(nc(CCc3ccc(F)cc3)c(-c3noc(=O)[nH]3)c2-c2cc3ccnc(NC4CCCc5ccccc54)c3s2)C2CCCN12]
TABLE 2-continued
Structure
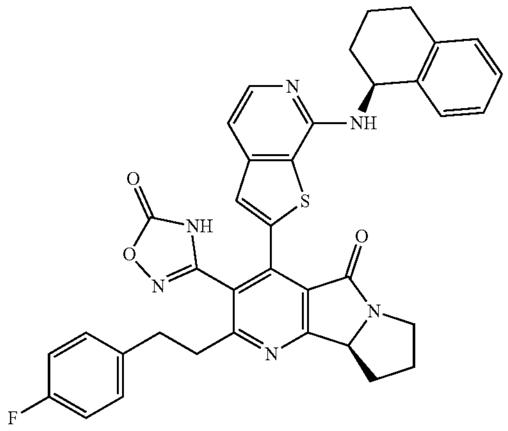 [SMILES: O=C1c2c(nc(CCc3ccc(F)cc3)c(-c3noc(=O)[nH]3)c2-c2cc3ccnc(N[C@H]4CCCc5ccccc54)c3s2)[C@@H]2CCCN12]
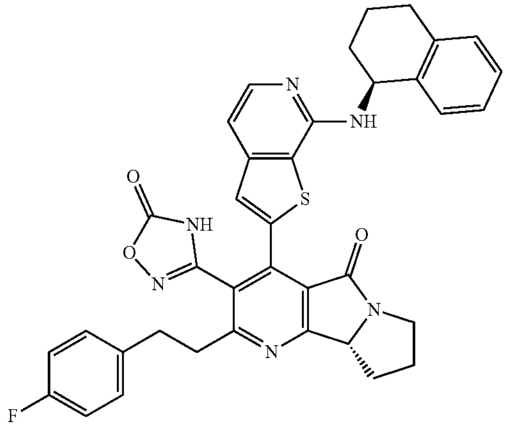 [SMILES: O=C1c2c(nc(CCc3ccc(F)cc3)c(-c3noc(=O)[nH]3)c2-c2cc3ccnc(N[C@H]4CCCc5ccccc54)c3s2)[C@H]2CCCN12]
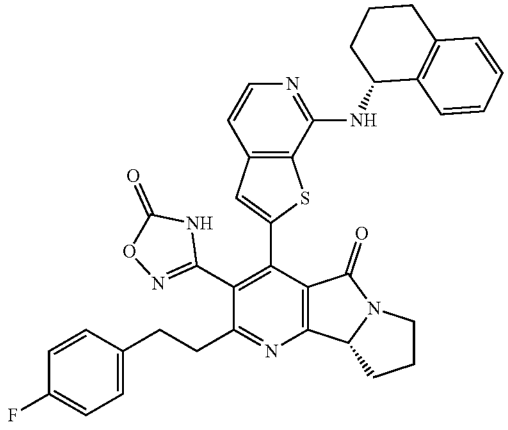 [SMILES: O=C1c2c(nc(CCc3ccc(F)cc3)c(-c3noc(=O)[nH]3)c2-c2cc3ccnc(N[C@@H]4CCCc5ccccc54)c3s2)[C@H]2CCCN12]

| Structure |
|---|
| 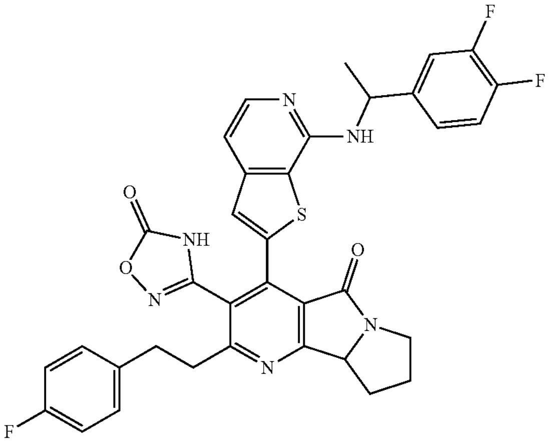 [SMILES: CC(Nc1nccc2cc(-c3c4c(nc(CCc5ccc(F)cc5)c3-c3noc(=O)[nH]3)C3CCCN3C4=O)sc12)c1ccc(F)c(F)c1] |
| 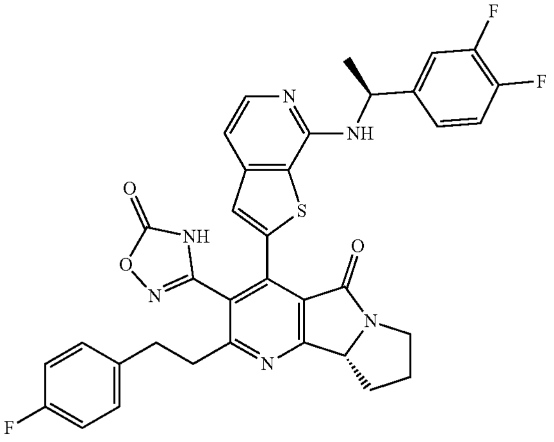 [SMILES: C[C@H](Nc1nccc2cc(-c3c4c(nc(CCc5ccc(F)cc5)c3-c3noc(=O)[nH]3)[C@H]3CCCN3C4=O)sc12)c1ccc(F)c(F)c1] |
| 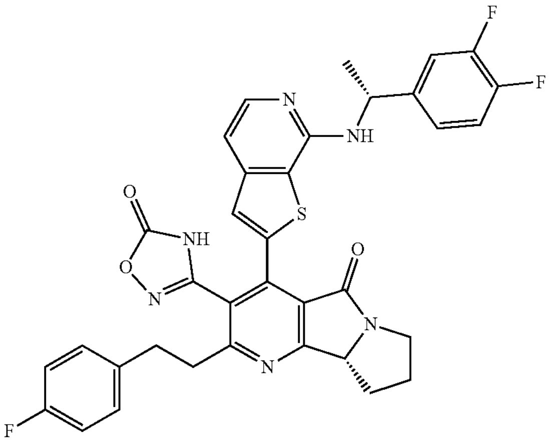 [SMILES: C[C@@H](Nc1nccc2cc(-c3c4c(nc(CCc5ccc(F)cc5)c3-c3noc(=O)[nH]3)[C@H]3CCCN3C4=O)sc12)c1ccc(F)c(F)c1] |
| Structure |
|---|
| 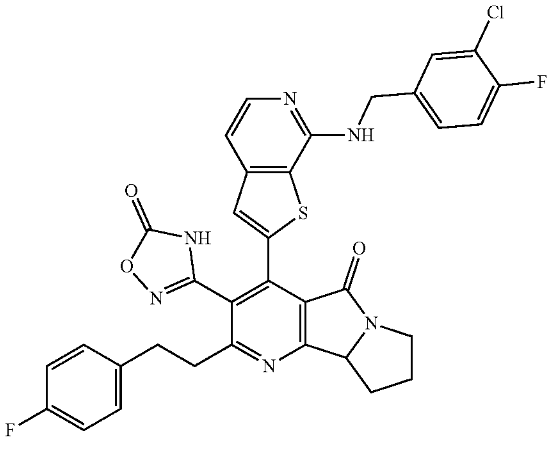 [SMILES: O=C1c2c(nc(CCc3ccc(F)cc3)c(-c3noc(=O)[nH]3)c2-c2cc3ccnc(NCc4ccc(F)c(Cl)c4)c3s2)C2CCCN12] |
| 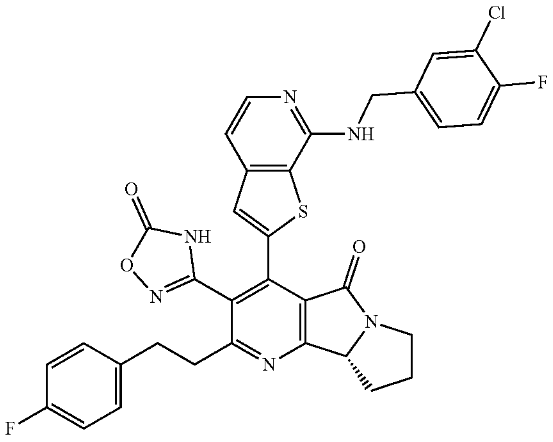 [SMILES: O=C1c2c(nc(CCc3ccc(F)cc3)c(-c3noc(=O)[nH]3)c2-c2cc3ccnc(NCc4ccc(F)c(Cl)c4)c3s2)[C@H]2CCCN12] |
| 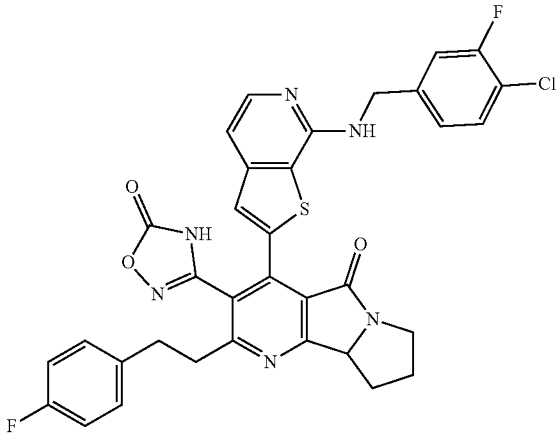 [SMILES: O=C1c2c(nc(CCc3ccc(F)cc3)c(-c3noc(=O)[nH]3)c2-c2cc3ccnc(NCc4ccc(Cl)c(F)c4)c3s2)C2CCCN12] |

TABLE 2-continued
| Structure |
|---|
| 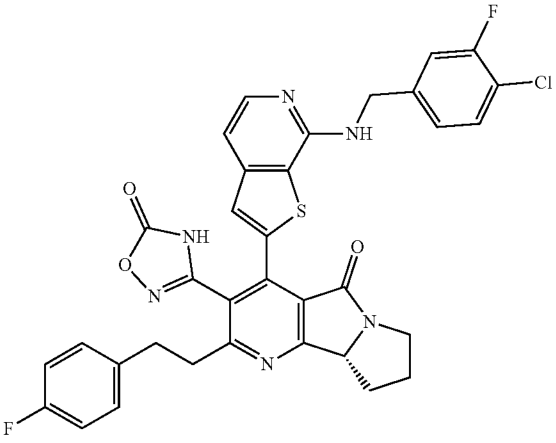 [SMILES: O=C1c2c(nc(CCc3ccc(F)cc3)c(-c3noc(=O)[nH]3)c2-c2cc3ccnc(NCc4ccc(Cl)c(F)c4)c3s2)[C@H]2CCCN12] |
| 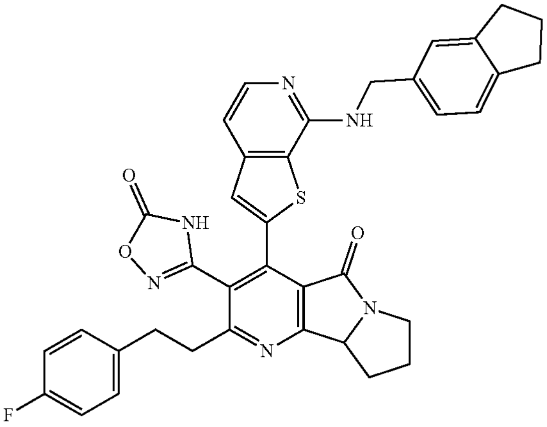 [SMILES: O=C1c2c(nc(CCc3ccc(F)cc3)c(-c3noc(=O)[nH]3)c2-c2cc3ccnc(NCc4ccc5c(c4)CCC5)c3s2)C2CCCN12] |
| 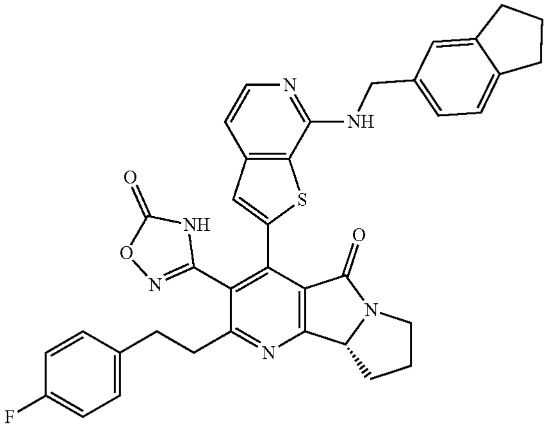 [SMILES: O=C1c2c(nc(CCc3ccc(F)cc3)c(-c3noc(=O)[nH]3)c2-c2cc3ccnc(NCc4ccc5c(c4)CCC5)c3s2)[C@H]2CCCN12] |
TABLE 2-continued
| Structure |
|---|
| 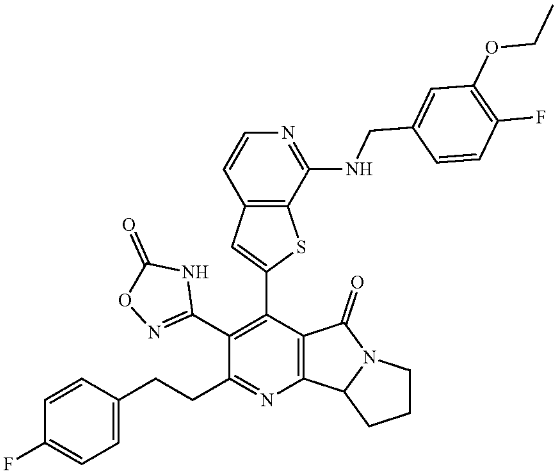 [SMILES: CCOc1cc(CNc2nccc3cc(-c4c5c(nc(CCc6ccc(F)cc6)c4-c4noc(=O)[nH]4)C4CCCN4C5=O)sc23)ccc1F] |
| 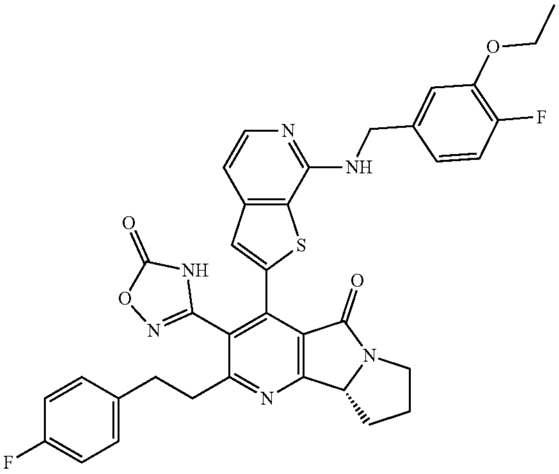 [SMILES: CCOc1cc(CNc2nccc3cc(-c4c5c(nc(CCc6ccc(F)cc6)c4-c4noc(=O)[nH]4)[C@H]4CCCN4C5=O)sc23)ccc1F] |
| 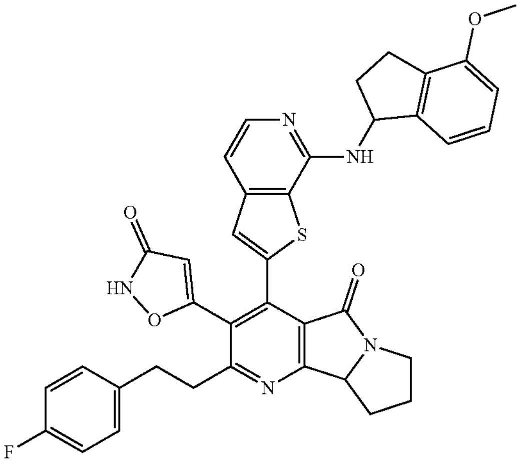 [SMILES: COc1cccc2c1CCC2Nc1nccc2cc(-c3c4c(nc(CCc5ccc(F)cc5)c3-c3cc(=O)[nH]o3)C3CCCN3C4=O)sc12] |

TABLE 2-continued
| Structure |
|---|
| 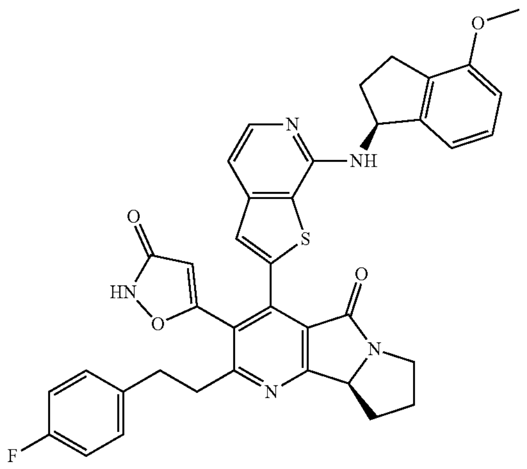 [SMILES: COc1cccc2c1CC[C@@H]2Nc1nccc2cc(-c3c4c(nc(CCc5ccc(F)cc5)c3-c3cc(=O)[nH]o3)[C@@H]3CCCN3C4=O)sc12] |
| 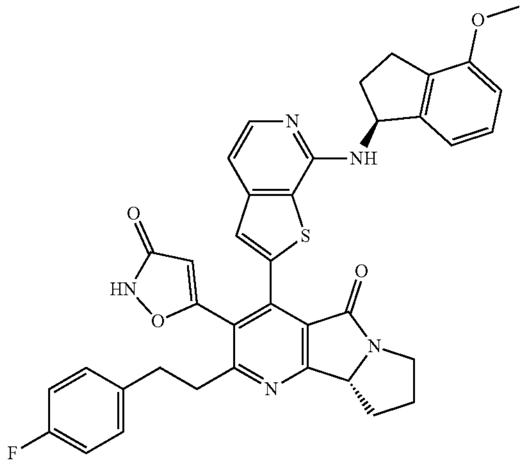 [SMILES: COc1cccc2c1CC[C@@H]2Nc1nccc2cc(-c3c4c(nc(CCc5ccc(F)cc5)c3-c3cc(=O)[nH]o3)[C@H]3CCCN3C4=O)sc12] |
| 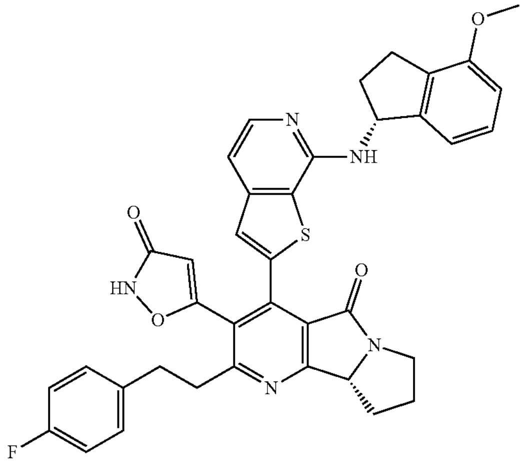 [SMILES: COc1cccc2c1CC[C@H]2Nc1nccc2cc(-c3c4c(nc(CCc5ccc(F)cc5)c3-c3cc(=O)[nH]o3)[C@H]3CCCN3C4=O)sc12] |
TABLE 2-continued
| Structure |
|---|
| 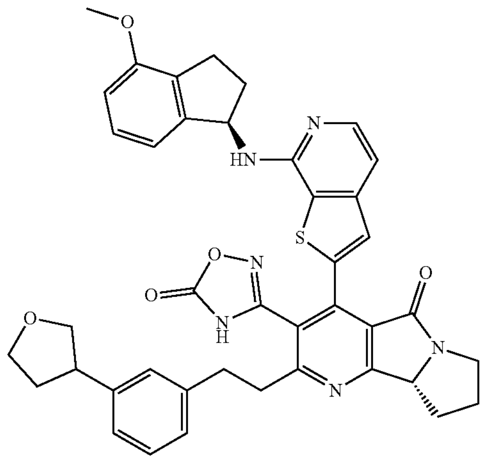 [SMILES: COc1cccc2c1CC[C@H]2Nc1nccc2cc(-c3c4c(nc(CCc5cccc(C6CCOC6)c5)c3-c3noc(=O)[nH]3)[C@H]3CCCN3C4=O)sc12] |
| 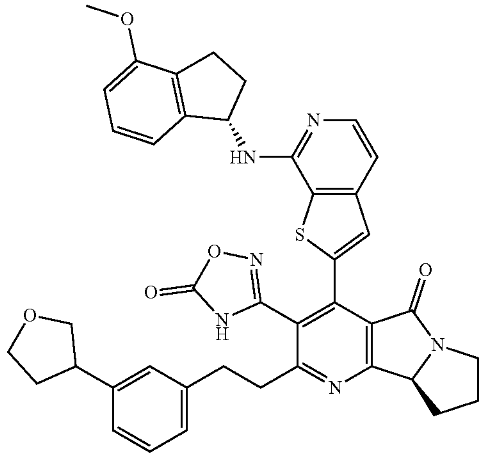 [SMILES: COc1cccc2c1CC[C@@H]2Nc1nccc2cc(-c3c4c(nc(CCc5cccc(C6CCOC6)c5)c3-c3noc(=O)[nH]3)[C@@H]3CCCN3C4=O)sc12] |
| 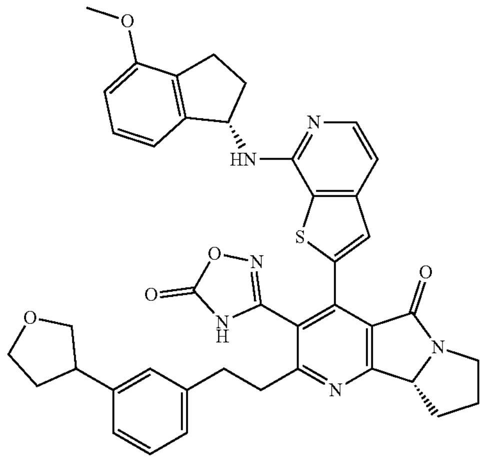 [SMILES: COc1cccc2c1CC[C@@H]2Nc1nccc2cc(-c3c4c(nc(CCc5cccc(C6CCOC6)c5)c3-c3noc(=O)[nH]3)[C@H]3CCCN3C4=O)sc12] |

TABLE 2-continued
| Structure |
| --- |
| 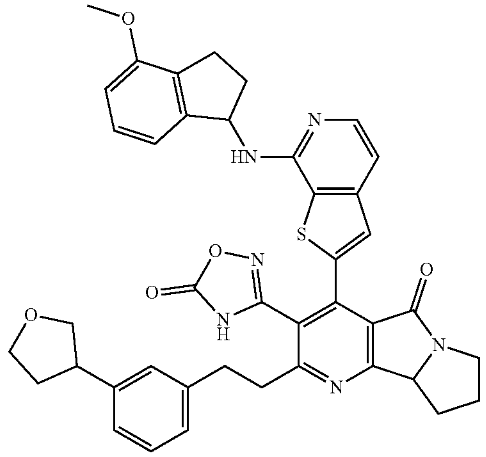 [SMILES: COc1cccc2c1CCC2Nc1nccc2cc(-c3c4c(nc(CCc5cccc(C6CCOC6)c5)c3-c3noc(=O)[nH]3)C3CCCN3C4=O)sc12] |
| 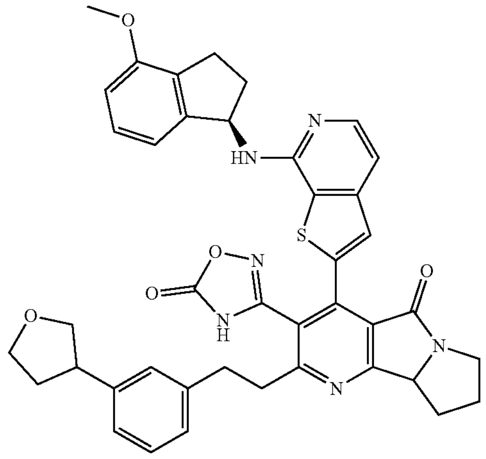 [SMILES: COc1cccc2c1CC[C@H]2Nc1nccc2cc(-c3c4c(nc(CCc5cccc(C6CCOC6)c5)c3-c3noc(=O)[nH]3)C3CCCN3C4=O)sc12] |
| 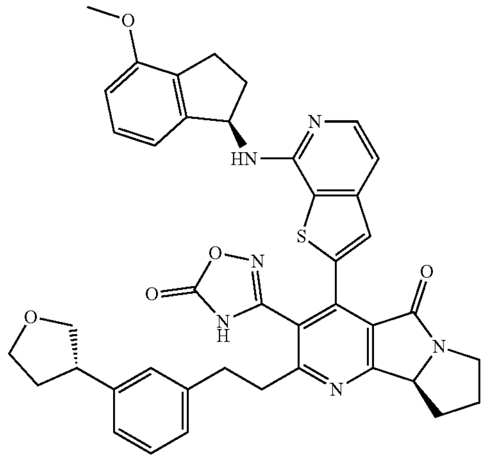 [SMILES: COc1cccc2c1CC[C@H]2Nc1nccc2cc(-c3c4c(nc(CCc5cccc([C@@H]6CCOC6)c5)c3-c3noc(=O)[nH]3)[C@@H]3CCCN3C4=O)sc12] |
TABLE 2-continued
| Structure |
| --- |
| 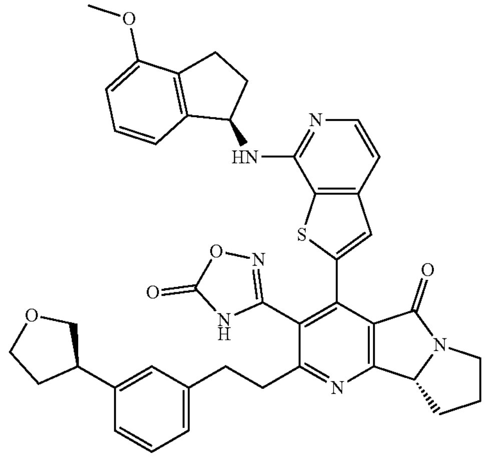 [SMILES: COc1cccc2c1CC[C@H]2Nc1nccc2cc(-c3c4c(nc(CCc5cccc([C@H]6CCOC6)c5)c3-c3noc(=O)[nH]3)[C@H]3CCCN3C4=O)sc12] |
| 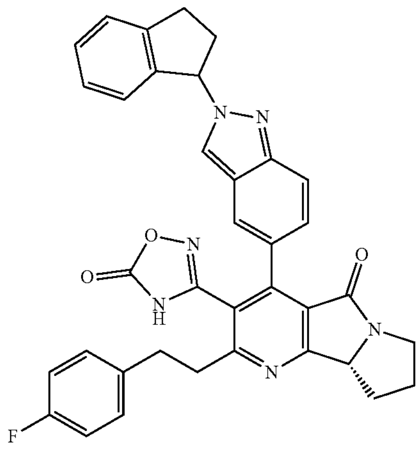 [SMILES: O=C1c2c(nc(CCc3ccc(F)cc3)c(-c3noc(=O)[nH]3)c2-c2ccc3nn(C4CCc5ccccc54)cc3c2)[C@H]2CCCN12] |
| 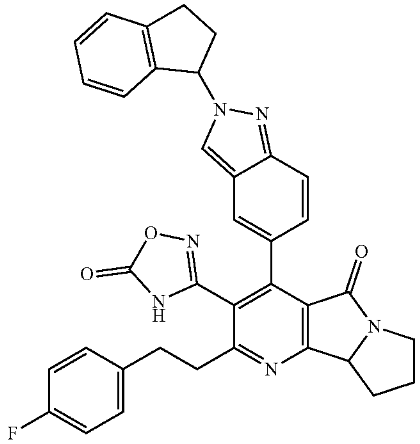 [SMILES: O=C1c2c(nc(CCc3ccc(F)cc3)c(-c3noc(=O)[nH]3)c2-c2ccc3nn(C4CCc5ccccc54)cc3c2)C2CCCN12] |

TABLE 2-continued
| Structure |
| --- |
| 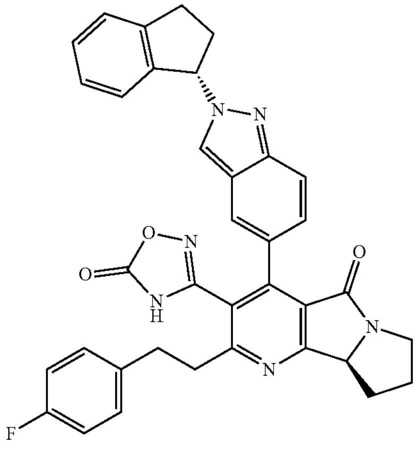 [SMILES: O=C1c2c(nc(CCc3ccc(F)cc3)c(-c3noc(=O)[nH]3)c2-c2ccc3nn([C@H]4CCc5ccccc54)cc3c2)[C@@H]2CCCN12] |
| 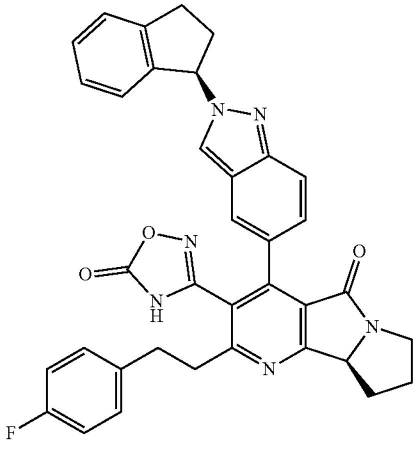 [SMILES: O=C1c2c(nc(CCc3ccc(F)cc3)c(-c3noc(=O)[nH]3)c2-c2ccc3nn([C@@H]4CCc5ccccc54)cc3c2)[C@@H]2CCCN12] |
| 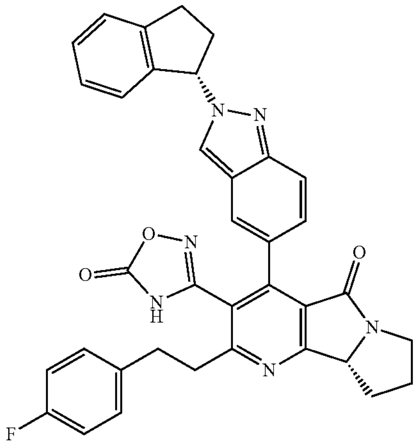 [SMILES: O=C1c2c(nc(CCc3ccc(F)cc3)c(-c3noc(=O)[nH]3)c2-c2ccc3nn([C@H]4CCc5ccccc54)cc3c2)[C@H]2CCCN12] |
TABLE 2-continued
| Structure |
| --- |
| 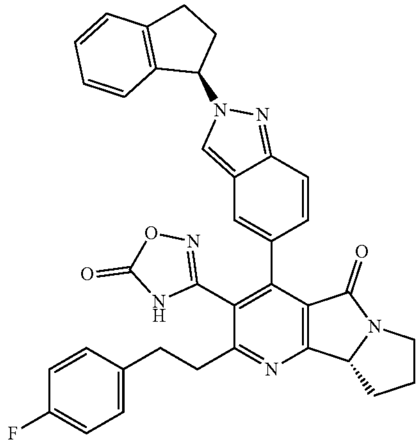 [SMILES: O=C1c2c(nc(CCc3ccc(F)cc3)c(-c3noc(=O)[nH]3)c2-c2ccc3nn([C@@H]4CCc5ccccc54)cc3c2)[C@H]2CCCN12] |
| 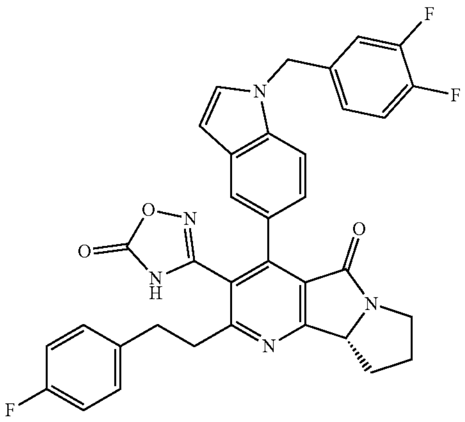 [SMILES: O=C1c2c(nc(CCc3ccc(F)cc3)c(-c3noc(=O)[nH]3)c2-c2ccc3c(ccn3Cc3ccc(F)c(F)c3)c2)[C@H]2CCCN12] |
| 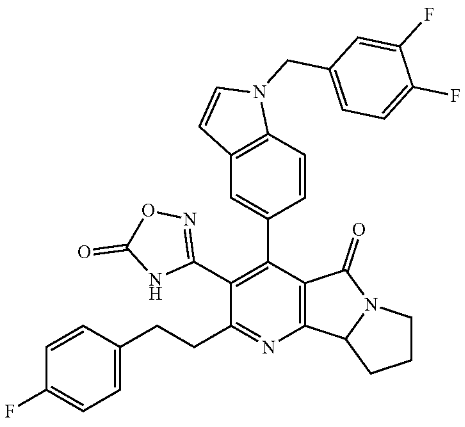 [SMILES: O=C1c2c(nc(CCc3ccc(F)cc3)c(-c3noc(=O)[nH]3)c2-c2ccc3c(ccn3Cc3ccc(F)c(F)c3)c2)C2CCCN12] |

TABLE 2-continued
| Structure |
|---|
| 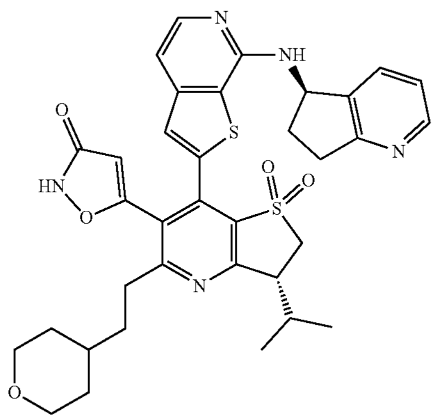 |
| 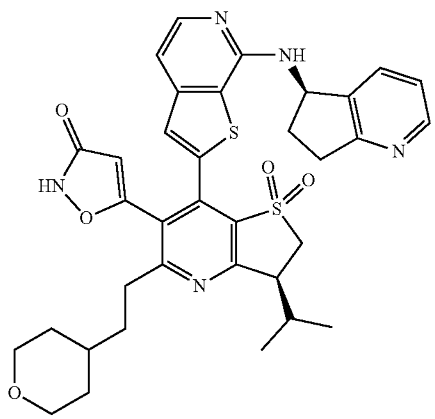 [SMILES: CC(C)[C@@H]1CS(=O)(=O)c2c1nc(CCC1CCOCC1)c(-c1cc(=O)[nH]o1)c2-c1cc2ccnc(N[C@@H]3CCc4ncccc43)c2s1] |
| 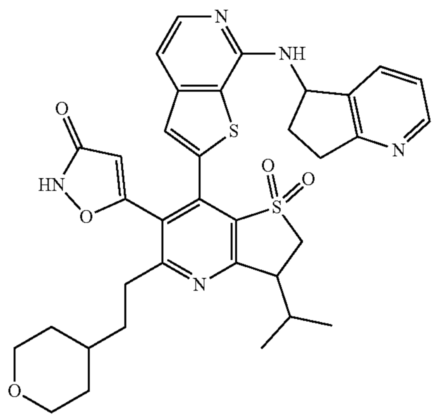 [SMILES: CC(C)C1CS(=O)(=O)c2c1nc(CCC1CCOCC1)c(-c1cc(=O)[nH]o1)c2-c1cc2ccnc(NC3CCc4ncccc43)c2s1] |
TABLE 2-continued
| Structure |
|---|
| 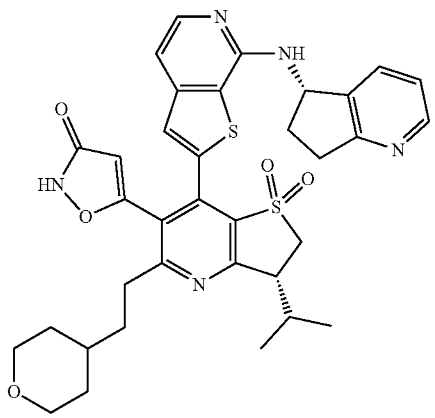 [SMILES: CC(C)[C@H]1CS(=O)(=O)c2c1nc(CCC1CCOCC1)c(-c1cc(=O)[nH]o1)c2-c1cc2ccnc(N[C@H]3CCc4ncccc43)c2s1] |
| 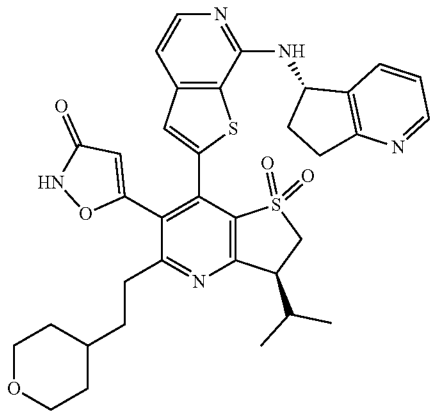 [SMILES: CC(C)[C@@H]1CS(=O)(=O)c2c1nc(CCC1CCOCC1)c(-c1cc(=O)[nH]o1)c2-c1cc2ccnc(N[C@H]3CCc4ncccc43)c2s1] |
| 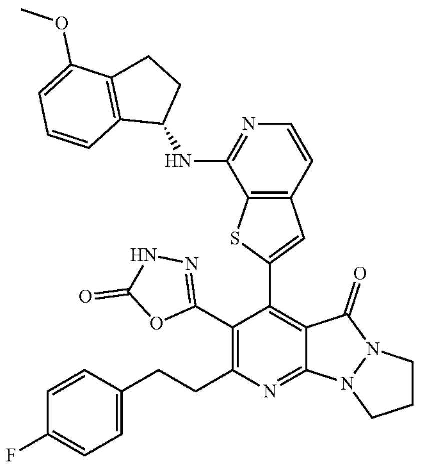 [SMILES: COc1cccc2c1CC[C@@H]2Nc1nccc2cc(-c3c(-c4n[nH]c(=O)o4)c(CCc4ccc(F)cc4)nc4c3c(=O)n3n4CCC3)sc12] |

TABLE 2-continued
| Structure |
| --- |
| 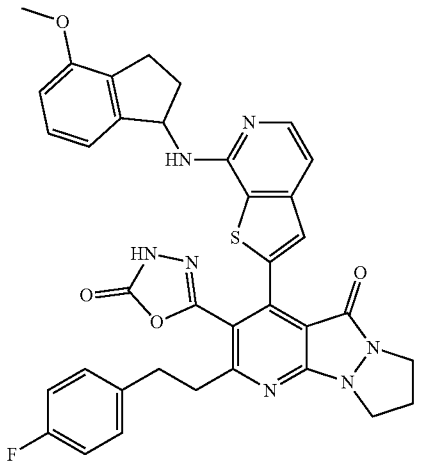 [SMILES: COc1cccc2c1CCC2Nc1nccc2cc(-c3c(-c4n[nH]c(=O)o4)c(CCc4ccc(F)cc4)nc4c3c(=O)n3n4CCC3)sc12] |
| 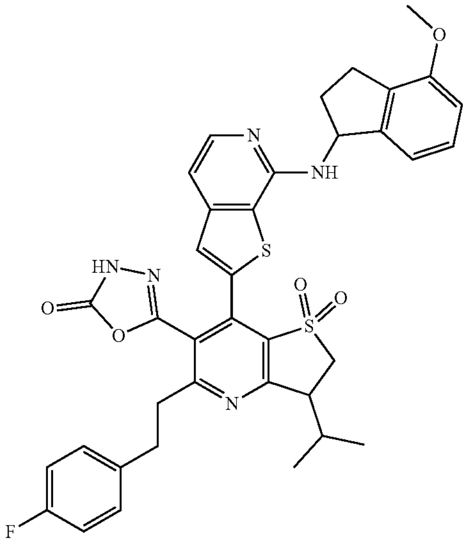 [SMILES: COc1cccc2c1CCC2Nc1nccc2cc(-c3c(-c4n[nH]c(=O)o4)c(CCc4ccc(F)cc4)nc4c3S(=O)(=O)CC4C(C)C)sc12] |
| 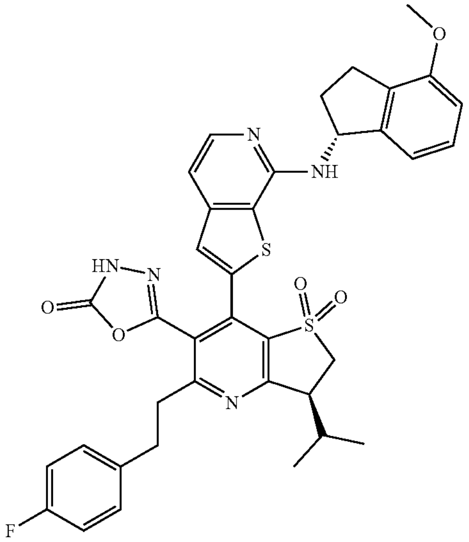 [SMILES: COc1cccc2c1CC[C@H]2Nc1nccc2cc(-c3c(-c4n[nH]c(=O)o4)c(CCc4ccc(F)cc4)nc4c3S(=O)(=O)C[C@H]4C(C)C)sc12] |
TABLE 2-continued
| Structure |
| --- |
| 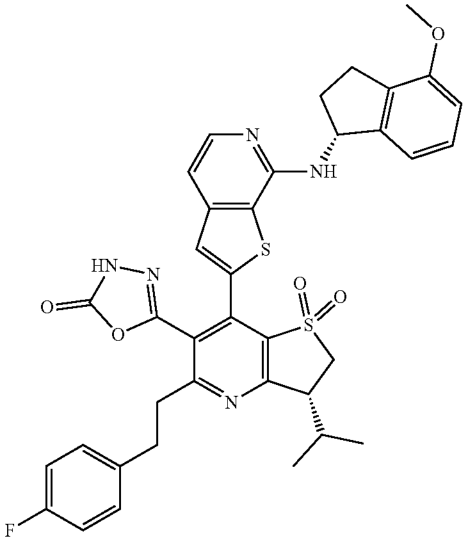 [SMILES: COc1cccc2c1CC[C@H]2Nc1nccc2cc(-c3c(-c4n[nH]c(=O)o4)c(CCc4ccc(F)cc4)nc4c3S(=O)(=O)C[C@@H]4C(C)C)sc12] |
| 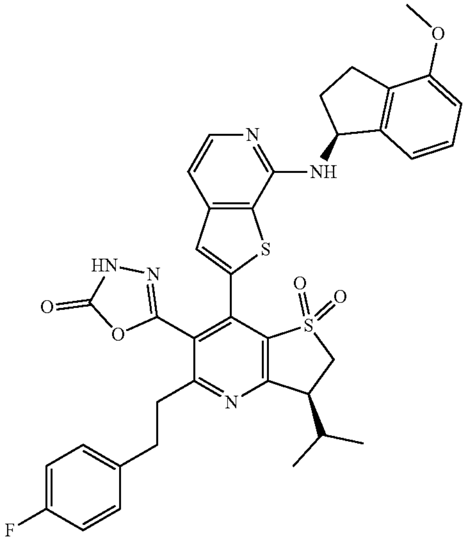 [SMILES: COc1cccc2c1CC[C@@H]2Nc1nccc2cc(-c3c(-c4n[nH]c(=O)o4)c(CCc4ccc(F)cc4)nc4c3S(=O)(=O)C[C@H]4C(C)C)sc12] |
| 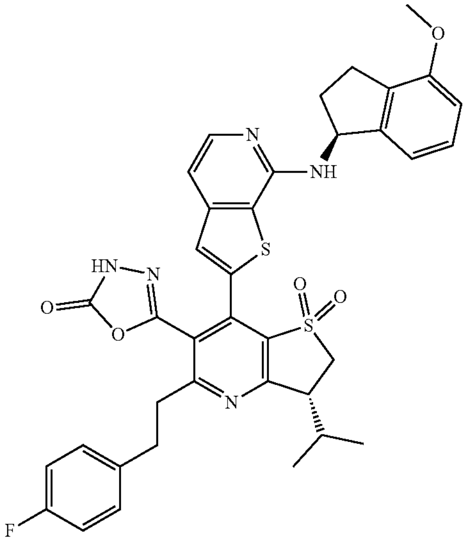 [SMILES: COc1cccc2c1CC[C@@H]2Nc1nccc2cc(-c3c(-c4n[nH]c(=O)o4)c(CCc4ccc(F)cc4)nc4c3S(=O)(=O)C[C@@H]4C(C)C)sc12] |

TABLE 2-continued
| Structure |
| --- |
| 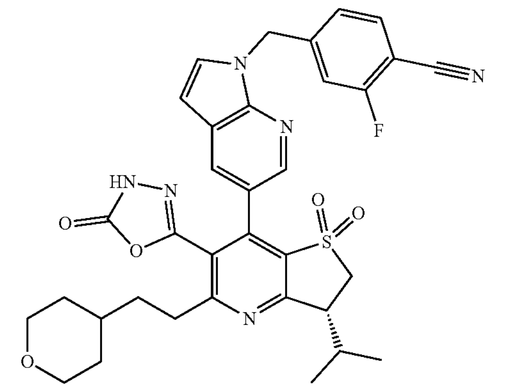 [SMILES: CC(C)[C@H]1CS(=O)(=O)c2c1nc(CCC1CCOCC1)c(-c1n[nH]c(=O)o1)c2-c1cnc2c(ccn2Cc2ccc(C#N)c(F)c2)c1] |
| 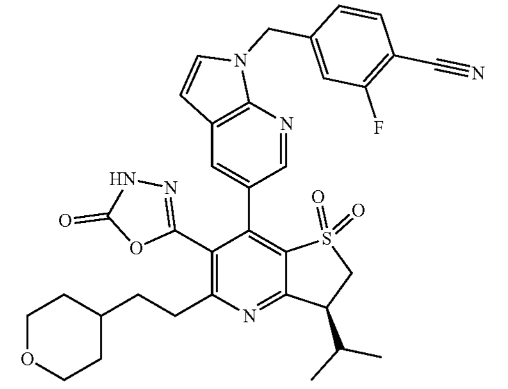 [SMILES: CC(C)[C@@H]1CS(=O)(=O)c2c1nc(CCC1CCOCC1)c(-c1n[nH]c(=O)o1)c2-c1cnc2c(ccn2Cc2ccc(C#N)c(F)c2)c1] |
| 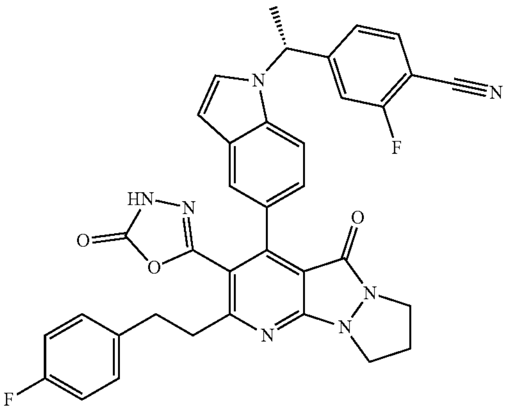 [SMILES: C[C@H](c1ccc(C#N)c(F)c1)n1ccc2cc(-c3c(-c4n[nH]c(=O)o4)c(CCc4ccc(F)cc4)nc4c3c(=O)n3n4CCC3)ccc21] |
| 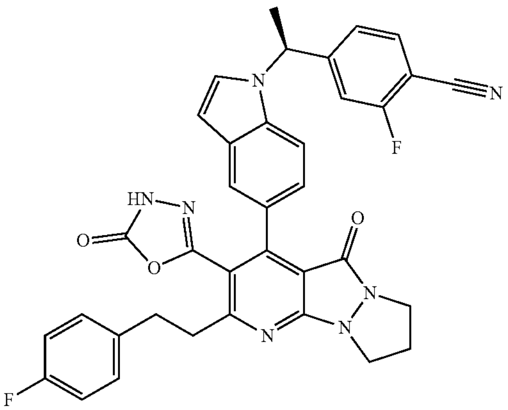 [SMILES: C[C@@H](c1ccc(C#N)c(F)c1)n1ccc2cc(-c3c(-c4n[nH]c(=O)o4)c(CCc4ccc(F)cc4)nc4c3c(=O)n3n4CCC3)ccc21] |
TABLE 2-continued
| Structure |
| --- |
| 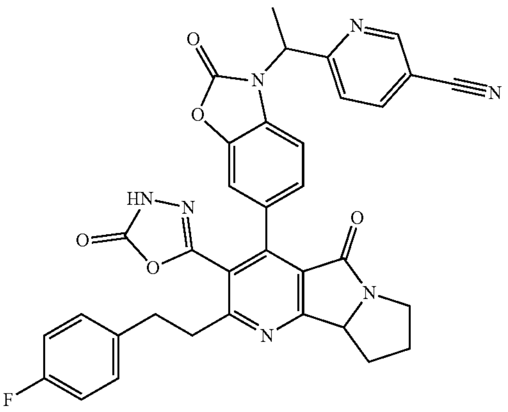 [SMILES: CC(c1ccc(C#N)cn1)n1c(=O)oc2cc(-c3c4c(nc(CCc5ccc(F)cc5)c3-c3n[nH]c(=O)o3)C3CCCN3C4=O)ccc21] |
| 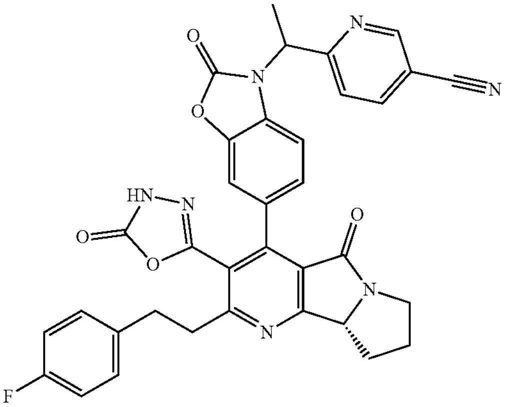 [SMILES: CC(c1ccc(C#N)cn1)n1c(=O)oc2cc(-c3c4c(nc(CCc5ccc(F)cc5)c3-c3n[nH]c(=O)o3)[C@H]3CCCN3C4=O)ccc21] |
| 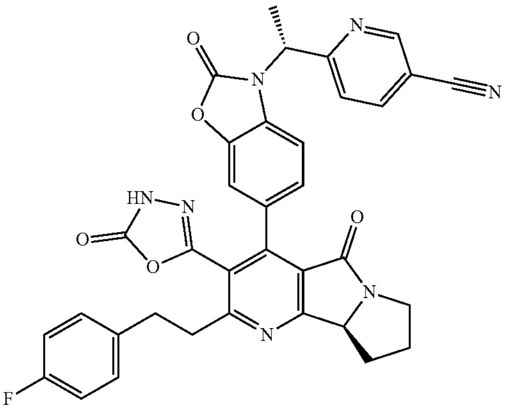 [SMILES: C[C@H](c1ccc(C#N)cn1)n1c(=O)oc2cc(-c3c4c(nc(CCc5ccc(F)cc5)c3-c3n[nH]c(=O)o3)[C@@H]3CCCN3C4=O)ccc21] |

TABLE 2-continued
| Structure |
| --- |
| 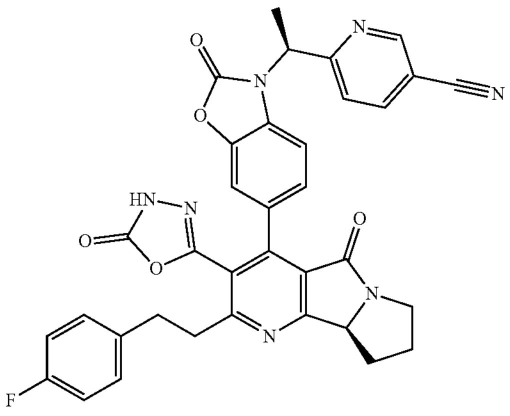 [SMILES: C[C@@H](c1ccc(C#N)cn1)n1c(=O)oc2cc(-c3c4c(nc(CCc5ccc(F)cc5)c3-c3n[nH]c(=O)o3)[C@@H]3CCCN3C4=O)ccc21] |
| 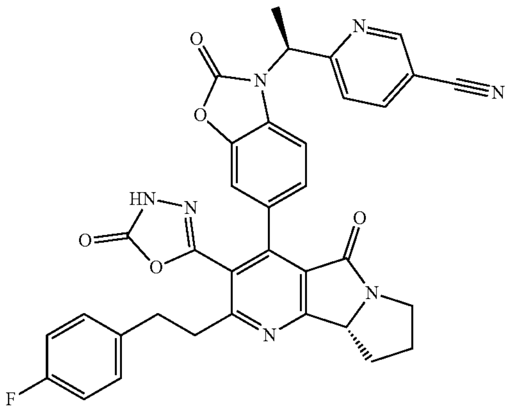 [SMILES: C[C@@H](c1ccc(C#N)cn1)n1c(=O)oc2cc(-c3c4c(nc(CCc5ccc(F)cc5)c3-c3n[nH]c(=O)o3)[C@H]3CCCN3C4=O)ccc21] |
| 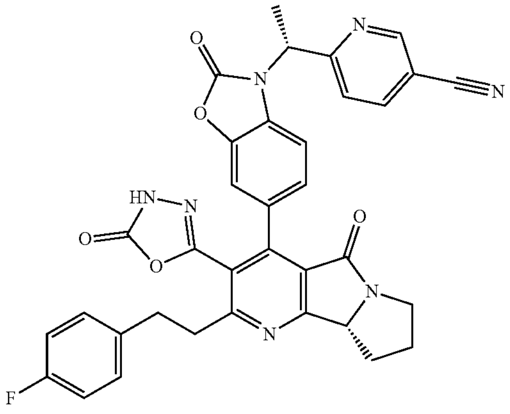 [SMILES: C[C@H](c1ccc(C#N)cn1)n1c(=O)oc2cc(-c3c4c(nc(CCc5ccc(F)cc5)c3-c3n[nH]c(=O)o3)[C@H]3CCCN3C4=O)ccc21] |
TABLE 2-continued
| Structure |
| --- |
| 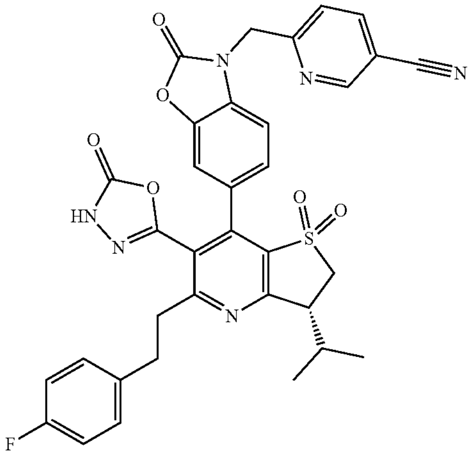 [SMILES: CC(C)[C@H]1CS(=O)(=O)c2c1nc(CCc1ccc(F)cc1)c(-c1n[nH]c(=O)o1)c2-c1ccc2c(c1)oc(=O)n2Cc1ccc(C#N)cn1] |
| 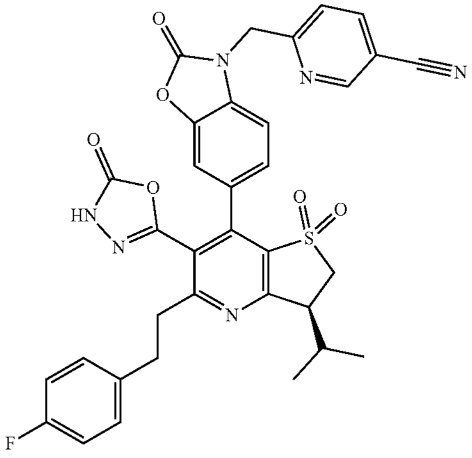 [SMILES: CC(C)[C@@H]1CS(=O)(=O)c2c1nc(CCc1ccc(F)cc1)c(-c1n[nH]c(=O)o1)c2-c1ccc2c(c1)oc(=O)n2Cc1ccc(C#N)cn1] |
| 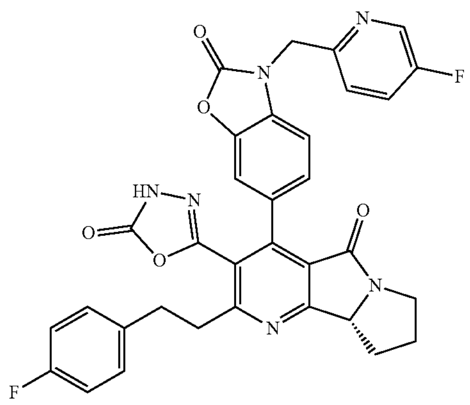 [SMILES: O=C1c2c(nc(CCc3ccc(F)cc3)c(-c3n[nH]c(=O)o3)c2-c2ccc3c(c2)oc(=O)n3Cc2ccc(F)cn2)[C@H]2CCCN12] |

TABLE 2-continued
| Structure |
| --- |
| 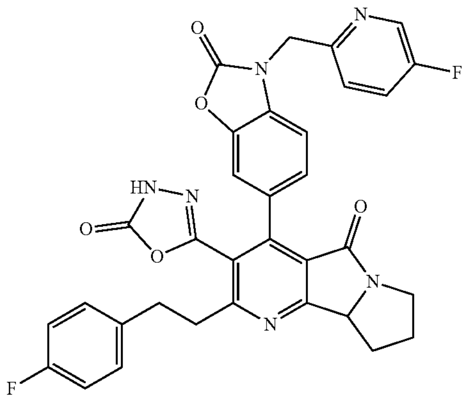 [SMILES: O=C1c2c(nc(CCc3ccc(F)cc3)c(-c3n[nH]c(=O)o3)c2-c2ccc3c(c2)oc(=O)n3Cc2ccc(F)cn2)C2CCCN12] |
| 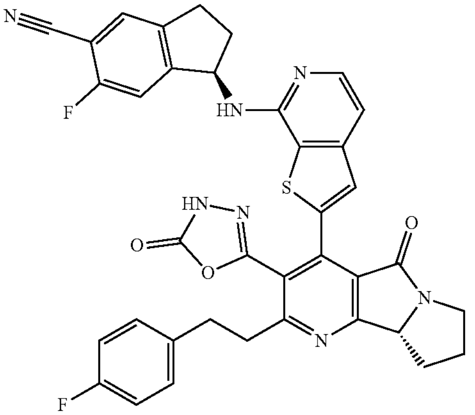 [SMILES: N#Cc1cc2c(cc1F)[C@H](Nc1nccc3cc(-c4c5c(nc(CCc6ccc(F)cc6)c4-c4n[nH]c(=O)o4)[C@H]4CCCN4C5=O)sc13)CC2] |
| 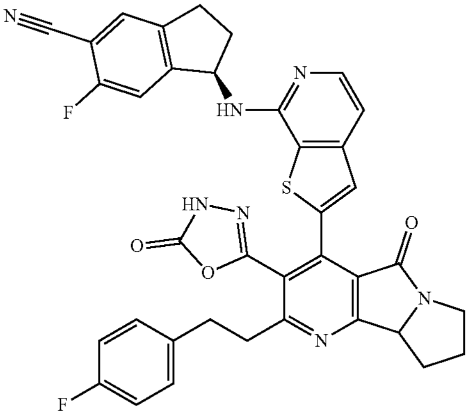 [SMILES: N#Cc1cc2c(cc1F)[C@H](Nc1nccc3cc(-c4c5c(nc(CCc6ccc(F)cc6)c4-c4n[nH]c(=O)o4)C4CCCN4C5=O)sc13)CC2] |
TABLE 2-continued
| Structure |
| --- |
| 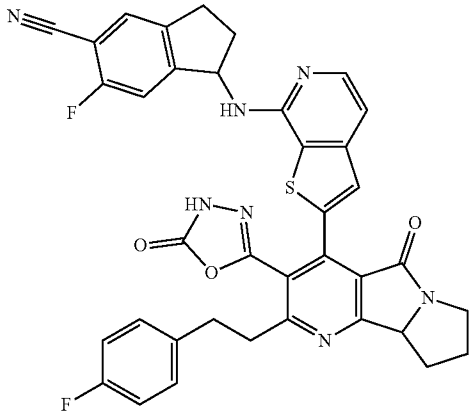 [SMILES: N#Cc1cc2c(cc1F)C(Nc1nccc3cc(-c4c5c(nc(CCc6ccc(F)cc6)c4-c4n[nH]c(=O)o4)C4CCCN4C5=O)sc13)CC2] |
| 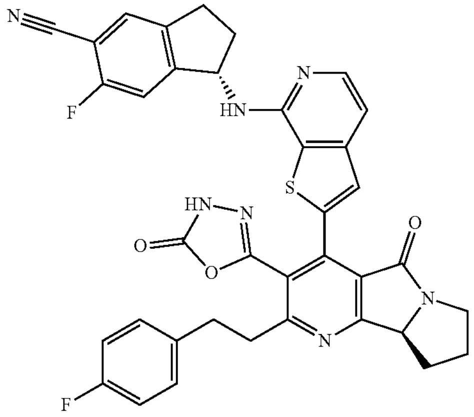 [SMILES: N#Cc1cc2c(cc1F)[C@@H](Nc1nccc3cc(-c4c5c(nc(CCc6ccc(F)cc6)c4-c4n[nH]c(=O)o4)[C@@H]4CCCN4C5=O)sc13)CC2] |
| 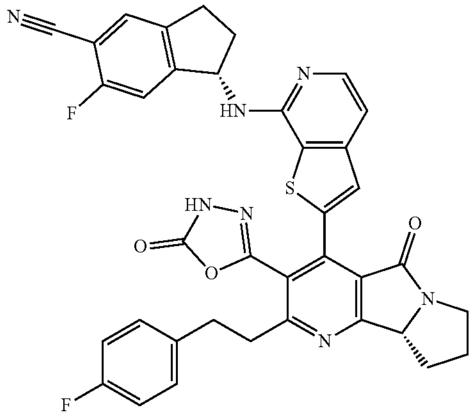 [SMILES: N#Cc1cc2c(cc1F)[C@@H](Nc1nccc3cc(-c4c5c(nc(CCc6ccc(F)cc6)c4-c4n[nH]c(=O)o4)[C@H]4CCCN4C5=O)sc13)CC2] |

TABLE 2-continued
| Structure |
| --- |
| 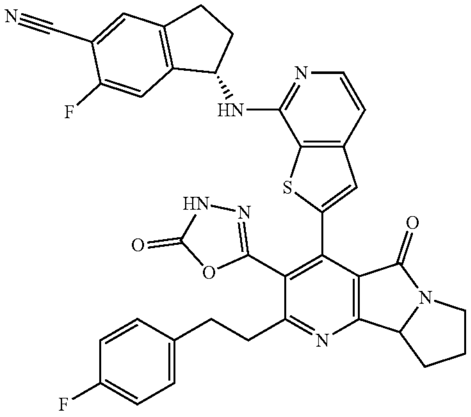 [SMILES: N#Cc1cc2c(cc1F)[C@@H](Nc1nccc3cc(-c4c5c(nc(CCc6ccc(F)cc6)c4-c4n[nH]c(=O)o4)C4CCCN4C5=O)sc13)CC2] |
| 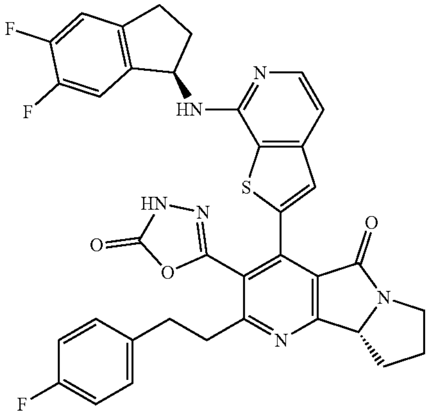 [SMILES: O=C1c2c(nc(CCc3ccc(F)cc3)c(-c3n[nH]c(=O)o3)c2-c2cc3ccnc(N[C@@H]4CCc5cc(F)c(F)cc54)c3s2)[C@H]2CCCN12] |
| 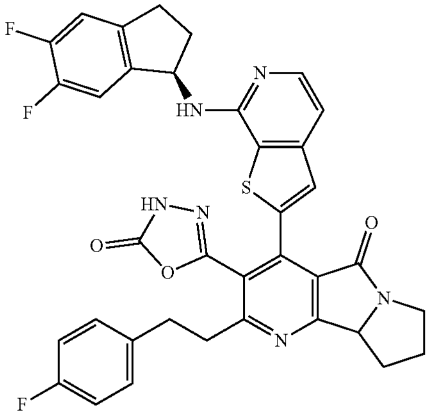 [SMILES: O=C1c2c(nc(CCc3ccc(F)cc3)c(-c3n[nH]c(=O)o3)c2-c2cc3ccnc(N[C@@H]4CCc5cc(F)c(F)cc54)c3s2)C2CCCN12] |
TABLE 2-continued
| Structure |
| --- |
| 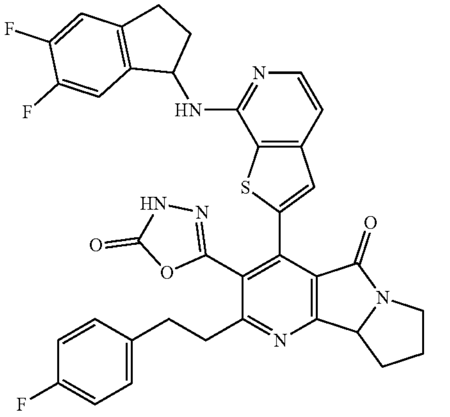 [SMILES: O=C1c2c(nc(CCc3ccc(F)cc3)c(-c3n[nH]c(=O)o3)c2-c2cc3ccnc(NC4CCc5cc(F)c(F)cc54)c3s2)C2CCCN12] |
| 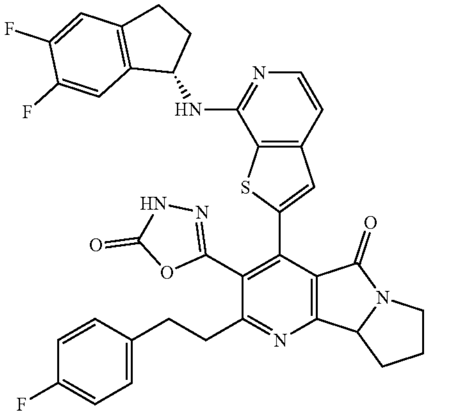 [SMILES: O=C1c2c(nc(CCc3ccc(F)cc3)c(-c3n[nH]c(=O)o3)c2-c2cc3ccnc(N[C@H]4CCc5cc(F)c(F)cc54)c3s2)C2CCCN12] |
| 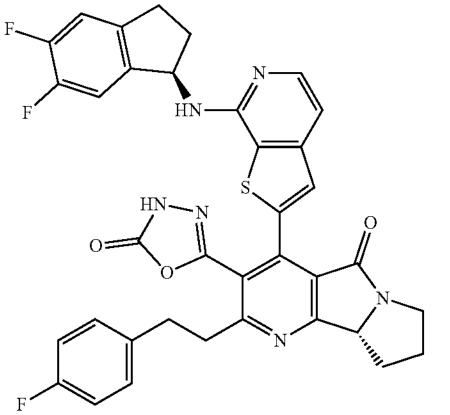 [SMILES: O=C1c2c(nc(CCc3ccc(F)cc3)c(-c3n[nH]c(=O)o3)c2-c2cc3ccnc(N[C@@H]4CCc5cc(F)c(F)cc54)c3s2)[C@H]2CCCN12] |

TABLE 2-continued
| Structure |
|---|
| 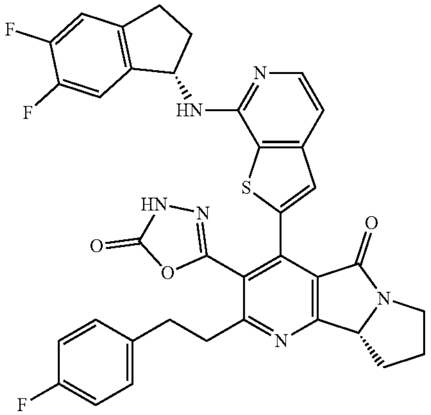 [SMILES: O=C1c2c(nc(CCc3ccc(F)cc3)c(-c3n[nH]c(=O)o3)c2-c2cc3ccnc(N[C@H]4CCc5cc(F)c(F)cc54)c3s2)[C@H]2CCCN12] |
| 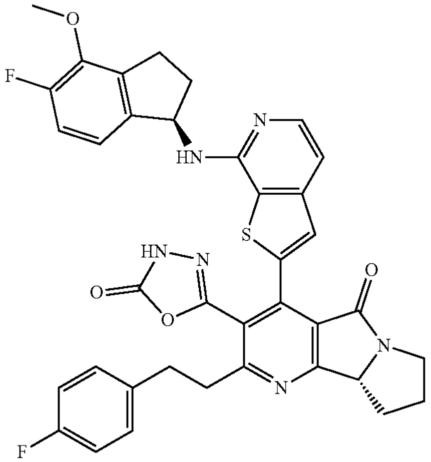 [SMILES: COc1c(F)ccc2c1CC[C@H]2Nc1nccc2cc(-c3c4c(nc(CCc5ccc(F)cc5)c3-c3n[nH]c(=O)o3)[C@H]3CCCN3C4=O)sc12] |
| 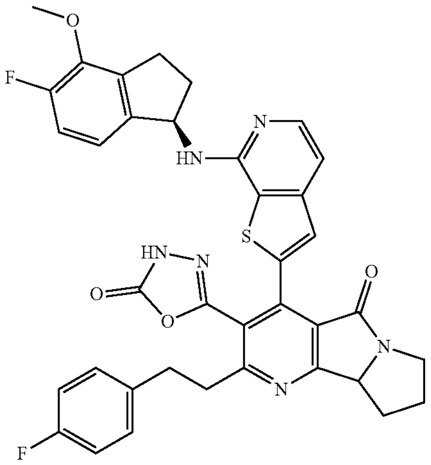 [SMILES: COc1c(F)ccc2c1CC[C@H]2Nc1nccc2cc(-c3c4c(nc(CCc5ccc(F)cc5)c3-c3n[nH]c(=O)o3)C3CCCN3C4=O)sc12] |
TABLE 2-continued
| Structure |
|---|
| 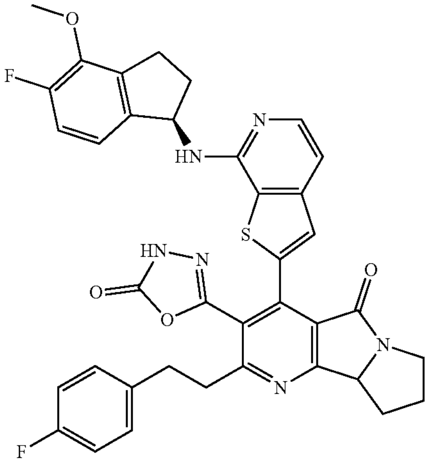 [SMILES: COc1c(F)ccc2c1CC[C@H]2Nc1nccc2cc(-c3c4c(nc(CCc5ccc(F)cc5)c3-c3n[nH]c(=O)o3)C3CCCN3C4=O)sc12] |
| 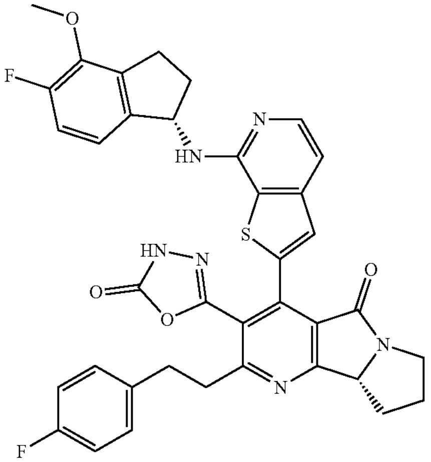 [SMILES: COc1c(F)ccc2c1CC[C@@H]2Nc1nccc2cc(-c3c4c(nc(CCc5ccc(F)cc5)c3-c3n[nH]c(=O)o3)[C@H]3CCCN3C4=O)sc12] |
| 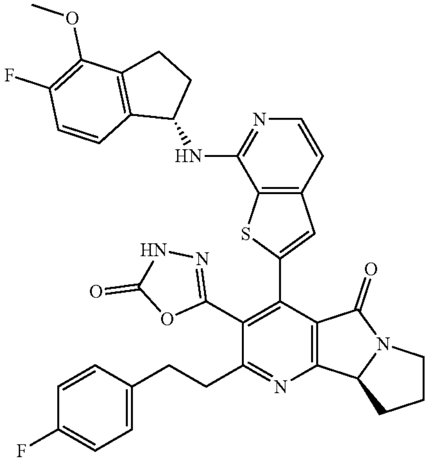 [SMILES: COc1c(F)ccc2c1CC[C@@H]2Nc1nccc2cc(-c3c4c(nc(CCc5ccc(F)cc5)c3-c3n[nH]c(=O)o3)[C@@H]3CCCN3C4=O)sc12] |

TABLE 2-continued
| Structure |
|---|
| 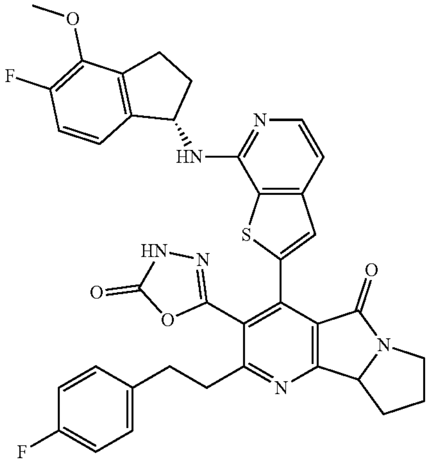 [SMILES: COc1c(F)ccc2c1CC[C@@H]2Nc1nccc2cc(-c3c4c(nc(CCc5ccc(F)cc5)c3-c3n[nH]c(=O)o3)C3CCCN3C4=O)sc12] |
| 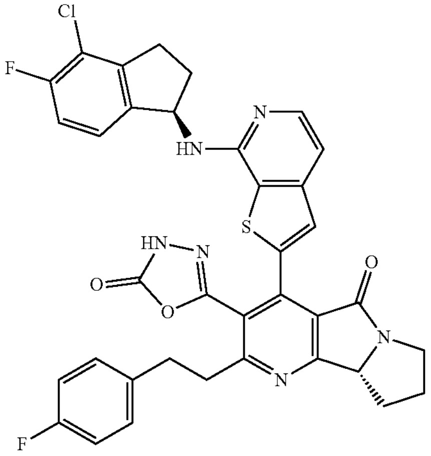 [SMILES: O=C1c2c(nc(CCc3ccc(F)cc3)c(-c3n[nH]c(=O)o3)c2-c2cc3ccnc(N[C@@H]4CCc5c4ccc(F)c5Cl)c3s2)[C@H]2CCCN12] |
| 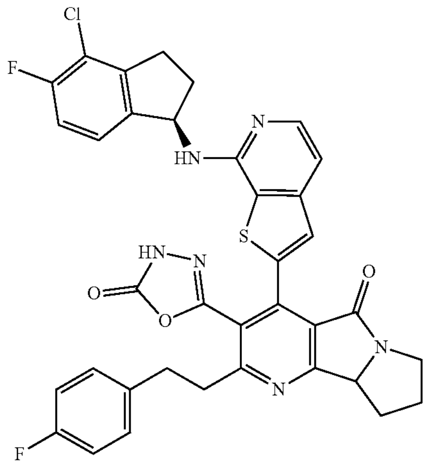 [SMILES: O=C1c2c(nc(CCc3ccc(F)cc3)c(-c3n[nH]c(=O)o3)c2-c2cc3ccnc(N[C@@H]4CCc5c4ccc(F)c5Cl)c3s2)C2CCCN12] |
TABLE 2-continued
| Structure |
|---|
| 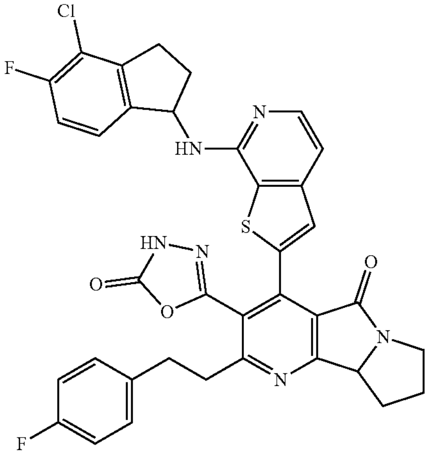 [SMILES: O=C1c2c(nc(CCc3ccc(F)cc3)c(-c3n[nH]c(=O)o3)c2-c2cc3ccnc(NC4CCc5c4ccc(F)c5Cl)c3s2)C2CCCN12] |
| 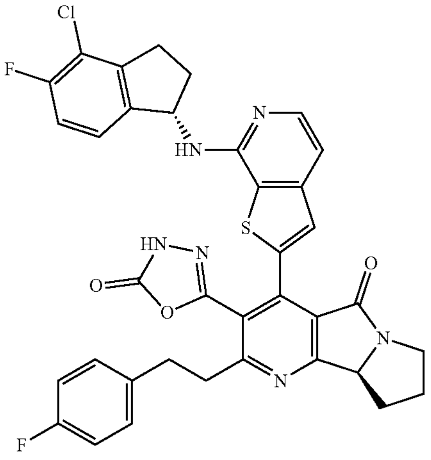 [SMILES: O=C1c2c(nc(CCc3ccc(F)cc3)c(-c3n[nH]c(=O)o3)c2-c2cc3ccnc(N[C@H]4CCc5c4ccc(F)c5Cl)c3s2)[C@@H]2CCCN12] |
| 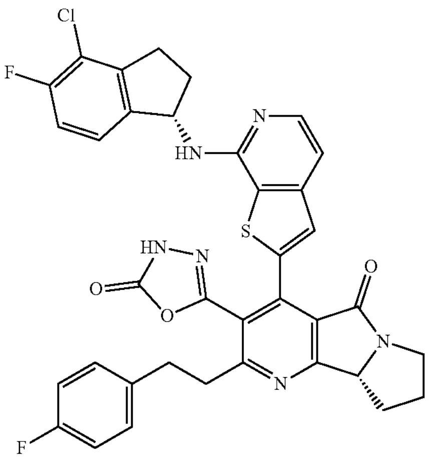 [SMILES: O=C1c2c(nc(CCc3ccc(F)cc3)c(-c3n[nH]c(=O)o3)c2-c2cc3ccnc(N[C@H]4CCc5c4ccc(F)c5Cl)c3s2)[C@H]2CCCN12] |

TABLE 2-continued
| Structure |
| --- |
| 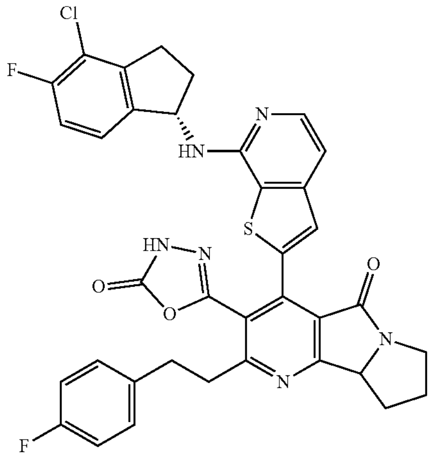 [SMILES: O=C1c2c(nc(CCc3ccc(F)cc3)c(-c3n[nH]c(=O)o3)c2-c2cc3ccnc(N[C@H]4CCc5c4ccc(F)c5Cl)c3s2)C2CCCN12] |
| 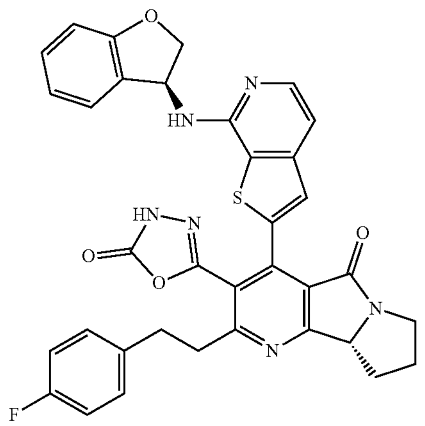 [SMILES: O=C1c2c(nc(CCc3ccc(F)cc3)c(-c3n[nH]c(=O)o3)c2-c2cc3ccnc(N[C@@H]4COc5ccccc54)c3s2)[C@H]2CCCN12] |
| 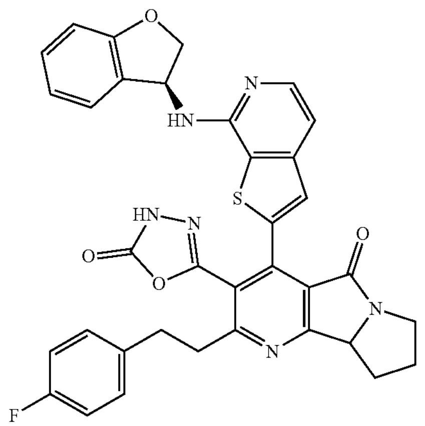 [SMILES: O=C1c2c(nc(CCc3ccc(F)cc3)c(-c3n[nH]c(=O)o3)c2-c2cc3ccnc(N[C@@H]4COc5ccccc54)c3s2)C2CCCN12] |
TABLE 2-continued
| Structure |
| --- |
| 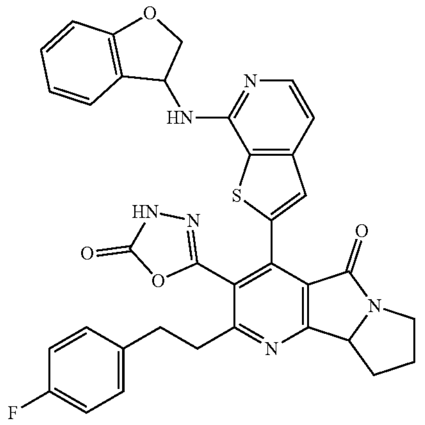 [SMILES: O=C1c2c(nc(CCc3ccc(F)cc3)c(-c3n[nH]c(=O)o3)c2-c2cc3ccnc(NC4COc5ccccc54)c3s2)C2CCCN12] |
| 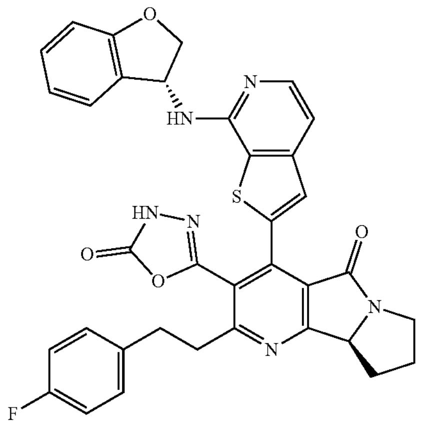 [SMILES: O=C1c2c(nc(CCc3ccc(F)cc3)c(-c3n[nH]c(=O)o3)c2-c2cc3ccnc(N[C@H]4COc5ccccc54)c3s2)[C@@H]2CCCN12] |
| 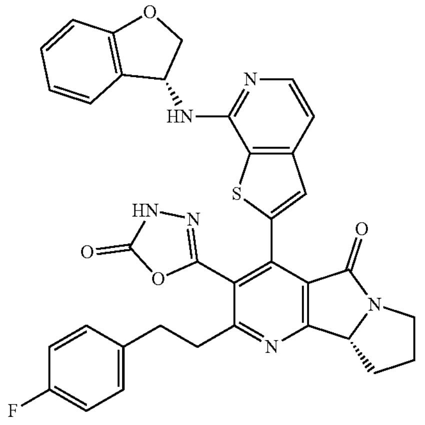 [SMILES: O=C1c2c(nc(CCc3ccc(F)cc3)c(-c3n[nH]c(=O)o3)c2-c2cc3ccnc(N[C@H]4COc5ccccc54)c3s2)[C@H]2CCCN12] |

TABLE 2-continued
| Structure |
| --- |
| 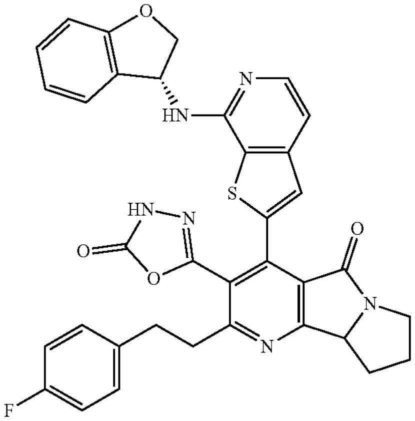 [SMILES: O=C1c2c(nc(CCc3ccc(F)cc3)c(-c3n[nH]c(=O)o3)c2-c2cc3ccnc(N[C@H]4COc5ccccc54)c3s2)C2CCCN12] |
| 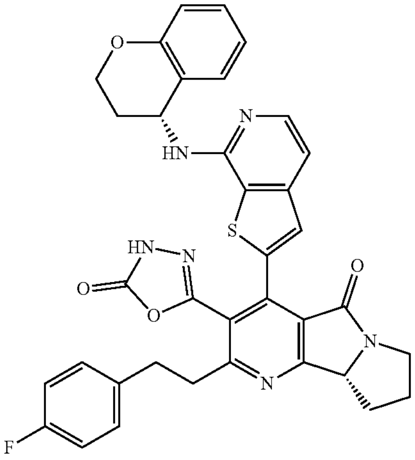 [SMILES: O=C1c2c(nc(CCc3ccc(F)cc3)c(-c3n[nH]c(=O)o3)c2-c2cc3ccnc(N[C@@H]4CCOc5ccccc54)c3s2)[C@H]2CCCN12] |
| 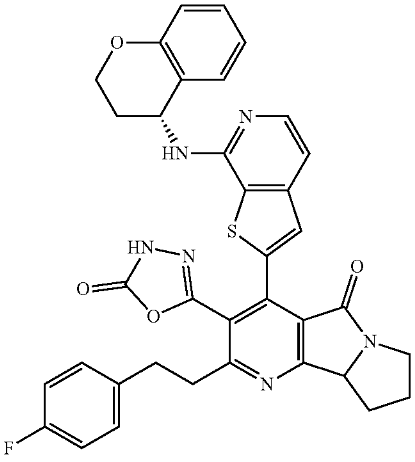 [SMILES: O=C1c2c(nc(CCc3ccc(F)cc3)c(-c3n[nH]c(=O)o3)c2-c2cc3ccnc(N[C@@H]4CCOc5ccccc54)c3s2)C2CCCN12] |
TABLE 2-continued
| Structure |
| --- |
| 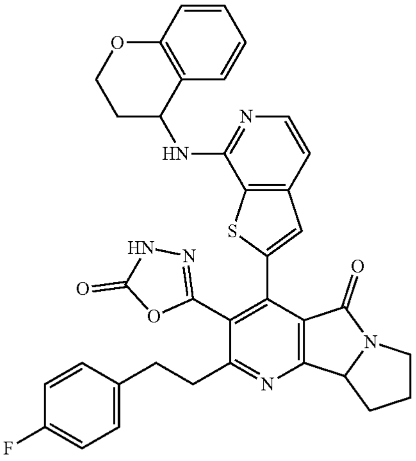 [SMILES: O=C1c2c(nc(CCc3ccc(F)cc3)c(-c3n[nH]c(=O)o3)c2-c2cc3ccnc(NC4CCOc5ccccc54)c3s2)C2CCCN12] |
| 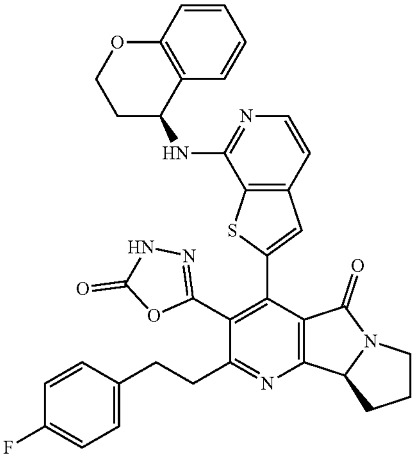 [SMILES: O=C1c2c(nc(CCc3ccc(F)cc3)c(-c3n[nH]c(=O)o3)c2-c2cc3ccnc(N[C@H]4CCOc5ccccc54)c3s2)[C@@H]2CCCN12] |
| 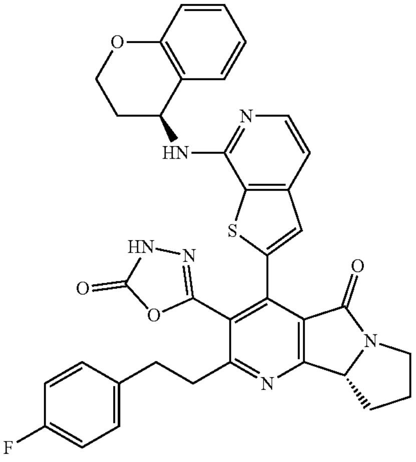 [SMILES: O=C1c2c(nc(CCc3ccc(F)cc3)c(-c3n[nH]c(=O)o3)c2-c2cc3ccnc(N[C@H]4CCOc5ccccc54)c3s2)C2CCCN12] |

TABLE 2-continued
| Structure |
| --- |
| 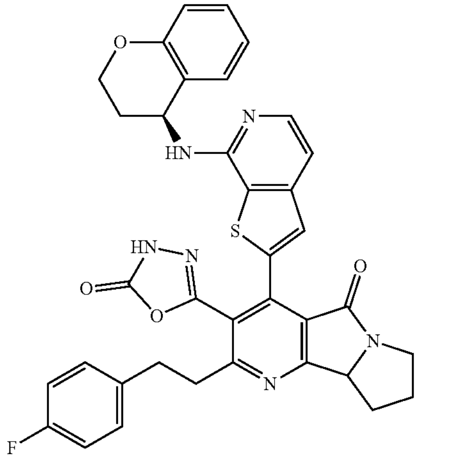 |
| 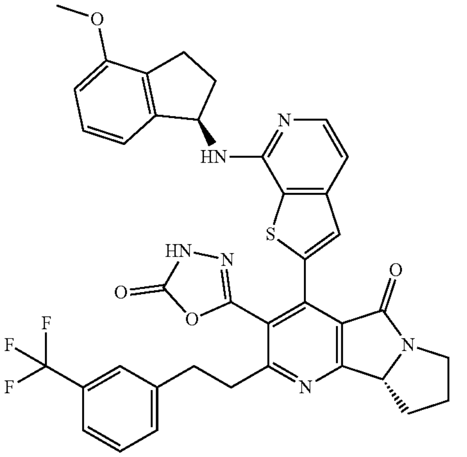 |
| 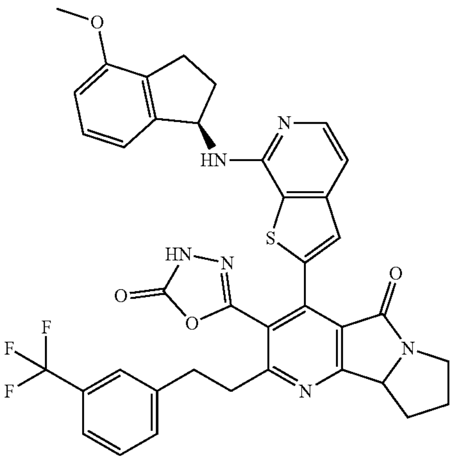 [SMILES: COc1cccc2c1CC[C@H]2Nc1nccc2cc(-c3c4c(nc(CCc5cccc(C(F)(F)F)c5)c3-c3n[nH]c(=O)o3)[C@H]3CCCN3C4=O)sc12] |
TABLE 2-continued
| Structure |
| --- |
| 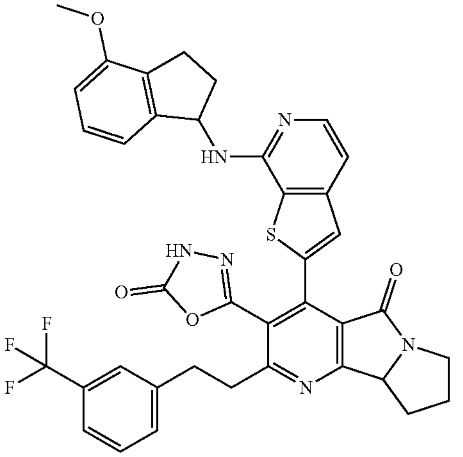 |
| 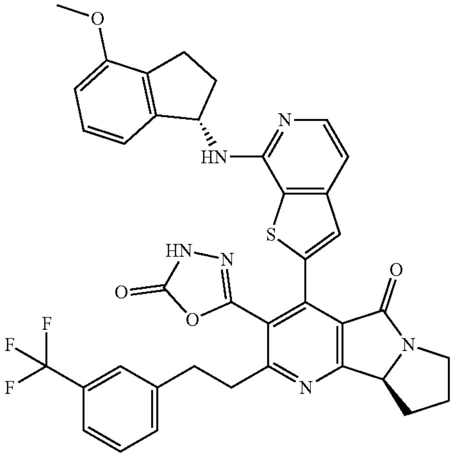 [SMILES: COc1cccc2c1CC[C@@H]2Nc1nccc2cc(-c3c4c(nc(CCc5cccc(C(F)(F)F)c5)c3-c3n[nH]c(=O)o3)[C@@H]3CCCN3C4=O)sc12] |
| 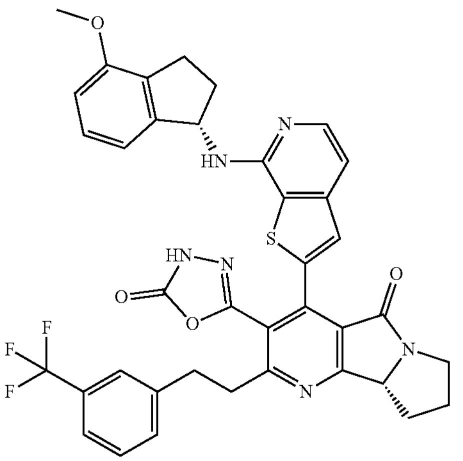 |

TABLE 2-continued
| Structure |
| --- |
| 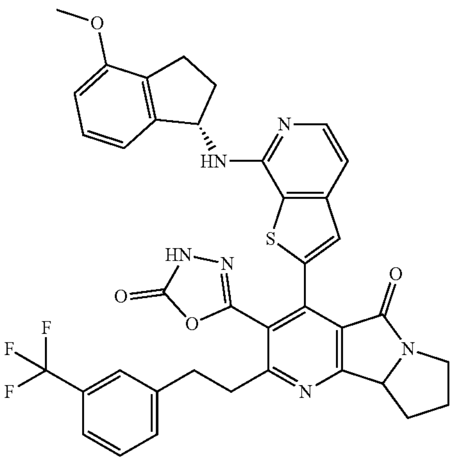 [SMILES: COc1cccc2c1CC[C@@H]2Nc1nccc2cc(-c3c4c(nc(CCc5cccc(C(F)(F)F)c5)c3-c3n[nH]c(=O)o3)[C@H]3CCCN3C4=O)sc12] |
| 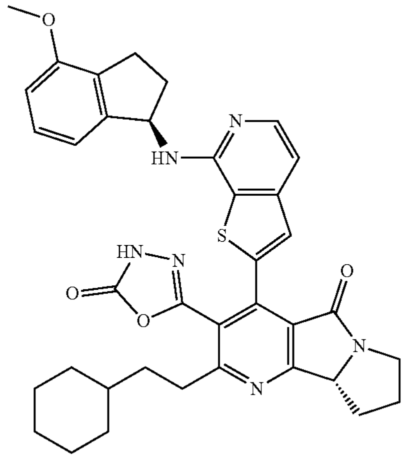 [SMILES: COc1cccc2c1CC[C@H]2Nc1nccc2cc(-c3c4c(nc(CCC5CCCCC5)c3-c3n[nH]c(=O)o3)[C@H]3CCCN3C4=O)sc12] |
| 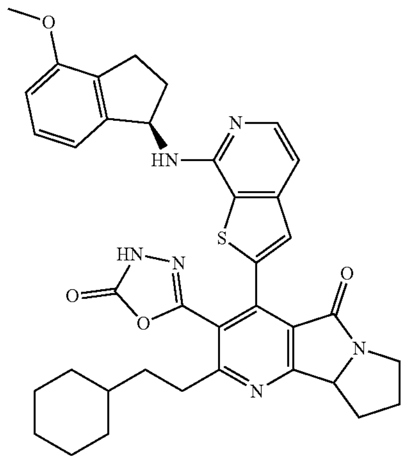 [SMILES: COc1cccc2c1CC[C@H]2Nc1nccc2cc(-c3c4c(nc(CCC5CCCCC5)c3-c3n[nH]c(=O)o3)C3CCCN3C4=O)sc12] |
TABLE 2-continued
| Structure |
| --- |
| 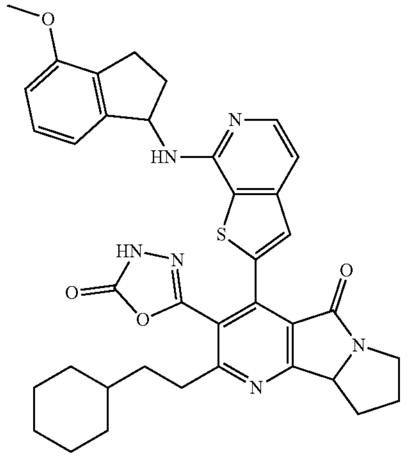 [SMILES: COc1cccc2c1CCC2Nc1nccc2cc(-c3c4c(nc(CCC5CCCCC5)c3-c3n[nH]c(=O)o3)C3CCCN3C4=O)sc12] |
| 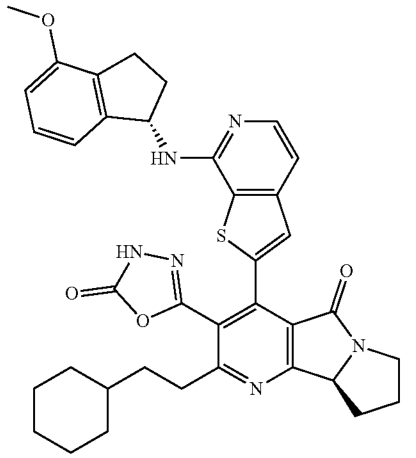 [SMILES: COc1cccc2c1CC[C@@H]2Nc1nccc2cc(-c3c4c(nc(CCC5CCCCC5)c3-c3n[nH]c(=O)o3)[C@@H]3CCCN3C4=O)sc12] |
| 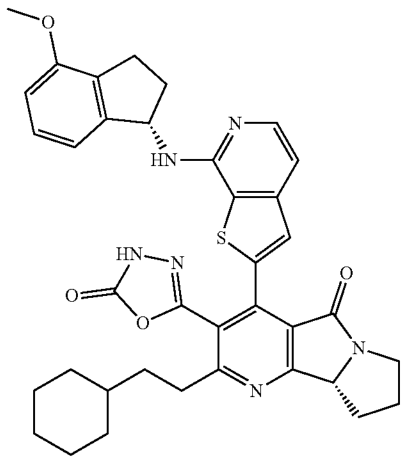 [SMILES: COc1cccc2c1CC[C@@H]2Nc1nccc2cc(-c3c4c(nc(CCC5CCCCC5)c3-c3n[nH]c(=O)o3)[C@H]3CCCN3C4=O)sc12] |

TABLE 2-continued
| Structure |
|---|
| 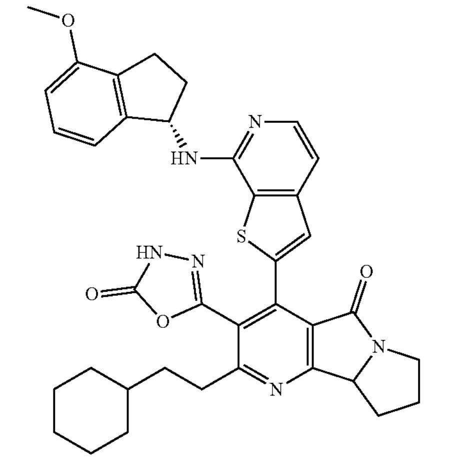 |
| 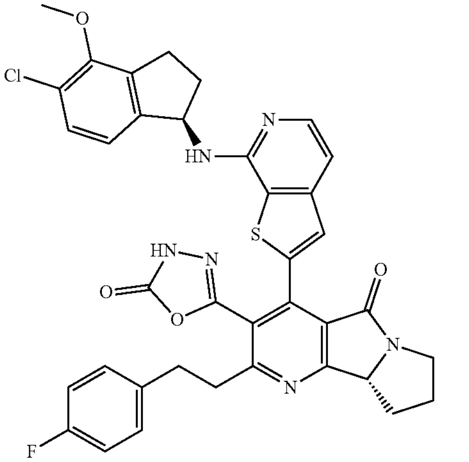 [SMILES: COc1c(Cl)ccc2c1CC[C@H]2Nc1nccc2cc(-c3c4c(nc(CCc5ccc(F)cc5)c3-c3n[nH]c(=O)o3)[C@H]3CCCN3C4=O)sc12] |
| 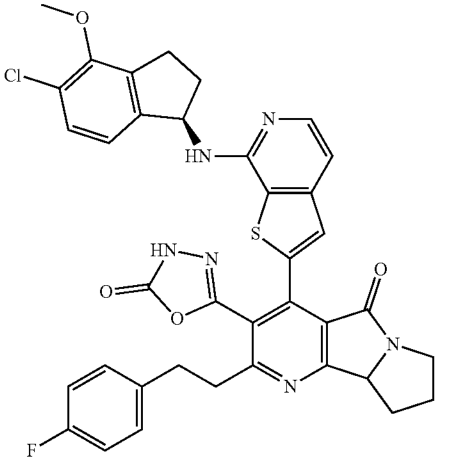 [SMILES: COc1c(Cl)ccc2c1CC[C@H]2Nc1nccc2cc(-c3c4c(nc(CCc5ccc(F)cc5)c3-c3n[nH]c(=O)o3)C3CCCN3C4=O)sc12] |
TABLE 2-continued
| Structure |
|---|
| 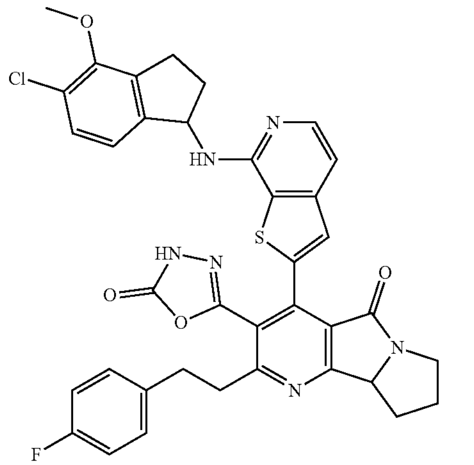 [SMILES: COc1c(Cl)ccc2c1CCC2Nc1nccc2cc(-c3c4c(nc(CCc5ccc(F)cc5)c3-c3n[nH]c(=O)o3)C3CCCN3C4=O)sc12] |
| 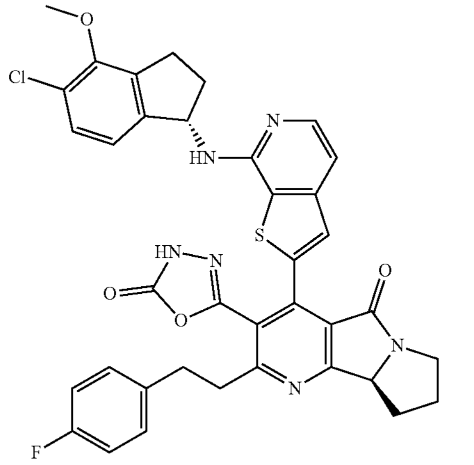 [SMILES: COc1c(Cl)ccc2c1CC[C@@H]2Nc1nccc2cc(-c3c4c(nc(CCc5ccc(F)cc5)c3-c3n[nH]c(=O)o3)[C@@H]3CCCN3C4=O)sc12] |
| 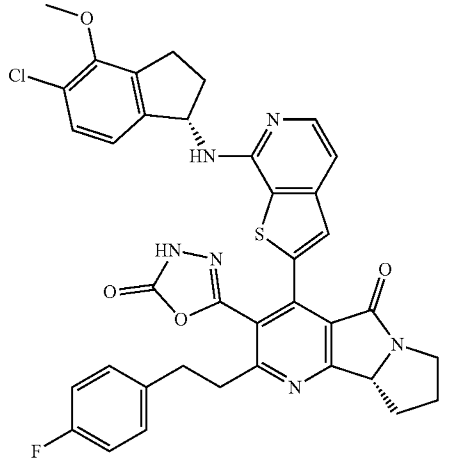 [SMILES: COc1c(Cl)ccc2c1CC[C@@H]2Nc1nccc2cc(-c3c4c(nc(CCc5ccc(F)cc5)c3-c3n[nH]c(=O)o3)[C@H]3CCCN3C4=O)sc12] |

TABLE 2-continued
| Structure |
| --- |
| 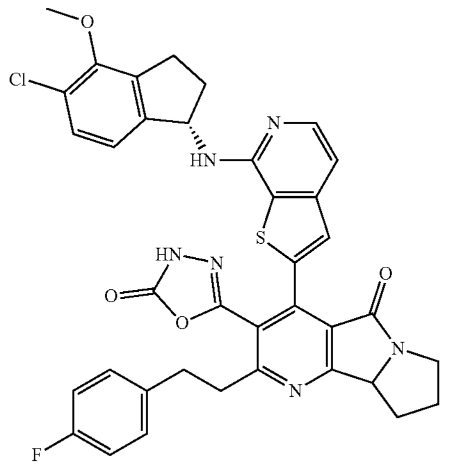 [SMILES: COc1c(Cl)ccc2c1CC[C@@H]2Nc1nccc2cc(-c3c4c(nc(CCc5ccc(F)cc5)c3-c3n[nH]c(=O)o3)C3CCCN3C4=O)sc12] |
| 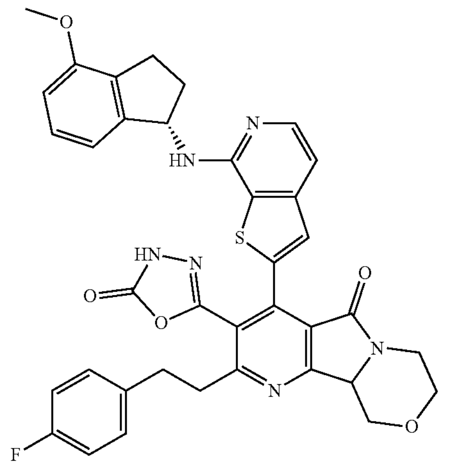 [SMILES: COc1cccc2c1CC[C@@H]2Nc1nccc2cc(-c3c4c(nc(CCc5ccc(F)cc5)c3-c3n[nH]c(=O)o3)C3COCCN3C4=O)sc12] |
| 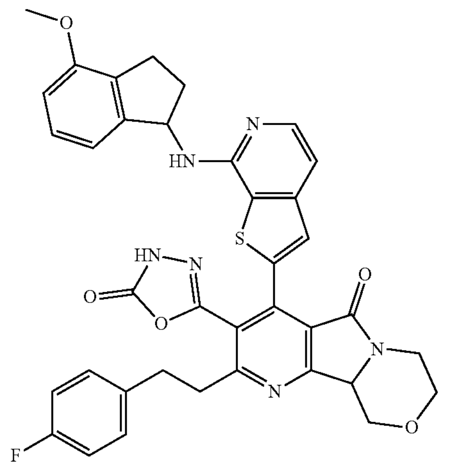 [SMILES: COc1cccc2c1CCC2Nc1nccc2cc(-c3c4c(nc(CCc5ccc(F)cc5)c3-c3n[nH]c(=O)o3)C3COCCN3C4=O)sc12] |
TABLE 2-continued
| Structure |
| --- |
| 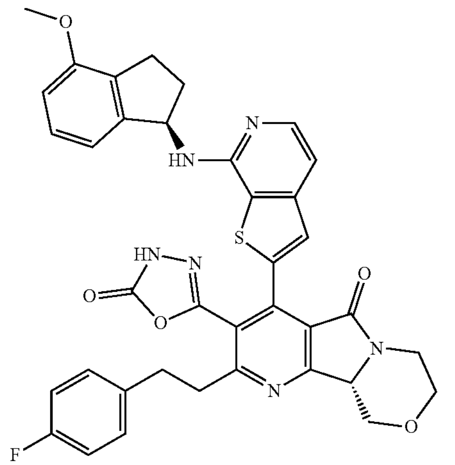 [SMILES: COc1cccc2c1CC[C@H]2Nc1nccc2cc(-c3c4c(nc(CCc5ccc(F)cc5)c3-c3n[nH]c(=O)o3)[C@H]3COCCN3C4=O)sc12] |
| 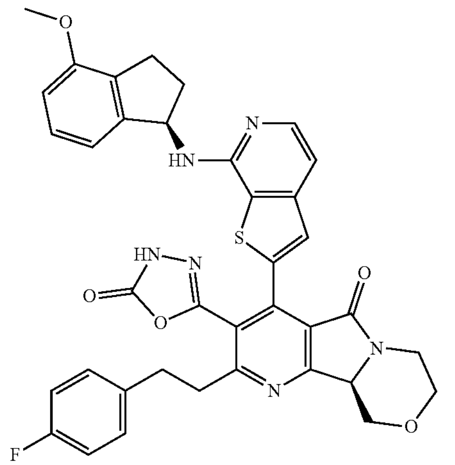 [SMILES: COc1cccc2c1CC[C@H]2Nc1nccc2cc(-c3c4c(nc(CCc5ccc(F)cc5)c3-c3n[nH]c(=O)o3)[C@@H]3COCCN3C4=O)sc12] |
| 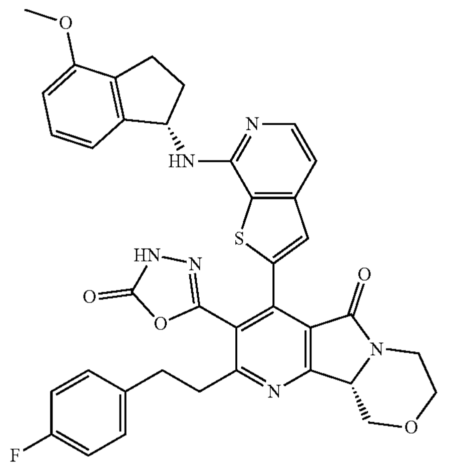 [SMILES: COc1cccc2c1CC[C@@H]2Nc1nccc2cc(-c3c4c(nc(CCc5ccc(F)cc5)c3-c3n[nH]c(=O)o3)[C@H]3COCCN3C4=O)sc12] |

| Structure |
|---|
| 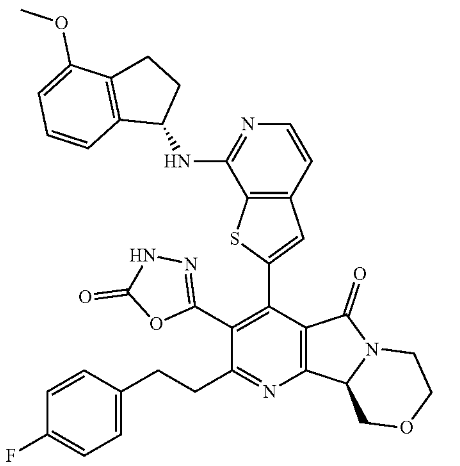 [SMILES: COc1cccc2c1CC[C@@H]2Nc1nccc2cc(-c3c4c(nc(CCc5ccc(F)cc5)c3-c3n[nH]c(=O)o3)[C@@H]3COCCN3C4=O)sc12] |
| 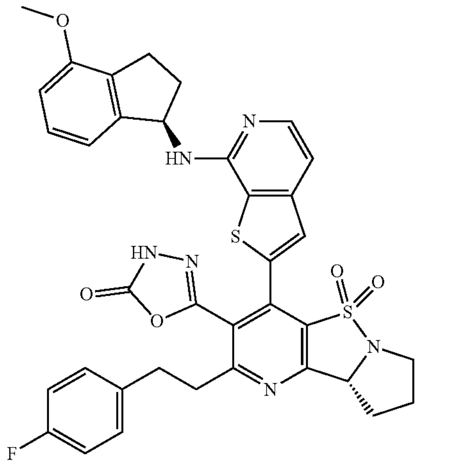 [SMILES: COc1cccc2c1CC[C@H]2Nc1nccc2cc(-c3c(-c4n[nH]c(=O)o4)c(CCc4ccc(F)cc4)nc4c3S(=O)(=O)N3CCC[C@H]43)sc12] |
| 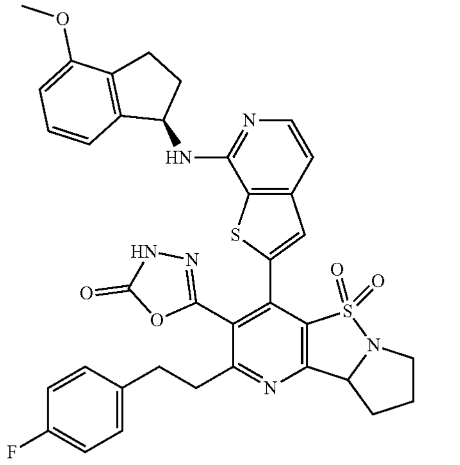 [SMILES: COc1cccc2c1CC[C@H]2Nc1nccc2cc(-c3c(-c4n[nH]c(=O)o4)c(CCc4ccc(F)cc4)nc4c3S(=O)(=O)N3CCCC43)sc12] |
| Structure |
|---|
| 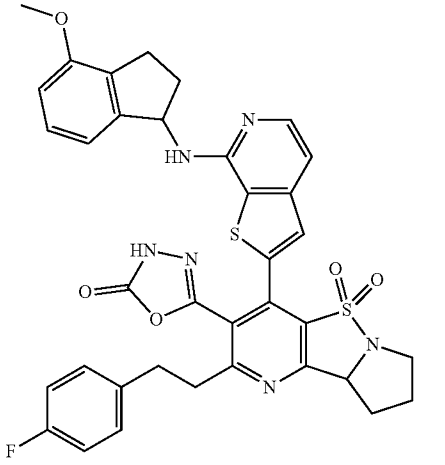 |
| 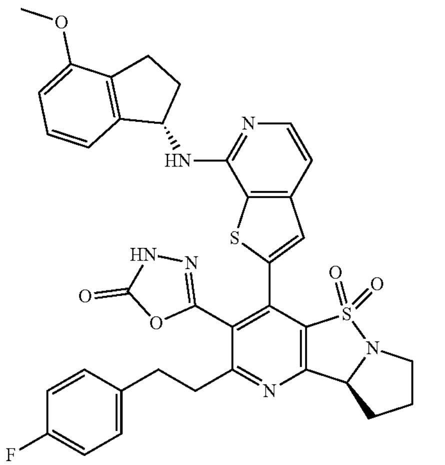 [SMILES: COc1cccc2c1CC[C@@H]2Nc1nccc2cc(-c3c(-c4n[nH]c(=O)o4)c(CCc4ccc(F)cc4)nc4c3S(=O)(=O)N3CCC[C@@H]43)sc12] |
| 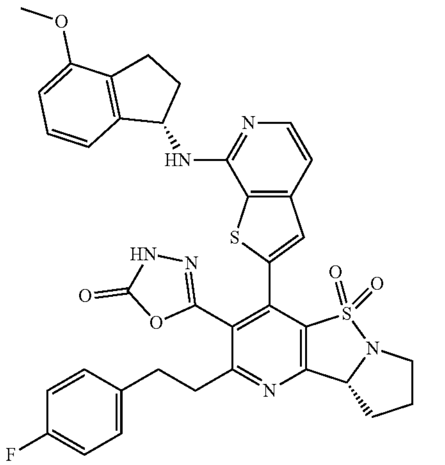 [SMILES: COc1cccc2c1CC[C@@H]2Nc1nccc2cc(-c3c(-c4n[nH]c(=O)o4)c(CCc4ccc(F)cc4)nc4c3S(=O)(=O)N3CCC[C@H]43)sc12] |

TABLE 2-continued
| Structure |
|---|
| 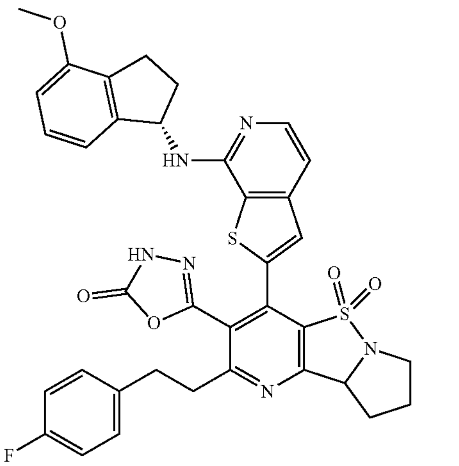 [SMILES: COc1cccc2c1CC[C@@H]2Nc1nccc2cc(-c3c(-c4n[nH]c(=O)o4)c(CCc4ccc(F)cc4)nc4c3S(=O)(=O)N3CCCC43)sc12] |
| 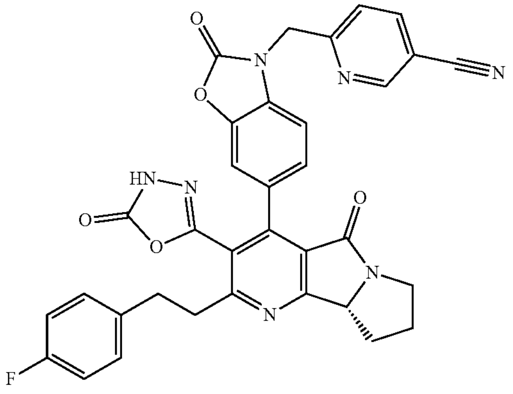 |
| 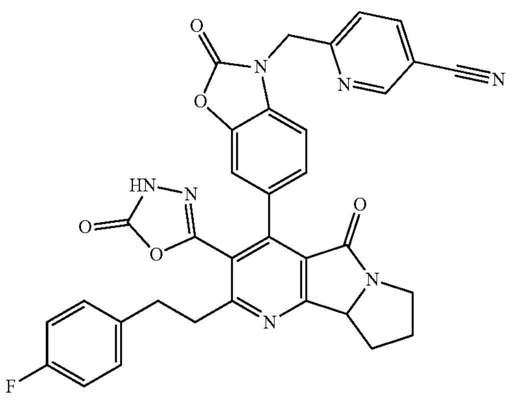 [SMILES: N#Cc1ccc(Cn2c(=O)oc3cc(-c4c5c(nc(CCc6ccc(F)cc6)c4-c4n[nH]c(=O)o4)[C@H]4CCCN4C5=O)ccc32)nc1] |
TABLE 2-continued
| Structure |
|---|
| 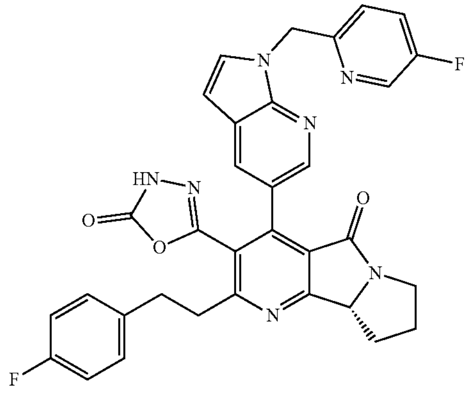 |
| 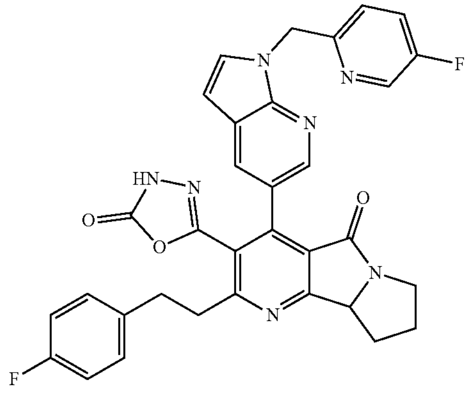 [SMILES: O=C1c2c(nc(CCc3ccc(F)cc3)c(-c3n[nH]c(=O)o3)c2-c2cnc3c(ccn3Cc3ccc(F)cn3)c2)C2CCCN12] |
| 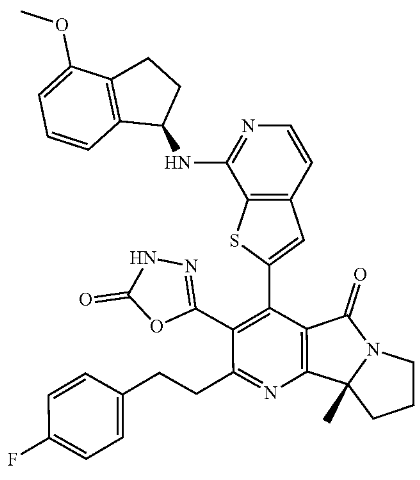 [SMILES: COc1cccc2c1CC[C@H]2Nc1nccc2cc(-c3c4c(nc(CCc5ccc(F)cc5)c3-c3n[nH]c(=O)o3)[C@@]3(C)CCCN3C4=O)sc12] |

TABLE 2-continued
| Structure |
|---|
| 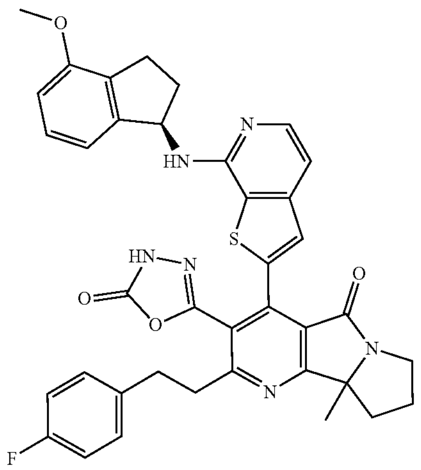 [SMILES: COc1cccc2c1CC[C@H]2Nc1nccc2cc(-c3c4c(nc(CCc5ccc(F)cc5)c3-c3n[nH]c(=O)o3)C3(C)CCCN3C4=O)sc12] |
| 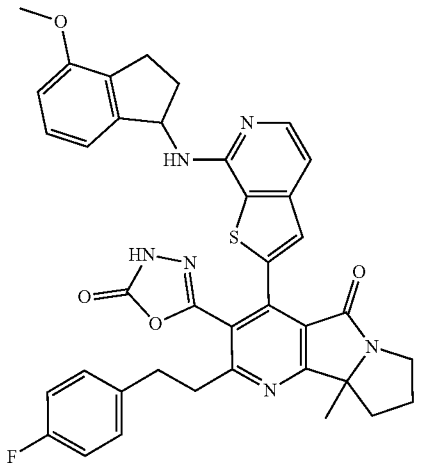 [SMILES: COc1cccc2c1CCC2Nc1nccc2cc(-c3c4c(nc(CCc5ccc(F)cc5)c3-c3n[nH]c(=O)o3)C3(C)CCCN3C4=O)sc12] |
| 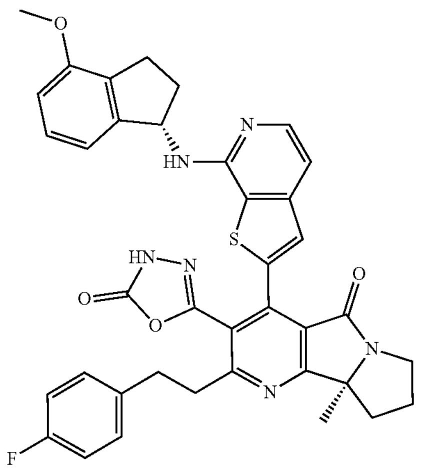 [SMILES: COc1cccc2c1CC[C@@H]2Nc1nccc2cc(-c3c4c(nc(CCc5ccc(F)cc5)c3-c3n[nH]c(=O)o3)[C@]3(C)CCCN3C4=O)sc12] |
TABLE 2-continued
| Structure |
|---|
| 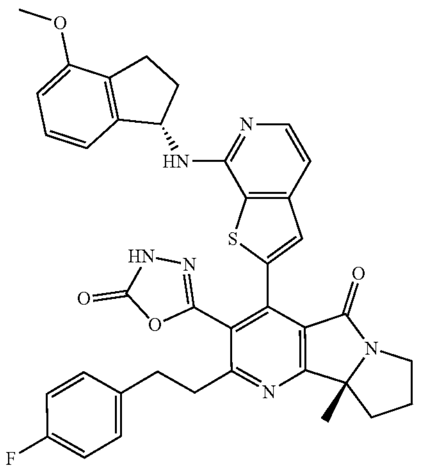 [SMILES: COc1cccc2c1CC[C@@H]2Nc1nccc2cc(-c3c4c(nc(CCc5ccc(F)cc5)c3-c3n[nH]c(=O)o3)[C@@]3(C)CCCN3C4=O)sc12] |
| 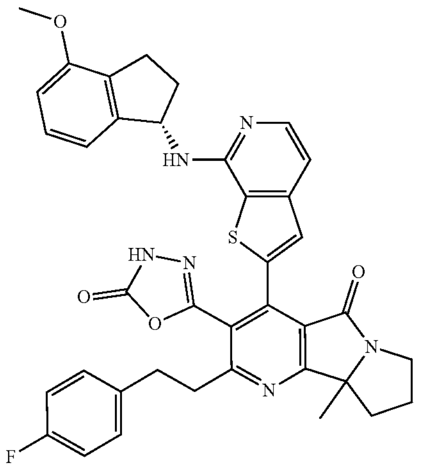 [SMILES: COc1cccc2c1CC[C@@H]2Nc1nccc2cc(-c3c4c(nc(CCc5ccc(F)cc5)c3-c3n[nH]c(=O)o3)C3(C)CCCN3C4=O)sc12] |
| 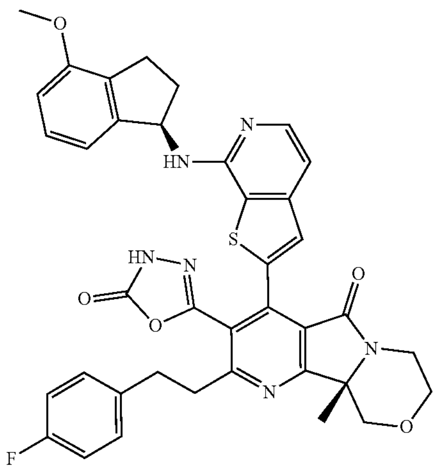 [SMILES: COc1cccc2c1CC[C@H]2Nc1nccc2cc(-c3c4c(nc(CCc5ccc(F)cc5)c3-c3n[nH]c(=O)o3)[C@@]3(C)COCCN3C4=O)sc12] |

TABLE 2-continued
| Structure |
| --- |
| 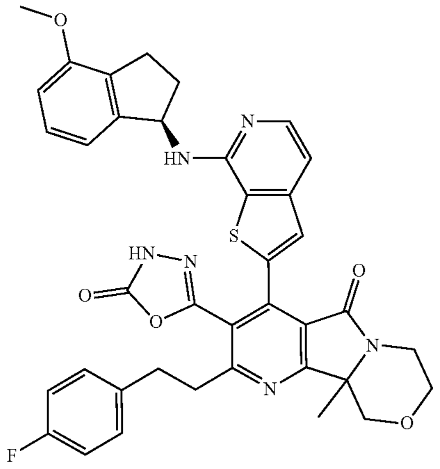 [SMILES: COc1cccc2c1CC[C@H]2Nc1nccc2cc(-c3c4c(nc(CCc5ccc(F)cc5)c3-c3n[nH]c(=O)o3)C3(C)COCCN3C4=O)sc12] |
| 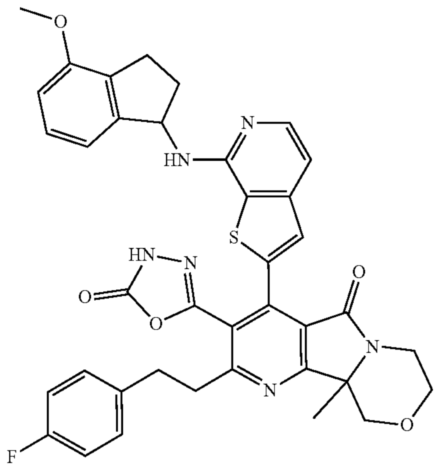 [SMILES: COc1cccc2c1CCC2Nc1nccc2cc(-c3c4c(nc(CCc5ccc(F)cc5)c3-c3n[nH]c(=O)o3)C3(C)COCCN3C4=O)sc12] |
| 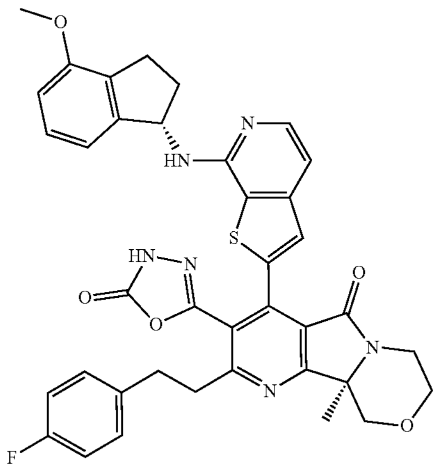 [SMILES: COc1cccc2c1CC[C@@H]2Nc1nccc2cc(-c3c4c(nc(CCc5ccc(F)cc5)c3-c3n[nH]c(=O)o3)[C@]3(C)COCCN3C4=O)sc12] |
TABLE 2-continued
| Structure |
| --- |
| 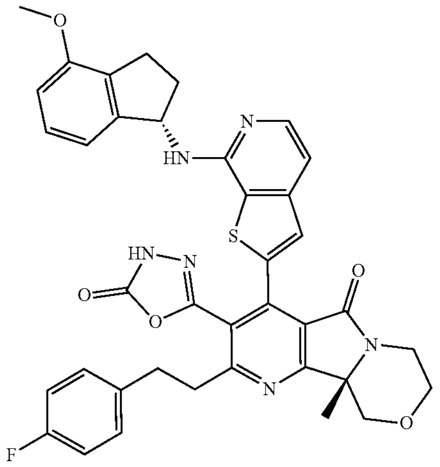 [SMILES: COc1cccc2c1CC[C@@H]2Nc1nccc2cc(-c3c4c(nc(CCc5ccc(F)cc5)c3-c3n[nH]c(=O)o3)[C@@]3(C)COCCN3C4=O)sc12] |
| 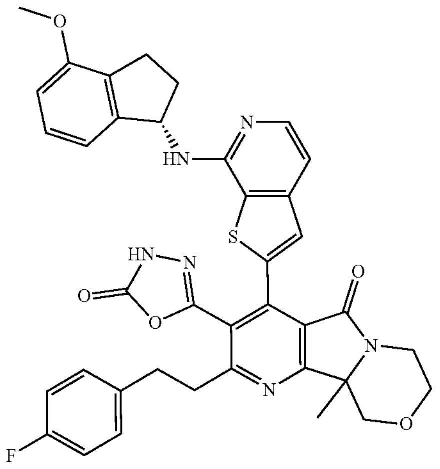 [SMILES: COc1cccc2c1CC[C@@H]2Nc1nccc2cc(-c3c4c(nc(CCc5ccc(F)cc5)c3-c3n[nH]c(=O)o3)C3(C)COCCN3C4=O)sc12] |
| 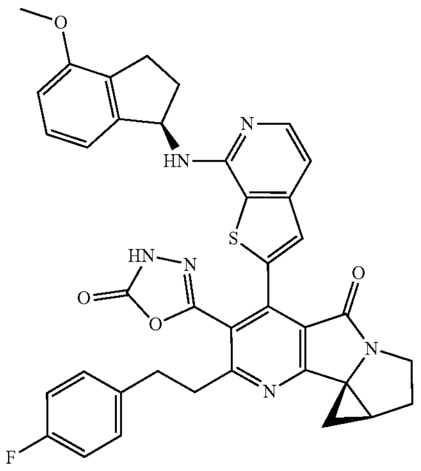 [SMILES: COc1cccc2c1CC[C@H]2Nc1nccc2cc(-c3c4c(nc(CCc5ccc(F)cc5)c3-c3n[nH]c(=O)o3)[C@@]35C[C@@H]3CCN5C4=O)sc12] |

TABLE 2-continued
| Structure |
|---|
| 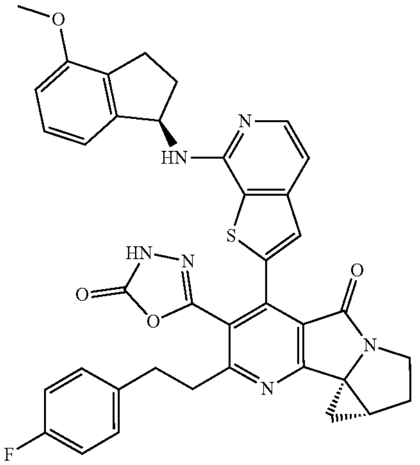 |
| 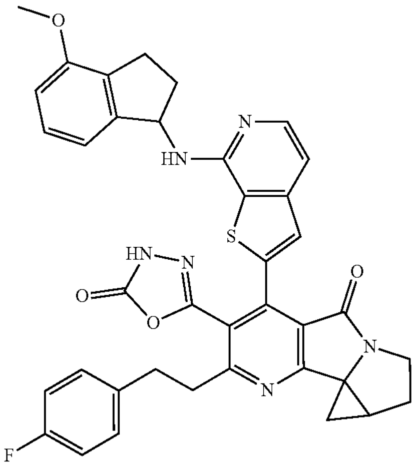 |
| 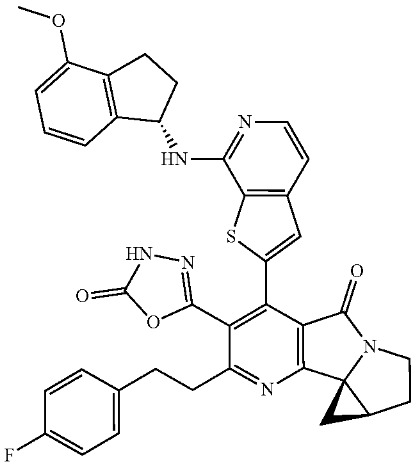 [SMILES: COc1cccc2c1CC[C@@H]2Nc1nccc2cc(-c3c4c(nc(CCc5ccc(F)cc5)c3-c3n[nH]c(=O)o3)[C@@]35C[C@@H]3CCN5C4=O)sc12] |
TABLE 2-continued
| Structure |
|---|
| 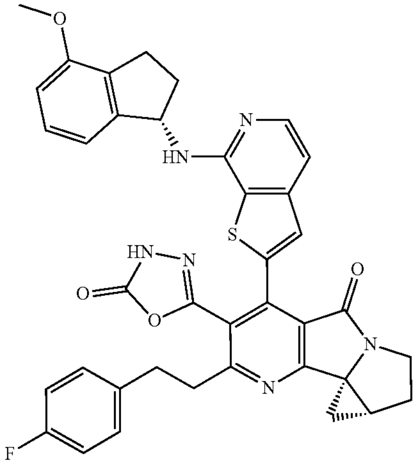 [SMILES: COc1cccc2c1CC[C@@H]2Nc1nccc2cc(-c3c4c(nc(CCc5ccc(F)cc5)c3-c3n[nH]c(=O)o3)[C@]35C[C@H]3CCN5C4=O)sc12] |
| 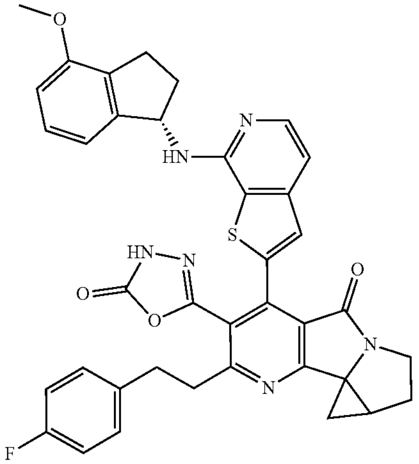 [SMILES: COc1cccc2c1CC[C@@H]2Nc1nccc2cc(-c3c4c(nc(CCc5ccc(F)cc5)c3-c3n[nH]c(=O)o3)C35CC3CCN5C4=O)sc12] |
| 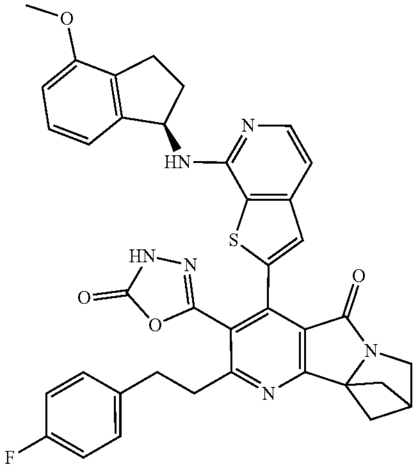 [SMILES: COc1cccc2c1CC[C@H]2Nc1nccc2cc(-c3c4c(nc(CCc5ccc(F)cc5)c3-c3n[nH]c(=O)o3)C35CC(CN3C4=O)C5)sc12] |

| Structure |
|---|
| 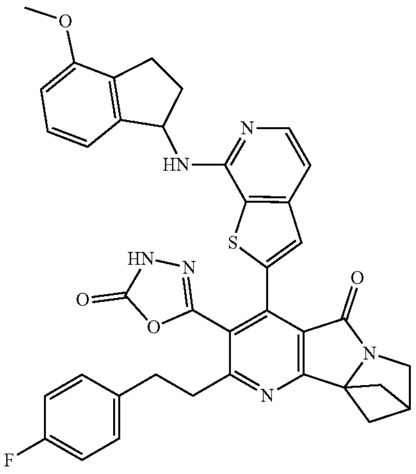 [SMILES: COc1cccc2c1CCC2Nc1nccc2cc(-c3c4c(nc(CCc5ccc(F)cc5)c3-c3n[nH]c(=O)o3)C35CC(CN3C4=O)C5)sc12] |
| 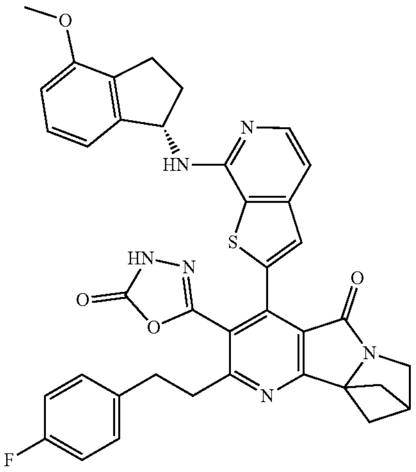 [SMILES: COc1cccc2c1CC[C@@H]2Nc1nccc2cc(-c3c4c(nc(CCc5ccc(F)cc5)c3-c3n[nH]c(=O)o3)C35CC(CN3C4=O)C5)sc12] |
| 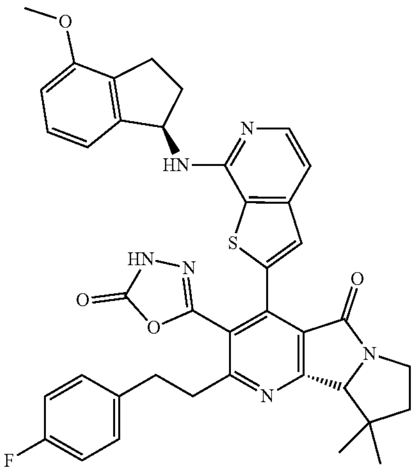 |
| Structure |
|---|
| 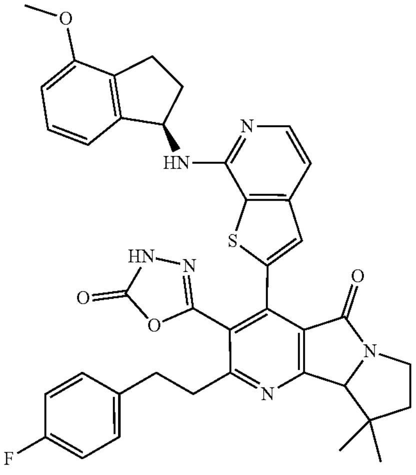 [SMILES: COc1cccc2c1CC[C@H]2Nc1nccc2cc(-c3c4c(nc(CCc5ccc(F)cc5)c3-c3n[nH]c(=O)o3)C3N(CCC3(C)C)C4=O)sc12] |
| 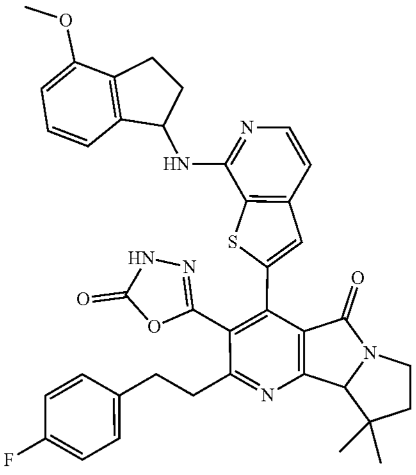 [SMILES: COc1cccc2c1CCC2Nc1nccc2cc(-c3c4c(nc(CCc5ccc(F)cc5)c3-c3n[nH]c(=O)o3)C3N(CCC3(C)C)C4=O)sc12] |
| 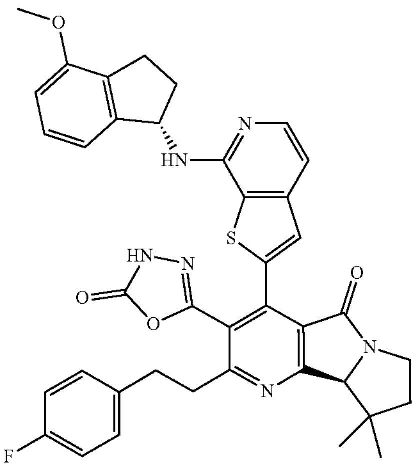 [SMILES: COc1cccc2c1CC[C@@H]2Nc1nccc2cc(-c3c4c(nc(CCc5ccc(F)cc5)c3-c3n[nH]c(=O)o3)[C@H]3N(CCC3(C)C)C4=O)sc12] |

| Structure |
|---|
| 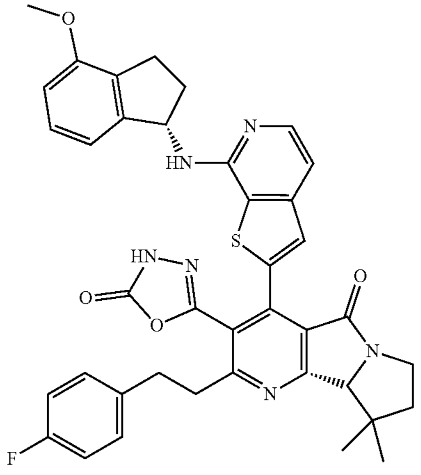 |
| 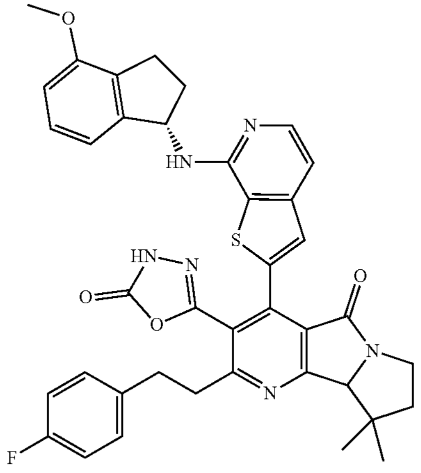 [SMILES: COc1cccc2c1CC[C@@H]2Nc1nccc2cc(-c3c4c(nc(CCc5ccc(F)cc5)c3-c3n[nH]c(=O)o3)C3N(CCC3(C)C)C4=O)sc12] |
| 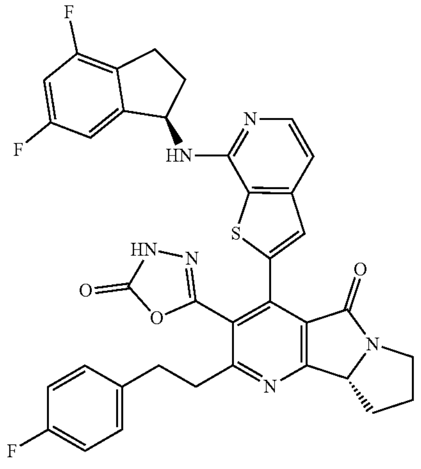 [SMILES: O=C1c2c(nc(CCc3ccc(F)cc3)c(-c3n[nH]c(=O)o3)c2-c2cc3ccnc(N[C@@H]4CCc5c(F)cc(F)cc54)c3s2)[C@H]2CCCN12] |
TABLE 2-continued
| Structure |
|---|
| 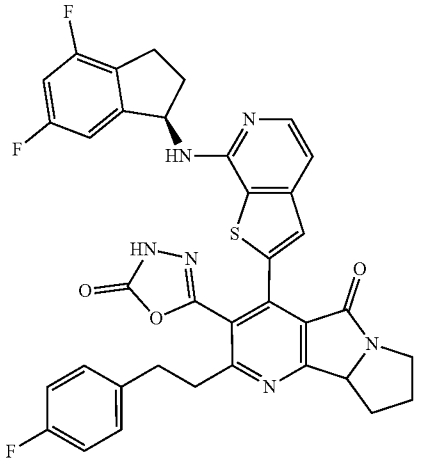 [SMILES: O=C1c2c(nc(CCc3ccc(F)cc3)c(-c3n[nH]c(=O)o3)c2-c2cc3ccnc(N[C@@H]4CCc5c(F)cc(F)cc54)c3s2)C2CCCN12] |
| 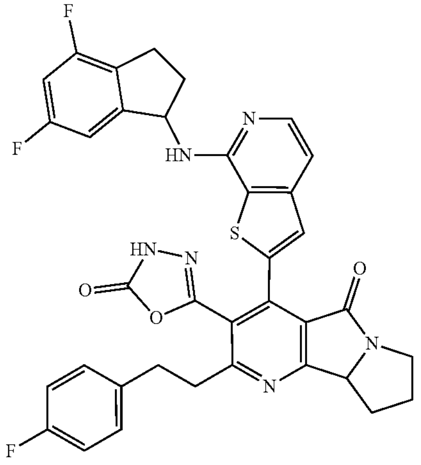 [SMILES: O=C1c2c(nc(CCc3ccc(F)cc3)c(-c3n[nH]c(=O)o3)c2-c2cc3ccnc(NC4CCc5c(F)cc(F)cc54)c3s2)C2CCCN12] |
| 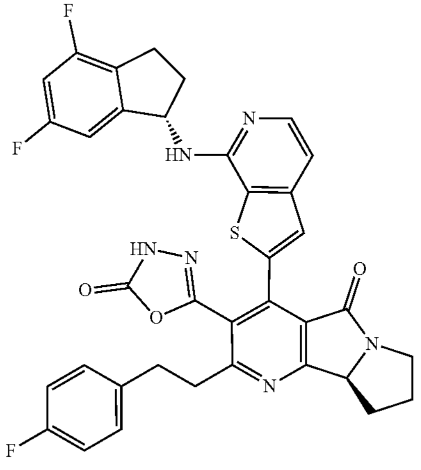 [SMILES: O=C1c2c(nc(CCc3ccc(F)cc3)c(-c3n[nH]c(=O)o3)c2-c2cc3ccnc(N[C@H]4CCc5c(F)cc(F)cc54)c3s2)[C@@H]2CCCN12] |

TABLE 2-continued
| Structure |
| --- |
| 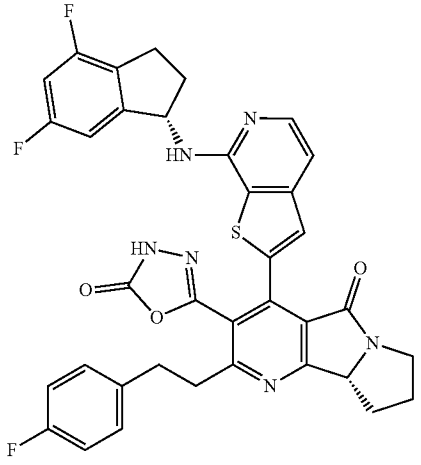 [SMILES: O=C1c2c(nc(CCc3ccc(F)cc3)c(-c3n[nH]c(=O)o3)c2-c2cc3ccnc(N[C@H]4CCc5c(F)cc(F)cc54)c3s2)[C@H]2CCCN12] |
| 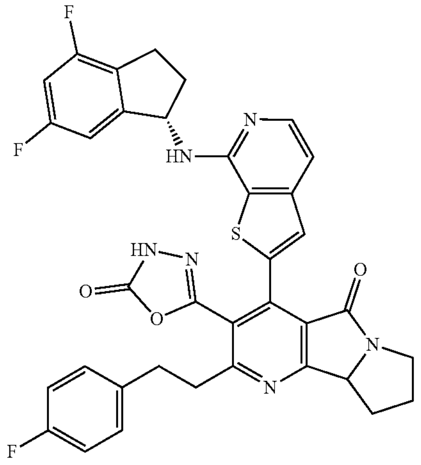 [SMILES: O=C1c2c(nc(CCc3ccc(F)cc3)c(-c3n[nH]c(=O)o3)c2-c2cc3ccnc(N[C@H]4CCc5c(F)cc(F)cc54)c3s2)C2CCCN12] |
| 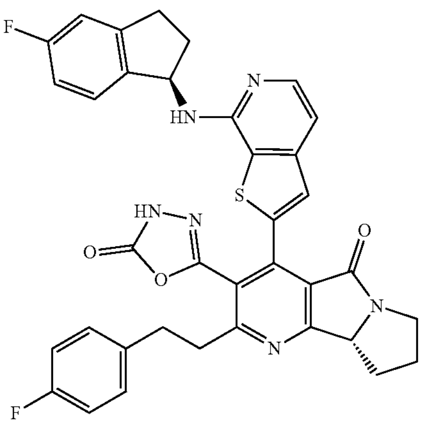 [SMILES: O=C1c2c(nc(CCc3ccc(F)cc3)c(-c3n[nH]c(=O)o3)c2-c2cc3ccnc(N[C@@H]4CCc5cc(F)ccc54)c3s2)[C@H]2CCCN12] |
TABLE 2-continued
| Structure |
| --- |
| 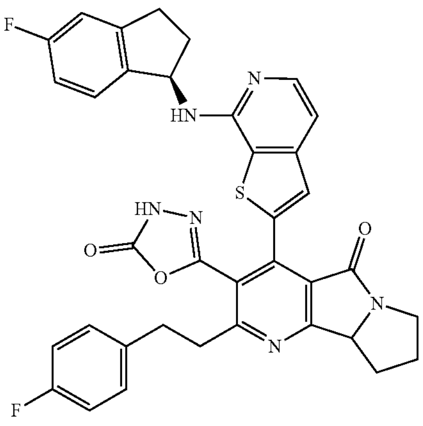 [SMILES: O=C1c2c(nc(CCc3ccc(F)cc3)c(-c3n[nH]c(=O)o3)c2-c2cc3ccnc(N[C@@H]4CCc5cc(F)ccc54)c3s2)C2CCCN12] |
| 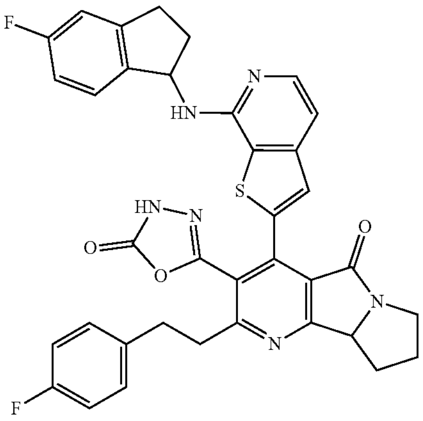 [SMILES: O=C1c2c(nc(CCc3ccc(F)cc3)c(-c3n[nH]c(=O)o3)c2-c2cc3ccnc(NC4CCc5cc(F)ccc54)c3s2)C2CCCN12] |
| 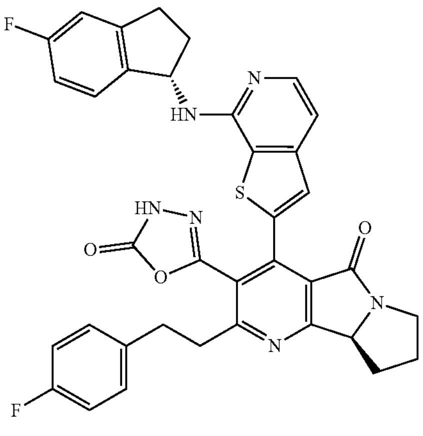 [SMILES: O=C1c2c(nc(CCc3ccc(F)cc3)c(-c3n[nH]c(=O)o3)c2-c2cc3ccnc(N[C@H]4CCc5cc(F)ccc54)c3s2)[C@@H]2CCCN12]

TABLE 2-continued
| Structure |
| --- |
| 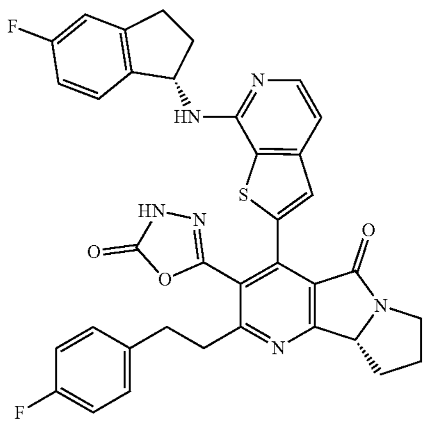 [SMILES: O=C1c2c(nc(CCc3ccc(F)cc3)c(-c3n[nH]c(=O)o3)c2-c2cc3ccnc(N[C@H]4CCc5cc(F)ccc54)c3s2)[C@H]2CCCN12] |
| 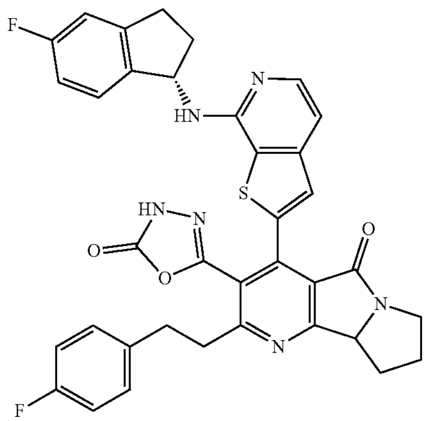 [SMILES: O=C1c2c(nc(CCc3ccc(F)cc3)c(-c3n[nH]c(=O)o3)c2-c2cc3ccnc(N[C@H]4CCc5cc(F)ccc54)c3s2)C2CCCN12] |
| 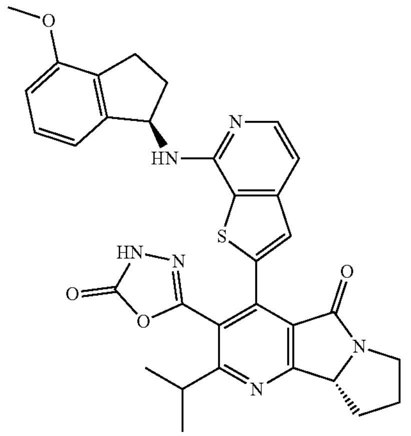 [SMILES: COc1cccc2c1CC[C@H]2Nc1nccc2cc(-c3c4c(nc(C(C)C)c3-c3n[nH]c(=O)o3)[C@H]3CCCN3C4=O)sc12] |
| 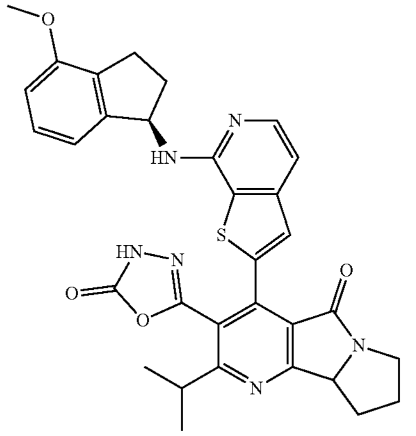 [SMILES: COc1cccc2c1CC[C@H]2Nc1nccc2cc(-c3c4c(nc(C(C)C)c3-c3n[nH]c(=O)o3)C3CCCN3C4=O)sc12] |
| 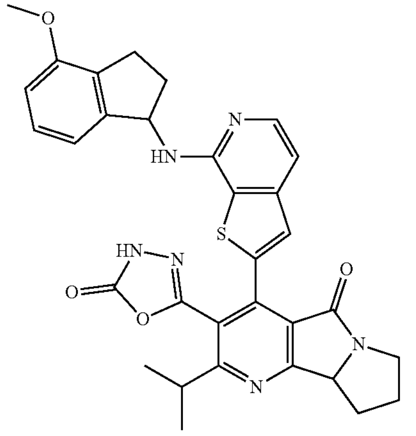 [SMILES: COc1cccc2c1CCC2Nc1nccc2cc(-c3c4c(nc(C(C)C)c3-c3n[nH]c(=O)o3)C3CCCN3C4=O)sc12] |
| 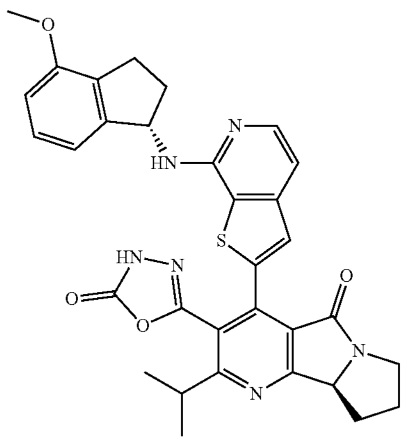 [SMILES: COc1cccc2c1CC[C@@H]2Nc1nccc2cc(-c3c4c(nc(C(C)C)c3-c3n[nH]c(=O)o3)[C@@H]3CCCN3C4=O)sc12] |

TABLE 2-continued
| Structure |
|---|
| 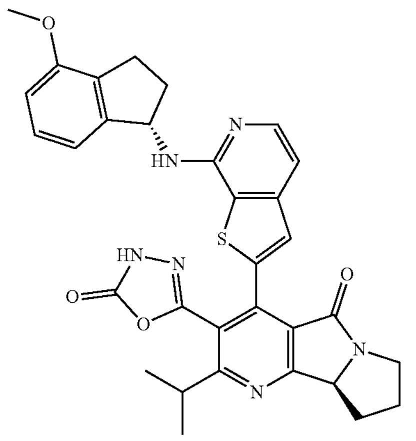 [SMILES: COc1cccc2c1CC[C@@H]2Nc1nccc2cc(-c3c4c(nc(C(C)C)c3-c3n[nH]c(=O)o3)[C@@H]3CCCN3C4=O)sc12] |
| 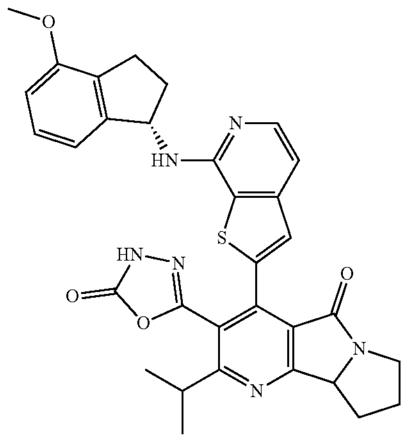 [SMILES: COc1cccc2c1CC[C@@H]2Nc1nccc2cc(-c3c4c(nc(C(C)C)c3-c3n[nH]c(=O)o3)C3CCCN3C4=O)sc12] |
| 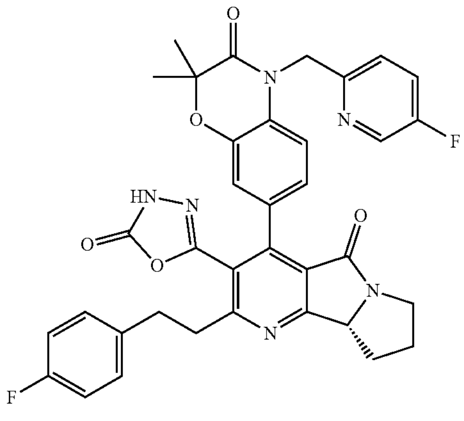 [SMILES: CC1(C)Oc2cc(-c3c4c(nc(CCc5ccc(F)cc5)c3-c3n[nH]c(=O)o3)[C@H]3CCCN3C4=O)ccc2N(Cc2ccc(F)cn2)C1=O] |
TABLE 2-continued
| Structure |
|---|
| 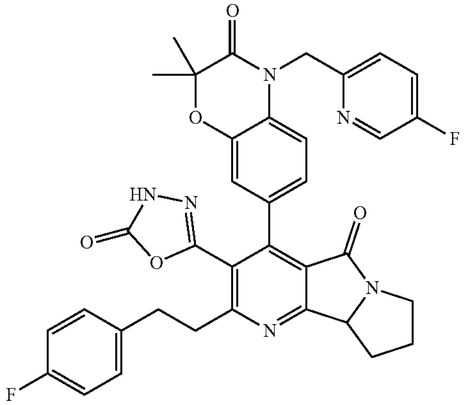 [SMILES: CC1(C)Oc2cc(-c3c4c(nc(CCc5ccc(F)cc5)c3-c3n[nH]c(=O)o3)C3CCCN3C4=O)ccc2N(Cc2ccc(F)cn2)C1=O] |
| 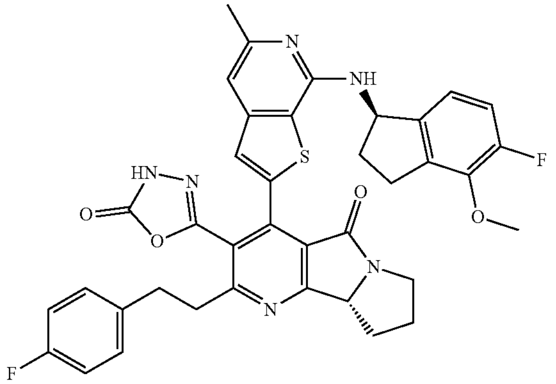 [SMILES: COc1c(F)ccc2c1CC[C@H]2Nc1nc(C)cc2cc(-c3c4c(nc(CCc5ccc(F)cc5)c3-c3n[nH]c(=O)o3)[C@H]3CCCN3C4=O)sc12] |
| 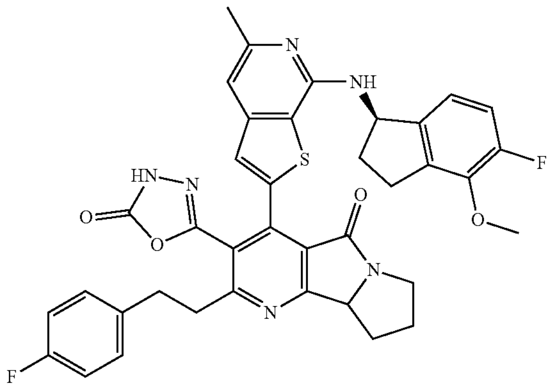 |
| 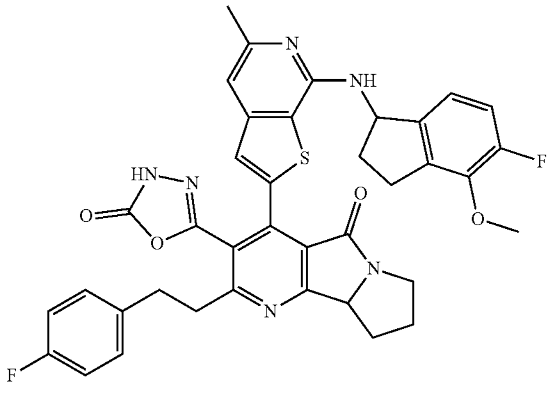 [SMILES: COc1c(F)ccc2c1CCC2Nc1nc(C)cc2cc(-c3c4c(nc(CCc5ccc(F)cc5)c3-c3n[nH]c(=O)o3)C3CCCN3C4=O)sc12] |

| Structure |
|---|
| 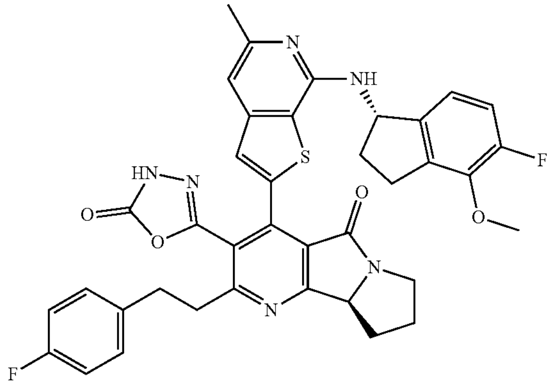 [SMILES: COc1c(F)ccc2c1CC[C@@H]2Nc1nc(C)cc2cc(-c3c4c(nc(CCc5ccc(F)cc5)c3-c3n[nH]c(=O)o3)[C@@H]3CCCN3C4=O)sc12] |
| 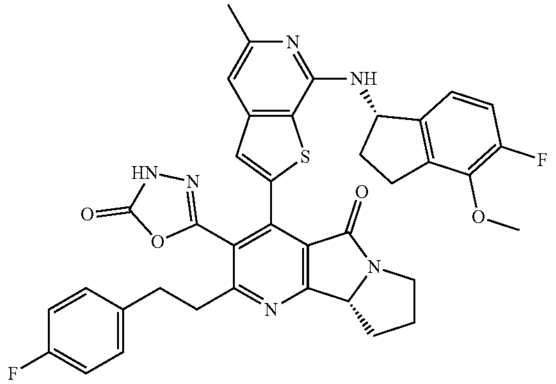 |
| 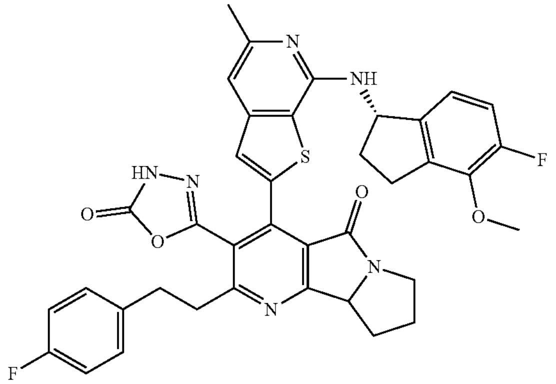 |
| 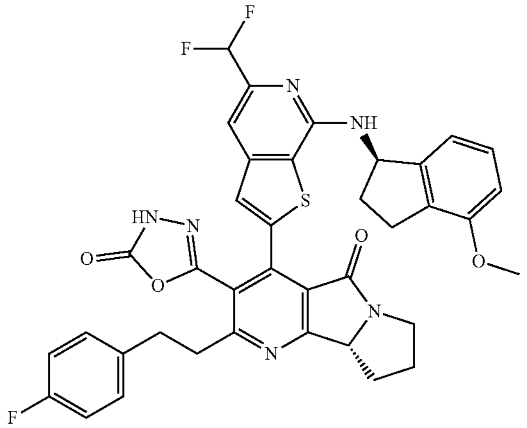 |
| Structure |
|---|
| 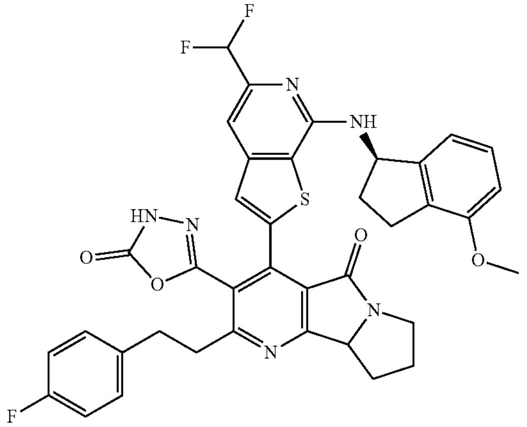 [SMILES: COc1cccc2c1CC[C@H]2Nc1nc(C(F)F)cc2cc(-c3c4c(nc(CCc5ccc(F)cc5)c3-c3n[nH]c(=O)o3)[C@H]3CCCN3C4=O)sc12] |
| 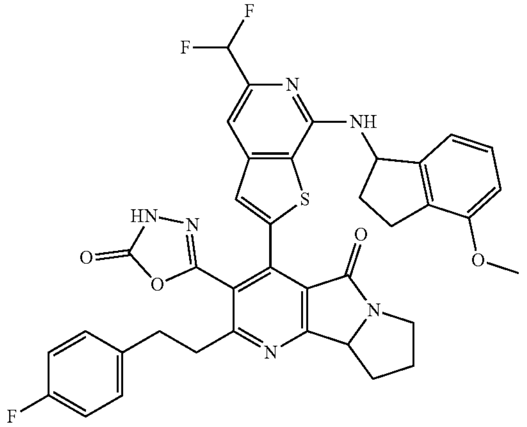 [SMILES: COc1cccc2c1CCC2Nc1nc(C(F)F)cc2cc(-c3c4c(nc(CCc5ccc(F)cc5)c3-c3n[nH]c(=O)o3)C3CCCN3C4=O)sc12] |
| 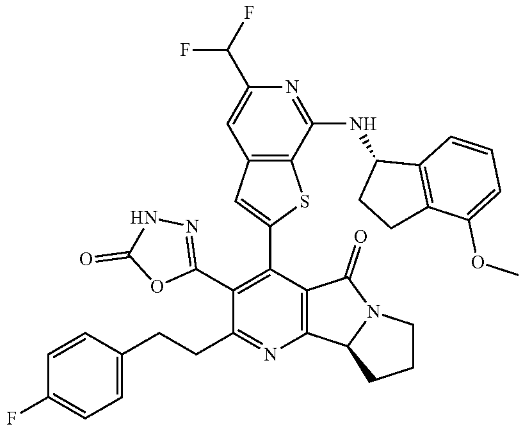 [SMILES: COc1cccc2c1CC[C@@H]2Nc1nc(C(F)F)cc2cc(-c3c4c(nc(CCc5ccc(F)cc5)c3-c3n[nH]c(=O)o3)[C@@H]3CCCN3C4=O)sc12]

TABLE 2-continued
| Structure |
|---|
| 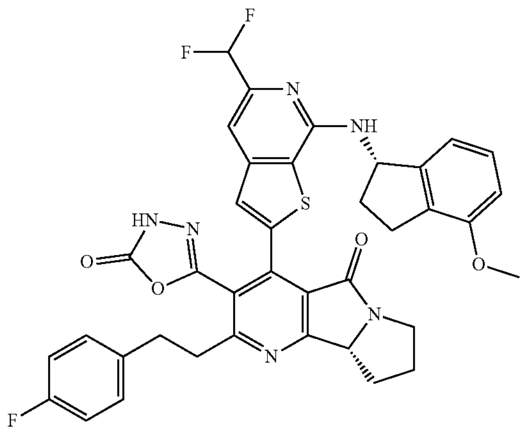 [SMILES: COc1cccc2c1CC[C@@H]2Nc1nc(C(F)F)cc2cc(-c3c4c(nc(CCc5ccc(F)cc5)c3-c3n[nH]c(=O)o3)[C@H]3CCCN3C4=O)sc12] |
| 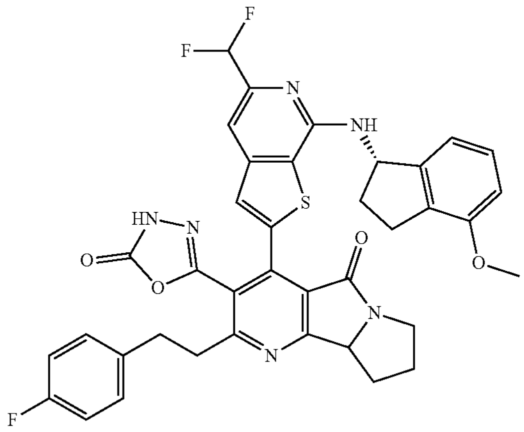 [SMILES: COc1cccc2c1CC[C@@H]2Nc1nc(C(F)F)cc2cc(-c3c4c(nc(CCc5ccc(F)cc5)c3-c3n[nH]c(=O)o3)C3CCCN3C4=O)sc12] |
| 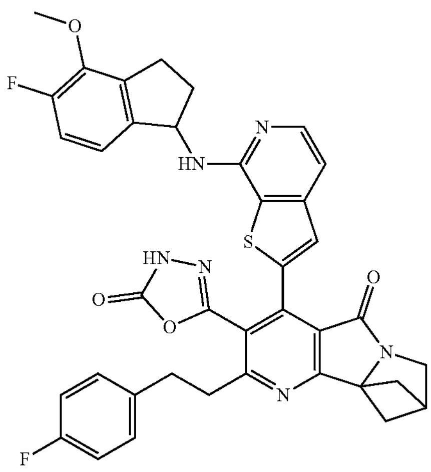 [SMILES: COc1c(F)ccc2c1CCC2Nc1nccc2cc(-c3c4c(nc(CCc5ccc(F)cc5)c3-c3n[nH]c(=O)o3)C35CC(CN3C4=O)C5)sc12] |
TABLE 2-continued
| Structure |
|---|
| 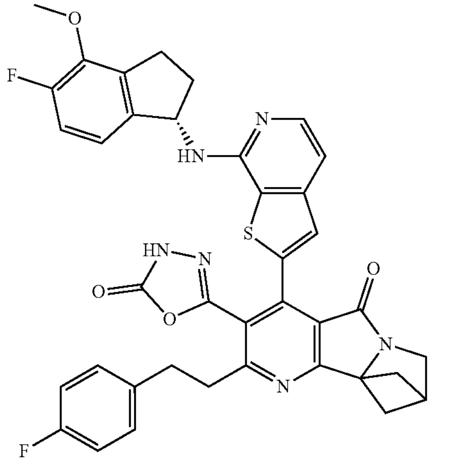 [SMILES: COc1c(F)ccc2c1CC[C@@H]2Nc1nccc2cc(-c3c4c(nc(CCc5ccc(F)cc5)c3-c3n[nH]c(=O)o3)C35CC(CN3C4=O)C5)sc12] |
| 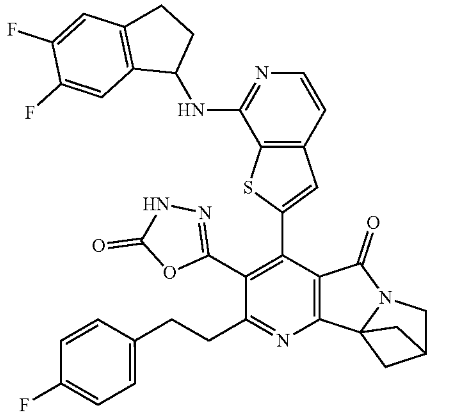 [SMILES: O=C1c2c(nc(CCc3ccc(F)cc3)c(-c3n[nH]c(=O)o3)c2-c2cc3ccnc(NC4CCc5cc(F)c(F)cc54)c3s2)C23CC(CN12)C3] |
| 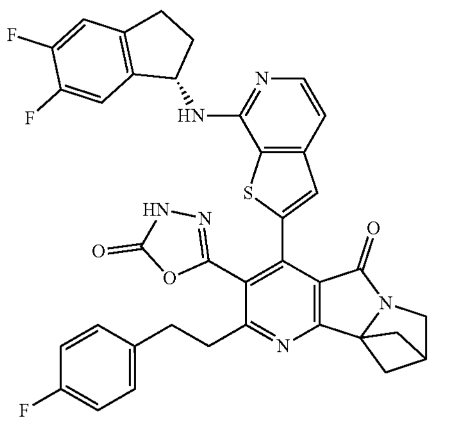 [SMILES: O=C1c2c(nc(CCc3ccc(F)cc3)c(-c3n[nH]c(=O)o3)c2-c2cc3ccnc(N[C@H]4CCc5cc(F)c(F)cc54)c3s2)C23CC(CN12)C3] |

TABLE 2-continued
| Structure |
|---|
| 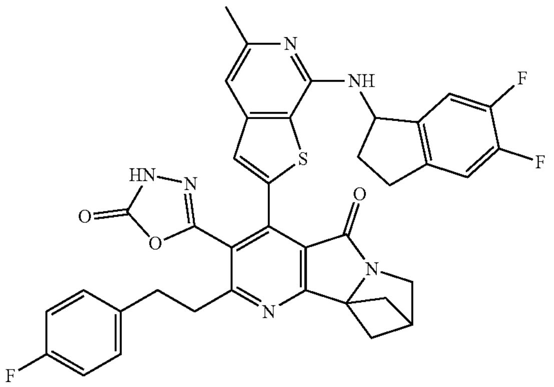 [SMILES: Cc1cc2cc(-c3c4c(nc(CCc5ccc(F)cc5)c3-c3n[nH]c(=O)o3)C35CC(CN3C4=O)C5)sc2c(NC2CCc3cc(F)c(F)cc32)n1] |
| 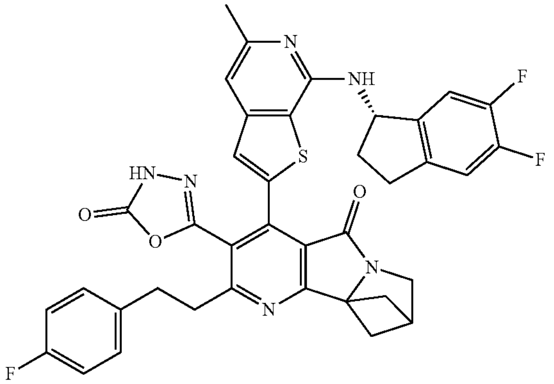 [SMILES: Cc1cc2cc(-c3c4c(nc(CCc5ccc(F)cc5)c3-c3n[nH]c(=O)o3)C35CC(CN3C4=O)C5)sc2c(N[C@H]2CCc3cc(F)c(F)cc32)n1] |
| 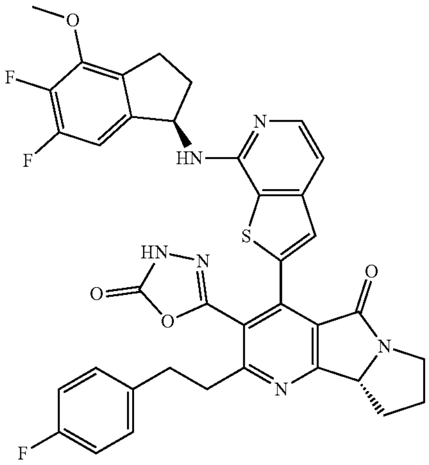 [SMILES: COc1c(F)c(F)cc2c1CC[C@H]2Nc1nccc2cc(-c3c4c(nc(CCc5ccc(F)cc5)c3-c3n[nH]c(=O)o3)[C@H]3CCCN3C4=O)sc12] |
TABLE 2-continued
| Structure |
|---|
| 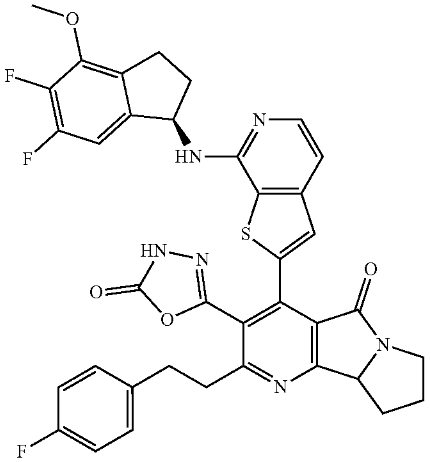 [SMILES: COc1c(F)c(F)cc2c1CC[C@H]2Nc1nccc2cc(-c3c4c(nc(CCc5ccc(F)cc5)c3-c3n[nH]c(=O)o3)C3CCCN3C4=O)sc12] |
| 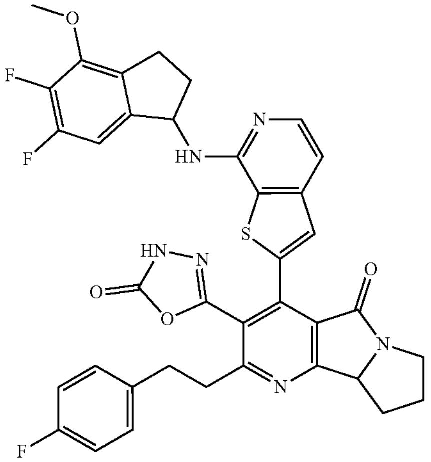 [SMILES: COc1c(F)c(F)cc2c1CCC2Nc1nccc2cc(-c3c4c(nc(CCc5ccc(F)cc5)c3-c3n[nH]c(=O)o3)C3CCCN3C4=O)sc12] |
| 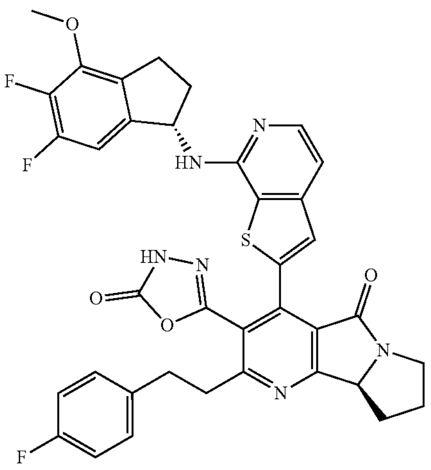 [SMILES: COc1c(F)c(F)cc2c1CC[C@@H]2Nc1nccc2cc(-c3c4c(nc(CCc5ccc(F)cc5)c3-c3n[nH]c(=O)o3)[C@@H]3CCCN3C4=O)sc12] |

TABLE 2-continued
| Structure |
| --- |
| 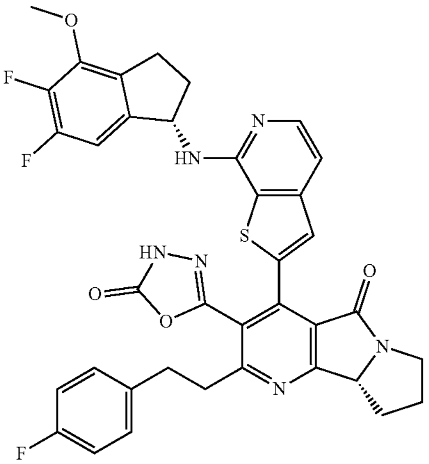 |
| 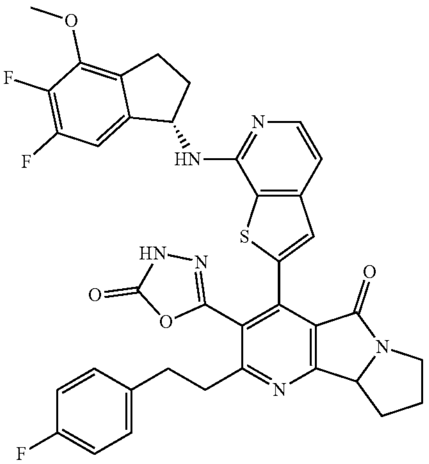 |
| 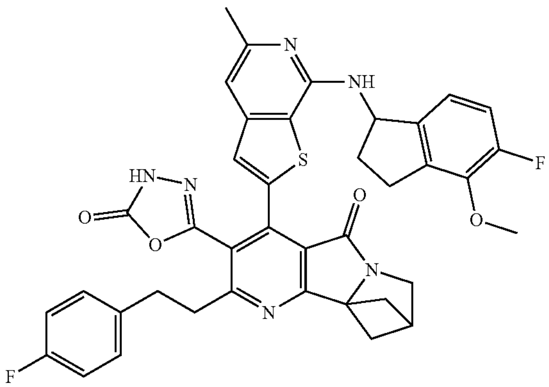 [SMILES: COc1c(F)ccc2c1CCC2Nc1nc(C)cc2cc(-c3c4c(nc(CCc5ccc(F)cc5)c3-c3n[nH]c(=O)o3)C35CC(CN3C4=O)C5)sc12] |
TABLE 2-continued
| Structure |
| --- |
| 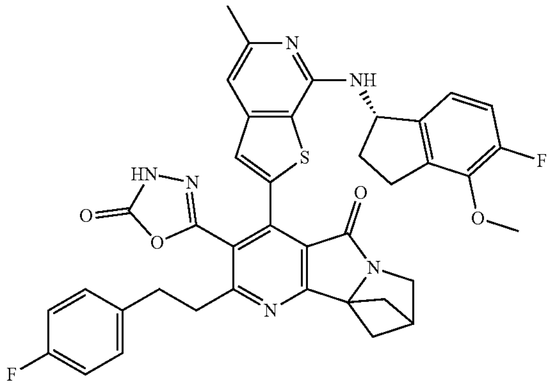 [SMILES: COc1c(F)ccc2c1CC[C@@H]2Nc1nc(C)cc2cc(-c3c4c(nc(CCc5ccc(F)cc5)c3-c3n[nH]c(=O)o3)C35CC(CN3C4=O)C5)sc12] |
| 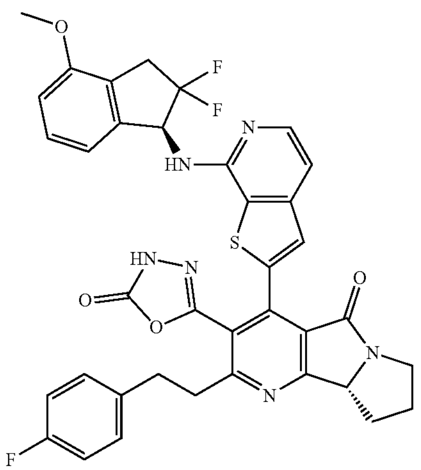 [SMILES: COc1cccc2c1CC(F)(F)[C@H]2Nc1nccc2cc(-c3c4c(nc(CCc5ccc(F)cc5)c3-c3n[nH]c(=O)o3)[C@H]3CCCN3C4=O)sc12] |
| 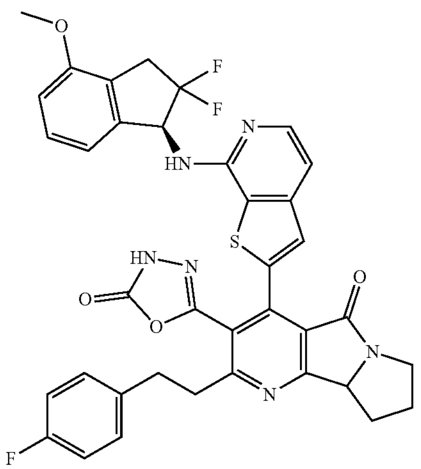 [SMILES: COc1cccc2c1CC(F)(F)[C@H]2Nc1nccc2cc(-c3c4c(nc(CCc5ccc(F)cc5)c3-c3n[nH]c(=O)o3)C3CCCN3C4=O)sc12] |

| Structure |
| --- |
| 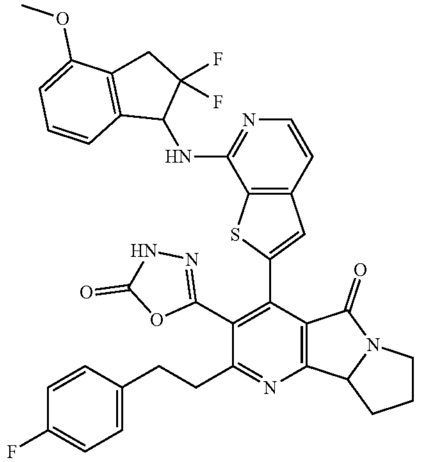 [SMILES: COc1cccc2c1CC(F)(F)C2Nc1nccc2cc(-c3c4c(nc(CCc5ccc(F)cc5)c3-c3n[nH]c(=O)o3)C3CCCN3C4=O)sc12] |
| 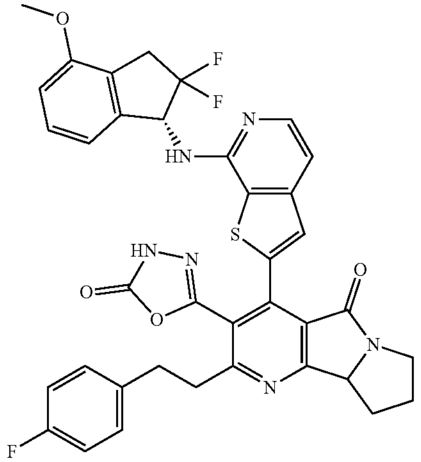 [SMILES: COc1cccc2c1CC(F)(F)[C@@H]2Nc1nccc2cc(-c3c4c(nc(CCc5ccc(F)cc5)c3-c3n[nH]c(=O)o3)C3CCCN3C4=O)sc12] |
| 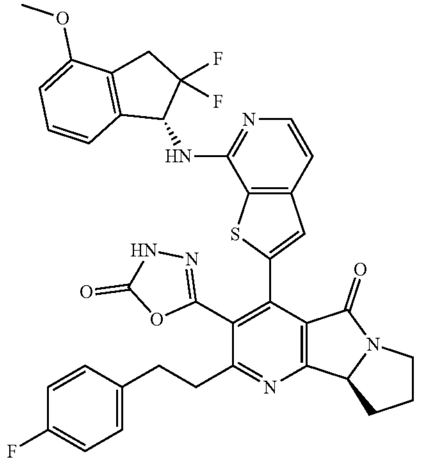 [SMILES: COc1cccc2c1CC(F)(F)[C@@H]2Nc1nccc2cc(-c3c4c(nc(CCc5ccc(F)cc5)c3-c3n[nH]c(=O)o3)[C@@H]3CCCN3C4=O)sc12] |
| Structure |
| --- |
| 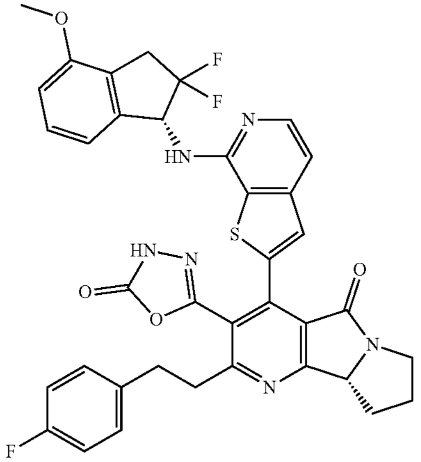 [SMILES: COc1cccc2c1CC(F)(F)[C@@H]2Nc1nccc2cc(-c3c4c(nc(CCc5ccc(F)cc5)c3-c3n[nH]c(=O)o3)[C@H]3CCCN3C4=O)sc12] |
| 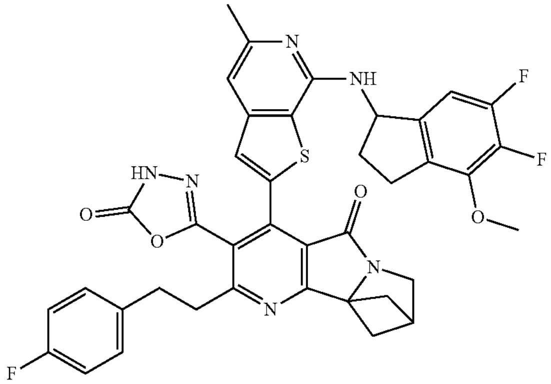 [SMILES: COc1c(F)c(F)cc2c1CCC2Nc1nc(C)cc2cc(-c3c4c(nc(CCc5ccc(F)cc5)c3-c3n[nH]c(=O)o3)C35CC(CN3C4=O)C5)sc12] |
| 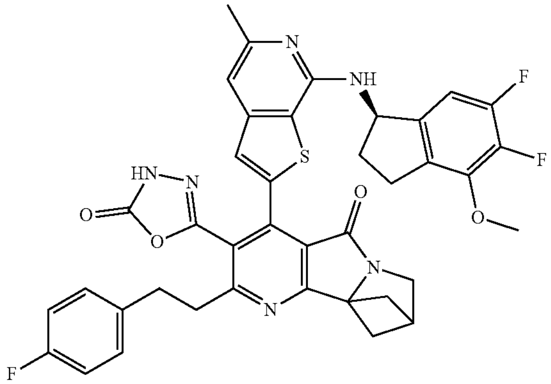 [SMILES: COc1c(F)c(F)cc2c1CC[C@H]2Nc1nc(C)cc2cc(-c3c4c(nc(CCc5ccc(F)cc5)c3-c3n[nH]c(=O)o3)C35CC(CN3C4=O)C5)sc12] |

TABLE 2-continued
| Structure |
| --- |
| 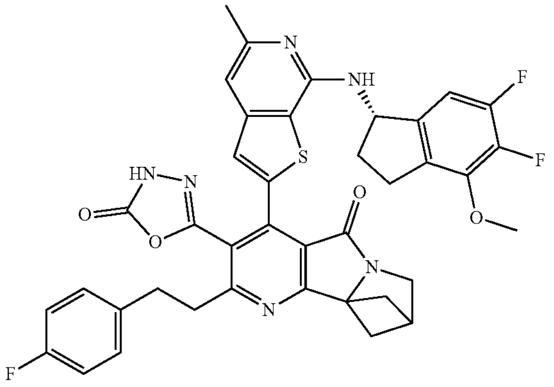 [SMILES: COc1c(F)c(F)cc2c1CC[C@@H]2Nc1nc(C)cc2cc(-c3c4c(nc(CCc5ccc(F)cc5)c3-c3n[nH]c(=O)o3)C35CC(CN3C4=O)C5)sc12] |
| 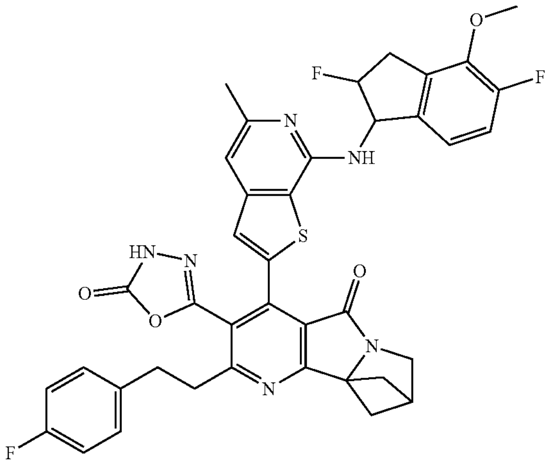 [SMILES: COc1c(F)ccc2c1CC(F)C2Nc1nc(C)cc2cc(-c3c4c(nc(CCc5ccc(F)cc5)c3-c3n[nH]c(=O)o3)C35CC(CN3C4=O)C5)sc12] |
| 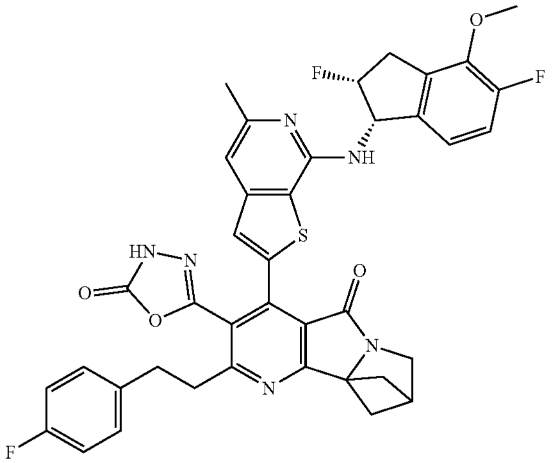 [SMILES: COc1c(F)ccc2c1C[C@@H](F)[C@H]2Nc1nc(C)cc2cc(-c3c4c(nc(CCc5ccc(F)cc5)c3-c3n[nH]c(=O)o3)C35CC(CN3C4=O)C5)sc12] |
TABLE 2-continued
| Structure |
| --- |
| 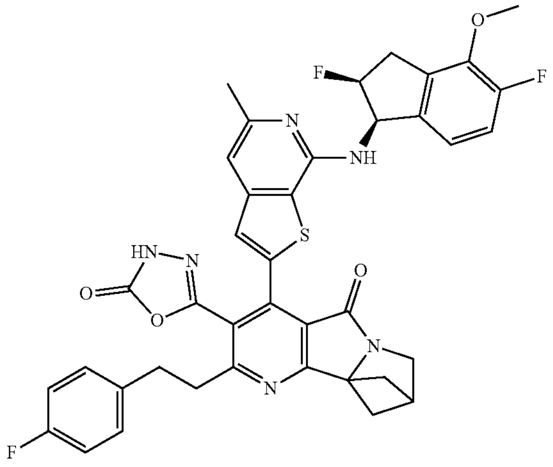 [SMILES: COc1c(F)ccc2c1C[C@H](F)[C@@H]2Nc1nc(C)cc2cc(-c3c4c(nc(CCc5ccc(F)cc5)c3-c3n[nH]c(=O)o3)C35CC(CN3C4=O)C5)sc12] |
| 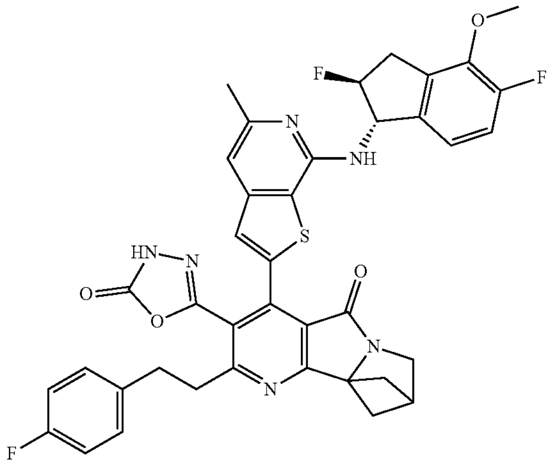 [SMILES: COc1c(F)ccc2c1C[C@H](F)[C@H]2Nc1nc(C)cc2cc(-c3c4c(nc(CCc5ccc(F)cc5)c3-c3n[nH]c(=O)o3)C35CC(CN3C4=O)C5)sc12] |
| 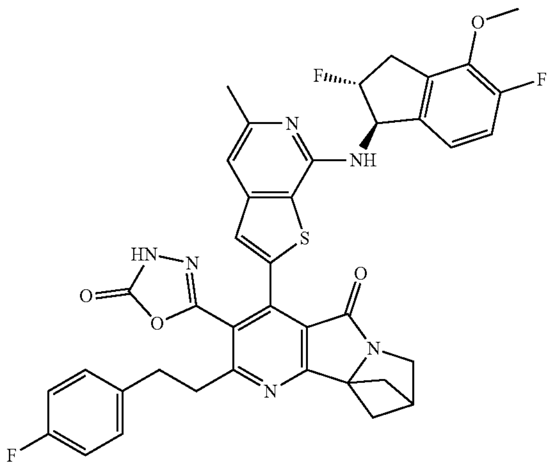 [SMILES: COc1c(F)ccc2c1C[C@@H](F)[C@@H]2Nc1nc(C)cc2cc(-c3c4c(nc(CCc5ccc(F)cc5)c3-c3n[nH]c(=O)o3)C35CC(CN3C4=O)C5)sc12] |

TABLE 2-continued
| Structure |
| --- |
| 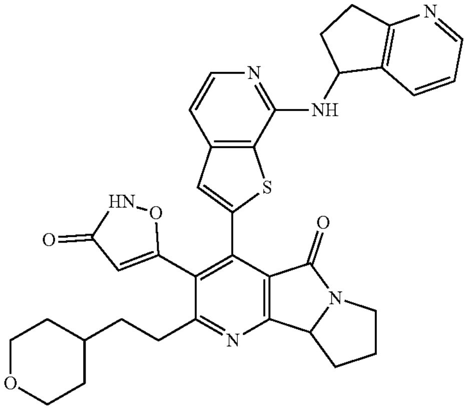 [SMILES: O=C1c2c(nc(CCC3CCOCC3)c(-c3cc(=O)[nH]o3)c2-c2cc3ccnc(NC4CCc5ncccc54)c3s2)C2CCCN12] |
| 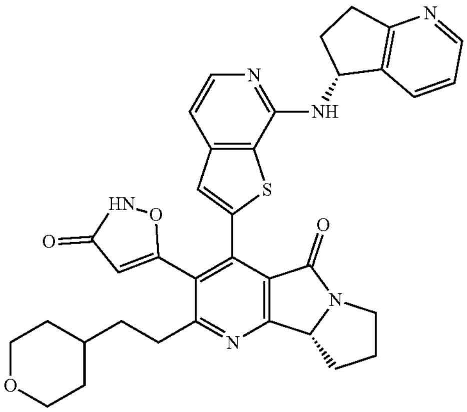 |
| 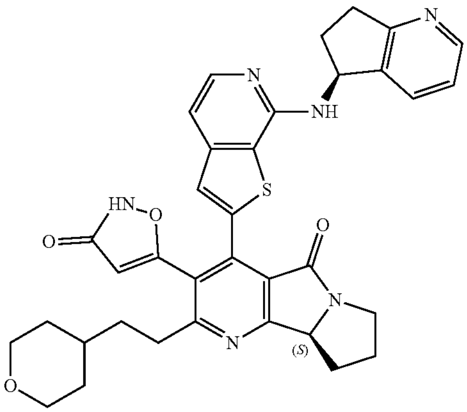 |
TABLE 2-continued
| Structure |
| --- |
| 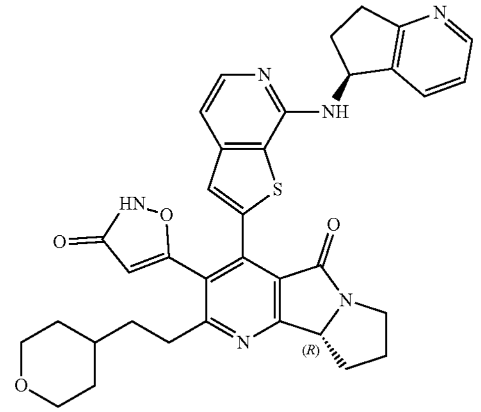 |
| 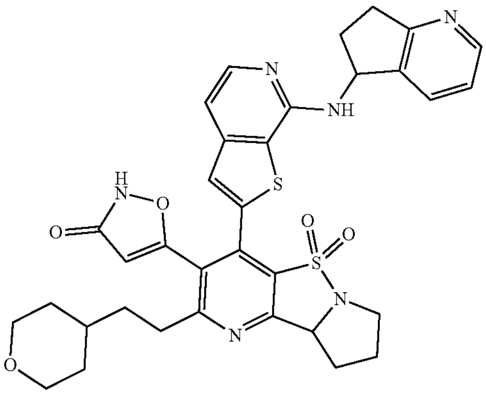 [SMILES: O=c1cc(-c2c(CCC3CCOCC3)nc3c(c2-c2cc4ccnc(NC5CCc6ncccc65)c4s2)S(=O)(=O)N2CCCC32)o[nH]1] |
| 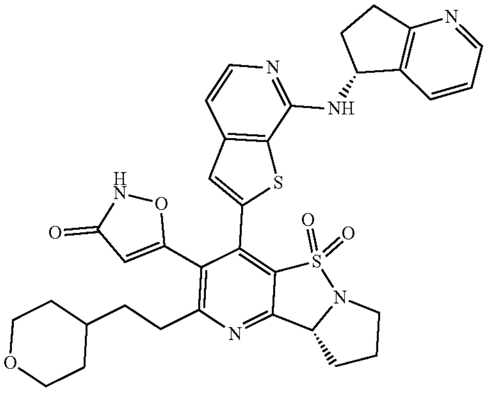 [SMILES: O=c1cc(-c2c(CCC3CCOCC3)nc3c(c2-c2cc4ccnc(N[C@@H]5CCc6ncccc65)c4s2)S(=O)(=O)N2CCC[C@H]32)o[nH]1] |
| 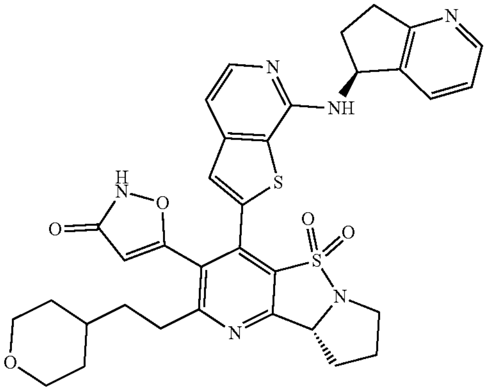 [SMILES: O=c1cc(-c2c(CCC3CCOCC3)nc3c(c2-c2cc4ccnc(N[C@H]5CCc6ncccc65)c4s2)S(=O)(=O)N2CCC[C@H]32)o[nH]1] |

TABLE 2-continued
| Structure |
|---|
| 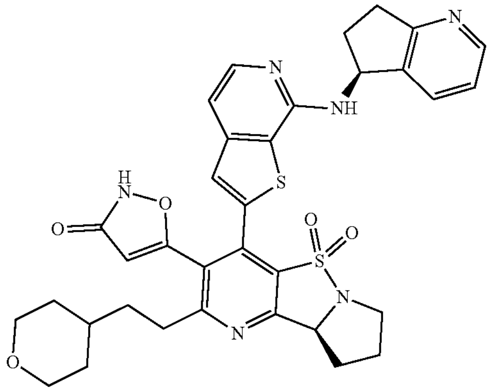 [SMILES: O=c1cc(-c2c(CCC3CCOCC3)nc3c(c2-c2cc4ccnc(N[C@H]5CCc6ncccc65)c4s2)S(=O)(=O)N2CCC[C@@H]32)o[nH]1] |
| 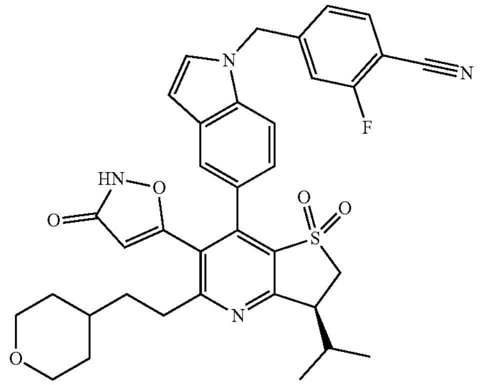 [SMILES: CC(C)[C@@H]1CS(=O)(=O)c2c1nc(CCC1CCOCC1)c(-c1cc(=O)[nH]o1)c2-c1ccc2c(ccn2Cc2ccc(C#N)c(F)c2)c1] |
| 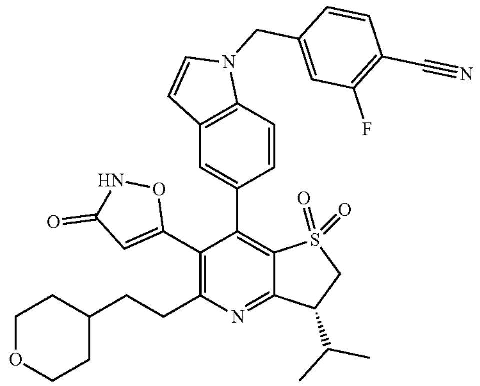 |
| 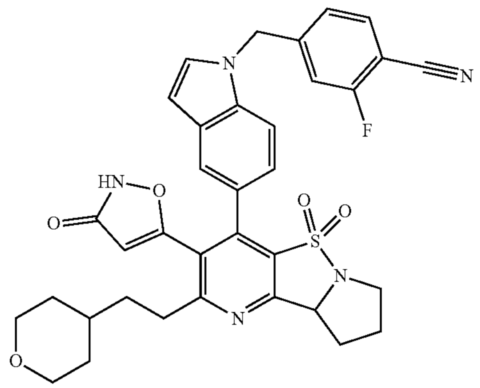 [SMILES: N#Cc1ccc(Cn2ccc3cc(-c4c(-c5cc(=O)[nH]o5)c(CCC5CCOCC5)nc5c4S(=O)(=O)N4CCCC54)ccc32)cc1F] |
TABLE 2-continued
| Structure |
|---|
| 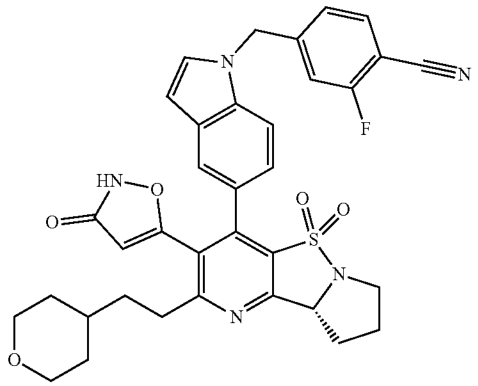 [SMILES: N#Cc1ccc(Cn2ccc3cc(-c4c(-c5cc(=O)[nH]o5)c(CCC5CCOCC5)nc5c4S(=O)(=O)N4CCC[C@H]54)ccc32)cc1F] |
| 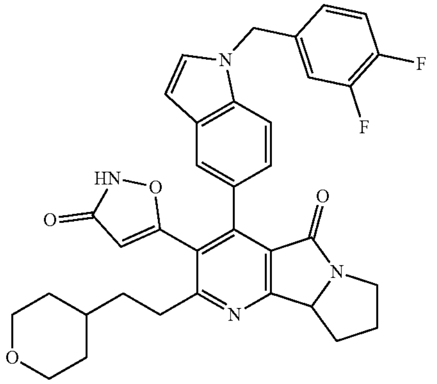 |
| 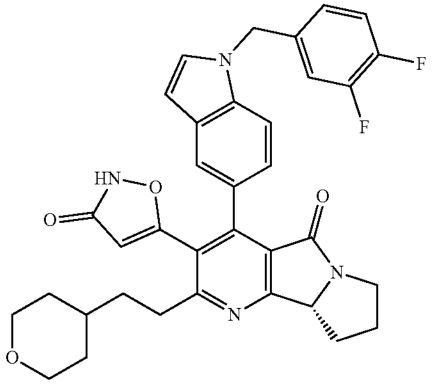 [SMILES: O=C1c2c(nc(CCC3CCOCC3)c(-c3cc(=O)[nH]o3)c2-c2ccc3c(ccn3Cc3ccc(F)c(F)c3)c2)[C@H]2CCCN12] |
| 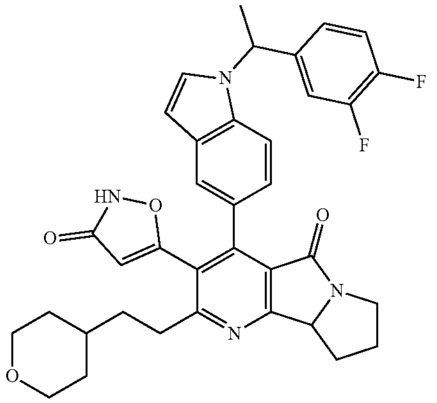 [SMILES: CC(c1ccc(F)c(F)c1)n1ccc2cc(-c3c4c(nc(CCC5CCOCC5)c3-c3cc(=O)[nH]o3)C3CCCN3C4=O)ccc21] |

TABLE 2-continued
| Structure |
|---|
| 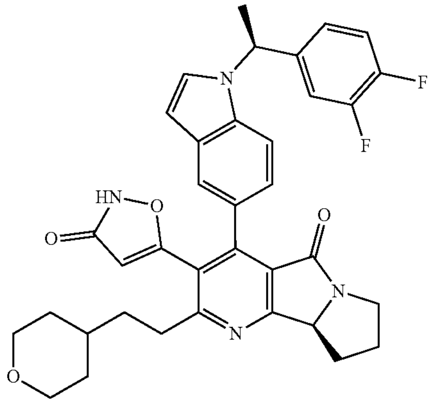 [SMILES: C[C@@H](c1ccc(F)c(F)c1)n1ccc2cc(-c3c4c(nc(CCC5CCOCC5)c3-c3cc(=O)[nH]o3)[C@@H]3CCCN3C4=O)ccc21] |
| 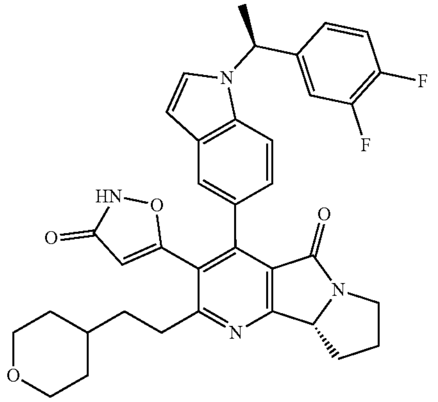 [SMILES: C[C@@H](c1ccc(F)c(F)c1)n1ccc2cc(-c3c4c(nc(CCC5CCOCC5)c3-c3cc(=O)[nH]o3)[C@H]3CCCN3C4=O)ccc21] |
| 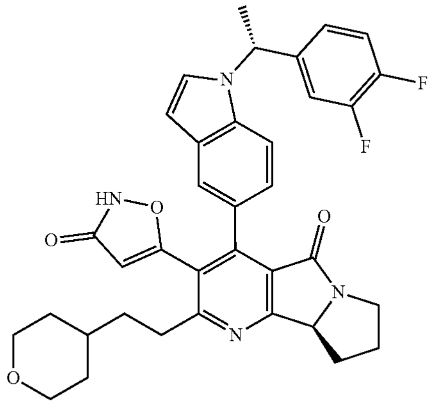 [SMILES: C[C@H](c1ccc(F)c(F)c1)n1ccc2cc(-c3c4c(nc(CCC5CCOCC5)c3-c3cc(=O)[nH]o3)[C@@H]3CCCN3C4=O)ccc21] |
| 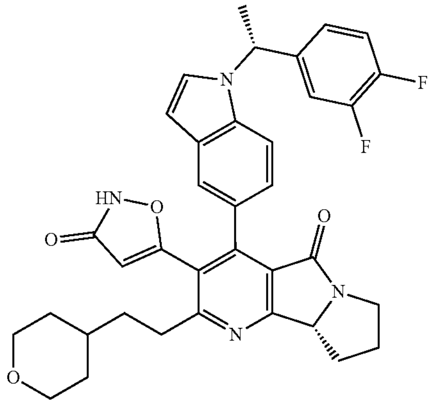 [SMILES: C[C@H](c1ccc(F)c(F)c1)n1ccc2cc(-c3c4c(nc(CCC5CCOCC5)c3-c3cc(=O)[nH]o3)[C@H]3CCCN3C4=O)ccc21] |
TABLE 2-continued
| Structure |
|---|
| 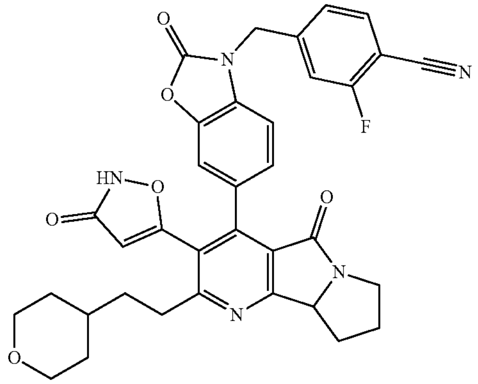 |
| 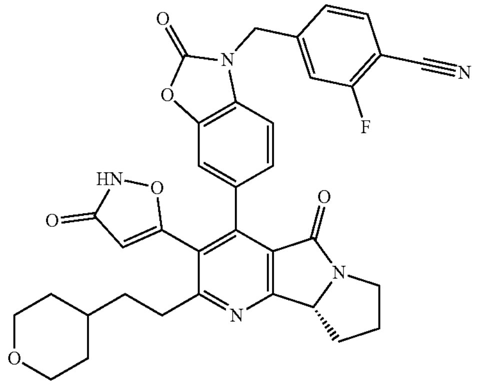 [SMILES: N#Cc1ccc(Cn2c(=O)oc3cc(-c4c5c(nc(CCC6CCOCC6)c4-c4cc(=O)[nH]o4)[C@H]4CCCN4C5=O)ccc32)cc1F] |
| 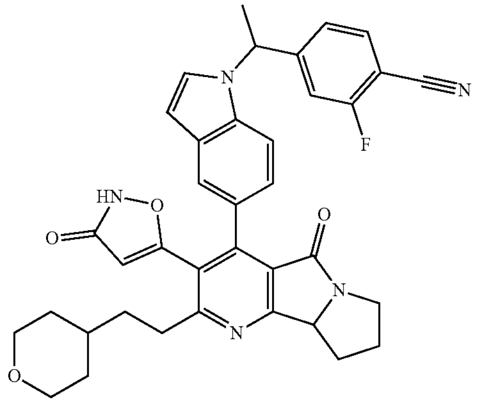 [SMILES: CC(c1ccc(C#N)c(F)c1)n1ccc2cc(-c3c4c(nc(CCC5CCOCC5)c3-c3cc(=O)[nH]o3)C3CCCN3C4=O)ccc21] |
| 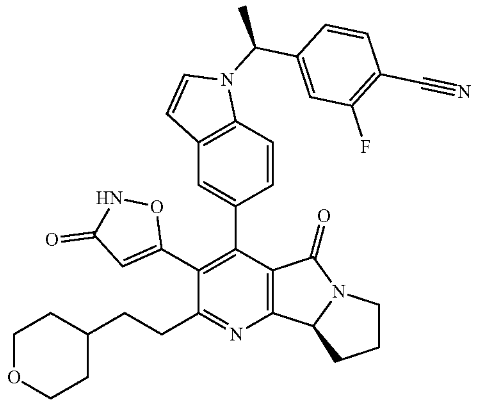 [SMILES: C[C@@H](c1ccc(C#N)c(F)c1)n1ccc2cc(-c3c4c(nc(CCC5CCOCC5)c3-c3cc(=O)[nH]o3)[C@@H]3CCCN3C4=O)ccc21]

TABLE 2-continued
| Structure |
| --- |
| 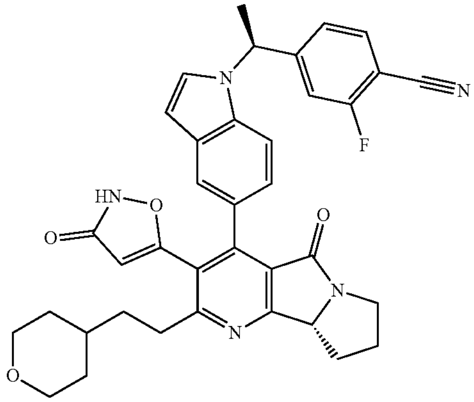 [SMILES: C[C@@H](c1ccc(C#N)c(F)c1)n1ccc2cc(-c3c4c(nc(CCC5CCOCC5)c3-c3cc(=O)[nH]o3)[C@H]3CCCN3C4=O)ccc21] |
| 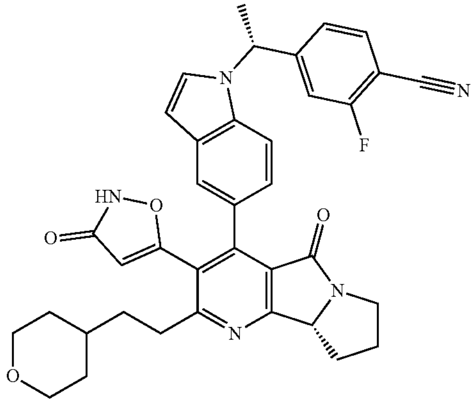 [SMILES: C[C@H](c1ccc(C#N)c(F)c1)n1ccc2cc(-c3c4c(nc(CCC5CCOCC5)c3-c3cc(=O)[nH]o3)[C@H]3CCCN3C4=O)ccc21] |
| 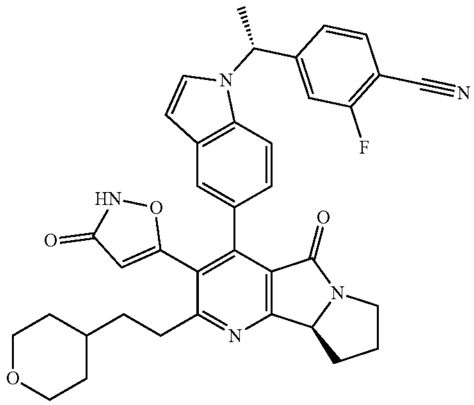 [SMILES: C[C@H](c1ccc(C#N)c(F)c1)n1ccc2cc(-c3c4c(nc(CCC5CCOCC5)c3-c3cc(=O)[nH]o3)[C@@H]3CCCN3C4=O)ccc21] |
TABLE 2-continued
| Structure |
| --- |
| 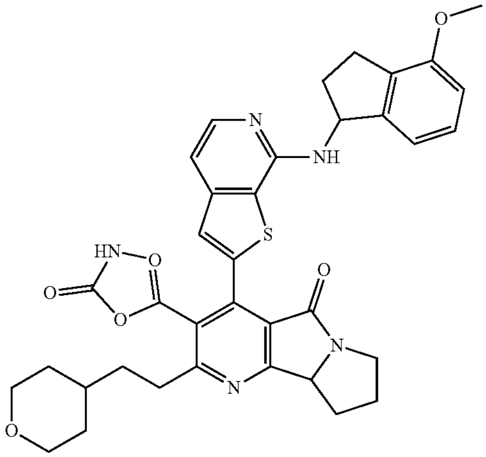 |
| 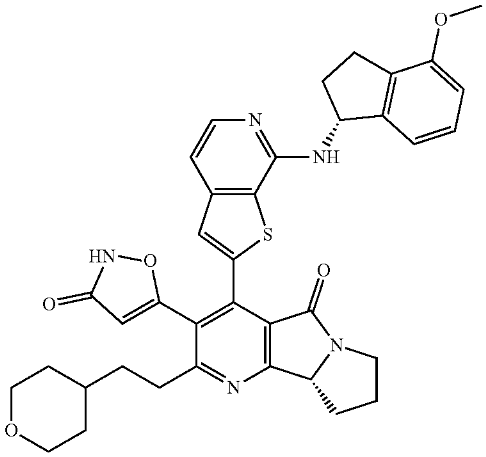 [SMILES: COc1cccc2c1CC[C@H]2Nc1nccc2cc(-c3c4c(nc(CCC5CCOCC5)c3-c3cc(=O)[nH]o3)[C@H]3CCCN3C4=O)sc12] |
| 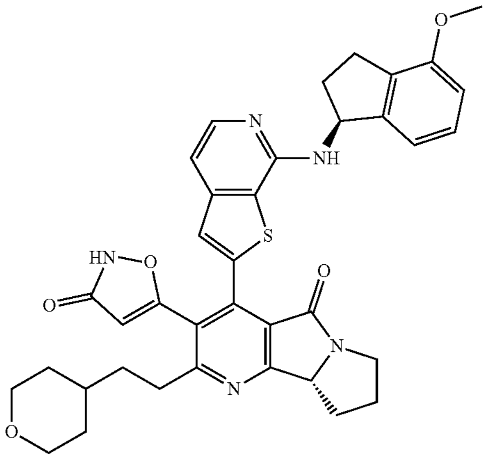 [SMILES: COc1cccc2c1CC[C@@H]2Nc1nccc2cc(-c3c4c(nc(CCC5CCOCC5)c3-c3cc(=O)[nH]o3)[C@H]3CCCN3C4=O)sc12] |

TABLE 2-continued
| Structure |
| --- |
| 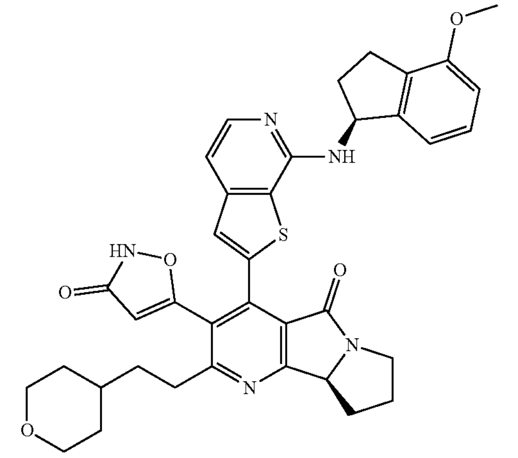 [SMILES: COc1cccc2c1CC[C@@H]2Nc1nccc2cc(-c3c4c(nc(CCC5CCOCC5)c3-c3cc(=O)[nH]o3)[C@@H]3CCCN3C4=O)sc12] |
| 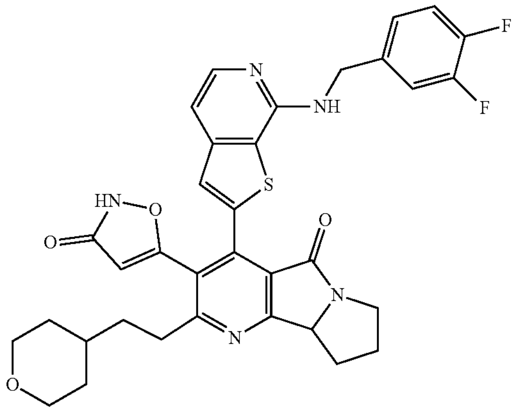 |
| 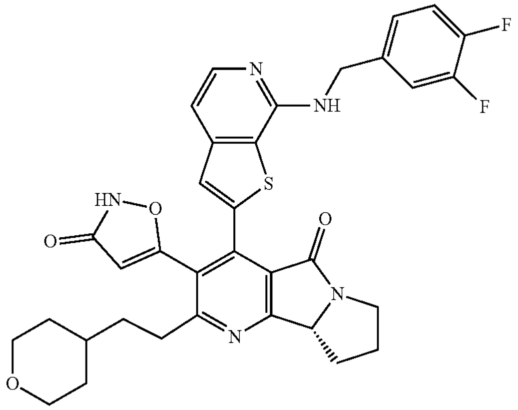 [SMILES: O=C1c2c(nc(CCC3CCOCC3)c(-c3cc(=O)[nH]o3)c2-c2cc3ccnc(NCc4ccc(F)c(F)c4)c3s2)[C@H]2CCCN12] |
TABLE 2-continued
| Structure |
| --- |
| 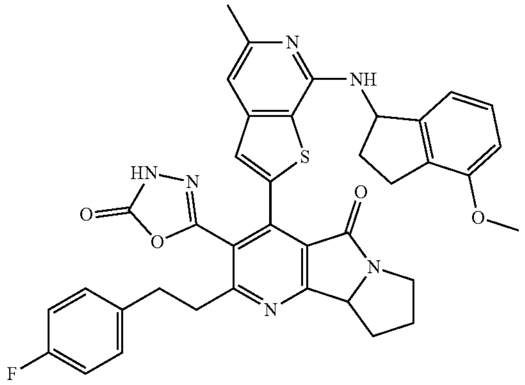 [SMILES: COc1cccc2c1CCC2Nc1nc(C)cc2cc(-c3c4c(nc(CCc5ccc(F)cc5)c3-c3n[nH]c(=O)o3)C3CCCN3C4=O)sc12] |
| 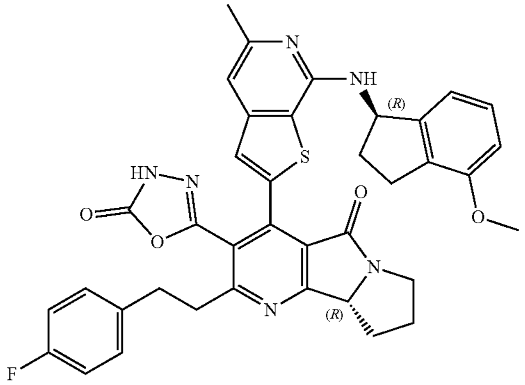 |
| 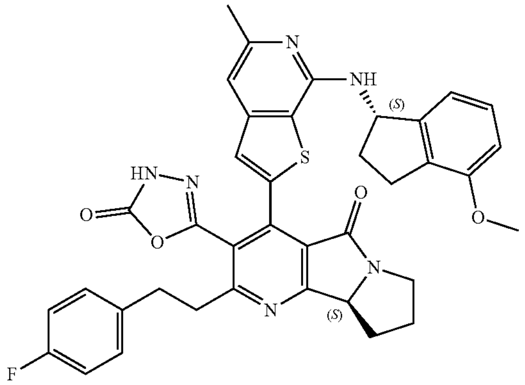 |
| 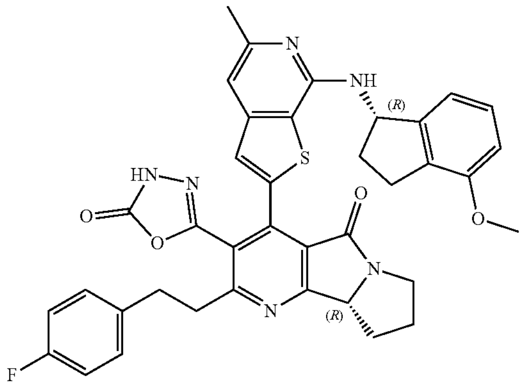

TABLE 2-continued
| Structure |
| --- |
| 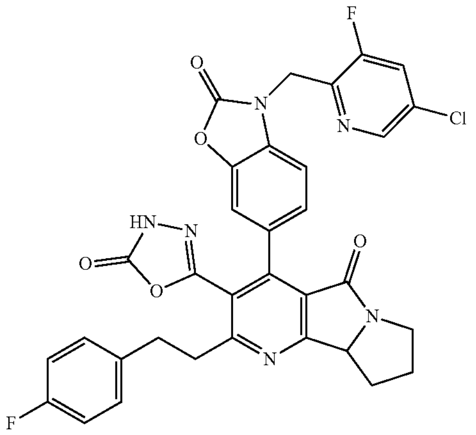 |
| 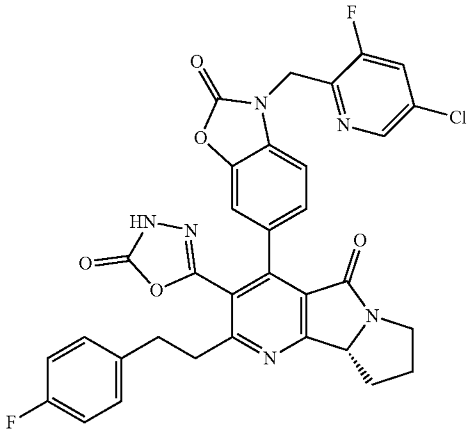 |
| 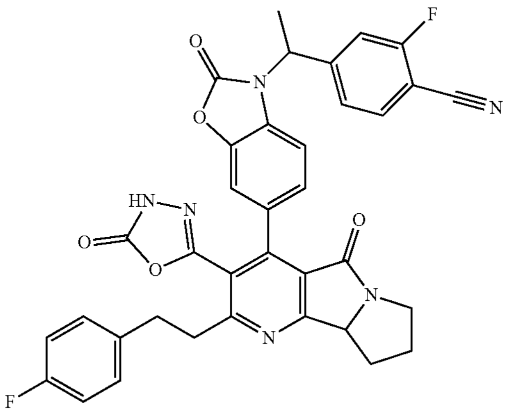 |
TABLE 2-continued
| Structure |
| --- |
| 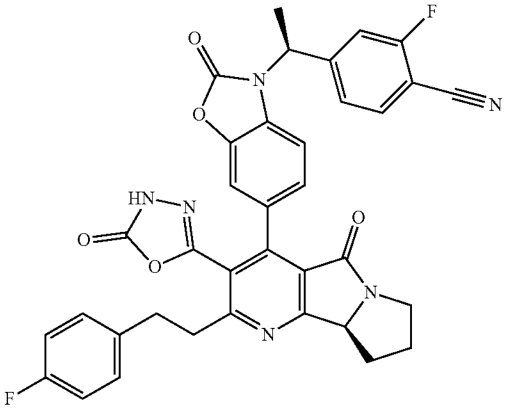 |
| 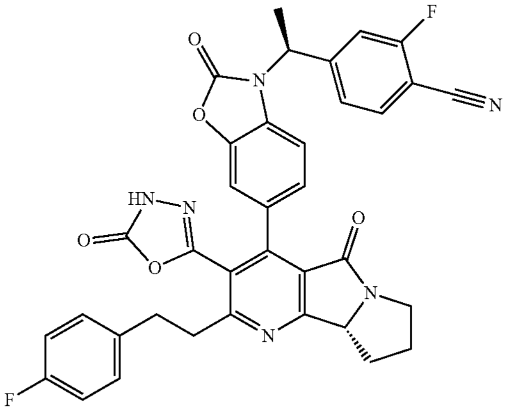 |
| 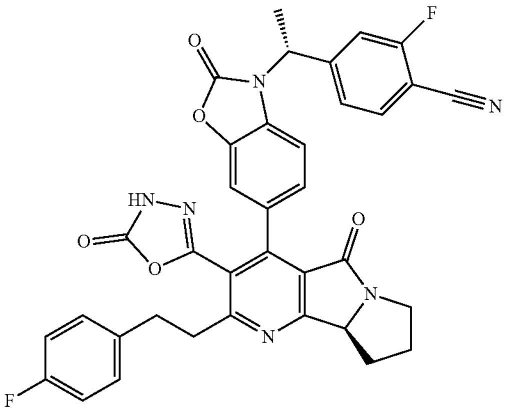 |

TABLE 2-continued
| Structure |
| --- |
| 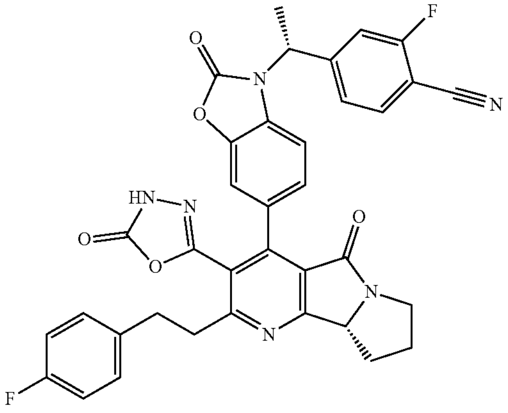 |
| 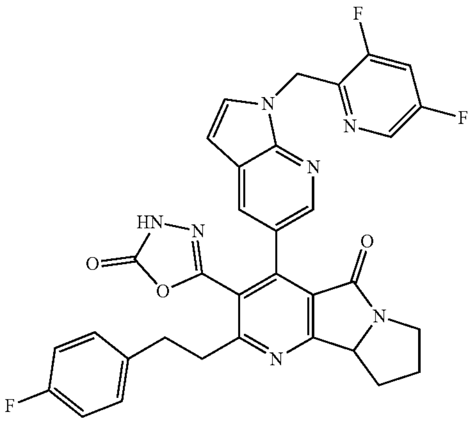 |
| 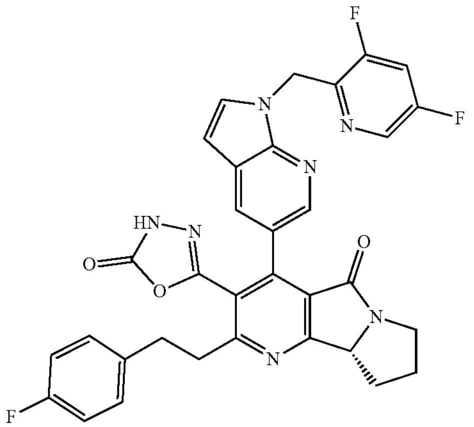 |
TABLE 2-continued
| Structure |
| --- |
| 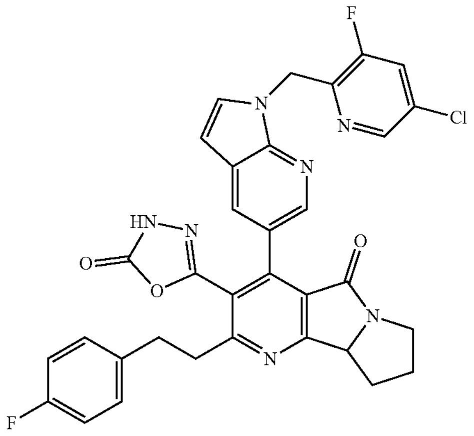 |
| 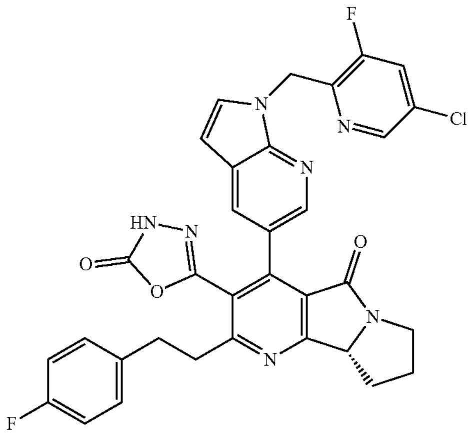 |
| 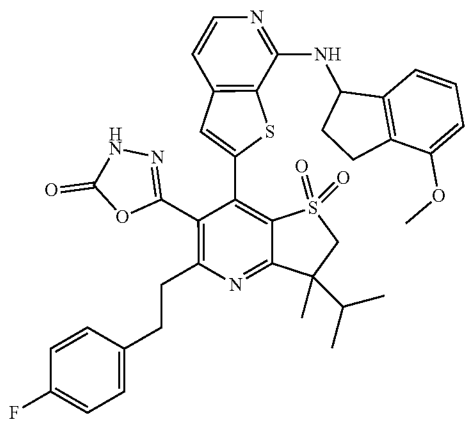 [SMILES: COc1cccc2c1CCC2Nc1nccc2cc(-c3c(-c4n[nH]c(=O)o4)c(CCc4ccc(F)cc4)nc4c3S(=O)(=O)CC4(C)C(C)C)sc12] |

TABLE 2-continued
| Structure |
|---|
| 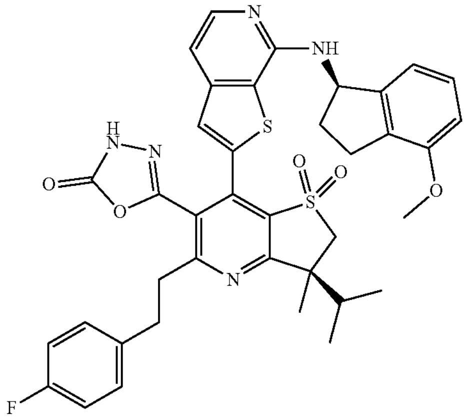 [SMILES: COc1cccc2c1CC[C@H]2Nc1nccc2cc(-c3c(-c4n[nH]c(=O)o4)c(CCc4ccc(F)cc4)nc4c3S(=O)(=O)C[C@@]4(C)C(C)C)sc12] |
| 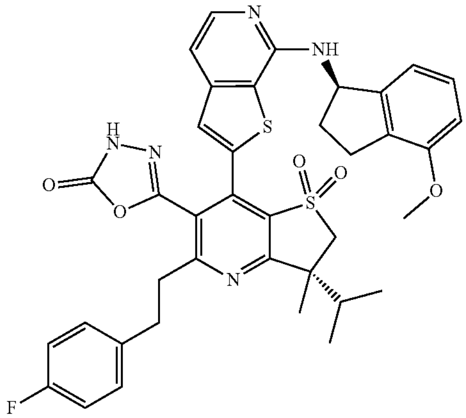 [SMILES: COc1cccc2c1CC[C@H]2Nc1nccc2cc(-c3c(-c4n[nH]c(=O)o4)c(CCc4ccc(F)cc4)nc4c3S(=O)(=O)C[C@]4(C)C(C)C)sc12] |
| 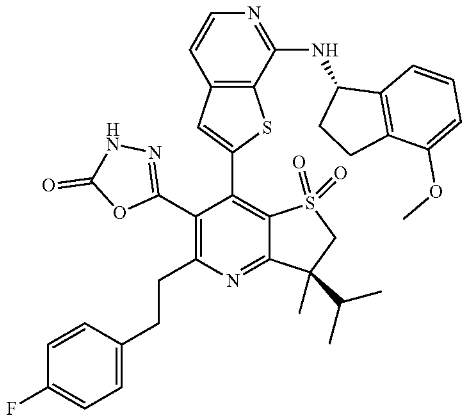 [SMILES: COc1cccc2c1CC[C@@H]2Nc1nccc2cc(-c3c(-c4n[nH]c(=O)o4)c(CCc4ccc(F)cc4)nc4c3S(=O)(=O)C[C@@]4(C)C(C)C)sc12] |
TABLE 2-continued
| Structure |
|---|
| 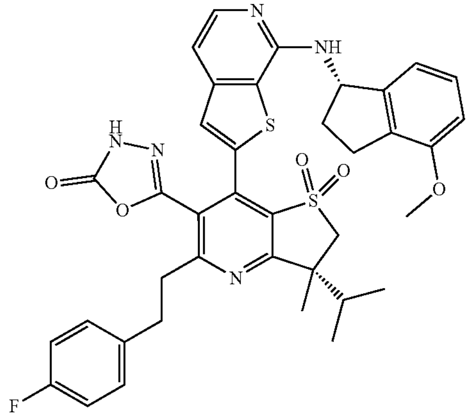 |
| 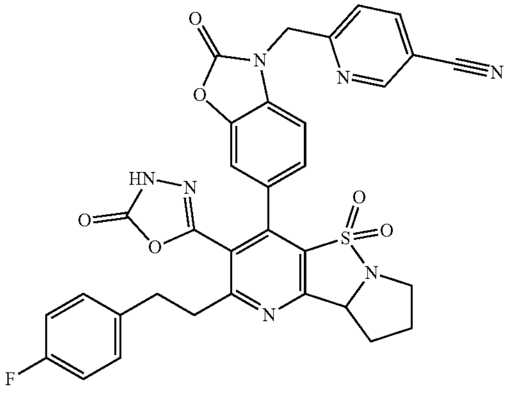 [SMILES: N#Cc1ccc(Cn2c(=O)oc3cc(-c4c(-c5n[nH]c(=O)o5)c(CCc5ccc(F)cc5)nc5c4S(=O)(=O)N4CCCC54)ccc32)nc1] |
| 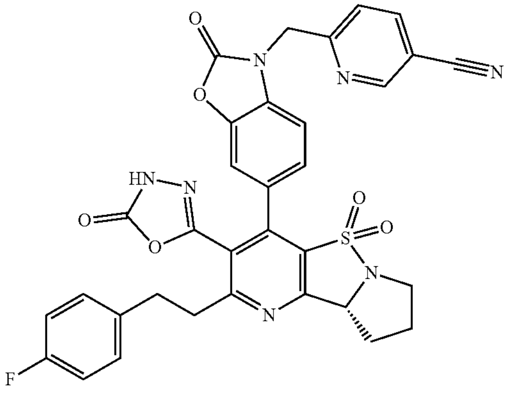 [SMILES: N#Cc1ccc(Cn2c(=O)oc3cc(-c4c(-c5n[nH]c(=O)o5)c(CCc5ccc(F)cc5)nc5c4S(=O)(=O)N4CCC[C@H]54)ccc32)nc1] |
| 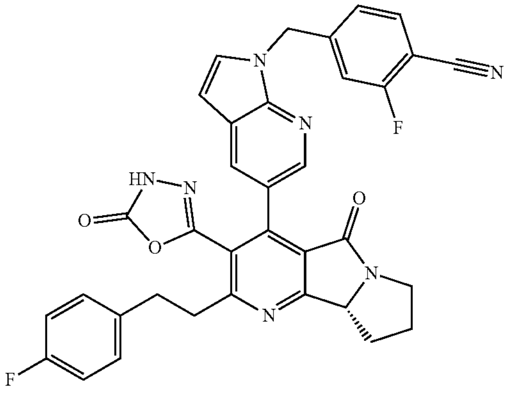 [SMILES: N#Cc1ccc(Cn2ccc3cc(-c4c5c(nc(CCc6ccc(F)cc6)c4-c4n[nH]c(=O)o4)[C@H]4CCCN4C5=O)cnc32)cc1F] |

TABLE 2-continued
| Structure |
| --- |
| 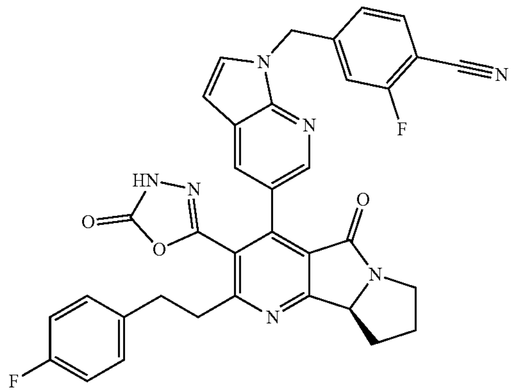 [SMILES: N#Cc1ccc(Cn2ccc3cc(-c4c5c(nc(CCc6ccc(F)cc6)c4-c4n[nH]c(=O)o4)[C@@H]4CCCN4C5=O)cnc32)cc1F] |
| 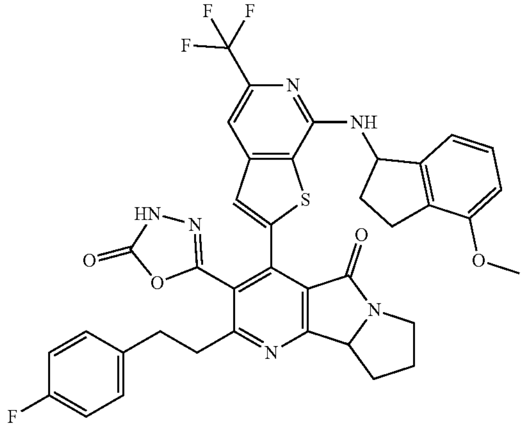 [SMILES: COc1cccc2c1CCC2Nc1nc(C(F)(F)F)cc2cc(-c3c4c(nc(CCc5ccc(F)cc5)c3-c3n[nH]c(=O)o3)C3CCCN3C4=O)sc12] |
| 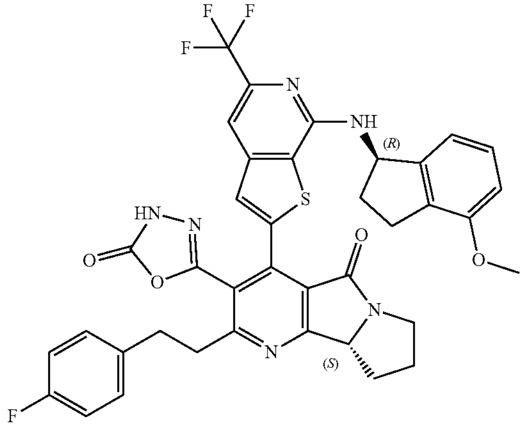 |
TABLE 2-continued
| Structure |
| --- |
| 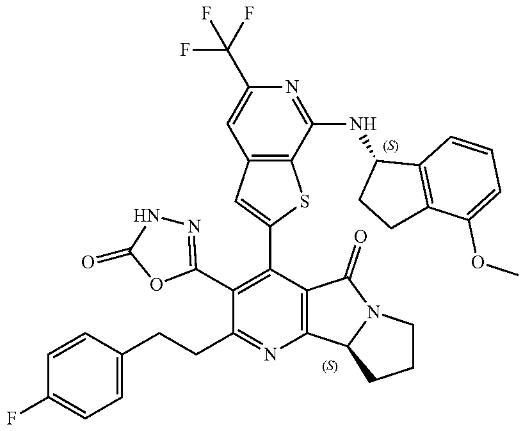 |
| 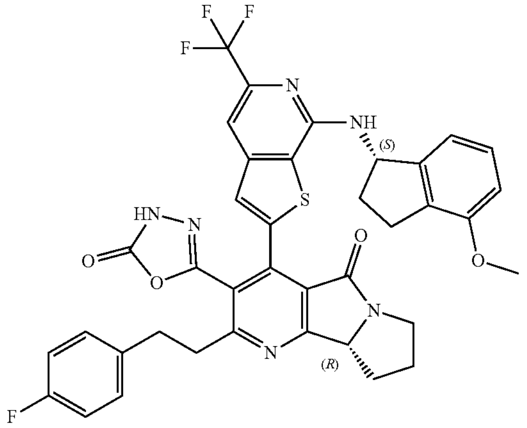 |
| 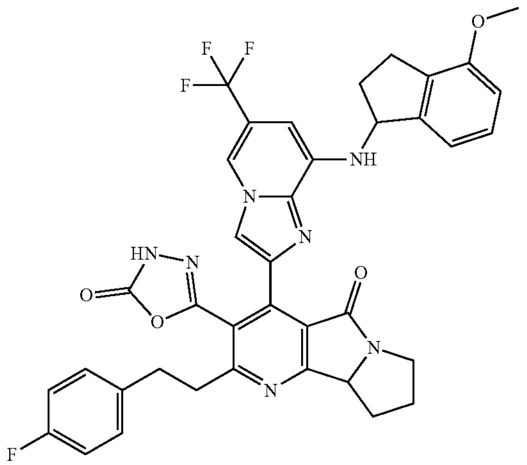 [SMILES: COc1cccc2c1CCC2Nc1cc(C(F)(F)F)cn2cc(-c3c4c(nc(CCc5ccc(F)cc5)c3-c3n[nH]c(=O)o3)C3CCCN3C4=O)nc12] |

TABLE 2-continued
| Structure |
|---|
| 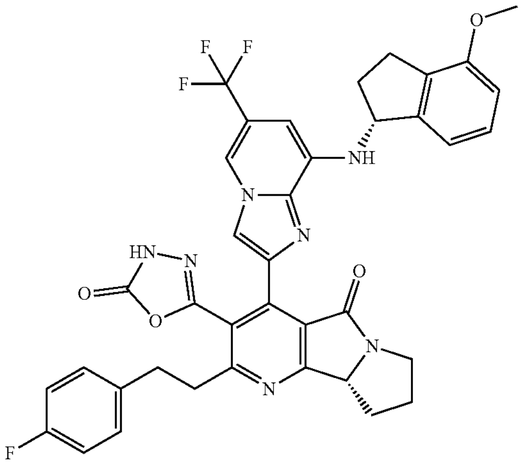 [SMILES: COc1cccc2c1CC[C@H]2Nc1cc(C(F)(F)F)cn2cc(-c3c4c(nc(CCc5ccc(F)cc5)c3-c3n[nH]c(=O)o3)[C@H]3CCCN3C4=O)nc12] |
| 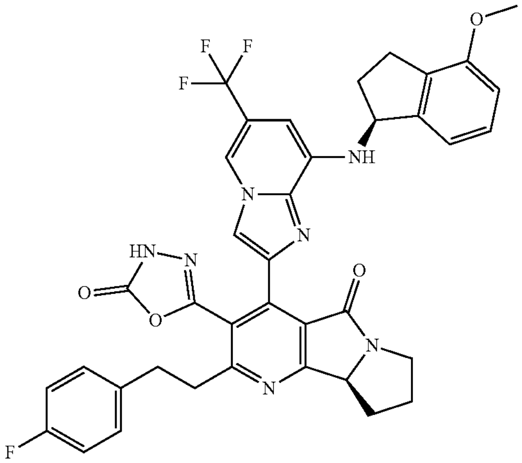 [SMILES: COc1cccc2c1CC[C@@H]2Nc1cc(C(F)(F)F)cn2cc(-c3c4c(nc(CCc5ccc(F)cc5)c3-c3n[nH]c(=O)o3)[C@@H]3CCCN3C4=O)nc12] |
| 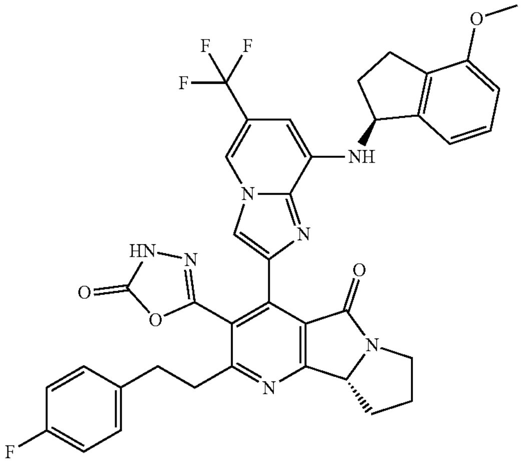 [SMILES: COc1cccc2c1CC[C@@H]2Nc1cc(C(F)(F)F)cn2cc(-c3c4c(nc(CCc5ccc(F)cc5)c3-c3n[nH]c(=O)o3)[C@H]3CCCN3C4=O)nc12] |
TABLE 2-continued
| Structure |
|---|
| 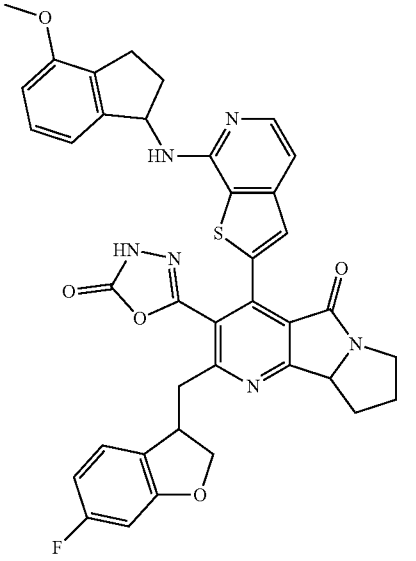 [SMILES: COc1cccc2c1CCC2Nc1nccc2cc(-c3c4c(nc(CC5COc6cc(F)ccc65)c3-c3n[nH]c(=O)o3)C3CCCN3C4=O)sc12] |
| 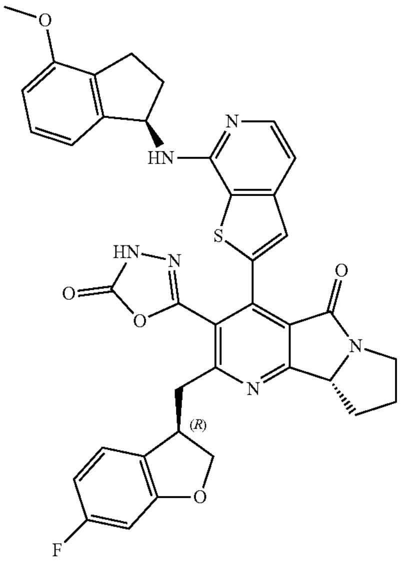 |

| Structure |
| --- |
| 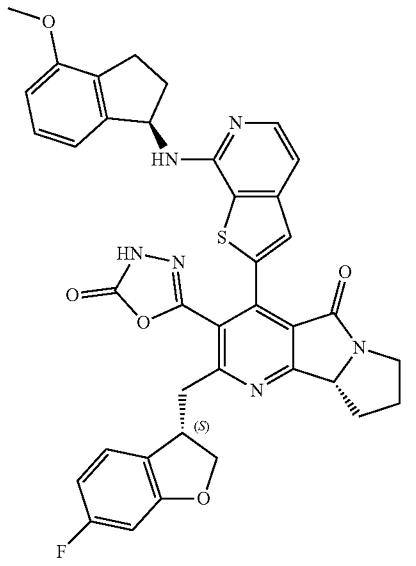 |
| 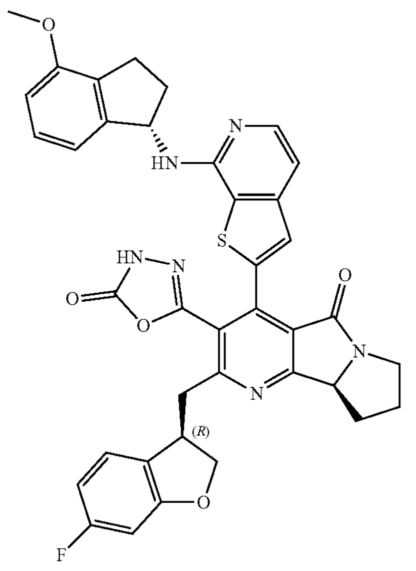 |
| Structure |
| --- |
| 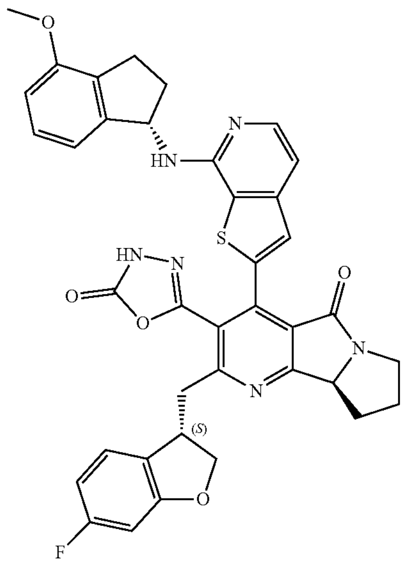 |
| 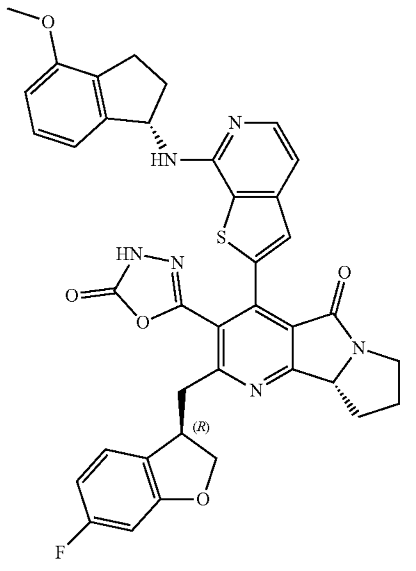 |

TABLE 2-continued
| Structure |
| --- |
| 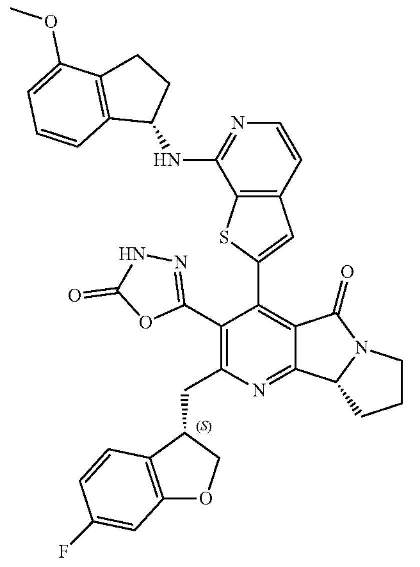 |
| 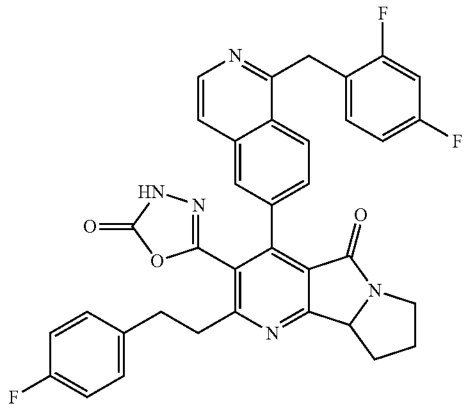 [SMILES: O=C1c2c(nc(CCc3ccc(F)cc3)c(-c3n[nH]c(=O)o3)c2-c2ccc3c(Cc4ccc(F)cc4F)nccc3c2)C2CCCN12] |
| 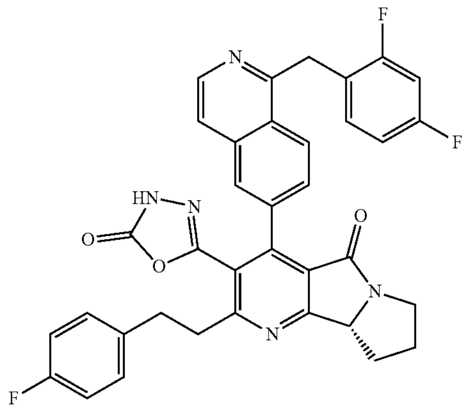 [SMILES: O=C1c2c(nc(CCc3ccc(F)cc3)c(-c3n[nH]c(=O)o3)c2-c2ccc3c(Cc4ccc(F)cc4F)nccc3c2)[C@H]2CCCN12] |
TABLE 2-continued
| Structure |
| --- |
| 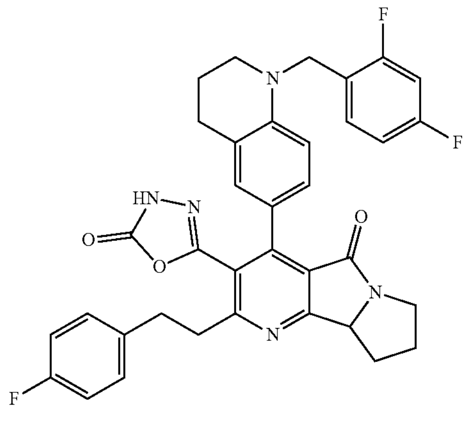 [SMILES: O=C1c2c(nc(CCc3ccc(F)cc3)c(-c3n[nH]c(=O)o3)c2-c2ccc3c(c2)CCCN3Cc2ccc(F)cc2F)C2CCCN12] |
| 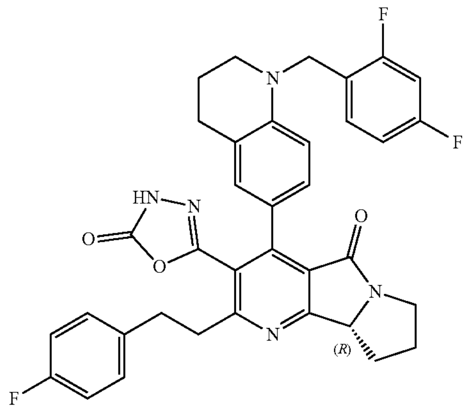 |
| 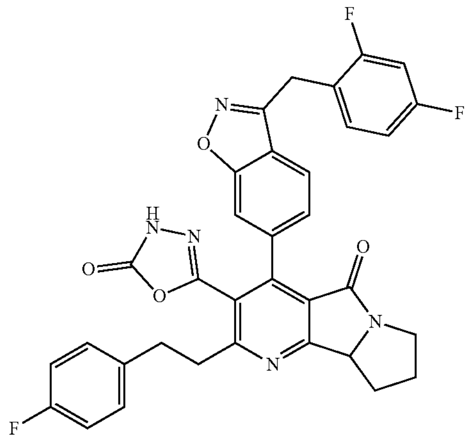 [SMILES: O=C1c2c(nc(CCc3ccc(F)cc3)c(-c3n[nH]c(=O)o3)c2-c2ccc3c(Cc4ccc(F)cc4F)noc3c2)C2CCCN12]

TABLE 2-continued
| Structure |
| --- |
| 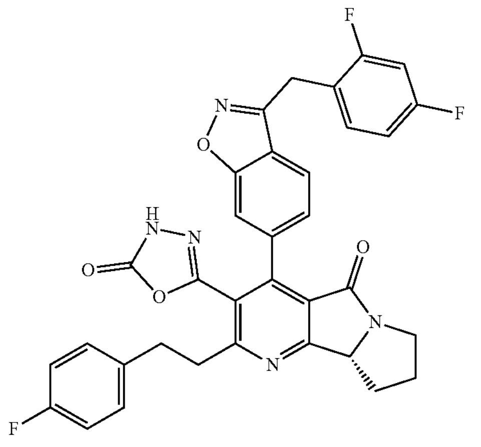 [SMILES: O=C1c2c(nc(CCc3ccc(F)cc3)c(-c3n[nH]c(=O)o3)c2-c2ccc3c(Cc4ccc(F)cc4F)noc3c2)[C@H]2CCCN12] |
| 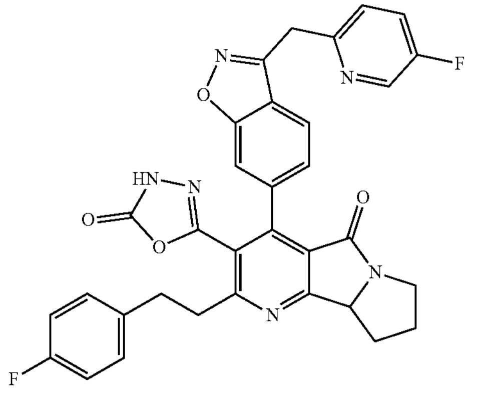 [SMILES: O=C1c2c(nc(CCc3ccc(F)cc3)c(-c3n[nH]c(=O)o3)c2-c2ccc3c(Cc4ccc(F)cn4)noc3c2)C2CCCN12] |
| 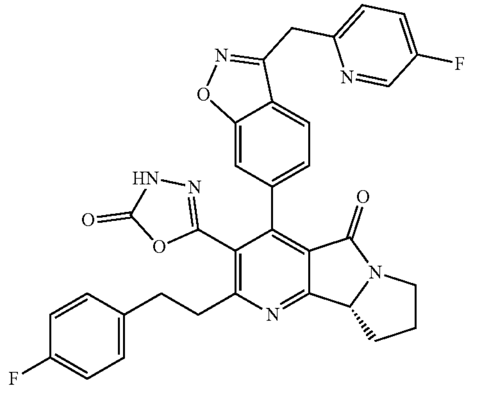 [SMILES: O=C1c2c(nc(CCc3ccc(F)cc3)c(-c3n[nH]c(=O)o3)c2-c2ccc3c(Cc4ccc(F)cn4)noc3c2)[C@H]2CCCN12] |
| 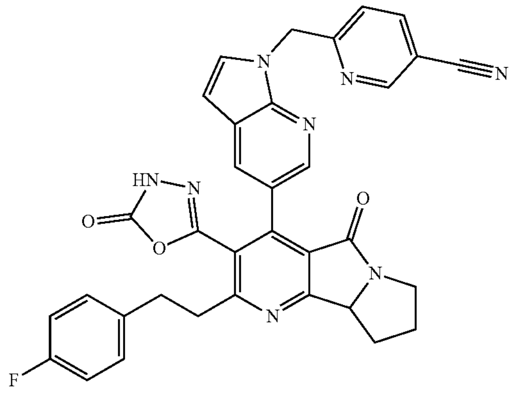 [SMILES: N#Cc1ccc(Cn2ccc3cc(-c4c5c(nc(CCc6ccc(F)cc6)c4-c4n[nH]c(=O)o4)C4CCCN4C5=O)cnc32)nc1] |
TABLE 2-continued
| Structure |
| --- |
| 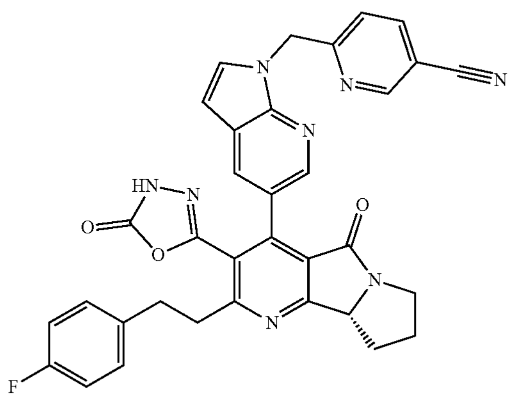 [SMILES: N#Cc1ccc(Cn2ccc3cc(-c4c5c(nc(CCc6ccc(F)cc6)c4-c4n[nH]c(=O)o4)[C@H]4CCCN4C5=O)cnc32)nc1] |
| 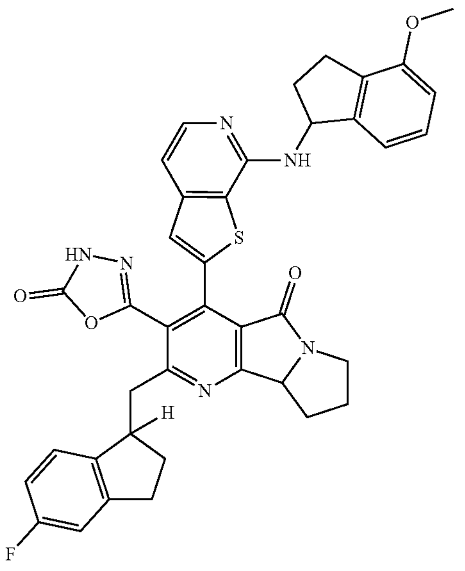 [SMILES: COc1cccc2c1CCC2Nc1nccc2cc(-c3c4c(nc(CC5CCc6cc(F)ccc65)c3-c3n[nH]c(=O)o3)C3CCCN3C4=O)sc12] |
| 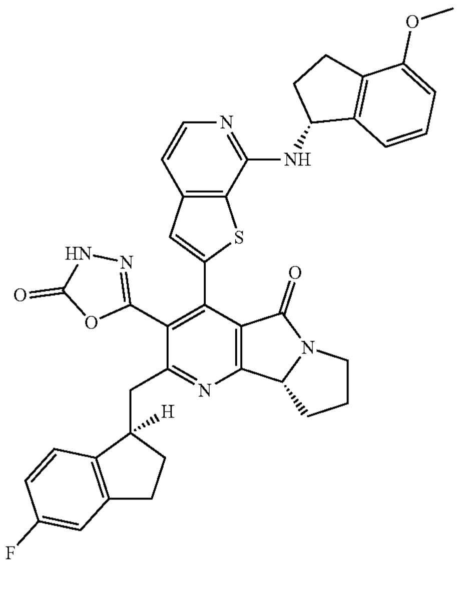 [SMILES: COc1cccc2c1CC[C@H]2Nc1nccc2cc(-c3c4c(nc(C[C@H]5CCc6cc(F)ccc65)c3-c3n[nH]c(=O)o3)[C@H]3CCCN3C4=O)sc12] |

TABLE 2-continued
| Structure |
| --- |
| 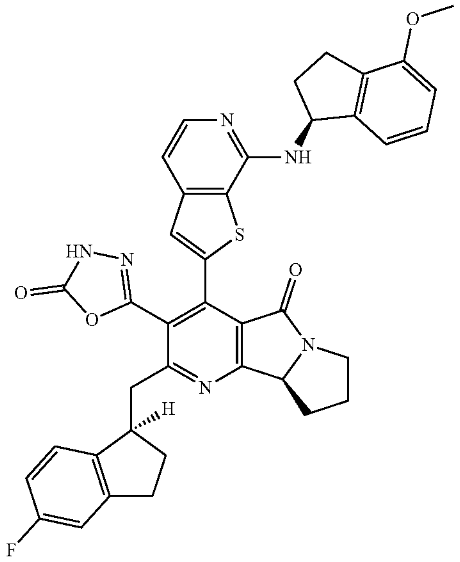 [SMILES: COc1cccc2c1CC[C@@H]2Nc1nccc2cc(-c3c4c(nc(C[C@H]5CCc6cc(F)ccc65)c3-c3n[nH]c(=O)o3)[C@@H]3CCCN3C4=O)sc12] |
| 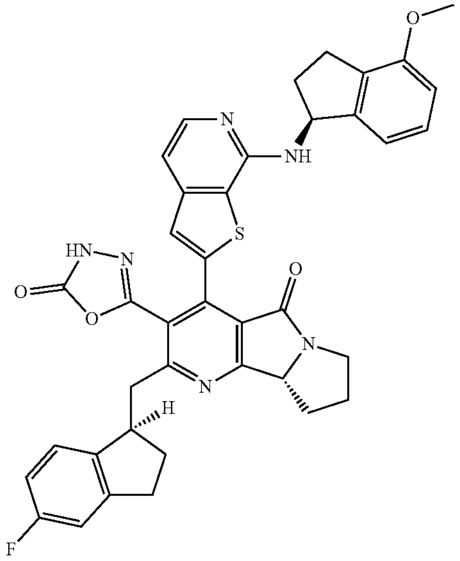 [SMILES: COc1cccc2c1CC[C@@H]2Nc1nccc2cc(-c3c4c(nc(C[C@H]5CCc6cc(F)ccc65)c3-c3n[nH]c(=O)o3)[C@H]3CCCN3C4=O)sc12] |
TABLE 2-continued
| Structure |
| --- |
| 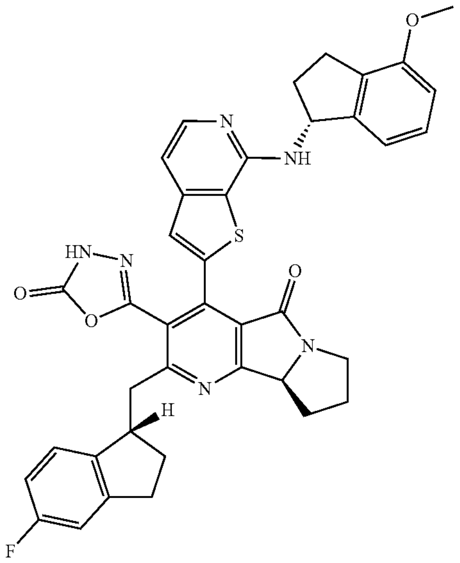 [SMILES: COc1cccc2c1CC[C@H]2Nc1nccc2cc(-c3c4c(nc(C[C@@H]5CCc6cc(F)ccc65)c3-c3n[nH]c(=O)o3)[C@@H]3CCCN3C4=O)sc12] |
| 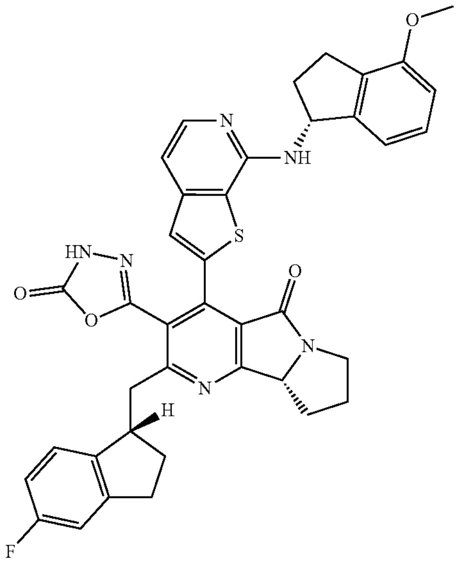 [SMILES: COc1cccc2c1CC[C@H]2Nc1nccc2cc(-c3c4c(nc(C[C@@H]5CCc6cc(F)ccc65)c3-c3n[nH]c(=O)o3)[C@H]3CCCN3C4=O)sc12] |

TABLE 2-continued
| Structure |
| --- |
| 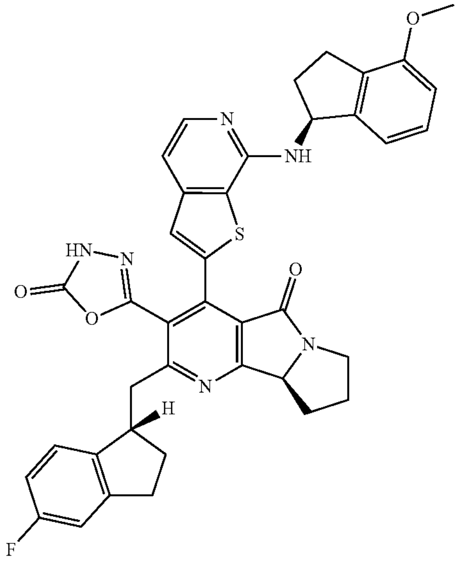 |
| 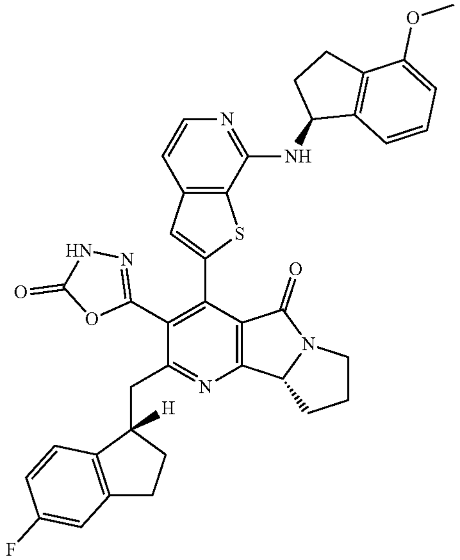 [SMILES: COc1cccc2c1CC[C@@H]2Nc1nccc2cc(-c3c4c(nc(C[C@@H]5CCc6cc(F)ccc65)c3-c3n[nH]c(=O)o3)[C@H]3CCCN3C4=O)sc12] |
| 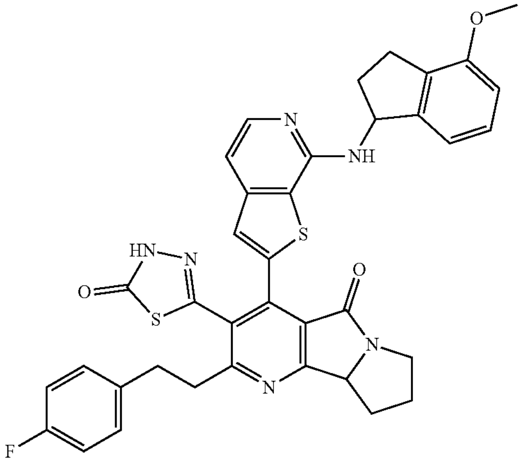 [SMILES: COc1cccc2c1CCC2Nc1nccc2cc(-c3c4c(nc(CCc5ccc(F)cc5)c3-c3n[nH]c(=O)s3)C3CCCN3C4=O)sc12] |
TABLE 2-continued
| Structure |
| --- |
| 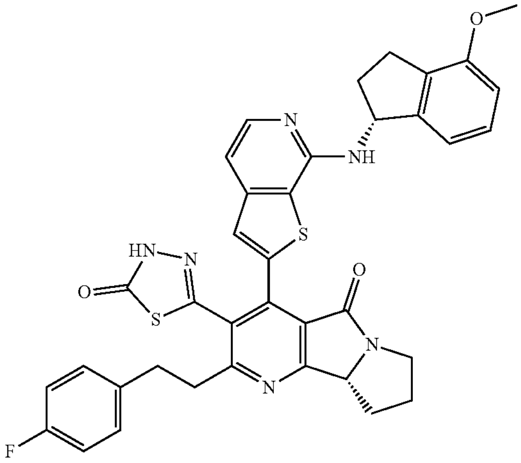 [SMILES: COc1cccc2c1CC[C@H]2Nc1nccc2cc(-c3c4c(nc(CCc5ccc(F)cc5)c3-c3n[nH]c(=O)s3)[C@H]3CCCN3C4=O)sc12] |
| 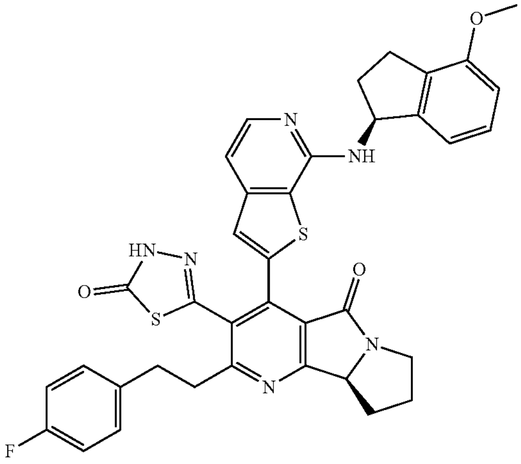 [SMILES: COc1cccc2c1CC[C@@H]2Nc1nccc2cc(-c3c4c(nc(CCc5ccc(F)cc5)c3-c3n[nH]c(=O)s3)[C@@H]3CCCN3C4=O)sc12] |
| 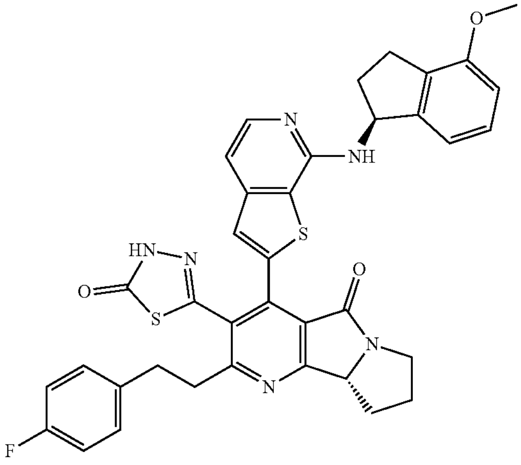 [SMILES: COc1cccc2c1CC[C@@H]2Nc1nccc2cc(-c3c4c(nc(CCc5ccc(F)cc5)c3-c3n[nH]c(=O)s3)[C@H]3CCCN3C4=O)sc12] |

TABLE 2-continued
| Structure |
| --- |
| 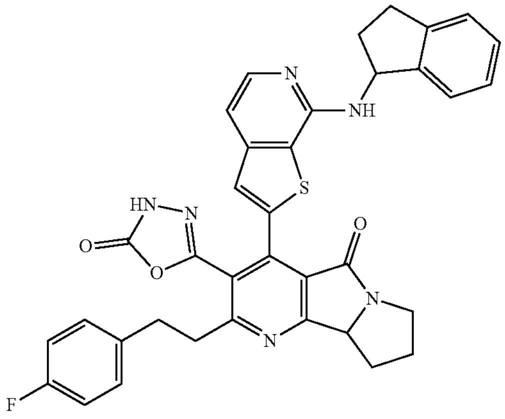 [SMILES: O=C1c2c(nc(CCc3ccc(F)cc3)c(-c3n[nH]c(=O)o3)c2-c2cc3ccnc(NC4CCc5ccccc54)c3s2)C2CCCN12] |
| 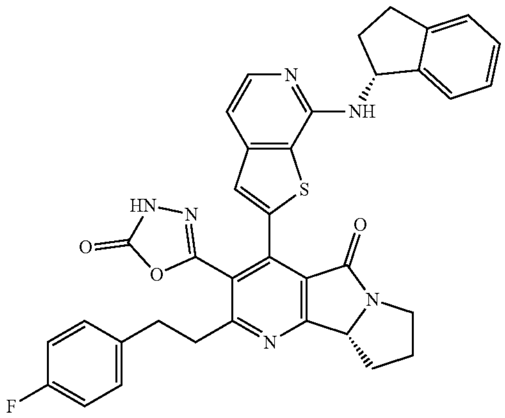 [SMILES: O=C1c2c(nc(CCc3ccc(F)cc3)c(-c3n[nH]c(=O)o3)c2-c2cc3ccnc(N[C@@H]4CCc5ccccc54)c3s2)[C@H]2CCCN12] |
| 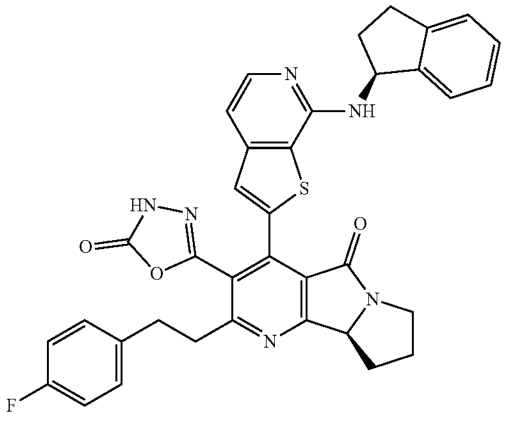 [SMILES: O=C1c2c(nc(CCc3ccc(F)cc3)c(-c3n[nH]c(=O)o3)c2-c2cc3ccnc(N[C@H]4CCc5ccccc54)c3s2)[C@@H]2CCCN12] |
TABLE 2-continued
| Structure |
| --- |
| 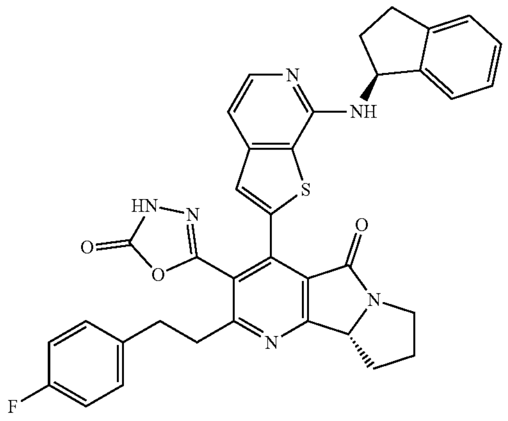 [SMILES: O=C1c2c(nc(CCc3ccc(F)cc3)c(-c3n[nH]c(=O)o3)c2-c2cc3ccnc(N[C@H]4CCc5ccccc54)c3s2)[C@H]2CCCN12] |
| 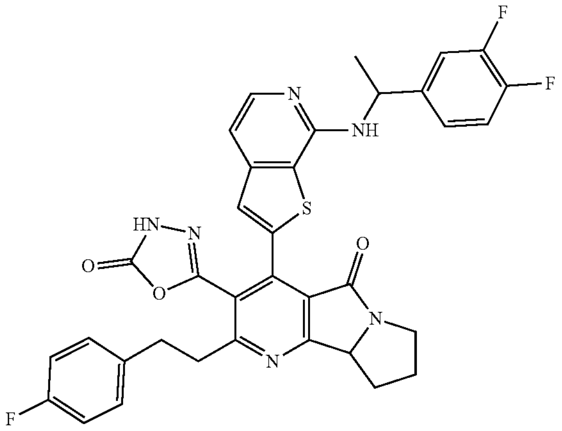 [SMILES: CC(Nc1nccc2cc(-c3c4c(nc(CCc5ccc(F)cc5)c3-c3n[nH]c(=O)o3)C3CCCN3C4=O)sc12)c1ccc(F)c(F)c1] |
| 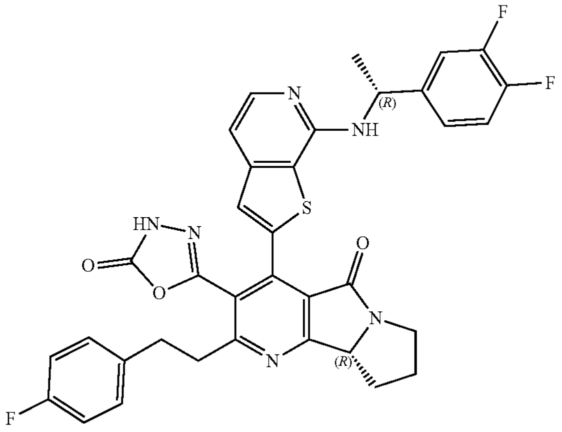 |

TABLE 2-continued
| Structure |
|---|
| 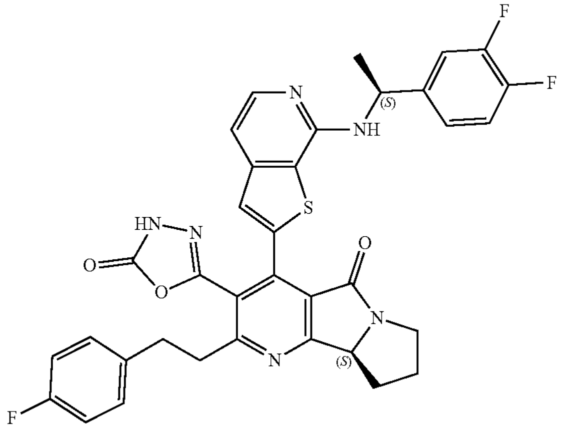 |
| 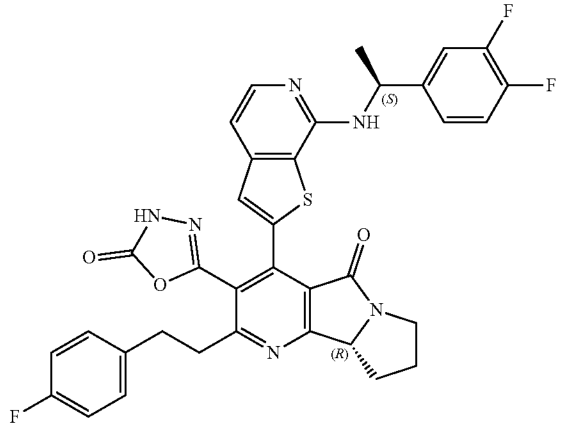 |
| 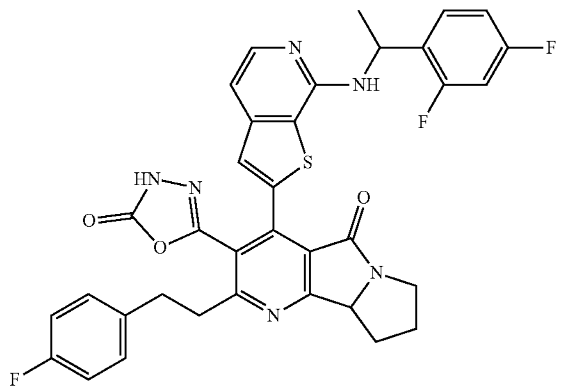 [SMILES: CC(Nc1nccc2cc(-c3c4c(nc(CCc5ccc(F)cc5)c3-c3n[nH]c(=O)o3)C3CCCN3C4=O)sc12)c1ccc(F)cc1F] |
TABLE 2-continued
| Structure |
|---|
| 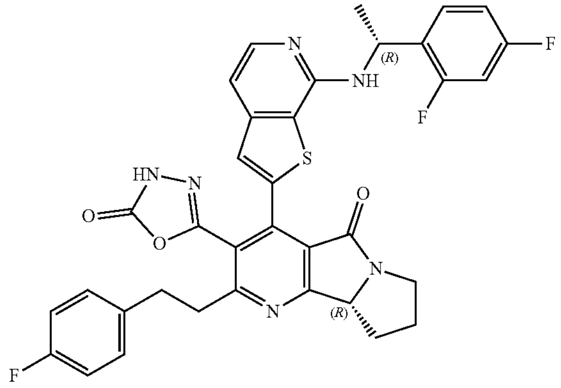 |
| 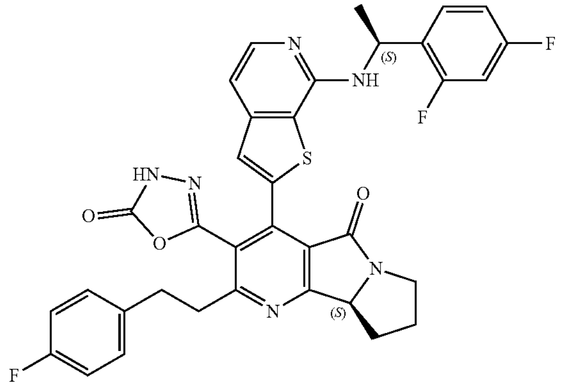 |
| 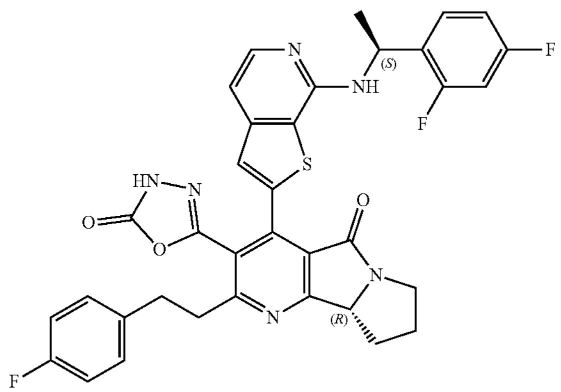 |

TABLE 2-continued
| Structure |
| --- |
| 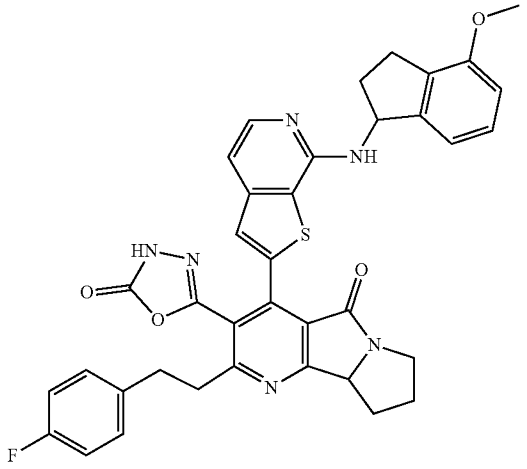 [SMILES: COc1cccc2c1CCC2Nc1nccc2cc(-c3c4c(nc(CCc5ccc(F)cc5)c3-c3n[nH]c(=O)o3)C3CCCN3C4=O)sc12] |
| 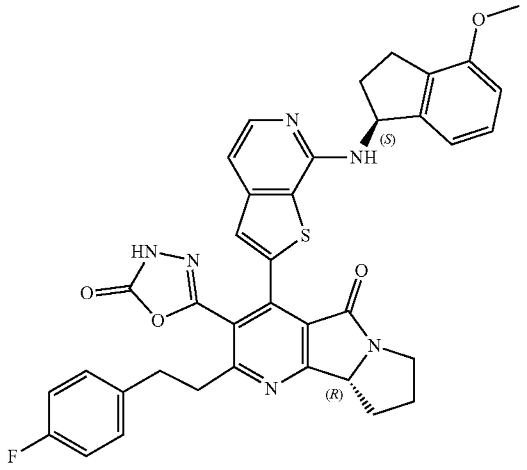 |
| 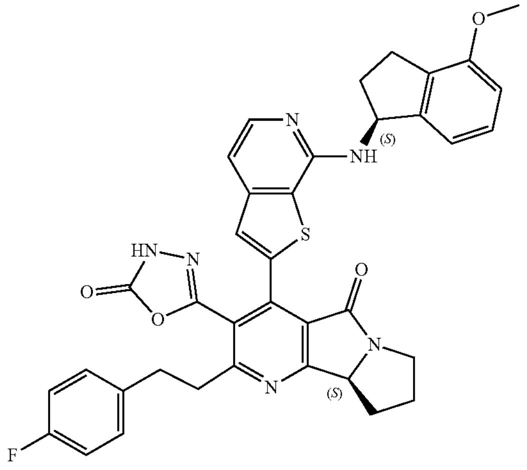 |
TABLE 2-continued
| Structure |
| --- |
| 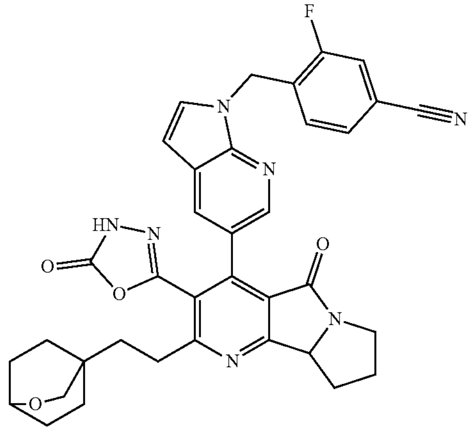 [SMILES: N#Cc1ccc(Cn2ccc3cc(-c4c5c(nc(CCC67CCC(CC6)OC7)c4-c4n[nH]c(=O)o4)C4CCCN4C5=O)cnc32)c(F)c1] |
| 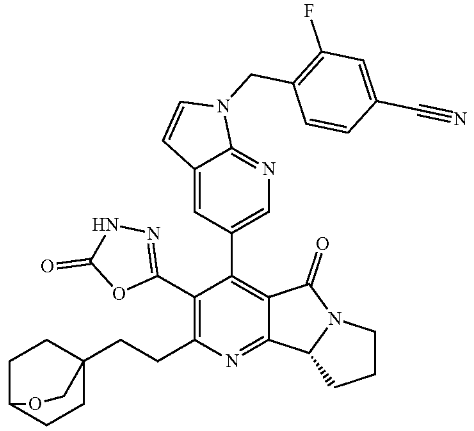 [SMILES: N#Cc1ccc(Cn2ccc3cc(-c4c5c(nc(CCC67CCC(CC6)OC7)c4-c4n[nH]c(=O)o4)[C@H]4CCCN4C5=O)cnc32)c(F)c1] |
| 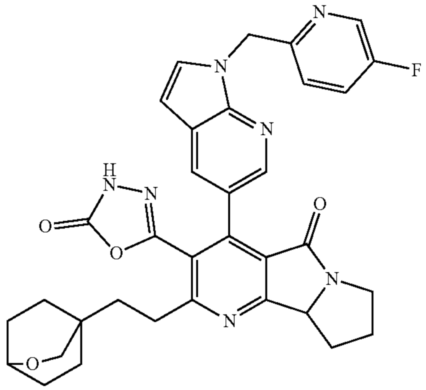 [SMILES: O=C1c2c(nc(CCC34CCC(CC3)OC4)c(-c3n[nH]c(=O)o3)c2-c2cnc3c(ccn3Cc3ccc(F)cn3)c2)C2CCCN12] |

TABLE 2-continued
| Structure |
| --- |
| 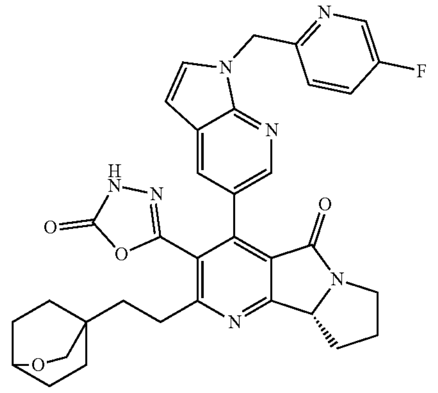 [SMILES: O=C1c2c(nc(CCC34CCC(CC3)OC4)c(-c3n[nH]c(=O)o3)c2-c2cnc3c(ccn3Cc3ccc(F)cn3)c2)[C@H]2CCCN12] |
| 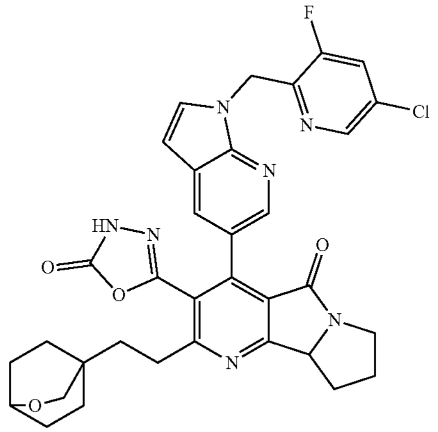 [SMILES: O=C1c2c(nc(CCC34CCC(CC3)OC4)c(-c3n[nH]c(=O)o3)c2-c2cnc3c(ccn3Cc3ncc(Cl)cc3F)c2)C2CCCN12] |
| 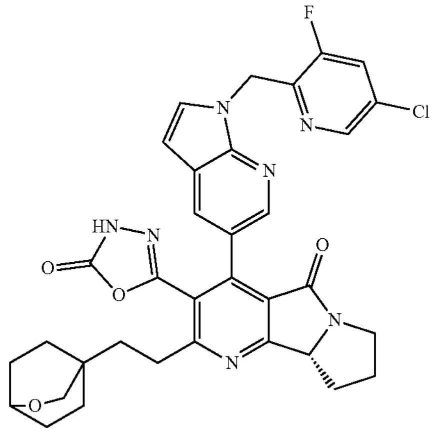 [SMILES: O=C1c2c(nc(CCC34CCC(CC3)OC4)c(-c3n[nH]c(=O)o3)c2-c2cnc3c(ccn3Cc3ncc(Cl)cc3F)c2)[C@H]2CCCN12] |
TABLE 2-continued
| Structure |
| --- |
| 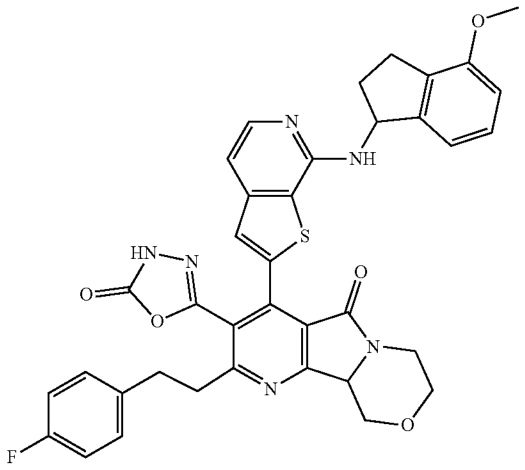 [SMILES: COc1cccc2c1CCC2Nc1nccc2cc(-c3c4c(nc(CCc5ccc(F)cc5)c3-c3n[nH]c(=O)o3)C3COCCN3C4=O)sc12] |
| 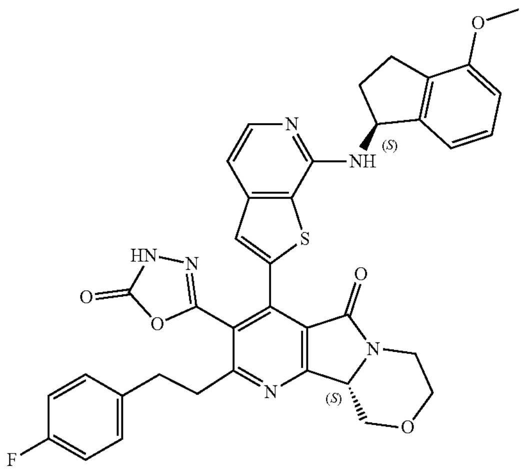 |
| 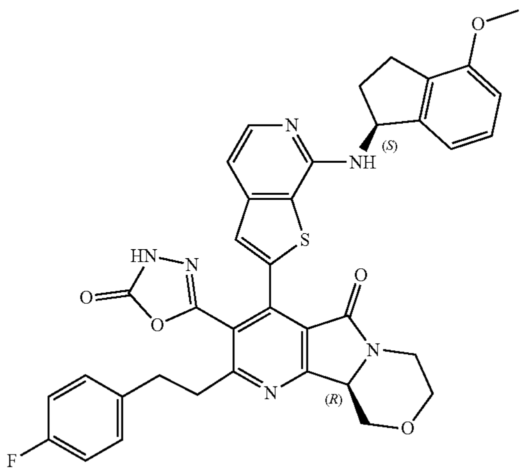 |

TABLE 2-continued
| Structure |
|---|
| 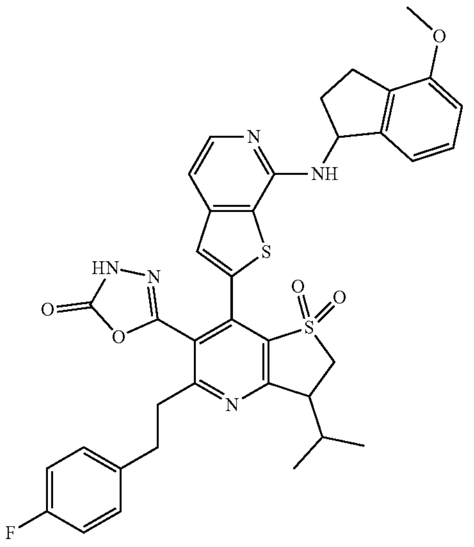 [SMILES: COc1cccc2c1CCC2Nc1nccc2cc(-c3c(-c4n[nH]c(=O)o4)c(CCc4ccc(F)cc4)nc4c3S(=O)(=O)CC4C(C)C)sc12] |
| 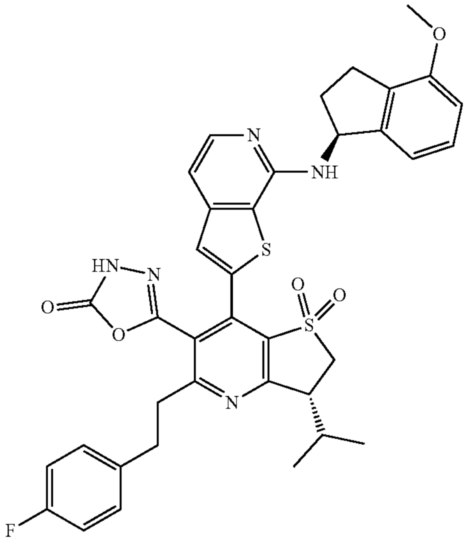 [SMILES: COc1cccc2c1CC[C@@H]2Nc1nccc2cc(-c3c(-c4n[nH]c(=O)o4)c(CCc4ccc(F)cc4)nc4c3S(=O)(=O)C[C@@H]4C(C)C)sc12] |
| 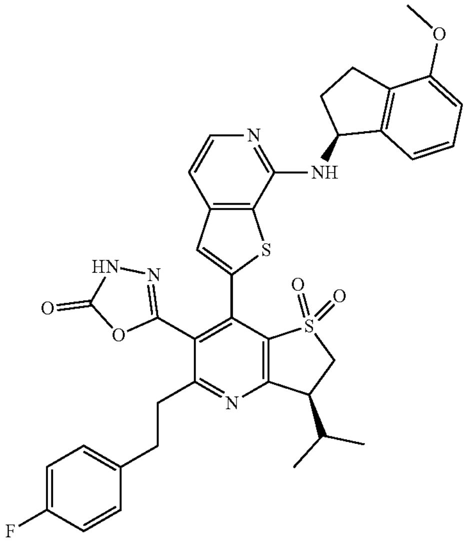 [SMILES: COc1cccc2c1CC[C@@H]2Nc1nccc2cc(-c3c(-c4n[nH]c(=O)o4)c(CCc4ccc(F)cc4)nc4c3S(=O)(=O)C[C@H]4C(C)C)sc12] |
TABLE 2-continued
| Structure |
|---|
| 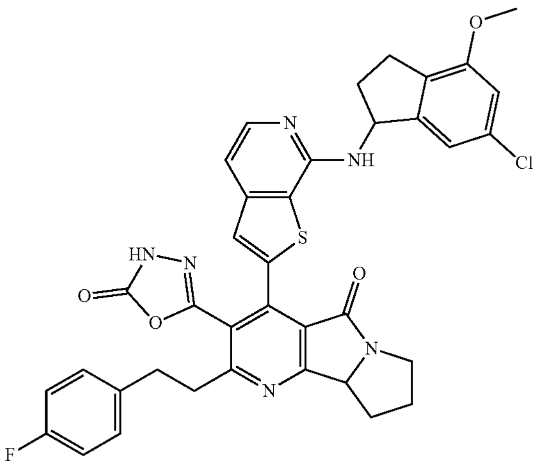 [SMILES: COc1cc(Cl)cc2c1CCC2Nc1nccc2cc(-c3c4c(nc(CCc5ccc(F)cc5)c3-c3n[nH]c(=O)o3)C3CCCN3C4=O)sc12] |
| 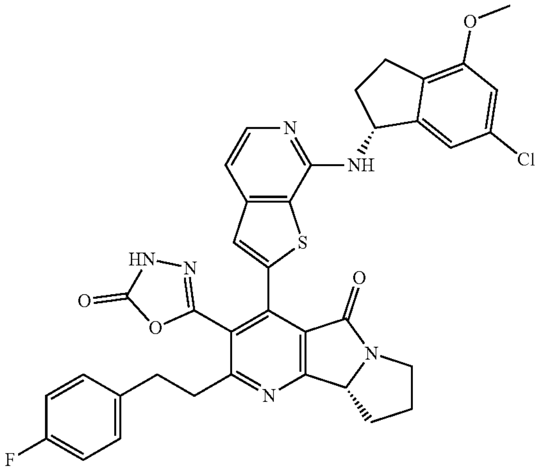 [SMILES: COc1cc(Cl)cc2c1CC[C@H]2Nc1nccc2cc(-c3c4c(nc(CCc5ccc(F)cc5)c3-c3n[nH]c(=O)o3)[C@H]3CCCN3C4=O)sc12] |
| 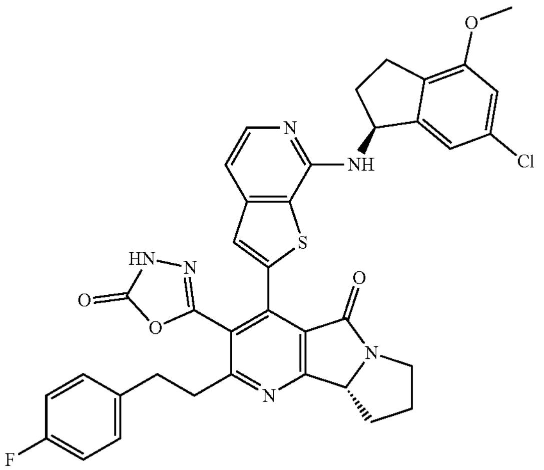 [SMILES: COc1cc(Cl)cc2c1CC[C@@H]2Nc1nccc2cc(-c3c4c(nc(CCc5ccc(F)cc5)c3-c3n[nH]c(=O)o3)[C@H]3CCCN3C4=O)sc12] |

TABLE 2-continued
| Structure |
| --- |
| 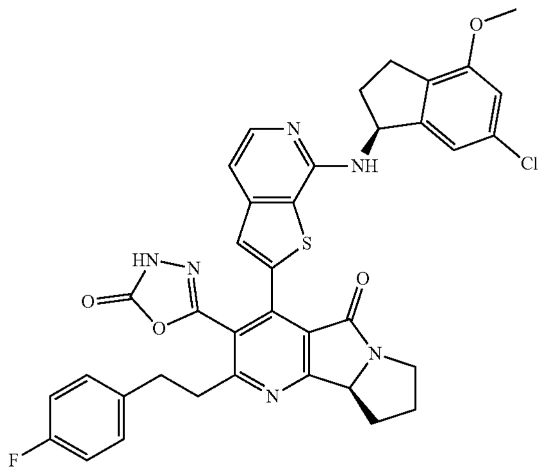 [SMILES: COc1cc(Cl)cc2c1CC[C@@H]2Nc1nccc2cc(-c3c4c(nc(CCc5ccc(F)cc5)c3-c3n[nH]c(=O)o3)[C@@H]3CCCN3C4=O)sc12] |
| 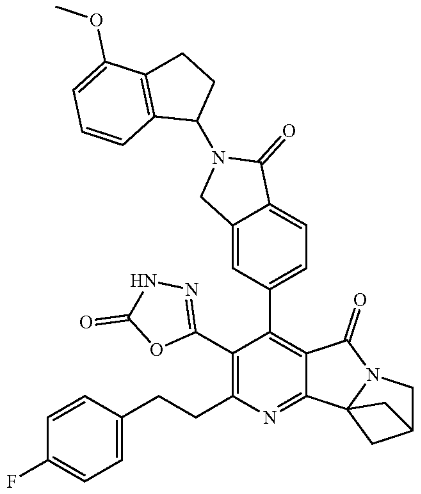 [SMILES: COc1cccc2c1CCC2N1Cc2cc(-c3c4c(nc(CCc5ccc(F)cc5)c3-c3n[nH]c(=O)o3)C35CC(CN3C4=O)C5)ccc2C1=O] |
| 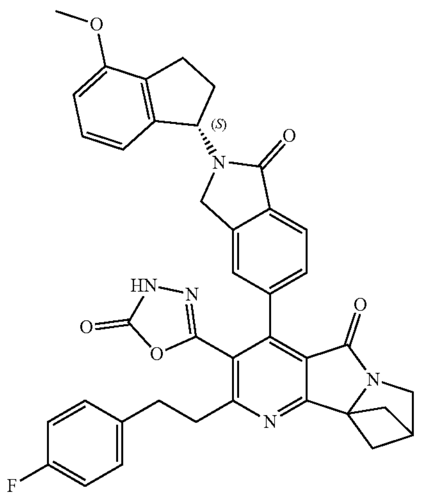 |
TABLE 2-continued
| Structure |
| --- |
| 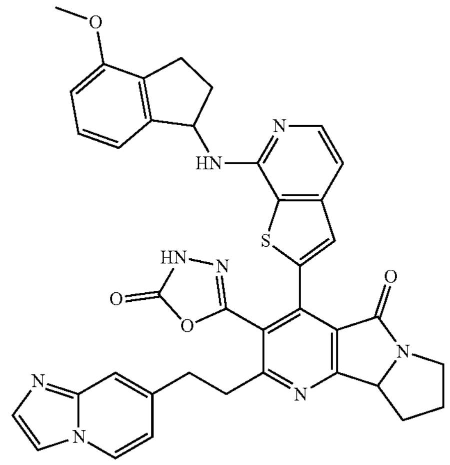 [SMILES: COc1cccc2c1CCC2Nc1nccc2cc(-c3c4c(nc(CCc5ccn6ccnc6c5)c3-c3n[nH]c(=O)o3)C3CCCN3C4=O)sc12] |
| 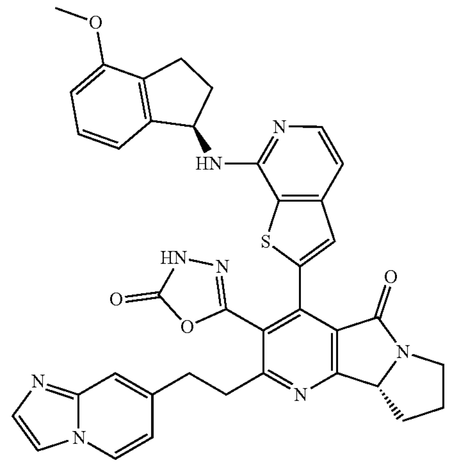 [SMILES: COc1cccc2c1CC[C@H]2Nc1nccc2cc(-c3c4c(nc(CCc5ccn6ccnc6c5)c3-c3n[nH]c(=O)o3)[C@H]3CCCN3C4=O)sc12] |
| 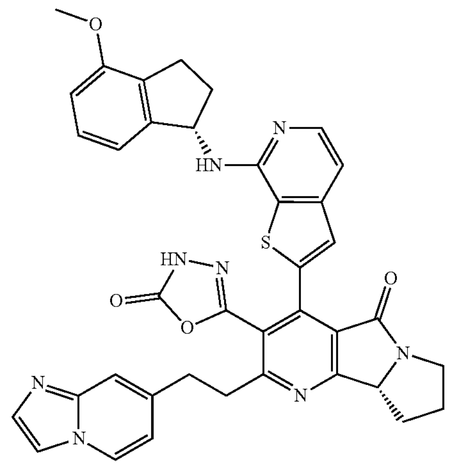 [SMILES: COc1cccc2c1CC[C@@H]2Nc1nccc2cc(-c3c4c(nc(CCc5ccn6ccnc6c5)c3-c3n[nH]c(=O)o3)[C@H]3CCCN3C4=O)sc12] |

TABLE 2-continued
| Structure |
| --- |
| 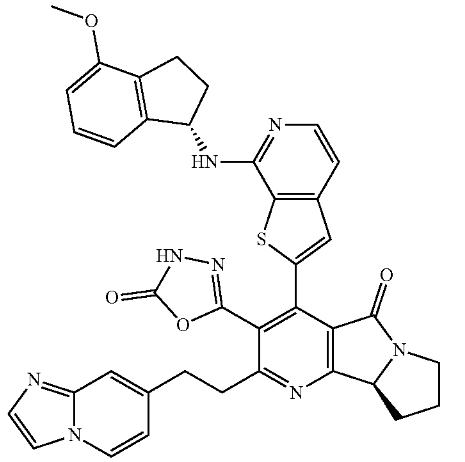 [SMILES: COc1cccc2c1CC[C@@H]2Nc1nccc2cc(-c3c4c(nc(CCc5ccn6ccnc6c5)c3-c3n[nH]c(=O)o3)[C@@H]3CCCN3C4=O)sc12] |
| 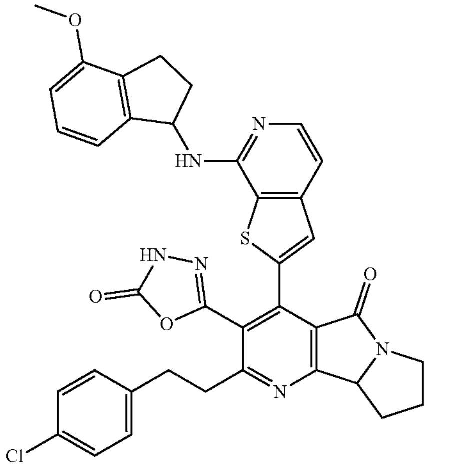 [SMILES: COc1cccc2c1CCC2Nc1nccc2cc(-c3c4c(nc(CCc5ccc(Cl)cc5)c3-c3n[nH]c(=O)o3)C3CCCN3C4=O)sc12] |
| 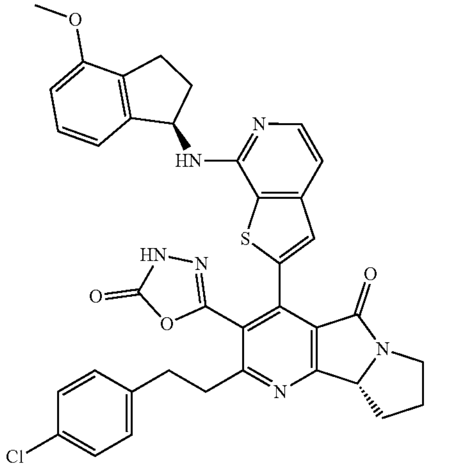 [SMILES: COc1cccc2c1CC[C@H]2Nc1nccc2cc(-c3c4c(nc(CCc5ccc(Cl)cc5)c3-c3n[nH]c(=O)o3)[C@H]3CCCN3C4=O)sc12] |
TABLE 2-continued
| Structure |
| --- |
| 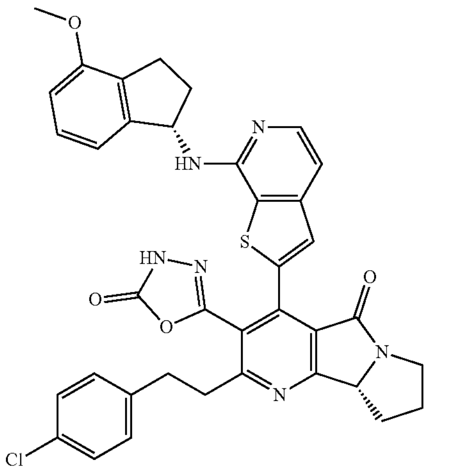 [SMILES: COc1cccc2c1CC[C@@H]2Nc1nccc2cc(-c3c4c(nc(CCc5ccc(Cl)cc5)c3-c3n[nH]c(=O)o3)[C@H]3CCCN3C4=O)sc12] |
| 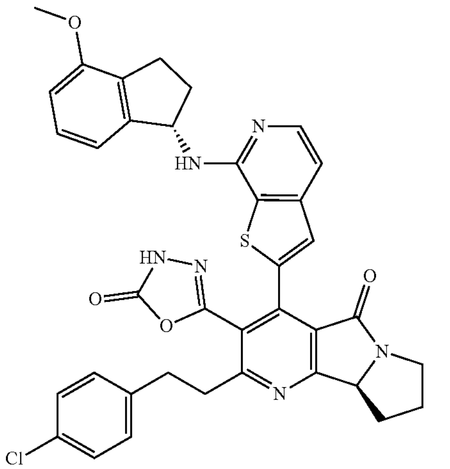 [SMILES: COc1cccc2c1CC[C@@H]2Nc1nccc2cc(-c3c4c(nc(CCc5ccc(Cl)cc5)c3-c3n[nH]c(=O)o3)[C@@H]3CCCN3C4=O)sc12] |
| 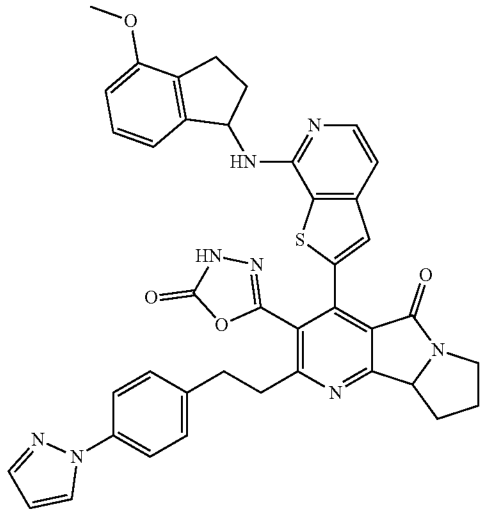 [SMILES: COc1cccc2c1CCC2Nc1nccc2cc(-c3c4c(nc(CCc5ccc(-n6cccn6)cc5)c3-c3n[nH]c(=O)o3)C3CCCN3C4=O)sc12] |

TABLE 2-continued
| Structure |
| --- |
| 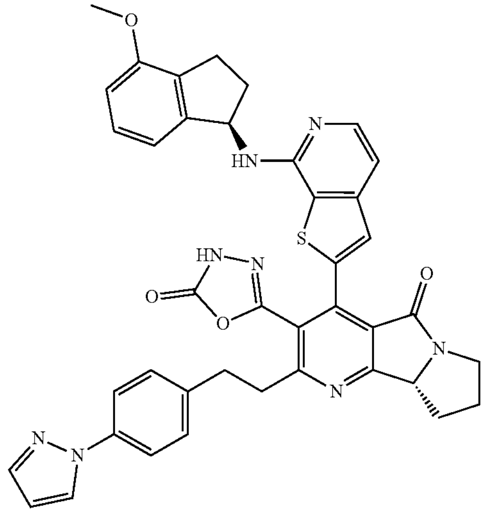 [SMILES: COc1cccc2c1CC[C@H]2Nc1nccc2cc(-c3c4c(nc(CCc5ccc(-n6cccn6)cc5)c3-c3n[nH]c(=O)o3)[C@H]3CCCN3C4=O)sc12] |
| 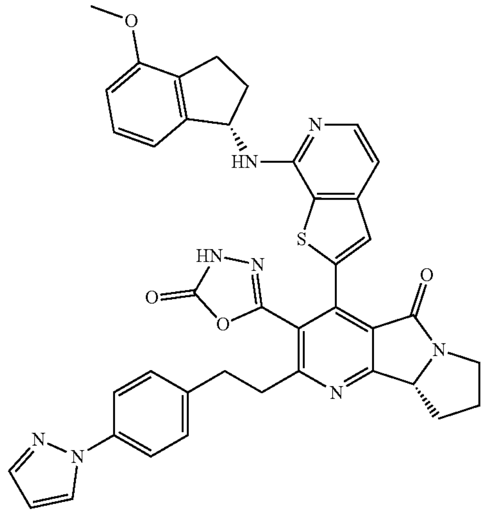 [SMILES: COc1cccc2c1CC[C@@H]2Nc1nccc2cc(-c3c4c(nc(CCc5ccc(-n6cccn6)cc5)c3-c3n[nH]c(=O)o3)[C@H]3CCCN3C4=O)sc12] |
| 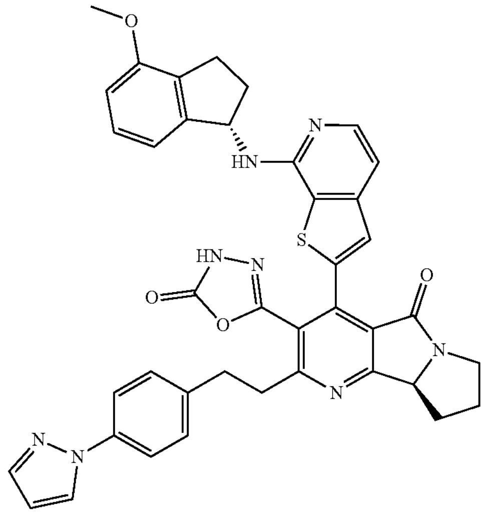 [SMILES: COc1cccc2c1CC[C@@H]2Nc1nccc2cc(-c3c4c(nc(CCc5ccc(-n6cccn6)cc5)c3-c3n[nH]c(=O)o3)[C@@H]3CCCN3C4=O)sc12] |
TABLE 2-continued
| Structure |
| --- |
| 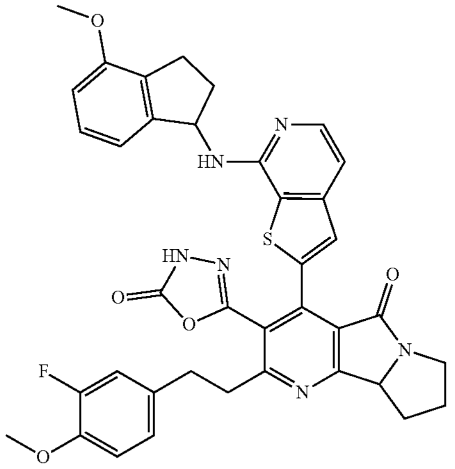 [SMILES: COc1ccc(CCc2nc3c(c(-c4cc5ccnc(NC6CCc7c(OC)cccc76)c5s4)c2-c2n[nH]c(=O)o2)C(=O)N2CCCC32)cc1F] |
| 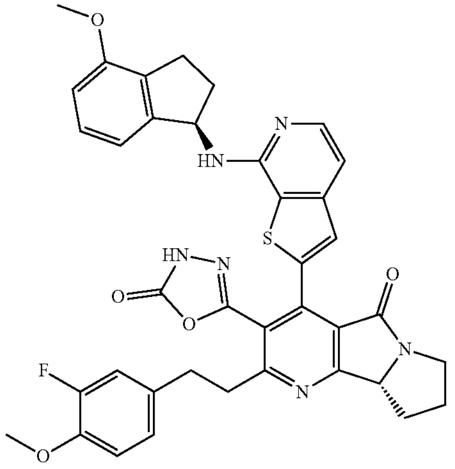 [SMILES: COc1ccc(CCc2nc3c(c(-c4cc5ccnc(N[C@@H]6CCc7c(OC)cccc76)c5s4)c2-c2n[nH]c(=O)o2)C(=O)N2CCC[C@H]32)cc1F] |
| 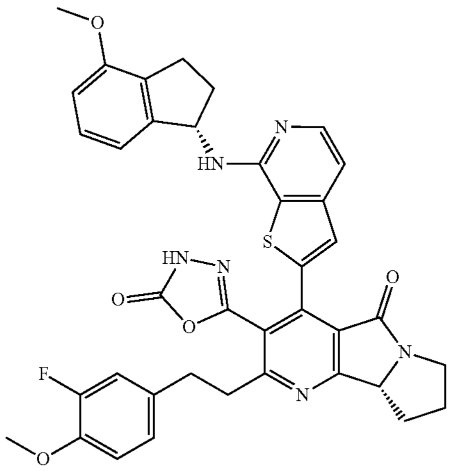 [SMILES: COc1ccc(CCc2nc3c(c(-c4cc5ccnc(N[C@H]6CCc7c(OC)cccc76)c5s4)c2-c2n[nH]c(=O)o2)C(=O)N2CCC[C@H]32)cc1F] |

TABLE 2-continued
| Structure |
|---|
| 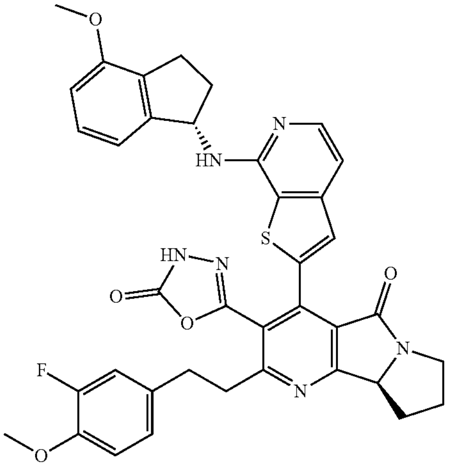 [SMILES: COc1ccc(CCc2nc3c(c(-c4cc5ccnc(N[C@H]6CCc7c(OC)cccc76)c5s4)c2-c2n[nH]c(=O)o2)C(=O)N2CCC[C@@H]32)cc1F] |
| 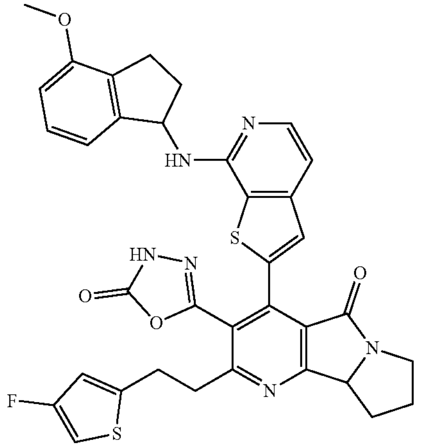 [SMILES: COc1cccc2c1CCC2Nc1nccc2cc(-c3c4c(nc(CCc5cc(F)cs5)c3-c3n[nH]c(=O)o3)C3CCCN3C4=O)sc12] |
| 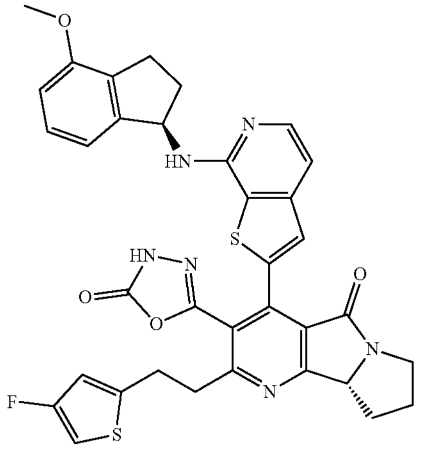 [SMILES: COc1cccc2c1CC[C@H]2Nc1nccc2cc(-c3c4c(nc(CCc5cc(F)cs5)c3-c3n[nH]c(=O)o3)[C@H]3CCCN3C4=O)sc12] |
TABLE 2-continued
| Structure |
|---|
| 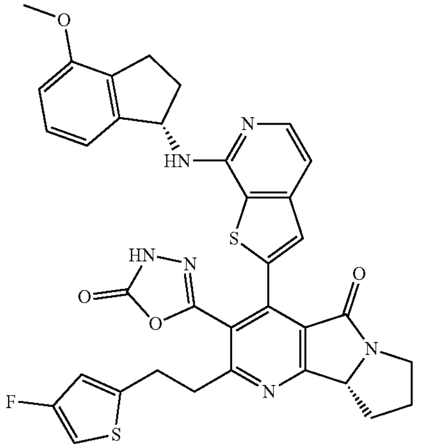 [SMILES: COc1cccc2c1CC[C@@H]2Nc1nccc2cc(-c3c4c(nc(CCc5cc(F)cs5)c3-c3n[nH]c(=O)o3)[C@H]3CCCN3C4=O)sc12] |
| 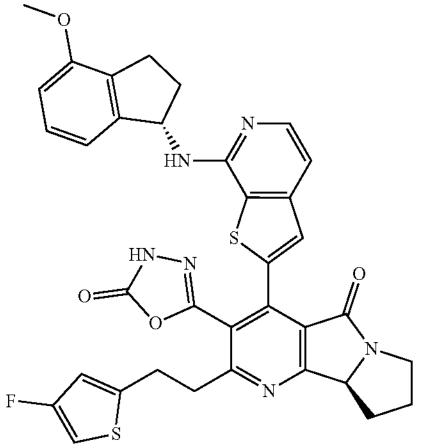 [SMILES: COc1cccc2c1CC[C@@H]2Nc1nccc2cc(-c3c4c(nc(CCc5cc(F)cs5)c3-c3n[nH]c(=O)o3)[C@@H]3CCCN3C4=O)sc12] |
| 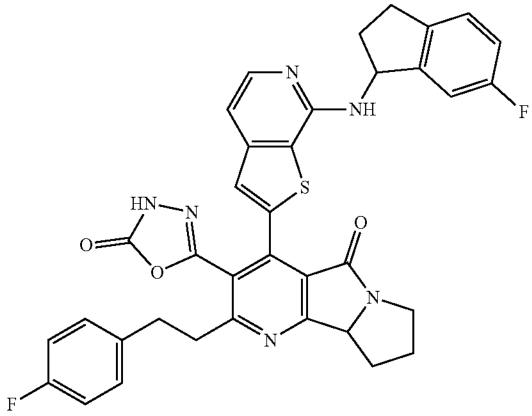 [SMILES: O=C1c2c(nc(CCc3ccc(F)cc3)c(-c3n[nH]c(=O)o3)c2-c2cc3ccnc(NC4CCc5ccc(F)cc54)c3s2)C2CCCN12] |

TABLE 2-continued
| Structure |
|---|
| 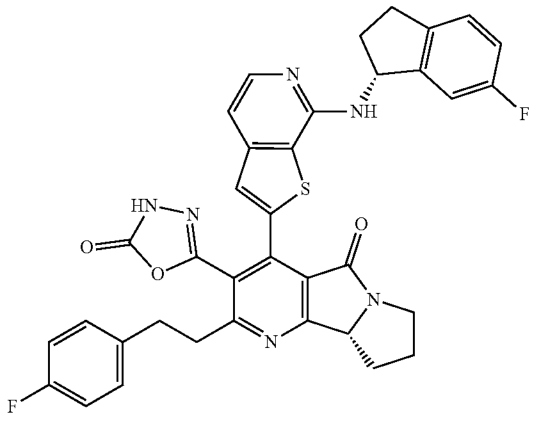 [SMILES: O=C1c2c(nc(CCc3ccc(F)cc3)c(-c3n[nH]c(=O)o3)c2-c2cc3ccnc(N[C@@H]4CCc5ccc(F)cc54)c3s2)[C@H]2CCCN12] |
| 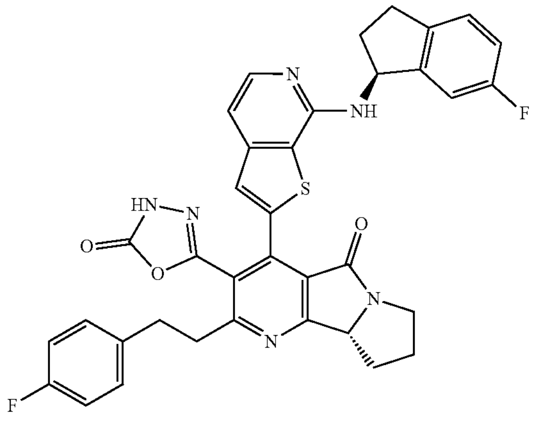 [SMILES: O=C1c2c(nc(CCc3ccc(F)cc3)c(-c3n[nH]c(=O)o3)c2-c2cc3ccnc(N[C@H]4CCc5ccc(F)cc54)c3s2)[C@H]2CCCN12] |
| 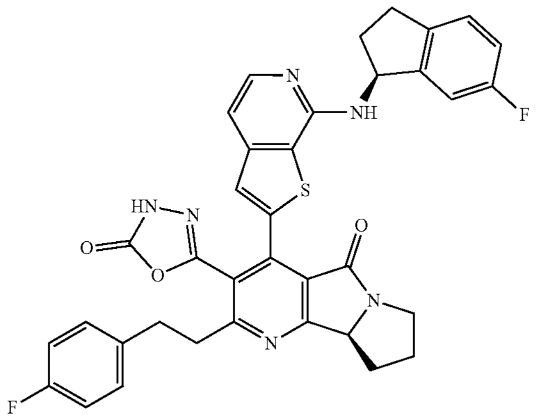 [SMILES: O=C1c2c(nc(CCc3ccc(F)cc3)c(-c3n[nH]c(=O)o3)c2-c2cc3ccnc(N[C@H]4CCc5ccc(F)cc54)c3s2)[C@@H]2CCCN12] |
TABLE 2-continued
| Structure |
|---|
| 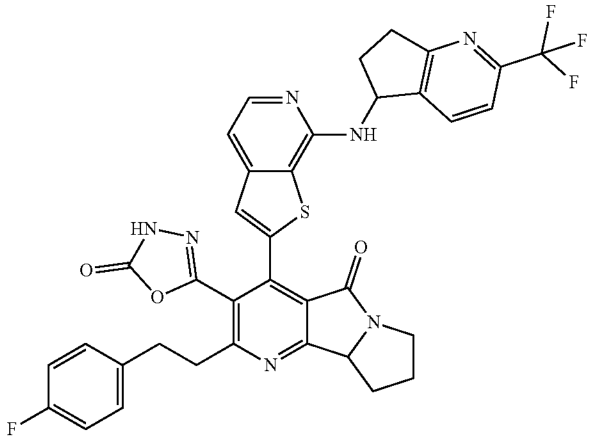 [SMILES: O=C1c2c(nc(CCc3ccc(F)cc3)c(-c3n[nH]c(=O)o3)c2-c2cc3ccnc(NC4CCc5nc(C(F)(F)F)ccc54)c3s2)C2CCCN12] |
| 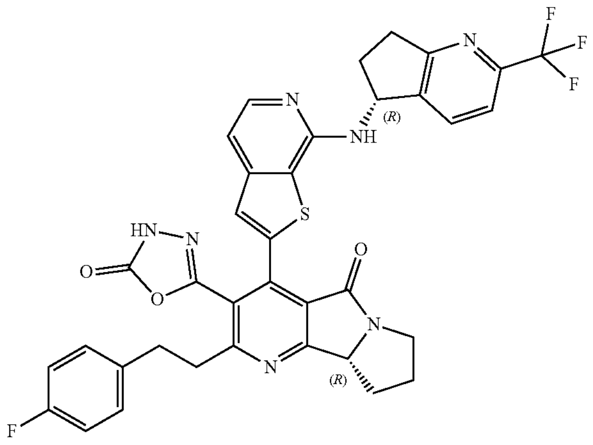 |
| 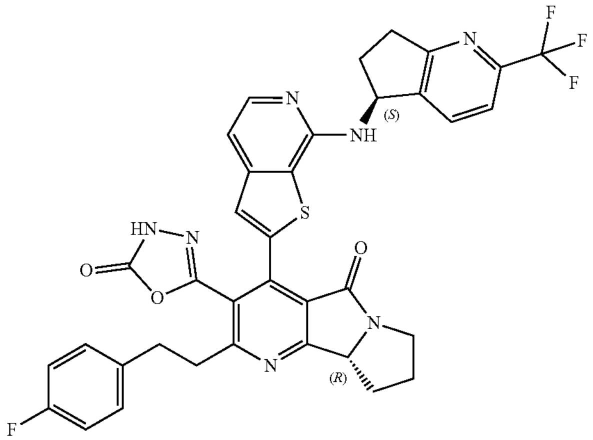 |

| Structure |
| --- |
| 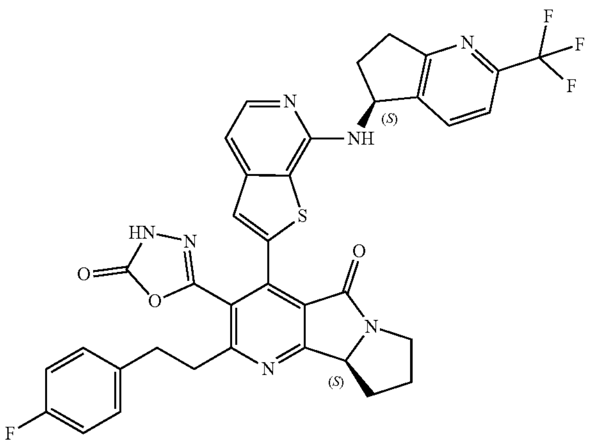 |
| 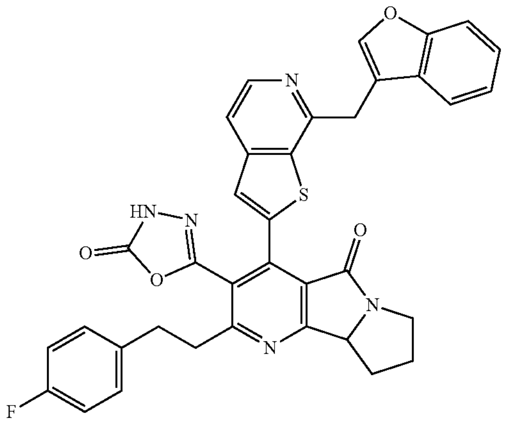 [SMILES: O=C1c2c(nc(CCc3ccc(F)cc3)c(-c3n[nH]c(=O)o3)c2-c2cc3ccnc(Cc4coc5ccccc45)c3s2)C2CCCN12] |
| 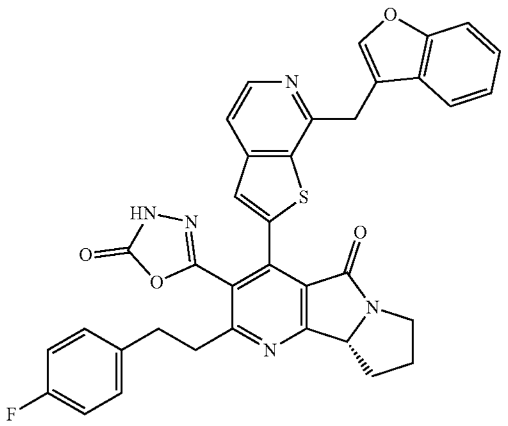 [SMILES: O=C1c2c(nc(CCc3ccc(F)cc3)c(-c3n[nH]c(=O)o3)c2-c2cc3ccnc(Cc4coc5ccccc45)c3s2)[C@H]2CCCN12] |
| Structure |
| --- |
| 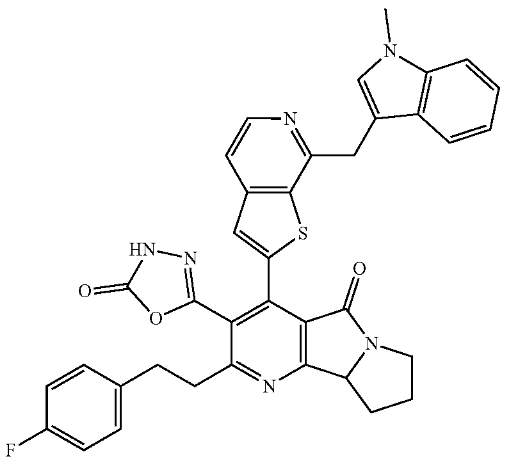 [SMILES: Cn1cc(Cc2nccc3cc(-c4c5c(nc(CCc6ccc(F)cc6)c4-c4n[nH]c(=O)o4)C4CCCN4C5=O)sc23)c2ccccc21] |
| 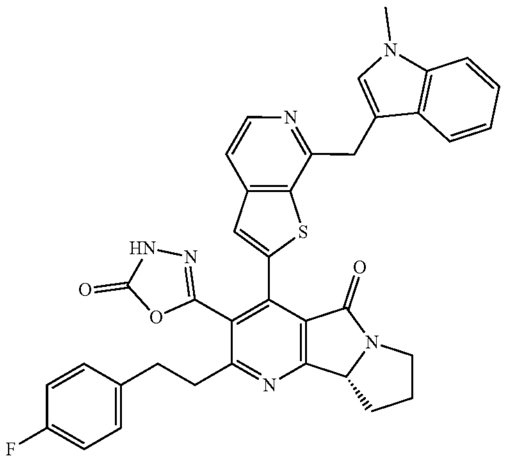 [SMILES: Cn1cc(Cc2nccc3cc(-c4c5c(nc(CCc6ccc(F)cc6)c4-c4n[nH]c(=O)o4)[C@H]4CCCN4C5=O)sc23)c2ccccc21] |
| 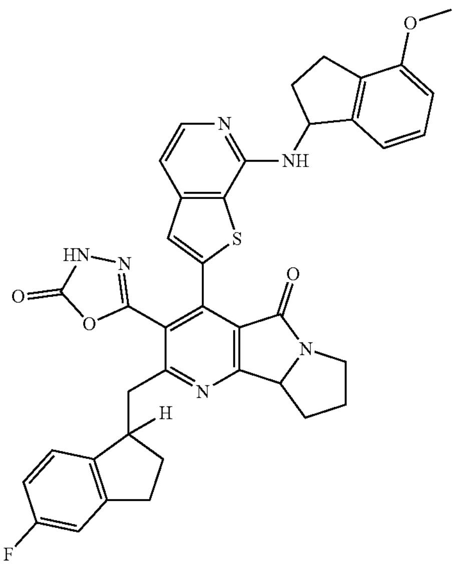 [SMILES: COc1cccc2c1CCC2Nc1nccc2cc(-c3c4c(nc(CC5CCc6cc(F)ccc65)c3-c3n[nH]c(=O)o3)C3CCCN3C4=O)sc12] |

TABLE 2-continued
| Structure |
| --- |
| 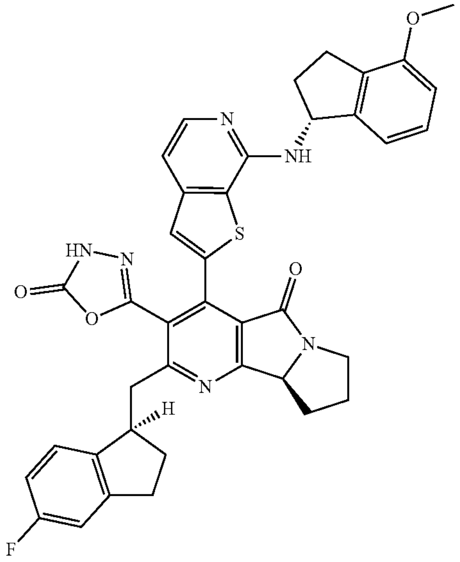 [SMILES: COc1cccc2c1CC[C@H]2Nc1nccc2cc(-c3c4c(nc(C[C@H]5CCc6cc(F)ccc65)c3-c3n[nH]c(=O)o3)[C@@H]3CCCN3C4=O)sc12] |
| 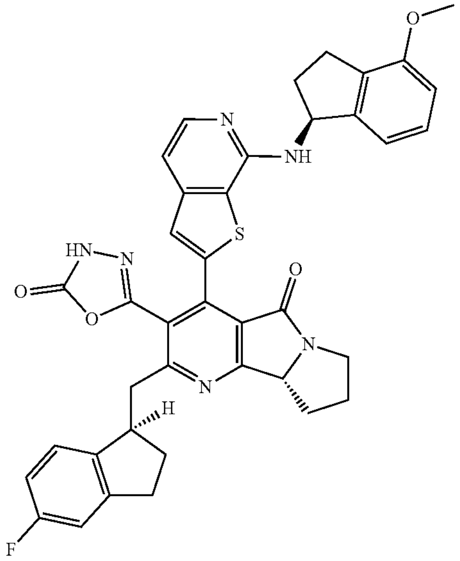 [SMILES: COc1cccc2c1CC[C@@H]2Nc1nccc2cc(-c3c4c(nc(C[C@H]5CCc6cc(F)ccc65)c3-c3n[nH]c(=O)o3)[C@H]3CCCN3C4=O)sc12] |
TABLE 2-continued
| Structure |
| --- |
| 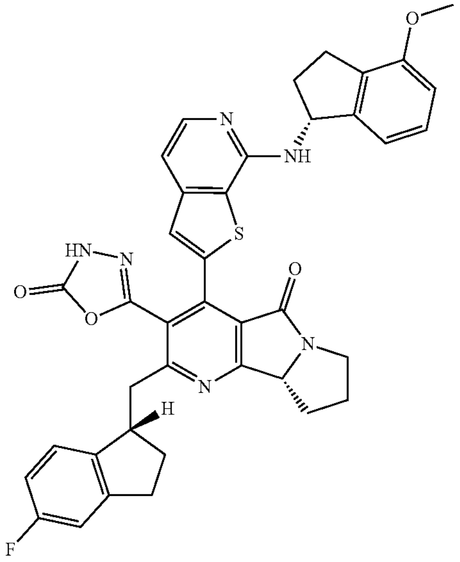 [SMILES: COc1cccc2c1CC[C@H]2Nc1nccc2cc(-c3c4c(nc(C[C@@H]5CCc6cc(F)ccc65)c3-c3n[nH]c(=O)o3)[C@H]3CCCN3C4=O)sc12] |
| 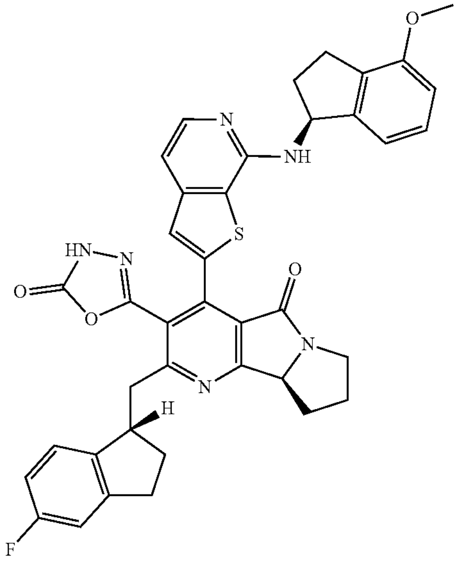 [SMILES: COc1cccc2c1CC[C@@H]2Nc1nccc2cc(-c3c4c(nc(C[C@@H]5CCc6cc(F)ccc65)c3-c3n[nH]c(=O)o3)[C@@H]3CCCN3C4=O)sc12] |

TABLE 2-continued
| Structure |
| --- |
| 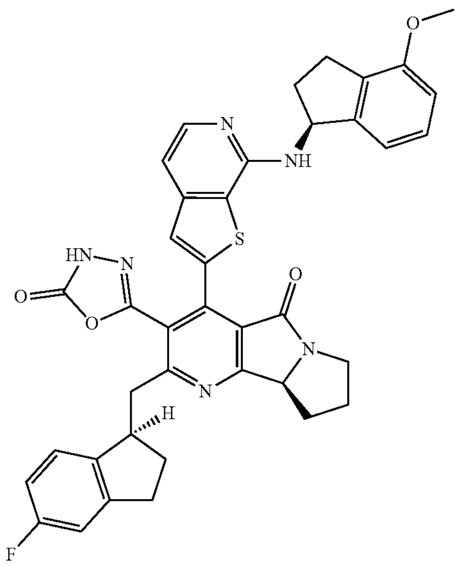 [SMILES: COc1cccc2c1CC[C@@H]2Nc1nccc2cc(-c3c4c(nc(C[C@H]5CCc6cc(F)ccc65)c3-c3n[nH]c(=O)o3)[C@@H]3CCCN3C4=O)sc12] |
| 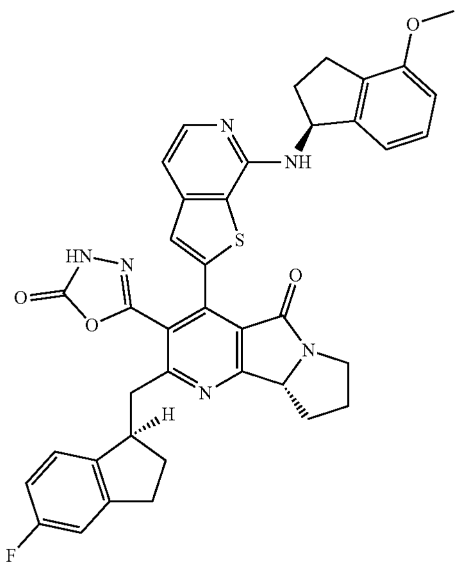 [SMILES: COc1cccc2c1CC[C@@H]2Nc1nccc2cc(-c3c4c(nc(C[C@H]5CCc6cc(F)ccc65)c3-c3n[nH]c(=O)o3)[C@H]3CCCN3C4=O)sc12] |
TABLE 2-continued
| Structure |
| --- |
| 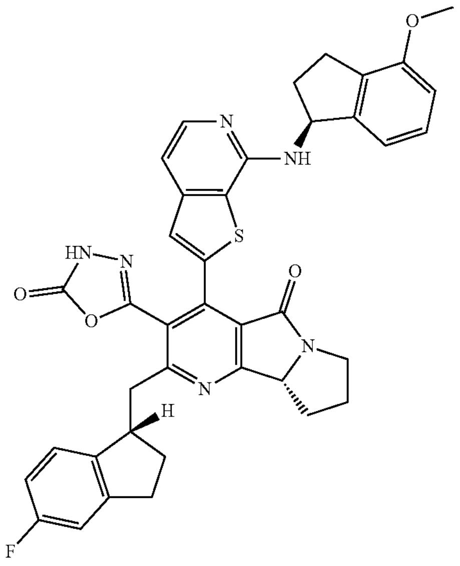 [SMILES: COc1cccc2c1CC[C@@H]2Nc1nccc2cc(-c3c4c(nc(C[C@@H]5CCc6cc(F)ccc65)c3-c3n[nH]c(=O)o3)[C@H]3CCCN3C4=O)sc12] |
| 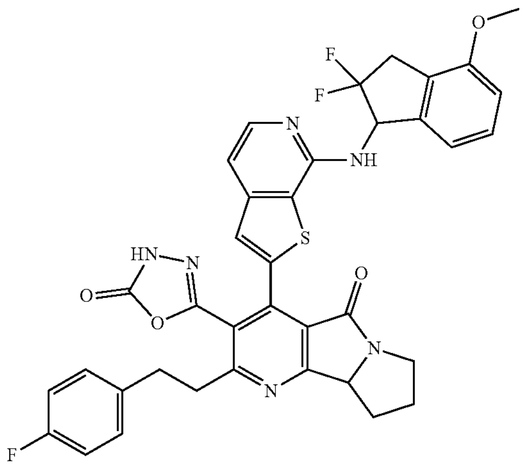 [SMILES: COc1cccc2c1CC(F)(F)C2Nc1nccc2cc(-c3c4c(nc(CCc5ccc(F)cc5)c3-c3n[nH]c(=O)o3)C3CCCN3C4=O)sc12] |
| 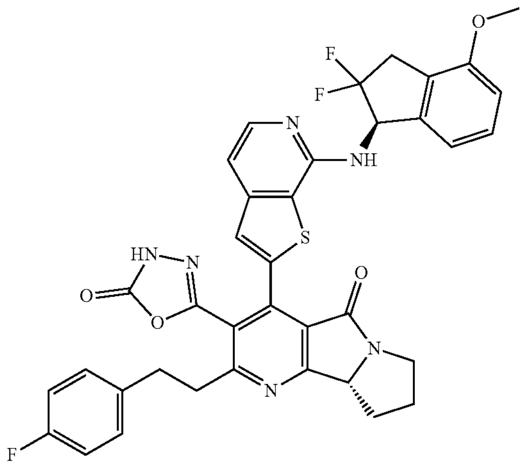 [SMILES: COc1cccc2c1CC(F)(F)[C@@H]2Nc1nccc2cc(-c3c4c(nc(CCc5ccc(F)cc5)c3-c3n[nH]c(=O)o3)[C@H]3CCCN3C4=O)sc12] |

TABLE 2-continued
Structure
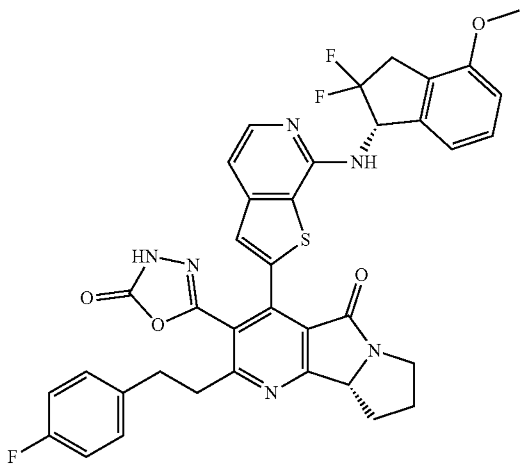 [SMILES: COc1cccc2c1CC(F)(F)[C@H]2Nc1nccc2cc(-c3c4c(nc(CCc5ccc(F)cc5)c3-c3n[nH]c(=O)o3)[C@H]3CCCN3C4=O)sc12]
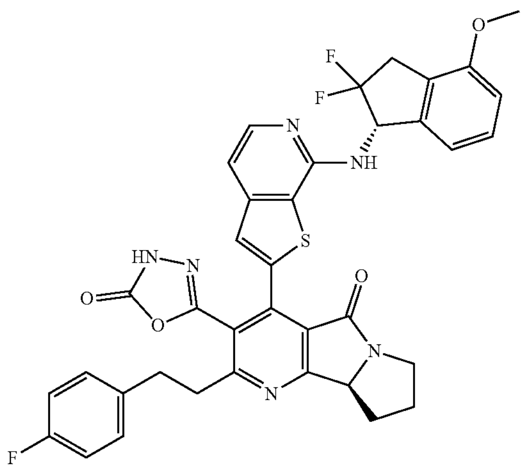 [SMILES: COc1cccc2c1CC(F)(F)[C@H]2Nc1nccc2cc(-c3c4c(nc(CCc5ccc(F)cc5)c3-c3n[nH]c(=O)o3)[C@@H]3CCCN3C4=O)sc12]
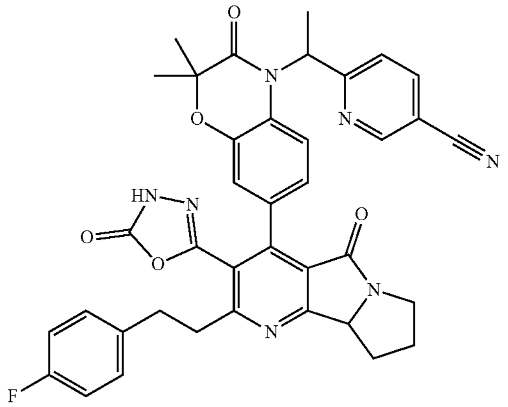 [SMILES: CC(c1ccc(C#N)cn1)N1C(=O)C(C)(C)Oc2cc(-c3c4c(nc(CCc5ccc(F)cc5)c3-c3n[nH]c(=O)o3)C3CCCN3C4=O)ccc21]
TABLE 2-continued
Structure
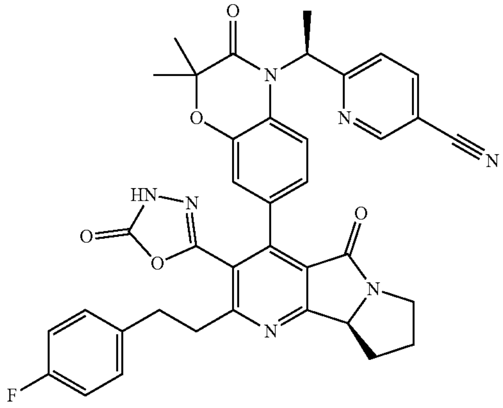 [SMILES: C[C@@H](c1ccc(C#N)cn1)N1C(=O)C(C)(C)Oc2cc(-c3c4c(nc(CCc5ccc(F)cc5)c3-c3n[nH]c(=O)o3)[C@@H]3CCCN3C4=O)ccc21]
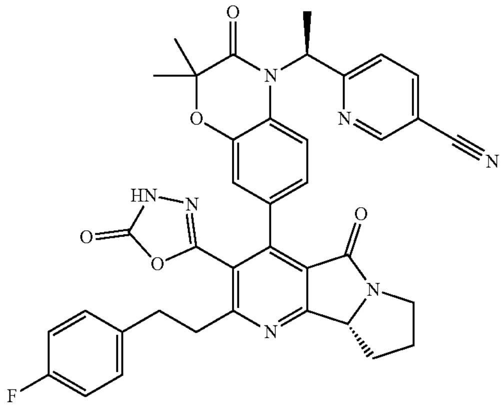 [SMILES: C[C@@H](c1ccc(C#N)cn1)N1C(=O)C(C)(C)Oc2cc(-c3c4c(nc(CCc5ccc(F)cc5)c3-c3n[nH]c(=O)o3)[C@H]3CCCN3C4=O)ccc21]
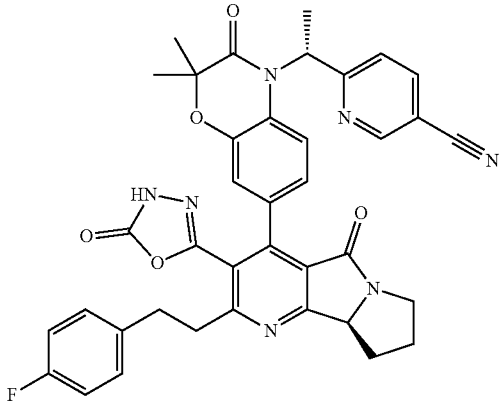

TABLE 2-continued
| Structure |
|---|
| 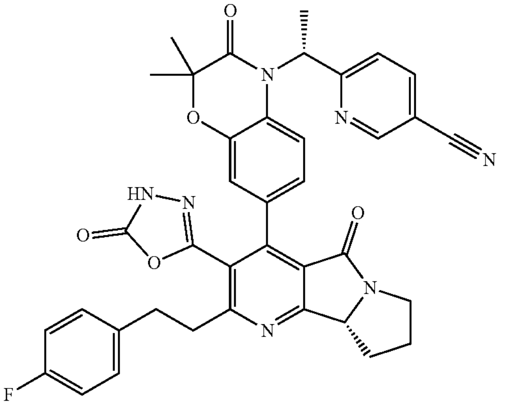 [SMILES: C[C@H](c1ccc(C#N)cn1)N1C(=O)C(C)(C)Oc2cc(-c3c4c(nc(CCc5ccc(F)cc5)c3-c3n[nH]c(=O)o3)[C@H]3CCCN3C4=O)ccc21] |
| 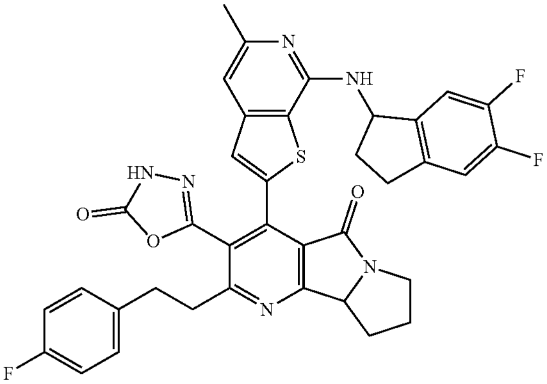 [SMILES: Cc1cc2cc(-c3c4c(nc(CCc5ccc(F)cc5)c3-c3n[nH]c(=O)o3)C3CCCN3C4=O)sc2c(NC2CCc3cc(F)c(F)cc32)n1] |
| 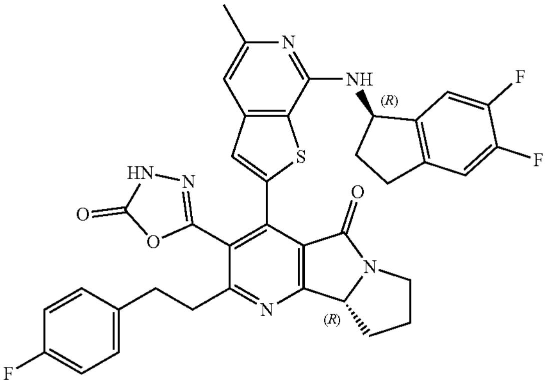 |
| 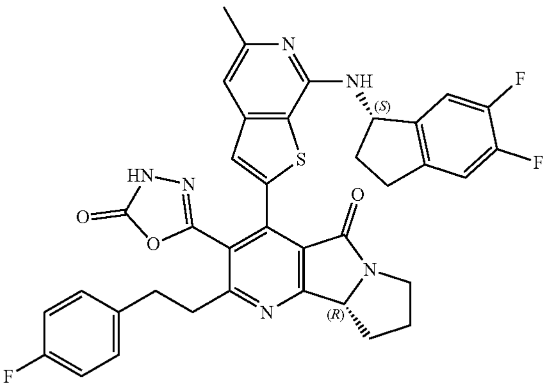 |
TABLE 2-continued
| Structure |
|---|
| 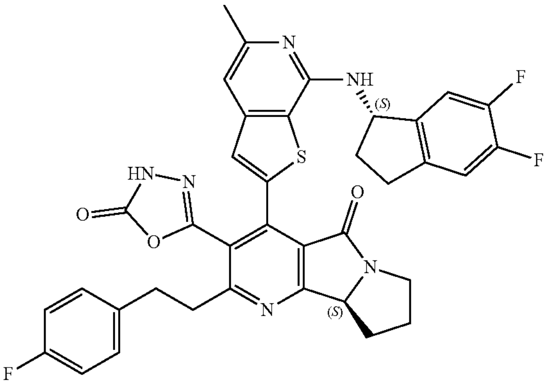 |
| 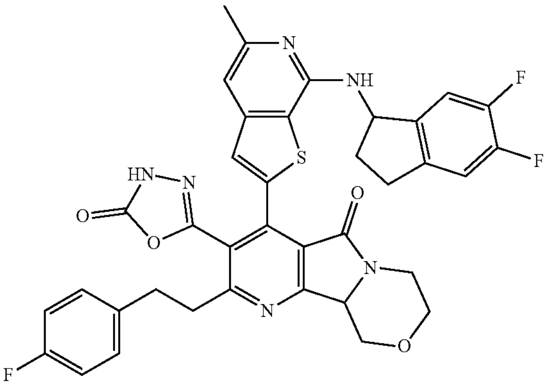 [SMILES: Cc1cc2cc(-c3c4c(nc(CCc5ccc(F)cc5)c3-c3n[nH]c(=O)o3)C3COCCN3C4=O)sc2c(NC2CCc3cc(F)c(F)cc32)n1] |
| 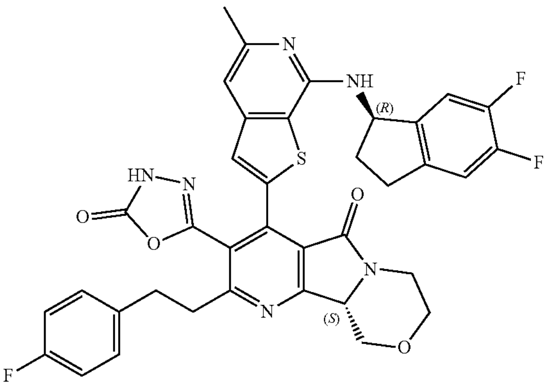 |
| 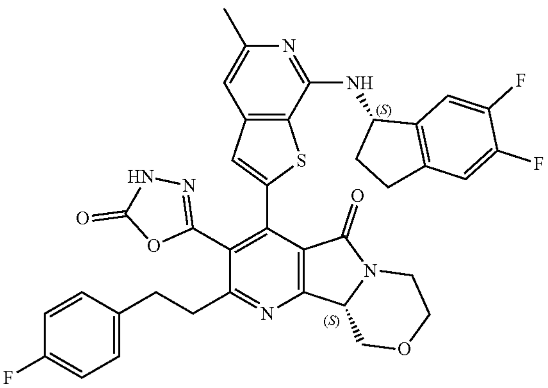 |

TABLE 2-continued
| Structure |
| --- |
| 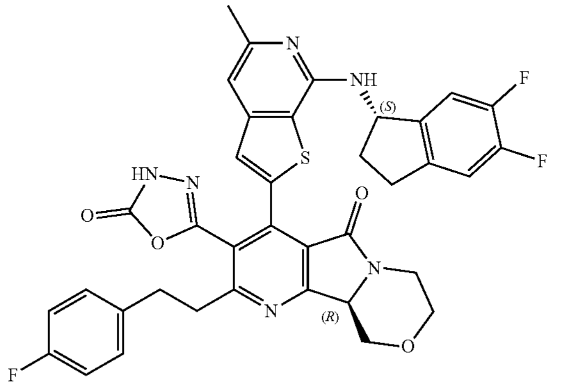 |
| 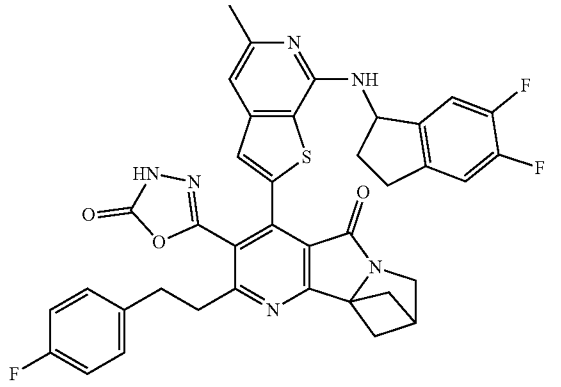 [SMILES: Cc1cc2cc(-c3c4c(nc(CCc5ccc(F)cc5)c3-c3n[nH]c(=O)o3)C35CC(CN3C4=O)C5)sc2c(NC2CCc3cc(F)c(F)cc32)n1] |
| 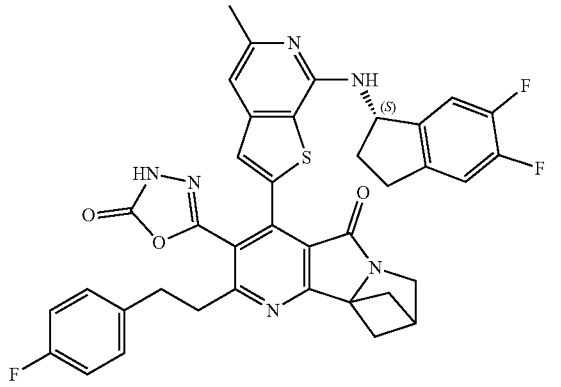 |
| 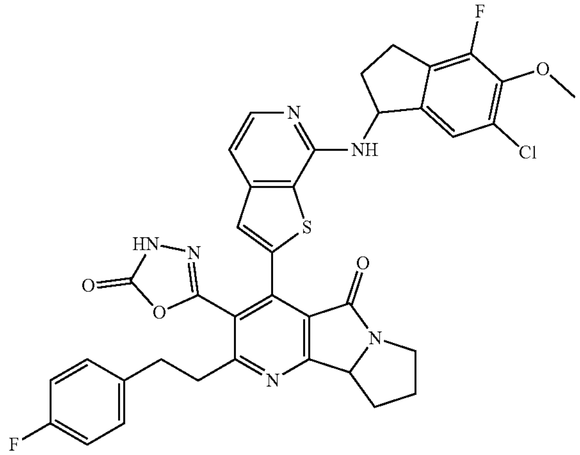 [SMILES: COc1c(Cl)cc2c(c1F)CCC2Nc1nccc2cc(-c3c4c(nc(CCc5ccc(F)cc5)c3-c3n[nH]c(=O)o3)C3CCCN3C4=O)sc12] |
TABLE 2-continued
| Structure |
| --- |
| 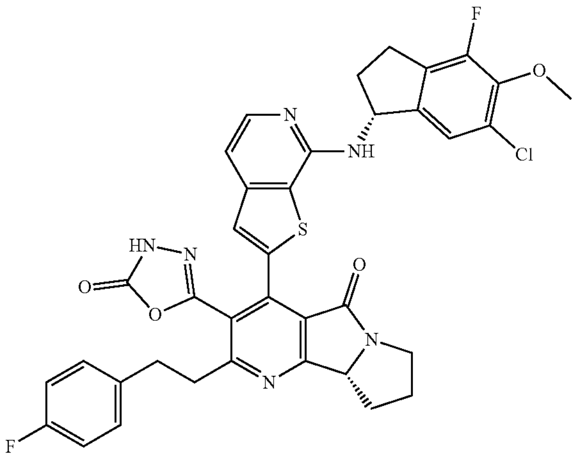 [SMILES: COc1c(Cl)cc2c(c1F)CC[C@H]2Nc1nccc2cc(-c3c4c(nc(CCc5ccc(F)cc5)c3-c3n[nH]c(=O)o3)[C@H]3CCCN3C4=O)sc12] |
| 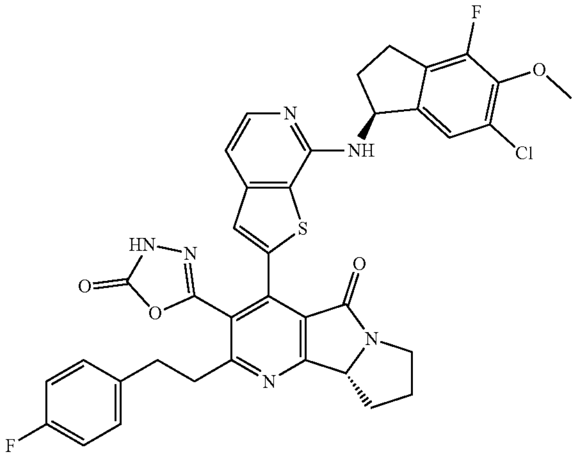 [SMILES: COc1c(Cl)cc2c(c1F)CC[C@@H]2Nc1nccc2cc(-c3c4c(nc(CCc5ccc(F)cc5)c3-c3n[nH]c(=O)o3)[C@H]3CCCN3C4=O)sc12] |
| 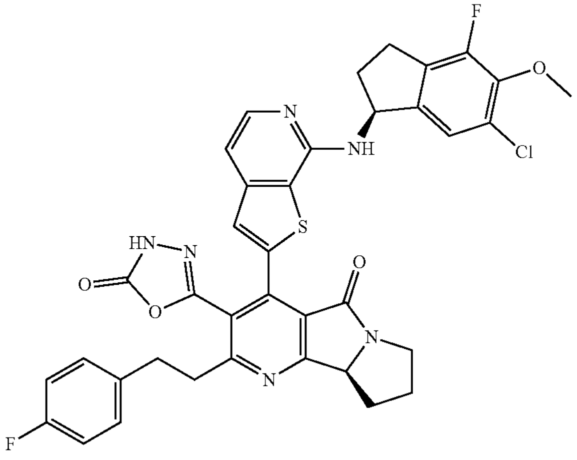 [SMILES: COc1c(Cl)cc2c(c1F)CC[C@@H]2Nc1nccc2cc(-c3c4c(nc(CCc5ccc(F)cc5)c3-c3n[nH]c(=O)o3)[C@@H]3CCCN3C4=O)sc12] |

TABLE 2-continued
| Structure |
| --- |
| 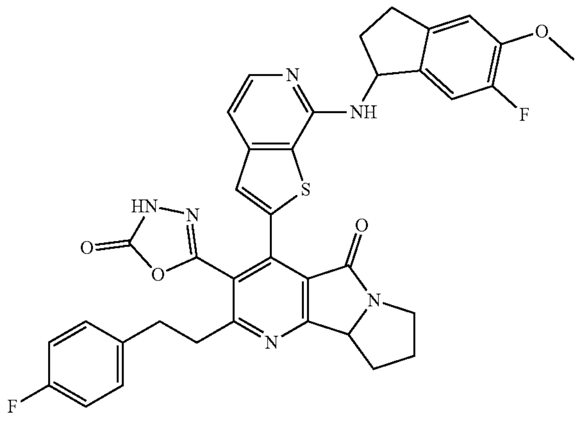 [SMILES: COc1cc2c(cc1F)C(Nc1nccc3cc(-c4c5c(nc(CCc6ccc(F)cc6)c4-c4n[nH]c(=O)o4)C4CCCN4C5=O)sc13)CC2] |
| 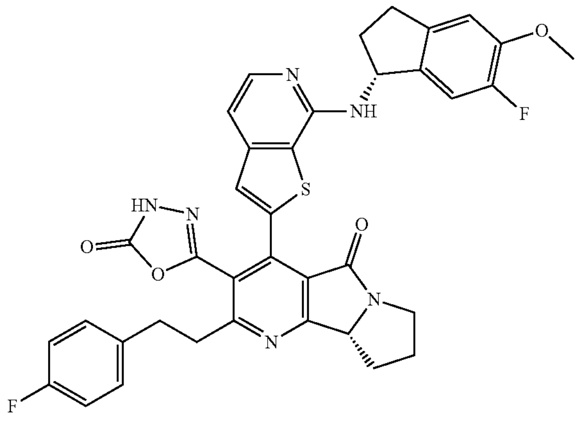 [SMILES: COc1cc2c(cc1F)[C@H](Nc1nccc3cc(-c4c5c(nc(CCc6ccc(F)cc6)c4-c4n[nH]c(=O)o4)[C@H]4CCCN4C5=O)sc13)CC2] |
| 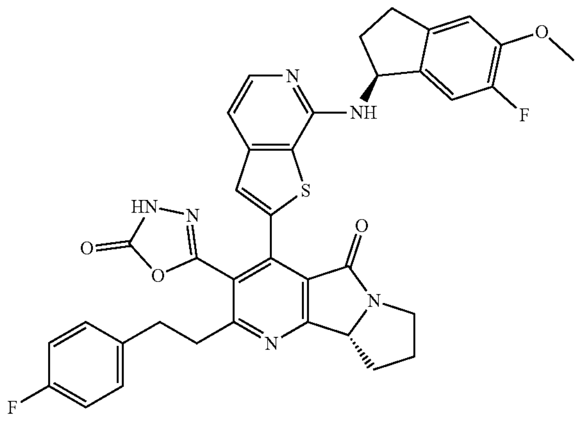 [SMILES: COc1cc2c(cc1F)[C@@H](Nc1nccc3cc(-c4c5c(nc(CCc6ccc(F)cc6)c4-c4n[nH]c(=O)o4)[C@H]4CCCN4C5=O)sc13)CC2] |
TABLE 2-continued
| Structure |
| --- |
| 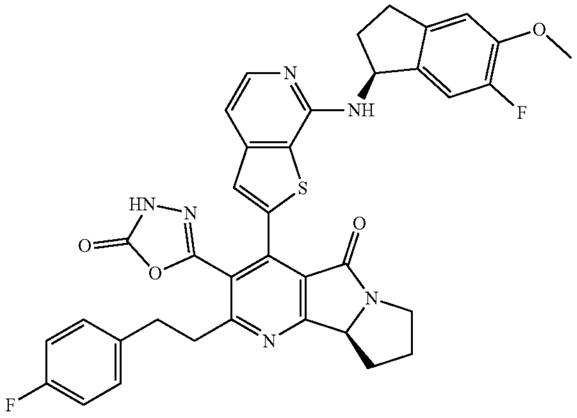 [SMILES: COc1cc2c(cc1F)[C@@H](Nc1nccc3cc(-c4c5c(nc(CCc6ccc(F)cc6)c4-c4n[nH]c(=O)o4)[C@@H]4CCCN4C5=O)sc13)CC2] |
| 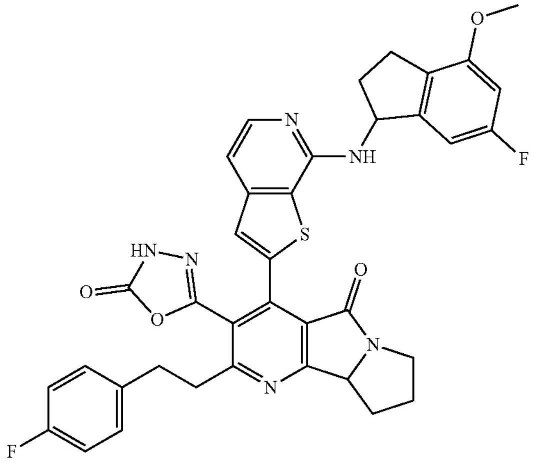 [SMILES: COc1cc(F)cc2c1CCC2Nc1nccc2cc(-c3c4c(nc(CCc5ccc(F)cc5)c3-c3n[nH]c(=O)o3)C3CCCN3C4=O)sc12] |
| 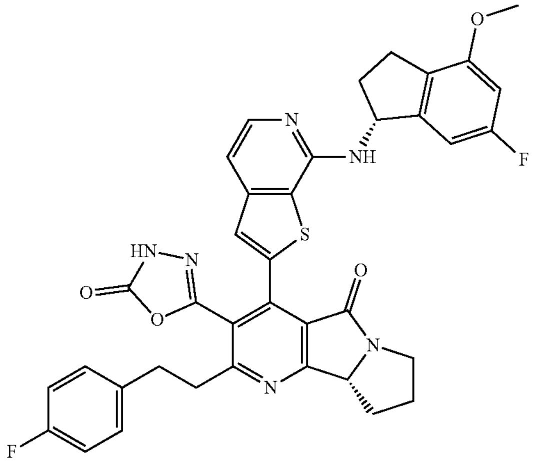 [SMILES: COc1cc(F)cc2c1CC[C@H]2Nc1nccc2cc(-c3c4c(nc(CCc5ccc(F)cc5)c3-c3n[nH]c(=O)o3)[C@H]3CCCN3C4=O)sc12] |

TABLE 2-continued
| Structure |
|---|
| 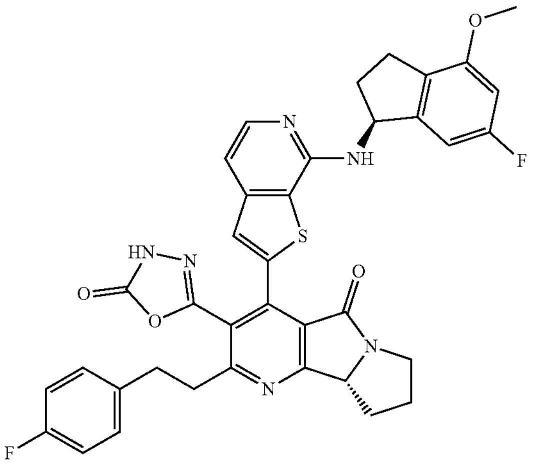 [SMILES: COc1cc(F)cc2c1CC[C@@H]2Nc1nccc2cc(-c3c4c(nc(CCc5ccc(F)cc5)c3-c3n[nH]c(=O)o3)[C@H]3CCCN3C4=O)sc12] |
| 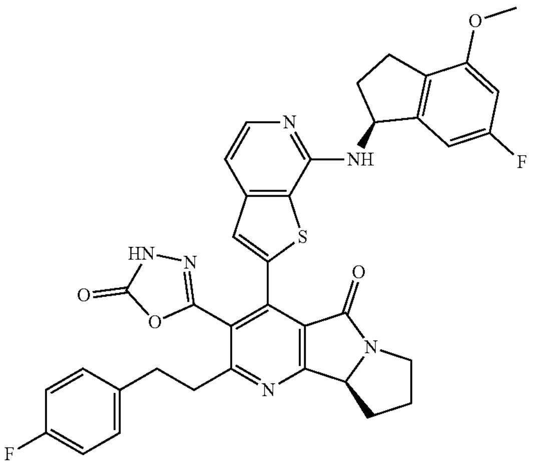 [SMILES: COc1cc(F)cc2c1CC[C@@H]2Nc1nccc2cc(-c3c4c(nc(CCc5ccc(F)cc5)c3-c3n[nH]c(=O)o3)[C@@H]3CCCN3C4=O)sc12] |
| 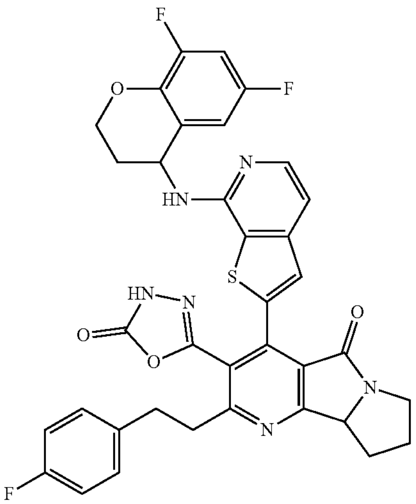 [SMILES: O=C1c2c(nc(CCc3ccc(F)cc3)c(-c3n[nH]c(=O)o3)c2-c2cc3ccnc(NC4CCOc5c(F)cc(F)cc54)c3s2)C2CCCN12] |
TABLE 2-continued
| Structure |
|---|
| 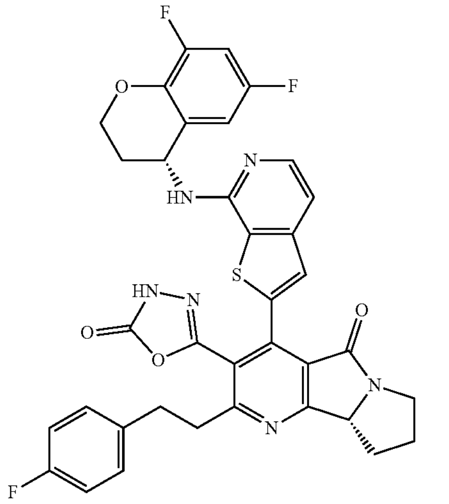 [SMILES: O=C1c2c(nc(CCc3ccc(F)cc3)c(-c3n[nH]c(=O)o3)c2-c2cc3ccnc(N[C@@H]4CCOc5c(F)cc(F)cc54)c3s2)[C@H]2CCCN12] |
| 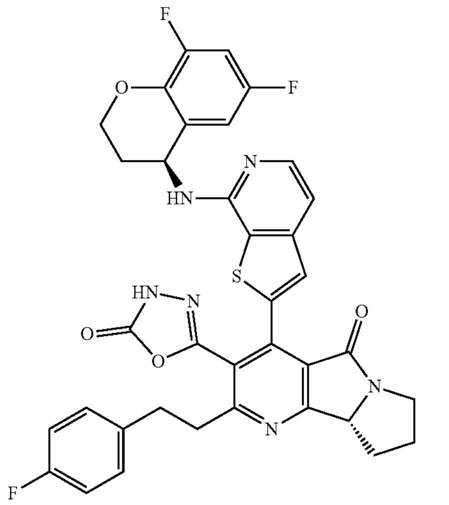 [SMILES: O=C1c2c(nc(CCc3ccc(F)cc3)c(-c3n[nH]c(=O)o3)c2-c2cc3ccnc(N[C@H]4CCOc5c(F)cc(F)cc54)c3s2)[C@H]2CCCN12] |
| 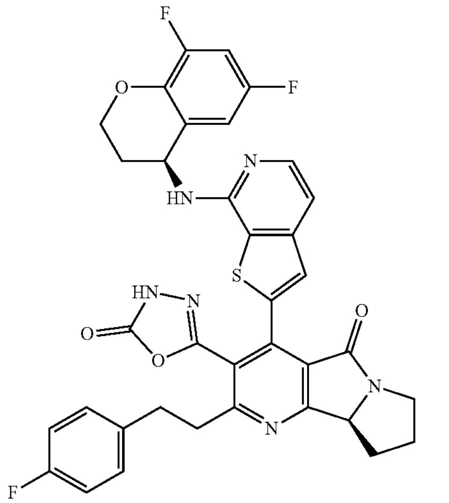 [SMILES: O=C1c2c(nc(CCc3ccc(F)cc3)c(-c3n[nH]c(=O)o3)c2-c2cc3ccnc(N[C@H]4CCOc5c(F)cc(F)cc54)c3s2)[C@@H]2CCCN12] |

TABLE 2-continued
| Structure |
|---|
| 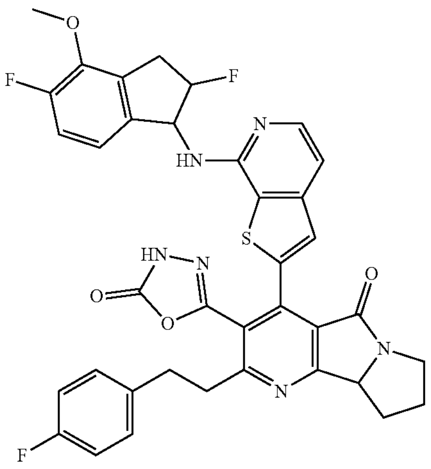 [SMILES: COc1c(F)ccc2c1CC(F)C2Nc1nccc2cc(-c3c4c(nc(CCc5ccc(F)cc5)c3-c3n[nH]c(=O)o3)C3CCCN3C4=O)sc12] |
| 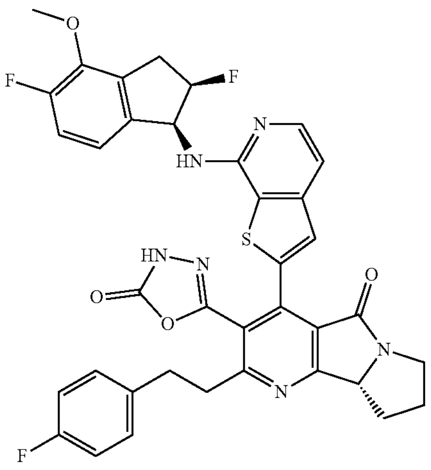 [SMILES: COc1c(F)ccc2c1C[C@@H](F)[C@H]2Nc1nccc2cc(-c3c4c(nc(CCc5ccc(F)cc5)c3-c3n[nH]c(=O)o3)[C@H]3CCCN3C4=O)sc12] |
| 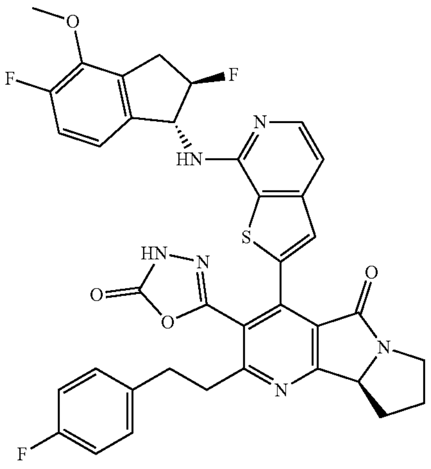 [SMILES: COc1c(F)ccc2c1C[C@@H](F)[C@@H]2Nc1nccc2cc(-c3c4c(nc(CCc5ccc(F)cc5)c3-c3n[nH]c(=O)o3)[C@@H]3CCCN3C4=O)sc12] |
TABLE 2-continued
| Structure |
|---|
| 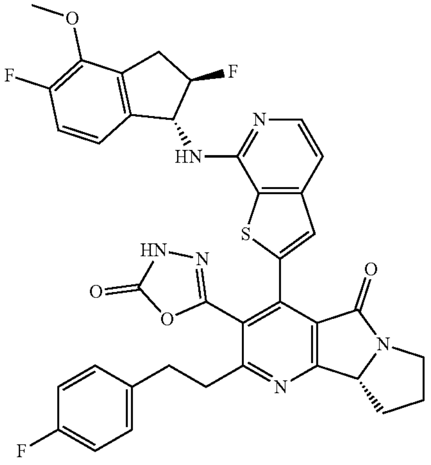 [SMILES: COc1c(F)ccc2c1C[C@@H](F)[C@@H]2Nc1nccc2cc(-c3c4c(nc(CCc5ccc(F)cc5)c3-c3n[nH]c(=O)o3)[C@H]3CCCN3C4=O)sc12] |
| 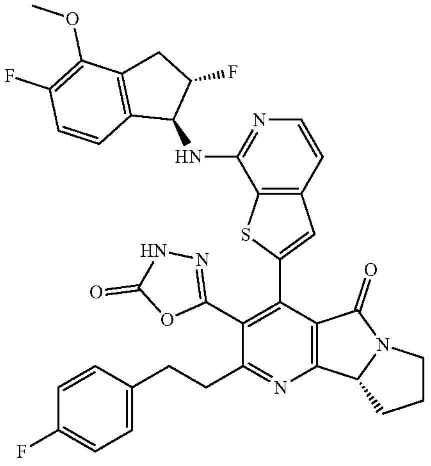 [SMILES: COc1c(F)ccc2c1C[C@H](F)[C@H]2Nc1nccc2cc(-c3c4c(nc(CCc5ccc(F)cc5)c3-c3n[nH]c(=O)o3)[C@H]3CCCN3C4=O)sc12] |
| 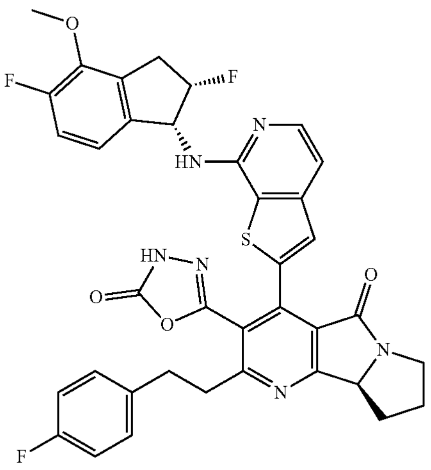 [SMILES: COc1c(F)ccc2c1C[C@H](F)[C@@H]2Nc1nccc2cc(-c3c4c(nc(CCc5ccc(F)cc5)c3-c3n[nH]c(=O)o3)[C@@H]3CCCN3C4=O)sc12] |

TABLE 2-continued
| Structure |
| --- |
| 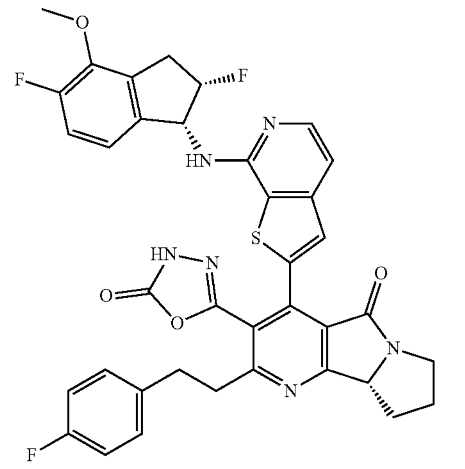 [SMILES: COc1c(F)ccc2c1C[C@H](F)[C@@H]2Nc1nccc2cc(-c3c4c(nc(CCc5ccc(F)cc5)c3-c3n[nH]c(=O)o3)[C@H]3CCCN3C4=O)sc12] |
| 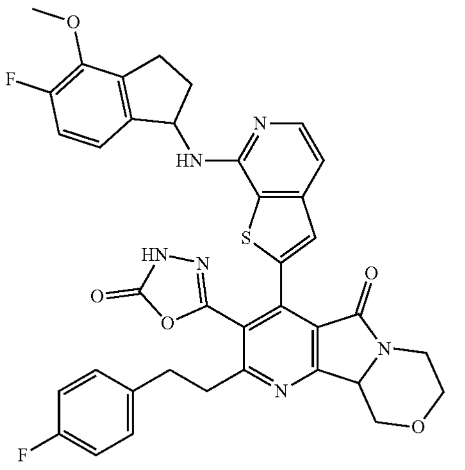 |
| 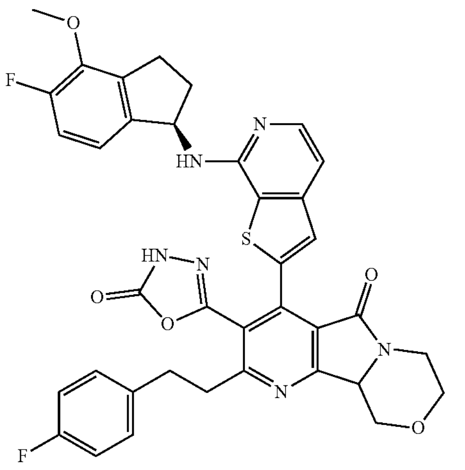 [SMILES: COc1c(F)ccc2c1CC[C@H]2Nc1nccc2cc(-c3c4c(nc(CCc5ccc(F)cc5)c3-c3n[nH]c(=O)o3)C3COCCN3C4=O)sc12] |
TABLE 2-continued
| Structure |
| --- |
| 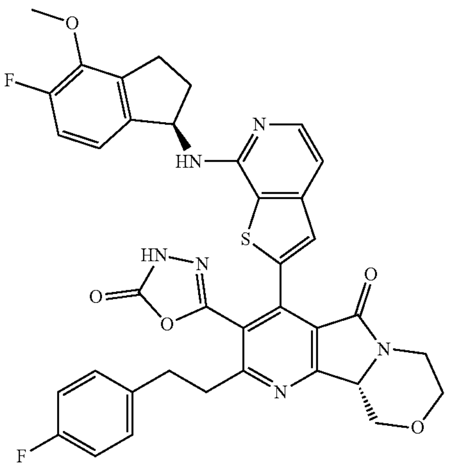 [SMILES: COc1c(F)ccc2c1CC[C@H]2Nc1nccc2cc(-c3c4c(nc(CCc5ccc(F)cc5)c3-c3n[nH]c(=O)o3)[C@H]3COCCN3C4=O)sc12] |
| 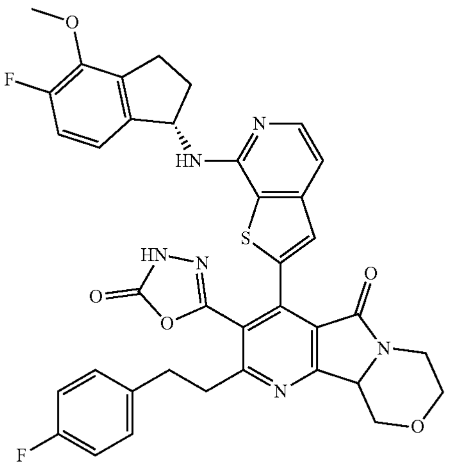 |
| 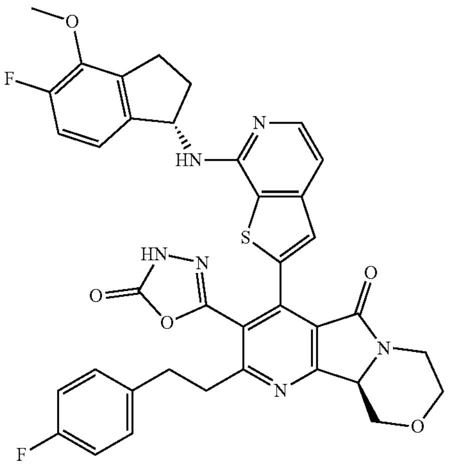 [SMILES: COc1c(F)ccc2c1CC[C@@H]2Nc1nccc2cc(-c3c4c(nc(CCc5ccc(F)cc5)c3-c3n[nH]c(=O)o3)[C@@H]3COCCN3C4=O)sc12] |

TABLE 2-continued
| Structure |
| --- |
| 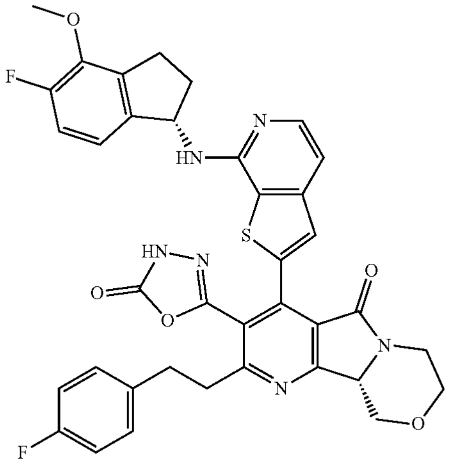 [SMILES: COc1c(F)ccc2c1CC[C@@H]2Nc1nccc2cc(-c3c4c(nc(CCc5ccc(F)cc5)c3-c3n[nH]c(=O)o3)[C@H]3COCCN3C4=O)sc12] |
| 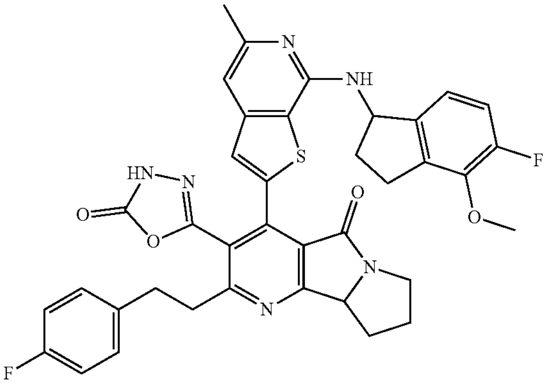 [SMILES: COc1c(F)ccc2c1CCC2Nc1nc(C)cc2cc(-c3c4c(nc(CCc5ccc(F)cc5)c3-c3n[nH]c(=O)o3)C3CCCN3C4=O)sc12] |
| 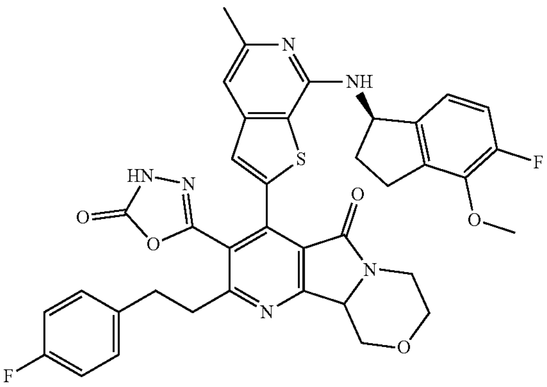 [SMILES: COc1c(F)ccc2c1CC[C@H]2Nc1nc(C)cc2cc(-c3c4c(nc(CCc5ccc(F)cc5)c3-c3n[nH]c(=O)o3)C3COCCN3C4=O)sc12] |
TABLE 2-continued
| Structure |
| --- |
| 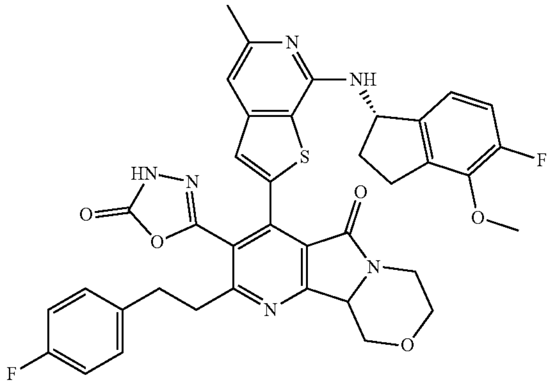 [SMILES: COc1c(F)ccc2c1CC[C@@H]2Nc1nc(C)cc2cc(-c3c4c(nc(CCc5ccc(F)cc5)c3-c3n[nH]c(=O)o3)C3COCCN3C4=O)sc12] |
| 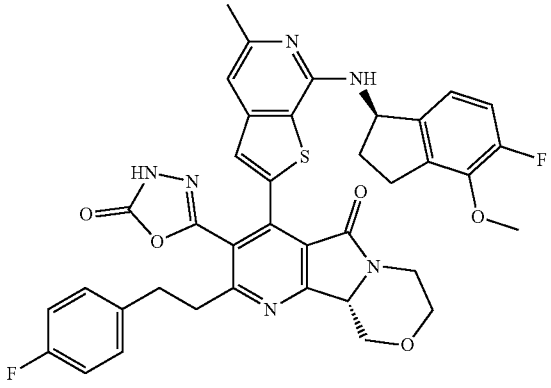 [SMILES: COc1c(F)ccc2c1CC[C@H]2Nc1nc(C)cc2cc(-c3c4c(nc(CCc5ccc(F)cc5)c3-c3n[nH]c(=O)o3)[C@H]3COCCN3C4=O)sc12] |
| 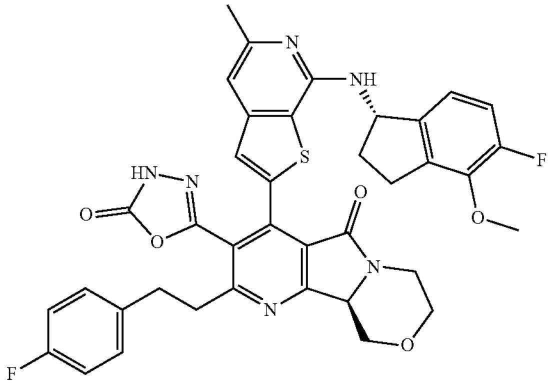 [SMILES: COc1c(F)ccc2c1CC[C@@H]2Nc1nc(C)cc2cc(-c3c4c(nc(CCc5ccc(F)cc5)c3-c3n[nH]c(=O)o3)[C@@H]3COCCN3C4=O)sc12] |
| 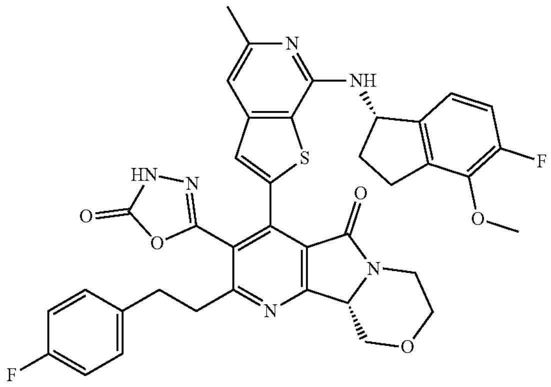 [SMILES: COc1c(F)ccc2c1CC[C@@H]2Nc1nc(C)cc2cc(-c3c4c(nc(CCc5ccc(F)cc5)c3-c3n[nH]c(=O)o3)[C@H]3COCCN3C4=O)sc12] |

TABLE 2-continued
| Structure |
| --- |
| 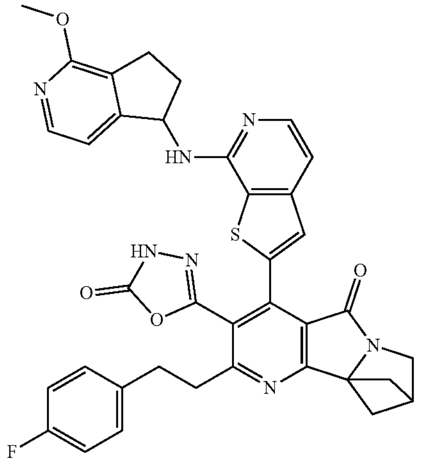 [SMILES: COc1nccc2c1CCC2Nc1nccc2cc(-c3c4c(nc(CCc5ccc(F)cc5)c3-c3n[nH]c(=O)o3)C35CC(CN3C4=O)C5)sc12] |
| 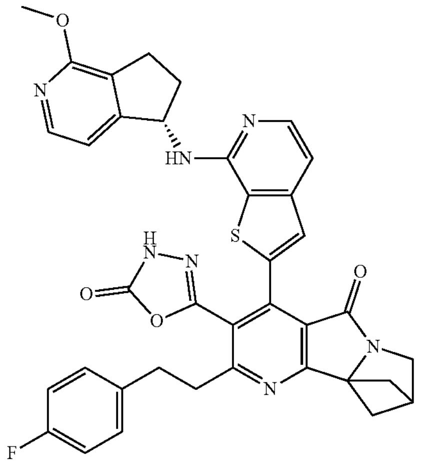 [SMILES: COc1nccc2c1CC[C@@H]2Nc1nccc2cc(-c3c4c(nc(CCc5ccc(F)cc5)c3-c3n[nH]c(=O)o3)C35CC(CN3C4=O)C5)sc12] |
| 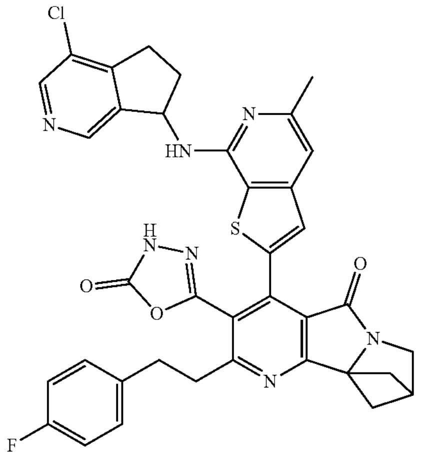 [SMILES: Cc1cc2cc(-c3c4c(nc(CCc5ccc(F)cc5)c3-c3n[nH]c(=O)o3)C35CC(CN3C4=O)C5)sc2c(NC2CCc3c(Cl)cncc32)n1] |
TABLE 2-continued
| Structure |
| --- |
| 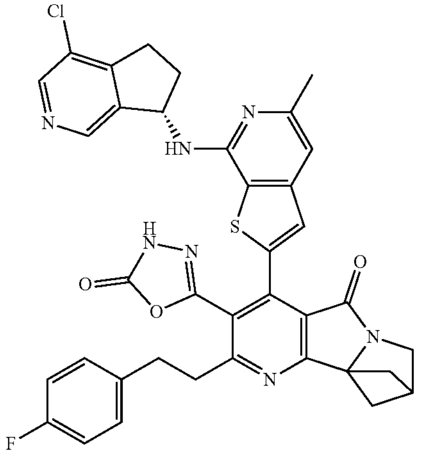 [SMILES: Cc1cc2cc(-c3c4c(nc(CCc5ccc(F)cc5)c3-c3n[nH]c(=O)o3)C35CC(CN3C4=O)C5)sc2c(N[C@H]2CCc3c(Cl)cncc32)n1] |
| 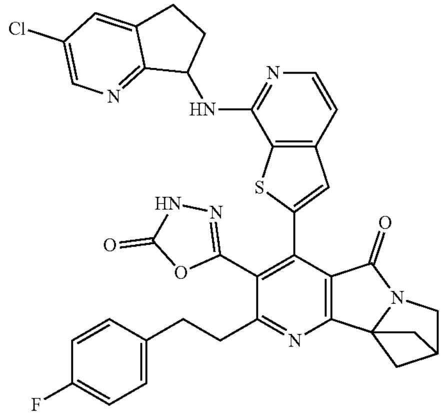 [SMILES: O=C1c2c(nc(CCc3ccc(F)cc3)c(-c3n[nH]c(=O)o3)c2-c2cc3ccnc(NC4CCc5cc(Cl)cnc54)c3s2)C23CC(CN12)C3] |
| 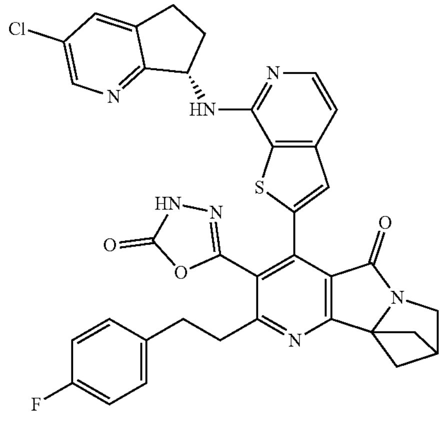 [SMILES: O=C1c2c(nc(CCc3ccc(F)cc3)c(-c3n[nH]c(=O)o3)c2-c2cc3ccnc(N[C@H]4CCc5cc(Cl)cnc54)c3s2)C23CC(CN12)C3] |

TABLE 2-continued
| Structure |
| --- |
| 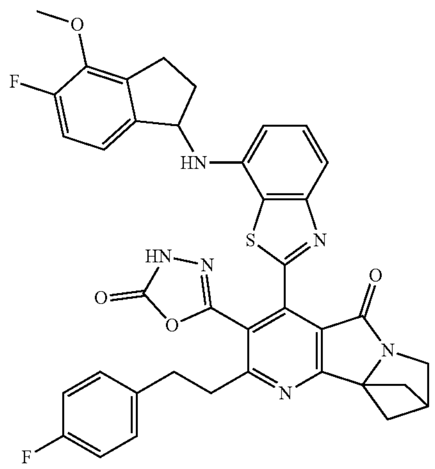 [SMILES: COc1c(F)ccc2c1CCC2Nc1cccc2nc(-c3c4c(nc(CCc5ccc(F)cc5)c3-c3n[nH]c(=O)o3)C35CC(CN3C4=O)C5)sc12] |
| 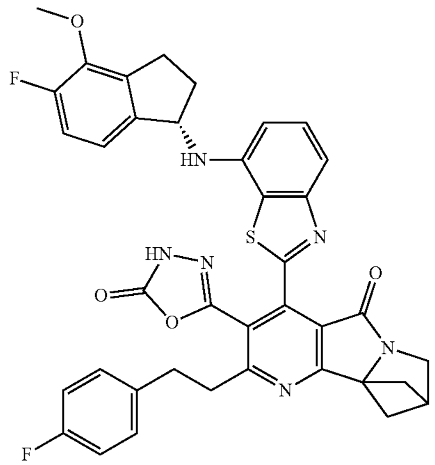 [SMILES: COc1c(F)ccc2c1CC[C@@H]2Nc1cccc2nc(-c3c4c(nc(CCc5ccc(F)cc5)c3-c3n[nH]c(=O)o3)C35CC(CN3C4=O)C5)sc12] |
| 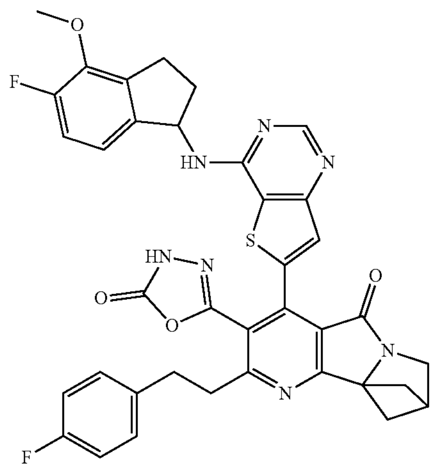 [SMILES: COc1c(F)ccc2c1CCC2Nc1ncnc2cc(-c3c4c(nc(CCc5ccc(F)cc5)c3-c3n[nH]c(=O)o3)C35CC(CN3C4=O)C5)sc12] |
TABLE 2-continued
| Structure |
| --- |
| 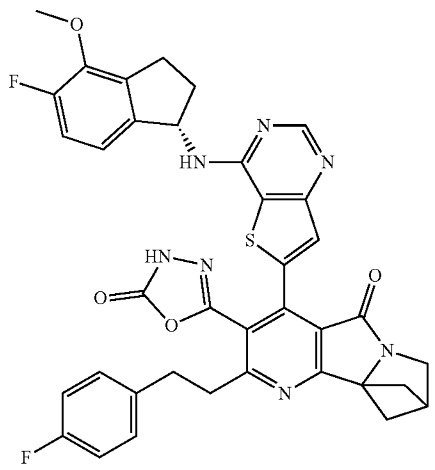 [SMILES: COc1c(F)ccc2c1CC[C@@H]2Nc1ncnc2cc(-c3c4c(nc(CCc5ccc(F)cc5)c3-c3n[nH]c(=O)o3)C35CC(CN3C4=O)C5)sc12] |
| 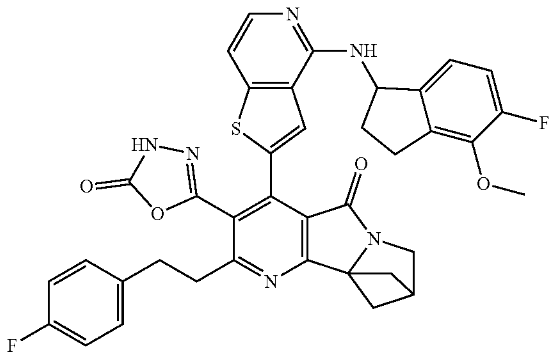 [SMILES: COc1c(F)ccc2c1CCC2Nc1nccc2sc(-c3c4c(nc(CCc5ccc(F)cc5)c3-c3n[nH]c(=O)o3)C35CC(CN3C4=O)C5)cc12] |
| 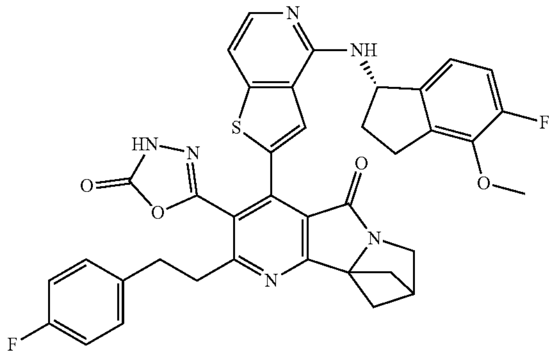 [SMILES: COc1c(F)ccc2c1CC[C@@H]2Nc1nccc2sc(-c3c4c(nc(CCc5ccc(F)cc5)c3-c3n[nH]c(=O)o3)C35CC(CN3C4=O)C5)cc12] |
| 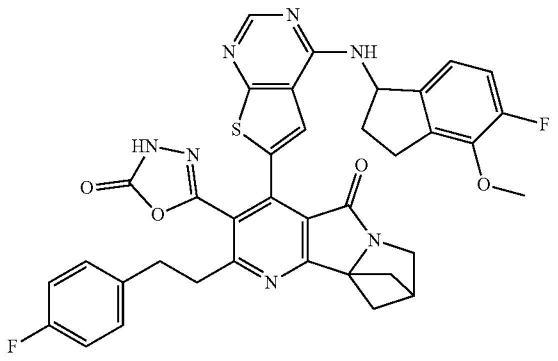 [SMILES: COc1c(F)ccc2c1CCC2Nc1ncnc2sc(-c3c4c(nc(CCc5ccc(F)cc5)c3-c3n[nH]c(=O)o3)C35CC(CN3C4=O)C5)cc12] |

TABLE 2-continued
| Structure |
| --- |
| 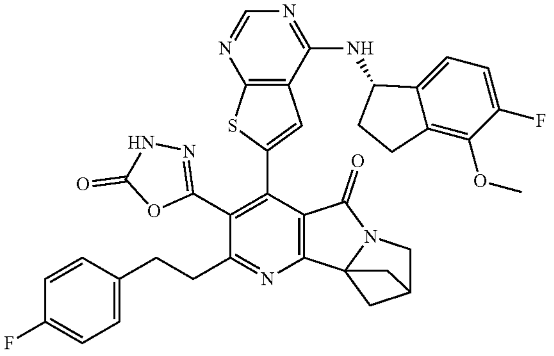 [SMILES: COc1c(F)ccc2c1CC[C@@H]2Nc1ncnc2sc(-c3c4c(nc(CCc5ccc(F)cc5)c3-c3n[nH]c(=O)o3)C35CC(CN3C4=O)C5)cc12] |
| 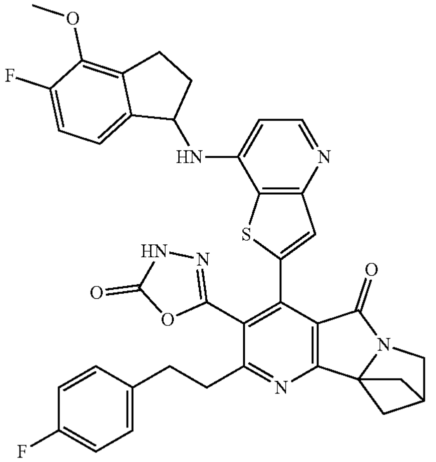 [SMILES: COc1c(F)ccc2c1CCC2Nc1ccnc2cc(-c3c4c(nc(CCc5ccc(F)cc5)c3-c3n[nH]c(=O)o3)C35CC(CN3C4=O)C5)sc12] |
| 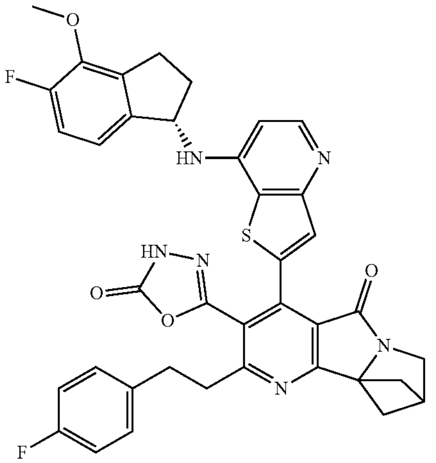 [SMILES: COc1c(F)ccc2c1CC[C@@H]2Nc1ccnc2cc(-c3c4c(nc(CCc5ccc(F)cc5)c3-c3n[nH]c(=O)o3)C35CC(CN3C4=O)C5)sc12] |
TABLE 2-continued
| Structure |
| --- |
| 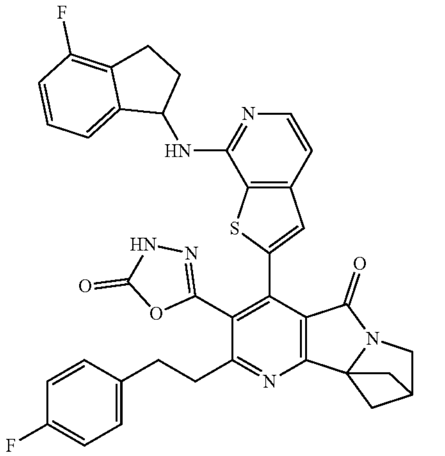 [SMILES: O=C1c2c(nc(CCc3ccc(F)cc3)c(-c3n[nH]c(=O)o3)c2-c2cc3ccnc(NC4CCc5c(F)cccc54)c3s2)C23CC(CN12)C3] |
| 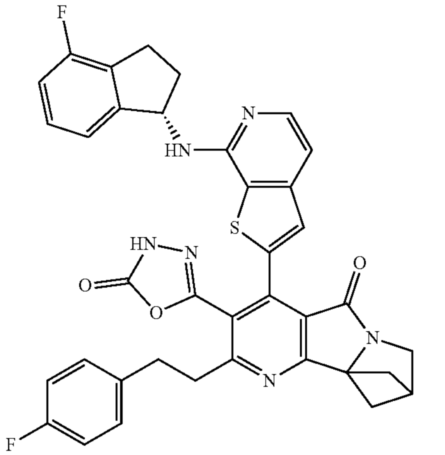 [SMILES: O=C1c2c(nc(CCc3ccc(F)cc3)c(-c3n[nH]c(=O)o3)c2-c2cc3ccnc(N[C@H]4CCc5c(F)cccc54)c3s2)C23CC(CN12)C3] |
| 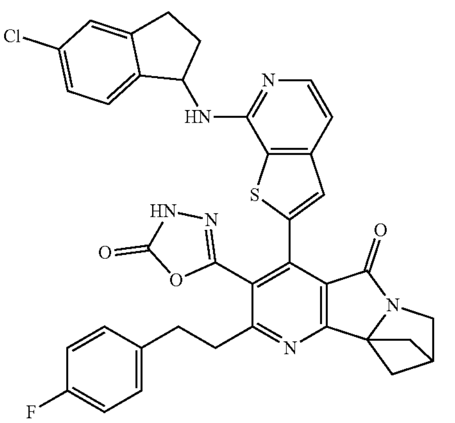 [SMILES: O=C1c2c(nc(CCc3ccc(F)cc3)c(-c3n[nH]c(=O)o3)c2-c2cc3ccnc(NC4CCc5cc(Cl)ccc54)c3s2)C23CC(CN12)C3] |

TABLE 2-continued
| Structure |
|---|
| 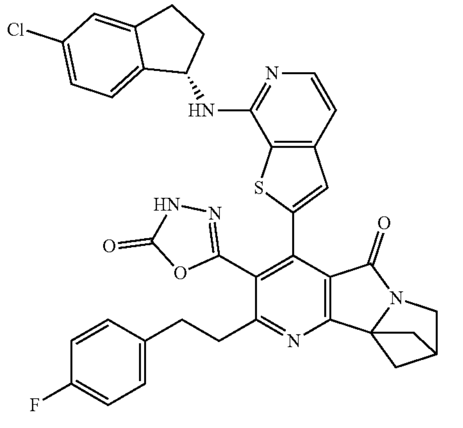 [SMILES: O=C1c2c(nc(CCc3ccc(F)cc3)c(-c3n[nH]c(=O)o3)c2-c2cc3ccnc(N[C@H]4CCc5cc(Cl)ccc54)c3s2)C23CC(CN12)C3] |
| 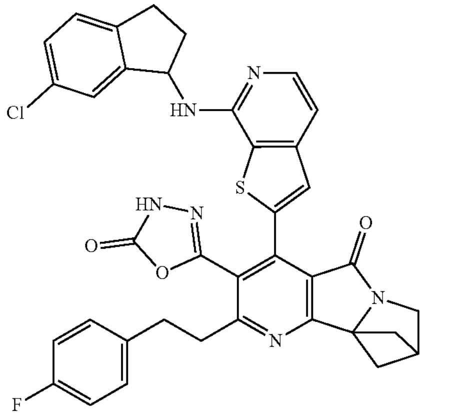 [SMILES: O=C1c2c(nc(CCc3ccc(F)cc3)c(-c3n[nH]c(=O)o3)c2-c2cc3ccnc(NC4CCc5ccc(Cl)cc54)c3s2)C23CC(CN12)C3] |
| 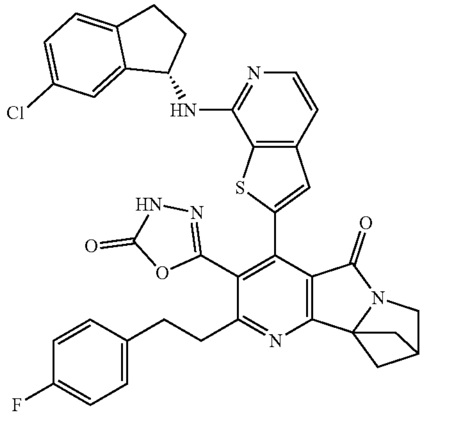 [SMILES: O=C1c2c(nc(CCc3ccc(F)cc3)c(-c3n[nH]c(=O)o3)c2-c2cc3ccnc(N[C@H]4CCc5ccc(Cl)cc54)c3s2)C23CC(CN12)C3] |
TABLE 2-continued
| Structure |
|---|
| 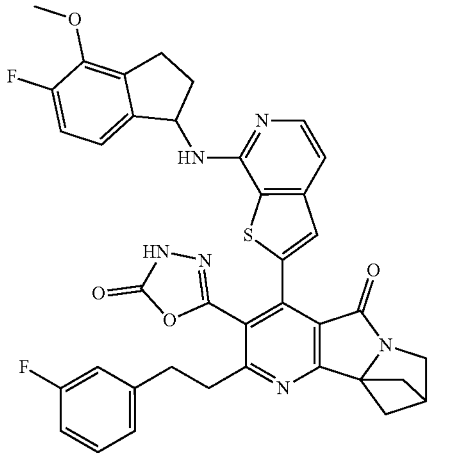 [SMILES: COc1c(F)ccc2c1CCC2Nc1nccc2cc(-c3c4c(nc(CCc5cccc(F)c5)c3-c3n[nH]c(=O)o3)C35CC(CN3C4=O)C5)sc12] |
| 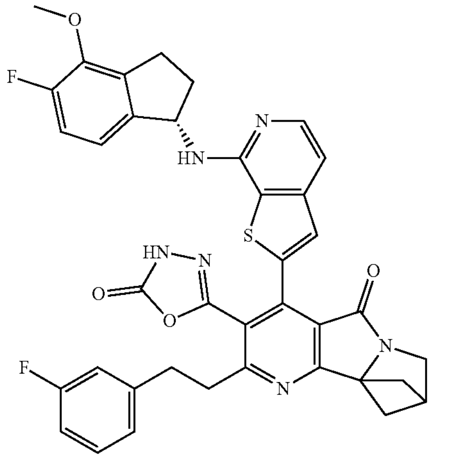 [SMILES: COc1c(F)ccc2c1CC[C@@H]2Nc1nccc2cc(-c3c4c(nc(CCc5cccc(F)c5)c3-c3n[nH]c(=O)o3)C35CC(CN3C4=O)C5)sc12] |
| 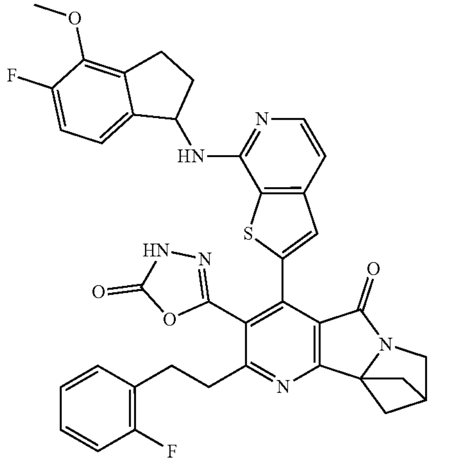

TABLE 2-continued
| Structure |
| --- |
| 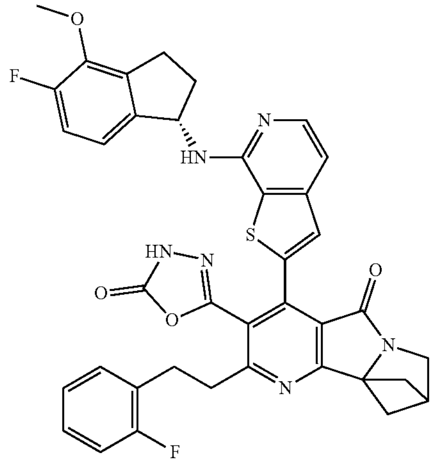 [SMILES: COc1c(F)ccc2c1CCC2Nc1nccc2cc(-c3c4c(nc(CCc5ccccc5F)c3-c3n[nH]c(=O)o3)C35CC(CN3C4=O)C5)sc12] |
| 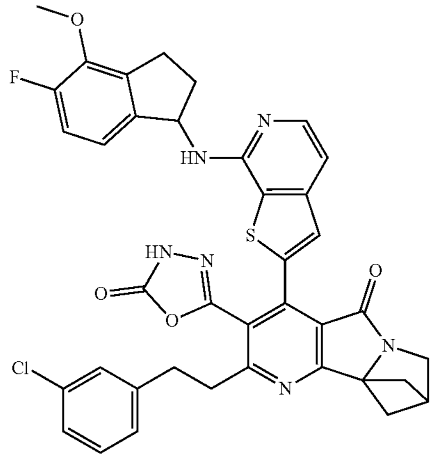 [SMILES: COc1c(F)ccc2c1CCC2Nc1nccc2cc(-c3c4c(nc(CCc5cccc(Cl)c5)c3-c3n[nH]c(=O)o3)C35CC(CN3C4=O)C5)sc12] |
| 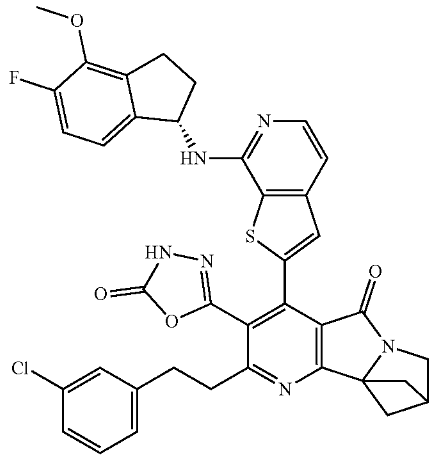 [SMILES: COc1c(F)ccc2c1CC[C@@H]2Nc1nccc2cc(-c3c4c(nc(CCc5cccc(Cl)c5)c3-c3n[nH]c(=O)o3)C35CC(CN3C4=O)C5)sc12] |
TABLE 2-continued
| Structure |
| --- |
| 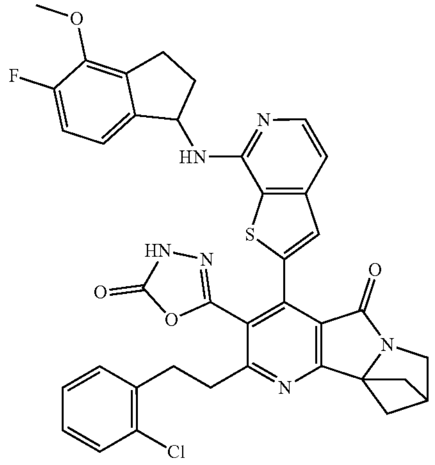 [SMILES: COc1c(F)ccc2c1CCC2Nc1nccc2cc(-c3c4c(nc(CCc5ccccc5Cl)c3-c3n[nH]c(=O)o3)C35CC(CN3C4=O)C5)sc12] |
| 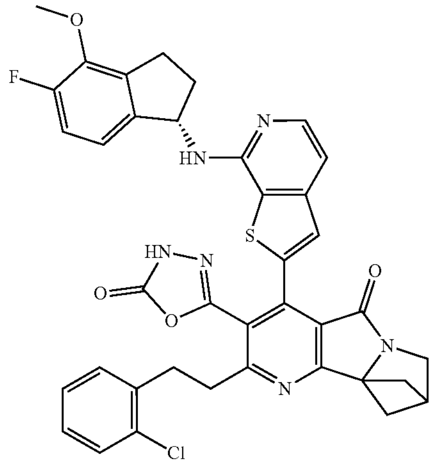 [SMILES: COc1c(F)ccc2c1CC[C@@H]2Nc1nccc2cc(-c3c4c(nc(CCc5ccccc5Cl)c3-c3n[nH]c(=O)o3)C35CC(CN3C4=O)C5)sc12] |
| 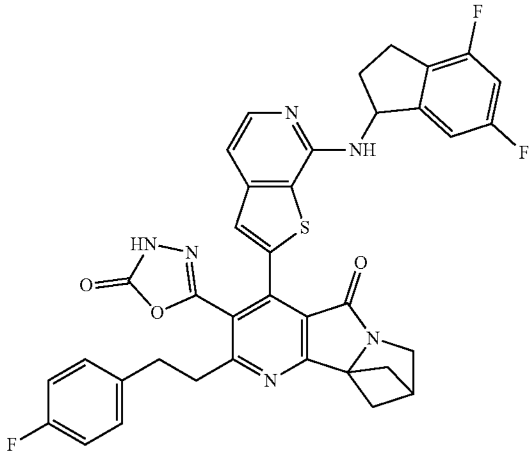 [SMILES: O=C1c2c(nc(CCc3ccc(F)cc3)c(-c3n[nH]c(=O)o3)c2-c2cc3ccnc(NC4CCc5c(F)cc(F)cc54)c3s2)C23CC(CN12)C3] |

TABLE 2-continued
| Structure |
|---|
| 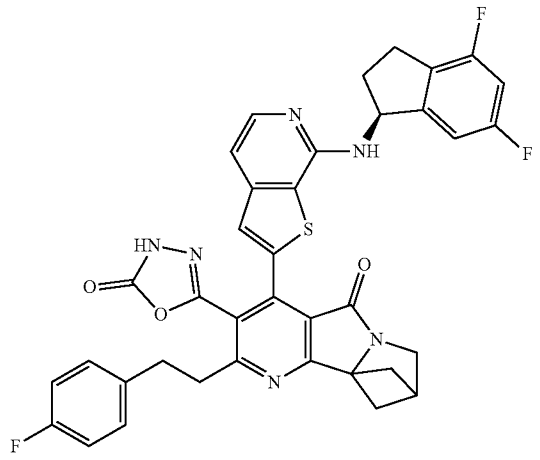 [SMILES: O=C1c2c(nc(CCc3ccc(F)cc3)c(-c3n[nH]c(=O)o3)c2-c2cc3ccnc(N[C@H]4CCc5c(F)cc(F)cc54)c3s2)C23CC(CN12)C3] |
| 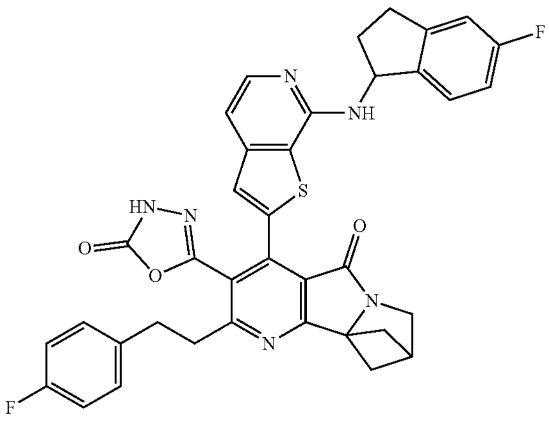 [SMILES: O=C1c2c(nc(CCc3ccc(F)cc3)c(-c3n[nH]c(=O)o3)c2-c2cc3ccnc(NC4CCc5cc(F)ccc54)c3s2)C23CC(CN12)C3] |
| 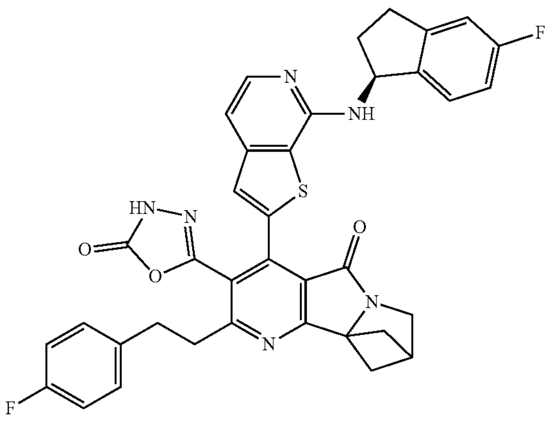 [SMILES: O=C1c2c(nc(CCc3ccc(F)cc3)c(-c3n[nH]c(=O)o3)c2-c2cc3ccnc(N[C@H]4CCc5cc(F)ccc54)c3s2)C23CC(CN12)C3] |
TABLE 2-continued
| Structure |
|---|
| 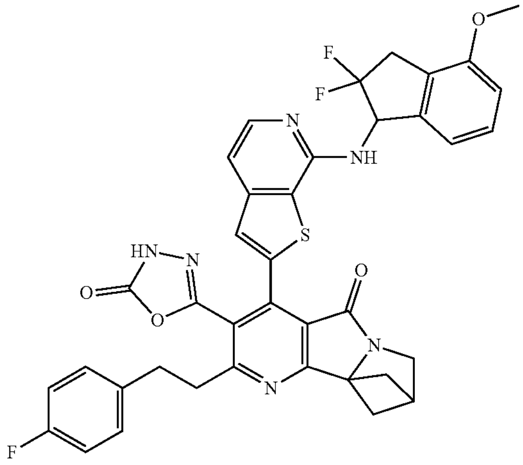 [SMILES: COc1cccc2c1CC(F)(F)C2Nc1nccc2cc(-c3c4c(nc(CCc5ccc(F)cc5)c3-c3n[nH]c(=O)o3)C35CC(CN3C4=O)C5)sc12] |
| 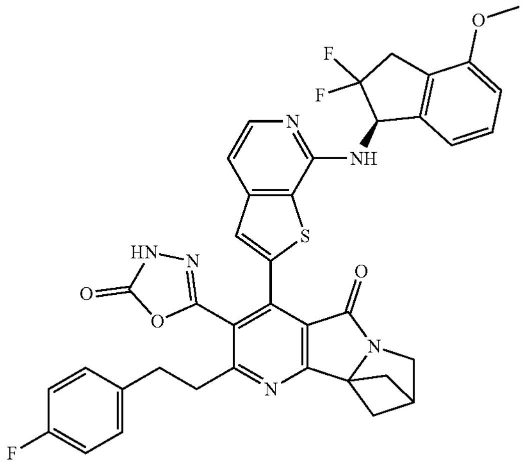 [SMILES: COc1cccc2c1CC(F)(F)[C@@H]2Nc1nccc2cc(-c3c4c(nc(CCc5ccc(F)cc5)c3-c3n[nH]c(=O)o3)C35CC(CN3C4=O)C5)sc12] |
| 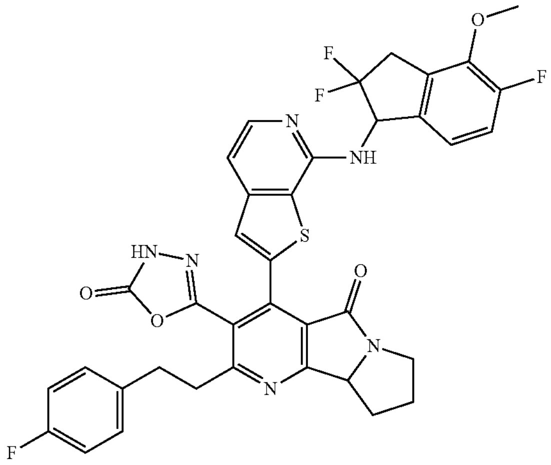 [SMILES: COc1c(F)ccc2c1CC(F)(F)C2Nc1nccc2cc(-c3c4c(nc(CCc5ccc(F)cc5)c3-c3n[nH]c(=O)o3)C3CCCN3C4=O)sc12] |

TABLE 2-continued
Structure
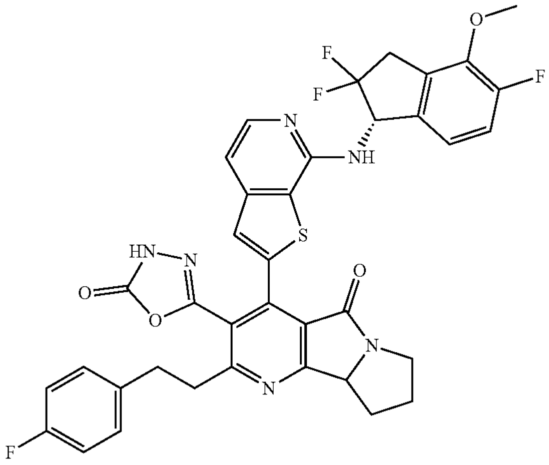 [SMILES: COc1c(F)ccc2c1CC(F)(F)[C@H]2Nc1nccc2cc(-c3c4c(nc(CCc5ccc(F)cc5)c3-c3n[nH]c(=O)o3)C3CCCN3C4=O)sc12]
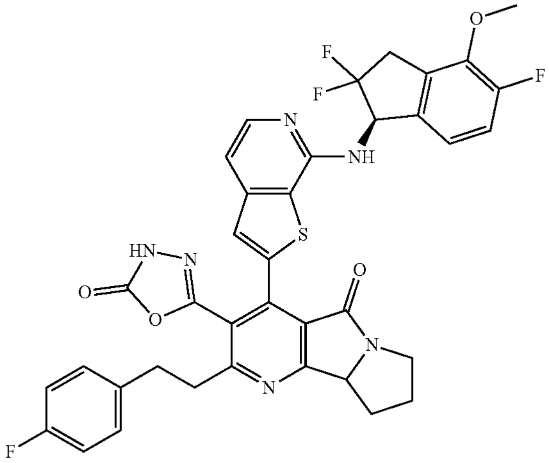 [SMILES: COc1c(F)ccc2c1CC(F)(F)[C@@H]2Nc1nccc2cc(-c3c4c(nc(CCc5ccc(F)cc5)c3-c3n[nH]c(=O)o3)C3CCCN3C4=O)sc12]
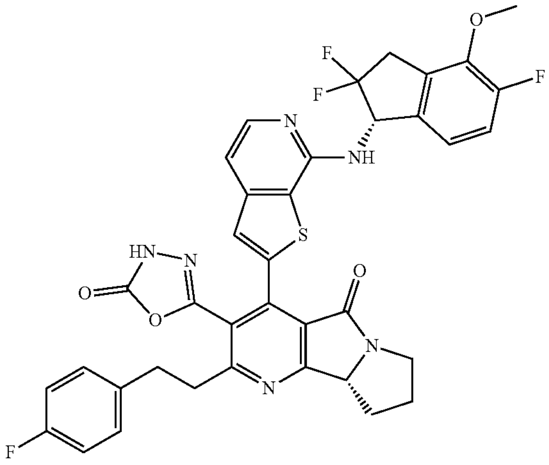 [SMILES: COc1c(F)ccc2c1CC(F)(F)[C@H]2Nc1nccc2cc(-c3c4c(nc(CCc5ccc(F)cc5)c3-c3n[nH]c(=O)o3)[C@H]3CCCN3C4=O)sc12]
TABLE 2-continued
Structure
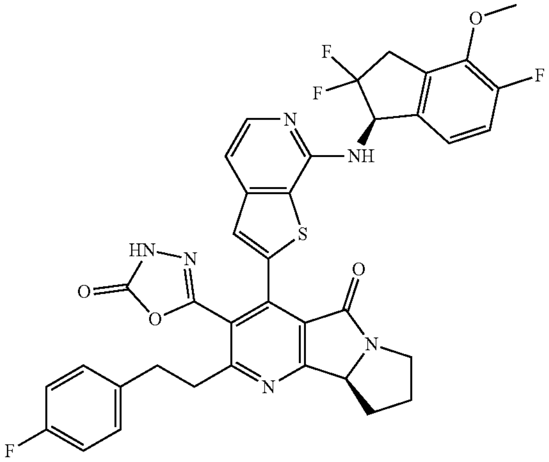 [SMILES: COc1c(F)ccc2c1CC(F)(F)[C@@H]2Nc1nccc2cc(-c3c4c(nc(CCc5ccc(F)cc5)c3-c3n[nH]c(=O)o3)[C@@H]3CCCN3C4=O)sc12]
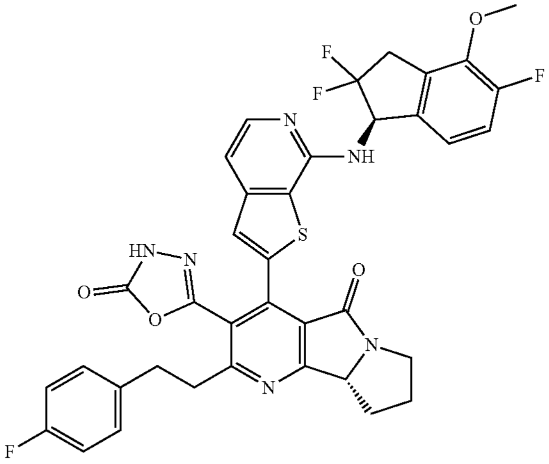 [SMILES: COc1c(F)ccc2c1CC(F)(F)[C@@H]2Nc1nccc2cc(-c3c4c(nc(CCc5ccc(F)cc5)c3-c3n[nH]c(=O)o3)[C@H]3CCCN3C4=O)sc12]
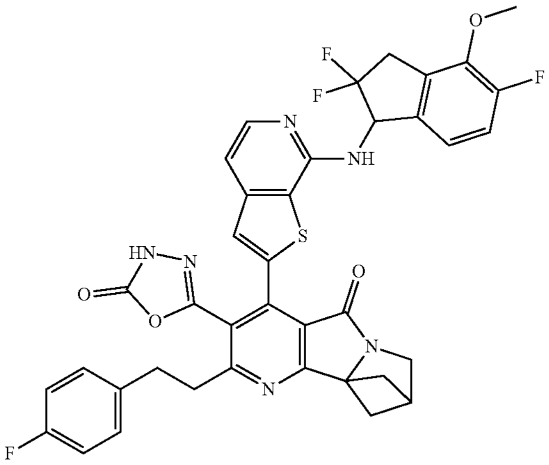

TABLE 2-continued
| Structure |
| --- |
| 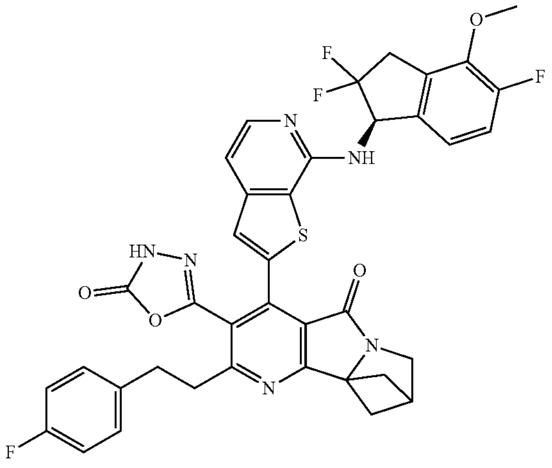 [SMILES: COc1c(F)ccc2c1CC(F)(F)[C@@H]2Nc1nccc2cc(-c3c4c(nc(CCc5ccc(F)cc5)c3-c3n[nH]c(=O)o3)C35CC(CN3C4=O)C5)sc12] |
| 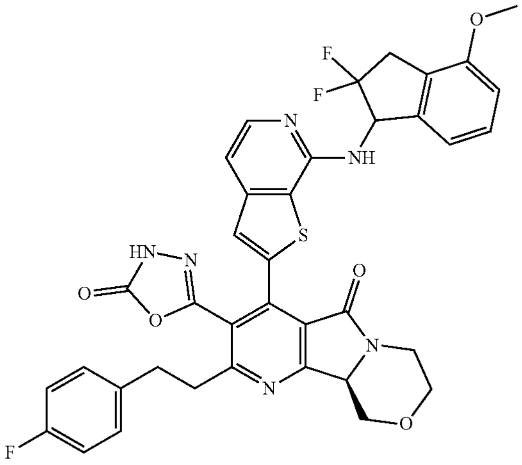 [SMILES: COc1cccc2c1CC(F)(F)C2Nc1nccc2cc(-c3c4c(nc(CCc5ccc(F)cc5)c3-c3n[nH]c(=O)o3)[C@@H]3COCCN3C4=O)sc12] |
| 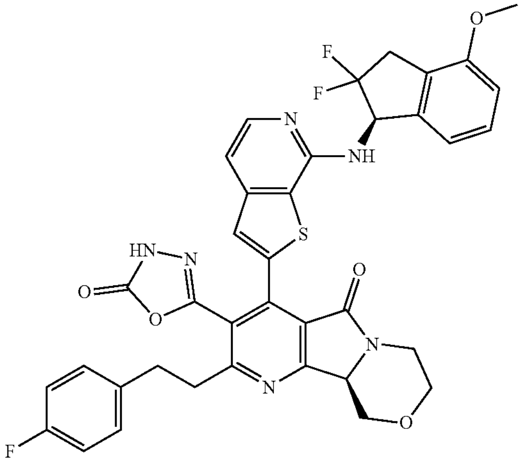 [SMILES: COc1cccc2c1CC(F)(F)[C@@H]2Nc1nccc2cc(-c3c4c(nc(CCc5ccc(F)cc5)c3-c3n[nH]c(=O)o3)[C@@H]3COCCN3C4=O)sc12] |
TABLE 2-continued
| Structure |
| --- |
| 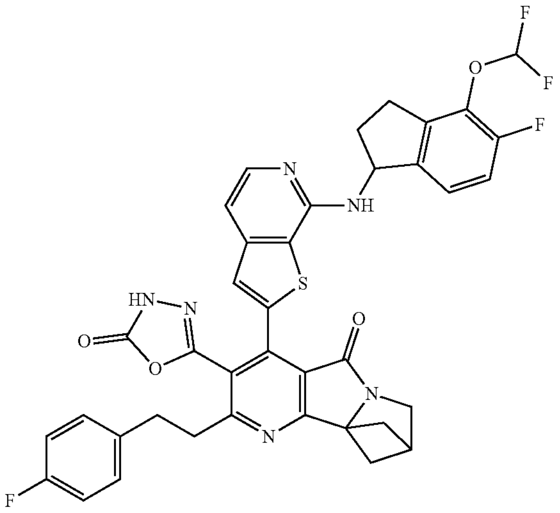 |
| 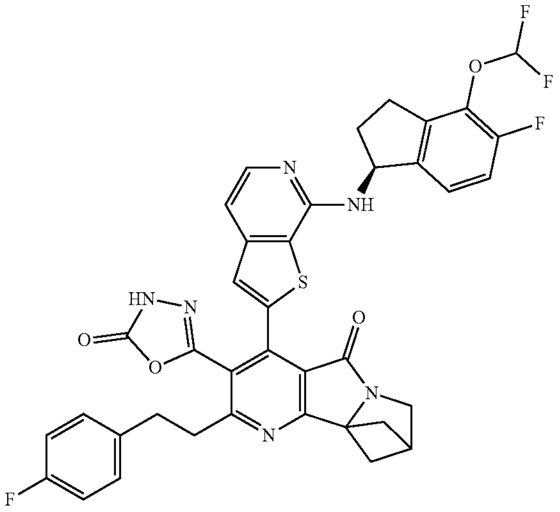 [SMILES: O=C1c2c(nc(CCc3ccc(F)cc3)c(-c3n[nH]c(=O)o3)c2-c2cc3ccnc(N[C@H]4CCc5c4ccc(F)c5OC(F)F)c3s2)C23CC(CN12)C3] |
| 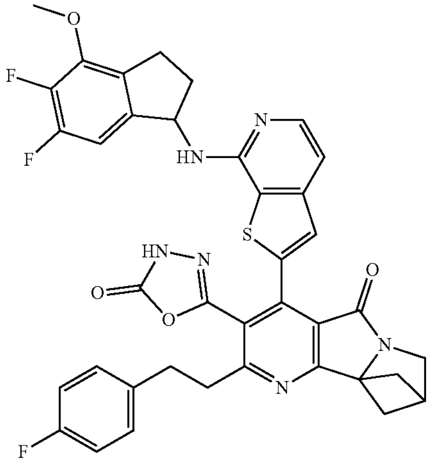 |

TABLE 2-continued
| Structure |
| --- |
| 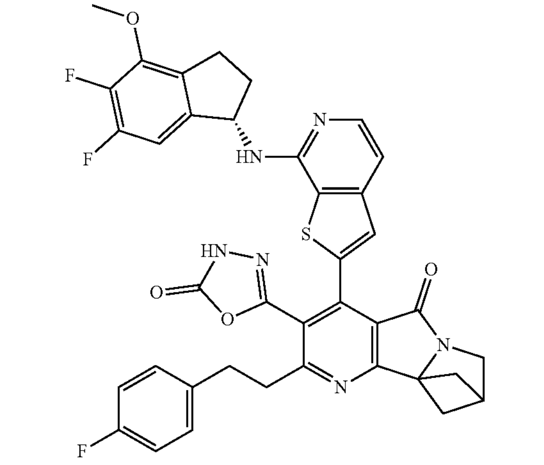 [SMILES: COc1c(F)c(F)cc2c1CC[C@@H]2Nc1nccc2cc(-c3c4c(nc(CCc5ccc(F)cc5)c3-c3n[nH]c(=O)o3)C35CC(CN3C4=O)C5)sc12] |
| 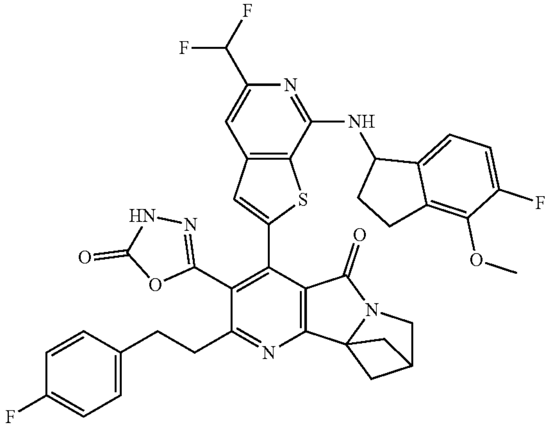 [SMILES: COc1c(F)ccc2c1CCC2Nc1nc(C(F)F)cc2cc(-c3c4c(nc(CCc5ccc(F)cc5)c3-c3n[nH]c(=O)o3)C35CC(CN3C4=O)C5)sc12] |
| 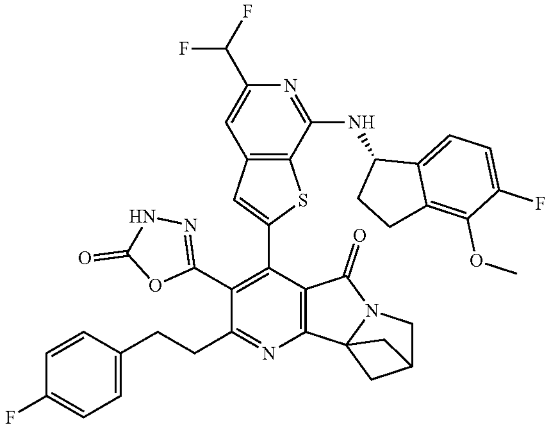 |
TABLE 2-continued
| Structure |
| --- |
| 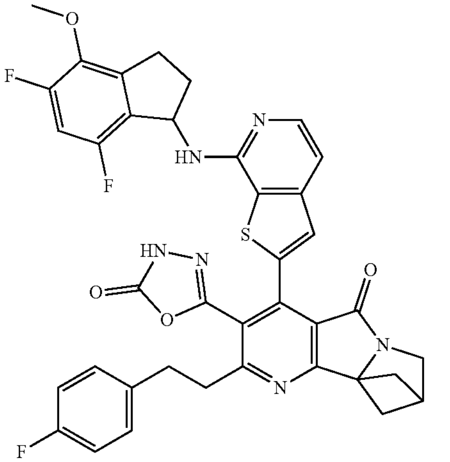 [SMILES: COc1c(F)cc(F)c2c1CCC2Nc1nccc2cc(-c3c4c(nc(CCc5ccc(F)cc5)c3-c3n[nH]c(=O)o3)C35CC(CN3C4=O)C5)sc12] |
| 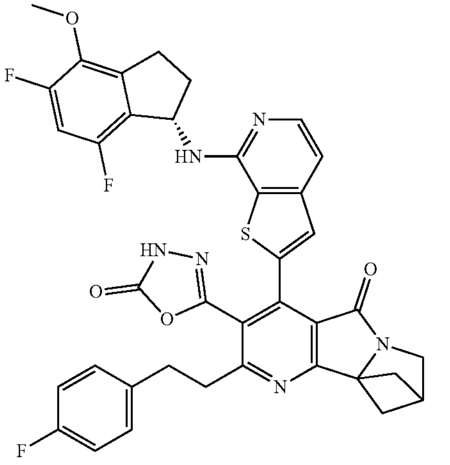 [SMILES: COc1c(F)cc(F)c2c1CC[C@@H]2Nc1nccc2cc(-c3c4c(nc(CCc5ccc(F)cc5)c3-c3n[nH]c(=O)o3)C35CC(CN3C4=O)C5)sc12] |
| 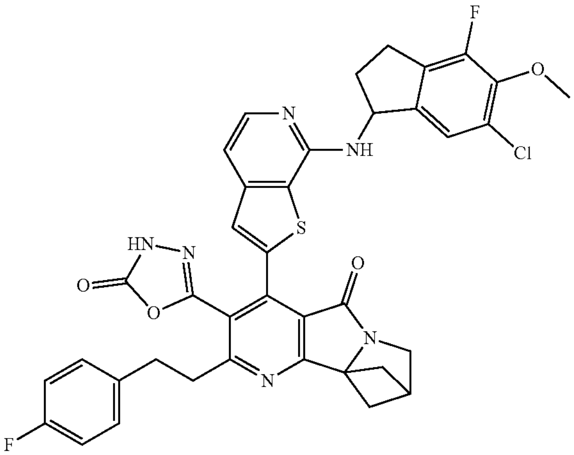 [SMILES: COc1c(Cl)cc2c(c1F)CCC2Nc1nccc2cc(-c3c4c(nc(CCc5ccc(F)cc5)c3-c3n[nH]c(=O)o3)C35CC(CN3C4=O)C5)sc12] |

TABLE 2-continued
| Structure |
| --- |
| 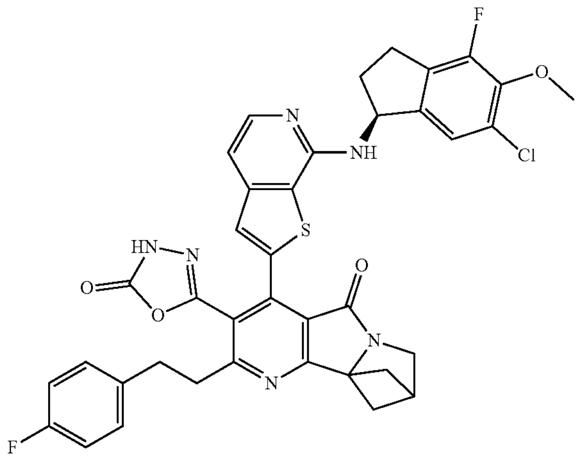 [SMILES: COc1c(Cl)cc2c(c1F)CC[C@@H]2Nc1nccc2cc(-c3c4c(nc(CCc5ccc(F)cc5)c3-c3n[nH]c(=O)o3)C35CC(CN3C4=O)C5)sc12] |
| 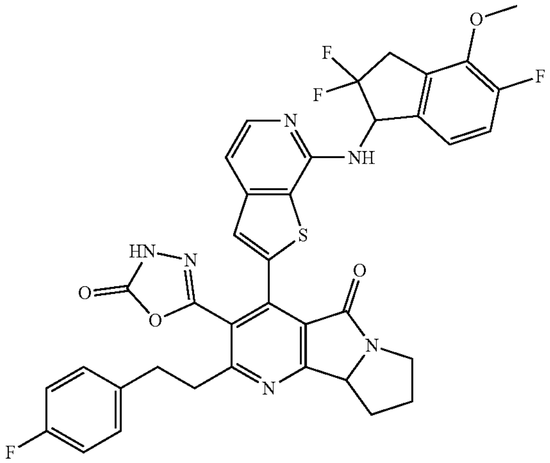 |
| 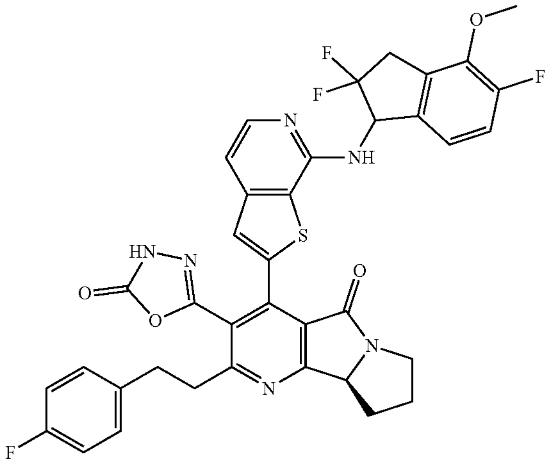 [SMILES: COc1c(F)ccc2c1CC(F)(F)C2Nc1nccc2cc(-c3c4c(nc(CCc5ccc(F)cc5)c3-c3n[nH]c(=O)o3)[C@@H]3CCCN3C4=O)sc12] |
TABLE 2-continued
| Structure |
| --- |
| 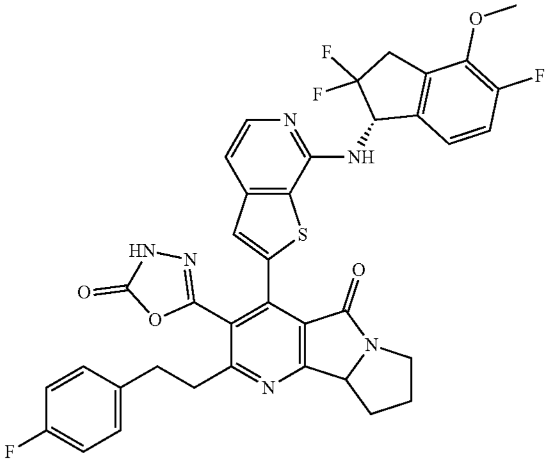 |
| 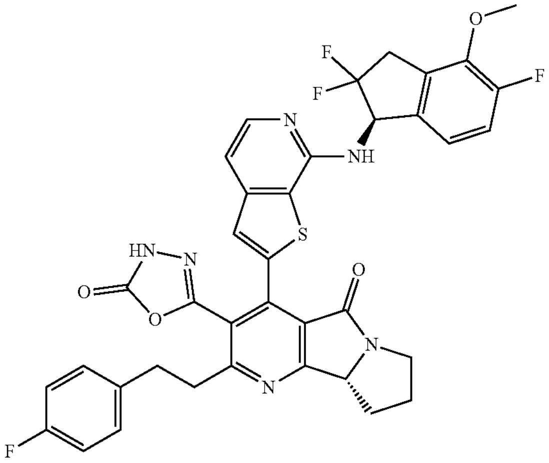 |
| 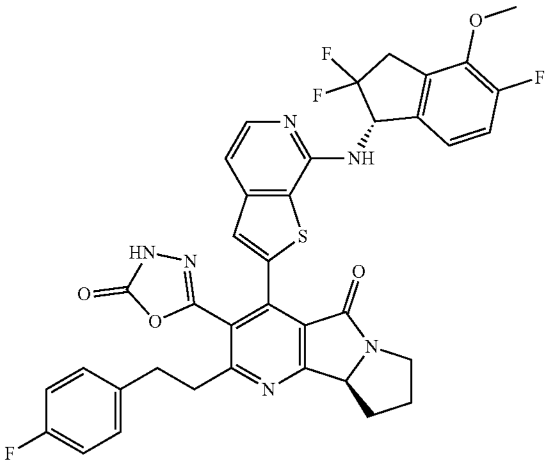 [SMILES: COc1c(F)ccc2c1CC(F)(F)[C@H]2Nc1nccc2cc(-c3c4c(nc(CCc5ccc(F)cc5)c3-c3n[nH]c(=O)o3)[C@@H]3CCCN3C4=O)sc12] |

TABLE 2-continued
| Structure |
| --- |
| 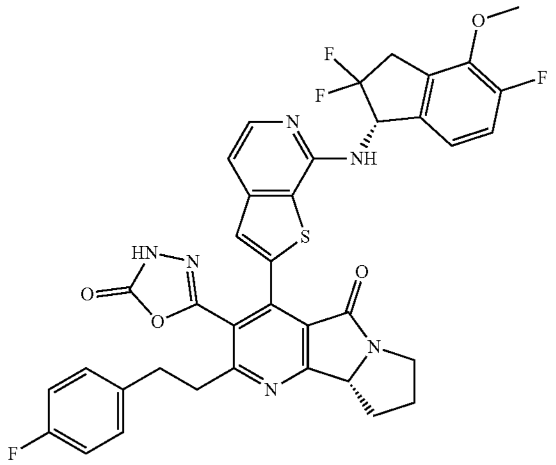 |
| 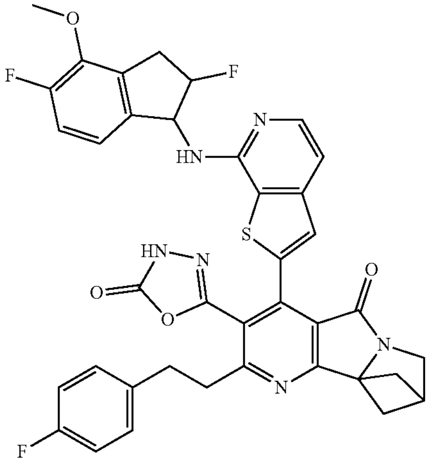 [SMILES: COc1c(F)ccc2c1CC(F)C2Nc1nccc2cc(-c3c4c(nc(CCc5ccc(F)cc5)c3-c3n[nH]c(=O)o3)C35CC(CN3C4=O)C5)sc12] |
| 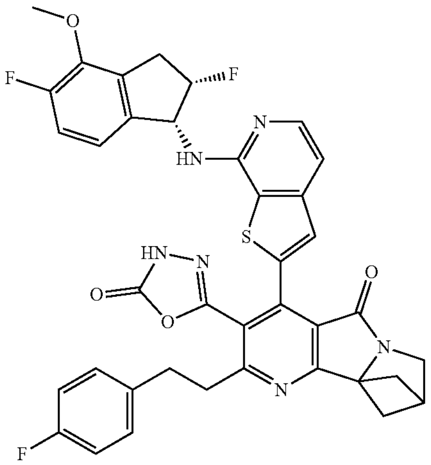 [SMILES: COc1c(F)ccc2c1C[C@H](F)[C@@H]2Nc1nccc2cc(-c3c4c(nc(CCc5ccc(F)cc5)c3-c3n[nH]c(=O)o3)C35CC(CN3C4=O)C5)sc12] |
TABLE 2-continued
| Structure |
| --- |
| 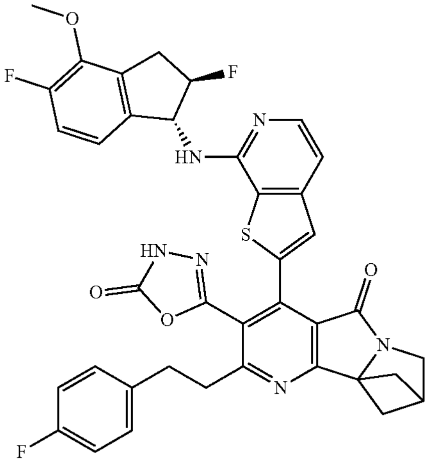 [SMILES: COc1c(F)ccc2c1C[C@@H](F)[C@@H]2Nc1nccc2cc(-c3c4c(nc(CCc5ccc(F)cc5)c3-c3n[nH]c(=O)o3)C35CC(CN3C4=O)C5)sc12] |
| 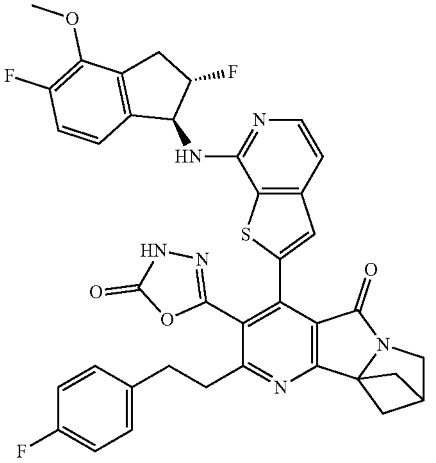 [SMILES: COc1c(F)ccc2c1C[C@H](F)[C@H]2Nc1nccc2cc(-c3c4c(nc(CCc5ccc(F)cc5)c3-c3n[nH]c(=O)o3)C35CC(CN3C4=O)C5)sc12] |
| 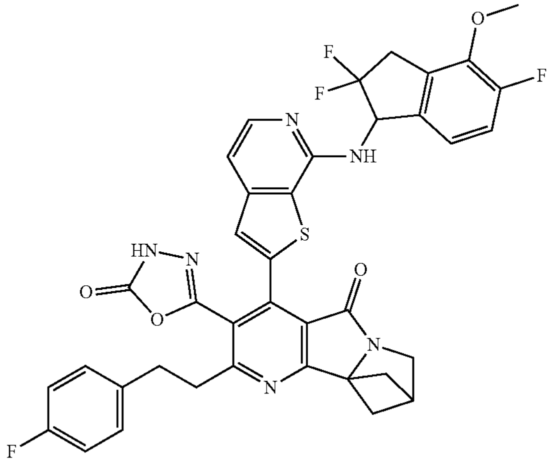 [SMILES: COc1c(F)ccc2c1CC(F)(F)C2Nc1nccc2cc(-c3c4c(nc(CCc5ccc(F)cc5)c3-c3n[nH]c(=O)o3)C35CC(CN3C4=O)C5)sc12]

TABLE 2-continued
| Structure |
| --- |
| 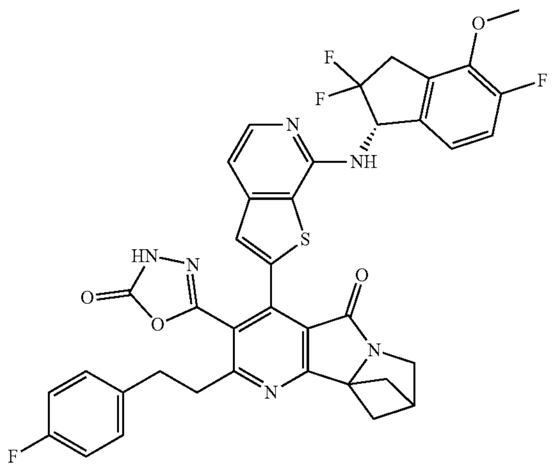 [SMILES: COc1c(F)ccc2c1CC(F)(F)[C@H]2Nc1nccc2cc(-c3c4c(nc(CCc5ccc(F)cc5)c3-c3n[nH]c(=O)o3)C35CC(CN3C4=O)C5)sc12] |
| 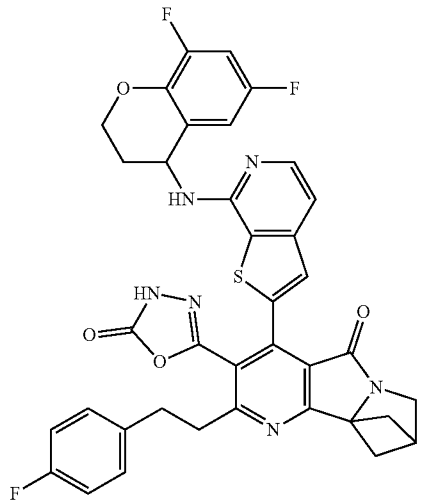 [SMILES: O=C1c2c(nc(CCc3ccc(F)cc3)c(-c3n[nH]c(=O)o3)c2-c2cc3ccnc(NC4CCOc5c(F)cc(F)cc54)c3s2)C23CC(CN12)C3] |
| 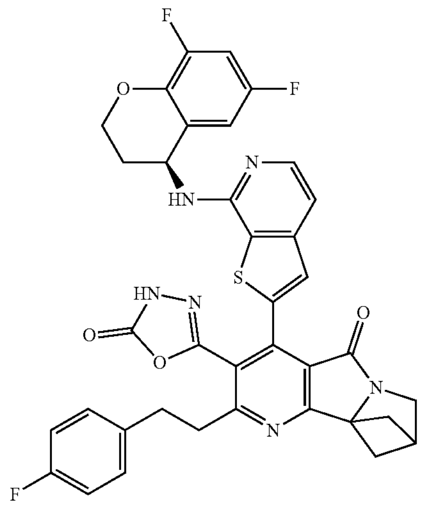 [SMILES: O=C1c2c(nc(CCc3ccc(F)cc3)c(-c3n[nH]c(=O)o3)c2-c2cc3ccnc(N[C@H]4CCOc5c(F)cc(F)cc54)c3s2)C23CC(CN12)C3] |
TABLE 2-continued
| Structure |
| --- |
| 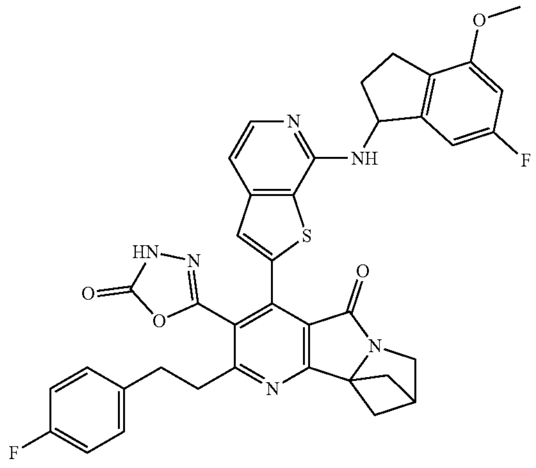 [SMILES: COc1cc(F)cc2c1CCC2Nc1nccc2cc(-c3c4c(nc(CCc5ccc(F)cc5)c3-c3n[nH]c(=O)o3)C35CC(CN3C4=O)C5)sc12] |
| 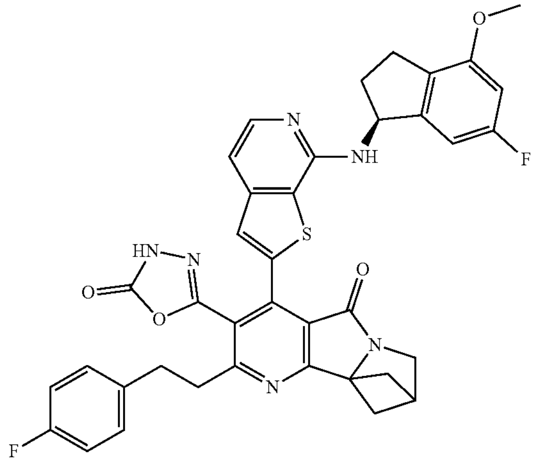 [SMILES: COc1cc(F)cc2c1CC[C@@H]2Nc1nccc2cc(-c3c4c(nc(CCc5ccc(F)cc5)c3-c3n[nH]c(=O)o3)C35CC(CN3C4=O)C5)sc12] |
| 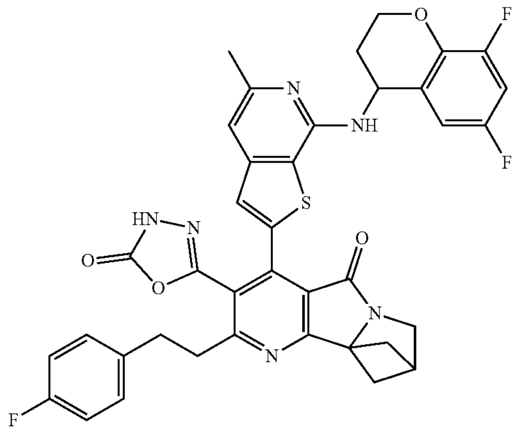 [SMILES: Cc1cc2cc(-c3c4c(nc(CCc5ccc(F)cc5)c3-c3n[nH]c(=O)o3)C35CC(CN3C4=O)C5)sc2c(NC2CCOc3c(F)cc(F)cc32)n1] |

TABLE 2-continued
| Structure |
| --- |
| 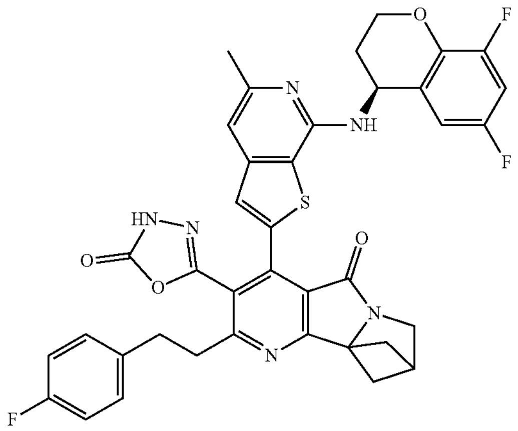 [SMILES: Cc1cc2cc(-c3c4c(nc(CCc5ccc(F)cc5)c3-c3n[nH]c(=O)o3)C35CC(CN3C4=O)C5)sc2c(N[C@H]2CCOc3c(F)cc(F)cc32)n1] |
| 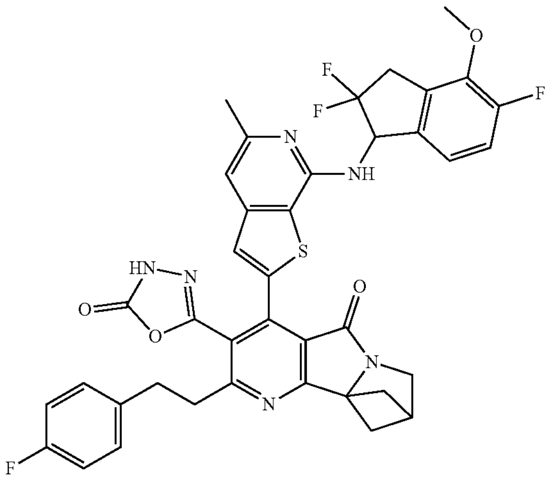 [SMILES: COc1c(F)ccc2c1CC(F)(F)C2Nc1nc(C)cc2cc(-c3c4c(nc(CCc5ccc(F)cc5)c3-c3n[nH]c(=O)o3)C35CC(CN3C4=O)C5)sc12] |
| 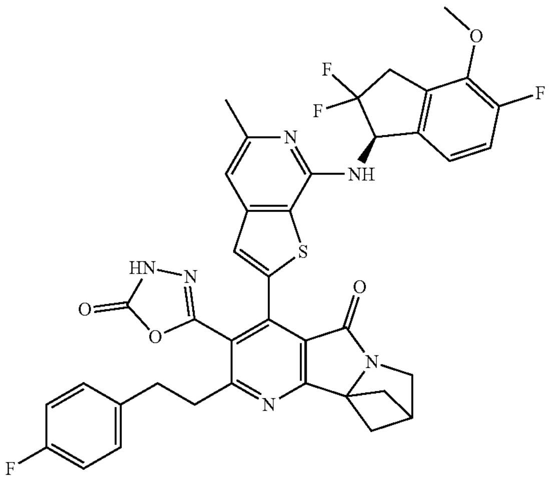 [SMILES: COc1c(F)ccc2c1CC(F)(F)[C@@H]2Nc1nc(C)cc2cc(-c3c4c(nc(CCc5ccc(F)cc5)c3-c3n[nH]c(=O)o3)C35CC(CN3C4=O)C5)sc12] |
TABLE 2-continued
| Structure |
| --- |
| 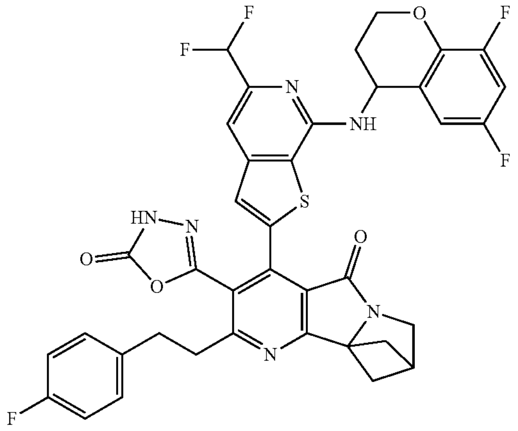 [SMILES: O=C1c2c(nc(CCc3ccc(F)cc3)c(-c3n[nH]c(=O)o3)c2-c2cc3cc(C(F)F)nc(NC4CCOc5c(F)cc(F)cc54)c3s2)C23CC(CN12)C3] |
| 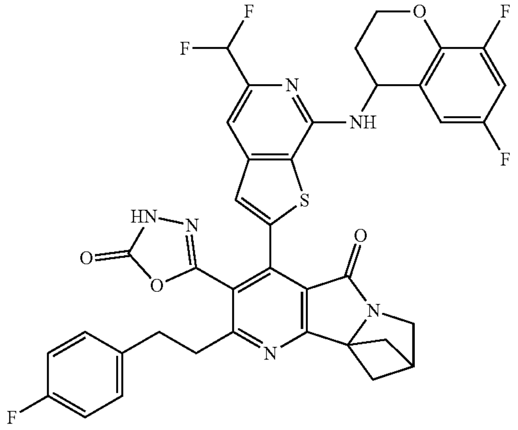 [SMILES: O=C1c2c(nc(CCc3ccc(F)cc3)c(-c3n[nH]c(=O)o3)c2-c2cc3cc(C(F)F)nc(NC4CCOc5c(F)cc(F)cc54)c3s2)C23CC(CN12)C3] |
| 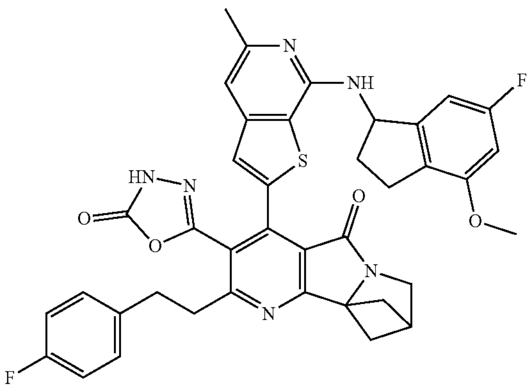 [SMILES: COc1cc(F)cc2c1CCC2Nc1nc(C)cc2cc(-c3c4c(nc(CCc5ccc(F)cc5)c3-c3n[nH]c(=O)o3)C35CC(CN3C4=O)C5)sc12] |

TABLE 2-continued
| Structure |
|---|
| 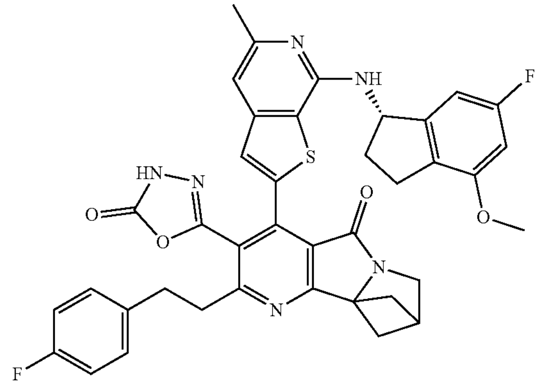 [SMILES: COc1cc(F)cc2c1CC[C@@H]2Nc1nc(C)cc2cc(-c3c4c(nc(CCc5ccc(F)cc5)c3-c3n[nH]c(=O)o3)C35CC(CN3C4=O)C5)sc12] |
| 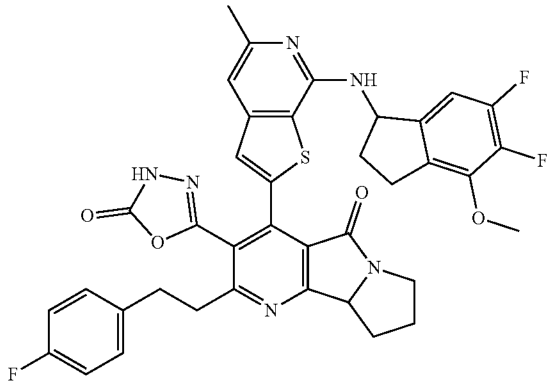 [SMILES: COc1c(F)c(F)cc2c1CCC2Nc1nc(C)cc2cc(-c3c4c(nc(CCc5ccc(F)cc5)c3-c3n[nH]c(=O)o3)C3CCCN3C4=O)sc12] |
| 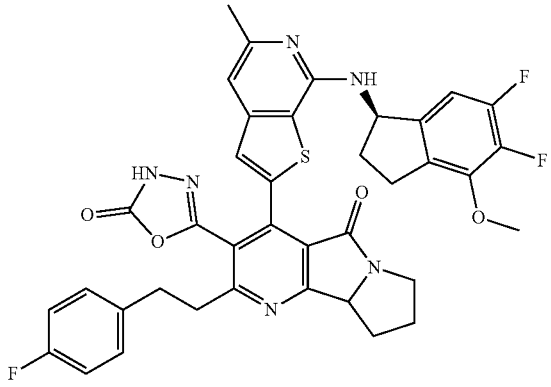 [SMILES: COc1c(F)c(F)cc2c1CC[C@H]2Nc1nc(C)cc2cc(-c3c4c(nc(CCc5ccc(F)cc5)c3-c3n[nH]c(=O)o3)C3CCCN3C4=O)sc12] |
| 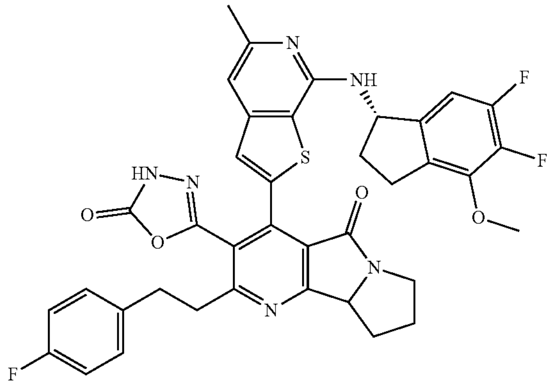 [SMILES: COc1c(F)c(F)cc2c1CC[C@@H]2Nc1nc(C)cc2cc(-c3c4c(nc(CCc5ccc(F)cc5)c3-c3n[nH]c(=O)o3)C3CCCN3C4=O)sc12] |
TABLE 2-continued
| Structure |
|---|
| 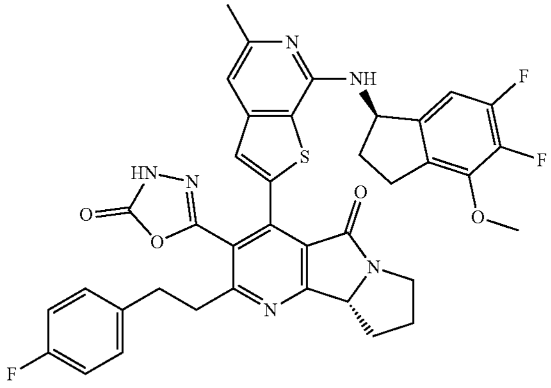 [SMILES: COc1c(F)c(F)cc2c1CC[C@H]2Nc1nc(C)cc2cc(-c3c4c(nc(CCc5ccc(F)cc5)c3-c3n[nH]c(=O)o3)[C@H]3CCCN3C4=O)sc12] |
| 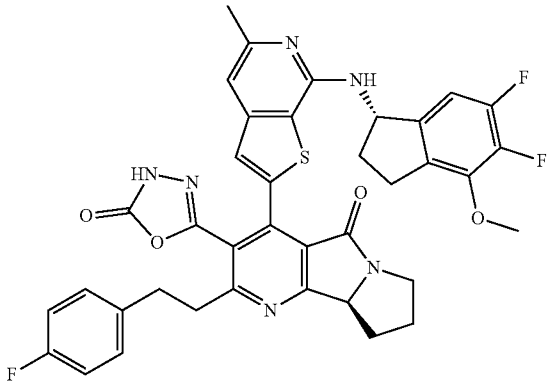 [SMILES: COc1c(F)c(F)cc2c1CC[C@@H]2Nc1nc(C)cc2cc(-c3c4c(nc(CCc5ccc(F)cc5)c3-c3n[nH]c(=O)o3)[C@@H]3CCCN3C4=O)sc12] |
| 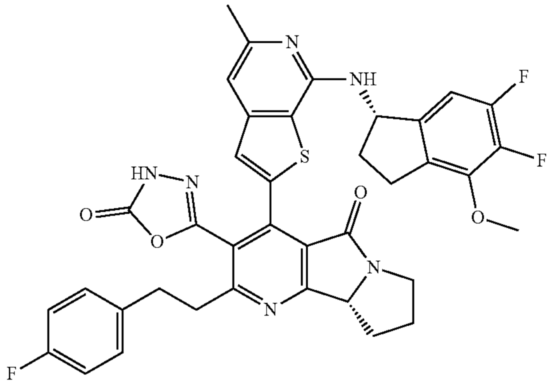 [SMILES: COc1c(F)c(F)cc2c1CC[C@@H]2Nc1nc(C)cc2cc(-c3c4c(nc(CCc5ccc(F)cc5)c3-c3n[nH]c(=O)o3)[C@H]3CCCN3C4=O)sc12] |
| 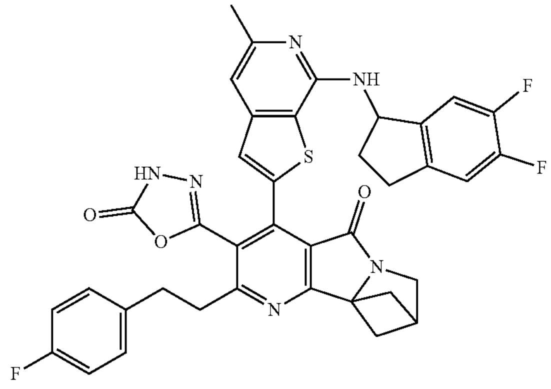 [SMILES: Cc1cc2cc(-c3c4c(nc(CCc5ccc(F)cc5)c3-c3n[nH]c(=O)o3)C35CC(CN3C4=O)C5)sc2c(NC2CCc3cc(F)c(F)cc32)n1] |

TABLE 2-continued
| Structure |
|---|
| 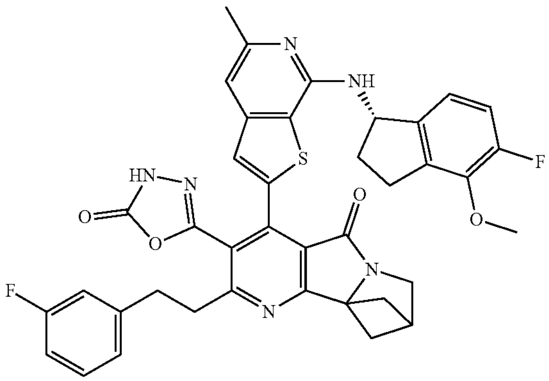 [SMILES: COc1c(F)ccc2c1CC[C@@H]2Nc1nc(C)cc2cc(-c3c4c(nc(CCc5cccc(F)c5)c3-c3n[nH]c(=O)o3)C35CC(CN3C4=O)C5)sc12] |
| 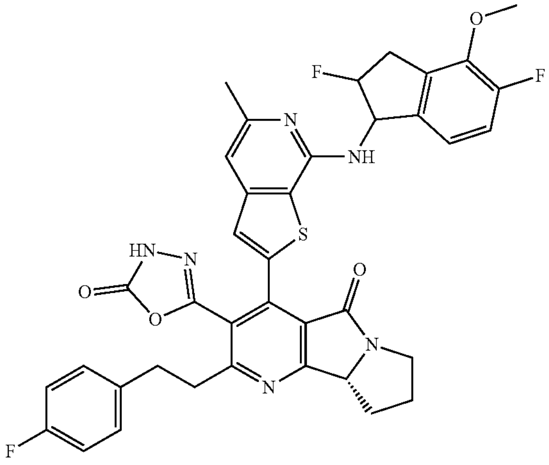 [SMILES: COc1c(F)ccc2c1CC(F)C2Nc1nc(C)cc2cc(-c3c4c(nc(CCc5ccc(F)cc5)c3-c3n[nH]c(=O)o3)[C@H]3CCCN3C4=O)sc12] |
| 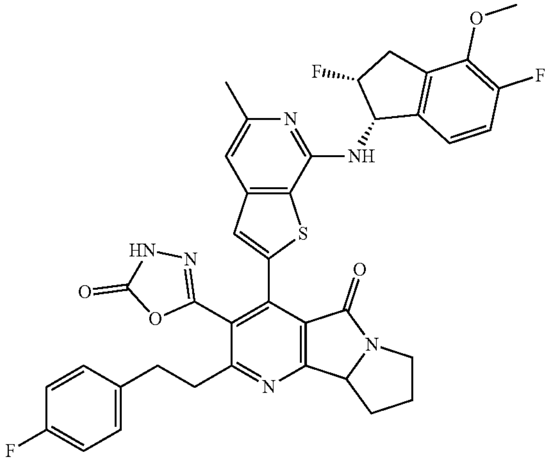 [SMILES: COc1c(F)ccc2c1C[C@@H](F)[C@H]2Nc1nc(C)cc2cc(-c3c4c(nc(CCc5ccc(F)cc5)c3-c3n[nH]c(=O)o3)C3CCCN3C4=O)sc12] |
TABLE 2-continued
| Structure |
|---|
| 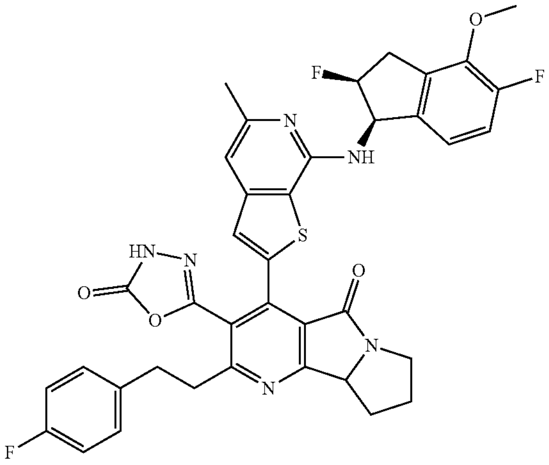 [SMILES: COc1c(F)ccc2c1C[C@H](F)[C@@H]2Nc1nc(C)cc2cc(-c3c4c(nc(CCc5ccc(F)cc5)c3-c3n[nH]c(=O)o3)C3CCCN3C4=O)sc12] |
| 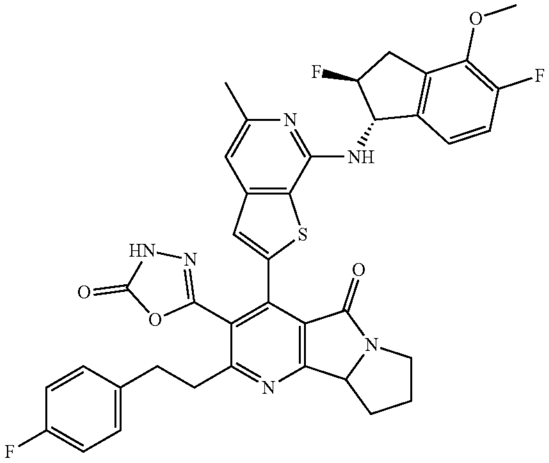 [SMILES: COc1c(F)ccc2c1C[C@H](F)[C@H]2Nc1nc(C)cc2cc(-c3c4c(nc(CCc5ccc(F)cc5)c3-c3n[nH]c(=O)o3)C3CCCN3C4=O)sc12] |
| 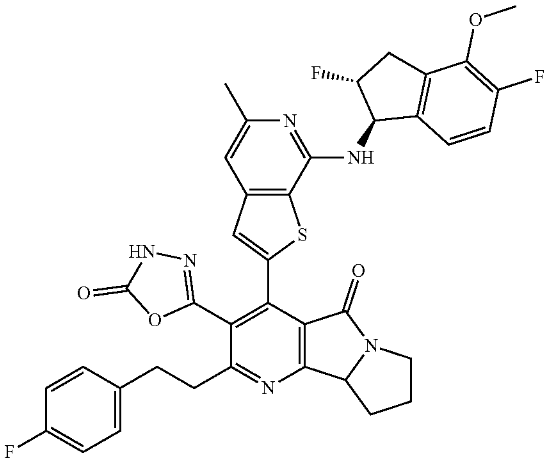 [SMILES: COc1c(F)ccc2c1C[C@@H](F)[C@@H]2Nc1nc(C)cc2cc(-c3c4c(nc(CCc5ccc(F)cc5)c3-c3n[nH]c(=O)o3)C3CCCN3C4=O)sc12] |

TABLE 2-continued
| Structure |
|---|
| 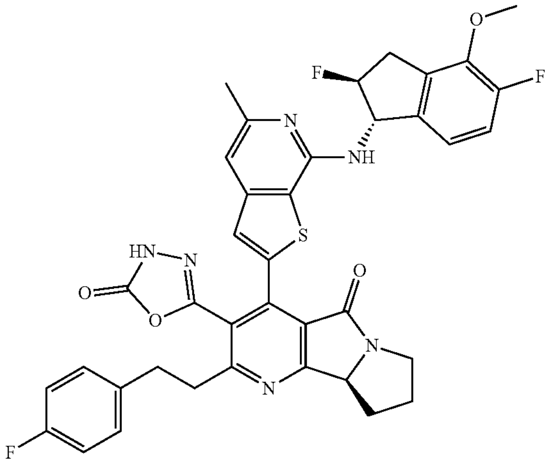 [SMILES: COc1c(F)ccc2c1C[C@H](F)[C@H]2Nc1nc(C)cc2cc(-c3c4c(nc(CCc5ccc(F)cc5)c3-c3n[nH]c(=O)o3)[C@@H]3CCCN3C4=O)sc12] |
| 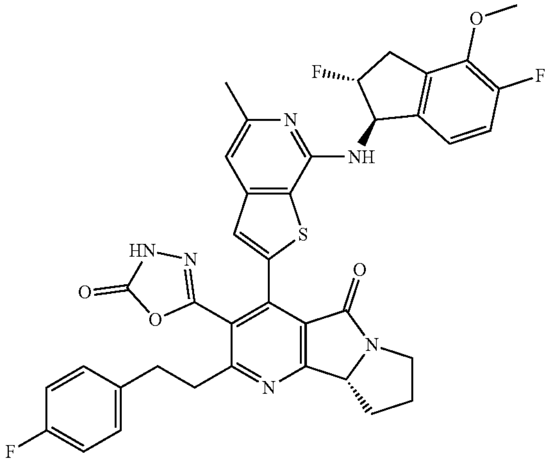 [SMILES: COc1c(F)ccc2c1C[C@@H](F)[C@@H]2Nc1nc(C)cc2cc(-c3c4c(nc(CCc5ccc(F)cc5)c3-c3n[nH]c(=O)o3)[C@H]3CCCN3C4=O)sc12] |
| 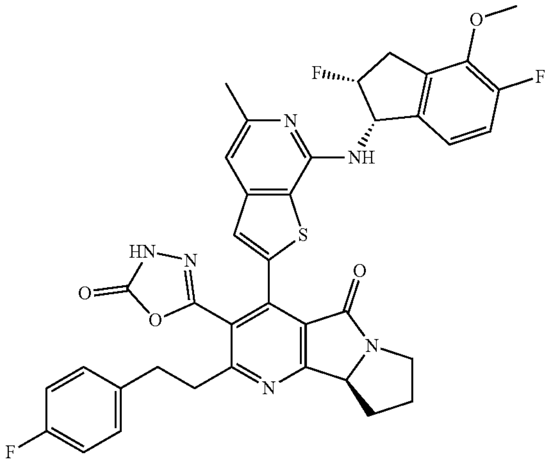 [SMILES: COc1c(F)ccc2c1C[C@@H](F)[C@H]2Nc1nc(C)cc2cc(-c3c4c(nc(CCc5ccc(F)cc5)c3-c3n[nH]c(=O)o3)[C@@H]3CCCN3C4=O)sc12] |
TABLE 2-continued
| Structure |
|---|
| 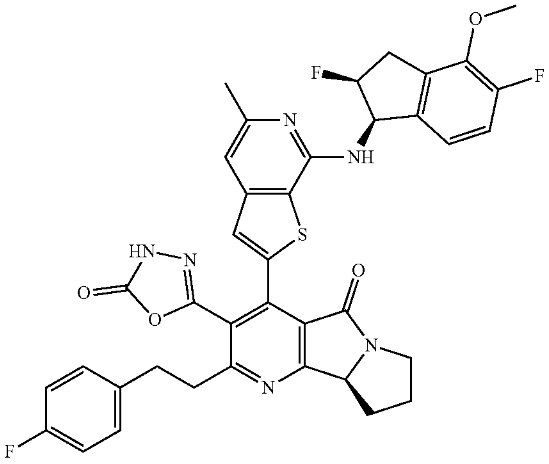 [SMILES: COc1c(F)ccc2c1C[C@H](F)[C@@H]2Nc1nc(C)cc2cc(-c3c4c(nc(CCc5ccc(F)cc5)c3-c3n[nH]c(=O)o3)[C@@H]3CCCN3C4=O)sc12] |
| 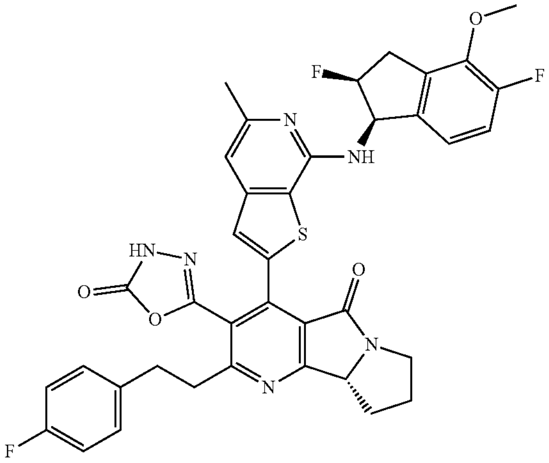 [SMILES: COc1c(F)ccc2c1C[C@H](F)[C@@H]2Nc1nc(C)cc2cc(-c3c4c(nc(CCc5ccc(F)cc5)c3-c3n[nH]c(=O)o3)[C@H]3CCCN3C4=O)sc12] |
| 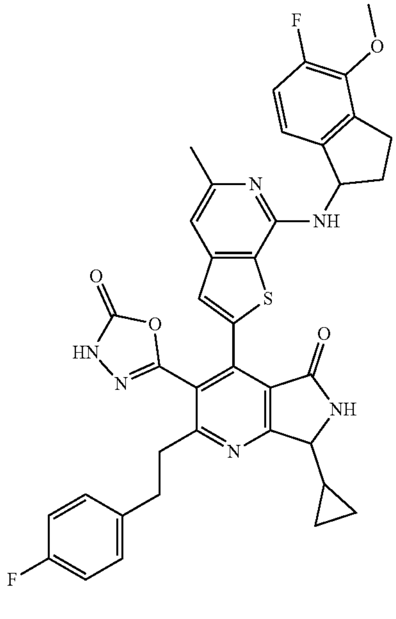 [SMILES: COc1c(F)ccc2c1CCC2Nc1nc(C)cc2cc(-c3c4c(nc(CCc5ccc(F)cc5)c3-c3n[nH]c(=O)o3)C(C3CC3)NC4=O)sc12] |

TABLE 2-continued
| Structure |
| --- |
| 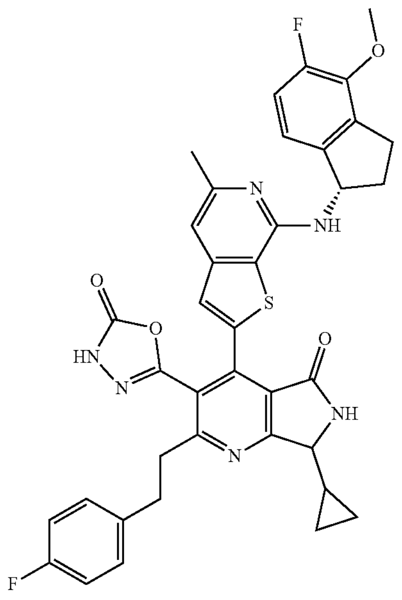 [SMILES: COc1c(F)ccc2c1CC[C@@H]2Nc1nc(C)cc2cc(-c3c4c(nc(CCc5ccc(F)cc5)c3-c3n[nH]c(=O)o3)C(C3CC3)NC4=O)sc12] |
| 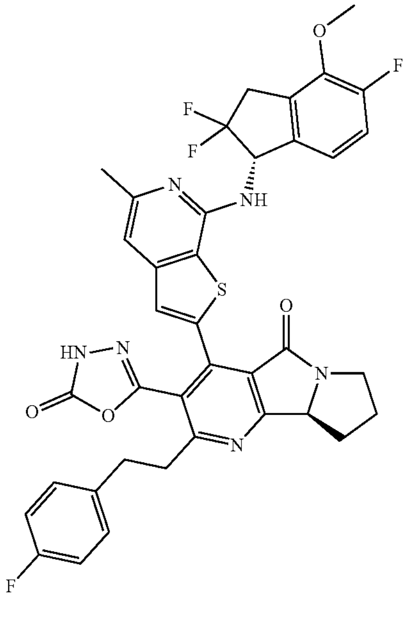 [SMILES: COc1c(F)ccc2c1CC(F)(F)[C@H]2Nc1nc(C)cc2cc(-c3c4c(nc(CCc5ccc(F)cc5)c3-c3n[nH]c(=O)o3)[C@@H]3CCCN3C4=O)sc12] |
TABLE 2-continued
| Structure |
| --- |
| 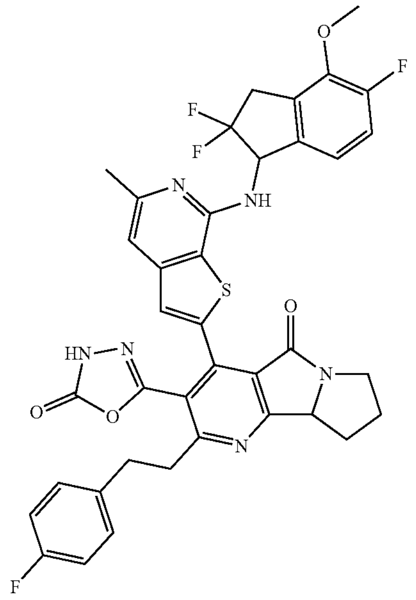 [SMILES: COc1c(F)ccc2c1CC(F)(F)C2Nc1nc(C)cc2cc(-c3c4c(nc(CCc5ccc(F)cc5)c3-c3n[nH]c(=O)o3)C3CCCN3C4=O)sc12] |
| 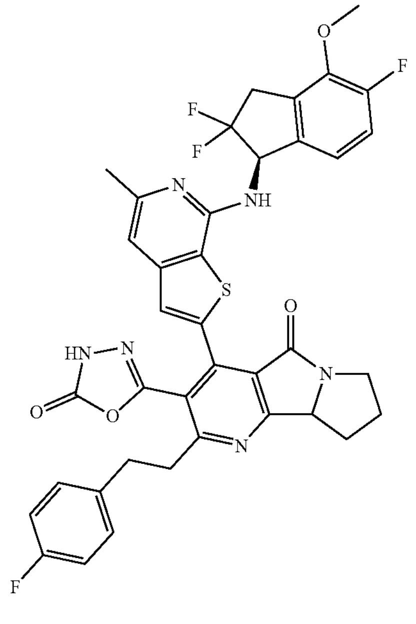 [SMILES: COc1c(F)ccc2c1CC(F)(F)[C@@H]2Nc1nc(C)cc2cc(-c3c4c(nc(CCc5ccc(F)cc5)c3-c3n[nH]c(=O)o3)C3CCCN3C4=O)sc12] |

TABLE 2-continued

| Structure |
| --- |
| 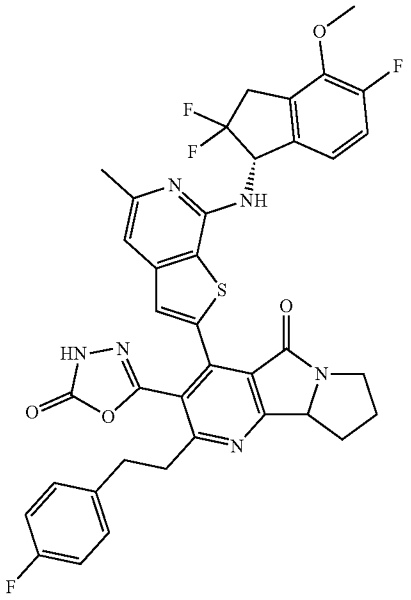 [SMILES: COc1c(F)ccc2c1CC(F)(F)[C@H]2Nc1nc(C)cc2cc(-c3c4c(nc(CCc5ccc(F)cc5)c3-c3n[nH]c(=O)o3)C3CCCN3C4=O)sc12] |
| 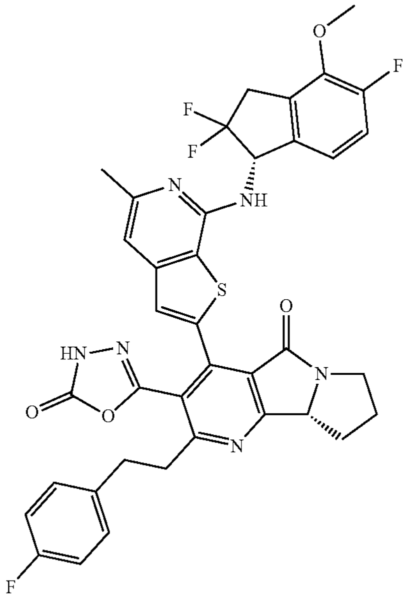 [SMILES: COc1c(F)ccc2c1CC(F)(F)[C@H]2Nc1nc(C)cc2cc(-c3c4c(nc(CCc5ccc(F)cc5)c3-c3n[nH]c(=O)o3)[C@H]3CCCN3C4=O)sc12] |

TABLE 2-continued

| Structure |
| --- |
| 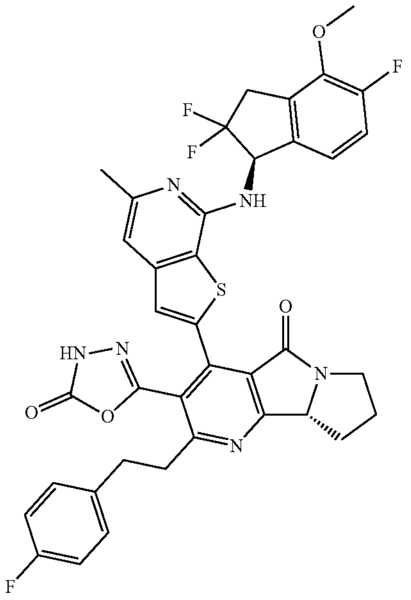 [SMILES: COc1c(F)ccc2c1CC(F)(F)[C@@H]2Nc1nc(C)cc2cc(-c3c4c(nc(CCc5ccc(F)cc5)c3-c3n[nH]c(=O)o3)[C@H]3CCCN3C4=O)sc12] |
| 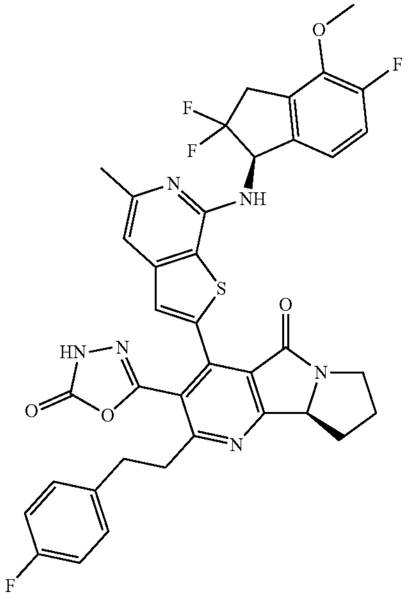 [SMILES: COc1c(F)ccc2c1CC(F)(F)[C@@H]2Nc1nc(C)cc2cc(-c3c4c(nc(CCc5ccc(F)cc5)c3-c3n[nH]c(=O)o3)[C@@H]3CCCN3C4=O)sc12] |

The compounds of Formula I and subformulas thereof include pharmaceutically acceptable salts thereof. In addition, the compounds of Formula I and subformulas thereof also include other salts of such compounds which are not necessarily pharmaceutically acceptable salts, and which may be useful as intermediates for preparing and/or purifying compounds of Formula I and subformulas thereof and/or for separating enantiomers of compounds of Formula I and subformulas thereof.

It will further be appreciated that the compounds of Formula I and subformulas or their salts may be isolated in the form of solvates, and accordingly that any such solvate is included within the scope of the present disclosure. For example, compounds of Formula I and subformulas thereof and salts of each thereof can exist in unsolvated as well as solvated forms with pharmaceutically acceptable solvents such as water, ethanol, and the like.

Pharmaceutical Compositions and Administration

When employed as pharmaceuticals, compounds as described herein (e.g., one or more compounds as disclosed herein, or a stereoisomer or mixture of stereoisomers thereof) can be administered in the form of a pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, one or more compounds as disclosed herein, or a stereoisomer or mixture of stereoisomers thereof, in combination with one or more pharmaceutically acceptable excipients (carriers). For example, a pharmaceutical composition prepared using one or more compounds as disclosed herein, or a stereoisomer or mixture of stereoisomers thereof.

In one embodiment, provided is a pharmaceutical composition comprising a compound, or a stereoisomer or mixture of stereoisomers thereof, or pharmaceutically acceptable salt thereof, as disclosed herein, and a pharmaceutically acceptable excipient. In one embodiment, provided is a pharmaceutical composition comprising a compound, or a stereoisomer or mixture of stereoisomers thereof, or pharmaceutically acceptable salt thereof, as disclosed herein, and a pharmaceutically acceptable excipient, wherein a compound, or a stereoisomer or mixture of stereoisomers thereof, or pharmaceutically acceptable salt thereof, is present in the pharmaceutical composition in an amount greater than about 0.1%, greater than about 1%, greater than about 5%, greater than about 10%, greater than about 15%, greater than about 20%, greater than about 25%, greater than about 35%, or greater than about 40%, or greater than about 45%, or greater than about 50%, or greater than about 55%, or greater than about 60%, or greater than about 65%, or greater than about 70%, or greater than about 75%, or greater than about 80%, or greater than about 85%, or greater than about 90%, or greater than about 95% purity, or about 40%, or about 45%, or about 50%, or about 55%, or about 60%, or about 65%, or about 70%, or about 75%, or about 80%, or about 85%, or about 90%, or about 95%, by weight.

In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing one or more compounds as disclosed herein, or a stereoisomer or mixture of stereoisomers thereof with a pharmaceutically acceptable excipient. Pharmaceutical compositions containing one or more compounds as disclosed herein, or a stereoisomer or mixture of stereoisomers thereof as the active ingredient can be prepared by intimately mixing one or more compounds as disclosed herein, or a stereoisomer or mixture of stereoisomers thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in The Handbook of Pharmaceutical Excipients, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

In some embodiments, the compound or pharmaceutical composition can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22nd Edition (Pharmaceutical Press, London, U K. 2012).

In some embodiments, the compounds and pharmaceutical compositions described herein or a pharmaceutical composition thereof can be administered to patient in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal (e.g., intranasal), nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In some embodiments, a route of administration is parenteral (e.g., intratumoral).

In some embodiments, one or more compounds as disclosed herein, or a stereoisomer or mixture of stereoisomers thereof as described herein or pharmaceutical compositions thereof can be formulated for parenteral administration, e.g., formulated for injection via the intraarterial, intrasternal, intracranial, intravenous, intramuscular, sub-cutaneous, or intraperitoneal routes. For example, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure. In some embodiments, devices are used for parenteral administration. For example, such devices may include needle injectors, microneedle injectors, needle-free injectors, and infusion techniques.

In some embodiments, the pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In some embodiments, the form must be sterile and must be fluid to the extent that it may be easily injected. In some embodiments, the form should be stable under the conditions of manufacture and storage and must be preserved against the contaminating action of microorganisms, such as bacteria and fungi.

In some embodiments, the carrier also can be a solvent or dispersion medium containing, for example, water, ethanol, polyol (for example, glycerol, propylene glycol, and liquid polyethylene glycol, and the like), suitable mixtures thereof, and vegetable oils. In some embodiments, the proper fluidity can be maintained, for example, by the use of a coating, such as lecithin, by the maintenance of the required particle size in the case of dispersion, and by the use of surfactants. In some embodiments, the prevention of the action of microorganisms can be brought about by various antibacterial and antifungal agents, for example, parabens, chlorobutanol, phenol, sorbic acid, thimerosal, and the like. In some embodiments, isotonic agents, for example, sugars or sodium chloride are included. In some embodiments, prolonged absorption of the injectable compositions can be brought about by the use in the compositions of agents delaying absorption, for example, aluminum monostearate and gelatin.

In some embodiments, sterile injectable solutions are prepared by incorporating one or more compounds as disclosed herein, or a stereoisomer or mixture of stereoisomers thereof in the required amount in the appropriate solvent with various of the other ingredients enumerated above, as required, followed by filtered sterilization. In some embodiments, dispersions are prepared by incorporating the various sterilized active ingredients into a sterile vehicle which contains the basic dispersion medium and the required other ingredients from those enumerated above. In some embodiments, sterile powders are used for the preparation of sterile injectable solutions. In some embodiments, the methods of preparation are vacuum-drying and freeze-drying techniques, which yield a powder of the active ingredient, plus any additional desired ingredient from a previously sterile-filtered solution thereof.

In some embodiments, pharmacologically acceptable excipients usable in a rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol, Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In some embodiments, suppositories can be prepared by mixing one or more compounds as disclosed herein, or a stereoisomer or mixture of stereoisomers thereof, or pharmaceutical compositions as described herein with suitable non-irritating excipients or carriers such as cocoa butter, polyethylene glycol or a suppository wax which are solid at ambient temperature but liquid at body temperature and therefore melt in the rectum and release the active compound. In some embodiments, compositions for rectal administration are in the form of an enema.

In some embodiments, one or more compounds as disclosed herein, or a stereoisomer or mixture of stereoisomers thereof, as described herein or a pharmaceutical composition thereof is formulated for local delivery to the digestive or GI tract by way of oral administration (e.g., solid or liquid dosage forms).

In some embodiments, solid dosage forms for oral administration include capsules, tablets, pills, powders, and granules. In some embodiments, one or more compounds as disclosed herein, or a stereoisomer or mixture of stereoisomers thereof, is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For example, in the case of capsules, tablets and pills, the dosage form may also comprise buffering agents. In some embodiments, solid compositions of a similar type may also be employed as fillers in soft and hard-filled gelatin capsules using such excipients as lactose or milk sugar as well as high molecular weight polyethylene glycols and the like.

In some embodiments, the pharmaceutical compositions will take the form of a unit dosage form such as a pill or tablet and thus the composition may contain, along with one or more compounds as disclosed herein, or a stereoisomer or mixture of stereoisomers thereof as provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In some embodiments, another solid dosage form, a powder, marume, solution or suspension (e.g., in propylene carbonate, vegetable oils, PEG's, poloxamer 124 or triglycerides) is encapsulated in a capsule (gelatin or cellulose base capsule). In some embodiments, unit dosage forms in which one or more compounds and pharmaceutical compositions as provided herein or additional active agents are physically separated are also contemplated; e.g., capsules with granules (or tablets in a capsule) of each drug; two-layer tablets; two-compartment gel caps, etc. In some embodiments, enteric coated or delayed release oral dosage forms are also contemplated.

In some embodiments, other physiologically acceptable compounds may include wetting agents, emulsifying agents, dispersing agents or preservatives that are particularly useful for preventing the growth or action of microorganisms. For example, various preservatives are well known and include, for example, phenol and ascorbic acid.

In some embodiments, the excipients are sterile and generally free of undesirable matter. For example, these compositions can be sterilized by conventional, well-known sterilization techniques. In some embodiments, for various oral dosage form excipients such as tablets and capsules, sterility is not required. For example, the United States Pharmacopeia/National Formulary (USP/NF) standard can be sufficient.

In some embodiments, one or more compounds as disclosed herein, or a stereoisomer or mixture of stereoisomers thereof as described herein or a pharmaceutical composition thereof is formulated for ocular administration. In some embodiments, ocular compositions can include, without limitation, one or more of any of the following: viscogens (e.g., carboxymethylcellulose, glycerin, polyvinylpyrrolidone, polyethylene glycol); stabilizers (e.g., Pluronic (triblock copolymers), cyclodextrins); preservatives (e.g., benzalkonium chloride, EDTA, SofZia (boric acid, propylene glycol, sorbitol, and zinc chloride; Alcon Laboratories, Inc.), Purite (stabilized oxychloro complex; Allergan, Inc.).

In some embodiments, one or more compounds as disclosed herein, or a stereoisomer or mixture of stereoisomers thereof as described herein or a pharmaceutical composition thereof is formulated for topical administration to the skin or mucosa (e.g., dermally or transdermally). In some embodiments, topical compositions can include ointments and creams. In some embodiments, ointments are semisolid preparations that are typically based on petrolatum or other petroleum derivatives. In some embodiments, creams containing the selected active agent are typically viscous liquid or semisolid emulsions, often either oil-in-water or water-in-oil. For example, cream bases are typically water-washable, and contain an oil phase, an emulsifier and an aqueous phase. For example, the oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. In some embodiments, the emulsifier in a cream formulation is generally a nonionic, anionic, cationic or amphoteric surfactant. In some embodiments, as with other carriers or vehicles, an ointment base should be inert, stable, nonirritating and non-sensitizing.

In any of the foregoing embodiments, pharmaceutical compositions as described herein can include one or more one or more of the following: lipids, interbilayer crosslinked multilamellar vesicles, biodegradable poly(D,L-lactic-co-glycolic acid) (PLGA)-based or poly anhydride-based nanoparticles or microparticles, and nanoporous particle-supported lipid bilayers.

The amount of the compound in a pharmaceutical composition or formulation can vary within the full range employed by those skilled in the art. Typically, the formulation will contain, on a weight percent (wt %) basis, from about 0.01-99.99 wt % of a compound of this disclosure based on the total formulation, with the balance being one or more suitable pharmaceutical excipients. In one embodiment, the compound is present at a level of about 1-80 wt %. Representative pharmaceutical formulations are described below.

Formulation Example 1—Tablet Formulation

The following ingredients are mixed intimately and pressed into single scored tablets.

| Ingredient | Quantity per tablet, mg |
| --- | --- |
| compound of this disclosure | 400 |
| cornstarch | 50 |
| croscarmellose sodium | 25 |
| lactose | 120 |
| magnesium stearate | 5 |

Formulation Example 2—Capsule Formulation

| The following ingredients are mixed intimately and loaded into a hard-shell gelatin capsule | |
|---|---|
| Ingredient | Quantity per capsule, mg |
| compound of this disclosure | 200 |
| lactose, spray-dried | 148 |
| magnesium stearate | 2 |

Formulation Example 3—Suspension Formulation

| The following ingredients are mixed to form a suspension for oral administration. | |
|---|---|
| Ingredient | Amount |
| compound of this disclosure | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| coloring | 0.5 mg |
| distilled water | q.s. to 100 mL |

Formulation Example 4—Injectable Formulation

| The following ingredients are mixed to form an injectable formulation. | |
|---|---|
| Ingredient | Amount |
| compound of this disclosure | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5—Suppository Formulation

| A suppository of total weight 2.5 g is prepared by mixing the compound of this disclosure with Witepsol ® H-15 (triglycerides of saturated vegetable fatty acid; Riches-Nelson, Inc., New York), and has the following composition: | |
|---|---|
| Ingredient | Amount |
| compound of this disclosure | 500 mg |
| Witepsol ® H-15 | balance |

In some embodiments, the dosage for one or more compounds as disclosed herein, or a stereoisomer or mixture of stereoisomers thereof, is determined based on a multiple factors including, but not limited to, type, age, weight, sex, medical condition of the patient, severity of the medical condition of the patient, route of administration, and activity of the compound or pharmaceutically acceptable s salt, stereoisomer, mixture of stereoisomers, or solvate thereof. In some embodiments, proper dosage for a particular situation can be determined by one skilled in the medical arts. In some embodiments, the total daily dosage may be divided and administered in portions throughout the day or by means providing continuous delivery.

In some embodiments, one or more compounds as disclosed herein, or a stereoisomer or mixture of stereoisomers thereof, is administered at a dose from about 0.01 to about 1000 mg. For example, from about 0.1 to about 30 mg, about 10 to about 80 mg, about 0.5 to about 15 mg, about 50 mg to about 200 mg, about 100 mg to about 300 mg, about 200 to about 400 mg, about 300 mg to about 500 mg, about 400 mg to about 600 mg, about 500 mg to about 800 mg, about 600 mg to about 900 mg, or about 700 mg to about 1000 mg. In some embodiments, the dose is a therapeutically effective amount.

In some embodiments, one or more compounds as disclosed herein, or a stereoisomer or mixture of stereoisomers thereof as described herein is administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg). In some embodiments, one or more compounds as disclosed herein, or a stereoisomer or mixture of stereoisomers thereof as described herein is administered as a dosage of about 100 mg/Kg.

In some embodiments, the foregoing dosages of one or more compounds as disclosed herein, or a stereoisomer or mixture of stereoisomers thereof, can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of one or more compounds as disclosed herein, or a stereoisomer or mixture of stereoisomers thereof as described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, one or more compounds as disclosed herein, or a stereoisomer or mixture of stereoisomers thereof is administered to a patient for a period of time followed by a separate period of time where administration of one or more compounds as disclosed herein, or a stereoisomer or mixture of stereoisomers thereof is stopped. In some embodiments, one or more compounds as disclosed herein, or a stereoisomer or mixture of stereoisomers thereof is administered for a first period and a second period following the first period, with administration stopped during the second period, followed by a third period where administration of one or more compounds as disclosed herein, or a stereoisomer or mixture of stereoisomers thereof is started and then a fourth period following the third period where administration is stopped. For example, the period of administration of one or more compounds as disclosed herein, or a stereoisomer or mixture of stereoisomers thereof followed by a period where administration is stopped is repeated for a determined or undetermined period of time. In some embodiments, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In some embodiments, one or more compounds as disclosed herein, or a stereoisomer or mixture of stereoisomers thereof, is orally administered to the patient one or more times per day (e.g., one time per day, two times per day, three times per day, four times per day per day or a single daily dose).

In some embodiments, one or more compounds as disclosed herein, or a stereoisomer or mixture of stereoisomers thereof, is administered by parenteral administration to the patient one or more times per day (e.g., 1 to 4 times, one time per day, two times per day, three times per day, four times per day or a single daily dose).

In some embodiments, one or more compounds as disclosed herein, or a stereoisomer or mixture of stereoisomers thereof, is administered by parenteral administration to the patient weekly.

Methods of Treatment

In some embodiments, this disclosure provides methods for treating a subject (e.g., a human) having a disease, disorder, or condition in which inhibition of one or more calcitonin receptor and/or amylin receptor is beneficial for the treatment of the underlying pathology and/or symptoms and/or progression of the disease, disorder, or condition. In some embodiments, the methods provided herein can include treating one or more conditions associated, co-morbid or sequela with any one or more of the conditions provided herein.

Provided herein is a method for treating a calcitonin receptor and/or an amylin receptor associated disease or disorder, the method comprising administering to a subject in need thereof an effective amount of a compound disclosed herein (e.g., a compound of Formula I, or any subformula thereof or a pharmaceutically acceptable salt, stereoisomer, mixture of stereoisomers, or solvate thereof), or a pharmaceutical composition as disclosed herein. Also provided herein are methods for treating or preventing a calcitonin receptor and/or an amylin receptor associated disease or disorder in a subject in need thereof, the method comprising administering to a subject in need thereof a therapeutically effective amount of a compound disclosed herein (e.g., a compound of Formula I or any subformula thereof, or a pharmaceutically acceptable salt, stereoisomer, mixture of stereoisomers, or solvate thereof), or a pharmaceutical composition thereof.

In some embodiments, the calcitonin receptor and/or amylin receptor associated disease or disorder is a bone disorder, a metabolic disorder, pain, a neurodegenerative disease or disorder, a cardiovascular disease, or other disease or disorder as described herein.

In some embodiments, the disease or disorder includes, but is not limited to type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, and Polycystic Ovary Syndrome (PCOS).

In some embodiments, the disease or disorder includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof.

In some embodiments, the disease or disorder includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

In some embodiments, the compounds and pharmaceutical compositions and methods for treating a patient described herein induce one or more of blood glucose reduction (e.g., reduce blood glucose levels), reduce blood hemoglobin A1c (HbA1c) levels, promote insulin synthesis, stimulate insulin secretion, increase the mass of β-cells, modulate gastric acid secretion, modulate gastric emptying, decrease the body mass index (BMI), and/or decrease glucagon production (e.g., level). In certain embodiments, the compounds and pharmaceutical compositions and methods for treating a patient described herein stabilize serum glucose and serum insulin levels (e.g., serum glucose and serum insulin concentrations). Also provided herein are methods for modulating glucose or insulin levels in a patient in need of such modulating, the method comprising administering to the patient an effective amount of one or more compounds as disclosed herein, or a stereoisomer or mixture of stereoisomers thereof, or a pharmaceutical composition as disclosed herein.

In some embodiments, provided herein is a method for reducing the risk (e.g., by about at least 20%, at least 30%, at least 40%, at least 50%, at least 60%, at least 70%, or at least 80%) of major adverse cardiovascular events (MACE) in a patient in need thereof, the method comprising administering to the patient an effective amount of one or more compounds as disclosed herein, or a stereoisomer or mixture of stereoisomers thereof, or a pharmaceutical composition as disclosed herein. In certain of these embodiments, the patient is an adult that has been diagnosed with type 2 diabetes (T2D). In certain embodiments, the patient is an adult that has been diagnosed with a heart disease. In certain embodiments, the patient is an adult that has been diagnosed with type 2 diabetes (T2D) and a heart disease. In certain embodiments, the patient is an adult that has type 2 diabetes (T2D). In certain embodiments, the patient is an adult that has a heart disease. In certain embodiments, the patient has type 2 diabetes (T2D) and a heart disease.

In some embodiments, the calcitonin receptor and/or amylin receptor associated disease or disorder is a bone disorder, including, but not limited to, osteoporosis, Paget's disease, hypercalcemia, Sudeck's atrophy, polystatic fibrous displasia, intersemocostoclavicular ossification, osteogenesis imperfecta, osteopenia, periodontal disease or defect, osteolytic bone disease, metastatic bone disorder, or bone loss resulting from a malignancy, autoimmune arthritides, a breakage or fracture, or immobility or disuse.

In some embodiments, the calcitonin receptor and/or amylin receptor associated disease or disorder is pain, including, but not limited to, osteopathic pain, phantom limb pain, general pain, hyperalgesia, or pain associated with diabetic neuropathy.

In some embodiments, the calcitonin receptor and/or amylin receptor associated disease or disorder is a neurodegenerative disease or disorder, including, but not limited to, Alzheimer's disease.

In some embodiments, the calcitonin receptor and/or amylin receptor associated disease or disorder is a metabolic disorder, including, but not limited to, non-alcoholic fatty liver disease (NAFLD), non-alcoholic steatohepatitis (NASH), insulin dependent diabetes, non-insulin dependent diabetes, impaired glucose tolerance, obesity, syndrome X, or other diabetic complication.

In some embodiments, the calcitonin receptor and/or amylin receptor associated disease or disorder is include primary or secondary hyperthyroidism, endocrine disorder, conditions associated with inhibiting gastric secretion, gastrointestinal disorders, renal osteodystrophy, or male infertility.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to alleviate insulin suppression in pancreatic tissue.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to treat alleviate insulin resistance.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to treat impaired glucose tolerance.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to treat obesity and symptoms thereof.

In some embodiments, provided is a method for reducing body fat or body fat gain, comprising administering to a subject in need thereof a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, provided is a method of altering a body composition of a subject in need of treatment, wherein body fat is reduced and lean body mass is maintained or increased, comprising administering to the subject a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, provided is a method for reducing body weight in a subject in need of, comprising administering to the subject a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, provided is a method for reducing caloric intake in a subject in need of reduction thereof, comprising administering to the subject a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, provided is a method for reducing body fat or body fat gain in a subject in need of treatment while maintaining or increasing lean body mass, comprising administering to the subject a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to treat hypertension.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to treat essential hypertension.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to treat a subject suffering from hypertension and hyperamylinemia.

In some embodiments, provided is a method for treating hyperinsulinemia, comprising administering to a subject in need thereof a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, provided is a method for treating a hypertensive, insulin-resistant subject suffering from coronary artery disease and having hyperamylinemia or hyperinsulinemia, comprising administering to a subject in need thereof a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, provided is a method for decreasing basal and submaximally stimulated rates of glycogen synthesis in a subject, comprising administering to a subject in need thereof a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, provided is a method for decreasing the rate of incorporation of glucose into glycogen in muscle tissue of a subject, comprising administering to a subject in need thereof a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, provided is a method for treating obesity and hypertension, and the lipid disorders and atherosclerosis associated therewith, in a subject, comprising administering to a subject in need thereof a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to modulate renin activity in a subject in need thereof.

In some embodiments, provided is a method for treating or preventing the development of cardiac failure, in a subject, comprising administering to a subject in need thereof a therapeutically effective amount of a compound disclosed herein (e.g., a compound of Formula I, or a pharmaceutically acceptable salt, stereoisomer, mixture of stereoisomers, or solvate thereof), or a pharmaceutical composition as provided herein.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to beneficially regulate gastrointestinal motility in a subject in need thereof. In some embodiments, the beneficial regulation of gastrointestinal motility comprises delaying gastric emptying.

In some embodiments, a compound disclosed herein (e.g., a compound of Formula I, or a pharmaceutically acceptable salt, stereoisomer, mixture of stereoisomers, or solvate thereof), or a pharmaceutical composition as provided herein is useful to treat postprandial hyperglycemia in a subject in need thereof.

Obesity

In some embodiments, the condition, disease or disorder is obesity and conditions, diseases or disorders that are associated with or related to obesity. Non-limiting examples of obesity and obesity related conditions include symptomatic obesity, simple obesity, childhood obesity, morbid obesity, and abdominal obesity (central obesity characterized by abdominal adiposity). Non-limiting examples of symptomatic obesity include endocrine obesity (e.g., Cushing syndrome, hypothyroidism, insulinoma, obese type II diabetes, pseudohypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or β-blocker-induced obesity).

In some embodiments, the condition, disease or disorder is associated with obesity. Examples of such conditions, diseases or disorders include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catamenial symptom), visceral obesity syndrome, and metabolic syndrome. In some embodiments, the chemical compound and pharmaceutical compositions described herein can be used to treat patients exhibiting symptoms of both obesity and insulin deficiency.

Diabetes

In some embodiments, the condition, disease or disorder is diabetes. Non-limiting examples of diabetes include type 1 diabetes mellitus, type 2 diabetes mellitus (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes. In some embodiments, the condition, disease or disorder is type 2 diabetes mellitus (e.g., diet-treated type 2-diabetes, sulfonylurea-treated type 2-diabetes, a far-advanced stage type 2-diabetes, long-term insulin-treated type 2-diabetes).

Provided herein is a method of treating a diabetes mellitus in a patient, the method comprising (a) determining that the patient has type 2 diabetes mellitus, and (b) administering to the patient a therapeutically effective amount of one or more compounds as disclosed herein, or a stereoisomer or mixture of stereoisomers thereof, or a pharmaceutical composition as disclosed herein.

Provided herein is a method for treating type 2 diabetes mellitus in a patient, the method comprising administering to a patient identified or diagnosed as having type 2 diabetes mellitus a therapeutically effective amount of one or more compounds as disclosed herein, or a stereoisomer or mixture of stereoisomers thereof, or a pharmaceutical composition as disclosed herein.

Also provided herein is a method of treating type 2 diabetes mellitus in a patient in need thereof, the method comprising administering to the patient a therapeutically effective amount of one or more compounds as disclosed herein, or a stereoisomer or mixture of stereoisomers thereof, or a pharmaceutical composition as disclosed herein.

In some embodiments, the compounds and pharmaceutical compositions and methods for treating a patient with a condition, disease, or disorder (e.g., type 2 diabetes mellitus) described herein reduce fasting plasma glucose levels. In some embodiments, the compounds and pharmaceutical compositions and methods for treating a patient with a condition, disease, or disorder (e.g., type 2 diabetes mellitus) described herein reduce non-fasting plasma glucose levels. In some embodiments, the compounds and pharmaceutical compositions and methods for treating a patient with a condition, disease, or disorder (e.g., type 2 diabetes mellitus) described herein reduce HbA1c levels. In some embodiments, the compounds and pharmaceutical compositions and methods for treating a patient with a condition, disease, or disorder (e.g., type 2 diabetes mellitus) described herein reduce glucagon levels. In some embodiments, the compounds and pharmaceutical compositions and methods for treating a patient with a condition, disease, or disorder (e.g., type 2 diabetes mellitus) described herein increase insulin levels. In some embodiments, the compounds and pharmaceutical compositions and methods for treating a patient with a condition, disease, or disorder (e.g., type 2 diabetes mellitus) described herein reduce BMI.

In some embodiments, a reduction in fasting plasma glucose levels of about 5% to about 95% indicates treatment of type 2 diabetes mellitus. In some embodiments, a reduction in fasting plasma glucose levels of about 15% to about 80% indicates treatment of type 2 diabetes mellitus. In some embodiments, a reduction in fasting plasma glucose levels of about 25% to about 60% indicates treatment of type 2 diabetes mellitus. In some embodiments, a reduction in fasting plasma glucose levels to about or below 126 mg/dL, about or below 110 mg/dL, or about or below 90 mg/dL indicates treatment of the type 2 diabetes mellitus.

In some embodiments, a reduction in non-fasting plasma glucose levels of about 5% to about 95% indicates treatment of type 2 diabetes mellitus. In some embodiments, a reduction in non-fasting plasma glucose levels of about 15% to about 80% indicates treatment of type 2 diabetes mellitus. In some embodiments, a reduction in non-fasting plasma glucose levels of about 25% to about 60% indicates treatment of type 2 diabetes mellitus. In some embodiments, a reduction in non-fasting plasma glucose levels to about or below 200 mg/dL, about or below 150 mg/dL, or about or below 130 mg/dL indicates treatment of type 2 diabetes mellitus.

In some embodiments, a reduction in HbA1c levels of about 5% to about 95% indicates treatment of type 2 diabetes mellitus. In some embodiments, a reduction in HbA1c levels of about 15% to about 80% indicates treatment of type 2 diabetes mellitus. In some embodiments, a reduction in HbA1c levels of about 25% to about 60% indicates treatment of type 2 diabetes mellitus. In some embodiments, reduction in HbA1c levels to about or below 6.5%, about or below 6.0%, or about or below 5.0% indicates treatment of type 2 diabetes mellitus.

In some embodiments, a reduction in glucagon levels of about 5% to about 95% indicates treatment of type 2 diabetes mellitus. In some embodiments, a reduction in glucagon levels of about 15% to about 80% indicates treatment of type 2 diabetes mellitus. In some embodiments, a reduction in glucagon levels of about 25% to about 60% indicates treatment of type 2 diabetes mellitus. In some embodiments, an increase in insulin levels of about 5% to about 95% indicates treatment of type 2 diabetes mellitus. In some embodiments, an increase in insulin levels of about 15% to about 80% indicates treatment of type 2 diabetes mellitus. In some embodiments, an increase in insulin levels of about 25% to about 60% indicates treatment of type 2 diabetes mellitus.

In some embodiments, a reduction in BMI of about 5% to about 95% indicates treatment of type 2 diabetes mellitus. In some embodiments, a reduction in BMI of about 15% to about 80% indicates treatment of the type 2 diabetes mellitus. In some embodiments, a reduction in BMI of about 25% to about 60% indicates treatment of type 2 diabetes mellitus. In some embodiments, a reduction in BMI of about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of type 2 diabetes mellitus. In some embodiments, a reduction in BMI to about or below 40, about or below 30, or about or below 20 indicates treatment of type 2 diabetes mellitus.

In some embodiments, the condition, disease or disorder is associated with diabetes (e.g., a complication of diabetes). Non-limiting examples of disorders associated with diabetes include obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors. (e.g., coronary artery disease, peripheral artery disease, cerebrovascular disease, hypertension, and risk factors related to unmanaged cholesterol and/or lipid levels, and/or inflammation), NASH, bone fracture, and cognitive dysfunction Other non-limiting examples of disorders related to diabetes include pre-diabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the condition, disease or disorder is diabetes and obesity (diabesity). In some embodiments, the compounds described herein are also useful in improving the therapeutic effectiveness of metformin.

Disorders of Metabolically Important Tissues

In some embodiments, the condition, disease or disorder is a disorder of a metabolically important tissue. Non-limiting examples of metabolically important tissues include liver, fat, pancreas, kidney, and gut.

In some embodiments, the condition, disease or disorder is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolman's disease, acute fatty liver of pregnancy, and lipodystrophy.

Non-alcoholic fatty liver disease (NAFLD) represents a spectrum of disease occurring in the absence of alcohol abuse and is typically characterized by the presence of steatosis (fat in the liver). NAFLD is believed to be linked to a variety of conditions, e.g., metabolic syndrome (including obesity, diabetes and hypertriglyceridemia) and insulin resistance. It can cause liver disease in adults and children and may ultimately lead to cirrhosis (Skelly et al., J Hepatol 2001; 35: 195-9; Chitturi et al., Hepatology 2002; 35(2): 373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol 2002; 17 Suppl:S186-90). In some embodiments, the patient is a pediatric patient. The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age. In some embodiments, the patient is an adult patient.

Other non-limiting examples of disorders in metabolically important tissues include joint disorders (e.g., osteoarthritis, secondary osteoarthritis), steatosis (e.g. in the liver); gall stones; gallbladder disorders; gastroesophageal reflux; sleep apnea; hepatitis; fatty liver; bone disorder characterized by altered bone metabolism, such as osteoporosis, including post-menopausal osteoporosis, poor bone strength, osteopenia, Paget's disease, osteolytic metastasis in cancer patients, osteodistrophy in liver disease and the altered bone metabolism caused by renal failure or hemodialysis, bone fracture, bone surgery, aging, pregnancy, protection against bone fractures, and malnutrition polycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute or chronic diarrhea, testicular dysfunction, respiratory dysfunction, frailty, sexual dysfunction (e.g., erectile dysfunction), and geriatric syndrome. In some embodiments, the compounds and pharmaceutical compositions described herein can be used for treating surgical trauma by improving recovery after surgery and/or by preventing the catabolic reaction caused by surgical trauma.

Cardiovascular and Vascular Diseases

In some embodiments, the disease or disorder is a cardiovascular disease. Non-limiting examples of cardiovascular disease include congestive heart failure, atherosclerosis, arteriosclerosis, coronary heart disease, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen or plasminogen activator inhibitor in the blood).

In some embodiments, the disease or disorder is related to a vascular disease. Non-limiting examples of vascular diseases include peripheral vascular disease, macrovascular complications (e.g., stroke), vascular dysfunction, peripheral artery disease, abdominal aortic aneurysm, carotid artery disease, cerebrovascular disorder (e.g., cerebral infarction), pulmonary embolism, chronic venous insufficiency, critical limb ischemia, retinopathy, nephropathy, and neuropathy.

Neurological Diseases

In some embodiments, the disease or disorder is a neurological disorder (e.g., neurodegenerative disorder) or a psychiatric disorder. Non-limiting examples of neurological disorders include brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld- Jakob Disease, bovine spongiform encephalopathy (mad cow disease), and chronic wasting syndrome). See, e.g., US2006/0275288A1.

Non-limiting examples of psychiatric disorders include drug dependence/addiction (narcotics and amphetamines and attention deficit/hyperactivity disorder (ADHD). The compounds and pharmaceutical compositions described herein can be useful in improving behavioral response to addictive drugs, decreasing drug dependence, prevention drug abuse relapse, and relieving anxiety caused by the absence of a given addictive substance. See, e.g., US2012/0021979A1.

In some embodiments, the compounds and pharmaceutical compositions described herein are useful in improving learning and memory by enhancing neuronal plasticity and facilitation of cellular differentiation, and also in preserving dopamine neurons and motor function in Morbus Parkinson.

Insulin-Related Conditions and Disorders

In some embodiments, the disease or disorder is impaired fasting glucose (IFG), impaired fasting glycemia (IFG), hyperglycemia, insulin resistance (impaired glucose homeostasis), hyperinsulinemia, elevated blood levels of fatty acids or glycerol, a hypoglycemic condition, insulin resistant syndrome, paresthesia caused by hyperinsulinemia, hyperlipidemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperprolactinemia, hypoglycemia (e.g., nighttime hypoglycemia), and concomitant comatose endpoint associated with insulin.

In some embodiments, the compounds and pharmaceutical compositions described herein can reduce or slow down the progression of borderline type, impaired fasting glucose or impaired fasting glycemia into diabetes.

Autoimmune Disorders

In some embodiments, the disease or disorder is an autoimmune disorder. Non-limiting examples of autoimmune disorders include multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves' disease. See, e.g., US20120148586A1.

Stomach and Intestine-Related Disorders

In some embodiments, the disease or disorder is a stomach or intestine related disorder. Non-limiting examples of these disorders include ulcers of any etiology (e.g. peptic ulcers, Zollinger-Ellison syndrome, drug-induced ulcers, ulcers related to infections or other pathogens), digestion disorders, malabsorption, short bowel syndrome, cul-de-sac syndrome, inflammatory bowel diseases (Crohn's disease and ulcerative colitis), celiac sprue, hypogammaglobulinemic sprue, chemotherapy and/or radiation therapy-induced mucositis and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, and cachexia caused by acquired immunodeficiency syndrome).

Body Weight

In some embodiments, the compounds and pharmaceutical compositions described herein can be used to reduce body weight (e.g., excess body weight), prevent body weight gain, induce weight loss, decrease body fat, or reduce food intake in a patient (e.g., a patient in need thereof). In some embodiments, the weight increase in a patient may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). In some embodiments, the weight increase may be weight increase before reaching obesity, or may be weight increase in an obese patient. In some embodiments, the weight increase may also be medication-induced weight gain or weight gain subsequent to cessation of smoking.

In some embodiments, the disease or disorder is an eating disorder, such as hyperphagia, binge eating, bulimia, or compulsive eating.

Inflammatory Diseases

In some embodiments, the disease or disorder is an inflammatory disorder. Non-limiting examples of inflammatory disorders include chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney and gut, and a proinflammatory state (e.g., elevated levels of proinflammatory cytokines or markers of inflammation-like C-reactive protein in the blood).

Cancer

In some embodiments, the disease or disorder is cancer. Suitable examples of cancer include breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

Hypothalamic-Pituitary Disorders

In some embodiments, the disease or disorder is related to the hypothalamic-pituitary-gonadal axis. For example, the condition, disease or disorder is related to the hypothalamus-pituitary-ovary axis. In another example, the condition, disease or disorder is related to the hypothalamus-pituitary-testis axis. Hypothalamic-pituitary-gonadal axis diseases include, but are not limited to, hypogonadism, polycystic ovary syndrome, hypothyroidism, hypopituitarism, sexual dysfunction, and Cushing's disease.

In some embodiments, the disease or disorder associated with diabetes is related to the hypothalamic-pituitary-gonadal axis.

Pulmonary Disease

In some embodiments, the disease or disorder is related to a pulmonary disease. Pulmonary diseases include, but are not limited to, asthma, idiopathic pulmonary fibrosis, pulmonary hypertension, obstructive sleep apnoea-hypopnoea syndrome, and chronic obstructive pulmonary disease (COPD) (e.g., emphysema, chronic bronchitis, and refractory (non-reversible) asthma).

In some embodiments, the disease or disorder associated with diabetes is a pulmonary disease.

Combination Therapy

In some embodiments, this disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the methods described herein include administering a compound described herein in combination with one or more of a diet therapy (e.g., dietary monitoring, diet therapy for diabetes), an exercise therapy (e.g., physical activity), blood sugar monitoring, gastric electrical stimulation (e.g., TANTALUS®), and diet modifications.

In some embodiments, one or more compounds as disclosed herein, or a stereoisomer or mixture of stereoisomers thereof can be administered in combination with one or more additional therapeutic agents.

Representative additional therapeutic agents include, but are not limited to, anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, anti-oxidants, therapeutic agents for osteoporosis, vitamins, antidementia drugs, erectile dysfunction drugs, therapeutic drugs for urinary frequency or urinary incontinence, therapeutic agents for NAFLD, therapeutic agents for NASH, therapeutic agents for dysuria and anti-emetic agents.

In some embodiments, the one or more additional therapeutic agents include those useful, for example, as anti-obesity agents. Non-limiting examples include monoamine uptake inhibitors (e.g., tramadol, phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), including GABA receptor agonists (e.g., gabapentin, pregabalin), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017, BVT-3498, INCB-13739), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), sodium-glucose cotransporter 2 (SGLT-2) inhibitors (e.g., JNJ-28431754, dapagliflozin, AVE2268, TS-033, YM543, TA-7284, ASP1941, remogliflozin), NFK inhibitors (e.g., HE-3286), PPAR agonists (e.g., GFT-505, DRF-11605, gemfibrozil and fenofibrate), phosphotyrosine phosphatase inhibitors (e.g., sodium vanadate, trodusquemin), GPR119 agonists (e.g., PSN-821, MBX-2982, APD597), glucokinase activators (e.g., piragliatin, AZD-1656, AZD6370, TTP-355, compounds described in W0006/112549, W0007/028135, W0008/047821, W0008/050821, W0008/136428 and W0008/156757), leptin, leptin derivatives (e.g., metreleptin), leptin resistance improving drugs, CNTF (ciliary neurotrophic factor), BDNF (brain-derived neurotrophic factor), cholecystokinin agonists, amylin preparations (e.g., pramlintide, AC-2307), neuropeptide Y agonists (e.g., PYY3-36, derivatives of PYY3-36, obineptide, TM-30339, TM-30335), oxyntomodulin (OXM) preparations, appetite suppressants (e.g. ephedrine), FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57), human proislet peptide (HIP), farnesoid X receptor (FXR) agonist, phentermine, zonisamide, norepinephrine/dopamine reuptake inhibitor, GDF-15 analog, methionine aminopeptidase 2 (MetAP2) inhibitor, diethylpropion, phendimetrazine, benzphetamine, fibroblast growth factor receptor (FGFR) modulator, and AMP-activated protein kinase (AMPK) activator.

In some embodiments, one or more compounds as disclosed herein, or a stereoisomer or mixture of stereoisomers thereof can be administered in combination with one or more additional therapeutic agents, wherein the additional therapeutic agent is a GLP-1 agonist or exhibits GLP-1 agonist activity.

In some embodiments, the additional therapeutic agent is TTP273, LY2944876 (pegapamodutide), HDM1002, K-757, K-833, retatrutide, IBI362 (mazdutide), cotadutide, AMG133, CT-868, HRS9531, HS-20094, dapiglutide, efinopegdutide, efocipegtrutide, pemvidutide, survodutide, AP026, AZD9550, BGM0504, CT-388, DD01, DR10624, G3215, GMA106, HEC88473, HZ010, LY3493269, MWN101, NN9487, NN9541, RAY1225, SCO-094, SHR-1816, TB001, VK2735, ZP2929, ecnoglutide, GX-G6, GZR18, HRS-7535, YH14617, avexitide, froniglutide, pegsebrenatide, vurolenatide, JY09, NB1001, Byetalog, GW002, HL08, KN056, SAL0112, SHR2042, VCT220, ZT002, ZYOG1, or utreglutide.

In some embodiments, the additional therapeutic agent is endogenous GLP-1, endogenous glucagon, oxyntomodulin, exendin-4, exenatide, lixisenatide, albiglutide, beinaglutide, dulaglutide, efpeglenatide, langlenatide, liraglutide, semaglutide, taspoglutide, tirzepatide, pegapamodutide, lithium chloride, PF-06882961 (danuglipron), LY3502970 (orforglipron), ECC-5004, GSBR-1290, AZD0186, PF-07081532 (lotiglipron), VCT220, TERN-601, RGT-075, CT-996, MDR-001, SAL0112, XW014, AVE-0010, S4P, or Boc5), In some embodiments, one or more compounds as disclosed herein, or a stereoisomer or mixture of stereoisomers thereof can be administered in combination with one or more additional therapeutic agents, wherein the additional therapeutic agent is selected from a compound disclosed in WO2021/155841, WO/2018/109607, WO/2018/056453, WO/2019/239319, or WO/2019/239371.

In some embodiments, the one or more additional therapeutic agents include those useful, for example, as antidiabetic agents. Non-limiting examples include insulin and insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation, synthetic human insulin), insulin sensitizers (e.g., pioglitazone or a salt thereof), biguanides (e.g., metformin, buformin or a salt thereof (e.g., hydrochloride, fumarate, succinate)), glucagon analogs (e.g., any of glucagon analogs described, e.g., in WO 2010/011439), agents which antagonize the actions of or reduce secretion of glucagon, sulfonylurea agents (e.g., chlorpropamide, tolazamide, gliclazide, glimepiride, tolbutamide, glibenclamide, gliclazide, acetohexamide, glyclopyramide, glybuzole, glyburide), thiazolidinedione agents (e.g. rosiglitazone or pioglitazone), α-glucosidase inhibitors (e.g., voglibose, acarbose, miglitol, emiglitate), insulin secretagogues, such as prandial glucose regulators (sometimes called "short-acting secretagogues"), e.g., meglitinides (e.g. repaglinide and nateglinide), cholinesterase inhibitors (e.g., donepezil, galantamine, rivastigmine, tacrine), NMDA receptor antagonists, dual GLP-1/GIP receptor agonists (e.g., LBT-2000, ZPD1-70), GLP-1R agonists (e.g., exenatide, liraglutide, albiglutide, dulaglutide, abiglutide, taspoglutide, lixisenatide, semaglutide, AVE-0010, S4P and Boc5), and dipeptidyl peptidase IV (DPP-4) inhibitors (e.g., vildagliptin, dutogliptin, gemigliptin, alogliptin, saxagliptin, sitagliptin, linagliptin, berberine, adogliptin, BI1356, GRC8200, MP-513, PF-00734200, PHX1149, SK-0403, ALS2-0426, TA-6666, TS-021, KRP-104, trelagliptin).

In some embodiments, the one or more additional therapeutic agents include those useful, for example, for treating NAFL and NASH. Non-limiting examples include FXR agonists, PF-05221304, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21), a niacin analogue, a leukotriene D4 (LTD4) receptor antagonist, an acetyl-CoA carboxylase (ACC) inhibitor, a ketohexokinase (KHK) inhibitor, an apoptosis signal-regulating kinase 1 (ASK1) inhibitor, an ileal bile acid transporter (IBAT) inhibitor, glycyrrhizin, Schisandra extract, ascorbic acid, glutathione, silymarin, lipoic acid, and d-alpha-tocopherol, ascorbic acid, glutathione, vitamin B-complex, glitazones/thiazolidinediones (e.g., troglitazone, rosiglitazone, pioglitazone), metformin, cysteamine, sulfonylureas, alpha-glucosidase inhibitors, meglitinides, vitamin E, tetrahydrolipstatin, milk thistle protein, anti-virals, and anti-oxidants.

In some embodiments, the one or more additional therapeutic agents include those useful, for example, for treating diabetic complications. Non-limiting examples include aldose reductase inhibitors (e.g., tolrestat, epalrestat, zopolrestat, fidarestat, CT-112, ranirestat, lidorestat), neurotrophic factor and increasing agents thereof (e.g., NGF, NT-3, BDNF, neurotrophic production/secretion promoting agents described in WO01/14372 (e.g., 4-(4-chlorophenyl)-2-(2-methyl-1-imidazolyl)-5-[3-(2-methylphenoxyl)propyl]oxazole), compounds described in WO2004/039365), PKC inhibitors (e.g., ruboxistaurin mesylate), AGE inhibitors (e.g., ALT946, N-phenacylthiazolium bromide (ALT766), EXO-226, pyridorin, pyridoxamine), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

In some embodiments, the one or more additional therapeutic agents include those useful, for example, for treating hyperlipidemia. Non-limiting examples include HMG-COA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compounds described in WO97/10224, e.g., N-[[(3R,5S)-1-(3-acetoxy-2,2-dimethylpropyl)-7-chloro-5-(2,3-dimethoxyphenyl)-2-oxo-1,2,3,5-tetrahydro-4, 1-benzoxazepin-3-yl]acetyl]piperidin-4-acetic acid), fibrate compounds (e.g., bezafibrate, clofibrate, simfibrate, clinofibrate), anion exchange resin (e.g., colestyramine), nicotinic acid drugs (e.g., nicomol, niceritrol, niaspan), phytosterols (e.g., soysterol, gamma oryzanol (γ-oryzanol)), cholesterol absorption inhibitors (e.g., zechia), CETP inhibitors (e.g., dalcetrapib, anacetrapib) and ω-3 fatty acid preparations (e.g., ω-3-fatty acid ethyl esters 90).

In some embodiments, the one or more additional therapeutic agents include those useful, for example, as antihypertensive agents. Non-limiting examples include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine) and β-blockers (e.g., metoprolol, atenolol, propranolol, carvedilol, pindolol).

In some embodiments, the one or more additional therapeutic agents include those useful, for example, as diuretics. Non-limiting examples include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide), antialdosterone preparations (e.g., spironolactone, triamterene), carbonic anhydrase inhibitors (e.g., acetazolamide) and chlorobenzenesulfonamide agents (e.g., chlortalidone, mefruside, indapamide).

In some embodiments, the one or more additional therapeutic agents include those useful, for example, as immunotherapeutic agents. Non-limiting examples include microbial or bacterial compounds (e.g., muramyl dipeptide derivative, picibanil), polysaccharides having immunoenhancing activity (e.g., lentinan, sizofiran, krestin), cytokines obtained by genetic engineering approaches (e.g., interferon, interleukin (IL) such as IL-1, IL-2, IL-12), and colony-stimulating factors (e.g., granulocyte colony-stimulating factor, erythropoietin).

In some embodiments, the one or more additional therapeutic agents include those useful, for example, as antithrombotic agents. Non-limiting examples include heparins (e.g., heparin sodium, heparin calcium, enoxaparin sodium, dalteparin sodium) warfarin (e.g., warfarin potassium); antithrombin drugs (e.g., aragatroban, dabigatran) FXa inhibitors (e.g., rivaroxaban, apixaban, edoxaban, betrixaban, YM150, compounds described in WO02/06234, WO2004/048363, WO2005/030740, WO2005/058823, and WO2005/113504) thrombolytic agents (e.g., urokinase, tisokinase, alteplase, nateplase, monteplase, pamiteplase), and platelet aggregation inhibitors (e.g., ticlopidine hydrochloride, clopidogrel, prasugrel, E5555, SHC530348, cilostazol, ethyl icosapentate, beraprost sodium, and sarpogrelate hydrochloride).

In some embodiments, the one or more additional therapeutic agents include those useful, for example, for treating osteoporosis. Non-limiting examples include alfacalcidol, calcitriol, elcatonin, calcitonin salmon, estriol, ipriflavone, pamidronate disodium, alendronate sodium hydrate, incadronate disodium, and risedronate disodium. Suitable examples of vitamins include vitamin B1 and vitamin B12. Suitable examples of erectile dysfunction drugs include apomorphine and sildenafil citrate. Suitable examples of therapeutic agents for urinary frequency or urinary incontinence include flavorxate hydrochloride, oxybutynin hydrochloride and propiverine hydrochloride. Suitable examples of therapeutic agents for dysuria include acetylcholine esterase inhibitors (e.g., distigmine). Suitable examples of anti-inflammatory agents include nonsteroidal anti-inflammatory drugs such as aspirin, acetaminophen, indomethacin.

Other exemplary additional therapeutic agents include agents that modulate hepatic glucose balance (e.g., fructose 1,6-bisphosphatase inhibitors, glycogen phosphorylase inhibitors, glycogen synthase kinase inhibitors, glucokinase activators), agents designed to treat the complications of prolonged hyperglycemia, such as aldose reductase inhibitors (e.g. epalrestat and ranirestat), agents used to treat complications related to micro-angiopathies, anti-dyslipidemia agents, such as HMG-CoA reductase inhibitors (statins, e.g. rosuvastatin), cholesterol-lowering agents, bile acid sequestrants (e.g., cholestyramine), cholesterol absorption inhibitors (e.g. plant sterols such as phytosterols), cholesteryl ester transfer protein (CETP) inhibitors, inhibitors of the ileal bile acid transport system (IBAT inhibitors), bile acid binding resins, nicotinic acid (niacin) and analogues thereof, anti-oxidants (e.g., probucol), omega-3 fatty acids, antihypertensive agents, including adrenergic receptor antagonists, such as beta blockers (e.g. atenolol), alpha blockers (e.g. doxazosin), and mixed alpha/beta blockers (e.g. labetalol), adrenergic receptor agonists, including alpha-2 agonists (e.g. clonidine), angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem), angiotensin II receptor antagonists (e.g. candesartan), aldosterone receptor antagonists (e.g. eplerenone), centrally acting adrenergic drugs, such as central alpha agonists (e.g. clonidine), diuretic agents (e.g. furosemide), haemostasis modulators, including antithrombotics (e.g., activators of fibrinolysis), thrombin antagonists, factor VIIa inhibitors, anticoagulants (e.g., vitamin K antagonists such as warfarin), heparin and low molecular weight analogues thereof, factor Xa inhibitors, and direct thrombin inhibitors (e.g. argatroban), antiplatelet agents (e.g., cyclooxygenase inhibitors (e.g. aspirin)), adenosine diphosphate (ADP) receptor inhibitors (e.g. clopidogrel), phosphodiesterase inhibitors (e.g. cilostazol), glycoprotein IIB/IIA inhibitors (e.g. tirofiban), adenosine reuptake inhibitors (e.g. dipyridamole), noradrenergic agents (e.g. phentermine), serotonergic agents (e.g. sibutramine), diacyl glycerolacyltransferase (DGAT) inhibitors, feeding behavior modifying agents, pyruvate dehydrogenase kinase (PDK) modulators, serotonin receptor modulators, monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), and monoamine oxidase inhibitors (MAOI) (e.g. toloxatone and amiflamine), compounds described in W0007/013694, WO2007/018314, WO2008/093639 and WO2008/099794, GPR40 agonists (e.g., fasiglifam or a hydrate thereof, compounds described in WO2004/041266, WO2004/106276, WO2005/063729, WO2005/063725, WO2005/087710, WO2005/095338, WO2007/013689 and WO2008/001931), SGLT1 inhibitors, adiponectin or agonist thereof, IKK inhibitors (e.g., AS-2868), somatostatin receptor agonists, ACC2 inhibitors, cachexia-ameliorating agents, such as a cyclooxygenase inhibitors (e.g., indomethacin), progesterone derivatives (e.g., megestrol acetate), glucocorticoids (e.g., dexamethasone), metoclopramide agents, tetrahydrocannabinol agents, agents for improving fat metabolism (e.g., eicosapentaenoic acid), growth hormones, IGF-1, antibodies against a cachexia-inducing factor TNF-α, LIF, IL-6, and oncostatin M, metabolism-modifying proteins or peptides such as glucokinase (GK), glucokinase regulatory protein (GKRP), uncoupling proteins 2 and 3 (UCP2 and UCP3), peroxisome proliferator-activated receptor α (PPARα), MC4r agonists, insulin receptor agonist, PDE 5 inhibitors, glycation inhibitors (e.g., ALT-711), nerve regeneration-promoting drugs (e.g., Y-128, VX853, prosaptide), antidepressants (e.g., desipramine, amitriptyline, imipramine), antiepileptic drugs (e.g., lamotrigine, trileptal, keppra, zonegran, pregabalin, harkoseride, carbamazepine), antiarrhythmic drugs (e.g., mexiletine), acetylcholine receptor ligands (e.g., ABT-594), endothelin receptor antagonists (e.g., ABT-627), narcotic analgesics (e.g., morphine), α2 receptor agonists (e.g., clonidine), local analgesics (e.g., capsaicin), antianxiety drugs (e.g., benzothiazepine), phosphodiesterase inhibitors (e.g., sildenafil), dopamine receptor agonists (e.g., apomorphine), cytotoxic antibodies (e.g., T-cell receptor and IL-2 receptor-specific antibodies), B cell depleting therapies (e.g., anti-CD20 antibody (e.g., rituxan), i-BLyS antibody), drugs affecting T cell migration (e.g., anti-integrin alpha 4/beta 1 antibody (e.g., tysabri), drugs that act on immunophilins (e.g., cyclosporine, tacrolimus, sirolimus, rapamicin), interferons (e.g., IFN—P), immunomodulators (e.g., glatiramer), TNF-binding proteins (e.g., circulating receptors), immunosupressants (e.g., mycophenolate), and metaglidasen, AMG-131, balaglitazone, MBX-2044, rivoglitazone, aleglitazar, chiglitazar, lobeglitazone, PLX-204, PN-2034, GFT-505, THR-0921, exenatide, exendin-4, memantine, midazolam, ketoconazole, ethyl icosapentate, clonidine, azosemide, isosorbide, ethacrynic acid, piretanide, bumetanide, etoposide, piroxicam, NO donating agents (e.g., organonitrates), and NO promoting agents (e.g., phosphodiesterase inhibitors).

In some embodiments, the one or more additional therapeutic agents include those useful, for example, as anti-emetic agents. As used herein, an "anti-emetic" agent refers to any agent that counteracts (e.g., reduces or removes) nausea or emesis (vomiting). It is to be understood that when referring to a therapeutically effective amount of an anti-emetic agent, the amount administered is an amount needed to counteract (e.g., reduce or remove) nausea or emesis (vomiting). While not wishing to be bound by theory, it is believed that administering one or more anti-emetic agents in combination with the formula (I) compounds described herein may allow higher dosages of the formula (I) compounds to be administered, e.g., because the patient may be able to have a normal food intake and thereby respond faster to the treatment.

Non-limiting examples of anti-emetic agents include 5HT3-receptor antagonists (serotonin receptor antagonists), neuroleptics/anti-psychotics, antihistamines, anticholinergic agents, steroids (e.g., corticosteroids), NK1-receptor antagonists (e.g., Neurokinin 1 substance P receptor antagonists), antidopaminergic agents/dopamine receptor antagonists, benzodiazepines, cannabinoids.

For example, the antiemetic agent can be selected from the group consisting of; neuroleptics, antihistamines, anticholinergic agents, steroids, 5HT-3-receptor antagonists, NK1-receptor antagonists, anti-dopaminergic agents/dopamine receptor antagonists, benzodiazepines and non-psychoactive cannabinoids.

In some embodiments, the anti-emetic agent is a 5HT3-receptor antagonist (serotonin receptor antagonist). Non-limiting examples of 5HT3-receptor antagonists (serotonin receptor antagonists) include: granisetron (Kytril), dolasetron, ondansetron (Zofran), tropisetron, ramosetron, palonosetron, alosetron, azasetron, bemesetron, zatisetron, batanopirde, MDL-73147EF; Metoclopramide, N-3389 (endo-3,9-dimethyl-3,9-diazabicyclo[3,3,1]non-7-yl-1H-indazole-3-carboxamide dihydrochloride), Y-25130 hydrochloride, MDL 72222, Tropanyl-3,5-dimethylbenzoate, 3-(4-Allylpiperazin-1-yl)-2-quinoxalinecarbonitrile maleate, zacopride hydrochloride, and mirtazepine. Other non-limiting examples of 5HT3-receptor antagonists (serotonin receptor antagonists) include: cilansetron, clozapine, cyproheptadine, dazopride, hydroxyzine, lerisetron, metoclopramide, mianserin, olanzapine, palonosetron (+netupitant), quetiapine, qamosetron, ramosteron, ricasetron, risperidone, ziprasidone, and zatosetron.

In certain embodiments, the 5HT-3-receptor antagonist is granisetron, dolasetron, ondansetron hydrochloride, tropisetron, ramosetron, palonosetron, alosetron, bemesetron, zatisetron, batanopirde, MDL-73147EF, metoclopramide, N-3389, Y—25130 hydrochloride, MDL 72222, tropanyl-3,5-dimethylbenzoate 3-(4-AIlyl-piperazin-1-yl)-2-quinoxalinecarbonitrile maleate, zacopride hydrochloride and mirtazepine.

In certain embodiments, the 5HT-3-receptor antagonist is granisetron, dolasetron, ondansetron hydrochloride, tropisetron, ramosetron, palonosetron, alosetron, bemesetron, and zatisetron.

In certain embodiments, the 5HT-3-receptor antagonist is granisetron, dolasetron and ondansetron.

In certain embodiments, the 5HT-3-receptor antagonist is granisetron.

In certain embodiments, the 5HT-3-receptor antagonist is ondansetron.

In some embodiments, the anti-emetic agent is an antihistamine. Non-limiting examples of antihistamines include: piperazine derivatives (e.g., cyclizine, meclizine, and cinnarizine); promethazine; dimenhydrinate (Dramamine, Gravol); diphenhydramine; hydroxyzine; buclizine; and meclizine hydrochloride (Bonine, Antivert), doxylamine, and mirtazapine.

In some embodiments, the anti-emetic agent is an anticholinergic agent (inhibitors of the acetylcholine receptors). Non-limiting examples of anticholinergic agents include: atropine, scopolamine, glycopyrron, hyoscine, artane (trihexy-5 trihexyphenidyl hydrochloride), cogentin (benztropine mesylate), akineton (biperiden hydrochloride), disipal (norflex orphenadrine citrate), diphenhydramine, hydroxyzine, hyoscyamine, and kemadrin (procyclidine hydrochloride).

In some embodiments, the anti-emetic agent is a steroid (e.g., a corticosteroid). Non-limiting examples of steroids include: betamethasone, dexamethasone, methylprednisolone, Prednisone®, and trimethobenzamide (Tigan).

In some embodiments, the anti-emetic agent is an NK1-receptor antagonists (e.g., Neurokinin 1 substance P receptor antagonists). Non-limiting examples of NK1-receptor antagonists include: aprepitant, casopitant, ezlopitant, fosaprepitant, maropitant, netupitant, rolapitant, and vestipitant.

Other non-limiting examples of NK1-receptor antagonists include: MPC-4505, GW597599, MPC-4505, GR205171, L-759274, SR 140333, CP-96,345, BIIF 1149, NKP 608C, NKP 608A, CGP 60829, SR 140333 (Nolpitantium besilate/chloride), LY 303870 (Lanepitant), MDL-105172A, MDL-103896, MEN-11149, MEN-11467, DNK 333A, YM-49244, YM-44778, ZM-274773, MEN-10930, S-19752, Neuronorm, YM-35375, DA-5018, MK-869, L-754030, CJ-11974, L-758298, DNK-33A, 6b-1, CJ-11974 j. Benserazide and carbidopa k. TAK-637 [(aR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphth- yridine-6,13-dione], PD 154075, ([(2-benzofuran)-CH2OCO]—(R)-alpha-MeTrp-(S)-NHCH($CH_3$)Ph), FK888, and (D-Pro4, D-Trp7,9,10, Phe11)SP4-11.

In some embodiments, the anti-emetic agent is an anti-dopaminergic agents/dopamine receptor antagonist (e.g., dopamine receptor antagonist, e.g., D2 or D3 antagonists). Non-limiting examples include phenothiazines (e.g., promethazine, chlorpromazine, prochlorperazine, perphenazine, hydroxyzine, thiethylperazine, metopimazine,); benzamides (e.g., metoclopramide, domperidone), butyrophenones (e.g., haloperidol, droperidol); alizapride, bromopride, clebopride, domperidone, itopride, metoclopramide, trimethobenzamide, and amisulpride.

In some embodiments, the anti-emetic agent is a non-psychoactive cannabinoids (e.g., Cannabidiol (CBD), Cannabidiol dimethylheptyl (CBD-DMH), Tetra-hydro-cannabinol (THC), Cannabinoid agonists such as WIN 55-212 (a CB1 and CB2 receptor agonist), Dronabinol (Marinol®), and Nabilone (Cesamet)).

Other exemplary anti-emetic agents include: c-9280 (Merck); benzodiazepines (diazepam, midazolam, lorazepam); neuroleptics/anti-psychotics (e.g., dixyrazine, haloperidol, and Prochlorperazine (Compazine®)); cerium oxalate; propofol; sodium citrate; dextrose; fructose (Nauzene); orthophosphoric acid; fructose; glucose (Emetrol); bismuth subsalicylate (Pepto Bismol); ephedrine; vitamin B6; peppermint, lavender, and lemon essential oils; and ginger.

Still other exemplary anti-emetic agents include those disclosed in US 20120101089A1; U.S. Pat. No. 10,071,088 B2; U.S. Pat. No. 6,673,792 B1; U.S. Pat. No. 6,197,329 B1; U.S. Pat. No. 10,828,297 B2; U.S. Pat. No. 10,322,106 B2; U.S. Pat. No. 10,525,033 B2; WO 2009080351 A1; WO 2019203753 A2; WO 2002020001 A2; U.S. Pat. No. 8,119,697 B2; U.S. Pat. No. 5,039,528; US20090305964A1; and WO 2006/111169, each of which is incorporated by reference in its entirety.

In some embodiments, the additional therapeutic agent or regimen is administered to the patient prior to contacting with or administering the compounds and pharmaceutical compositions (e.g., about one hour prior, or about 6 hours prior, or about 12 hours prior, or about 24 hours prior, or about 48 hours prior, or about 1 week prior, or about 1 month prior).

In some embodiments, the additional therapeutic agent or regimen is administered to the patient at about the same time as contacting with or administering the compounds and pharmaceutical compositions. By way of example, the additional therapeutic agent or regimen and the compounds and pharmaceutical compositions are provided to the patient simultaneously in the same dosage form. As another example, the additional therapeutic agent or regimen and the compounds and pharmaceutical compositions are provided to the patient concurrently in separate dosage forms.

Patient Selection

In some embodiments, the methods described herein further include the step of identifying a patient (e.g., a subject) in need of such treatment (e.g., by way of blood assay, body mass index, or other conventional method known in the art).

In some embodiments, the methods described herein further include the step of identifying a patient (e.g., patient) that has type 2 diabetes mellitus. In some embodiments, determining if the patient has type 2 diabetes mellitus includes performing an assay to determine the level of hemoglobin A1c (HbA1c), fasting plasma glucose, non-fasting plasma glucose, or any combination thereof. In some embodiments, the level of HbA1c is about 6.5% to about 24.0%. In some embodiments, the level of HbA1c is greater than or about 6.5%. In some embodiments, the level of HbA1c is greater than or about 8.0%. In some embodiments, the level of HbA1c is greater than or about 10.0%. In some embodiments, the level of HbA1c is greater than or about 12.0%. In some embodiments, the level of HbA1c is greater than or about 14.0%. In some embodiments, the level of HbA1c is greater than or about 16.0%. In some embodiments, the level of HbA1c is greater than or about 18.0%. In some embodiments, the level of HbA1c is greater than or about 20.0%. In some embodiments, the level of HbA1c is greater than or about 22.0%. In some embodiments, the level of HbA1c is greater than or about 24.0%.

In some embodiments, the level of fasting plasma glucose is greater than or about 120 mg/dL to greater than or about 750 mg/dL. In some embodiments, the level of fasting plasma glucose is greater than or about 200 mg/dL to greater than or about 500 mg/dL. In some embodiments, the level of fasting plasma glucose is greater than or about 300 mg/dL to greater than or about 700 mg/dL.

In some embodiments, the level of non-fasting plasma glucose is greater than or about 190 mg/dL to greater than or about 750 mg/dL. In some embodiments, the level of non-fasting plasma glucose is greater than or about 250 mg/dL to greater than or about 450 mg/dL. In some embodiments, the level of non-fasting plasma glucose is greater than or about 400 mg/dL to greater than or about 700 mg/dL.

In some embodiments, determining if the patient has type 2 diabetes mellitus further includes determining the patient's BMI. In some embodiments, the BMI of the patient is greater than or about 22 kg/m$^2$ to greater than or about 100 kg/m$^2$. In some embodiments, the BMI of the patient is greater than or about 30 kg/m$^2$ to greater than or about 90 kg/m$^2$. In some embodiments, the BMI of the patient is greater than or about 40 kg/m$^2$ to greater than or about 80 kg/m$^2$. In some embodiments, the BMI of the patient is greater than or about 50 kg/m$^2$ to greater than or about 70 kg/m$^2$.

In some embodiments, additional factors (e.g. risk factors) used for determining if the patient has type 2 diabetes mellitus further includes age and ethnicity of the patient. In some embodiments, the patient's age is greater than or about 10 years. In some embodiments, the patient's age is greater than or about 15 years. In some embodiments, the patient's age is greater than or about 20 years. In some embodiments, the patient's age is greater than or about 25 years. In some embodiments, the patient's age is greater than or about 30 years. In some embodiments, the patient's age is greater than or about 35 years. In some embodiments, the patient's age is greater than or about 40 years. In some embodiments, the patient's age is greater than or about 42 years. In some embodiments, the patient's age is greater than or about 44 years. In some embodiments, the patient's age is greater than or about 46 years. In some embodiments, the patient's age is greater than or about 48 years. In some embodiments, the patient's age is greater than or about 50 years. In some embodiments, the patient's age is greater than or about 52 years. In some embodiments, the patient's age is greater than or about 54 years. In some embodiments, the patient's age is greater than or about 56 years. In some embodiments, the patient's age is greater than or about 58 years. In some embodiments, the patient's age is greater than or about 60 years. In some embodiments, the patient's age is greater than or about 62 years. In some embodiments, the patient's age is greater than or about 64 years. In some embodiments, the patient's age is greater than or about 66 years. In some embodiments, the patient's age is greater than or about 68 years. In some embodiments, the patient's age is greater than or about 70 years. In some embodiments, the patient's age is greater than or about 72 years. In some embodiments, the patient's age is greater than or about 74 years. In some embodiments, the patient's age is greater than or about 76 years. In some embodiments, the patient's age is greater than or about 78 years. In some embodiments, the patient's age is greater than or about 80 years. In some embodiments, the patient's age is greater than or about 85 years. In some embodiments, the patient's age is greater than or about 90 years. In some embodiments, the patient's age is greater than or about 95 years. In some embodiments, the ethnicity of the patient may be African American, American Indian or Alaska Native, Asian American, Hispanics or Latinos, or Native Hawaiian or Pacific Islander.

Synthesis of the Compounds

The compounds of this disclosure can be prepared from readily available starting materials using, for example, the following general methods, and procedures. It will be appreciated that where certain process conditions (i.e., reaction temperatures, times, mole ratios of reactants, solvents, pressures, etc.) are given, other process conditions can also be used unless otherwise stated. Optimum reaction conditions may vary with the reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting certain functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance CA USA), EMKA-Chemie Gmbh & Co. KG (Eching Germany), or Millipore Sigma (Burlington MA USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Scheme I illustrates a general method which can be employed for the synthesis of compounds described herein, wherein each of A, $X^1$, $X^2$, $X^3$, $X^4$, $L^1$, $L^2$, $Y^1$, $Y^2$, $Y^3$, $R^4$, and $R^5$, are independently as defined herein, and $R^{50}$ is an alkyl or substituted alkyl.

Scheme I

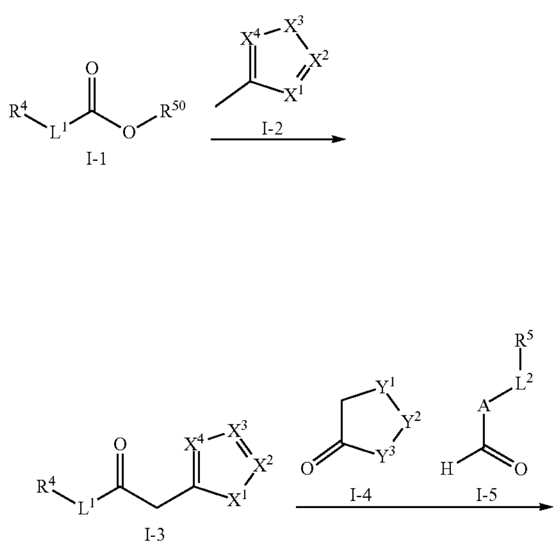

I-1 I-2

I-3 I-4 I-5

-continued

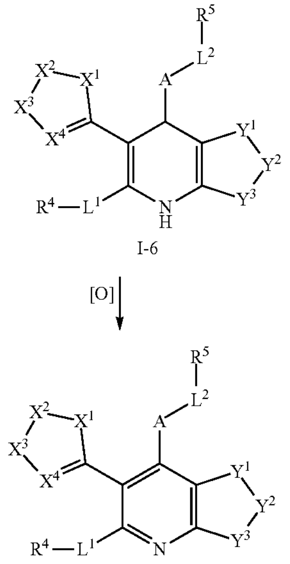

I-6

I

As shown in Scheme I, coupling compound I-1 with compound I-2 provides compound I-3. Compound I-3 may then undergo a Hantzsch style pyridine reaction with compound I-4 and compound I-5 to provide compound I-6. In some embodiments, the reaction is performed under heated conditions in a suitable solvent. Oxidation of I-6, such as by CAN or DDQ, provides compounds of Formula I.

For any compound shown in Scheme I, it should be understood that various derivatives can be provided by functional group interconversion at any step. In some embodiments, the various substituents of compounds I-1, I-2, I-3, I-4, I-5, or I-6 (e.g., A, $X^1$, $X^2$, $X^3$, $X^4$, $L^1$, $L^2$, $Y^1$, $Y^2$, $Y^3$, $R^4$, and $R^5$) are as defined herein. However, derivatization of compounds I-1, I-2, I-3, I-4, I-5, or I-6 prior to reacting in any step, and/or further derivatization of the resulting reaction product, provides various compounds of Formula I. Appropriate starting materials and reagents can be purchased or prepared by methods known to one of skill in the art.

Upon reaction completion, compounds of Formula I can be recovered by conventional techniques such as neutralization, extraction, precipitation, chromatography, filtration and the like. In certain embodiments, when control of stereochemistry is desired, proper control of reaction conditions and selection of substituents for the reagents can at least partially dictate or preserve the formation of the various stereoisomers.

Furthermore, compounds of Formula IB may be synthesized according to the route shown in Scheme II, wherein each of A, $X^1$, $X^2$, $X^3$, $X^4$, Ring B, $L^1$, $L^2$, $Y^1$, $Y^2$, $Y^3$, $R^4$, and $R^5$, are independently as defined herein, $R^{50}$ is an alkyl or substituted alkyl, and PG is a suitable protecting group (such as tert-butoxycarbonyl).

Scheme II

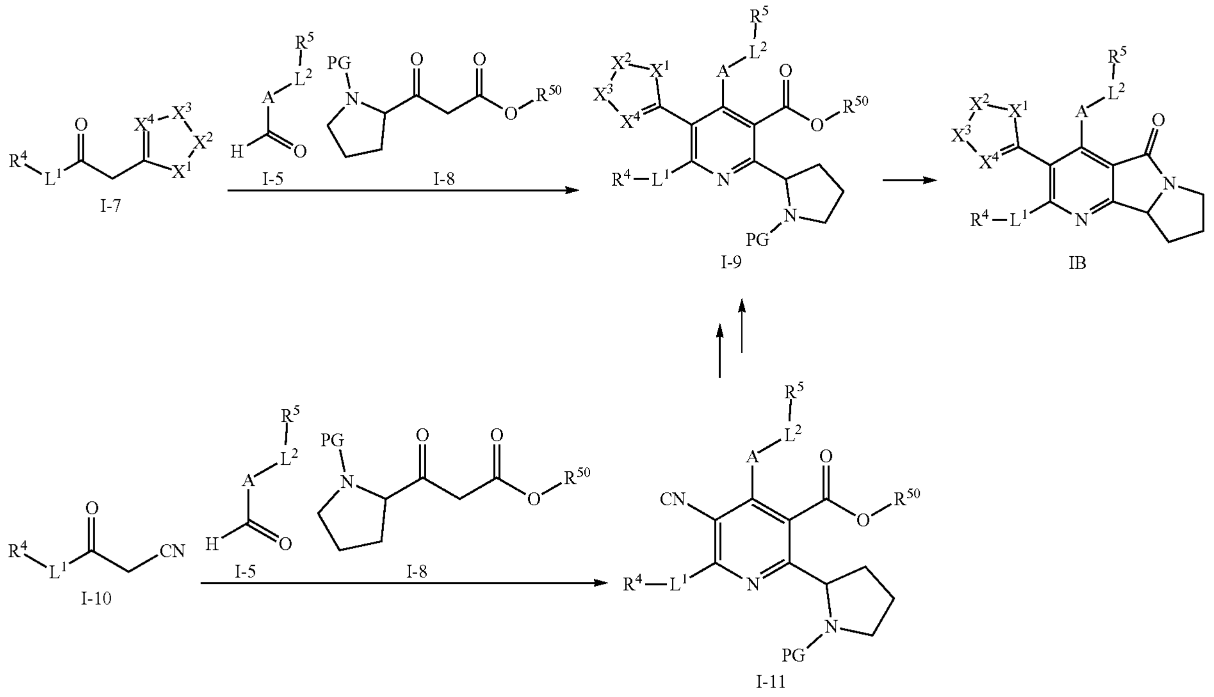

As shown in Scheme II, compound I-7 can undergo Hantzsch style pyridine reaction with compound I-5 and compound I-8, followed by oxidation under suitable conditions (such as in the presence of CAN or DDQ) to provide compound I-9. Alternatively, compound I-10 may be reacted with compound I-5 and compound I-8 under similar conditions to provide compound I-11. Compound I-11 can then be reacted sequentially with hydroxylamine to provide a N-hydroxycarboximidamide intermediate, followed by reaction with CDI to provide compound I-9.

Compound I-9 may then undergo deprotection and subsequent cyclization under suitable conditions (such as in the presence of TFA) to provide compounds of Formula IB. In certain embodiments, when control of stereochemistry is desired, proper control of reaction conditions and selection of substituents for the reagents can at least partially dictate or preserve the formation of the various stereoisomers.

Upon each reaction completion, each of the intermediates or final compounds can be recovered, and optionally purified, by conventional techniques such as neutralization, extraction, precipitation, chromatography, filtration, and the like. Other modifications to arrive at compounds of this disclosure are within the skill of the art.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General information: All evaporations or concentrations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (100-200 mesh). Solvent systems were reported as mixtures by volume. NMR spectra were recorded on a Bruker 400 or Varian (400 MHz) spectrometer. $^{1}H$ chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on SHIMADZU LC20-MS2020 or Agilent 1260 series 6125B mass spectrometer or Agilent 1200 series, 6110 or 6120 mass spectrometer with electrospray ionization and excepted as otherwise indicated.

Unless otherwise indicated in the examples described herein, certain compounds comprise a stereocenter at the carbon atom indicated below (e.g., compounds with stereochemistry at C3 or the C9a fusion), the composition obtained and tested in the assays which follow was a scalemic composition with respect to that stereocenter. It is contemplated that a certain amount of racemization (e.g., less than 50%, or less than 20%) occurs during the Hantzsch style pyridine synthesis. However, the compositions tested favor the stereoisomer indicated in the Examples and Table 1.

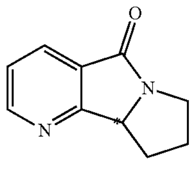

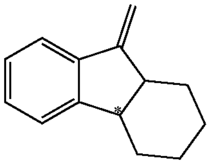

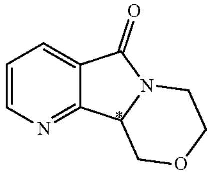

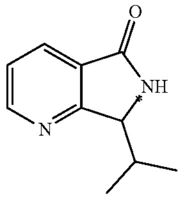

-continued

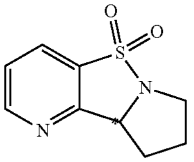

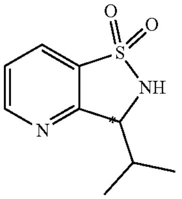

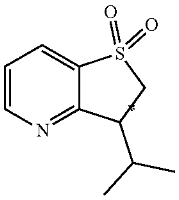

For certain compounds which were prepared without a chiral influence, the stereochemistry as indicated in the Examples and Table 1 may have been assigned based on expected potencies (e.g., the compounds of Examples 33, 34, 35, and 42).

Separation of the stereoisomers is or can, be, performed using standard techniques (e.g., SFC). For example:

| Column name: | ChiralPak IH |
|---|---|
| Column size: | 250 * 30 mm 10 μm |
| Mobile Phase A: | Supercritical $CO_2$, |
| Mobile Phase B: | EtOH (0.1% $NH_3H_2O$) |
| A:B: | 70:30 |
| Flow: | 150 mL/min |
| Gradient Time | 4 min |

Example 1: Compound 101

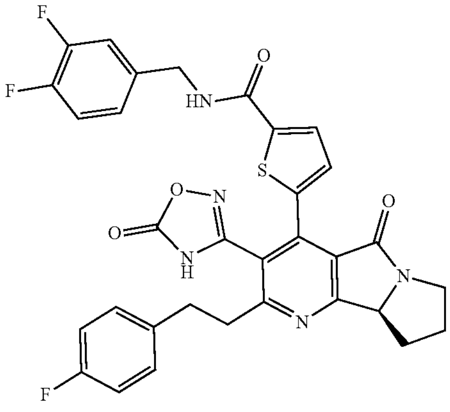

-continued
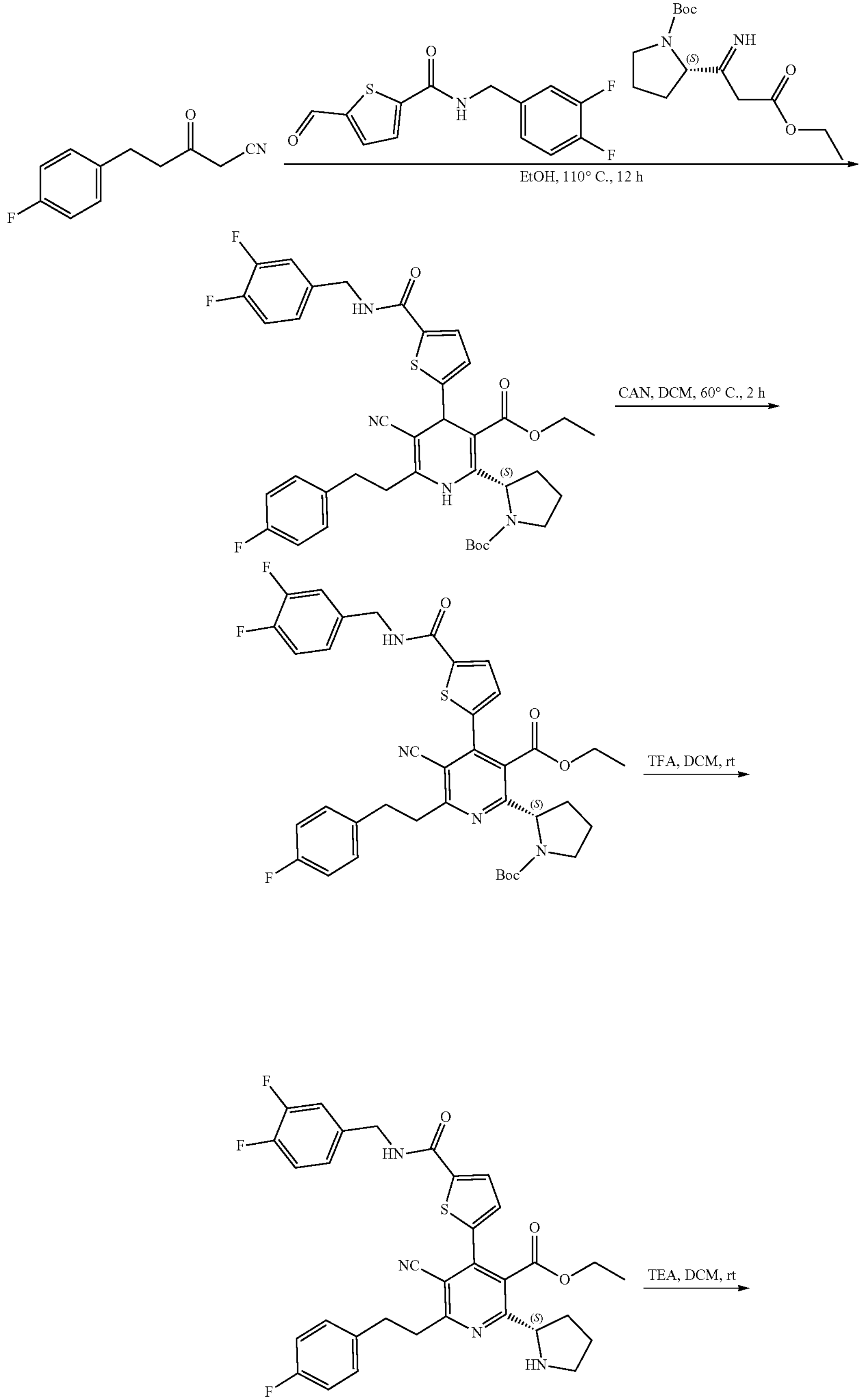

-continued

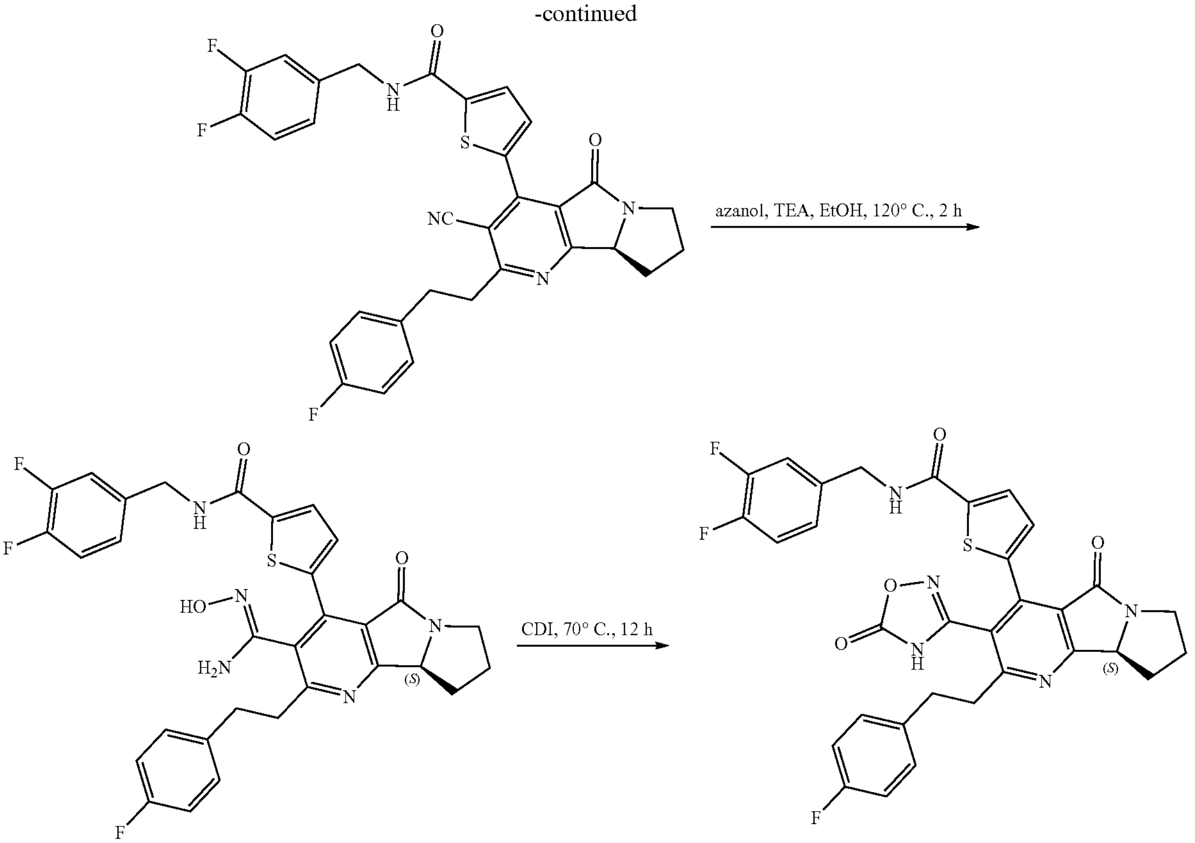

Step A ethyl 2-((S)-1-(tert-butoxycarbonyl)pyrrolidin-2-yl)-5-cyano-4-(5-((3,4-difluorobenzyl)carbamoyl)thiophen-2-yl)-6-(4-fluorophenethyl)-1,4-dihydropyridine-3-carboxylate

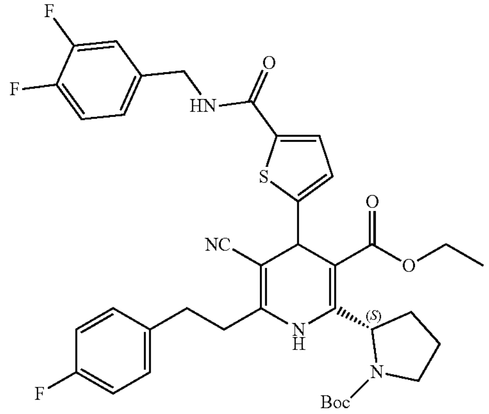

A mixture of 5-(4-fluorophenyl)-3-oxopentanenitrile (350 mg, 1.830 mmol), N-(3,4-difluorobenzyl)-5-formylthiophene-2-carboxamide (514.87 mg, 1.830 mmol) and tert-butyl (S)-2-(3-ethoxy-1-imino-3-oxopropyl)pyrrolidine-1-carboxylate (520.51 mg, 1.830 mmol) in EtOH (1 mL) was stirred at 110° C. for 12 h. The mixture reaction was concentrated under reduced pressure to afford ethyl 2-((S)-1-(tert-butoxycarbonyl)pyrrolidin-2-yl)-5-cyano-4-(5-((3,4-difluorobenzyl)carbamoyl)thiophen-2-yl)-6-(4-fluorophenethyl)-1,4-dihydropyridine-3-carboxylate (1.2 g, crude). LC-MS: m/z 721.0 $(M+H)^+$.

Step B ethyl (S)-2-(1-(tert-butoxycarbonyl)pyrrolidin-2-yl)-5-cyano-4-(5-((3,4-difluorobenzyl)carbamoyl)thiophen-2-yl)-6-(4-fluorophenethyl)nicotinate

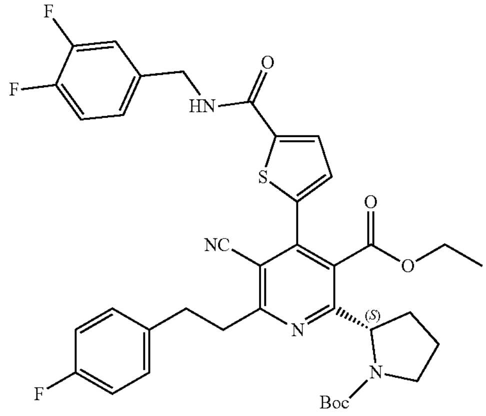

To a mixture of ethyl 2-((S)-1-(tert-butoxycarbonyl)pyrrolidin-2-yl)-5-cyano-4-(5-((3,4-difluorobenzyl)carbamoyl)thiophen-2-yl)-6-(4-fluorophenethyl)-1,4-dihydropyridine-3-carboxylate (1.2 g, 1.665 mmol) and diammonium cerium (IV) nitrate (1.37 g, 2.497 mmol) in EtOH (10 mL) was stirred at 50° C. for 2 hr. After the reaction was completed, the reaction was washed with $H_2O$ (100 mL) and extracted with EA (60 mL×3), the organic layer dried over sodium sulfate, filtered and concentrated in vacuum. The reaction was purified by column chromatography (PE/EA=1/1) to afford ethyl (S)-2-(1-(tert-butoxycarbonyl)pyrrolidin-2-yl)-5-cyano-4-(5-((3,4-difluorobenzyl)carbamoyl)thiophen-2-yl)-6-(4-fluorophenethyl)nicotinate (200 mg, 0.278 mmol, 16.71%). LC-MS: m/z 618.7 $(M-100)^+$.

Step C ethyl (S)-5-cyano-4-(5-((3,4-difluorobenzyl) carbamoyl)thiophen-2-yl)-6-(4-fluorophenethyl)-2-(pyrrolidin-2-yl)nicotinate

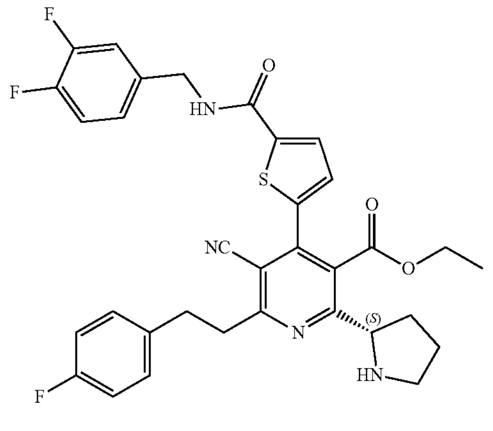

To a mixture of ethyl (S)-2-(1-(tert-butoxycarbonyl)pyrrolidin-2-yl)-5-cyano-4-(5-((3,4-difluorobenzyl)carbamoyl) thiophen-2-yl)-6-(4-fluorophenethyl)nicotinate (200 mg, 0.278 mmol) in DCM (2 mL) was added TFA (2 mL) and stirred at room temperature for 1 hour. After the reaction was completed, the reaction was concentrated in vacuum to afford ethyl (S)-5-cyano-4-(5-((3,4-difluorobenzyl)carbamoyl)thiophen-2-yl)-6-(4-fluorophenethyl)-2-(pyrrolidin-2-yl)nicotinate TFA (170 mg crude). LC-MS: m/z 618.8 $(M+H)^+$.

Step D (S)-5-(3-cyano-2-(4-fluorophenethyl)-5-oxo-7,8,9,9a-tetrahydro-5H-pyrido[2,3-a]pyrrolizin-4-yl)-N-(3,4-difluorobenzyl)thiophene-2-carboxamide

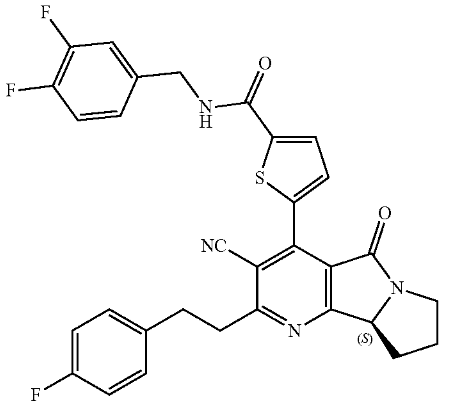

To a mixture of ethyl (S)-5-cyano-4-(5-((3,4-difluorobenzyl)carbamoyl)thiophen-2-yl)-6-(4-fluorophenethyl)-2-(pyrrolidin-2-yl)nicotinate TFA (170 mg, 0.275 mmol) in DCM (1.5 mL) was added TEA (0.3 mL, 2.158 mmol) and stirred at room temperature for 1 hour. The reaction was concentrated in vacuum and purified by reversed phase chromatography (0.1% FA) to afford (S)-5-(3-cyano-2-(4-fluorophenethyl)-5-oxo-7,8,9,9a-tetrahydro-5H-pyrido[2,3-a]pyrrolizin-4-yl)-N-(3,4-difluorobenzyl)thiophene-2-carboxamide (80 mg, 0.140 mmol, 50.84%). LC-MS: m/z 573.2 $(M+H)^+$.

Step E (S,Z)—N-(3,4-difluorobenzyl)-5-(2-(4-fluorophenethyl)-3-(N'-hydroxycarbamimidoyl)-5-oxo-7,8,9,9a-tetrahydro-5H-pyrido[2,3-a]pyrrolizin-4-yl) thiophene-2-carboxamide

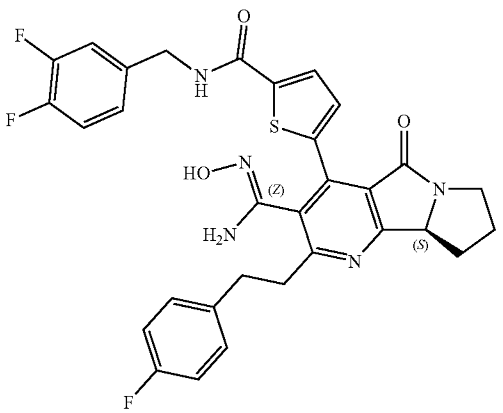

A mixture of(S)-5-(3-cyano-2-(4-fluorophenethyl)-5-oxo-7,8,9,9a-tetrahydro-5H-pyrido[2,3-a]pyrrolizin-4-yl)-N-(3,4-difluorobenzyl)thiophene-2-carboxamide (60 mg, 0.105 mmol), $NH_2OH$ in water (0.5 mL, 0.017 mmol) and TEA (0.044 mL, 0.314 mmol) in EtOH (1.0 mL) was stirred at 120° C. for 2 hr. The reaction was diluted with $H_2O$ (40 mL) and extracted with EA (30 mL×3), the organic layer dried over sodium sulfate, filtered and concentrated in vacuum. The reaction was purified by column chromatography (DCM/MeOH=15/1) to afford (S,Z)—N-(3,4-difluorobenzyl)-5-(2-(4-fluorophenethyl)-3-(N'-hydroxycarbamimidoyl)-5-oxo-7,8,9,9a-tetrahydro-5H-pyrido[2,3-a]pyrrolizin-4-yl)thiophene-2-carboxamide (15 mg, 0.025 mmol, 23.64%). LC-MS: m/z 605.7 $(M+H)^+$.

Step F Compound 101

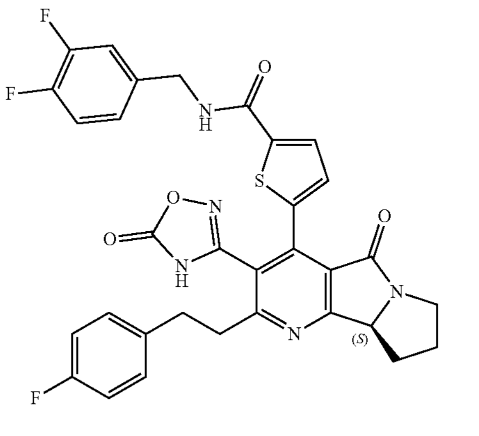

To a mixture of (S,Z)—N-(3,4-difluorobenzyl)-5-(2-(4-fluorophenethyl)-3-(N'-hydroxycarbamimidoyl)-5-oxo-7,8,9,9a-tetrahydro-5H-pyrido[2,3-a]pyrrolizin-4-yl)thiophene-2-carboxamide (15 mg, 0.025 mmol), CDI (4.02 mg, 0.025 mmol) and TEA (0.010 mL, 0.074 mmol) in THF (2 mL) was stirred at 70° C. for 6 hr. The reaction was washed with $H_2O$ (40 mL) and extracted with EA (40 mL×3), the organic layer dried over sodium sulfate, filtered and concentrated in vacuum. The reaction was purified by Prep-HPLC to afford Compound 101 (1.02 mg, 0.002 mmol, 6.52%).

$^1H$ NMR (400 MHz, $CDCl_3$-d+$CD_3OD$): δ 7.45-7.50 (m, 1H), 7.10-7.22 (m, 6H), 6.97 (t, J-8.0 Hz, 2H), 4.72-4.82 (m, 1H), 4.52 (s, 2H), 3.69-3.76 (m, 1H), 3.37-3.47 (m, 1H), 3.01-3.20 (m, 4H), 2.20-2.34 (m, 3H), 1.39-1.46 (m, 1H). $^{19}F$ NMR (377 MHz, $CDCl_3$-d+$CD_3OD$-d4): −116.83, −137.52, −139.81. LC-MS: m/z 632.2 $(M+H)^+$.

Compound 110

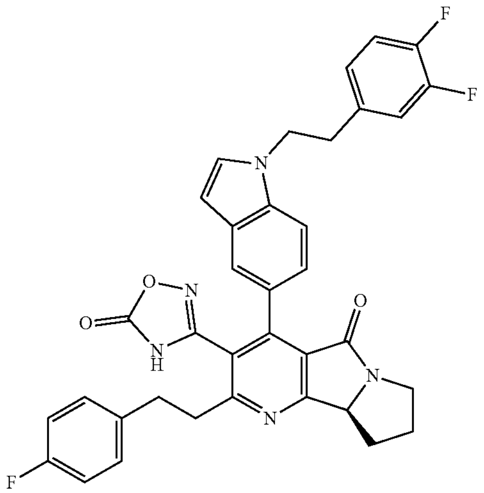

Compound 110 was synthesized using similar procedure as described in Example 1 above by using the appropriate materials.

$^1H$ NMR (400 MHz, DMSO-d6): δ 7.43-7.54 (m, 3H), 7.28-7.35 (m, 2H), 7.20-7.24 (m, 2H), 7.05-7.15 (m, 4H), 4.87 (d, J=3.2 Hz, 1H), 4.74 (dd, J=6.0 Hz, J=10.0 Hz, 1H), 4.39 (t, J=7.6 Hz, 2H), 3.49-3.52 (m, 1H), 3.23-3.25 (m, 1H), 3.09 (t, J=8.0 Hz, 2H), 2.97-3.04 (m, 4H), 2.33-2.39 (m, 1H), 2.20-2.25 (m, 2H), 1.31-1.36 (m, 1H). $^{19}F$ NMR (377 MHz, DMSO-d6): δ −117.45, −139.15, −142.17. LC-MS: m/z 636.3 $(M+H)^+$.

Compound 111

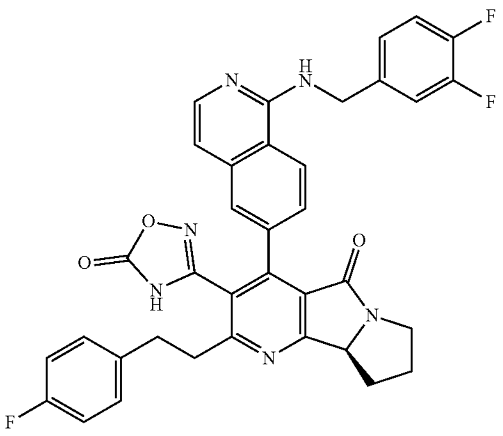

Compound 111 was synthesized using similar procedure as described in Example 1 above by using the appropriate materials.

$^1H$ NMR (400 MHz, DMSO-d6): δ 12.72 (br s, 1H), 8.27 (d, J=8.8 Hz, 1H), 8.10-8.17 (m, 1H), 7.87 (d, J=5.6 Hz, 1H), 7.63 (br s, 1H), 7.31-7.44 (m, 3H), 7.19-7.28 (m, 3H), 7.10 (t, J=8.8 Hz, 2H), 6.90 (d, J=5.6 Hz, 1H), 4.87 (dd, J=5.6 Hz, J=10.0 Hz, 1H), 4.73 (d, J=5.6 Hz, 2H), 3.48-3.59 (m, 1H), 3.24-3.27 (m, 1H), 2.98-3.17 (m, 4H), 2.22-2.41 (m, 3H), 1.32-2.46 (m, 1H). $^{19}F$ NMR (377 MHz, DMSO-d6): −117.10, −139.25, −142.13. LC-MS: m/z 649.1 $(M+H)^+$.

Compound 113

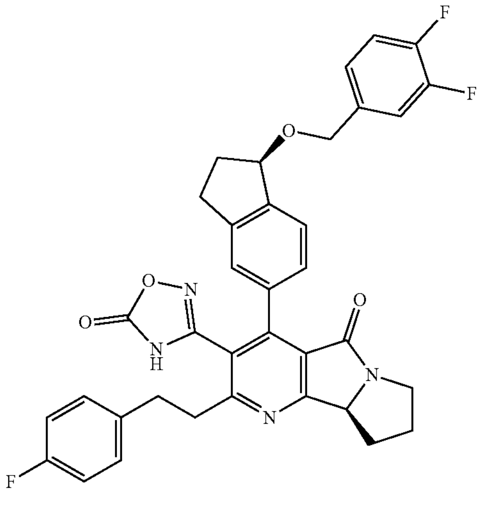

Compound 113 was synthesized using similar procedure as described in Example 1 above by using the appropriate materials.

$^1H$ NMR (400 MHz, DMSO-d6): δ 12.65 (br s, 1H), 7.38-7.46 (m, 3H), 7.20-7.25 (m, 4H), 7.05-7.12 (m, 3H), 5.06 (t, J=5.6 Hz, 1H), 4.83 (dd, J=6.4 Hz, J=10.4 Hz, 1H), 4.55-4.65 (m, 2H), 3.49-3.56 (m, 1H), 3.21-3.25 (m, 1H), 2.95-3.13 (m, 5H), 2.75-2.84 (m, 1H), 2.21-2.43 (m, 4H), 1.98-2.10 (m, 1H), 1.31-1.43 (m, 1H). $^{19}F$ NMR (377 MHz, DMSO-d6): −117.10, −138.93, −140.74. LC-MS: m/z 639.2 $(M+H)^+$.

Compound 114

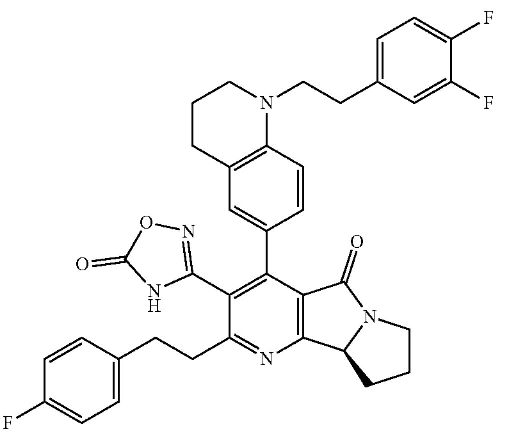

Compound 114 was synthesized using similar procedure as described in Example 1 above by using the appropriate materials.

$^{1}$H NMR (400 MHz, DMSO-d6): δ 12.52 (br s, 1H), 7.39-7.51 (m, 1H), 7.31-7.38 (m, 1H), 7.18-7.25 (m, 2H), 7.06-7.16 (m, 3H), 6.97 (dd, J=8.4 Hz, J=2.4 Hz, 1H), 6.89-6.93 (m, 1H), 6.60-6.71 (m, 1H), 4.78 (dd, J=10.0 Hz, J=6.0 Hz, 1H), 3.48-3.53 (m, 2H), 3.20-3.31 (m, 3H), 3.01-3.12 (m, 3H), 2.78-2.86 (m, 2H), 2.57-2.66 (m, 2H), 2.18-2.40 (m, 4H), 1.74-1.86 (m, 2H), 1.18-1.37 (m, 2H). $^{19}$F NMR (377 MHz, DMSO-d6): −74.40, −117.10, −139.21, −142.51. LC-MS: m/z 652.3 $(M+H)^{+}$

Example 2

5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 102)

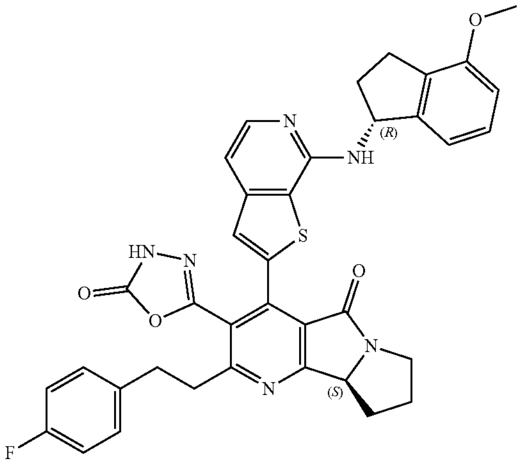

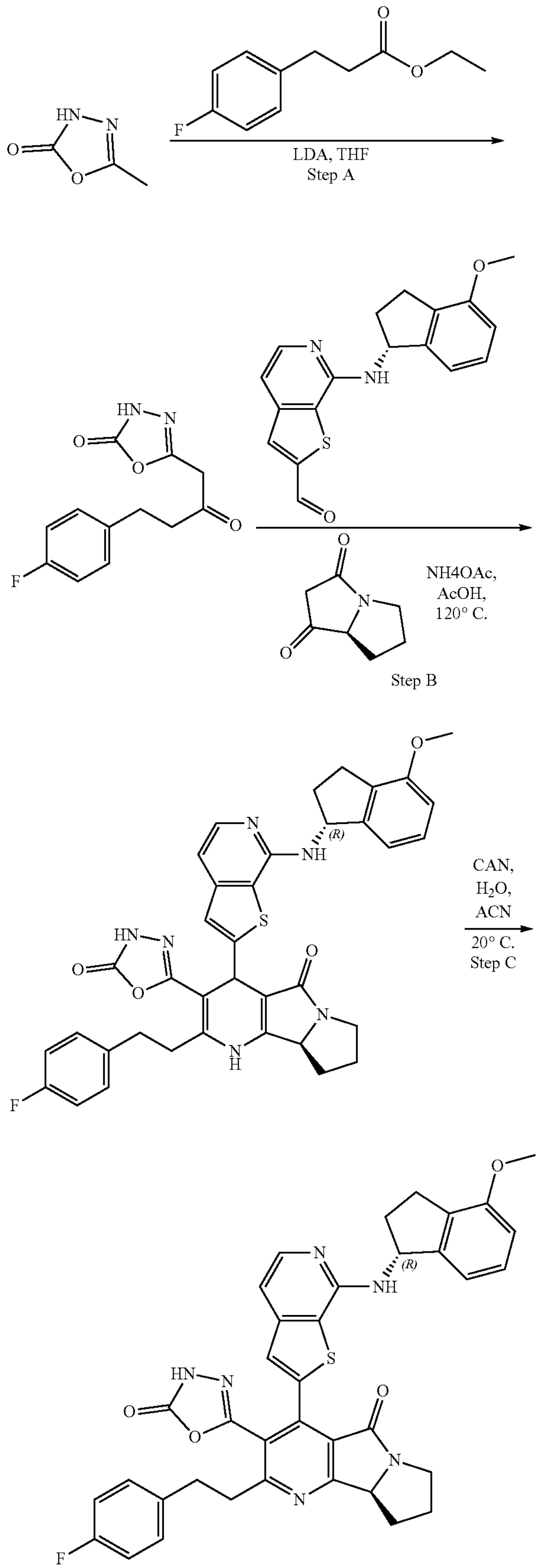

Step A 5-(4-(4-fluorophenyl)-2-oxobutyl)-1,3,4-oxadiazol-2(3H)-one

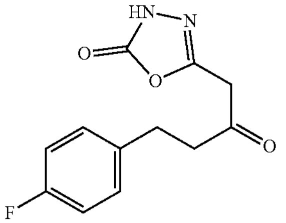

To a solution of LDA (2.0 M, 10.70 mL) in THF (25 mL) was added 5-methyl-3H-1,3,4-oxadiazol-2-one (1.02 g, 10.19 mmol) at −10° C. under $N_2$. The mixture was stirred at −10° C. for 30 min. Ethyl 3-(4-fluorophenyl)propanoate (1.0 g, 5.10 mmol) in THF (5.0 mL) was added into the reaction solution. The mixture was stirred at −10° C. for 1 hr. To the solution was added HCl (1 M) until pH=6~7. The mixture was extracted with EtOAc (100 mL). The organic layer was washed with brine (80 mL), dried over anhydrous of $Na_2SO_4$, filtered and concentrated in vacuum. The residue was purified by flash silica gel chromatography (ISCO®; 20 g SepaFlash® Silica Flash Column, Eluent of 0~60% Ethyl acetate/Petroleum ether, gradient @25 mL/min) to give 5-(4-(4-fluorophenyl)-2-oxobutyl)-1,3,4-oxadiazol-2(3H)-one (166 mg, 663.40 μmol, 13.02% yield, 80% purity by TLC). LC-MS: m/z 250.0 $(M+H)^+$.

Step B 5-((9aS)-2-(4-fluorophenethyl)-4-(7-(((R)-4-methoxy-2,3-dihydro-1H-inden-1-yl)amino)thieno[2,3-c]pyridin-2-yl)-5-oxo-1,5,7,8,9,9a-hexahydro-4H-pyrido[2,3-a]pyrrolizin-3-yl)-1,3,4-oxadiazol-2(3H)-one

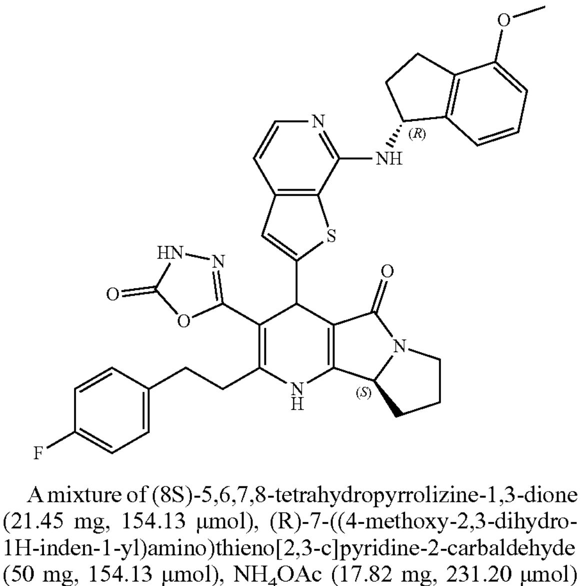

A mixture of (8S)-5,6,7,8-tetrahydropyrrolizine-1,3-dione (21.45 mg, 154.13 μmol), (R)-7-((4-methoxy-2,3-dihydro-1H-inden-1-yl)amino)thieno[2,3-c]pyridine-2-carbaldehyde (50 mg, 154.13 μmol), $NH_4OAc$ (17.82 mg, 231.20 μmol) and 5-(4-(4-fluorophenyl)-2-oxobutyl)-1,3,4-oxadiazol-2(3H)-one (38.57 mg, 154.13 μmol) in AcOH (0.5 mL) was degassed and purged with $N_2$ for 3 times, and then the mixture was stirred at 120° C. for 2 hrs under $N_2$ atmosphere. The mixture was cooled to room temperature and poured into water (5 mL), extracted with EtOAc (25 mL). The organic layer was washed with the aqueous of $NaHCO_3$ solution (25 mL), then brine (25 mL), dried over anhydrous of $Na_2SO_4$, concentrated in vacuum. The crude product 5-((9aS)-2-(4-fluorophenethyl)-4-(7-(((R)-4-methoxy-2,3-dihydro-1H-inden-1-yl)amino)thieno[2,3-c]pyridin-2-yl)-5-oxo-1,5,7,8,9,9a-hexahydro-4H-pyrido[2,3-a]pyrrolizin-3-yl)-1,3,4-oxadiazol-2(3H)-one (56 mg, crude) was obtained. LC-MS: m/z 677.7 $(M+H)^+$.

Step C 5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one

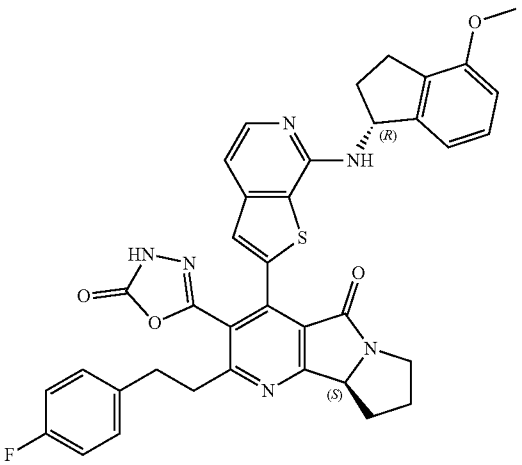

To a solution of 5-((9aS)-2-(4-fluorophenethyl)-4-(7-(((R)-4-methoxy-2,3-dihydro-1H-inden-1-yl)amino)thieno[2,3-c]pyridin-2-yl)-5-oxo-1,5,7,8,9,9a-hexahydro-4H-pyrido[2,3-a]pyrrolizin-3-yl)-1,3,4-oxadiazol-2(3H)-one (56.00 mg, crude) in ACN (5 mL) and water (2.5 mL) was added CAN (90.73 mg, 165.49 μmol). The mixture was stirred at 20° C. for 16 hrs. The mixture was poured into water (25 mL), extracted with EtOAc (25 mL). The organic layer was washed with brine (25 mL), dried over $Na_2SO_4$, filtered and concentrated in vacuum, The residue was purified by flash silica gel chromatography (ISCO®; 12 g SepaFlash® Silica Flash Column, Eluent of 0~10% MeOH/DCM gradient @12 mL/min), then re-purified by prep-HPLC (FA condition). Column: Kromasil C18 150*30 mm*5 μm; Condition: water (0.2% Formic acid)-ACN; Begin B: 25 End B: 55; Gradient Time (min): 10; 100% B Hold Time (Time): 5; Flow Rate (mL/min): 25; Detection wavelength: 220 nm and 254 nm) to give 5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (1.77 mg, 2.49 μmol, 3.01% yield, 95% purity).

$^1H$ NMR (400 MHz, $CDCl_3$) δ ppm 8.06 (d, J=5.6 Hz, 1H), 7.39 (s, 1H), 7.17-7.22 (m, 1H), 7.09-7.16 (m, 2H), 7.06 (d, J=5.60 Hz, 1H), 6.93-7.02 (m, 3H), 6.76 (d, J=8.0 Hz, 1H), 5.83 (s, 1H) 4.74-4.78 (m, 1H), 3.85 (s, 3H), 3.71-3.80 (m, 1H), 3.39-3.43 (m, 1H), 2.95-3.22 (m, 5H), 2.79-2.88 (m, 1H), 2.72-2.78 (m, 1H), 2.48-2.55 (m, 1H), 2.32-2.41 (m, 2H), 1.91-1.99 (m, 2H), 1.47 (m, 1H). LC-MS: m/z 675.2 $(M+H)^+$.

(S)—N-(3,4-difluorobenzyl)-5-(2-(4-fluorophenethyl)-5-oxo-3-(3-oxo-2,3-dihydroisoxazol-5-yl)-7,8,9,9a-tetrahydro-5H-pyrido[2,3-a]pyrrolizin-4-yl)thiophene-2-carboxamide (Compound 103)
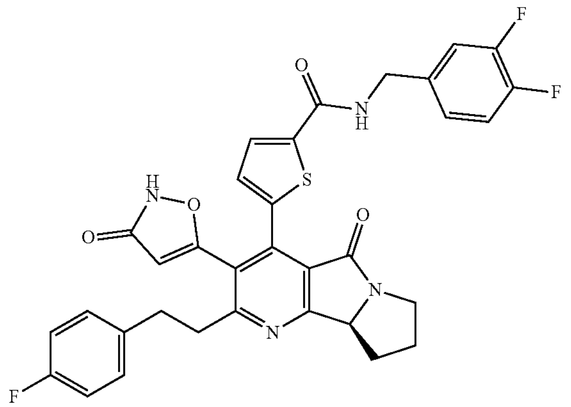 [SMILES: O=C(NCc1ccc(F)c(F)c1)c1ccc(-c2c3c(nc(CCc4ccc(F)cc4)c2-c2cc(=O)[nH]o2)[C@@H]2CCCN2C3=O)s1]
Compound 103 was synthesized using similar procedure as described in Example 2 above by using the appropriate materials.
$^1$H NMR (400 MHz, DMSO-$d_6$) δ ppm 11.42 (s, 1H), 9.11-9.39 (m, 1H), 7.70 (d, J=4.0 Hz, 1H), 7.35-7.44 (m, 2H), 7.03-7.20 (m, 6H), 6.04 (s, 1H), 4.81-4.85 (m, 1H), 4.38-4.49 (m, 2H), 3.51-3.60 (m, 1H), 2.88-3.08 (m, 4H), 2.11-2.44 (m, 4H), 1.33-1.45 (m, 1H). LC-MS: m/z 633.2 $(M+H)^+$.
Example 3: Compound 104
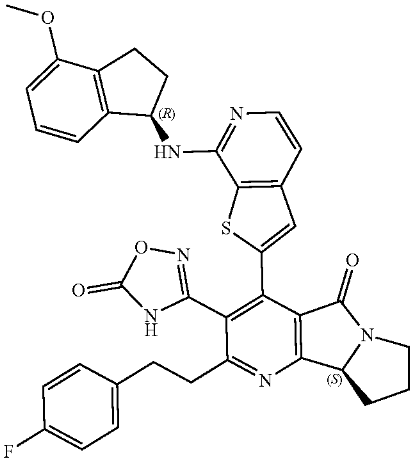
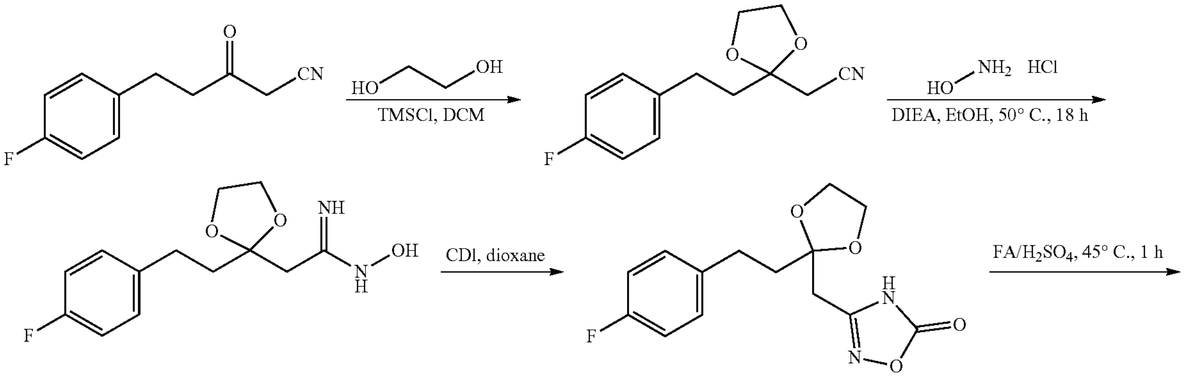

-continued
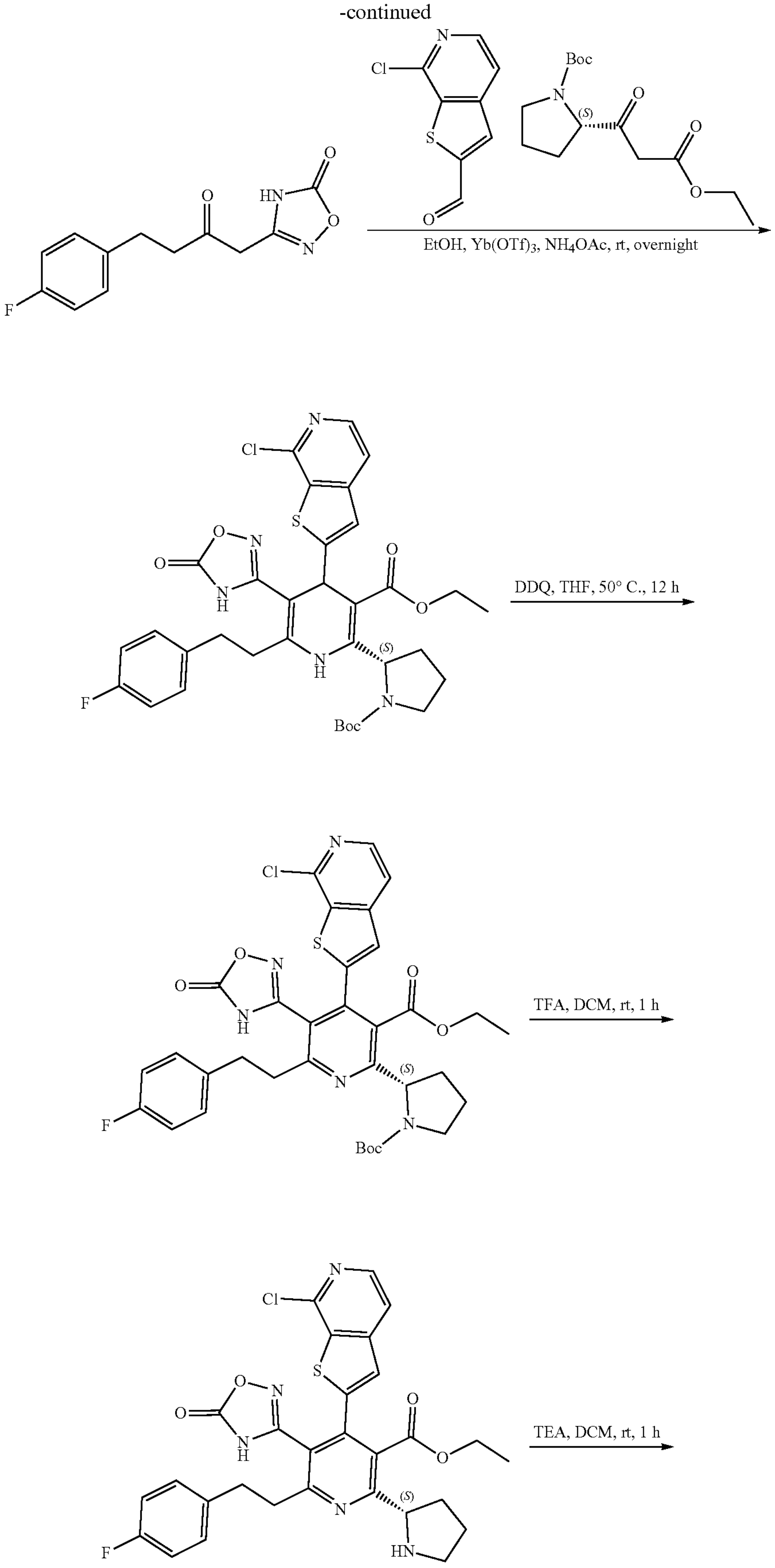

-continued

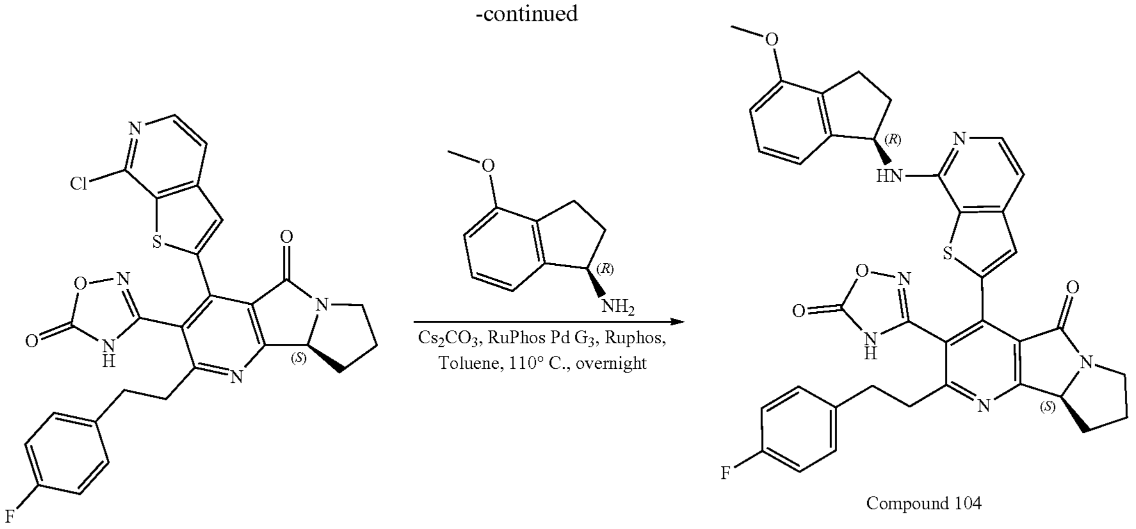

Compound 104

Step A {2-[2-(4-fluorophenyl)ethyl]-1,3-dioxolan-2-yl}acetonitrile

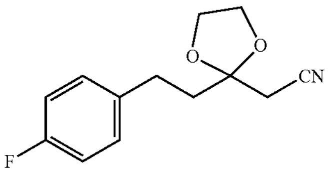 [SMILES: N#CCC1(CCc2ccc(F)cc2)OCCO1]

To a solution of 5-(4-fluorophenyl)-3-oxopentanenitrile (5 g, 26.149 mmol) in DCM (130 mL) were added ethylene glycol (4.375 mL, 78.448 mmol) and TMSCl (8.52 g, 78.448 mmol), and the reaction was stirred at 40° C. for 48 hr. The reaction was diluted with EA (200 mL) and water (100 mL). The organic layer was separated, washed with further water (100 mL×2) and saturated NaCl (100 mL). The organic layer was separated, dried with $Na_2SO_4$ and then filtered. The organic layer was collected, concentrated in vacuo. The residue was purified using silica gel column chromatography eluting with PE:EA=3:1. The organic layer was collected, concentrated in vacuo, and dried to afford the title compound {2-[2-(4-fluorophenyl)ethyl]-1,3-dioxolan-2-yl}acetonitrile (5.8 g, 24.654 mmol, 94.28%). LC-MS: m/z 257.9 $(M+Na)^+$.

Step B [(Z)-1-amino-2-{2-[2-(4-fluorophenyl) ethyl]-1,3-dioxolan-2-yl}ethylidene]hydroxylamine

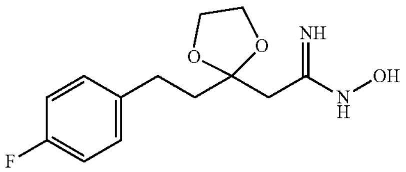 [SMILES: N=C(CC1(CCc2ccc(F)cc2)OCCO1)NO]

To a solution of {2-[2-(4-fluorophenyl)ethyl]-1,3-dioxolan-2-yl}acetonitrile (5.8 g, 24.654 mmol) in EtOH (110 mL) were added hydroxyaminehydrochloride (5.14 g, 73.962 mmol) and DIEA (19.12 g, 147.921 mmol), and the reaction was stirred at 50° C. for 18 hr. The reaction was diluted with EA (100 mL) and water (50 mL). The organic layer was separated, washed with further water (100 mL×2) and saturated NaCl (50 mL). The organic layer was dried with $Na_2SO_4$ and then filtered. The organic layer was collected, concentrated in vacuo. The residue was purified using silica gel column chromatography eluting with PE:EA=1:1. The organic layer was collected, concentrated in vacuo, and dried to afford the title compound [(1Z)-1-amino-2-{2-[2-(4-fluorophenyl)ethyl]-1,3-dioxolan-2-yl}ethylidene]hydroxylamine (4.7 g, 17.518 mmol, 71.06%). LC-MS: m/z 269.1 $(M+H)^+$.

Step C 3-({2-[2-(4-fluorophenyl)ethyl]-1,3-dioxolan-2-yl}methyl)-4H,5H-1,2,4-oxadiazol-5-one

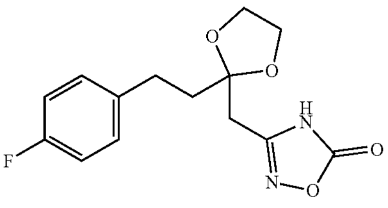 [SMILES: O=c1[nH]c(CC2(CCc3ccc(F)cc3)OCCO2)no1]

To a solution of [(1Z)-1-amino-2-{2-[2-(4-fluorophenyl) ethyl]-1,3-dioxolan-2-yl}ethylidene]hydroxyl amine (2 g, 7.455 mmol) in dioxane (100 mL) were added CDI (1.21 g, 7.455 mmol), and the reaction was stirred at 70° C. for 18 hr. The reaction was diluted with EA (100 mL) and water (50 mL). The organic layer was separated, washed with further water (100 mL×2) and saturated NaCl (50 mL). The organic layer was dried with $Na_2SO_4$ and then filtered. The organic layer was collected, concentrated in vacuo. The residue was purified using silica gel column chromatography eluting with DCM:MeOH=96:4. The organic layer was collected, concentrated in vacuo, and dried to afford the title compound 3-({2-[2-(4-fluorophenyl)ethyl]-1,3-dioxolan-2-yl}methyl)-4H,5H-1,2,4-oxadiazol-5-one (1.7 g, 5.777 mmol, 77.49%). LC-MS: m/z 317.2 $(M+Na)^+$.

Step D 3-[4-(4-fluorophenyl)-2-oxobutyl]-4H,5H-1,2,4-oxadiazol-5-one

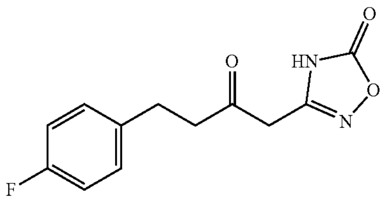 [SMILES: O=C(CCc1ccc(F)cc1)Cc1noc(=O)[nH]1]

To a solution of 3-({2-[2-(4-fluorophenyl)ethyl]-1,3-dioxolan-2-yl}methyl)-4H,5H-1,2,4-oxadiazol-5-one (700 mg, 2.379 mmol) in FA (7 mL) were added conc. $H_2SO_4$ (0.127 mL, 2.379 mmol), and the reaction was stirred at 45° C. for 1 hr. The reaction was diluted with EA (50 mL) and water (20 mL). The organic layer was separated, washed with further water (20 mL×2) and saturated NaCl (20 mL). The organic layer was dried with $Na_2SO_4$ and then filtered. The organic layer was collected, concentrated in vacuo. The residue was purified using silica gel column chromatography eluting with DCM:MeOH=96:4. The organic layer was collected, concentrated in vacuo, and dried to afford the title compound 3-[4-(4-fluorophenyl)-2-oxobutyl]-4H,5H-1,2,4-oxadiazol-5-one (490 mg, 1.958 mmol, 82.32%). LC-MS: m/z 273.0 $(M+Na)^+$.

Step E ethyl 2-((S)-1-(tert-butoxycarbonyl)pyrrolidin-2-yl)-4-(7-chlorothieno[2,3-c]pyridin-2-yl)-6-(4-fluorophenethyl)-5-(5-oxo-4,5-dihydro-1,2,4-oxadiazol-3-yl)-1,4-dihydropyridine-3-carboxylate

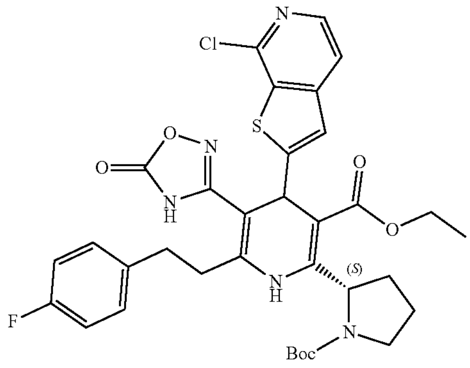

A mixture of 3-(4-(4-fluorophenyl)-2-oxobutyl)-1,2,4-oxadiazol-5(4H)-one (1000 mg, 3.996 mmol), 7-chlorothieno[2,3-c]pyridine-2-carbaldehyde (789.83 mg, 3.996 mmol), tert-butyl (S)-2-(3-ethoxy-3-oxopropanoyl)pyrrolidine-1-carboxylate (1140.31 mg, 3.996 mmol), $NH_4OAC$ (616.07 mg, 7.993 mmol) and $Yb((OTf)_3$ (247.77 mg, 0.400 mmol) in EtOH (20 mL) was stirred at room temperature for overnight. After the reaction was completed, the mixture was diluted with EA (50 mL) and washed with water (150 mL). The organic layers were dried over $Na_2SO_4$, filtered and concentrated to give ethyl 2-((S)-1-(tert-butoxycarbonyl)pyrrolidin-2-yl)-4-(7-chlorothieno[2,3-c]pyridin-2-yl)-6-(4-fluorophenethyl)-5-(5-oxo-4,5-dihydro-1,2,4-oxadiazol-3-yl)-1,4-dihydropyridine-3-carboxylate (2800 mg, crude). LC-MS: m/z 695.4 $(M+H)^+$.

Step F ethyl (S)-2-(1-(tert-butoxycarbonyl)pyrrolidin-2-yl)-4-(7-chlorothieno[2,3-c]pyridin-2-yl)-6-(4-fluorophenethyl)-5-(5-oxo-4,5-dihydro-1,2,4-oxadiazol-3-yl)nicotinate

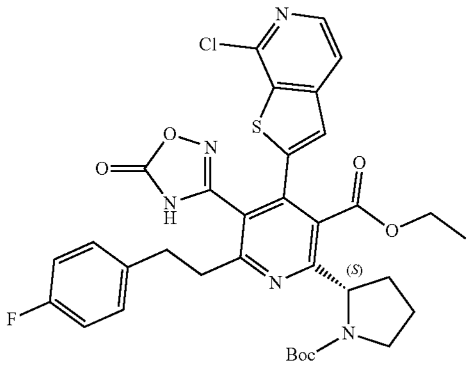

To a solution of ethyl 2-((S)-1-(tert-butoxycarbonyl)pyrrolidin-2-yl)-4-(7-chlorothieno[2,3-c]pyridin-2-yl)-6-(4-fluorophenethyl)-5-(5-oxo-4,5-dihydro-1,2,4-oxadiazol-3-yl)-1,4-dihydropyridine-3-carboxylate (2800 mg, crude) in THF (30 mL) was added DDQ (1278.16 mg, 5.631 mmol), and the reaction was stirred at 50° C. for 12 hr. After the reaction was completed, the mixture was diluted with EA (50 mL) and washed with water (200 mL). The organic layers were dried over $Na_2SO_4$, filtered and concentrated under vacuum to dryness. The residue was purified by column chromatography on silica gel (DCM/MeOH=20/1) to give ethyl (S)-2-(1-(tert-butoxycarbonyl)pyrrolidin-2-yl)-4-(7-chlorothieno[2,3-c]pyridin-2-yl)-6-(4-fluorophenethyl)-5-(5-oxo-4,5-dihydro-1,2,4-oxadiazol-3-yl)nicotinate (2 g, impure). LC-MS: m/z 693.4 $(M+H)^+$.

Step G ethyl (S)-4-(7-chlorothieno[2,3-c]pyridin-2-yl)-6-(4-fluorophenethyl)-5-(5-oxo-4,5-dihydro-1,2,4-oxadiazol-3-yl)-2-(pyrrolidin-2-yl)nicotinate TFA salt

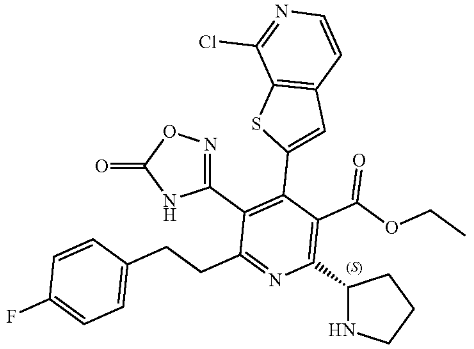

To a solution of ethyl (S)-2-(1-(tert-butoxycarbonyl)pyrrolidin-2-yl)-4-(7-chlorothieno[2,3-c]pyridin-2-yl)-6-(4-fluorophenethyl)-5-(5-oxo-4,5-dihydro-1,2,4-oxadiazol-3-yl)nicotinate (2.0 g, impure) in DCM (30 mL) was added TFA (7 mL, 91.414 mmol) and the reaction was stirred at room temperature for 1 hr. After the reaction was completed, the mixture was concentrated to give ethyl (S)-4-(7-chloro-thieno[2,3-c]pyridin-2-yl)-6-(4-fluorophenethyl)-5-(5-oxo-4,5-dihydro-1,2,4-oxadiazol-3-yl)-2-(pyrrolidin-2-yl)nicotinate TFA salt (2.5 g, crude). LC-MS: m/z 593.4 $(M+H)^+$.

Step H (S)-3-(4-(7-chlorothieno[2,3-c]pyridin-2-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one

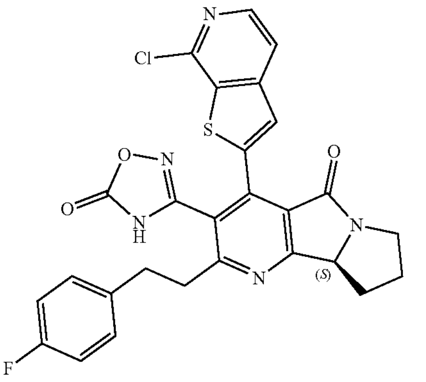

To a solution of ethyl (S)-4-(7-chlorothieno[2,3-c]pyridin-2-yl)-6-(4-fluorophenethyl)-5-(5-oxo-4,5-dihydro-1,2,4-oxadiazol-3-yl)-2-(pyrrolidin-2-yl)nicotinate TFA salt (2.5 g, crude) in DCM (30 mL) was added TEA (12 mL, 86.333 mmol), and the reaction was stirred at room temperature for 1 hr. After the reaction was completed, the mixture was diluted with EA (100 mL), washed with water (300 mL). The organic layers were dried over $Na_2SO_4$, filtered and concentrated under vacuum to dryness. The residue was purified by column chromatography on silica gel (DCM/MeOH=20/1) to give (S)-3-(4-(7-chlorothieno[2,3-c]pyridin-2-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one (640 mg, 1.168 mmol, 29.22%). LC-MS: m/z 547.4 $(M+H)^+$.

Step I—Compound 104

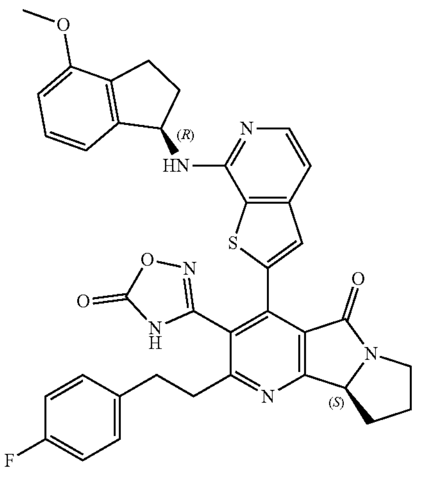

To a solution of (S)-3-(4-(7-chlorothieno[2,3-c]pyridin-2-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one (100 mg, 0.183 mmol), (R)-4-methoxy-2,3-dihydro-1H-inden-1-amine (61.85 mg, 0.311 mmol), RuPhos Pd $G_3$ (15.29 mg, 0.018 mmol), RuPhos (16.80 mg, 0.036 mmol) and $Cs_2CO_3$ (119.20 mg, 0.366 mmol) in toluene (3 mL) in a 10 mL sealed tube under $N_2$. The mixture was stirred at 110° C. for overnight. After the reaction was completed, the mixture was filtered and concentrated under vacuum to dryness. The residue was purified by column chromatography on silica gel (DCM/MeOH=20/1) to give Compound 104 (20 mg, crude). The residue was purified by column chromatography on C18-25g (FA 0.1%/ACN=36%) to give Compound 104 (2.98 mg, 2.43%).

$^1H$ NMR (400 MHz, DMSO-d6): δ 12.79 (br s, 1H), 7.98 (d, J=5.2 Hz, 1H), 7.41 (s, 1H), 7.19-7.33 (m, 3H), 7.04-7.17 (m, 4H), 6.79-6.88 (m, 2H), 5.90 (q, J=8.0 Hz, 1H), 4.87 (dd, J=6.0 Hz, J=10.0 Hz, 1H), 3.79 (s, 3H), 3.50-3.59 (m, 1H), 3.26-3.28 (m, 1H), 2.89-3.18 (m, 6H), 2.65-2.75 (m, 1H), 2.22-2.40 (m, 3H), 1.95-2.07 (m, 1H), 1.33-1.46 (m, 1H). $^{19}F$ NMR (377 MHz, DMSO-d6): −117.07. LC-MS: m/z 675.3 $(M+H)^+$.

4-(5-((3,4-difluorobenzyl)carbamoyl)thiophen-2-yl)-6-(4-fluorobenzyl)-2-isobutyl-5-(5-methyl-1,3,4-oxadiazol-2-yl)nicotinamide (Compound 123)

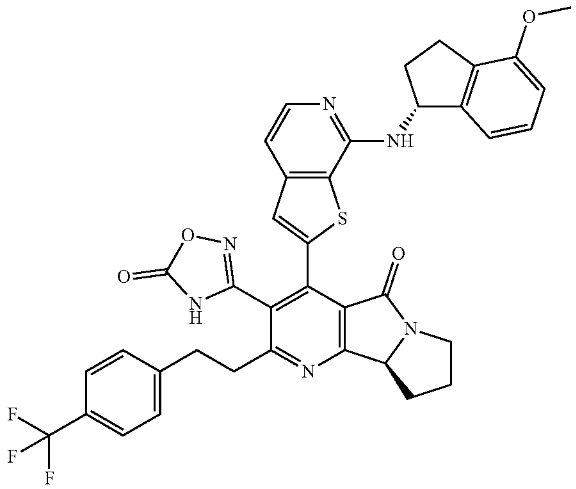 [SMILES: COc1cccc2c1CC[C@H]2Nc1nccc2cc(-c3c4c(nc(CCc5ccc(C(F)(F)F)cc5)c3-c3noc(=O)[nH]3)[C@@H]3CCCN3C4=O)sc12]

Compound 123 was synthesized using a similar procedure described in the Example 3 above by using the appropriate materials.

$^1H$ NMR (400 MHz, MeOD-$d_4$) δ 7.78 (d, J=6.85 Hz, 1H), 7.65 (s, 1H), 7.57 (br d, J=7.95 Hz, 2H), 7.37-7.45 (m, 1H), 7.41 (dd, J=7.64, 10.33 Hz, 3H), 7.28 (t, J=7.89 Hz, 1H), 6.98 (d, J=7.46 Hz, 1H), 6.92 (d, J=8.19 Hz, 1H), 5.52 (br t, J=6.85 Hz, 1H), 3.86 (s, 3H), 3.61-3.73 (m, 1H), 3.40-3.52 (m, 1H), 3.26-3.30 (m, 4H), 3.17-3.26 (m, 1H), 3.05-3.17 (m, 1H), 2.83-2.96 (m, 1H), 2.69-2.70 (m, 1H), 2.68-2.81 (m, 1H), 2.37-2.53 (m, 3H), 2.10-2.22 (m, 1H), 1.37-1.50 (m, 1H). LC-MS: m/z 725.4 $(M+H)^+$.

3-((S)-4-(7-(((R)-4-methoxy-2,3-dihydro-1H-inden-1-yl)amino)thieno[2,3-c]pyridin-2-yl)-5-oxo-2-(3-(trifluoromethyl)phenethyl)-7,8,9,9a-tetrahydro-5H-pyrido[2,3-a]pyrrolizin-3-yl)-1,2,4-oxadiazol-5(4H)-one (Compound 124)

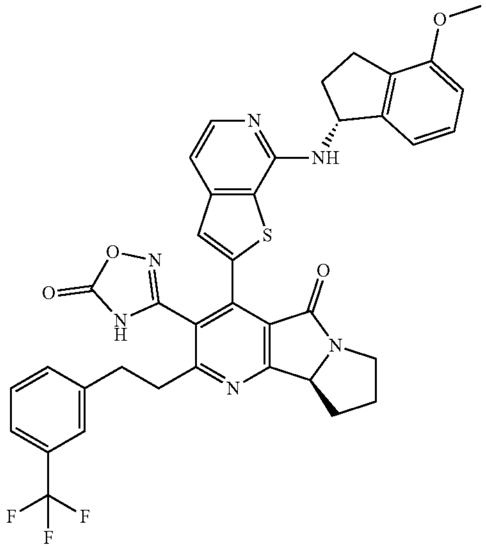 [SMILES: COc1cccc2c1CC[C@H]2Nc1nccc2cc(-c3c4c(nc(CCc5cccc(C(F)(F)F)c5)c3-c3noc(=O)[nH]3)[C@@H]3CCCN3C4=O)sc12]

Compound 124 was synthesized using a similar procedure described in the Example 3 above by using the appropriate materials.

$^1$H NMR (400 MHz, MeOD) δ ppm 8.24 (s, 1H), 7.79 (d, J=6.36 Hz, 1H), 7.44-7.55 (m, 5H), 7.16-7.30 (m, 2H), 6.94 (d, J=7.34 Hz, 1H), 6.87 (d, J=8.07 Hz, 1H), 5.61 (t, J=6.91 Hz, 1H), 4.65 (m, 1H), 3.85 (s, 3H), 3.55-3.73 (m, 1H), 3.35-3.51 (m, 1H), 3.04-3.25 (m, 5H), 2.83 (dt, J=16.11, 7.90 Hz, 1H), 2.65-2.75 (m, 1H), 2.42 (d, J=13.69 Hz, 3H), 2.04-2.15 (m, 1H). 1.34-1.46 (m, 1H). LC-MS: m/z 725.4 $(M+H)^+$.

3-((S)-4-(7-(((R)-4-methoxy-2,3-dihydro-1H-inden-1-yl)amino)thieno[2,3-c]pyridin-2-yl)-5-oxo-2-(2-(trifluoromethyl)phenethyl)-7,8,9,9a-tetrahydro-5H-pyrido[2,3-a]pyrrolizin-3-yl)-1,2,4-oxadiazol-5(4H)-one (Compound 125)

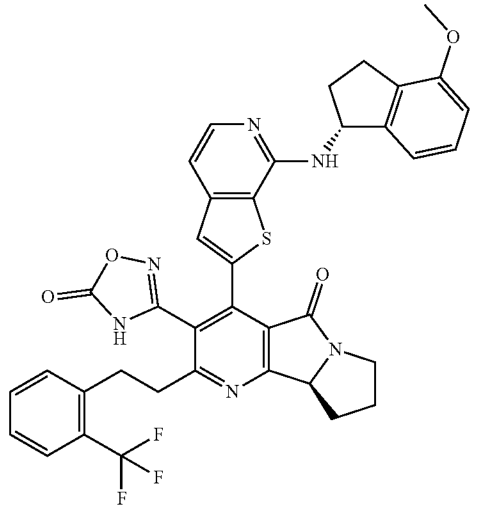 [SMILES: COc1cccc2c1CC[C@H]2Nc1nccc2cc(-c3c4c(nc(CCc5ccccc5C(F)(F)F)c3-c3noc(=O)[nH]3)[C@@H]3CCCN3C4=O)sc12]

Compound 125 was synthesized using a similar procedure described in the Example 3 above by using the appropriate materials.

$^1$H NMR (400 MHz, MeOD-$d_4$) δ 7.66-7.71 (m, 1H), 7.53-7.59 (m, 2H), 7.42-7.50 (m, 1H), 7.25-7.37 (m, 3H), 7.14-7.21 (m, 1H), 6.80-6.92 (m, 2H), 5.37-5.47 (m, 1H), 3.73-3.81 (m, 3H), 3.49-3.63 (m, 1H), 3.30-3.40 (m, 1H), 3.17 (d, J=1.71 Hz, 4H), 2.97-3.05 (m, 1H), 2.75-2.82 (m, 1H), 2.58-2.71 (m, 1H), 2.27-2.47 (m, 3H), 2.00-2.13 (m, 1H), 1.31-1.45 (m, 1H), 1.21-1.24 (m, 1H). LC-MS: m/z 725.4 $(M+H)^+$.

3-((S)-2-(4-isopropylphenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,2,4-oxadiazol-5(4H)-one (Compound 126)

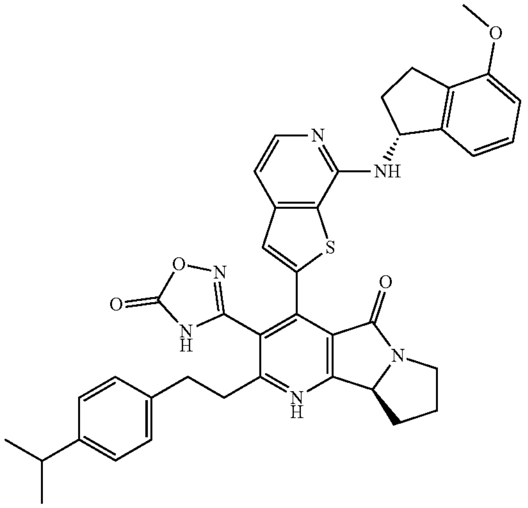 [SMILES: COc1cccc2c1CC[C@H]2Nc1nccc2cc(-c3c4c(nc(CCc5ccc(C(C)C)cc5)c3-c3noc(=O)[nH]3)[C@@H]3CCCN3C4=O)sc12]

Compound 126 was synthesized using a similar procedure described in the Example 3 above by using the appropriate materials.

$^1$H NMR (400 MHz, DMSO-$d_6$) δ 9.24 (s, 1H), 7.89 (d, J=6.60 Hz, 1H), 7.63 (s, 1H), 7.40 (d, J=6.60 Hz, 1H), 7.23 (t, J=7.82 Hz, 1H), 7.11-7.16 (m, 5H), 6.94 (dd, J=7.83, 15.16 Hz, 2H), 5.64 (q, J=7.09 Hz, 1H), 4.91 (dd, J=6.30, 10.21 Hz, 1H), 3.81 (s, 3H), 3.12-3.17 (m, 2H), 3.05 (d, J=5.50 Hz, 1H), 2.94-3.00 (m, 2H), 2.71-2.86 (m, 4H), 2.62 (td, J=4.55, 12.65 Hz, 1H), 2.32-2.38 (m, 1H), 2.23-2.31 (m, 2H), 2.10 (dd, J=7.89, 12.78 Hz, 1H), 1.35-1.47 (m, 1H), 1.16 (d, J=6.85 Hz, 6H). LC-MS: m/z 699.4 $(M+H)^+$.

3-((S)-2-(4-cyclopropylphenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,2,4-oxadiazol-5(4H)-one (Compound 127)

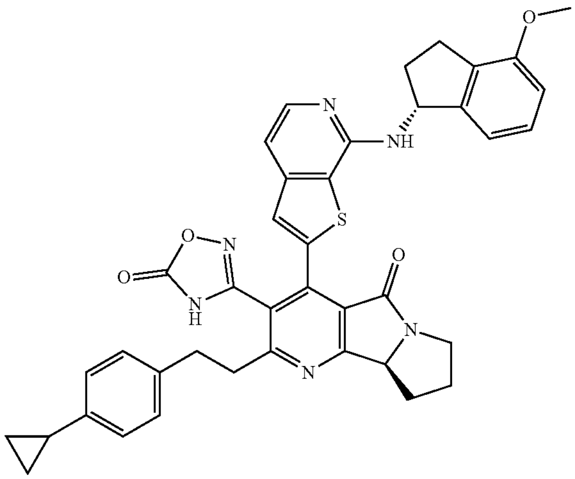 [SMILES: COc1cccc2c1CC[C@H]2Nc1nccc2cc(-c3c4c(nc(CCc5ccc(C6CC6)cc5)c3-c3noc(=O)[nH]3)[C@@H]3CCCN3C4=O)sc12]

Compound 127 was synthesized using a similar procedure described in the Example 3 above by using the appropriate materials.

$^1$H NMR (400 MHz, MeOD-$d_4$) δ ppm 8.32 (s, 1H), 7.84 (d, J=6.24 Hz, 1H), 7.51 (s, 1H), 7.19-7.28 (m, 2H), 7.07 (d, J=7.95 Hz, 2H), 6.93-7.01 (m, 3H), 6.87 (d, J=7.44 Hz, 1H), 5.67 (t, J=6.79 Hz, 1H), 4.63 (s, 1H), 3.86 (m, 3H), 3.62-3.73 (m, 1H), 3.38-3.48 (m, 1H), 3.13-3.20 (m, 2H), 2.98-3.12 (m, 3H), 2.84 (dt, J=16.11, 8.15 Hz, 1H), 2.67-2.76 (m, 1H), 2.37-2.54 (m, 3H), 2.09 (br dd, J=12.41, 8.13 Hz, 1H), 1.83-1.90 (m, 1H), 1.38-1.50 (m, 1H), 0.89-0.95 (m, 2H), 0.64 (d, J=4.89 Hz, 2H). LC-MS: m/z 697.5 $(M+H)^+$.

4-(5-((3,4-difluorobenzyl)carbamoyl)thiophen-2-yl)-6-(4-fluorobenzyl)-2-isobutyl-5-(5-methyl-1,3,4-oxadiazol-2-yl)nicotinamide (Compound 128)

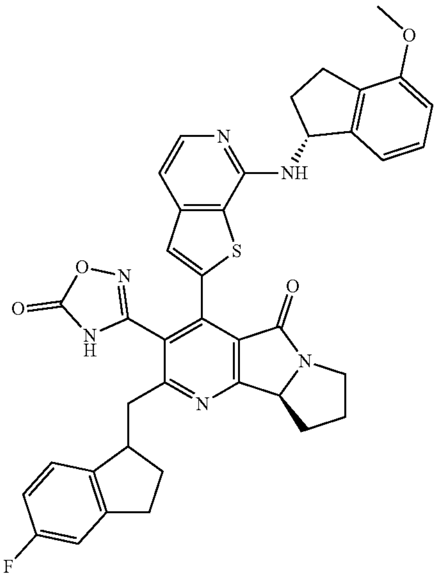 [SMILES: COc1cccc2c1CC[C@H]2Nc1nccc2cc(-c3c4c(nc(CC5CCc6cc(F)ccc65)c3-c3noc(=O)[nH]3)[C@@H]3CCCN3C4=O)sc12]

Compound 128 synthesized using a similar procedure described in the Example 3 above by using the appropriate materials.

$^1$H NMR (400 MHz, MeOD-$d_4$) δ 7.78 (d, J=6.85 Hz, 1H), 7.67 (d, J=2.57 Hz, 1H), 7.43 (d, J=6.85 Hz, 1H), 7.28 (t, J=7.83 Hz, 1H), 6.90-7.10 (m, 3H), 6.78-6.88 (m, 1H), 5.52 (t, J=6.66 Hz, 1H), 3.86 (s, 3H), 3.63-3.81 (m, 2H), 3.46 (dd, J=5.93, 11.19 Hz, 1H), 3.36-3.43 (m, 1H), 3.36-3.42 (m, 1H), 3.07-3.16 (m, 1H), 2.65-3.06 (m, 6H), 2.39-2.56 (m, 3H), 2.10-2.27 (m, 2H), 1.80-1.98 (m, 1H), 1.50 (d, J=3.91 Hz, 1H). LC-MS: m/z 701.4 $(M+H)^+$.

Compound 130

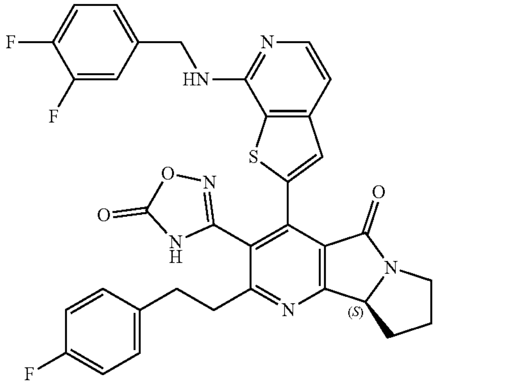

Compound 130 was synthesized using a similar procedure described in the Example 3 above by using the appropriate materials.

$^1$H NMR (400 MHz, DMSO-d6): δ 12.84 (br s, 1H), 7.85-7.95 (m, 1H), 7.17-7.66 (m, 8H), 7.10 (t, J=8.8 Hz, 2H), 4.86-4.97 (m, 1H), 4.64-4.79 (m, 2H), 3.54-3.58 (m, 1H), 3.16-3.21 (m, 2H), 3.03-3.15 (m, 3H), 2.36-2.40 (m, 1H), 2.26-2.34 (m, 2H), 1.36-1.48 (m, 1H). $^{19}$F NMR (377 MHz, DMSO-d6): −117.01, −71.08, −69.19. LC-MS: m/z 655.2 $(M+H)^+$.

(S)-3-(4-(7-((3,4-difluorobenzyl)oxy)thieno[2,3-c]pyridin-2-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one (Compound 133)

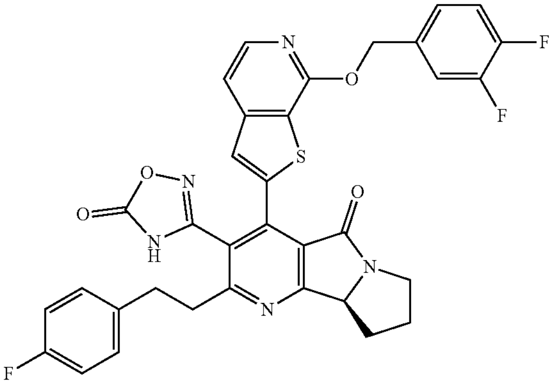 [SMILES: O=C1c2c(nc(CCc3ccc(F)cc3)c(-c3noc(=O)[nH]3)c2-c2cc3ccnc(OCc4ccc(F)c(F)c4)c3s2)[C@@H]2CCCN12]

Compound 133 was synthesized using a similar procedure described in the Example 3 above by using the appropriate materials.

$^1$H NMR (400 MHz, MeOD-$d_4$) δ 7.92-7.99 (m, 1H), 7.40-7.49 (m, 1H), 7.29-7.38 (m, 2H), 7.14-7.24 (m, 2H), 7.06-7.12 (m, 2H), 6.84-6.93 (m, 2H), 5.45 (s, 2H), 3.51-3.62 (m, 1H), 3.28-3.39 (m, 1H), 3.07-3.14 (m, 2H), 2.91-3.04 (m, 2H), 2.23-2.45 (m, 3H), 1.29-1.45 (m, 1H), 1.19 (m, 1H). LC-MS: m/z 656.1 $(M+H)^+$.

(S)-3-(4-(7-(4-fluoroisoindolin-2-yl)thieno[2,3-c]pyridin-2-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one (Compound 137)

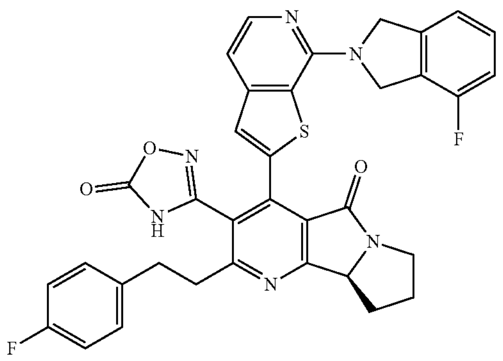 [SMILES: O=C1c2c(nc(CCc3ccc(F)cc3)c(-c3noc(=O)[nH]3)c2-c2cc3ccnc(N4Cc5cccc(F)c5C4)c3s2)[C@@H]2CCCN12]

Compound 137 was synthesized using a similar procedure described in the Example 3 above by using the appropriate materials.

$^1$H NMR (400 MHz, MeOD-$d_4$) δ 7.79-7.89 (m, 1H), 7.72 (s, 1H), 7.44-7.56 (m, 2H), 7.35 (d, J=7.70 Hz, 1H), 7.16-7.27 (m, 3H), 6.94-7.07 (m, 2H), 5.39-5.54 (m, 4H), 3.64-3.77 (m, 1H), 3.43-3.53 (m, 1H), 3.23-3.31 (m, 3H), 3.22 (m, 2H), 2.40-2.59 (m, 3H), 1.43-1.57 (m, 1H). LC-MS: m/z 649.3 $(M+H)^+$.

(S)-3-(4-(7-(6-fluoro-3,4-dihydroisoquinolin-2(1H)-yl)thieno[2,3-c]pyridin-2-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one (Compound 138)

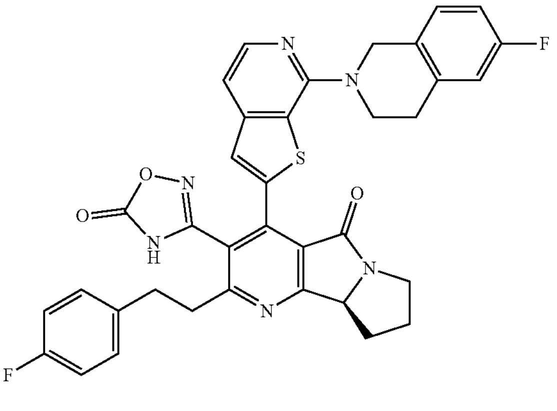 [SMILES: O=C1c2c(nc(CCc3ccc(F)cc3)c(-c3noc(=O)[nH]3)c2-c2cc3ccnc(N4CCc5cc(F)ccc5C4)c3s2)[C@@H]2CCCN12]

Compound 138 was synthesized using a similar procedure described in the Example 3 above by using the appropriate materials.

$^1$H NMR (400 MHz, MeOD-$d_4$) δ 7.83-7.90 (m, 1H), 7.70-7.76 (m, 1H), 7.50 (d, J=6.72 Hz, 1H), 7.32-7.40 (m, 1H), 7.18-7.25 (m, 2H), 7.06-7.15 (m, 2H), 7.01 (t, J=8.74 Hz, 2H), 5.06 (s, 2H), 4.14 (s, 2H), 3.63-3.76 (m, 1H), 3.39-3.53 (m, 1H), 3.19-3.28 (m, 5H), 3.10-3.19 (m, 2H), 2.41-2.60 (m, 3H), 1.41-1.56 (m, 1H). LC-MS: m/z 663.3 $(M+H)^+$.

Compound 139

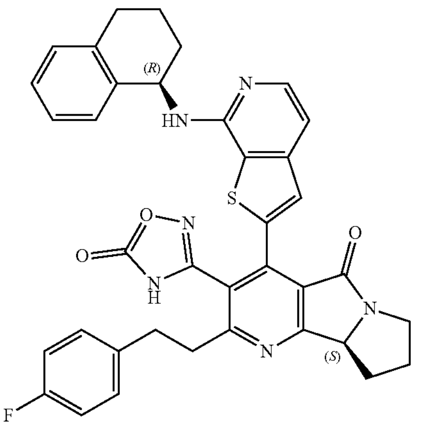

Compound 139 was synthesized using a similar procedure described in the Example 3 above by using the appropriate materials.

$^1$H NMR (400 MHz, DMSO-d6): δ 12.79 (br s, 1H), 7.97 (d, J=5.6 Hz, 1H), 7.41 (s, 1H), 7.20-7.37 (m, 4H), 7.05-7.17 (m, 6H), 5.57-5.67 (m, 1H), 4.89 (dd, J=10.0 Hz, J=6.0 Hz, 1H), 3.49-3.60 (m, 1H), 3.24-3.28 (m, 1H), 2.99-3.18 (m, 4H), 2.72-2.84 (m, 2H), 2.23-2.38 (m, 3H), 1.71-2.04 (m, 4H), 1.34-1.47 (m, 1H). $^{19}$F NMR (377 MHz, DMSO-d6): δ -117.06. LC-MS: m/z 659.3 $(M+H)^+$.

Example 4 (Compound 148)

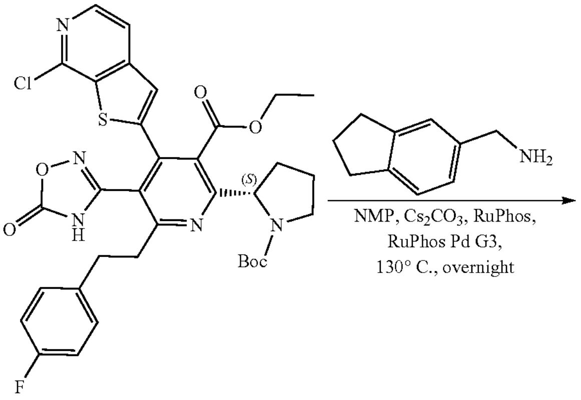

-continued

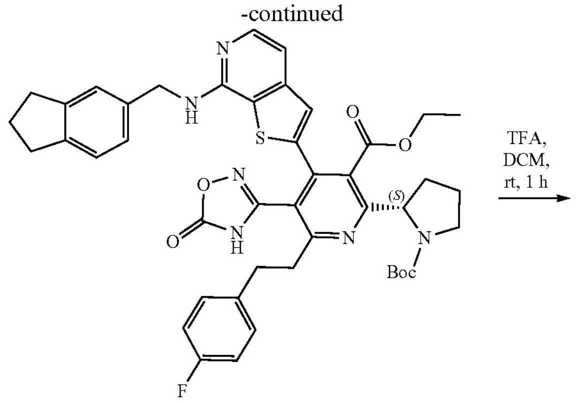

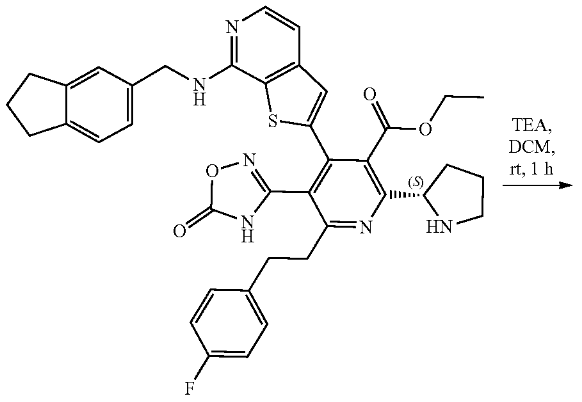

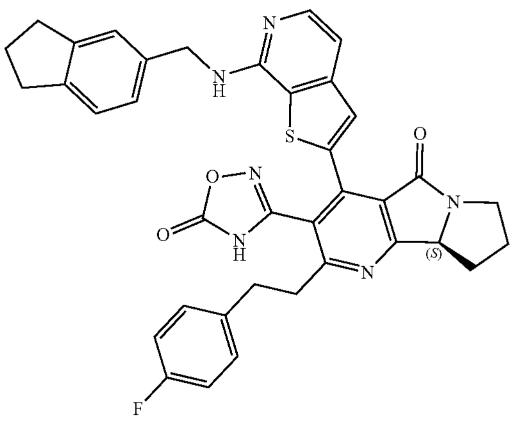

Step A ethyl (S)-2-(1-(tert-butoxycarbonyl)pyrrolidin-2-yl)-4-(7-(((2,3-dihydro-1H-inden-5-yl)methyl)amino)thieno[2,3-c]pyridin-2-yl)-6-(4-fluorophenethyl)-5-(5-oxo-4,5-dihydro-1,2,4-oxadiazol-3-yl)nicotinate

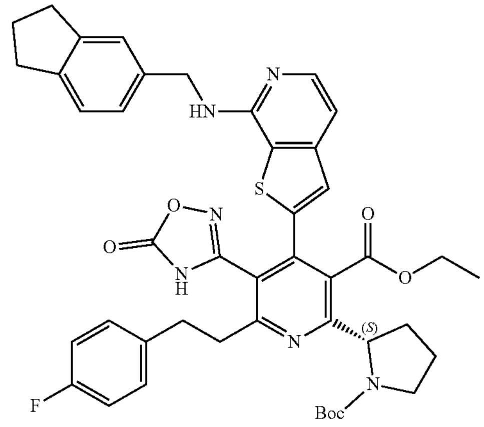

A mixture of ethyl (S)-2-(1-(tert-butoxycarbonyl)pyrrolidin-2-yl)-4-(7-chlorothieno[2,3-c]pyridin-2-yl)-6-(4-fluorophenethyl)-5-(5-oxo-4,5-dihydro-1,2,4-oxadiazol-3-yl)nicotinate (100 mg, 0.144 mmol), (2,3-dihydro-1H-inden-5-yl)methanamine (106.04 mg, 0.720 mmol), $Cs_2CO_3$ (234.68 mg, 0.720 mmol), RuPhos (13.44 mg, 0.029 mmol) and RuPhos-Pd-G3 (12.06 mg, 0.014 mmol) in NMP (2 mL) in was stirred at 130° C. overnight under $N_2$. After the reaction was completed, the mixture was filtered, diluted with EA (20 mL), washed with water (40 mL). The organic layers were dried over $Na_2SO_4$, filtered and concentrated under vacuum to dryness. The residue was purified by Prep-TLC (DCM/MeOH=15/1) to give ethyl (S)-2-(1-(tert-butoxycarbonyl)pyrrolidin-2-yl)-4-(7-(((2,3-dihydro-1H-inden-5-yl)methyl)amino)thieno[2,3-c]pyridin-2-yl)-6-(4-fluorophenethyl)-5-(5-oxo-4,5-dihydro-1,2,4-oxadiazol-3-yl)nicotinate (40 mg, 0.050 mmol, 34.49%). LC-MS: m/z 804.4 $(M+H)^+$.

Step B ethyl (S)-4-(7-(((2,3-dihydro-1H-inden-5-yl)methyl)amino)thieno[2,3-c]pyridin-2-yl)-6-(4-fluorophenethyl)-5-(5-oxo-4,5-dihydro-1,2,4-oxadiazol-3-yl)-2-(pyrrolidin-2-yl)nicotinate TFA salt

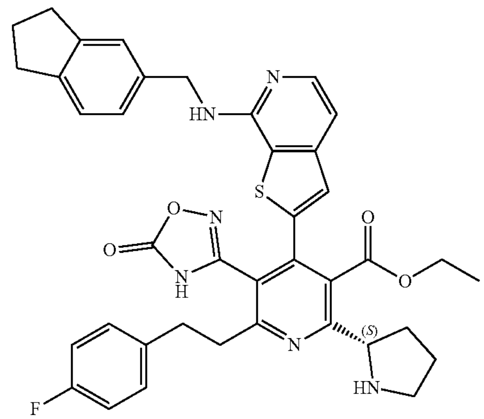

To a solution of ethyl (S)-2-(1-(tert-butoxycarbonyl)pyrrolidin-2-yl)-4-(7-(((2,3-dihydro-1H-inden-5-yl)methyl)amino)thieno[2,3-c]pyridin-2-yl)-6-(4-fluorophenethyl)-5-(5-oxo-4,5-dihydro-1,2,4-oxadiazol-3-yl)nicotinate (40 mg, 0.050 mmol) in DCM (3 mL) was added TFA (1 mL) and the reaction was stirred at room temperature for 1 h. After the reaction was completed, the mixture was concentrated to give ethyl (S)-4-(7-(((2,3-dihydro-1H-inden-5-yl)methyl)amino)thieno[2,3-c]pyridin-2-yl)-6-(4-fluorophenethyl)-5-(5-oxo-4,5-dihydro-1,2,4-oxadiazol-3-yl)-2-(pyrrolidin-2-yl)nicotinate TFA salt (50 mg, crude). LC-MS: m/z 704.5 $(M+H)^+$.

Step C Compound 148

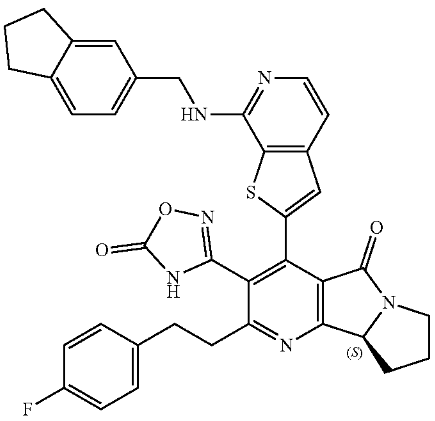

To a solution of ethyl (S)-4-(7-(((2,3-dihydro-1H-inden-5-yl)methyl)amino)thieno[2,3-c]pyridin-2-yl)-6-(4-fluorophenethyl)-5-(5-oxo-4,5-dihydro-1,2,4-oxadiazol-3-yl)-2-(pyrrolidin-2-yl)nicotinate TFA salt (50 mg, crude) in DCM (2 mL) was added TEA (1 mL), and the reaction was stirred at room temperature for 1 h. After the reaction was completed, the mixture was filtered, diluted with EA (20 mL), washed with water (40 mL). The organic layers were dried over $Na_2SO_4$, filtered and concentrated under vacuum to dryness. The residue was purified by Prep-HPLC to give Compound 148 (9.99 mg, 0.015 mmol, 30.54%).

$^1$H NMR (400 MHz, DMSO-d6): δ 12.79 (bs, 1H), 7.97 (d, J=5.2 Hz, 1H), 7.52 (s, 1H), 7.44 (s, 1H), 7.17-7.30 (m, 3H), 7.01-7.16 (m, 5H), 4.85-4.94 (m, 1H), 4.65 (d, J=5.6 Hz, 2H), 3.49-3.65 (m, 1H), 2.95-3.22 (m, 5H), 2.72-2.86 (m, 4H), 2.20-2.42 (m, 3H), 1.88-2.07 (m, 2H), 1.31-1.48 (m, 1H). $^{19}$F NMR (377 MHz, DMSO-d6): −117.05. LC-MS: m/z 659.3 $(M+H)^+$.

(S)-3-(4-(7-((3,4-difluorobenzyl)(methyl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one (Compound 107)

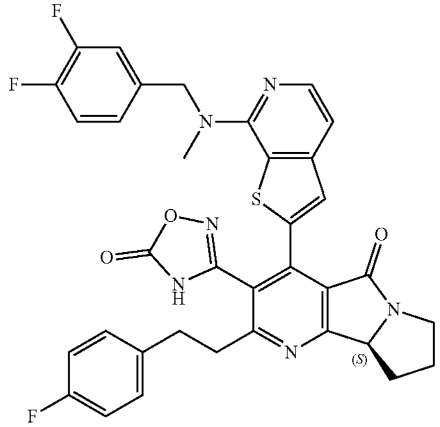

Compound 107 was synthesized using a similar procedure described in the Example 4 above by using the appropriate materials.

$^1$H NMR (400 MHz, DMSO-d6): δ 12.81 (br s, 1H), 8.04 (d, J=5.2 Hz, 1H), 7.53 (s, 1H), 7.30-7.42 (m, 2H), 7.19-7.27 (m, 3H), 7.04-7.16 (m, 3H), 4.80-4.95 (m, 3H), 3.51-3.60 (m, 1H), 3.25 (s, 3H), 2.95-3.18 (m, 5H), 2.23-2.39 (m, 3H), 1.31-1.46 (m, 1H). $^{19}$F NMR (377 MHz, DMSO-d6): −141.23, −138.54, −117.07. LC-MS: m/z 669.3 $(M+H)^+$.

Compound 117

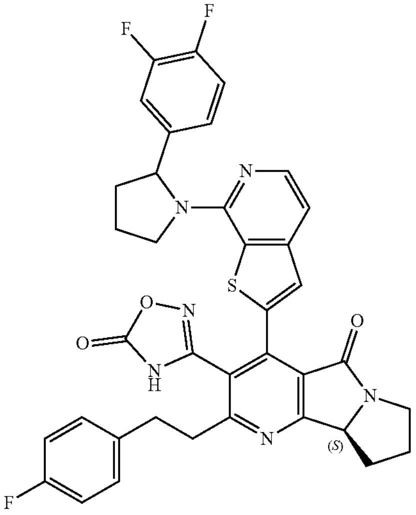

Compound 117 was synthesized using a similar procedure described in the Example 4 above by using the appropriate materials.

$^1$H NMR (400 MHz, DMSO-d6): δ 12.77 (br s, 1H), 7.79-7.85 (m, 1H), 7.41 (s, 1H), 7.19-7.33 (m, 4H), 7.00-7.17 (m, 4H), 5.44-5.53 (m, 1H), 4.79-4.89 (m, 1H), 4.13-4.26 (m, 1H), 3.91-4.01 (m, 1H), 3.51-3.57 (m, 1H), 2.93-3.16 (m, 4H), 2.32-2.38 (m, 2H), 2.22-2.31 (m, 2H), 1.77-

2.06 (m, 4H), 1.33-1.43 (m, 1H). $^{19}F$ NMR (377 MHz, DMSO-d6): −142.17, −138.87, −117.17. LC-MS: m/z 695.2 $(M+H)^+$.

Compound 140

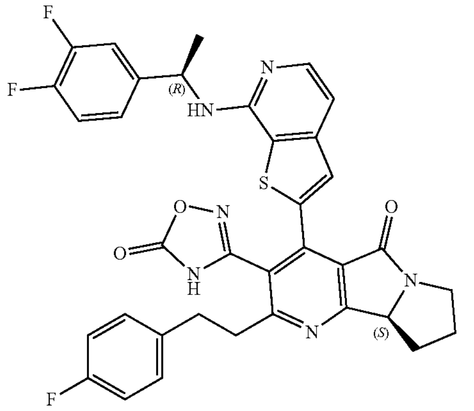

Compound 140 was synthesized using a similar procedure described in the Example 4 above by using the appropriate materials.

$^1H$ NMR (400 MHz, DMSO-d6): δ 12.77 (br s, 1H), 7.86 (d, J=5.2 Hz, 1H), 7.44-7.55 (m, 2H), 7.18-7.43 (m, 5H), 7.04-7.17 (m, 3H), 5.35-5.47 (m, 1H), 4.87-4.95 (m, 1H), 3.51-3.59 (m, 1H), 2.98-3.22 (m, 5H), 2.36-2.42 (m, 1H), 2.25-2.33 (m, 2H), 1.47-1.59 (m, 3H), 1.36-1.46 (m, 1H). $^{19}F$ NMR (377 MHz, DMSO-d6): −142.39, −139.21, −117.02. LC-MS: m/z 669.3 $(M+H)^+$.

Compound 141

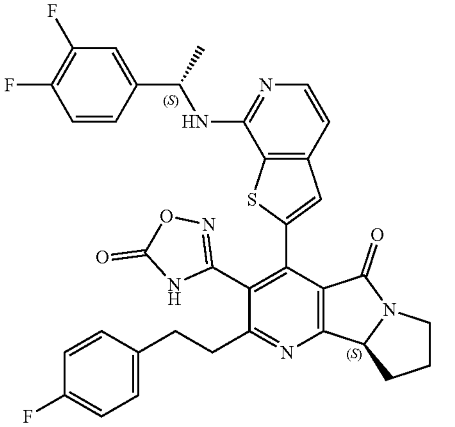

Compound 141 was synthesized using a similar procedure described in the Example 4 above by using the appropriate materials.

$^1H$ NMR (400 MHz, DMSO-d6): δ 12.81 (br s, 1H), 7.86 (d, J=6.0 Hz, 1H), 7.45-7.53 (m, 2H), 7.18-7.44 (m, 5H), 7.05-7.17 (m, 3H), 5.36-5.47 (m, 1H), 4.91 (dd, J=10.0 Hz, J=6.0 Hz, 1H), 3.51-3.60 (m, 1H), 3.29-3.31 (m, 1H), 3.00-3.21 (m, 4H), 2.24-2.40 (m, 3H), 1.54 (d, J=6.8 Hz, 3H), 1.34-1.48 (m, 1H). $^{19}F$ NMR (377 MHz, DMSO-d6): −142.03, −139.00, −117.02. LC-MS: m/z 669.3 $(M+H)^+$.

Compound 146

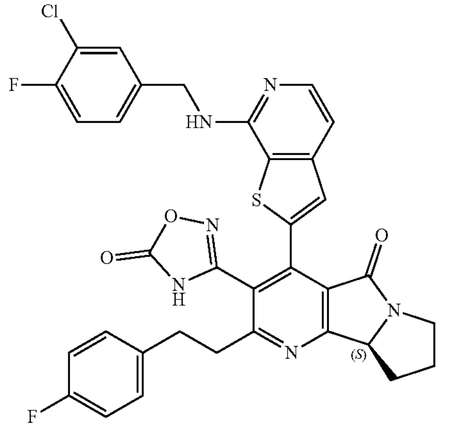

Compound 146 was synthesized using a similar procedure described in the Example 4 above by using the appropriate materials.

$^1H$ NMR (400 MHz, DMSO-d6): δ 12.81 (br s, 1H), 7.92 (d, J=5.6 Hz, 1H), 7.51-7.68 (m, 2H), 7.47 (s, 1H), 7.29-7.38 (m, 2H), 7.21-7.27 (m, 2H), 7.04-7.16 (m, 3H), 4.90 (dd, J=10.4 Hz, J=6.8 Hz, 1H), 4.66 (d, J=5.6 Hz, 2H), 3.52-3.61 (m, 1H), 3.00-3.19 (m, 5H), 2.24-2.40 (m, 3H), 1.36-1.46 (m, 1H). $^{19}F$ NMR (377 MHz, DMSO-d6): δ −117.03, −119.79. LC-MS: m/z 671.1 $(M+H)^+$.

Compound 147

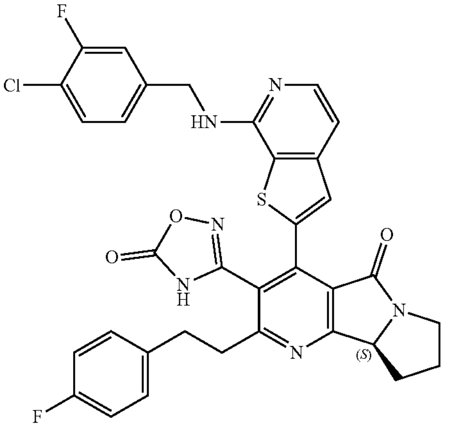

Compound 147 was synthesized using a similar procedure described in the Example 4 above by using the appropriate materials.

$^1H$ NMR (400 MHz, DMSO-d6): δ 12.80 (br s, 1H), 7.91 (d, J=5.6 Hz, 1H), 7.58-7.65 (m, 1H), 7.50 (t, J=8.0 Hz, 1H), 7.45 (s, 1H), 7.35 (d, J=10.0 Hz, 1H), 7.18-7.28 (m, 3H), 7.05-7.13 (m, 3H), 4.89 (dd, J=10.0 Hz, J=6.0 Hz, 1H), 4.64-4.72 (m, 2H), 3.50-3.61 (m, 1H), 2.95-3.23 (m, 5H), 2.20-2.44 (m, 3H), 1.34-1.49 (m, 1H). $^{19}F$ NMR (377 MHz, DMSO-d6): δ −116.94, −117.05. LC-MS: m/z 671.2 $(M+H)^+$.

Compound 149
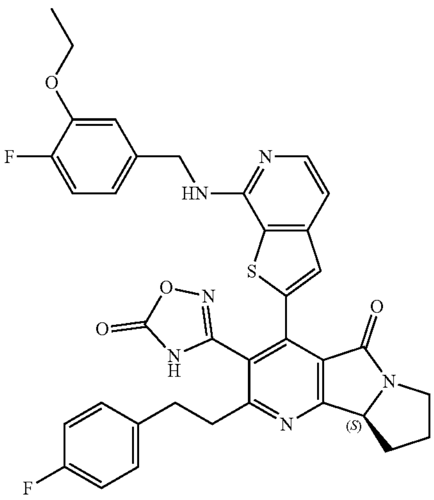
Compound 149 was synthesized using a similar procedure described in the Example 4 above by using the appropriate materials.
$^1$H NMR (400 MHz, DMSO-d6): δ 12.79 (br s, 1H), 7.91 (d, J=5.2 Hz, 1H), 7.51 (t, J=6.0 Hz, 1H), 7.43 (s, 1H), 7.22-7.26 (m, 2H), 7.16 (dd, J=8.4 Hz, 5.6 Hz, 1H), 7.04-7.11 (m, 4H), 6.85-6.89 (m, 1H), 4.87 (dd, J=10.4 Hz, J=6.4 Hz, 1H), 4.64 (d, J=5.6 Hz, 2H), 4.05 (q, J=7.2 Hz, 2H), 3.51-3.59 (m, 1H), 3.22-3.30 (m, 1H), 2.97-3.17 (m, 4H), 2.22-2.40 (m, 3H), 1.34-1.47 (m, 1H), 1.32 (t, J=6.8 Hz, 3H). $^{19}$F NMR (377 MHz, DMSO-d6): δ −117.10, −138.13. LC-MS: m/z 681.2 $(M+H)^+$.
Example 5: Compound 109
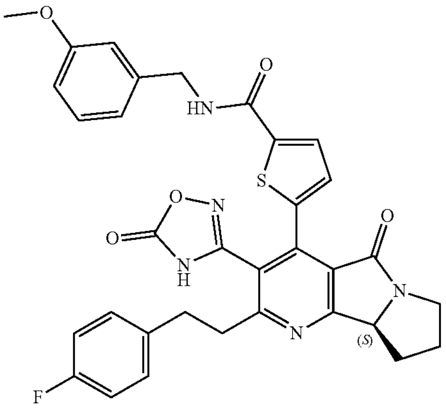
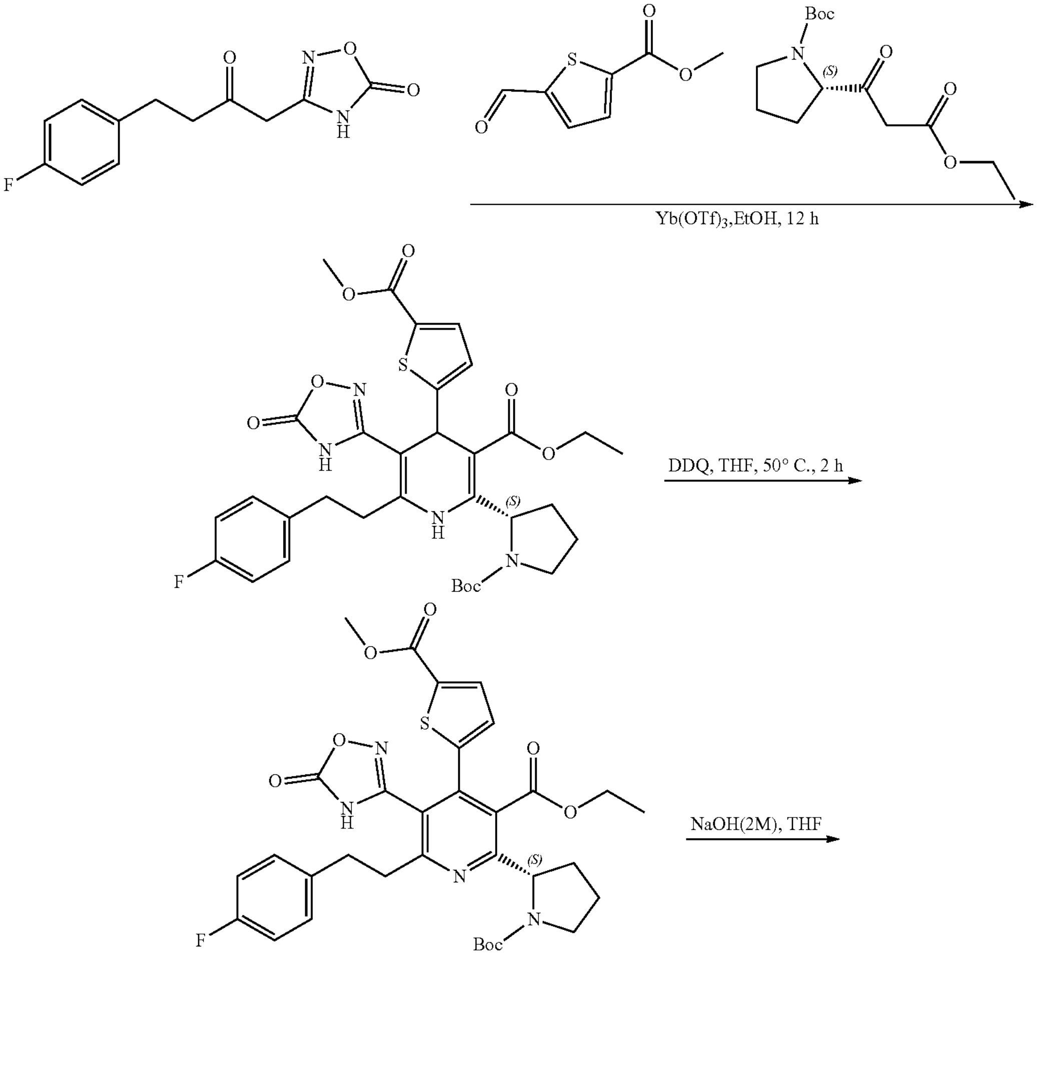

-continued
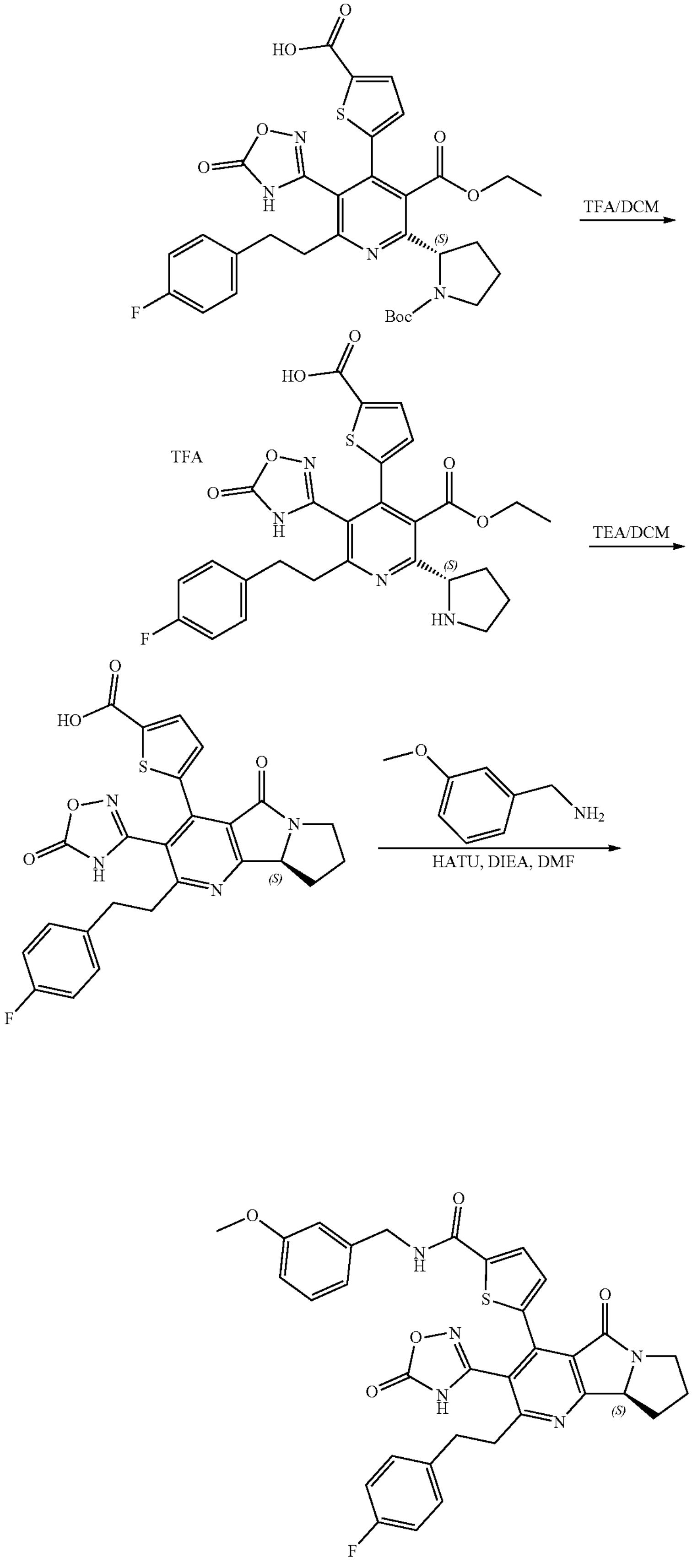

Step A ethyl 2-((S)-1-(tert-butoxycarbonyl)pyrrolidin-2-yl)-6-(4-fluorophenethyl)-4-(5-(methoxycarbonyl)thiophen-2-yl)-5-(5-oxo-4,5-dihydro-1,2,4-oxadiazol-3-yl)-1,4-dihydropyridine-3-carboxylate

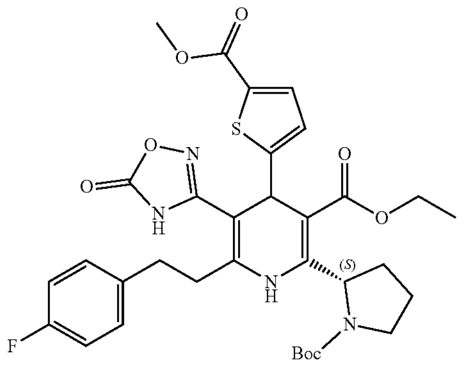

To a solution of 3-(4-(4-fluorophenyl)-2-oxobutyl)-1,2,4-oxadiazol-5(4H)-one (1 g, 4.00 mmol) in EtOH (10 mL) were added methyl 5-formylthiophene-2-carboxylate (680 mg, 4.00 mmol), tert-butyl (S)-2-(3-ethoxy-3-oxopropanoyl)pyrrolidine-1-carboxylate (1140 mg, 4.00 mmol), $Yb(OTf)_3$ (248 mg, 0.40 mmol) and $NH_4OAc$ (616 mg, 8.00 mmol). The reaction was stirred at room temperature for 12 hours. The mixture was diluted with EA (200 mL×2), washed with water (50 mL). The organic layer was dried over $Na_2SO_4$, filtered and concentrated under reduced pressure. The reaction was concentrated in vacuo to afford the crude ethyl 2-((S)-1-(tert-butoxycarbonyl)pyrrolidin-2-yl)-6-(4-fluorophenethyl)-4-(5-(methoxycarbonyl)thiophen-2-yl)-5-(5-oxo-4,5-dihydro-1,2,4-oxadiazol-3-yl)-1,4-dihydropyridine-3-carboxylate (2.5 g, crude). LC-MS: m/z 669.3 $(M+H)^+$.

Step B ethyl (S)-2-(1-(tert-butoxycarbonyl)pyrrolidin-2-yl)-6-(4-fluorophenethyl)-4-(5-(methoxycarbonyl)thiophen-2-yl)-5-(5-oxo-4,5-dihydro-1,2,4-oxadiazol-3-yl)nicotinate

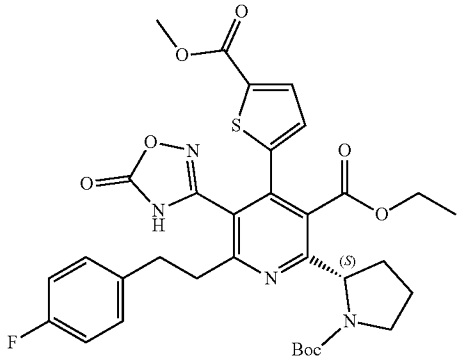

A mixture of ethyl 4-(5-((benzyloxy)carbonyl)thiophen-2-yl)-2-((S)-1-(tert-butoxycarbonyl)pyrrolidin-2-yl)-5-(5-methyl-1,3,4-oxadiazol-2-yl)-6-(2-(tetrahydro-2H-pyran-4-yl)ethyl)-1,4-dihydropyridine-3-carboxylate (2.5 g, crude), DDQ (1816 mg, 8.0 mmol) in THF (50 mL) was stirred at 50° C. for 2 hours. The mixture was diluted with EA (500 mL) and washed with water (100 mL). The organic layer was dried over $Na_2SO_4$, filtered and concentrated under reduced pressure. The residue was purified by silica gel column chromatography, eluted with MeOH/DCM (1/20) to give ethyl (S)-2-(1-(tert-butoxycarbonyl)pyrrolidin-2-yl)-6-(4-fluorophenethyl)-4-(5-(methoxycarbonyl)thiophen-2-yl)-5-(5-oxo-4,5-dihydro-1,2,4-oxadiazol-3-yl)nicotinate (1.1 g, yield: 41.4%). LC-MS: m/z 667.3 $(M+H)^+$.

Step C (S)-5-(2-(1-(tert-butoxycarbonyl)pyrrolidin-2-yl)-3-(ethoxycarbonyl)-6-(4-fluorophenethyl)-5-(5-oxo-4,5-dihydro-1,2,4-oxadiazol-3-yl)pyridin-4-yl)thiophene-2-carboxylic acid

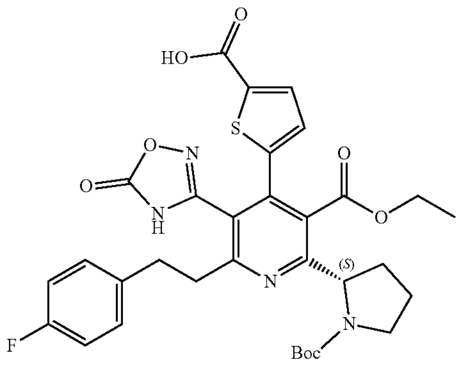

To a solution of ethyl (S)-2-(1-(tert-butoxycarbonyl)pyrrolidin-2-yl)-6-(4-fluorophenethyl)-4-(5-(methoxycarbonyl)thiophen-2-yl)-5-(5-oxo-4,5-dihydro-1,2,4-oxadiazol-3-yl)nicotinate (1.1 g, 1.65 mmol) in THF (50 mL) was added NaOH (5 mL, 2 M in water) at room temperature and stirred at room temperature for 3 hours. The mixture was diluted with EA (100 mL) and adjusted by 1 M HCl (15 mL) until the pH<7. Then, the mixture was washed with $H_2O$ (50 mL) and extracted with EA (100 mL×3). The organic layer was concentrated under reduced pressure to give (S)-5-(2-(1-(tert-butoxycarbonyl)pyrrolidin-2-yl)-3-(ethoxycarbonyl)-6-(4-fluorophenethyl)-5-(5-oxo-4,5-dihydro-1,2,4-oxadiazol-3-yl)pyridin-4-yl)thiophene-2-carboxylic acid (900 mg, yield: 83.6%). LC-MS: m/z 653.1 $(M+H)^+$.

Step D (S)-5-(3-(ethoxycarbonyl)-6-(4-fluorophenethyl)-5-(5-oxo-4,5-dihydro-1,2,4-oxadiazol-3-yl)-2-(pyrrolidin-2-yl)pyridin-4-yl)thiophene-2-carboxylic acid TFA salt

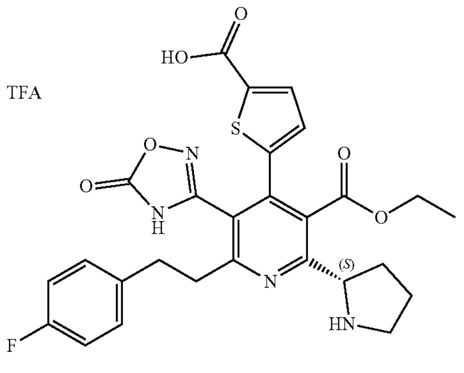

To a solution of (S)-5-(2-(1-(tert-butoxycarbonyl)pyrrolidin-2-yl)-3-(ethoxycarbonyl)-6-(4-fluorophenethyl)-5-(5-oxo-4,5-dihydro-1,2,4-oxadiazol-3-yl)pyridin-4-yl)thiophene-2-carboxylic acid (900 mg, 1.38 mmol) in DCM (9 mL) was added TFA (9 mL) at room temperature and stirred at room temperature for 1 hour. The mixture was concentrated under reduced pressure to give (S)-5-(3-(ethoxycarbonyl)-6-(4-fluorophenethyl)-5-(5-oxo-4,5-dihydro-1,2,4-oxadiazol-3-yl)-2-(pyrrolidin-2-yl)pyridin-4-yl)thiophene-2-carboxylic acid TFA salt (1 g, crude). LC-MS: m/z 553.2 $(M+H)^+$.

Step E (S)-5-(2-(4-fluorophenethyl)-5-oxo-3-(5-oxo-4,5-dihydro-1,2,4-oxadiazol-3-yl)-7,8,9,9a-tetrahydro-5H-pyrido[2,3-a]pyrrolizin-4-yl)thiophene-2-carboxylic acid

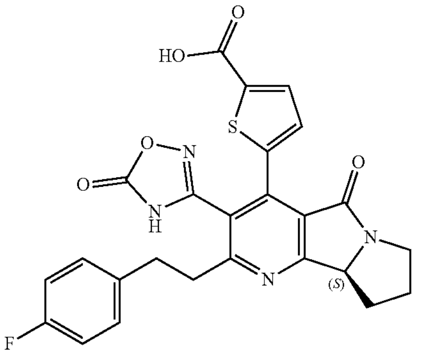

To a solution of (S)-5-(3-(ethoxycarbonyl)-6-(4-fluorophenethyl)-5-(5-oxo-4,5-dihydro-1,2,4-oxadiazol-3-yl)-2-(pyrrolidin-2-yl)pyridin-4-yl)thiophene-2-carboxylic acid TFA salt (1 g, crude) in DCM (5 mL) was added TEA (10 mL) at room temperature and stirred at room temperature for 1 hour. The mixture was concentrated under reduced pressure and purified by prep-HPLC to give (S)-5-(2-(4-fluorophenethyl)-5-oxo-3-(5-oxo-4,5-dihydro-1,2,4-oxadiazol-3-yl)-7,8,9,9a-tetrahydro-5H-pyrido[2,3-a]pyrrolizin-4-yl) thiophene-2-carboxylic acid (500 mg, yield: 71.6%). LC-MS: m/z 507.1 $(M+H)^+$.

Step F Compound 109

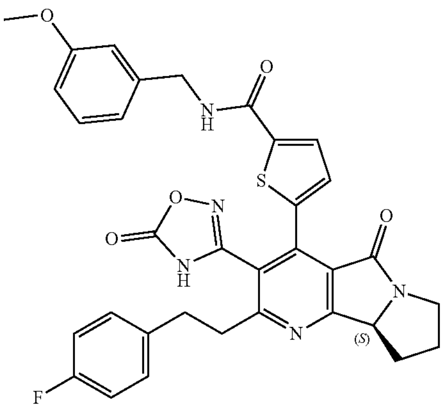

To a solution of (S)-5-(2-(4-fluorophenethyl)-5-oxo-3-(5-oxo-4,5-dihydro-1,2,4-oxadiazol-3-yl)-7,8,9,9a-tetrahydro-5H-pyrido[2,3-a]pyrrolizin-4-yl)thiophene-2-carboxylic acid (40 mg, 0.079 mmol) in DMA (1 mL) were added HATU (36 mg, 0.0949 mmol), (3-methoxyphenyl)methanamine (14 mg, 0.103 mmol), and DIEA (39 mg, 0.103 mmol). The reaction was stirred at room temperature for 2 hours. The residue was purified by prep-HPLC to afford the Compound 109 (26.52 mg, yield: 54.1%).

$^1$H NMR (400 MHz, DMSO-d6): δ 12.78 (br s, 1H), 9.18 (t, J=6.0 Hz, 1H), 7.79 (d, J=4.0 Hz, 1H), 7.19-7.30 (m, 4H), 7.05-7.13 (m, 2H), 6.89-6.91 (m, 2H), 6.80-6.85 (m, 1H), 4.86 (dd, J=6.0 Hz, J=10.0 Hz, 1H), 4.44 (d, J=6.0 Hz, 2H), 3.74 (s, 3H), 3.53-3.61 (m, 1H), 3.31-3.32 (m, 1H), 2.94-3.15 (m, 4H), 2.24-2.38 (m, 3H), 1.34-1.45 (m, 1H). $^{19}$F NMR (377 MHz, DMSO-d6): −117.05. LC-MS: m/z 626.2 $(M+H)^+$.

5-((S)-2-(4-fluorophenethyl)-5-oxo-3-(5-oxo-4,5-dihydro-1,2,4-oxadiazol-3-yl)-7,8,9,9a-tetrahydro-5H-pyrido[2,3-a]pyrrolizin-4-yl)-N—((R)-4-methoxy-2,3-dihydro-1H-inden-1-yl)thiophene-2-carboxamide (Compound 108)

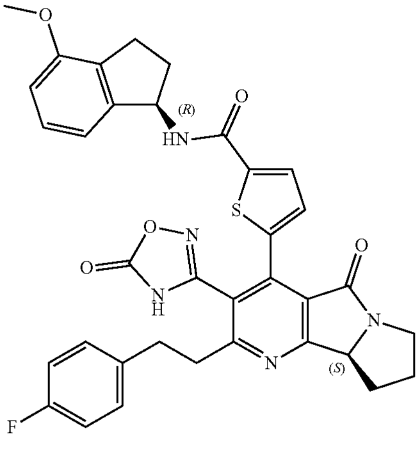

Compound 108 was synthesized using a similar procedure described in the Example 5 above by using the appropriate materials.

$^1$H NMR (400 MHz, DMSO-d6): δ 12.80 (br s, 1H), 8.94 (d, J=8.4 Hz, 1H), 7.78 (d, J=3.6 Hz, 1H), 7.17-7.28 (m, 4H), 7.04-7.13 (m, 2H), 6.86 (d, J=7.6 Hz, 2H), 5.46-5.56 (m, 1H), 4.79-4.89 (m, 1H), 3.80 (s, 3H), 3.49-3.62 (m, 2H), 2.91-3.05 (m, 3H), 2.66-2.75 (m, 2H), 2.22-2.39 (m, 4H), 1.87-2.05 (m, 2H), 1.33-1.45 (m, 1H). $^{19}$F NMR (377 MHz, DMSO-d6): −117.09. LC-MS: m/z 652.3 $(M+H)^+$.

Compound 115

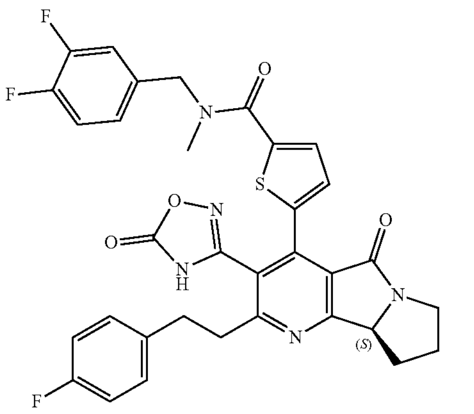

Compound 115 was synthesized using a similar procedure described in the Example 5 above by using the appropriate materials.

$^{1}$H NMR (400 MHz, DMSO-d6): δ 12.80 (br s, 1H), 7.34-7.70 (m, 3H), 7.19-7.28 (m, 3H), 7.05-7.18 (m, 3H), 4.85 (dd, J=10.4 Hz, J=6.0 Hz, 1H), 4.69 (s, 2H), 3.52-3.62 (m, 1H), 3.26-3.29 (m, 1H), 2.95-3.20 (m, 7H), 2.20-2.40 (m, 3H), 1.34-1.43 (m, 1H). $^{19}$F NMR (377 MHz, DMSO-d6): −117.05, −138.50, −140.71. LC-MS: m/z 646.2 $(M+H)^{+}$.

Compound 116

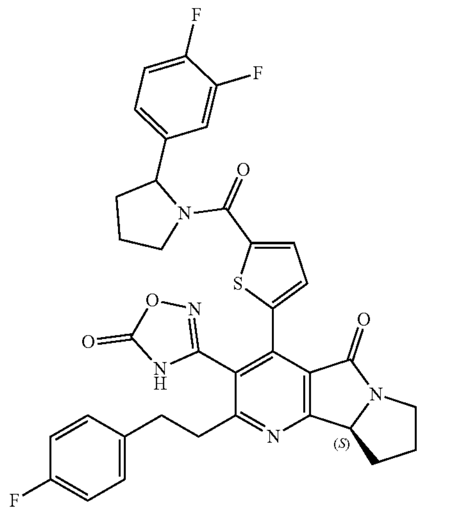

Compound 116 was synthesized using a similar procedure described in the Example 5 above by using the appropriate materials.

$^{1}$H NMR (400 MHz, DMSO-d6): δ 12.80 (br s, 1H), 7.73 (s, 1H), 7.31-7.41 (m, 2H), 7.19-7.29 (m, 3H), 7.03-7.15 (m, 3H), 5.13-5.21 (m, 1H), 4.80-4.90 (m, 1H), 4.11-4.22 (m, 1H), 3.85-3.97 (m, 1H), 3.49-3.63 (m, 1H), 2.95-3.18 (m, 4H), 2.65-2.70 (m, 1H), 2.21-2.36 (m, 4H) 1.93-2.02 (m, 2H), 1.67-1.79 (m, 1H), 1.30-1.43 (m, 1H). $^{19}$F NMR (377 MHz, DMSO-d6): −117.06, −139.00, −141.97. LC-MS: m/z 672.2 $(M+H)^{+}$.

Compound 118

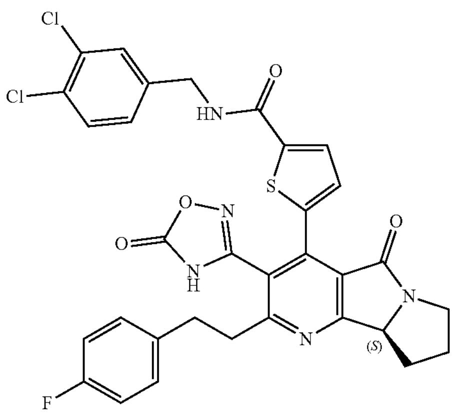

Compound 118 was synthesized using a similar procedure described in the Example 5 above by using the appropriate materials.

$^{1}$H NMR (400 MHz, DMSO-d6): δ 12.79 (br s, 1H), 9.25 (t, J=6.0 Hz, 1H), 7.77 (d, J=4.0 Hz, 1H), 7.58-7.61 (m, 2H), 7.32 (dd, J=1.6 Hz, J=8.0 Hz, 1H), 7.21-7.37 (m, 3H), 7.08 (t, J=8.8 Hz, 2H), 4.85 (dd, J=5.6 Hz, J=9.6 Hz, 1H), 4.46 (d, J=5.6 Hz, 2H), 3.54-3.59 (m, 1H), 3.27-3.33 (m, 1H), 2.97-3.15 (m, 4H), 2.27-2.36 (m, 3H), 1.36-1.40 (m, 1H). $^{19}$F NMR (377 MHz, DMSO-d6): −117.04. LC-MS: m/z 664.3 $(M+H)^{+}$.

Compound 119

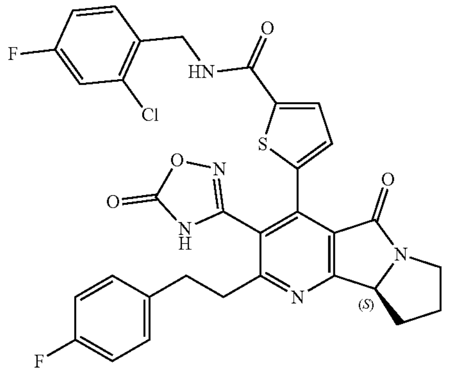

Compound 119 was synthesized using a similar procedure described in the Example 5 above by using the appropriate materials.

$^{1}$H NMR (400 MHz, DMSO-d6): δ 12.80 (br s, 1H), 9.02 (t, J=6.0 Hz, 1H), 7.82 (d, J=4.0 Hz, 1H), 7.41-7.49 (m, 2H), 7.20-7.28 (m, 4H), 7.06-7.12 (m, 2H), 4.82-4.92 (m, 1H), 4.50 (d, J=5.6 Hz, 2H), 3.50-3.64 (m, 1H), 3.25-3.30 (m, 1H), 2.98-3.18 (m, 4H), 2.24-2.40 (m, 3H), 1.32-1.47 (m, 1H). $^{19}$F NMR (377 MHz, DMSO-d6): −113.52, −117.05. LC-MS: m/z 648.1 $(M+H)^{+}$.

Compound 120

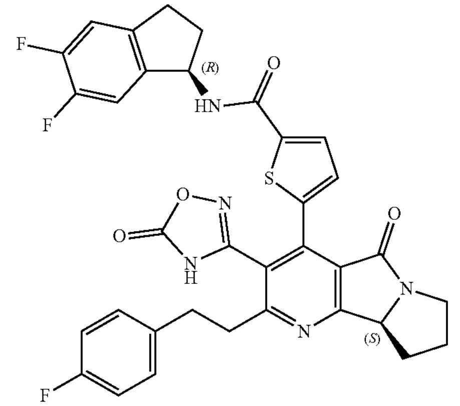

Compound 120 was synthesized using a similar procedure described in the Example 5 above by using the appropriate materials.

$^1$H NMR (400 MHz, DMSO-d6): δ 12.81 (br s, 1H), 8.99 (d, J=8.0 Hz, 1H), 7.80 (d, J=4.0 Hz, 1H), 7.20-7.40 (m, 5H), 7.05-7.13 (m, 2H), 5.45 (q, J=8.0 Hz, 1H), 4.86 (dd, J=6.0 Hz, J=10.0 Hz, 1H), 3.53-3.60 (m, 1H), 3.28-3.34 (m, 2H), 2.94-3.17 (m, 5H), 2.78-2.88 (m, 1H), 2.26-2.38 (m, 3H), 1.97-2.06 (m, 1H), 1.34-1.44 (m, 1H). $^{19}$F NMR (377 MHz, DMSO-d6): −117.05, −139.94, −141.15. LC-MS: m/z 658.4 $(M+H)^+$.

Compound 121

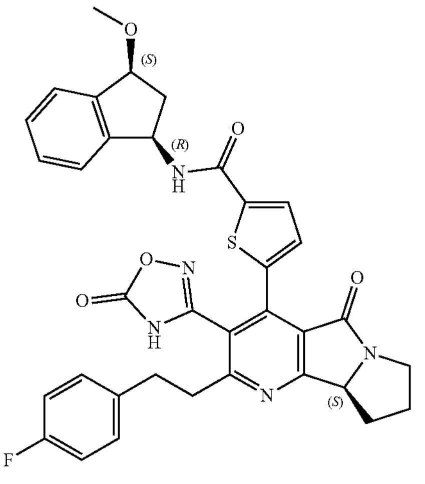

Compound 121 was synthesized using a similar procedure described in the Example 5 above by using the appropriate materials.

$^1$H NMR (400 MHz, DMSO-d6): δ 12.80 (br s, 1H), 9.05 (d, J=8.8 Hz, 1H), 7.81 (dd, J=1.2 Hz, J=4.0 Hz, 1H), 7.37-7.42 (m, 1H), 7.19-7.34 (m, 6H), 7.06-7.12 (m, 2H), 5.39 (q, J=8.4 Hz, 1H), 4.78-4.89 (m, 2H), 3.52-3.62 (m, 1H), 3.44 (s, 3H), 3.28-3.29 (m, 1H), 2.91-3.13 (m, 5H), 2.24-2.38 (m, 3H), 1.81-1.92 (m, 1H), 1.33-1.44 (m, 1H). $^{19}$F NMR (377 MHz, DMSO-d6): −117.13. LC-MS: m/z 652.3 $(M+H)^+$.

Compound 122

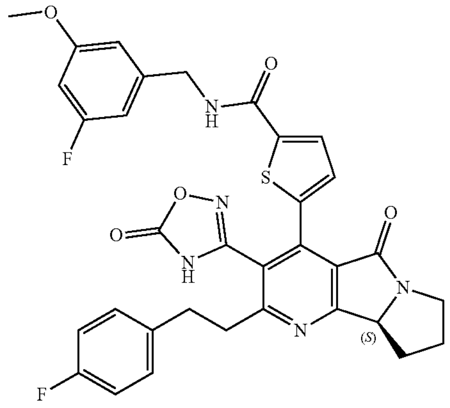

Compound 122 was synthesized using a similar procedure described in the Example 5 above by using the appropriate materials.

$^1$H NMR (400 MHz, DMSO-d6): δ 12.76 (br s, 1H), 9.15 (t, J=6.0 Hz, 1H), 7.75 (d, J=4.0 Hz, 1H), 7.21-7.26 (m, 3H), 7.08 (t, J=17.6 Hz, 2H), 6.66-6.77 (m, 3H), 4.82 (dd, J=6.0 Hz, J=10.0 Hz, 1 H), 4.43 (d, J=5.60 Hz, 2H), 3.76 (s, 3H), 3.52-3.57 (m, 1H), 2.90-3.15 (m, 5H), 2.20-2.40 (m, 3H), 1.30-1.43 (m, 1H). $^{19}$F NMR (377 MHz, DMSO-d6): −111.86, −117.19. LC-MS: m/z 644.3 $(M+H)^+$.

Example 6

3-((S)-2-(4-fluorophenethyl)-4-(7-((®-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-4-methyl-1,2,4-oxadiazol-5(4H)-one (Compound 112)

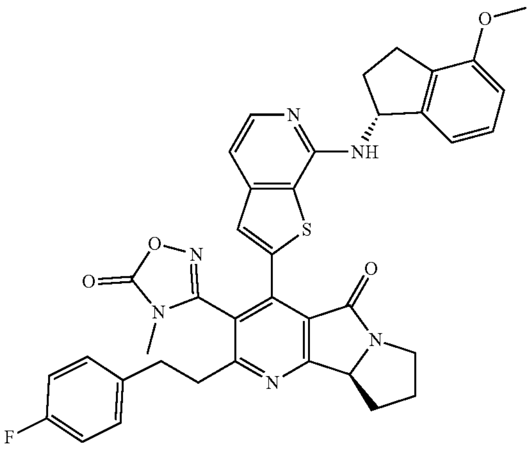 [SMILES: COc1cccc2c1CC[C@H]2Nc1nccc2cc(-c3c4c(nc(CCc5ccc(F)cc5)c3-c3noc(=O)n3C)[C@@H]3CCCN3C4=O)sc12]

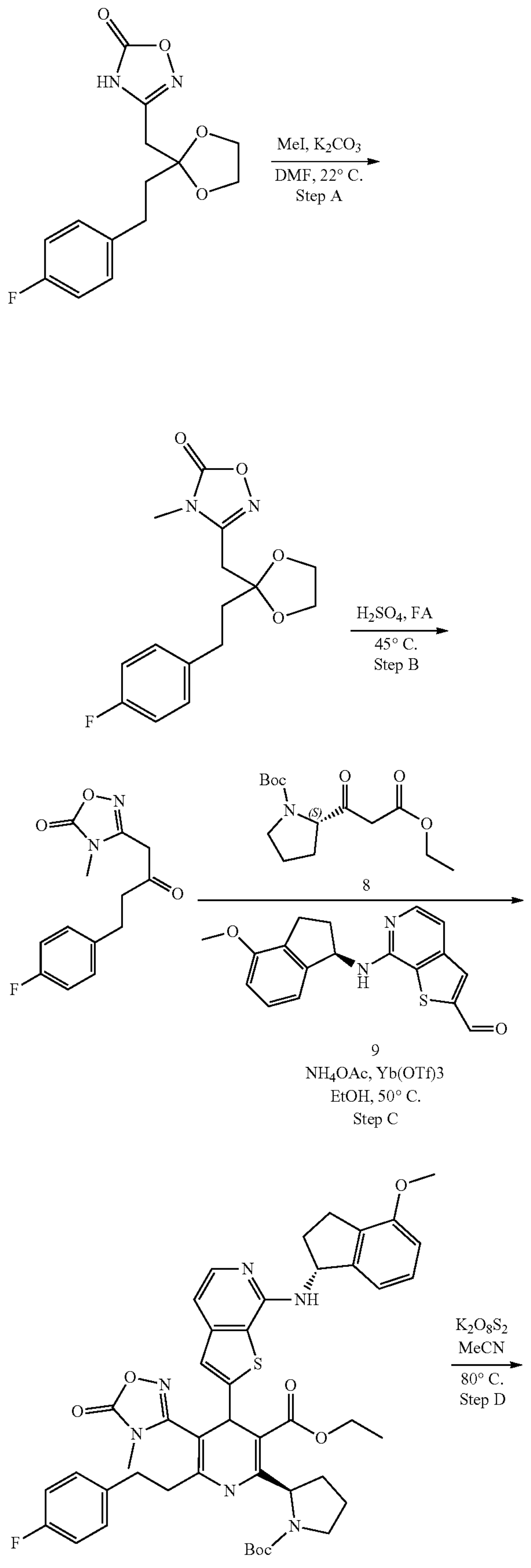
-continued
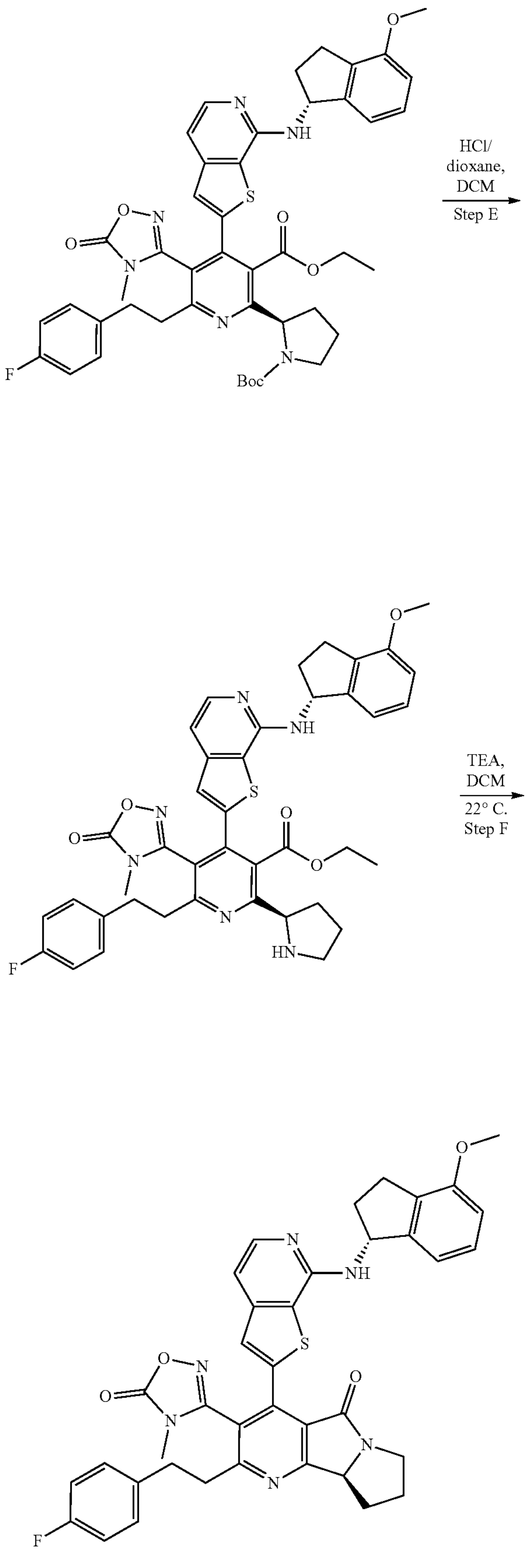

Step A 3-((2-(4-fluorophenethyl)-1,3-dioxolan-2-yl)methyl)-4-methyl-1,2,4-oxadiazol-5(4H)-one

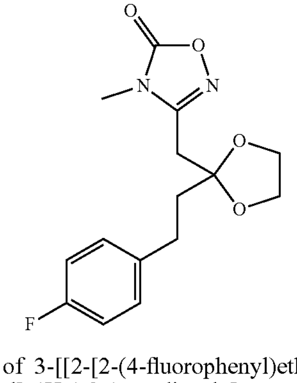

A mixture of 3-[[2-[2-(4-fluorophenyl)ethyl]-1,3-dioxolan-2-yl]methyl]-4H-1,2,4-oxadiazol-5-one (500 mg, 1.70 mmol), $CH_3I$ (1.37 g, 9.64 mmol, 0.6 mL), $K_2CO_3$ (705 mg, 5.10 mmol) in DMF (5 mL) was degassed and purged with $N_2$ for 3 times, and then the mixture was stirred at 22° C. for 16 hrs under $N_2$ atmosphere. The reaction mixture was diluted with water (100 mL) and extracted with EtOAc (100 mL). The organic layer was washed with brine (50 mL×2), dried over $Na_2SO_4$, filtered and concentrated under reduced pressure to give a residue. The residue was purified by column chromatography on silica gel (eluted with 0-30% EA in PE). 3-[[2-[2-(4-fluorophenyl)ethyl]-1,3-dioxolan-2-yl]methyl]-4-methyl-1,2,4-oxadiazol-5-one (352 mg, 1.14 mmol, 67.2% yield) was obtained.

$^1H$ NMR (400 MHz, $CDCl_3$) δ ppm 7.07 (dd, J=8.44, 5.50 Hz, 2H), 6.86-6.96 (m, 2H), 3.82-3.97 (m, 4H), 3.20 (s, 3H), 2.82-2.89 (m, 1H), 2.86 (s, 2H), 2.61-2.71 (m, 2H), 1.88-2.02 (m, 2H).

Step B 3-(4-(4-fluorophenyl)-2-oxobutyl)-4-methyl-1,2,4-oxadiazol-5(4H)-one

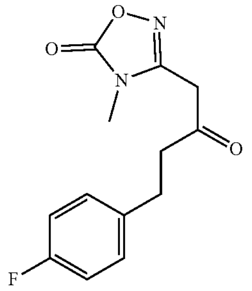 [SMILES: Cn1c(CC(=O)CCc2ccc(F)cc2)noc1=O]

A mixture of 3-[[2-[2-(4-fluorophenyl)ethyl]-1,3-dioxolan-2-yl]methyl]-4-methyl-1,2,4-oxadiazol-5-one (350 mg, 1.14 mmol) in formic acid (5 mL) and $H_2SO_4$ (1 mL) was degassed and purged with $N_2$ for 3 times, and then the mixture was stirred at 45° C. for 2 hrs under $N_2$ atmosphere. The reaction mixture was concentrated under reduced pressure to remove solvent. The residue was diluted with water (80 mL) and extracted with EtOAc (100 mL×2). The combined organic layers were washed with brine (50 mL), dried over $Na_2SO_4$, filtered and concentrated under reduced pressure to give a residue. Crude compound 3-[4-(4-fluorophenyl)-2-oxo-butyl]-4-methyl-1,2,4-oxadiazol-5-one (291 mg) was obtained.

$^1H$ NMR (400 MHz, $CDCl_3$) δ ppm 7.07 (dd, J=8.44, 5.50 Hz, 2H), 6.91 (t, J=8.62 Hz, 2H), 3.61 (s, 2H), 2.99 (s, 3H), 2.79-2.91 (m, 4H). LC-MS: m/z 263.4 $(M+H)^+$.

Step C ethyl 2-((R)-1-(tert-butoxycarbonyl)pyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(4-methyl-5-oxo-4,5-dihydro-1,2,4-oxadiazol-3-yl)-1,4-dihydropyridine-3-carboxylate

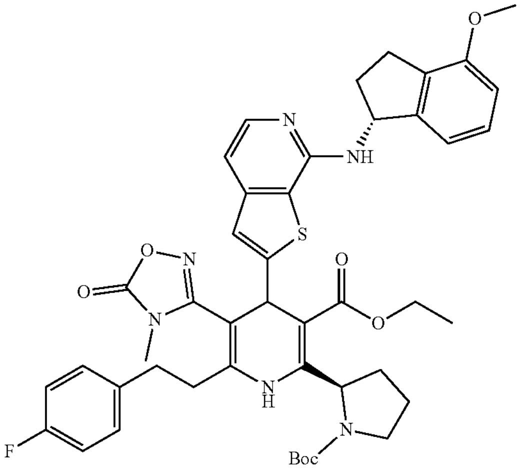 [SMILES: CCOC(=O)C1=C([C@H]2CCCN2C(=O)OC(C)(C)C)NC(CCc2ccc(F)cc2)=C(c2noc(=O)n2C)C1c1cc2ccnc(N[C@@H]3CCc4c(OC)cccc43)c2s1]

A mixture of 3-[4-(4-fluorophenyl)-2-oxo-butyl]-4-methyl-1,2,4-oxadiazol-5-one (50 mg, 189.21 μmol), 7-[[(1R)-4-methoxyindan-1-yl]amino]thieno[2,3-c]pyridine-2-carbaldehyde (62 mg, 191.12 μmol), tris(trifluoromethylsulfonyloxy)ytterbium (59 mg, 95.12 μmol), $NH_4OAc$ (30 mg, 389.19 μmol) and tert-butyl (2S)-2-(3-ethoxy-3-oxo-propanoyl)pyrrolidine-1-carboxylate (54 mg, 189.25 μmol) in EtOH (5 mL) was degassed and purged with $N_2$ for 3 times, and then the mixture was stirred at 50° C. for 16 hrs under $N_2$ atmosphere. The reaction mixture was concentrated under reduced pressure to give crude ethyl 2-[(2R)-1-tert-butoxycarbonylpyrrolidin-2-yl]-6-[2-(4-fluorophenyl)ethyl]-4-[7-[[(1R)-4-methoxyindan-1-yl]amino]thieno[2,3-c]pyridin-2-yl]-5-(4-methyl-5-oxo-1,2,4-oxadiazol-3-yl)-1,4-dihydropyridine-3-carboxylate (170 mg, crude) was obtained. LC-MS: m/z 837.9 $(M+H)^+$.

Step D ethyl 2-((R)-1-(tert-butoxycarbonyl)pyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(4-methyl-5-oxo-4,5-dihydro-1,2,4-oxadiazol-3-yl)nicotinate

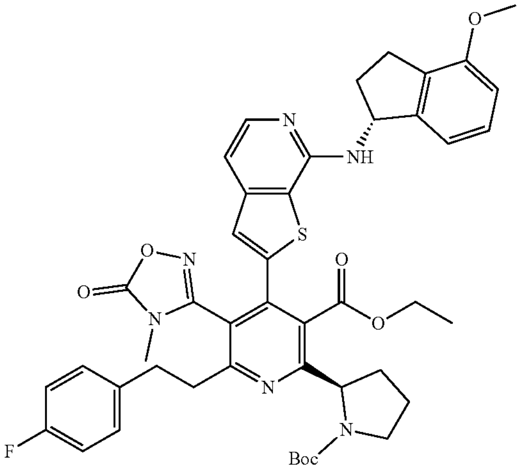 [SMILES: CCOC(=O)c1c([C@H]2CCCN2C(=O)OC(C)(C)C)nc(CCc2ccc(F)cc2)c(-c2noc(=O)n2C)c1-c1cc2ccnc(N[C@@H]3CCc4c(OC)cccc43)c2s1]

A mixture of ethyl 2-[(2R)-1-tert-butoxycarbonylpyrrolidin-2-yl]-6-[2-(4-fluorophenyl)ethyl]-4-[7-[[(1R)-4-methoxyindan-1-yl]amino]thieno[2,3-c]pyridin-2-yl]-5-(4-methyl-5-oxo-1,2,4-oxadiazol-3-yl)-1,4-dihydropyridine-3-carboxylate (170 mg, 203.11 μmol), dipotassium; sulfonatooxy sulfate (55 mg, 203.46 μmol) in MeCN (6 mL) and $H_2O$ (2 mL) was degassed and purged with $N_2$ for 3 times, and then the mixture was stirred at 85° C. for 2 hrs under $N_2$ atmosphere. The reaction mixture was diluted with $H_2O$ (50 mL) and extracted with EtOAc (100 mL×2). The combined organic layers were washed with brine (50 mL×3), dried over $Na_2SO_4$, filtered and concentrated under reduced pressure to give a residue. The residue was purified by prep-TLC ($SiO_2$, PE/EA=1:1). Crude ethyl 2-[(2R)-1-tert-butoxycarbonylpyrrolidin-2-yl]-6-[2-(4-fluorophenyl)ethyl]-4-[7-[[(1R)-4-methoxyindan-1-yl]amino]thieno[2,3-c]pyridin-2-yl]-5-(4-methyl-5-oxo-1,2,4-oxadiazol-3-yl)pyridine-3-carboxylate (38 mg) was obtained. LC-MS: m/z 835.9 $(M+H)^+$.

Step E ethyl 6-(4-fluorophenethyl)-4-(7-(((R)-4-methoxy-2,3-dihydro-1H-inden-1-yl)amino)thieno[2,3-c]pyridin-2-yl)-5-(4-methyl-5-oxo-4,5-dihydro-1,2,4-oxadiazol-3-yl)-2-((R)-pyrrolidin-2-yl)nicotinate

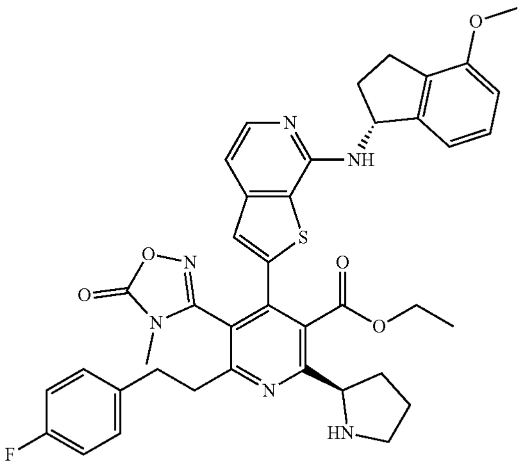 [SMILES: CCOC(=O)c1c([C@H]2CCCN2)nc(CCc2ccc(F)cc2)c(-c2noc(=O)n2C)c1-c1cc2ccnc(N[C@@H]3CCc4c(OC)cccc43)c2s1]

A mixture of ethyl 6-[2-(4-fluorophenyl)ethyl]-5-(4-methyl-5-oxo-1,2,4-oxadiazol-3-yl)-2-[rac-(2R)-1-tert-butoxycarbonylpyrrolidin-2-yl]-4-[7-[[rac-(1R)-4-methoxyindan-1-yl]amino]thieno[2,3-c]pyridin-2-yl]pyridine-3-carboxylate (20 mg, crude) in DCM (2 mL) and HCl/dioxane (4 M, 2 mL) was degassed and purged with $N_2$ for 3 times, and then the mixture was stirred at 22° C. for 1 hr under $N_2$ atmosphere. The reaction mixture was concentrated under reduced pressure to give crude compound ethyl 6-[2-(4-fluorophenyl)ethyl]-5-(4-methyl-5-oxo-1,2,4-oxadiazol-3-yl)-4-[7-[[rac-(1R)-4-methoxyindan-1-yl]amino]thieno[2,3-c]pyridin-2-yl]-2-[rac-(2R)-pyrrolidin-2-yl]pyridine-3-carboxylate (18 mg, crude). LC-MS: m/z 735 $(M+H)^+$.

Step I 3-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-4-methyl-1,2,4-oxadiazol-5(4H)-one

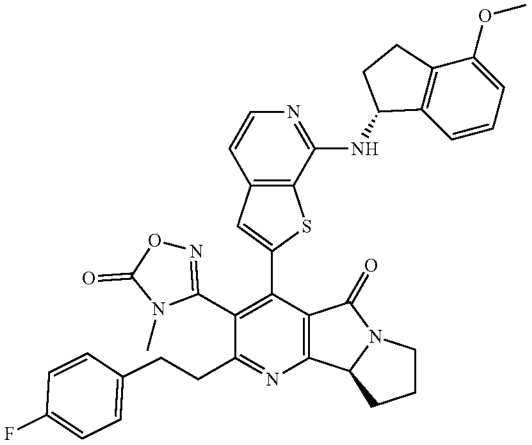 [SMILES: COc1cccc2c1CC[C@H]2Nc1nccc2cc(-c3c4c(nc(CCc5ccc(F)cc5)c3-c3noc(=O)n3C)[C@@H]3CCCN3C4=O)sc12]

A mixture of ethyl 6-[2-(4-fluorophenyl)ethyl]-5-(4-methyl-5-oxo-1,2,4-oxadiazol-3-yl)-4-[7-[[rac-(1R)-4-methoxyindan-1-yl]amino]thieno[2,3-c]pyridin-2-yl]-2-[rac-(2R)-pyrrolidin-2-yl]pyridine-3-carboxylate (18 mg, crude), TEA (363.50 mg, 3.59 mmol, 0.5 mL) in DCM (5 mL) was degassed and purged with $N_2$ for 3 times, and then the mixture was stirred at 22° C. for 16 hrs under $N_2$ atmosphere. The reaction mixture was concentrated under reduced pressure to remove solvent. The residue was purified by reversed-phase HPLC (Column: Kromasil 100-5-C18; Eluent: 30% to 60% water (0.1% $NH_3{\cdot}H_2O$)-ACN). 4-methyl-3-[rac-(9aS)-2-[2-(4-fluorophenyl)ethyl]-5-oxo-4-[7-[[rac-(1R)-4-methoxyindan-1-yl]amino]thieno[2,3-c]pyridin-2-yl]-7,8,9,9a-tetrahydropyrido[2,3-a]pyrrolizin-3-yl]-1,2,4-oxadiazol-5-one (1.2 mg, 1.70 μmol, 6.25% yield, 97.7% purity) was obtained.

$^1H$ NMR (400 MHz, MeOD) δ ppm 7.94 (d, J=5.62 Hz, 1H), 7.52 (s, 1H), 7.07-7.22 (m, 4H), 6.97 (t, J=8.19 Hz, 2H), 6.89 (d, J=9.05 Hz, 1H), 6.81 (d, J=8.07 Hz, 1H), 5.80 (d, J=7.82 Hz, 1H), 3.83 (s, 3H), 3.69 (s, 1H), 3.46 (s, 1H), 3.29-3.30 (m, 3H), 3.10-3.23 (m, 4H), 3.02 (d, J=12.47 Hz, 1H), 2.59-2.84 (m, 3H), 2.43 (s, 2H), 2.16-2.22 (m, 1H), 2.03 (m, 1H), 1.60 (m, 1H). LC-MS: m/z 689.2 $(M+H)^+$.

Example 7

(S)-3-(4-(2-(3,4-difluorobenzyl)-1-oxo-1,2,3,4-tetrahydropyrrolo[1,2-a]pyrazin-6-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one (Compound 129)

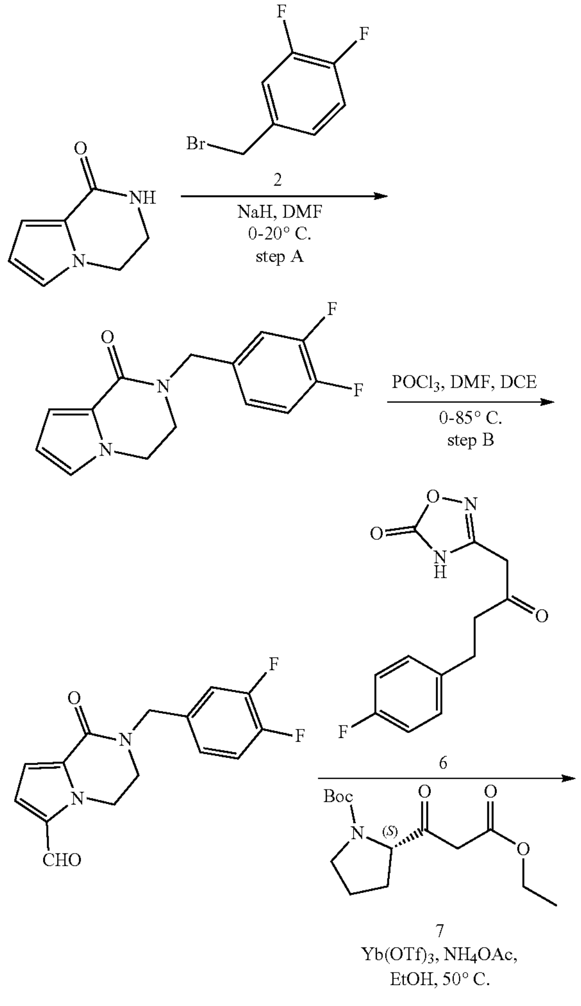

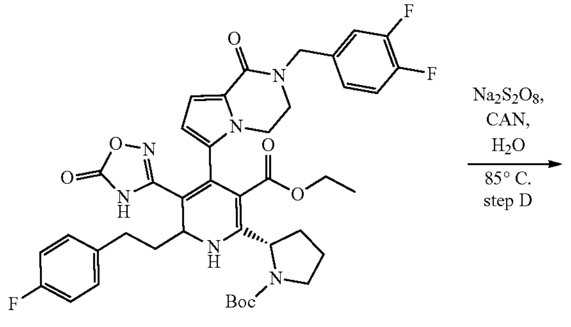

-continued

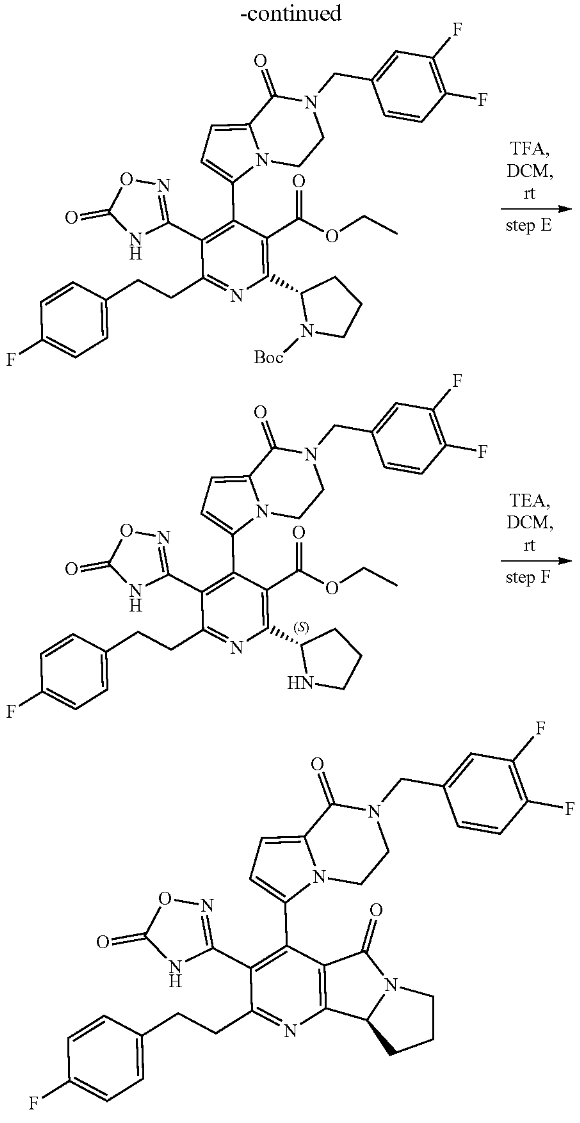

Step A 2-(3,4-difluorobenzyl)-3,4-dihydropyrrolo[1,2-a]pyrazin-1(2H)-one

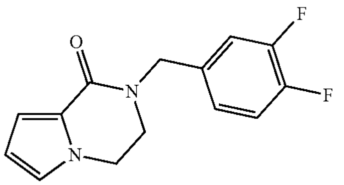 [SMILES: O=C1c2cccn2CCN1Cc1ccc(F)c(F)c1]

To a solution of 3,4-dihydro-2H-pyrrolo[1,2-a]pyrazin-1-one (200 mg, 1.47 mmol) in DMF (5 mL) was added NaH (235 mg, 5.88 mmol, 60% purity) and 4-(chloromethyl)-1,2-difluoro-benzene (239 mg, 1.47 mmol). The mixture was stirred at 0-20° C. for 16 hrs. The reaction mixture was quenched with ice-water (5 mL) at 0° C., then diluted with EtOAc (15 mL) and extracted with EtOAc (20 mL×3). The combined organic layer was washed with brine (30 mL), dried over $Na_2SO_4$, filtered and concentrated under reduced pressure to give a residue. The residue was purified by flash silica gel chromatography (ISCO®; 12 g SepaFlash® Silica Flash Column, Eluent of 0~30% Ethyl acetate/Petroleum ether gradient @40 mL/min). 2-(3,4-difluorobenzyl)-3,4-dihydropyrrolo[1,2-a]pyrazin-1(2H)-one (328 mg, 1.25 mmol, 85.1% yield) was obtained.

$^1$H NMR (400 MHz, $CDCl_3$) δ ppm 7.03-7.20 (m, 3H), 6.96-7.02 (m, 1H), 6.73 (s, 1H), 6.21-6.28 (m, 1H), 4.70 (s, 2H), 4.05-4.16 (m, 2H), 3.50-3.62 (m, 2H).

Step B 2-(3,4-difluorobenzyl)-1-oxo-1,2,3,4-tetrahydropyrrolo[1,2-a]pyrazine-6-carbaldehyde

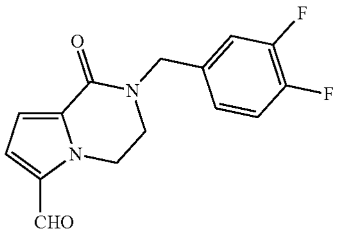 [SMILES: O=Cc1ccc2n1CCN(Cc1ccc(F)c(F)c1)C2=O]

To a solution of 2-[(3,4-difluorophenyl)methyl]-3,4-dihydropyrrolo[1,2-a]pyrazin-1-one (250 mg, 953 μmol) in DCE (5 mL) was added DMF (139 mg, 1.91 mmol) and $POCl_3$ (292 mg, 1.91 mmol). The mixture was stirred at 0-85° C. for 16 hrs. The reaction mixture was quenched with ice-water (5 mL) at 0° C., then diluted with EtOAc (15 mL) and extracted with EtOAc (20 mL×3). The combined organic layers were washed with brine (30 mL), dried over $Na_2SO_4$, filtered and concentrated under reduced pressure to give a residue. The residue was purified by flash silica gel chromatography (ISCO®; 4 g SepaFlash® Silica Flash Column, Eluent of 0~40% Ethyl acetate/Petroleum ether gradient @20 mL/min). 2-(3,4-difluorobenzyl)-1-oxo-1,2,3,4-tetrahydropyrrolo[1,2-a]pyrazine-6-carbaldehyde (254 mg, 875 μmol, 91.8% yield) was obtained.

$^1$H NMR (400 MHz, $CDCl_3$) δ ppm 9.68 (s, 1H), 7.13-7.19 (m, 2H), 7.07 (m, 1H) 7.00-7.03 (m, 1H), 6.97 (d, J=4.16 Hz, 1H), 4.71 (s, 2H), 4.62 (t, J=6.05 Hz, 2H), 3.61 (t, J=6.05 Hz, 2H).

Step C ethyl 2-(1-(tert-butoxycarbonyl)pyrrolidin-2-yl)-4-(2-(3,4-difluorobenzyl)-1-oxo-1,2,3,4-tetrahydropyrrolo[1,2-a]pyrazin-6-yl)-6-(4-fluorophenethyl)-5-(5-oxo-4,5-dihydro-1,2,4-oxadiazol-3-yl)-1,6-dihydropyridine-3-carboxylate

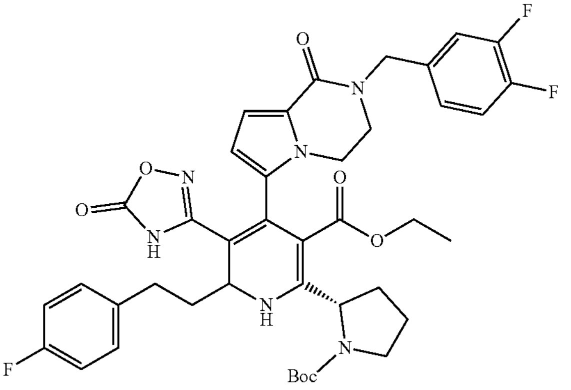 [SMILES: CCOC(=O)C1=C([C@@H]2CCCN2C(=O)OC(C)(C)C)NC(CCc2ccc(F)cc2)C(c2noc(=O)[nH]2)=C1c1ccc2n1CCN(Cc1ccc(F)c(F)c1)C2=O]

To a solution of 2-[(3,4-difluorophenyl)methyl]-1-oxo-3,4-dihydropyrrolo[1,2-a]pyrazine-6-carbaldehyde (100 mg, 345 μmol) in EtOH (3 mL) was added tris(trifluoromethylsulfonyloxy)ytterbium (21.4 mg, 34.5 μmol), 3-(4-(4-fluorophenyl)-2-oxobutyl)-1,2,4-oxadiazol-5(4H)-one (86.2 mg, 345 μmol), tert-butyl (S)-2-(3-ethoxy-3-oxopropanoyl)pyrrolidine-1-carboxylate (98.3 mg, 345 μmol) and $NH_4OAc$ (53.1 mg, 689 μmol). The mixture was stirred at 50° C. for 16 hrs. The reaction mixture was concentrated under reduced pressure. Crude product ethyl 2-(1-(tert-butoxycarbonyl)pyrrolidin-2-yl)-4-(2-(3,4-difluorobenzyl)-1-oxo-1,2,3,4-tetrahydropyrrolo[1,2-a]pyrazin-6-yl)-6-(4-fluorophenethyl)-5-(5-oxo-4,5-dihydro-1,2,4-oxadiazol-3-yl)-1,6-dihydropyridine-3-carboxylate (272 mg) was obtained.

Step D ethyl 2-(1-tert-butoxycarbonylpyrrolidin-2-yl)-4-[2-[(3,4-difluorophenyl)methyl]-1-oxo-3,4-dihydropyrrolo[1,2-a]pyrazin-6-yl]-6-[2-(4-fluorophenyl)ethyl]-5-(5-oxo-4H-1,2,4-oxadiazol-3-yl)pyridine-3-carboxylate

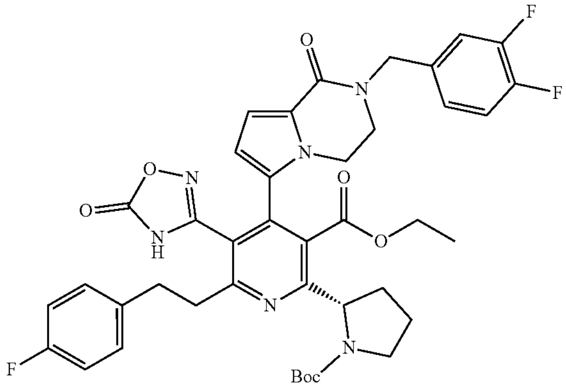 [SMILES: CCOC(=O)c1c([C@@H]2CCCN2C(=O)OC(C)(C)C)nc(CCc2ccc(F)cc2)c(-c2noc(=O)[nH]2)c1-c1ccc2n1CCN(Cc1ccc(F)c(F)c1)C2=O]

To a solution of ethyl 6-(1-tert-butoxycarbonylpyrrolidin-2-yl)-4-[2-[(3,4-difluorophenyl)methyl]-1-oxo-3,4-dihydropyrrolo[1,2-a]pyrazin-6-yl]-2-[2-(4-fluorophenyl)ethyl]-3-(5-oxo-4H-1,2,4-oxadiazol-3-yl)-1,2-dihydropyridine-5-carboxylate (272 mg, 344 μmol) in MeCN (3 mL)/$H_2O$ (1 mL) was added dipotassium sulfonatooxy sulfate (186 mg, 689 μmol, 138 μL). The mixture was stirred at 85° C. for 2 hrs. The reaction mixture was diluted with $H_2O$ (10 mL) and extracted with EtOAc (15 mL×3). The combined organic layers were washed with brine (20 mL×3), dried over $Na_2SO_4$, filtered and concentrated under reduced pressure to give a residue. The residue was purified by prep-TLC ($SiO_2$, Ethyl acetate). ethyl 2-(1-tert-butoxycarbonylpyrrolidin-2-yl)-4-[2-[(3,4-difluorophenyl)methyl]-1-oxo-3,4-dihydropyrrolo[1,2-a]pyrazin-6-yl]-6-[2-(4-fluorophenyl)ethyl]-5-(5-oxo-4H-1,2,4-oxadiazol-3-yl)pyridine-3-carboxylate (80 mg, 101.68 μmol, 29.52% yield) was obtained. LC-MS: m/z 787.8 $(M+H)^+$.

Step E ethyl 4-[2-[(3,4-difluorophenyl)methyl]-1-oxo-3,4-dihydropyrrolo[1,2-a]pyrazin-6-yl]-6-[2-(4-fluorophenyl)ethyl]-5-(5-oxo-4H-1,2,4-oxadiazol-3-yl)-2-pyrrolidin-2-yl-pyridine-3-carboxylate

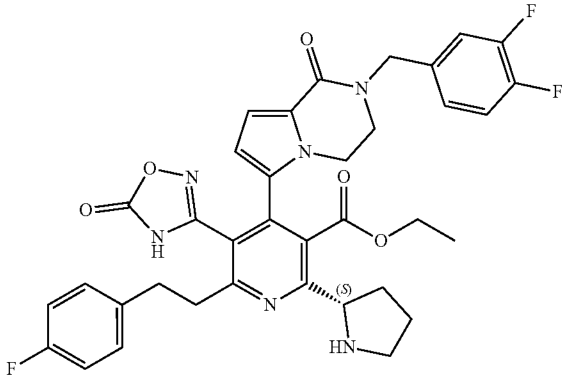

To a solution of ethyl 2-(1-tert-butoxycarbonylpyrrolidin-2-yl)-4-[2-[(3,4-difluorophenyl)methyl]-1-oxo-3,4-dihydro-pyrrolo[1,2-a]pyrazin-6-yl]-6-[2-(4-fluorophenyl)ethyl]-5-(5-oxo-4H-1,2,4-oxadiazol-3-yl)pyridine-3-carboxylate (80 mg, 102 μmol) in DCM (5 mL) was added TFA (1.54 g, 13.5 mmol, 1 mL). The mixture was stirred at 20° C. for 16 hrs. The reaction mixture was concentrated under reduced pressure to remove solvent. The crude ethyl 4-[2-[(3,4-difluorophenyl)methyl]-1-oxo-3,4-dihydropyrrolo[1,2-a]pyrazin-6-yl]-6-[2-(4-fluorophenyl)ethyl]-5-(5-oxo-4H-1,2,4-oxadiazol-3-yl)-2-pyrrolidin-2-yl-pyridine-3-carboxylate (69.8 mg).

Step F (S)-3-(4-(2-(3,4-difluorobenzyl)-1-oxo-1,2,3,4-tetrahydropyrrolo[1,2-a]pyrazin-6-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one

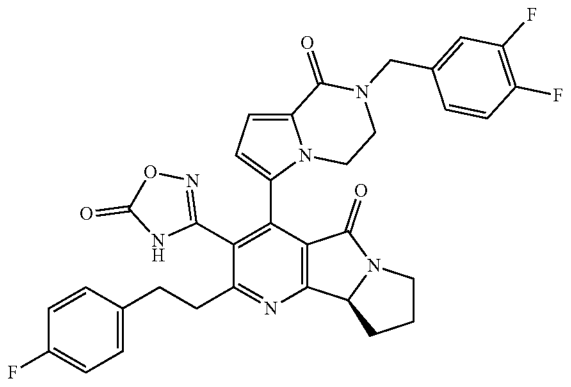 [SMILES: O=C1c2ccc(-c3c4c(nc(CCc5ccc(F)cc5)c3-c3noc(=O)[nH]3)[C@@H]3CCCN3C4=O)n2CCN1Cc1ccc(F)c(F)c1]

To a solution of ethyl 4-[2-[(3,4-difluorophenyl)methyl]-1-oxo-3,4-dihydropyrrolo[1,2-a]pyrazin-6-yl]-6-[2-(4-fluorophenyl)ethyl]-5-(5-oxo-4H-1,2,4-oxadiazol-3-yl)-2-pyrrolidin-2-yl-pyridine-3-carboxylate (69.8 mg, 102 μmol) in DCM (5 mL) was added TEA (2.18 g, 21.5 mmol, 3 mL). The mixture was stirred at 20° C. for 16 hrs. The reaction mixture was concentrated under reduced pressure to remove solvent. The residue was purified by prep-TLC ($SiO_2$, Ethyl acetate), and further purified by prep-HPLC (Column: Kromasil 100-5-C18; Eluent: 45% to 70% water (0.1% FA)-ACN). (S)-3-(4-(2-(3,4-difluorobenzyl)-1-oxo-1,2,3,4-tetrahydropyrrolo[1,2-a]pyrazin-6-yl)-2-(4-fluorophenethyl)-5-oxo-7,8,9,9a-tetrahydro-5H-pyrido[2,3-a]pyrrolizin-3-yl)-1,2,4-oxadiazol-5(4H)-one (4.7 mg, 6.96 μmol, 7.43% yield, 94.8% purity) was obtained.

$^1$H NMR (400 MHz, $CDCl_3$) δ ppm 7.00-7.16 (m, 7H), 6.92 (t, J=8.50 Hz, 3H), 6.08-6.22 (m, 1H), 4.75-4.85 (m, 1H), 4.52-4.68 (m, 2H), 3.92-4.09 (m, 1H), 3.64-3.87 (m, 3H), 3.42 (s, 2H), 3.05-3.26 (m, 3H), 2.28-2.57 (m, 3H), 1.40-1.50 (m, 1H). LC-MS: m/z 641.4 $(M+H)^+$.

Example 8

5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)isoxazol-3(2H)-one (Compound 150)

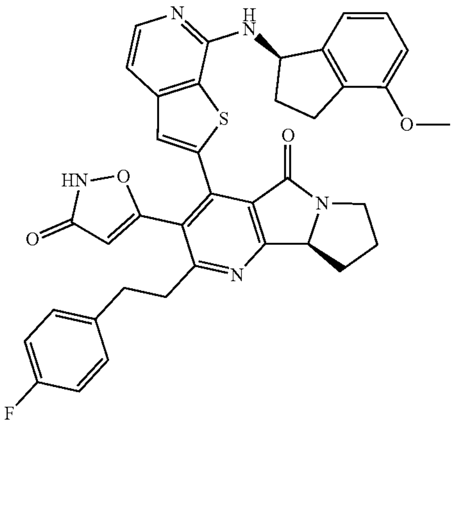

-continued
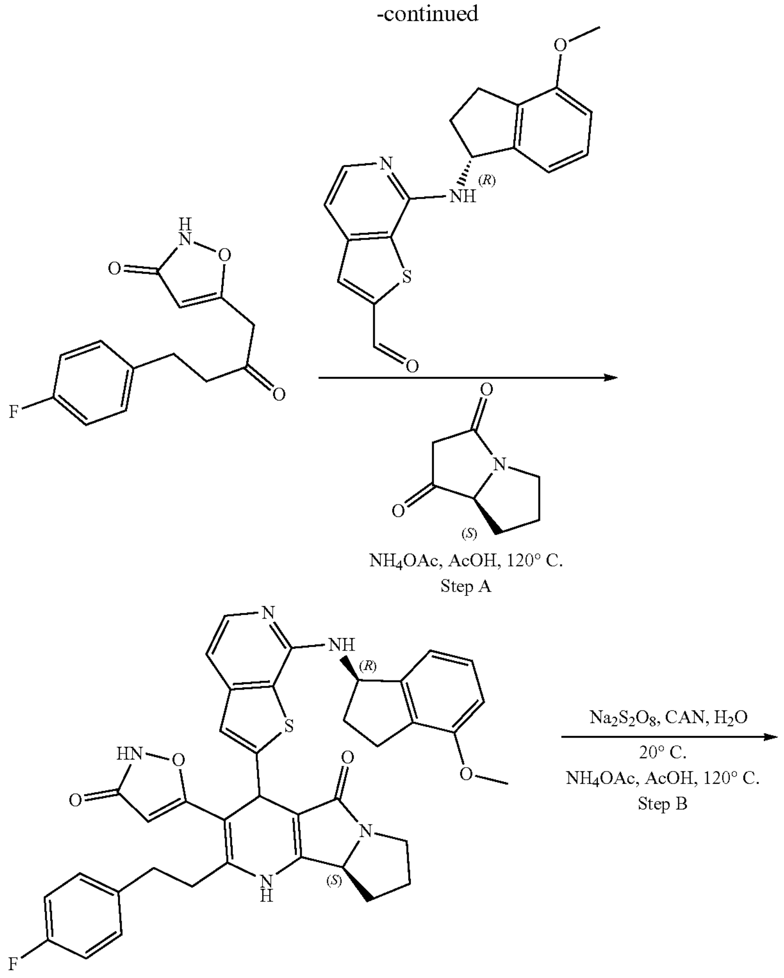
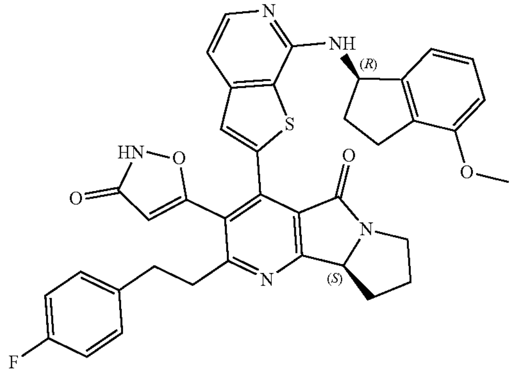

Step A 5-((9aS)-2-(4-fluorophenethyl)-4-(7-(((R)-4-methoxy-2,3-dihydro-1H-inden-1-yl)amino)thieno[2,3-c]pyridin-2-yl)-5-oxo-1,5,7,8,9,9a-hexahydro-4H-pyrido[2,3-a]pyrrolizin-3-yl)isoxazol-3(2H)-one

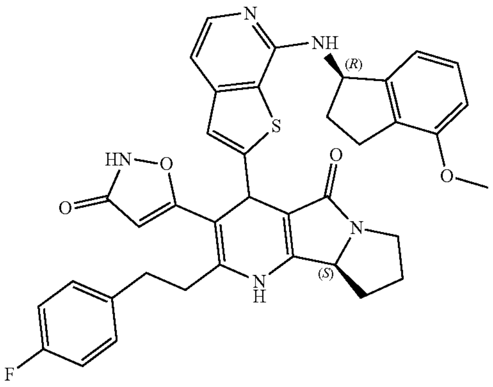

A mixture of (8S)-5,6,7,8-tetrahydropyrrolizine-1,3-dione (17.16 mg, 123.31 μmol), (R)-7-((4-methoxy-2,3-dihydro-1H-inden-1-yl)amino)thieno[2,3-c]pyridine-2-carbaldehyde (40 mg, 123.31 μmol), $NH_4OAc$ (14.26 mg, 184.96 μmaol) and 5-(4-(4-fluorophenyl)-2-oxobutyl)isoxazol-3(2H)-one (30.73 mg, 123.31 μmol) in AcOH (1.5 mL) was degassed and purged with $N_2$ for 3 times, and then the mixture was stirred at 120° C. for 2 hrs under $N_2$ atmosphere. The solution was cooled to room temperature and poured into water (25 mL), extracted with EtOAc (25 mL). The organic layer was washed with the aqueous $NaHCO_3$ solution (25 mL), then brine (25 mL), dried over anhydrous of $Na_2SO_4$, filtered and concentrated in vacuum. The residue was purified by flash silica gel chromatography (ISCO®; 4 g Sepa-Flash® Silica Flash Column, Eluent of 0~10% MeOH/DCM gradient @12 mL/min) to give 5-((9aS)-2-(4-fluorophenethyl)-4-(7-(((R)-4-methoxy-2,3-dihydro-1H-inden-1-yl)amino)thieno[2,3-c]pyridin-2-yl)-5-oxo-1,5,7,8,9,9a-hexahydro-4H-pyrido[2,3-a]pyrrolizin-3-yl)isoxazol-3(2H)-one (47 mg, 69.55 μmol, 56.40% yield). LC-MS: m/z 676.7 $(M+H)^+$.

Step B 5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)isoxazol-3(2H)-one

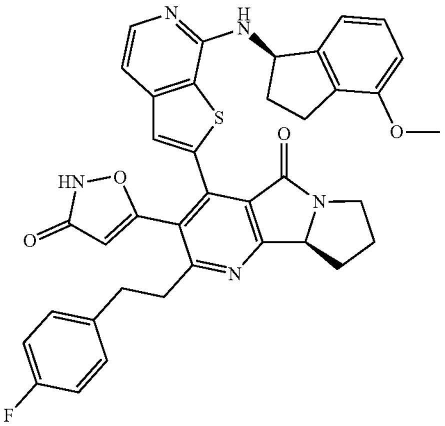 [SMILES: COc1cccc2c1CC[C@H]2Nc1nccc2cc(-c3c4c(nc(CCc5ccc(F)cc5)c3-c3cc(=O)[nH]o3)[C@@H]3CCCN3C4=O)sc12]

To a solution of 5-((9aS)-2-(4-fluorophenethyl)-4-(7-(((R)-4-methoxy-2,3-dihydro-1H-inden-1-yl)amino)thieno[2,3-c]pyridin-2-yl)-5-oxo-1,5,7,8,9,9a-hexahydro-4H-pyrido[2,3-a]pyrrolizin-3-yl)isoxazol-3(2H)-one (47 mg, 69.55 μmol) in ACN (10 mL) and water (5 mL) was added CAN (76.26 mg, 139.10 μmol). The mixture was stirred at 20° C. for 2 hrs. Water (25 mL) was added and the mixture was extracted with EtOAc (25 mL). The organic layer was washed with brine (25 mL), dried over $Na_2SO_4$, filtered and concentrated in vacuum. The residue was purified by flash silica gel chromatography (ISCO®; 12 g SepaFlash® Silica Flash Column, Eluent of 0~10% MeOH/DCM gradient @12 mL/min), then re-purified by prep-HPLC (FA condition). Column: Kromasil C18 150*30 mm*5 um; Condition: water (0.2% Formic acid)-ACN; Begin B: 30; End B: 85; Gradient Time (min): 20; 100% B Hold Time (Time): 5; Flow Rate (ml/min): 20; Detection wavelength: 220 nm and 254 nm) to give 5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)isoxazol-3(2H)-one (2.58 mg, 3.83 μmol, 5.51% yield).

$^1H$ NMR (400 MHz, DMSO-$d_6$) δ ppm 11.47 (s, 1H), 7.88 (d, J=6.0 Hz, 1H), 7.51 (s, 1H), 7.31 (s, 1H), 7.02-7.25 (m, 6H), 6.88-6.99 (m, 2H), 6.06 (s, 1H), 5.57-5.73 (m, 1H), 4.87-4.91 (m, 1H), 3.81 (s, 3H), 2.90-3.06 (m, 6H), 2.72-2.79 (m, 1H), 2.55-2.65 (m, 2H), 2.37-2.39 (m, 1H), 2.26-2.29 (m, 2H), 2.06-2.09 (m, 1H), 1.33-1.50 (m, 1H). LC-MS: m/z 674.4 $(M+H)^+$.

3-((9aS)-4-(7-(((R)-4-methoxy-2,3-dihydro-1H-inden-1-yl)amino)thieno[2,3-c]pyridin-2-yl)-5-oxo-2-(3-(tetrahydrofuran-3-yl)phenethyl)-7,8,9,9a-tetrahydro-5H-pyrido[2,3-a]pyrrolizin-3-yl)-1,2,4-oxadiazol-5(4H)-one (Compound 151)

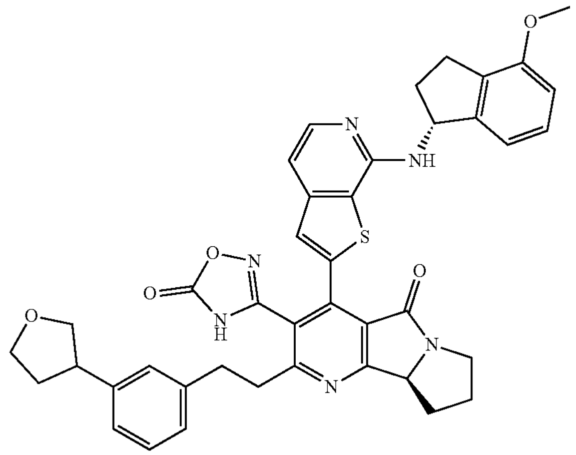 [SMILES: COc1cccc2c1CC[C@H]2Nc1nccc2cc(-c3c4c(nc(CCc5cccc(C6CCOC6)c5)c3-c3noc(=O)[nH]3)[C@@H]3CCCN3C4=O)sc12]

Compound 151 was synthesized using a similar procedure described in the Example 3 above by using the appropriate materials.

$^1$H NMR (400 MHz, MeOD-$d_4$) δ ppm 7.78 (d, J=6.72 Hz, 1H), 7.66 (s, 1H), 7.41 (d, J=6.72 Hz, 1H), 7.22-7.31 (m, 1H), 7.14-7.20 (m, 2H), 7.08-7.13 (m, 2H), 6.97 (d, J=7.21 Hz, 1H), 6.93-6.94 (m, 1H), 6.88-6.93 (m, 1H), 5.53 (t, J=6.48 Hz, 1H), 4.30-4.72 (m, 1H), 3.99-4.10 (m, 2H), 3.86-3.91 (m, 1H) 3.86 (s, 3H), 3.59-3.68 (m, 2H), 3.35-3.47 (m, 2H), 3.21 (d, J=7.58 Hz, 2H), 3.02-3.16 (m, 3H), 2.83-2.95 (m, 1H), 2.75 (d, J=6.60 Hz, 1H), 2.37-2.54 (m, 3H), 2.33 (d, J=5.99 Hz, 1H), 2.15 (dd, J=12.65, 6.54 Hz, 1H), 1.91-2.04 (m, 1H), 1.45 (q, J=10.21 Hz, 1H). LC-MS: m/z 727.4 $(M+H)^+$.

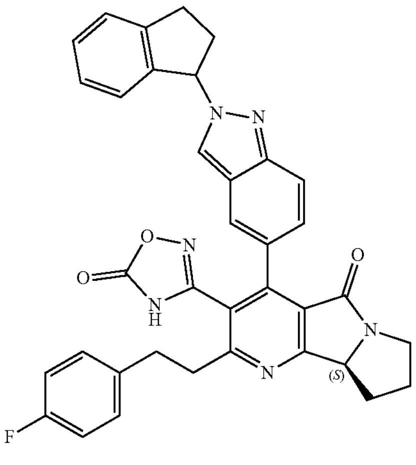

Compound 152 was synthesized using similar procedure as described in Example 1 above by using the appropriate materials.

$^1$H NMR (400 MHz, DMSO-d6): δ 8.38 (d, J=3.6 Hz, 1H), 8.24 (s, 1H), 7.64 (s, 1H), 7.37-7.42 (m, 2H), 7.30 (t, J=7.2 Hz, 1H), 7.05-7.23 (m, 7H), 6.22 (dd, J=6.0 Hz, J=8.0 Hz, 1H), 4.75 (dd, J=6.0 Hz, J=8.8 Hz, 1H), 3.46-3.53 (m, 1H), 3.19-3.25 (m, 2H), 2.95-3.06 (m, 5H), 2.71-2.76 (m, 1H), 2.57-2.62 (m, 1H), 2.31-2.36 (m, 1H), 2.19-2.27 (m, 2H), 1.32-1.36 (m, 1H). $^{19}$F NMR (377 MHz, DMSO-d6): δ −117.43. LC-MS: m/z 613.3 $(M+H)^+$

Compound 153

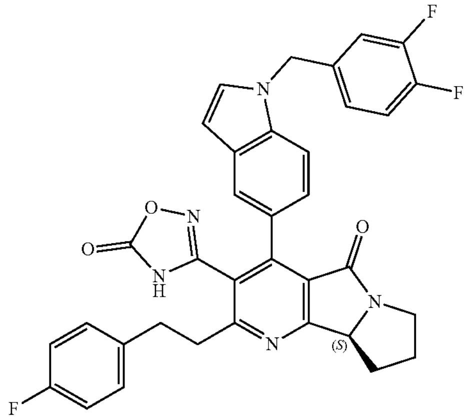

Compound 153 was synthesized using similar procedure as described in Example 1 above by using the appropriate materials.

$^1$H NMR (400 MHz, DMSO-d6): δ 12.51 (s, 1H), 7.61 (d, J=3.2 Hz, 1H), 7.52-7.56 (m, 2H), 7.34-7.49 (m, 2H), 7.19-7.27 (m, 2H), 7.06-7.15 (m, 3H), 7.02 (dd, J=8.4 Hz, J=1.2 Hz, 1H), 6.54 (d, J=3.2 Hz, 1H), 5.44 (s, 2H), 4.83 (dd, J=10.0 Hz, J=6.0 Hz, 1H), 3.46-3.58 (m, 1H), 3.21-3.31 (m, 1H), 2.95-3.16 (m, 4H), 2.18-2.42 (m, 3H), 1.30-1.43 (m, 1H). $^{19}$F NMR (377 MHz, DMSO-d6): δ −117.09, −138.27, −140.28. LC-MS: m/z 622.3 $(M+H)^+$ 5-(7-(7-(((R)-6,7-dihydro-5H-cyclopenta[b]pyridin-5-yl)amino)thieno[2,3-c]pyridin-2-yl)-3-isopropyl-1,1-dioxido-5-(2-(tetrahydro-2H-pyran-4-yl)ethyl)-2,3-dihydrothieno[3,2-b]pyridin-6-yl)isoxazol-3(2H)-one (Compound 154)

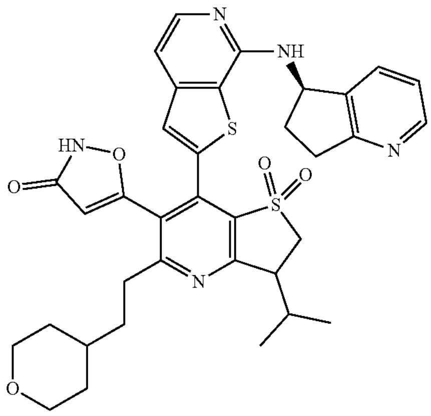 [SMILES: CC(C)C1CS(=O)(=O)c2c1nc(CCC1CCOCC1)c(-c1cc(=O)[nH]o1)c2-c1cc2ccnc(N[C@@H]3CCc4ncccc43)c2s1]

Compound 154 was synthesized using similar procedure as described in Example 2 above by using the appropriate materials.

$^1$H NMR (400 MHz, MeOD-$d_4$) δ 8.32-8.40 (m, 1H), 7.93-8.01 (m, 1H), 7.71-7.79 (m, 1H), 7.57-7.63 (m, 1H), 7.19-7.27 (m, 1H), 7.11-7.18 (m, 1H), 5.94-6.00 (m, 1H), 5.85-5.93 (m, 1H), 3.88-3.95 (m, 2H), 3.77-3.82 (m, 1H), 3.37-3.43 (m, 2H), 3.11-3.17 (m, 1H), 2.99-3.09 (m, 1H), 2.86-2.96 (m, 2H), 2.70-2.84 (m, 2H), 2.04-2.25 (m, 2H), 1.68-1.78 (m, 2H), 1.56-1.67 (m, 3H), 1.35 (d, J=1.34 Hz, 2H), 1.22-1.29 (m, 2H), 1.12-1.20 (m, 3H), 0.91 (d, J=6.36 Hz, 3H). LC-MS: m/z 672.2 $(M+H)^+$.

Compound 155

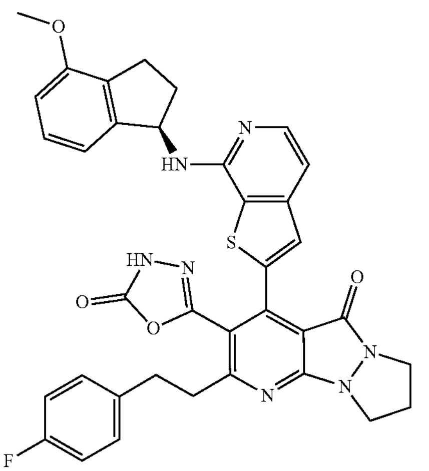

Compound 155 was synthesized using similar procedure as described in Example 2 above by using the appropriate materials.

$^1$H NMR (400 MHz, DMSO-d6): δ 7.98 (d, J=5.6 Hz, 1H), 7.51 (s, 1H), 7.20-7.30 (m, 3H), 7.04-7.15 (m, 4H), 6.83 (t, J=8.8 Hz, 2H), 5.90 (q, J=8.0 Hz, 1H), 3.97 (t, J=6.8 Hz, 2H), 3.85 (t, J=6.8 Hz, 2H), 3.79 (s, 3H), 3.07-3.10 (m, 2H), 2.89-3.05 (m, 3H), 2.58-2.74 (m, 4H), 1.97-2.06 (m, 1H). $^{19}$F NMR (377 MHz, DMSO-d6): −117.08. LC-MS: m/z 676.0 $(M+H)^+$.

5-(5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3-dihydrothieno[3,2-b]pyridin-6-yl)-1,3,4-oxadiazol-2(3H)-one (Compound 156)

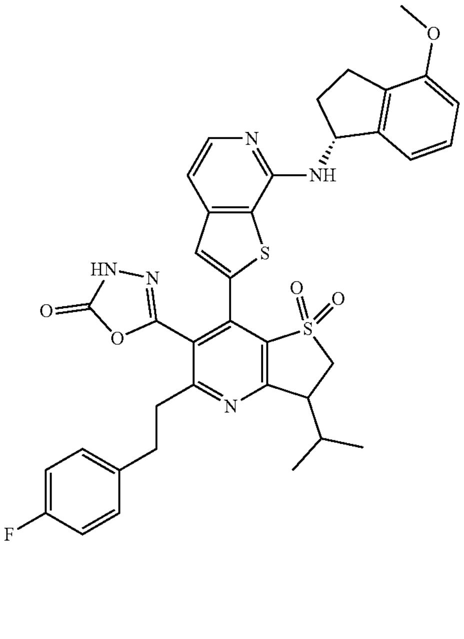

Compound 156 was synthesized using similar procedure as described in Example 2 above by using the appropriate materials.

$^1$H NMR (400 MHz, MeOD-$d_4$) δ ppm 7.92-7.97 (m, 1H), 7.65-7.71 (m, 1H), 7.12-7.17 (m, 4H), 6.93-6.99 (m, 2H), 6.86-6.91 (m, 1H), 6.79 (d, J=7.87 Hz, 1H), 5.77-5.83 (m, 1H), 3.82-3.84 (m, 3H), 3.72-3.81 (m, 2H), 3.52-3.59 (m, 1H), 3.21-3.29 (m, 1H), 2.99-3.15 (m, 3H), 2.71-2.82 (m, 2H), 2.60-2.69 (m, 1H), 1.96-2.04 (m, 1H), 1.12-1.16 (m, 3H), 0.84 (dd, J=6.56, 3.22 Hz, 3H). LC-MS: m/z 712.2 $(M+H)^+$.

2-fluoro-4-((5-(3-isopropyl-1,1-dioxido-6-(5-oxo-4,5-dihydro-1,3,4-oxadiazol-2-yl)-5-(2-(tetrahydro-2H-pyran-4-yl)ethyl)-2,3-dihydrothieno[3,2-b]pyridin-7-yl)-1H-pyrrolo[2,3-b]pyridin-1-yl)methyl)benzonitrile (Compound 157)

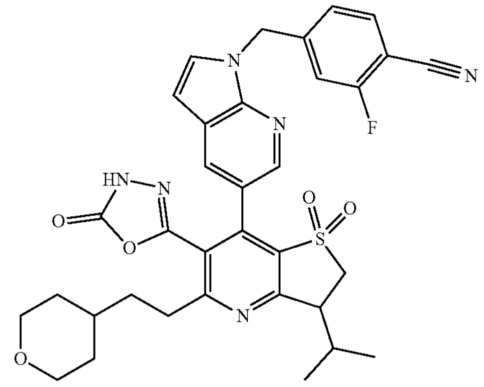 [SMILES: CC(C)C1CS(=O)(=O)c2c1nc(CCC1CCOCC1)c(-c1n[nH]c(=O)o1)c2-c1cnc2c(ccn2Cc2ccc(C#N)c(F)c2)c1]

Compound 157 was synthesized using similar procedure as described in Example 2 above by using the appropriate materials.

$^1$H NMR (400 MHz, $CDCl_3$) δ ppm 8.93-9.08 (m, 1H), 8.31 (d, J=1.79 Hz, 1H), 8.12-8.23 (m, 1H), 7.54-7.66 (m, 1H), 7.26 (d, J=3.70 Hz, 1H), 7.03-7.14 (m, 2H), 6.56-6.73 (m, 1H), 5.48-5.66 (m, 2H), 3.93-4.02 (m, 2H), 3.70-3.80 (m, 1H), 3.55-3.66 (m, 1H), 3.30-3.46 (m, 3H), 2.80-3.01 (m, 3H), 1.72-1.80 (m, 2H), 1.65 (dd, J=8.17, 1.97 Hz, 3H), 1.30-1.39 (m, 2H), 1.16 (d, J=6.91 Hz, 3H), 0.86-0.94 (m, 3H). LC-MS: m/z 657.2 $(M+H)^+$.

2-fluoro-4-((5-(2-(4-fluorophenethyl)-5-oxo-3-(5-oxo-4,5-dihydro-1,3,4-oxadiazol-2-yl)-8,9-dihydro-5H,7H-pyrazolo[1',2':1,2]pyrazolo[3,4-b]pyridin-4-yl)-1H-indol-1-yl)methyl)benzonitrile (Compound 158)

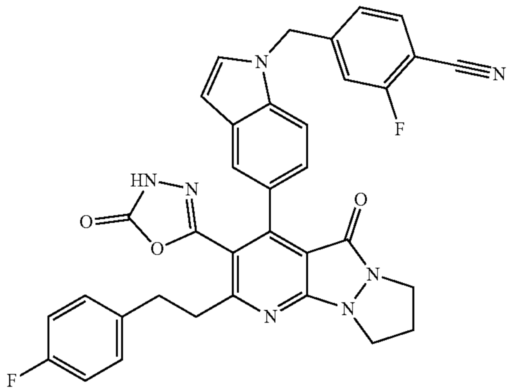 [SMILES: N#Cc1ccc(Cn2ccc3cc(-c4c(-c5n[nH]c(=O)o5)c(CCc5ccc(F)cc5)nc5c4c(=O)n4n5CCC4)ccc32)cc1F]

Compound 158 was synthesized using similar procedure as described in Example 2 above by using the appropriate materials.

$^1$H NMR (400 MHz, MeOD-$d_4$) δ ppm 7.64-7.69 (m, 2H), 7.36-7.40 (m, 1H), 7.30-7.34 (m, 1H), 7.14-7.19 (m, 2H), 7.07-7.13 (m, 2H), 7.02-7.06 (m, 1H), 6.93-7.00 (m, 2H), 6.59-6.63 (m, 1H), 5.52-5.56 (m, 2H), 4.08-4.13 (m, 2H), 3.96-4.02 (m, 2H), 3.10-3.14 (m, 2H), 3.03-3.09 (m, 2H), 2.72-2.80 (m, 2H). LC-MS: m/z 630.1 $(M+H)^+$.

2-fluoro-4-[1-[5-[11-[2-(4-fluorophenyl)ethyl]-7-oxo-10-(2-oxo-3H-1,3,4-oxadiazol-5-yl)-2,6,12-triazatricyclo[6.4.0.02,6]dodeca-1(8),9,11-trien-9-yl]indol-1-yl]ethyl]benzonitrile (Compound 159)

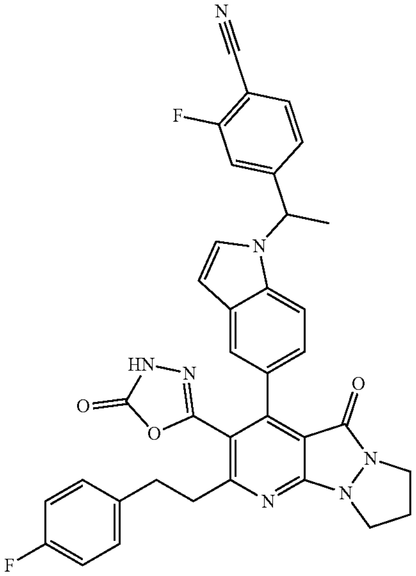 [SMILES: CC(c1ccc(C#N)c(F)c1)n1ccc2cc(-c3c(-c4n[nH]c(=O)o4)c(CCc4ccc(F)cc4)nc4c3c(=O)n3n4CCC3)ccc21]

Compound 159 was synthesized using similar procedure as described in Example 2 above by using the appropriate materials.

$^1$H NMR (400 MHz, MeOD-$d_4$) δ ppm 7.61-7.70 (m, 2H), 7.55-7.60 (m, 1H), 7.26-7.31 (m, 1H), 7.13-7.21 (m, 3H), 7.06-7.13 (m, 2H), 6.94-6.99 (m, 2H), 6.59-6.68 (m, 1H), 5.85-5.95 (m, 1H), 4.04-4.14 (m, 2H), 3.93-4.02 (m, 2H), 3.02-3.16 (m, 4H), 2.70-2.81 (m, 2H), 1.94-2.00 (m, 3H). LC-MS: m/z 644.3 $(M+H)^+$.

Compound 161

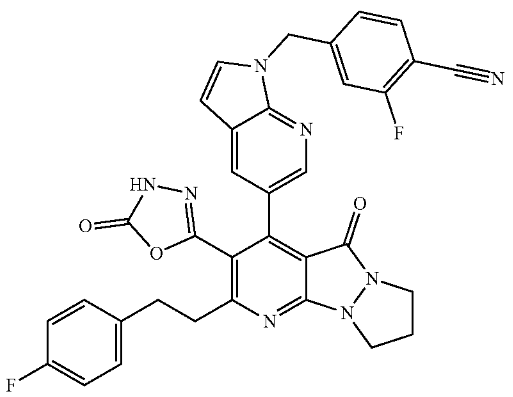

Compound 161 was synthesized using similar procedure as described in Example 2 above by using the appropriate materials.

$^1$H NMR (400 MHz, DMSO-d6): 12.45 (br s, 1H), 8.13 (d, J=2.0 Hz, 1H), 7.99 (d, J=2.0 Hz, 1H), 7.87 (t, J=7.6 Hz, 1H), 7.75 (d, J=3.6 Hz, 1H), 7.41 (d, J=10.0 Hz, 1H), 7.21-7.27 (m, 2H), 7.19 (d, J=7.6 Hz, 1H), 7.04-7.12 (m, 2H), 6.62 (d, J=3.2 Hz, 1H), 5.62 (s, 2H), 3.97 (t, J=6.8 Hz, 2H), 3.82 (t, J=6.8 Hz, 2H), 3.05-3.13 (m, 2H), 2.98-3.05 (m, 2H), 2.60 (t, J=7.2 Hz, 2H). $^{19}$F NMR (377 MHz, DMSO-d6): δ −108.14, −117.12. LC-MS: m/z 631.1 $(M+H)^+$.

6-[[6-[(9aS)-2-[2-(4-fluorophenyl)ethyl]-5-oxo-3-(2-oxo-3H-1,3,4-oxadiazol-5-yl)-7,8,9,9a-tetrahydro-pyrido[2,3-a]pyrrolizin-4-yl]-2-oxo-1,3-benzoxazol-3-yl]methyl]pyridine-3-carbonitrile (Compound 176)

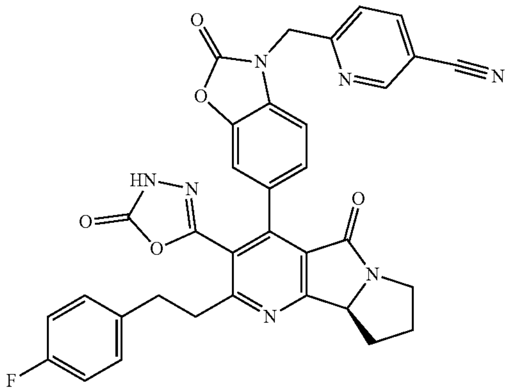

Compound 176 was synthesized using similar procedure as described in Example 2 above by using the appropriate materials.

$^1H$ NMR (400 MHz, DMSO-$d_6$) δ ppm 8.94 (d, J=1.6 Hz, 1H), 8.35 (dd, J=2.0, 8.4 Hz, 1H), 7.73 (d, J=8.0 Hz, 1H), 7.40 (s, 1H), 7.18-7.24 (m, 3H), 7.04-7.10 (m, 2H), 6.98-7.03 (m, 1H), 5.33 (s, 2H), 4.83 (dd, J=6.4, 10.2 Hz, 1H), 3.43-3.57 (m, 2H), 3.11-3.17 (m, 2H), 2.96-3.09 (m, 2H), 2.22-2.36 (m, 3H), 1.32-1.45 (m, 1H). $^{19}F$ NMR (400 MHz, DMSO-$d_6$) δ ppm −117.067. LC-MS: m/z 630.1 $(M+H)^+$.

2-fluoro-4-((6-(2-(4-fluorophenethyl)-5-oxo-3-(5-oxo-4,5-dihydro-1,3,4-oxadiazol-2-yl)-8,9-dihydro-5H,7H-pyrazolo[1',2':1,2]pyrazolo[3,4-b]pyridin-4-yl)-2-oxobenzo[d]oxazol-3(2H)-yl)methyl)benzonitrile (Compound 162)

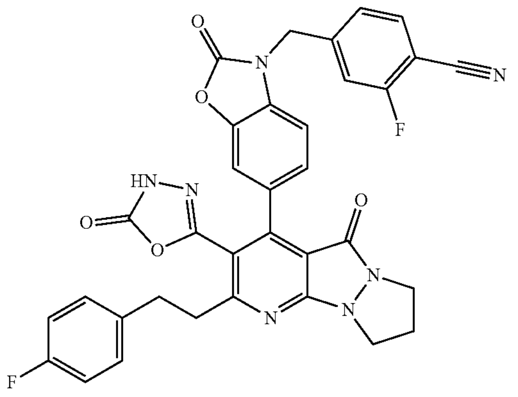 [SMILES: N#Cc1ccc(Cn2c(=O)oc3cc(-c4c(-c5n[nH]c(=O)o5)c(CCc5ccc(F)cc5)nc5c4c(=O)n4n5CCC4)ccc32)cc1F]

Compound 162 was synthesized using similar procedure as described in Example 2 above by using the appropriate materials.

$^1H$ NMR (400 MHz, DMSO-$d_6$) δ 12.52 (s, 1H), 7.94 (t, J=7.2 Hz, 1H), 7.63 (d, J=10.0 Hz, 1H), 7.40-7.46 (m, 2H), 7.29 (d, J=8.0 Hz, 1H), 7.19-7.26 (m, 2H), 7.04-7.11 (m, 3H), 5.19 (s, 2H), 3.96 (t, J=6.8 Hz, 2H), 3.82 (t, J=6.8 Hz, 2H), 2.97-3.11 (m, 4H), 2.55-2.64 (m, 2H). $^{19}F$ NMR (377 MHz, DMSO-$d_6$) δ −107.78, −117.09. LC-MS: m/z 648.2 $(M+H)^+$.

6-((6-(5-(4-fluorophenethyl)-3-isopropyl-1,1-dioxido-6-(5-oxo-4,5-dihydro-1,3,4-oxadiazol-2-yl)-2,3-dihydrothieno[3,2-b]pyridin-7-yl)-2-oxobenzo[d]oxazol-3(2H)-yl)methyl)nicotinonitrile (Compound 163)

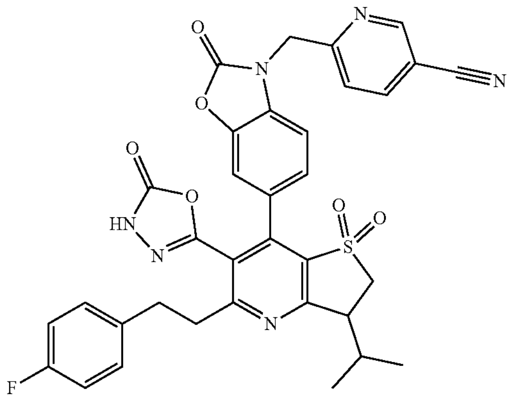 [SMILES: CC(C)C1CS(=O)(=O)c2c1nc(CCc1ccc(F)cc1)c(-c1n[nH]c(=O)o1)c2-c1ccc2c(c1)oc(=O)n2Cc1ccc(C#N)cn1]

Compound 163 was synthesized using similar procedure as described in Example 2 above by using the appropriate materials.

$^1H$ NMR (400 MHz, DMSO-$d_6$) δ 12.67 (s, 1H), 8.94 (dd, J=2.0 Hz, J=0.8 Hz, 1H), 8.36 (dd, J=8.4 Hz, J=2.4 Hz, 1H), 7.74 (d, J=8.0 Hz, 1H), 7.41 (s, 1H), 7.30 (d, J=8.4 Hz, 1H), 7.15-7.24 (m, 2H), 7.02-7.09 (m, 3H), 5.34 (s, 2H), 3.71-3.87 (m, 2H), 3.59 (dd, J=13.6 Hz, J=4.8 Hz, 1H), 3.17-3.28 (m, 2H), 3.00-3.10 (m, 2H) 2.54-2.64 (m, 1H), 1.05 (d, J=6.8 Hz, 3H), 0.76 (d, J=6.8 Hz, 3H). $^{19}F$ NMR (377 MHz, DMSO-$d_6$) δ −117.09. LC-MS: m/z 667.2 $(M+H)^+$.

6-[1-[6-[(9aS)-2-[2-(4-fluorophenyl)ethyl]-5-oxo-3-(2-oxo-3H-1,3,4-oxadiazol-5-yl)-7,8,9,9a-tetrahydropyrido[2,3-a]pyrrolizin-4-yl]-2-oxo-1,3-benzoxazol-3-yl]ethyl]pyridine-3-carbonitrile (Compound 160)

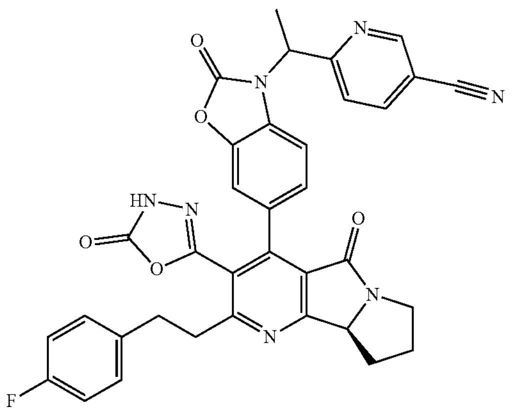

Compound 160 was synthesized using similar procedure as described in Example 2 above by using the appropriate materials.

$^1H$ NMR (400 MHz, DMSO-$d_6$) δ ppm 8.97 (s, 1H), 8.29-8.51 (m, 1H), 7.77 (d, J=8.4 Hz, 1H), 7.33-7.51 (m, 1H), 7.13-7.30 (m, 3H), 7.01-7.12 (m, 2H), 6.97 (d, J=8.0 Hz, 1H), 5.80 (q, J=7.2 Hz, 1H), 4.70-4.90 (m, 1H), 3.49-3.61 (m, 2H), 3.09-3.19 (m, 2H), 2.92-3.07 (m, 2H), 2.20-2.40 (m, 3H), 1.93 (d, J=7.2 Hz, 3H), 1.30-1.47 (m, 1H). $^{19}F$ NMR (400 MHz, DMSO-$d_6$) δ ppm −117.059. LC-MS: m/z 644.1 $(M+H)^+$.

(S)-6-(2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)-3-((5-fluoropyridin-2-yl)methyl)benzo[d]oxazol-2(3H)-one (Compound 164)

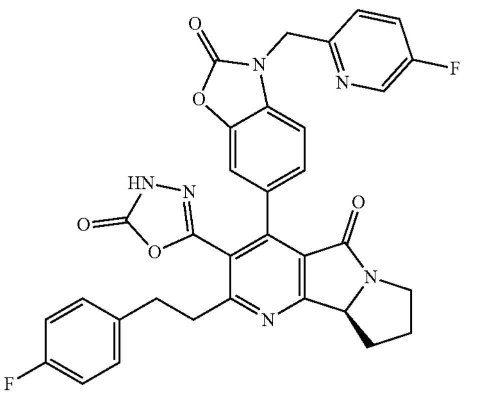

Compound 164 was synthesized using similar procedure as described in Example 2 above by using the appropriate materials.

$^1$H NMR (400 MHz, $CDCl_3$) δ ppm 8.47-8.58 (m, 1H), 8.43 (s, 1H), 7.39-7.45 (m, 2H), 7.22 (s, 1H), 7.13 (dd, J=8.46, 5.60 Hz, 2H), 7.08 (s, 2H), 6.94-7.00 (m, 2H), 5.08-5.19 (m, 2H), 4.71-4.82 (m, 1H), 3.65-3.80 (m, 1H), 3.34-3.49 (m, 1H), 3.02-3.19 (m, 4H), 2.46-2.55 (m, 1H), 2.32-2.41 (m, 2H), 1.39-1.48 (m, 1H). LC-MS: m/z 623.2 $(M+H)^+$.

Example 9: (R)-6-fluoro-1-((2-((S)-2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)thieno[2,3-c]pyridin-7-yl)amino)-2,3-dihydro-1H-indene-5-carbonitrile (Compound 165)

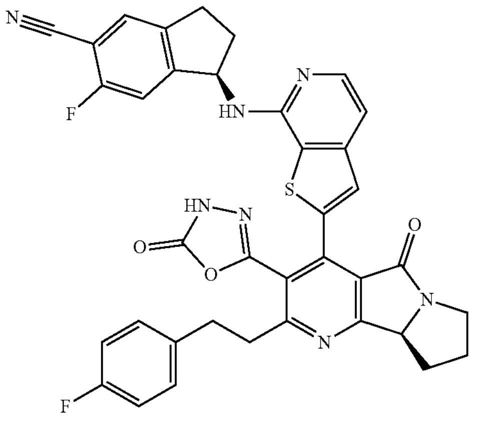 [SMILES: N#Cc1cc2c(cc1F)[C@H](Nc1nccc3cc(-c4c5c(nc(CCc6ccc(F)cc6)c4-c4n[nH]c(=O)o4)[C@@H]4CCCN4C5=O)sc13)CC2]

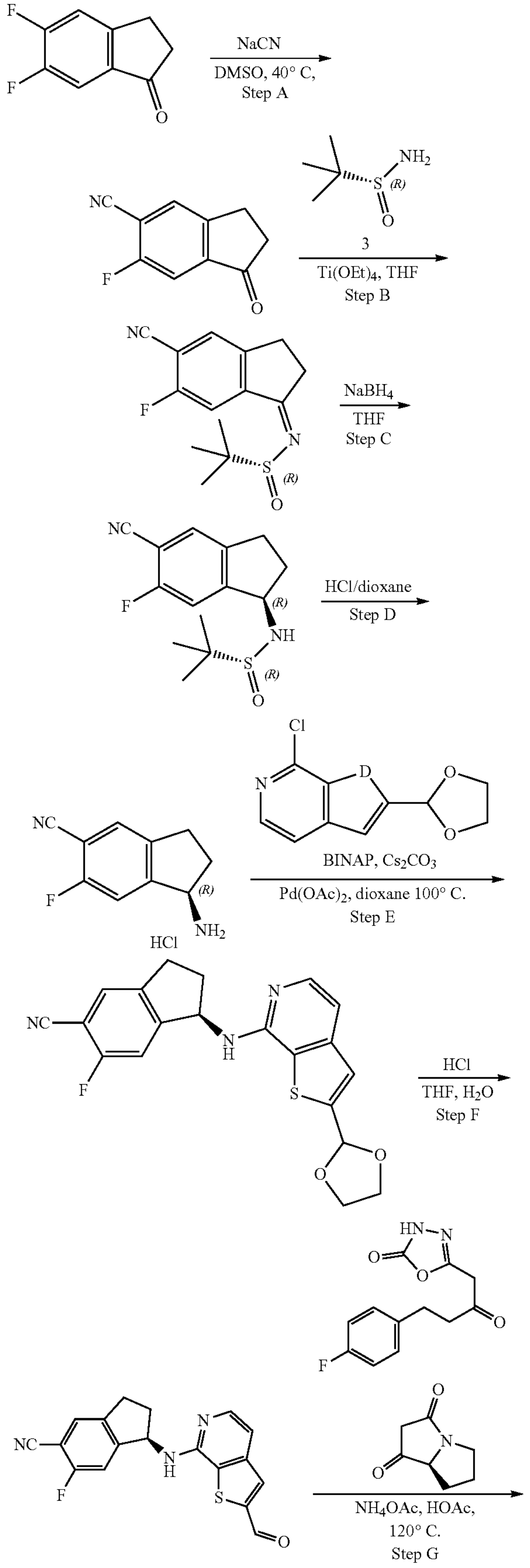

-continued

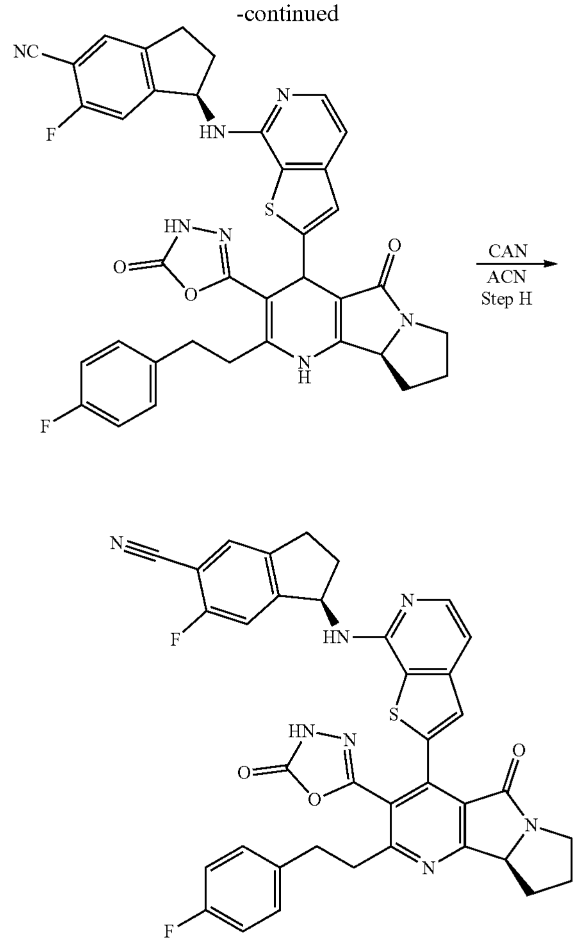

Step A 6-fluoro-1-oxo-2,3-dihydro-1H-indene-5-carbonitrile

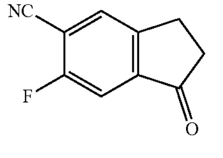 [SMILES: N#Cc1cc2c(cc1F)C(=O)CC2]

To a solution of 5,6-difluoroindan-1-one (3.4 g, 20.22 mmol) in DMSO (40 mL) was added NaCN (991 mg, 20.22 mmol). The mixture was stirred at 40° C. for 16 hrs. The solution was diluted with water (40 mL) and filtered by Celite. The filtrate was extracted with ethyl acetate (50 mL×2). The combined organic phases were washed with brine (50 mL), dried over anhydrous sodium sulfate, filtered, concentrated in vacuum to give a residue. The residue was purified by column chromatography ($SiO_2$, 16% ethyl acetate in petroleum ether) to give 6-fluoro-1-oxo-2,3-dihydro-1H-indene-5-carbonitrile (560 mg, 15.81% yield) as a black oil.

$^1$H NMR (400 MHz, $CDCl_3$) δ 7.79 (d, J=5.2 Hz, 1H), 7.54 (d, J=7.2 Hz, 1H), 3.13-3.29 (m, 2H), 2.72-2.99 (m, 2H). $^{19}$F NMR (377 MHz, chloroform-d) δ −107.985. LC-MS: m/z 176.1 $(M+H)^+$.

Step B (R,Z)—N-(5-cyano-6-fluoro-2,3-dihydro-1H-inden-1-ylidene)-2-methylpropane-2-sulfinamide

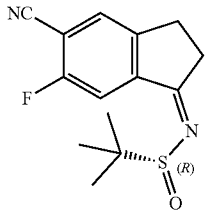

To a solution of 6-fluoro-1-oxo-2,3-dihydro-1H-indene-5-carbonitrile (280 mg, 1.60 mmol) and (R)-2-methylpropane-2-sulfinamide (200 mg, 1.65 mmol) in 2-methyltetrahydrofuran (5 mL) was added $Ti(OEt)_4$ (663 μL, 3.20 mmol). The mixture was stirred at 80° C. for 16 hrs. The mixture was combined with another batch from ES28217-38 (280 mg of compound ketone) was poured into water (50 mL) at 0° C., and diluted with ethyl acetate (50 mL). The mixture was added with diatomite (10 g) and stirred for 10 min. Then the mixture was filtered to remove the precipitate. The filtrate was extracted with ethyl acetate (50 mL×2). The combined organic phases were washed with brine (50 mL), dried over anhydrous sodium sulfate, filtered, concentrated in vacuum to give a residue. The residue was purified by flash column chromatography ($SiO_2$, 27% ethyl acetate in petroleum ether) to give (R,Z)—N-(5-cyano-6-fluoro-2,3-dihydro-1H-inden-1-ylidene)-2-methylpropane-2-sulfinamide (275 mg, 30.90% average yield) as a brown oil.

$^1$H NMR (400 MHz, $CDCl_3$) δ 7.68 (d, J=5.2 Hz, 1H), 7.54 (d, J=8.0 Hz, 1H), 3.52-3.65 (m, 1H), 3.27 (s, 1H), 3.14-3.19 (m, 2H), 1.34 (s, 9H). LC-MS: m/z 279.1 $(M+H)^+$.

Step C (R)—N—((R)-5-cyano-6-fluoro-2,3-dihydro-1H-inden-1-yl)-2-methylpropane-2-sulfinamide

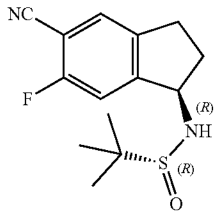

To a solution of (R,Z)—N-(5-cyano-6-fluoro-2,3-dihydro-1H-inden-1-ylidene)-2-methylpropane-2-sulfinamide (275 mg, 0.99 mmol) in THF (5 mL) was added $NaBH_4$ (150 mg, 3.97 mmol) at −70° C. under nitrogen atmosphere. The reaction mixture was stirred at −70° C. for 30 mins, then warmed to 0° C. naturally. The mixture was stirred at 0° C. for 1 hr under nitrogen atmosphere. The reaction mixture was quenched with saturated $NH_4Cl$ solution (20 mL), and extracted with ethyl acetate (20 mL×2). The combined organic phases were washed with brine (20 mL), dried over anhydrous sodium sulfate, filtered, concentrated in vacuum to give a residue. The residue was purified by column chromatography ($SiO_2$, 30-40% ethyl acetate in petroleum ether) to give (R)—N—((R)-5-cyano-6-fluoro-2,3-dihydro-1H-inden-1-yl)-2-methylpropane-2-sulfinamide (100 mg, 36.10% yield).

$^1H$ NMR (400 MHz, $CDCl_3$) δ 7.58 (d, J=8.4 Hz, 1H), 7.44 (d, J=5.6 Hz, 1H), 4.91 (q, J=7.2 Hz, 1H), 3.54 (d, J=6.4 Hz, 1H), 2.94-3.06 (m, 1H), 2.77-2.88 (m, 1H), 2.54-2.67 (m, 1H), 2.00-2.08 (m, 1H), 1.26 (s, 9H). LC-MS: m/z 281.1 $(M+H)^+$.

Step D (R)-1-amino-6-fluoro-2,3-dihydro-1H-indene-5-carbonitrile

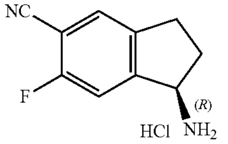

A mixture of (R,Z)—N-(5-cyano-6-fluoro-2,3-dihydro-1H-inden-1-ylidene)-2-methylpropane-2-sulfinamide (100 mg, 0.36 mmol) in HCl/dioxane (2M, 2 mL) was stirred at 20° C. for 1.5 hrs. The mixture was concentrated to give (R)-1-amino-6-fluoro-2,3-dihydro-1H-indene-5-carbonitrile (130 mg, 99.49% yield, 68% purity, 2HCl).

$^1H$ NMR (400 MHz, chloroform-d) δ 7.76 (d, J=6.0 Hz, 1H), 7.49 (d, J=9.2 Hz, 1H), 4.84-4.90 (m, 1H), 3.11-3.22 (m, 1H), 2.95-3.07 (m, 1H), 2.65-2.75 (m, 1H), 2.08-2.23 (m, 1H).

Step E (R)-1-((2-(1,3-dioxolan-2-yl)thieno[2,3-c]pyridin-7-yl)amino)-6-fluoro-2,3-dihydro-1H-indene-5-carbonitrile

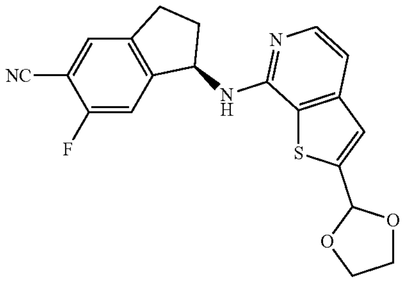 [SMILES: N#Cc1cc2c(cc1F)[C@H](Nc1nccc3cc(C4OCCO4)sc13)CC2]

A mixture of (R)—N—((R)-5-cyano-6-fluoro-2,3-dihydro-1H-inden-1-yl)-2-methylpropane-2-sulfinamide (110 mg, 0.30 mmol, 2HCl), 7-chloro-2-(1,3-dioxolan-2-yl)thieno[2,3-c]pyridine (73 mg, 0.30 mmol), $Cs_2CO_3$ (300 mg, 0.92 mmol), $Pd(OAc)_2$ (7 mg, 0.03 mmol) and BINAP (40 mg, 0.06 mmol) in dioxane (5 mL) was degassed and purged with nitrogen for 3 times, and then the mixture was stirred at 100° C. for 16 hrs under nitrogen atmosphere. The mixture was combined with ES28217-44 (20 mg of heterocyclic compound), and concentrated. The residue was purified by flash column chromatography ($SiO_2$, 34% ethyl acetate in petroleum ether) to give (R)-1-((2-(1,3-dioxolan-2-yl)thieno[2,3-c]pyridin-7-yl)amino)-6-fluoro-2,3-dihydro-1H-indene-5-carbonitrile (120 mg, 88.79% average yield).

$^1H$ NMR (400 MHz, DMSO-$d_6$) δ 7.96 (d, J=5.6 Hz, 1H), 7.81 (d, J=6.4 Hz, 1H), 7.50 (s, 1H), 7.29 (d, J=8.0 Hz, 1H), 7.21-7.26 (m, 1H), 7.09 (d, J=5.6 Hz, 1H), 6.21 (s, 1H), 5.89 (q, J=8.4 Hz, 1H), 3.92-4.14 (m, 4H), 2.95-3.07 (m, 1H), 2.79-2.93 (m, 1H), 2.54-2.60 (m, 1H), 2.03-2.17 (m, 1H). LC-MS: m/z 382.1 $(M+H)^+$.

Step F (R)-6-fluoro-1-((2-formylthieno[2,3-c]pyridin-7-yl)amino)-2,3-dihydro-1H-indene-5-carbonitrile

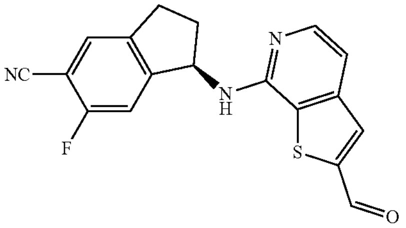 [SMILES: N#Cc1cc2c(cc1F)[C@H](Nc1nccc3cc(C=O)sc13)CC2]

A mixture of (R)-1-amino-6-fluoro-2,3-dihydro-1H-indene-5-carbonitrile (120 mg, 0.31 mmol), aqueous HCl solution (4 M, 400 μL) in THF (2 mL) was stirred at 45° C. for 16 hrs. The reaction mixture was quenched by addition of aq. $NaHCO_3$ (10 mL) at 0° C., then diluted with ethyl acetate (50 mL) and extracted with ethyl acetate (10 mL×3). The combined organic layers were washed with brine (10 mL), dried over anhydrous sodium sulfate, filtered and concentrated under reduced pressure to give a residue. The residue was purified by flash column chromatography ($SiO_2$, 34% ethyl acetate in petroleum ether) to give (R)-1-((2-(1,3-dioxolan-2-yl)thieno[2,3-c]pyridin-7-yl)amino)-6-fluoro-2,3-dihydro-1H-indene-5-carbonitrile (70 mg, 8.2% yield).

$^1H$ NMR (400 MHz, DMSO-$d_6$) δ 10.18 (s, 1H), 8.34 (s, 1H), 8.05 (d, J=5.6 Hz, 1H), 7.82 (d, J=5.6 Hz, 1H), 7.63 (d, J=8.0 Hz, 1H), 7.24-7.31 (m, 2H), 5.91 (q, J=8.0 Hz, 1H), 2.96-3.07 (m, 1H), 2.81-2.94 (m, 1H), 2.55-2.64 (m, 1H), 2.02-2.22 (m, 1H). $^{19}F$ NMR (377 MHz, DMSO-$d_6$) δ −112.17. LC-MS: m/z 338.1 $(M+H)^+$.

Step G (1R)-6-fluoro-1-((2-((9aS)-2-(4-fluorophenethyl)-5-oxo-3-(5-oxo-4,5-dihydro-1,3,4-oxadiazol-2-yl)-4,5,7,8,9,9a-hexahydro-1H-pyrido[2,3-a]pyrrolizin-4-yl)thieno[2,3-c]pyridin-7-yl)amino)-2,3-dihydro-1H-indene-5-carbonitrile

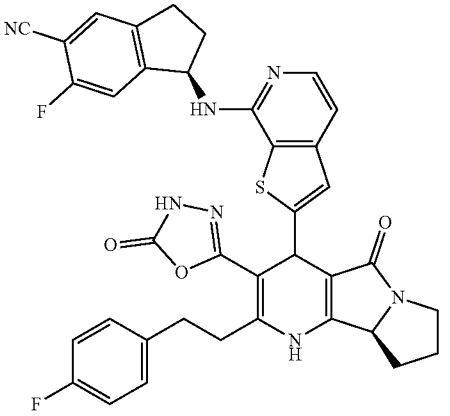 [SMILES: N#Cc1cc2c(cc1F)[C@H](Nc1nccc3cc(C4C5=C(NC(CCc6ccc(F)cc6)=C4c4n[nH]c(=O)o4)[C@@H]4CCCN4C5=O)sc13)CC2]

To a solution of (R)-1-((2-(1,3-dioxolan-2-yl)thieno[2,3-c]pyridin-7-yl)amino)-6-fluoro-2,3-dihydro-1H-indene-5-carbonitrile (65 mg, 0.19 mmol) and 5-(4-(4-fluorophenyl)-2-oxobutyl)-1,3,4-oxadiazol-2(3H)-one (52 mg, 0.21 mmol) and (S)-tetrahydro-1H-pyrrolizine-1,3(2H)-dione (39 mg, 0.28 mmol) in HOAc (3 mL) was added $NH_4OAc$ (40 mg, 0.52 mmol). The mixture was stirred at 120° C. for 1 hr. The mixture was combined with ES28217-49 (5 mg of nitrile compound) was concentrated in vacuum to give a residue. The residue was purified by column chromatography (SiO2, ethyl acetate) to give (1R)-6-fluoro-1-((2-((9aS)-2-(4-fluorophenethyl)-5-oxo-3-(5-oxo-4,5-dihydro-1,3,4-oxadiazol-2-yl)-4,5,7,8,9,9a-hexahydro-1H-pyrido[2,3-a]pyrrolizin-4-yl)thieno[2,3-c]pyridin-7-yl)amino)-2,3-dihydro-1H-indene-5-carbonitrile (35 mg, 24.61% average yield).

$^1H$ NMR (400 MHz, DMSO-$d_6$) δ 12.19 (d, J=8.4 Hz, 1H), 9.69-10.06 (m, 1H), 7.88 (d, J=5.6 Hz, 1H), 7.78 (d, J=6.0 Hz, 1H), 7.19-7.29 (m, 4H), 7.06-7.13 (m, 3H), 6.99 (dd, J=2.4, 5.6 Hz, 1H), 5.77-5.96 (m, 1H), 5.08-5.24 (m, 1H), 4.18-4.34 (m, 1H), 3.24-3.29 (m, 1H), 2.93-3.04 (m, 2H), 2.79-2.92 (m, 6H), 2.03-2.15 (m, 4H), 1.22-1.35 (m, 1H). LC-MS: m/z 690.2 $(M+H)^+$.

Step H (R)-6-fluoro-1-((2-((S)-2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)thieno[2,3-c]pyridin-7-yl)amino)-2,3-dihydro-1H-indene-5-carbonitrile

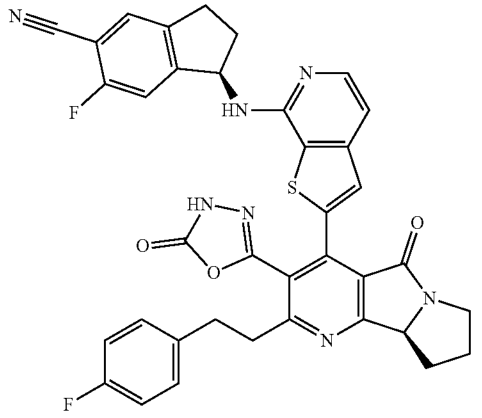 [SMILES: N#Cc1cc2c(cc1F)[C@H](Nc1nccc3cc(-c4c5c(nc(CCc6ccc(F)cc6)c4-c4n[nH]c(=O)o4)[C@@H]4CCCN4C5=O)sc13)CC2]

A mixture of (1R)-6-fluoro-1-((2-((9aS)-2-(4-fluorophenethyl)-5-oxo-3-(5-oxo-4,5-dihydro-1,3,4-oxadiazol-2-yl)-4,5,7,8,9,9a-hexahydro-1H-pyrido[2,3-a]pyrrolizin-4-yl)thieno[2,3-c]pyridin-7-yl)amino)-2,3-dihydro-1H-indene-5-carbonitrile (35 mg, 0.05 mmol), CAN (28 mg, 0.05 mmol) in acetonitrile (2 mL) was stirred at 50° C. for 1 hr. The reaction mixture was concentrated. The mixture was purified by reversed-phase HPLC (column: Welch Xtimate C18 150*25 mm*5 um; mobile phase: [water($NH_3H_2O$ +$NH_4HCO_3$)-ACN]; gradient: 26%-566% B over 8 min) and lyophilized to give (R)-6-fluoro-1-((2-((S)-2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)thieno[2,3-c]pyridin-7-yl)amino)-2,3-dihydro-1H-indene-5-carbonitrile (5.97 mg, 17.11% yield).

$^1H$ NMR (400 MHz, DMSO-$d_6$) δ 7.99 (d, J=5.6 Hz, 1H), 7.81 (d, J=5.6 Hz, 1H), 7.41-7.47 (m, 2H), 7.28 (dd, J=9.2, 2.4 Hz, 1H), 7.21 (dd, J=8.8, 5.6 Hz, 2H), 7.14 (d, J=5.6 Hz, 1H), 7.01-7.10 (m, 2H), 5.81-6.02 (m, 1H), 4.87 (dd, J=6.4, 10.2 Hz, 1H), 3.51-3.57 (m, 1H), 3.16-3.23 (m, 2H), 2.97-3.13 (m, 3H), 2.80-2.93 (m, 1H), 2.54-2.63 (m, 2H), 2.35-2.39 (m, 1H), 2.23-2.30 (m, 2H), 2.08-2.16 (m, 1H), 1.37-1.49 (m, 1H). $^{19}F$ NMR (377 MHz, DMSO-$d_6$) δ −112.11, −117.04. LC-MS: m/z 688.0 $(M+H)^+$.

Example 10

5-((S)-4-(7-(((R)-5,6-difluoro-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 166)

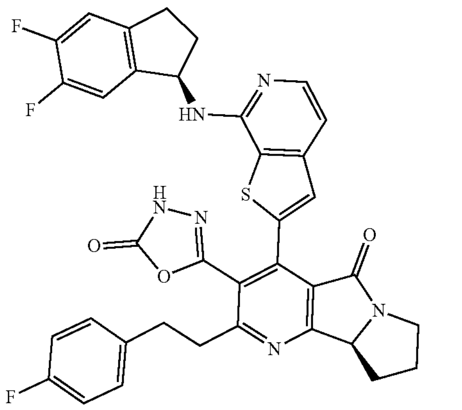

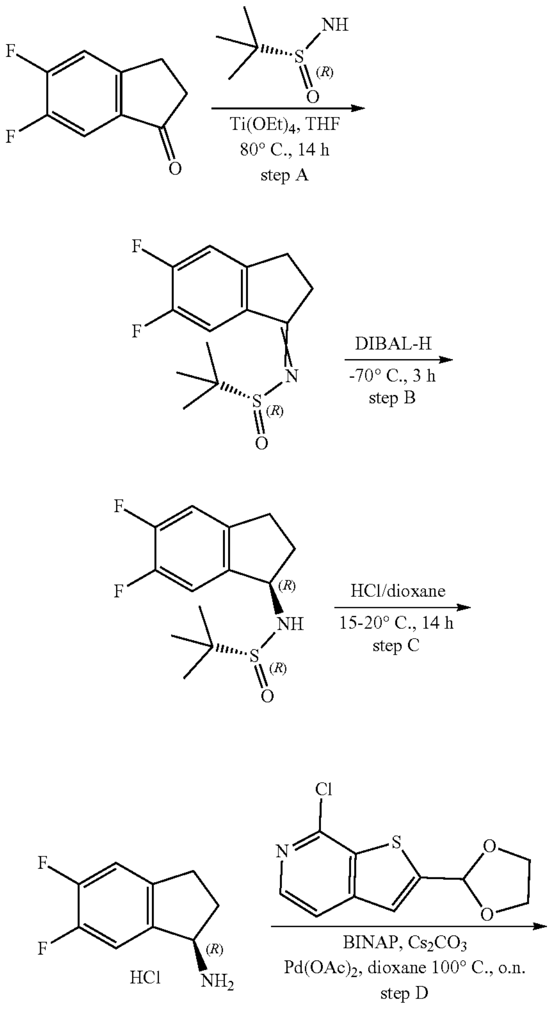

-continued

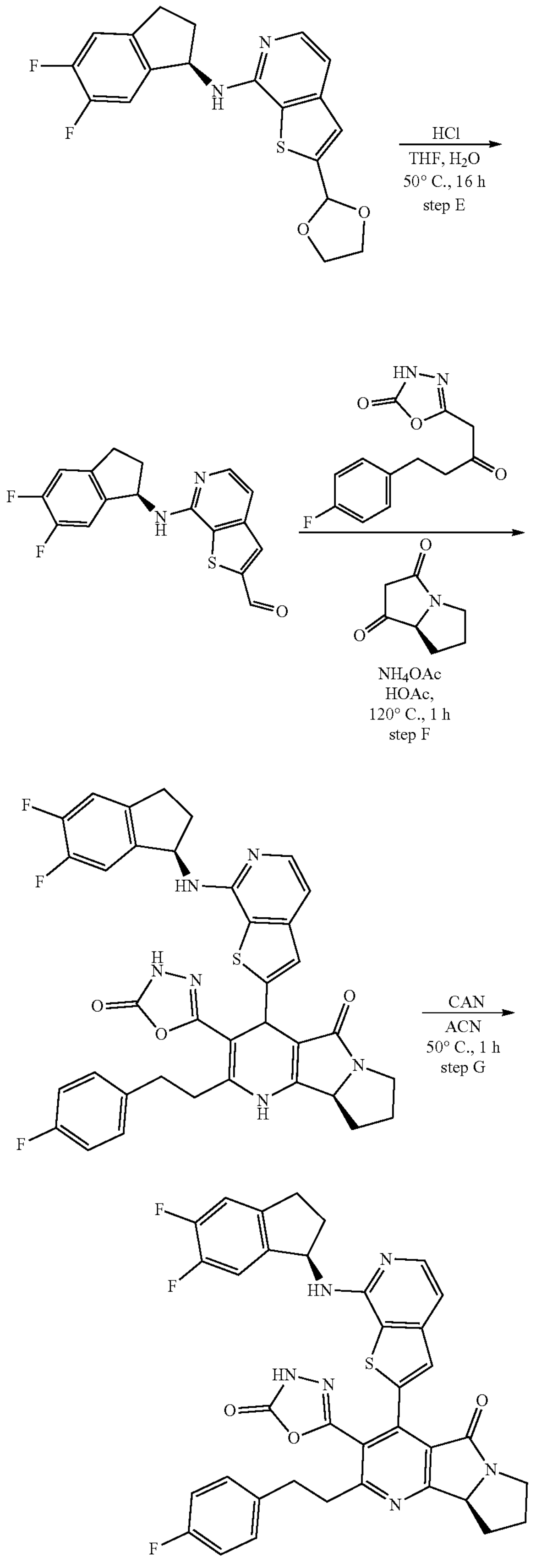

Step A (R)—N-(5,6-difluoro-2,3-dihydro-1H-inden-1-ylidene)-2-methylpropane-2-sulfinamide

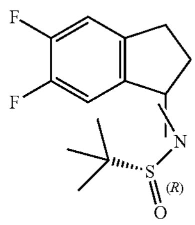

To a mixture of 5,6-difluoroindan-1-one (2 g, 11.89 mmol) and (R)-2-methylpropane-2-sulfinamide (1.51 g, 12.49 mmol) in 2-MeTHF (20 mL) was added tetraethoxytitanium (4.93 mL, 23.79 mmol) under nitrogen and stirred at 80° C. for 14 hrs. The reaction was diluted with water (500 mL) and ethyl acetate (500 mL) and filtered through Celite. The mixture was extracted with ethyl acetate (300 mL×3). The combined organic layers were dried over anhydrous sodium sulfate, filtered and concentrated in vacuum. The crude product was purified by silica gel column chromatography (35% ethyl acetate in petroleum ether) to give (R)—N-(5,6-difluoro-2,3-dihydro-1H-inden-1-ylidene)-2-methylpropane-2-sulfinamide (2.73 g, 42.29% yield).

$^1H$ NMR (400 MHz, DMSO-$d_6$) δ 7.59-7.71 (m, 2H), 3.32-3.29 (m, 1H), 3.08-3.14 (m, 2H), 2.98-3.08 (m, 1H), 1.22 (s, 9H). $^{19}F$ NMR (377 MHz, DMSO-$d_6$) δ −129.75, −138.67. LC-MS: m/z 272.1 $(M+H)^+$.

Step B (R)—N—((R)-5,6-difluoro-2,3-dihydro-1H-inden-1-yl)-2-methylpropane-2-sulfinamide

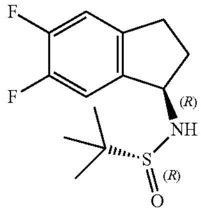

To a mixture of (R)—N-(5,6-difluoro-2,3-dihydro-1H-inden-1-ylidene)-2-methylpropane-2-sulfinamide (2.73 g, 10.06 mmol) in DCM (150 mL) was added DIBAL-H (1 M in toluene, 30.19 mL) dropwise under nitrogen at −70° C. and stirred for 3 hrs. The reaction was quenched with MeOH (10 mL) slowly, then warmed to 0° C. 50 mL of saturated $NH_4Cl$ solution was added and the resulting mixture was stirred for 30 min. Then the organic layer was separated. The aqueous layer was washed with DCM (300 mL). The combined organic layers were washed with brine (500 mL), dried over anhydrous sodium sulfate, filtered and concentrated in vacuum to give a residue. The crude product was purified by silica gel column chromatography (50% ethyl acetate in petroleum ether) to give (R)—N—((R)-5,6-difluoro-2,3-dihydro-1H-inden-1-yl)-2-methylpropane-2-sulfinamide (1.19 g, 43.27% yield).

$^1H$ NMR (400 MHz, DMSO-$d_6$) δ 7.56 (dd, J=7.9, 10.7 Hz, 1H), 7.29 (dd, J=7.5, 10.5 Hz, 1H), 5.86 (d, J=8.8 Hz, 1H), 4.71 (q, J=8.4 Hz, 1H), 2.80-2.92 (m, 1H), 2.67-2.77 (m, 1H), 2.36-2.45 (m, 1H), 1.91-2.00 (m, 1H), 1.15 (s, 9H).

$^{19}$F NMR (377 MHz, DMSO-$d_6$) δ −140.55, −141.44. LC-MS: m/z 274.1 (M+H)$^+$. SFC $t_R$=1.712 min, 100%.

Step C
(R)-5,6-difluoro-2,3-dihydro-1H-inden-1-amine

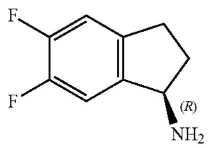

A mixture of (R)—N—((R)-5,6-difluoro-2,3-dihydro-1H-inden-1-yl)-2-methylpropane-2-sulfinamide (1.19 g, 4.35 mmol, 1 eq) in HCl/dioxane (20 mL) was stirred at 15-20° C. for 14 hrs. The reaction was concentrated in vacuum to give (R)-5,6-difluoro-2,3-dihydro-1H-inden-1-amine (960 mg, 99.73% yield, HCl).

$^1$H NMR (400 MHz, DMSO-$d_6$) δ 8.71 (s, 3H), 7.77 (dd, J=7.8, 10.8 Hz, 1H), 7.41 (dd, J=7.7, 10.6 Hz, 1H), 4.58-4.84 (m, 1H), 3.00-3.11 (m, 1H), 2.78-2.90 (m, 1H), 2.51-2.56 (m, 1H), 2.43-2.49 (m, 1H), 1.99-2.11 (m, 1H). $^{19}$F NMR (377 MHz, DMSO-$d_6$) δ −137.90, −140.58.

Step D (R)—N-(5,6-difluoro-2,3-dihydro-1H-inden-1-yl)-2-(1,3-dioxolan-2-yl)thieno[2,3-c]pyridin-7-amine

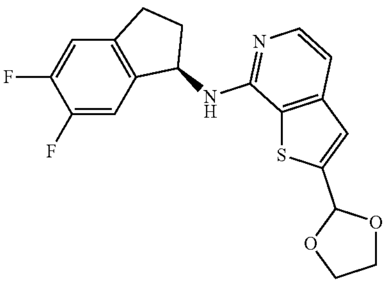 [SMILES: Fc1cc2c(cc1F)[C@H](Nc1nccc3cc(C4OCCO4)sc13)CC2]

To a mixture of (R)-5,6-difluoro-2,3-dihydro-1H-inden-1-amine (204 mg, 0.99 mmol, HCl), 7-chloro-2-(1,3-dioxolan-2-yl)thieno[2,3-c]pyridine (200 mg, 0.83 mmol), $Pd(OAc)_2$ (20 mg, 0.09 mmol), BINAP (104 mg, 0.17 mmol) and $Cs_2CO_3$ (800 mg, 2.46 mmol) under nitrogen was added dioxane (6 mL) and stirred at 100° C. for 16 hrs under nitrogen. The reaction was filtered and concentrated in vacuum. The crude product was purified by silica gel column chromatography (50% ethyl acetate in petroleum ether) to give (R)—N-(5,6-difluoro-2,3-dihydro-1H-inden-1-yl)-2-(1,3-dioxolan-2-yl)thieno[2,3-c]pyridin-7-amine (353 mg, 91.15% yield).

$^1$H NMR (400 MHz, DMSO-$d_6$) δ ppm 7.96 (d, J=5.5 Hz, 1H), 7.48 (s, 1H), 7.33 (dd, J=7.6, 10.7 Hz, 1H), 7.14-7.21 (m, 2H), 7.07 (d, J=5.5 Hz, 1H), 6.21 (s, 1H), 5.80 (q, J=7.9 Hz, 1H), 4.03-4.06 (m, 2H), 3.99-4.03 (m, 2H), 2.94-3.04 (m, 1H), 2.76-2.90 (m, 1H), 2.52-2.58 (m, 1H), 2.01-2.13 (m, 1H). $^{19}$F NMR (377 MHz, DMSO-$d_6$) δ −140.59, −140.65, −141.71, −141.77. LC-MS: m/z 375.0 (M+H)$^+$.

Step E (R)-7-((5,6-difluoro-2,3-dihydro-1H-inden-1-yl)amino)thieno[2,3-c]pyridine-2-carbaldehyde

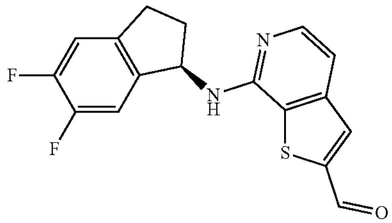 [SMILES: O=Cc1cc2ccnc(N[C@@H]3CCc4cc(F)c(F)cc43)c2s1]

To a mixture of (R)—N-(5,6-difluoro-2,3-dihydro-1H-inden-1-yl)-2-(1,3-dioxolan-2-yl)thieno[2,3-c]pyridin-7-amine (353 mg, 0.94 mmol) in THF (3 mL) was added 4M aqueous HCl (1.18 mL) and stirred at 50° C. for 16 hrs under nitrogen. The reaction was diluted with $NaHCO_3$ solution (aq., 30 mL) and extracted with ethyl acetate (20 mL×3). The combined organic layers were dried over anhydrous sodium sulfate, filtered and concentrated in vacuum. The crude product was purified by silica gel column chromatography (35% ethyl acetate in petroleum ether) to give (R)-7-((5,6-difluoro-2,3-dihydro-1H-inden-1-yl)amino)thieno[2,3-c]pyridine-2-carbaldehyde (300 mg, 96.32% yield).

$^1$H NMR (400 MHz, DMSO-$d_6$) δ 10.18 (s, 1H), 8.33 (s, 1H), 8.06 (d, J=5.6 Hz, 1H), 7.53 (d, J=7.9 Hz, 1H), 7.34 (dd, J=7.6, 10.7 Hz, 1H), 7.26 (d, J=5.5 Hz, 1H), 7.20 (dd, J=7.9, 10.3 Hz, 1H), 5.82 (q, J=8.0 Hz, 1H), 2.95-3.05 (m, 1H), 2.75-2.90 (m, 1H), 2.54-2.60 (m, 1H), 2.01-2.16 (m, 1H). $^{19}$F NMR (377 MHz, DMSO-$d_6$) δ −140.41, −140.47, −141.60, −141.66.

Step F 5-((9aS)-4-(7-(((R)-5,6-difluoro-2,3-dihydro-1H-inden-1-yl)amino)thieno[2,3-c]pyridin-2-yl)-2-(4-fluorophenethyl)-5-oxo-4,5,7,8,9,9a-hexahydro-1H-pyrido[2,3-a]pyrrolizin-3-yl)-1,3,4-oxadiazol-2(3H)-one

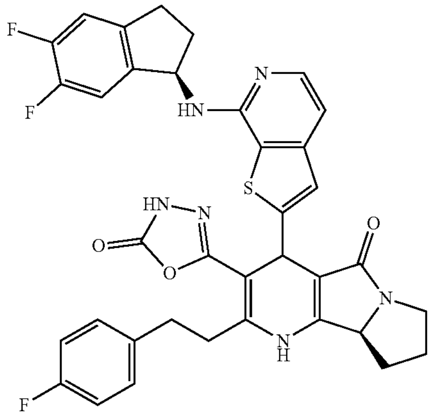 [SMILES: O=C1C2=C(NC(CCc3ccc(F)cc3)=C(c3n[nH]c(=O)o3)C2c2cc3ccnc(N[C@@H]4CCc5cc(F)c(F)cc54)c3s2)[C@@H]2CCCN12]

To a mixture of (R)-7-((5,6-difluoro-2,3-dihydro-1H-inden-1-yl)amino)thieno[2,3-c]pyridine-2-carbaldehyde (50 mg, 0.15 mmol), (S)-tetrahydro-1H-pyrrolizine-1,3(2H)-dione (25 mg, 0.18 mmol) and 5-(4-(4-fluorophenyl)-2-oxobutyl)-1,3,4-oxadiazol-2(3H)-one (40 mg, 0.16 mmol) in HOAc (5 mL) was added $NH_4OAc$ (25 mg, 0.32 mmol) and stirred at 120° C. for 1 hr. The reaction was filtered and concentrated in vacuum. The crude product was purified by silica gel column chromatography (100% ethyl acetate in petroleum ether) to give 5-((9aS)-4-(7-(((R)-5,6-difluoro-2,3-dihydro-1H-inden-1-yl)amino)thieno[2,3-c]pyridin-2-yl)-2-(4-fluorophenethyl)-5-oxo-4,5,7,8,9,9a-hexahydro-1H-pyrido[2,3-a]pyrrolizin-3-yl)-1,3,4-oxadiazol-2(3H)-one (36 mg, 34.84% yield). LC-MS: m/z 683.1 $(M+H)^+$.

Step G 5-((S)-4-(7-(((R)-5,6-difluoro-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one

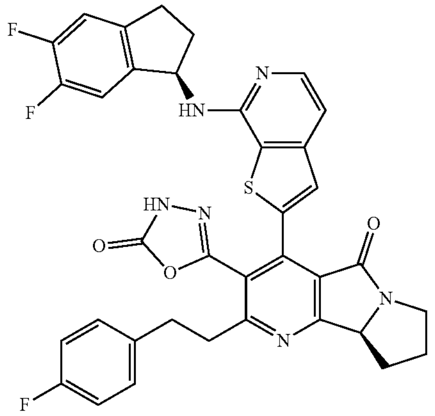 [SMILES: O=C1c2c(nc(CCc3ccc(F)cc3)c(-c3n[nH]c(=O)o3)c2-c2cc3ccnc(N[C@@H]4CCc5cc(F)c(F)cc54)c3s2)[C@@H]2CCCN12]

To a mixture of 5-((9aS)-4-(7-(((R)-5,6-difluoro-2,3-dihydro-1H-inden-1-yl)amino)thieno[2,3-c]pyridin-2-yl)-2-(4-fluorophenethyl)-5-oxo-4,5,7,8,9,9a-hexahydro-1H-pyrido[2,3-a]pyrrolizin-3-yl)-1,3,4-oxadiazol-2(3H)-one (36 mg, 0.05 mmol) in DCM (2 mL) was added CAN (29 mg, 0.05 mmol) and stirred at 50° C. for 1 hr. The reaction was filtered and concentrated in vacuum. The crude product was purified by prep-HPLC [column: Welch Xtimate C18 150*25 mm*5 um; mobile phase: [water($NH_3H_2O$+$NH_4HCO_3$)-ACN]; gradient: 34%-64% B over 8 min] and fractions containing the desired compound was lyophilized to give 5-((S)-4-(7-(((R)-5,6-difluoro-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (2.89 mg, 8.05% yield).

$^1$H NMR (400 MHz, DMSO-$d_6$) δ 12.69 (s, 1H), 8.00 (d, J=5.6 Hz, 1H), 7.45 (d, J=2.3 Hz, 1H), 7.29-7.38 (m, 2H), 7.17-7.26 (m, 3H), 7.02-7.11 (m, 3H), 5.81 (q, J=7.6 Hz, 1H), 4.87 (dd, J=6.3, 10.1 Hz, 1H), 3.50-3.59 (m, 1H), 3.26-3.30 (m, 1H), 3.16-3.23 (m, 2H), 3.04-3.13 (m, 1H), 2.95-3.04 (m, 2H), 2.77-2.89 (m, 1H), 2.54-2.59 (m, 1H), 2.32-2.40 (m, 1H), 2.23-2.32 (m, 2H), 2.01-2.13 (m, 1H), 1.37-1.47 (m, 1H). $^{19}$F NMR (377 MHz, DMSO-$d_6$) δ −117.02, −140.55, −141.60. LC-MS: m/z 681.1 $(M+H)^+$.

5-((S)-4-(7-(((R)-5-fluoro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 167)

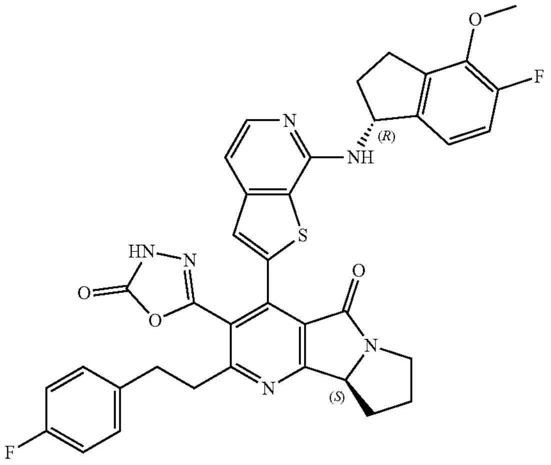

Compound 167 was synthesized using similar procedure as described in Example 10 above by using the appropriate materials.

$^1$H NMR (400 MHz, MeOD-$d_4$) δ ppm 7.78-7.83 (m, 1H), 7.63-7.67 (m, 1H), 7.43-7.46 (m, 1H), 7.12-7.19 (m, 2H), 7.06-7.10 (m, 2H), 6.95-7.01 (m, 2H), 5.47-5.53 (m, 1H), 4.91-4.97 (m, 1H), 3.98-3.99 (m, 3H), 3.64-3.74 (m, 1H), 3.41-3.52 (m, 1H), 2.90-3.25 (m, 6H), 2.75-2.83 (m, 1H), 2.40-2.56 (m, 3H), 2.18-2.27 (m, 1H), 1.45-1.56 (m, 1H). $^{19}$F NMR (377 MHz, MeOD-$d_4$) δ −77.16, −118.97, −134.63. LC-MS: m/z 693.1 $(M+H)^+$.

5-((S)-4-(7-(((R)-4-chloro-5-fluoro-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 168)

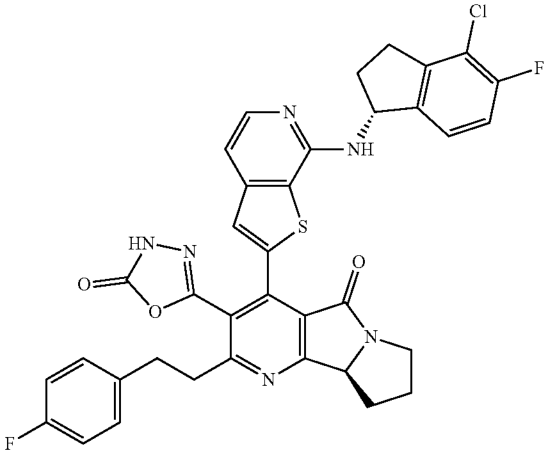 [SMILES: O=C1c2c(nc(CCc3ccc(F)cc3)c(-c3n[nH]c(=O)o3)c2-c2cc3ccnc(N[C@@H]4CCc5c4ccc(F)c5Cl)c3s2)[C@@H]2CCCN12]

Compound 168 was synthesized using similar procedure as described in Example 10 above by using the appropriate materials.

$^1$H NMR (400 MHz, $CDCl_3$) δ ppm 7.95-8.06 (m, 1H), 7.40-7.40 (m, 1H), 7.34-7.44 (m, 1H), 7.23 (dd, J=7.93, 4.83 Hz, 1H), 7.12 (td, J=9.09, 5.66 Hz, 3H), 6.94-7.01 (m, 3H), 5.78-5.95 (m, 1 H), 4.74-4.84 (m, 1H), 3.69-3.86 (m, 1H), 3.37-3.50 (m, 1H), 3.05-3.21 (m, 5H), 2.89-2.98 (m, 1H), 2.73-2.82 (m, 1H), 2.50-2.56 (m, 1H), 2.33-2.43 (m, 2H), 2.00-2.09 (m, 1H), 1.43-1.50 (m, 1H). $^{19}$F NMR (377 MHz, DMSO-d6) δ −116.57. LC-MS: m/z 697.0 $(M+H)^+$.
Example 11
5-((S)-4-(7-(((S)-2,3-dihydrobenzofuran-3-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 169)
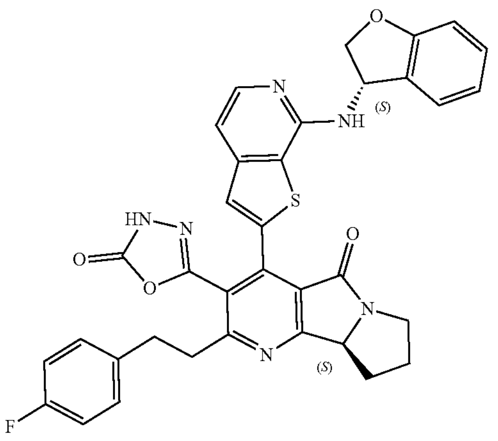
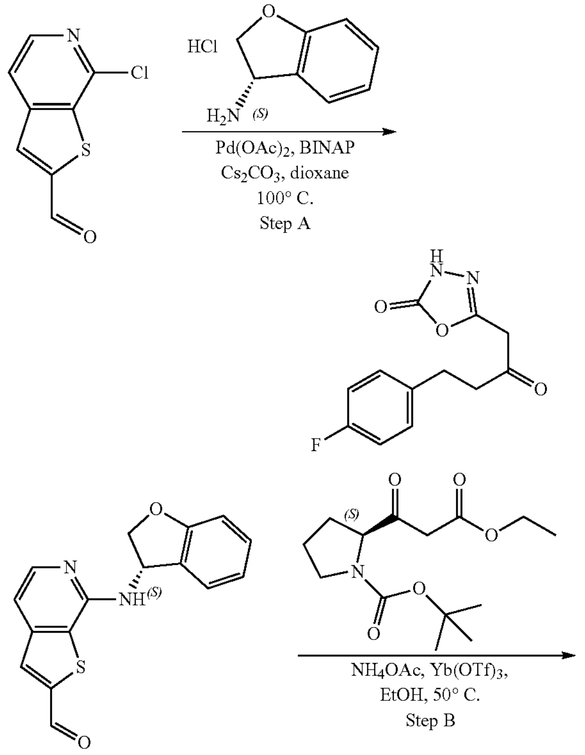
-continued
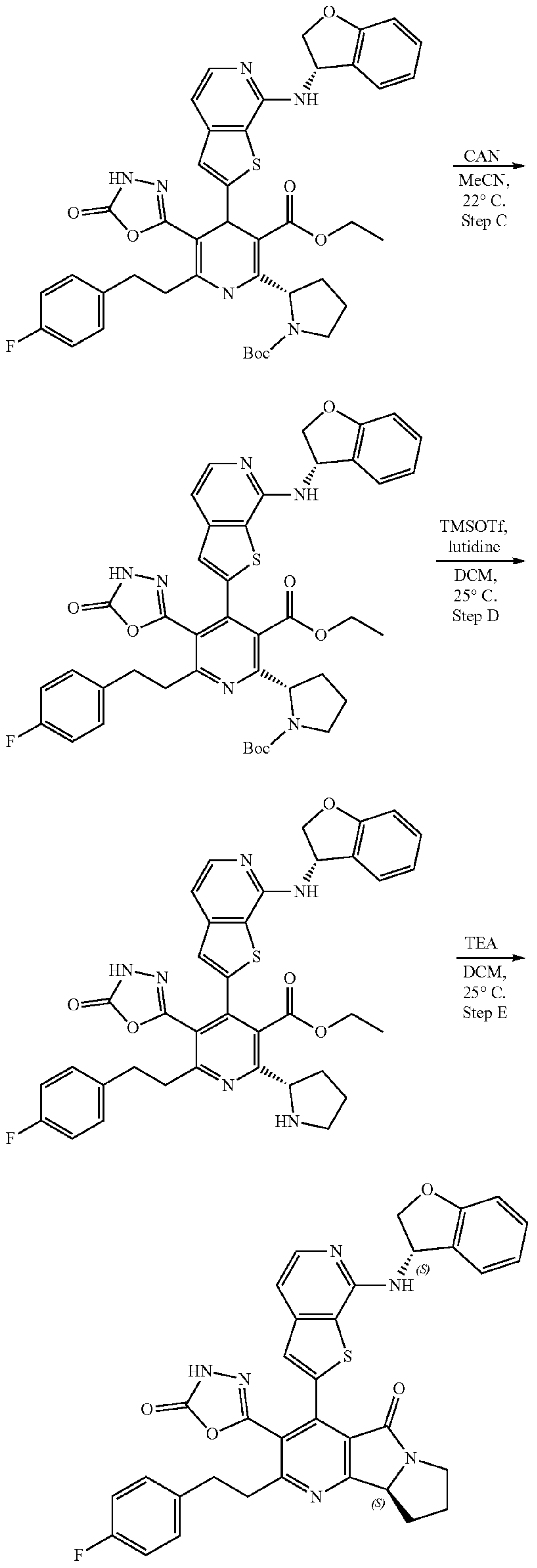

Step A (S)-7-((2,3-dihydrobenzofuran-3-yl)amino)thieno[2,3-c]pyridine-2-carbaldehyde

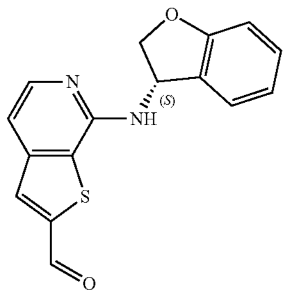

A mixture of (3S)-2,3-dihydrobenzofuran-3-amine (50 mg, 369.92 μmol), 7-chlorothieno[2,3-c]pyridine-2-carbaldehyde (74 mg, 374.42 μmol), $Pd(OAc)_2$ (9 mg, 40.09 μmol), BINAP (24 mg, 38.54 μmol and $Cs_2CO_3$ (241. mg, 739.67 μmol) in dioxane (5 mL) was degassed and purged with $N_2$ for 3 times, and then the mixture was stirred at 100° C. for 16 hrs under $N_2$ atmosphere. The reaction mixture was concentrated under reduced pressure to remove solvent. The residue was purified by column chromatography on silica gel (eluted with 0~30% PE in EA). Compound (S)-7-((2,3-dihydrobenzofuran-3-yl)amino)thieno[2,3-c]pyridine-2-carbaldehyde (40 mg, 32.84% yield, 90% purity) was obtained. $^1H$ NMR (400 MHz, DMSO-$d_6$) δ ppm 10.18 (s, 1H), 8.27 (dd, J=5.19, 3.04 Hz, 1H), 8.01-8.13 (m, 1H), 7.72-7.90 (m, 1H), 7.35-7.44 (m, 1H), 7.29-7.33 (m, 1H), 7.18-7.26 (m, 1H), 6.84-6.92 (m, 2H), 5.97-6.06 (m, 1H), 4.83 (t, J=9.12 Hz, 1H), 4.40 (br dd, J=9.54, 5.25 Hz, 1H). LC-MS: m/z 296.8 $(M+H)^+$.

Step B ethyl 2-((S)-1-(tert-butoxycarbonyl)pyrrolidin-2-yl)-4-(7-(((S)-2,3-dihydrobenzofuran-3-yl)amino)thieno[2,3-c]pyridin-2-yl)-6-(4-fluorophenethyl)-5-(5-oxo-4,5-dihydro-1,3,4-oxadiazol-2-yl)-1,4-dihydropyridine-3-carboxylate

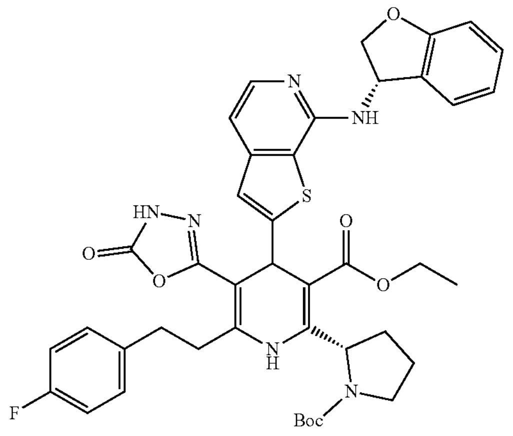 [SMILES: CCOC(=O)C1=C([C@@H]2CCCN2C(=O)OC(C)(C)C)NC(CCc2ccc(F)cc2)=C(c2n[nH]c(=O)o2)C1c1cc2ccnc(N[C@@H]3COc4ccccc43)c2s1]

A mixture of (S)-7-((2,3-dihydrobenzofuran-3-yl)amino)thieno[2,3-c]pyridine-2-carbaldehyde (40 mg, 134.98 μmol), tert-butyl (S)-2-(3-ethoxy-3-oxopropanoyl)pyrrolidine-1-carboxylate (39 mg, 136.68 μmol), $NH_4OAc$ (21 mg, 272.44 μmol), tris(trifluoromethylsulfonyloxy)ytterbium (9 mg, 14.51 μmol), 5-(4-(4-fluorophenyl)-2-oxobutyl)-1,3,4-oxadiazol-2(3H)-one (34 mg, 135.88 μmol) in EtOH (50 mL) was degassed and purged with $N_2$ for 3 times, and then the mixture was stirred at 50° C. for 16 hrs under $N_2$ atmosphere. The reaction mixture was concentrated under reduced pressure to remove solvent. Crude compound ethyl 2-((S)-1-(tert-butoxycarbonyl)pyrrolidin-2-yl)-4-(7-(((S)-2,3-dihydrobenzofuran-3-yl)amino)thieno[2,3-c]pyridin-2-yl)-6-(4-fluorophenethyl)-5-(5-oxo-4,5-dihydro-1,3,4-oxadiazol-2-yl)-1,4-dihydropyridine-3-carboxylate (108 mg, crude) was obtained. LC-MS: m/z 795.3 $(M+H)^+$.

Step C ethyl 2-((S)-1-(tert-butoxycarbonyl)pyrrolidin-2-yl)-4-(7-(((S)-2,3-dihydrobenzofuran-3-yl)amino)thieno[2,3-c]pyridin-2-yl)-6-(4-fluorophenethyl)-5-(5-oxo-4,5-dihydro-1,3,4-oxadiazol-2-yl)nicotinate

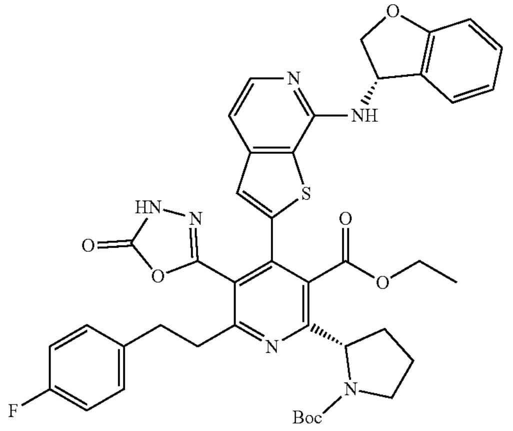 [SMILES: CCOC(=O)c1c([C@@H]2CCCN2C(=O)OC(C)(C)C)nc(CCc2ccc(F)cc2)c(-c2n[nH]c(=O)o2)c1-c1cc2ccnc(N[C@@H]3COc4ccccc43)c2s1]

A mixture of ethyl 2-((S)-1-(tert-butoxycarbonyl)pyrrolidin-2-yl)-4-(7-(((S)-2,3-dihydrobenzofuran-3-yl)amino)thieno[2,3-c]pyridin-2-yl)-6-(4-fluorophenethyl)-5-(5-oxo-4,5-dihydro-1,3,4-oxadiazol-2-yl)-1,4-dihydropyridine-3-carboxylate (108 mg, 135.87 μmol), CAN (148 mg, 269.96 μmol) in MeCN (3 mL) and $H_2O$ (3 mL) was degassed and purged with $N_2$ for 3 times, and then the mixture was stirred at 22° C. for 16 hrs under $N_2$ atmosphere. The reaction mixture was quenched by addition $NaHCO_3$ (50 mL) at 22° C., and then diluted with $H_2O$ (100 mL) and extracted with EtOAc (100 mL×2). The combined organic layer was washed with brine (50 mL), dried over $Na_2SO_4$, filtered and concentrated under reduced pressure to give a residue. The residue was purified by column chromatography on silica gel (eluted with 0~30% PE in EA). Compound ethyl 2-((S)-1-(tert-butoxycarbonyl)pyrrolidin-2-yl)-4-(7-(((S)-2,3-dihydrobenzofuran-3-yl)amino)thieno[2,3-c]pyridin-2-yl)-6-(4-fluorophenethyl)-5-(5-oxo-4,5-dihydro-1,3,4-oxadiazol-2-yl)nicotinate (70 mg, 45.49% yield, 70% purity) was obtained. LC-MS: m/z 793.3 $(M+H)^+$.

Step D ethyl 4-(7-(((S)-2,3-dihydrobenzofuran-3-yl)amino)thieno[2,3-c]pyridin-2-yl)-6-(4-fluorophenethyl)-5-(5-oxo-4,5-dihydro-1,3,4-oxadiazol-2-yl)-2-((S)-pyrrolidin-2-yl)nicotinate

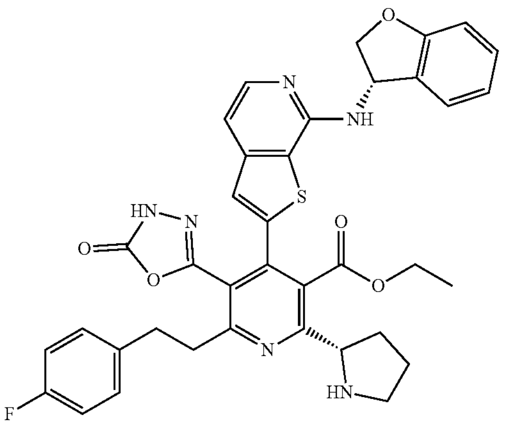 [SMILES: CCOC(=O)c1c([C@@H]2CCCN2)nc(CCc2ccc(F)cc2)c(-c2n[nH]c(=O)o2)c1-c1cc2ccnc(N[C@@H]3COc4ccccc43)c2s1]

To a solution of ethyl 2-((S)-1-(tert-butoxycarbonyl)pyrrolidin-2-yl)-4-(7-(((S)-2,3-dihydrobenzofuran-3-yl)amino)thieno[2,3-c]pyridin-2-yl)-6-(4-fluorophenethyl)-5-(5-oxo-4,5-dihydro-1,3,4-oxadiazol-2-yl)nicotinate (60 mg, 75.67 μmol) in DCM (5 mL)) was added trimethylsilyl trifluoromethanesulfonate (369.00 mg, 1.66 mmol) and 2,6-dimethylpyridine (184.00 mg, 1.72 mmol). The mixture was stirred at 25° C. for 0.5 hr. The reaction mixture was concentrated under reduced pressure to remove solvent. Crude compound ethyl 4-(7-(((S)-2,3-dihydrobenzofuran-3-yl)amino)thieno[2,3-c]pyridin-2-yl)-6-(4-fluorophenethyl)-5-(5-oxo-4,5-dihydro-1,3,4-oxadiazol-2-yl)-2-((S)-pyrrolidin-2-yl)nicotinate (80 mg, crude) was obtained. LC-MS: m/z 693.1 $(M+H)^+$.

Step E 5-((S)-4-(7-(((S)-2,3-dihydrobenzofuran-3-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one

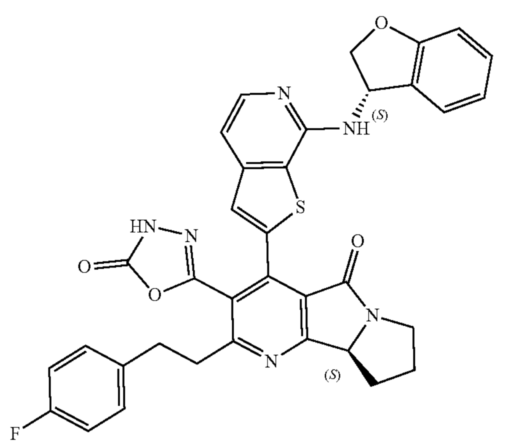

A mixture of ethyl 4-(7-(((S)-2,3-dihydrobenzofuran-3-yl)amino)thieno[2,3-c]pyridin-2-yl)-6-(4-fluorophenethyl)-5-(5-oxo-4,5-dihydro-1,3,4-oxadiazol-2-yl)-2-((S)-pyrrolidin-2-yl)nicotinate (80 mg, 115.48 μmol), TEA (545.25 mg, 5.39 mmol) in DCM (2 mL) was degassed and purged with $N_2$ for 3 times, and then the mixture was stirred at 25° C. for 2 hrs under $N_2$ atmosphere. The reaction mixture was concentrated under reduced pressure to remove solvent. The crude product was purified by reversed-phase HPLC (column: Boston Green ODS 150*30 mm*5 um; mobile phase: [water(FA)-ACN]; gradient: 45%-65% B over 10 min). Compound 5-((S)-4-(7-(((S)-2,3-dihydrobenzofuran-3-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (0.97 mg, 1.30% yield) was obtained.

$^1H$ NMR (400 MHz, $CDCl_3$) δ ppm 8.05-8.14 (m, 1H), 7.40-7.48 (m, 1H), 7.34-7.40 (m, 1H), 7.24 (s, 1H), 7.10-7.16 (m, 3H), 6.93-7.00 (m, 3H), 6.72-6.84 (m, 1H), 5.88-5.97 (m, 1H), 4.82-4.91 (m, 1H), 4.70-4.80 (m, 2H), 4.41-4.50 (m, 1H), 3.70-3.82 (m, 1H), 3.35-3.48 (m, 1H), 3.15 (br s, 4H), 2.48-2.56 (m, 1H), 2.34-2.45 (m, 2H), 1.46 (m, 1H). LC-MS: m/z 647.3 $(M+H)^+$.

5-((S)-4-(7-(((R)-4-methoxy-2,3-dihydro-1H-inden-1-yl)amino)thieno[2,3-c]pyridin-2-yl)-5-oxo-2-(3-(trifluoromethyl)phenethyl)-7,8,9,9a-tetrahydro-5H-pyrido[2,3-a]pyrrolizin-3-yl)-1,3,4-oxadiazol-2(3H)-one (Compound 171)

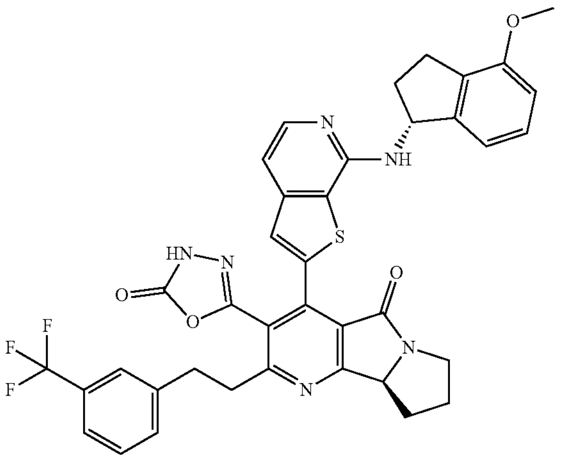 [SMILES: COc1cccc2c1CC[C@H]2Nc1nccc2cc(-c3c4c(nc(CCc5cccc(C(F)(F)F)c5)c3-c3n[nH]c(=O)o3)[C@@H]3CCCN3C4=O)sc12]

Compound 171 was synthesized using similar procedure as described in Example 2 above by using the appropriate materials.

$^1H$ NMR (400 MHz, MeOD-$d_4$) δ 7.74-7.83 (m, 1H), 7.60-7.66 (m, 1H), 7.38-7.51 (m, 5H), 7.22-7.31 (m, 1H), 6.89-7.00 (m, 2H), 5.47-5.57 (m, 1H), 4.91-4.94 (m, 1H), 3.83-3.90 (m, 3H), 3.60-3.74 (m, 1H), 3.42-3.49 (m, 1H), 3.34-3.39 (m, 2H), 3.19-3.29 (m, 2H), 3.07-3.15 (m, 1H), 2.85-2.97 (m, 1H), 2.70-2.79 (m, 1H), 2.38-2.53 (m, 3H), 2.11-2.21 (m, 1H), 1.41-1.53 (m, 1H). $^{19}F$ NMR (376 MHz, $CDCl_3$) δ −64.01 (s, 3 F). LC-MS: m/z 725.1 $(M+H)^+$.

5-((S)-2-(2-cyclohexylethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 172)

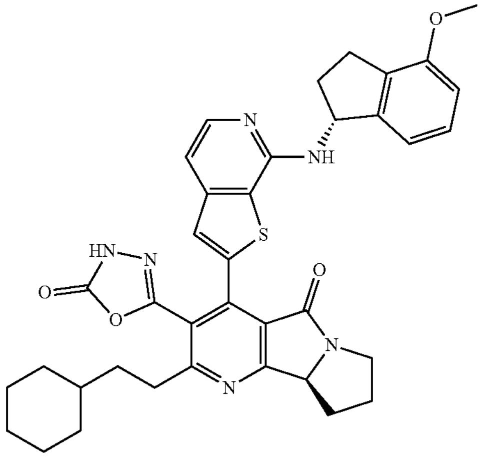 [SMILES: COc1cccc2c1CC[C@H]2Nc1nccc2cc(-c3c4c(nc(CCC5CCCCC5)c3-c3n[nH]c(=O)o3)[C@@H]3CCCN3C4=O)sc12]

Compound 172 was synthesized using similar procedure as described in Example 2 above by using the appropriate materials.

$^1$H NMR (500 MHz, MeOD-$d_4$) δ 7.90-8.00 (d, J=4.8 Hz, 1H), 7.49 (s, 1H), 7.12-7.22 (m, 2H), 6.88-6.96 (m, 1H), 6.82 (dd, J=8.09, 2.44 Hz, 1H), 5.75-5.86 (t, J=6 Hz, 1H), 3.84 (s, 3H), 3.63-3.74 (m, 1H), 3.40-3.50 (m, 1H), 3.01-3.10 (m, 1H), 2.90-3.01 (m, 2H), 2.75-2.84 (m, 1H), 2.64-2.72 (m, 1H), 2.46-2.55 (m, 1H), 2.38-2.46 (m, 2H), 1.98-2.07 (m, 1H), 1.71-1.80 (m, 4H), 1.60-1.70 (m, 3H), 1.43-1.56 (m, 1H), 1.15-1.38 (m, 5H), 0.90-1.01 (m, 2H). LC-MS: m/z 663.2 $(M+H)^+$.

5—((S)-4-(7-(((R)-5-chloro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 173)

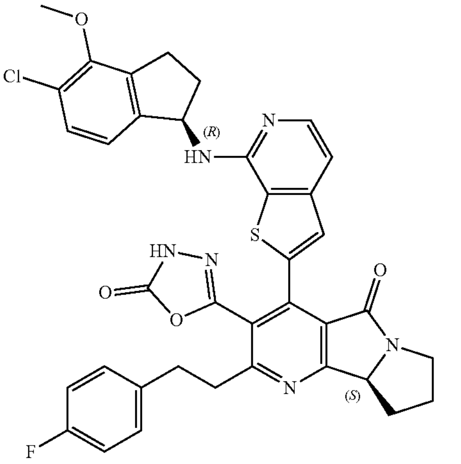

Compound 173 was synthesized using similar procedure as described in Example 10 above by using the appropriate materials.

$^1$H NMR (400 MHz, $CDCl_3$) δ ppm 7.99-8.11 (m, 1H), 7.34-7.45 (m, 1H), 7.18-7.24 (m, 1H), 7.01-7.16 (m, 4H), 6.91-7.01 (m, 2H), 5.60-5.99 (m, 1H), 4.75-4.81 (m, 1H), 3.90 (s, 3H), 3.69-3.82 (m, 1H), 3.35-3.49 (m, 1H), 3.03 (m, 5H), 2.87-2.99 (m, 1H), 2.67-2.79 (m, 1H), 2.47-2.56 (m, 1H), 2.33-2.44 (m, 2H), 1.95-2.02 (m, 1H), 1.43-1.51 (m, 1H). LC-MS: m/z 709.1 $(M+H)^+$.

Example 12

(R)-2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 174)

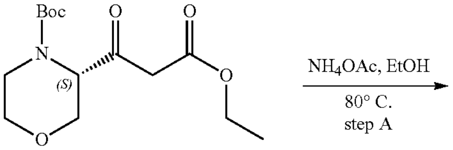

1

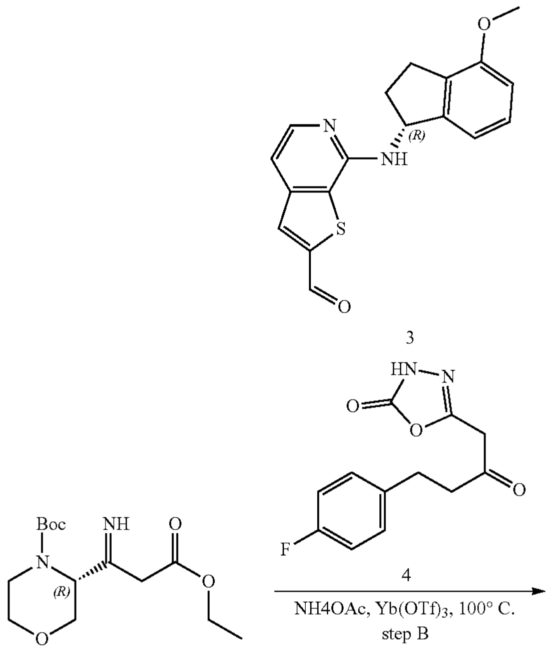

2

-continued

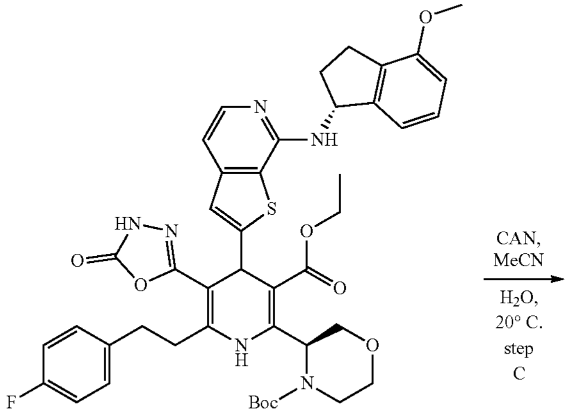

5

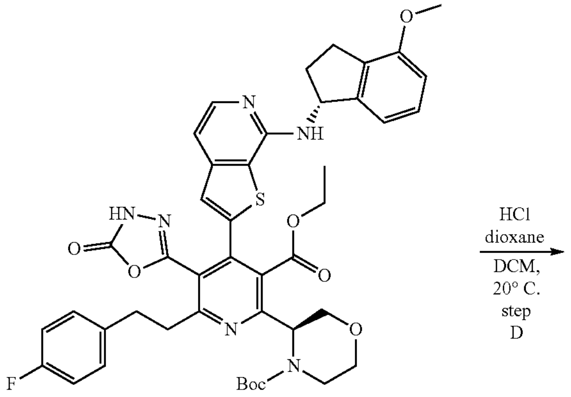

6

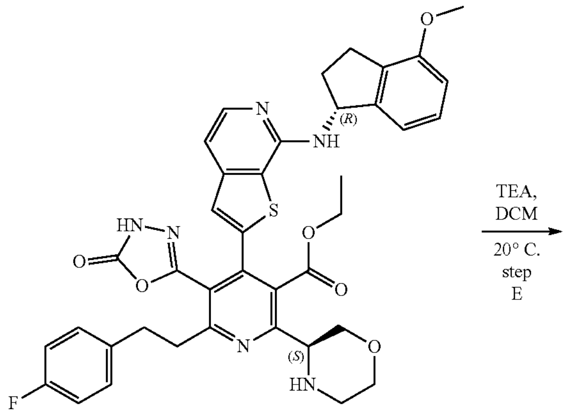

7

-continued

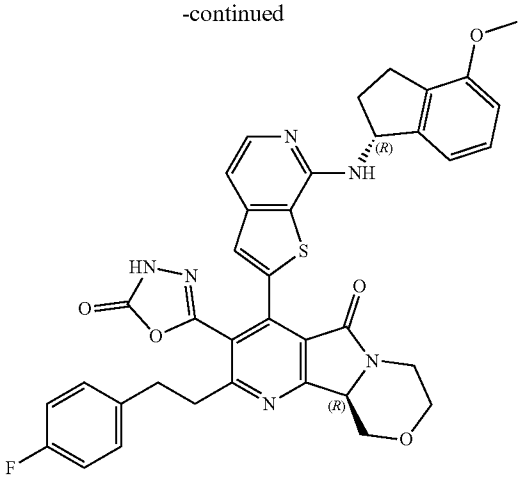

Step A tert-butyl (3R)-3-[(Z)-1-amino-3-ethoxy-3-oxo-prop-1-enyl]morpholine-4-carboxylate

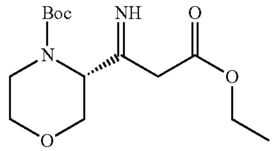 [SMILES: CCOC(=O)CC(=N)[C@@H]1COCCN1C(=O)OC(C)(C)C]

To a solution of tert-butyl (3S)-3-(3-ethoxy-3-oxo-propanoyl)morpholine-4-carboxylate (2 g, 6.64 mmol) in EtOH (20 mL) was added $NH_4OAc$ (2.56 g, 33.19 mmol). The mixture was stirred at 80° C. for 16 hrs. The reaction mixture was concentrated under reduced pressure to remove solvent. The residue was purified by flash silica gel chromatography (ISCO®; 12 g SepaFlash® Silica Flash Column, Eluent of 0~18% Ethyl acetate/Petroleum ether gradient @40 mL/min). Compound tert-butyl (3R)-3-[(Z)-1-amino-3-ethoxy-3-oxo-prop-1-enyl]morpholine-4-carboxylate (1.12 g, 3.73 mmol, 56.18% yield) was obtained as a colorless oil.

$^1H$ NMR (400 MHz, $CDCl_3$) δ ppm 4.39-4.49 (m, 1H), 4.17-4.23 (m, 1H), 4.07-4.16 (m, 2H), 3.86-3.93 (m, 1H), 3.76-3.85 (m, 1H), 3.63-3.71 (m, 1H), 3.49-3.57 (m, 1H), 3.20-3.31 (m, 1H), 1.49 (s, 9H), 1.24-1.27 (m, 3H).

Step B tert-butyl (3S)-3-(3-(ethoxycarbonyl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl)-1,4-dihydropyridin-2-yl)morpholine-4-carboxylate

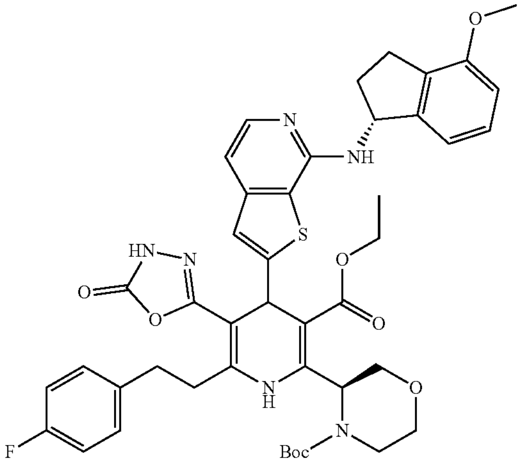 [SMILES: CCOC(=O)C1=C([C@H]2COCCN2C(=O)OC(C)(C)C)NC(CCc2ccc(F)cc2)=C(c2n[nH]c(=O)o2)C1c1cc2ccnc(N[C@@H]3CCc4c(OC)cccc43)c2s1]

A mixture of 5-(4-(4-fluorophenyl)-2-oxobutyl)-1,3,4-oxadiazol-2(3H)-one (100 mg, 399.64 μmol), (R)-7-((4-methoxy-2,3-dihydro-1H-inden-1-yl)amino)thieno[2,3-c]pyridine-2-carbaldehyde (129.64 mg, 399.64 μmol), $NH_4OAc$ (61.61 mg, 799.28 μmol), $Yb(OTf)_3$ (24.79 mg, 39.96 μmol) and tert-butyl (3R)-3-[(Z)-1-amino-3-ethoxy-3-oxo-prop-1-enyl]morpholine-4-carboxylate (120.03 mg, 399.64 μmol) was degassed and purged with $N_2$ for 3 times, and then the mixture was stirred at 100° C. for 1 hr under $N_2$ atmosphere. The reaction mixture was concentrated under reduced pressure to remove solvent. The residue was purified by flash silica gel chromatography (ISCO®; 4 g SepaFlash® Silica Flash Column, Eluent of 0~100% Ethyl acetate/Petroleum ether gradient @40 mL/min). Compound tert-butyl (3S)-3-(3-(ethoxycarbonyl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl)-1,4-dihydropyridin-2-yl)morpholine-4-carboxylate (357 mg, 255.32 μmol, 63.89% yield, 60% purity) was obtained. LC-MS: m/z 839.5 $(M+H)^+$.

Step C tert-butyl (3S)-3-[3-ethoxycarbonyl-6-[2-(4-fluorophenyl)ethyl]-4-[7-[[(JR)-4-methoxyindan-1-yl]amino]thieno[2,3-c]pyridin-2-yl]-5-(2-oxo-3H-1,3,4-oxadiazol-5-yl)-2-pyridyl]morpholine-4-carboxylate

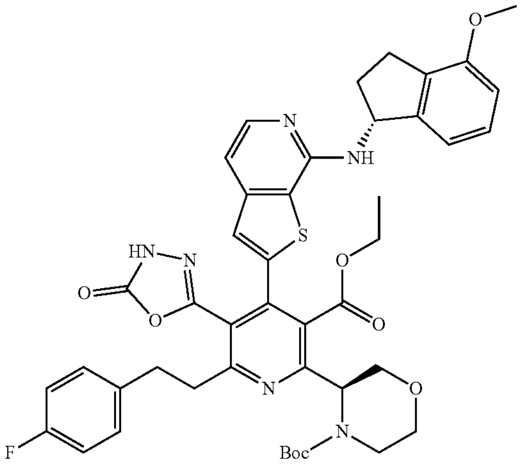 [SMILES: CCOC(=O)c1c([C@H]2COCCN2C(=O)OC(C)(C)C)nc(CCc2ccc(F)cc2)c(-c2n[nH]c(=O)o2)c1-c1cc2ccnc(N[C@@H]3CCc4c(OC)cccc43)c2s1]

To a solution of tert-butyl (3S)-3-[3-ethoxycarbonyl-6-[2-(4-fluorophenyl)ethyl]-4-[7-[[(1R)-4-methoxyindan-1-yl]amino]thieno[2,3-c]pyridin-2-yl]-5-(2-oxo-3H-1,3,4-oxadiazol-5-yl)-1,4-dihydropyridin-2-yl]morpholine-4-carboxylate (357 mg, 425.54 μmol) in MeCN (2 mL)/$H_2O$ (2 mL) was added CAN (466.58 mg, 851.07 μmol). The mixture was stirred at 20° C. for 2 hrs. The reaction mixture was concentrated under reduced pressure to remove solvent. The residue was purified by flash silica gel chromatography (ISCO®; 4 g SepaFlash® Silica Flash Column, Eluent of 0~100% Ethyl acetate/Petroleum ether gradient @20 mL/min). Compound tert-butyl (3S)-3-[3-ethoxycarbonyl-6-[2-(4-fluorophenyl)ethyl]-4-[7-[[(1R)-4-methoxyindan-1-yl]amino]thieno[2,3-c]pyridin-2-yl]-5-(2-oxo-3H-1,3,4-oxadiazol-5-yl)-2-pyridyl]morpholine-4-carboxylate (356.1 mg, 425.49 μmol, 99.99% yield) was obtained. LC-MS: m/z 837.3 $(M+H)^+$.

Step D ethyl 6-[2-(4-fluorophenyl)ethyl]-4-[7-[[(JR)-4-methoxyindan-1-yl]amino]thieno[2,3-c]pyridin-2-yl]-2-[(3S)-morpholin-3-yl]-5-(2-oxo-3H-1,3,4-oxadiazol-5-yl)pyridine-3-carboxylate

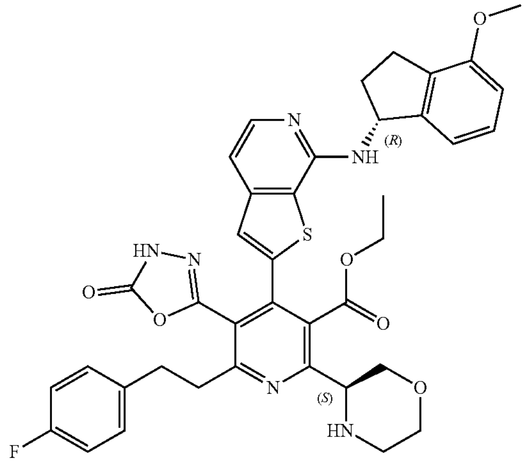

To a solution of tert-butyl (3S)-3-[3-ethoxycarbonyl-6-[2-(4-fluorophenyl)ethyl]-4-[7-[[(1R)-4-methoxyindan-1-yl]amino]thieno[2,3-c]pyridin-2-yl]-5-(2-oxo-3H-1,3,4-oxadiazol-5-yl)-2-pyridyl]morpholine-4-carboxylate (356.1 mg, 425.49 μmol) in DCM (4 mL) was added HCl/dioxane (3 M, 17 mL). The mixture was stirred at 20° C. for 2 hrs. The reaction mixture was concentrated under reduced pressure to remove solvent. The crude product ethyl 6-[2-(4-fluorophenyl)ethyl]-4-[7-[[(1R)-4-methoxyindan-1-yl]amino]thieno[2,3-c]pyridin-2-yl]-2-[(3S)-morpholin-3-yl]-5-(2-oxo-3H-1,3,4-oxadiazol-5-yl)pyridine-3-carboxylate (313.5 mg, 425.48 μmol, 100.00% yield) was used into the next step without further purification. LC-MS: m/z 737.1 $(M+H)^+$.

Step E (R)-2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one

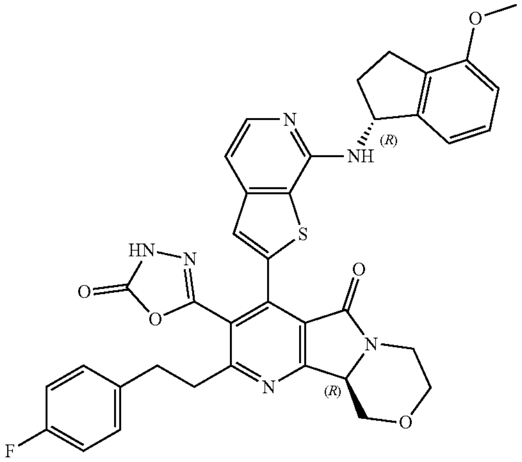

To a solution of ethyl 6-[2-(4-fluorophenyl)ethyl]-4-[7-[[(1R)-4-methoxyindan-1-yl]amino]thieno[2,3-c]pyridin-2-yl]-2-[(3S)-morpholin-3-yl]-5-(2-oxo-3H-1,3,4-oxadiazol-5-yl)pyridine-3-carboxylate (313.5 mg, 425.48 μmol) in DCM (2 mL) was added TEA (43.05 mg, 425.48 μmol). The mixture was stirred at 20° C. for 16 hrs. The reaction mixture was concentrated under reduced pressure to remove solvent. The residue was purified by prep-HPLC (column: Boston Green ODS 150*30 mm*5 um; mobile phase: [water(TFA)-ACN]; gradient: 38%-58% B over 11 min). Compound (R)-2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (11.66 mg, 16.66 μmol, 3.92% yield, 98.7% purity) was obtained.

$^1$H NMR (400 MHz, $CDCl_3$) δ ppm 7.75-7.84 (m, 1H), 7.64-7.69 (m, 1H), 7.41-7.46 (m, 1H), 7.26-7.33 (m, 1H), 7.11-7.18 (m, 2H), 6.89-7.02 (m, 4H), 5.47-5.60 (m, 1H), 4.60-4.69 (m, 1H), 4.18-4.26 (m, 1H), 4.03-4.10 (m, 1H), 3.81-3.93 (m, 3H), 3.34-3.48 (m, 5H), 3.19-3.27 (m, 1H), 3.06-3.17 (m, 3H), 2.86-2.99 (m, 1H), 2.71-2.83 (m, 1H), 2.09-2.25 (m, 1H). LC-MS: m/z 691.3 $(M+H)^+$.

Example 13

5-((S)-2-(4-fluorophenethyl)-4-(7-(((R)-4-methoxy-2,3-dihydro-1H-inden-1-yl)amino)thieno[2,3-c]pyridin-2-yl)-5,5-dioxido-7,8,9,9a-tetrahydropyrrolo[1',2':2,3]isothiazolo[4,5-b]pyridin-3-yl)-1,3,4-oxadiazol-2(3H)-one (Compound 175)

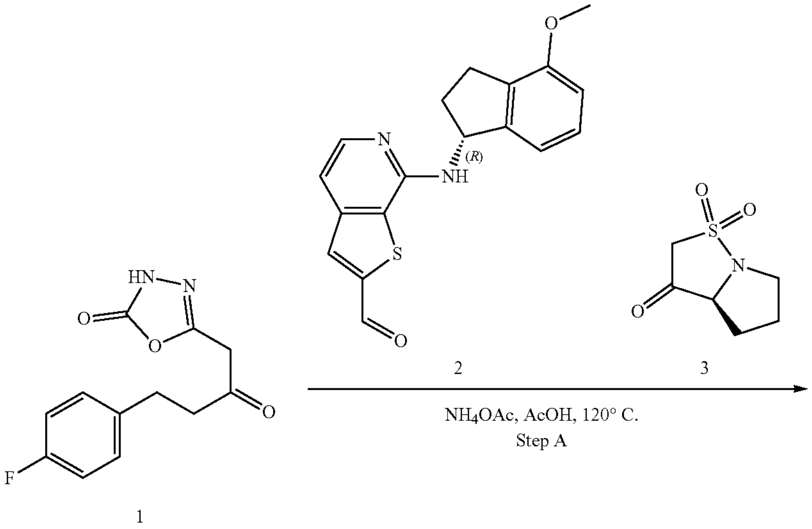

-continued
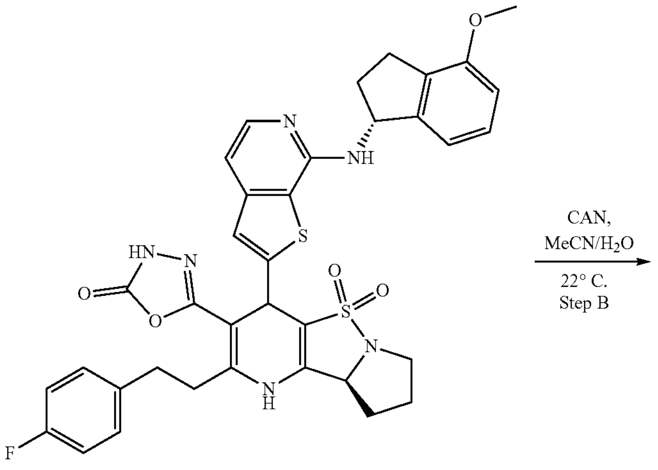
4
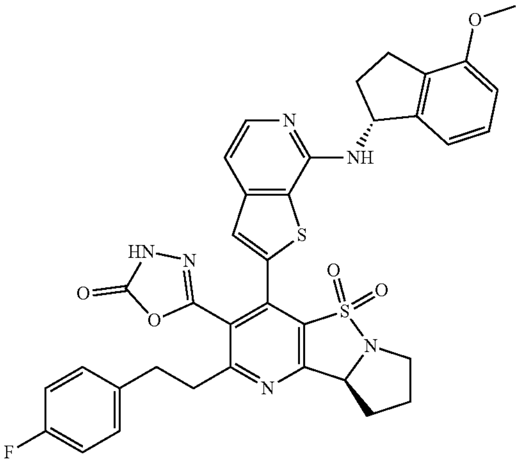

Step A 5-((9aS)-2-(4-fluorophenethyl)-4-(7-(((R)-4-methoxy-2,3-dihydro-1H-inden-1-yl)amino)thieno[2,3-c]pyridin-2-yl)-5,5-dioxido-1,4,7,8,9,9a-hexahydropyrrolo[1',2':2,3]isothiazolo[4,5-b]pyridin-3-yl)-1,3,4-oxadiazol-2(3H)-one

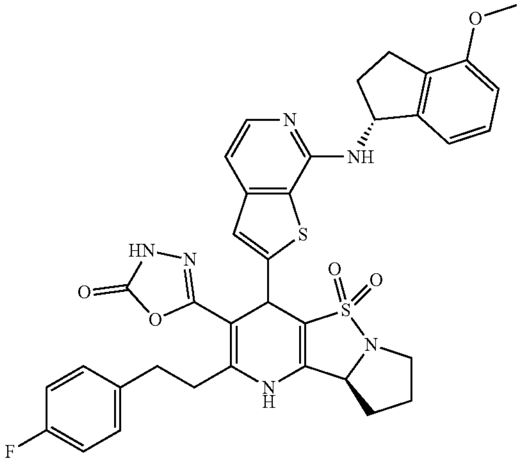 [SMILES: COc1cccc2c1CC[C@H]2Nc1nccc2cc(C3C(c4n[nH]c(=O)o4)=C(CCc4ccc(F)cc4)NC4=C3S(=O)(=O)N3CCC[C@@H]43)sc12]

A mixture of 5-[4-(4-fluorophenyl)-2-oxo-butyl]-3H-1,3,4-oxadiazol-2-one (40 mg, 159.86 μmol), 7-[[(1R)-4-methoxyindan-1-yl]amino]thieno[2,3-c]pyridine-2-carbaldehyde (52 mg, 160.30 μmol), (3aS)-1,1-dioxo-3a,4,5,6-tetrahydropyrrolo[1,2-b]isothiazol-3-one (28.0 mg, 159.81 μmol), $NH_4OAc$ (25 mg, 324.33 μmol) in AcOH (2 mL) was degassed and purged with $N_2$ for 3 times, and then the mixture was stirred at 120° C. for 2 hrs under $N_2$ atmosphere. The reaction mixture was concentrated under reduced pressure to remove solvent. The residue was diluted with $H_2O$ (100 mL) and extracted with EtOAc (50 mL×2). The combined organic layer was washed with brine (50 mL), dried over $Na_2SO_4$, filtered and concentrated under reduced pressure to give a residue. The residue was purified by prep-TLC ($SiO_2$, EA). Compound 5-((9aS)-2-(4-fluorophenethyl)-4-(7-(((R)-4-methoxy-2,3-dihydro-1H-inden-1-yl)amino)thieno[2,3-c]pyridin-2-yl)-5,5-dioxido-1,4,7,8,9,9a-hexahydropyrrolo[1',2':2,3]isothiazolo[4,5-b]pyridin-3-yl)-1,3,4-oxadiazol-2(3H)-one (18 mg, 22.73 μmol, 14.22% yield, 90% purity) was obtained. LC-MS: m/z 713.1 $(M+H)^+$.

Step B 5-((S)-2-(4-fluorophenethyl)-4-(7-(((R)-4-methoxy-2,3-dihydro-1H-inden-1-yl)amino)thieno[2,3-c]pyridin-2-yl)-5,5-dioxido-7,8,9,9a-tetrahydropyrrolo[1',2':2,3]isothiazolo[4,5-b]pyridin-3-yl)-1,3,4-oxadiazol-2(3H)-one

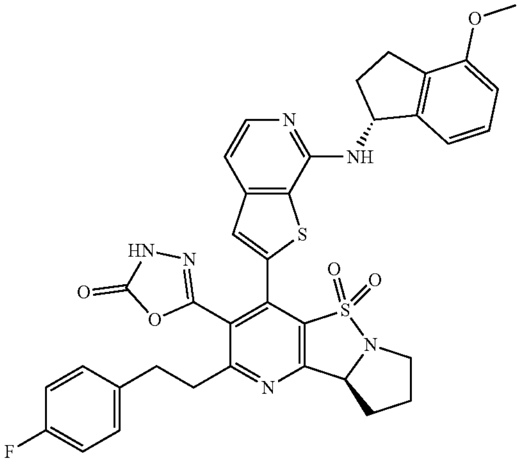 [SMILES: COc1cccc2c1CC[C@H]2Nc1nccc2cc(-c3c(-c4n[nH]c(=O)o4)c(CCc4ccc(F)cc4)nc4c3S(=O)(=O)N3CCC[C@@H]43)sc12]

A mixture of 5-((9aS)-2-(4-fluorophenethyl)-4-(7-(((R)-4-methoxy-2,3-dihydro-1H-inden-1-yl)amino)thieno[2,3-c]pyridin-2-yl)-5,5-dioxido-1,4,7,8,9,9a-hexahydropyrrolo[1',2':2,3]isothiazolo[4,5-b]pyridin-3-yl)-1,3,4-oxadiazol-2(3H)-one (18 mg, 25.25 μmol), CAN (28 mg, 51.07 μmol) in MeCN (2 mL) and $H_2O$ (2 mL) was degassed and purged with $N_2$ for 3 times, and then the mixture was stirred at 22° C. for 1 hr under $N_2$ atmosphere. The reaction mixture was quenched by aq. $NaHCO_3$ (30 mL) at 22° C., and then diluted with $H_2O$ (50 mL) and extracted with EtOAc (50 mL×2). The combined organic layer was washed with brine (50 mL), dried over $Na_2SO_4$, filtered and concentrated under reduced pressure to give a residue. The residue was purified by prep-HPLC (column: Boston Green ODS 150*30 mm*5 um; mobile phase: [water(FA)-ACN]; gradient: 45%-65% B over 10 min). Compound 5-((S)-2-(4-fluorophenethyl)-4-(7-(((R)-4-methoxy-2,3-dihydro-1H-inden-1-yl)amino)thieno[2,3-c]pyridin-2-yl)-5,5-dioxido-7,8,9,9a-tetrahydropyrrolo[1',2':2,3]isothiazolo[4,5-b]pyridin-3-yl)-1,3,4-oxadiazol-2(3H)-one (4.77 mg, 6.64 μmol, 26.31% yield, 99% purity) was obtained.

$^1H$ NMR (400 MHz, $CDCl_3$) δ ppm 8.01-8.11 (m, 1H), 7.69-7.78 (m, 1H), 7.16-7.23 (m, 1H), 7.08-7.14 (m, 3H), 6.94-7.01 (m, 3H), 6.73-6.80 (m, 1H), 5.68-5.84 (m, 1H), 5.02-5.07 (m, 1H), 3.81-3.89 (m, 4H), 3.44 (dt, J=11.47, 6.90 Hz, 1H), 3.23 (br s, 5H), 2.81 (dt, J=16.06, 7.88 Hz, 1H), 2.64-2.73 (m, 1H), 2.51-2.60 (m, 1H), 2.28-2.35 (m, 1H), 1.91-2.05 (m, 2H), 1.73-1.82 (m, 1H). LC-MS: m/z 711.2 $(M+H)^+$.

Example 14
6-[[6-[(9aS)-2-[2-(4-fluorophenyl)ethyl]-5-oxo-3-(2-oxo-3H-1,3,4-oxadiazol-5-yl)-7,8,9,9a-tetrahydro-pyrido[2,3-a]pyrrolizin-4-yl]-2-oxo-1,3-benzoxazol-3-yl]methyl]pyridine-3-carbonitrile
(Compound 176)
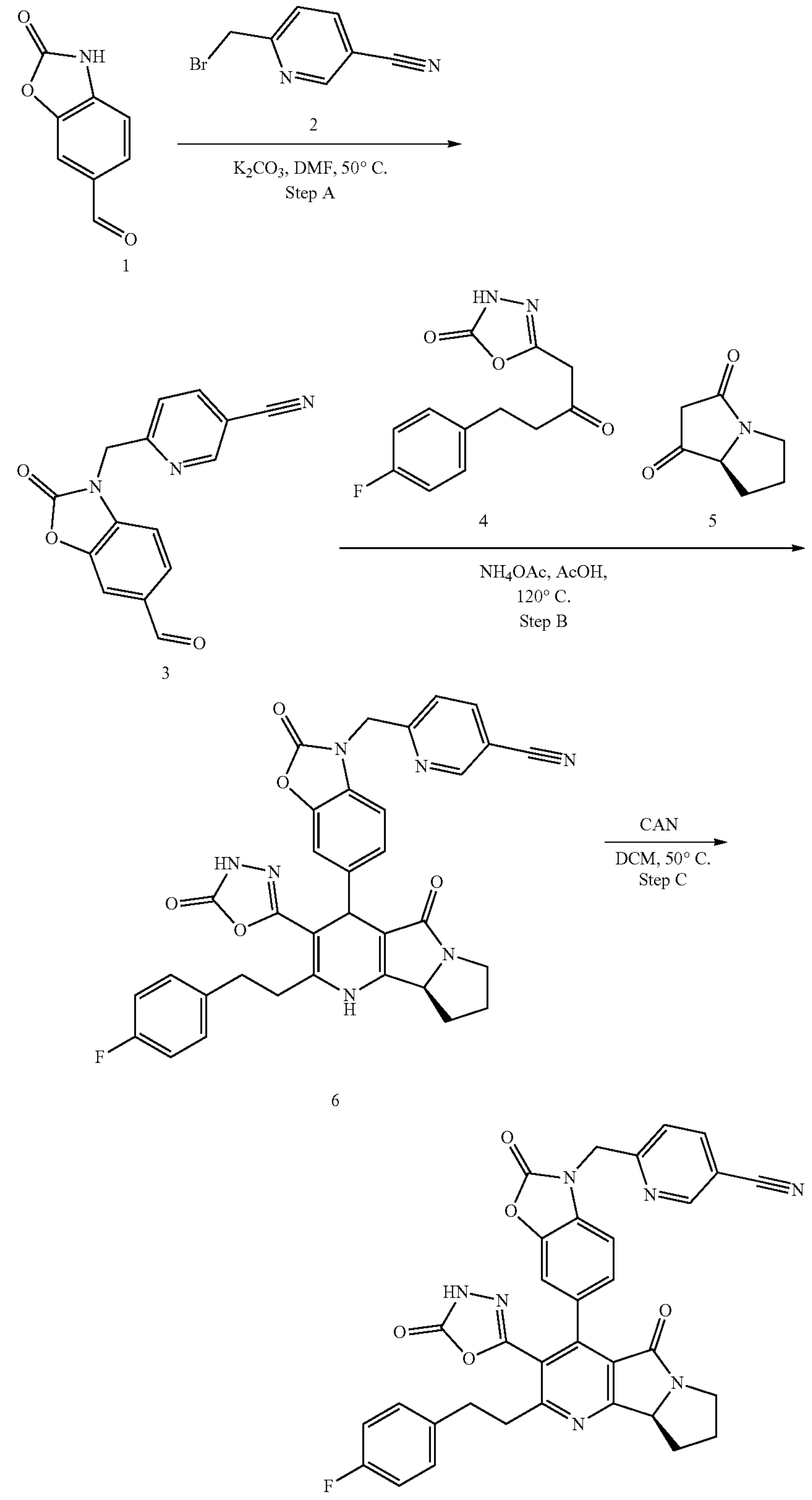
1
2
3
4
5
6

Step A 6-[(6-formyl-2-oxo-1,3-benzoxazol-3-yl) methyl]pyridine-3-carbonitrile

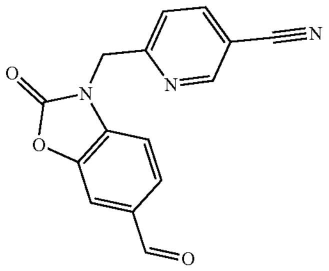 [SMILES: N#Cc1ccc(Cn2c(=O)oc3cc(C=O)ccc32)nc1]

To a mixture of 2-oxo-3H-1,3-benzoxazole-6-carbaldehyde (100 mg, 0.61 mmol), 6-(bromomethyl)pyridine-3-carbonitrile (363 mg, 1.84 mmol) and $K_2CO_3$ (170 mg, 1.23 mmol) in DMF (10 mL) was stirred at 50° C. for 14 hrs. The reaction was diluted with water (20 mL) and extracted with ethyl acetate (20 mL×3). The reaction mixture (combined with another batch from 100 mg of 2-oxo-3H-1,3-benzoxazole-6-carbaldehyde) were washed by 4% LiCl solution (aq., 20 mL), dried over anhydrous sodium sulfate, filtered and concentrated in vacuum. The crude product was purified by silica gel column chromatography (50% ethyl acetate in petroleum ether) to give 6-[(6-formyl-2-oxo-1,3-benzoxazol-3-yl)methyl]pyridine-3-carbonitrile (260 mg, 0.93 mmol, 75.94% average yield).

$^1$H NMR (400 MHz, DMSO-$d_6$) δ ppm 9.93 (s, 1H), 8.93 (d, J=1.6 Hz, 1H), 8.35 (dd, J=2.0, 8.0 Hz, 1H), 7.86 (s, 1H), 7.82 (dd, J=1.2, 8.0 Hz, 1H), 7.74 (d, J=8.2 Hz, 1H), 7.40 (d, J=8.0 Hz, 1H), 5.37 (s, 2H). LC-MS: m/z 280.0 $(M+H)^+$.

Step B: 6-[[6-[(9aS)-2-[2-(4-fluorophenyl)ethyl]-5-oxo-3-(2-oxo-3H-1,3,4-oxadiazol-5-yl)-1,4,7,8,9,9a-hexahydropyrido[2,3-a]pyrrolizin-4-yl]-2-oxo-1,3-benzoxazol-3-yl]methyl]pyridine-3-carbonitrile

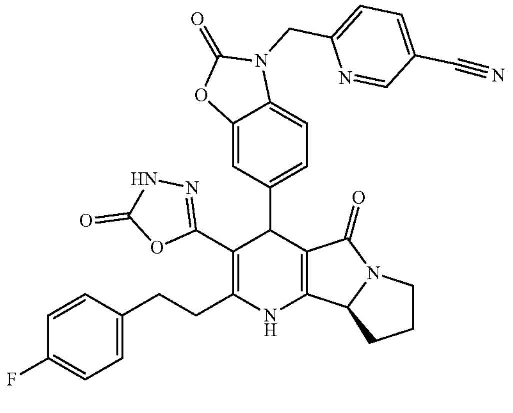 [SMILES: N#Cc1ccc(Cn2c(=O)oc3cc(C4C5=C(NC(CCc6ccc(F)cc6)=C4c4n[nH]c(=O)o4)[C@@H]4CCCN4C5=O)ccc32)nc1]

To a mixture of 6-[(6-formyl-2-oxo-1,3-benzoxazol-3-yl) methyl]pyridine-3-carbonitrile (50 mg, 0.18 mmol), 5-[4-(4-fluorophenyl)-2-oxo-butyl]-3H-1,3,4-oxadiazol-2-one (46 mg, 0.18 mmol) and (8S)-5,6,7,8-tetrahydropyrrolizine-1,3-dione (28 mg, 0.20 mmol) in acetic acid (5 mL) was added $NH_4OAc$ (28 mg, 0.36 mmol) and stirred at 120° C. for 1 hr. The reaction was concentrated in vacuum and the residue was purified by silica gel column chromatography (100% ethyl acetate) to give 6-[[6-[(9aS)-2-[2-(4-fluorophenyl)ethyl]-5-oxo-3-(2-oxo-3H-1,3,4-oxadiazol-5-yl)-1,4,7,8,9,9a-hexahydropyrido[2,3-a]pyrrolizin-4-yl]-2-oxo-1,3-benzoxazol-3-yl]methyl]pyridine-3-carbonitrile (51 mg, 0.081 mmol, 45.10% yield).

$^1$H NMR (400 MHz, DMSO-$d_6$) δ ppm 12.07 (d, J=12.4 Hz, 1H), 9.63-9.77 (m, 1H), 8.94 (t, J=2.8 Hz, 1H), 8.30-8.35 (m, 1H), 7.65-7.72 (m, 1H), 7.26-7.32 (m, 2H), 7.06-7.15 (m, 3H), 6.93-7.01 (m, 2H), 5.22 (d, J=2.0 Hz, 2H), 4.68 (s, 1H), 4.16-4.29 (m, 1H), 3.06-3.21 (m, 1H), 2.93-3.05 (m, 1H), 2.85-2.92 (m, 3H), 2.35-2.44 (m, 1H), 2.01-2.13 (m, 3H). $^{19}$F NMR (400 MHz, DMSO-$d_6$) δ ppm −116.926. LC-MS: m/z 632.1 $(M+H)^+$.

Step C: 6-[[6-[(9aS)-2-[2-(4-fluorophenyl)ethyl]-5-oxo-3-(2-oxo-3H-1,3,4-oxadiazol-5-yl)-7,8,9,9a-tetrahydropyrido[2,3-a]pyrrolizin-4-yl]-2-oxo-1,3-benzoxazol-3-yl]methyl]pyridine-3-carbonitrile

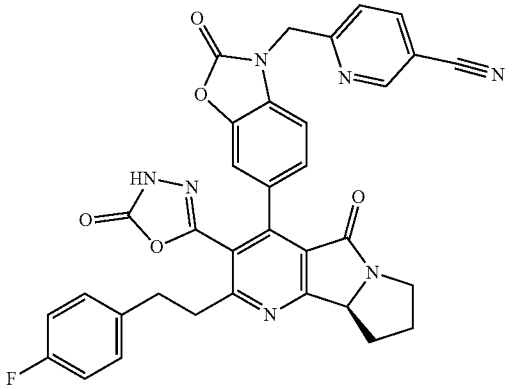 [SMILES: N#Cc1ccc(Cn2c(=O)oc3cc(-c4c5c(nc(CCc6ccc(F)cc6)c4-c4n[nH]c(=O)o4)[C@@H]4CCCN4C5=O)ccc32)nc1]

To a mixture of 6-[[6-[(9aS)-2-[2-(4-fluorophenyl)ethyl]-5-oxo-3-(2-oxo-3H-1,3,4-oxadiazol-5-yl)-1,4,7,8,9,9a-hexahydropyrido[2,3-a]pyrrolizin-4-yl]-2-oxo-1,3-benzoxazol-3-yl]methyl]pyridine-3-carbonitrile (51 mg, 0.081 mmol) in DCM (3 mL) was added CAN (45 mg, 0.082 mmol) and the mixture was stirred at 50° C. for 1 hr. The reaction mixture was concentrated in vacuum and the residue was purified by prep-HPLC {column: Welch Xtimate C18 150*25 mm*5 um; mobile phase: [water($NH_3H_2O$+$NH_4HCO_3$)-ACN]; gradient: 11%-41% B over 8 min} and fractions containing the desired compound was lyophilized to give 6-[[6-[(9aS)-2-[2-(4-fluorophenyl)ethyl]-5-oxo-3-(2-oxo-3H-1,3,4-oxadiazol-5-yl)-7,8,9,9a-tetrahydropyrido [2,3-a]pyrrolizin-4-yl]-2-oxo-1,3-benzoxazol-3-yl]methyl] pyridine-3-carbonitrile (19.22 mg, 30.53 μmol, 37.81% yield, 100% purity).

$^1$H NMR (400 MHz, DMSO-$d_6$) δ ppm 8.94 (d, J=1.6 Hz, 1H), 8.35 (dd, J=2.0, 8.4 Hz, 1H), 7.73 (d, J=8.0 Hz, 1H), 7.40 (s, 1H), 7.18-7.24 (m, 3H), 7.04-7.10 (m, 2H), 6.98-7.03 (m, 1H), 5.33 (s, 2H), 4.83 (dd, J=6.4, 10.2 Hz, 1H), 3.43-3.57 (m, 2H), 3.11-3.17 (m, 2H), 2.96-3.09 (m, 2H), 2.22-2.36 (m, 3H), 1.32-1.45 (m, 1H). $^{19}$F NMR (400 MHz, DMSO-$d_6$) δ ppm −117.067. LC-MS: m/z 630.1 $(M+H)^+$.

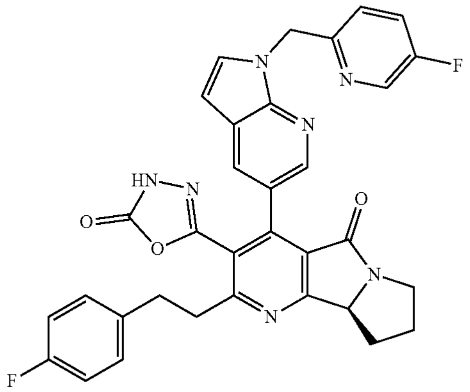

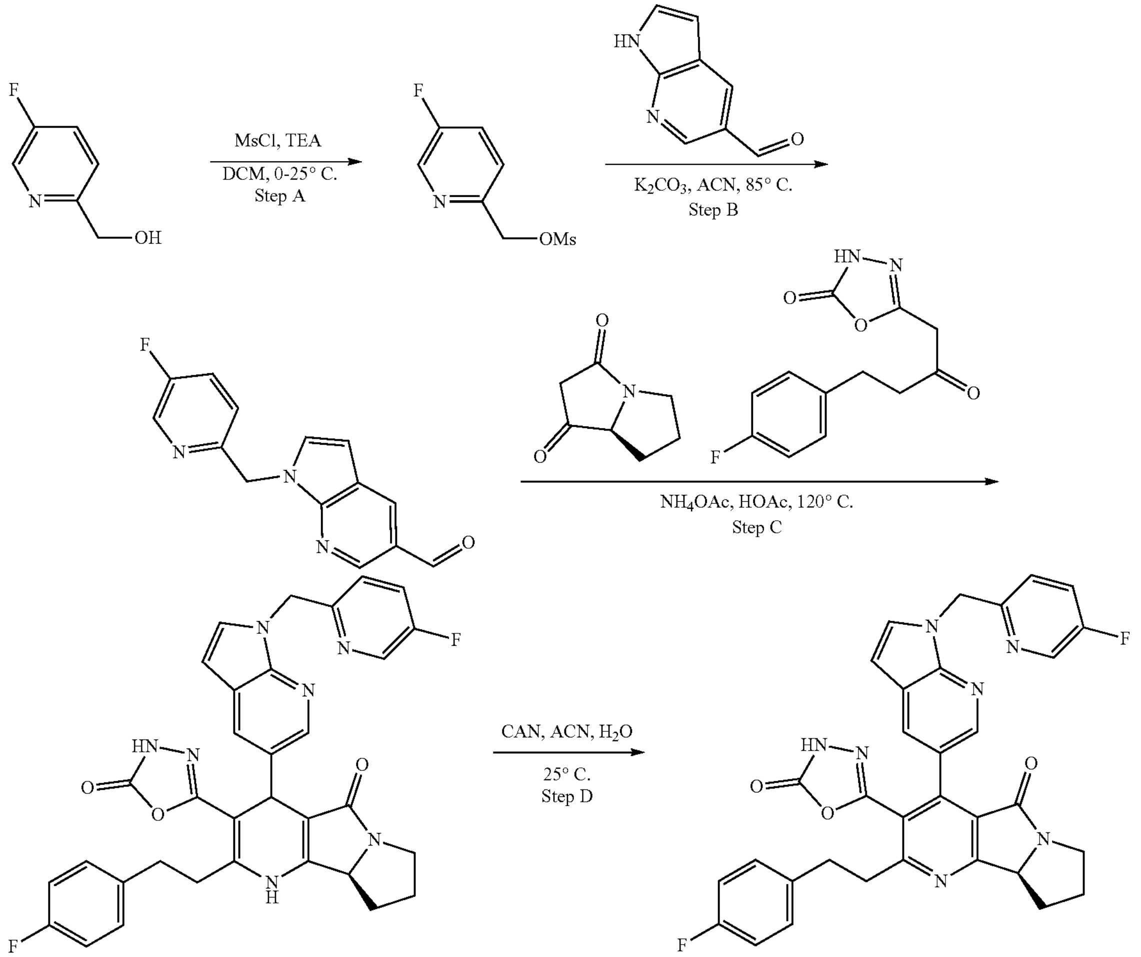

Step A (5-fluoropyridin-2-yl)methyl methanesulfonate

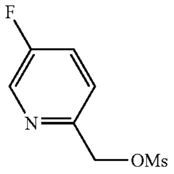 [SMILES: CS(=O)(=O)OCc1ccc(F)cn1]

To a solution of (5-fluoro-2-pyridyl)methanol (300 mg, 2.36 mmol) in DCM (5 mL) was added TEA (7.08 mmol, 985.47 μL) at 0° C. To the mixture was added MsCl (2.01 mmol, 155.41 μL) and the mixture was stirred at 25° C. for 30 min. The reaction mixture was added $H_2O$ (10 mL) and extracted with DCM (10 mL×2). The combined organic layers were washed with brine (10 mL), dried over $Na_2SO_4$, filtered and concentrated under reduced pressure. The crude (5-fluoropyridin-2-yl)methyl methanesulfonate (530 mg, 98.49% yield) was obtained as a yellow oil.

Step B 1-((5-fluoropyridin-2-yl)methyl)-1H-pyrrolo [2,3-b]pyridine-5-carbaldehyde

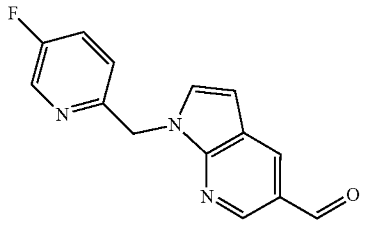 [SMILES: O=Cc1cnc2c(ccn2Cc2ccc(F)cn2)c1]

To a solution of 1H-pyrrolo[2,3-b]pyridine-5-carbaldehyde (200 mg, 1.37 mmol) in ACN (3 mL) was added $K_2CO_3$ (567.42 mg, 4.11 mmol) and (5-fluoro-2-pyridyl) methyl methanesulfonate (530 mg, 2.58 mmol). The mixture was stirred at 85° C. for 16 hrs. The reaction mixture was filtered and the filtrate was concentrated under reduced pressure to give a residue. The residue was purified by flash silica gel chromatography (Biotage®; 4 g SepaFlash® Silica Flash Column, Eluent of 0~37% Ethylacetate/Petroleum ether gradient @18 mL/min) to give 1-((5-fluoropyridin-2-yl)methyl)-1H-pyrrolo[2,3-b]pyridine-5-carbaldehyde (130 mg, 37.22% yield) as a pink oil.

$^1$H NMR (400 MHz, $CDCl_3$) δ ppm 10.06 (s, 1H), 8.76 (d, J=1.79 Hz, 1H), 8.31-8.38 (m, 1H), 8.29-8.47 (m, 2H), 7.37 (d, J=3.70 Hz, 1H), 7.25 (m, 1H), 7.08 (m, 1H), 6.60 (d, J=3.58 Hz, 1H), 5.57 (s, 2H). LC-MS: m/z 256.1 $(M+H)^+$.

Step C 5-((9aS)-2-(4-fluorophenethyl)-4-(1-((5-fluoropyridin-2-yl)methyl)-1H-pyrrolo[2,3-b]pyridin-5-yl)-5-oxo-1,5,7,8,9,9a-hexahydro-4H-pyrido[2,3-a] pyrrolizin-3-yl)-1,3,4-oxadiazol-2(3H)-one

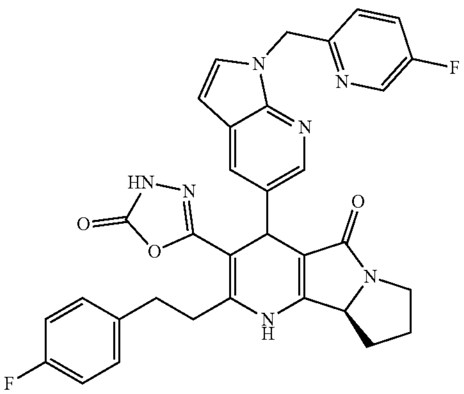 [SMILES: O=C1C2=C(NC(CCc3ccc(F)cc3)=C(c3n[nH]c(=O)o3)C2c2cnc3c(ccn3Cc3ccc(F)cn3)c2)[C@@H]2CCCN12]

A mixture of 1-((5-fluoropyridin-2-yl)methyl)-1H-pyrrolo[2,3-b]pyridine-5-carbaldehyde (70 mg, 230.37 μmol), (8S)-5,6,7,8-tetrahydropyrrolizine-1,3-dione (32.06 mg, 230.37 μmol), 5-[4-(4-fluorophenyl)-2-oxo-butyl]-3H-1,3,4-oxadiazol-2-one (57.64 mg, 230.37 μmol) and $NH_4OAc$ (35.51 mg, 460.73 μmol) in HOAc (2 mL) was stirred at 120° C. for 1 hr. The mixture was added $H_2O$ (10 mL) and extracted with ethyl acetate (10 mL×3). The combined organic layers were washed with brine (10 mL), dried over $Na_2SO_4$, filtered and concentrated under reduced pressure to give a residue. The residue was purified by flash silica gel chromatography (Biotage®; 4 g SepaFlash® Silica Flash Column, Eluent of 0~100% Ethylacetate/Petroleum ether gradient @18 mL/min) to give 5-((9aS)-2-(4-fluorophenethyl)-4-(1-((5-fluoropyridin-2-yl)methyl)-1H-pyrrolo[2,3-b]pyridin-5-yl)-5-oxo-1,5,7,8,9,9a-hexahydro-4H-pyrido[2,3-a]pyrrolizin-3-yl)-1,3,4-oxadiazol-2(3H)-one (60 mg, 98.75 μmol, 42.87% yield). LC-MS: m/z 608.2 $(M+H)^+$.

Step D (S)-5-(2-(4-fluorophenethyl)-4-(1-((5-fluoropyridin-2-yl)methyl)-1H-pyrrolo[2,3-b]pyridin-5-yl)-5-oxo-7,8,9,9a-tetrahydro-5H-pyrido[2,3-a]pyrrolizin-3-yl)-1,3,4-oxadiazol-2(3H)-one

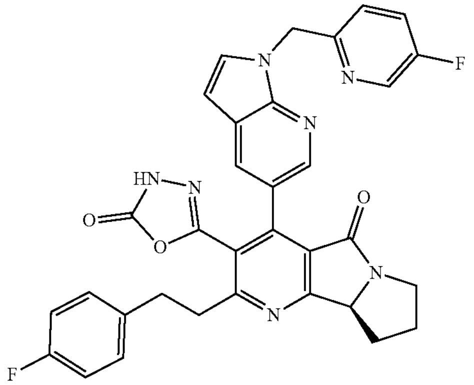 [SMILES: O=C1c2c(nc(CCc3ccc(F)cc3)c(-c3n[nH]c(=O)o3)c2-c2cnc3c(ccn3Cc3ccc(F)cn3)c2)[C@@H]2CCCN12]

To a solution of 5-((9aS)-2-(4-fluorophenethyl)-4-(1-((5-fluoropyridin-2-yl)methyl)-1H-pyrrolo[2,3-b]pyridin-5-yl)-5-oxo-1,5,7,8,9,9a-hexahydro-4H-pyrido[2,3-a]pyrrolizin-3-yl)-1,3,4-oxadiazol-2(3H)-one (60 mg, 98.75 μmol) in ACN (2 mL) and $H_2O$ (2 mL) was added CAN (54.14 mg, 98.75 μmol). The mixture was stirred at 25° C. for 1 hr. The mixture was added $H_2O$ (5 mL) and extracted with ethyl acetate (5 mL×3). The combined organic layers were washed with brine (5 mL), dried over $Na_2SO_4$, filtered and concentrated under reduced pressure to give a residue. The residue was further purification by pre-HPLC (Boston Green ODS 150*30 mm*5 um, water (0.2% FA)-ACN) to give (S)-5-(2-(4-fluorophenethyl)-4-(1-((5-fluoropyridin-2-yl) methyl)-1H-pyrrolo[2,3-b]pyridin-5-yl)-5-oxo-7,8,9,9a-tetrahydro-5H-pyrido[2,3-a]pyrrolizin-3-yl)-1,3,4-oxadiazol-2 (3H)-one (12.7 mg, 20.97 μmol, 21.24% yield).

$^1$H NMR (400 MHz, MeOD-$d_4$) δ ppm 8.44 (d, J=2.98 Hz, 1H), 8.15 (d, J=2.03 Hz, 1H), 8.03 (d, J=2.15 Hz, 1H), 7.56 (d, J=3.46 Hz, 1H), 7.54-7.58 (m, 1H), 7.52 (m, 1H), 7.17 (m, 2H), 7.07 (m, 1H), 6.93-7.01 (m, 2H), 6.64 (d, J=3.58 Hz, 1H), 5.64 (s, 2H), 4.92-4.92 (m, 1H), 4.92 (br s, 1H), 3.67 (m, 1H), 3.43 (m, 1H), 3.26 (m, 2H), 3.06-3.18 (m, 2H), 2.52 (m, 1H), 2.38-2.47 (m, 2H), 1.43-1.57 (m, 1H). $^{19}$F NMR (376 MHz, MeOD-$d_4$) δ ppm −119.06 (s, 1 F), −130.86 (s, 1 F). LC-MS: m/z 606.1 $(M+H)^+$.

5-((S)-2-(4-fluorophenethyl)-4-(7-(((R)-4-methoxy-2,3-dihydro-1H-inden-1-yl)amino)thieno[2,3-c]pyridin-2-yl)-9a-methyl-5-oxo-7,8,9,9a-tetrahydro-5H-pyrido[2,3-a]pyrrolizin-3-yl)-1,3,4-oxadiazol-2(3H)-one (Compound 178)

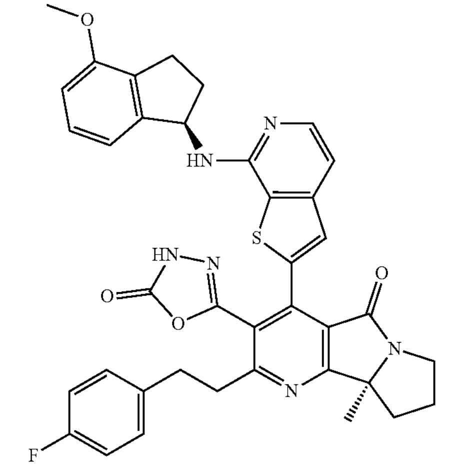 [SMILES: COc1cccc2c1CC[C@H]2Nc1nccc2cc(-c3c4c(nc(CCc5ccc(F)cc5)c3-c3n[nH]c(=O)o3)[C@]3(C)CCCN3C4=O)sc12]

Compound 178 was synthesized using similar procedure as described in Example 2 above by using the appropriate materials.

$^1$H NMR (400 MHz, DMSO-$d_6$): δ 12.71 (br s, 1H), 7.98 (d, J=5.2 Hz, 1H), 7.44 (s, 1H), 7.18-7.25 (m, 3H), 7.13 (t, J=7.6 Hz, 1H), 7.04-7.09 (m, 3H), 6.84 (dd, J=7.6 Hz, J=9.2 Hz, 2H), 5.86-5.93 (m, 1H), 3.79 (s, 3H), 3.58-3.67 (m, 1H), 3.27-3.30 (m, 1H), 3.19-3.23 (m, 2H), 2.92-3.07 (m, 3H), 2.66-2.72 (m, 1H), 2.20-2.43 (m, 3H), 1.97-2.08 (m, 2H), 1.54-1.65 (m, 4H). $^{19}$F NMR (377 MHz, DMSO-$d_6$): −117.07. LC-MS: m/z 689.1 $(M+H)^+$.

Example 16

(R)-2-(4-fluorophenethyl)-4-(7-(((R)-4-methoxy-2,3-dihydro-1H-inden-1-yl)amino)thieno[2,3-c]pyridin-2-yl)-10a-methyl-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 179)

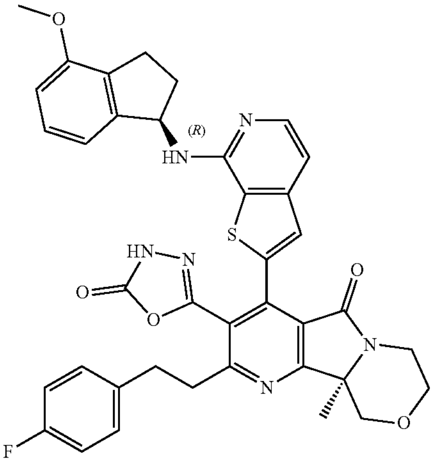

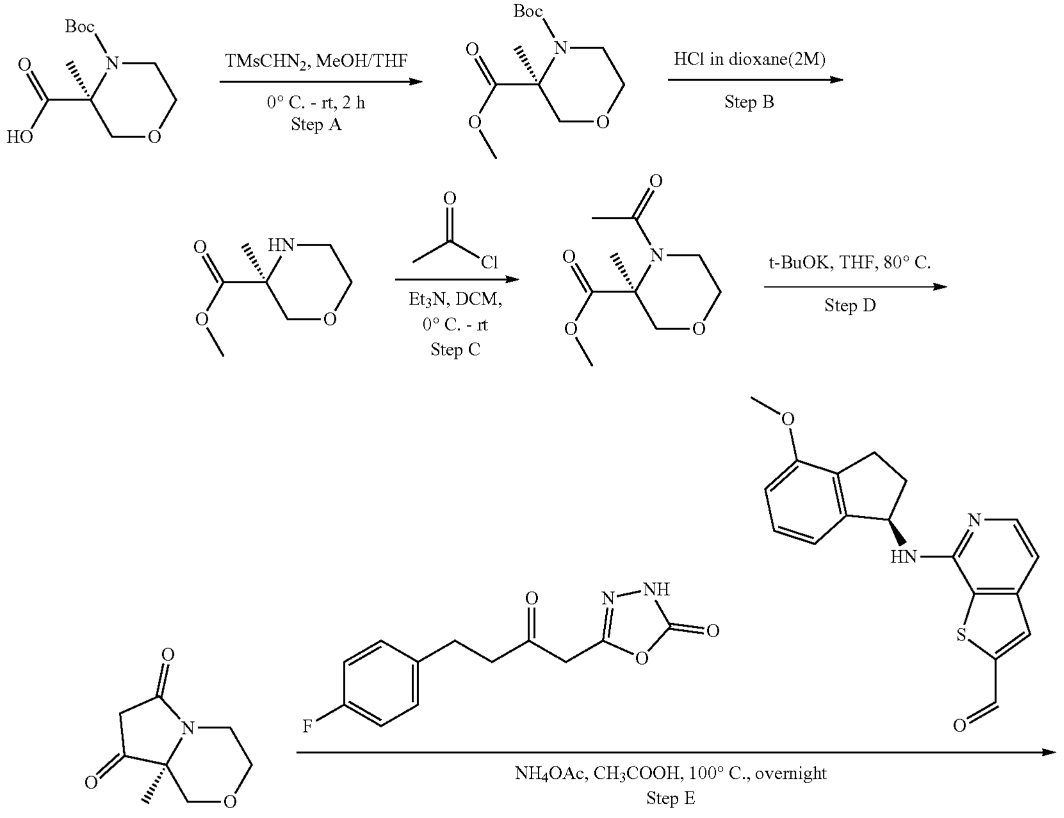

-continued

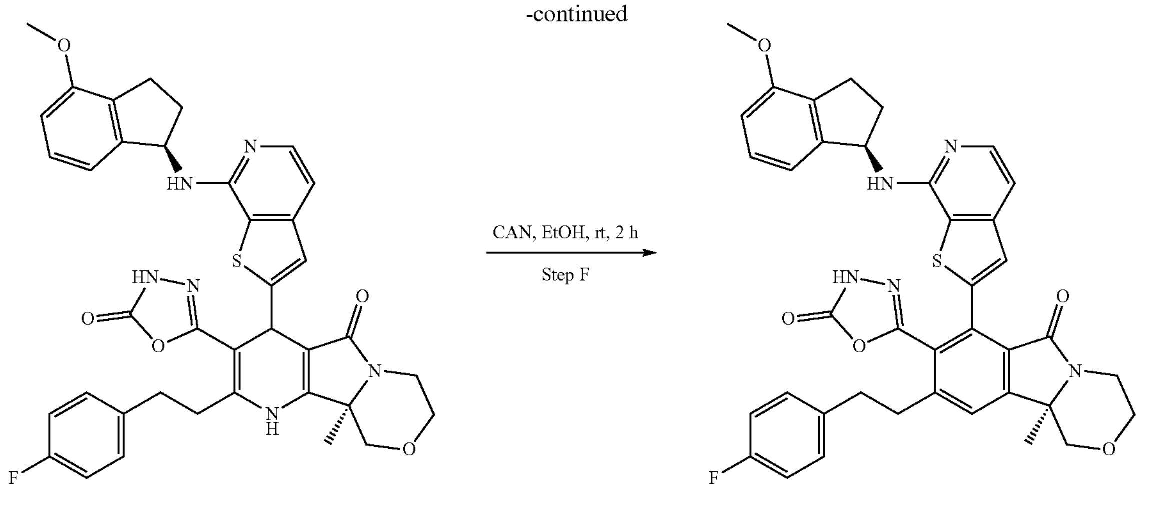

Step A: 4-(tert-butyl) 3-methyl (S)-3-methylmorpholine-3,4-dicarboxylate

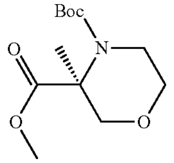 [SMILES: COC(=O)[C@]1(C)COCCN1C(=O)OC(C)(C)C]

To a solution of (S)-4-(tert-butoxycarbonyl)-3-methylmorpholine-3-carboxylic acid (1.1 g, 4.485 mmol) in Acetonitrile (120 mL) was added potassium carbonate (1.24 g, 8.969 mmol) and iodomethane (0.728 mL, 8.969 mmol), and the reaction was stirred at 60° C. for 18 hours. The reaction was concentrated in vacuo. The residue was purified by silica gel column chromatography eluting with 10% ethyl acetate in petroleum ether to afford 4-(tert-butyl) 3-methyl (S)-3-methylmorpholine-3,4-dicarboxylate (1.12 g, 4.319 mmol, 96.31%).

$^1$H NMR (400 MHz, $CDCl_3$): 3.82-3.91 (m, 1H), 3.66-3.76 (m, 5H), 3.58-3.66 (m, 1H), 3.52-3.56 (m, 1H), 3.20-3.30 (m, 1H), 1.54 (s, 3H), 1.44 (s, 9H).

Step B: methyl (S)-3-methylmorpholine-3-carboxylate

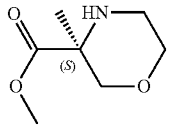

To a solution of 4-(tert-butyl) 3-methyl (S)-3-methylmorpholine-3,4-dicarboxylate (1.12 g, 4.319 mmol) in dioxane (6 mL) was added HCl-dioxane (4 M, 6 mL). The reaction was stirred at room temperature for 2 hrs. The reaction was concentrated to afford methyl (S)-3-methylmorpholine-3-carboxylate HCl salt (943 mg, crude). LC-MS: m/z 160.0 $(M+H)^+$.

Step C: methyl (S)-4-acetyl-3-methylmorpholine-3-carboxylate

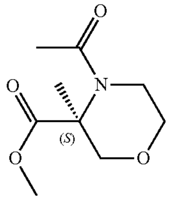

To a solution of methyl (S)-3-methylmorpholine-3-carboxylate HCl salt (943 mg, crude) in DCM (10 mL) was added TEA (2.470 mL, 17.771 mmol) and acetyl chloride (0.631 mL, 8.886 mmol), and the reaction was stirred at room temperature for 3 hours. After the reaction was completed, the mixture was quenched with ice water (10 ml), extracted with DCM (20 mL*3). The organic layers were combined, dried over $Na_2SO_4$, filtered and concentrated under vacuum to dryness. The crude product was purified by column chromatography on silica gel eluted with ($CH_2Cl_2$/MeOH 20:1) to give methyl (S)-4-acetyl-3-methylmorpholine-3-carboxylate (657 mg, 3.265 mmol, 55.12%). LC-MS: m/z 202.0 $(M+H)^+$.

Step D: (S)-8a-methyltetrahydro-6H-pyrrolo[2,1-c][1,4]oxazine-6,8(7H)-dione

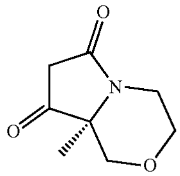

To a solution of methyl (S)-4-acetyl-3-methylmorpholine-3-carboxylate (150 mg, 0.745 mmol) in THF (2 mL) was added Potassium tert-butoxide solution 1.0 M in THF (0.894 mL, 0.894 mmol), and the reaction was stirred at 80° C. for 30 minutes. The reaction was concentrated in vacuo to afford (S)-8a-methyltetrahydro-6H-pyrrolo[2,1-c][1,4]oxazine-6,8(7H)-dione (160 mg, crude). LC-MS: m/z 170.1 $(M+H)^+$.

Step E: (10aR)-2-(4-fluorophenethyl)-4-(7-(((R)-4-methoxy-2,3-dihydro-1H-inden-1-yl)amino)thieno[2,3-c]pyridin-2-yl)-10a-methyl-3-(5-oxo-4,5-dihydro-1,3,4-oxadiazol-2-yl)-1,4,7,8,10,10a-hexahydro-5H-pyrido[2',3':3,4]pyrrolo[2,1-c][1,4]oxazin-5-one

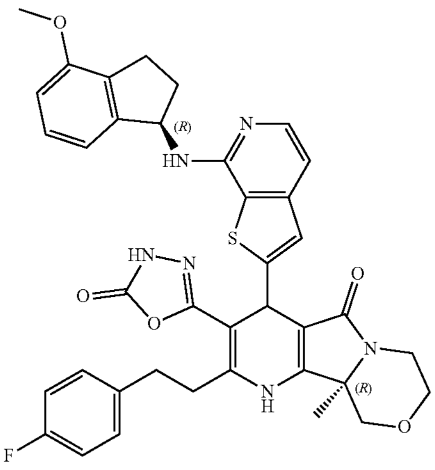

To a solution of (S)-8a-methyltetrahydro-6H-pyrrolo[2,1-c][1,4]oxazine-6,8(7H)-dione (10.43 mg, crude) in HOAc (1 mL) was added 5-(4-(4-fluorophenyl)-2-oxobutyl)-1,3,4-oxadiazol-2(3H)-one (15.43 mg, 0.062 mmol), (R)-7-((4-methoxy-2,3-dihydro-1H-inden-1-yl)amino)thieno[2,3-c]pyridine-2-carbaldehyde (20 mg, 0.062 mmol) and $NH_4OAc$ (9.50 mg, 0.123 mmol). The reaction was stirred at 100° C. for overnight. The reaction was concentrated in vacuo to afford (10aR)-2-(4-fluorophenethyl)-4-(7-(((R)-4-methoxy-2,3-dihydro-1H-inden-1-yl)amino)thieno[2,3-c]pyridin-2-yl)-10a-methyl-3-(5-oxo-4,5-dihydro-1,3,4-oxadiazol-2-yl)-1,4,7,8,10,10a-hexahydro-5H-pyrido[2',3':3,4]pyrrolo[2,1-c][1,4]oxazin-5-one (50 mg, crude). LC-MS: m/z 707.0 $(M+H)^+$.

Step F: (R)-2-(4-fluorophenethyl)-4-(7-(((R)-4-methoxy-2,3-dihydro-1H-inden-1-yl)amino)thieno[2,3-c]pyridin-2-yl)-10a-methyl-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 179)

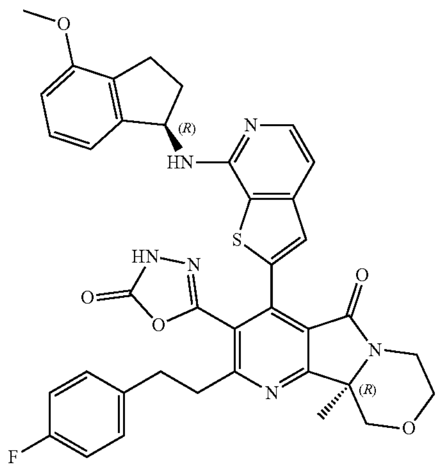

To a solution of (10aR)-2-(4-fluorophenethyl)-4-(7-(((R)-4-methoxy-2,3-dihydro-1H-inden-1-yl)amino)thieno[2,3-c]pyridin-2-yl)-10a-methyl-3-(5-oxo-4,5-dihydro-1,3,4-oxadiazol-2-yl)-1,4,7,8,10,10a-hexahydro-5H-pyrido[2',3':3,4]pyrrolo[2,1-c][1,4]oxazin-5-one (50 mg, crude) in EtOH (3 mL) was added cerium ammonium nitrate (77.57 mg, 0.141 mmol). The reaction was stirred at room temperature for 1 hour. The reaction mixture was purified by prep-HPLC to afford (R)-2-(4-fluorophenethyl)-4-(7-(((R)-4-methoxy-2,3-dihydro-1H-inden-1-yl)amino)thieno[2,3-c]pyridin-2-yl)-10a-methyl-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 179) (2.21 mg, 0.003 mmol, 4.23%).

$^1H$ NMR (400 MHz, DMSO-$d_6$): δ 7.94 (d, J=5.2 Hz, 1H), 7.35 (s, 1H), 7.18-7.24 (m, 2H), 7.09-7.15 (m, 2H), 7.02-7.09 (m, 3H), 6.86 (d, J=7.6 Hz, 1H), 6.82 (d, J=8.0 Hz, 1H), 5.87-5.94 (m, 1H), 4.09 (d, J=10.8 Hz, 1H), 3.97-4.02 (m, 1H), 3.89-3.95 (m, 1H), 3.79 (s, 3H), 3.26-3.28 (m, 1H), 3.22-3.26 (m, 1H), 3.10-3.20 (m, 4H), 2.90-3.00 (m, 3H), 2.64-2.72 (m, 1H), 1.96-2.07 (m, 1H), 1.62 (s, 3H). $^{19}F$ NMR (377 MHz, DMSO-$d_6$): −117.33. LC-MS: m/z 705.2 $(M+H)^+$.

5-(8-(4-fluorophenethyl)-6-(7-(((R)-4-methoxy-2,3-dihydro-1H-inden-1-yl)amino)thieno[2,3-c]pyridin-2-yl)-5-oxo-1,1a,2,3-tetrahydro-5H-cyclopropa[g]pyrido[2,3-a]pyrrolizin-7-yl)-1,3,4-oxadiazol-2(3H)-one (Compound 180)

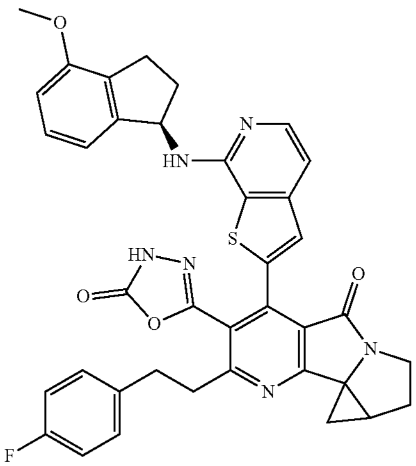 [SMILES: COc1cccc2c1CC[C@H]2Nc1nccc2cc(-c3c4c(nc(CCc5ccc(F)cc5)c3-c3n[nH]c(=O)o3)C35CC3CCN5C4=O)sc12]

Compound 180 was synthesized using similar procedure as described in Example 2 above by using the appropriate materials.

$^1$H NMR (400 MHz, DMSO-$d_6$): δ 7.94 (d, J=5.6 Hz, 1H), 7.32 (d, J=0.8 Hz, 1H), 7.22 (dd, J=6.0 Hz, J=8.8 Hz, 2H), 7.02-7.13 (m, 5H), 6.87 (t, J=7.2 Hz, 1H), 6.81 (dd, J=4.0 Hz, J=8.4 Hz, 1H), 5.86-5.95 (m, 1H), 3.84-3.91 (m, 1H), 3.79 (d, J=1.2 Hz, 3H), 3.01-3.10 (m, 3H), 2.88-2.97 (m, 3H), 2.64-2.73 (m, 2H), 2.30-2.35 (m, 2H), 2.14-2.21 (m, 1H), 2.01-2.06 (m, 1H), 1.88-1.95 (m, 1H), 1.78 (t, J=5.6 Hz, 1H). $^{19}$F NMR (377 MHz, DMSO-$d_6$): −117.30. LC-MS: m/z 687.1 $(M+H)^+$.

Example 17

(R)-5-(2-(4-fluorophenethyl)-4-(7-((4-methoxy-2,3-dihydro-1H-inden-1-yl)amino)thieno[2,3-c]pyridin-2-yl)-5-oxo-8,9-dihydro-5H,7H-8,9a-methanopyrido[2,3-a]pyrrolizin-3-yl)-1,3,4-oxadiazol-2(3H)-one (Compound 181)

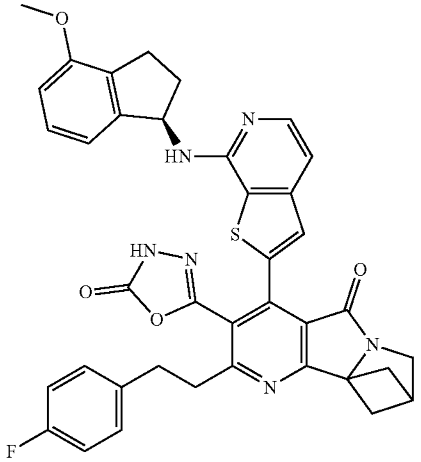

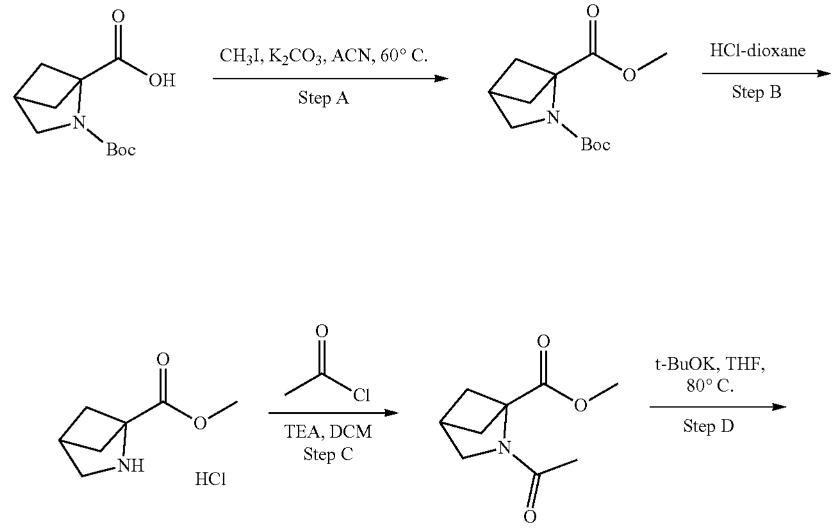

-continued

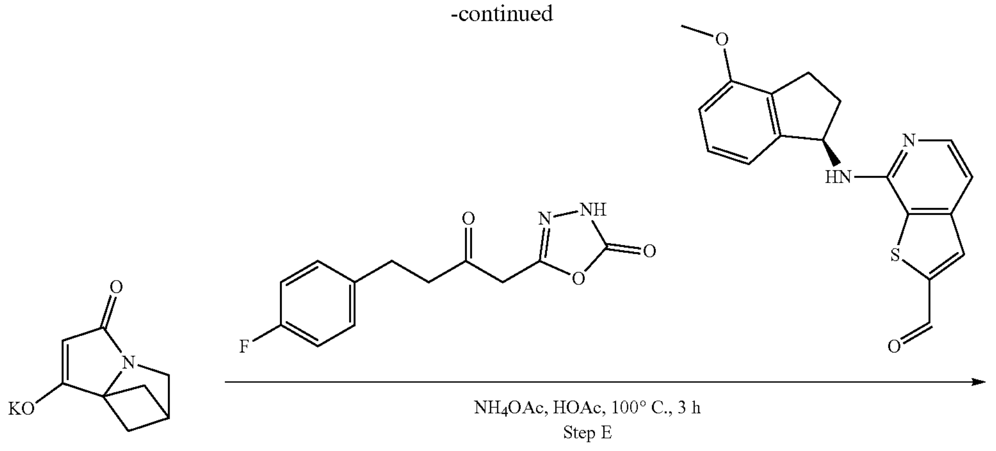

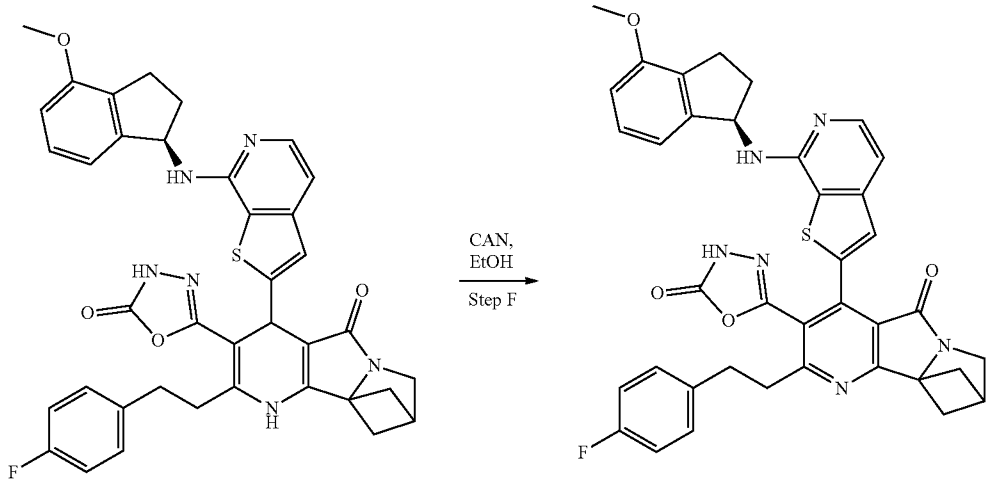

Step A: 2-(tert-butyl) 1-methyl 2-azabicyclo[2.1.1] hexane-1,2-dicarboxylate

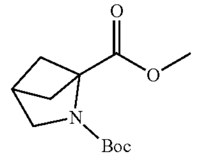 [SMILES: COC(=O)C12CC(CN1C(=O)OC(C)(C)C)C2]

To a solution of 2-(tert-butoxycarbonyl)-2-azabicyclo [2.1.1]hexane-1-carboxylic acid (500 mg, 2.20 mmol) in ACN (2 mL) was added potassium carbonate (608 mg, 4.40 mmol) and iodomethane (0.357 mL, 4.40 mmol), and the reaction was stirred at 60° C. for 18 hours. The reaction was concentrated in vacuo. The residue was purified by silica gel column chromatography eluting with 10% ethyl acetate in petroleum ether to afford 2-(tert-butyl) 1-methyl 2-azabicyclo[2.1.1]hexane-1,2-dicarboxylate (450 mg, 84.8%). LC-MS: m/z 242.1 $(M+H)^+$.

Step B: methyl 2-azabicyclo[2.1.1]hexane-1-carboxylate HC salt

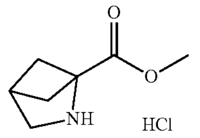

To a solution of 2-(tert-butyl) 1-methyl 2-azabicyclo [2.1.1]hexane-1,2-dicarboxylate (400 mg, 1.66 mmol) in dioxane (4 mL) was added HCl-dioxane (4 M, 4 mL). The reaction was stirred at room temperature for 18 hours. The reaction was concentrated to afford methyl 2-azabicyclo [2.1.1]hexane-1-carboxylate HCl salt (300 mg, crude). LC-MS: m/z 142.1 $(M+H)^+$.

Step C: methyl 2-acetyl-2-azabicyclo[2.1.1]hexane-1-carboxylate

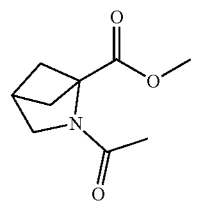

To a solution of methyl 2-azabicyclo[2.1.1]hexane-1-carboxylate HCl salt (300 mg, crude) in DCM (3 mL) were added TEA (0.87 mL, 6.38 mmol) and acetyl chloride (0.23 mL, 3.20 mmol), and the reaction was stirred at room temperature for 3 hours. After the reaction was completed, the mixture was quenched with ice water (5 ml), extracted with DCM (20 mL*3). The organic layers were combined, dried over $Na_2SO_4$, filtered and concentrated under vacuum to dryness. The crude product was purified by column chromatography on silica gel eluted with ($CH_2Cl_2$/MeOH 20:1) to give methyl 2-acetyl-2-azabicyclo[2.1.1]hexane-1-carboxylate (300 mg, 77.1%). LC-MS: m/z 184.1 $(M+H)^+$.

Step D: dihydro-1H,5H-2,7a-methanopyrrolizine-5,7(6H)-dione

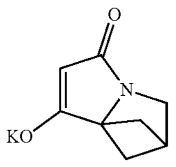

To a solution of methyl 2-acetyl-2-azabicyclo[2.1.1]hexane-1-carboxylate (50 mg, 0.273 mmol) in THF (2 mL) were added t-BuOK (61 mg, 0.546 mmol), and the reaction was stirred at 80° C. for 30 minutes. The reaction was concentrated in vacuo to afford dihydro-1H,5H-2,7a-methanopyrrolizine-5,7(6H)-dione (41 mg, crude). LC-MS: m/z 208.0 $(M+H_2O+H)^+$.

Step E: 5-(2-(4-fluorophenethyl)-4-(7-(((R)-4-methoxy-2,3-dihydro-1H-inden-1-yl)amino)thieno[2,3-c]pyridin-2-yl)-5-oxo-1,5,8,9-tetrahydro-4H,7H-8,9a-methanopyrido[2,3-a]pyrrolizin-3-yl)-1,3,4-oxadiazol-2(3H)-one

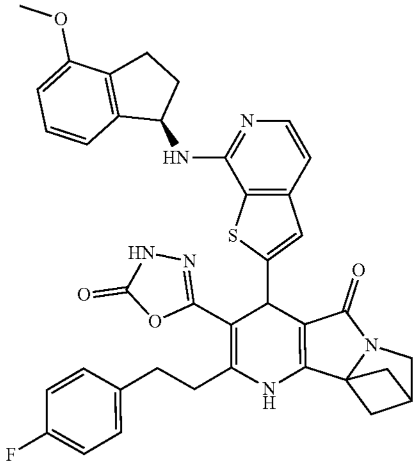 [SMILES: COc1cccc2c1CC[C@H]2Nc1nccc2cc(C3C4=C(NC(CCc5ccc(F)cc5)=C3c3n[nH]c(=O)o3)C35CC(CN3C4=O)C5)sc12]

To a solution of dihydro-1H,5H-2,7a-methanopyrrolizine-5,7(6H)-dione (20 mg, crude) in HOAc (1 mL) was added 5-(4-(4-fluorophenyl)-2-oxobutyl)-1,3,4-oxadiazol-2(3H)-one (17 mg, 0.053 mmol), (R)-7-((4-methoxy-2,3-dihydro-1H-inden-1-yl)amino)thieno[2,3-c]pyridine-2-carbaldehyde (13 mg, 0.053 mmol) and $NH_4OAc$ (8 mg, 0.106 mmol). The reaction was stirred at 100° C. for 3 hours. The reaction was concentrated in vacuo to afford 5-(2-(4-fluorophenethyl)-4-(7-(((R)-4-methoxy-2,3-dihydro-1H-inden-1-yl)amino)thieno[2,3-c]pyridin-2-yl)-5-oxo-1,5,8,9-tetrahydro-4H,7H-8,9a-methanopyrido[2,3-a]pyrrolizin-3-yl)-1,3,4-oxadiazol-2(3H)-one (91 mg, crude). LC-MS: m/z 689.5 $(M+H)^+$.

Step F: (R)-5-(2-(4-fluorophenethyl)-4-(7-((4-methoxy-2,3-dihydro-1H-inden-1-yl)amino)thieno[2,3-c]pyridin-2-yl)-5-oxo-8,9-dihydro-5H,7H-8,9a-methanopyrido[2,3-a]pyrrolizin-3-yl)-1,3,4-oxadiazol-2(3H)-one (Compound 181)

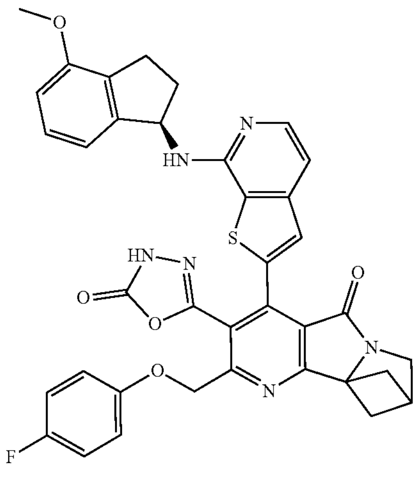 [SMILES: COc1cccc2c1CC[C@H]2Nc1nccc2cc(-c3c4c(nc(COc5ccc(F)cc5)c3-c3n[nH]c(=O)o3)C35CC(CN3C4=O)C5)sc12]

To a solution of 5-(2-(4-fluorophenethyl)-4-(7-(((R)-4-methoxy-2,3-dihydro-1H-inden-1-yl)amino)thieno[2,3-c]pyridin-2-yl)-5-oxo-1,5,8,9-tetrahydro-4H,7H-8,9a-methanopyrido[2,3-a]pyrrolizin-3-yl)-1,3,4-oxadiazol-2(3H)-one (91 mg, crude) in EtOH (3 mL) was added cerium ammonium nitrate (72 mg, 0.132 mmol). The reaction was stirred at room temperature for 1 hour. The reaction mixture was purified by prep-HPLC to afford (R)-5-(2-(4-fluorophenethyl)-4-(7-((4-methoxy-2,3-dihydro-1H-inden-1-yl)amino)thieno[2,3-c]pyridin-2-yl)-5-oxo-8,9-dihydro-5H,7H-8,9a-methanopyrido[2,3-a]pyrrolizin-3-yl)-1,3,4-oxadiazol-2(3H)-one (Compound 181) (5.50 mg, 6.06%).

$^1$H NMR (400 MHz, DMSO-$d_6$): δ 12.69 (br s, 1H), 7.98 (d, J=5.2 Hz, 1H), 7.41 (s, 1H), 7.18-7.24 (m, 3H), 7.02-7.14 (m, 4H), 6.84 (dd, J=7.6 Hz, J=11.6 Hz, 2H), 5.90 (q, J=8.0 Hz, 1H), 3.79 (s, 3H), 3.56 (s, 2H), 3.17-3.22 (m, 3H), 3.01-3.05 (m, 2H), 2.89-2.97 (m, 1H), 2.62-2.72 (m, 4H), 1.96-2.07 (m, 1H), 1.71-1.78 (m, 2H). $^{19}$F NMR (377 MHz, DMSO-$d_6$): −117.03. LC-MS: m/z 687.2 $(M+H)^+$.

Example 18

5-((S)-2-(4-fluorophenethyl)-4-(7-(((R)-4-methoxy-2,3-dihydro-1H-inden-1-yl)amino)thieno[2,3-c]pyridin-2-yl)-9,9-dimethyl-5-oxo-7,8,9,9a-tetrahydro-5H-pyrido[2,3-a]pyrrolizin-3-yl)-1,3,4-oxadiazol-2(3H)-one (Compound 182)

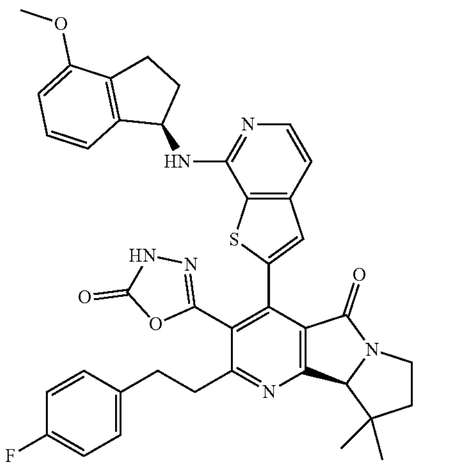

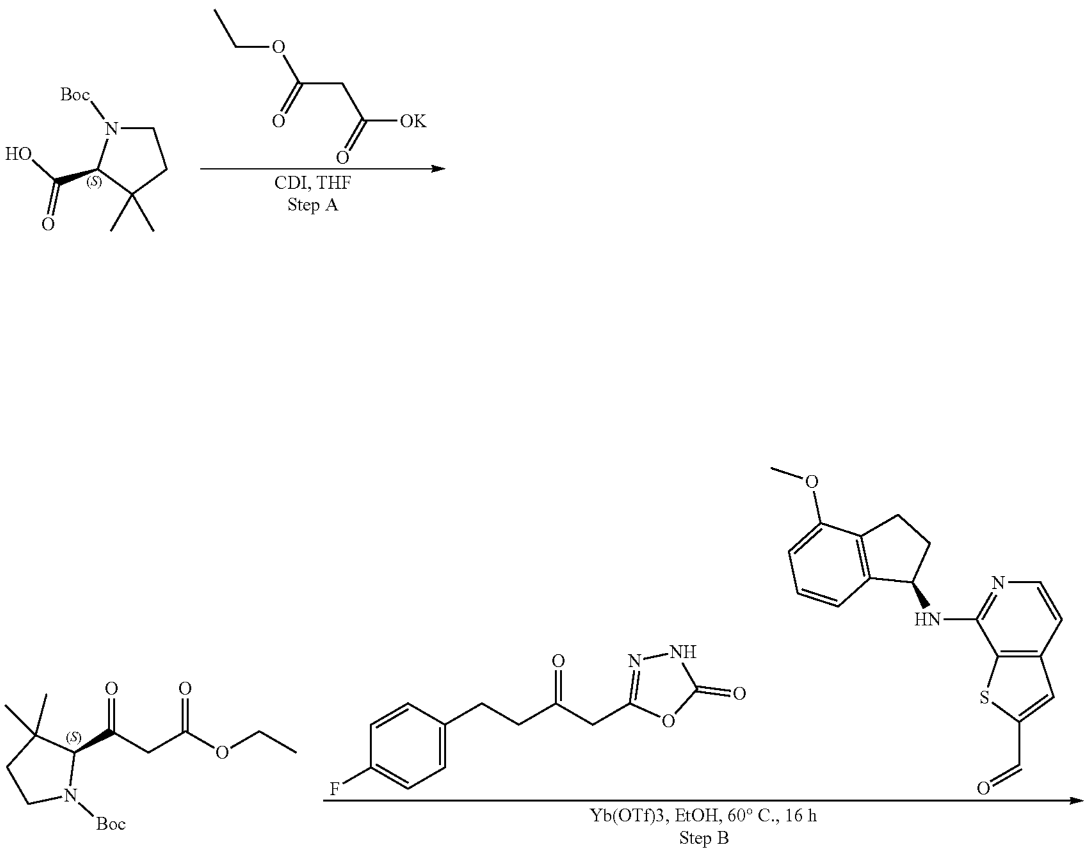

-continued
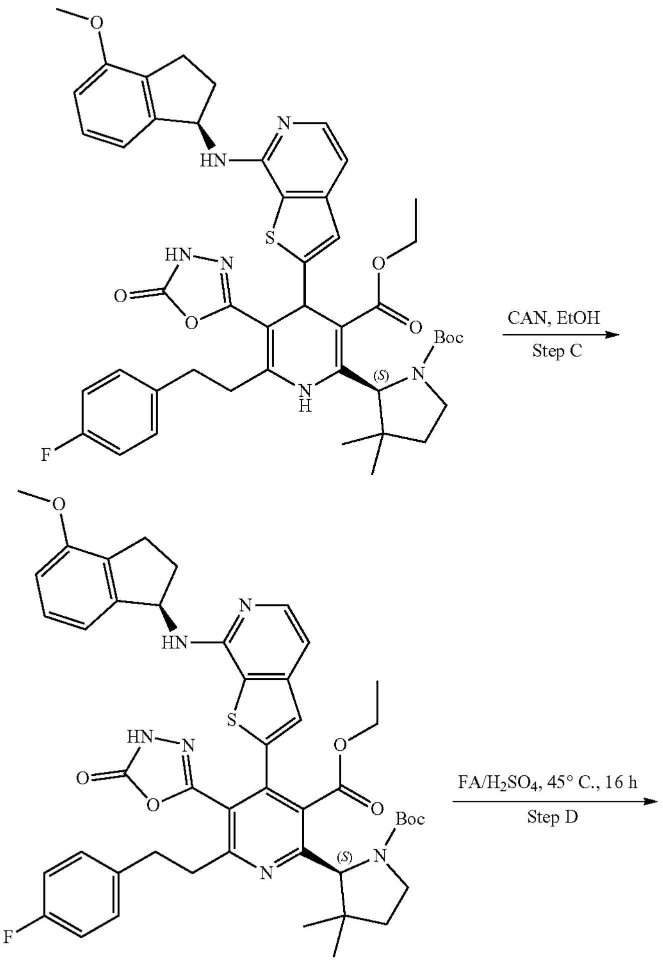
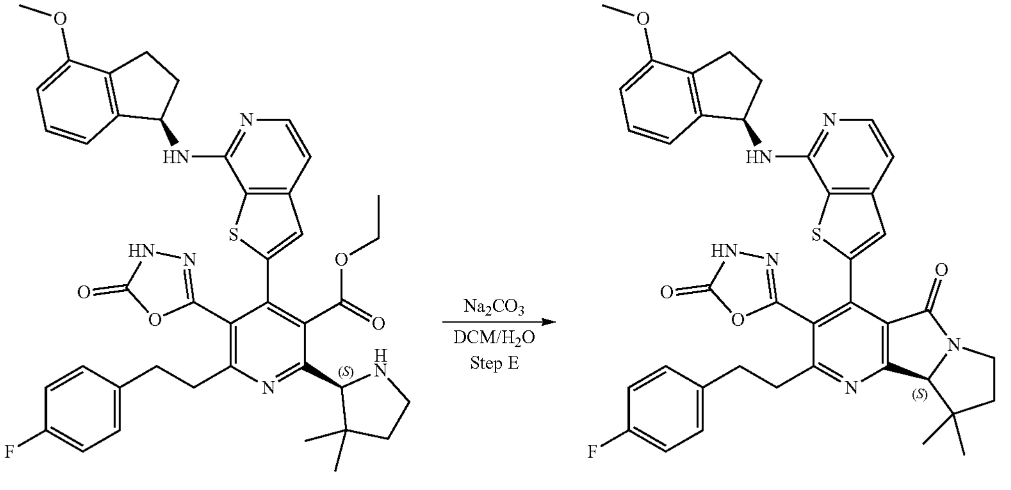

Step A tert-butyl (S)-2-(3-ethoxy-3-oxopropanoyl)-3,3-dimethylpyrrolidine-1-carboxylate

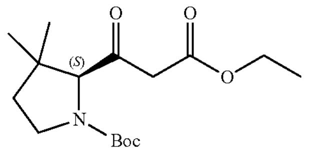

To a solution of (S)-1-(tert-butoxycarbonyl)-3,3-dimethylpyrrolidine-2-carboxylic acid (300 mg, 1.233 mmol) in THF (3 mL) and Acetonitrile (3 mL) were added CDI (239.93 mg, 1.480 mmol) and the reaction was stirred at room temperature for 1 hr. Then potassium 3-ethoxy-3-oxopropanoate (314.82 mg, 1.850 mmol) and magnesium chloride (140.86 mg, 1.480 mmol) was added and the reaction was stirred at 50° C. for 18 hr. The reaction was diluted with EA (50 mL) and water (20 mL). The organic layer was separated, washed with further water (20 mL×2) and saturated NaCl (20 mL). The organic layer was separated, dried with $Na_2SO_4$ and then filtered. The organic layer was collected, concentrated in vacuo. The residue was purified using silica gel column chromatography eluting with PE:EA=1:1. The organic layer was collected, concentrated in vacuo to afford the title compound tert-butyl (S)-2-(3-ethoxy-3-oxopropanoyl)-3,3-dimethylpyrrolidine-1-carboxylate (170 mg, 0.542 mmol, 43.99%). LC-MS: m/z 314.2 $(M+H)^+$.

Step B ethyl 2-((S)-1-(tert-butoxycarbonyl)-3,3-dimethylpyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl)-1,4-dihydropyridine-3-carboxylate

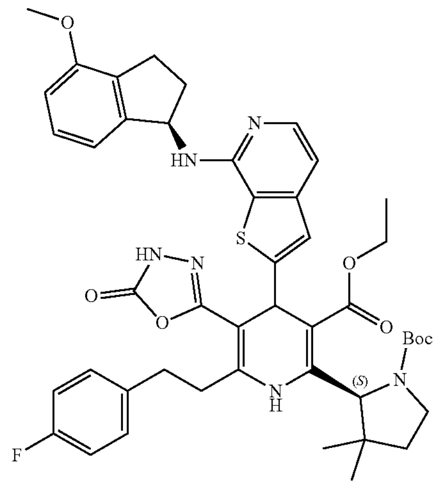

A solution of tert-butyl (S)-2-(3-ethoxy-3-oxopropanoyl)-3,3-dimethylpyrrolidine-1-carboxylate (170 mg, 0.542 mmol), 5-(4-(4-fluorophenyl)-2-oxobutyl)-1,3,4-oxadiazol-2(3H)-one (135.74 mg, 0.542 mmol) and (R)-7-((4-methoxy-2,3-dihydro-1H-inden-1-yl)amino)thieno[2,3-c]pyridine-2-carbaldehyde (175.97 mg, 0.542 mmol) in EtOH (2 mL) were added $NH_4OAc$ (167.25 mg, 2.170 mmol) and $Yb(OTf)_3$ (33.63 mg, 0.054 mmol). The reaction was stirred at 60° C. for 18 hr. The reaction was diluted with EA (50 mL) and water (20 mL). The organic layer was separated, washed with further water (20 mL×2) and saturated NaCl (20 mL). The organic layer was separated, dried with $Na_2SO_4$ and then filtered. The organic layer was collected, concentrated in vacuo to give ethyl 2-((S)-1-(tert-butoxycarbonyl)-3,3-dimethylpyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl)-1,4-dihydropyridine-3-carboxylate (crude 200 mg, 0.235 mmol, 43.32%). LC-MS: m/z 851.3 $(M+H)^+$.

Step C ethyl 2-((S)-1-(tert-butoxycarbonyl)-3,3-dimethylpyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl)nicotinate

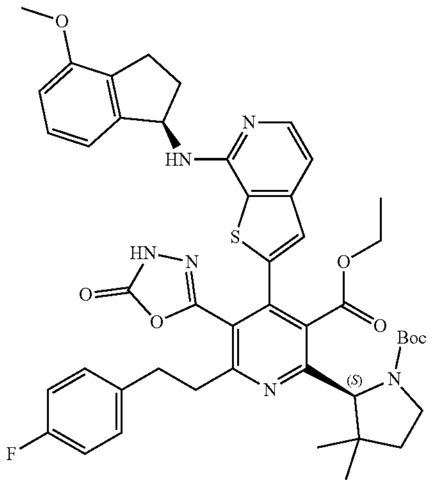

A solution of ethyl 2-((S)-1-(tert-butoxycarbonyl)-3,3-dimethylpyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl)-1,4-dihydropyridine-3-carboxylate (crude 200 mg, 0.235 mmol) in EtOH (2 mL) were added ammonium cerium(IV) nitrate (257.68 mg, 0.470 mmol). The reaction was stirred at R.T. for 2 hr. The reaction was concentrated and purified by chromatography on C18 (FA) to give ethyl 2-((S)-1-(tert-butoxycarbonyl)-3,3-dimethylpyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl)nicotinate (100 mg, 0.118 mmol, 50.12%). LC-MS: m/z 849.3 $(M+H)^+$.

Step D ethyl 2-((S)-3,3-dimethylpyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl) nicotinate

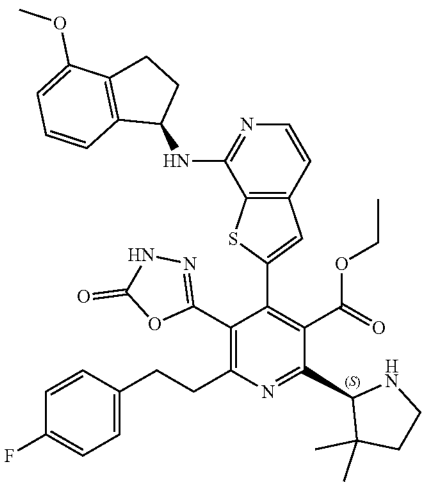

A solution of ethyl 2-((S)-1-(tert-butoxycarbonyl)-3,3-dimethylpyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl) nicotinate (100 mg, 0.118 mmol) in AcOH (4 mL) and $H_2O$ (2 mL) were added $H_2SO_4$ (0.006 mL, 0.118 mmol). The reaction was stirred at 40° C. for 18 hr. The reaction was diluted with EA (50 mL) and water (20 mL). The organic layer was separated, washed with further water (20 mL×2) and saturated NaCl (20 mL). The organic layer was separated, dried with $Na_2SO_4$ and then filtered. The organic layer was collected, concentrated in vacuo. The residue was concentrated give ethyl 2-((S)-3,3-dimethylpyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl)nicotinate (crude 80 mg, 0.107 mmol, 90.69%). LC-MS: m/z 749.2 $(M+H)^+$.

Step E 5-((S)-2-(4-fluorophenethyl)-4-(7-(((R)-4-methoxy-2,3-dihydro-1H-inden-1-yl)amino)thieno[2,3-c]pyridin-2-yl)-9,9-dimethyl-5-oxo-7,8,9,9a-tetrahydro-5H-pyrido[2,3-a]pyrrolizin-3-yl)-1,3,4-oxadiazol-2(3H)-one (Compound 182)

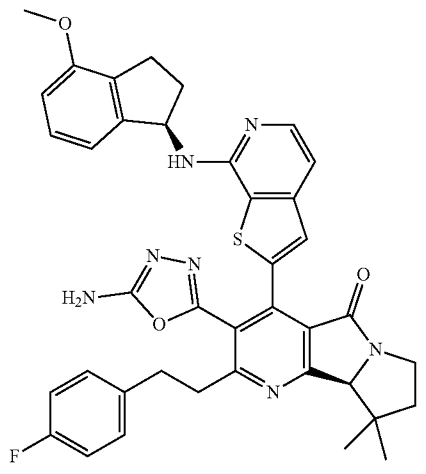 [SMILES: COc1cccc2c1CC[C@H]2Nc1nccc2cc(-c3c4c(nc(CCc5ccc(F)cc5)c3-c3nnc(N)o3)[C@H]3N(CCC3(C)C)C4=O)sc12]

A solution of ethyl 2-((S)-3,3-dimethylpyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-oxadiazol-2-yl)nicotinate (50 mg, 0.067 mmol) in DCM (2 mL) and $H_2O$ (2 mL) were added $Na_2CO_3$ (21.30 mg, 0.201 mmol). The reaction was stirred at R.T. for 1 hr. The reaction was purified by Prep-HPLC (FA) to give 5-((S)-2-(4-fluorophenethyl)-4-(7-(((R)-4-methoxy-2,3-dihydro-1H-inden-1-yl)amino)thieno[2,3-c]pyridin-2-yl)-9,9-dimethyl-5-oxo-7,8,9,9a-tetrahydro-5H-pyrido[2,3-a]pyrrolizin-3-yl)-1,3,4-oxadiazol-2(3H)-one (Compound 182) (14.45 mg, 0.021 mmol, 30.80%).

$^1H$ NMR (400 MHz, DMSO-$d_6$): δ 7.97 (d, J=5.2 Hz, 1H), 7.44 (s, 1H), 7.19-7.25 (m, 3H), 7.11-7.15 (m, 1H), 7.02-7.08 (m, 3H), 6.81-6.86 (m, 2H), 5.86-5.92 (m, 1H), 4.61 (s, 1H), 3.79 (s, 3H), 3.43-3.51 (m, 1H), 3.19-3.26 (m, 3H), 3.08-3.14 (m, 1H), 3.00-3.05 (m, 1H), 2.91-2.98 (m, 1H), 2.66-2.74 (m, 2H), 2.53-2.55 (m, 1H), 2.17-2.28 (m, 1H), 1.94-2.06 (m, 2H), 1.40 (s, 3H), 0.31 (s, 3H). 19F NMR (377 MHz, DMSO-d6): δ −117.19. LC-MS: m/z 703.3 $(M+H)^+$.

5-((S)-4-(7-(((R)-4,6-difluoro-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 183)

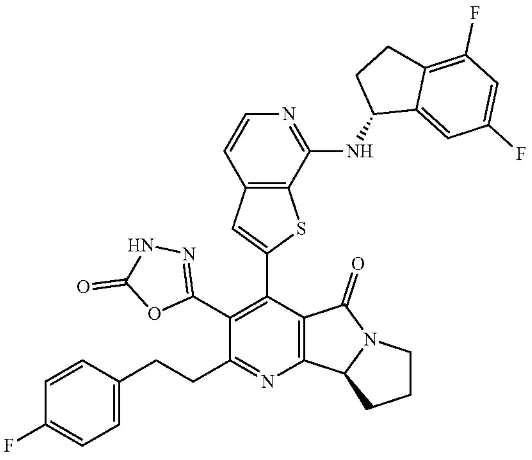 [SMILES: O=C1c2c(nc(CCc3ccc(F)cc3)c(-c3n[nH]c(=O)o3)c2-c2cc3ccnc(N[C@@H]4CCc5c(F)cc(F)cc54)c3s2)[C@@H]2CCCN12]

Compound 183 was synthesized using similar procedure as described in Example 10 above by using the appropriate materials.

$^1H$ NMR (400 MHz, $CDCl_3$) δ ppm 8.05-8.10 (m, 1H), 7.40 (s, 1H), 7.09-7.17 (m, 3H), 6.90-7.00 (m, 3H), 6.65-6.74 (m, 1H), 5.75-6.03 (m, 1H), 4.56-4.88 (m, 2H), 3.70-3.81 (m, 1H), 3.39-3.50 (m, 1H), 3.02-3.21 (m, 5H), 2.75-2.89 (m, 2H), 2.48-2.56 (m, 1H), 2.35-2.45 (m, 2H), 2.01 (m, 1H), 1.45 (m, 1H). LC-MS: m/z 681.1 $(M+H)^+$.

5-((S)-4-(7-(((R)-5-fluoro-2,3-dihydro-1H-inden-1-yl)amino)thieno[2,3-c]pyridin-2-yl)-2-(4-fluoro-phenethyl)-5-oxo-7,8,9,9a-tetrahydro-5H-pyrido[2,3-a]pyrrolizin-3-yl)-1,3,4-oxadiazol-2(3H)-one (Compound 184)

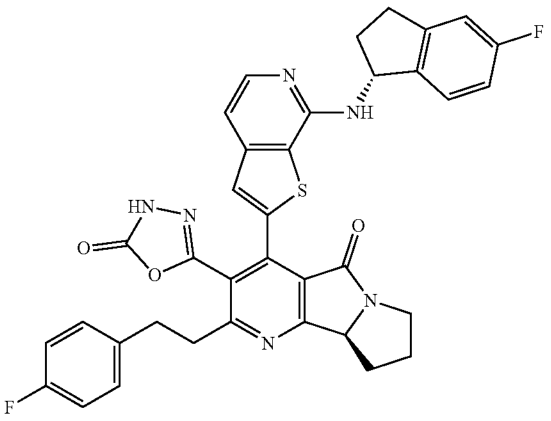 [SMILES: O=C1c2c(nc(CCc3ccc(F)cc3)c(-c3n[nH]c(=O)o3)c2-c2cc3ccnc(N[C@@H]4CCc5cc(F)ccc54)c3s2)[C@@H]2CCCN12]

Compound 184 was synthesized using similar procedure as described in Example 10 above by using the appropriate materials.

$^{1}$H NMR (400 MHz, $CDCl_3$) δ 8.04 (d, J=6 Hz, 1H) 7.40 (s, 1H) 7.29-7.36 (m, 1H) 7.11-7.18 (m, 2H) 7.07 (d, J=5.60 Hz, 1H) 6.93-7.01 (m, 3H) 6.89 (m, 1H) 5.73-5.83 (m, 1H) 4.86-4.97 (m, 1H) 4.75-4.83 (m, 1H) 3.73-3.83 (m, 1H) 3.38-3.48 (m, 1H) 3.16-3.23 (m, 2H) 3.06-3.14 (m, 2H) 2.97-3.04 (m, 1H) 2.84-2.94 (m, 1H) 2.67-2.79 (m, 1H) 2.49-2.59 (m, 1H) 2.33-2.45 (m, 2H) 1.97-2.04 (m, 1H) 1.41-1.53 (m, 1H). $^{19}$F NMR (376 MHz, $CDCl_3$) δ −115.13 (s, 1 F) −116.62 (s, 1 F). LC-MS: m/z 663.1 $(M+H)^+$.

5-((S)-2-isopropyl-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 185)

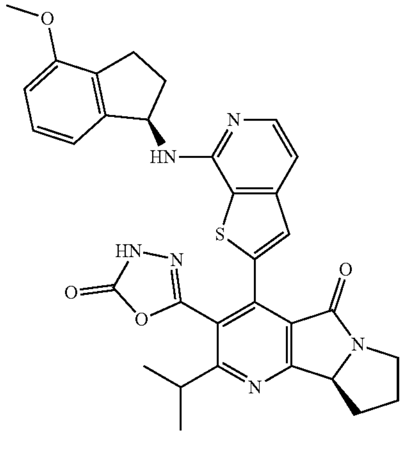 [SMILES: COc1cccc2c1CC[C@H]2Nc1nccc2cc(-c3c4c(nc(C(C)C)c3-c3n[nH]c(=O)o3)[C@@H]3CCCN3C4=O)sc12]

Compound 185 was synthesized using similar procedure as described in Example 2 above by using the appropriate materials.

$^{1}$H NMR (400 MHz, DMSO-$d_6$): δ 7.98 (d, J=5.2 Hz, 1H), 7.42 (s, 1H), 7.25 (d, J=8.4 Hz, 1H), 7.13 (t, J=7.6 Hz, 1H), 7.07 (d, J=5.6 Hz, 1H), 6.84 (dd, J=7.2 Hz, J=11.2 Hz, 2H), 5.90 (q, J=8.4 Hz, 1H), 4.87 (dd, J=6.4 Hz, J=9.6 Hz, 1H), 3.79 (s, 3H), 3.51-3.56 (m, 1H), 3.25-3.28 (m, 1H), 3.16-3.20 (m, 1H), 2.92-2.98 (m, 1H), 2.68-2.72 (m, 1H), 2.22-2.41 (m, 4H), 1.96-2.05 (m, 1H), 1.45 (t, J=10.4 Hz, 1H), 1.28 (dd, J=3.2 Hz, J=6.4 Hz, 6H). LC-MS: m/z 595.2 $(M+H)^+$.

Example 19

(S)-7-(2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)-4-((5-fluoropyridin-2-yl)methyl)-2,2-dimethyl-2H-benzo[b][1,4]oxazin-3(4H)-one (Compound 186)

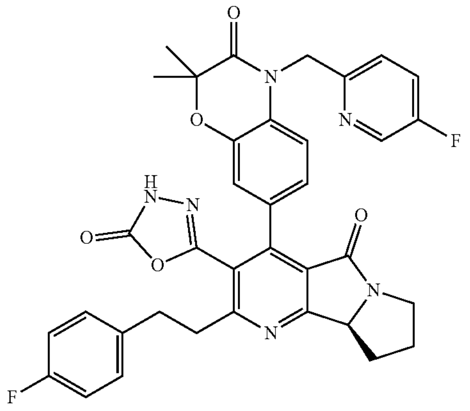 [SMILES: CC1(C)Oc2cc(-c3c4c(nc(CCc5ccc(F)cc5)c3-c3n[nH]c(=O)o3)[C@@H]3CCCN3C4=O)ccc2N(Cc2ccc(F)cn2)C1=O]

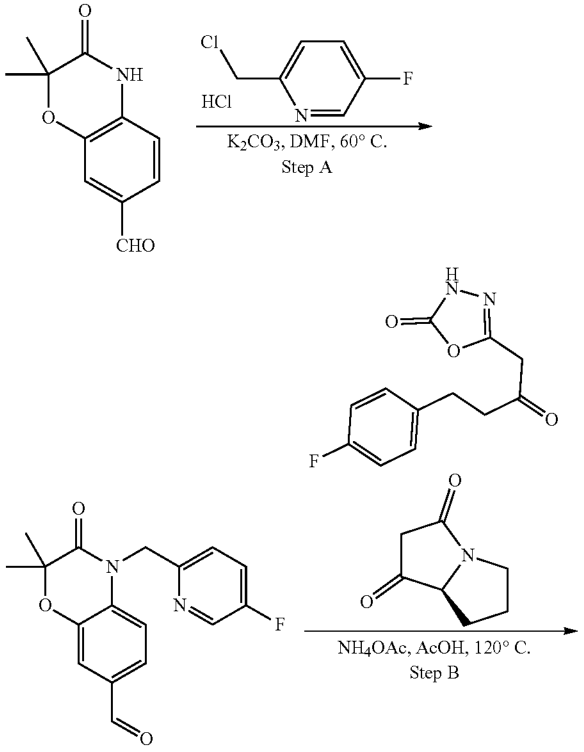

-continued

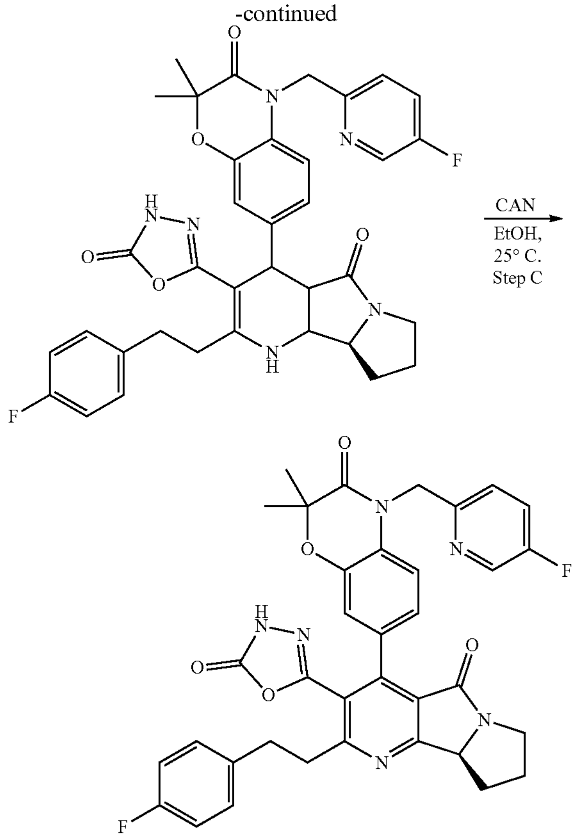

Step A 4-((5-fluoropyridin-2-yl)methyl)-2,2-dimethyl-3-oxo-3,4-dihydro-2H-benzo[b][1,4]oxazine-7-carbaldehyde

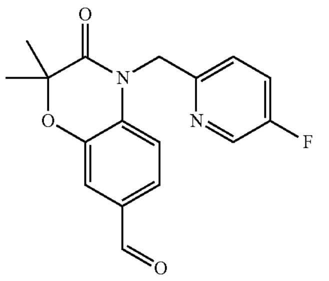 [SMILES: CC1(C)Oc2cc(C=O)ccc2N(Cc2ccc(F)cn2)C1=O]

To a solution of 2,2-dimethyl-3-oxo-4H-1,4-benzoxazine-7-carbaldehyde (65 mg, 316.75 μmol) in DMF (3 mL) was added $K_2CO_3$ (131.0 mg, 950.25 μmol) and 2-(chloromethyl)-5-fluoro-pyridine (69.0 mg, 380.10 μmol, HCl salt). The mixture was stirred at 60° C. for 2 hrs. The reaction mixture was concentrated under reduced pressure to give a residue. The residue was purified by column chromatography ($SiO_2$, Petroleum ether/Ethyl acetate=1/0 to 5/1). Compound 4-((5-fluoropyridin-2-yl)methyl)-2,2-dimethyl-3-oxo-3,4-dihydro-2H-benzo[b][1,4]oxazine-7-carbaldehyde (80 mg, 80.36% yield) was obtained. LC-MS: m/z 315.0 $(M+H)^+$.

Step B 7-((9aS)-2-(4-fluorophenethyl)-5-oxo-3-(5-oxo-4,5-dihydro-1,3,4-oxadiazol-2-yl)-4,4a,5,7,8,9,9a,9b-octahydro-1H-pyrido[2,3-a]pyrrolizin-4-yl)-4-((5-fluoropyridin-2-yl)methyl)-2,2-dimethyl-2H-benzo[b][1,4]oxazin-3(4H)-one

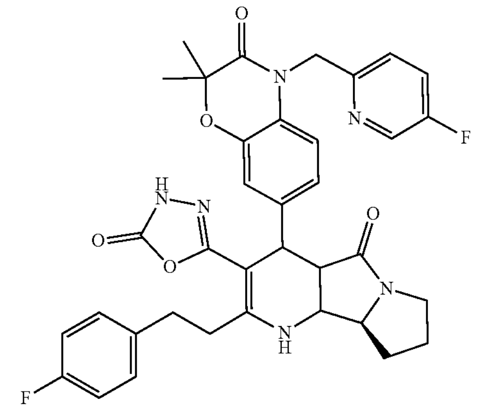 [SMILES: CC1(C)Oc2cc(C3C(c4n[nH]c(=O)o4)=C(CCc4ccc(F)cc4)NC4C3C(=O)N3CCC[C@@H]43)ccc2N(Cc2ccc(F)cn2)C1=O]

To a solution of 4-[(5-fluoro-2-pyridyl)methyl]-2,2-dimethyl-3-oxo-1,4-benzoxazine-7-carbaldehyde (70 mg, 222.71 μmol), 5-[4-(4-fluorophenyl)-2-oxo-butyl]-3H-1,3,4-oxadiazol-2-one (55.0 mg, 222.71 μmol), (8S)-5,6,7,8-tetrahydropyrrolizine-1,3-dione (31.0 mg, 222.71 μmol) in AcOH (2 mL) was added $NH_4OAc$ (34.0 mg, 445.42 μmol). The mixture was stirred at 120° C. for 1 hr. The reaction mixture was concentrated under reduced pressure to give crude product 7-((9aS)-2-(4-fluorophenethyl)-5-oxo-3-(5-oxo-4,5-dihydro-1,3,4-oxadiazol-2-yl)-4,4a,5,7,8,9,9a,9b-octahydro-1H-pyrido[2,3-a]pyrrolizin-4-yl)-4-((5-fluoropyridin-2-yl)methyl)-2,2-dimethyl-2H-benzo[b][1,4]oxazin-3(4H)-one (150 mg, crude). LC-MS: m/z 667.2 $(M+H)^+$.

Step C (S)-7-(2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)-4-((5-fluoropyridin-2-yl)methyl)-2,2-dimethyl-2H-benzo[b][1,4]oxazin-3(4H)-one (Compound 186)

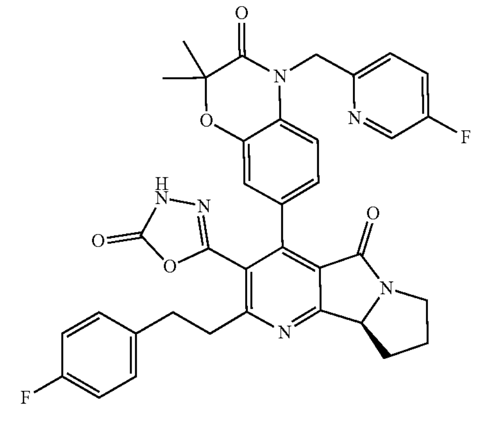 [SMILES: CC1(C)Oc2cc(-c3c4c(nc(CCc5ccc(F)cc5)c3-c3n[nH]c(=O)o3)[C@@H]3CCCN3C4=O)ccc2N(Cc2ccc(F)cn2)C1=O]

To a solution of 7-((9aS)-2-(4-fluorophenethyl)-5-oxo-3-(5-oxo-4,5-dihydro-1,3,4-oxadiazol-2-yl)-4,4a,5,7,8,9,9a, 9b-octahydro-1H-pyrido[2,3-a]pyrrolizin-4-yl)-4-((5-fluoropyridin-2-yl)methyl)-2,2-dimethyl-2H-benzo[b][1,4]oxazin-3(4H)-one (60 mg, 90.00 μmol) in MeCN (3 mL) was added CAN (49.34 mg, 90.00 μmol). The mixture was stirred at 25° C. for 1 hr. The reaction mixture was concentrated under reduced pressure to give a residue. The residue was purified by prep-HPLC (column: YMC-Actus Triart C18 150*30 mm*5 um; mobile phase: [water(TFA)-ACN]; gradient: 46%-66% B over 11.5 min). Compound (S)-7-(2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)-4-((5-fluoropyridin-2-yl)methyl)-2,2-dimethyl-2H-benzo[b][1,4]oxazin-3(4H)-one (4.38 mg, 7.32% yield) was obtained.

$^1H$ NMR (400 MHz, MeOD-$d_4$) δ ppm 8.39-8.48 (m, 1H), 7.54-7.65 (m, 1H), 7.32-7.38 (m, 1H), 7.11-7.17 (m, 2H), 7.03-7.08 (m, 1H), 6.89-7.01 (m, 4H), 5.25-5.32 (m, 2H), 4.83-4.87 (m, 1H), 3.61-3.71 (m, 1H), 3.39-3.48 (m, 1H), 3.19-3.27 (m, 2H), 3.01-3.16 (m, 2H), 2.38-2.55 (m, 3H), 1.52-1.58 (m, 6H), 1.42-1.50 (m, 1H). LC-MS: m/z 665.2 $(M+H)^+$.

Example 20

(R)-5-(4-(7-((5,6-difluoro-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 191)

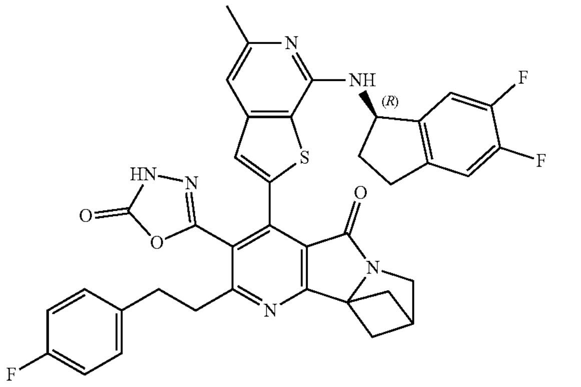

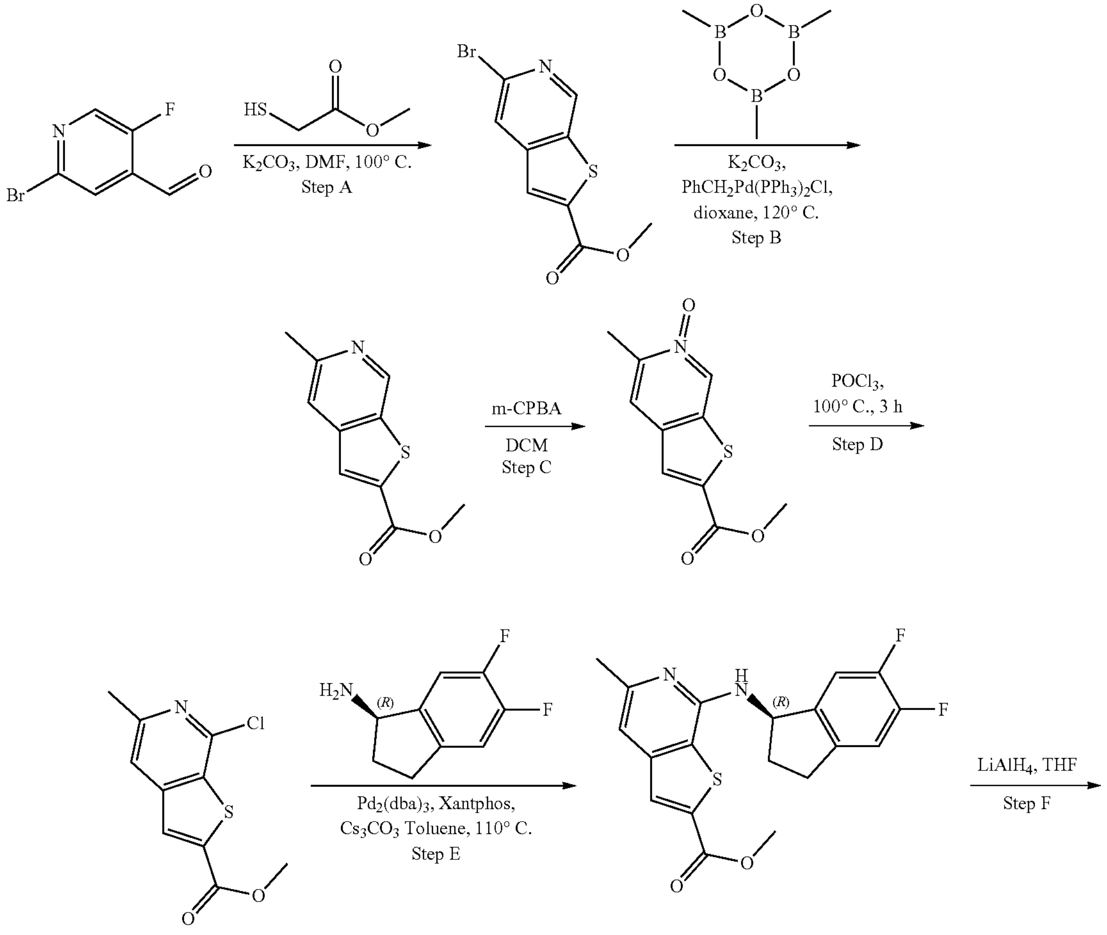

-continued

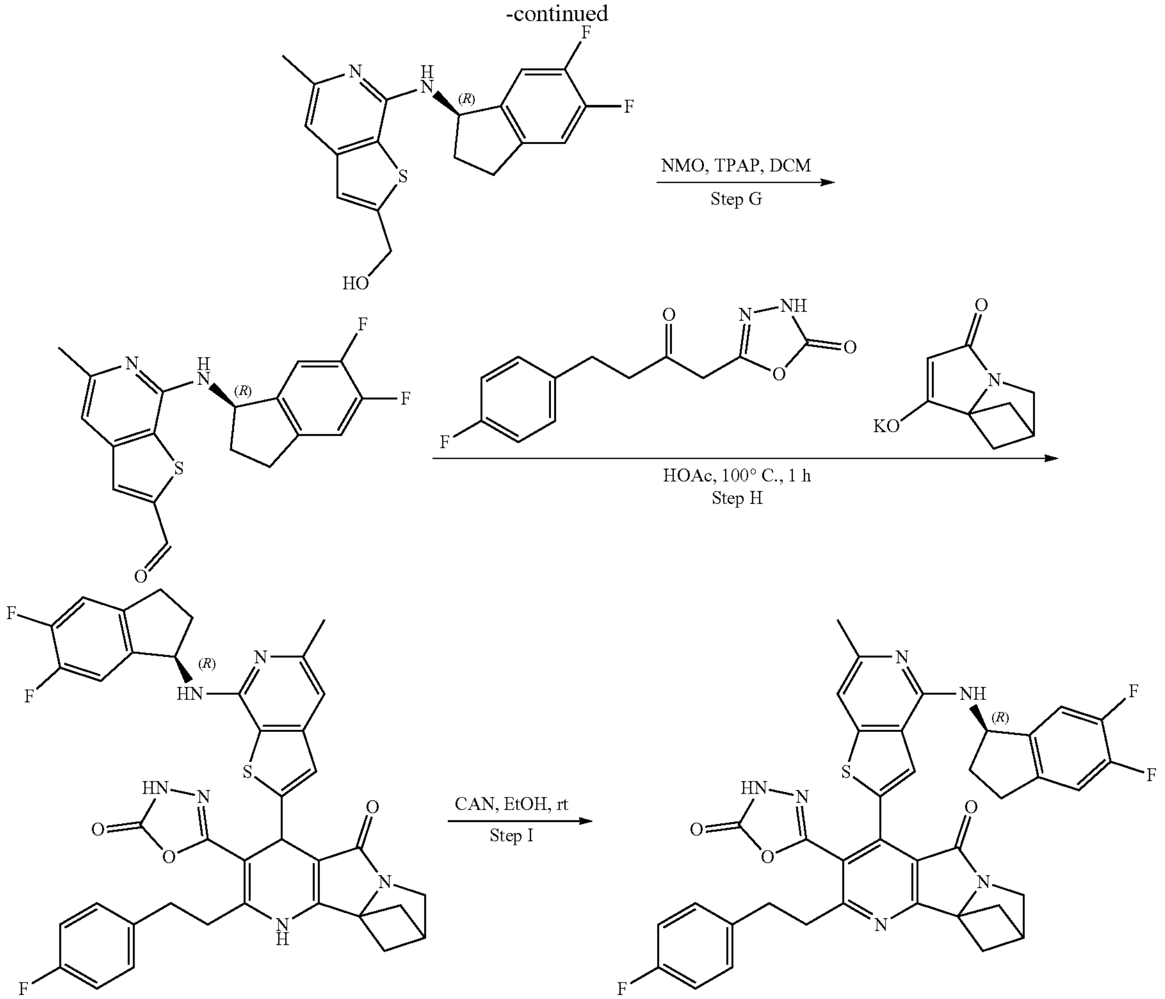

Step A: methyl 5-bromothieno[2,3-c]pyridine-2-carboxylate

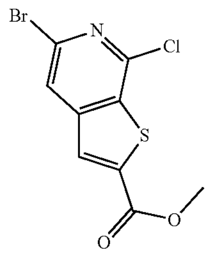

A mixture of 2-bromo-5-fluoroisonicotinaldehyde (10 g, 49.0 mmol), $K_2CO_3$ (20.3 g, 147 mmol) in DMF (100 mL) was stirred at room temperature for 30 minutes. Then, methyl 2-mercaptoacetate (10.4 g, 98.0 mmol) was added and the reaction was stirred at 100° C. for 2 hours. The reaction was poured into 1 L water, filtered and dried to give methyl 5-bromothieno[2,3-c]pyridine-2-carboxylate (10.8 g, 81.0%). LC-MS: m/z 271.9 $(M+H)^+$.

Step B: methyl 5-methylthieno[2,3-c]pyridine-2-carboxylate

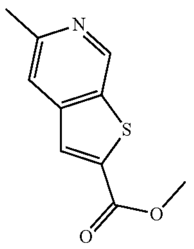

To a solution of 5-bromothieno[2,3-c]pyridine-2-carboxylate (5 g, 18.4 mmol) in dioxane (100 mL) was added 2,4,6-trimethyl-1,3,5,2,4,6-trioxatriborinane (23.1 g, 183 mmol), $K_2CO_3$ (7.62 g, 55.1 mmol), and Pd(dppf) $Cl_2 \cdot CH_2Cl_2$ (1.50 g, 1.84 mmol). The reaction was stirred at 90° C. for 18 hours under $N_2$. The reaction was concentrated in vacuo and purified by silica gel column chromatography eluting with 10% ethyl acetate in petroleum ether to afford methyl 5-methylthieno[2,3-c]pyridine-2-carboxylate (3.8 g, 99.8%). LC-MS: m/z 208.0 $(M+H)^+$.

Step C: 2-(methoxycarbonyl)-5-methylthieno[2,3-c] pyridine 6-oxide

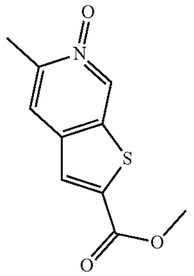

To a solution of methyl 5-methylthieno[2,3-c]pyridine-2-carboxylate (2 g, 9.65 mmol) in DCM (30 mL) was added m-CPBA (2.50 g, 14.48 mmol). The reaction was stirred at room temperature for 18 hours. The reaction was diluted with DCM (100 mL) and water (50 mL). The organic layer was separated, washed with further saturated NaCl solution (50 mL), and concentrated in vacuo. The residue was purified by silica gel column chromatography eluting with 1% methanol in dichloroform to afford 2-(methoxycarbonyl)-5-methylthieno[2,3-c]pyridine 6-oxide (4 g, impure). LC-MS: m/z 224.1 $(M+H)^+$.

Step D: methyl 7-chloro-5-methylthieno[2,3-c]pyridine-2-carboxylate

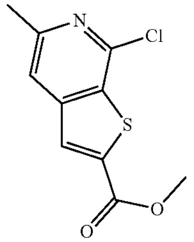

A solution of 2-(methoxycarbonyl)-5-methylthieno[2,3-c] pyridine 6-oxide (3.5 g, impure) in $POCl_3$ (30 mL) was stirred at 100° C. for 3 hours. The reaction was concentrated and diluted with DCM (50 mL), adjusted by saturated $Na_2CO_3$ solution (100 mL) to pH>7. The organic phase was separated, the aqueous phase was extracted with DCM (100 mL*2). The combined organic layer was washed with saturated NaCl solution (50 mL), and concentrated in vacuo. The residue was purified by silica gel column chromatography eluting with 6% ethyl acetate in petroleum ether to afford methyl 7-chloro-5-methylthieno[2,3-c]pyridine-2-carboxylate (1 g, 26.39%). LC-MS: m/z 242.0 $(M+H)^+$.

Step E: methyl (R)-7-((5,6-difluoro-2,3-dihydro-1H-inden-1-yl)amino)-5-methylthieno[2,3-c]pyridine-2-carboxylate

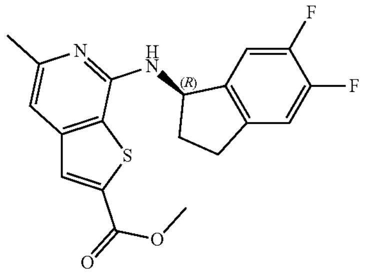

To a solution of methyl 7-chloro-5-methylthieno[2,3-c] pyridine-2-carboxylate (500 mg, 2.07 mmol) in Toluene (10 mL) was added (R)-5,6-difluoro-2,3-dihydro-1H-inden-1-amine (412 mg, 2.48 mmol), $Pd_2(dba)_3$ (167 mg, 0.207 mmol), and Xantphos (120 mg, 0.207 mmol), $Cs_2CO_3$ (2.02 g, 6.21 mmol). The mixture reaction was stirred at 110° C. for 18 hours under $N_2$. The mixture reaction was concentrated and purified by silica gel column chromatography eluting with 6% ethyl acetate in petroleum ether to afford methyl (R)-7-((5,6-difluoro-2,3-dihydro-1H-inden-1-yl) amino)-5-methylthieno[2,3-c]pyridine-2-carboxylate (400 mg, 51.6%). LC-MS: m/z 374.9 $(M+H)^+$.

Step F: (R)-(7-((5,6-difluoro-2,3-dihydro-1H-inden-1-yl)amino)-5-methylthieno[2,3-c]pyridin-2-yl) methanol

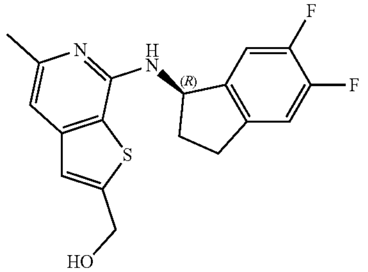

To a solution of methyl (R)-7-((5,6-difluoro-2,3-dihydro-1H-inden-1-yl)amino)-5-methylthieno[2,3-c]pyridine-2-carboxylate (350 mg, 0.935 mmol) in THF (5 mL) was added $LiAlH_4$ (107 mg, 2.80 mmol) slowly at 0° C. The reaction was stirred at room temperature for 10 minutes. The reaction was diluted with EA (10 mL) and water (20 mL). The organic layer was separated, washed with further saturated NaCl solution, and concentrated to afford (R)-(7-((5,6-difluoro-2,3-dihydro-1H-inden-1-yl)amino)-5-methylthieno[2,3-c]pyridin-2-yl)methanol (320 mg, crude). LC-MS: m/z 347.0 $(M+H)^+$.

Step G: (R)-7-((5,6-difluoro-2,3-dihydro-1H-inden-1-yl)amino)-5-methylthieno[2,3-c]pyridine-2-carbaldehyde

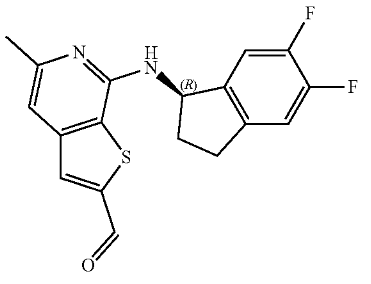

To a solution of (R)-(7-((5,6-difluoro-2,3-dihydro-1H-inden-1-yl)amino)-5-methylthieno[2,3-c]pyridin-2-yl) methanol (320 mg, 0.924 mmol) in DCM (5 mL) was added 4-Methylmorpholine N-oxide (230 mg, 1.96 mmol), Tetrapropylammonium Perruthenate (34 mg, 0.098 mmol). The reaction was stirred at room temperature for 3 hours. The reaction was diluted with EA (10 mL), washed with water (30 mL*3), then the organic phase was concentrated in vacuo. The residue was purified by silica gel column chromatography eluting with 5% ethyl acetate in petroleum ether to afford (R)-7-((5,6-difluoro-2,3-dihydro-1H-inden-1-yl)amino)-5-methylthieno[2,3-c]pyridine-2-carbaldehyde (310 mg, 97.44%). LC-MS: m/z 345.1 $(M+H)^+$.

Step H: 5-(4-(7-(((R)-5,6-difluoro-2,3-dihydro-1H-inden-1-yl)amino)-5-methylthieno[2,3-c]pyridin-2-yl)-2-(4-fluorophenethyl)-5-oxo-1,5,8,9-tetrahydro-4H,7H-8,9a-methanopyrido[2,3-a]pyrrolizin-3-yl)-1,3,4-oxadiazol-2(3H)-one

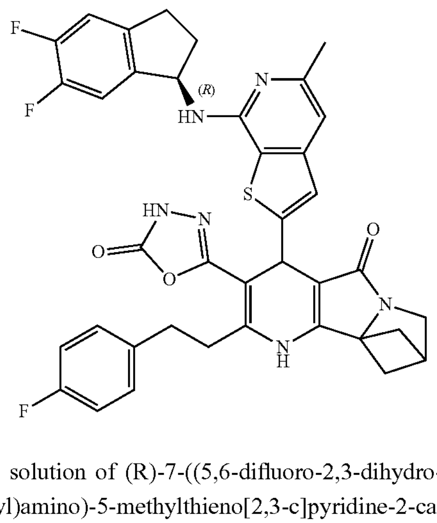

To a solution of (R)-7-((5,6-difluoro-2,3-dihydro-1H-inden-1-yl)amino)-5-methylthieno[2,3-c]pyridine-2-carbaldehyde (30 mg, 0.0872 mmol) in HOAc (1 mL) was added 5-(4-(4-fluorophenyl)-2-oxobutyl)-1,3,4-oxadiazol-2(3H)-one (22 mg, 0.0872 mmol), potassium 5-oxo-2,3-dihydro-1H,5H-2,7a-methanopyrrolizin-7-olate (20 mg, 0.105 mmol), and $NH_4OAc$ (13 mg, 0.174 mmol). The reaction was stirred at 100° C. for 1 hour. The reaction was concentrated in vacuo to afford 5-(4-(7-(((R)-5,6-difluoro-2,3-dihydro-1H-inden-1-yl)amino)-5-methylthieno[2,3-c]pyridin-2-yl)-2-(4-fluorophenethyl)-5-oxo-1,5,8,9-tetrahydro-4H,7H-8,9a-methanopyrido[2,3-a]pyrrolizin-3-yl)-1,3,4-oxadiazol-2(3H)-one (41 mg, crude). LC-MS: m/z 709.2 $(M+H)^+$.

Step I: (R)-5-(4-(7-((5,6-difluoro-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 191)

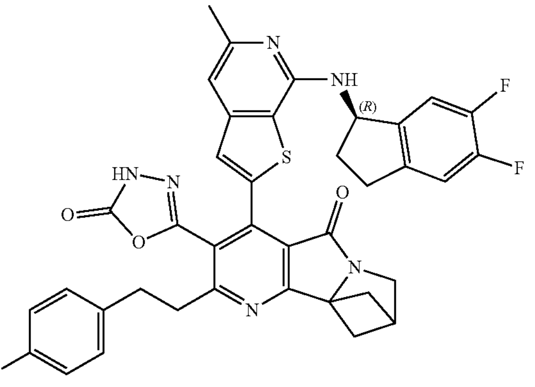

To a solution of 5-(4-(7-(((R)-5,6-difluoro-2,3-dihydro-1H-inden-1-yl)amino)-5-methylthieno[2,3-c]pyridin-2-yl)-2-(4-fluorophenethyl)-5-oxo-1,5,8,9-tetrahydro-4H,7H-8,9a-methanopyrido[2,3-a]pyrrolizin-3-yl)-1,3,4-oxadiazol-2(3H)-one (41 mg, crude) in EtOH (2 mL) were added ceric ammonium nitrate (63 mg, 0.116 mmol). The reaction was stirred at room temperature for 1 hour. The reaction was diluted with EA (10 mL) and water (20 mL). The organic layer was separated, washed with further saturated NaCl solution (10 mL), and concentrated in vacuo. The residue was purified by prep-HPLC to afford (R)-5-(4-(7-((5,6-difluoro-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (3.13 mg, 7.66%).

$^1$H NMR (400 MHz, DMSO-$d_6$): δ 7.30-7.35 (m, 2H), 7.17-7.25 (m, 4H), 7.07 (t, J=8.8 Hz, 2H), 6.94 (s, 1H), 5.79-5.85 (m, 1H), 3.56 (s, 2H), 3.15-3.22 (m, 3H), 2.97-3.07 (m, 3H), 2.79-2.88 (m, 1H), 2.61-2.68 (m, 2H), 2.55-2.57 (m, 1H), 2.41 (s, 3H), 2.03-2.14 (m, 1H), 1.74 (d, J=4.0 Hz, 2H). 19F NMR (377 MHz, DMSO-$d_6$): δ −117.03, −140.59, −141.547. LC-MS: m/z 707.3 $(M+H)^+$.

5-((S)-4-(7-(((R)-5-fluoro-4-methoxy-2,3-dihydro-1H-inden-1-yl)amino)-5-methylthieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 187)

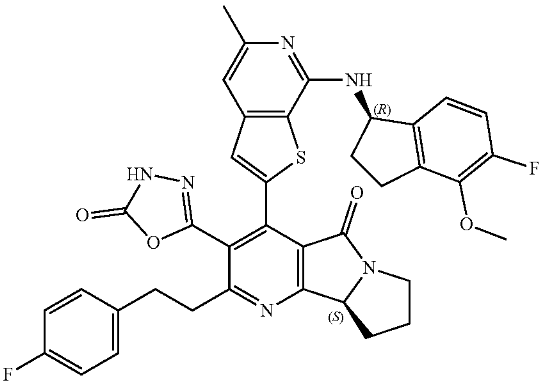

Compound 187 was synthesized using similar procedure as described in Example 20 above by using the appropriate materials.

$^1$H NMR (400 MHz, DMSO-$d_6$): δ 7.32 (s, 1H), 7.18-7.25 (m, 2H), 7.16 (d, J=8.4 Hz, 1H), 7.07 (t, J=8.8 Hz, 2H), 6.98-7.03 (m, 1H), 6.90-6.95 (m, 2H), 5.83-5.88 (m, 1H), 4.86 (dd, J=6.0 Hz, J=10.4 Hz, 1H), 3.87 (s, 3H), 3.50-3.59 (m, 2H), 3.16-3.19 (m, 2H), 2.97-3.10 (m, 4H), 2.81-2.89 (m, 2H), 2.40 (s, 3H), 2.27-2.31 (m, 2H), 2.00-2.12 (m, 1H), 1.37-1.47 (m, 1H). $^{19}$F NMR (377 MHz, DMSO-$d_6$): δ −117.04, −135.41. LC-MS: m/z 707.3 $(M+H)^+$.

Example 21

5-((S)-4-(5-(difluoromethyl)-7-(((R)-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 188)

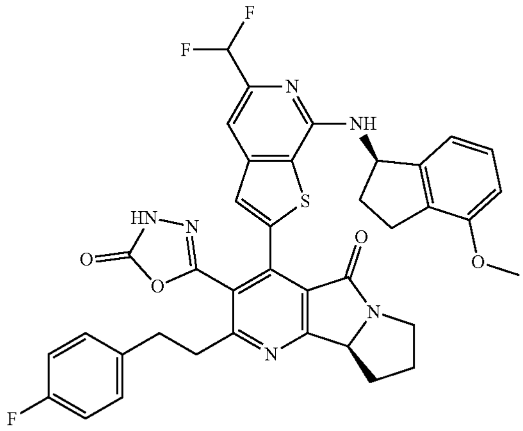 [SMILES: COc1cccc2c1CC[C@H]2Nc1nc(C(F)F)cc2cc(-c3c4c(nc(CCc5ccc(F)cc5)c3-c3n[nH]c(=O)o3)[C@@H]3CCCN3C4=O)sc12]

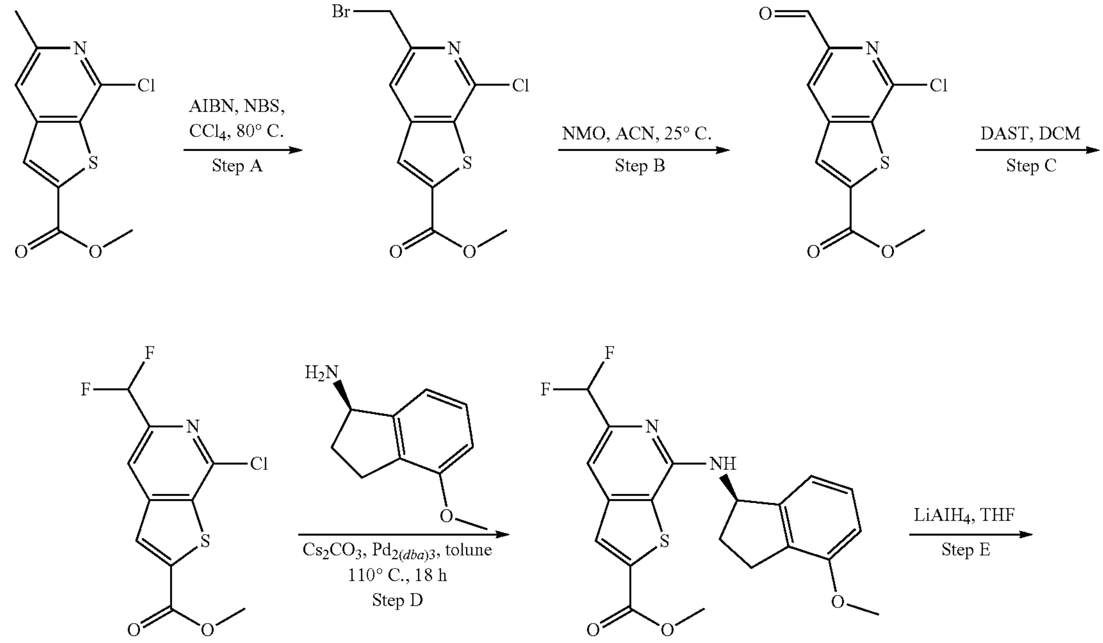

-continued
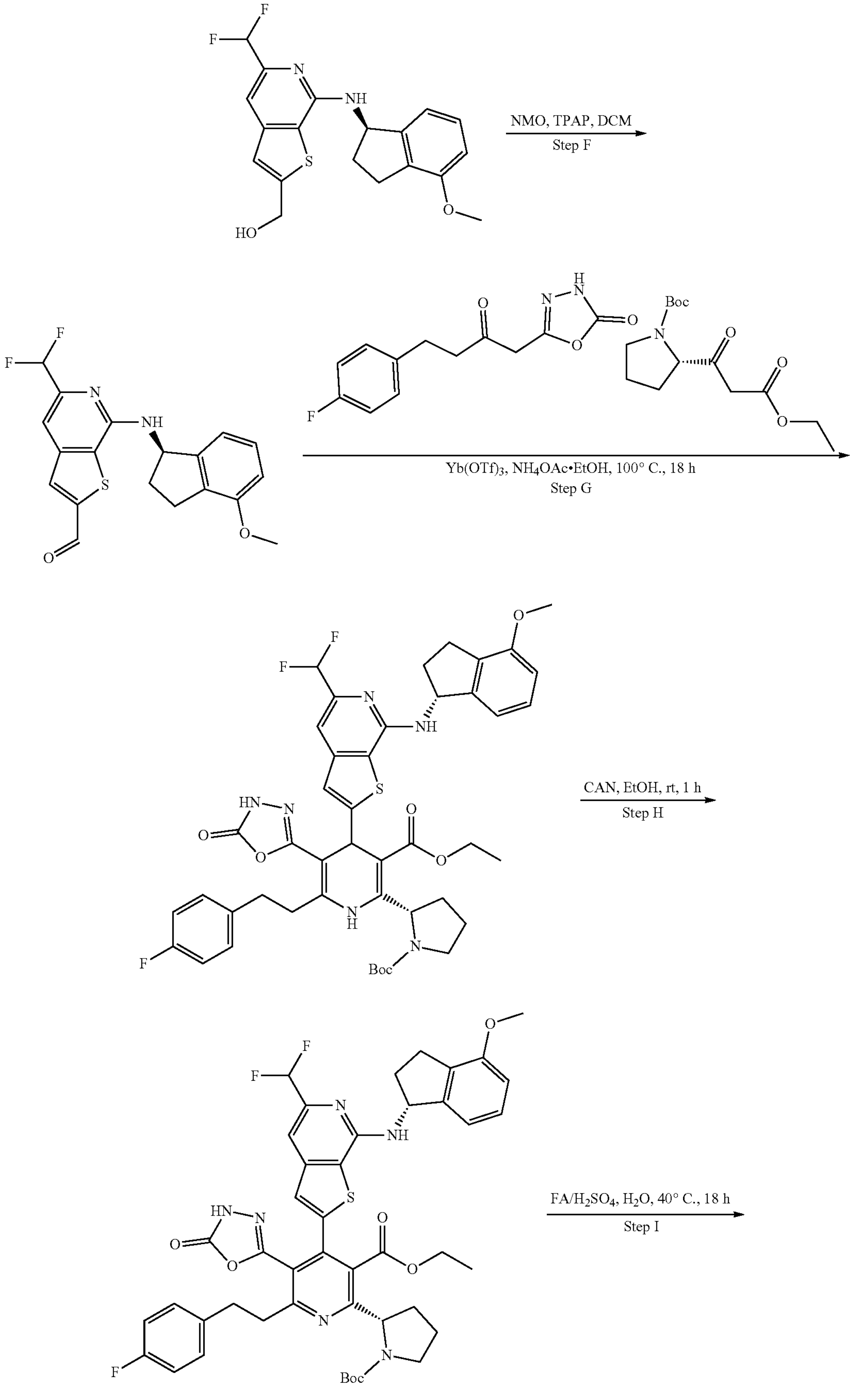

-continued

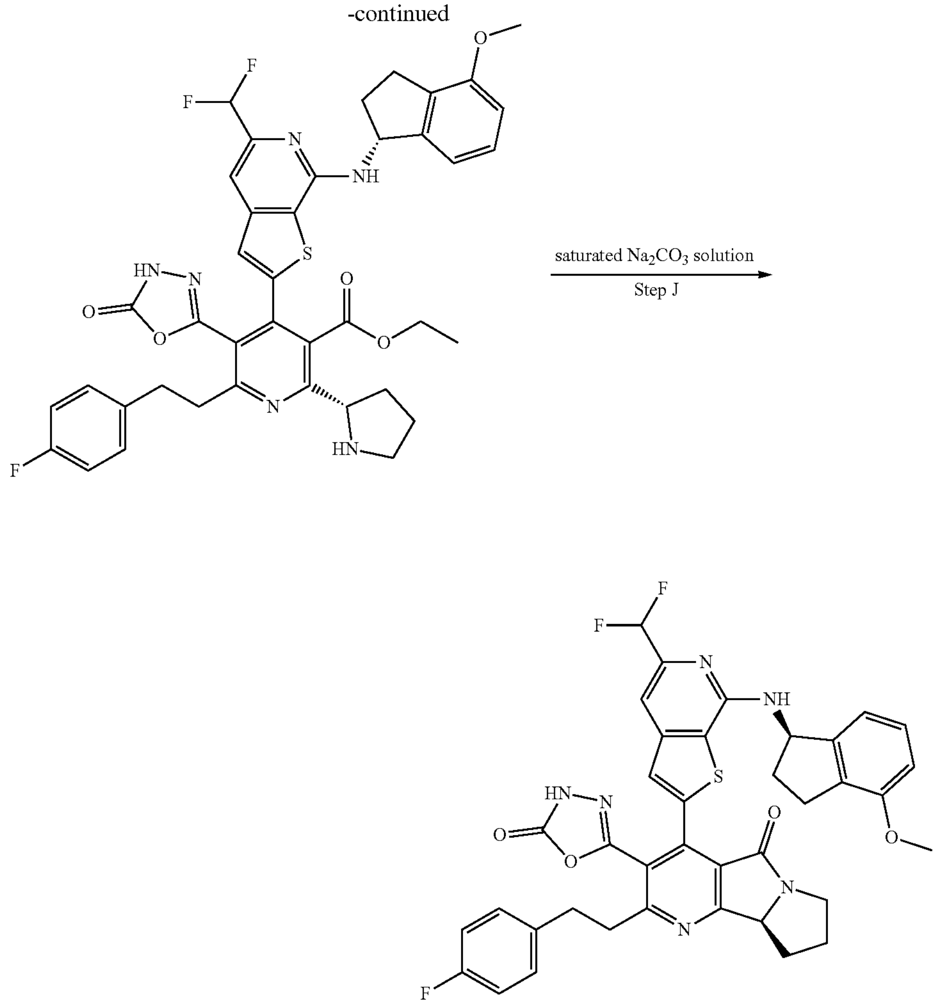

Step A: methyl 5-(bromomethyl)-7-chlorothieno[2,3-c]pyridine-2-carboxylate

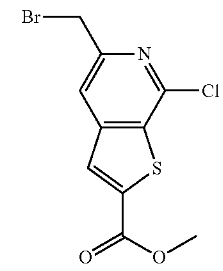 [SMILES: COC(=O)c1cc2cc(CBr)nc(Cl)c2s1]

To a solution of methyl 7-chloro-5-methylthieno[2,3-c]pyridine-2-carboxylate (500 mg, 2.07 mmol) in $CCl_4$ (5 mL) was added NBS (405 mg, 2.28 mmol), AIBN (68 mg, 0.414 mmol). The reaction was stirred at 80° C. for 18 hours. The reaction was diluted with DCM (50 mL), washed with further saturated NaCl solution (20 mL*2), dried over $Na_2SO_4$ and concentrated to afford methyl 5-(bromomethyl)-7-chlorothieno[2,3-c]pyridine-2-carboxylate (663 mg, crude). LC-MS: m/z 319.8 $(M+H)^+$.

Step B: methyl 7-chloro-5-formylthieno[2,3-c]pyridine-2-carboxylate

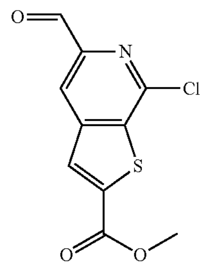 [SMILES: COC(=O)c1cc2cc(C=O)nc(Cl)c2s1]

To a solution of methyl 5-(bromomethyl)-7-chlorothieno[2,3-c]pyridine-2-carboxylate (663 mg, 2.07 mmol) in Acetonitrile (10 mL) was added 4-Methylmorpholine N-oxide (485 mg, 4.14 mmol). The reaction was stirred at 25° C. for 1 hour. The reaction was diluted with DCM (50 mL), washed with further saturated NaCl solution (20 mL*3) and concentrated in vacuo. The residue was purified by prep-TLC eluting with 10% ethyl acetate in petroleum ether to afford methyl 7-chloro-5-formylthieno[2,3-c]pyridine-2-carboxylate (240 mg, 45.4%). LC-MS: m/z 255.9 $(M+H)^+$.

Step C: methyl 7-chloro-5-(difluoromethyl)thieno[2,3-c]pyridine-2-carboxylate

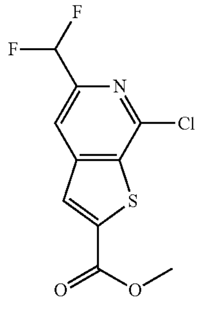 [SMILES: COC(=O)c1cc2cc(C(F)F)nc(Cl)c2s1]

To a solution of methyl 7-chloro-5-formylthieno[2,3-c]pyridine-2-carboxylate (240 mg, 0.939 mmol) in DCM (1 mL) were added DAST (1513 mg, 9.39 mmol), and the reaction was stirred at room temperature for 30 minutes. The reaction was diluted with DCM (30 mL), washed with further saturated NaCl solution (20 mL*3) and concentrated in vacuo. The residue was purified by silica gel column chromatography eluting with 8% ethyl acetate in petroleum ether to afford methyl 7-chloro-5-(difluoromethyl)thieno[2,3-c]pyridine-2-carboxylate (200 mg, 76.7%). LC-MS: m/z 278.0 $(M+H)^+$.

5-((S)-4-(5-(difluoromethyl)-7-(((R)-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 188)

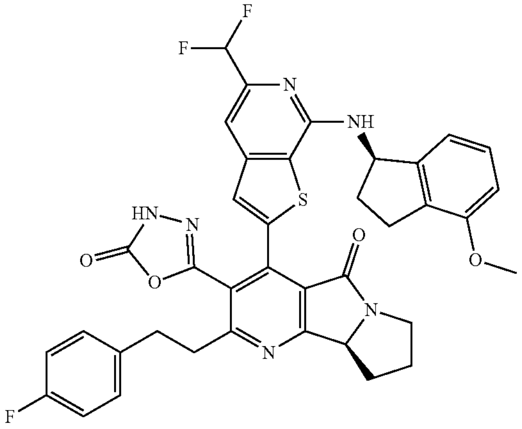 [SMILES: COc1cccc2c1CC[C@H]2Nc1nc(C(F)F)cc2cc(-c3c4c(nc(CCc5ccc(F)cc5)c3-c3n[nH]c(=O)o3)[C@@H]3CCCN3C4=O)sc12]

Compound 188 was synthesized using similar procedure as described in Example 20 above by using the appropriate materials.

$^1$H NMR (400 MHz, DMSO-$d_6$): δ 12.70 (br s, 1H), 7.65 (d, J=8.0 Hz, 1H), 7.53 (s, 1H), 7.38 (s, 1H), 7.22 (dd, J=5.6 Hz, J=8.8 Hz, 2H), 7.13 (t, J=8.0 Hz, 1H), 7.07 (t, J=8.8 Hz, 2H), 6.71-6.99 (m, 3H), 5.90 (q, J=8.0 Hz, 1H), 4.88 (dd, J=6.0 Hz, J=10.0 Hz, 1H), 3.79 (s, 3H), 3.51-3.59 (m, 1H), 3.20 (t, J=8.0 Hz, 2H), 2.95-3.10 (m, 3H), 2.67-2.77 (m, 2H), 2.54-2.56 (m, 1H), 2.24-2.38 (m, 3H), 1.99-2.08 (m, 1H), 1.39-1.49 (m, 1H). $^{19}$F NMR (377 MHz, DMSO-$d_6$): δ −114.68, −117.02. LC-MS: m/z 725.3 $(M+H)^+$.

(R)-5-(4-(7-((5-fluoro-4-methoxy-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 189)

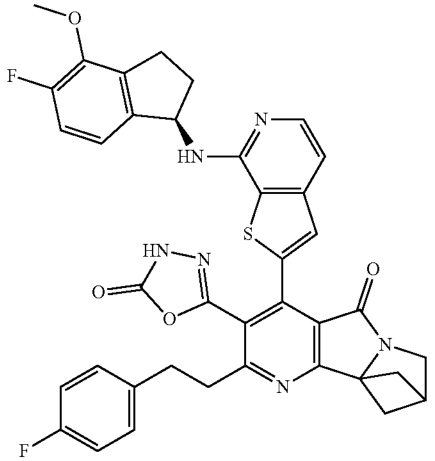

Compound 189 was synthesized using similar procedure as described in Example 17 above by using the appropriate materials.

$^1$H NMR (400 MHz, DMSO-$d_6$) δ 8.36 (br s, 1H), 7.96 (d, J=5.6 Hz, 1H), 7.37 (s, 1H), 7.17-7.25 (m, 3H), 7.04-7.12 (m, 3H), 6.90-7.02 (m, 2H), 5.80-5.90 (m, 1H), 3.87 (d, J=1.2 Hz, 3H), 3.55 (s, 2H), 3.12-3.21 (m, 3H), 2.96-3.07 (m, 3H), 2.78-2.90 (m, 1H), 2.60-2.65 (m, 2H), 2.53-2.56 (m, 1H), 2.02-2.15 (m, 1H), 1.70-1.76 (m, 2H). $^{19}$F NMR (377 MHz, DMSO-$d_6$): −117.11, −135.40. LC-MS: m/z 705.3 $(M+H)^+$.

(R)-5-(4-(7-((5,6-difluoro-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 190)

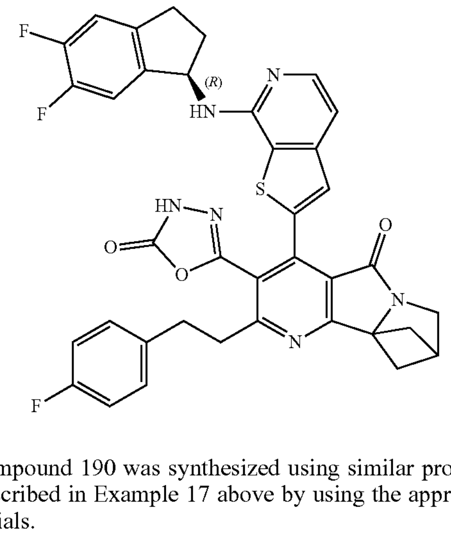

Compound 190 was synthesized using similar procedure as described in Example 17 above by using the appropriate materials.

$^1$H NMR (400 MHz, DMSO-$d_6$): δ 12.71 (br s, 1H), 8.00 (d, J=5.2 Hz, 1H), 7.43 (s, 1H), 7.30-7.36 (m, 2H), 7.19-7.25 (m, 3H), 7.05-7.11 (m, 3H), 5.81 (q, J=7.6 Hz, 1H), 3.56 (s, 2H), 3.18-3.22 (m, 3H), 2.95-3.06 (m, 3H), 2.79-2.88 (m, 1H), 2.63-2.67 (m, 2H), 2.54-2.58 (m, 1H), 2.02-2.12 (m, 1H), 1.75 (d, J=4.0 Hz, 2H). $^{19}$F NMR (377 MHz, DMSO-$d_6$): −117.01, −140.53-141.58. LC-MS: m/z 693.1 $(M+H)^+$.

5-((S)-4-(7-(((R)-5,6-difluoro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 192)

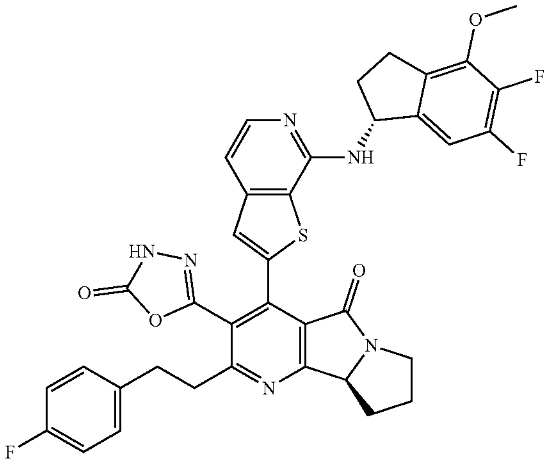 [SMILES: COc1c(F)c(F)cc2c1CC[C@H]2Nc1nccc2cc(-c3c4c(nc(CCc5ccc(F)cc5)c3-c3n[nH]c(=O)o3)[C@@H]3CCCN3C4=O)sc12]

Compound 192 was synthesized using similar procedure as described in Example 10 above by using the appropriate materials.

$^1$H NMR (400 MHz, DMSO-$d_6$) δ ppm 8.00 (d, J=5.48 Hz, 1H), 7.43-7.47 (m, 1H), 7.31-7.35 (m, 1H), 7.19-7.25 (m, 2H), 7.04-7.15 (m, 3H), 6.91-6.97 (m, 1H), 5.76-5.86 (m, 1H), 4.89 (dd, J=10.19, 6.26 Hz, 1H), 3.96 (d, J=1.43 Hz, 3H), 3.48-3.61 (m, 1H), 3.30 (br s, 2H), 3.17-3.24 (m, 2H), 2.98-3.12 (m, 3H), 2.80-2.89 (m, 1H), 2.25-2.39 (m, 3H), 2.02-2.09 (m, 1H), 1.39-1.50 (m, 1H). $^{19}$F NMR (376 MHz, DMSO-$d_6$) δ ppm −117.01 (s, 1 F), −140.71--136.40 (s, 1 F), −160.23--156.59 (s, 1 F). LC-MS: m/z 711.1 $(M+H)^+$.

(R)-5-(4-(7-((5-fluoro-4-methoxy-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 193)

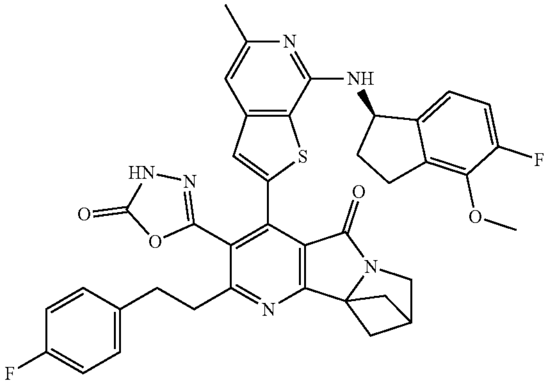 [SMILES: COc1c(F)ccc2c1CC[C@H]2Nc1nc(C)cc2cc(-c3c4c(nc(CCc5ccc(F)cc5)c3-c3n[nH]c(=O)o3)C35CC(CN3C4=O)C5)sc12]

Compound 193 was synthesized using similar procedure as described in Example 20 above by using the appropriate materials.

$^1$H NMR (400 MHz, DMSO-$d_6$): δ 12.70 (br s, 1H), 7.32 (s, 1H), 7.20-7.23 (m, 2H), 7.15 (d, J=8.4 Hz, 1H), 7.05-7.09 (m, 2H), 6.96-7.03 (m, 1H), 6.90-6.93 (m, 2H), 5.86 (q, J=8.0 Hz, 1H), 3.87 (d, J=1.2 Hz, 3H), 3.56 (s, 2H), 3.16-3.21 (m, 3H), 2.96-3.07 (m, 3H), 2.78-2.90 (m, 1H), 2.60-2.67 (m, 2H), 2.53-2.56 (m, 1H), 2.34 (s, 3H), 2.00-2.14 (m, 1H), 1.75 (d, J=4.4 Hz, 2H). $^{19}$F NMR (377 MHz, DMSO-$d_6$): δ −117.01, −135.42. LC-MS: m/z 719.3 $(M+H)^+$.

Example 22

5-((S)-4-(7-(((S)-2,2-difluoro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 194)

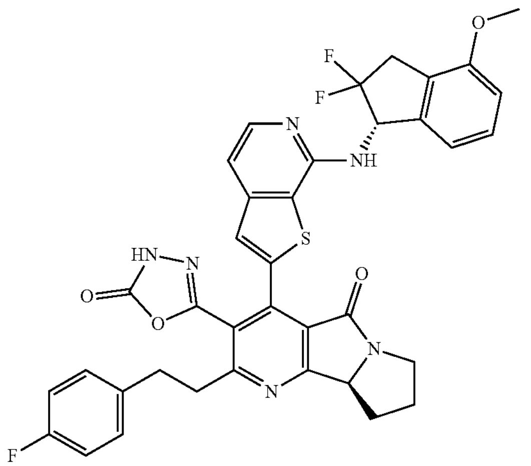

-continued
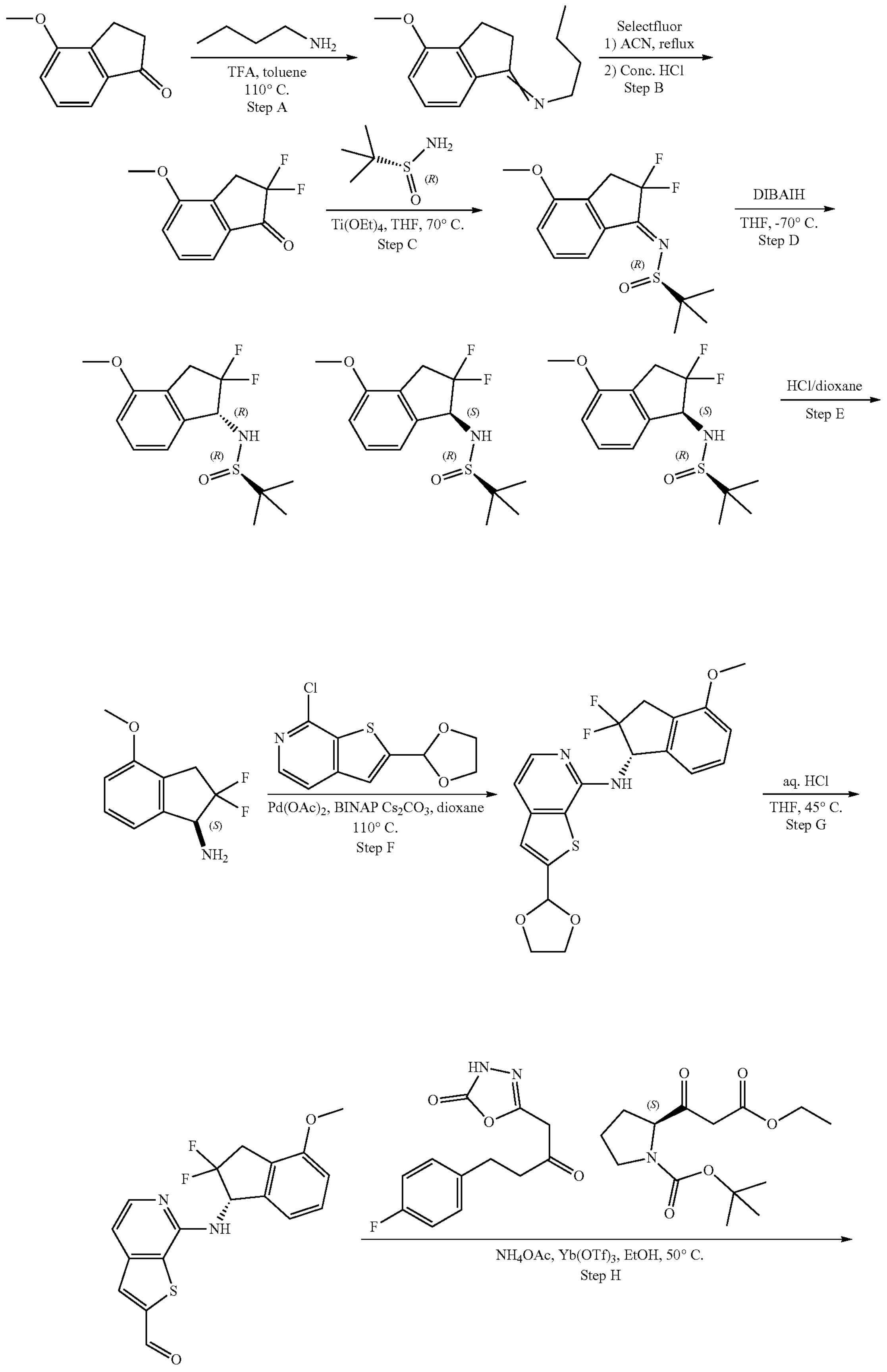

-continued
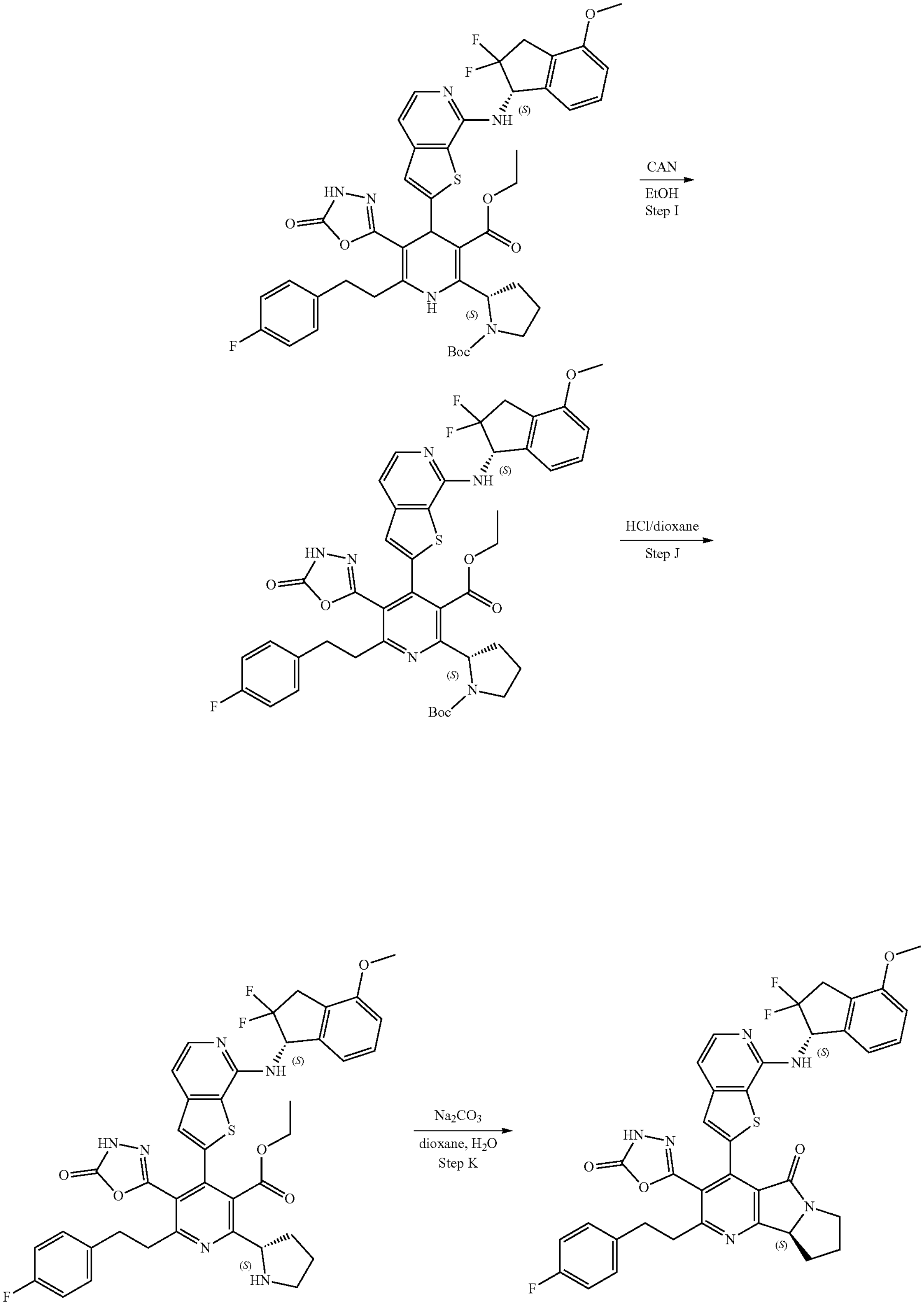

Step A N-(4-methoxy-2,3-dihydro-1H-inden-1-ylidene)butan-1-amine

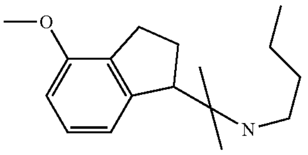 [SMILES: CCCCNC(C)(C)C1CCc2c(OC)cccc21]

The solution of 4-methoxy-2,3-dihydro-1H-inden-1-one (5 g, 30.83 mmol), butan-1-amine (2.71 g, 36.99 mmol) and TFA (703.04 mg, 6.17 mmol) in toluene (60 mL) was refluxed at 110° C. for 16 hrs. The reaction mixture was concentrated to remove the solvent, and to the residue was added ethyl acetate (100 mL). The resulting mixture was washed with saturated aqueous sodium bicarbonate (30 mL). The organic layer was dried over $Na_2SO_4$ and concentrated to give N-(4-methoxy-2,3-dihydro-1H-inden-1-ylidene)butan-1-amine (6.7 g, crude). LC-MS: m/z 218.1 $(M+H)^+$.

Step B 2,2-difluoro-4-methoxy-2,3-dihydro-1H-inden-1-one

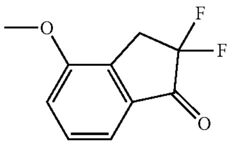

N-(4-methoxy-2,3-dihydro-1H-inden-1-ylidene)butan-1-amine (6.7 g, 30.83 mmol) was dissolved in acetonitrile (100 mL). Then to the solution was added 1-(chloromethyl)-4-fluoro-1,4-diazoniabicyclo[2.2.2]octane ditetrafluoroborate (21.85 g, 61.66 mmol). The solution was refluxed at 80° C. for 16 hrs. The reaction solution was cooled to rt, and con. HCl (18.74 g, 184.99 mmol, 36% purity) wad added dropwise slowly. The resulting mixture was stirred for 10 min. Then ethyl acetate (100 mL) was added. The mixture was washed with water (50 mL×2). The organic layer was dried over anhydrous sodium sulfate and concentrated. The residue was purified by column chromatography ($SiO_2$, petroleum ether/ethyl acetate=1/0 to 5/1) to give 2,2-difluoro-4-methoxy-2,3-dihydro-1H-inden-1-one (1.58 g, 7.97 mmol, 25.86% yield). $^1H$ NMR (400 MHz, $CDCl_3$) δ 7.41-7.54 (m, 2H), 7.15-7.23 (m, 1H), 3.94 (s, 3H), 3.41-3.55 (m, 2H).

Step C (R,E)-N-(2,2-difluoro-4-methoxy-2,3-dihydro-1H-inden-1-ylidene)-2-methylpropane-2-sulfinamide

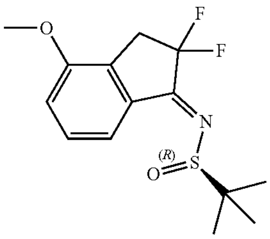

tetraethoxytitanium (4.83 g, 21.19 mmol) was added to a mixture of 2,2-difluoro-4-methoxy-2,3-dihydro-1H-inden-1-one (1.4 g, 7.06 mmol) and (R)-2-methylpropane-2-sulfinamide (899.07 mg, 7.42 mmol) in THF (20 mL). The mixture was stirred for 16 hrs at 70° C. Ethyl acetate (25 mL) and water (5 mL) were added to the mixture, and the formed precipitate was removed by filtration. The filtrate was concentrated in vacuo to give a residue. The residue was purified by column chromatography ($SiO_2$, petroleum ether/ethyl acetate=1/0 to 0/1) to give (R,E)-N-(2,2-difluoro-4-methoxy-2,3-dihydro-1H-inden-1-ylidene)-2-methylpropane-2-sulfinamide (1.8 g, 76.28% yield, 90.22% purity). LC-MS: m/z 301.9 $(M+H)^+$.

Step D (R)—N—((S)-2,2-difluoro-4-methoxy-2,3-dihydro-1H-inden-1-yl)-2-methylpropane-2-sulfinamide and (R)—N—((R)-2,2-difluoro-4-methoxy-2,3-dihydro-1H-inden-1-yl)-2-methylpropane-2-sulfinamide

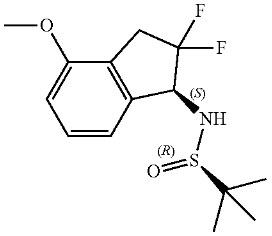

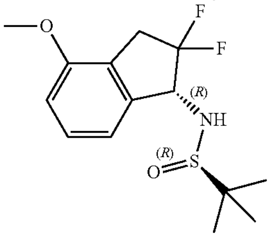

To a solution of (R,E)-N-(2,2-difluoro-4-methoxy-2,3-dihydro-1H-inden-1-ylidene)-2-methylpropane-2-sulfinamide (1.8 g, 5.97 mmol) in DCM (40 mL) was added dropwise DIBAL-H (1.5 M, 7.96 mL) at −70° C. After addition, the mixture was stirred at this temperature for 2 hrs. The reaction mixture was quenched by addition (MeOH 10 mL) at 0° C., and then diluted with $H_2O$ (10 mL) and extracted with DCM (20 mL×2). The combined organic layers were washed with brine (10 mL), dried over $Na_2SO_4$, filtered and concentrated under reduced pressure to give a residue. The residue was purified by column chromatography ($SiO_2$, petroleum ether/ethyl acetate=1/0 to 1/1) to give (R)—N—((S)-2,2-difluoro-4-methoxy-2,3-dihydro-1H-inden-1-yl)-2-methylpropane-2-sulfinamide (470 mg, 24.49% yield, 94.43% purity) and (R)—N—((R)-2,2-difluoro-4-methoxy-2,3-dihydro-1H-inden-1-yl)-2-methylpropane-2-sulfinamide (680 mg, 37.07% yield, 98.78% purity).

$^1H$ NMR (400 MHz, $CDCl_3$) δ 7.20-7.25 (m, 1H), 6.89-6.94 (m, 1H), 6.72-6.78 (m, 1H), 4.82-4.93 (m, 1H), 3.82-3.88 (m, 1H), 3.77 (s, 3H), 3.30-3.43 (m, 1H), 3.11-3.27 (m, 1H), 1.22-1.26 (m, 9H). LC-MS: m/z 304.0 $(M+H)^+$.

$^1H$ NMR (400 MHz, $CDCl_3$) δ 7.30-7.36 (m, 1H), 7.24-7.28 (m, 1H), 6.80-6.88 (m, 1H), 4.94-5.05 (m, 1H), 3.83-3.88 (m, 3H), 3.63-3.70 (m, 1H), 3.37-3.50 (m, 1H), 3.18-3.32 (m, 1H), 1.32 (s, 9H). LC-MS: m/z 304.0 $(M+H)^+$.

Step E (S)-2,2-difluoro-4-methoxy-2,3-dihydro-1H-inden-1-amine

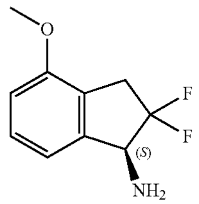

A mixture of (R)—N—((S)-2,2-difluoro-4-methoxy-2,3-dihydro-1H-inden-1-yl)-2-methylpropane-2-sulfinamide (470.00 mg, 1.55 mmol) and HCl/MeOH (2 M, 3.87 mL) in MeOH (3 mL) was degassed and purged with $N_2$ for 3 times, and then the mixture was stirred at 20° C. for 2 hr under $N_2$ atmosphere. The reaction mixture was concentrated under reduced pressure to give a residue. The resulting product was dissolved in petroleum ether/ethyl acetate=3/1 (10 mL) and filtered to give (S)-2,2-difluoro-4-methoxy-2,3-dihydro-1H-inden-1-amine (310 mg, crude, HCl). $^1$H NMR (400 MHz, MeOD-$d_4$) δ 7.41-7.51 (m, 1H), 7.06-7.18 (m, 2H), 5.04-5.15 (m, 1H), 3.90 (s, 3H), 3.45-3.62 (m, 2H).

Step F (S)—N-(2,2-difluoro-4-methoxy-2,3-dihydro-1H-inden-1-yl)-2-(1,3-dioxolan-2-yl)thieno[2,3-c]pyridin-7-amine

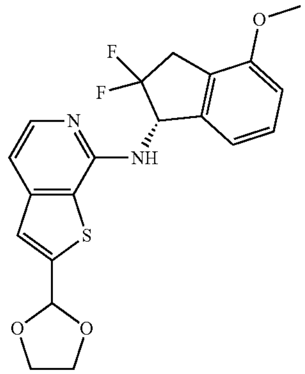 [SMILES: COc1cccc2c1CC(F)(F)[C@H]2Nc1nccc2cc(C3OCCO3)sc12]

A mixture of 7-chloro-2-(1,3-dioxolan-2-yl)thieno[2,3-c]pyridine (200.00 mg, 827.49 μmol), (S)-2,2-difluoro-4-methoxy-2,3-dihydro-1H-inden-1-amine (195.01 mg, 827.49 μmol, HCl salt), $Cs_2CO_3$ (808.84 mg, 2.48 mmol), $Pd(OAc)_2$ (18.58 mg, 82.75 μmol) and BINAP (103.05 mg, 165.50 μmol) in dioxane (5 mL) was degassed and purged with $N_2$ for 3 times, and then the mixture was stirred at 110° C. for 16 hrs under $N_2$ atmosphere. The reaction mixture was filtered and concentrated under reduced pressure to give a residue. The residue was purified by column chromatography ($SiO_2$, petroleum ether/ethyl acetate=1/0 to 1/1) to give (S)—N-(2,2-difluoro-4-methoxy-2,3-dihydro-1H-inden-1-yl)-2-(1,3-dioxolan-2-yl)thieno[2,3-c]pyridin-7-amine (220 mg, 60.58% yield, 92.15% purity). LC-MS: m/z 405.2 $(M+H)^+$.

Step G (S)-7-((2,2-difluoro-4-methoxy-2,3-dihydro-1H-inden-1-yl)amino)thieno[2,3-c]pyridine-2-carbaldehyde

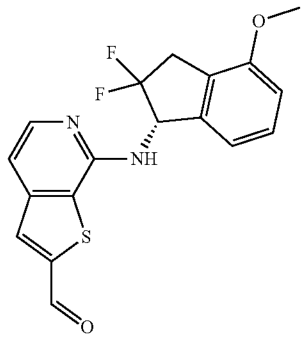 [SMILES: COc1cccc2c1CC(F)(F)[C@H]2Nc1nccc2cc(C=O)sc12]

A mixture of(S)—N-(2,2-difluoro-4-methoxy-2,3-dihydro-1H-inden-1-yl)-2-(1,3-dioxolan-2-yl)thieno[2,3-c]pyridin-7-amine (220.00 mg, 543.98 μmol) and HCl (2 M, 2.72 mL) in THF (2 mL) was degassed and purged with $N_2$ for 3 times, and then the mixture was stirred at 45° C. for 16 hrs under $N_2$ atmosphere. The reaction mixture was filtered and quenched by addition aq. $NaHCO_3$ (10 mL) at 0° C., and then diluted with ethyl acetate (10 mL) and extracted with ethyl acetate (10 mL×3). The combined organic layers were washed with brine (10 mL), dried over $Na_2SO_4$, filtered and concentrated under reduced pressure to give (S)-7-((2,2-difluoro-4-methoxy-2,3-dihydro-1H-inden-1-yl)amino)thieno[2,3-c]pyridine-2-carbaldehyde (190 mg, 527.23 μmol).

$^1$H NMR (400 MHz, $CDCl_3$) δ 10.05-10.13 (s, 1H), 8.06-8.14 (d, J=5.6 Hz, 1H), 7.93 (s, 1H), 7.16-7.19 (m, 1H), 6.82-6.88 (m, 1H), 6.73-6.78 (m, 1H), 6.27-6.40 (m, 1H), 4.8p-4.91 (d, J=9.6 Hz, 1H), 3.79 (s, 3H), 3.76-3.77 (m, 1H), 3.22-3.47 (m, 2H).

Step H ethyl 2-((S)-1-(tert-butoxycarbonyl)pyrrolidin-2-yl)-4-(7-(((S)-2,2-difluoro-4-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-1,4-dihydropyridine-3-carboxylate

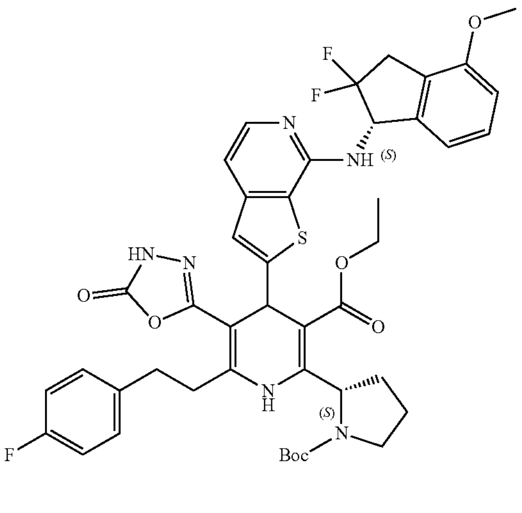

A mixture of tert-butyl (S)-2-(3-ethoxy-3-oxopropanoyl)pyrrolidine-1-carboxylate (45 mg, 157.71 μmol), 5-(4-(4-fluorophenyl)-2-oxobutyl)-1,3,4-oxadiazol-2(3H)-one (39.46 mg, 157.71 μmol), (S)-7-((2,2-difluoro-4-methoxy-2,3-dihydro-1H-inden-1-yl)amino)thieno[2,3-c]pyridine-2-carbaldehyde (56.83 mg, 157.71 μmol), $NH_4OAc$ (24.31 mg, 315.42 μmol) and $Yb(oTf)_3$ (9.78 mg, 15.77 μmol) in EtOH (2 mL) was degassed and purged with $N_2$ for 3 times, and then the mixture was stirred at 50° C. for 16 hr under $N_2$ atmosphere. The reaction mixture was concentrated under reduced pressure to give ethyl 2-((S)-1-(tert-butoxycarbonyl)pyrrolidin-2-yl)-4-(7-(((S)-2,2-difluoro-4-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-1,4-dihydropyridine-3-carboxylate (140 mg, crude). LC-MS: m/z 859.2 $(M+H)^+$.

Step J ethyl 2-((S)-1-(tert-butoxycarbonyl)pyrrolidin-2-yl)-4-(7-(((S)-2,2-difluoro-4-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)nicotinate

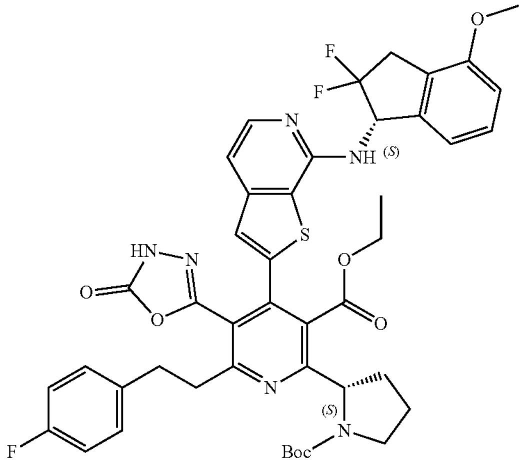

A mixture of ethyl 2-((S)-1-(tert-butoxycarbonyl)pyrrolidin-2-yl)-4-(7-(((S)-2,2-difluoro-4-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-1,4-dihydropyridine-3-carboxylate (140.00 mg, 162.99 μmol) and CAN (178.71 mg, 325.99 μmol) in EtOH (4 mL) was degassed and purged with $N_2$ for 3 times, and then the mixture was stirred at 20° C. for 1 hr under $N_2$ atmosphere. The reaction mixture was diluted with ethyl acetate (20 mL) and washed with brine (5 mL×2), dried over $Na_2SO_4$, filtered and concentrated under reduced pressure to give ethyl 2-((S)-1-(tert-butoxycarbonyl)pyrrolidin-2-yl)-4-(7-(((S)-2,2-difluoro-4-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)nicotinate (150 mg, crude). LC-MS: m/z 857.3 $(M+H)^+$.

Step J ethyl 4-(7-(((S)-2,2-difluoro-4-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-2-((S)-pyrrolidin-2-yl)nicotinate

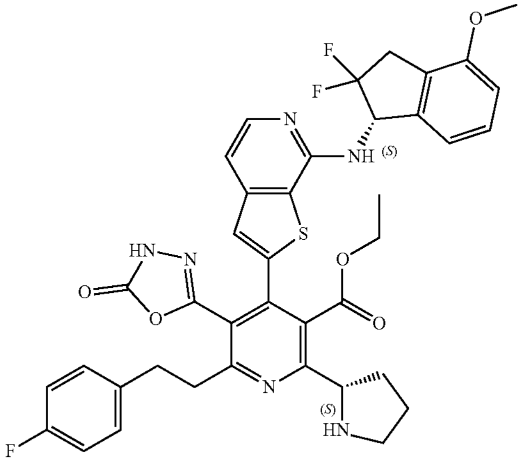

A mixture of ethyl 2-((S)-1-(tert-butoxycarbonyl)pyrrolidin-2-yl)-4-(7-(((S)-2,2-difluoro-4-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)nicotinate (150.00 mg, 175.05 μmol) and HCl/dioxane (2 M, 1.75 mL) in dioxane (2 mL) was degassed and purged with $N_2$ for 3 times, and then the mixture was stirred at 20° C. for 2 hrs under $N_2$ atmosphere. The reaction mixture was concentrated under reduced pressure to give ethyl 4-(7-(((S)-2,2-difluoro-4-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-2-((S)-pyrrolidin-2-yl)nicotinate (150 mg, crude). LC-MS: m/z 757.3 $(M+H)^+$.

Step K 5-((S)-4-(7-(((S)-2,2-difluoro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one

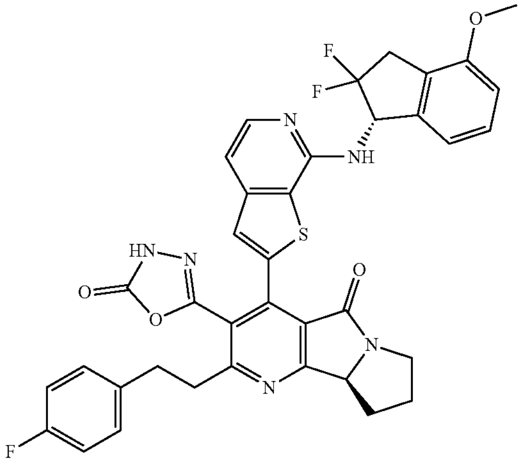 [SMILES: COc1cccc2c1CC(F)(F)[C@H]2Nc1nccc2cc(-c3c4c(nc(CCc5ccc(F)cc5)c3-c3n[nH]c(=O)o3)[C@@H]3CCCN3C4=O)sc12]

A mixture of ethyl 4-(7-(((S)-2,2-difluoro-4-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-2-((S)-pyrrolidin-2-yl)nicotinate (150 mg, 189.09 μmol, HCl salt) and $Na_2CO_3$ (400.84 mg, 3.78 mmol) in dioxane (4 mL) and $H_2O$ (4 mL) was degassed and purged with $N_2$ for 3 times. Then the mixture was stirred at 20° C. for 16 hrs under $N_2$ atmosphere. The reaction mixture was extracted with ethyl acetate (10 mL×3). The combined organic layers were washed with brine (10 mL), dried over $Na_2SO_4$, filtered and concentrated under reduced pressure to give a residue. The residue was purified by prep-HPLC (column: C18 150×30 mm; mobile phase: [water(FA)-ACN]; gradient: 45%-75% B over 7 min) to give 5-((S)-4-(7-(((S)-2,2-difluoro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (7.61 mg, 5.30% yield, 93.64% purity).

$^1$H NMR (400 MHz, MeOD-$d_4$) δ 7.96-8.04 (d, J=14 Hz, 1H), 7.46 (s, 1H), 7.26-7.33 (m, 1H), 7.14-7.21 (m, 3H), 6.90-7.02 (m, 4H), 6.26 (t, J=11.32 Hz, 1H), 3.88 (s, 3H), 3.69 (dt, J=11.44, 8.46 Hz, 1H), 3.36-3.52 (m, 3H), 3.21-3.30 (m, 2H), 3.03-3.19 (m, 2H), 2.37-2.57 (m, 3H), 1.45-1.50 (m, 1H). $^{19}$F NMR (376 MHz, MeOD-$d_4$) δ −103.35-101.50 (m, 1 F) −110.55--109.05 (m, 1 F) −119.03 (s, 1 F). LC-MS: m/z 711.1 $(M+H)^+$.

Example 23

(R)-5-(4-(7-((5,6-difluoro-4-methoxy-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (195)

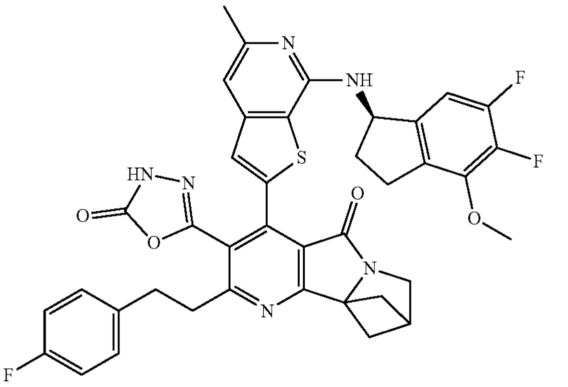

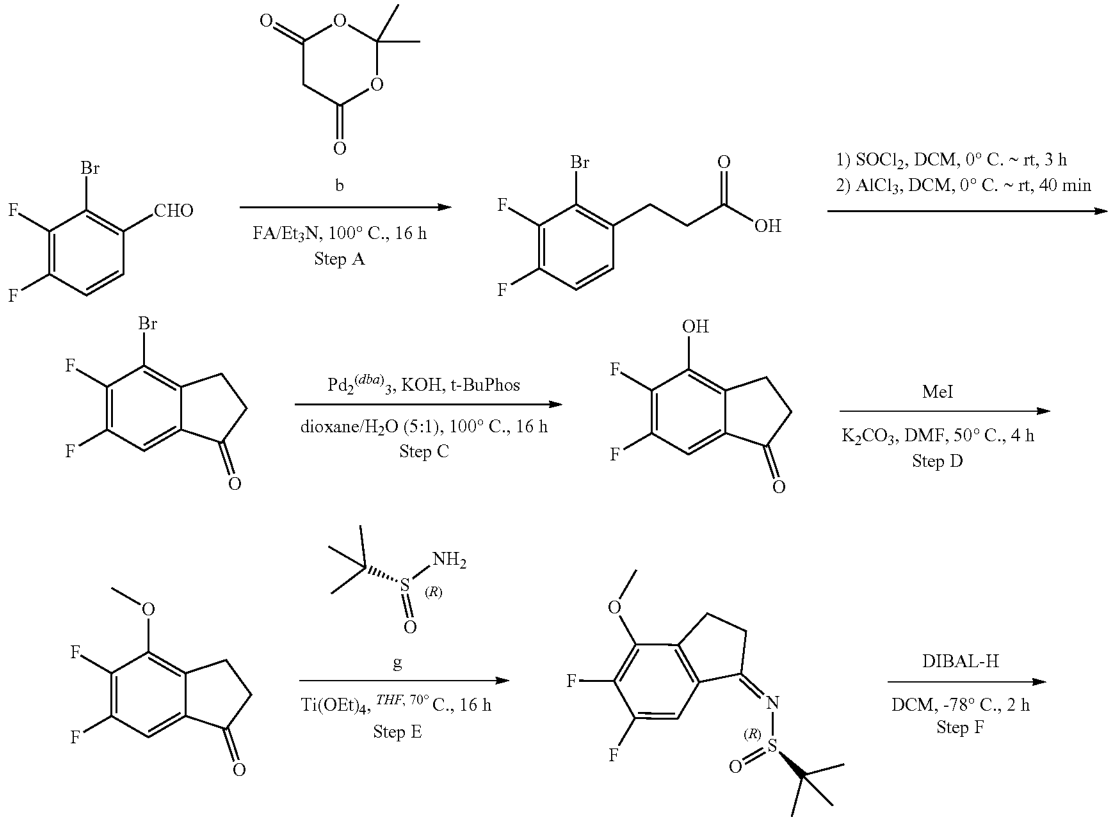

-continued
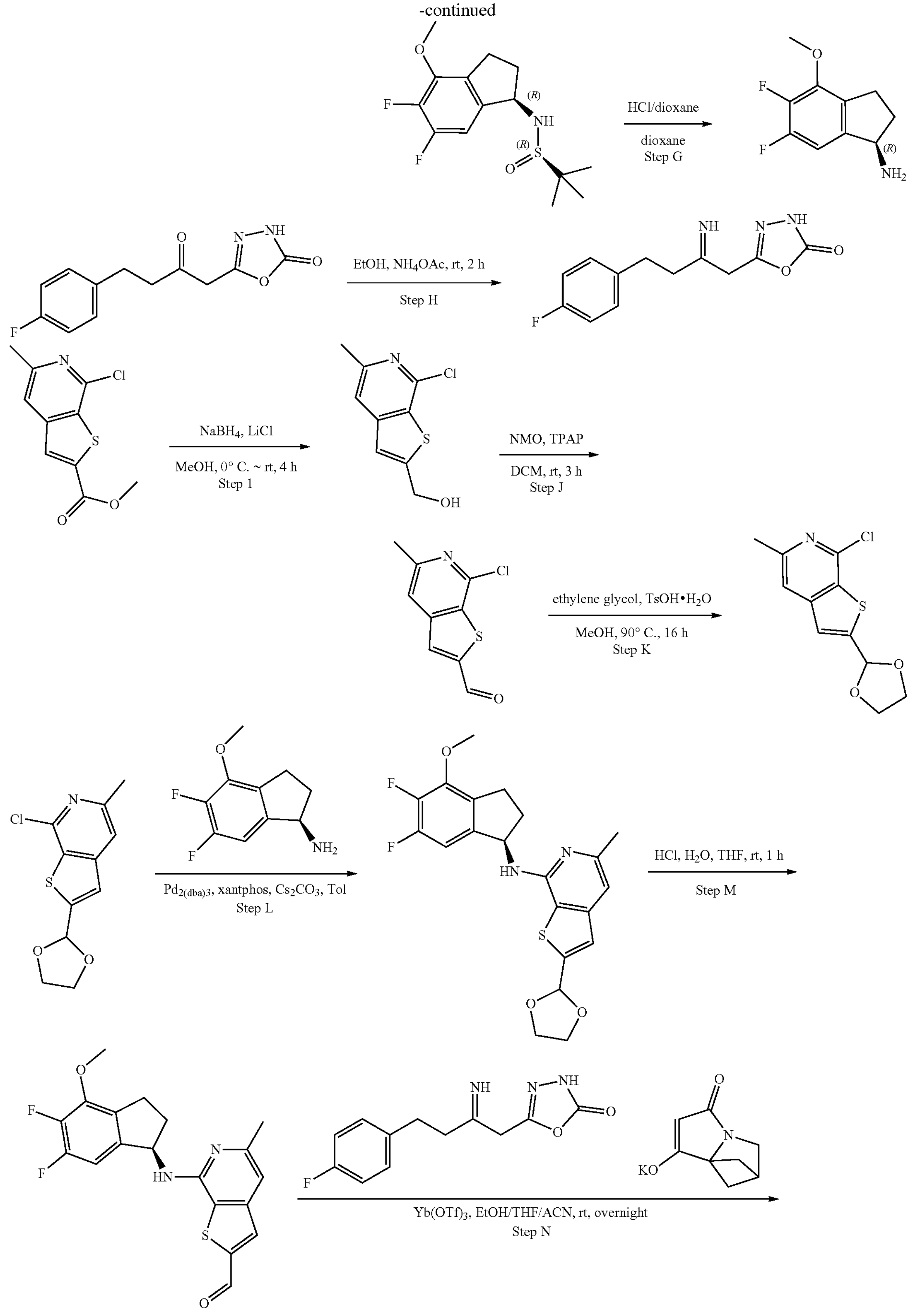

-continued

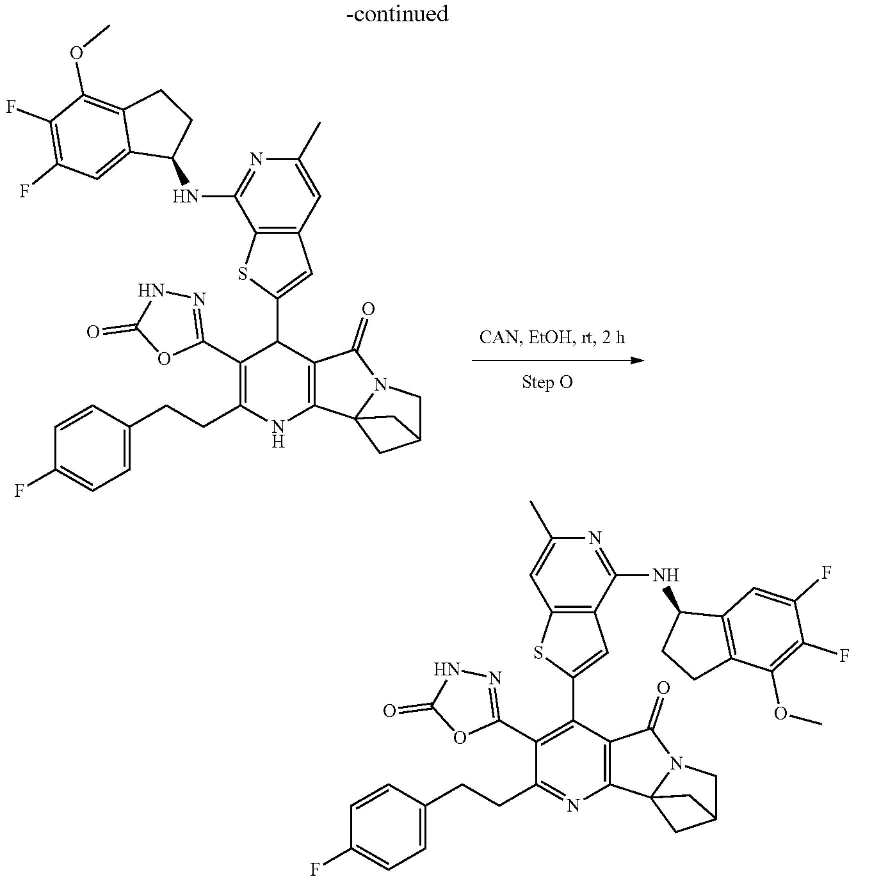

Step A 3-(2-bromo-3,4-difluorophenyl)propanoic acid

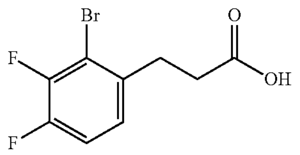 [SMILES: O=C(O)CCc1ccc(F)c(F)c1Br]

To a solution of FA (10.40 mL) in $Et_3N$ (12.60 mL) was added 2-bromo-3,4-difluorobenzene-1-carbaldehyde (10.0 g, 45.249 mmol) at 0° C. and the 2,2-dimethyl-1,3-dioxane-4,6-dione (7.83 g, 54.299 mmol) was added slowly for stirring 30 min at the same temperature and the reaction was warmed to stir at 100° C. overnight under $N_2$. LCMS showed raw material had disappeared and the product was detected. The reaction was diluted with DCM (1000 mL) and water (500 mL). The organic layer was separated, washed with further brine (500 mL×2), dried over $Na_2SO_4$ and concentrated in vacuum to afford the title compound 3-(2-bromo-3,4-difluorophenyl)propanoic acid (9.50 g, 35.842 mmol, 79.21%). $^1$H NMR (400 MHz, DMSO-$d_6$) δ ppm 12.28 (s, 1H), 7.40-7.47 (m, 1H), 7.23-7.27 (m, 1H), 2.95 (t, J=7.60 Hz, 2H), 2.51-2.57 (m, 2H).

Step B 4-bromo-5,6-difluoro-2,3-dihydro-1H-inden-1-one

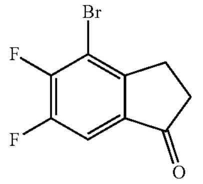 [SMILES: O=C1CCc2c1cc(F)c(F)c2Br]

To a solution of 3-(2-bromo-3,4-difluorophenyl)propanoic acid (8.10 g, 30.560 mmol) in DCM (100.00 mL) were added $(COCl)_2$ (5.245 mL, 61.121 mmol) and DMF (0.246 mL, 3.056 mmol) at 0° C. and warmed to rt and stirred for 3 h under $N_2$. The mixture was concentrated in vacuo to afford 3-(2-bromo-3,4-difluorophenyl)propanoyl chloride (8.60 g, 30.335 mmol, 99.26%). To a solution of 3-(2-bromo-3,4-difluorophenyl)propanoyl chloride (8.60 g, 30.335 mmol) in DCM (100.00 mL) was added $AlCl_3$ (6.05 g, 45.503 mmol) at 0° C. with stirring for 10 min and the reaction was warmed to stir at rt for 40 min under $N_2$. The mixture was poured into the ice-water and stirred for 30 min. The reaction was diluted with DCM (500 mL). The organic layer was separated, washed with further brine (500 mL×2), dried over $Na_2SO_4$ and concentrated in vacuo. The residue was purified using silica gel column chromatography eluting with PE:EA=40:1 to 20:1. The organic product was concentrated in vacuum to afford the title compound 4-bromo-5,6-difluoro-2,3-dihydro-1H-inden-1-one (4.50 g, 18.216 mmol, 60.05%). $^1$H NMR (400 MHz, DMSO-$d_6$) δ ppm 7.30 (dd, $J_1$=7.20 Hz/$J_2$=8.80 Hz, 1H), 3.00 (t, J=5.20 Hz, 2H), 2.73-2.76 (m, 2H).

Step C
5,6-difluoro-4-hydroxy-2,3-dihydro-1H-inden-1-one

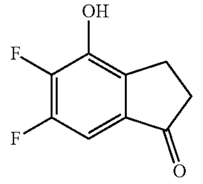 [SMILES: O=C1CCc2c1cc(F)c(F)c2O]

To a solution of 4-bromo-5,6-difluoro-2,3-dihydro-1H-inden-1-one (4.50 g, 18.29 mmol) in dioxane (50 mL) and water (10.0 mL) were added $Pd_2(dba)_3$ (1.68 g, 1.83 mmol), KOH (2.05 g, 36.58 mmol) and t-Buphos (1.56 g, 3.66 mmol), and the reaction was stirred at 100° C. overnight. The mixture was poured into water (500 mL) and DCM (2×500 mL) was added. The inorganic layer was separated, and the pH was adjusted to 6.0-7.0. DCM (500 mL×2) and water (250 mL) were added to the inorganic phase, the organic layer was separated, combined and washed with brine (1000 mL×2), dried over $Na_2SO_4$ and concentrated in vacuum to afford the title compound 5,6-difluoro-4-hydroxy-2,3-dihydro-1H-inden-1-one (2.40 g, 13.04 mmol, 61.75%). $^1$H NMR (400 MHz, DMSO-$d_6$) δ ppm 10.82 (s, 1H), 7.09 (dd, $J_1$=6.40 Hz/$J_2$=8.40 Hz, 1H), 2.97 (t, J=5.60 Hz, 2H), 2.62-2.65 (m, 2H). LC-MS: m/z 185.20 $(M+H)^+$ Step D
5,6-difluoro-4-methoxy-2,3-dihydro-1H-inden-1-one

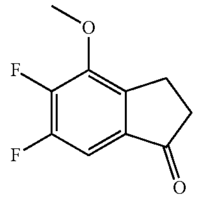

To a solution of 5,6-difluoro-4-hydroxy-2,3-dihydro-1H-inden-1-one (2.40 g, 13.034 mmol) in DMF (80.00 mL) was added $K_2CO_3$ (5.40 g, 39.101 mmol) at rt. Then iodomethane (4.463 mL, 71.685 mmol) was added slowly and the mixture was stirred 30 min at the same temperature before it was warmed to 50° C. and stirred overnight under $N_2$. LCMS showed raw material had disappeared and the product was detected. The reaction was diluted with DCM (700 mL) and water (500 mL). The organic layer was separated, washed with brine (500 mL×2), dried over $Na_2SO_4$ and concentrated in vacuum to afford the title crude compound 5,6-difluoro-4-methoxy-2,3-dihydro-1H-inden-1-one (2.60 g, 13.120 mmol, >99.99%). LC-MS: m/z 199.20 $(M+H)^+$. $^1$H NMR (400 MHz, $CDCl_3$-d) δ ppm 7.21 (dd, $J_1$=6.80 Hz/$J_2$=8.00 Hz, 1H), 4.09 (d, J=2.80 Hz, 3H), 3.06 (t, J=6.40 Hz, 2H), 2.66-2.69 (m, 2H).

Step E (R,Z)—N-(5,6-difluoro-4-methoxy-2,3-dihydro-1H-inden-1-ylidene)-2-methylpropane-2-sulfinamide

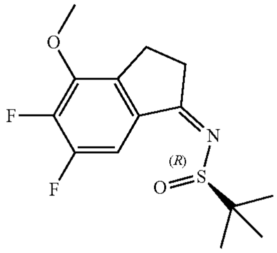

To a solution of 5,6-difluoro-4-methoxy-2,3-dihydro-1H-inden-1-one (2.60 g, 13.120 mmol) in THF (20.00 mL) were added (R)-2-methylpropane-2-sulfinamide (1.83 g, 15.088 mmol) and $Ti(OEt)_4$ (5.489 mL, 26.240 mmol) at rt and the reaction was warmed to stir at 80° C. overnight under $N_2$. LCMS showed raw materials had disappeared and the product was detected. The reaction was diluted with EA (200 mL) and water (250 mL). The organic layer was separated, washed with further brine (250 mL×2), dried over $Na_2SO_4$ and concentrated in vacuo. The residue was purified using silica gel column chromatography eluting with PE:EA=10:1 to 5:1. The organic product was concentrated in vacuum to afford the title compound (R,Z)—N-(5,6-difluoro-4-methoxy-2,3-dihydro-1H-inden-1-ylidene)-2-methylpropane-2-sulfinamide (1.30 g, 4.314 mmol, 32.88%). LC-MS: m/z 302.20 $(M+H)^+$ Step F (R)—N—((R)-5,6-difluoro-4-methoxy-2,3-dihydro-1H-inden-1-yl)-2-methylpropane-2-sulfinamide

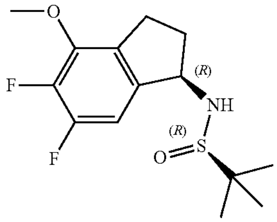

To a solution of (R,Z)—N-(5,6-difluoro-4-methoxy-2,3-dihydro-1H-inden-1-ylidene)-2-methylpropane-2-sulfinamide (1.30 g, 4.314 mmol) in DCM (55.00 mL) was added dropwise DIBAL-H (17.256 mL, 17.256 mmol, 1.0 M in toluene) at −78° C. The mixture was stirred at −78° C. under Ar for 2 h. TLC showed reaction was completed and the product was detected by LCMS. The mixture was added dropwise $H_2O$ (0.50 mL), NaOH aq (15% in water, 0.15 mL) and another water (0.15 mL) in turn at −78° C. Then, $Na_2SO_4$ was added to the mixture and filtered, the filtrate was concentrated in vacuum. The residue was purified by column chromatography (PE/EtOAc=10/1 to 5/1) on silica gel to obtain (R)—N—((R)-5,6-difluoro-4-methoxy-2,3-dihydro-1H-inden-1-yl)-2-methylpropane-2-sulfinamide (1.10 g, 3.626 mmol, 84.05%). LC-MS: m/z 304.20 $(M+H)^+$.

Step G (R)-5,6-difluoro-4-methoxy-2,3-dihydro-1H-inden-1-amine hydrochloride

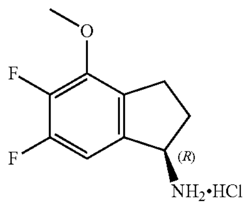

A mixture of (R)—N—((R)-5,6-difluoro-4-methoxy-2,3-dihydro-1H-inden-1-yl)-2-methylpropane-2-sulfinamide (1.00 g, 3.296 mmol) and HCl in dioxane (9.971 mL, 39.885 mmol, 4 M in dioxane) in 1,4-dioxane (5.00 mL) was stirred at 0° C. for 30 min and the reaction was warmed to rt and stirred for 1 h. TLC showed reaction was completed. The mixture was concentrated to obtain (1R)-5,6-difluoro-4-methoxy-2,3-dihydro-1H-inden-1-amine (0.900 g, 3.30 mmol, >99.99%) after being washed with MTBE (60 mL). LC-MS: m/z 200.20 $(M+H)^+$ Step H 5-(4-(4-fluorophenyl)-2-iminobutyl)-1,3,4-oxadiazol-2(3H)-one

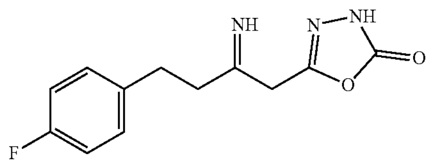 [SMILES: N=C(CCc1ccc(F)cc1)Cc1n[nH]c(=O)o1]

To a solution of 5-(4-(4-fluorophenyl)-2-oxobutyl)-1,3,4-oxadiazol-2(3H)-one (20 g, 79.926 mmol) in EtOH (200 mL) was added $NH_4OAc$ (24.64 g, 319.706 mmol), and the reaction was stirred at room temperature for 2 hr. After the reaction was completed, the mixture was added to aqueous ammonia (200 mL) at 0° C., filtered and concentrated to give 5-(4-(4-fluorophenyl)-2-iminobutyl)-1,3,4-oxadiazol-2(3H)-one (17 g, 68.205 mmol, 85.33%). $^1H$ NMR (400 MHz, DMSO-$d_6$) δ 7.26-7.30 (m, 2H), 7.08-7.13 (m, 2H), 6.66 (br s, 2H), 4.51 (s, 1H), 2.80-2.85 (m, 2H), 2.40-2.44 (m, 2H).

Step I (7-chloro-5-methylthieno[2,3-c]pyridin-2-yl) methanol

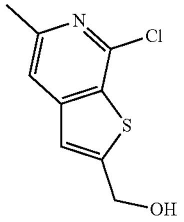

To a solution of methyl 7-chloro-5-methylthieno[2,3-c]pyridine-2-carboxylate (1000 mg, 4.138 mmol) in THF (15 mL) and $H_2O$ (2.5 mL) were added LiCl (526.17 mg, 12.413 mmol) and $NaBH_4$ (469.57 mg, 12.413 mmol). The reaction was stirred at rt for 3 hr. The reaction was concentrated in vacuo. The residue was purified using silica gel column chromatography eluting with ethyl acetate in petroleum ether. The collected fraction was concentrated in vacuo to afford the title compound (7-chloro-5-methylthieno[2,3-c]pyridin-2-yl)methanol (556 mg, 2.602 mmol, 62.89%). LC-MS: m/z 214.1 $(M+H)^+$.

Step J 7-chloro-5-methylthieno[2,3-c]pyridine-2-carbaldehyde

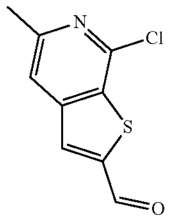

To a solution of (7-chloro-5-methylthieno[2,3-c]pyridin-2-yl)methanol (5000 mg, 23.399 mmol) in DCM (80 mL) were added Dess-martin periodinane (19849.31 mg, 46.799 mmol), and the reaction was stirred at 0° C. for 10 min, and the reaction was stirred at 0° C. for 2 hr. LCMS showed the reaction was completed. The $NaHCO_3$ solution (saturated, 55 mL) was added and the reaction mixture was extracted with DCM (2×50 mL), The organic extract was washed with brine (2×50 mL), dried over $Na_2SO_4$, filtered and concentrated. The residue was purified by flash column chromatography using silica gel and eluting with DCM/MeOH (10/1, v/v) to give compound 7-chloro-5-methylthieno[2,3-c]pyridine-2-carbaldehyde (4900 mg, 23.150 mmol, 98.94%). LC-MS: m/z 212.1 $(M+H)^+$.

Step K 7-chloro-2-(1,3-dioxolan-2-yl)-5-methylthieno[2,3-c]pyridine

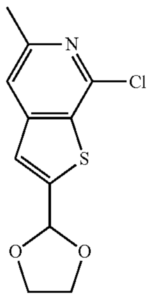 [SMILES: Cc1cc2cc(C3OCCO3)sc2c(Cl)n1]

To a solution of 7-chloro-5-methylthieno[2,3-c]pyridine-2-carbaldehyde (10600 mg, 50.080 mmol) in Toluene (150 mL) was added ethylene glycol (13.964 mL, 250.400 mmol), 4-Methylbenzenesulfonic acid hydrate (952.57 mg, 5.008 mmol), the reaction was stirred at 110° C. for 4 hr under $N_2$. LCMS showed raw materials had disappeared and the product was detected. The reaction was diluted with EA (2000 mL) and saturated $NaHCO_3$ solution. The organic layer was separated, washed with brine (2000 mL×2), dried over $Na_2SO_4$ and concentrated in vacuo. The residue was purified using silica gel column chromatography eluting with PE:EA=5:1. The residue was concentrated in vacuo to afford the title compound 7-chloro-2-(1,3-dioxolan-2-yl)-5-methylthieno[2,3-c]pyridine (7600 mg, 29.720 mmol, 59.34%). $^1$H NMR (400 MHz, $CD_3OD$-$d_4$): δ 7.72 (s, 1H), 7.66 (s, 1H), 6.25 (s, 1H), 3.97-4.12 (m, 4H), 2.55 (s, 3H). LC-MS: m/z 256.1 $(M+H)^+$.

Step L (R)—N-(5,6-difluoro-4-methoxy-2,3-dihydro-1H-inden-1-yl)-2-(1,3-dioxolan-2-yl)-5-methylthieno[2,3-c]pyridin-7-amine

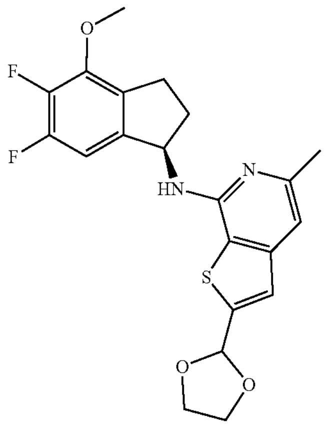 [SMILES: COc1c(F)c(F)cc2c1CC[C@H]2Nc1nc(C)cc2cc(C3OCCO3)sc12]

To a solution of 7-chloro-2-(1,3-dioxolan-2-yl)-5-methylthieno[2,3-c]pyridine (3.83 g, 14.974 mmol) in toluene (120 mL) was added (R)-5,6-difluoro-4-methoxy-2,3-dihydro-1H-inden-1-amine (3.132 g, 15.723 mmol), $Pd_2(dba)_3$ (29.14 mg, 0.036 mmol), Xantphos (0.87 g, 1.497 mmol) and $Cs_2CO_3$ (12.20 g, 37.435 mmol). The reaction was stirred at 110° C. for 18 hr under $N_2$. After the reaction was completed, the mixture was diluted with EA (100 mL), washed with water (150 mL). The organic layers were separated, dried over $Na_2SO_4$, filtered and concentrated under vacuum to dryness. The residue was purified by column chromatography on silica gel (PE/EA=10/1) to give (R)—N-(5,6-difluoro-4-methoxy-2,3-dihydro-1H-inden-1-yl)-2-(1,3-dioxolan-2-yl)-5-methylthieno[2,3-c]pyridin-7-amine (5.175 g, 12.367 mmol, 82.59%). LC-MS: m/z 419.2 $(M+H)^+$.

Step M (R)-7-((5,6-difluoro-4-methoxy-2,3-dihydro-1H-inden-1-yl)amino)-5-methylthieno[2,3-c]pyridine-2-carbaldehyde

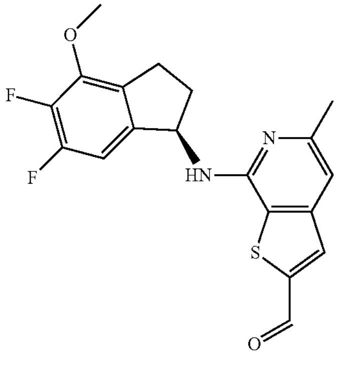 [SMILES: COc1c(F)c(F)cc2c1CC[C@H]2Nc1nc(C)cc2cc(C=O)sc12]

To a solution of (R)—N-(5,6-difluoro-4-methoxy-2,3-dihydro-1H-inden-1-yl)-2-(1,3-dioxolan-2-yl)-5-methylthieno[2,3-c]pyridin-7-amine (5.175 g, 12.38 mmol) in THF (12 mL), $H_2O$ (12 mL) was added 4 N HCl (12 mL), the reaction was stirred at room temperature for 1 h. After the reaction was completed, the mixture reaction was basified with $Na_2CO_3$ to pH=8, the mixture was extracted with EA. The organic phase was washed with water, concentrated to give (R)-7-((5,6-difluoro-4-methoxy-2,3-dihydro-1H-inden-1-yl)amino)-5-methylthieno[2,3-c]pyridine-2-carbaldehyde (4.2 g, 11.218 mmol). LC-MS: m/z 375.1 $(M+H)^+$.

Step N 5-(4-(7-(((R)-5,6-difluoro-4-methoxy-2,3-dihydro-1H-inden-1-yl)amino)-5-methylthieno[2,3-c]pyridin-2-yl)-2-(4-fluorophenethyl)-5-oxo-1,5,8,9-tetrahydro-4H,7H-8,9a-methanopyrido[2,3-a]pyrrolizin-3-yl)-1,3,4-oxadiazol-2(3H)-one

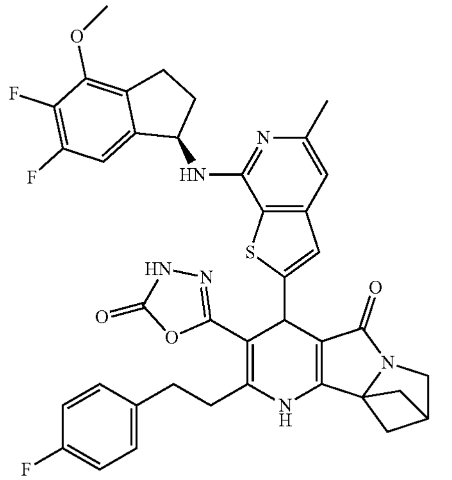 [SMILES: COc1c(F)c(F)cc2c1CC[C@H]2Nc1nc(C)cc2cc(C3C4=C(NC(CCc5ccc(F)cc5)=C3c3n[nH]c(=O)o3)C35CC(CN3C4=O)C5)sc12]

A mixture of (R)-7-((5,6-difluoro-4-methoxy-2,3-dihydro-1H-inden-1-yl)amino)-5-methylthieno[2,3-c]pyridine-2-carbaldehyde (4000 mg, 10.683 mmol), 5-(4-(4-fluorophenyl)-2-iminobutyl)-1,3,4-oxadiazol-2(3H)-one (2662.86 mg, 10.683 mmol), 7-hydroxy-2,3-dihydro-1H,5H-2,7a-methanopyrrolizin-5-one (1614.91 mg, 10.683 mmol), and $Yb(OTf)_3$ (662.63 mg, 1.068 mmol) in ethanol (16 mL), tetrahydrofuran (16 mL), acetonitrile (16 mL) was stirred at room temperature overnight. Then 7-hydroxy-2,3-dihydro-1H,5H-2,7a-methanopyrrolizin-5-one (645.97 mg, 4.273 mmol) was added and stirred for 2 hr. After the reaction was completed, the mixture was concentrated and the residue was dissolved in HOAc (50 mL), heated to 100° C. and stirred for 0.5 hr. After the reaction was completed, the mixture reaction was concentrated and purified by column chromatography on silica gel (MeOH/DCM/=0% to 10%) to give 5-(4-(7-(((R)-5,6-difluoro-4-methoxy-2,3-dihydro-1H-inden-1-yl)amino)-5-methylthieno[2,3-c]pyridin-2-yl)-2-(4-fluorophenethyl)-5-oxo-1,5,8,9-tetrahydro-4H,7H-8,9a-methanopyrido[2,3-a]pyrrolizin-3-yl)-1,3,4-oxadiazol-2(3H)-one (5.6 g). LC-MS: m/z 739.2 $(M+H)^+$.

Step O (R)-5-(4-(7-((5,6-difluoro-4-methoxy-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (195)

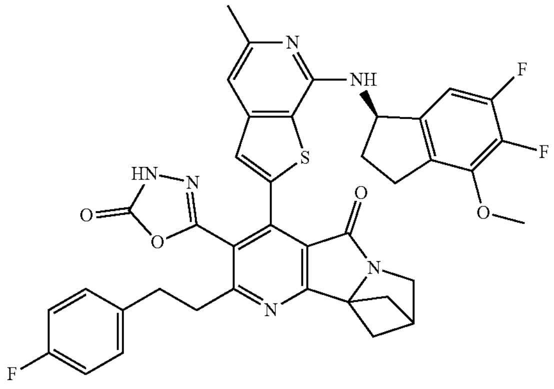 [SMILES: COc1c(F)c(F)cc2c1CC[C@H]2Nc1nc(C)cc2cc(-c3c4c(nc(CCc5ccc(F)cc5)c3-c3n[nH]c(=O)o3)C35CC(CN3C4=O)C5)sc12]

To a mixture of 5-(4-(7-(((R)-5,6-difluoro-4-methoxy-2,3-dihydro-1H-inden-1-yl)amino)-5-methylthieno[2,3-c]pyridin-2-yl)-2-(4-fluorophenethyl)-5-oxo-1,5,8,9-tetra-hydro-4H,7H-8,9a-methanopyrido[2,3-a]pyrrolizin-3-yl)-1,3,4-oxadiazol-2(3H)-one (5.62 g, 7.607 mmol) in ethanol (60 mL) was added Ceric ammonium nitrate (8.07 g, 15.214 mmol) in portions at 0° C., the mixture was stirred at room temperature for 1 hr. After the reaction was completed, the mixture reaction was diluted with EA, washed with water, dried, concentrated. The residue was purified by column chromatography on silica gel (MeOH/DCM/=0% to 10%) to give crude product (5.3 g). The crude product was purified by Prep-HPLC ($NH_3H_2O$) to give (R)-5-(4-(7-((5,6-difluoro-4-methoxy-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (4267.98 mg, 5.697 mmol, 74.89%). $^1$H NMR (400 MHz, DMSO-d6): δ 12.70 (br s, 1H), 7.33 (s, 1H), 7.17-7.25 (m, 3H), 7.03-7.11 (m, 2H), 6.90-6.97 (m, 2H), 5.82 (q, J=8.0 Hz, 1H), 3.94 (d, J=1.2 Hz, 3H), 3.56 (s, 2H), 3.16-3.22 (m, 3H), 3.00-3.09 (m, 3H), 2.79-2.90 (m, 1H), 2.61-2.67 (m, 2H), 2.52-2.57 (m, 1H), 2.41 (s, 3H), 2.00-2.11 (m, 1H), 1.70-1.79 (m, 2H). $^{19}$F NMR (377 MHz, DMSO-d6): −117.01, −138.68, −158.74. LC-MS: m/z 737.2 $(M+H)^+$.

Example 24

5-(4-(7-(((1S,2R)-2,5-difluoro-4-methoxy-2,3-di-hydro-1H-inden-1-yl)amino)-5-methylthieno[2,3-c]pyridin-2-yl)-2-(4-fluorophenethyl)-5-oxo-8,9-di-hydro-5H,7H-8,9a-methanopyrido[2,3-a]pyrrolizin-3-yl)-1,3,4-oxadiazol-2(3H)-one (196)

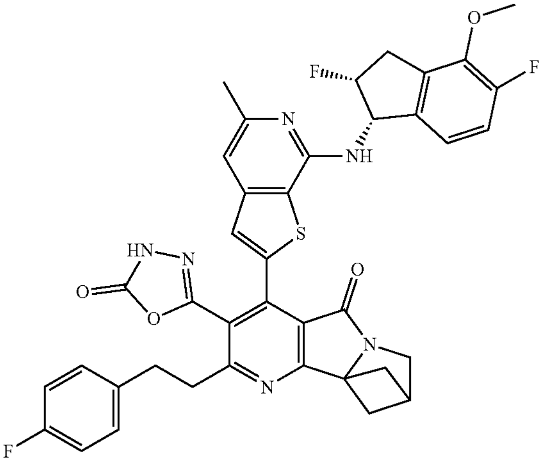

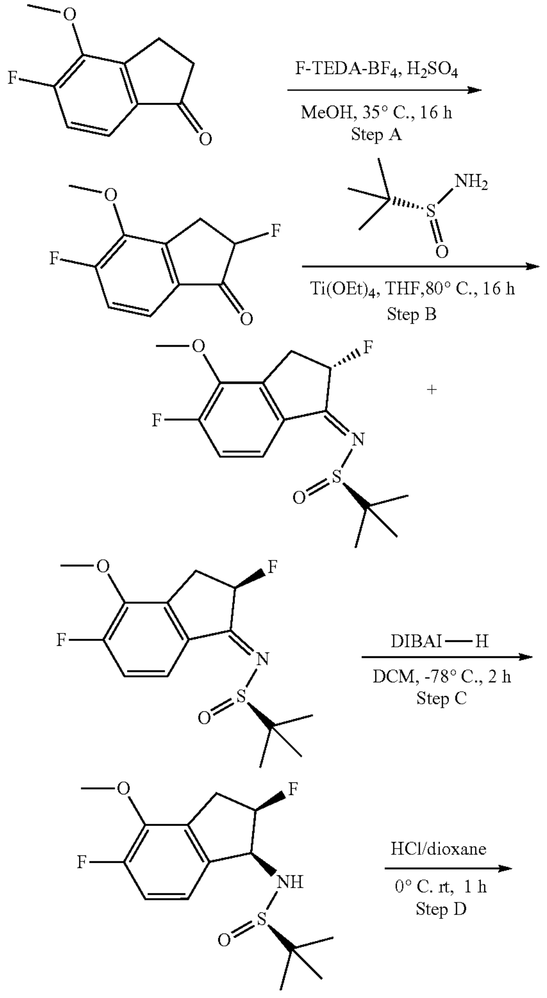

-continued

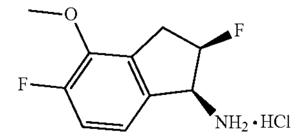

Step A
2,5-difluoro-4-methoxy-2,3-dihydro-1H-inden-1-one

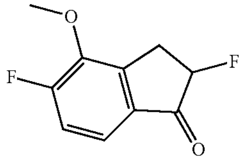

A mixture of 5-fluoro-4-methoxy-2,3-dihydro-1H-inden-1-one (49 g, 271.950 mmol), Selectfluor (192.68 g, 543.901 mmol) and $H_2SO_4$ (2.913 mL, 54.390 mmol) in MeOH (350 mL) was stirred at 35° C. for 16 h under $N_2$ atmosphere. The mixture was poured into water (1 μL) and extracted with EtOAc (2×1 L), the combined organic layer was washed with brine, dried over sodium sulfate, filtered and the residue was purified by column chromatography (PE/EtOAc=5/1) on silica gel to obtain 2,5-difluoro-4-methoxy-2,3-dihydro-1H-inden-1-one (52.30 g, 263.915 mmol, 97.05%). LC-MS: m/z 199.20 $(M+H)^+$.

Step B (R)—N—((R,E)-2,5-difluoro-4-methoxy-2,3-dihydro-1H-inden-1-ylidene)-2-methylpropane-2-sulfinamide

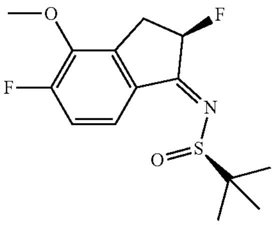 [SMILES: COc1c(F)ccc2c1C[C@@H](F)/C2=N/[S@](=O)C(C)(C)C]

A mixture of 2,5-difluoro-4-methoxy-2,3-dihydro-1H-inden-1-one (52.30 g, 263.915 mmol), (R)-2-methylpropane-2-sulfinamide (31.99 g, 263.915 mmol) and $Ti(OEt)_4$ (120.40 g, 527.830 mmol) in THF (500 mL) was stirred at 80° C. for 16 h under $N_2$ atmosphere. LCMS showed reaction was completed. The reaction was concentrated in vacuo. The residue was purified by column chromatography (PE/EtOAc=5/1) on silica gel to obtain (R)—N—((S,E)-2,5-difluoro-4-methoxy-2,3-dihydro-1H-inden-1-ylidene)-2-methylpropane-2-sulfinamide (25.3 g, 83.956 mmol, 31.81%) as a brown oil and (R)—N—((R,E)-2,5-difluoro-4-methoxy-2,3-dihydro-1H-inden-1-ylidene)-2-methylpropane-2-sulfinamide (23.4 g, 77.651 mmol, 29.42%) as a brown oil. LC-MS: m/z 302.20 $(M+H)^+$.

Step C (R)—N-((1S,2R)-2,5-difluoro-4-methoxy-2,3-dihydro-1H-inden-1-yl)-2-methylpropane-2-sulfinamide

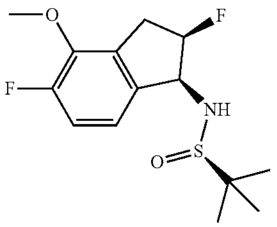 [SMILES: COc1c(F)ccc2c1C[C@@H](F)[C@H]2N[S@](=O)C(C)(C)C]

To a solution of (R)—N—((R,E)-2,5-difluoro-4-methoxy-2,3-dihydro-1H-inden-1-ylidene)-2-methylpropane-2-sulfinamide (11.2 g, 37.166 mmol) in DCM (500 mL) was added DIBAL-H (1.5 M in toluene, 99.110 mL, 148.664 mmol) at −78° C. for 2 h under $N_2$. The reaction mixture was diluted with water (3.7 mL), 15% NaOH aq (11.1 mL, 15% in water) and water (11.1 mL) in turn at −78° C. The organic layer was dried by $Na_2SO_4$, filtered and the residue was purified by column chromatography (PE/EtOAc=5/1) on silica gel to obtain (R)—N-((1S,2R)-2,5-difluoro-4-methoxy-2,3-dihydro-1H-inden-1-yl)-2-methylpropane-2-sulfinamide (7 g, 23.074 mmol, 62.06%). LC-MS: m/z 304.20 $(M+H)^+$.

Step D (1S,2R)-2,5-difluoro-4-methoxy-2,3-dihydro-1H-inden-1-amine hydrochloride

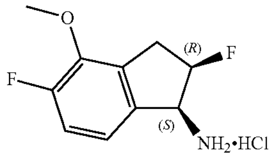

To a solution of (R)—N-((1S,2R)-2,5-difluoro-4-methoxy-2,3-dihydro-1H-inden-1-yl)-2-methylpropane-2-sulfinamide (7.00 g, 23.074 mmol) in dioxane (20 mL) was added HCl (6 M in dioxane, 40 mL) at 0° C. for 10 min, then the reaction was stirred at rt 1 h under $N_2$. The reaction was concentrated in vacuo to afford the title compound (1S,2R)-2,5-difluoro-4-methoxy-2,3-dihydro-1H-inden-1-amine hydrochloride (4.80 g, 20.368 mmol, 88.27%) after being washed with MTBE (50 mL). LC-MS: m/z 200.20 $(M+H)^+$. $^1H$ NMR (400 MHz, DMSO-$d_6$) δ 9.08 (s, 3H), 7.41 (q, J=4.0 Hz, 1H), 7.26 (dd, J=12.0 Hz/J=8.4 Hz, 1H), 5.62 (t, J=4.4 Hz, 0.5H), 5.49 (t, J=4.4 Hz, 0.5H), 4.83 (dd, J=22.4 Hz/J =4.0 Hz, 1H), 3.89 (d, J=1.2 Hz, 3H), 3.19-3.39 (m, 2H). $^{19}F$ NMR (400 MHz, DMSO-$d_6$) δ −132.14, −193.89.

5-(4-(7-(((1S,2R)-2,5-difluoro-4-methoxy-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (196)

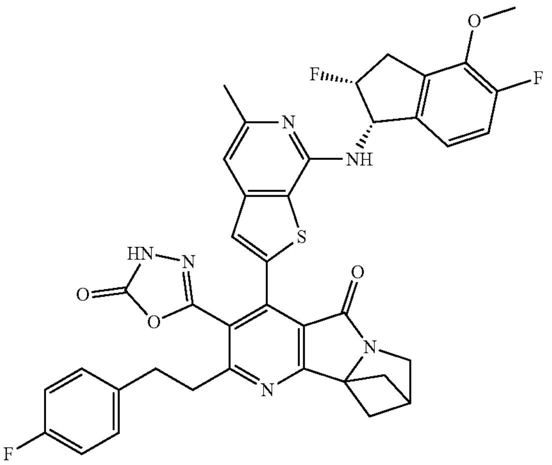

Compound 196 was synthesized using similar procedure as described in Example 23 above by using the appropriate materials. $^1H$ NMR (400 MHz, DMSO-$d_6$) δ 12.69 (br s, 1H), 7.33 (s, 1H), 7.20-7.24 (m, 2H), 7.17-7.19 (m, 1H), 7.15-7.16 (m, 1H), 7.05-7.10 (m, 2H), 6.95-7.01 (m, 2H), 5.88-6.00 (m, 1H), 5.47-5.65 (m, 1H), 3.90 (d, J=1.2 Hz, 3H), 3.57 (s, 2H), 3.56-3.44 (m, 1H), 3.25-3.29 (m, 1H), 3.15-3.23 (m, 3H), 3.00-3.07 (m, 2H), 2.62-2.67 (m, 2H), 2.42 (s, 3H), 1.71-1.79 (m, 2H). $^{19}F$ NMR (377 MHz, DMSO-$d_6$): −117.02, −134.35, −191.64. LC-MS: m/z 737.3 $(M+H)^+$.

Example 25

5-((S)-4-(7-(((R)-6,7-dihydro-5H-cyclopenta[b]pyridin-5-yl)amino)thieno[2,3-c]pyridin-2-yl)-5-oxo-2-(2-(tetrahydro-2H-pyran-4-yl)ethyl)-7,8,9,9a-tetrahydro-5H-pyrido[2,3-a]pyrrolizin-3-yl)isoxazol-3(2H)-one (Compound 197)

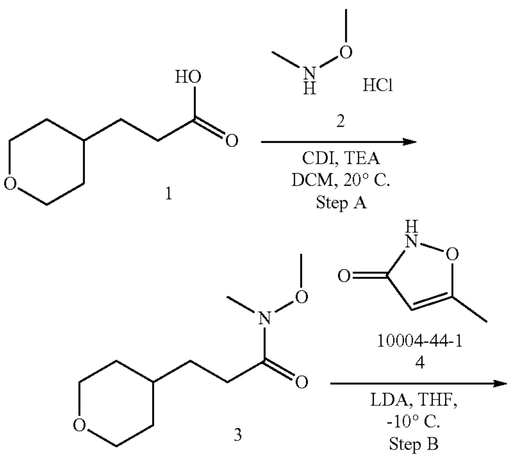

-continued

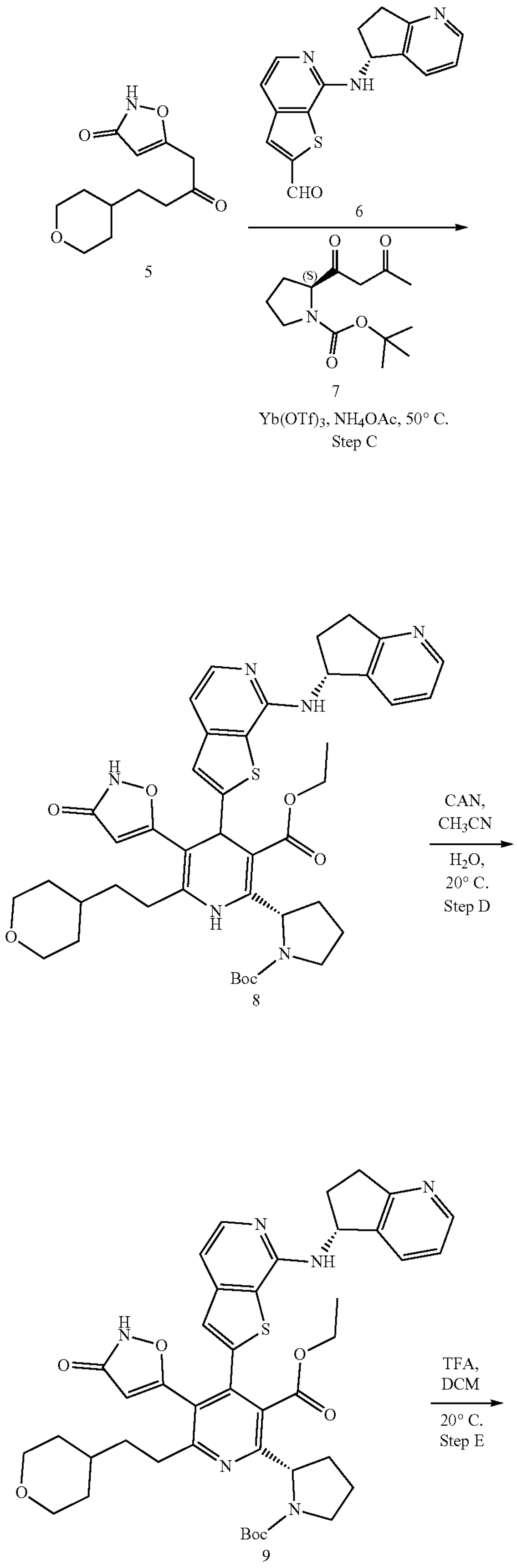

-continued

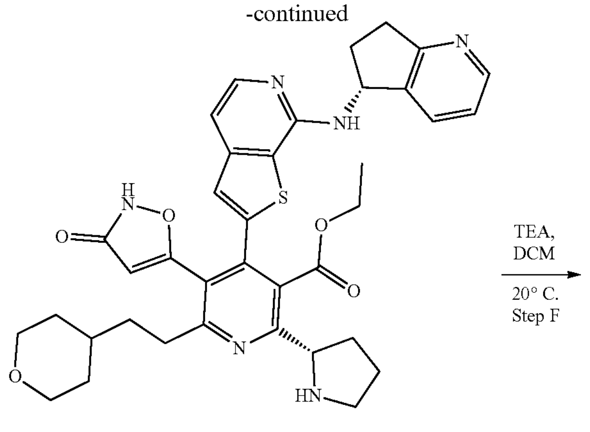

10

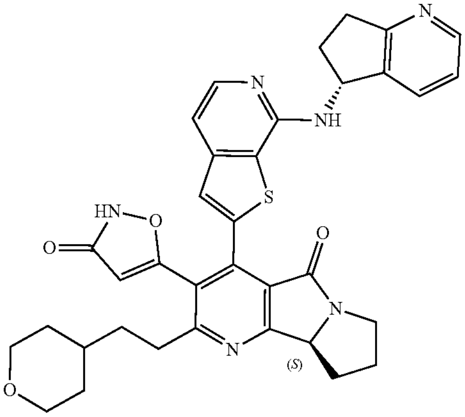

Compound 197

Step A N-methoxy-N-methyl-3-(tetrahydro-2H-pyran-4-yl)propanamide

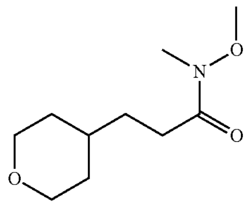

3-(tetrahydro-2H-pyran-4-yl)propanoic acid (500 mg, 3.16 mmol) was dissolved in DCM (10 mL). Carbonyldiimidazole (563.75 mg, 3.48 mmol) was added slowly and the reaction was stirred at 20° C. for 1 hr. N, O-dimethylhydroxylamine hydrochloride (339.13 mg, 3.48 mmol) and TEA (351.81 mg, 3.48 mmol) were added and the reaction was stirred at 20° C. for 16 hrs. The mixture was diluted with DCM (20 mL) and washed with HCl (10 mL, 1M), saturated aqueous $NaHCO_3$ (10 mL) and saturated brine (10 mL). The organic phase is dried over anhydrous $Na_2SO_4$. The solvent was filtered and concentrated under reduced pressure to give N-methoxy-N-methyl-3-(tetrahydro-2H-pyran-4-yl)propanamide (560 mg, 2.78 mmol, 88.03% yield).

$^1$H NMR (400 MHz, MeOD-$d_4$) δ 3.90-3.99 (m, 2H), 3.69-3.78 (m, 3H), 3.37-3.49 (m, 2H), 3.20 (s, 3H), 2.45-2.57 (m, 2H), 1.63-1.72 (m, 2H), 1.57 (t, J=5.99 Hz, 3H), 1.19-1.36 (m, 2H).

Step B 5-(2-oxo-4-(tetrahydro-2H-pyran-4-yl)butyl) isoxazol-3(2H)-one

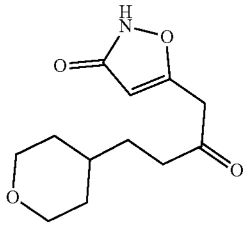 [SMILES: O=C(CCC1CCOCC1)Cc1cc(=O)[nH]o1]

To a mixture of LDA (2.0 M, 2.61 mL) in THF (5 mL) was added 5-methylisoxazol-3-one (246.17 mg, 2.48 mmol) at −10° C. under $N_2$. The mixture was stirred at −10° C. for 30 min. N-methoxy-N-methyl-3-(tetrahydro-2H-pyran-4-yl) propanamide (250 mg, 1.24 mmol) in THF (2 mL) was added into the reaction solution. The solution was stirred at −10° C. for 1 hr. The solution was quenched with 1 M HCl until pH=1. The mixture was poured into water (20 mL), washed with ethyl acetate (20 mL) to remove the impurities. The aqueous layer was adjusted with the sat. $NaHCO_3$ solution until pH=7, extracted with ethyl acetate (30 mL×3), then brine (50 mL), dried over anhydrous of $Na_2SO_4$, filtered and concentrated in vacuum to a residue. The residue was purified by flash silica gel chromatography (ISCO®; 20 g SepaFlash® Silica Flash Column, Eluent of 0~80% Ethyl acetate/Petroleum ether gradient @25 mL/min) to give 5-(2-oxo-4-(tetrahydro-2H-pyran-4-yl)butyl)isoxazol-3(2H)-one (114 mg, 476.46 μmol, 38.36% yield, 100% purity).

$^1$H NMR (400 MHz, DMSO-$d_6$) δ 5.85-5.92 (m, 1H), 3.90-3.98 (m, 2H), 3.77-3.86 (m, 2H), 3.18-3.29 (m, 2H), 2.52-2.58 (m, 2H), 1.49-1.57 (m, 2H), 1.35-1.46 (m, 3H), 1.03-1.17 (m, 2H). LC-MS: m/z 240.0 $(M+H)^+$.

Step C ethyl 2-((S)-1-(tert-butoxycarbonyl)pyrrolidin-2-yl)-4-(7-(((R)-6,7-dihydro-5H-cyclopenta[b]pyridin-5-yl)amino)thieno[2,3-c]pyridin-2-yl)-5-(3-oxo-2,3-dihydroisoxazol-5-yl)-6-(2-(tetrahydro-2H-pyran-4-yl)ethyl)-1,4-dihydropyridine-3-carboxylate

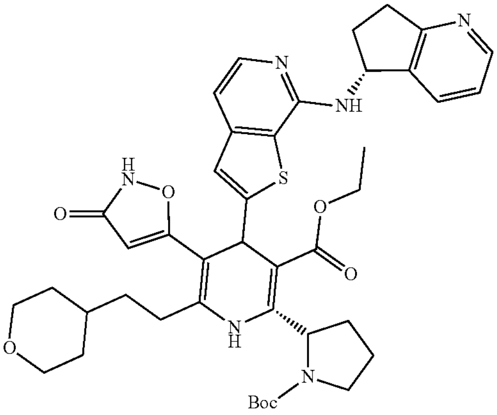

A mixture of tert-butyl (S)-2-(3-ethoxy-3-oxopropanoyl)pyrrolidine-1-carboxylate (50 mg, 175.23 μmol), 5-(2-oxo-4-(tetrahydro-2H-pyran-4-yl)butyl)isoxazol-3(2H)-one (41.93 mg, 175.23 μmol), (R)-7-((6,7-dihydro-5H-cyclopenta[b]pyridin-5-yl)amino)thieno[2,3-c]pyridine-2-carbaldehyde (51.76 mg, 175.23 μmol), $NH_4OAc$ (14.86 mg, 192.76 μmol) and $Yb(OTf)_3$ (10.87 mg, 17.52 μmol) in EtOH (2 mL) was degassed and purged with $N_2$ for 3 times, and then the mixture was stirred at 50° C. for 16 hrs under $N_2$ atmosphere. The reaction mixture was concentrated under reduced pressure to give a residue. The residue was purified by column chromatography ($SiO_2$, petroleum ether/ethyl acetate=1/0 to 0/1) to give ethyl 2-((S)-1-(tert-butoxycarbonyl)pyrrolidin-2-yl)-4-(7-(((R)-6,7-dihydro-5H-cyclopenta[b]pyridin-5-yl)amino)thieno[2,3-c]pyridin-2-yl)-5-(3-oxo-2,3-dihydroisoxazol-5-yl)-6-(2-(tetrahydro-2H-pyran-4-yl)ethyl)-1,4-dihydropyridine-3-carboxylate (90 mg, 58.51 μmol, 33.39% yield, 50.90% purity). LC-MS: m/z 793.3 $(M+H)^+$.

Step D ethyl 2-((S)-1-(tert-butoxycarbonyl)pyrrolidin-2-yl)-4-(7-(((R)-6,7-dihydro-5H-cyclopenta[b]pyridin-5-yl)amino)thieno[2,3-c]pyridin-2-yl)-5-(3-oxo-2,3-dihydroisoxazol-5-yl)-6-(2-(tetrahydro-2H-pyran-4-yl)ethyl)nicotinate

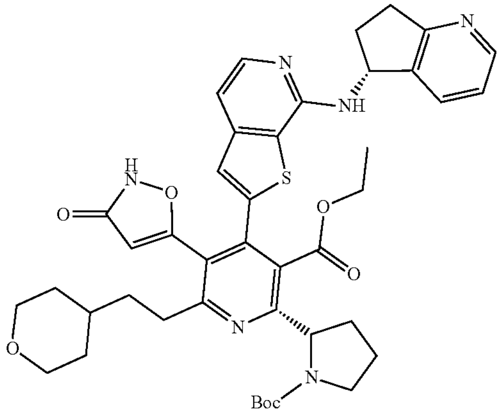

A mixture of ethyl 2-((S)-1-(tert-butoxycarbonyl)pyrrolidin-2-yl)-4-(7-(((R)-6,7-dihydro-5H-cyclopenta[b]pyridin-5-yl)amino)thieno[2,3-c]pyridin-2-yl)-5-(3-oxo-2,3-dihydroisoxazol-5-yl)-6-(2-(tetrahydro-2H-pyran-4-yl)ethyl)-1,4-dihydropyridine-3-carboxylate (90 mg, 114.95 μmol) and CAN (126.04 mg, 229.90 μmol) in $CH_3CN$ (2 mL) and $H_2O$ (2 mL) was degassed and purged with $N_2$ for 3 times, and then the mixture was stirred at 20° C. for 2 hrs under $N_2$ atmosphere. The reaction mixture was diluted with ethyl acetate (10 mL) and washed with brine (5 mL), dried over $Na_2SO_4$, filtered and concentrated under reduced pressure to give ethyl 5-(3-oxoisoxazol-5-yl)-2-[rac-(2S)-1-tert-butoxycarbonylpyrrolidin-2-yl]-4-[7-[[rac-(5R)-6,7-dihydro-5H-cyclopenta[b]pyridin-5-yl]amino]thieno[2,3-c]pyridin-2-yl]-6-(2-tetrahydropyran-4-ylethyl)pyridine-3-carboxylate (62 mg, 32.02 μmol, 27.85% yield, 40.33% purity). LC-MS: m/z 781.3 $(M+H)^+$.

Step E ethyl 4-(7-(((R)-6,7-dihydro-5H-cyclopenta[b]pyridin-5-yl)amino)thieno[2,3-c]pyridin-2-yl)-5-(3-oxo-2,3-dihydroisoxazol-5-yl)-2-((S)-pyrrolidin-2-yl)-6-(2-(tetrahydro-2H-pyran-4-yl)ethyl)nicotinate

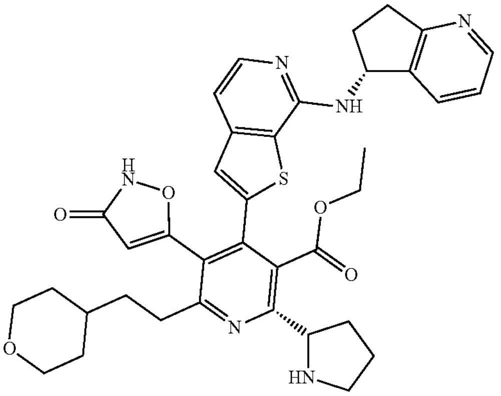

A mixture of ethyl 2-((S)-1-(tert-butoxycarbonyl)pyrrolidin-2-yl)-4-(7-(((R)-6,7-dihydro-5H-cyclopenta[b]pyridin-5-yl)amino)thieno[2,3-c]pyridin-2-yl)-5-(3-oxo-2,3-dihydroisoxazol-5-yl)-6-(2-(tetrahydro-2H-pyran-4-yl)ethyl)nicotinate (62 mg, 79.39 μmol) and TFA (460.50 mg, 4.04 mmol) in DCM (3 mL) was degassed and purged with $N_2$ for 3 times, and then the mixture was stirred at 20° C. for 2 hrs under $N_2$ atmosphere. The reaction mixture was concentrated under reduced pressure to give ethyl 4-(7-(((R)-6,7-dihydro-5H-cyclopenta[b]pyridin-5-yl)amino)thieno[2,3-c]pyridin-2-yl)-5-(3-oxo-2,3-dihydroisoxazol-5-yl)-2-((S)-pyrrolidin-2-yl)-6-(2-(tetrahydro-2H-pyran-4-yl)ethyl)nicotinate (65 mg, crude, TFA). LC-MS: m/z 681.2 $(M+H)^+$.

Step F 5-((S)-4-(7-(((R)-6,7-dihydro-5H-cyclopenta[b]pyridin-5-yl)amino)thieno[2,3-c]pyridin-2-yl)-5-oxo-2-(2-(tetrahydro-2H-pyran-4-yl)ethyl)-7,8,9,9a-tetrahydro-5H-pyrido[2,3-a]pyrrolizin-3-yl)isoxazol-3(2H)-one

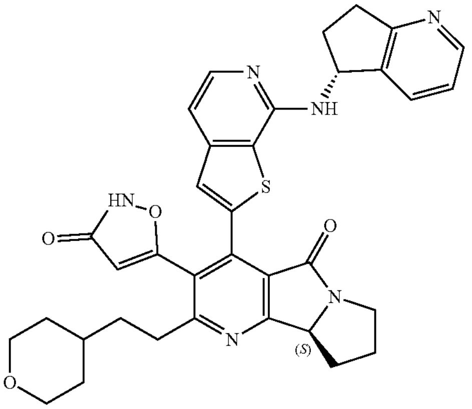

To a solution of ethyl 4-(7-(((R)-6,7-dihydro-5H-cyclopenta[b]pyridin-5-yl)amino)thieno[2,3-c]pyridin-2-yl)-5-(3-oxo-2,3-dihydroisoxazol-5-yl)-2-((S)-pyrrolidin-2-yl)-6-(2-(tetrahydro-2H-pyran-4-yl)ethyl)nicotinate (65 mg, 95.47 μmol) in DCM (2 mL) was added TEA (1.45 g, 14.37 mmol). The mixture was stirred at 20° C. for 16 hrs. The reaction mixture was concentrated under reduced pressure to give a residue. The residue was purified by prep-HPLC (FA) to give 5-((S)-4-(7-(((R)-6,7-dihydro-5H-cyclopenta[b]pyridin-5-yl)amino)thieno[2,3-c]pyridin-2-yl)-5-oxo-2-(2-(tetrahydro-2H-pyran-4-yl)ethyl)-7,8,9,9a-tetrahydro-5H-pyrido[2,3-a]pyrrolizin-3-yl)isoxazol-3(2H)-one (6.78 mg, 10.54 μmol, 11.04% yield, 98.68% purity).

$^1H$ NMR (400 MHz, $CDCl_3$) δ 8.36-8.46 (m, 1H), 7.95-8.06 (m, 1H), 7.85 (d, J=1.47 Hz, 1H), 7.35-7.45 (m, 1H), 7.07-7.17 (m, 2H), 5.80-5.94 (m, 1H), 5.68-5.78 (m, 1H), 4.67-4.81 (m, 1H), 3.88-3.98 (m, 2H), 3.69-3.79 (m, 1H), 3.30-3.44 (m, 3H), 2.82 (d, J=3.18 Hz, 2H), 2.67-2.75 (m, 2H), 2.47-2.54 (m, 2H), 2.35-2.41 (m, 2H), 1.76-1.86 (m, 2H), 1.65-1.73 (m, 2H), 1.55-1.61 (m, 2H), 1.38-1.51 (m, 2H), 1.23-1.33 (m, 2H). LC-MS: m/z 635.4 $(M+H)^+$.

5-[(2S)-9-[7-[[(5R)-6,7-dihydro-5H-cyclopenta[b]pyridin-5-yl]amino]thieno[2,3-c]pyridin-2-yl]-7,7-dioxo-11-(2-tetrahydropyran-4-ylethyl)-7thia-6,12-diazatricyclo[6.4.0.02,6]dodeca-1(12),8,10-trien-10-yl]isoxazol-3-one (Compound 198)

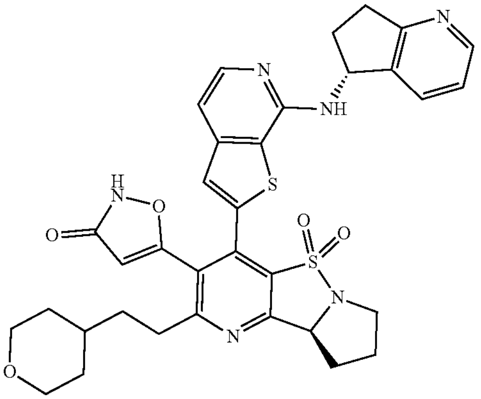 [SMILES: O=c1cc(-c2c(CCC3CCOCC3)nc3c(c2-c2cc4ccnc(N[C@@H]5CCc6ncccc65)c4s2)S(=O)(=O)N2CCC[C@@H]32)o[nH]1]

Compound 198 was synthesized using a similar procedure described in the Example 13 above by using the appropriate materials.

$^1H$ NMR (500 MHz, MeOD-$d_4$) δ ppm 8.36 (d, J=5.19 Hz, 1H), 7.99 (d, J=5.80 Hz, 1H), 7.76 (d, J=7.63 Hz, 1H), 7.65 (s, 1H), 7.23 (dd, J=7.55, 5.11 Hz, 1H), 7.16 (d, J=5.65 Hz, 1H), 6.03 (s, 1H), 5.90 (t, J=7.78 Hz, 1H), 5.09 (dd, J=8.16, 4.96 Hz, 1H), 3.89-3.94 (m, 2H), 3.76-3.83 (m, 1H), 3.35-3.47 (m, 4H), 3.13-3.19 (m, 1H), 3.04 (dt, J=16.94, 8.62 Hz, 1H), 2.86-2.93 (m, 2H), 2.70-2.77 (m, 1H), 2.56-2.63 (m, 1H), 2.35 (dq, J=12.26, 6.14 Hz, 1H), 2.09-2.18 (m, 1H), 1.98-2.06 (m, 1H), 1.77-1.84 (m, 1H), 1.52-1.74 (m, 5H), 1.21-1.40 (m, 3H). LC-MS: m/z 671.2 $(M+H)^+$.

Example 26

3-((9aS)-4-(7-(((R)-4-methoxy-2,3-dihydro-1H-inden-1-yl)amino)thieno[2,3-c]pyridin-2-yl)-5-oxo-2-(3-(tetrahydrofuran-3-yl)phenethyl)-7,8,9,9a-tetrahydro-5H-pyrido[2,3-a]pyrrolizin-3-yl)-1,2,4-oxadiazol-5(4H)-one (Compound 199)

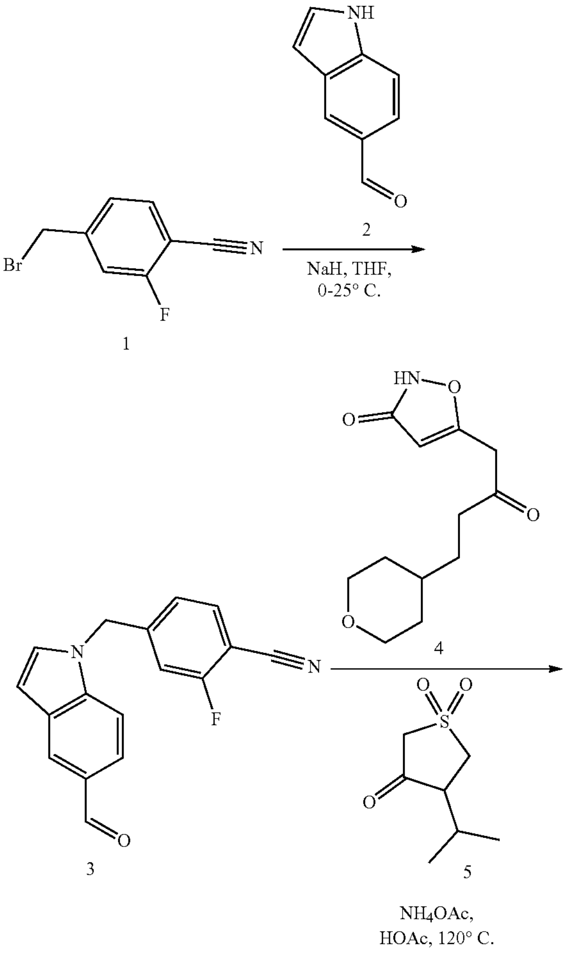

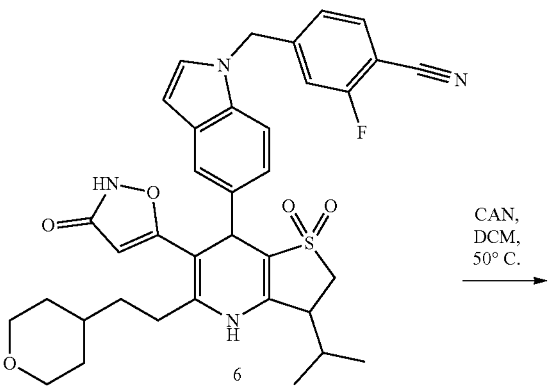

-continued

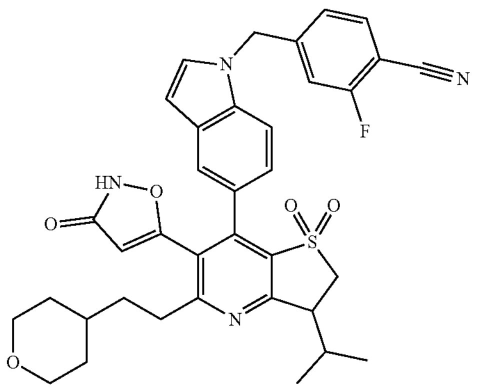

Step A 2-fluoro-4-[(5-formylindol-1-yl)methyl]benzonitrile

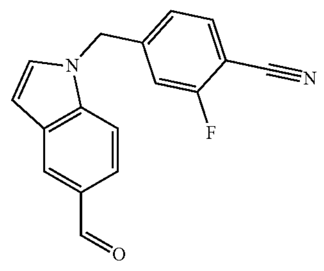 [SMILES: N#Cc1ccc(Cn2ccc3cc(C=O)ccc32)cc1F]

To a solution of 1H-indole-5-carbaldehyde (500 mg, 3.44 mmol) in THF (10 mL) was added NaH (206.65 mg, 5.17 mmol, 60% purity) at 0° C. The mixture was stirred at 0° C. for 30 mins. Then 4-(bromomethyl)-2-fluoro-benzonitrile (1.11 g, 5.17 mmol) was added. The mixture was stirred at 25° C. for 90 mins. The reaction mixture was quenched by addition aqueous $NH_4Cl$ (20 mL) at 0° C., and then extracted with EtOAc (20 mL×2). The combined organic layer was washed with brine (20 mL×2), dried over $Na_2SO_4$, filtered and concentrated under reduced pressure to give a residue. The residue was purified by column chromatography ($SiO_2$, Petroleum ether/Ethyl acetate=1/10 to 3/1) to give 2-fluoro-4-[(5-formylindol-1-yl)methyl]benzonitrile (700 mg, 2.52 mmol, 73.03% yield).

$^1$H NMR (500 MHz, DMSO-$d_6$) δ ppm 9.94-10.05 (m, 1H), 8.14-8.27 (m, 1H), 7.82-7.93 (m, 1H), 7.70-7.75 (m, 1H), 7.63-7.68 (m, 2H), 7.33-7.38 (m, 1H), 7.08-7.14 (m, 1H), 6.75-6.81 (m, 1H), 5.57-5.72 (m, 2H).

Step B 2-fluoro-4-[[5-[3-isopropyl-1,1-dioxo-6-(3-oxoisoxazol-5-yl)-5-(2-tetrahydropyran-4-ylethyl)-2,3,4,7-tetrahydrothieno[3,2-b]pyridin-7-yl]indol-1-yl]methyl]benzonitrile

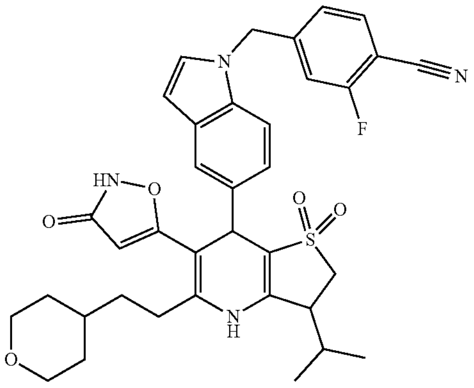 [SMILES: CC(C)C1CS(=O)(=O)C2=C1NC(CCC1CCOCC1)=C(c1cc(=O)[nH]o1)C2c1ccc2c(ccn2Cc2ccc(C#N)c(F)c2)c1]

To a solution of 4-isopropyl-1,1-dioxo-thiolan-3-one (28.50 mg, 161.71 μmol), 5-(2-oxo-4-tetrahydropyran-4-yl-butyl)isoxazol-3-one (38.69 mg, 161.71 μmol), 2-fluoro-4-[(5-formylindol-1-yl)methyl]benzonitrile (45 mg, 161.71 μmol) in AcOH (3 mL) was added $NH_4OAc$ (12.46 mg, 161.71 μmol). The mixture was stirred at 120° C. for 1 hr. The reaction mixture was concentrated under reduced pressure to give crude product 2-fluoro-4-[[5-[3-isopropyl-1,1-dioxo-6-(3-oxoisoxazol-5-yl)-5-(2-tetrahydropyran-4-yl-ethyl)-2,3,4,7-tetrahydrothieno[3,2-b]pyridin-7-yl]indol-1-yl]methyl]benzonitrile (110 mg, crude). LC-MS: m/z 657.2 $(M+H)^+$.

Step C 2-fluoro-4-[[5-[3-isopropyl-1,1-dioxo-6-(3-oxoisoxazol-5-yl)-5-(2-tetrahydropyran-4-ylethyl)-2,3-dihydrothieno[3,2-b]pyridin-7-yl]indol-1-yl]methyl]benzonitrile

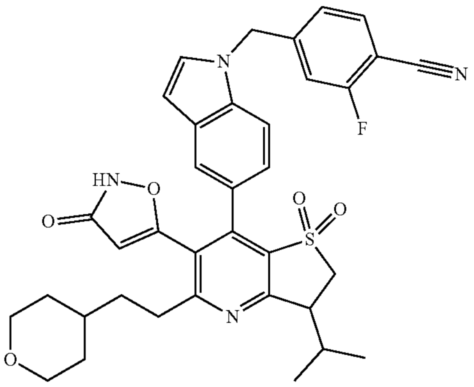 [SMILES: CC(C)C1CS(=O)(=O)c2c1nc(CCC1CCOCC1)c(-c1cc(=O)[nH]o1)c2-c1ccc2c(ccn2Cc2ccc(C#N)c(F)c2)c1]

To a solution of 2-fluoro-4-[[5-[3-isopropyl-1,1-dioxo-6-(3-oxoisoxazol-5-yl)-5-(2-tetrahydropyran-4-ylethyl)-2,3,4,7-tetrahydrothieno[3,2-b]pyridin-7-yl]indol-1-yl]methyl]benzonitrile (100 mg, 152.26 μmol) in DCM (3 mL) was added CAN (83.47 mg, 152.26 μmol). The mixture was stirred at 50° C. for 1 hr. The reaction mixture was concentrated under reduced pressure to give a residue. The crude product was purified by prep-HPLC (column: Boston Prime C18 150*30 mm*5 um; mobile phase: [water (NH3H2O +NH4HCO3)-ACN]; gradient: 22%-52% B over 11 min). 2-fluoro-4-[[5-[3-isopropyl-1,1-dioxo-6-(3-oxoisoxazol-5-yl)-5-(2-tetrahydropyran-4-ylethyl)-2,3-dihydrothieno[3,2-b]pyridin-7-yl]indol-1-yl]methyl]benzonitrile (1.86 mg, 2.84 μmol, 1.87% yield) was obtained.

$^1$H NMR (400 MHz, MeOD-$d_4$) δ ppm 7.64-7.71 (m, 2H), 7.34-7.39 (m, 1H), 7.25-7.30 (m, 1H), 7.02-7.13 (m, 3H), 6.57-6.60 (m, 1H), 5.57-5.63 (m, 1H), 5.48-5.53 (m, 2H), 3.87-3.94 (m, 2H), 3.67-3.77 (m, 2H), 3.44-3.50 (m, 1H), 3.36-3.41 (m, 2H), 2.76-2.86 (m, 3H), 1.67-1.75 (m, 2H), 1.54-1.66 (m, 3H), 1.22-1.29 (m, 2H), 1.13-1.16 (m, 3H), 0.88-0.92 (m, 3H). LC-MS: m/z 655.4 (M+H)$^+$.

4-[[5-[(2S)-7,7-dioxo-10-(3-oxoisoxazol-5-yl)-11-(2-tetrahydropyran-4-ylethyl)-7thia-6,12-diazatricyclo [6.4.0.02,6]dodeca-1(8),9,11-trien-9-yl]indol-1-yl] methyl]-2-fluoro-benzonitrile (Compound 200)

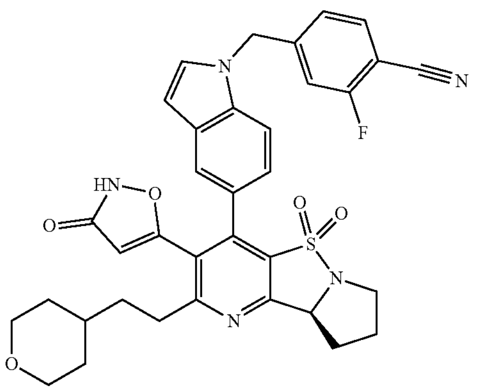

Compound 200 was synthesized using a similar procedure described in the Example 13 above by using the appropriate materials.

$^1$H NMR (400 MHz, MeOD-$d_4$) δ ppm 8.50-8.59 (m, 1H), 7.62-7.75 (m, 2H), 7.35-7.39 (m, 1H), 7.26-7.32 (m, 1H), 7.03-7.15 (m, 3H), 6.57-6.61 (m, 1H), 5.49-5.57 (m, 3H), 5.00-5.05 (m, 1H), 3.86-3.95 (m, 2H), 3.71-3.78 (m, 1H), 3.56-3.67 (m, 1H), 3.35-3.41 (m, 2H), 2.81-2.87 (m, 2H), 2.51-2.62 (m, 1H), 2.18-2.37 (m, 2H), 1.95-2.01 (m, 1H), 1.75-1.84 (m, 1H), 1.66-1.72 (m, 2H), 1.46-1.53 (m, 1H), 1.19 (s, 2H). LC-MS: m/z 654.4 (M+H)$^+$.

(S)-5-(4-(1-(3,4-difluorobenzyl)-1H-indol-5-yl)-5-oxo-2-(2-(tetrahydro-2H-pyran-4-yl)ethyl)-7,8,9,9a-tetrahydro-5H-pyrido[2,3-a]pyrrolizin-3-yl)isoxazol-3(2H)-one (Compound 201)

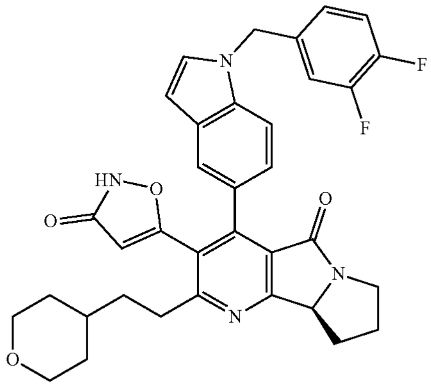 [SMILES: O=C1c2c(nc(CCC3CCOCC3)c(-c3cc(=O)[nH]o3)c2-c2ccc3c(ccn3Cc3ccc(F)c(F)c3)c2)[C@@H]2CCCN12]

Compound 201 was synthesized using a similar procedure described in the Example 26 above by using the appropriate materials.

$^1$H NMR (500 MHz, MeOD-$d_4$) δ 8.32-8.40 (m, 1H), 7.34-7.41 (m, 1H), 7.20-7.23 (m, 1H), 7.17 (d, J=8.39 Hz, 1H), 7.05-7.10 (m, 1H), 6.93-6.99 (m, 1H), 6.84-6.90 (m, 2H), 6.39-6.44 (m, 1H), 5.44-5.47 (m, 1H), 5.22-5.30 (m, 3H), 3.77-3.82 (m, 2H), 3.50-3.55 (m, 1H), 3.26-3.31 (m, 3H), 2.65-2.75 (m, 2H), 2.37-2.42 (m, 1H), 2.26-2.32 (m, 2H), 2.09 (t, J=7.63 Hz, 1H), 1.54-1.60 (m, 2H), 1.51 (m, 2H), 1.41-1.45 (m, 1H) 1.30-1.39 (m, 2H). LC-MS: m/z 611.2 (M+H)$^+$.

5-((9aS)-4-(1-(1-(3,4-difluorophenyl)ethyl)-1H-indol-5-yl)-5-oxo-2-(2-(tetrahydro-2H-pyran-4-yl) ethyl)-7,8,9,9a-tetrahydro-5H-pyrido[2,3-a]pyrrolizin-3-yl)isoxazol-3(2H)-one (Compound 202)

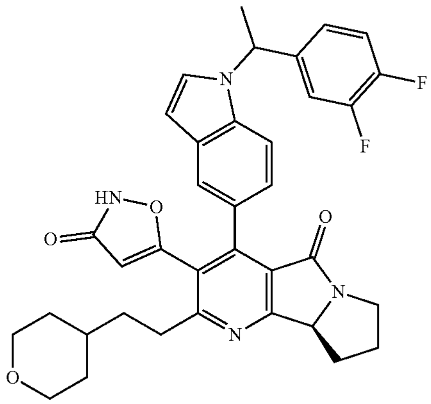 [SMILES: CC(c1ccc(F)c(F)c1)n1ccc2cc(-c3c4c(nc(CCC5CCOCC5)c3-c3cc(=O)[nH]o3)[C@@H]3CCCN3C4=O)ccc21]

Compound 202 was synthesized using a similar procedure described in the Example 25 above by using the appropriate materials.

$^1$H NMR (500 MHz, MeOD-$d_4$) δ 7.34-7.41 (m, 2H), 7.12-7.17 (m, 1H), 7.04-7.09 (m, 1H), 6.96-7.02 (m, 1H), 6.88-6.92 (m, 1H), 6.80-6.85 (m, 1H), 6.41-6.47 (m, 1H), 5.62-5.72 (m, 1H), 5.44-5.52 (m, 1H), 5.21-5.28 (m, 1H), 3.77-3.83 (m, 2H), 3.48-3.56 (m, 1H), 3.30 (m, 2H), 2.65-2.76 (m, 2H), 2.36-2.42 (m, 1H), 2.25-2.33 (m, 2H), 1.81 (m, 3H), 1.55-1.62 (m, 2H), 1.49 (d, J=13.28 Hz, 3H), 1.41 (m, 2H), 1.28-1.37 (m, 2H). LC-MS: m/z 625.2 $(M+H)^+$.

4-[[6-[(9aS)-5-oxo-3-(3-oxoisoxazol-5-yl)-2-(2-tetrahydropyran-4-ylethyl)-1,4,7,8,9,9a-hexahydropyrido[2,3-a]pyrrolizin-4-yl]-2-oxo-1,3-benzoxazol-3-yl]methyl]-2-fluoro-benzonitrile (Compound 203)

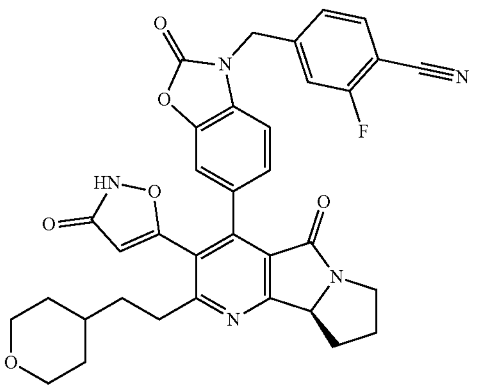

Compound 203 was synthesized using a similar procedure described in the Example 25 above by using the appropriate materials.

$^1$H NMR (500 MHz, MeOD-$d_4$) δ ppm 7.71-7.81 (m, 1H), 7.41-7.46 (m, 1H), 7.36-7.41 (m, 1H), 7.22-7.27 (m, 1H), 6.93-7.08 (m, 2H), 5.63-5.85 (m, 1H), 5.11-5.21 (m, 2H), 4.80-4.85 (m, 1H), 3.85-3.95 (m, 2H), 3.59-3.68 (m, 1H), 3.35-3.42 (m, 3H), 2.77-2.88 (m, 2H), 2.44-2.52 (m, 1H), 2.32-2.43 (m, 2H), 1.63 (s, 2H), 1.59 (d, J=13.89 Hz, 2H), 1.48-1.54 (m, 1H), 1.39-1.47 (m, 1H), 1.17-1.27 (m, 2H). LC-MS: m/z 636.3 $(M+H)^+$.

2-fluoro-4-(1-(5-((S)-5-oxo-3-(3-oxo-2,3-dihydroisoxazol-5-yl)-2-(2-(tetrahydro-2H-pyran-4-yl)ethyl)-7,8,9,9a-tetrahydro-5H-pyrido[2,3-a]pyrrolizin-4-yl)-1H-indol-1-yl)ethyl)benzonitrile (compound 204)

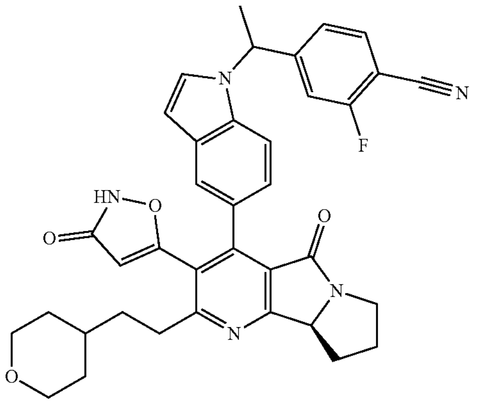

Compound 204 was synthesized using a similar procedure described in the Example 25 above by using the appropriate materials.

$^1$H NMR (500 MHz, MeOD-$d_4$) δ ppm 7.64-7.70 (m, 1H), 7.45-7.55 (m, 2H), 7.13-7.23 (m, 3H), 6.89-7.00 (m, 1H), 6.53-6.64 (m, 1H), 5.81-5.94 (m, 1H), 5.35-5.61 (m, 1H), 3.88-3.93 (m, 2H), 3.57-3.66 (m, 1H), 3.36-3.40 (m, 3H), 2.74-2.90 (m, 2H), 2.46-2.54 (m, 1H), 2.36-2.42 (m, 2H), 1.92-1.96 (m, 3H), 1.58-1.71 (m, 5H), 1.50-1.54 (m, 1H), 1.41-1.46 (m, 1H), 1.21-1.28 (m, 2H). LC-MS: m/z 632.4 $(M+H)^+$.

5-((S)-4-(7-(((R)-4-methoxy-2,3-dihydro-1H-inden-1-yl)amino)thieno[2,3-c]pyridin-2-yl)-5-oxo-2-(2-(tetrahydro-2H-pyran-4-yl)ethyl)-7,8,9,9a-tetrahydro-5H-pyrido[2,3-a]pyrrolizin-3-yl)isoxazol-3(2H)-one (Compound 205)

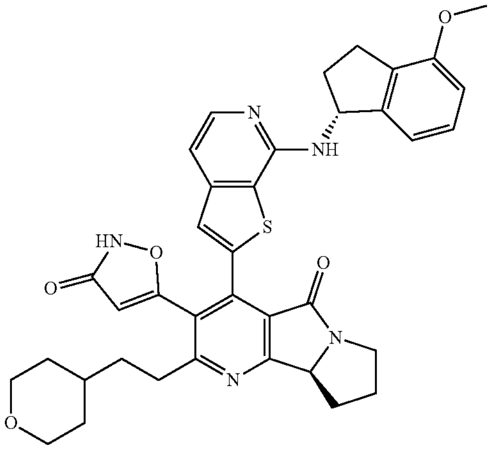 [SMILES: COc1cccc2c1CC[C@H]2Nc1nccc2cc(-c3c4c(nc(CCC5CCOCC5)c3-c3cc(=O)[nH]o3)[C@@H]3CCCN3C4=O)sc12]

Compound 205 was synthesized using a similar procedure described in the Example 25 above by using the appropriate materials.

$^1$H NMR (400 MHz, MeOD-$d_4$) δ ppm 7.88 (d, J=6.0 Hz, 1H), 7.31 (s, 1H), 7.16 (t, J=7.2 Hz, 1H), 7.09 (d, J=6.0 Hz, 1H), 6.89 (d, J=7.2 Hz, 1H), 6.81 (d, J=8.0 Hz, 1H), 5.93 (s, 1H), 5.75 (t, J=7.2 Hz, 1H), 3.89-3.92 (m, 1H), 3.87-3.89 (m, 1H), 3.83 (s, 3H), 3.61-3.69 (m, 1H), 3.35-3.45 (m, 3H), 2.99-3.07 (m, 1H), 2.81-2.89 (m, 2H), 2.74-2.80 (m, 1H), 2.35-2.71 (m, 5H), 1.95-2.03 (m, 1H), 1.63-1.71 (m, 2H), 1.59 (d, J=12.0 Hz, 2H), 1.41-1.48 (m, 1H), 1.20-1.32 (m, 3H). LC-MS: m/z 664.3 $(M+H)^+$.

(S)-5-(4-(7-((3,4-difluorobenzyl)amino)thieno[2,3-c]pyridin-2-yl)-5-oxo-2-(2-(tetrahydro-2H-pyran-4-yl)ethyl)-7,8,9,9a-tetrahydro-5H-pyrido[2,3-a]pyrrolizin-3-yl)isoxazol-3(2H)-one (Compound 206)

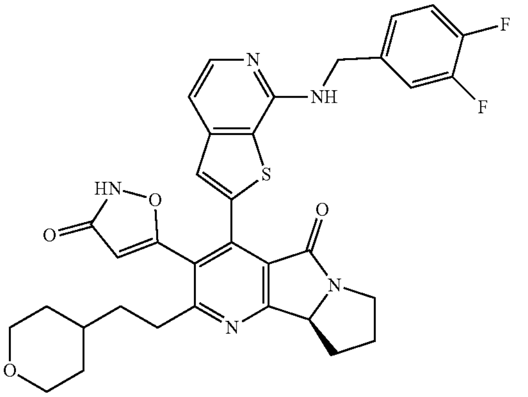 [SMILES: O=C1c2c(nc(CCC3CCOCC3)c(-c3cc(=O)[nH]o3)c2-c2cc3ccnc(NCc4ccc(F)c(F)c4)c3s2)[C@@H]2CCCN12]

Compound 206 was synthesized using a similar procedure described in the Example 25 above by using the appropriate materials.

$^1$H NMR (400 MHz, MeOD-$d_4$) δ 7.81-7.89 (m, 1H), 7.32-7.37 (m, 1H), 7.22-7.30 (m, 1H), 7.14-7.21 (m, 2H), 7.04-7.10 (m, 1H), 5.93-5.99 (m, 1H), 3.89-3.96 (m, 2H), 3.63-3.73 (m, 1H), 3.35-3.49 (m, 4H), 2.80-2.93 (m, 2H), 2.48-2.57 (m, 1H), 2.38-2.48 (m, 2H), 1.67-1.78 (m, 2H), 1.62 (d, J=12.99 Hz, 2H), 1.44-1.56 (m, 2H), 1.19-1.33 (m, 4H). LC-MS: m/z 644.1 $(M+H)^+$.

5-((S)-2-(4-fluorophenethyl)-4-(7-(((R)-4-methoxy-2,3-dihydro-1H-inden-1-yl)amino)-5-methylthieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 207)

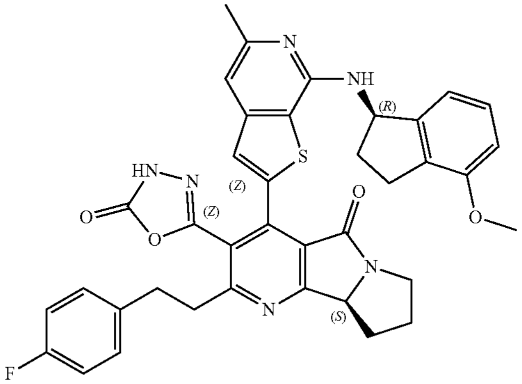

Compound 207 was synthesized using a similar procedure described in the Example 20 above by using the appropriate materials.

$^1$H NMR (400 MHz, DMSO-$d_6$): δ 7.29 (s, 1H), 7.18-7.24 (m, 2H), 7.03-7.15 (m, 4H), 6.90 (s, 1H), 6.86 (d, J=7.6 Hz, 1H), 6.82 (d, J=8.0 Hz, 1H), 5.92 (q, J=8.0 Hz, 1H), 4.84 (dd, J=6.0 Hz, J=9.6 Hz, 1H), 3.79 (s, 3H), 3.49-3.59 (m, 1H), 3.23-3.28 (m, 1H), 3.10-3.18 (m, 2H), 2.89-3.09 (m, 3H), 2.67-2.75 (m, 1H), 2.43-2.47 (m, 1H), 2.40 (s, 3H), 2.22-2.30 (m, 2H), 1.94-2.05 (m, 1H), 1.35-1.47 (m, 1H), 0.94 (t, J=7.2 Hz, 1H). $^{19}$F NMR (377 MHz, DMSO-$d_6$): −117.10. LC-MS: m/z 689.1 $(M+H)^+$.

(S)-3-((5-chloro-3-fluoropyridin-2-yl)methyl)-6-(2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)benzo[d]oxazol-2(3H)-one (Compound 208)

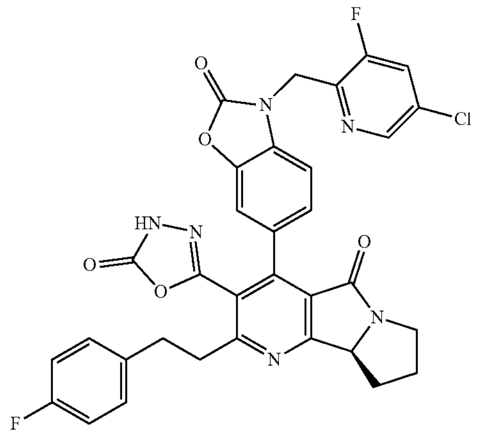

Compound 208 was synthesized using a similar procedure described in the Example 14 above by using the appropriate materials.

$^1$H NMR (400 MHz, $CDCl_3$) δ ppm 8.52-8.65 (m, 1H), 8.35-8.43 (m, 1H), 7.48-7.55 (m, 1H), 7.20-7.23 (m, 1H), 7.11-7.17 (m, 2H), 7.03-7.11 (m, 2H), 6.95-7.01 (m, 2H), 5.14-5.29 (m, 2H), 4.68-4.89 (m, 1H), 3.68-3.79 (m, 1H), 3.42 (ddd, J=11.80, 8.17, 3.87 Hz, 1H), 3.03-3.26 (m, 4H), 2.48-2.58 (m, 1H), 2.33-2.43 (m, 2H), 1.42-1.50 (m, 1H). LC-MS: m/z 657.2 $(M+H)^+$.

2-fluoro-4-(1-(6-((S)-2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)-2-oxobenzo[d]oxazol-3(2H)-yl)ethyl)benzonitrile (Compound 209)

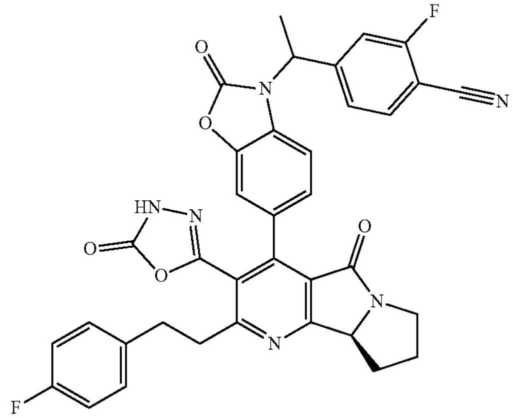 [SMILES: CC(c1ccc(C#N)c(F)c1)n1c(=O)oc2cc(-c3c4c(nc(CCc5ccc(F)cc5)c3-c3n[nH]c(=O)o3)[C@@H]3CCCN3C4=O)ccc21]

Compound 209 was synthesized using a similar procedure described in the Example 14 above by using the appropriate materials.

$^1$H NMR (400 MHz, $CDCl_3$) δ ppm 8.60-8.75 (m, 1H), 7.62-7.72 (m, 1H), 7.31-7.36 (m, 2H), 7.26-7.28 (m, 1H), 7.14 (dd, J=8.46, 5.48 Hz, 2H), 7.02-7.08 (m, 1H), 6.94-7.01 (m, 2H), 6.72-6.80 (m, 1H), 5.59-5.70 (m, 1H), 4.72-4.85 (m, 1H), 3.68-3.80 (m, 1H), 3.36-3.50 (m, 1H), 3.02-3.24 (m, 4H), 2.49-2.61 (m, 1H), 2.34-2.46 (m, 2H), 1.98 (br d, J=6.79 Hz, 3H), 1.39-1.53 (m, 1H). LC-MS: m/z 661.2 $(M+H)^+$.

(S)-5-(4-(1-((3,5-difluoropyridin-2-yl)methyl)-1H-pyrrolo[2,3-b]pyridin-5-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 210)

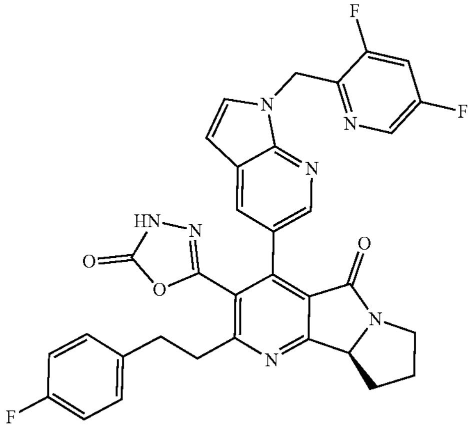 [SMILES: O=C1c2c(nc(CCc3ccc(F)cc3)c(-c3n[nH]c(=O)o3)c2-c2cnc3c(ccn3Cc3ncc(F)cc3F)c2)[C@@H]2CCCN12]

Compound 210 was synthesized using a similar procedure described in the Example 15 above by using the appropriate materials.

$^1$H NMR (400 MHz, DMSO-$d_6$) δ ppm 12.61 (s, 1H), 8.42 (d, J=2.38 Hz, 1H), 8.06 (d, J=2.03 Hz, 1H), 8.00 (td, J=9.48, 2.38 Hz, 1H), 7.93 (d, J=2.03 Hz, 1H), 7.64 (d, J=3.46 Hz, 1H), 7.19-7.27 (m, 2H), 7.08 (t, J=8.88 Hz, 2H), 6.57 (d, J=3.58 Hz, 1H), 5.69 (s, 2H), 4.86 (dd, J=10.37, 6.20 Hz, 1H), 3.45-3.57 (m, 1H), 3.29 (dd, J=11.50, 5.90 Hz, 1H), 3.15-3.20 (m, 2H), 2.97-3.12 (m, 1H), 2.96-3.12 (m, 1H), 2.32-2.42 (m, 2H), 2.22-2.31 (m, 2H), 1.34-1.49 (m, 1H). $^{19}$F NMR (376 MHz, DMSO-$d_6$) δ ppm −117.05 (s, 1 F), −121.62 (d, J=4.49 Hz, 1 F), −124.87 (d, J=6.73 Hz, 1 F). LC-MS: m/z 624.1 $(M+H)^+$.

(S)-5-(4-(1-((5-chloro-3-fluoropyridin-2-yl)methyl)-1H-pyrrolo[2,3-b]pyridin-5-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 211)

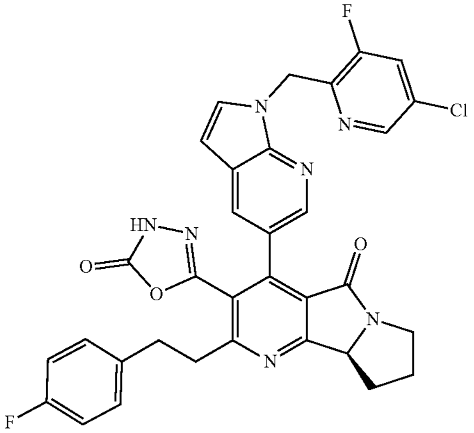 [SMILES: O=C1c2c(nc(CCc3ccc(F)cc3)c(-c3n[nH]c(=O)o3)c2-c2cnc3c(ccn3Cc3ncc(Cl)cc3F)c2)[C@@H]2CCCN12]

Compound 211 was synthesized using a similar procedure described in the Example 15 above by using the appropriate materials.

$^1$H NMR (400 MHz, DMSO-$d_6$) δ 12.57 (br s, 1H), 8.41 (d, J=1.2 Hz, 1H), 8.13 (dd, J=2.0 Hz, J=9.6 Hz, 1H), 8.04 (d, J=2.0 Hz, 1H), 7.92 (d, J=1.6 Hz, 1H), 7.63 (d, J=3.6 Hz, 1H), 7.20-7.24 (m, 2H), 7.05-7.10 (m, 2H), 6.56 (d, J=3.6 Hz, 1H), 5.69 (s, 2H), 4.85 (dd, J=10.0 Hz, J=6.4 Hz, 1H), 3.47-3.55 (m, 1H), 3.24-3.29 (m, 1H), 2.98-3.18 (m, 4H), 2.23-2.39 (m, 3H), 1.36-1.46 (m, 1H). $^{19}$F NMR (377 MHz, DMSO-$d_6$) δ −117.06, −122.91. LC-MS: m/z 640.2 $(M+H)^+$.

Example 27

5-(5-(4-fluorophenethyl)-3-isopropyl-7-(7-(((R)-4-methoxy-2,3-dihydro-1H-inden-1-yl)amino)thieno[2,3-c]pyridin-2-yl)-3-methyl-1,1-dioxido-2,3-dihydrothieno[3,2-b]pyridin-6-yl)-1,3,4-oxadiazol-2(3H)-one (Compound 212)

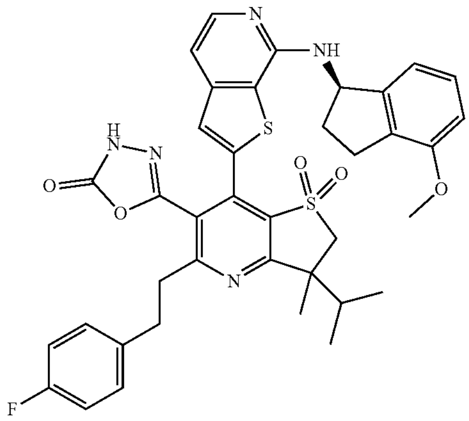

-continued
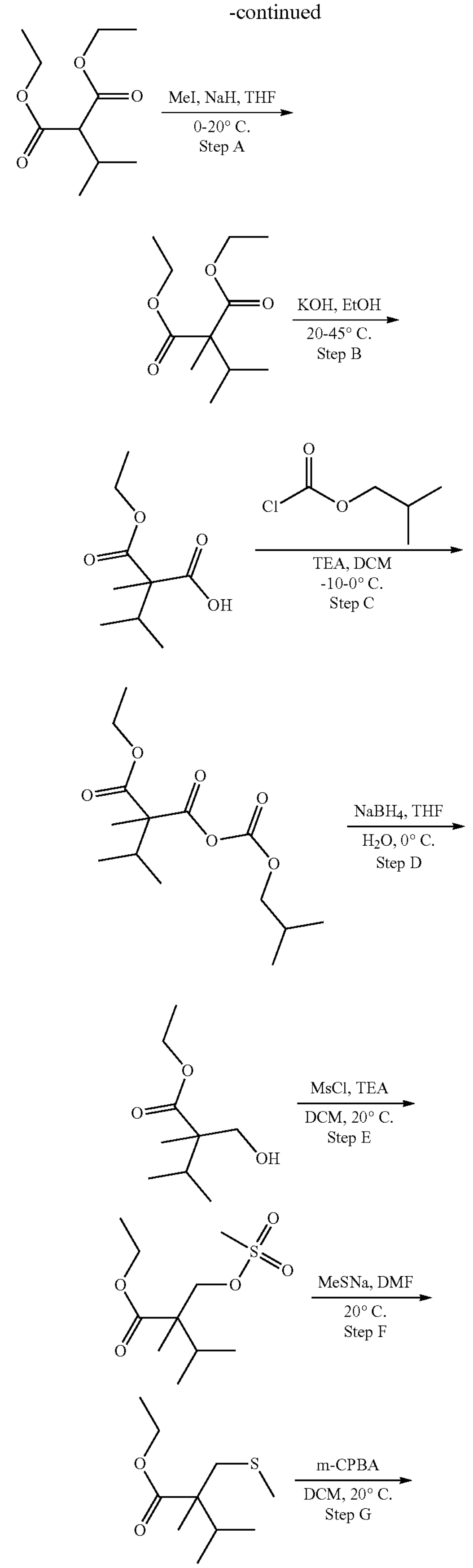
-continued
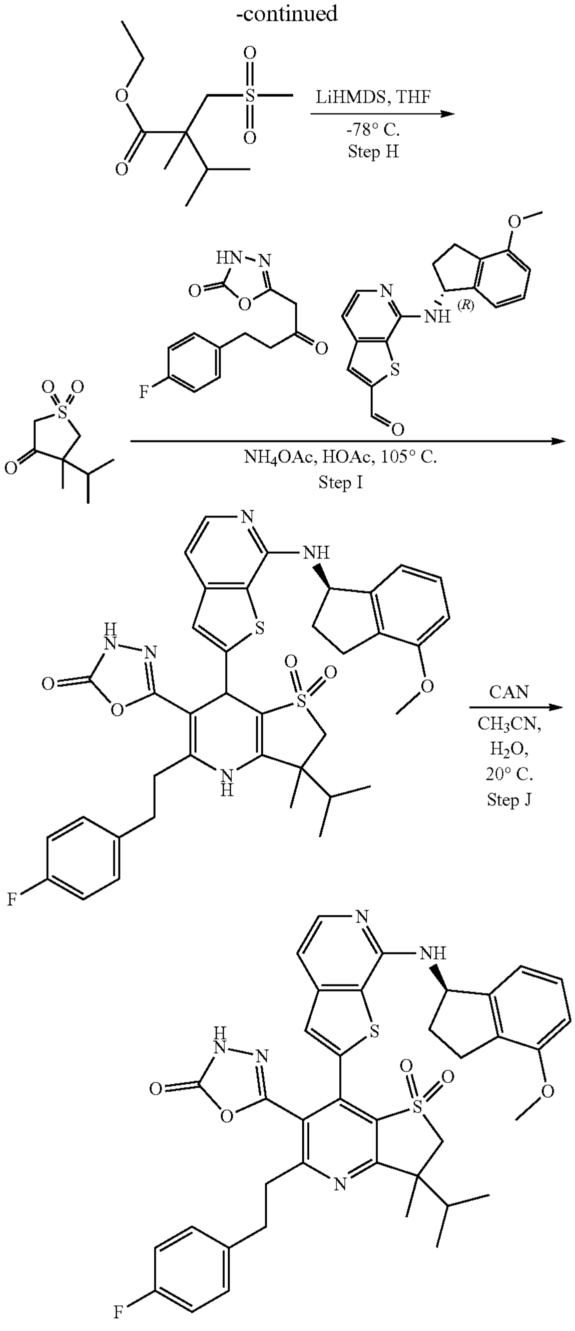
Step A diethyl 2-isopropyl-2-methylmalonate
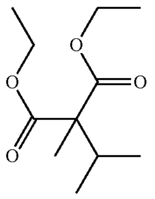
To a solution of diethyl 2-isopropylmalonate (5 g, 24.72 mmol) in THF (50 mL) was added NaH (1.09 g, 27.19 mmol, 60% purity) at 0° C. After addition, the mixture was stirred at this temperature for 0.5 hr, and then MeI (14.04 g, 98.89 mmol) was added at 0° C. The resulting mixture was stirred at 20° C. for 2 hrs. The reaction mixture was quenched by addition aq. $NH_4Cl$ (20 mL) at 0° C., and then diluted with ethyl acetate (20 mL) and extracted with ethyl acetate (50 mL×2). The combined organic layers were washed with brine (50 mL), dried over $Na_2SO_4$, filtered and concentrated under reduced pressure to give diethyl 2-isopropyl-2-methylmalonate (5.5 g, crude).

$^1H$ NMR (400 MHz, $CDCl_3$) δ 4.01-4.16 (m, 4H), 2.36-2.49 (m, 1H), 1.25 (m, 3H), 1.18 (t, J=7.09 Hz, 6H), 0.83-0.89 (m, 6H).

Step B 2-(ethoxycarbonyl)-2,3-dimethylbutanoic acid

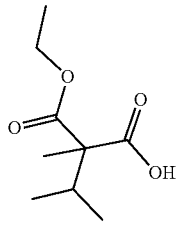

aq. KOH (1 M, 5.55 mL) was added under nitrogen dropwise to a solution of diethyl 2-isopropyl-2-methylmalonate (1.2 g, 5.55 mmol) in EtOH (10 mL) at 0° C. After the addition, the reaction was allowed to stir at 20° C. for 16 hrs. Then the reaction was allowed to stir at 45° C. for 16 hrs. The reaction was concentrated under reduced pressure to remove most of the ethanol. The residue was partitioned between water (10 mL) and ethyl acetate (10 mL). The aqueous layer was separated and acidified with 2 M HCl and extracted with ethyl acetate (10 mL×3). The combined extracts were dried (anhydrous $Na_2SO_4$) and the solvent removed under reduced pressure to give 2-ethoxycarbonyl-2,3-dimethyl-butanoic acid (650 mg, 62.24% yield).

$^1H$ NMR (400 MHz, $CDCl_3$) δ 4.12-4.22 (m, 2H), 2.31-2.47 (m, 1H), 1.30 (s, 3H), 1.21 (t, J=7.15 Hz, 3H), 0.90 (t, J=6.44 Hz, 6H).

Step C 2-(ethoxycarbonyl)-2,3-dimethylbutanoic (isobutyl carbonic) anhydride

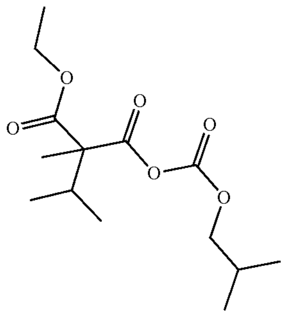 [SMILES: CCOC(=O)C(C)(C(=O)OC(=O)OCC(C)C)C(C)C]

To a stirring solution of 2-ethoxycarbonyl-2,3-dimethylbutanoic acid (0.65 g, 3.45 mmol) and triethylamine (419.34 mg, 4.14 mmol) in THF (10 mL) at −10° C., was added isobutyl carbonochloridate (518.82 mg, 3.80 mmol) dropwise. Then the reaction mixture was stirred 1 hr at 0° C. The insoluble material was filtered off, and the filtrate was directly used later.

Step D ethyl 2-(hydroxymethyl)-2,3-dimethylbutanoate

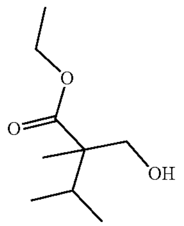

To an ice-cooling solution of $NaBH_4$ (392.13 mg, 10.36 mmol) in THF (7 mL) and $H_2O$ (1.5 mL) was added abbvie 2-(ethoxycarbonyl)-2,3-dimethylbutanoic (isobutyl carbonic) anhydride (THF solution) dropwise. After the reaction mixture was allowed to stirred at 0° C. for 1 h. Then reaction mixture was poured into 10% of aqueous solution HOAc (1 mL), the aqueous phase was extracted with ethyl acetate (20 ml×3), and the combined organic phase was washed with brine (10 mL), dried over $Na_2SO_4$, filtered and concentrated. The residue was purified by column chromatography ($SiO_2$, petroleum ether/ethyl acetate=1/0 to 1/1) to give ethyl 2-(hydroxymethyl)-2,3-dimethylbutanoate (350 mg, 58.15% yield).

$^1H$ NMR (500 MHz, $CDCl_3$) δ 4.14-4.23 (m, 2H), 3.72-3.81 (m, 1H), 3.44-3.52 (m, 1H), 2.04-2.15 (m, 1H), 1.25-1.32 (m, 3H), 1.08 (s, 3H), 0.85-0.93 (m, 6H).

Step E ethyl 2,3-dimethyl-2-(((methylsulfonyl)oxy)methyl)butanoate

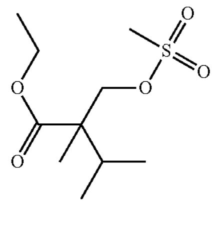 [SMILES: CCOC(=O)C(C)(COS(C)(=O)=O)C(C)C]

Under ice bath condition, MsCl (345.16 mg, 3.01 mmol) was added dropwise to ethyl 2-(hydroxymethyl)-2,3-dimethylbutanoate (350 mg, 2.01 mmol) and TEA (406.53 mg, 4.02 mmol) in a solution of DCM (5 mL). The mixture was stirred at 20° C. for 2 hrs. The reaction solution was diluted with dichloromethane (20 mL), washed with hydrochloric acid (10 mL, 1 M) and brine (10 mL). The organic phase was dried over anhydrous sodium sulfate, filtered and concentrated under reduced pressure to give ethyl 2,3-dimethyl-2-(methylsulfonyloxymethyl)butanoate (520 mg, crude).

$^1H$ NMR (400 MHz, $CDCl_3$) δ 4.34-4.47 (m, 1H), 4.02-4.19 (m, 3H), 2.93 (s, 3H), 1.89-2.01 (m, 1H), 1.18-1.25 (m, 3H), 1.12-1.16 (m, 3H), 0.81-0.90 (m, 6H).

Step F ethyl 2,3-dimethyl-2-((methylthio)methyl)butanoate

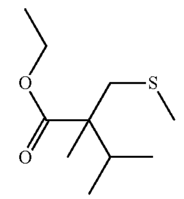

NaSMe (277.77 mg, 3.96 mmol) was added to a stirred solution of ethyl 2,3-dimethyl-2-(methylsulfonyloxymethyl) butanoate (500 mg, 1.98 mmol) in DMF (5 mL) at 20° C. The resulting brown suspension was stirred at 20° C. for 16 hrs. The reaction mixture was diluted with water (20 mL) and extracted with ethyl acetate (20 mL×3). The combined organic layer was dried over $Na_2SO_4$, filtered, and concentrated under vacuum to give ethyl 2,3-dimethyl-2-((methylthio)methyl)butanoate (350 mg, 86.44% yield).

$^1$H NMR (500 MHz, $CDCl_3$) δ 4.11-4.16 (m, 2H), 3.00 (s, 3H), 2.84-2.89 (m, 1H), 2.77-2.79 (m, 1H), 2.11 (s, 2H), 1.96-2.01 (m, 1H), 1.24-1.27 (m, 3H), 1.17-1.21 (m, 3H), 0.89-0.92 (m, 6H).

Step G ethyl 2,3-dimethyl-2-((methylsulfonyl)methyl)butanoate

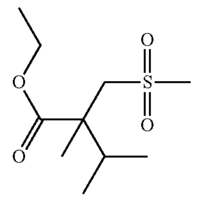

A mixture of ethyl 2,3-dimethyl-2-(methylsulfanylmethyl)butanoate (350 mg, 1.71 mmol) and m-CPBA (1.04 g, 5.14 mmol, 85% purity) in DCM (5 mL) was degassed and purged with $N_2$ for 3 times, and then the mixture was stirred at 20° C. for 16 hrs under $N_2$ atmosphere. The reaction mixture was quenched by addition aq. $NaS_2O_3$ (20 mL) at 0° C., and then diluted with DCM (20 mL) and extracted with DCM (20 mL×2). The combined organic layer was dried over $Na_2SO_4$, filtered and concentrated under reduced pressure to give a residue. The residue was purified by column chromatography ($SiO_2$, petroleum ether/ethyl acetate=1/0 to 50/50) to give ethyl 2,3-dimethyl-2-((methylsulfonyl) methyl)butanoate (290 mg, 71.64% yield).

$^1$H NMR (400 MHz, $CDCl_3$) δ 4.09-4.21 (m, 2H), 3.56-3.67 (m, 1H), 3.03-3.12 (m, 1H), 2.87 (s, 3H), 1.78-1.90 (m, 1H), 1.34 (s, 3H), 1.19-1.27 (m, 3H), 0.77-0.88 (m, 6H).

Step H 4-isopropyl-4-methyldihydrothiophen-3(2H)-one 1,1-dioxide

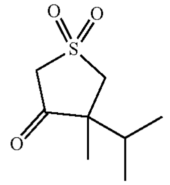

To a stirred solution of ethyl 2,3-dimethyl-2-(methylsulfonylmethyl)butanoate (290 mg, 1.23 mmol) in THF (3 mL) was added dropwise LiHMDS (1 M, 2.93 mL) at −78° C. with stirring under $N_2$. The reaction mixture was left to stir at −78° C. for 1 hr. The reaction mixture was quenched by addition of a saturated aqueous solution of $NH_4Cl$ (10 mL) at −10° C. with stirring. The resulting solution was concentrated in vacuo. The residue was purified by column chromatography ($SiO_2$, petroleum ether/ethyl acetate=1/0 to 1/1) to give 4-isopropyl-4-methyldihydrothiophen-3(2H)-one 1,1-dioxide (70 mg, 367.92 μmol, 29.98% yield).

$^1$H NMR (400 MHz, $CDCl_3$) δ 3.61-3.82 (m, 2H), 3.47-3.57 (m, 1H), 3.05-3.13 (m, 1H), 2.09-2.24 (m, 1H), 1.30-1.36 (m, 3H), 0.84-0.90 (m, 6H).

Step I 5-(5-(4-fluorophenethyl)-3-isopropyl-7-(7-(((R)-4-methoxy-2,3-dihydro-1H-inden-1-yl)amino) thieno[2,3-c]pyridin-2-yl)-3-methyl-1,1-dioxido-2,3,4,7-tetrahydrothieno[3,2-b]pyridin-6-yl)-1,3,4-oxadiazol-2(3H)-one

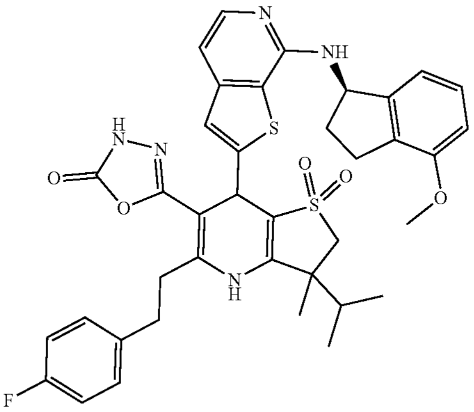 [SMILES: COc1cccc2c1CC[C@H]2Nc1nccc2cc(C3C(c4n[nH]c(=O)o4)=C(CCc4ccc(F)cc4)NC4=C3S(=O)(=O)CC4(C)C(C)C)sc12]

A HOAc (2 mL) solution of 4-isopropyl-4-methyldihydrothiophen-3(2H)-one 1,1-dioxide (26.61 mg, 139.87 μmol),5-(4-(4-fluorophenyl)-2-oxobutyl)-1,3,4-oxadiazol-2 (3H)-one (35 mg, 139.87 μmol), (R)-7-((4-methoxy-2,3-dihydro-1H-inden-1-yl)amino)thieno[2,3-c]pyridine-2-carbaldehyde (45.37 mg, 139.87 μmol) and acetic acid ammonia (21.56 mg, 279.75 μmol) was heated to 105° C. for 1 hr. The reaction mixture was quenched by addition $H_2O$ (5 mL) at 0° C., and then extracted with ethyl acetate (10 mL×2). The combined organic layer was washed with brine (10 mL), dried over $Na_2SO_4$, filtered and concentrated under reduced pressure to give 5-(5-(4-fluorophenethyl)-3-isopropyl-7-(7-(((R)-4-methoxy-2,3-dihydro-1H-inden-1-yl)

amino)thieno[2,3-c]pyridin-2-yl)-3-methyl-1,1-dioxido-2,3,4,7-tetrahydrothieno[3,2-b]pyridin-6-yl)-1,3,4-oxadiazol-2(3H)-one (100 mg, crude). LC-MS: m/z 728.1 $(M+H)^+$.

Step J 5-(5-(4-fluorophenethyl)-3-isopropyl-7-(7-(((R)-4-methoxy-2,3-dihydro-1H-inden-1-yl)amino)thieno[2,3-c]pyridin-2-yl)-3-methyl-1,1-dioxido-2,3-dihydrothieno[3,2-b]pyridin-6-yl)-1,3,4-oxadiazol-2(3H)-one

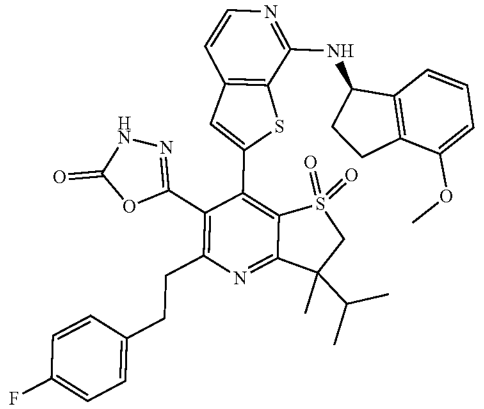 [SMILES: COc1cccc2c1CC[C@H]2Nc1nccc2cc(-c3c(-c4n[nH]c(=O)o4)c(CCc4ccc(F)cc4)nc4c3S(=O)(=O)CC4(C)C(C)C)sc12]

A mixture of 5-(5-(4-fluorophenethyl)-3-isopropyl-7-(7-(((R)-4-methoxy-2,3-dihydro-1H-inden-1-yl)amino)thieno[2,3-c]pyridin-2-yl)-3-methyl-1,1-dioxido-2,3,4,7-tetrahydrothieno[3,2-b]pyridin-6-yl)-1,3,4-oxadiazol-2(3H)-one (100 mg, 137.39 μmol) and CAN (150.64 mg, 274.78 μmol) in $CH_3CN$ (2 mL) and $H_2O$ (2 mL) was degassed and purged with $N_2$ for 3 times, and then the mixture was stirred at 20° C. for 2 hrs under $N_2$ atmosphere. The reaction mixture was filtered and concentrated under reduced pressure to give a residue. The residue was purified by column chromatography ($SiO_2$, DCM: MeOH=1/0 to 95/5) to give crude product. The crude product was purified by prep-HPLC (column: C18 150×30 mm; mobile phase: [water(FA)-ACN]; gradient: 35%-65% B over 6 min) to give 5-(5-(4-fluorophenethyl)-3-isopropyl-7-(7-(((R)-4-methoxy-2,3-dihydro-1H-inden-1-yl)amino)thieno[2,3-c]pyridin-2-yl)-3-methyl-1,1-dioxido-2,3-dihydrothieno[3,2-b]pyridin-6-yl)-1,3,4-oxadiazol-2(3H)-one (1.23 mg, 1.23% yield, 100% purity).

$^1$H NMR (500 MHz, MeOD-$d_4$) δ 7.83-7.88 (d, J=4.4 Hz, 1H), 7.58 (s, 1H), 6.99-7.08 (m, 4H), 6.82-6.89 (m, 2H), 6.77-6.78 (d, J=6 Hz, 1H), 6.68-6.69 (d, J=6.4 Hz, 1H), 5.67-5.73 (m, 1H), 3.72 (s, 3H), 3.56-3.62 (m, 1H), 3.27-3.32 (m, 1H), 2.98-3.04 (m, 2H), 2.88-2.96 (m, 1H), 2.62-2.71 (m, 1H), 2.50-2.58 (m, 1H), 2.41-2.49 (m, 1H), 1.93 (s, 2H), 1.49-1.55 (m, 1H), 1.47 (d, J=1.53 Hz, 3H), 0.94-0.98 (m, 3H), 0.66 (dd, J=6.79, 2.82 Hz, 3H). $^{19}$F NMR (376 MHz, MeOD-$d_4$) δ ppm −119.15 (s, 1 F). LC-MS: m/z 726.2 $(M+H)^+$.

(S)-6-((6-(2-(4-fluorophenethyl)-5,5-dioxido-3-(5-oxo-4,5-dihydro-1,3,4-oxadiazol-2-yl)-7,8,9,9a-tetrahydropyrrolo[1',2':2,3]isothiazolo[4,5-b]pyridin-4-yl)-2-oxobenzo[d]oxazol-3(2H)-yl)methyl)nicotinonitrile (Compound 213) 2

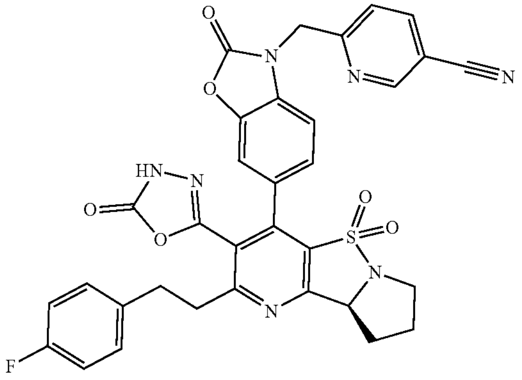 [SMILES: N#Cc1ccc(Cn2c(=O)oc3cc(-c4c(-c5n[nH]c(=O)o5)c(CCc5ccc(F)cc5)nc5c4S(=O)(=O)N4CCC[C@@H]54)ccc32)nc1]

Compound 213 was synthesized using a similar procedure described in the Example 14 above by using the appropriate materials.

$^1$H NMR (400 MHz, $CDCl_3$) δ ppm 8.82-8.89 (m, 1H), 8.15-8.22 (m, 1H), 7.59-7.70 (m, 1H), 7.41-7.50 (m, 1H), 7.13-7.21 (m, 4H), 6.95-7.01 (m, 2H), 5.29-5.33 (m, 2H), 5.07 (br dd, J=7.03, 4.65 Hz, 1H), 3.73-3.82 (m, 1H), 3.38-3.43 (m, 1H), 3.26-3.31 (m, 2H), 3.07-3.15 (m, 2H), 2.52-2.60 (m, 1H), 2.24-2.34 (m, 1H), 1.95-2.07 (m, 1H), 1.70-1.80 (m, 1H). LC-MS: m/z 666.1 $(M+H)^+$.

2-fluoro-4-((5-(2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)-1H-pyrrolo[2,3-b]pyridin-1-yl)methyl)benzonitrile (Compound 214)

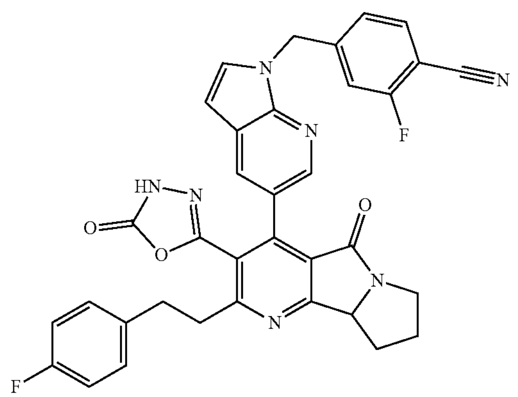

Compound 214 was synthesized using a similar procedure described in the Example 15 above by using the appropriate materials.

$^1$H NMR (400 MHz, DMSO-$d_6$) δ ppm 7.83-8.05 (m, 2H), 7.59-7.80 (m, 2H), 7.15-7.28 (m, 1H), 6.91-7.10 (m, 5H), 6.52-6.67 (m, 1H), 5.48-5.66 (m, 2H), 4.72-4.89 (m, 1H), 3.39-3.55 (m, 1H), 3.09-3.32 (m, 3H), 2.88-3.05 (m, 2H), 2.21-2.38 (m, 3H), 1.22-1.40 (m, 1H). $^{19}$F NMR (376 MHz, MeOD-$d_4$) δ ppm −77.28 (s, 1 F), −109.22 (s, 1 F), −118.93 (s, 1 F). LC-MS: m/z 630.1 $(M+H)^+$.

Example 28
5-((S)-2-(4-fluorophenethyl)-4-(7-(((R)-4-methoxy-2,3-dihydro-1H-inden-1-yl)amino)-5-(trifluoromethyl)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 215)
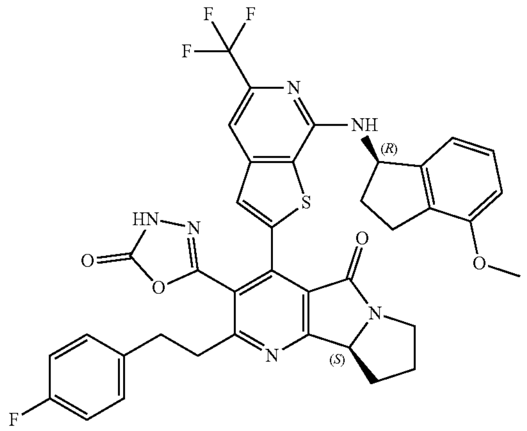
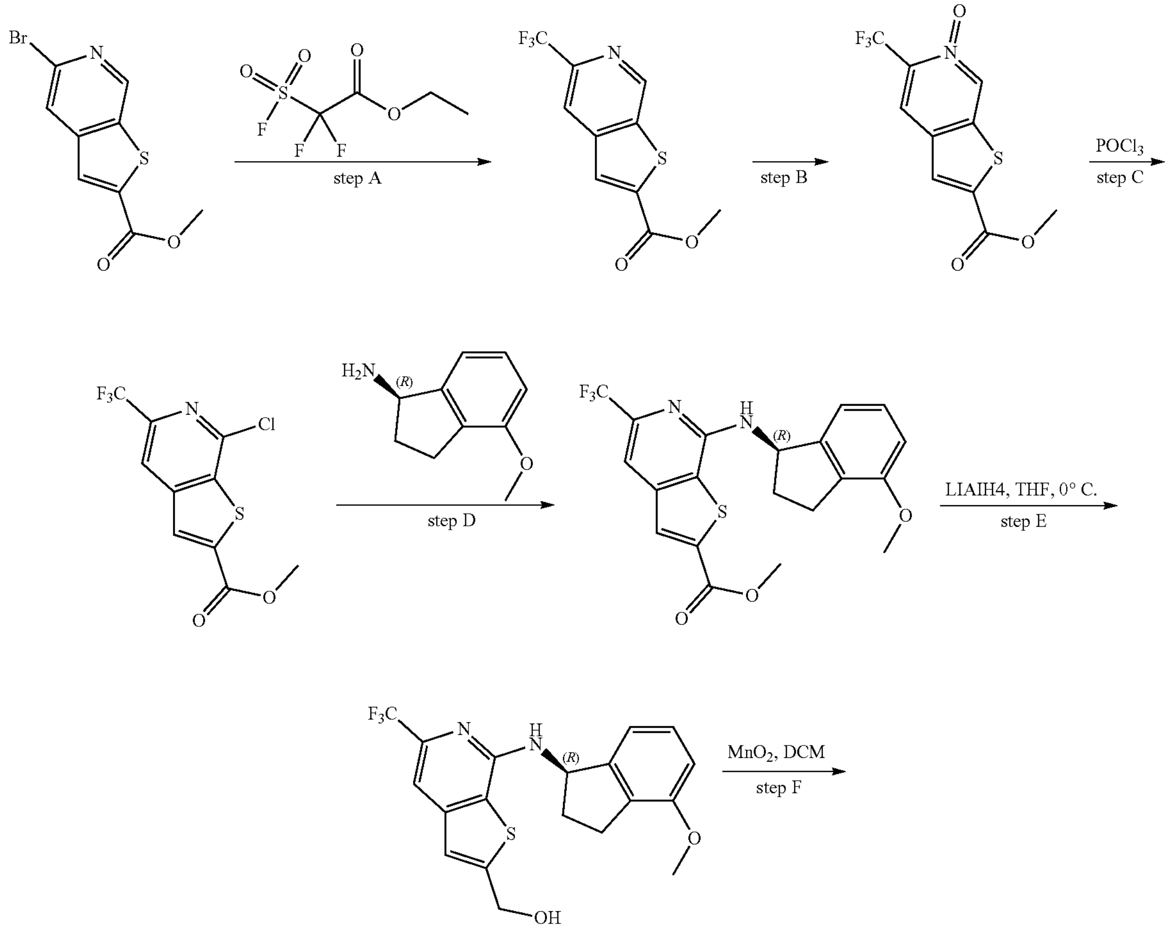

-continued
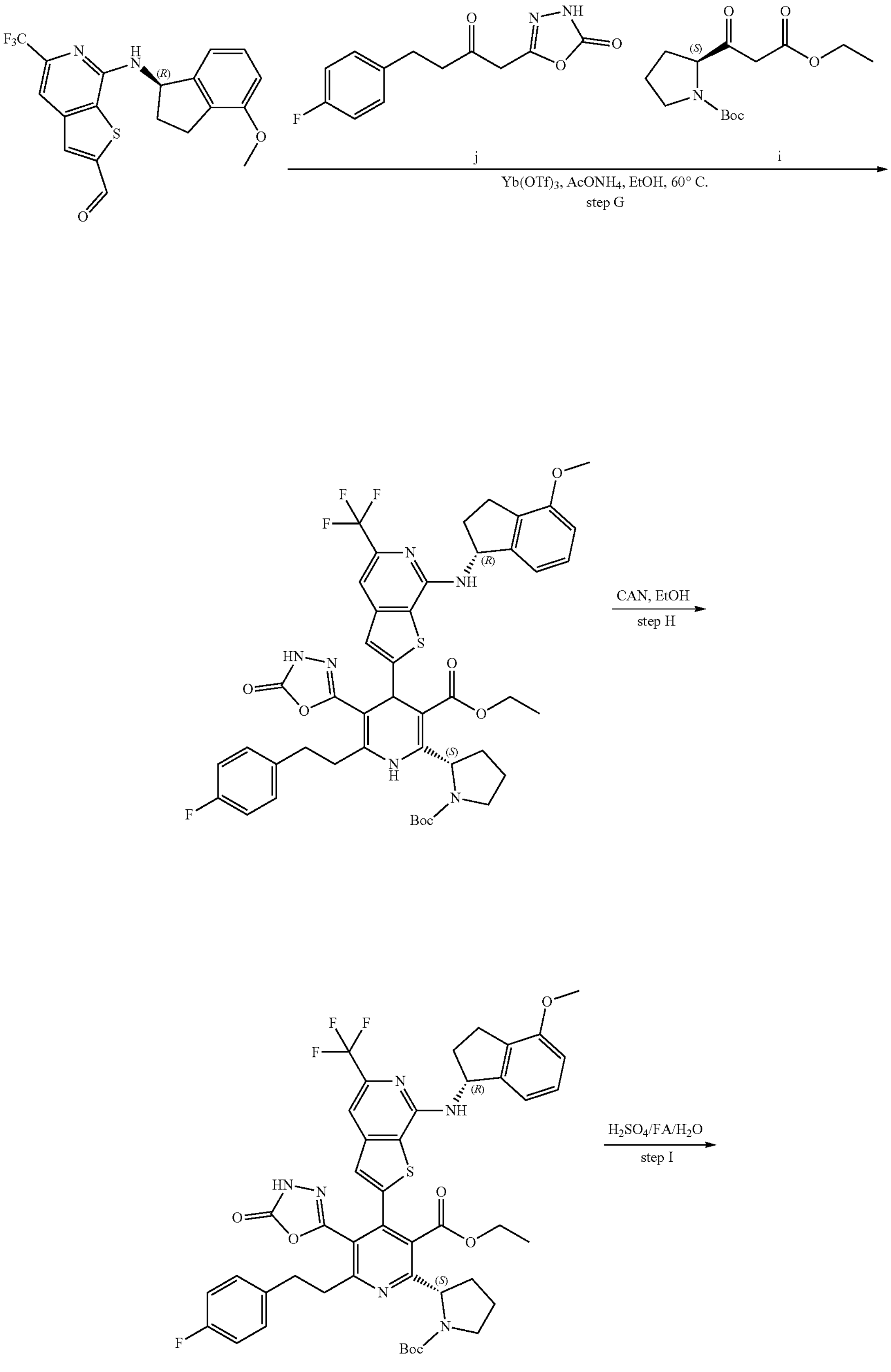

-continued

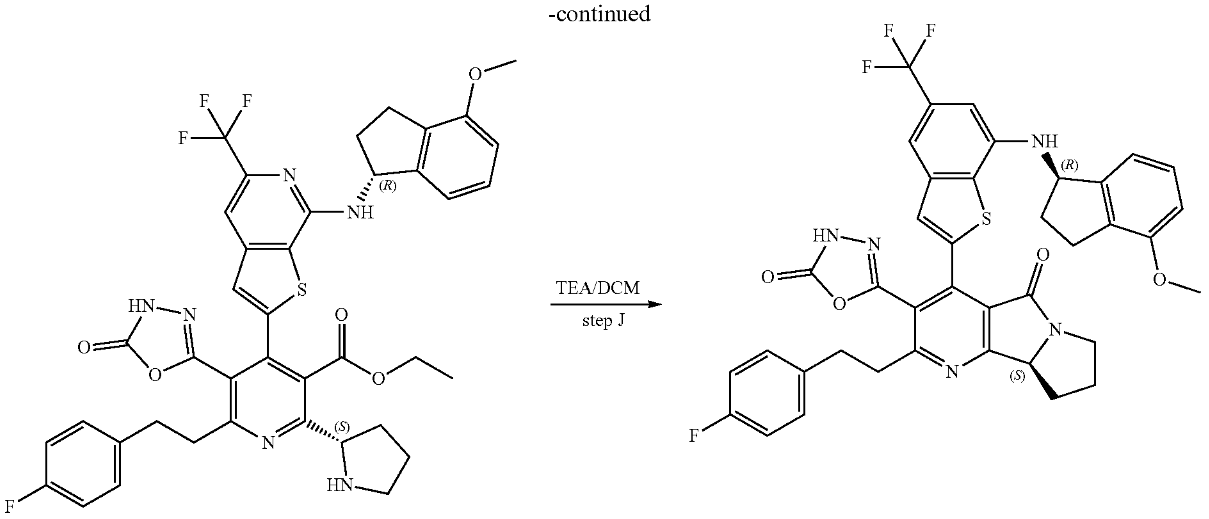

Step A methyl 5-(trifluoromethyl)thieno[2,3-c]pyridine-2-carboxylate

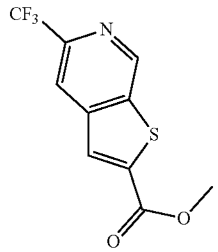 [SMILES: COC(=O)c1cc2cc(C(F)(F)F)ncc2s1]

A mixture of methyl 5-bromothieno[2,3-c]pyridine-2-carboxylate (500 mg, 1.837 mmol), ethyl 2,2-difluoro-2-(fluorosulfonyl)acetate (1764.94 mg, 9.187 mmol), CuI (1749.69 mg, 9.187 mmol), Cu (700.61 mg, 11.025 mmol) in DMF (20 mL) was stirred at 100° C. for 2h in seal tube, After the reaction was completed. The mixture reaction was diluted with EA, filtered and the filtrate was washed with water*3, dried and concentrated. The residue was purified by column chromatography on silica gel (PE/EA=10/1) to give methyl 5-(trifluoromethyl)thieno[2,3-c]pyridine-2-carboxylate (267 mg, 1.022 mmol, 55.63%). LC-MS: m/z 303.1 $(M+CH3CN+H)^+$.

Step B 2-(methoxycarbonyl)-5-(trifluoromethyl) thieno[2,3-c]pyridine 6-oxide

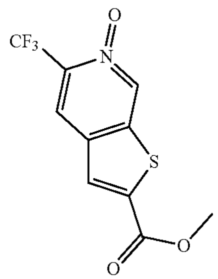 [SMILES: COC(=O)c1cc2cc(C(F)(F)F)[n+]([O-])cc2s1]

A mixture of methyl 5-(trifluoromethyl)thieno[2,3-c]pyridine-2-carboxylate (1.7 g, 6.508 mmol), dioxidane oxomethanediamine (82.83 mg, 0.880 mmol), TFAA (1.835 mL, 13.016 mmol) in DCM (5 mL) was stirred at room temperature overnight. After the reaction was completed, the mixture reaction was diluted with EA, washed with aq. $Na_2CO_3$, dried over $Na_2SO_4$. The organic layers were concentrated and purified by column chromatography on silica gel (MeOH/DCM=0% to 5%) to give 2-(methoxycarbonyl)-5-(trifluoromethyl)thieno[2,3-c]pyridine 6-oxide (1.1 g, 3.968 mmol, 60.97%). LC-MS: m/z 278.1 $(M+H)^+$.

Step C methyl 7-chloro-5-(trifluoromethyl)thieno[2,3-c]pyridine-2-carboxylate

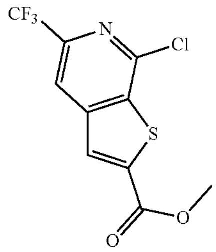 [SMILES: COC(=O)c1cc2cc(C(F)(F)F)nc(Cl)c2s1]

A mixture of 2-(methoxycarbonyl)-5-(trifluoromethyl) thieno[2,3-c]pyridine 6-oxide (1.1 g, 3.968 mmol), $POCl_3$ (3.643 mL, 39.680 mmol) in $CHCl_3$ (30 mL) was stirred at 60° C. overnight. After the reaction was completed, the mixture reaction was diluted with DCM, washed with aq. $Na_2CO_3$, filtered and the filtrate was and concentrated. The residue was purified by column chromatography on silica gel (PE/EA=10/1) to give methyl 7-chloro-5-(trifluoromethyl)thieno[2,3-c]pyridine-2-carboxylate (1.0 g, 3.382 mmol, 85.24%). LC-MS: m/z 295.9 $(M+H)^+$.

Step D methyl (R)-7-((4-methoxy-2,3-dihydro-1H-inden-1-yl)amino)-5-(trifluoromethyl)thieno[2,3-c]pyridine-2-carboxylate

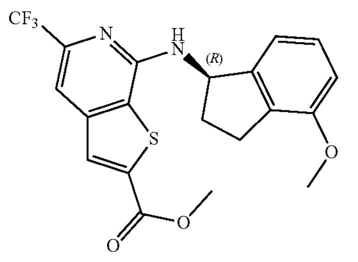

A mixture of methyl 7-chloro-5-(trifluoromethyl)thieno[2,3-c]pyridine-2-carboxylate (300 mg, 1.015 mmol), (R)-4-methoxy-2,3-dihydro-1H-inden-1-amine dihydrochloride (287.53 mg, 1.218 mmol), $Cs_2CO_3$ (991.81 mg, 3.044 mmol), $Pd_2(dba)_3$ (92.92 mg, 0.101 mmol), Xantphos (58.71 mg, 0.101 mmol) in Toluene (10 mL) was stirred at 110° C. overnight in seal tube. After the reaction was completed. The mixture reaction was concentrated. The residue was purified by column chromatography on silica gel (PE/EA=10/1) to give methyl (R)-7-((4-methoxy-2,3-dihydro-1H-inden-1-yl)amino)-5-(trifluoromethyl)thieno[2,3-c]pyridine-2-carboxylate (260 mg, 0.616 mmol, 60.66%). LC-MS: m/z 423.2 $(M+H)^+$.

Step E (R)-(7-((4-methoxy-2,3-dihydro-1H-inden-1-yl)amino)-5-(trifluoromethyl)thieno[2,3-c]pyridin-2-yl)methanol

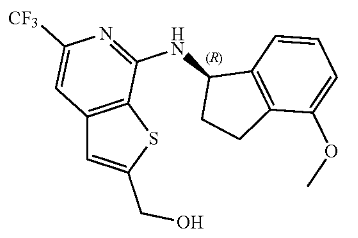

To a mixture of methyl (R)-7-((4-methoxy-2,3-dihydro-1H-inden-1-yl)amino)-5-(trifluoromethyl)thieno[2,3-c]pyridine-2-carboxylate (230 mg, 0.544 mmol) in THF (4 mL) was added $LiAlH_4$ (61.99 mg, 1.633 mmol) at 0° C., and stirred at room temperature for 3 h, After the reaction was completed. The mixture reaction was diluted with DCM, washed with aq. $NH_4Cl$, the organic phase was dried over $Na_2SO_4$, filtered and the filtrate was concentrated. The residue was purified by column chromatography on silica gel (PE/EA=20/1) to give (R)-(7-((4-methoxy-2,3-dihydro-1H-inden-1-yl)amino)-5-(trifluoromethyl)thieno[2,3-c]pyridin-2-yl)methanol (171 mg, 0.434 mmol, 79.63%). LC-MS: m/z 395.1 $(M+H)^+$.

Step F (R)-7-((4-methoxy-2,3-dihydro-1H-inden-1-yl)amino)-5-(trifluoromethyl)thieno[2,3-c]pyridine-2-carbaldehyde

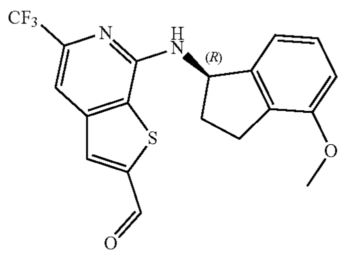

A mixture of (R)-(7-((4-methoxy-2,3-dihydro-1H-inden-1-yl)amino)-5-(trifluoromethyl)thieno[2,3-c]pyridin-2-yl)methanol (187 mg, 0.474 mmol), $MnO_2$ (824.41 mg, 9.483 mmol) in DCM (8 mL) was stirred at room temperature overnight. After the reaction was completed. The mixture reaction was concentrated. The residue was purified by column chromatography on silica gel (PE/EA=20/1) to give (R)-7-((4-methoxy-2,3-dihydro-1H-inden-1-yl)amino)-5-(trifluoromethyl)thieno[2,3-c]pyridine-2-carbaldehyde (150 mg, 0.382 mmol, 80.62%). LC-MS: m/z 393.1 $(M+H)^+$.

Step G 5-((S)-2-(4-fluorophenethyl)-4-(7-(((R)-4-methoxy-2,3-dihydro-1H-inden-1-yl)amino)-5-(trifluoromethyl)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one

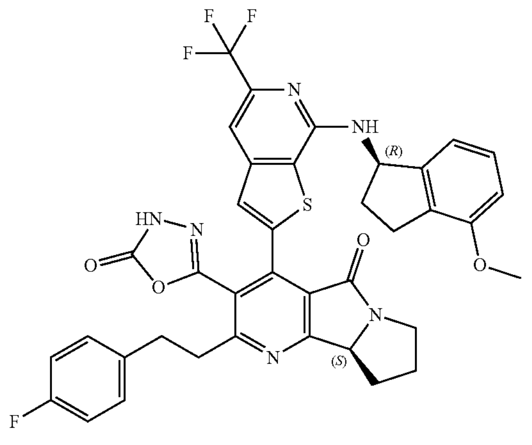

Compound 215 was synthesized using a similar procedure described in Example 21 by using the appropriate materials. (6.03 mg)

$^1H$ NMR (400 MHz, DMSO-d6): δ 12.72 (br s, 1H), 7.87 (d, J=8.0 Hz, 1H), 7.57 (d, J=9.2 Hz, 2H), 7.18-7.25 (m, 2H), 7.14 (t, J=8.0 Hz, 1H), 7.04-7.10 (m, 2H), 6.88 (d, J=7.6 Hz, 1H), 6.84 (d, J=8.4 Hz, 1H), 5.85 (q, J=7.6 Hz, 1H), 4.88 (dd, J=10.0 Hz, J=6.0 Hz, 1H), 3.79 (s, 3H), 3.48-3.60 (m, 1H), 3.23-3.32 (m, 1H), 3.20 (t, J=7.6 Hz, 2H), 2.93-3.12 (m, 3H), 2.67-2.79 (m, 1H), 2.22-2.43 (m, 4H), 2.00-2.10 (m, 1H), 1.38-1.50 (m, 1H). $^{19}F$ NMR (377 MHz, DMSO-d6): −66.31, −117.03. LC-MS: m/z 743.4 $(M+H)^+$.

Example 29
5-((S)-2-(4-fluorophenethyl)-4-(8-(((R)-4-methoxy-2,3-dihydro-1H-inden-1-yl)amino)-6-(trifluoromethyl)imidazo[1,2-a]pyridin-2-yl)-5-oxo-7,8,9,9a-tetrahydro-5H-pyrido[2,3-a]pyrrolizin-3-yl)-1,3,4-oxadiazol-2(3H)-one (Compound 216)
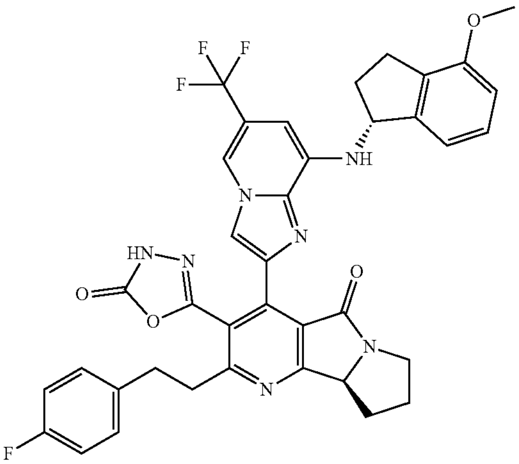
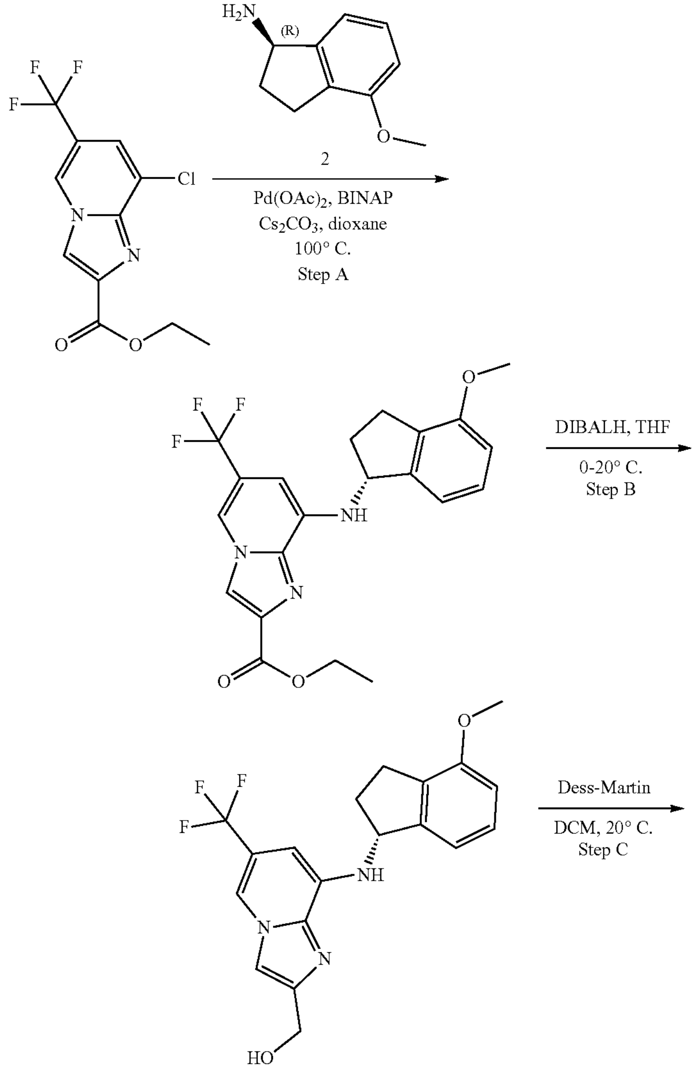

-continued
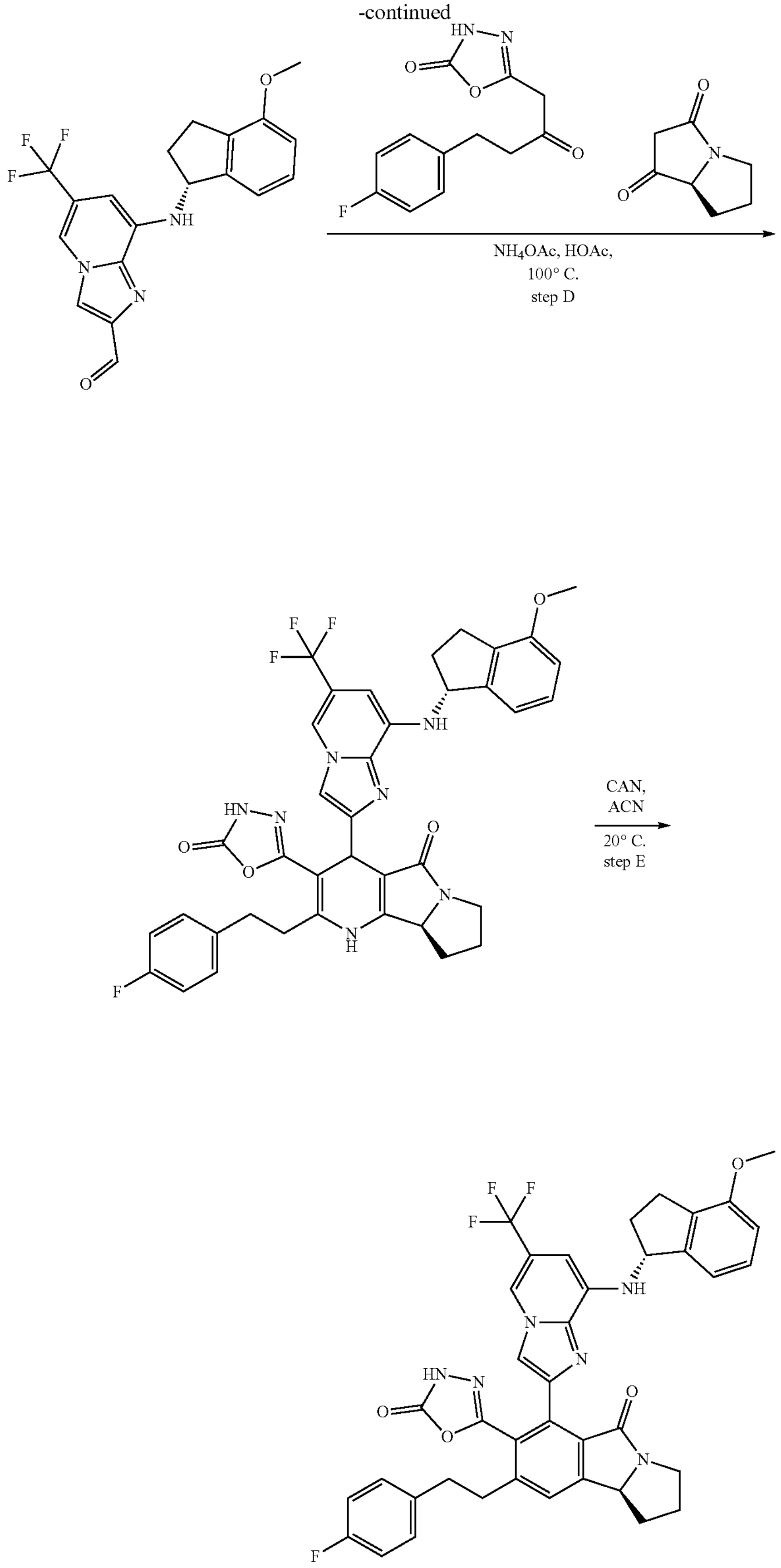

Step A ethyl (R)-8-((4-methoxy-2,3-dihydro-1H-inden-1-yl)amino)-6-(trifluoromethyl)imidazo[1,2-a]pyridine-2-carboxylate

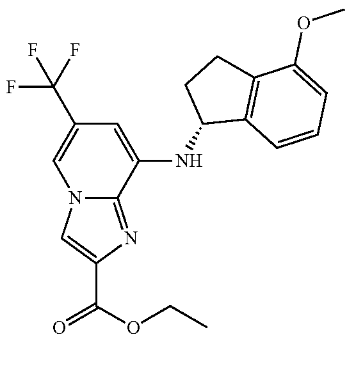 [SMILES: CCOC(=O)c1cn2cc(C(F)(F)F)cc(N[C@@H]3CCc4c(OC)cccc43)c2n1]

To a solution of ethyl 8-chloro-6-(trifluoromethyl)imidazo[1,2-a]pyridine-2-carboxylate (1 g, 3.42 mmol) in dioxane (5 mL) was added $Pd(OAc)_2$ (76.72 mg, 341.72 μmol), (R)-4-methoxy-2,3-dihydro-1H-inden-1-amine (613.51 mg, 3.76 mmol), $Cs_2CO_3$ (2.23 g, 6.83 mmol) and BINAP (255.33 mg, 410.06 μmol). The mixture was stirred at 100° C. for 16 hrs under $N_2$. The reaction mixture was concentrated under reduced pressure to remove solvent. The residue was purified by flash silica gel chromatography (ISCO®; 12 g SepaFlash® Silica Flash Column, Eluent of 0-60% Ethyl acetate/Petroleum ether gradient @40 mL/min). Compound ethyl (R)-8-((4-methoxy-2,3-dihydro-1H-inden-1-yl)amino)-6-(trifluoromethyl)imidazo[1,2-a]pyridine-2-carboxylate (953 mg, 2.27 mmol, 66.50% yield) was obtained.

$^1H$ NMR (400 MHz, $CDCl_3$) δ ppm 8.00-8.13 (m, 1H), 7.72-7.85 (m, 1H), 7.10-7.16 (m, 1H), 6.89-7.01 (m, 1H), 6.65-6.80 (m, 1H), 6.20-6.32 (m, 1H), 5.73-5.82 (m, 1H), 5.02-5.15 (m, 1H), 4.24-4.42 (m, 2H), 3.74-3.86 (m, 3H), 2.94-3.06 (m, 1H), 2.76-2.89 (m, 1H), 2.44-2.70 (m, 1H), 1.98-2.09 (m, 1H), 1.27-1.37 (m, 3H). LC-MS: m/z 420.0 $(M+H)^+$.

Step B (R)-(8-((4-methoxy-2,3-dihydro-1H-inden-1-yl)amino)-6-(trifluoromethyl)imidazo[1,2-a]pyridin-2-yl)methanol

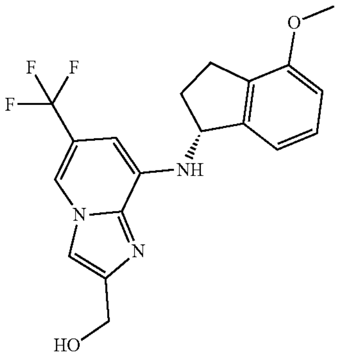 [SMILES: COc1cccc2c1CC[C@H]2Nc1cc(C(F)(F)F)cn2cc(CO)nc12]

To a solution of ethyl 8-[[(1R)-4-methoxyindan-1-yl]amino]-6-(trifluoromethyl)imidazo[1,2-a]pyridine-2-carboxylate (453 mg, 1.08 mmol) in THF (5 mL) was added dropwise DIBAL (1 M, 3.24 mL) at 0° C. over 3 min. The resulting mixture was stirred at 0-20° C. for 16 hrs. The reaction mixture was quenched by 1N HCl (5 mL) at 0° C., and then diluted with $H_2O$ (10 mL) and extracted with EtOAc (15 mL×3). The combined organic layers were washed with brine (20 mL), dried over $Na_2SO_4$, filtered and concentrated under reduced pressure to give a residue. The residue was purified by flash silica gel chromatography (ISCO®; 4 g SepaFlash® Silica Flash Column, Eluent of 0~80% Ethyl acetate/Petroleum ether gradient @40 mL/min). Compound (R)-(8-((4-methoxy-2,3-dihydro-1H-inden-1-yl)amino)-6-(trifluoromethyl)imidazo[1,2-a]pyridin-2-yl)methanol (300 mg, 73.60% yield) was obtained.

$^1H$ NMR (400 MHz, $CDCl_3$) δ ppm 7.67-7.78 (m, 1H), 7.29-7.39 (m, 1H), 7.08-7.15 (m, 1H), 6.86-7.00 (m, 1H), 6.65-6.77 (m, 1H), 6.23-6.31 (m, 1H), 5.88-6.06 (m, 1H), 4.96-5.11 (m, 1H), 4.47-4.71 (m, 2H), 3.69-3.84 (m, 3H), 2.91-3.02 (m, 1H), 2.73-2.82 (m, 1H), 2.41-2.63 (m, 1H), 1.87-2.03 (m, 1H), 1.12-1.25 (m, 1H).

Step C (R)-8-((4-methoxy-2,3-dihydro-1H-inden-1-yl)amino)-6-(trifluoromethyl)imidazo[1,2-a]pyridine-2-carbaldehyde

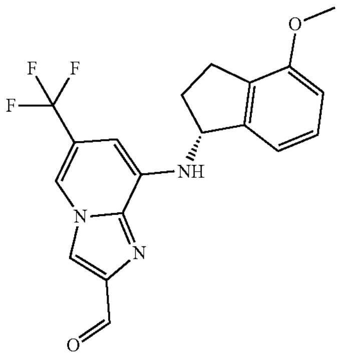 [SMILES: COc1cccc2c1CC[C@H]2Nc1cc(C(F)(F)F)cn2cc(C=O)nc12]

To a solution of (R)-(8-((4-methoxy-2,3-dihydro-1H-inden-1-yl)amino)-6-(trifluoromethyl)imidazo[1,2-a]pyridin-2-yl)methanol (300 mg, 795.00 μmol) in DCM (2 mL) was added Dess-Martin (674.38 mg, 1.59 mmol). The mixture was stirred at 20° C. for 16 hrs. The reaction mixture was quenched by addition $Na_2SO_3$ (10 mL) at 0° C., and then diluted with $H_2O$ (5 mL) and extracted with EtOAc (15 mL×3). The combined organic layers were washed with $Na_2SO_3$ (30 mL×3), dried over $Na_2SO_4$, filtered and concentrated under reduced pressure to give a residue. The residue was purified by flash silica gel chromatography (ISCO®; 12 g SepaFlash® Silica Flash Column, Eluent of 0~50% Ethyl acetate/Petroleum ether gradient @40 mL/min). Compound (R)-8-((4-methoxy-2,3-dihydro-1H-inden-1-yl)amino)-6-(trifluoromethyl)imidazo[1,2-a]pyridine-2-carbaldehyde (105 mg, 35.19% yield) was obtained.

$^1H$ NMR (400 MHz, $CDCl_3$) δ ppm 10.02-10.13 (m, 1H), 8.07-8.22 (m, 1H), 7.79-8.02 (m, 1H), 7.20-7.26 (m, 1H), 6.98-7.03 (m, 1H), 6.77-6.84 (m, 1H), 6.34-6.41 (m, 1H), 5.71-5.94 (m, 1 H), 5.06-5.23 (m, 1H), 3.81-3.99 (m, 3H), 3.02-3.11 (m, 1H), 2.83-2.97 (m, 1H), 2.62-2.70 (m, 1H), 2.09-2.14 (m, 1H), 2.04-2.13 (m, 1H).

Step D 5-((9aS)-2-(4-fluorophenethyl)-4-(8-(((R)-4-methoxy-2,3-dihydro-1H-inden-1-yl)amino)-6-(trifluoromethyl)imidazo[1,2-a]pyridin-2-yl)-5-oxo-1,5,7,8,9,9a-hexahydro-4H-pyrido[2,3-a]pyrrolizin-3-yl)-1,3,4-oxadiazol-2(3H)-one

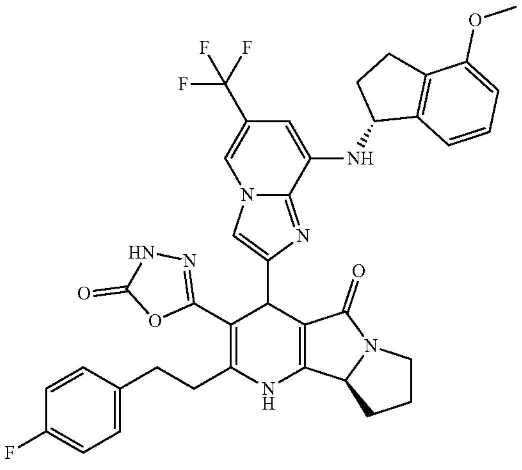 [SMILES: COc1cccc2c1CC[C@H]2Nc1cc(C(F)(F)F)cn2cc(C3C4=C(NC(CCc5ccc(F)cc5)=C3c3n[nH]c(=O)o3)[C@@H]3CCCN3C4=O)nc12]

To a solution of (R)-8-((4-methoxy-2,3-dihydro-1H-inden-1-yl)amino)-6-(trifluoromethyl)imidazo[1,2-a]pyridine-2-carbaldehyde (50 mg, 133.21 μmol) in HOAc (2 mL) was added $NH_4OAc$ (20.54 mg, 266.42 μmol), (S)-tetrahydro-1H-pyrrolizine-1,3(2H)-dione (27.80 mg, 199.82 μmol) and 5-(4-(4-fluorophenyl)-2-oxobutyl)-1,3,4-oxadiazol-2(3H)-one (33.33 mg, 133.21 μmol). The mixture was stirred at 100° C. for 1.5 hrs. The reaction mixture was concentrated under reduced pressure to remove solvent. The crude product 5-((9aS)-2-(4-fluorophenethyl)-4-(8-(((R)-4-methoxy-2,3-dihydro-1H-inden-1-yl)amino)-6-(trifluoromethyl)imidazo[1,2-a]pyridin-2-yl)-5-oxo-1,5,7,8,9,9a-hexahydro-4H-pyrido[2,3-a]pyrrolizin-3-yl)-1,3,4-oxadiazol-2(3H)-one (78 mg, 80.46% yield).

Step E 5-((S)-2-(4-fluorophenethyl)-4-(8-(((R)-4-methoxy-2,3-dihydro-1H-inden-1-yl)amino)-6-(trifluoromethyl)imidazo[1,2-a]pyridin-2-yl)-5-oxo-7,8,9,9a-tetrahydro-5H-pyrido[2,3-a]pyrrolizin-3-yl)-1,3,4-oxadiazol-2(3H)-one

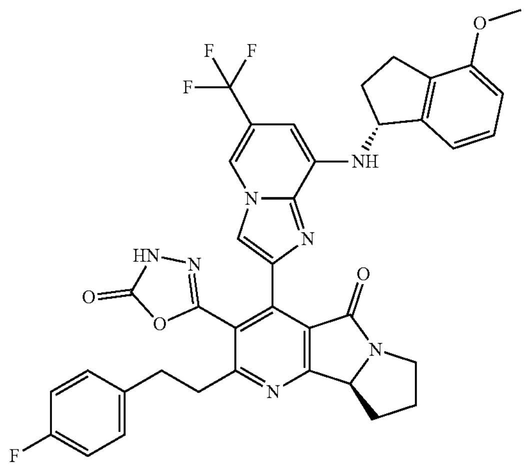 [SMILES: COc1cccc2c1CC[C@H]2Nc1cc(C(F)(F)F)cn2cc(-c3c4c(nc(CCc5ccc(F)cc5)c3-c3n[nH]c(=O)o3)[C@@H]3CCCN3C4=O)nc12]

To a solution of 5-((9aS)-2-(4-fluorophenethyl)-4-(8-(((R)-4-methoxy-2,3-dihydro-1H-inden-1-yl)amino)-6-(trifluoromethyl)imidazo[1,2-a]pyridin-2-yl)-5-oxo-1,5,7,8,9,9a-hexahydro-4H-pyrido[2,3-a]pyrrolizin-3-yl)-1,3,4-oxadiazol-2(3H)-one (83 mg, 114.06 μmol) in MeCN (2 mL) was added CAN (125.06 mg, 228.11 μmol). The mixture was stirred at 20° C. for 16 hrs. The reaction mixture was concentrated under reduced pressure to remove solvent. The residue was purified by prep-HPLC (column: Boston Green ODS 150*30 mm*5 um; mobile phase: [water(TFA)-ACN]; gradient: 75%-95% B over 11 min), further purified by prep-HPLC (column: Waters Xbridge BEH C18 100*30 mm*10 um; mobile phase: [water(NH4HCO3)-ACN]; gradient: 32%-62% B over 11 min). Compound 5-((S)-2-(4-fluorophenethyl)-4-(8-(((R)-4-methoxy-2,3-dihydro-1H-inden-1-yl)amino)-6-(trifluoromethyl)imidazo[1,2-a]pyridin-2-yl)-5-oxo-7,8,9,9a-tetrahydro-5H-pyrido[2,3-a]pyrrolizin-3-yl)-1,3,4-oxadiazol-2(3H)-one (1.3 mg, 1.79 μmol, 1.57% yield, 100% purity) was obtained.

$^1H$ NMR (400 MHz, MeOD-$d_6$) δ ppm 8.58-8.66 (m, 1H), 8.26-8.33 (m, 1H), 7.20-7.26 (m, 1H), 7.13-7.18 (m, 2H), 6.93-6.99 (m, 3H), 6.83-6.89 (m, 1H), 6.40-6.44 (m, 1H), 5.20-5.25 (m, 1H), 3.85-3.87 (m, 3H), 3.70-3.78 (m, 1H), 3.44-3.47 (m, 2H), 3.18-3.21 (m, 2H), 3.04-3.08 (m, 2H), 2.80-2.90 (m, 1H), 2.63-2.76 (m, 1H), 2.38-2.53 (m, 3H), 2.17-2.23 (m, 1H), 2.03-2.05 (m, 1H), 1.62-1.64 (m, 1H). LC-MS: m/z 726.2 $(M+H)^+$.

Example 30
5-((S)-2-(((R)-6-fluoro-2,3-dihydrobenzofuran-3-yl)methyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 217)
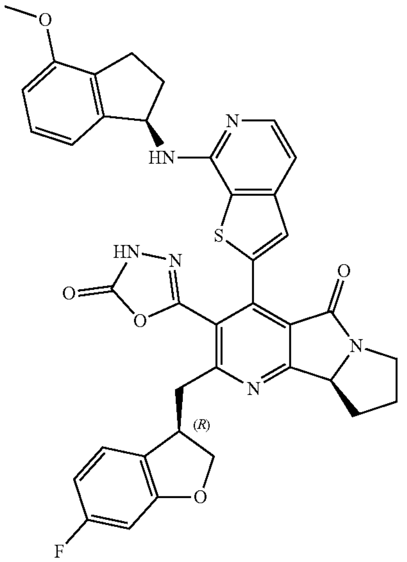
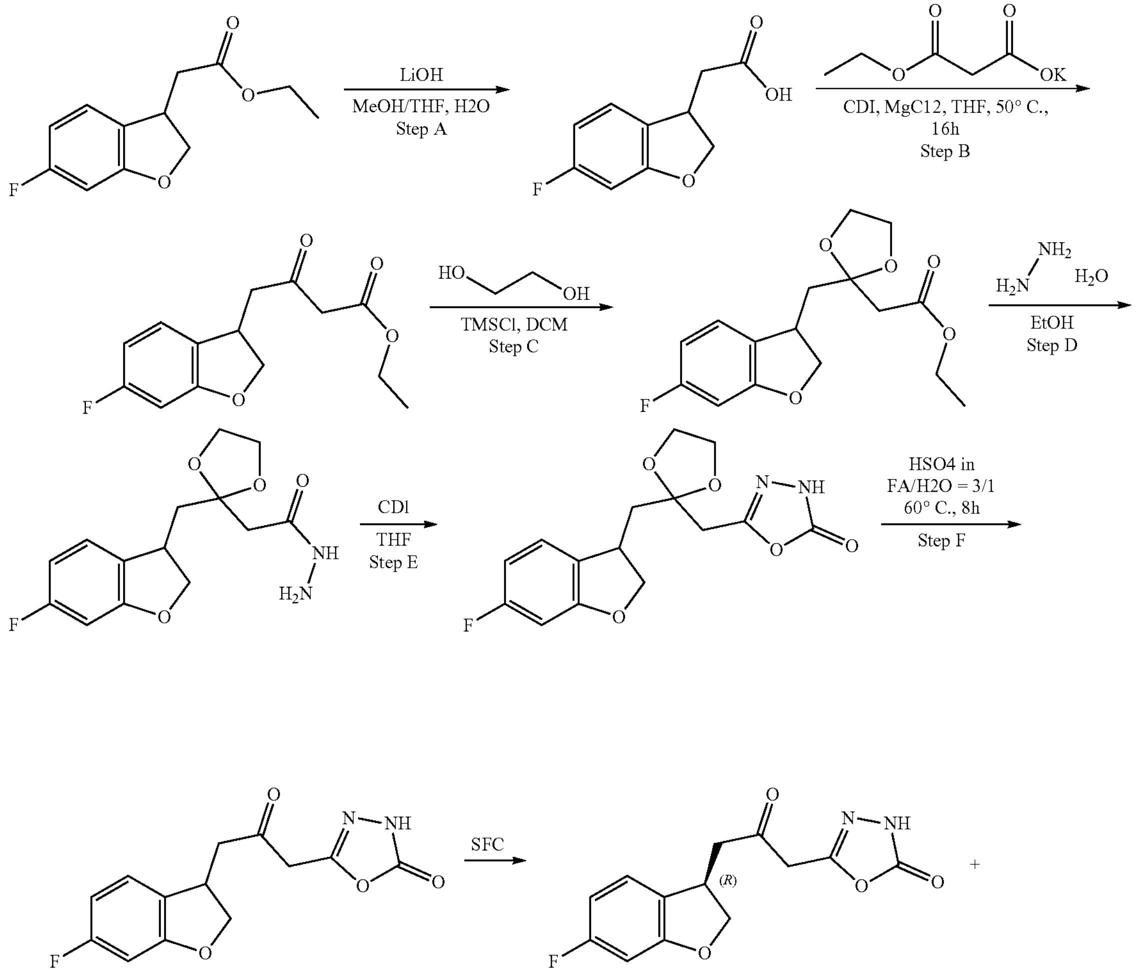

-continued

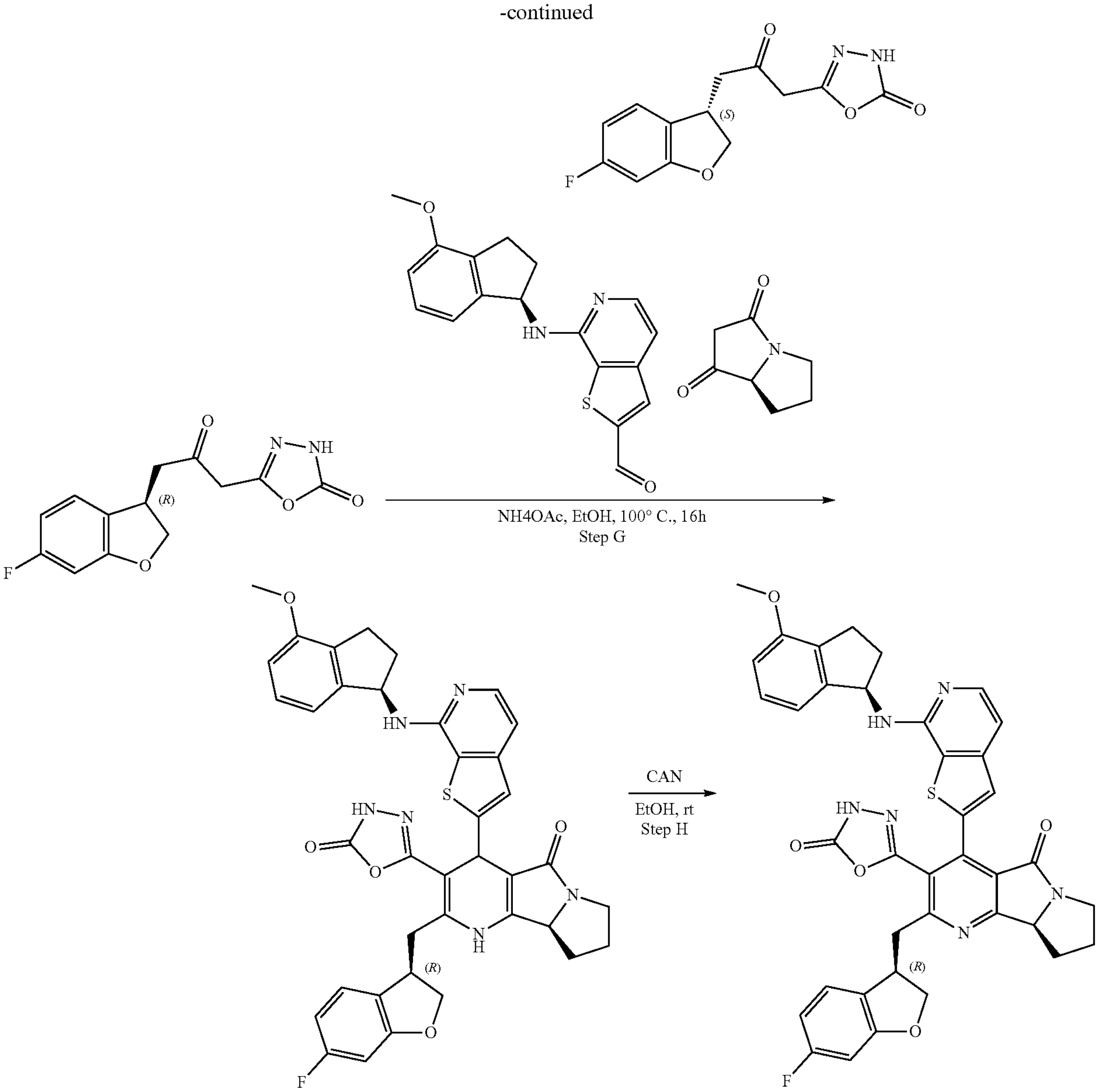

Step A
2-(6-fluoro-2,3-dihydrobenzofuran-3-yl)acetic acid

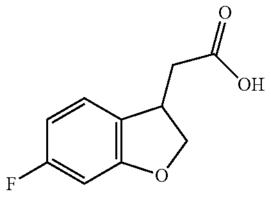 [SMILES: O=C(O)CC1COc2cc(F)ccc21]

To a solution of ethyl 2-(6-fluoro-2,3-dihydrobenzofuran-3-yl)acetate (4.7 g, 20.961 mmol) in MeOH/THF/H2O (20 mL/20 mL/10 mL) was added LiOH·$H_2O$ (4.4 g, 104.803 mmol). The reaction mixture was stirred at room temperature for 16 hours. The mixture was adjusted to pH=1 with 1N aq. HCl. Then the mixture was the reaction was diluted with water and extracted EtOAc. The organic layer was dried over $Na_2SO_4$, filtered and concentrated under reduced pressure to give 2-(6-fluoro-2,3-dihydrobenzofuran-3-yl)acetic acid (4.0 g, 97.28%).

Step B ethyl 4-(6-fluoro-2,3-dihydrobenzofuran-3-yl)-3-oxobutanoate

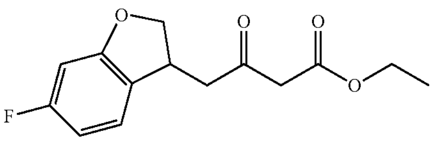 [SMILES: CCOC(=O)CC(=O)CC1COc2cc(F)ccc21]

To a solution of 2-(6-fluoro-2,3-dihydrobenzofuran-3-yl) acetic acid (3.9 g, 19.880 mmol) in THF (50 mL) were added CDI (4.84 g, 29.820 mmol) and the reaction was stirred at room temperature for 1 hr. Then added potassium 3-ethoxy-3-oxopropanoate (3.38 g, 19.880 mmol), $MgCl_2$ (1.95 g, 19.880 mmol) and the reaction was stirred at 50° C. for 18 hr. After the reaction was completed, the mixture was filtered and concentrated in vacuum, the residue was purified by silica gel column chromatography, eluting with ethyl acetate in petroleum ether to give ethyl 4-(6-fluoro-2,3-dihydrobenzofuran-3-yl)-3-oxobutanoate (4.8 g, 90.68%). LC-MS: m/z 267.1 $(M+H)^+$.

Step C ethyl 2-(2-((6-fluoro-2,3-dihydrobenzofuran-3-yl)methyl)-1,3-dioxolan-2-yl)acetate

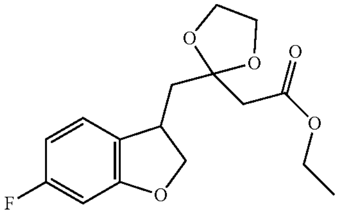 [SMILES: CCOC(=O)CC1(CC2COc3cc(F)ccc32)OCCO1]

A mixture of 4-(6-fluoro-2,3-dihydrobenzofuran-3-yl)-3-oxobutanoate (4.3 g, 16.149 mmol), ethane-1,2-diol (3.01 g, 48.447 mmol) and TMSCl (5.26 g, 48.447 mmol) in DCM (50 mL) was stirred at 40° C. for 16 hours. The reaction mixture was diluted with water and extracted EtOAc. The organic layer was separated, washed with brine, and concentrated in vacuo. The residue was purified by silica gel column chromatography, eluting with ethyl acetate in petroleum ether to give ethyl 2-(2-((6-fluoro-2,3-dihydrobenzofuran-3-yl)methyl)-1,3-dioxolan-2-yl)acetate (3.4 g, 67.85%). LC-MS: m/z 311.2 $(M+H)^+$.

Step D 2-(2-((6-fluoro-2,3-dihydrobenzofuran-3-yl)methyl)-1,3-dioxolan-2-yl)acetohydrazide

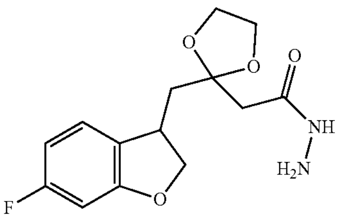 [SMILES: NNC(=O)CC1(CC2COc3cc(F)ccc32)OCCO1]

A mixture of ethyl 2-(2-((6-fluoro-2,3-dihydrobenzofuran-3-yl)methyl)-1,3-dioxolan-2-yl)acetate (3.4 g, 10.956 mmol) and $N_2H_4$·H2O (5.48 g, 109.564 mmol) in EtOH (50 mL) was stirred at 80° C. for 16 hours. The reaction mixture was diluted with water and extracted EtOAc. The organic layer was separated, washed with brine, and concentrated in vacuo. The residue was purified by silica gel column chromatography, eluting with ethyl acetate in petroleum ether to give ethyl 2-(2-((6-fluoro-2,3-dihydrobenzofuran-3-yl)methyl)-1,3-dioxolan-2-yl)acetate (2.4 g, 74.93%). LC-MS: m/z 297.2 $(M+H)^+$.

Step E 5-((2-((6-fluoro-2,3-dihydrobenzofuran-3-yl)methyl)-1,3-dioxolan-2-yl)methyl)-1,3,4-oxadiazol-2(3H)-one

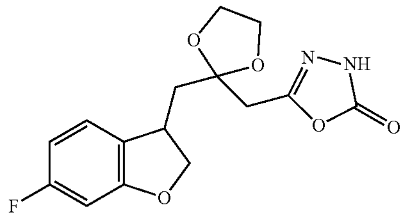 [SMILES: O=c1[nH]nc(CC2(CC3COc4cc(F)ccc43)OCCO2)o1]

A mixture of ethyl 2-(2-((6-fluoro-2,3-dihydrobenzofuran-3-yl)methyl)-1,3-dioxolan-2-yl)acetate (2.4 g, 8.100 mmol) and CDI (1.97 g, 12.150 mmol) in THF (40 mL) was stirred at 40° C. for 16 hours. The reaction mixture was diluted with water and extracted EtOAc. The organic layer was separated, washed with brine, and concentrated in vacuo. The residue was purified by silica gel column chromatography, eluting with ethyl acetate in petroleum ether to give 5-((2-((6-fluoro-2,3-dihydrobenzofuran-3-yl)methyl)-1,3-dioxolan-2-yl)methyl)-1,3,4-oxadiazol-2(3H)-one (3.4 g, 67.85%). LC-MS: m/z 345.2 $(M+Na)^+$.

Step F 5-(3-(6-fluoro-2,3-dihydrobenzofuran-3-yl)-2-oxopropyl)-1,3,4-oxadiazol-2(3H)-one

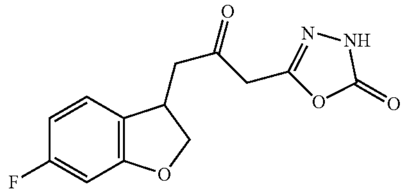 [SMILES: O=C(Cc1n[nH]c(=O)o1)CC1COc2cc(F)ccc21]

A mixture of 5-((2-((6-fluoro-2,3-dihydrobenzofuran-3-yl)methyl)-1,3-dioxolan-2-yl)methyl)-1,3,4-oxadiazol-2(3H)-one (2.3 g, 7.136 mmol) in 0.066 M $H_2SO_4$ in FA (15 mL) and $H_2O$ (5 mL), The reaction mixture was stirred at 60° C. for 8 hours. The reaction mixture was diluted with water and extracted EtOAc. The organic layer was separated, washed with brine, and concentrated in vacuo. The residue was purified by silica gel column chromatography, eluting with ethyl acetate in petroleum ether to give 5-(3-(6-fluoro-2,3-dihydrobenzofuran-3-yl)-2-oxopropyl)-1,3,4-oxadiazol-2(3H)-one (1.97 g, 99.21%). LC-MS: m/z 301.0 $(M+Na)^+$.

Compound 217 was synthesized using a similar procedure described in Example 10 by using the appropriate materials. (1.56 mg, 7.80%)

$^1H$ NMR (400 MHz, DMSO-$d_6$) δ 7.97 (d, J=5.6 Hz, 1H), 7.41 (d, J=5.2 Hz, 1H), 7.21 (d, J=8.4 Hz, 1H), 7.01-7.15 (m, 3H), 6.79-6.87 (m, 2H), 6.57-6.69 (m, 2H), 5.90 (q, J=8.0 Hz, 1H), 4.83-4.90 (m, 1H), 4.67-4.78 (m, 1H), 4.38-4.46 (m, 1H), 3.99-4.13 (m, 1H), 3.79 (s, 3H), 3.50-3.58 (m, 1H), 3.38-3.42 (m, 1H), 3.10-3.20 (m, 1H), 2.90-2.98 (m, 1H), 2.64-2.74 (m, 2H), 2.23-2.40 (m, 4H), 1.97-2.07 (m, 1H), 1.41-1.52 (m, 1H). $^{19}F$ NMR (377 MHz, DMSO-$d_6$) δ −114.04. LC-MS: m/z 703.1 $(M+H)^+$.

5-((S)-2-(((S)-6-fluoro-2,3-dihydrobenzofuran-3-yl)methyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 218)

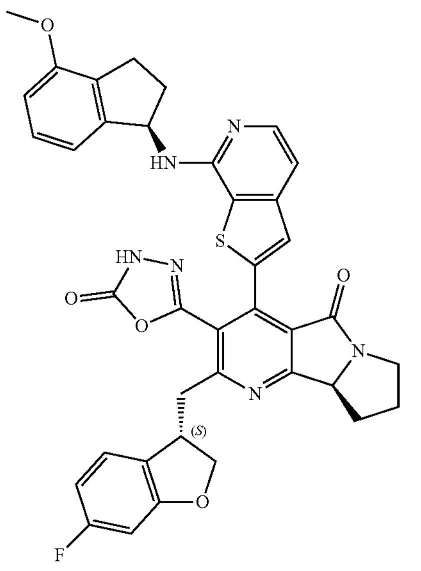

Compound 218 was synthesized using a similar procedure described in Example 30 by using the appropriate materials. (3.77 mg, 18.85%)

$^1$H NMR (400 MHz, DMSO-$d_6$) δ 7.97 (d, J=5.6 Hz, 1H), 7.42 (s, 1H), 7.23 (d, J=7.2 Hz, 1H), 7.02-7.13 (m, 3H), 6.79-6.87 (m, 2H), 6.57-6.68 (m, 2H), 5.90 (q, J=8.0 Hz, 1H), 4.94-4.91 (m, 1H), 4.68-4.78 (m, 1H), 4.38-4.47 (m, 1H), 3.99-4.15 (m, 1H), 3.79 (d, J=1.2 Hz, 3H), 3.51-3.59 (m, 1H), 3.36-3.42 (m, 1H), 3.11-3.22 (m, 1H), 2.90-2.99 (m, 1H), 2.54-2.74 (m, 2H), 2.23-2.41 (m, 4H), 1.97-2.07 (m, 1H), 1.42-1.54 (m, 1H). $^{19}$F NMR (377 MHz, DMSO-$d_6$) δ −114.02. LC-MS: m/z 703.1 $(M+H)^+$.

Example 31

(S)-5-(4-(1-(2,4-difluorobenzyl)isoquinolin-6-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 219)

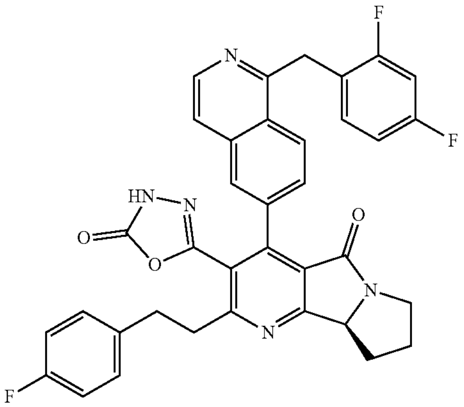

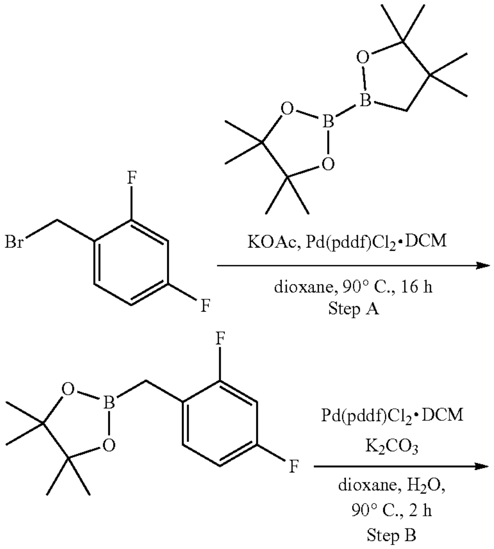

-continued

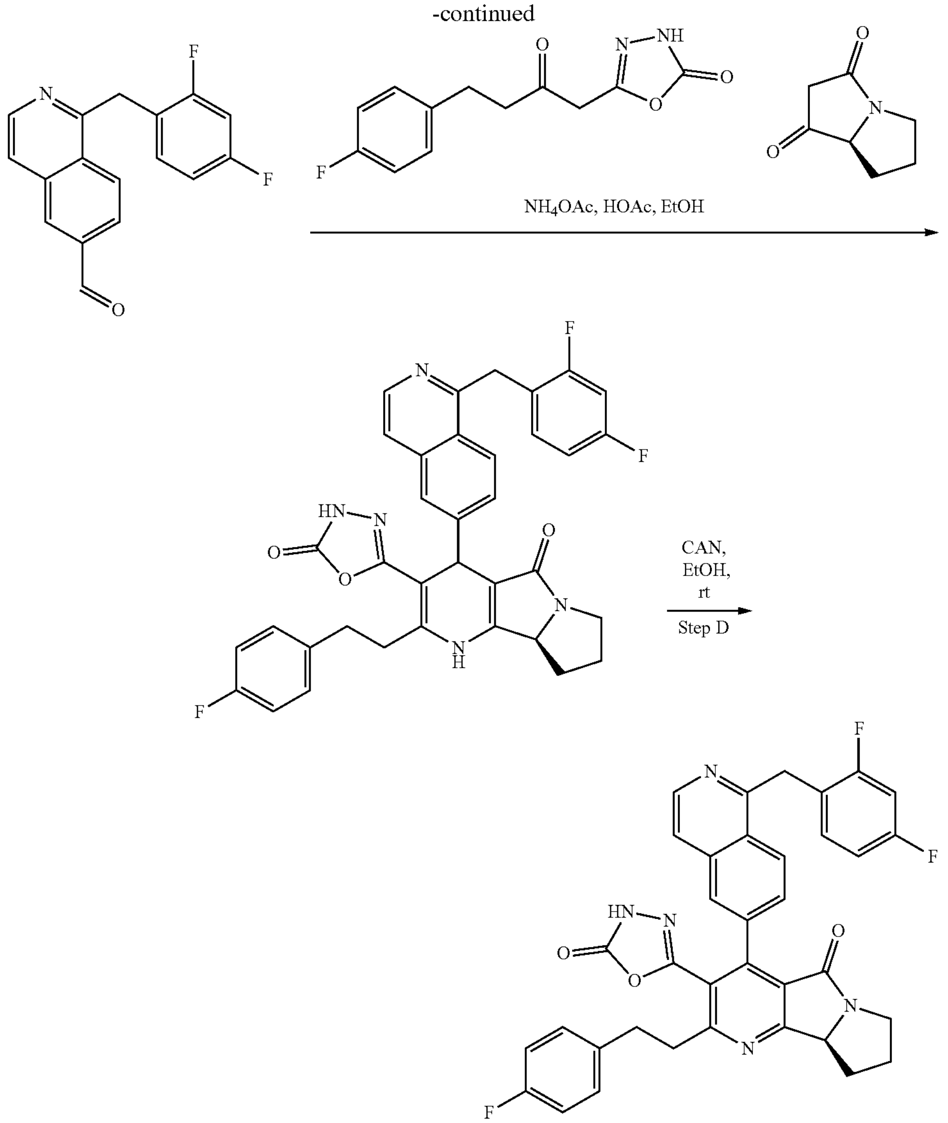

Step A 2-(2,4-difluorobenzyl)-4,4,5,5-tetramethyl-1,3,2-dioxaborolane

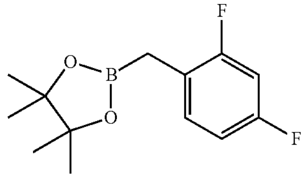 [SMILES: CC1(C)OB(Cc2ccc(F)cc2F)OC1(C)C]

To a solution of 1-(bromomethyl)-2,4-difluorobenzene (2 g, 9.67 mmol) in dioxane (50 mL) was added potassium acetate (2.84 g, 30.0 mmol), 4,4,4',4',5,5,5',5'-octamethyl-2,2'-bi(1,3,2-dioxaborolane) (3.48 g, 14.5 mmol), and Pd(pddf)$Cl_2$·DCM (0.79 g, 0.97 mmol). The reaction was stirred at 90° C. for 18 hours under $N_2$. The reaction was concentrated in vacuo. The residue was purified by silica gel column chromatography eluting with petroleum ether to afford 2-(2,4-difluorobenzyl)-4,4,5,5-tetramethyl-1,3,2-dioxaborolane (1 g, 40.74%). LC-MS: m/z 296.2 $(M+CH_3CN+H)^+$.

Step B
1-(2,4-difluorobenzyl)isoquinoline-6-carbaldehyde

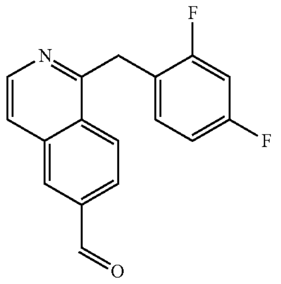 [SMILES: O=Cc1ccc2c(Cc3ccc(F)cc3F)nccc2c1]

To a solution of 2-(2,4-difluorobenzyl)-4,4,5,5-tetramethyl-1,3,2-dioxaborolane (796 mg, 3.13 mmol) in dioxane (10 mL) and water (1 mL) was added 1-chloroisoquinoline-6-carbaldehyde (200 mg, 1.04 mmol), potassium carbonate (433 mg, 3.13 mmol), and Pd(pddf)Cl2·DCM (91 mg, 0.10 mmol). The reaction was stirred at 90° C. for 2 hours under $N_2$. The reaction was concentrated in vacuo. The residue was purified by silica gel column chromatography eluting with ethyl acetate (5%) in petroleum ether to afford 1-(2,4-difluorobenzyl)isoquinoline-6-carbaldehyde (80 mg, 27.1%). LC-MS: m/z 284.0 $(M+H)^+$.

(S)-5-(4-(1-(2,4-difluorobenzyl)isoquinolin-6-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one

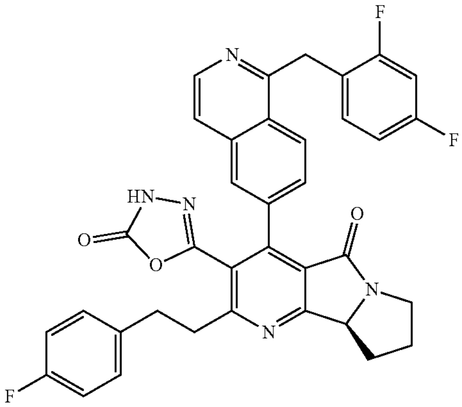 [SMILES: O=C1c2c(nc(CCc3ccc(F)cc3)c(-c3n[nH]c(=O)o3)c2-c2ccc3c(Cc4ccc(F)cc4F)nccc3c2)[C@@H]2CCCN12]

Compound 219 was synthesized using a similar procedure described in Example 15 by using the appropriate materials. $^1H$ NMR (400 MHz, DMSO-$d_6$): δ 8.38 (d, J=5.6 Hz, 1H), 8.31 (d, J=8.4 Hz, 1H), 7.86 (s, 1H), 7.69 (d, J=5.6 Hz, 1H), 7.53 (d, J=8.0 Hz, 1H), 7.29-7.36 (m, 1H), 7.19-7.26 (m, 3H), 7.06-7.12 (m, 2H), 6.98-7.04 (m, 1H), 4.86 (dd, J=6.8 Hz, J=10.4 Hz, 1H), 4.68 (s, 2H), 3.47-3.54 (m, 1H), 3.24-3.28 (m, 1H), 3.14-3.19 (m, 2H), 2.96-3.09 (m, 2H), 2.37-2.41 (m, 1H), 2.19-2.30 (m, 2H), 1.38-1.44 (m, 1H). $^{19}F$ NMR (377 MHz, DMSO-$d_6$): −112.29, −113.04, −117.13. LC-MS: m/z 634.1 $(M+H)^+$.

(S)-5-(4-(1-(2,4-difluorobenzyl)-1,2,3,4-tetrahydroquinolin-6-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 220)

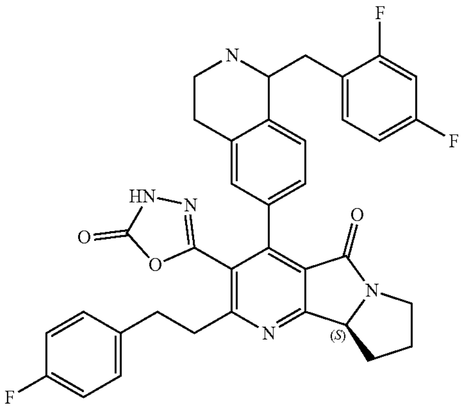

Compound 220 was synthesized using a similar procedure described in Example 15 by using the appropriate materials.

$^1H$ NMR (400 MHz, DMSO-$d_6$) δ 7.22-7.30 (m, 2H), 7.16-7.22 (m, 2H), 6.99-7.10 (m, 3H), 6.90 (d, J=2.0 Hz, 1H), 6.85 (dd, J=8.8 Hz, J=2.4 Hz, 1H), 6.46 (d, J=8.8 Hz, 1H), 4.75 (dd, J=9.6 Hz, J=6.0, 1H), 4.54 (s, 2H), 3.48-3.59 (m, 2H), 2.98-3.08 (m, 4H), 2.89-2.97 (m, 1H), 2.46-2.72 (m, 3H), 2.18-2.38 (m, 3H), 1.86-1.98 (m, 2H), 1.30-1.37 (in, 1H). $^{19}F$ NMR (377 MHz, DMSO-$d_6$) δ −112.40, −113.54, −117.17. LC-MS: m/z 638.4 $(M+H)^+$.

(S)-5-(4-(3-(2,4-difluorobenzyl)benzo[d]isoxazol-6-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 221)

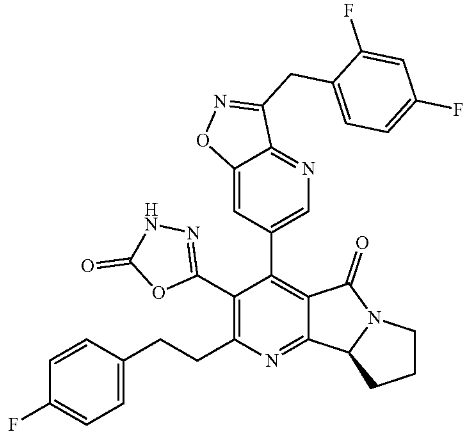 [SMILES: O=C1c2c(nc(CCc3ccc(F)cc3)c(-c3n[nH]c(=O)o3)c2-c2cnc3c(Cc4ccc(F)cc4F)noc3c2)[C@@H]2CCCN12]

Compound 221 was synthesized using a similar procedure described in Example 31 by using the appropriate materials.

$^1H$ NMR (400 MHz, DMSO-$d_6$): δ 12.56 (br s, 1H), 7.76 (d, J=7.6 Hz, 1H), 7.69 (br s, 1H), 7.55-7.63 (m, 1H), 7.16-7.31 (m, 4H), 7.04-7.12 (m, 3H), 4.86 (dd, J=6.0 Hz, J=10.0 Hz, 1H), 4.45 (s, 2H), 3.46-3.55 (m, 1H), 3.24-3.29 (m, 1H), 3.17-3.21 (m, 2H), 3.05-3.13 (m, 1H), 2.96-3.04 (m, 1H), 2.32-2.41 (m, 1H), 2.22-2.31 (m, 2H), 1.33-1.47 (m, 1H). 19F NMR (377 MHz, DMSO-d6): −111.39, −112.23, −117.05. LC-MS: m/z 624.4 $(M+H)^+$.

(S)-5-(2-(4-fluorophenethyl)-4-(3-((5-fluoropyridin-2-yl)methyl)benzo[d]isoxazol-6-yl)-5-oxo-7,8,9,9a-tetrahydro-5H-pyrido[2,3-a]pyrrolizin-3-yl)-1,3,4-oxadiazol-2(3H)-one (Compound 222)

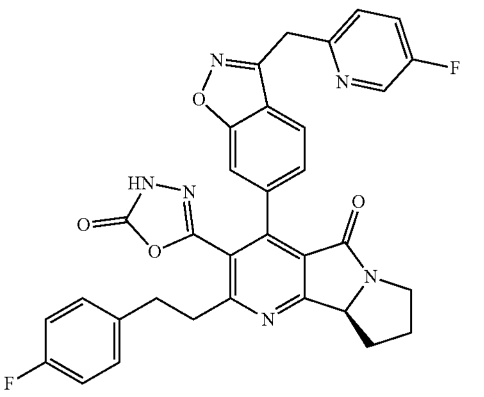 [SMILES: O=C1c2c(nc(CCc3ccc(F)cc3)c(-c3n[nH]c(=O)o3)c2-c2ccc3c(Cc4ccc(F)cn4)noc3c2)[C@@H]2CCCN12]

Compound 222 was synthesized using a similar procedure described in Example 31 by using the appropriate materials.

$^1$H NMR (400 MHz, DMSO-$d_6$): δ 12.57 (s, 1H), 8.49 (d, J=2.8 Hz, 1H), 7.73-7.77 (m, 1H), 7.62-7.72 (m, 3H), 7.18-7.24 (m, 2H), 7.10-7.15 (m, 1H), 7.04-7.10 (m, 2H), 4.86 (dd, J=10.4 Hz, J=6.4 Hz 1H), 4.60 (s, 2H), 3.53-3.59 (m, 1H), 3.24-3.30 (m, 1H), 3.17-3.21 (m, 2H), 2.99-3.12 (m, 2H), 2.32-2.40 (m, 1H), 3.24-3.31 (m, 2H), 1.34-1.46 (m, 1H). $^{19}$F NMR (377 MHz, DMSO-d6): −117.04, −129.94. LC-MS: m/z 607.2 $(M+H)^+$.

(S)-6-((5-(2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)-1H-pyrrolo[2,3-b]pyridin-1-yl)methyl)nicotinonitrile (Compound 223)

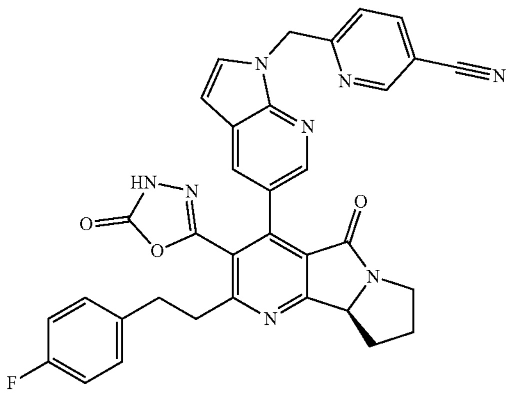

Compound 223 was synthesized using a similar procedure described in Example 15 by using the appropriate materials.

$^1$H NMR (400 MHz, DMSO-$d_6$) δ 12.57 (br s, 1H), 8.96 (d, J=1.6 Hz, 1H), 8.24 (dd, J=2.4 Hz, J=8.4 Hz, 1H), 8.04 (d, J=1.6 Hz, 1H), 7.96 (d, J=1.6 Hz, 1H), 7.72 (d, J=3.6 Hz, 1H), 7.19-7.25 (m, 3H), 7.04-7.10 (m, 2H), 6.61 (d, J=3.6 Hz, 1H), 5.72 (s, 2H), 4.85 (dd, J=10.4 Hz, J=6.4 Hz, 1H), 3.48-3.55 (m, 1H), 3.23-3.27 (m, 1H), 3.00-3.19 (m, 4H), 2.23-2.38 (m, 3H), 1.38-1.46 (m, 1H). 19F NMR (377 MHz, DMSO-d6): −117.07. $^{19}$F NMR (377 MHz, DMSO-$d_6$) δ −117.07. LC-MS: m/z 613.2 $(M+H)^+$.

5-((S)-2-(((R)-5-fluoro-2,3-dihydro-1H-inden-1-yl)methyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 224)

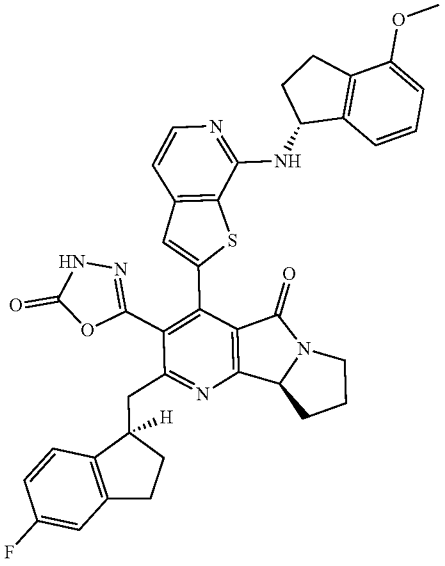 [SMILES: COc1cccc2c1CC[C@H]2Nc1nccc2cc(-c3c4c(nc(C[C@H]5CCc6cc(F)ccc65)c3-c3n[nH]c(=O)o3)[C@@H]3CCCN3C4=O)sc12]

Compound 224 was synthesized using a similar procedure described in Example 30 by using the appropriate materials.

$^1$H NMR (400 MHz, MeOD-$d_4$) δ ppm 7.88-7.97 (m, 1H), 7.41-7.49 (m, 1H), 6.98-7.19 (m, 3H), 6.87-6.96 (m, 2H), 6.75-6.84 (m, 2H), 5.75-5.86 (m, 1H), 3.79-3.88 (m, 3H), 3.64-3.74 (m, 2H), 3.37-3.49 (m, 2H), 2.96-3.05 (m, 2H), 2.87-2.95 (m, 1H), 2.72-2.84 (m, 2H), 2.60-2.70 (m, 1H), 2.37-2.54 (m, 3H), 2.14-2.22 (m, 1H), 1.97-2.03 (m, 1H), 1.86-1.92 (m, 1H), 1.52 (m, 1H), 0.88-0.92 (m, 1H). LC-MS: m/z 701.2 $(M+H)^+$.

Example 32
5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-thiadiazol-2(3H)-one (Compound 225)
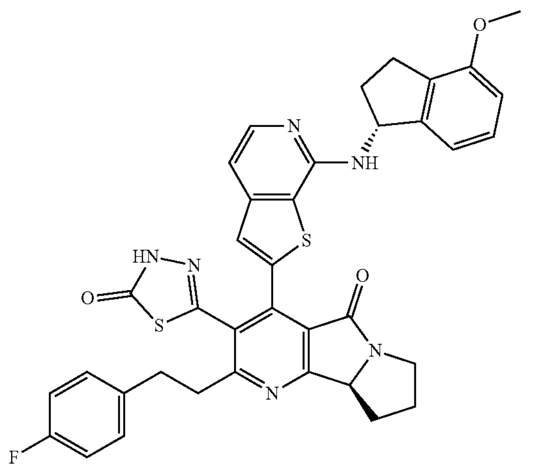
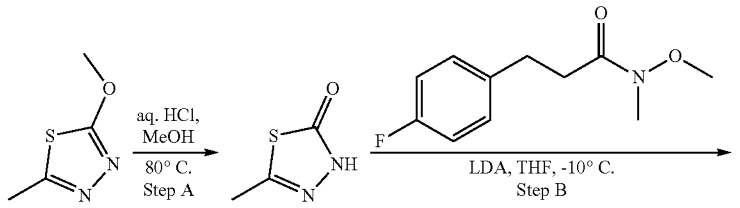
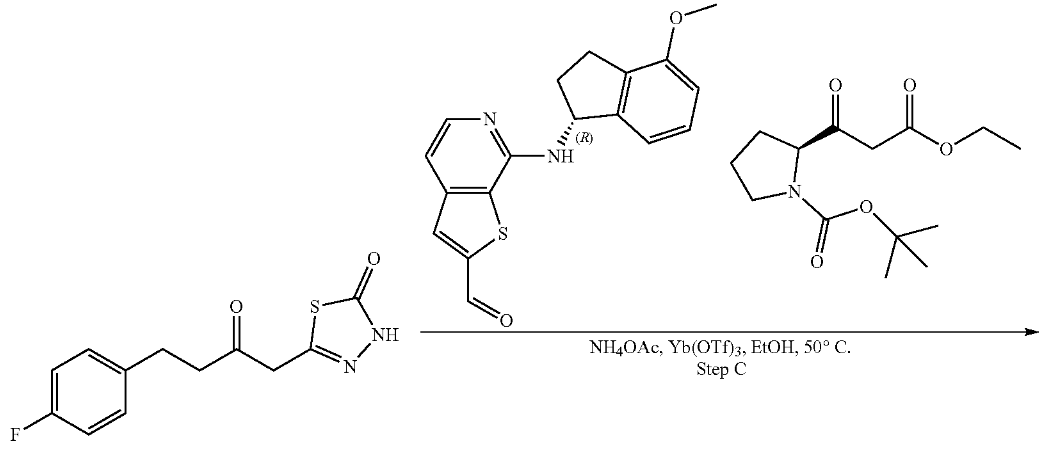

-continued
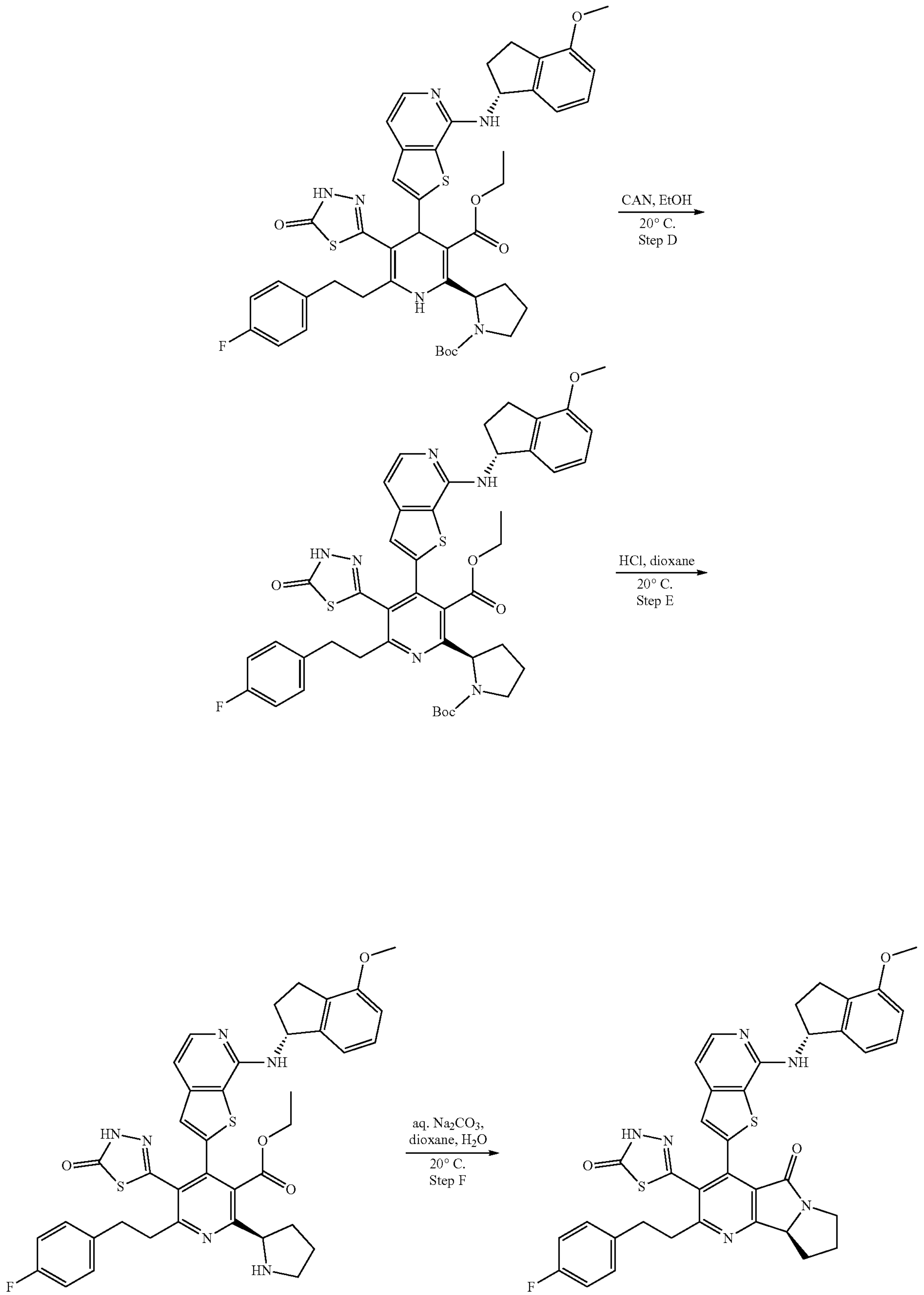

Step A 5-methyl-1,3,4-thiadiazol-2(3H)-one

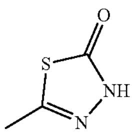

To a solution of 2-methoxy-5-methyl-1,3,4-thiadiazole (750 mg, 5.76 mmol) in MeOH (5 mL) was added HCl (15 mL) dropwise. The mixture was stirred at 80° C. for 2 hrs. To the solution was added $NaHCO_3$ until pH-7 at 0° C. Then the mixture was diluted with EtOAc (25 mL)/water (20 mL). The organic layer was separated, washed with brine (20 mL), dried over anhydrous of $Na_2SO_4$, filtered and concentrated under reduced pressure. The residue was purified by flash silica gel chromatography (Biotage®; 20 g Sepa-Flash® Silica Flash Column, Eluent of 0-100% Ethyl acetate/Petroleum ether gradient @25 mL/min) to give 5-methyl-1,3,4-thiadiazol-2(3H)-one (630 mg, 94.14% yield).

$^1H$ NMR (400 MHz, $CDCl_3$) δ 10.11 (s, 1H), 2.35 (s, 3H).

Step B 5-(4-(4-fluorophenyl)-2-oxobutyl)-1,3,4-thiadiazol-2(3H)-one

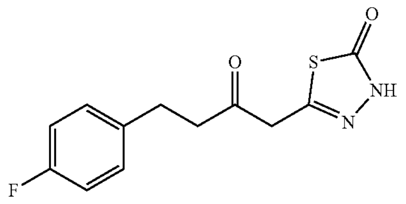 [SMILES: O=C(CCc1ccc(F)cc1)Cc1n[nH]c(=O)s1]

A mixture of 5-methyl-1,3,4-thiadiazol-2(3H)-one (109.97 mg, 946.83 μmol) in THF (3 mL) was added LDA (2.0 M, 1.18 mL) at −10° C. under $N_2$. The mixture was stirred at −10° C. for 30 min. 3-(4-fluorophenyl)-N-methoxy-N-methylpropanamide (100 mg, 473.41 μmol) in THF (1 mL) was added into the reaction solution. The solution was stirred at −10° C. for 1 hr. The solution was quenched with aq. $NH_4Cl$ (5 mL). The mixture was poured into water (5 mL), extracted with ethyl acetate (10 mL×2). The combined organic layer was washed with brine (10 mL), dried over $Na_2SO_4$, filtered and concentrated under reduced pressure to give a residue. The residue was purified by flash silica gel chromatography (ISCO®; 20 g SepaFlash® Silica Flash Column, Eluent of 0~40% Ethyl acetate/Petroleum ether gradient @25 mL/min) to give 5-(4-(4-fluorophenyl)-2-oxobutyl)-1,3,4-thiadiazol-2(3H)-one (30 mg, 22.88% yield, 96.153% purity).

$^1H$ NMR (400 MHz, $CDCl_3$) δ 9.17 (s, 1H), 6.99-7.11 (m, 2H), 6.85-6.95 (m, 2H), 3.69 (s, 2H), 2.72-2.93 (m, 4H). LC-MS: m/z 267.0 $(M+H)^+$.

Step C ethyl 2-((R)-1-(tert-butoxycarbonyl)pyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-thiadiazol-2-yl)-1,4-dihydropyridine-3-carboxylate

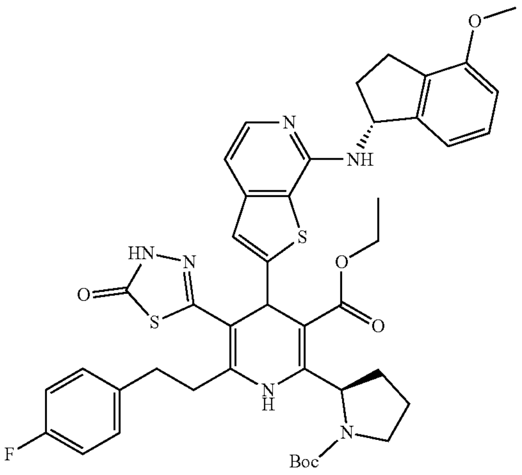 [SMILES: CCOC(=O)C1=C([C@H]2CCCN2C(=O)OC(C)(C)C)NC(CCc2ccc(F)cc2)=C(c2n[nH]c(=O)s2)C1c1cc2ccnc(N[C@@H]3CCc4c(OC)cccc43)c2s1]

A mixture of tert-butyl (S)-2-(3-ethoxy-3-oxopropanoyl) pyrrolidine-1-carboxylate (32 mg, 112.15 μmol), 5-(4-(4-fluorophenyl)-2-oxobutyl)-1,3,4-thiadiazol-2(3H)-one (29.86 mg, 112.15 μmol), (R)-7-((4-methoxy-2,3-dihydro-1H-inden-1-yl)amino)thieno[2,3-c]pyridine-2-carbaldehyde (36.38 mg, 112.15 μmol), $NH_4OAc$ (17.29 mg, 224.30 μmol) and $Yb(OTf)_3$ (6.96 mg, 11.21 μmol) in EtOH (2 mL) was degassed and purged with $N_2$ for 3 times, and then the mixture was stirred at 50° C. for 16 hrs under $N_2$ atmosphere. The reaction mixture was filtered and concentrated under reduced pressure to give ethyl 2-((R)-1-(tert-butoxycarbonyl)pyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-thiadiazol-2-yl)-1,4-dihydropyridine-3-carboxylate (100 mg, crude). LC-MS: m/z 839.2 $(M+H)^+$.

Step D ethyl 2-((R)-1-(tert-butoxycarbonyl)pyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-thiadiazol-2-yl)nicotinate

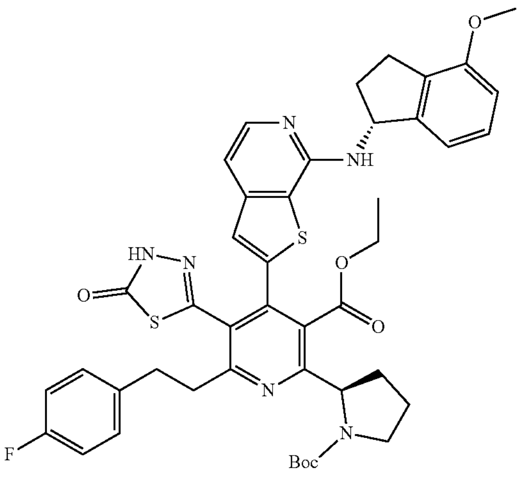 [SMILES: CCOC(=O)c1c([C@H]2CCCN2C(=O)OC(C)(C)C)nc(CCc2ccc(F)cc2)c(-c2n[nH]c(=O)s2)c1-c1cc2ccnc(N[C@@H]3CCc4c(OC)cccc43)c2s1]

A mixture of ethyl 2-((R)-1-(tert-butoxycarbonyl)pyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-thiadiazol-2-yl)-1,4-dihydropyridine-3-carboxylate (100 mg, 119.19 μmol) and CAN (130.68 mg, 238.38 μmol) in EtOH (3 mL) was degassed and purged with $N_2$ for 3 times, and then the mixture was stirred at 20° C. for 1 hr under $N_2$ atmosphere. The reaction mixture was diluted with ethyl acetate (20 mL) and washed with brine (5 mL*2), dried over $Na_2SO_4$, filtered and concentrated under reduced pressure to give ethyl 2-((R)-1-(tert-butoxycarbonyl)pyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-thiadiazol-2-yl)nicotinate (100 mg, crude). LC-MS: m/z 837.2 $(M+H)^+$.

Step E ethyl 6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-thiadiazol-2-yl)-2-((R)-pyrrolidin-2-yl)nicotinate

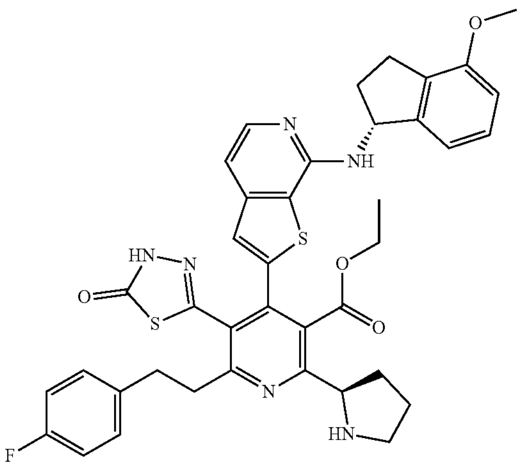 [SMILES: CCOC(=O)c1c([C@H]2CCCN2)nc(CCc2ccc(F)cc2)c(-c2n[nH]c(=O)s2)c1-c1cc2ccnc(N[C@@H]3CCc4c(OC)cccc43)c2s1]

A mixture of ethyl 2-((R)-1-(tert-butoxycarbonyl)pyrrolidin-2-yl)-6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-thiadiazol-2-yl)nicotinate (100 mg, 119.48 μmol) and HCl/dioxane (2 M, 2.39 mL) in dioxane (1 mL) was degassed and purged with $N_2$ for 3 times, and then the mixture was stirred at 20° C. for 2 hrs under $N_2$ atmosphere. The reaction mixture was concentrated under reduced pressure at 20° C. to give ethyl 6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-thiadiazol-2-yl)-2-((R)-pyrrolidin-2-yl)nicotinate (100 mg, crude). LC-MS: m/z 737.1 $(M+H)^+$.

Step F 5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-thiadiazol-2(3H)-one

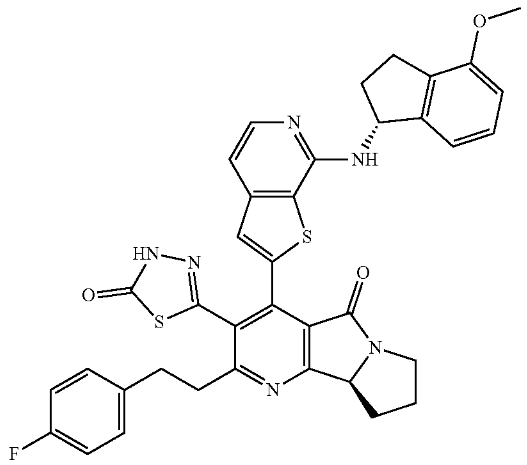 [SMILES: COc1cccc2c1CC[C@H]2Nc1nccc2cc(-c3c4c(nc(CCc5ccc(F)cc5)c3-c3n[nH]c(=O)s3)[C@@H]3CCCN3C4=O)sc12]

A mixture of ethyl 6-(4-fluorophenethyl)-4-(7-(((R)-4-methoxy-2,3-dihydro-1H-inden-1-yl)amino)thieno[2,3-c]pyridin-2-yl)-5-(5-oxo-4,5-dihydro-1,3,4-thiadiazol-2-yl)-2-((R)-pyrrolidin-2-yl)nicotinate (100 mg, 135.71 μmol) and $Na_2CO_3$ (287.6 mg, 2.71 mmol) in dioxane (4 mL) and $H_2O$ (4 mL) was degassed and purged with $N_2$ for 3 times, and then the mixture was stirred at 20° C. for 16 hrs under $N_2$ atmosphere. The reaction mixture was extracted with ethyl acetate (10 mL×3). The combined organic layer was washed with brine (10 mL), dried over $Na_2SO_4$, filtered and concentrated under reduced pressure to give a residue. The residue was purified by prep-HPLC (column: Xtimate C18 150*40 mm*10 um; mobile phase: [water(FA)-ACN]; gradient: 29%-59% B over 10 min) to give 5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-thiadiazol-2(3H)-one (14.87 mg, 15.84% yield, 99.88% purity).

$^1H$ NMR (400 MHz, MeOD-$d_4$) δ 7.93 (d, J=5.84 Hz, 1H), 7.35-7.45 (m, 1H), 7.11-7.23 (m, 4H), 6.95-7.05 (m, 2H), 6.93 (d, J=7.60 Hz, 1H), 6.86 (d, J=8.00 Hz, 1H), 5.79 (t, J=7.60 Hz, 1H), 3.82-3.88 (m, 3H), 3.63-3.73 (m, 1H), 3.39-3.47 (m, 1H), 3.37 (m, 1H) 3.17 (s, 2H), 3.00-3.16 (m, 3H), 2.74-2.86 (m, 1H), 2.63-2.73 (m, 1H), 2.47-2.57 (m, 1H), 2.36-2.46 (m, 2H), 1.98-2.07 (m, 1H), 1.41-1.54 (m, 1H). $^{19}F$ NMR (376 MHz, MeOD-$d_4$) δ ppm −119.12 (s, 1 F). LC-MS: m/z 691.1 $(M+H)^+$.

5-((S)-4-(7-(((R)-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 226)

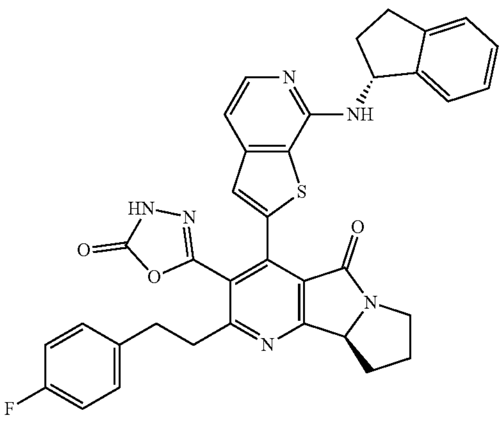 [SMILES: O=C1c2c(nc(CCc3ccc(F)cc3)c(-c3n[nH]c(=O)o3)c2-c2cc3ccnc(N[C@@H]4CCc5ccccc54)c3s2)[C@@H]2CCCN12]

Compound 226 was synthesized using a similar procedure described in Example 10 by using the appropriate materials. $^1$H NMR (400 MHz, $CDCl_3$) δ ppm 7.97 (s, 1H), 7.27-7.36 (m, 2H), 7.11-7.18 (m, 2H), 7.05 (dd, J=8.58, 5.48 Hz, 2H), 7.00 (d, J=5.84 Hz, 1H), 6.89 (t, J=8.64 Hz, 2H), 5.71-5.81 (m, 1H), 4.70 (dd, J=10.49, 6.20 Hz, 1H), 3.69 (dt, J=11.80, 8.58 Hz, 1H), 3.29-3.42 (m, 1H), 3.07-3.14 (m, 2H), 2.91-3.06 (m, 3H), 2.79-2.89 (m, 1H), 2.60-2.71 (m, 1H), 2.44 (dtd, J=12.32, 6.03, 6.03, 2.21 Hz, 1H), 2.24-2.36 (m, 2H), 1.83-1.97 (m, 2H), 1.33-1.43 (m, 1H), 1.32-1.44 (m, 1H). $^{19}$F NMR (376 MHz, $CDCl_3$) δ ppm −116.63 (s, 1 F). LC-MS: m/z 645.1 $(M+H)^+$.

5-((S)-4-(7-(((R)-1-(3,4-difluorophenyl)ethyl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 227)

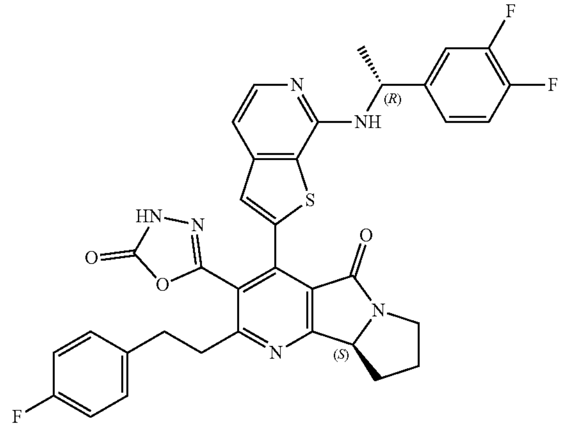

Compound 227 was synthesized using a similar procedure described in Example 10 by using the appropriate materials. $^1$H NMR (400 MHz, MeOD-$d_4$) δ ppm 7.83 (d, J=5.6 Hz, 1H), 7.43-7.50 (m, 1H), 7.29-7.35 (m, 1H), 7.14-7.24 (m, 4H), 7.10 (d, J=6.0 Hz, 1H), 6.99 (t, J=8.4 Hz, 2H), 5.32-5.43 (m, 1H), 4.90-4.94 (m, 1H), 3.60-3.81 (m, 1H), 3.41-3.52 (m, 1H), 3.24-3.30 (m, 2H), 3.05-3.21 (m, 2H), 2.40-2.60 (m, 3H), 1.61 (d, J=6.4 Hz, 3H), 1.48-1.53 (m, 1H). LC-MS: m/z 669.1 $(M+H)^+$.

5-((S)-4-(7-(((R)-1-(2,4-difluorophenyl)ethyl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 228)

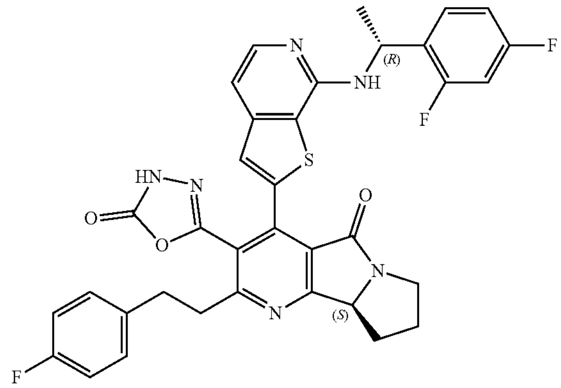

Compound 228 was synthesized using a similar procedure described in Example 10 by using the appropriate materials. $^1$H NMR (400 MHz, MeOD-$d_4$) δ ppm 7.68-7.72 (m, 1H), 7.63-7.66 (m, 1H), 7.43-7.47 (m, 1H), 7.37-7.41 (m, 1H), 7.19-7.26 (m, 1H), 7.11-7.17 (m, 2H), 7.02-7.10 (m, 1H), 6.95-6.99 (m, 3H), 5.36-5.46 (m, 1H), 4.90-4.98 (m, 1H), 3.63-3.74 (m, 1H), 3.41-3.52 (m, 1H), 3.08-3.16 (m, 2H), 2.85-2.94 (m, 1H), 2.43-2.60 (m, 3H), 1.74-1.77 (m, 3H), 1.46-1.55 (m, 1H), 1.39-1.45 (m, 1H). $^{19}$F NMR (377 MHz, MeOD-$d_4$) δ −77.01, −118.96. LC-MS: m/z 669.1 $(M+H)^+$.

Example 33

5—((R)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 229)

5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 230)

(Compound 229)

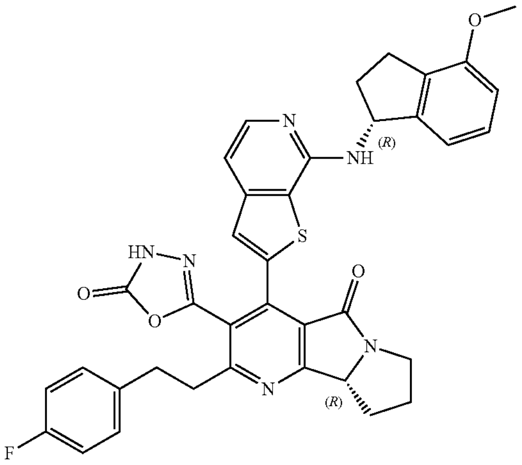

-continued
(Compound 230)
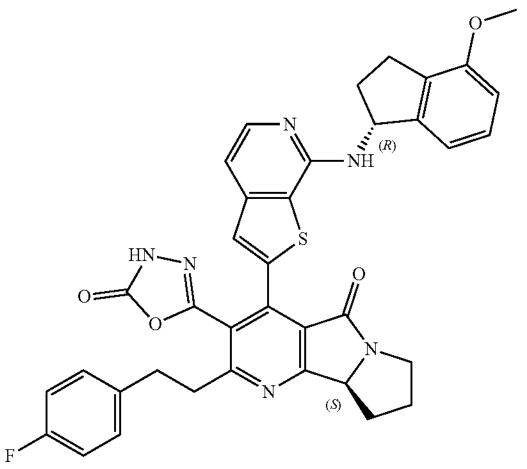
-continued
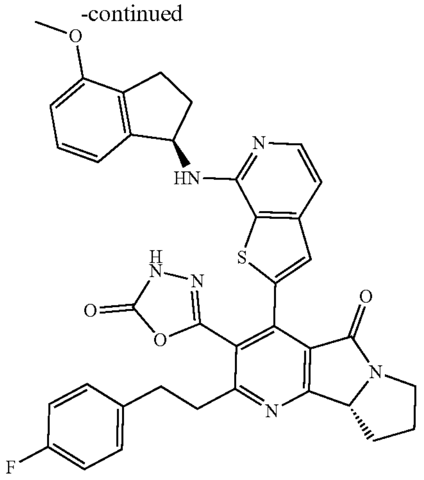
Step A 5-((R)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 229) and 5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 230)
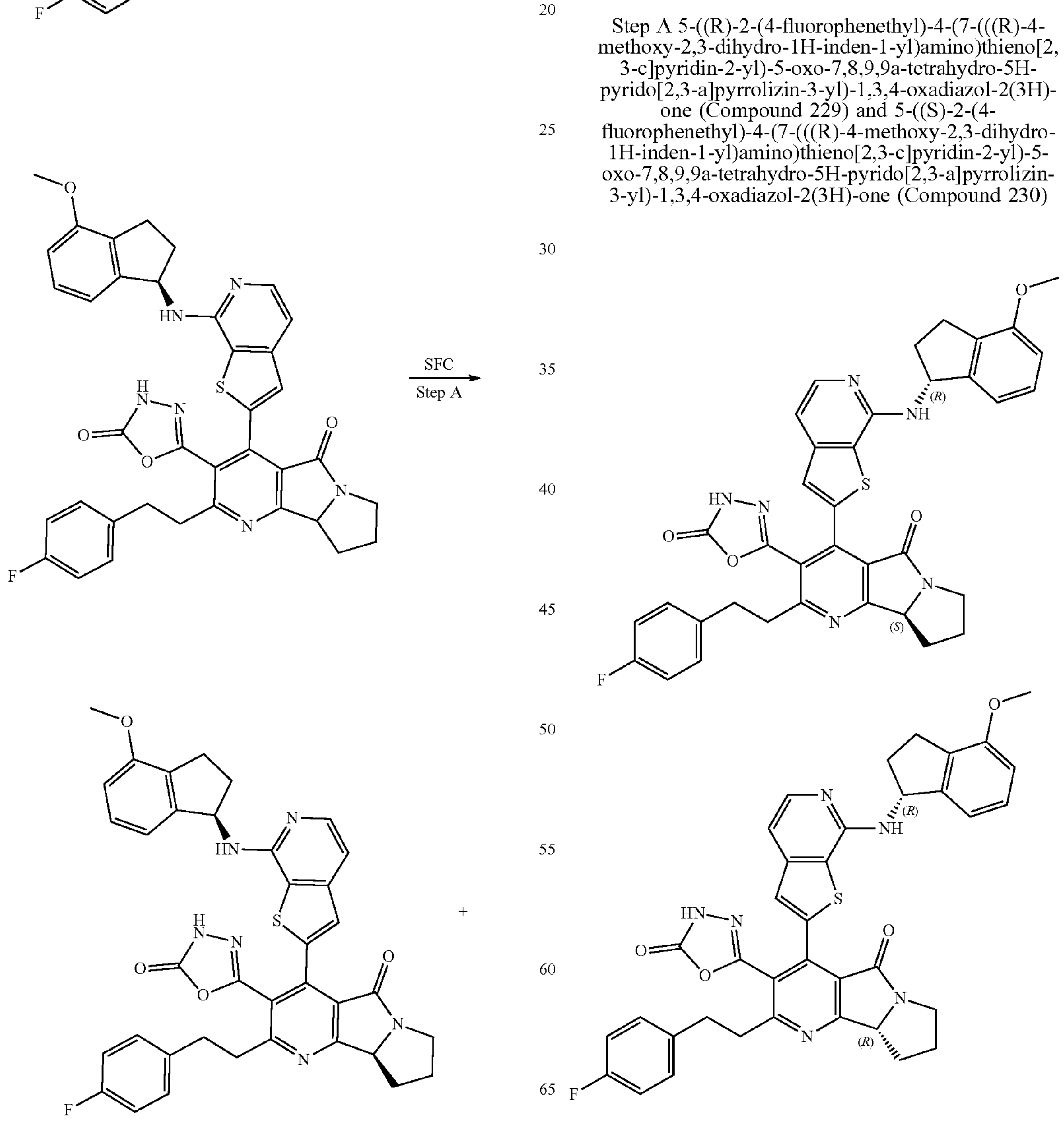

5-((S)-4-(7-(((R)-4-methoxy-2,3-dihydro-1H-inden-1-yl)amino)thieno[2,3-c]pyridin-2-yl)-5-oxo-2-(2-(tetrahydro-2H-pyran-4-yl)ethyl)-7,8,9,9a-tetrahydro-5H-pyrido[2,3-a]pyrrolizin-3-yl)isoxazol-3(2H)-one (30 mg) was further separated by chiral SFC (column: DAICEL CHIRALPAK AS (250 mm*30 mm, 10 um); mobile phase: [CO2-EtOH (0.1% NH3H2O)]; B %:40%%, isocratic elution mode) to give compound 5-((S)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (12.93 mg) and 5-((R)-2-(4-fluorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (10.47 mg).

Compound 230: $^1$H NMR (400 MHz, MeOD-$d_4$) δ ppm 7.95 (d, J=6.8 Hz, 1H), 7.46 (s, 1H), 7.12-7.17 (m, 4H), 6.98 (t, J=8.4 Hz, 2H), 6.90 (d, J=7.2 Hz, 1H), 6.82 (d, J=8.0 Hz, 1H), 5.82 (t, J=7.6 Hz, 1H), 4.87 (m, 1H), 3.85 (s, 3H), 3.63-3.74 (m, 1H), 3.40-3.49 (m, 1H), 3.26 (m, 2H), 3.01-3.16 (m, 3H), 2.73-2.84 (m, 1H), 2.61-2.71 (m, 1H), 2.37-2.55 (m, 3H), 2.01-2.04 (m, 1H), 1.46-1.54 (m, 1H). LC-MS: m/z 675.2 $(M+H)^+$.

Compound 229: $^1$H NMR (400 MHz, MeOD-$d_4$) δ ppm 7.95 (d, J=6.8 Hz, 1H), 7.45 (s, 1H), 7.12-7.17 (m, 4H), 6.98 (t, J=8.4 Hz, 2H), 6.90 (d, J=7.2 Hz, 1H), 6.82 (d, J=8.0 Hz, 1H), 5.82 (t, J=7.6 Hz, 1H), 4.87 (m, 1H), 3.85 (s, 3H), 3.63-3.74 (m, 1H), 3.40-3.49 (m, 1H), 3.26 (m, 2H), 3.01-3.16 (m, 3H), 2.73-2.84 (m, 1H), 2.61-2.71 (m, 1H), 2.37-2.55 (m, 3H), 1.98-2.06 (m, 1H), 1.47-1.53 (m, 1H). LC-MS: m/z 675.2 $(M+H)^+$.

(S)-4-((5-(2-(2-(2-oxabicyclo[2.2.2]octan-4-yl)ethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)-1H-pyrrolo[2,3-b]pyridin-1-yl)methyl)-3-fluorobenzonitrile (Compound 231)

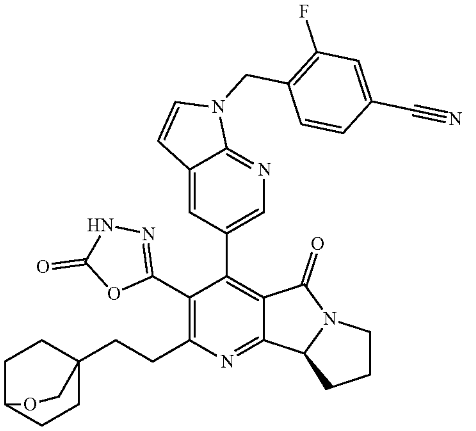 [SMILES: N#Cc1ccc(Cn2ccc3cc(-c4c5c(nc(CCC67CCC(CC6)OC7)c4-c4n[nH]c(=O)o4)[C@@H]4CCCN4C5=O)cnc32)c(F)c1]

Compound 231 was synthesized using a similar procedure described in the report of Example 25 by using the appropriate materials.

$^1$H NMR (400 MHz, DMSO-$d_6$): δ 12.58 (br s, 1H), 8.09 (d, J=2.0 Hz, 1H), 7.96 (d, J=2.0 Hz, 1H), 7.90 (dd, J=10.0 Hz, J=1.6 Hz, 1H), 7.68 (d, J=3.2 Hz, 1H), 7.62 (dd, J=8.0 Hz, J=1.2 Hz, 1H), 7.11 (t, J=7.6 Hz, 1H), 6.61 (d, J=3.6 Hz, 1H), 5.65 (s, 2H), 4.82 (dd, J=10.0 Hz, J=6.4 Hz, 1H), 3.63-3.70 (m, 1H), 3.45-3.54 (m, 3H), 3.20-3.29 (m, 1H), 2.71-2.80 (m, 2H), 2.31-2.39 (m, 1H), 2.19-2.29 (m, 2H), 1.80-1.92 (m, 2H), 1.32-1.63 (m, 9H). 19F NMR (377 MHz, DMSO-$d_6$): −115.11. LC-MS: m/z 646.3 $(M+H)^+$.

(S)-5-(2-(2-(2-oxabicyclo[2.2.2]octan-4-yl)ethyl)-4-(1-((5-fluoropyridin-2-yl)methyl)-1H-pyrrolo[2,3-b]pyridin-5-yl)-5-oxo-7,8,9,9a-tetrahydro-5H-pyrido[2,3-a]pyrrolizin-3-yl)-1,3,4-oxadiazol-2(3H)-one (Compound 232)

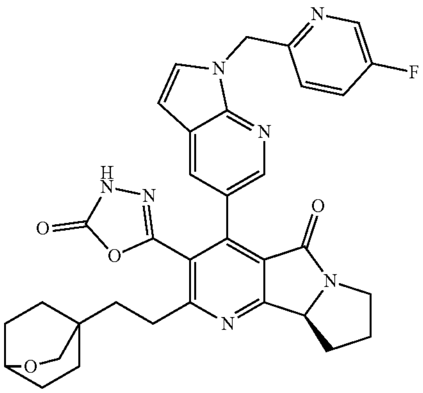 [SMILES: O=C1c2c(nc(CCC34CCC(CC3)OC4)c(-c3n[nH]c(=O)o3)c2-c2cnc3c(ccn3Cc3ccc(F)cn3)c2)[C@@H]2CCCN12]

Compound 232 was synthesized using a similar procedure described in the report of Example 25 by using the appropriate materials.

$^1$H NMR (400 MHz, DMSO-$d_6$): δ 8.51 (d, J=2.8 Hz, 1H), 8.07 (d, J=2.0 Hz, 1H), 7.94 (d, J=1.6 Hz, 1H), 7.64-7.72 (m, 2H), 7.21 (dd, J=4.4 Hz, J=8.8 Hz, 1H), 6.58 (d, J=3.6 Hz, 1H), 5.61 (s, 2H), 4.82 (dd, J=10.0 Hz, J=6.0 Hz, 1H), 3.63-3.69 (m, 1H), 3.46-3.56 (m, 3H), 3.23-3.29 (m, 1H), 2.70-2.79 (m, 2H), 2.29-2.39 (m, 1H), 2.20-2.29 (m, 2H), 1.81-1.91 (m, 2H), 1.36-1.61 (m, 9H). $^{19}$F NMR (377 MHz, DMSO-$d_6$): −129.35. LC-MS: m/z 622.2 $(M+H)^+$.

(S)-5-(2-(2-(2-oxabicyclo[2.2.2]octan-4-yl)ethyl)-4-(1-((5-chloro-3-fluoropyridin-2-yl)methyl)-1H-pyrrolo[2,3-b]pyridin-5-yl)-5-oxo-7,8,9,9a-tetrahydro-5H-pyrido[2,3-a]pyrrolizin-3-yl)-1,3,4-oxadiazol-2(3H)-one (Compound 233)

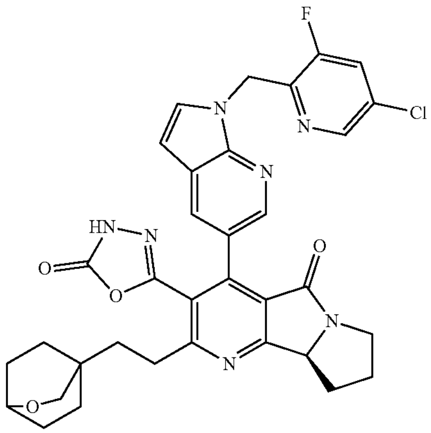 [SMILES: O=C1c2c(nc(CCC34CCC(CC3)OC4)c(-c3n[nH]c(=O)o3)c2-c2cnc3c(ccn3Cc3ncc(Cl)cc3F)c2)[C@@H]2CCCN12]

Compound 233 was synthesized using a similar procedure described in the report of Example 25 by using the appropriate materials.

$^1$H NMR (400 MHz, DMSO-$d_6$): δ 8.41 (d, J=2.0 Hz, 1H), 8.13 (dd, J=9.6 Hz, J=2.0 Hz, 1H), 8.05 (d, J=2.0 Hz, 1H), 7.92 (d, J=2.0 Hz, 1H), 7.63 (d, J=3.6 Hz, 1H), 6.56 (d, J=3.6 Hz, 1H), 5.69 (s, 2H), 4.82 (dd, J=10.0 Hz, J=6.4 Hz, 1H), 3.63-3.70 (m, 1H), 3.47-3.54 (m, 3H), 3.23-3.29 (m, 1H), 2.70-2.78 (m, 2H), 2.31-2.39 (m, 1H), 2.20-2.29 (m, 2H), 1.81-1.92 (m, 2H), 1.33-1.62 (m, 9H). $^{19}$F NMR (377 MHz, DMSO-$d_6$): −112.91. LC-MS: m/z 656.2 $(M+H)^+$.

Example 34

(S)-2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 234)

(R)-2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 235)

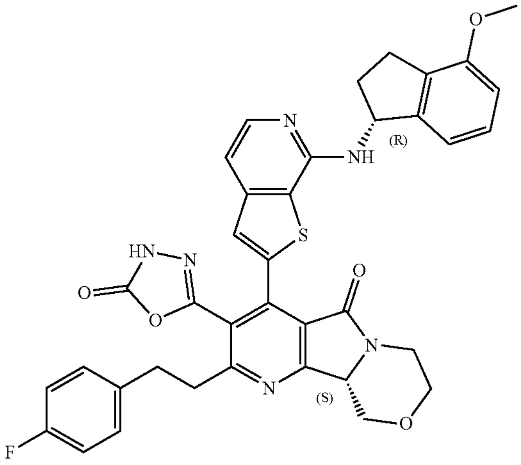

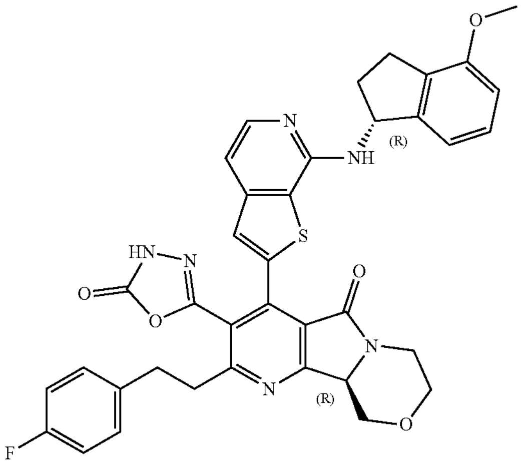

-continued

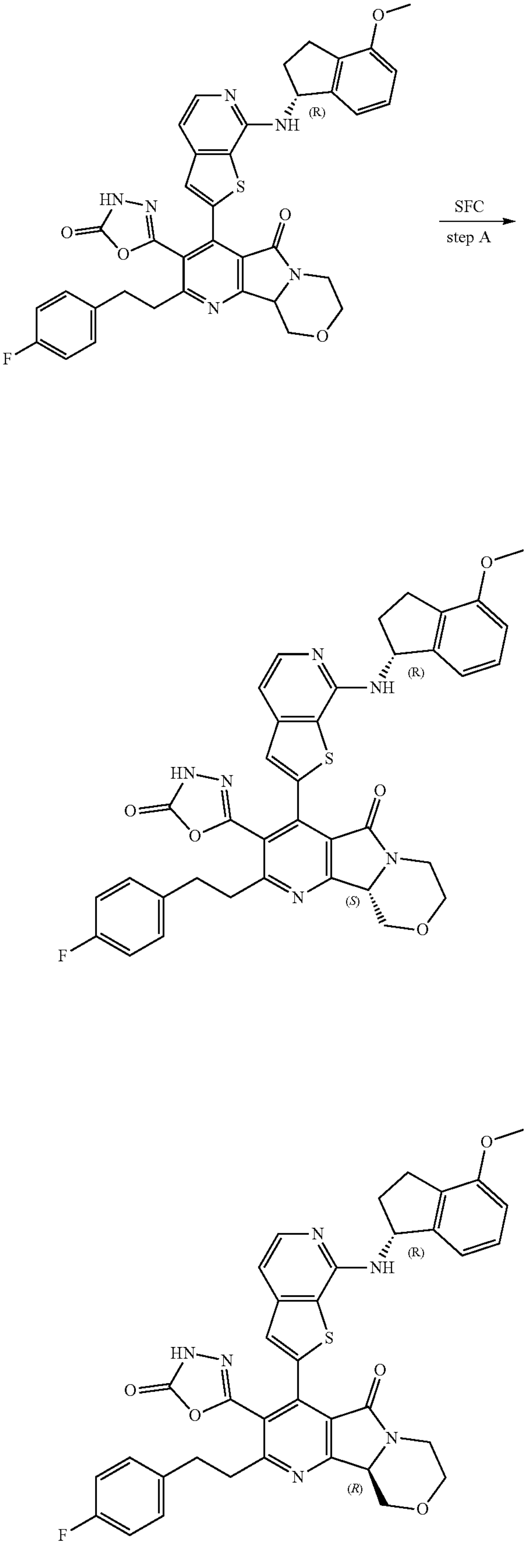

Step A (S)-2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 234) & (R)-2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 235)

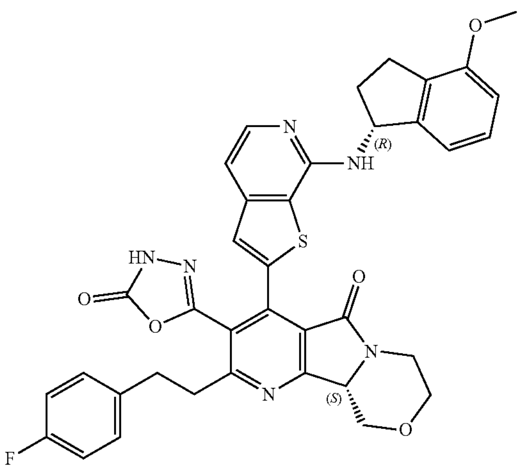

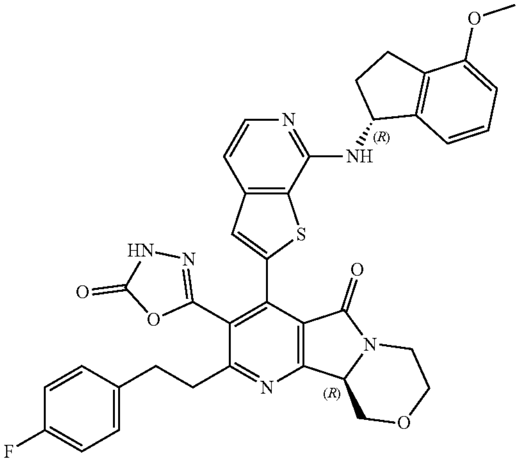

2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (150 mg) was separated by chiral SFC (column: Boston Green ODS 150*30 mm*5 um; mobile phase: [water(TFA)-ACN]; gradient: 35%-55% B over 11 min). (S)-2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (234) (10.71 mg, 7.14% yield) was obtained. (R)-2-(4-fluorophenethyl)-4-(7-(((R)-4-methoxy-2,3-dihydro-1H-inden-1-yl)amino)thieno[2,3-c]pyridin-2-yl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (235) (20.16 mg, 40.32% yield) was obtained.

Compound 234: $^{1}H$ NMR (400 MHz, MeOD-$d_4$) δ ppm 7.93-7.97 (m, 1H), 7.44-7.50 (m, 1H), 7.13-7.18 (m, 4H), 6.95-7.01 (m, 2H), 6.88-6.92 (m, 1H), 6.80-6.83 (m, 1H), 5.79-5.86 (m, 1H), 4.80 (br s, 2H), 4.60-4.65 (m, 2H), 4.20-4.24 (m, 1H), 4.02-4.07 (m, 1H), 3.84-3.86 (m, 3H), 3.38-3.40 (m, 2H), 3.02-3.16 (m, 4H), 2.74-2.84 (m, 1H), 2.64-2.71 (m, 1H), 2.00-2.06 (m, 1H). LC-MS: m/z 691.1 $(M+H)^+$.

Compound 235: $^{1}H$ NMR (400 MHz, MeOD-$d_4$) δ ppm 7.92-7.98 (m, 1H), 7.44-7.49 (m, 1H), 7.13-7.19 (m, 4H), 6.96-7.00 (m, 2H), 6.89-6.92 (m, 1H), 6.80-6.84 (m, 1H), 5.78-5.86 (m, 1H), 4.80-4.83 (m, 2H), 4.57-4.66 (m, 2H), 4.36-4.42 (m, 1H), 4.20-4.25 (m, 1H), 4.02-4.07 (m, 1H), 3.84-3.86 (m, 3H), 3.36-3.41 (m, 2H), 3.09-3.25 (m, 4H), 2.75-2.83 (m, 1H), 2.64-2.70 (m, 1H), 1.97-2.04 (m, 1H). LC-MS: m/z 691.1 $(M+H)^+$.

Example 35
5—((R)-5-(4-fluorophenethyl)-3-isopropyl-7-(7-(((R)-4-methoxy-2,3-dihydro-1H-inden-1l-yl)amino)thieno[2,3-c]pyridin-2-yl)-1,1-dioxido-2,3-dihydrothieno[3,2-b]pyridin-6-yl)-1,3,4-oxadiazol-2(3H)-one (Compound 236)
5-((S)-5-(4-fluorophenethyl)-3-isopropyl-7-(7-(((R)-4-methoxy-2,3-dihydro-1H-inden-1l-yl)amino)thieno[2,3-c]pyridin-2-yl)-1,1-dioxido-2,3-dihydrothieno[3,2-b]pyridin-6-yl)-1,3,4-oxadiazol-2(3H)-one (Compound 237)
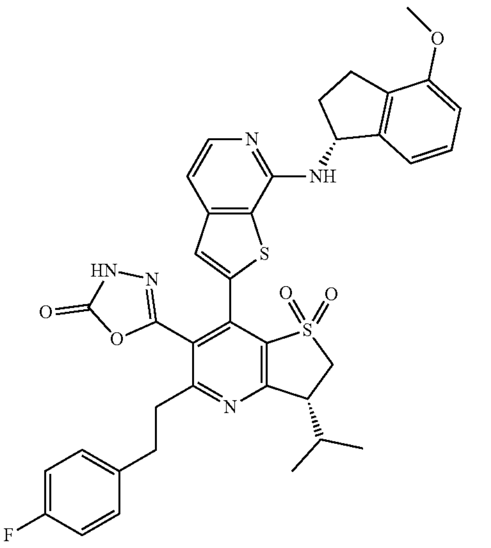
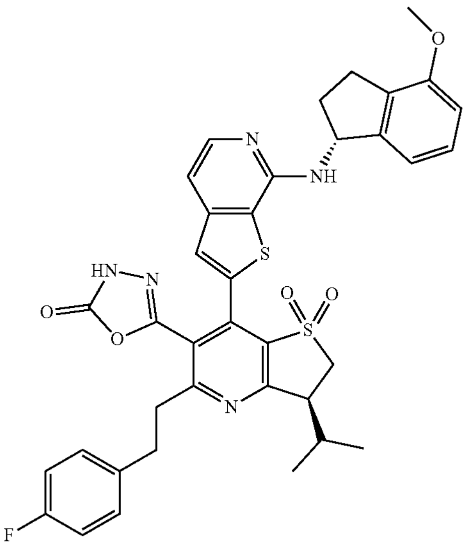
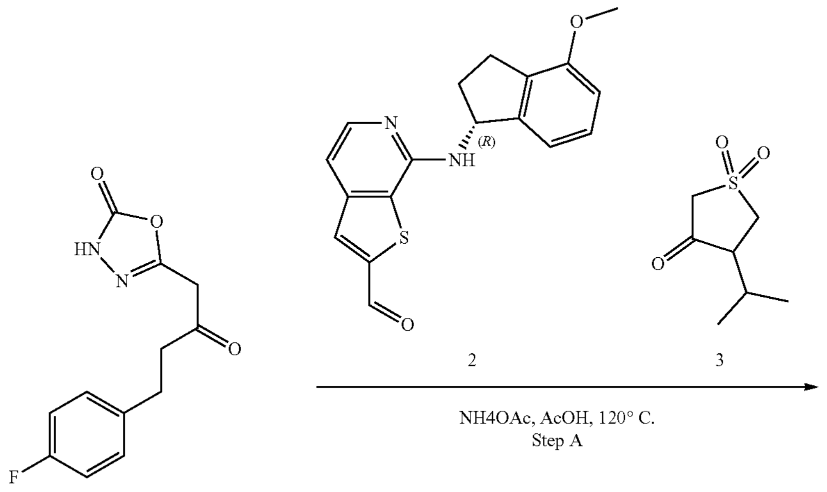

-continued
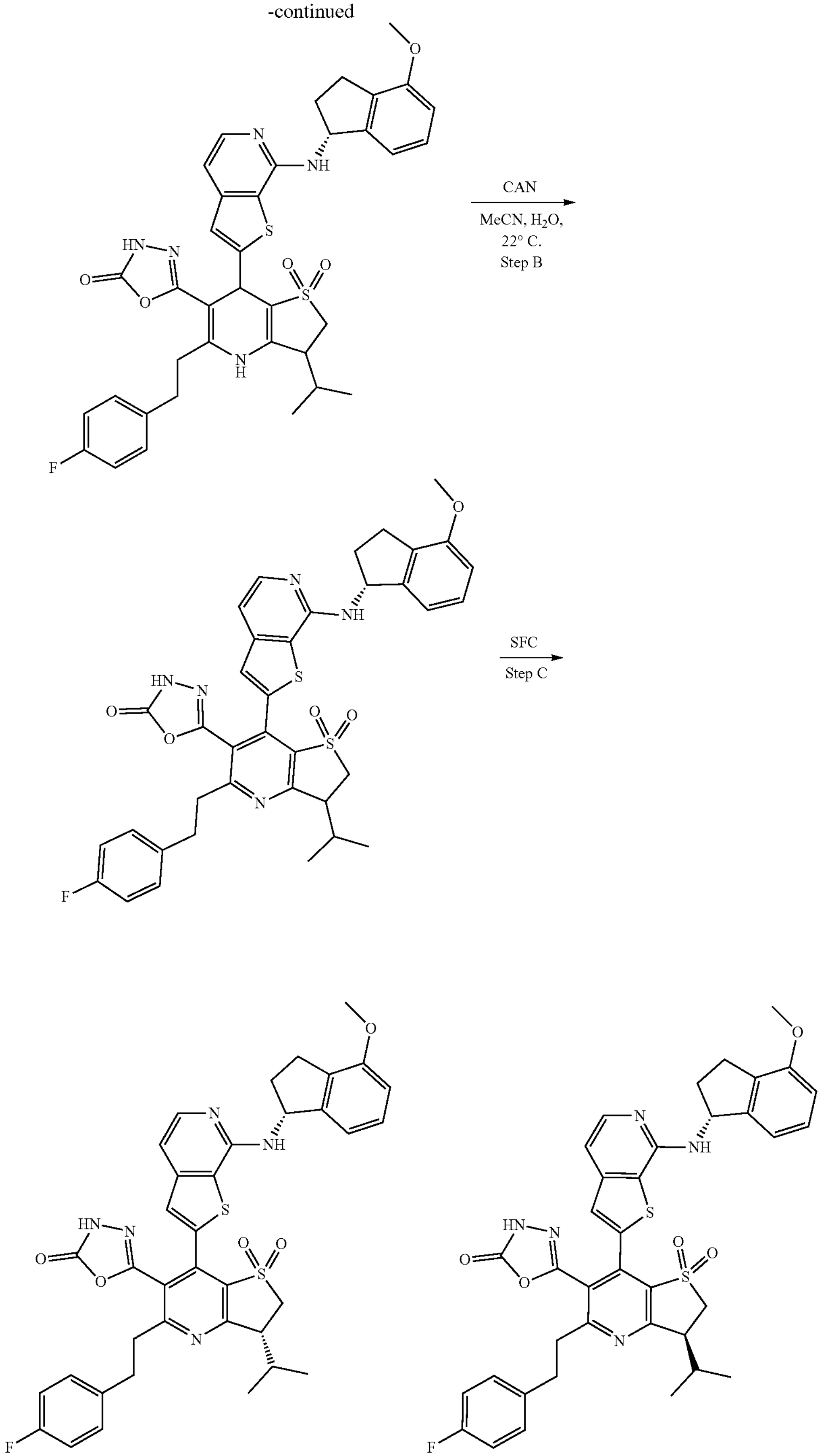

Step A 5-(5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3,4,7-tetrahydrothieno[3,2-b]pyridin-6-yl)-1,3,4-oxadiazol-2(3H)-one

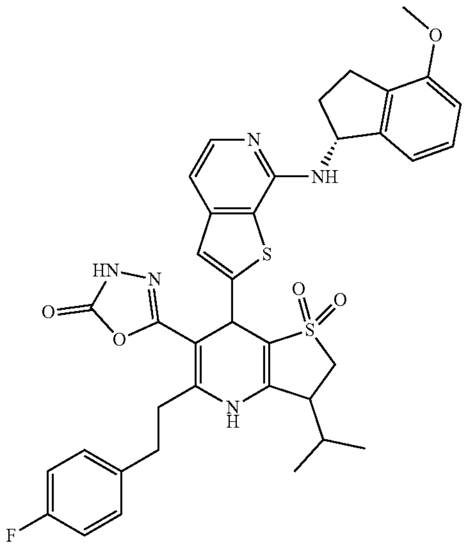 [SMILES: COc1cccc2c1CC[C@H]2Nc1nccc2cc(C3C(c4n[nH]c(=O)o4)=C(CCc4ccc(F)cc4)NC4=C3S(=O)(=O)CC4C(C)C)sc12]

A mixture of 5-[4-(4-fluorophenyl)-2-oxo-butyl]-3H-1,3,4-oxadiazol-2-one (500 mg, 2.00 mmol), 7-[[(1R)-4-methoxyindan-1-yl]amino]thieno[2,3-c]pyridine-2-carbaldehyde (650.00 mg, 2.00 mmol, 4-isopropyl-1,1-dioxothiolan-3-one (367.50 mg, 2.09 mmol), $NH_4OAc$ (325.00 mg, 4.22 mmol) in AcOH (10 mL) was degassed and purged with $N_2$ for 3 times, and then the mixture was stirred at 120° C. for 3 hrs under $N_2$ atmosphere. The reaction mixture was concentrated under reduced pressure to remove solvent. The residue was diluted with aqueous $NaHCO_3$ (200 mL) and extracted with EtOAc (200 mL×2). The combined organic layers were washed with aqueous NaCl (100 mL), dried over $Na_2SO_4$, filtered and concentrated under reduced pressure to give a residue. The crude product was purified by silica gel column chromatography (50% ethyl acetate in petroleum ether). Compound 5-(5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3,4,7-tetrahydrothieno[3,2-b]pyridin-6-yl)-1,3,4-oxadiazol-2(3H)-one (494 mg, 34.63% yield) was obtained. LC-MS: m/z 714.1 $(M+H)^+$.

Step B 5-(5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3-dihydrothieno[3,2-b]pyridin-6-yl)-1,3,4-oxadiazol-2(3H)-one

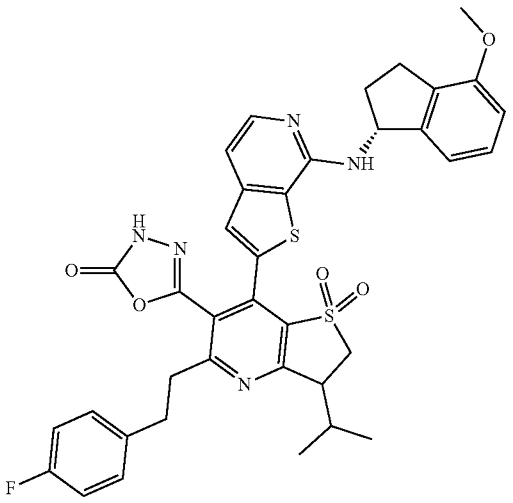 [SMILES: COc1cccc2c1CC[C@H]2Nc1nccc2cc(-c3c(-c4n[nH]c(=O)o4)c(CCc4ccc(F)cc4)nc4c3S(=O)(=O)CC4C(C)C)sc12]

A mixture of 5-(5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3,4,7-tetrahydrothieno[3,2-b]pyridin-6-yl)-1,3,4-oxadiazol-2(3H)-one (450 mg, 630.39 μmol), CAN (693.00 mg, 1.26 mmol) in MeCN (6 mL) and $H_2O$ (6 mL) was degassed and purged with $N_2$ for 3 times, and then the mixture was stirred at 22° C. for 2 hrs under $N_2$ atmosphere. The reaction mixture was quenched by addition $NaHCO_3$ (30 mL) at 22° C., and then diluted with $H_2O$ (50 mL) and extracted with EtOAc (50 mL×2). The combined organic layers were washed with aqueous NaCl (50 mL), dried over $Na_2SO_4$, filtered and concentrated under reduced pressure to give a residue. The residue was purified by column chromatography on silica gel (eluted with 0~50% PE in EA). Compound 5-(5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3-dihydrothieno[3,2-b]pyridin-6-yl)-1,3,4-oxadiazol-2(3H)-one (220 mg, 48.71% yield, 99.35% purity) was obtained. LC-MS: m/z 712.2 $(M+H)^+$.

Step C 5-((R)-5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3-dihydrothieno[3,2-b]pyridin-6-yl)-1,3,4-oxadiazol-2(3H)-one & 5-((S)-5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3-dihydrothieno[3,2-b]pyridin-6-yl)-1,3,4-oxadiazol-2(3H)-one

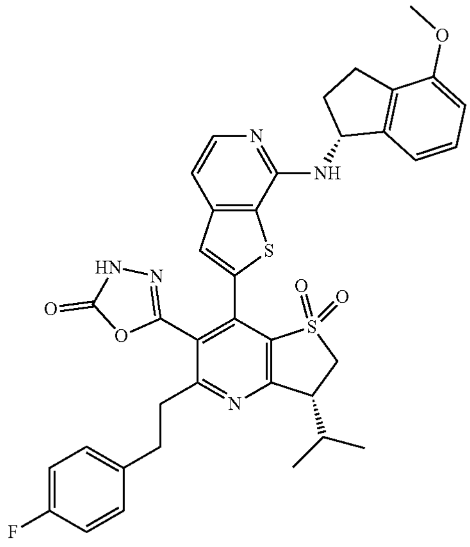

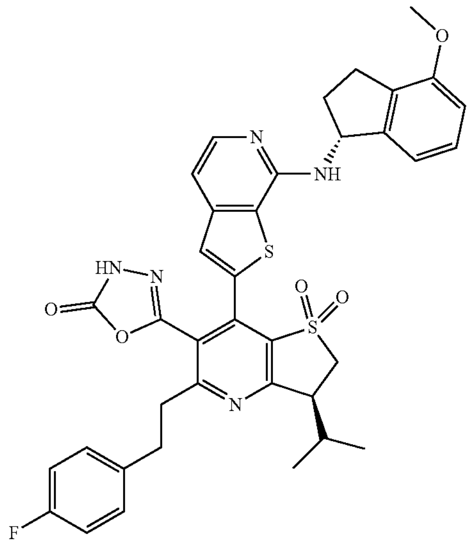

5-(5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3-dihydrothieno[3,2-b]pyridin-6-yl)-1,3,4-oxadiazol-2(3H)-one (220 mg) was separated by SFC (column: DAICEL CHIRALPAK AS (250 mm*30 mm, 10 um); mobile phase: [CO2-EtOH (0.1% NH3H2O)]; B %:50%%, isocratic elution mode). Compound 5-((R)-5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3-dihydrothieno[3,2-b]pyridin-6-yl)-1,3,4-oxadiazol-2(3H)-one (79.89 mg, 34.57% yield, 95.21% purity) was obtained. Compound 5-((S)-5-(4-fluorophenethyl)-3-isopropyl-7-(7-(((R)-4-methoxy-2,3-dihydro-1H-inden-1-yl)amino)thieno[2,3-c]pyridin-2-yl)-1,1-dioxido-2,3-dihydrothieno[3,2-b]pyridin-6-yl)-1,3,4-oxadiazol-2(3H)-one (71.93 mg, 32.70% yield) was obtained. LC-MS: m/z 712.1 (M+H)+

Compound 236: $^{1}H$ NMR (400 MHz, $CDCl_3$) δ ppm 8.03-8.16 (m, 1H), 7.59-7.75 (m, 1H), 7.18-7.23 (m, 1H), 7.10-7.16 (m, 3H), 6.94-7.01 (m, 3H), 6.74-6.84 (m, 1H), 5.72-5.89 (m, 1H), 3.80-3.95 (m, 3H), 3.61-3.75 (m, 2H), 3.40-3.51 (m, 1H), 3.18-3.31 (m, 2H), 2.97-3.13 (m, 3H), 2.69-2.88 (m, 3H), 1.91-2.02 (m, 1H), 1.08-1.18 (m, 3H), 0.85 (d, J=6.79 Hz, 3H). $^{19}F$ NMR (376 MHz, $CDCl_3$) δ −116.528 ppm.

Compound 237: H NMR (400 MHz, $CDCl_3$) δ ppm 8.04-8.15 (m, 1H), 7.65-7.71 (m, 1H), 7.17-7.24 (m, 1H), 7.09-7.16 (m, 3H), 6.93-7.02 (m, 3H), 6.78 (br d, J=8.34 Hz, 1H), 5.68-5.91 (m, 1H), 3.81-3.93 (m, 3H), 3.60-3.75 (m, 2H), 3.41-3.51 (m, 1H), 3.15-3.29 (m, 2H), 2.96-3.15 (m, 3H), 2.64-2.91 (m, 3H), 1.89-1.99 (m, 1H), 1.14 (d, J=6.91 Hz, 3H), 0.86 (d, J=6.68 Hz, 3H). $^{19}F$ NMR (376 MHz, $CDCl_3$) δ −116.546 ppm.

Example 36
6-((6-(5'-(4-fluorophenethyl)-1',1'-dioxido-6'-(5-oxo-4,5-dihydro-1,3,4-oxadiazol-2-yl)-2'H-spiro[cyclopropane-1,3'-thieno[3,2-b]pyridin]-7'-yl)-2-oxobenzo[d]oxazol-3(2H)-yl)methyl)nicotinonitrile (Compound 238)
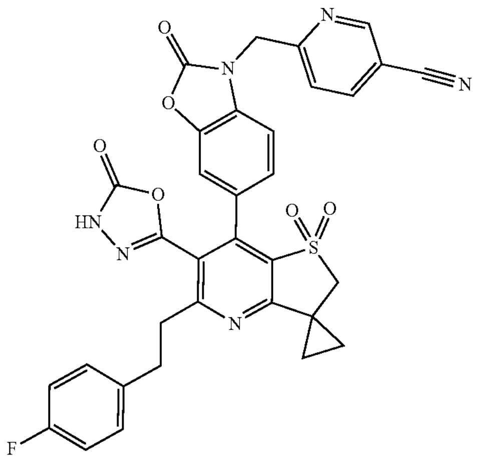
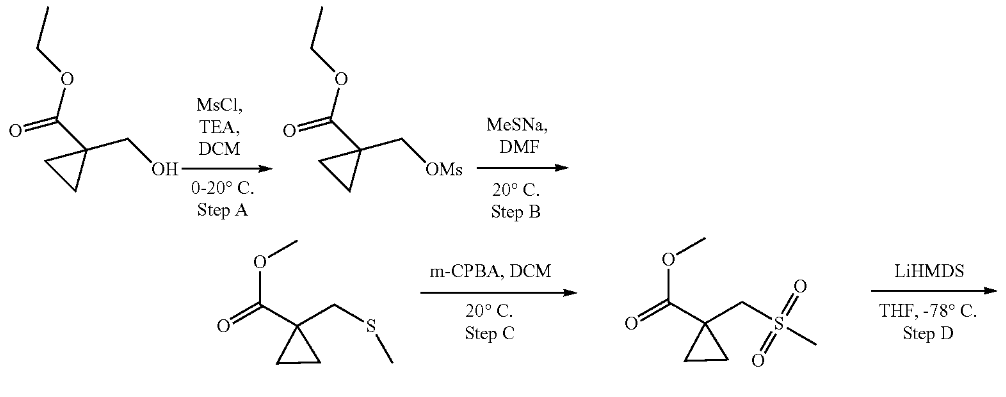
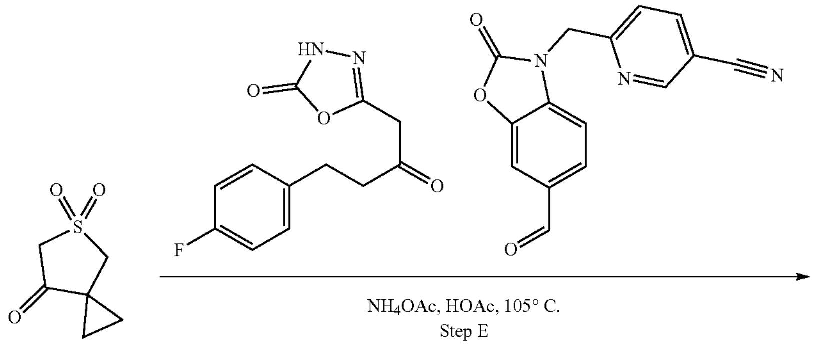

-continued

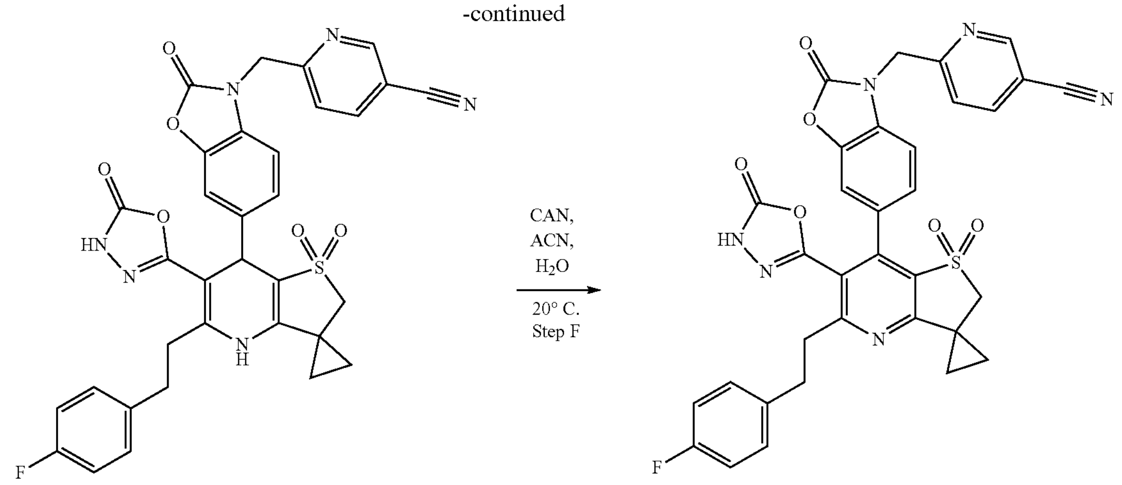

Step A ethyl 1-(((methylsulfonyl)oxy)methyl)cyclopropane-1-carboxylate

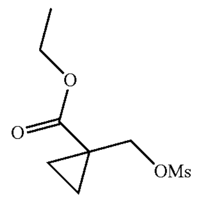

Under ice bath conditions, MsCl (1.32 g, 11.53 mmol) add dropwise to methyl 1-(hydroxymethyl)cyclopropane-1-carboxylate (1 g, 7.68 mmol) and TEA (1.56 g, 15.37 mmol) in dichloromethane (20 mL). The mixture was stirred at 20° C. for 2 hrs. The reaction solution was diluted with dichloromethane (20 mL), washed with hydrochloric acid (10 mL, 1 M) and saturated brine (10 mL). The organic phase was dried over anhydrous sodium sulfate. filtered and concentrated under reduced pressure to give methyl 1-(((methylsulfonyl)oxy)methyl)cyclopropane-1-carboxylate (1.6 g, crude).

$^1$H NMR (500 MHz, $CDCl_3$) δ 4.32 (s, 2H), 3.70 (s, 3H), 3.07 (s, 3H), 1.40-1.47 (m, 2H), 1.03-1.10 (m, 2H).

Step B methyl 1-((methylthio)methyl)cyclopropane-1-carboxylate

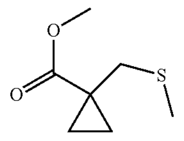

NaSMe (1.08 g, 15.37 mmol) was added to a stirred solution of ethyl 1-(((methylsulfonyl)oxy)methyl)cyclopropane-1-carboxylate (1.6 g, 7.68 mmol) in DMF (10 mL) at 20° C. The resulting brown suspension was stirred at 20° C. for 16 hrs. The reaction mixture was diluted with water (20 mL) and extracted with ethyl acetate (20 mL×3). The combined organic layer was dried over $Na_2SO_4$, filtered, and concentrated by evaporation to give methyl 1-((methylthio)methyl)cyclopropane-1-carboxylate (1.3 g, crude).

$^1$H NMR (400 MHz, $CDCl_3$) δ 3.70 (s, 3H), 2.85 (s, 2H), 2.18 (s, 3H), 1.31-1.39 (m, 2H), 0.88-0.97 (m, 2H).

Step C methyl 1-((methylsulfonyl)methyl)cyclopropane-1-carboxylate

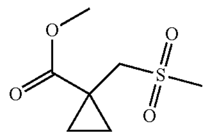

A mixture of methyl 1-((methylthio)methyl)cyclopropane-1-carboxylate (1.3 g, 8.11 mmol) and m-CPBA (4.94 g, 24.34 mmol, 85% purity) in dichloromethane (20 mL) was degassed and purged with $N_2$ for 3 times, and then the mixture was stirred at 20° C. for 16 hrs under $N_2$ atmosphere. The reaction mixture was quenched by addition aq. $NaS_2O_3$ (20 mL) at 0° C., and then diluted with dichloromethane (20 mL) and extracted with dichloromethane (20 mL×2). The combined organic layer was dried over $Na_2SO_4$, filtered and concentrated under reduced pressure to give a residue. The residue was purified by column chromatography ($SiO_2$, Petroleum ether/Ethyl acetate=1/0 to 50/50) to give methyl 1-((methylsulfonyl)methyl)cyclopropane-1-carboxylate (1.3 g, 83.35% yield).

$^1$H NMR (400 MHz, $CDCl_3$) δ 3.64 (s, 3H), 3.38 (s, 2H), 2.90 (s, 3H), 1.43-1.51 (m, 2H), 1.14-1.24 (m, 2H).

Step D 5-thiaspiro[2.4]heptan-7-one 5,5-dioxide

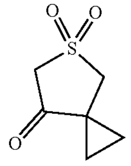

To a stirred solution of methyl 1-((methylsulfonyl)methyl)cyclopropane-1-carboxylate (600 mg, 3.12 mmol) in THF (6 mL) was added dropwise LiHMDS (1 M, 7.44 mL) at −78° C. with stirring under $N_2$. The reaction mixture was left to stir at this temperature for 1 hr. The reaction mixture was quenched by addition of a saturated aqueous solution of NHC (10 mL) at −10° C. with stirring. The resulting solution was concentrated in vacuo. The residue was purified by column chromatography ($SiO_2$, Petroleum ether/Ethyl acetate=1/0 to 1/1) to give 5-thiaspiro[2.4]heptan-7-one 5,5-dioxide (370 mg, 74.00% yield).

$^1$H NMR (500 MHz, $CDCl_3$) δ 3.82 (s, 2H) 3.57 (s, 2H) 1.65-1.74 (m, 2H) 1.26-1.32 (m, 2H).

Step E 6-((6-(5'-(4-fluorophenethyl)-1',1'-dioxido-6'-(5-oxo-4,5-dihydro-1,3,4-oxadiazol-2-yl)-4',7'-dihydro-2'H-spiro[cyclopropane-1,3'-thieno[3,2-b]pyridin]-7'-yl)-2-oxobenzo[d]oxazol-3(2H)-yl)methyl)nicotinonitrile

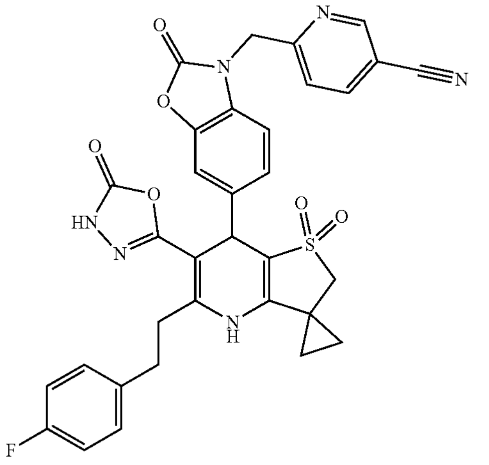 [SMILES: N#Cc1ccc(Cn2c(=O)oc3cc(C4C(c5n[nH]c(=O)o5)=C(CCc5ccc(F)cc5)NC5=C4S(=O)(=O)CC54CC4)ccc32)nc1]

A HOAc (1 mL) solution of 6-((6-formyl-2-oxobenzo[d]oxazol-3(2H)-yl)methyl)nicotinonitrile (43.58 mg, 156.06 μmol), 5-thiaspiro[2.4]heptan-7-one 5,5-dioxide (25 mg, 156.06 μmol), 5-(4-(4-fluorophenyl)-2-oxobutyl)-1,3,4-oxadiazol-2(3H)-one (39.05 mg, 156.06 μmol) and acetic acid ammonia (24.06 mg, 312.13 μmol) was stirred at 105° C. for 1 hr. The reaction mixture was quenched by addition $H_2O$ (5 mL) at 0° C., and then extracted with ethyl acetate (10 mL×2). The combined organic layer was washed with brine (10 mL), dried over $Na_2SO_4$, filtered and concentrated under reduced pressure to give 6-((6-(5'-(4-fluorophenethyl)-1',1'-dioxido-6'-(5-oxo-4,5-dihydro-1,3,4-oxadiazol-2-yl)-4',7'-dihydro-2'H-spiro[cyclopropane-1,3'-thieno[3,2-b]pyridin]-7'-yl)-2-oxobenzo[d]oxazol-3(2H)-yl)methyl)nicotinonitrile (100 mg, crude). LC-MS: m/z 653.1 (M+H)$^+$.

Step F 6-((6-(5'-(4-fluorophenethyl)-1',1'-dioxido-6'-(5-oxo-4,5-dihydro-1,3,4-oxadiazol-2-yl)-2'H-spiro[cyclopropane-1,3'-thieno[3,2-b]pyridin]-7'-yl)-2-oxobenzo[d]oxazol-3(2H)-yl)methyl)nicotinonitrile

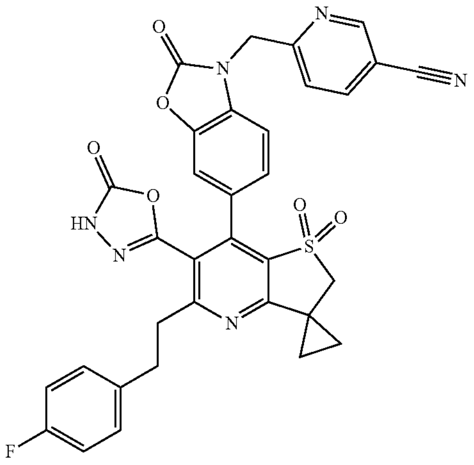 [SMILES: N#Cc1ccc(Cn2c(=O)oc3cc(-c4c(-c5n[nH]c(=O)o5)c(CCc5ccc(F)cc5)nc5c4S(=O)(=O)CC54CC4)ccc32)nc1]

A mixture of 6-[[6-[5-[2-(4-fluorophenyl)ethyl]-1,1-dioxo-6-(2-oxo-3H-1,3,4-oxadiazol-5-yl)spiro[4,7-dihydro-2H-thieno[3,2-b]pyridine-3,1'-cyclopropane]-7-yl]-2-oxo-1,3-benzoxazol-3-yl]methyl]pyridine-3-carbonitrile (100 mg, 153.22 μmol) and CAN (168.00 mg, 306.44 μmol) in $CH_3CN$ (2 mL) and $H_2O$ (2 mL) was degassed and purged with $N_2$ for 3 times, and then the mixture was stirred at 20° C. for 2 hrs under $N_2$ atmosphere. The reaction mixture was filtered and concentrated under reduced pressure to give a residue. The crude product was triturated with MeOH (2 mL) at 20° C. for 30 min and filtered to give 6-[[6-[5-[2-(4-fluorophenyl)ethyl]-1,1-dioxo-6-(2-oxo-3H-1,3,4-oxadiazol-5-yl)spiro[2H-thieno[3,2-b]pyridine-3,1'-cyclopropane]-7-yl]-2-oxo-1,3-benzoxazol-3-yl]methyl]pyridine-3-carbonitrile (37.55 mg, 37.67% yield).

$^1$H NMR (400 MHz, MeOD-$d_4$) δ 8.82-8.91 (m, 1H), 8.15-8.24 (m, 1H), 7.64 (d, J=7.75 Hz, 1H), 7.40-7.46 (m, 1H), 7.11-7.23 (m, 4H), 6.93-7.04 (m, 2H), 5.30 (s, 2H), 3.75 (s, 2H), 3.20-3.25 (m, 2H), 3.02-3.11 (m, 2H), 1.62-1.69 (m, 2H), 1.41-1.47 (m, 2H). $^{19}$F NMR (376 MHz, MeOD-$d_4$) δ −119.18 (s, 1 F). LC-MS: m/z 651.1 (M+H)$^+$.

5-((S)-4-(7-(((R)-6-chloro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 239)

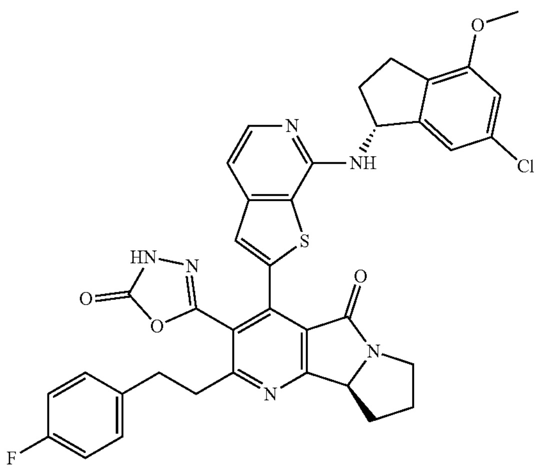 [SMILES: COc1cc(Cl)cc2c1CC[C@H]2Nc1nccc2cc(-c3c4c(nc(CCc5ccc(F)cc5)c3-c3n[nH]c(=O)o3)[C@@H]3CCCN3C4=O)sc12]

Compound 239 was synthesized using a similar procedure described in Example 10 by using the appropriate materials.

$^1$H NMR (400 MHz, MeOD-$d_4$) δ ppm 7.95 (d, J=5.84 Hz, 1H), 7.44-7.48 (m, 1H), 7.13-7.20 (m, 3H), 6.98 (t, J=8.82 Hz, 2H), 6.87-6.91 (m, 1H), 6.84 (d, J=1.67 Hz, 1H), 5.79-5.86 (m, 1H), 4.61-4.67 (m, 1H), 3.85 (s, 3H), 3.64-3.74 (m, 1H), 3.41-3.49 (m, 1H), 3.24-3.30 (m, 2H), 3.08-3.17 (m, 2H), 2.97-3.04 (m, 1H), 2.73-2.80 (m, 1H), 2.65-2.71 (m, 1H), 2.40-2.54 (m, 3H), 2.00-2.09 (m, 1H), 1.44-1.55 (m, 1H). $^{19}$F NMR (376 MHz, MeOD-$d_4$) δ ppm −119.02 (s, 1 F). LC-MS: m/z 709.1 $(M+H)^+$.

Example 37

(R)-5-(2-(4-fluorophenethyl)-4-(2-(4-methoxy-2,3-dihydro-1H-inden-1-yl)-1-oxoisoindolin-5-yl)-5-oxo-8,9-dihydro-5H,7H-8,9a-methanopyrido[2,3-a]pyrrolizin-3-yl)-1,3,4-oxadiazol-2(3H)-one (Compound 240)

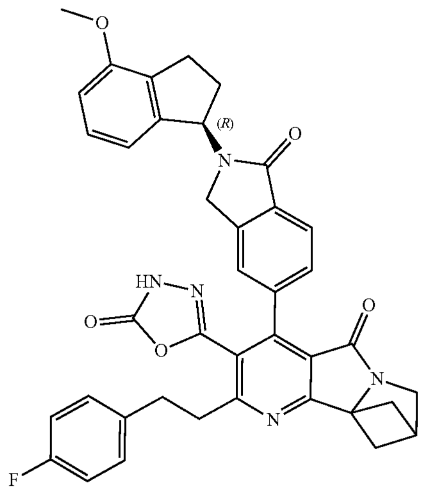

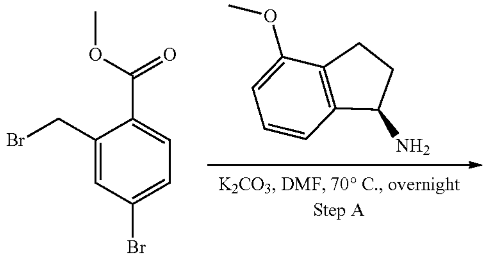

-continued
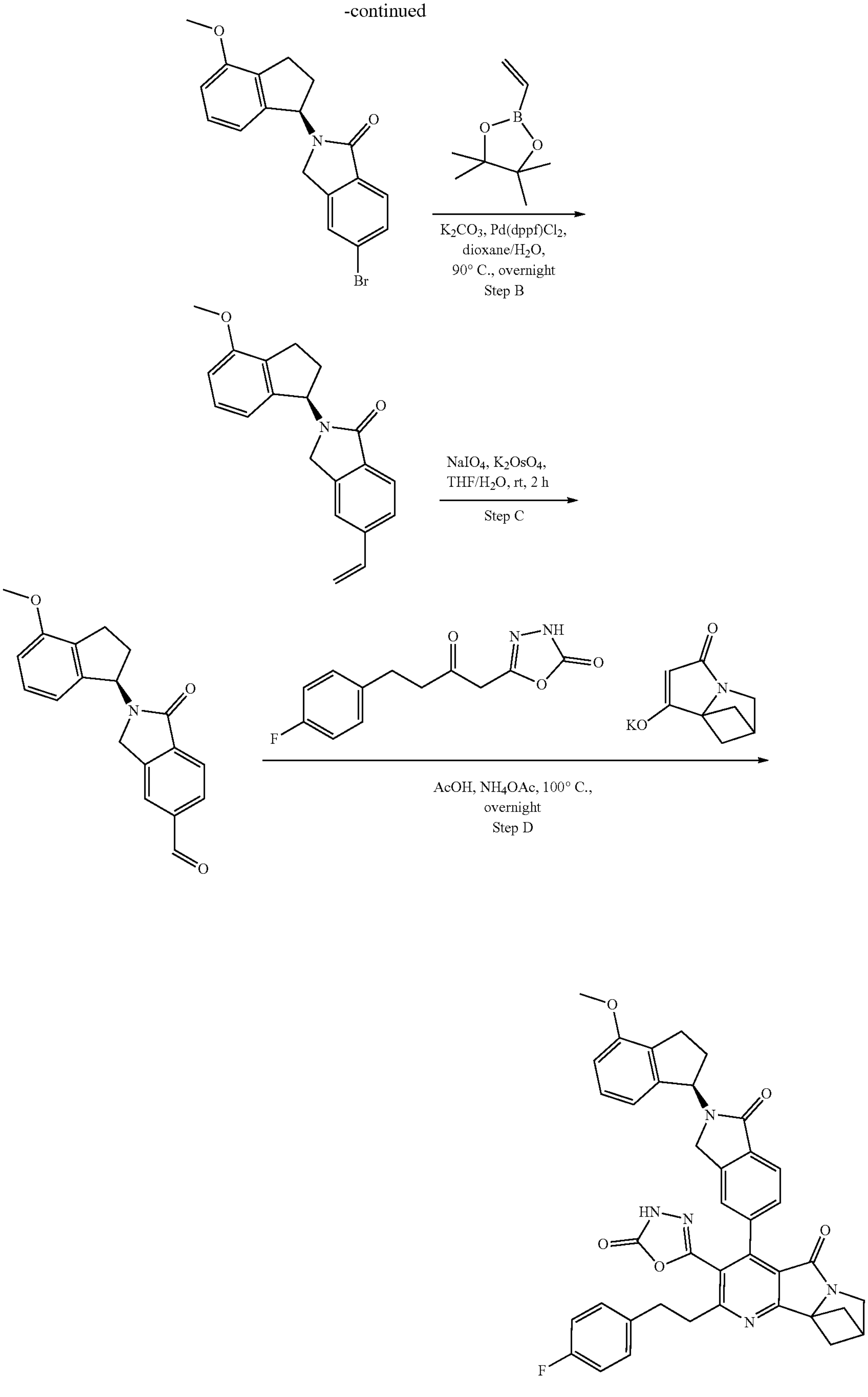

Step A (R)-5-bromo-2-(4-methoxy-2,3-dihydro-1H-inden-1-yl)isoindolin-1-one

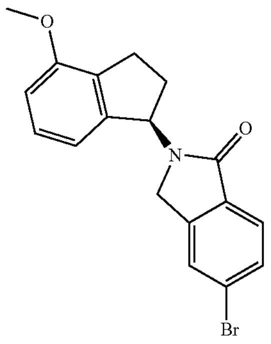 [SMILES: COc1cccc2c1CC[C@H]2N1Cc2cc(Br)ccc2C1=O]

To a solution of methyl 4-bromo-2-(bromomethyl)benzoate (150 mg, 0.487 mmol) in N,N-dimethylmethanamide (1 mL) was added (R)-4-methoxy-2,3-dihydro-1H-inden-1-amine (87.45 mg, 0.536 mmol), potassium carbonate (201.94 mg, 1.461 mmol) and the reaction was stirred at 70° C. for overnight. After the reaction was completed, the mixture was diluted with EA (30 mL), washed with water (30 mL). The organic layers were separated, dried over $Na_2SO_4$, filtered and concentrated under vacuum to dryness. The residue was purified by column chromatography on silica gel (PE/EA=10/1) to give (R)-5-bromo-2-(4-methoxy-2,3-dihydro-1H-inden-1-yl)isoindolin-1-one (144 mg, 0.402 mmol, 82.53%). LC-MS: m/z 358.0 $(M+H)^+$.

Step B (R)-2-(4-methoxy-2,3-dihydro-1H-inden-1-yl)-5-vinylisoindolin-1-one

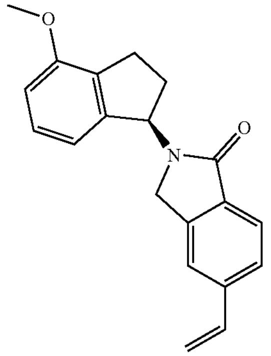 [SMILES: C=Cc1ccc2c(c1)CN([C@@H]1CCc3c(OC)cccc31)C2=O]

To a solution of (R)-5-bromo-2-(4-methoxy-2,3-dihydro-1H-inden-1-yl)isoindolin-1-one (104 mg, 0.290 mmol) and 4,4,5,5-tetramethyl-2-vinyl-1,3,2-dioxaborolane (223.57 mg, 1.452 mmol) in dioxane (5.00 mL) and $H_2O$ (0.5 mL) were added $K_2CO_3$ (120.36 mg, 0.871 mmol) and Pd(dppf) $Cl_2$ (11.85 mg, 0.016 mmol), and the reaction was stirred at 90° C. for 18 hr. After the reaction was completed, the mixture was diluted with EA (20 mL), washed with water (20 mL). The organic layers were separated, dried over $Na_2SO_4$, filtered and concentrated to give (R)-2-(4-methoxy-2,3-dihydro-1H-inden-1-yl)-5-vinylisoindolin-1-one (112 mg, crude). LC-MS: m/z 306.1 $(M+H)^+$.

Step C (R)-2-(4-methoxy-2,3-dihydro-1H-inden-1-yl)-1-oxoisoindoline-5-carbaldehyde

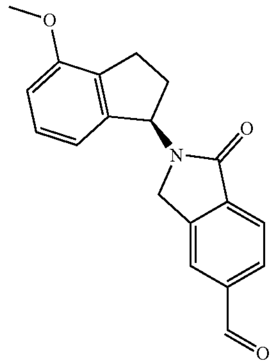 [SMILES: COc1cccc2c1CC[C@H]2N1Cc2cc(C=O)ccc2C1=O]

To a solution of (R)-2-(4-methoxy-2,3-dihydro-1H-inden-1-yl)-5-vinylisoindolin-1-one (112 mg, crude) in THF (2 mL), was added $NaIO_4$ (313.78 mg, 1.467 mmol) in $H_2O$ (2 mL), and $K_2OsO_4$ (13.51 mg, 0.037 mmol), and the reaction was stirred at room temperature for 2 h. After the reaction was completed, the mixture was diluted with EA (20 mL), washed with water (25 mL). The organic layers were separated, dried over $Na_2SO_4$, filtered and concentrated under vacuum to dryness. The residue was purified by column chromatography on silica gel (PE/EA=8/1) to give (R)-2-(4-methoxy-2,3-dihydro-1H-inden-1-yl)-1-oxoisoindoline-5-carbaldehyde (75 mg, 0.244 mmol, 66.54%). LC-MS: m/z 308.3 $(M+H)^+$.

Step D (R)-5-(2-(4-fluorophenethyl)-4-(2-(4-methoxy-2,3-dihydro-1H-inden-1-yl)-1-oxoisoindolin-5-yl)-5-oxo-8,9-dihydro-5H,7H-8,9a-methanopyrido[2,3-a]pyrrolizin-3-yl)-1,3,4-oxadiazol-2(3H)-one (240)

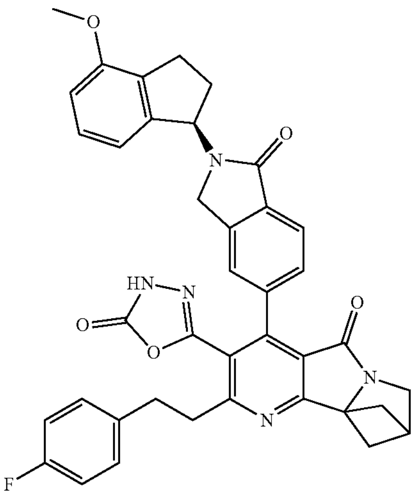 [SMILES: COc1cccc2c1CC[C@H]2N1Cc2cc(-c3c4c(nc(CCc5ccc(F)cc5)c3-c3n[nH]c(=O)o3)C35CC(CN3C4=O)C5)ccc2C1=O]

To a solution of (R)-2-(4-methoxy-2,3-dihydro-1H-inden-1-yl)-1-oxoisoindoline-5-carbaldehyde (50 mg, 0.163 mmol), 5-(4-(4-fluorophenyl)-2-oxobutyl)-1,3,4-oxadiazol-2(3H)-one (40.71 mg, 0.163 mmol), potassium 5-oxo-2,3-dihydro-1H,5H-2,7a-methanopyrrolizin-7-olate (36.90 mg, 0.195 mmol) in HOAc (1 mL) was added $NH_4OAc$ (25.08 mg, 0.325 mmol), the mixture reaction was stirred at 100° C. for overnight. After the reaction was completed, the mixture was diluted with EA (20 mL), washed with water (20 mL). The organic layers was separated, dried over $Na_2SO_4$, filtered and concentrated under vacuum to dryness. The residue was purified by prep-HPLC (TFA=0.1%) to afford the (R)-5-(2-(4-fluorophenethyl)-4-(2-(4-methoxy-2,3-dihydro-1H-inden-1-yl)-1-oxoisoindolin-5-yl)-5-oxo-8,9-dihydro-5H,7H-8,9a-methanopyrido[2,3-a]pyrrolizin-3-yl)-1,3,4-oxadiazol-2(3H)-one (9.89 mg, 0.015 mmol, 8.97%).

$^1$H NMR (400 MHz, DMSO-$d_6$) δ 12.60 (br s, 1H), 7.72 (d, J=8.0 Hz, 1H), 7.46 (s, 1H), 7.32 (d, J=8.4 Hz, 1H), 7.17-7.25 (m, 3H), 7.07 (t, J=8.8 Hz, 2H), 6.89 (d, J=8.0 Hz, 1H), 6.71 (d, J=7.2 Hz, 1H), 5.89 (t, J=7.6 Hz, 1H), 4.33-4.45 (m, 1H), 3.88-3.99 (m, 1H), 3.81 (s, 3H), 3.52 (s, 2H), 3.14-3.21 (m, 3H), 2.96-3.04 (m, 3H), 2.77-2.85 (m, 1H), 2.60-2.66 (m, 2H), 2.41-2.48 (m, 1H), 2.12-2.19 (m, 1H), 1.69-1.77 (m, 2H). $^{19}$F NMR (377 MHz, DMSO-$d_6$): −117.05. LC-MS: m/z 670.3 $(M+H)^+$.

5-((S)-2-(2-(imidazo[1,2-a]pyridin-7-yl)ethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 241)

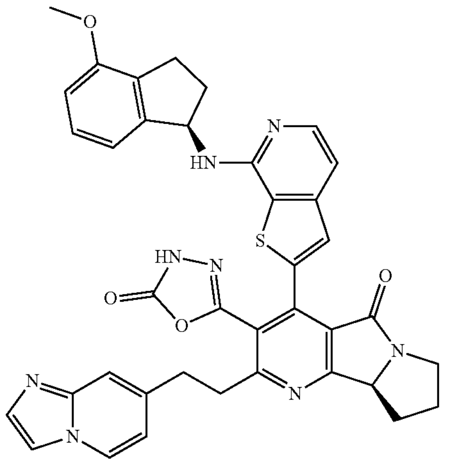 [SMILES: COc1cccc2c1CC[C@H]2Nc1nccc2cc(-c3c4c(nc(CCc5ccn6ccnc6c5)c3-c3n[nH]c(=O)o3)[C@@H]3CCCN3C4=O)sc12]

Compound 241 was synthesized using a similar procedure described in Example 10 by using the appropriate materials. (2.47 mg, 0.004 mmol, 8.72%)

$^1$H NMR (400 MHz, DMSO-$d_6$): δ 12.70 (br s, 1H), 8.42 (d, J=6.8 Hz, 1H), 7.98 (d, J=5.6 Hz, 1H), 7.84 (s, 1H), 7.48 (d, J=0.8 Hz, 1H), 7.43 (s, 1H), 7.32 (s, 1H), 7.25 (d, J=8.4 Hz, 1H), 7.13 (t, J=7.6 Hz, 1H), 7.07 (d, J=5.2 Hz, 1H), 6.80-6.88 (m, 2H), 6.77 (dd, J=6.8 Hz, J=1.6 Hz, 1H), 5.89 (q, J=8.0 Hz, 1H), 4.84-4.89 (m, 1H), 3.79 (s, 3H), 3.49-3.59 (m, 1H), 3.25-3.29 (m, 3H), 3.02-3.20 (m, 2H), 2.90-2.99 (m, 1H), 2.67-2.74 (m, 1H), 2.44-2.47 (m, 1H), 2.33-2.37 (m, 1H), 2.21-2.29 (m, 2H), 1.96-2.05 (m, 1H), 1.33-1.44 (m, 1H). LC-MS: m/z 697.3 $(M+H)^+$.

5-((S)-2-(4-chlorophenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 242)

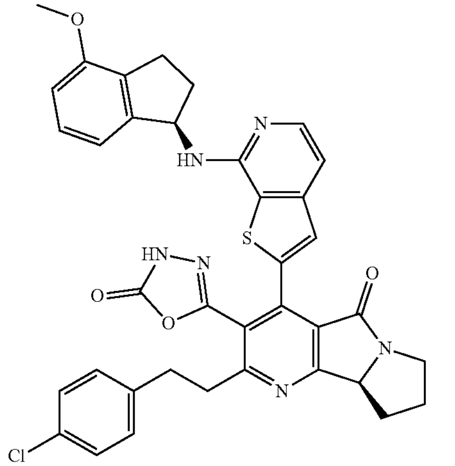 [SMILES: COc1cccc2c1CC[C@H]2Nc1nccc2cc(-c3c4c(nc(CCc5ccc(Cl)cc5)c3-c3n[nH]c(=O)o3)[C@@H]3CCCN3C4=O)sc12]

Compound 242 was synthesized using a similar procedure described in Example 10 by using the appropriate materials. $^1$H NMR (400 MHz, DMSO-$d_6$) δ 8.37 (br s, 1H), 7.96 (d, J=5.2 Hz, 1H), 7.37-7.39 (m, 1H), 7.29-7.33 (m, 2H), 7.19-7.25 (m, 3H), 7.13 (t, J=7.6 Hz, 1H), 7.06 (d, J=5.6 Hz, 1H), 6.84 (dd, J=15.2 Hz, J=7.6 Hz, 2H), 5.90 (q, J=8.0 Hz, 1H), 4.84 (dd, J=10.4 Hz, J=6.0, 1H), 3.79 (s, 3H), 3.52-3.59 (m, 1H), 3.16 (t, J=7.6 Hz, 2H), 2.93-3.07 (m, 3H), 2.65-2.73 (m, 2H), 2.24-2.38 (m, 4H), 1.96-2.06 (m, 1H), 1.36-1.46 (in, 1H). LC-MS: m/z 691.1 $(M+H)^+$.

5-((S)-2-(4-(1H-pyrazol-1-yl)phenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 243)

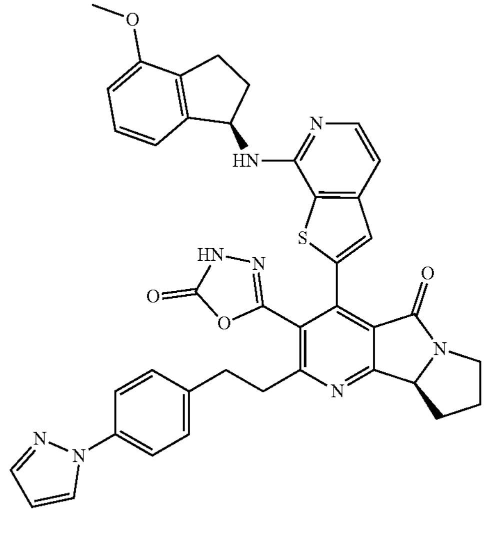 [SMILES: COc1cccc2c1CC[C@H]2Nc1nccc2cc(-c3c4c(nc(CCc5ccc(-n6cccn6)cc5)c3-c3n[nH]c(=O)o3)[C@@H]3CCCN3C4=O)sc12]

Compound 243 was synthesized using a similar procedure described in Example 10 by using the appropriate materials. (3.21 mg, 0.004 mmol, 4.46%)

$^1$H NMR (400 MHz, DMSO-$d_6$): δ 12.72 (br s, 1H), 8.43 (d, J=2.4 Hz, 1H), 7.98 (d, J=5.6 Hz, 1H), 7.68-7.73 (m, 3H), 7.44 (d, J=3.6 Hz, 1H), 7.31 (d, J=8.8 Hz, 2H), 7.25 (dd, J=8.8 Hz, J=2.4 Hz, 1H), 7.12 (dd, J=7.2 Hz, J=14.0 Hz, 1H), 7.08 (d, J=5.6 Hz, 1H), 6.79-6.86 (m, 2H), 6.51 (t, J=2.0 Hz, 1H), 5.86-5.93 (m, 1H), 4.88 (dd, J=6.8 Hz, J=10.4 Hz, 1H), 3.79 (s, 3H), 3.51-3.58 (m, 1H), 3.21-3.25 (m, 2H), 3.03-3.15 (m, 2H), 2.90-2.98 (m, 1H), 2.66-2.74 (m, 2H), 2.54-2.58 (m, 1H), 2.23-2.38 (m, 3H), 1.97-2.06 (m, 1H), 1.37-1.49 (m, 1H). LC-MS: m/z 723.3 $(M+H)^+$.

5-((S)-2-(3-fluoro-4-methoxyphenethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 244)

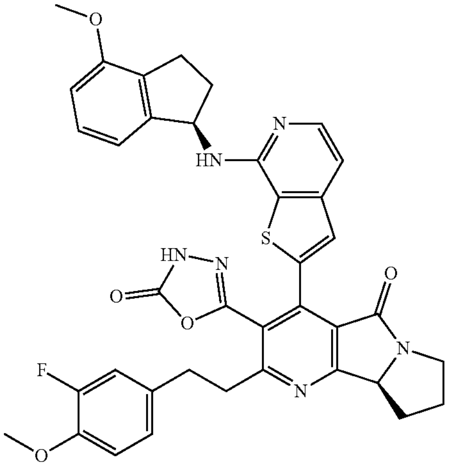 [SMILES: COc1ccc(CCc2nc3c(c(-c4cc5ccnc(N[C@@H]6CCc7c(OC)cccc76)c5s4)c2-c2n[nH]c(=O)o2)C(=O)N2CCC[C@@H]32)cc1F]

Compound 244 was synthesized using a similar procedure described in the report of Example 10 by using the appropriate materials. (5.19 mg, 0.00737 mmol, 20.9%)

$^1$H NMR (400 MHz, DMSO-$d_6$): δ 7.94 (d, J=5.6 Hz, 1H), 7.30 (s, 1H), 7.10-7.15 (m, 2H), 7.02-7.06 (m, 3H), 6.95 (d, J=9.6 Hz, 1H), 6.88 (d, J=7.2 Hz, 1H), 6.82 (d, J=8.0 Hz, 1H), 5.91 (q, J=8.0 Hz, 1H), 4.79 (dd, J=5.6 Hz, J=10.0 Hz, 1H), 3.79 (s, 6H), 3.49-3.55 (m, 1H), 3.23-3.27 (m, 1H), 3.03-3.08 (m, 2H), 2.84-2.97 (m, 3H), 2.66-2.71 (m, 1H), 2.17-2.42 (m, 4H), 1.99-2.04 (m, 1H), 1.32-1.44 (m, 1H). $^{19}$F NMR (377 MHz, DMSO-$d_6$): δ −135.63. LC-MS: m/z 705.2 $(M+H)^+$.

5-((S)-2-(2-(4-fluorothiophen-2-yl)ethyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 245)

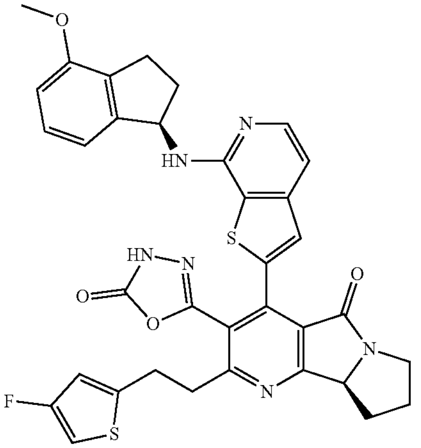 [SMILES: COc1cccc2c1CC[C@H]2Nc1nccc2cc(-c3c4c(nc(CCc5cc(F)cs5)c3-c3n[nH]c(=O)o3)[C@@H]3CCCN3C4=O)sc12]

Compound 245 was synthesized using a similar procedure described in Example 10 by using the appropriate materials. (3.53 mg, 0.005 mmol, 6.20%)

$^1$H NMR (400 MHz, DMSO-$d_6$) δ 7.96 (d, J=5.6 Hz, 1H), 7.38 (s, 1H), 7.20 (d, J=8.4 Hz, 1H), 7.13 (t, J=5.6 Hz, 1H), 7.06 (d, J=5.6 Hz, 1H), 6.91-6.92 (m, 1H), 6.86 (d, J=7.6 Hz, 1H), 6.80-6.85 (m, 2H), 5.89 (q, J=7.6 Hz, 1H), 4.85 (dd, J=9.6 Hz, J=6.4 Hz, 1H), 3.79 (s, 3H), 3.49-3.58 (m, 1H), 3.25-3.29 (m, 1H), 3.15-3.24 (m, 4H), 2.89-2.98 (m, 1H), 2.65-2.74 (m, 1H), 2.53-2.58 (m, 1H), 2.34-2.41 (m, 1H), 2.22-2.30 (m, 2H), 1.96-2.06 (m, 1H), 1.38-1.49 (m, 1H). $^{19}$F NMR (377 MHz, DMSO-d6): −127.97. LC-MS: m/z 681.1 $(M+H)^+$.

5-((S)-4-(7-(((R)-6-fluoro-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 246)

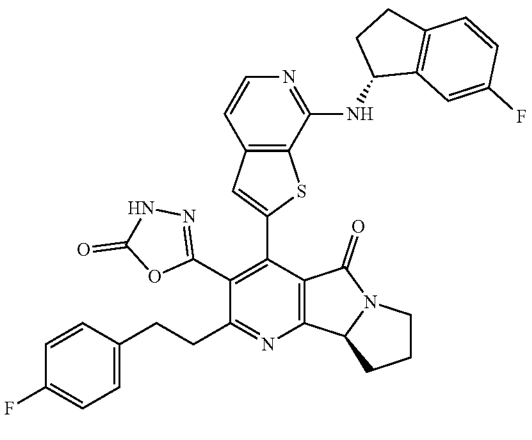 [SMILES: O=C1c2c(nc(CCc3ccc(F)cc3)c(-c3n[nH]c(=O)o3)c2-c2cc3ccnc(N[C@@H]4CCc5ccc(F)cc54)c3s2)[C@@H]2CCCN12]

Compound 246 was synthesized using a similar procedure described in Example 10 by using the appropriate materials.

$^1$H NMR (400 MHz, MeOD-$d_4$) δ ppm 7.93-7.99 (m, 1H), 7.41-7.47 (m, 1H), 7.22-7.26 (m, 1H), 7.13-7.19 (m, 3H), 6.91-7.01 (m, 4H), 5.79-5.86 (m, 1H), 3.65-3.74 (m, 1H), 3.41-3.49 (m, 1H), 3.21-3.29 (m, 3H), 3.00-3.16 (m, 3H), 2.86-2.94 (m, 1H), 2.66-2.73 (m, 1H), 2.40-2.54 (m, 3H), 1.97-2.12 (m, 2H), 1.45-1.52 (m, 1H). $^{19}$F NMR (377 MHz, MEOD-$d_4$) δ −119.00 (s, 1 F), −119.25 (s, 1 F). LC-MS: m/z 663.1 $(M+H)^+$.
Example 38
5-((S)-2-(4-fluorophenethyl)-5-oxo-4-(7-(((R)-2-(trifluoromethyl)-6,7-dihydro-5H-cyclopenta[b]pyridin-5-yl)amino)thieno[2,3-c]pyridin-2-yl)-7,8,9,9a-tetrahydro-5H-pyrido[2,3-a]pyrrolizin-3-yl)-1,3,4-oxadiazol-2(3H)-one (Compound 247)
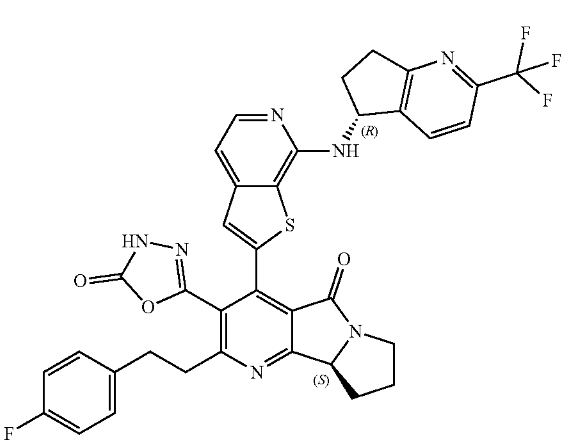
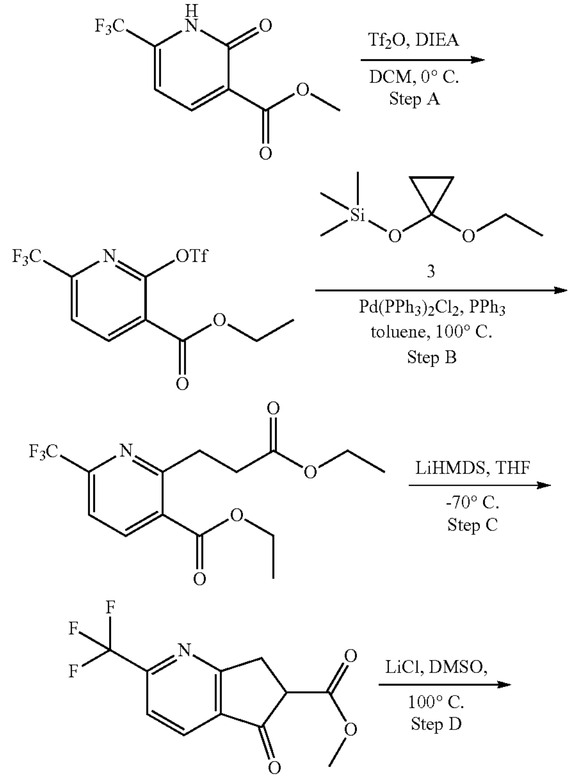
-continued
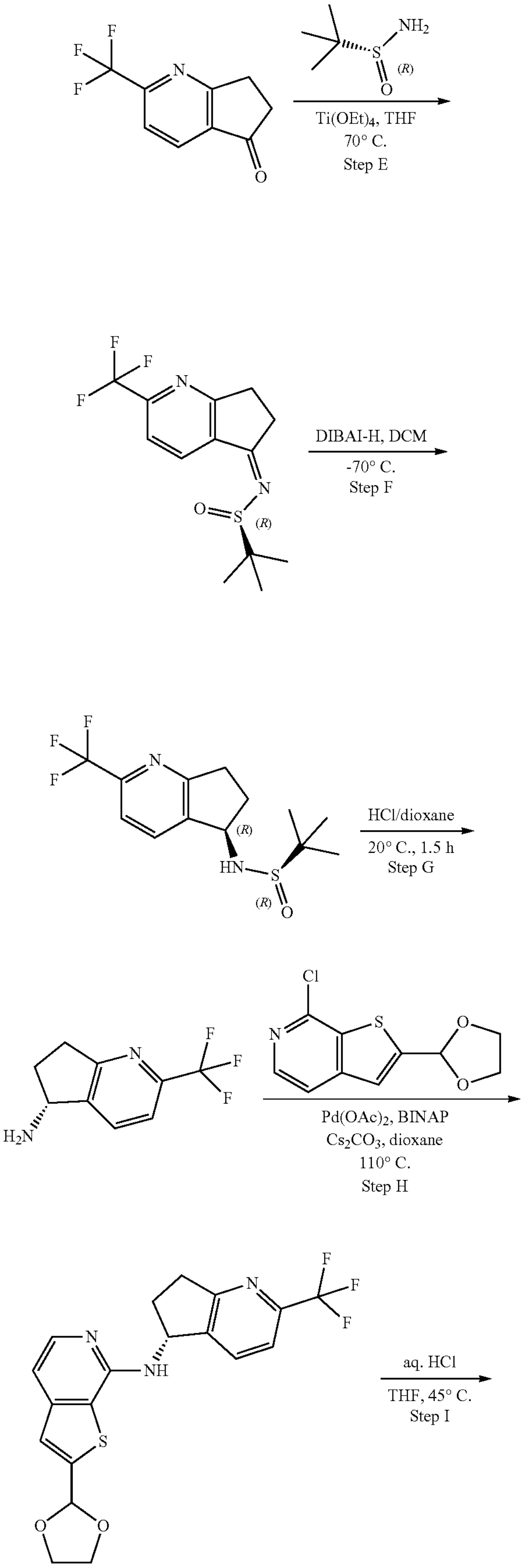

-continued

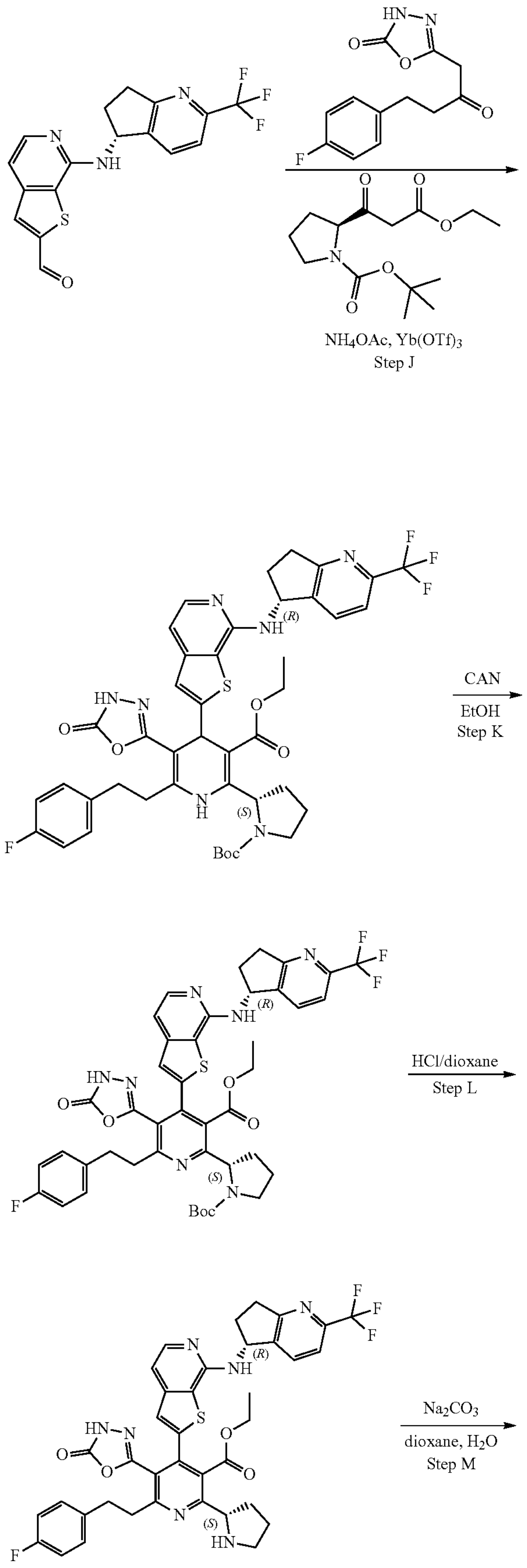

-continued

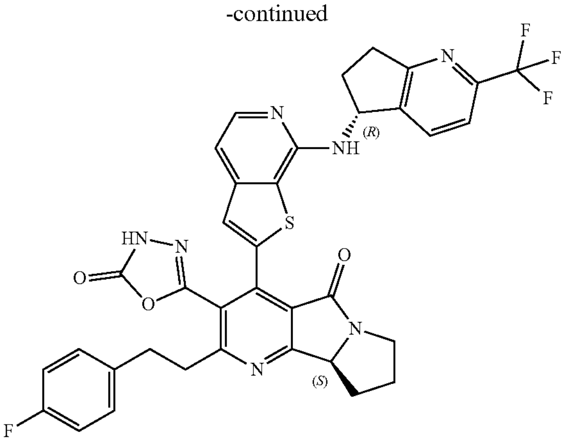

Step A ethyl 6-(trifluoromethyl)-2-(((trifluoromethyl)sulfonyl)oxy)nicotinate

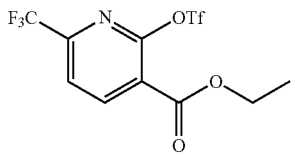 [SMILES: CCOC(=O)c1ccc(C(F)(F)F)nc1OS(=O)(=O)C(F)(F)F]

Ethyl 2-hydroxy-6-(trifluoromethyl)pyridine-3-carboxylate (4.5 g, 19.14 mmol) was suspended in DCM (45 mL) and treated with DIEA (4.95 g, 38.27 mmol). Then the mixture was cooled to 0° C. and $Tf_2O$ (8.10 g, 28.70 mmol) in DCM (10 mL) was added dropwise. The cooling bath was removed and the mixture was stirred at 20° C. for 3 hrs. DCM (10 mL) and water (5 mL) were added to the reaction and extracted with DCM (10 Ml×2). The organic layer was washed with brine (5 mL), dried over $Na_2SO_4$, filtered and concentrated. The residue was purified by column chromatography ($SiO_2$, petroleum ether/ethyl acetate=1/0 to 3/1) to give ethyl 6-(trifluoromethyl)-2-(((trifluoromethyl)sulfonyl)oxy)nicotinate (6 g, 85.38% yield).

$^1H$ NMR (400 MHz, $CDCl_3$) δ 8.70 (d, J=7.87 Hz, 1H) 7.89 (d, J=7.87 Hz, 1H) 4.53 (q, J=7.15 Hz, 2H) 1.48 (t, J=7.15 Hz, 3H).

Step B ethyl 2-(3-ethoxy-3-oxopropyl)-6-(trifluoromethyl)nicotinate

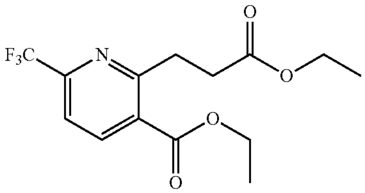 [SMILES: CCOC(=O)CCc1nc(C(F)(F)F)ccc1C(=O)OCC]

A mixture of ethyl 6-(trifluoromethyl)-2-(((trifluoromethyl)sulfonyl)oxy)nicotinate (6 g, 16.34 mmol), (1-ethoxycyclopropoxy)trimethylsilane (4.27 g, 24.51 mmol), $PPh_3$ (857.09 mg, 3.27 mmol), and $Pd(PPh_3)_2Cl_2$ (573.41 mg, 816.95 μmol) in toluene (120 mL) was degassed and purged with $N_2$ for 3 times, and then the mixture was stirred at 110° C. for 16 hrs under $N_2$ atmosphere. The reaction mixture was filtered and concentrated under reduced pressure to give a residue. The residue was purified by column chromatography ($SiO_2$, petroleum ether/ethyl acetate=1/0 to 5/1) to give ethyl 2-(3-ethoxy-3-oxopropyl)-6-(trifluoromethyl)nicotinate (2.9 g, 9.08 mmol, 55.59% yield).

$^1$H NMR (400 MHz, $CDCl_3$) δ 8.26 (d, J=7.2 Hz, 1H) 7.50 (d, J=7.2 Hz, 1H) 4.31-4.40 (m, 2H) 4.01-4.12 (m, 2H) 3.45-3.54 (m, 2H) 2.71-2.87 (m, 2H) 1.35 (t, J=7.09 Hz, 3H) 1.13-1.22 (m, 3H)

Step C methyl 5-oxo-2-(trifluoromethyl)-6,7-dihydro-5H-cyclopenta[b]pyridine-6-carboxylate

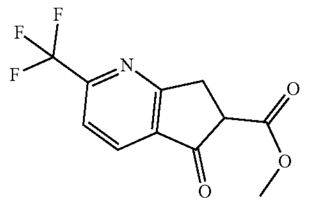 [SMILES: COC(=O)C1Cc2nc(C(F)(F)F)ccc2C1=O]

To a solution of ethyl 2-(3-ethoxy-3-oxopropyl)-6-(trifluoromethyl)nicotinate (2.8 g, 8.77 mmol) in THF (60 mL) was added LiHMDS (1 M, 17.54 mL). The mixture was stirred at −70° C. for 2 hrs. The reaction mixture was quenched by addition of a saturated aqueous solution of $NH_4Cl$ (10 mL) at −70° C. with stirring. The resulting solution was extracted with ethyl acetate (50 mL×3). The combined organic layers were washed with brine (50 mL), dried over $Na_2SO_4$, filtered and concentrated under reduced pressure to give methyl 5-oxo-2-(trifluoromethyl)-6,7-dihydro-5H-cyclopenta[b]pyridine-6-carboxylate (2.8 g, crude).

$^1$H NMR (400 MHz, $CDCl_3$) δ 7.79-7.97 (m, 1H) 7.34-7.52 (m, 1H) 4.02-4.18 (m, 2H) 3.25-3.66 (m, 3H) 1.14 (s, 3H).

Step D 2-(trifluoromethyl)-6,7-dihydro-5H-cyclopenta[b]pyridin-5-one

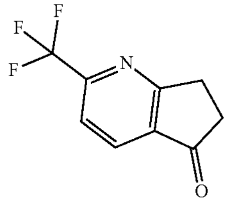 [SMILES: O=C1CCc2nc(C(F)(F)F)ccc21]

A solution of ethyl 5-oxo-2-(trifluoromethyl)-6,7-dihydrocyclopenta[b]pyridine-6-carboxylate (2.6 g, 9.52 mmol) and LiCl (2.02 g, 47.58 mmol) in DMSO (50 mL) and $H_2O$ (2.5 mL) was stirred at 100° C. for 1 hr. The reaction mixture was quenched by addition $H_2O$ (20 mL) at 0° C., and then extracted with ethyl acetate (30 mL×3). The combined organic layers were washed with brine (30 mL), dried over $Na_2SO_4$, filtered and concentrated under reduced pressure to give a residue. The residue was purified by column chromatography ($SiO_2$, petroleum ether/ethyl acetate=1/0 to 3/1) to give 2-(trifluoromethyl)-6,7-dihydro-5H-cyclopenta[b]pyridin-5-one (920 mg, 4.57 mmol, 48.06% yield).

$^1$H NMR (400 MHz, $CDCl_3$) δ 8.14 (d, J=8.00 Hz, 1H) 7.66 (d, J=8.00 Hz, 1H) 3.27-3.37 (m, 2H) 2.77-2.87 (m, 2H).

Step E (R,Z)-2-methyl-N-(2-(trifluoromethyl)-6,7-dihydro-5H-cyclopenta[b]pyridin-5-ylidene)propane-2-sulfinamide

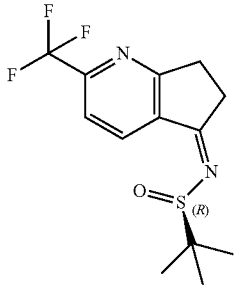

Tetraethoxytitanium (2.79 g, 12.23 mmol) was added to a mixture of 2-(trifluoromethyl)-6,7-dihydro-5H-cyclopenta[b]pyridin-5-one (820 mg, 4.08 mmol) and (R)-2-methylpropane-2-sulfinamide (518.80 mg, 4.28 mmol) in THF (15 mL). The mixture was stirred for 16 h at 70° C. Ethyl acetate (25 mL) and water (5 mL) were added to the mixture, and the formed precipitate was removed by filtration. The filtrate was concentrated in vacuo to give a residue. The residue was purified by column chromatography ($SiO_2$, petroleum ether/ethyl acetate=1/0 to 3/1) to give (R,Z)-2-methyl-N-(2-(trifluoromethyl)-6,7-dihydro-5H-cyclopenta[b]pyridin-5-ylidene)propane-2-sulfinamide (400 mg, 29.52% yield, 91.57% purity). LC-MS: m/z 305.1 $(M+H)^+$.

Step F (R)-2-methyl-N—((R)-2-(trifluoromethyl)-6,7-dihydro-5H-cyclopenta[b]pyridin-5-yl)propane-2-sulfinamide

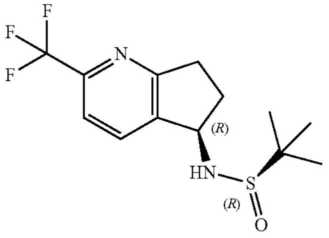

To a solution of (R,Z)-2-methyl-N-(2-(trifluoromethyl)-6,7-dihydro-5H-cyclopenta[b]pyridin-5-ylidene)propane-2-sulfinamide (400 mg, 1.31 mmol) in DCM (10 mL) was added dropwise DIBAL-H (1 M, 2.63 mL) at −70° C. After addition, the mixture was stirred at this temperature for 2 hrs. The reaction mixture was quenched by addition MeOH (5 mL) at 0° C., and then diluted with $H_2O$ (5 mL) and extracted with DCM (20 mL×2). The combined organic layers were washed with brine (10 mL), dried over $Na_2SO_4$, filtered and concentrated under reduced pressure to give a residue. The residue was purified by column chromatography ($SiO_2$, petroleum ether/ethyl acetate=1/0 to 1/1) to give (R)-2-methyl-N—((R)-2-(trifluoromethyl)-6,7-dihydro-5H-cyclopenta[b]pyridin-5-yl)propane-2-sulfinamide (288 mg, 71.53% yield). LC-MS: m/z 307.1 $(M+H)^+$.

Step G (R)-2-(trifluoromethyl)-6,7-dihydro-5H-cyclopenta[b]pyridin-5-amine

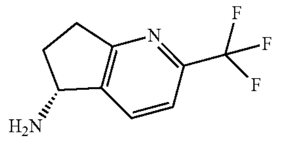

A mixture of (R)-2-methyl-N—((R)-2-(trifluoromethyl)-6,7-dihydro-5H-cyclopenta[b]pyridin-5-yl)propane-2-sulfinamide (288 mg, 940.11 μmol) and HCl/dioxane (2 M, 3.29 mL) in MeOH (3 mL) was degassed and purged with $N_2$ for 3 times, and then the mixture was stirred at 20° C. for 2 hrs under $N_2$ atmosphere. The reaction mixture was concentrated under reduced pressure to give a residue. The resulting product was dissolved in petroleum ether/ethyl acetate=3/1 (10 mL) and filtered to give (R)-2-(trifluoromethyl)-6,7-dihydro-5H-cyclopenta[b]pyridin-5-amine (150 mg, 65.85% yield, 98.48% purity, HCl salt).

$^1H$ NMR (400 MHz, MeOD-$d_4$) δ 8.14 (d, J=8 Hz, 1H) 7.77 (d, J=8 Hz, 1H) 4.96-4.99 (m, 1H) 3.26-3.32 (m, 1H) 3.13-3.23 (m, 1H) 2.73-2.84 (m, 1H) 2.16-2.28 (m, 1H). LC-MS: m/z 203.0 $(M+H)^+$.

Step H (R)-2-(1,3-dioxolan-2-yl)-N-(2-(trifluoromethyl)-6,7-dihydro-5H-cyclopenta[b]pyridin-5-yl)thieno[2,3-c]pyridin-7-amine

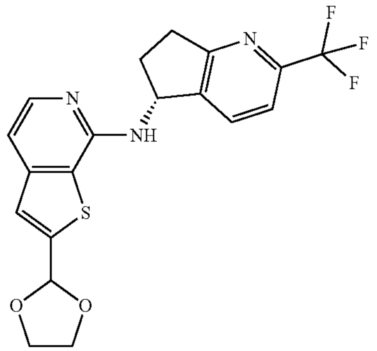 [SMILES: FC(F)(F)c1ccc2c(n1)CC[C@H]2Nc1nccc2cc(C3OCCO3)sc12]

A mixture of 7-chloro-2-(1,3-dioxolan-2-yl)thieno[2,3-c]pyridine (150 mg, 620.62 μmol), (R)-2-(trifluoromethyl)-6,7-dihydro-5H-cyclopenta[b]pyridin-5-amine (148.10 mg, 620.62 μmol, HCl), $Cs_2CO_3$ (606.63 mg, 1.86 mmol), $Pd(OAc)_2$ (13.93 mg, 62.06 μmol) and BINAP (77.29 mg, 124.12 μmol) in dioxane (4 mL) was degassed and purged with $N_2$ for 3 times, and then the mixture was stirred at 110° C. for 16 hrs under $N_2$ atmosphere. The reaction mixture was filtered and concentrated under reduced pressure to give a residue. The residue was purified by column chromatography ($SiO_2$, petroleum ether/ethyl acetate=1/0 to 2/1) to give (R)-2-(1,3-dioxolan-2-yl)-N-(2-(trifluoromethyl)-6,7-dihydro-5H-cyclopenta[b]pyridin-5-yl)thieno[2,3-c]pyridin-7-amine (190 mg, 75.14% yield, 100.00% purity). LC-MS: m/z 408.1 $(M+H)^+$.

Step I (R)-7-((2-(trifluoromethyl)-6,7-dihydro-5H-cyclopenta[b]pyridin-5-yl)amino)thieno[2,3-c]pyridine-2-carbaldehyde

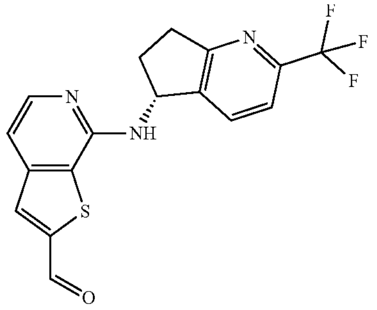 [SMILES: O=Cc1cc2ccnc(N[C@@H]3CCc4nc(C(F)(F)F)ccc43)c2s1]

A mixture of (R)-2-(1,3-dioxolan-2-yl)-N-(2-(trifluoromethyl)-6,7-dihydro-5H-cyclopenta[b]pyridin-5-yl)thieno[2,3-c]pyridin-7-amine (190 mg, 466.36 μmol) and HCl (2 M, 5 mL) in THF (3 mL) was degassed and purged with $N_2$ for 3 times, and then the mixture was stirred at 45° C. for 16 hrs under $N_2$ atmosphere. The reaction mixture was filtered and quenched by addition aq. $NaHCO_3$ (10 mL) at 0° C., and then diluted with ethyl acetate (10 mL) and extracted with ethyl acetate (10 mL). The combined organic layers were washed with brine 10 mL (10 mL), dried over $Na_2SO_4$, filtered and concentrated under reduced pressure to give (R)-7-((2-(trifluoromethyl)-6,7-dihydro-5H-cyclopenta[b]pyridin-5-yl)amino)thieno[2,3-c]pyridine-2-carbaldehyde (150 mg, 88.52% yield). LC-MS: m/z 364.0 $(M+H)^+$.

Step J ethyl 2-((S)-1-(tert-butoxycarbonyl)pyrrolidin-2-yl)-6-(4-fluorophenethyl)-5-(5-oxo-4,5-dihydro-1,3,4-oxadiazol-2-yl)-4-(7-(((R)-2-(trifluoromethyl)-6,7-dihydro-5H-cyclopenta[b]pyridin-5-yl)amino)thieno[2,3-c]pyridin-2-yl)-1,4-dihydropyridine-3-carboxylate

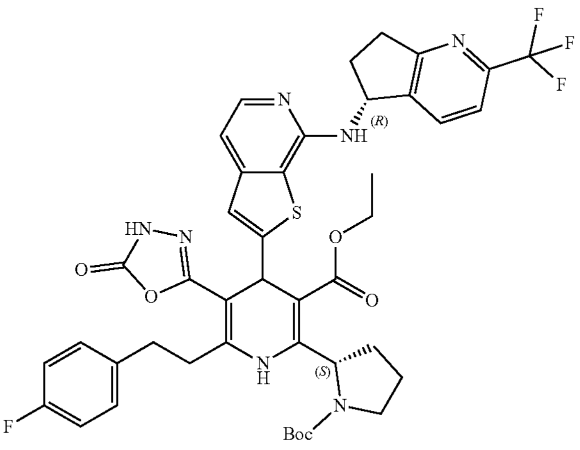

A mixture of tert-butyl (S)-2-(3-ethoxy-3-oxopropanoyl)pyrrolidine-1-carboxylate (40 mg, 140.19 μmol), 5-(4-(4-fluorophenyl)-2-oxobutyl)-1,3,4-oxadiazol-2(3H)-one (35.08 mg, 140.19 μmol), (R)-7-((2-(trifluoromethyl)-6,7-dihydro-5H-cyclopenta[b]pyridin-5-yl)amino)thieno[2,3-c]pyridine-2-carbaldehyde (50.94 mg, 140.19 μmol), $NH_4OAc$ (21.61 mg, 280.37 μmol) and $Yb(OTf)_3$ (8.70 mg, 14.02 μmol) in EtOH (2 mL) was degassed and purged with $N_2$ for 3 times, and then the mixture was stirred at 50° C. for 16 hrs under $N_2$ atmosphere. The reaction mixture was filtered and concentrated under reduced pressure to give ethyl 2-((S)-1-(tert-butoxycarbonyl)pyrrolidin-2-yl)-6-(4-fluorophenethyl)-5-(5-oxo-4,5-dihydro-1,3,4-oxadiazol-2-yl)-4-(7-(((R)-2-(trifluoromethyl)-6,7-dihydro-5H-cyclopenta[b]pyridin-5-yl)amino)thieno[2,3-c]pyridin-2-yl)-1,4-dihydropyridine-3-carboxylate (125 mg, crude). LC-MS: m/z 862.2 $(M+H)^+$.

Step K ethyl 2-((S)-1-(tert-butoxycarbonyl)pyrrolidin-2-yl)-6-(4-fluorophenethyl)-5-(5-oxo-4,5-dihydro-1,3,4-oxadiazol-2-yl)-4-(7-(((R)-2-(trifluoromethyl)-6,7-dihydro-5H-cyclopenta[b]pyridin-5-yl)amino)thieno[2,3-c]pyridin-2-yl)nicotinate

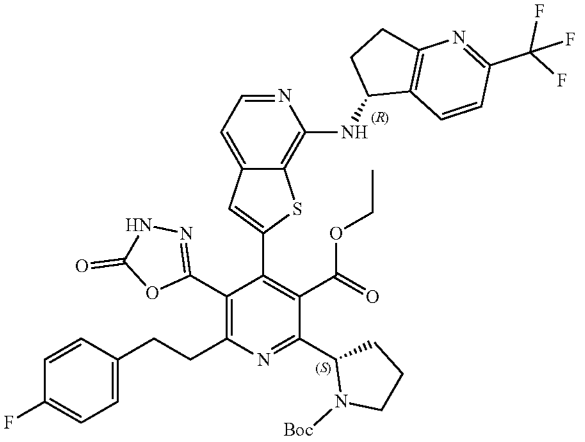

A mixture of ethyl 2-((S)-1-(tert-butoxycarbonyl)pyrrolidin-2-yl)-6-(4-fluorophenethyl)-5-(5-oxo-4,5-dihydro-1,3,4-oxadiazol-2-yl)-4-(7-(((R)-2-(trifluoromethyl)-6,7-dihydro-5H-cyclopenta[b]pyridin-5-yl)amino)thieno[2,3-c]pyridin-2-yl)-1,4-dihydropyridine-3-carboxylate (125 mg, 145.03 μmol) and CAN (159.02 mg, 290.06 μmol) in EtOH (4 mL) was degassed and purged with $N_2$ for 3 times, and then the mixture was stirred at 20° C. for 1 hr under $N_2$ atmosphere. The reaction mixture was diluted with ethyl acetate (20 mL) and washed with brine (5 mL×2), dried over $Na_2SO_4$, filtered and concentrated under reduced pressure to ethyl 2-((S)-1-(tert-butoxycarbonyl)pyrrolidin-2-yl)-6-(4-fluorophenethyl)-5-(5-oxo-4,5-dihydro-1,3,4-oxadiazol-2-yl)-4-(7-(((R)-2-(trifluoromethyl)-6,7-dihydro-5H-cyclopenta[b]pyridin-5-yl)amino)thieno[2,3-c]pyridin-2-yl) nicotinate (150 mg, crude). LC-MS: m/z 860.2 $(M+H)^+$.

Step L ethyl 6-(4-fluorophenethyl)-5-(5-oxo-4,5-dihydro-1,3,4-oxadiazol-2-yl)-2-((S)-pyrrolidin-2-yl)-4-(7-(((R)-2-(trifluoromethyl)-6,7-dihydro-5H-cyclopenta[b]pyridin-5-yl)amino)thieno[2,3-c]pyridin-2-yl)nicotinate

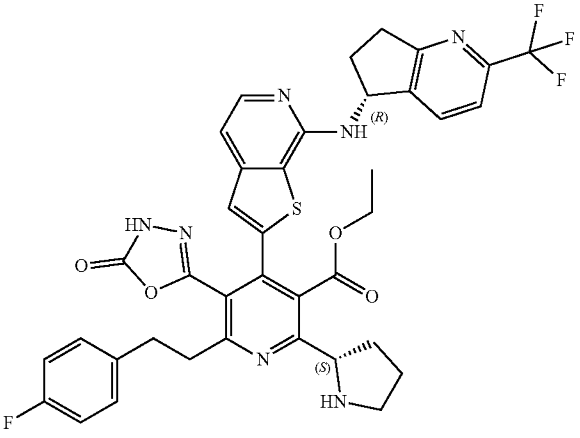

A mixture of ethyl 2-((S)-1-(tert-butoxycarbonyl)pyrrolidin-2-yl)-6-(4-fluorophenethyl)-5-(5-oxo-4,5-dihydro-1,3,4-oxadiazol-2-yl)-4-(7-(((R)-2-(trifluoromethyl)-6,7-dihydro-5H-cyclopenta[b]pyridin-5-yl)amino)thieno[2,3-c]pyridin-2-yl)nicotinate (150 mg, 174.44 μmol) and HCl (2 M, 1.74 mL) in dioxane (1 mL) was degassed and purged with $N_2$ for 3 times, and then the mixture was stirred at 20° C. for 4 hrs under $N_2$ atmosphere. The reaction mixture was concentrated under reduced pressure to give ethyl 6-(4-fluorophenethyl)-5-(5-oxo-4,5-dihydro-1,3,4-oxadiazol-2-yl)-2-((S)-pyrrolidin-2-yl)-4-(7-(((R)-2-(trifluoromethyl)-6,7-dihydro-5H-cyclopenta[b]pyridin-5-yl)amino)thieno[2,3-c]pyridin-2-yl)nicotinate (150 mg, crude). LC-MS: m/z 760.2 $(M+H)^+$.

Step M 5-((S)-2-(4-fluorophenethyl)-5-oxo-4-(7-(((R)-2-(trifluoromethyl)-6,7-dihydro-5H-cyclopenta[b]pyridin-5-yl)amino)thieno[2,3-c]pyridin-2-yl)-7,8,9,9a-tetrahydro-5H-pyrido[2,3-a]pyrrolizin-3-yl)-1,3,4-oxadiazol-2(3H)-one

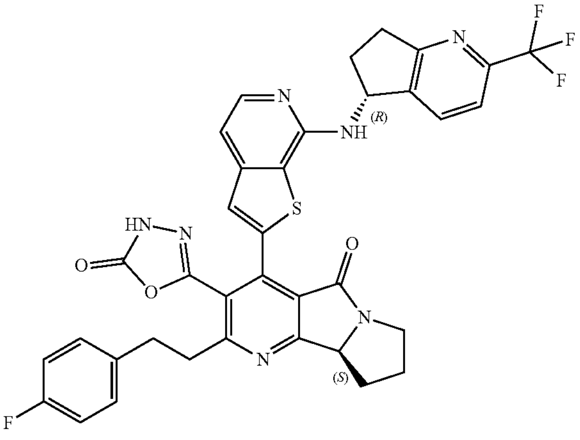

A mixture of ethyl 6-(4-fluorophenethyl)-5-(5-oxo-4,5-dihydro-1,3,4-oxadiazol-2-yl)-2-((S)-pyrrolidin-2-yl)-4-(7-(((R)-2-(trifluoromethyl)-6,7-dihydro-5H-cyclopenta[b]pyridin-5-yl)amino)thieno[2,3-c]pyridin-2-yl)nicotinate (150 mg, 197.43 μmol) and $Na_2CO_3$ (418.50 mg, 3.95 mmol) in dioxane (4 mL) and $H_2O$ (4 mL) was degassed and purged with $N_2$ for 3 times, and then the mixture was stirred at 20° C. for 16 hrs under $N_2$ atmosphere. The reaction mixture was extracted with ethyl acetate (10 mL×3). The combined organic layers were washed with brine (10 mL), dried over $Na_2SO_4$, filtered and concentrated under reduced pressure to give a residue. The residue was purified by prep-HPLC (column: C18 150×30 mm; mobile phase: [water(FA)-ACN]; gradient: 31%-61% B over 7 min) to give 5-((S)-2-(4-fluorophenethyl)-5-oxo-4-(7-(((R)-2-(trifluoromethyl)-6,7-dihydro-5H-cyclopenta[b]pyridin-5-yl)amino)thieno[2,3-c]pyridin-2-yl)-7,8,9,9a-tetrahydro-5H-pyrido[2,3-a]pyrrolizin-3-yl)-1,3,4-oxadiazol-2(3H)-one (8.41 mg, 5.97% yield).

$^1$H NMR (400 MHz, MeOD-$d_4$) δ 7.97-8.03 (d, J=5.6 Hz, 1H) 7.86-7.92 (m, 1H) 7.60-7.66 (m, 1H) 7.47 (s, 1H) 7.12-7.23 (m, 3H) 6.93-7.03 (m, 2H) 5.92-6.02 (m, 1H) 3.63-3.75 (m, 1H) 3.39-3.49 (m, 1H) 3.21-3.31 (m, 1H) 3.16-3.21 (m, 1H) 3.04-3.16 (m, 3H) 2.74-2.83 (m, 1H) 2.38-2.56 (m, 3H) 2.14-2.27 (m, 1H) 1.42-1.56 (m, 1H). $^{19}$F NMR (376 MHz, METHANOL-$d_4$) δ −68.69 (s, 1 F) −119.08 (s, 1 F). LC-MS: m/z 714.2 (M+H)$^+$.

(S)-5-(4-(7-(benzofuran-3-ylmethyl)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 248)

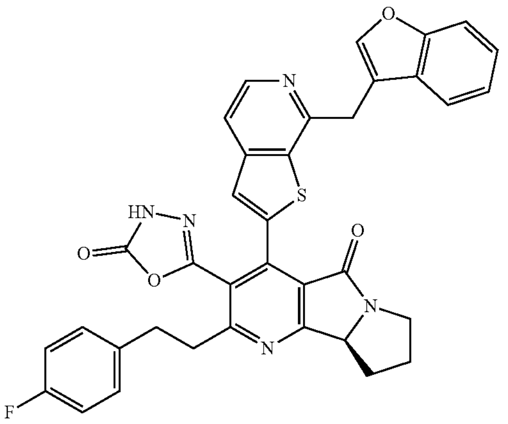 [SMILES: O=C1c2c(nc(CCc3ccc(F)cc3)c(-c3n[nH]c(=O)o3)c2-c2cc3ccnc(Cc4coc5ccccc45)c3s2)[C@@H]2CCCN12]

Compound 248 was synthesized using a similar procedure described in Example 10 by using the appropriate materials.

$^1$H NMR (400 MHz, MeOD-$d_4$) δ ppm 8.55-8.58 (m, 1H), 8.24-8.28 (m, 1H), 7.88-7.89 (m, 1H), 7.85-7.87 (m, 1H), 7.52-7.56 (m, 1H), 7.41-7.45 (m, 1H), 7.32-7.37 (m, 1H), 7.21-7.27 (m, 1H), 7.13-7.18 (m, 2H), 6.95-7.00 (m, 2H), 4.91-4.96 (m, 1H), 4.80-4.82 (m, 2H), 3.62-3.72 (m, 1H), 3.42-3.48 (m, 1H), 3.34-3.37 (m, 1H), 3.30-3.32 (m, 1H), 3.08-3.16 (m, 2H), 2.41-2.55 (m, 3H), 1.46-1.56 (m, 1H). $^{19}$F NMR (376 MHz, MeOD-$d_4$) δ −118.96 (s, 1 F). LC-MS: m/z 644.1 (M+H)$^+$.

(S)-5-(2-(4-fluorophenethyl)-4-(7-((1-methyl-1H-indol-3-yl)methyl)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 249)

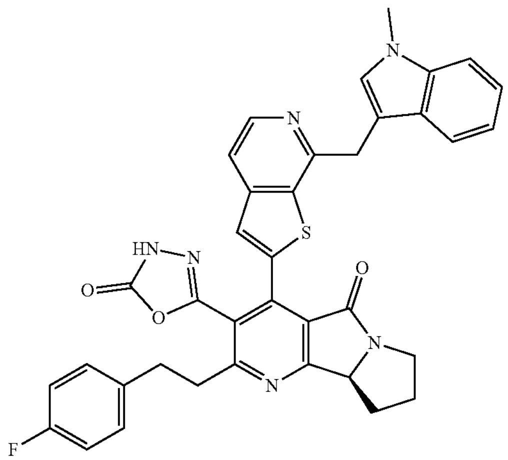 [SMILES: Cn1cc(Cc2nccc3cc(-c4c5c(nc(CCc6ccc(F)cc6)c4-c4n[nH]c(=O)o4)[C@@H]4CCCN4C5=O)sc23)c2ccccc21]

Compound 249 was synthesized using a similar procedure described in Example 10 by using the appropriate materials.

$^1$H NMR (400 MHz, $CDCl_3$) δ 8.51-8.55 (d, J=5.6 Hz, 1H), 7.67 (s, 1H), 7.55-7.64 (m, 2H), 7.40-7.47 (m, 1H), 7.30-7.33 (m, 1H), 7.14-7.19 (m, 1H), 7.06-7.12 (m, 2H), 6.92-7.00 (m, 3H), 4.71-4.79 (m, 1H), 4.53 (s, 2H), 3.71-3.83 (m, 4H), 3.39-3.53 (m, 1H), 2.96-3.18 (m, 4H), 2.47-2.59 (m, 1H), 2.30-2.45 (m, 2H), 1.39-1.50 (m, 2H). $^{19}$F NMR (376 MHz, $CDCl_3$) δ −116.70 (s, 1 F). LC-MS: m/z 657.2 (M+H)$^+$ 5-((S)-2-(((S)-5-fluoro-2,3-dihydro-1H-inden-1-yl)methyl)-4-(7-(((R)-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 250)

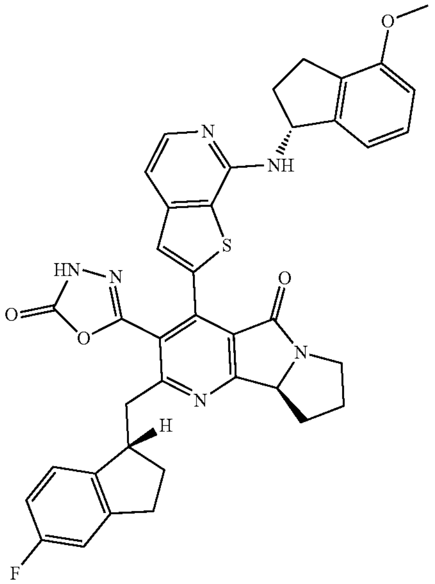 [SMILES: COc1cccc2c1CC[C@H]2Nc1nccc2cc(-c3c4c(nc(C[C@@H]5CCc6cc(F)ccc65)c3-c3n[nH]c(=O)o3)[C@@H]3CCCN3C4=O)sc12]

Compound 250 was synthesized using a similar procedure described in Example 30 by using the appropriate materials.

$^{1}H$ NMR (400 MHz, MeOD-$d_4$): δ 7.88-7.99 (m, 1H), 7.46-7.50 (m, 1H), 7.09-7.22 (m, 2H), 6.88-6.99 (m, 3H), 6.79-6.85 (m, 2H), 5.80-5.86 (m, 1H), 3.82-3.89 (m, 3H), 3.65-3.76 (m, 2H), 3.39-3.50 (m, 2H), 2.93-3.09 (m, 3H), 2.74-2.87 (m, 2H), 2.64-2.72 (m, 1H), 2.39-2.54 (m, 3H), 2.18-2.27 (m, 1H), 1.94-2.05 (m, 2H), 1.48-1.57 (m, 1H), 1.29-1.34 (m, 3H), 0.88-0.97 (m, 1H). $^{19}F$ NMR (400 MHz, MeOD-$d_4$): 120.0 (S, 1 F). LC-MS: m/z 701.2 $(M+H)^+$.

5-((S)-4-(7-(((R)-2,2-difluoro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 251)

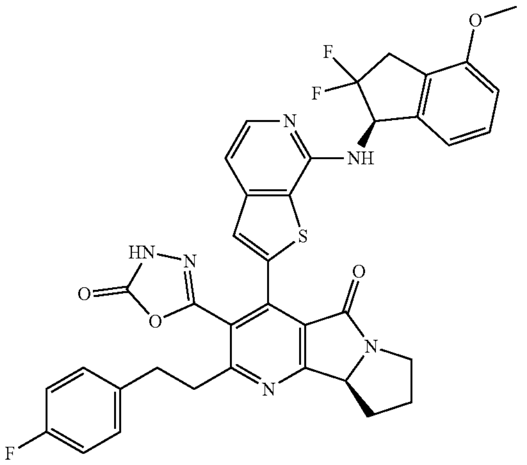 [SMILES: COc1cccc2c1CC(F)(F)[C@@H]2Nc1nccc2cc(-c3c4c(nc(CCc5ccc(F)cc5)c3-c3n[nH]c(=O)o3)[C@@H]3CCCN3C4=O)sc12]

Compound 251 was synthesized using a similar procedure described in Example 10 by using the appropriate materials.

$^{1}H$ NMR (400 MHz, MeOD-$d_4$) δ 7.97-8.03 (d, J=5.6 Hz, 1H), 7.46 (s, 1H), 7.26-7.34 (m, 1H), 7.13-7.22 (m, 3H), 6.96-7.03 (m, 2H), 6.89-6.95 (m, 2H), 6.22-6.32 (m, 1H), 3.87 (s, 3H), 3.64-3.73 (m, 1H), 3.39-3.54 (m, 3H), 3.36-3.38 (m, 1H), 3.23-3.29 (m, 2H), 3.05-3.19 (m, 2H), 2.39-2.56 (m, 3H), 1.43-1.55 (m, 1H). $^{19}F$ NMR (376 MHz, MeOD-$d_4$) δ −103.22--101.71 (m, 1 F) −109.86 (m, 1 F) −119.02 (s, 1 F). LC-MS: m/z 711.1 $(M+H)^+$.

6-(1-(7-((S)-2-(4-fluorophenethyl)-5-oxo-3-(5-oxo-4,5-dihydro-1,3,4-oxadiazol-2-yl)-7,8,9,9a-tetrahydro-5H-pyrido[2,3-a]pyrrolizin-4-yl)-2,2-dimethyl-3-oxo-2H-benzo[b][1,4]oxazin-4(3H)-yl)ethyl) nicotinonitrile (Compound 252)

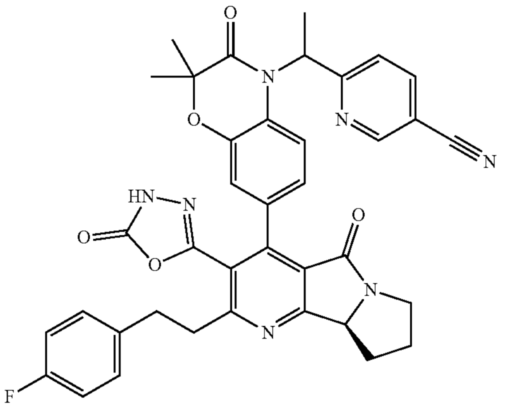 [SMILES: CC(c1ccc(C#N)cn1)N1C(=O)C(C)(C)Oc2cc(-c3c4c(nc(CCc5ccc(F)cc5)c3-c3n[nH]c(=O)o3)[C@@H]3CCCN3C4=O)ccc21]

Compound 252 was synthesized using a similar procedure described in Example 19 by using the appropriate materials. $^{1}H$ NMR (400 MHz, MeOD-$d_4$) δ ppm 8.84-8.92 (m, 1H), 8.10-8.15 (m, 1H), 7.52-7.56 (m, 1H), 7.12-7.16 (m, 2H), 6.95-7.00 (m, 2H), 6.83-6.93 (m, 2H), 6.11-6.19 (m, 1H), 4.84-4.87 (m, 1H), 3.60-3.74 (m, 1H), 3.39-3.49 (m, 1H), 3.20-3.27 (m, 2H), 3.01-3.15 (m, 2H), 2.37-2.54 (m, 3H), 1.87-1.96 (m, 3H), 1.47-1.51 (m, 6H), 1.42-1.47 (m, 1H). 19F NMR (377 MHz, MeOD-$d_4$) δ ppm −119.045. LC-MS: m/z 686.2 $(M+H)^+$.

5-((S)-4-(7-(((R)-5,6-difluoro-2,3-dihydro-1H-inden-1-yl)amino)-5-methylthieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 253)

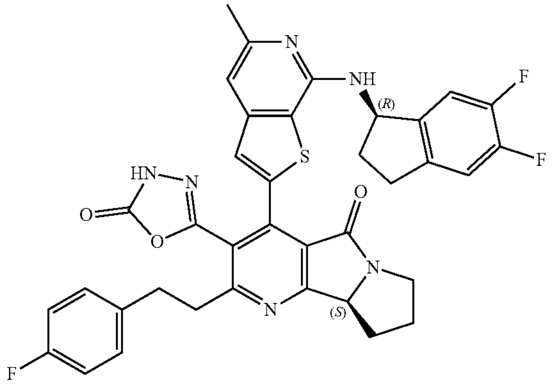

Compound 253 was synthesized using a similar procedure described in Example 20 by using the appropriate materials. $^{1}H$ NMR (400 MHz, DMSO-$d_6$): δ 12.69 (br s, 1H), 7.29-7.36 (m, 2H), 7.17-7.26 (m, 4H), 7.03-7.10 (m, 2H), 6.95 (s, 1H), 5.78-5.87 (m, 1H), 4.83-4.90 (m, 1H), 3.50-3.59 (m, 2H), 3.16-3.20 (m, 2H), 3.05-3.11 (m, 1H), 2.94-3.04 (m, 2H), 2.78-2.88 (m, 2H), 2.41 (s, 3H), 2.35-2.38 (m, 1H), 2.23-2.30 (m, 2H), 2.02-2.14 (m, 1H), 1.36-1.49 (m, 1H). 19F NMR (377 MHz, DMSO-d6): −117.03, −140.57, −141.53. LC-MS: m/z 695.3 (M+H)$^+$.

(R)-4-(7-(((R)-5,6-difluoro-2,3-dihydro-1H-inden-1-yl)amino)-5-methylthieno[2,3-c]pyridin-2-yl)-2-(4-fluorophenethyl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 254)

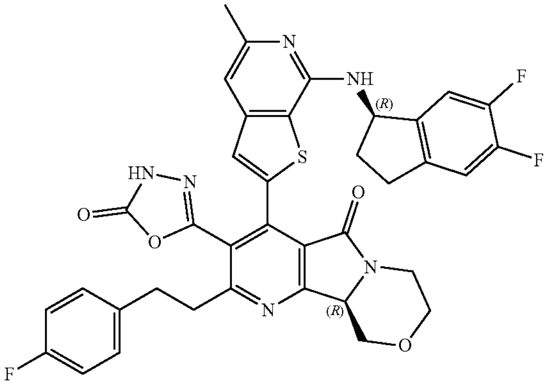

Compound 254 was synthesized using a similar procedure described in Example 20 by using the appropriate materials. (2.90 mg, 0.004 mmol, 3.54%)

$^1$H NMR (400 MHz, DMSO-$d_6$): δ 12.62 (br s, 1H), 7.30-7.36 (m, 2H), 7.16-7.25 (m, 4H), 7.047.09 (m, 2H), 6.96 (s, 1H), 5.79-5.86 (m, 1H), 4.81 (dd, J=10.4 Hz, J=4.4 Hz, 1H), 4.47 (dd, J=11.2 Hz, J=4.0 Hz, 1H), 4.03-4.10 (m, 1H), 3.92-3.99 (m, 1H), 3.24-3.27 (m, 2H), 3.16-3.21 (m, 3H), 2.96-3.07 (m, 3H), 2.79-2.87 (m, 1H), 2.42 (s, 3H), 2.02-2.12 (m, 1H), 1.05 (d, J=6.4 Hz, 1H). 19F NMR (377 MHz, DMSO-d6): −117.03, −140.58, −141.54. LC-MS: m/z 711.2 (M+H)$^+$.

(R)-5-(4-(7-((5,6-difluoro-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 255)

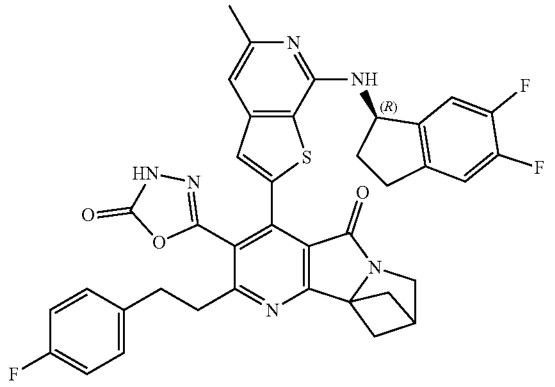

Compound 255 was synthesized using a similar procedure described in Example 20 by using the appropriate materials.

$^1$H NMR (400 MHz, DMSO-$d_6$): δ 7.30-7.35 (m, 2H), 7.17-7.25 (m, 4H), 7.07 (t, J=8.8 Hz, 2H), 6.94 (s, 1H), 5.79-5.85 (m, 1H), 3.56 (s, 2H), 3.15-3.22 (m, 3H), 2.97-3.07 (m, 3H), 2.79-2.88 (m, 1H), 2.61-2.68 (m, 2H), 2.55-2.57 (m, 1H), 2.41 (s, 3H), 2.03-2.14 (m, 1H), 1.74 (d, J=4.0 Hz, 2H). 19F NMR (377 MHz, DMSO-$d_6$): δ −117.03, −140.59, −141.547. LC-MS: m/z 707.3 (M+H)$^+$.

Example 39

5-[(9aS)-4-[7-[[(1R)-6-chloro-4-fluoro-5-methoxy-indan-1-yl]amino]thieno[2,3-c]pyridin-2-yl]-2-[2-(4-fluorophenyl)ethyl]-5-oxo-7,8,9,9a-tetrahydropyrido[2,3-a]pyrrolizin-3-yl]-3H-1,3,4-oxadiazol-2-one (Compound 256)

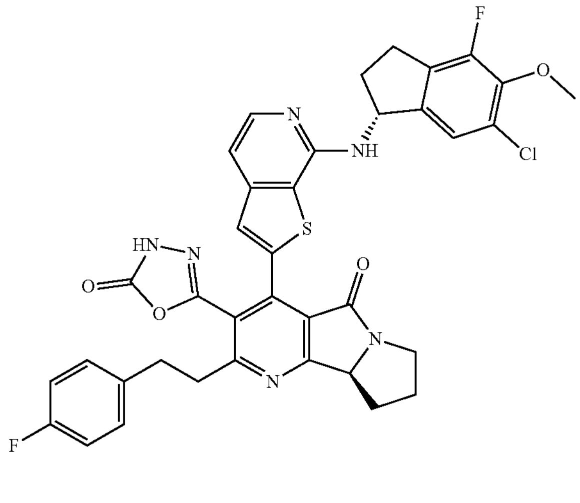 [SMILES: COc1c(Cl)cc2c(c1F)CC[C@H]2Nc1nccc2cc(-c3c4c(nc(CCc5ccc(F)cc5)c3-c3n[nH]c(=O)o3)[C@@H]3CCCN3C4=O)sc12]

-continued
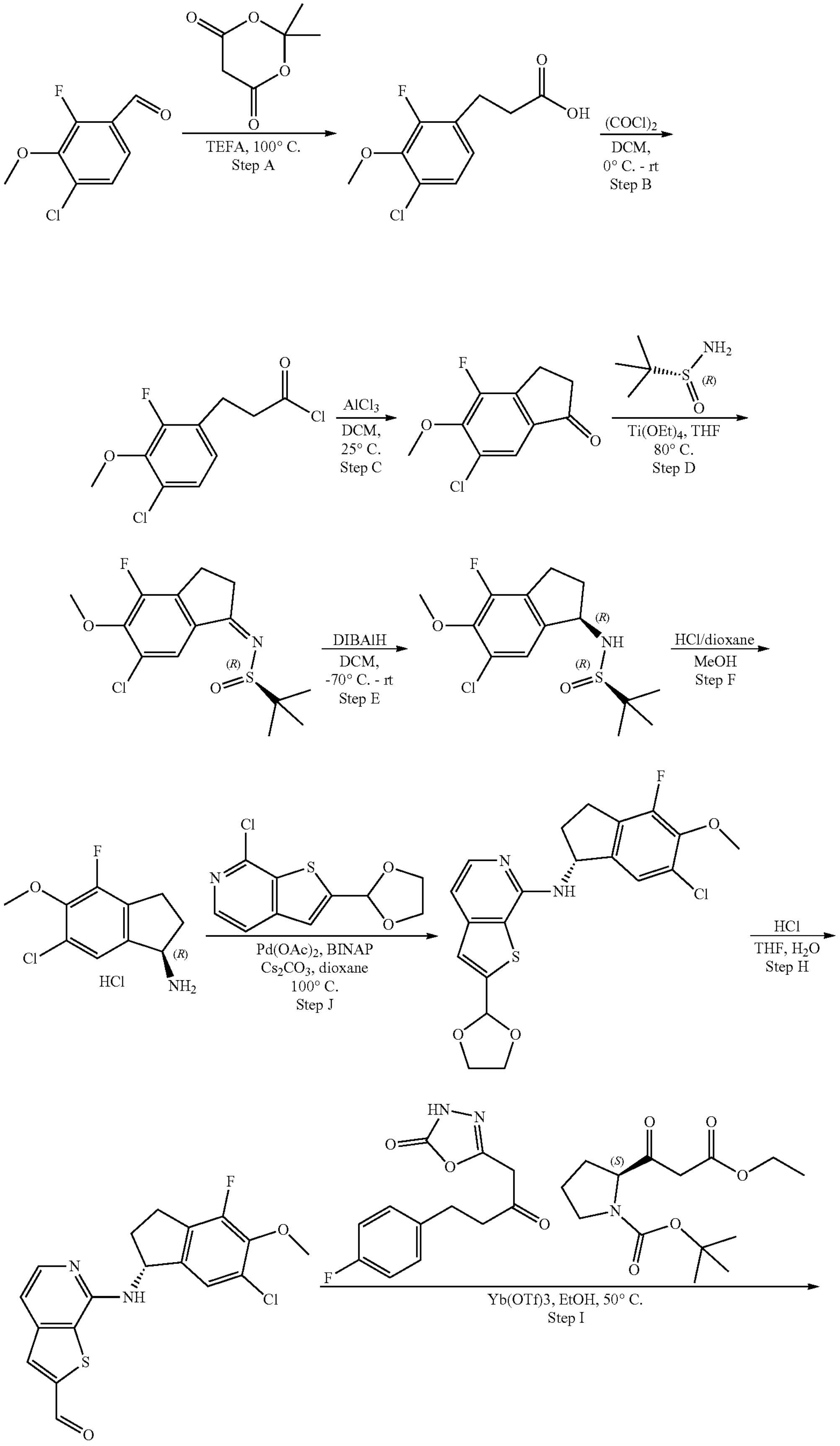

-continued
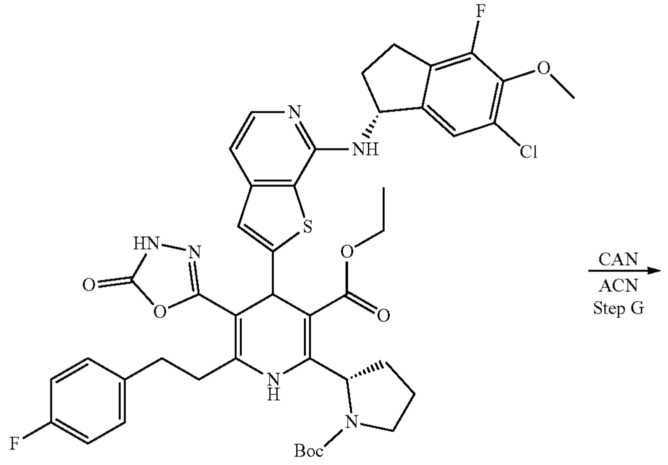
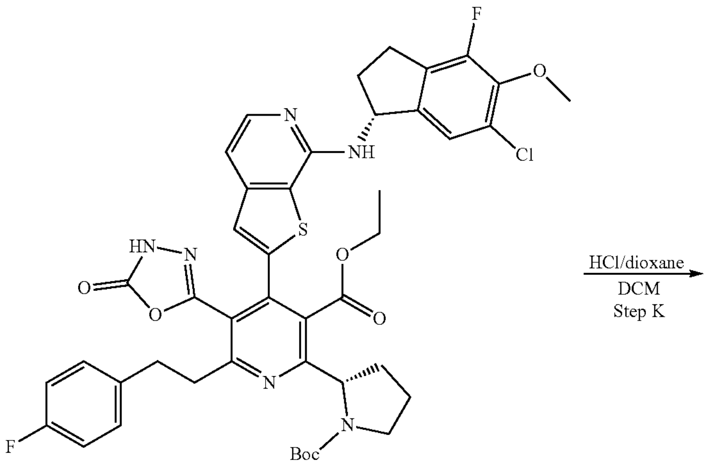
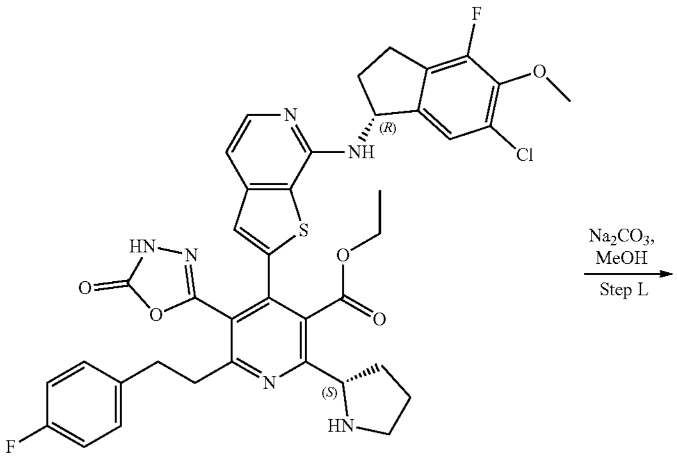

-continued

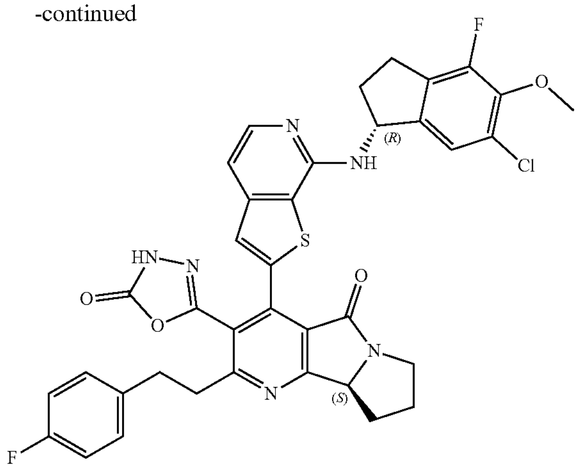

Step A 3-(4-chloro-2-fluoro-3-methoxy-phenyl) propanoic acid

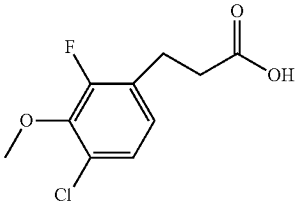

To a solution of TEA (5.37 g, 53.03 mmol, 7.38 mL) was added formic acid (7.32 g, 159.08 mmol, 6.00 mL) at 0° C. over 15 min. After addition, the mixture was stirred at this temperature for 10 min and then 2, 2-dimethyl-1, 3-dioxane-4, 6-dione (4.59 g, 31.82 mmol) and 4-chloro-2-fluoro-3-methoxy-benzaldehyde (5 g, 26.51 mmol) were added. The resulting mixture was stirred at 100° C. for 16 hours. The reaction mixture was diluted with $H_2O$ (80 mL) and adjusted pH to 10 by NaOH solid and then and washed with EtOAc (80 mL*2). The aqueous phase adjusted pH to 3 by HCl (12 M), extracted with EtOAc (100 mL*2). The combined organic layers were washed with brine (120 mL), dried over $Na_2SO_4$, filtered and concentrated under reduced pressure to give crude product 3-(4-chloro-2-fluoro-3-methoxy-phenyl) propanoic acid (6 g, 25.79 mmol, 97.28% yield), which was used for next step without further purification.

$^1H$ NMR (400 MHz, $CDCl_3$) δ ppm 7.21-7.26 (m, 1H), 7.06 (m, 1H), 3.83-3.88 (m, 3H), 2.82 (m, 2H), 2.54-2.69 (m, 2H).

Step B 3-(4-chloro-2-fluoro-3-methoxy-phenyl)propanoyl chloride

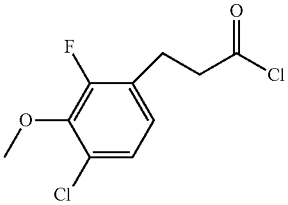

To a solution of 3-(4-chloro-2-fluoro-3-methoxy-phenyl) propanoic acid (6 g, 25.79 mmol) in DCM (40 mL) was added $(COCl)_2$ (9.82 g, 77.37 mmol, 6.77 mL) at 0° C., and then DMF (188.51 mg, 2.58 mmol) was added. The mixture was stirred at 25° C. for 12.5 hours. The reaction mixture was concentrated under reduced pressure to give 3-(4-chloro-2-fluoro-3-methoxy-phenyl) propanoyl chloride (6.48 g, 25.81 mmol, 100% yield), which was used into the next step without further purification.

Step C 6-chloro-4-fluoro-5-methoxy-indan-1-one

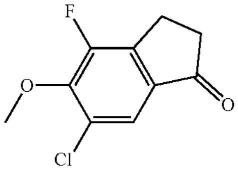

To a solution of 3-(4-chloro-2-fluoro-3-methoxy-phenyl) propanoyl chloride (6.4 g, 25.49 mmol) in DCM (40 mL) was added $AlCl_3$ (5.10 g, 38.23 mmol). The mixture was stirred at 25° C. for 0.5 hour. The reaction mixture was quenched by ice-water (50 mL) at 0° C., and then diluted with $H_2O$ (100 mL) and extracted with EtOAc (150 mL*3). The combined organic layers were washed with brine (200 mL), dried over $Na_2SO_4$, filtered and concentrated under reduced pressure to give a residue. The residue was purified by flash silica gel chromatography (ISCO®; 80 g SepaFlash® Silica Flash Column, Eluent of 0~30% Ethylacetate/Petroleum ether gradient @80 mL/min) to give 6-chloro-4-fluoro-5-methoxy-indan-1-one (4 g, 18.64 mmol, 73.12% yield).

$^1$H NMR (400 MHz, DMSO-$d_6$) δ ppm 7.50-7.65 (m, 1H), 4.03-4.04 (m, 3H), 3.02-3.16 (m, 2H), 2.64-2.72 (m, 2H), LC-MS: m/z 286.9 $(M+H)^+$.

Step D (NZ,R)—N-(6-chloro-4-fluoro-5-methoxy-indan-1-ylidene)-2-methyl-propane-2-sulfinamide

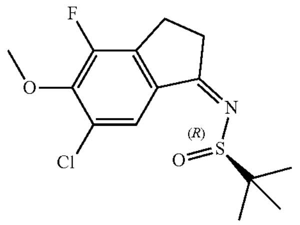

A mixture of 6-chloro-4-fluoro-5-methoxy-indan-1-one (4 g, 18.64 mmol, 1.68 eq), (R)-2-methylpropane-2-sulfinamide (1.41 g, 11.66 mmol), tetraethoxytitanium (5.06 g, 22.20 mmol, 4.60 mL) in THF (40 mL) was degassed and purged with $N_2$ for 3 times, and then the mixture was stirred at 80° C. for 12 hours under $N_2$ atmosphere. The reaction mixture was diluted with water (50 mL) and EtOAc (100 mL), filtered and extracted with EtOAc (100 mL*3). The combined organic layers were washed with brine (50 mL), dried over $Na_2SO_4$, filtered and concentrated under reduced pressure to give a residue. The residue was purified by flash silica gel chromatography (ISCO®; 80 g SepaFlash® Silica Flash Column, Eluent of 0~50% Ethylacetate/Petroleum ether gradient @80 mL/min) to give (NZ,R)—N-(6-chloro-4-fluoro-5-methoxy-indan-1-ylidene)-2-methyl-propane-2-sulfinamide (1.1 g, 3.46 mmol, 31.18% yield).

$^1$H NMR (400 MHz, DMSO-$d_6$) δ ppm 7.50-7.65 (m, 1H), 4.03-4.04 (m, 3H), 3.02-3.16 (m, 2H), 2.64-2.72 (m, 2H), LC-MS: m/z 318.1 $(M+H)^+$.

Step E (R)—N—[(JR)-6-chloro-4-fluoro-5-methoxy-indan-1-yl]-2-methyl-propane-2-sulfinamide

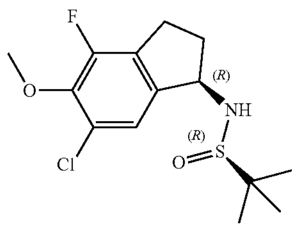

To a solution of (NZ,R)—N-(6-chloro-4-fluoro-5-methoxy-indan-1-ylidene)-2-methyl-propane-2-sulfinamide (1.1 g, 3.46 mmol) in DCM (10 mL) was added DIBALH (1.5 M, 2.31 mL) at −70° C. The mixture was stirred at 25° C. for 2 hours. The reaction mixture was quenched by addition MeOH (50 mL) at 0° C., and then diluted with $H_2O$ (100 mL) and extracted with DCM (100 mL×2). The combined organic layer was washed with brine (30 mL), dried over Na2SO4, filtered and concentrated under reduced pressure to give a residue. The residue was purified by flash silica gel chromatography (ISCO®; 40 g SepaFlash® Silica Flash Column, Eluent of 0~50% Ethylacetate/Petroleum ether gradient @60 mL/min) to give (R)—N-[(1R)-6-chloro-4-fluoro-5-methoxy-indan-1-yl]-2-methyl-propane-2-sulfinamide (700 mg, 2.19 mmol, 63.24% yield).

$^1$H NMR (400 MHz, DMSO) δ ppm 7.51 (s, 1H), 5.90 (d, J=9.2 Hz, 1H), 4.75 (q, J=8.4 Hz, 1H), 3.84 (d, J=0.8 Hz, 3H), 2.93 (ddd, J=2.4, 8.8, 16.0 Hz, 1H), 2.77-2.67 (m, 1H), 2.43 (dtd, J=2.4, 7.8, 12.7 Hz, 1H), 1.94 (dd, J=9.2, 12.7 Hz, 1H), 1.16-1.12 (m, 9H). LC-MS: m/z 320.1 $(M+H)^+$.

Step F (1R)-6-chloro-4-fluoro-5-methoxy-indan-1-amine

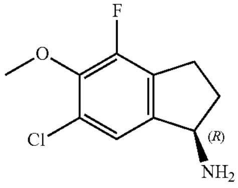

To a solution of (R)—N-[(1R)-6-chloro-4-fluoro-5-methoxy-indan-1-yl]-2-methyl-propane-2-sulfinamide (700 mg, 2.19 mmol) in MeOH (8 mL) was added HCl/dioxane (2 M, 4 mL). The mixture was stirred at 25° C. for 2 hours. LC (Petroleum ether: Ethyl acetate=3:1) indicated material was consumed completely and one major new spot formed. The reaction mixture was concentrated under reduced pressure to give (1R)-6-chloro-4-fluoro-5-methoxy-indan-1-amine (500 mg, 1.98 mmol, 90.61% yield, HCl), which was used into the next step without further purification.

$^1$H NMR (400 MHz, DMSO) δ ppm 10.21 (s, 1H), 9.85 (br d, J=8.2 Hz, 1H), 8.48 (s, 1H), 7.88 (d, J=6.8 Hz, 1H), 7.55 (d, J=6.8 Hz, 1H), 7.24-6.98 (m, 2H), 5.97-5.81 (m, 1H), 3.90 (d, J=1.3 Hz, 3H), 3.11 (dt, J=4.4, 8.1 Hz, 1H), 2.97-2.85 (m, 1H), 2.81-2.70 (m, 1H), 2.20-2.09 (m, 1H).

Step J N—[(R)-6-chloro-4-fluoro-5-methoxy-indan-1-yl]-2-(1,3-dioxolan-2-yl)thieno[2,3-c]pyridin-7-amine

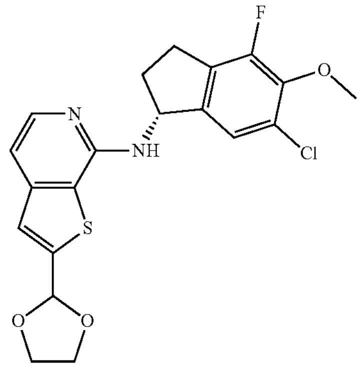 [SMILES: COc1c(Cl)cc2c(c1F)CC[C@H]2Nc1nccc2cc(C3OCCO3)sc12]

A mixture of (1R)-6-chloro-4-fluoro-5-methoxy-indan-1-amine (500 mg, 1.98 mmol, HCl), 7-chloro-2-(1,3-dioxolan- 2-yl)thieno[2,3-c]pyridine (479.3 mg, 1.98 mmol), Pd(OAc)2 (44.53 mg, 198.33 μmol), $Cs_2CO_3$ (1.29 g, 3.97 mmol) and BINAP (185.08 mg, 297.23 μmol) in dioxane (10 mL) was degassed and purged with $N_2$ for 3 times, and then the mixture was stirred at 100° C. for 2 hours under $N_2$ atmosphere. The reaction mixture was filtered and concentrated under reduced pressure to give a residue. The residue was purified by flash silica gel chromatography (ISCO®; 40 g SepaFlash® Silica Flash Column, Eluent of 0~50% Ethylacetate/Petroleum ether gradient @60 mL/min) to give N-[(1R)-6-chloro-4-fluoro-5-methoxy-indan-1-yl]-2-(1,3-dioxolan-2-yl)thieno[2,3-c]pyridin-7-amine (640 mg, 1.52 mmol, 76.67% yield). LC-MS: m/z 386.9 $(M+H)^+$.

$^1$H NMR (400 MHz, DMSO) δ ppm 7.96 (d, J=5.5 Hz, 1H), 7.49 (s, 1H), 7.22 (d, J=8.0 Hz, 1H), 7.13-6.99 (m, 2H), 6.21 (s, 1H), 5.83 (d, J=7.9 Hz, 1H), 4.07-4.03 (m, 2H), 4.01 (td, J=1.9, 5.8 Hz, 2H), 3.84 (s, 3H), 3.05 (ddd, J=3.4, 8.8, 16.0 Hz, 1H), 2.92-2.79 (m, 1H), 2.60-2.53 (m, 1H), 2.14-2.05 (m, 1H).

Step H 7-[[(JR)-6-chloro-4-fluoro-5-methoxy-indan-1-yl]amino]thieno[2,3-c]pyridine-2-carbaldehyde

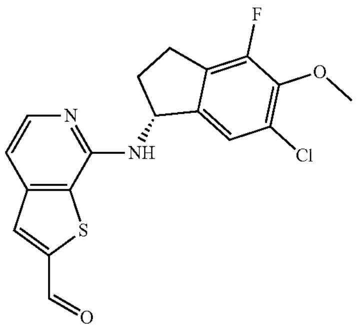 [SMILES: COc1c(Cl)cc2c(c1F)CC[C@H]2Nc1nccc2cc(C=O)sc12]

To a solution of N-[(1R)-6-chloro-4-fluoro-5-methoxy-indan-1-yl]-2-(1, 3-dioxolan-2-yl) thieno[2,3-c]pyridin-7-amine (640 mg, 1.52 mmol) in THF (5 mL) was added aq. HCl (4 M, 4 mL). The mixture was stirred at 25° C. for 2 hours. The reaction mixture was adjusted pH=10 by NaOH solid and then extracted with EtOAc (100 mL*3). The combined organic layers were washed with brine, dried over $Na_2SO_4$, filtered and concentrated under reduced pressure to give 7-[[(1R)-6-chloro-4-fluoro-5-methoxy-indan-1-yl]amino]thieno[2,3-c]pyridine-2-carbaldehyde (490 mg, 1.30 mmol, 85.51% yield), which was used into the next step without further purification.

$^1$H NMR (400 MHz, $CDCl_3$) δ ppm 10.24 (s, 1H), 8.40 (s, 1H), 8.12 (d, J=5.6 Hz, 1H), 7.62 (d, J=8.0 Hz, 1H), 7.33 (d, J=5.6 Hz, 1H), 7.18 (s, 1H), 5.92 (d, J=7.7 Hz, 1H), 3.91 (s, 3H), 3.13 (ddd, J=3.5, 8.9, 16.1 Hz, 1H), 3.00-2.87 (m, 1H), 2.68-2.61 (m, 1H), 2.17 (qd, J=8.3, 12.6 Hz, 1H). LC-MS: m/z 377.1 $(M+H)^+$.

Step I ethyl 2-((S)-1-(tert-butoxycarbonyl)pyrrolidin-2-yl)-4-(7-(((R)-6-chloro-4-fluoro-5-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-1,4-dihydropyridine-3-carboxylate

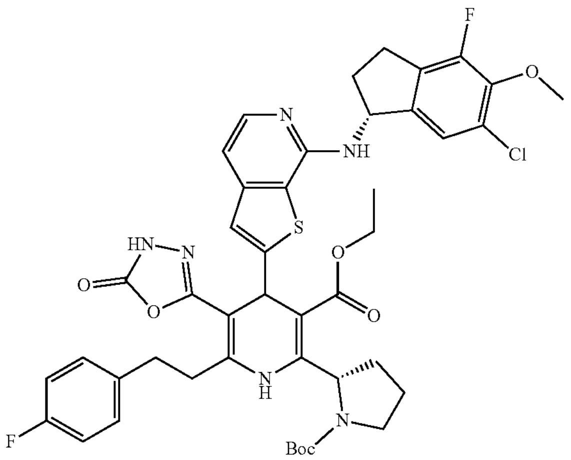 [SMILES: CCOC(=O)C1=C([C@@H]2CCCN2C(=O)OC(C)(C)C)NC(CCc2ccc(F)cc2)=C(c2n[nH]c(=O)o2)C1c1cc2ccnc(N[C@@H]3CCc4c3cc(Cl)c(OC)c4F)c2s1]

A mixture of 7-[[(1R)-6-chloro-4-fluoro-5-methoxy-indan-1-yl]amino]thieno[2,3-c]pyridine-2-carbaldehyde (250 mg, 663.43 μmol), 5-[4-(4-fluorophenyl)-2-oxo-butyl]-3H-1,3,4-oxadiazol-2-one (166 mg, 663.40 μmol), tert-butyl (2S)-2-(3-ethoxy-3-oxo-propanoyl)pyrrolidine-1-carboxylate (189 mg, 662.38 μmol), $NH_4OAc$ (105.3 mg, 1.37 mmol), tris(trifluoromethylsulfonyloxy)ytterbium (43.9 mg, 70.78 μmol) in EtOH (5 mL) was stirred at 50° C. for 2 hours. The reaction mixture was filtered and concentrated under reduced pressure to give ethyl 2-((S)-1-(tert-butoxycarbonyl)pyrrolidin-2-yl)-4-(7-(((R)-6-chloro-4-fluoro-5-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-1,4-dihydropyridine-3-carboxylate (580 mg, 662.57 μmol, 99.87% yield). LC-MS: m/z 875.3 $(M+H)^+$.

Step G ethyl 2-((S)-1-(tert-butoxycarbonyl)pyrrolidin-2-yl)-4-(7-(((R)-6-chloro-4-fluoro-5-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)nicotinate

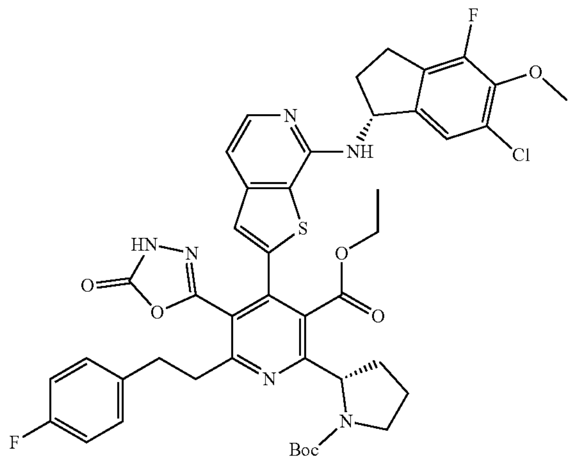 [SMILES: CCOC(=O)c1c([C@@H]2CCCN2C(=O)OC(C)(C)C)nc(CCc2ccc(F)cc2)c(-c2n[nH]c(=O)o2)c1-c1cc2ccnc(N[C@@H]3CCc4c3cc(Cl)c(OC)c4F)c2s1]

To a solution of ethyl 2-((S)-1-(tert-butoxycarbonyl)pyrrolidin-2-yl)-4-(7-(((R)-6-chloro-4-fluoro-5-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-1,4-dihydropyridine-3-carboxylate (580 mg, 662.57 μmol) in $CH_3CN$ (10 mL), $H_2O$ (5 mL) was added CAN (726.6 mg, 1.33 mmol). The mixture was stirred at 25° C. for 2 hours. The reaction mixture was quenched by addition of $NaHCO_3$, and then extracted with EtOAc (50 mL*3). The combined organic layers were washed with brine (25 mL*2), dried over $Na_2SO_4$, filtered and concentrated under reduced pressure to give a residue. The residue was purified by flash silica gel chromatography (ISCO®; 24 g SepaFlash® Silica Flash Column, Eluent of 0~100% Ethylacetate/Petroleum ether gradient @60 mL/min) to give compound ethyl 2-((S)-1-(tert-butoxycarbonyl)pyrrolidin-2-yl)-4-(7-(((R)-6-chloro-4-fluoro-5-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)nicotinate (300 mg, 343.50 μmol, 51.84% yield). LC-MS: m/z 873.2 $(M+H)^+$.

Step K ethyl 4-(7-(((R)-6-chloro-4-fluoro-5-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-2-((S)-pyrrolidin-2-yl)nicotinate

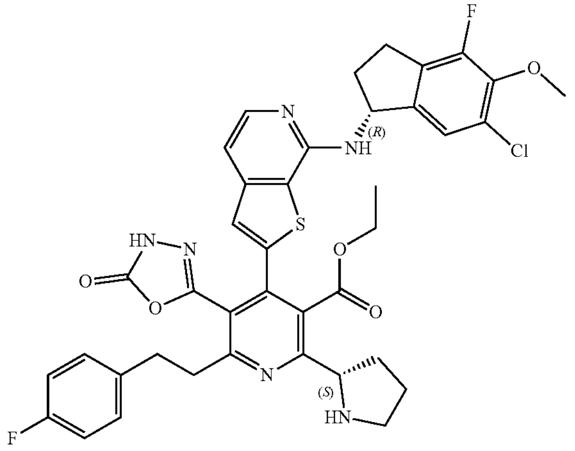

To a solution of ethyl 2-((S)-1-(tert-butoxycarbonyl)pyrrolidin-2-yl)-4-(7-(((R)-6-chloro-4-fluoro-5-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)nicotinate (300 mg, 343.50 μmol) in HCl/dioxane (2 M, 12.00 mL, 69.87 eq). The mixture was stirred at 25° C. for 2 hours. The reaction mixture was concentrated under reduced pressure to give crude ethyl 4-(7-(((R)-6-chloro-4-fluoro-5-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-2-((S)-pyrrolidin-2-yl) nicotinate (260 mg, 336.24 μmol, 97.89% yield) was obtained, which was used into the next step without further purification. LC-MS: m/z 773.1 $(M+H)^+$.

Step L 5-((S)-4-(7-(((R)-6-chloro-4-fluoro-5-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one

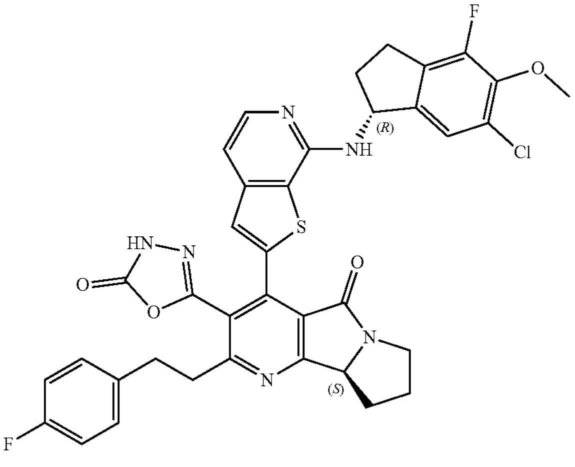

To a solution of ethyl 4-(7-(((R)-6-chloro-4-fluoro-5-methoxy-2,3-dihydro-1H-inden-1-yl)amino)thieno[2,3-c]pyridin-2-yl)-6-(4-fluorophenethyl)-5-(5-oxo-4,5-dihydro-1,3,4-oxadiazol-2-yl)-2-((S)-pyrrolidin-2-yl)nicotinate (260 mg, 336.24 μmol) in $H_2O$ (3 mL), MeOH (4 mL) was added $Na_2CO_3$ (356.3 mg, 3.36 mmol). The mixture was stirred at 25° C. for 2 hours. The reaction mixture was diluted with $H_2O$ (30 mL), and then extracted with EtOAc (20 mL*3). The combined organic layers were washed with brine, dried over $Na_2SO_4$, filtered and concentrated under reduced pressure to give a residue. The residue was purified by flash silica gel chromatography (ISCO®; 20 g SepaFlash® Silica Flash Column, Eluent of 0-100% Ethyl acetate/Petroleum ether gradient @30 mL/min) to give compound 5-((S)-4-(7-(((R)-6-chloro-4-fluoro-5-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (39.8 mg, 16.28% yield).

$^1$H NMR (400 MHz, MeOD-$d_4$) δ ppm 8.00 (d, J=5.6 Hz, 1H), 7.44 (s, 1H), 7.36 (br d, J=8.0 Hz, 1H), 7.23-7.18 (m, 2H), 7.17-7.11 (m, 2H), 7.07 (t, J=8.8 Hz, 2H), 5.84 (q, J=7.7 Hz, 1H), 4.87 (dd, J=6.3, 10.2 Hz, 1H), 3.85 (s, 3H), 3.57-3.51 (m, 1H), 3.25-3.16 (m, 3H), 3.14-2.96 (m, 4H), 2.89-2.81 (m, 1H), 2.39-2.33 (m, 1H), 2.31-2.23 (m, 2H), 2.09 (dt, J=3.9, 8.4 Hz, 1H), 1.48-1.37 (m, 1H). LC-MS: m/z 727.0 $(M+H)^+$.

5-((S)-4-(7-(((R)-6-fluoro-5-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 257)

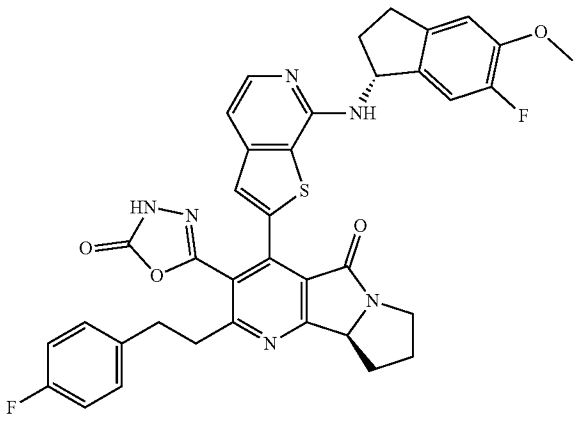 [SMILES: COc1cc2c(cc1F)[C@H](Nc1nccc3cc(-c4c5c(nc(CCc6ccc(F)cc6)c4-c4n[nH]c(=O)o4)[C@@H]4CCCN4C5=O)sc13)CC2]

Compound 257 was synthesized using a similar procedure described in Example 10 by using the appropriate materials.

$^1$H NMR (400 MHz, $CDCl_3$) δ=8.08 (d, J=5.6 Hz, 1H), 7.39 (s, 1H), 7.16-7.07 (m, 4H), 7.01-6.93 (m, 2H), 6.87 (d, J=7.6 Hz, 1H), 5.85-5.73 (m, 1H), 4.82-4.70 (m, 1H), 4.53-4.49 (m, 1H), 3.89 (s, 3H), 3.83-3.71 (m, 1H), 3.48-3.37 (m, 1H), 3.21-2.94 (m, 5H), 2.92-2.81 (m, 1H), 2.79-2.67 (m, 1H), 2.57-2.47 (m, 1H), 2.45-2.32 (m, 2H), 2.06-1.91 (m, 2H), 1.48-1.43 (m, 1H). $^{19}$F NMR (376 MHz, $CDCl_3$) δ −116.64 (s, 1F), −137.110 (s, 1F). LC-MS: m/z 693.2 $(M+H)^+$.

5-((S)-4-(7-(((R)-6-fluoro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 258)

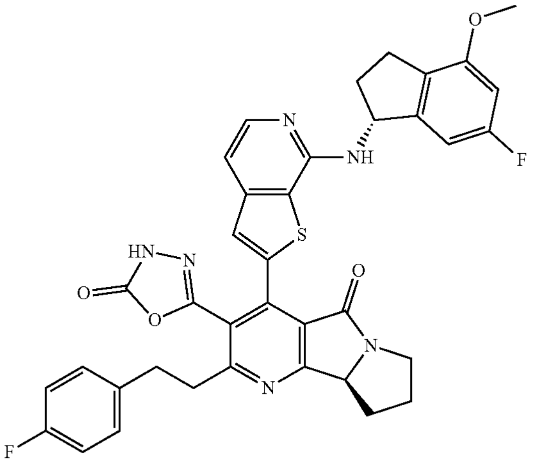 [SMILES: COc1cc(F)cc2c1CC[C@H]2Nc1nccc2cc(-c3c4c(nc(CCc5ccc(F)cc5)c3-c3n[nH]c(=O)o3)[C@@H]3CCCN3C4=O)sc12]

Compound 258 was synthesized using a similar procedure described in Example 39 by using the appropriate materials.

$^1$H NMR (400 MHz, MeOD-$d_4$) δ ppm 7.92 (d, J=5.96 Hz, 1H), 7.50 (s, 1H), 7.21 (d, J=5.96 Hz, 1H), 7.14-7.18 (m, 2H), 6.94-7.02 (m, 2H), 6.65 (q, J=2.42 Hz, 1H), 6.63 (s, 1H), 5.74 (br t, J=7.57 Hz, 1H), 4.59-4.70 (m, 1H), 3.85 (s, 3H), 3.69 (dt, J=11.12, 8.33 Hz, 1H), 3.41-3.49 (m, 1H), 3.25-3.30 (m, 2H), 3.07-3.17 (m, 2H), 2.96-3.05 (m, 1H), 2.67-2.81 (m, 2H), 2.41-2.55 (m, 3H), 2.03-2.10 (m, 1H), 1.43-1.55 (m, 1H). $^{19}$F NMR (376 MHz, METHANOL-d4) δ ppm −115.38 (s, 1 F), −119.00 (s, 1 F). LC-MS: m/z 693.1 $(M+H)^+$.

5-((S)-4-(7-(((R)-6,8-difluorochroman-4-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 259)

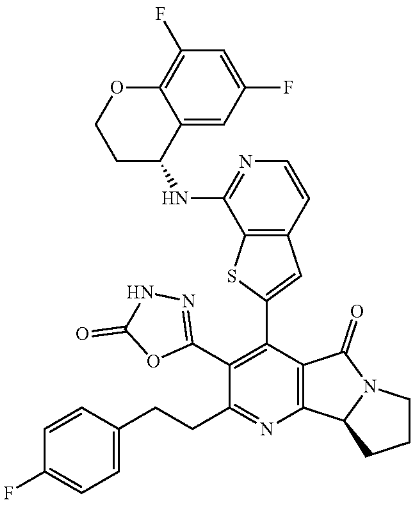 [SMILES: O=C1c2c(nc(CCc3ccc(F)cc3)c(-c3n[nH]c(=O)o3)c2-c2cc3ccnc(N[C@@H]4CCOc5c(F)cc(F)cc54)c3s2)[C@@H]2CCCN12]

Compound 259 was synthesized using a similar procedure described in Example 10 by using the appropriate materials. $^1$H NMR (400 MHz, DMSO-d6): δ 12.70 (br s, 1H), 8.00 (d, J=5.6 Hz, 1H), 7.48 (d, J=7.6 Hz, 1H), 7.45 (s, 1H), 7.05-7.24 (m, 3H), 7.14 (d, J=5.6 Hz, 1H), 7.03-7.09 (m, 2H), 6.86-6.93 (m, 1H), 5.60 (dd, J=6.0 Hz, J=13.2 Hz, 1H), 4.88 (dd, J=6.0 Hz, J=10.0 Hz, 1H), 4.24-4.43 (m, 2H), 3.51-3.57 (m, 1H), 3.25-3.29 (m, 1H), 3.19 (t, J=7.6 Hz, 2H), 2.95-3.12 (m, 2H), 2.22-2.40 (m, 3H), 2.12-2.21 (m, 2H), 1.40-1.48 (m, 1H). $^{19}$F NMR (377 MHz, DMSO-d6): −117.02, −121.77, −132.92. LC-MS: m/z 697.2 $(M+H)^+$.

5-((S)-4-(7-(((1S,2R)-2,5-difluoro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 260)

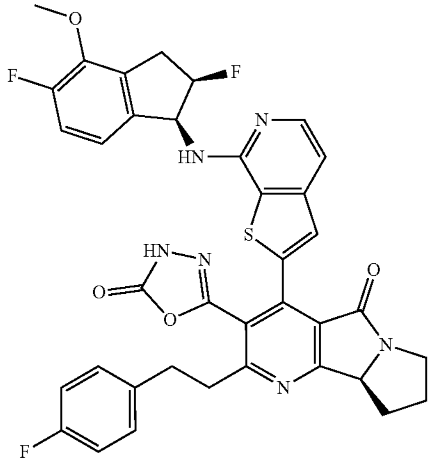 [SMILES: COc1c(F)ccc2c1C[C@@H](F)[C@H]2Nc1nccc2cc(-c3c4c(nc(CCc5ccc(F)cc5)c3-c3n[nH]c(=O)o3)[C@@H]3CCCN3C4=O)sc12]

Compound 260 was synthesized using a similar procedure described in Example 10 by using the appropriate materials.

$^1$H NMR (400 MHz, $CDCl_3$) δ=9.15 (s, 1H), 8.06 (d, J=5.6 Hz, 1H), 7.43 (s, 1H), 7.17-7.08 (m, 3H), 7.03-6.91 (m, 4H), 6.11-5.91 (m, 1H), 5.63-5.37 (m, 1H), 5.0-4.90 (m, 1H), 4.82-4.73 (m, 1H), 3.98 (s, 3H), 3.84-3.70 (m, 1H), 3.49-3.26 (m, 2H), 3.23-2.97 (m, 5H), 2.58-2.47 (m, 1H), 2.45-2.32 (m, 2H), 1.47-1.40 (m, 1H). $^{19}$F NMR (376 MHz, $CCl_3D$) δ −116.62, −133.15, −195.27. LC-MS: m/z 711.5 $(M+H)^+$.

5-((S)-4-(7-(((1S,2S)-2,5-difluoro-4-methoxy-2,3-dihydro-1H-inden-1-yl)amino)thieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 261)

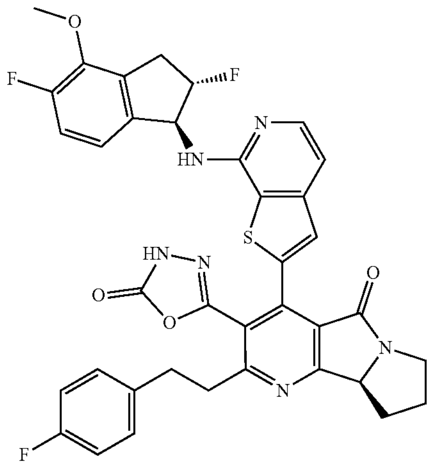 [SMILES: COc1c(F)ccc2c1C[C@H](F)[C@H]2Nc1nccc2cc(-c3c4c(nc(CCc5ccc(F)cc5)c3-c3n[nH]c(=O)o3)[C@@H]3CCCN3C4=O)sc12]

Compound 261 was synthesized using a similar procedure described in Example 10 by using the appropriate materials. $^1$H NMR (400 MHz, $CDCl_3$) δ=9.27 (br.s., 1H), 8.06 (d, J=5.6 Hz, 1H), 7.44 (s, 1H), 7.17-7.11 (m, 3H), 7.01-6.94 (m, 4H), 6.11-5.93 (m, 1H), 5.61-5.42 (m, 1H), 5.01-4.89 (m, 1H), 4.83-4.72 (m, 1H), 3.99 (s, 3H), 3.84-3.70 (m, 1H), 3.49-3.27 (m, 2H), 3.22-3.05 (m, 5H), 2.58-2.47 (m, 1H), 2.40-2.35 (m, 1H), 2.05-1.97 (m, 1H), 1.48-1.41 (m, 1H). $^{19}$F NMR (376 MHz, CHLOROFORM-d) δ −116.63, −133.18. LC-MS: m/z 711.2 $(M+H)^+$.

(R)-4-(7-(((R)-5-fluoro-4-methoxy-2,3-dihydro-1H-inden-1-yl)amino)thieno[2,3-c]pyridin-2-yl)-2-(4-fluorophenethyl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 262)

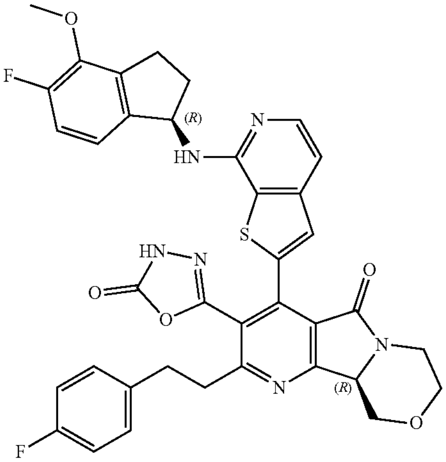

Compound 262 was synthesized using a similar procedure described in Example 10 by using the appropriate materials.

$^1$H NMR (400 MHz, DMSO-$d_6$) δ 7.98 (d, J=5.6 Hz, 1H), 7.42 (s, 1H), 7.17-7.25 (m, 3H), 7.07-7.10 (m, 3H), 6.97-7.04 (m, 1H), 6.91-6.96 (m, 1H), 5.81-5.90 (m, 1H), 4.77-4.84 (m, 1H), 4.45-4.51 (m, 1H), 4.02-4.10 (m, 1H), 3.92-3.98 (m, 1H), 3.88 (d, J=1.2 Hz, 3H), 3.22-3.27 (m, 2H), 3.16-3.20 (m, 3H), 2.99-3.09 (m, 3H), 2.81-2.89 (m, 1H), 2.53-2.57 (m, 1H), 2.02-2.13 (m, 1H). $^{19}$F NMR (377 MHz, DMSO-$d_6$): −117.08, −135.37. LC-MS: m/z 709.3 $(M+H)^+$.

(R)-4-(7-(((R)-5-fluoro-4-methoxy-2,3-dihydro-1H-inden-1-yl)amino)-5-methylthieno[2,3-c]pyridin-2-yl)-2-(4-fluorophenethyl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 263)

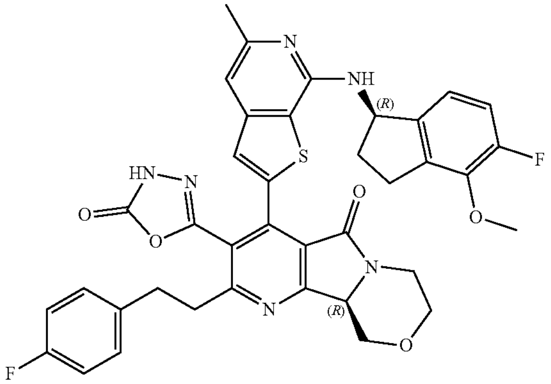

Compound 263 was synthesized using a similar procedure described in Example 20 by using the appropriate materials.

$^1$H NMR (400 MHz, DMSO-$d_6$): δ 7.35 (s, 1H), 7.15-7.22 (m, 3H), 6.97-7.10 (m, 3H), 6.90-6.96 (m, 2H), 5.85 (q, J=8.0 Hz, 1H), 4.81 (dd, J=4.8 Hz, J=10.0 Hz, 1H), 4.47 (dd, J=4.0 Hz, J=10.4 Hz, 1H), 4.06 (d, J=10.0 Hz, 1H), 3.95 (d, J=6.8 Hz, 1H), 3.87 (d, J=1.2 Hz, 3H), 3.24-3.27 (m, 2H), 3.16-3.23 (m, 3H), 2.98-3.10 (m, 3H), 2.80-2.90 (m, 1H), 2.54-2.57 (m, 1H), 2.40 (s, 3H), 2.02-2.12 (m, 1H). $^{19}$F NMR (377 MHz, DMSO-$d_6$): −117.02, −135.41. LC-MS: m/z 723.3 $(M+H)^+$.

(R)-5-(2-(4-fluorophenethyl)-4-(7-((1-methoxy-6,7-dihydro-5H-cyclopenta[c]pyridin-5-yl)amino)thieno[2,3-c]pyridin-2-yl)-5-oxo-8,9-dihydro-5H,7H-8,9a-methanopyrido[2,3-a]pyrrolizin-3-yl)-1,3,4-oxadiazol-2(3H)-one (Compound 264)

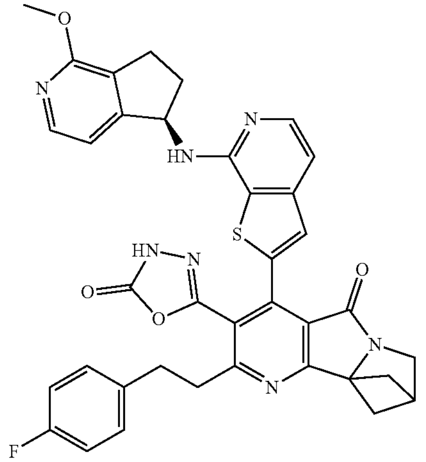 [SMILES: COc1nccc2c1CC[C@H]2Nc1nccc2cc(-c3c4c(nc(CCc5ccc(F)cc5)c3-c3n[nH]c(=O)o3)C35CC(CN3C4=O)C5)sc12]

Compound 264 was synthesized using a similar procedure described in Example 39 by using the appropriate materials. $^1$H NMR (400 MHz, DMSO-$d_6$) δ 12.71 (br s, 1H), 7.99 (d, J=5.6 Hz, 1H), 7.94 (d, J=5.2 Hz, 1H), 7.43 (s, 1H), 7.31 (d, J=8.4 Hz, 1H), 7.17-7.26 (m, 2H), 7.01-7.10 (m, 3H), 6.89 (d, J=4.8 Hz, 1H), 5.90 (q, J=7.6 Hz, 1H), 3.89 (s, 3H), 3.56 (s, 2H), 3.15-3.24 (m, 3H), 3.01-3.08 (m, 2H), 2.88-2.95 (m, 1H), 2.72-2.78 (m, 1H), 2.63-2.67 (m, 2H), 2.57-2.59 (m, 1H), 2.01-2.09 (m, 1H), 1.71-1.78 (m, 2H). $^{19}$F NMR (377 MHz, DMSO-$d_6$): −117.02. LC-MS: m/z 688.4 $(M+H)^+$.

(R)-5-(4-(7-((4-chloro-6,7-dihydro-5H-cyclopenta[c]pyridin-7-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 265)

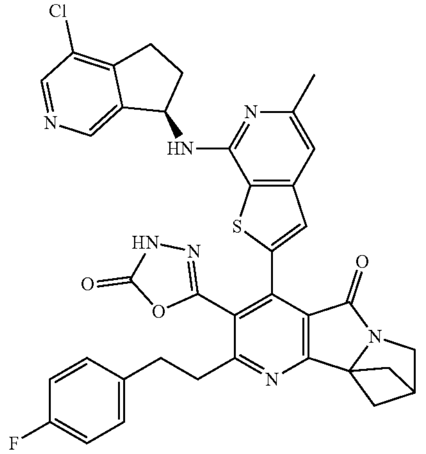 [SMILES: Cc1cc2cc(-c3c4c(nc(CCc5ccc(F)cc5)c3-c3n[nH]c(=O)o3)C35CC(CN3C4=O)C5)sc2c(N[C@@H]2CCc3c(Cl)cncc32)n1]

Compound 265 was synthesized using a similar procedure described in Example 39 by using the appropriate materials.

$^1$H NMR (400 MHz, DMSO-$d_6$) δ 12.68 (br s, 1H), 8.44 (d, J=4.4 Hz, 2H), 7.30-7.34 (m, 2H), 7.18-7.4 (m, 2H), 7.03-7.11 (m, 2H), 6.96 (s, 1H), 5.95-6.00 (m, 1H), 3.56 (s, 2H), 3.15-3.21 (m, 3H), 3.08-3.13 (m, 1H), 3.00-3.04 (m, 2H), 2.90-2.98 (m, 1H), 2.62-2.66 (m, 2H), 2.54-2.60 (m, 1H), 2.43 (s, 3H), 2.06-2.17 (m, 1H), 1.71-1.77 (m, 2H). 19F NMR (377 MHz, DMSO-$d_6$): −117.05. LC-MS: m/z 706.2 $(M+H)^+$.

(R)-5-(4-(7-((3-chloro-6,7-dihydro-5H-cyclopenta[b]pyridin-7-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 266)

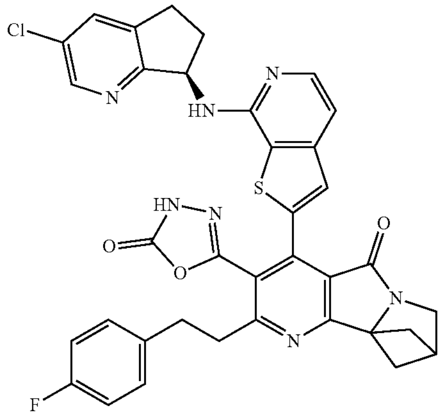 [SMILES: O=C1c2c(nc(CCc3ccc(F)cc3)c(-c3n[nH]c(=O)o3)c2-c2cc3ccnc(N[C@@H]4CCc5cc(Cl)cnc54)c3s2)C23CC(CN12)C3]

Compound 266 was synthesized using a similar procedure described in Example 39 by using the appropriate materials.

$^1$H NMR (400 MHz, DMSO-$d_6$) δ 12.72 (br s, 1H), 8.37 (s, 1H), 7.93 (d, J=5.6 Hz, 1H), 7.82 (s, 1H), 7.41 (s, 1H), 7.19-7.27 (m, 3H), 7.03-7.11 (m, 3H), 5.85 (dd, J=16.0 Hz, J=8.4 Hz 1H), 3.54-3.59 (m, 2H), 3.16-3.23 (m, 3H), 2.96-3.07 (m, 3H), 2.85-2.93 (m, 1H), 2.62-2.67 (m, 2H), 2.58-2.60 (m, 1H), 2.05-2.15 (m, 1H), 1.72-1.78 (m, 2H). 19F NMR (377 MHz, DMSO-$d_6$): −117.01. LC-MS: m/z 691.7 $(M+H)^+$.

(R)-5-(4-(7-((5-fluoro-4-methoxy-2,3-dihydro-1H-inden-1-yl)amino)benzo[d]thiazol-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 267)

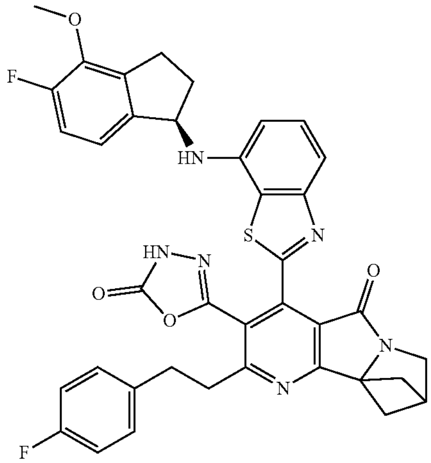 [SMILES: COc1c(F)ccc2c1CC[C@H]2Nc1cccc2nc(-c3c4c(nc(CCc5ccc(F)cc5)c3-c3n[nH]c(=O)o3)C35CC(CN3C4=O)C5)sc12]

Compound 267 was synthesized using a similar procedure described in Example 10 by using the appropriate materials. $^1$H NMR (400 MHz, DMSO-$d_6$) δ 12.61 (br s, 1H), 7.38 (t, J=8.0 Hz, 1H), 7.31 (d, J=8.0 Hz, 1H), 7.20-7.26 (m, 2H), 7.01-7.10 (m, 3H), 6.96-6.98 (m, 1H), 6.89 (d, J=7.6 Hz, 1H), 6.29-6.34 (m, 1H), 5.14-5.25 (m, 1H), 3.89 (d, J=1.2 Hz, 3H), 3.58 (s, 2H), 3.19-3.26 (m, 3H), 3.01-3.09 (m, 3H), 2.81-2.91 (m, 1H), 2.64-2.69 (m, 2H), 2.55-2.61 (m, 1H), 2.00-2.10 (m, 1H), 1.77-1.79 (m, 2H). $^{19}$F NMR (377 MHz, DMSO-$d_6$): −117.01, −134.94. LC-MS: m/z 705.3 $(M+H)^+$.

(R)-5-(4-(4-((5-fluoro-4-methoxy-2,3-dihydro-1H-inden-1-yl)amino)thieno[3,2-d]pyrimidin-6-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 268)

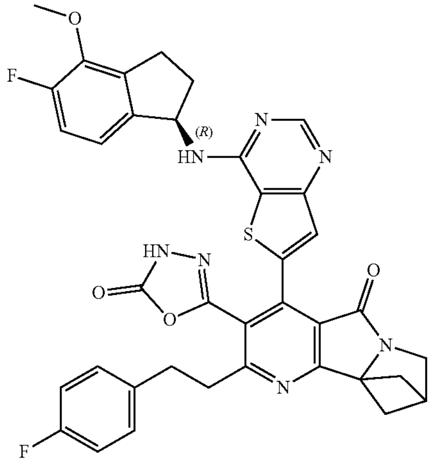

Compound 268 was synthesized using a similar procedure described in the Example 10 by using the appropriate materials.

$^{1}$H NMR (400 MHz, DMSO-$d_6$) δ 12.74 (br s, 1H), 8.35-8.76 (m, 2H), 7.42-7.47 (m, 1H), 7.18-7.26 (m, 2H), 7.01-7.11 (m, 3H), 6.93-6.99 (m, 1H), 5.87-5.97 (m, 1H), 3.89 (d, J=1.2 Hz, 3H), 3.57 (s, 2H), 3.18-3.21 (m, 2H), 3.00-3.07 (m, 3H), 2.86-2.94 (m, 1H), 2.64-2.67 (m, 3H), 2.57-2.59 (m, 1H), 2.04-2.15 (m, 1H), 1.74-1.76 (m, 2H). $^{19}$F NMR (377 MHz, DMSO-$d_6$): −117.00, −134.64. LC-MS: m/z 706.3 $(M+H)^+$.

(R)-5-(4-(4-((5-fluoro-4-methoxy-2,3-dihydro-1H-inden-1-yl)amino)thieno[3,2-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 269)

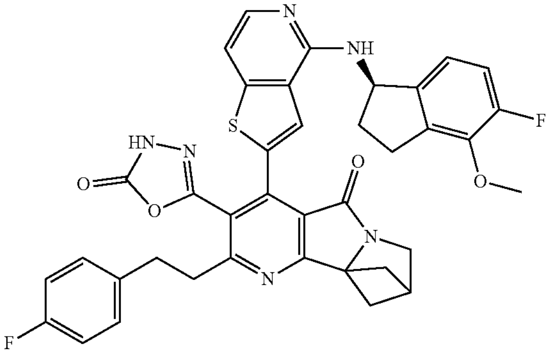 [SMILES: COc1c(F)ccc2c1CC[C@H]2Nc1nccc2sc(-c3c4c(nc(CCc5ccc(F)cc5)c3-c3n[nH]c(=O)o3)C35CC(CN3C4=O)C5)cc12]

Compound 269 was synthesized using a similar procedure described in the Example 10 by using the appropriate materials.

$^{1}$H NMR (400 MHz, DMSO-$d_6$): δ 7.90-7.93 (m, 2H), 7.48 (d, J=7.6 Hz, 1H), 7.15-7.24 (m, 3H), 6.99-7.10 (m, 3H), 6.93-6.98 (m, 1H), 5.81 (q, J=7.6 Hz, 1H), 3.88 (d, J=1.2 Hz, 3H), 3.55 (s, 2H), 3.12-3.21 (m, 3H), 2.98-3.11 (m, 3H), 2.81-2.91 (m, 1H), 2.61-2.66 (m, 2H), 2.54-2.57 (m, 1H), 1.98-2.07 (m, 1H), 1.69-1.73 (m, 2H). $^{19}$F NMR (377 MHz, DMSO-$d_6$): −117.06, −135.23. LC-MS: m/z 705.3 $(M+H)^+$.

(R)-5-(4-(4-((5-fluoro-4-methoxy-2,3-dihydro-1H-inden-1-yl)amino)thieno[2,3-d]pyrimidin-6-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 270)

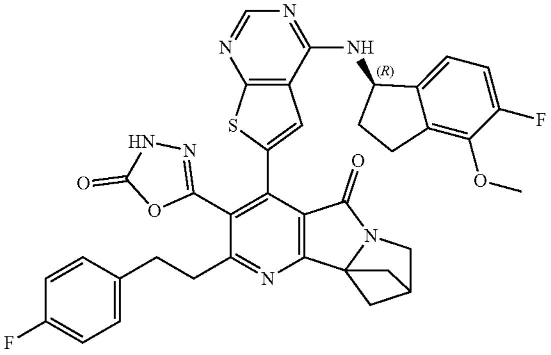

Compound 270 was synthesized using a similar procedure described in the Example 10 by using the appropriate materials.

$^{1}$H NMR (400 MHz, DMSO-$d_6$): δ 12.73 (br s, 1H), 8.42 (s, 1H), 8.38 (d, J=8.0 Hz, 1H), 7.80 (s, 1H), 7.19-7.24 (m, 2H), 7.03-7.09 (m, 3H), 6.96-7.00 (m, 1H), 5.83-5.91 (m, 1H), 3.89 (d, J=0.8 Hz, 3H), 3.55 (s, 2H), 3.12-3.21 (m, 3H), 3.05-3.10 (m, 1H), 2.97-3.01 (m, 2H), 2.87-2.91 (m, 1H), 2.62-2.64 (m, 2H), 2.55-2.57 (m, 1H), 2.01-2.09 (m, 1H), 1.66-1.75 (m, 2H). $^{19}$F NMR (377 MHz, DMSO-$d_6$): δ −117.11, −134.66. LC-MS: m/z 706.2 $(M+H)^+$.

(R)-5-(4-(7-((5-fluoro-4-methoxy-2,3-dihydro-1H-inden-1-yl)amino)thieno[3,2-b]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 271)

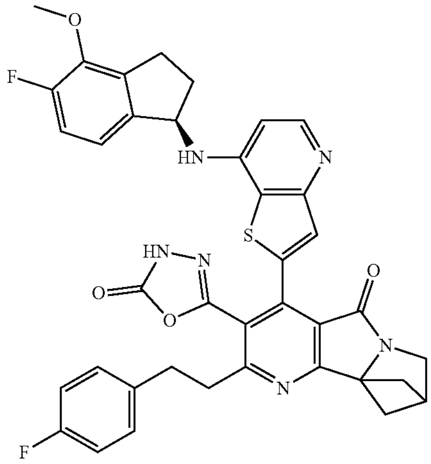

Compound 271 was synthesized using a similar procedure described in the Example 10 by using the appropriate materials.

$^{1}$H NMR (400 MHz, DMSO-$d_6$): δ 12.71 (br s, 1H), 8.26 (d, J=5.2 Hz, 1H), 7.40 (s, 1H), 7.19-7.26 (m, 2H), 7.02-7.14 (m, 4H), 6.91-6.96 (m, 1H), 6.73 (d, J=5.6 Hz, 1H), 5.29 (q, J=7.2 Hz, 1H), 3.88 (d, J=1.2 Hz, 3H), 3.57 (s, 2H), 3.11-3.21 (m, 3H), 3.00-3.06 (m, 3H), 2.81-2.92 (m, 1H), 2.62-2.67 (m, 2H), 2.54-2.60 (m, 1H), 2.03-2.14 (m, 1H), 1.71-1.79 (m, 2H). $^{19}$F NMR (377 MHz, DMSO-$d_6$): −117.03, −134.70. LC-MS: m/z 705.3 $(M+H)^+$.

(R)-5-(4-(7-((4-fluoro-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 272)

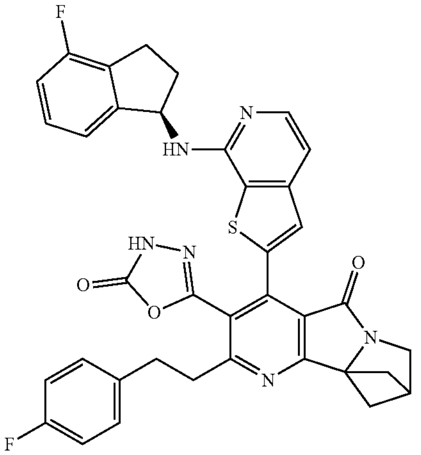 [SMILES: O=C1c2c(nc(CCc3ccc(F)cc3)c(-c3n[nH]c(=O)o3)c2-c2cc3ccnc(N[C@@H]4CCc5c(F)cccc54)c3s2)C23CC(CN12)C3]

Compound 272 was synthesized using a similar procedure described in Example 10 by using the appropriate materials. (8.30 mg, 0.012 mmol, 16.52%)

$^1$H NMR (400 MHz, DMSO-$d_6$): δ 12.71 (br s, 1H), 7.98 (d, J=5.2 Hz, 1H), 7.42 (s, 1H), 7.31 (d, J=8.4 Hz, 1H), 7.15-7.25 (m, 3H), 6.99-7.12 (m, 5H), 5.93 (q, J=8.0 Hz, 1H), 3.56 (s, 2H), 3.16-3.23 (m, 3H), 3.00-3.09 (m, 3H), 2.79-2.89 (m, 1H), 2.63-2.66 (m, 2H), 2.55-2.59 (m, 1H), 2.03-2.15 (m, 1H), 1.74 (d, J=4.0 Hz, 2H). $^{19}$F NMR (377 MHz, DMSO-$d_6$): −117.01, −119.17. LC-MS: m/z 675.3 $(M+H)^+$.

(R)-5-(4-(7-((5-chloro-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 273)

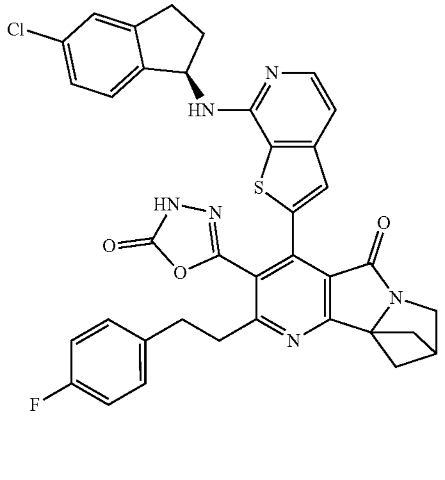 [SMILES: O=C1c2c(nc(CCc3ccc(F)cc3)c(-c3n[nH]c(=O)o3)c2-c2cc3ccnc(N[C@@H]4CCc5cc(Cl)ccc54)c3s2)C23CC(CN12)C3]

Compound 273 was synthesized using a similar procedure described in Example 10 by using the appropriate materials.

$^1$H NMR (400 MHz, DMSO-$d_6$) δ 12.71 (br s, 1H), 7.98 (d, J=6.0 Hz, 1H), 7.42 (s, 1H), 7.33 (s, 1H), 7.16-7.29 (m, 5H), 7.03-7.11 (m, 3H), 5.85 (q, J=8.0 Hz, 1H), 3.56 (s, 2H), 3.16-3.23 (m, 3H), 2.99-3.06 (m, 3H), 2.81-2.89 (m, 1H), 2.62-2.66 (m, 2H), 2.54-2.57 (m, 1H), 2.01-2.17 (m, 1H), 1.70-1.79 (m, 2H). $^{19}$F NMR (377 MHz, DMSO-$d_6$): −117.02. LC-MS: m/z 691.2 $(M+H)^+$.

(R)-5-(4-(7-((6-chloro-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 274)

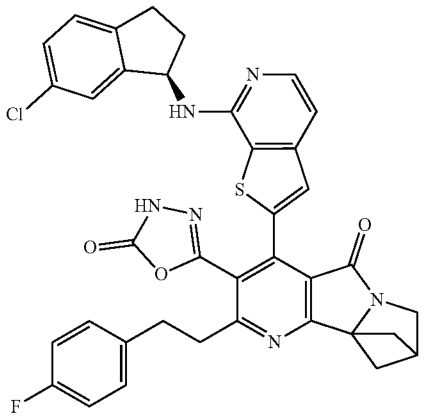 [SMILES: O=C1c2c(nc(CCc3ccc(F)cc3)c(-c3n[nH]c(=O)o3)c2-c2cc3ccnc(N[C@@H]4CCc5ccc(Cl)cc54)c3s2)C23CC(CN12)C3]

Compound 274 was synthesized using a similar procedure described in Example 10 by using the appropriate materials. (4.19 mg, 3.33%)

$^1$H NMR (400 MHz, DMSO-$d_6$): δ 12.71 (br s, 1H), 7.99 (d, J=5.6 Hz, 1H), 7.44 (s, 1H), 7.34 (d, J=8.4 Hz, 1H), 7.26-7.30 (m, 2H), 7.20-7.24 (m, 3H), 7.05-7.12 (m, 3H), 5.86 (q, J=8.0 Hz, 1H), 3.57 (s, 2H), 3.16-3.23 (m, 3H), 2.95-3.06 (m, 3H), 2.81-2.86 (m, 1H), 2.63-2.67 (m, 2H), 2.56-2.58 (m, 1H), 2.01-2.10 (m, 1H), 1.71-1.80 (m, 2H). $^{19}$F NMR (377 MHz, DMSO-$d_6$): δ −117.01. LC-MS: m/z 691.2 $(M+H)^+$.

(R)-5-(4-(7-((5-fluoro-4-methoxy-2,3-dihydro-1H-inden-1-yl)amino)thieno[2,3-c]pyridin-2-yl)-2-(3-fluorophenethyl)-5-oxo-8,9-dihydro-5H,7H-8,9a-methanopyrido[2,3-a]pyrrolizin-3-yl)-1,3,4-oxadiazol-2(3H)-one (Compound 275)

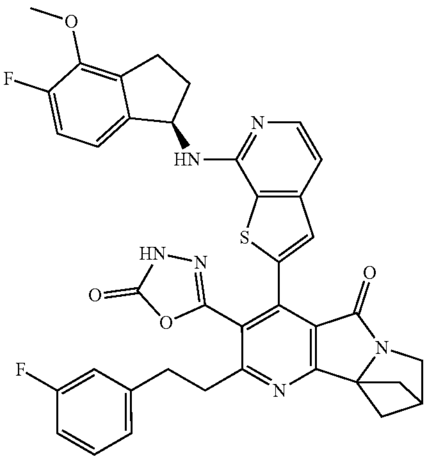

Compound 275 was synthesized using a similar procedure described in Example 10 by using the appropriate materials. (3.86 mg, 3.39%)

$^{1}$H NMR (400 MHz, DMSO-$d_6$): δ 12.61 (br s, 1H), 7.97 (d, J=5.2 Hz, 1H), 7.40 (s, 1H), 7.30 (dd, J=14.0 Hz, J=8.0 Hz, 1H), 7.22 (d, J=8.0 Hz, 1H), 7.08 (d, J=5.6 Hz, 1H), 6.98-7.06 (m, 4H), 6.90-6.94 (m, 1H), 5.81-5.87 (m, 1H), 3.88 (s, 3H), 3.56 (s, 2H), 3.17-3.23 (m, 3H), 3.02-3.10 (m, 3H), 2.82-2.86 (m, 1H), 2.61-2.67 (m, 2H), 2.56-2.59 (m, 1H), 2.03-2.11 (m, 1H), 1.70-1.79 (m, 2H). $^{19}$F NMR (377 MHz, DMSO-$d_6$): δ −113.58, −135.37. LC-MS: m/z 705.2 $(M+H)^+$.

(R)-5-(4-(7-((5-fluoro-4-methoxy-2,3-dihydro-1H-inden-1-yl)amino)thieno[2,3-c]pyridin-2-yl)-2-(2-fluorophenethyl)-5-oxo-8,9-dihydro-5H,7H-8,9a-methanopyrido[2,3-a]pyrrolizin-3-yl)-1,3,4-oxadiazol-2(3H)-one (Compound 276)

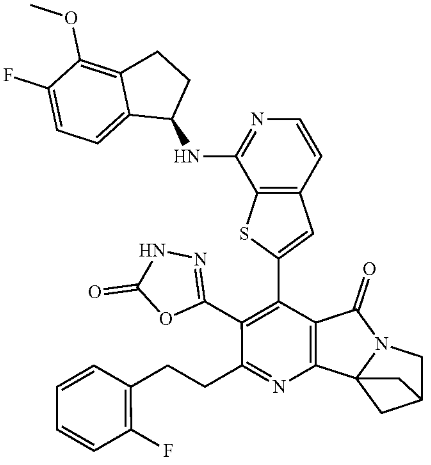 [SMILES: COc1c(F)ccc2c1CC[C@H]2Nc1nccc2cc(-c3c4c(nc(CCc5ccccc5F)c3-c3n[nH]c(=O)o3)C35CC(CN3C4=O)C5)sc12]

Compound 276 was synthesized using a similar procedure described in Example 10 by using the appropriate materials.

$^{1}$H NMR (400 MHz, DMSO-$d_6$) δ 12.72 (s, 1H), 7.98 (d, J=5.6 Hz, 1H), 7.42 (s, 1H), 7.20-7.30 (m, 3H), 7.06-7.13 (m, 3H), 6.98-7.05 (m, 1H), 6.91-6.96 (m, 1H), 5.84 (q, J=8.0 Hz, 1H), 3.88 (d, J=1.2 Hz, 3H), 3.56 (s, 2H), 3.16-3.22 (m, 3H), 3.01-3.09 (m, 3H), 2.79-2.90 (m, 1H), 2.62-2.65 (m, 2H), 2.56-2.58 (m, 1H), 2.03-2.12 (m, 1H), 1.70-1.78 (m, 2H). $^{19}$F NMR (377 MHz, DMSO-$d_6$): −119.24,-135.35. LC-MS: m/z 705.3 $(M+H)^+$.

(R)-5-(2-(3-chlorophenethyl)-4-(7-((5-fluoro-4-methoxy-2,3-dihydro-1H-inden-1-yl)amino)thieno[2,3-c]pyridin-2-yl)-5-oxo-8,9-dihydro-5H,7H-8,9a-methanopyrido[2,3-a]pyrrolizin-3-yl)-1,3,4-oxadiazol-2(3H)-one (Compound 277)

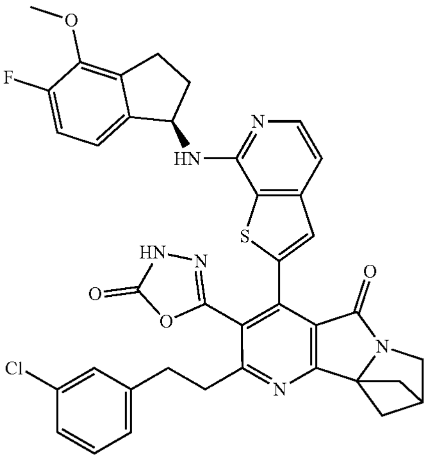 [SMILES: COc1c(F)ccc2c1CC[C@H]2Nc1nccc2cc(-c3c4c(nc(CCc5cccc(Cl)c5)c3-c3n[nH]c(=O)o3)C35CC(CN3C4=O)C5)sc12]

Compound 277 was synthesized using a similar procedure described in Example 10 by using the appropriate materials.

$^{1}$H NMR (400 MHz, DMSO-$d_6$) δ 12.71 (br s, 1H), 7.98 (d, J=5.6 Hz, 1H), 7.41 (s, 1H), 7.22-7.32 (m, 4H), 7.17 (d, J=8.0 Hz, 1H), 7.09 (d, J=5.6 Hz, 1H), 7.97-7.05 (m, 1H), 6.90-6.96 (m, 1H), 5.84 (q, J=8.0 Hz, 1H), 3.88 (s, 3H), 3.56 (s, 2H), 3.17-3.27 (m, 3H), 3.03-3.11 (m, 3H), 2.80-2.87 (m, 1H), 2.62-2.66 (m, 2H), 2.54-2.57 (m, 1H), 2.01-2.12 (m, 1H), 1.69-1.79 (m, 2H). $^{19}$F NMR (377 MHz, DMSO-$d_6$): −135.35. LC-MS: m/z 721.2 $(M+H)^+$.

(R)-5-(2-(2-chlorophenethyl)-4-(7-((5-fluoro-4-methoxy-2,3-dihydro-1H-inden-1-yl)amino)thieno[2,3-c]pyridin-2-yl)-5-oxo-8,9-dihydro-5H,7H-8,9a-methanopyrido[2,3-a]pyrrolizin-3-yl)-1,3,4-oxadiazol-2(3H)-one (Compound 278)

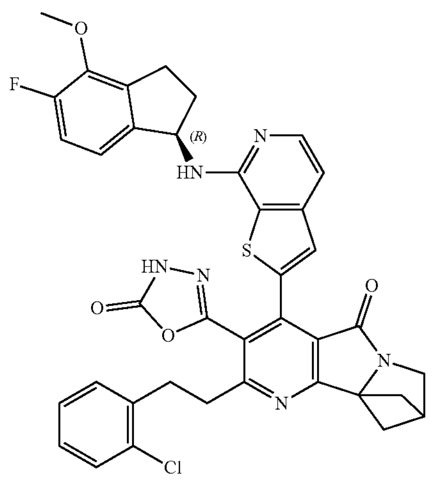

Compound 278 was synthesized using a similar procedure described in Example 10 by using the appropriate materials. (2.77 mg, 0.004 mmol, 5.48%)

$^1$H NMR (400 MHz, DMSO-$d_6$): δ 12.75 (br s, 1H), 7.93 (d, J=6.0 Hz, 1H), 7.50-7.59 (m, 1H), 7.36-7.40 (m, 1H), 7.20-7.32 (m, 4H), 6.99-7.12 (m, 2H), 5.62-5.75 (m, 1H), 3.89 (d, J=1.2 Hz, 3H), 3.56 (s, 2H), 3.18-3.27 (m, 3H), 3.04-3.16 (m, 3H), 2.83-2.94 (m, 1H), 2.63-2.67 (m, 2H), 2.57-2.62 (m, 1H), 2.05-2.18 (m, 1H), 1.74 (d, J=4.0 Hz, 2H). $^{19}$F NMR (377 MHz, DMSO-$d_6$): −135.67. LC-MS: m/z 721.2 $(M+H)^+$.

(R)-5-(4-(7-((4,6-difluoro-2,3-dihydro-1H-inden-1-yl)amino)thieno[2,3-c]pyridin-2-yl)-2-(4-fluorophenethyl)-5-oxo-5,7,8,9-tetrahydro-8,9a-methanopyrido[2,3-a]pyrrolizin-3-yl)-1,3,4-oxadiazol-2(3H)-one (Compound 279)

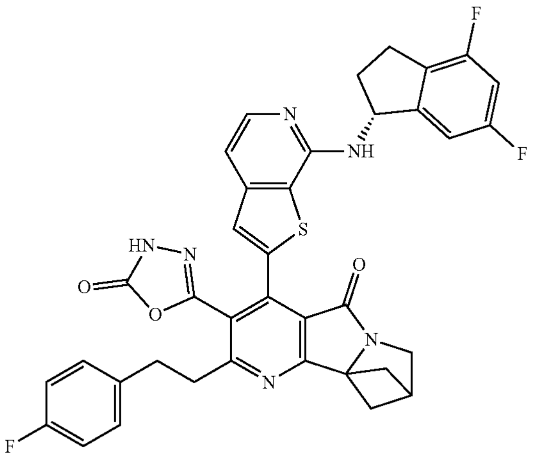

Compound 279 was synthesized using a similar procedure described in Example 10 by using the appropriate materials.

$^1$H NMR (400 MHz, $CDCl_3$) δ 7.98 (d, J=6 Hz, 1H), 7.29 (s, 1H), 7.00-7.09 (m, 3H), 6.93 (s, 1H), 6.56-6.64 (m, 1H), 5.75-5.87 (m, 1H), 4.33-4.59 (m, 1H), 3.58 (s, 2H), 3.16-3.21 (m, 1H), 3.08-3.14 (m, 2H), 2.94-3.06 (m, 3H), 2.71-2.83 (m, 2H), 2.64-2.69 (m, 2H), 1.86-1.94 (m, 1H), 1.69-1.73 (m, 2H). $^{19}$F NMR (376 MHz, $CDCl_3$) δ −112.23 (s, 1 F), −114.64 (s, 1 F), −116.65 (s, 1 F). LC-MS: m/z 693.1 $(M+H)^+$.

(R)-5-(4-(7-((5-fluoro-2,3-dihydro-1H-inden-1-yl)amino)thieno[2,3-c]pyridin-2-yl)-2-(4-fluorophenethyl)-5-oxo-5,7,8,9-tetrahydro-8,9a-methanopyrido[2,3-a]pyrrolizin-3-yl)-1,3,4-oxadiazol-2(3H)-one (Compound 280)

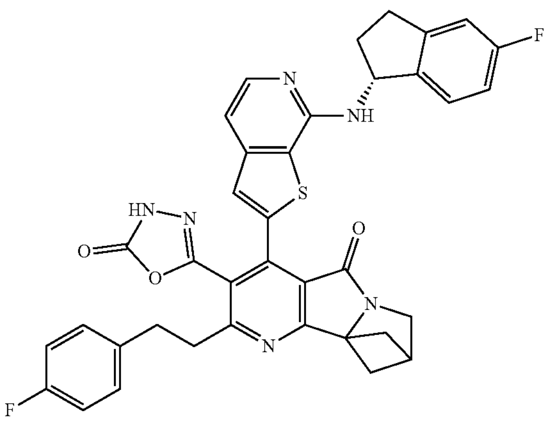 [SMILES: O=C1c2c(nc(CCc3ccc(F)cc3)c(-c3n[nH]c(=O)o3)c2-c2cc3ccnc(N[C@@H]4CCc5cc(F)ccc54)c3s2)C23CC(CN12)C3]

Compound 280 was synthesized using a similar procedure described in Example 10 by using the appropriate materials.

$^1$H NMR (400 MHz, MeOD-$d_4$) δ 7.79 (d, J=6.8 Hz, 1H), 7.66 (s, 1H), 7.35-7.48 (m, 2H), 7.09-7.20 (m, 3H), 6.92-7.06 (m, 3H), 5.47-5.57 (m, 1H), 3.66-3.71 (m, 2H), 3.34-3.36 (m, 1H), 3.28-3.32 (m, 2H), 3.10-3.23 (m, 3H), 2.98-3.09 (m, 1H), 2.75-2.86 (m, 3H), 2.18-2.31 (m, 1H), 1.83 (m, 2H). $^{19}$F NMR (376 MHz, MeOD-$d_4$) δ −115.90, −118.94. LC-MS: m/z 675.2 $(M+H)^+$.

(S)-5-(4-(7-((2,2-difluoro-4-methoxy-2,3-dihydro-1H-inden-1-yl)amino)thieno[2,3-c]pyridin-2-yl)-2-(4-fluorophenethyl)-5-oxo-5,7,8,9-tetrahydro-8,9a-methanopyrido[2,3-a]pyrrolizin-3-yl)-1,3,4-oxadiazol-2(3H)-one (Compound 281)

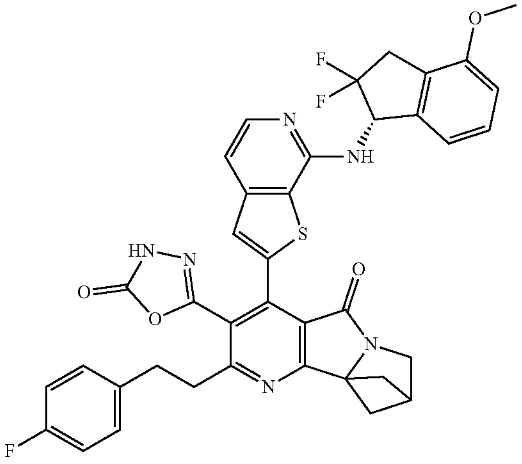 [SMILES: COc1cccc2c1CC(F)(F)[C@H]2Nc1nccc2cc(-c3c4c(nc(CCc5ccc(F)cc5)c3-c3n[nH]c(=O)o3)C35CC(CN3C4=O)C5)sc12]

Compound 281 was synthesized using a similar procedure described in Example 22 by using the appropriate materials. $^1$H NMR (400 MHz, MeOD-$d_4$) δ 7.98 (d, J=5.6 Hz, 1H), 7.47 (s, 1H), 7.26-7.30 (m, 1H), 7.13-7.22 (m, 3H), 6.89-7.03 (m, 4H), 6.19-6.33 (m, 1H), 3.87 (s, 3H), 3.68 (s, 2H), 3.37-3.53 (m, 2H), 3.21-3.30 (m, 3H), 3.06-3.16 (m, 2H), 2.73-2.85 (m, 2H), 1.75-1.86 (m, 2H). $^{19}$F NMR (376 MHz, MeOD-$d_4$) δ ppm −102.28 (d, J=230.86, 1 F) −109.85 (d, J=230.86 Hz, 1 F), −118.99 (s, 1 F). LC-MS: m/z 723.1 $(M+H)^+$.

5-((S)-2-(4-fluorophenethyl)-5-oxo-4-(7-(((S)-2,2,5-trifluoro-4-methoxy-2,3-dihydro-1H-inden-1-yl)amino)thieno[2,3-c]pyridin-2-yl)-7,8,9,9a-tetrahydro-5H-pyrido[2,3-a]pyrrolizin-3-yl)-1,3,4-oxadiazol-2(3H)-one (Compound 282)

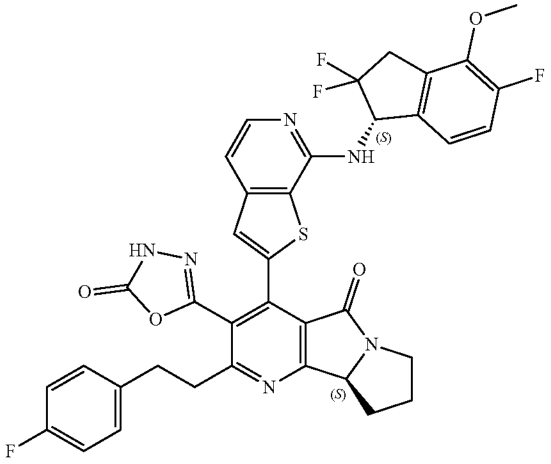

Compound 282 was synthesized using a similar procedure described in Example 22 by using the appropriate materials. $^1$H NMR (400 MHz, MeOD-$d_4$) δ 7.99 (d, J=5.72 Hz, 1H), 7.47 (s, 1H), 7.13-7.23 (m, 3H), 7.07-7.12 (m, 1H), 6.95-7.04 (m, 3H), 6.22 (t, J=10.91 Hz, 1H), 4.88 (m, 1H), 3.99 (d, J=2.15 Hz, 3H), 3.69 (dt, J=11.27, 8.31 Hz, 1H), 3.40-3.62 (m, 3H), 3.22-3.30 (m, 2H), 3.02-3.20 (m, 2H), 2.38-2.56 (m, 3H), 1.42-1.55 (m, 1H). $^{19}$F NMR (376 MHz, MeOD-$d_4$) δ −102.08 (d, J=246 Hz, 1 F), −109.84 (d, J=246 Hz, 1 F), −119.02 (s, 1 F), −133.84 (s, 1 F). LC-MS: m/z 729.1 $(M+H)^+$.

(S)-5-(2-(4-fluorophenethyl)-5-oxo-4-(7-((2,2,5-trifluoro-4-methoxy-2,3-dihydro-1H-inden-1-yl)amino)thieno[2,3-c]pyridin-2-yl)-5,7,8,9-tetrahydro-8,9a-methanopyrido[2,3-a]pyrrolizin-3-yl)-1,3,4-oxadiazol-2(3H)-one (Compound 283)

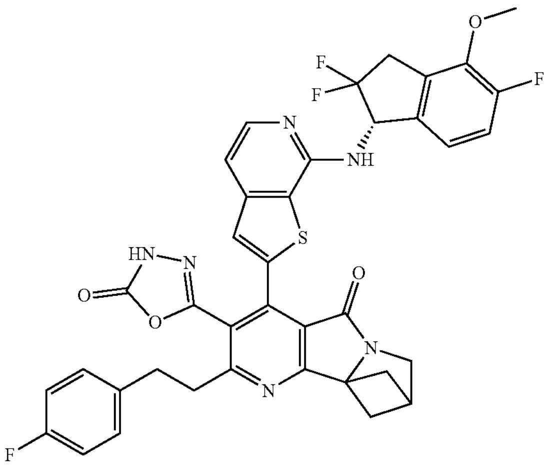 [SMILES: COc1c(F)ccc2c1CC(F)(F)[C@H]2Nc1nccc2cc(-c3c4c(nc(CCc5ccc(F)cc5)c3-c3n[nH]c(=O)o3)C35CC(CN3C4=O)C5)sc12]

Compound 283 was synthesized using a similar procedure described in Example 22 by using the appropriate materials. $^1$H NMR (400 MHz, MeOD-$d_4$) δ 7.88 (d, J=6.8 Hz, 1H), 7.68 (s, 1H), 7.52 (d, J=6.4 Hz, 1H), 7.12-7.25 (m, 4H), 6.93-7.02 (m, 2H), 5.79-5.88 (m, 1H), 3.98-4.06 (m, 3H), 3.69 (s, 2H), 3.52-3.67 (m, 2H), 3.35 (s, 1H), 3.27-3.32 (m, 2H), 3.09-3.17 (m, 2H), 2.76-2.85 (m, 2H), 1.83 (d, J=5.72 Hz, 2H). $^{19}$F NMR (376 MHz, MeOD-$d_4$) δ −100.75 (d, J=233.37 Hz, 1 F), −109.62 (d, J=233.37 Hz, 1 F), −118.94 (s, 1 F), −131.60 (s, 1 F). LC-MS: m/z 741.1 $(M+H)^+$.

(R)-4-(7-(((S)-2,2-difluoro-4-methoxy-2,3-dihydro-1H-inden-1-yl)amino)thieno[2,3-c]pyridin-2-yl)-2-(4-fluorophenethyl)-3-(5-oxo-4,5-dihydro-1,3,4-oxadiazol-2-yl)-7,8,10,10a-tetrahydro-5H-pyrido[2',3':3,4]pyrrolo[2,1-c][1,4]oxazin-5-one (Compound 284)

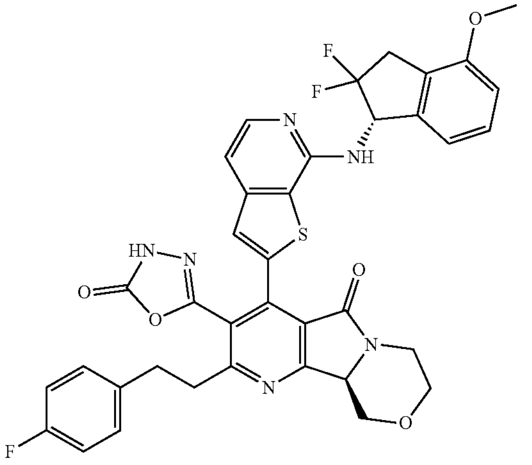

Compound 284 was synthesized using a similar procedure described in Example 22 by using the appropriate materials. $^1$H NMR (400 MHz, MeOD-$d_4$) δ 8.00 (d, J=5.72 Hz, 1H), 7.48 (s, 1H), 7.29 (t, J=7.93 Hz, 1H), 7.11-7.22 (m, 3H), 6.88-7.03 (m, 4H), 6.27 (t, J=11.21 Hz, 1H), 4.81 (dd, J=10.43, 4.59 Hz, 1H), 4.63 (dd, J=11.03, 4.59 Hz, 1H), 4.22 (d, J=10.73 Hz, 1H), 4.00-4.09 (m, 1H), 3.88 (s, 3H), 3.35-3.53 (m, 4H), 3.24-3.30 (m, 2H), 3.05-3.24 (m, 3H). $^{19}$F NMR (376 MHz, MeOD-$d_4$) δ −102.23 (d, J=231.12 Hz, 1F), −109.86 (d, J=231.12 Hz, 1 F), −119.03 (s, 1 F). LC-MS: m/z 727.1 $(M+H)^+$.

Example 40

(R)-5-(4-(7-((4-(difluoromethoxy)-5-fluoro-2,3-dihydro-1H-inden-1-yl)amino)thieno[2,3-c]pyridin-2-yl)-2-(4-fluorophenethyl)-5-oxo-5,7,8,9-tetrahydro-8,9a-methanopyrido[2,3-a]pyrrolizin-3-yl)-1,3,4-oxadiazol-2(3H)-one (Compound 285)

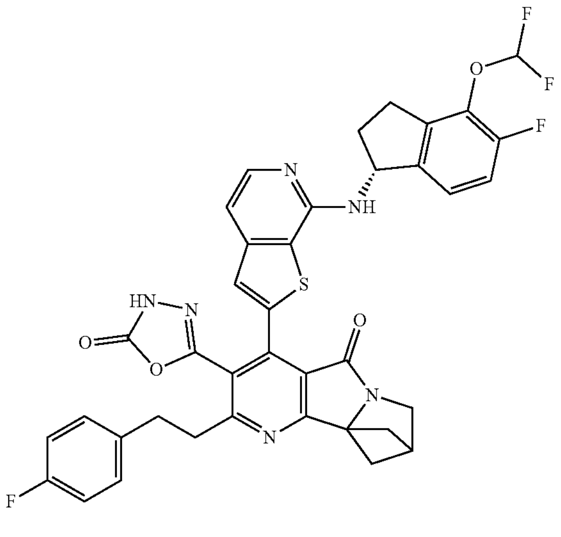 [SMILES: O=C1c2c(nc(CCc3ccc(F)cc3)c(-c3n[nH]c(=O)o3)c2-c2cc3ccnc(N[C@@H]4CCc5c4ccc(F)c5OC(F)F)c3s2)C23CC(CN12)C3]

-continued

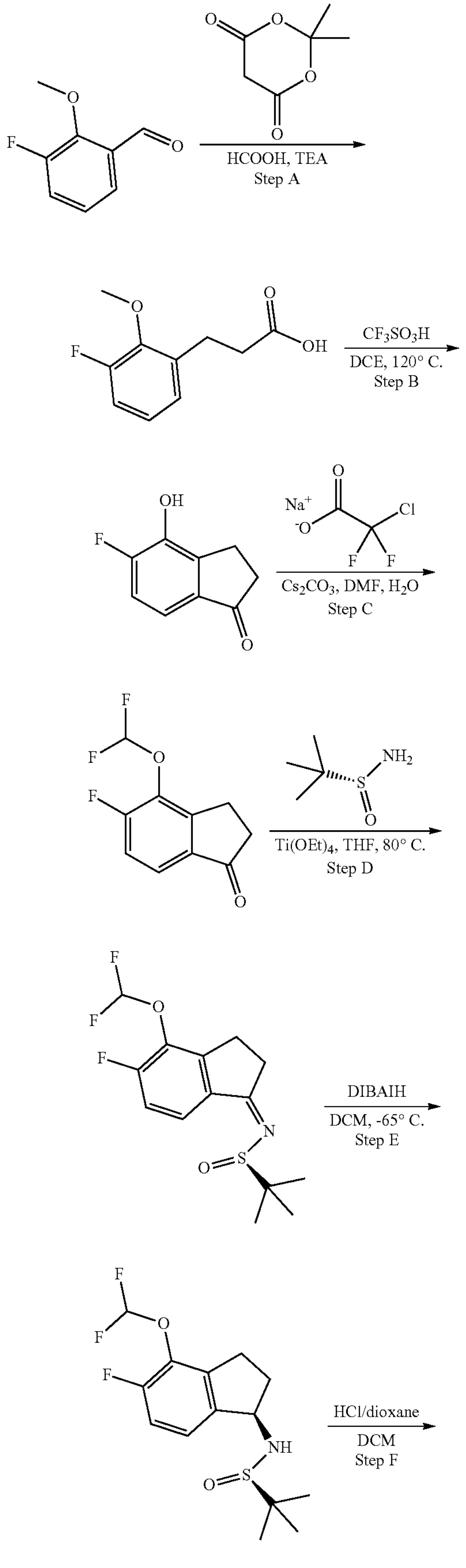

-continued

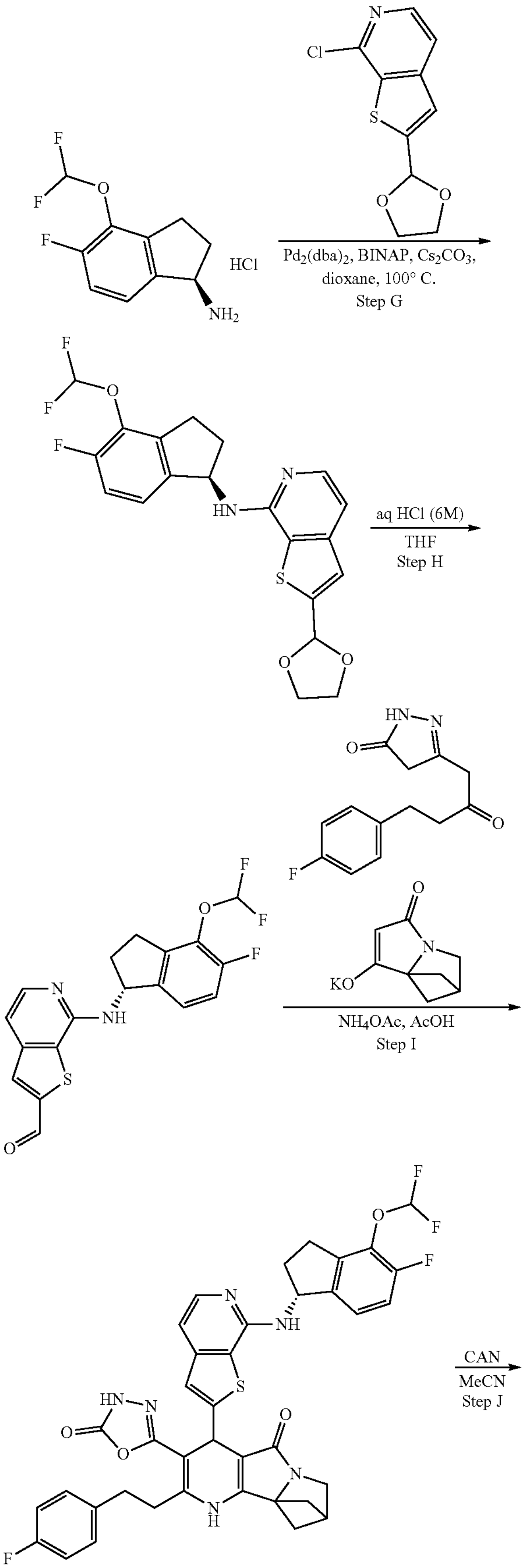

-continued

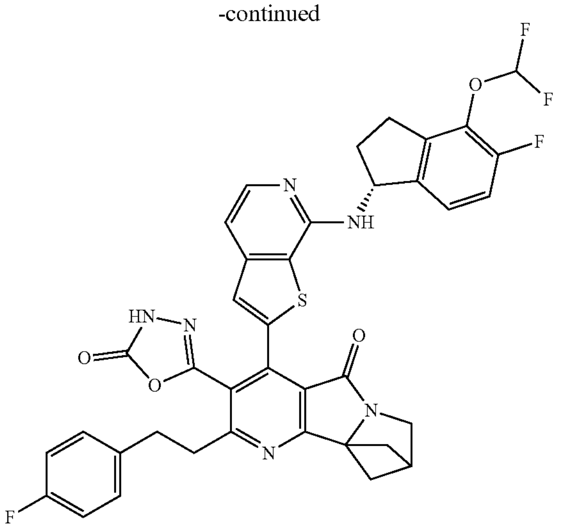

Step A 3-(3-fluoro-2-methoxyphenyl)propanoic acid

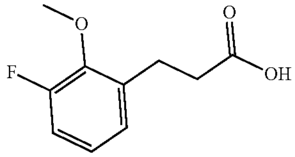

To stirred HCOOH (46.75 g, 973.15 mmol) was added TEA (45.15 mL, 324.38 mmol) dropwise at 0° C. and the mixture was stirred for 15 minutes. After 3-fluoro-2-methoxy-benzaldehyde (50.0 g, 324.38 mmol) and 2,2-dimethyl-1,3-dioxane-4,6-dione (49.09 g, 340.60 mmol) were added and the mixture was stirred at 100° C. for 11.75 hrs. After cooling to 10 ~20° C., the mixture was added dropwise to saturated $Na_2CO_3$ aqueous solution (200 mL) under stirring. The mixture was extracted with ethyl acetate (100 mL×2). To the aqueous layer was added HCl (150 mL, 3 M) dropwise under stirring and the mixture was extracted with ethyl acetate (100 mL×3). The combined organic layers were washed with brine (100 mL), dried over $Na_2SO_4$, filtered and the filtrate was concentrated under reduced pressure to give 3-(3-fluoro-2-methoxy-phenyl) propanoic acid (64.0 g, 89.59% yield, 90% purity by H NMR).

$^1H$ NMR (400 MHz, $CDCl_3$) δ=7.05-6.88 (m, 3H), 3.98-3.92 (m, 3H), 3.03-2.92 (m, 2H), 2.71-2.62 (m, 2H).

Step B
5-fluoro-4-hydroxy-2,3-dihydro-1H-inden-1-one

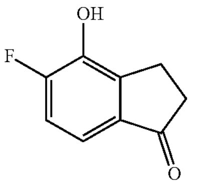 [SMILES: O=C1CCc2c1ccc(F)c2O]

To an ice cooled solution of 3-(3-fluoro-2-methoxyphenyl) propanoic acid (2.0 g, 10.09 mmol) in DCE (20.0 mL) was added trifluoromethanesulfonic acid (15.26 g, 101.71 mmol) and the reaction mixture was stirred at 120° C. for 16 hours. After cooling to room temperature, the reaction mixture was poured onto ice water (100 mL) and extracted with ethyl acetate (100 mL×2). The combined organic layers were washed with brine (100 mL), dried over anhydrous $Na_2SO_4$ and the filtrate was concentrated under reduced pressure to afford a crude. The crude product was purified by column chromatography ($SiO_2$, 30-90% ethyl acetate in petroleum ether) to give the product, which was triturated with DCM (30 mL) at 20-30° C. for 5 minutes to give 5-fluoro-4-hydroxy-2,3-dihydro-1H-inden-1-one (1.27 g, 75.75% yield). LC-MS: m/z 166.9 $(M+H)^+$.

$^1H$ NMR (400 MHz, $CDCl_3$) δ=7.40-7.30 (m, 1H), 7.21-7.08 (m, 1H), 5.54 (br.s., 1H), 3.13-3.09 (m, 2H), 2.76-2.72 (m, 2H).

Step C 4-(difluoromethoxy)-5-fluoro-2,3-dihydro-1H-inden-1-one

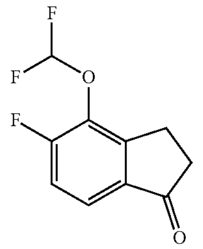

To a mixture of 5-fluoro-4-hydroxy-2,3-dihydro-1h-inden-1-one (1.07 g, 6.44 mmol) in DMF (70.0 mL) and water (10.0 mL) was added sodium sodium;2-chloro-2,2-difluoroacetate (2.54 g, 16.67 mmol) and cesium carbonate (4.15 g, 12.73 mmol). The mixture was stirred for 15 minutes at 25-30° C. and then heated to 100° C. for 12 hours under nitrogen. After cooling to room temperature, the mixture was diluted with water (100 mL) and extracted with ethyl acetate (100 mL×2). The combined organic layers were washed with brine (200 mL), dried over anhydrous sodium sulfate, filtered and the filtrate was concentrated to give a crude. The crude was purified by column chromatography ($SiO_2$, 23% ethyl acetate in petroleum ether) to give 4-(difluoromethoxy)-5-fluoro-2,3-dihydro-1H-inden-1-one (760.0 mg, 54.60% yield). LC-MS: m/z 216.8 $(M+H)^+$.

$^1H$ NMR (400 MHz, $CDCl_3$) δ=7.75-7.60 (m, 1H), 7.26-7.18 (m, 1H), 6.66 (t, J=73.6 Hz, 1H), 3.23-3.17 (m, 2H), 2.83-2.68 (m, 2H).

Step D (R,Z)—N-(4-(difluoromethoxy)-5-fluoro-2,3-dihydro-1H-inden-1-ylidene)-2-methylpropane-2-sulfinamide

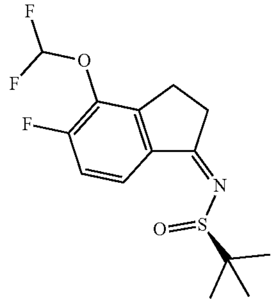 [SMILES: CC(C)(C)[S@@](=O)/N=C1/CCc2c1ccc(F)c2OC(F)F]

To a stirred solution of 4-(difluoromethoxy)-5-fluoro-2,3-dihydro-1H-inden-1-one (880.0 mg, 4.07 mmol) in THF (15.0 mL) was added (R)-2-methylpropane-2-sulfinamide (530.0 mg, 4.37 mmol) and $Ti(OEt)_4$ (2.10 g, 9.19 mmol) under $N_2$ and the mixture was stirred under $N_2$ at 80° C. for 12 hours. After cooling to room temperature, the mixture was diluted with cold water (50 mL) and extracted with ethyl acetate (50 mL×3). The combined organic layers were dried over anhydrous sodium sulfate, filtered and the filtrate was concentrated to give a crude. The crude was purified by column chromatography ($SiO_2$, 31-38% ethyl acetate in petroleum ether) to give (R,Z)—N-(4-(difluoromethoxy)-5-fluoro-2,3-dihydro-1H-inden-1-ylidene)-2-methylpropane-2-sulfinamide (490.0 mg, 37.69% yield).

$^1H$ NMR (400 MHz, $CDCl_3$) δ=7.81-7.61 (m, 1H), 7.24-7.14 (m, 1H), 6.63 (t, J=74.0 Hz, 1H), 3.61-3.41 (m, 1H), 3.24-3.06 (m, 3H), 1.33 (s, 9H).

Step E (R)—N—((R)-4-(difluoromethoxy)-5-fluoro-2,3-dihydro-1H-inden-1-yl)-2-methylpropane-2-sulfinamide

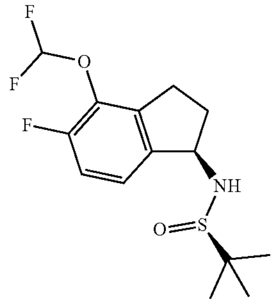 [SMILES: CC(C)(C)[S@@](=O)N[C@@H]1CCc2c1ccc(F)c2OC(F)F]

To a stirred solution of (R,Z)—N-(4-(difluoromethoxy)-5-fluoro-2,3-dihydro-1H-inden-1-ylidene)-2-methylpropane-2-sulfinamide (490.0 mg, 1.53 mmol) in DCM (10.0 mL) was added DIBAL-H (2.30 mL, 1 M) dropwise under $N_2$ at −65° C. and the mixture was stirred for 1 hour. The reaction mixture was quenched by addition MeOH (20 mL) at −65° C. and concentrated under reduced pressure to give a residue. The residue was purified by flash silica gel chromatography (45% ethyl acetate in petroleum ether) to give (R)—N—((R)-4-(difluoromethoxy)-5-fluoro-2,3-dihydro-1H-inden-1-yl)-2-methylpropane-2-sulfinamide (320.0 mg, 64.90% yield).

$^1$H NMR (400 MHz, $CDCl_3$) δ=7.54-7.42 (m, 1H), 7.11-7.00 (m, 1H), 6.57 (t, J=74.0 Hz, 1H), 5.00-4.79 (m, 1H), 3.49-3.39 (m, 1H), 3.23-2.96 (m, 1H), 2.93-2.76 (m, 1H), 2.63-2.46 (m, 1H), 2.05-1.91 (m, 1H), 1.24 (s, 9H).

Step F (R)-4-(difluoromethoxy)-5-fluoro-2,3-dihydro-1H-inden-1-amine

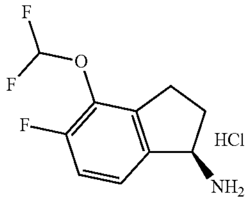 [SMILES: N[C@@H]1CCc2c1ccc(F)c2OC(F)F ; Cl]

To a solution of (R)—N—((R)-4-(difluoromethoxy)-5-fluoro-2,3-dihydro-1H-inden-1-yl)-2-methylpropane-2-sulfinamide (320.0 mg, 995.78 μmol) in DCM (2.0 mL) was added HCl/dioxane (4 mL, 4 M) dropwise at 0° C. and the mixture was stirred at 0-30° C. for 4 hours. The mixture was concentrated under reduced pressure to give (R)-4-(difluoromethoxy)-5-fluoro-2,3-dihydro-1H-inden-1-amine (250.0 mg, crude, HCl salt).

$^1$H NMR (400 MHz, DMSO-$d_6$) δ=8.61 (br.s., 3H), 7.67-7.55 (m, 1H), 7.45-7.30 (m, 1H), 7.19 (t, J=73.2 Hz, 2H), 4.74 (br.s., 1H), 3.17-3.10 (m, 1H), 2.97-2.88 (m, 1H), 2.61-2.53 (m, 1H), 2.15-1.95 (m, 1H).

Step G (R)—N-(4-(difluoromethoxy)-5-fluoro-2,3-dihydro-1H-inden-1-yl)-2-(1,3-dioxolan-2-yl)thieno[2,3-c]pyridin-7-amine

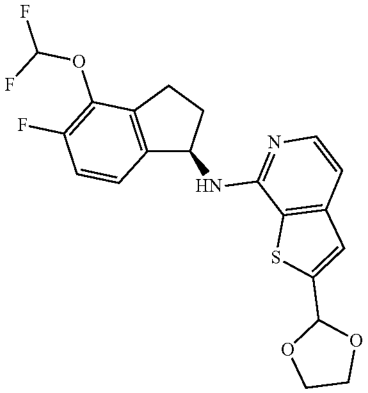 [SMILES: Fc1ccc2c(c1OC(F)F)CC[C@H]2Nc1nccc2cc(C3OCCO3)sc12]

A mixture of (R)-4-(difluoromethoxy)-5-fluoro-2,3-dihydro-1H-inden-1-amine (230.0 mg, 906.77 mol, HCl salt), 7-chloro-2-(1,3-dioxolan-2-yl)thieno[2,3-c]pyridine (230.0 mg, 951.62 μmol), $Cs_2CO_3$ (920.0 mg, 2.82 mmol), $Pd(dba)_2$ (60.0 mg, 104.35 μmol) and BINAP (90.0 mg, 144.54 μmol) in dioxane (10.0 mL) was stirred at 100° C. for 12 hours under $N_2$. The reaction mixture was concentrated to give a crude. The crude was purified by column chromatography ($SiO_2$, 11.1% ethyl acetate in petroleum ether) to give (R)—N-(4-(difluoromethoxy)-5-fluoro-2,3-dihydro-1H-inden-1-yl)-2-(1,3-dioxolan-2-yl)thieno[2,3-c]pyridin-7-amine (310.0 mg, 80.93% yield). LC-MS: m/z 422.9 $(M+H)^+$.

$^1$H NMR (400 MHz, $CDCl_3$) δ=8.08 (d, J=5.6 Hz, 1H), 7.37 (s, 1H), 7.24-7.18 (m, 1H), 7.08 (d, J=5.6 Hz, 1H), 7.05-6.96 (m, 1H), 6.60 (t, J=74.4 Hz, 1H), 6.22 (s, 1H), 5.98-5.85 (m, 1H), 4.71-4.44 (m, 1H), 4.15-4.12 (m, 2H), 4.11-4.07 (m, 2H), 3.24-3.12 (m, 1H), 2.99-2.90 (m, 1H), 2.87-2.77 (m, 1H), 2.03-1.97 (m, 1H).

Step H(R)-7-((4-(difluoromethoxy)-5-fluoro-2,3-dihydro-1H-inden-1-yl)amino)thieno[2,3-c]pyridine-2-carbaldehyde

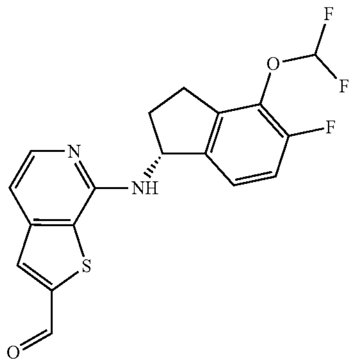 [SMILES: O=Cc1cc2ccnc(N[C@@H]3CCc4c3ccc(F)c4OC(F)F)c2s1]

To a stirred solution of (R)—N-(4-(difluoromethoxy)-5-fluoro-2,3-dihydro-1H-inden-1-yl)-2-(1,3-dioxolan-2-yl) thieno[2,3-c]pyridin-7-amine (290.0 mg, 686.52 μmol) in THF (10.0 mL) was added HCl (10.0 mL, 6 M) and the mixture was stirred for 2 hours at 10-15° C. The reaction mixture was concentrated under reduced pressure, neutralized to pH=7 with saturated $NaHCO_3$ aqueous solution and extracted with ethyl acetate (50 mL×3). The combined organic layers were washed with brine (200 mL), dried over anhydrous $Na_2SO_4$, filtered and the filtrate was concentrated to give a crude. The crude was purified by column chromatography ($SiO_2$, 30% ethyl acetate in petroleum ether) to give (R)-7-((4-(difluoromethoxy)-5-fluoro-2,3-dihydro-1H-inden-1-yl)amino)thieno[2,3-c]pyridine-2-carbaldehyde (240.0 mg, 92.39% yield).

$^1$H NMR (400 MHz, $CDCl_3$) δ=10.15 (s, 1H), 8.16 (d, J=6.0 Hz, 1H), 8.00 (s, 1H), 7.25-7.18 (m, 2H), 7.07-6.99 (m, 1H), 6.61 (t, J=74.4 Hz, 1H), 6.02-5.82 (m, 1H), 4.84-4.66 (m, 1H), 3.31-3.11 (m, 1H), 3.03-2.91 (m, 1H), 2.88-2.74 (m, 1H), 2.05-1.98 (m, 1H).

Step I 5-(4-(7-(((R)-4-(difluoromethoxy)-5-fluoro-2,3-dihydro-1H-inden-1-yl)amino)thieno[2,3-c]pyridin-2-yl)-2-(4-fluorophenethyl)-5-oxo-1,5,8,9-tetrahydro-4H,7H-8,9a-methanopyrido[2,3-a]pyrrolizin-3-yl)-1,3,4-oxadiazol-2(3H)-one

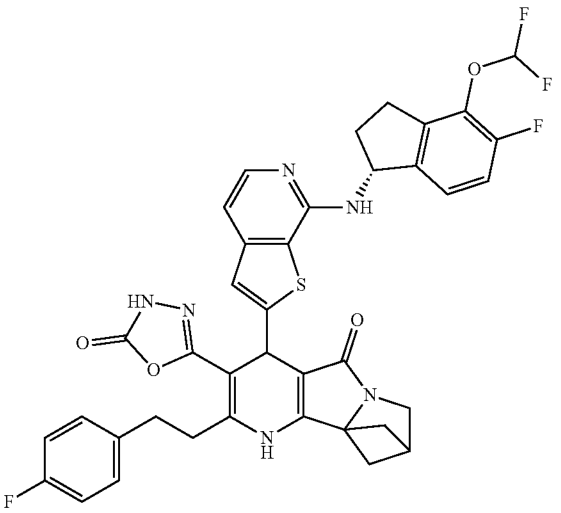 [SMILES: O=C1C2=C(NC(CCc3ccc(F)cc3)=C(c3n[nH]c(=O)o3)C2c2cc3ccnc(N[C@@H]4CCc5c4ccc(F)c5OC(F)F)c3s2)C23CC(CN12)C3]

A mixture of (R)-7-((4-(difluoromethoxy)-5-fluoro-2,3-dihydro-1H-inden-1-yl)amino)thieno[2,3-c]pyridine-2-carbaldehyde (100.0 mg, 264.29 μmol), 5-(4-(4-fluorophenyl)-2-oxobutyl)-1,3,4-oxadiazol-2(3H)-one (80.0 mg, 319.71 μmol), potassium 5-oxo-2,3-dihydro-1H,5H-2,7a-methanopyrrolizin-7-olate (100.0 mg, 264.20 μmol) and $NH_4OAc$ (50.0 mg, 648.66 μmol) in AcOH (5.0 mL) was stirred at 110° C. for 1 hour. After cooling to room temperature, the reaction mixture was added to water (100 mL). The precipitate was collected by filtration and the filter cake was washed with water (100 mL) to afford the desired compound. The desired compound was dissolved in ethyl acetate (100 mL). The organic layer was dried over anhydrous sodium sulfate, filtered and the filtrate was concentrated to give a crude. The crude was purified by combi flash ($SiO_2$, 4-6% methanol in dichloromethane) to afford 5-(4-(7-(((R)-4-(difluoromethoxy)-5-fluoro-2,3-dihydro-1H-inden-1-yl)amino)thieno[2,3-c]pyridin-2-yl)-2-(4-fluorophenethyl)-5-oxo-1,5,8,9-tetrahydro-4H,7H-8,9a-methanopyrido[2,3-a]pyrrolizin-3-yl)-1,3,4-oxadiazol-2(3H)-one (60.0 mg, 30.57% yield). LC-MS: m/z 743.2 $(M+H)^+$.

Step J (R)-5-(4-(7-((4-(difluoromethoxy)-5-fluoro-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 285)

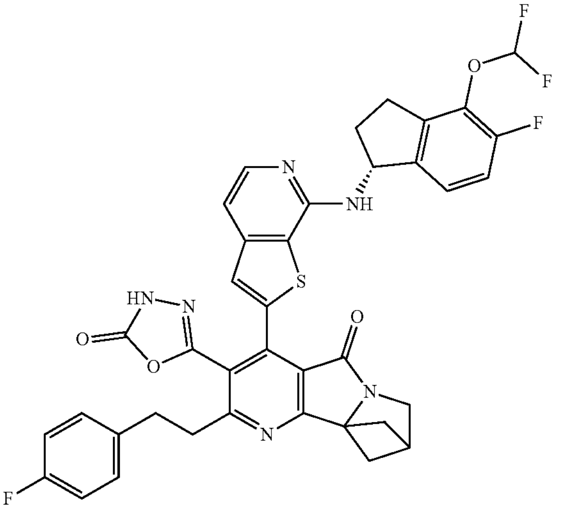 [SMILES: O=C1c2c(nc(CCc3ccc(F)cc3)c(-c3n[nH]c(=O)o3)c2-c2cc3ccnc(N[C@@H]4CCc5c4ccc(F)c5OC(F)F)c3s2)C23CC(CN12)C3]

To a solution of 5-(4-(7-(((R)-4-(difluoromethoxy)-5-fluoro-2,3-dihydro-1H-inden-1-yl)amino)thieno[2,3-c]pyridin-2-yl)-2-(4-fluorophenethyl)-5-oxo-1,5,8,9-tetrahydro-4H,7H-8,9a-methanopyrido[2,3-a]pyrrolizin-3-yl)-1,3,4-oxadiazol-2(3H)-one (50.0 mg, 67.32 μmol) in MeCN (5.0 mL) was added CAN (75.0 mg, 136.81 μmol) at 10-15° C. and the mixture was stirred at 25-30° C. for 1 hour. The reaction mixture was concentrated under reduced pressure, diluted with water (40 mL) and extracted with ethyl acetate (40 mL×2). The combined organic layers were washed with brine (100 mL), dried over anhydrous sodium sulfate, filtered and the filtrate was concentrated to give a crude. The crude was purified by prep-HPLC (column: $C_{18}$ 150×30 mm; mobile phase: [water (FA)-ACN]; gradient: 30%-60% B over 7 min), concentrated and lyophilized to give (R)-5-(4-(7-((4-(difluoromethoxy)-5-fluoro-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (285) (25.75 mg, 51.64% yield, 100.0% purity).

$^1H$ NMR (400 MHz, $CDCl_3$) δ=8.04 (d, J=5.6 Hz, 1H), 7.36 (s, 1H), 7.23-7.18 (m, 1H), 7.16-7.10 (m, 2H), 7.08 (d, J=5.6 Hz, 1H), 7.02-6.93 (m, 3H), 6.58 (t, J=74.4 Hz, 1H), 5.91-5.77 (m, 1H), 5.06-4.32 (m, 1H), 3.65 (s, 2H), 3.27-3.22 (m, 2H), 3.13-3.04 (m, 3H), 2.96-2.87 (m, 1H), 2.78-2.71 (m, 3H), 2.02-1.97 (m, 1H), 1.80-1.77 (m, 2H). $^{19}F$ NMR (400 MHz, $CDCl_3$) δ=−80.873, −116.668, −131.859. LC-MS: m/z 741.3 $(M+H)^+$.

(R)-5-(4-(7-((5,6-difluoro-4-methoxy-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 286)

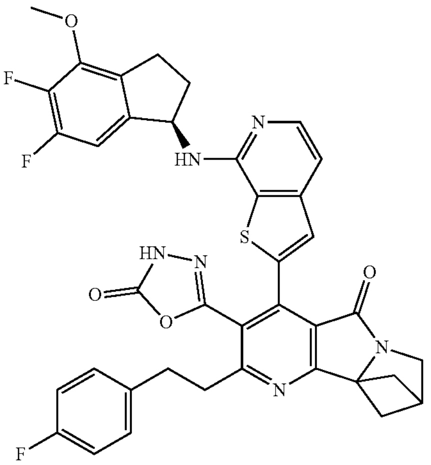 [SMILES: COc1c(F)c(F)cc2c1CC[C@H]2Nc1nccc2cc(-c3c4c(nc(CCc5ccc(F)cc5)c3-c3n[nH]c(=O)o3)C35CC(CN3C4=O)C5)sc12]

Compound 286 was synthesized using a similar procedure described in Example 10 by using the appropriate materials.

$^1$H NMR (400 MHz, DMSO-$d_6$) δ 7.98 (d, J=5.2 Hz, 1H), 7.40 (s, 1H), 7.20-7.27 (m, 3H), 7.04-7.11 (m, 3H), 6.91-6.97 (m, 1H), 5.78-5.85 (m, 1H), 3.94 (d, J=1.2 Hz, 3H), 3.55 (s, 2H), 3.13-3.21 (m, 3H), 2.97-3.06 (m, 3H), 2.80-2.89 (m, 1H), 2.62-2.66 (m, 2H), 2.53-2.55 (m, 1H), 2.01-2.11 (m, 1H), 1.73-1.74 (m, 2H). 19F NMR (377 MHz, DMSO-$d_6$): −117.06, −138.71, −158.73. LC-MS: m/z 723.3 $(M+H)^+$.

(R)-5-(4-(5-(difluoromethyl)-7-((5-fluoro-4-methoxy-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 287)

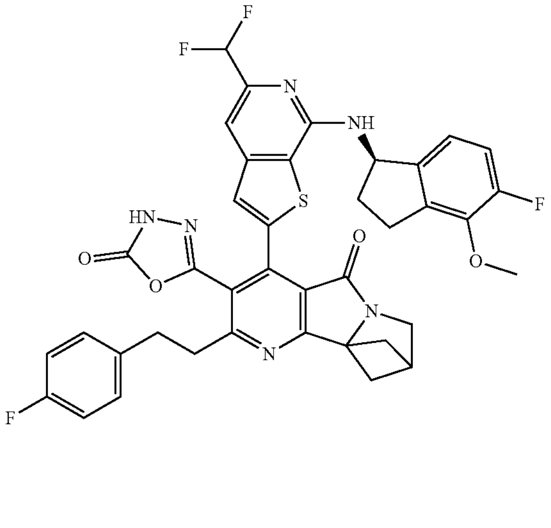 [SMILES: COc1c(F)ccc2c1CC[C@H]2Nc1nc(C(F)F)cc2cc(-c3c4c(nc(CCc5ccc(F)cc5)c3-c3n[nH]c(=O)o3)C35CC(CN3C4=O)C5)sc12]

Compound 287 was synthesized using a similar procedure described in Example 21 by using the appropriate materials.

$^1$H NMR (400 MHz, DMSO-$d_6$) δ 12.74 (br s, 1H), 7.64 (d, J=7.6 Hz, 1H), 7.53 (s, 1H), 7.39 (s, 1H), 7.19-7.26 (m, 2H), 7.04-7.11 (m, 2H), 6.95-7.02 (m, 2H), 6.68-6.94 (m, 1H), 5.83 (q, J=8.0 Hz, 1H), 3.88 (d, J=1.2 Hz, 3H), 3.56 (s, 2H), 3.17-3.23 (m, 3H), 3.01-3.09 (m, 3H), 2.84-2.92 (m, 1H), 2.63-2.66 (m, 2H), 2.54-2.56 (m, 1H), 2.07-2.13 (m, 1H), 1.73-1.78 (m, 2H). $^{19}$F NMR (377 MHz, DMSO-$d_6$): −114.68, −117.00, −135.17. LC-MS: m/z 755.3 $(M+H)^+$.

(R)-5-(4-(7-((5,7-difluoro-4-methoxy-2,3-dihydro-1H-inden-1-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 288)

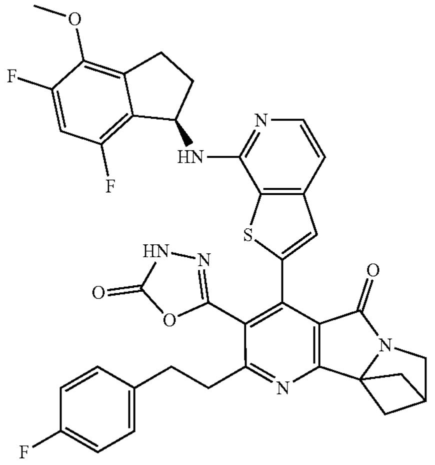 [SMILES: COc1c(F)cc(F)c2c1CC[C@H]2Nc1nccc2cc(-c3c4c(nc(CCc5ccc(F)cc5)c3-c3n[nH]c(=O)o3)C35CC(CN3C4=O)C5)sc12]

Compound 288 was synthesized using a similar procedure described in Example 10 by using the appropriate materials.

$^1$H NMR (400 MHz, DMSO-$d_6$) δ 12.70 (br s, 1H), 7.98 (d, J=5.6 Hz, 1H), 7.41 (s, 1H), 7.32 (d, J=8.0 Hz, 1H), 7.17-7.25 (m, 2H), 7.03-7.16 (m, 4H), 5.96-6.05 (m, 1H), 3.85 (s, 3H), 3.56 (s, 2H), 3.16-3.23 (m, 3H), 3.07-3.14 (m, 1H), 3.00-3.06 (m, 2H), 2.83-2.95 (m, 1H), 2.62-2.66 (m, 2H), 2.53-2.58 (m, 1H), 2.01-2.11 (m, 1H) 1.70-1.78 (m, 2H). $^{19}$F NMR (377 MHz, DMSO-$d_6$): −117.02, −120.84, −129.92. LC-MS: m/z 723.2 $(M+H)^+$.

(R)-5-(4-(7-((6-chloro-4-fluoro-5-methoxy-2,3-dihydro-1H-inden-1-yl)amino)thieno[2,3-c]pyridin-2-yl)-2-(4-fluorophenethyl)-5-oxo-5,7,8,9-tetrahydro-8,9a-methanopyrido[2,3-a]pyrrolizin-3-yl)-1,3,4-oxadiazol-2(3H)-one (Compound 289)

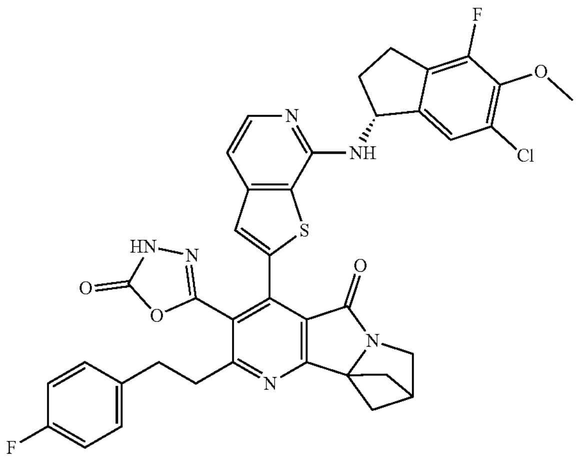 [SMILES: COc1c(Cl)cc2c(c1F)CC[C@H]2Nc1nccc2cc(-c3c4c(nc(CCc5ccc(F)cc5)c3-c3n[nH]c(=O)o3)C35CC(CN3C4=O)C5)sc12]

Compound 289 was synthesized using a similar procedure described in Example 39 by using the appropriate materials.

$^1$H NMR (400 MHz, DMSO-$d_6$) δ 12.96-12.50 (m, 1H), 8.00 (d, J=5.6 Hz, 1H), 7.44 (s, 1H), 7.34 (d, J=8.0 Hz, 1H), 7.22 (dd, J=5.6, 8.4 Hz, 2H), 7.15-7.06 (m, 4H), 5.85 (d, J=7.6 Hz, 1H), 3.86 (s, 3H), 3.57 (s, 2H), 3.23-3.18 (m, 3H), 3.08-3.02 (m, 3H), 2.86 (td, J=8.2, 16.0 Hz, 1H), 2.65 (br s, 2H), 2.58 (br dd, J=4.4, 8.4 Hz, 1H), 2.15-2.04 (m, 1H), 1.75 (br d, J=4.4 Hz, 2H). LC-MS: m/z 739.2 $(M+H)^+$.

5-((S)-2-(4-fluorophenethyl)-5-oxo-4-(7-(((R)-2,2,5-trifluoro-4-methoxy-2,3-dihydro-1H-inden-1-yl)amino)thieno[2,3-c]pyridin-2-yl)-7,8,9,9a-tetrahydro-5H-pyrido[2,3-a]pyrrolizin-3-yl)-1,3,4-oxadiazol-2(3H)-one (Compound 290)

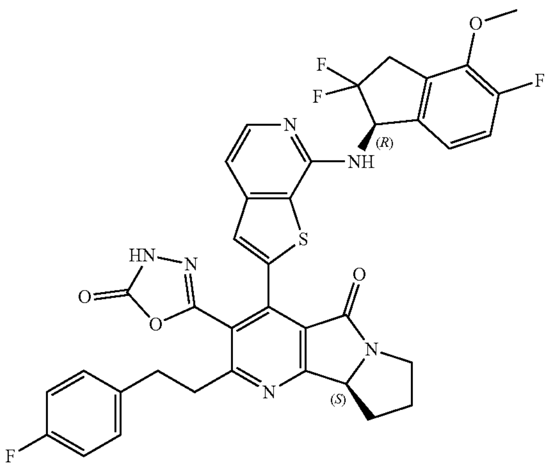

Compound 290 was synthesized using a similar procedure described in Example 22 by using the appropriate materials.

$^1$H NMR (400 MHz, MeOD-$d_4$) δ 7.99 (d, J=5.72 Hz, 1H), 7.47 (s, 1H), 7.13-7.23 (m, 3H), 7.05-7.12 (m, 1H), 6.94-7.04 (m, 3H), 6.22 (t, J=10.85 Hz, 1H), 4.87 (s, 1H), 3.99 (d, J=2.03 Hz, 3H), 3.61-3.73 (m, 1H), 3.39-3.60 (m, 3H), 3.23-3.29 (m, 2H), 3.04-3.19 (m, 2H), 2.37-2.55 (m, 3H), 1.45-1.50 (m, 1H). $^{19}$F NMR (376 MHz, MeOD-$d_4$) δ −102.41 (d, J=231.13 Hz, 1 F), −109.86 (d, J =231.13 Hz, 1 F), −119.00 (s, 1 F), −133.82 (s, 1 F). LC-MS: m/z 729.1 $(M+H)^+$.

5-(4-(7-(((1S,2R)-2,5-difluoro-4-methoxy-2,3-dihydro-1H-inden-1-yl)amino)thieno[2,3-c]pyridin-2-yl)-2-(4-fluorophenethyl)-5-oxo-5,7,8,9-tetrahydro-8,9a-methanopyrido[2,3-a]pyrrolizin-3-yl)-1,3,4-oxadiazol-2(3H)-one (Compound 291)

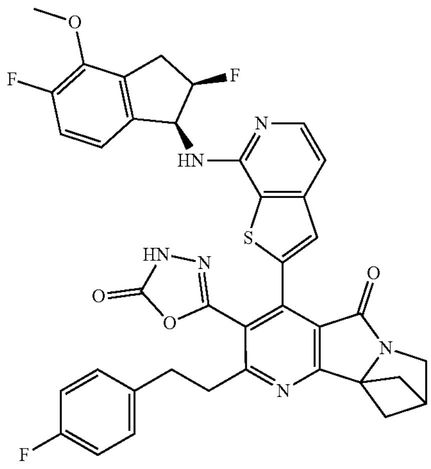 [SMILES: COc1c(F)ccc2c1C[C@@H](F)[C@H]2Nc1nccc2cc(-c3c4c(nc(CCc5ccc(F)cc5)c3-c3n[nH]c(=O)o3)C35CC(CN3C4=O)C5)sc12]

Compound 291 was synthesized using a similar procedure described in Example 24 by using the appropriate materials.

$^1$H NMR (400 MHz, $CDCl_3$) δ=8.06 (d, J=5.6 Hz, 1H), 7.41 (s, 1H), 7.18-7.10 (m, 3H), 7.00-6.93 (m, 4H), 6.11-5.93 (m, 1H), 5.60-5.40 (m, 1H), 5.00-4.89 (m, 1H), 4.02-3.94 (m, 3H), 3.67 (s, 2H), 3.42-3.28 (m, 1H), 3.27-3.23 (m, 1H), 3.23-3.05 (m, 5H), 2.79-2.71 (m, 2H), 1.82-1.77 (m, 2H). $^{19}$F NMR (376 MHz, $CCl_3D$) δ −116.69, −133.20, −195.27. LC-MS: m/z 723.4 $(M+H)^+$.

(R)-5-(2-(4-fluorophenethyl)-5-oxo-4-(7-((2,2,5-trifluoro-4-methoxy-2,3-dihydro-1H-inden-1-yl)amino)thieno[2,3-c]pyridin-2-yl)-5,7,8,9-tetrahydro-8,9a-methanopyrido[2,3-a]pyrrolizin-3-yl)-1,3,4-oxadiazol-2(3H)-one (Compound 292)

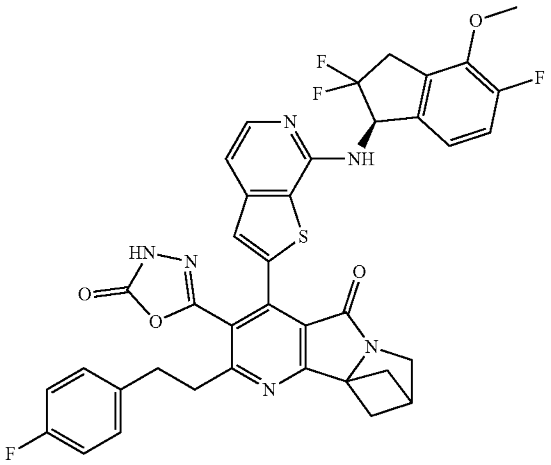 [SMILES: COc1c(F)ccc2c1CC(F)(F)[C@@H]2Nc1nccc2cc(-c3c4c(nc(CCc5ccc(F)cc5)c3-c3n[nH]c(=O)o3)C35CC(CN3C4=O)C5)sc12]

Compound 292 was synthesized using a similar procedure described in Example 22 by using the appropriate materials.

$^1$H NMR (400 MHz, MeOD-$d_4$) δ 7.88 (d, J=6.8 Hz 1H), 7.68 (s, 1H) 7.54 (d, J=10.8 Hz, 1H) 7.13-7.25 (m, 4H) 6.93-7.03 (m, 2H) 5.80-5.91 (m, 1H), 4.00-4.06 (m, 3H), 3.69 (s, 2H), 3.54-3.66 (m, 2H), 3.34-3.36 (m, 1H), 3.28-3.32 (m, 2H), 3.09-3.17 (m, 2H), 2.81 (br s, 2H), 1.83 (dd, J=4.53, 1.31 Hz, 2H). $^{19}$F NMR (376 MHz, MeOD-$d_4$) δ −100.78 (d, J=233.37 Hz, 1 F), −109.62 (d, J=233.37 Hz, 1 F), −118.93 (s, 1 F), −131.62 (s, 1 F). LC-MS: m/z 741.1 $(M+H)^+$.

(R)-5-(4-(7-((6,8-difluorochroman-4-yl)amino)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 293)

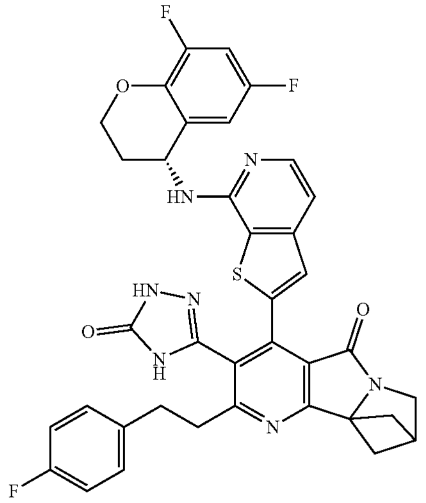

Compound 293 was synthesized using a similar procedure described in Example 10 by using the appropriate materials. $^1$H NMR (400 MHz, DMSO-d6): δ 12.70 (br s, 1H), 8.00 (d, J=5.6 Hz, 1H), 7.45 (d, J=8.0 Hz, 1H), 7.43 (s, 1H), 7.15-7.24 (m, 3H), 7.13 (d, J=5.6 Hz, 1H), 7.05-7.10 (m, 2H), 6.87-6.92 (m, 1H), 5.61 (q, J=6.4 Hz, 1H), 4.27-4.43 (m, 2H), 3.56 (s, 2H), 3.16-3.22 (m, 3H), 2.99-3.06 (m, 2H), 2.61-2.68 (m, 2H), 2.14-2.22 (m, 2H), 1.71-1.77 (m, 2H). $^{19}$F NMR (377 MHz, DMSO-d6): −117.04, −121.79, −132.93. LC-MS: m/z 709.3 $(M+H)^+$.

Example 41

(R)-5-(4-(7-((6-fluoro-4-methoxy-2,3-dihydro-1H-inden-1-yl)amino)thieno[2,3-c]pyridin-2-yl)-2-(4-fluorophenethyl)-5-oxo-5,7,8,9-tetrahydro-8,9a-methanopyrido[2,3-a]pyrrolizin-3-yl)-1,3,4-oxadiazol-2(3H)-one (Compound 294)

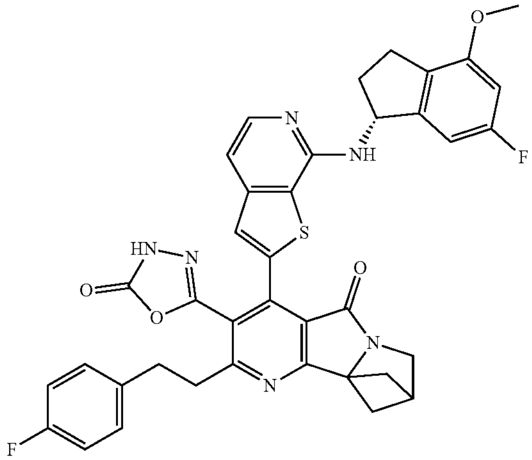

-continued
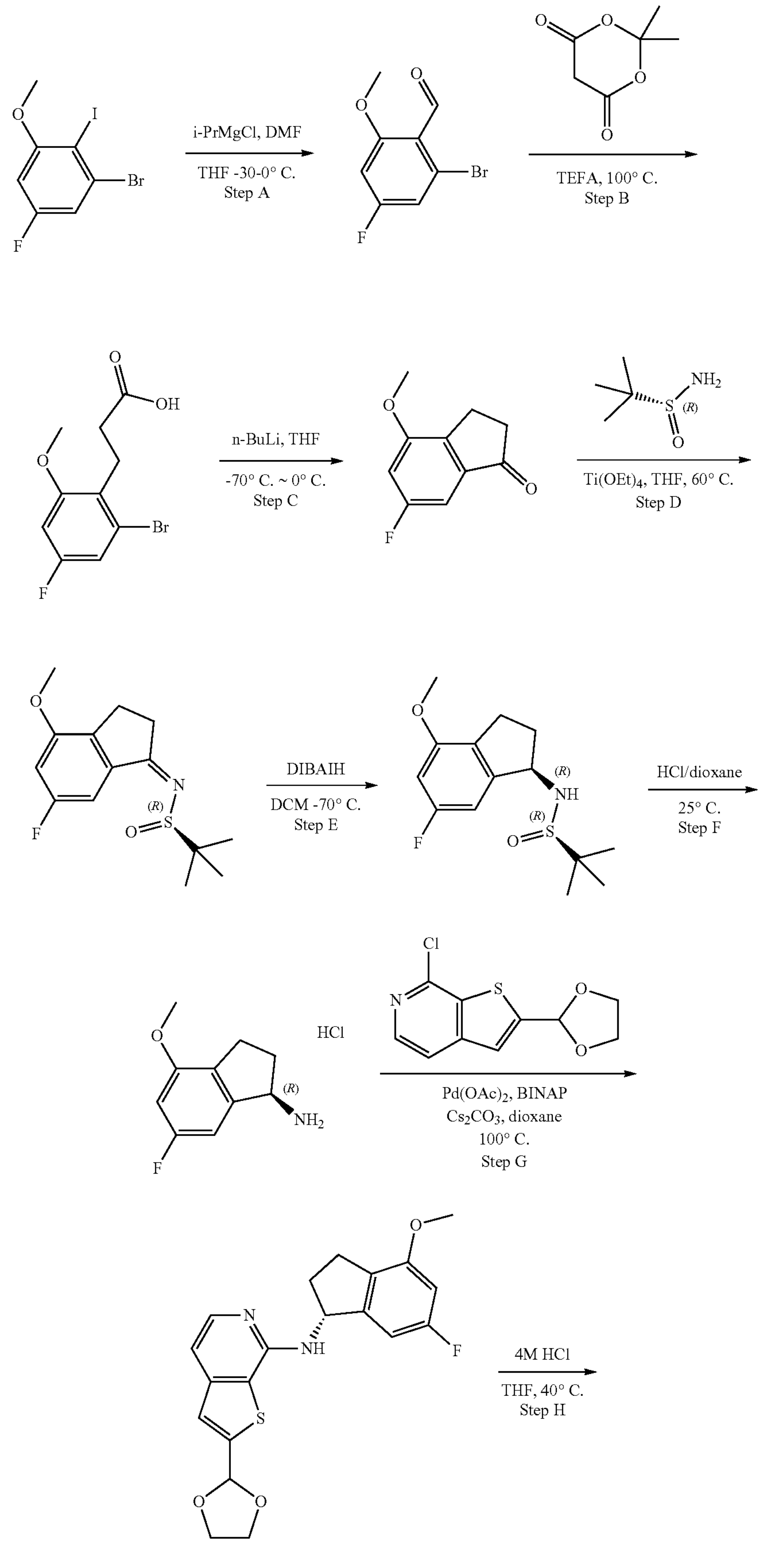

-continued

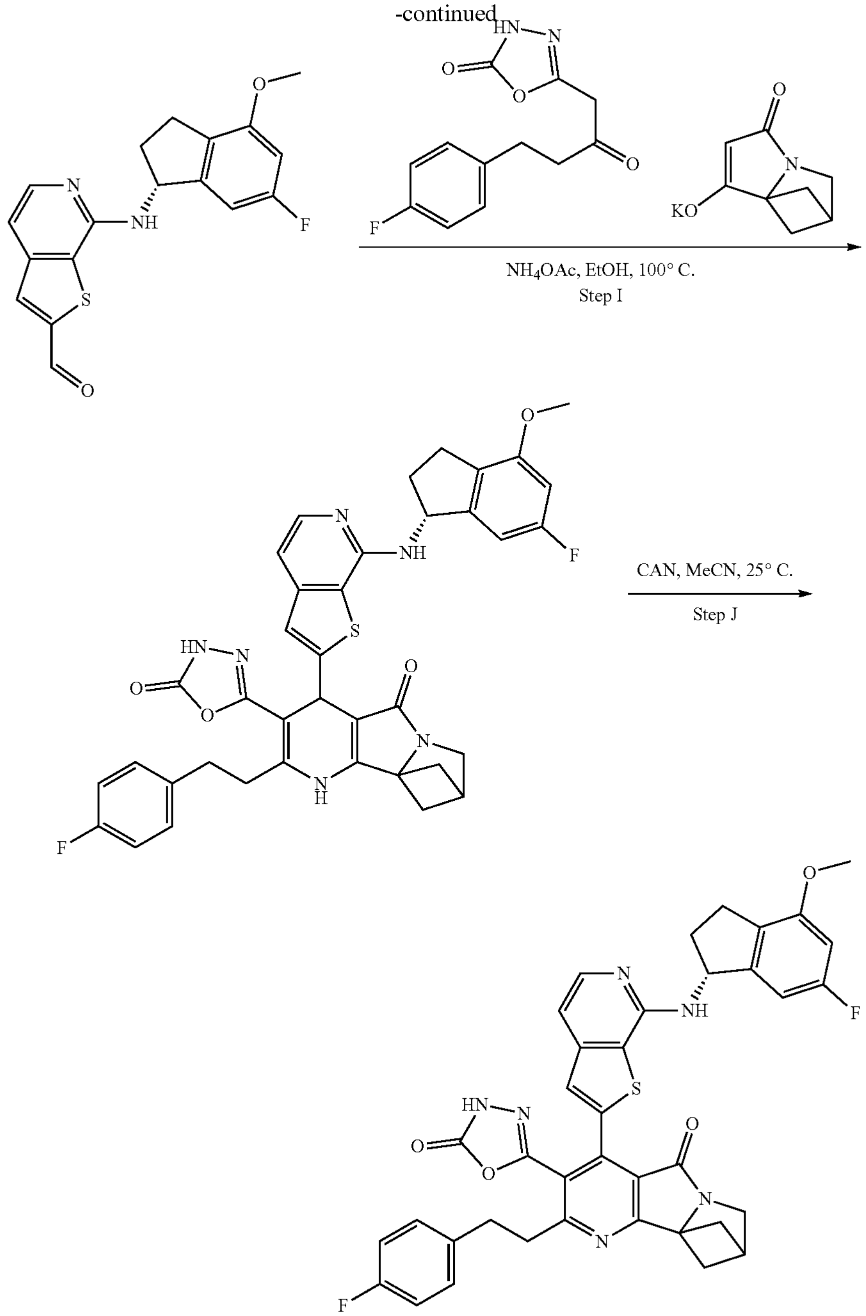

Step A 2-bromo-4-fluoro-6-methoxybenzaldehyde

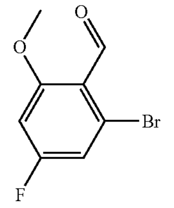

A solution of the 1-bromo-5-fluoro-2-iodo-3-methoxybenzene (5.1 g, 15.41 mmol) in toluene (70 mL) was cooled to a temperature of −30° C. Then, a solution of isopropylmagnesium chloride (2 M, 11.5 mL) was added slowly over 5 min. A clear brown solution was obtained. Stirring was continued for 1 hr. Anhydrous DMF (61.65 mmol, 4.7 mL) was added slowly over 5 min, the temperature of the reaction mixture increased to −19° C. The reaction mixture was warmed to 0° C. over 1 hr. The reaction was quenched into saturated aqueous $NH_4Cl$ (50 mL), and allowed to warm to room temperature. Ethyl acetate (100 mL*2) and water (100 mL) were added and the layers were separated. The organic layer was washed with brine, concentrated by rotary evaporator. The residue was purified by flash silica gel chromatography (Biotage®; 40 g SepaFlash® Silica Flash Column, Eluent of 0-30% Ethylacetate/Petroleum ether gradient @25 mL/min) to give 2-bromo-4-fluoro-6-methoxybenzaldehyde (2.7 g, 75.18% yield).

$^1H$ NMR (400 MHz, $CDCl_3$) δ ppm 10.27 (s, 1H), 6.94 (dd, J=7.99, 2.38 Hz, 1H), 6.62 (dd, J=10.43, 2.32 Hz, 1H), 3.85 (s, 3H).

Step B
3-(2-bromo-4-fluoro-6-methoxyphenyl)propanoic acid

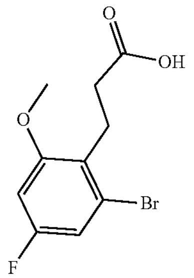

To a solution of formic acid (347.59 mmol, 13 mL) was added TEA (115.86 mmol, 16 mL) drop-wise at 0° C. To the mixture was added 2-bromo-4-fluoro-6-methoxybenzaldehyde (2.7 g, 11.59 mmol) and 2,2-dimethyl-1,3-dioxane-4,6-dione (1.67 g, 11.59 mmol). The reaction mixture was warmed to 100° C. and stirred at 100° C. for 16 hrs. The solution was added aqueous NaOH until pH=10~11. The mixture was washed with EtOAc (50 mL*2). The aqueous phase was added HCl until pH=1-2 and extracted with EtOAc (50 mL*3). The combined organic phase was washed with brine (100 mL), dried over anhydrous $Na_2SO_4$, filtered and concentrated in vacuo. Compound 3-(2-bromo-4-fluoro-6-methoxyphenyl)propanoic acid (2.05 g, 63.85% yield) was obtained.

$^1H$ NMR (400 MHz, $CDCl_3$) δ ppm 6.84 (dd, J=8.11, 2.50 Hz, 1H), 6.49 (dd, J=10.49, 2.38 Hz, 1H), 3.74 (s, 3H), 2.97-3.10 (m, 2H), 2.39-2.54 (m, 2H).

Step C
6-fluoro-4-methoxy-2,3-dihydro-1H-inden-1-one

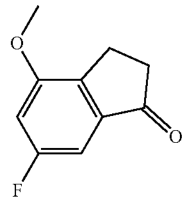

To a solution of 3-(2-bromo-4-fluoro-6-methoxyphenyl) propanoic acid (1.55 g, 5.59 mmol) in THF (30 mL) was added a solution of n-BuLi (2.5 M, 4.92 mL) drop-wise at −70° C. under $N_2$. The reaction mixture was warmed to 0° C. and stirred at 0° C. for 2 hrs. The solution was quenched with aqueous $NH_4Cl$ (40 mL) at 0° C., then extracted with EtOAc (40 mL*2). The organic layer was separated, washed with brine (50 mL), dried over anhydrous $Na_2SO_4$, filtered and concentrated under reduced pressure. The residue was purified by flash silica gel chromatography (Biotage®; 20 g SepaFlash® Silica Flash Column, Eluent of 0~40% Ethylacetate/Petroleum ether gradient @25 mL/min) to give 6-fluoro-4-methoxy-2,3-dihydro-1H-inden-1-one (779 mg, 77.29% yield).

$^1H$ NMR (400 MHz, $CDCl_3$) δ ppm 6.86 (dd, J=7.15, 2.15 Hz, 1H), 6.64 (dd, J=10.49, 2.15 Hz, 1H), 3.77 (s, 3H), 2.86 (td, J=5.66, 1.67 Hz, 2H), 2.55-2.61 (m, 2H).

Step D (R,Z)—N-(6-fluoro-4-methoxy-2,3-dihydro-1H-inden-1-ylidene)-2-methylpropane-2-sulfinamide

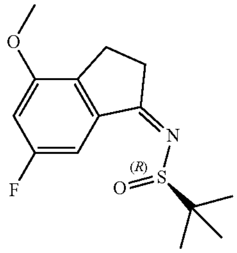

To a solution of 6-fluoro-4-methoxy-2,3-dihydro-1H-inden-1-one (825 mg, 4.58 mmol) in THF (10 mL) was added (R)-2-methylpropane-2-sulfinamide (582.71 mg, 4.81 mmol) and tetraethoxytitanium (9.16 mmol, 1.90 mL). The mixture was stirred at 60° C. for 16 hrs. Ethyl acetate (15 mL) and water (10 mL) were added to the mixture at 25° C., and the formed precipitate was removed by filtration. The filtrate was concentrated in vacuo to give a residue. The residue was purified by flash silica gel chromatography (Biotage®; 12 g SepaFlash® Silica Flash Column, Eluent of 0~40% Ethyl acetate/Petroleum ether gradient @18 mL/min) to give (R,Z)—N-(6-fluoro-4-methoxy-2,3-dihydro-1H-inden-1-ylidene)-2-methylpropane-2-sulfinamide (419 mg, 32.29% yield). LC-MS: m/z 284.4 $(M+H)^+$.

Step E (R)—N—((R)-6-fluoro-4-methoxy-2,3-dihydro-1H-inden-1-yl)-2-methylpropane-2-sulfinamide

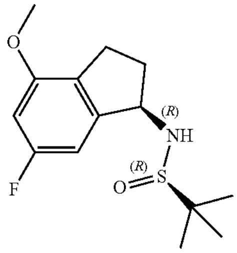

To a solution of (R,Z)—N-(6-fluoro-4-methoxy-2,3-dihydro-1H-inden-1-ylidene)-2-methylpropane-2-sulfinamide (419 mg, 1.48 mmol) in DCM (3 mL) was added dropwise DIBAL-H (1 M, 2.96 mL) at −70° C. After addition, the mixture was stirred at −70° C. for 2 hrs. The reaction mixture was quenched by addition MeOH (5 mL) at 0° C., and then diluted with $H_2O$ (20 mL) and extracted with DCM (20 mL*2). The combined organic layer was washed with brine (20 mL), dried over $Na_2SO_4$, filtered and concentrated under reduced pressure to give a residue. The residue was purified by flash silica gel chromatography (Biotage®; 12 g SepaFlash® Silica Flash Column, Eluent of 0~40% Ethyl acetate/Petroleum ether gradient @18 mL/min) to give (R)—N—((R)-6-fluoro-4-methoxy-2,3-dihydro-1H-inden- 1-yl)-2-methylpropane-2-sulfinamide (237 mg, 56.16% yield). LC-MS: m/z 286.0 $(M+H)^+$.

$^1H$ NMR (400 MHz, $CDCl_3$) δ ppm 6.83 (dd, J=8.29, 1.97 Hz, 1H), 6.41 (dd, J=10.91, 2.09 Hz, 1H), 4.79 (q, J=6.91 Hz, 1H), 3.74 (s, 3H), 3.39 (d, J=6.56 Hz, 1H), 2.83 (ddd, J=15.85, 8.64, 4.23 Hz, 1H), 2.55-2.66 (m, 1H), 2.37-2.47 (m, 1H), 1.87-1.99 (m, 1H), 1.16 (s, 9H).

Step F (R)-6-fluoro-4-methoxy-2,3-dihydro-1H-inden-1-amine

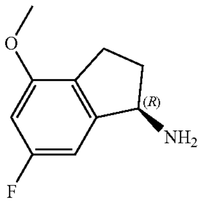

To a solution of (R)—N—((R)-6-fluoro-4-methoxy-2,3-dihydro-1H-inden-1-yl)-2-methylpropane-2-sulfinamide (237 mg, 830.48 μmol) in HCl/dioxane (2 M, 3 mL). The mixture was stirred at 25° C. for 30 min. The reaction mixture was concentrated under reduced pressure. The reaction was filtered to give Compound (R)-6-fluoro-4-methoxy-2,3-dihydro-1H-inden-1-amine (151 mg, 83.53% yield, HCl) was obtained.

$^1H$ NMR (400 MHz, MeOD-$d_4$) δ ppm 6.91 (dd, J=8.28, 2.01 Hz, 1H), 6.78 (dd, J=11.17, 2.13 Hz, 1H), 4.76-4.83 (m, 1H), 3.86 (s, 3H), 2.98-3.11 (m, 1H), 2.82-2.91 (m, 1H), 2.59-2.70 (m, 1H), 2.14 (ddt, J=13.99, 8.72, 5.33, 5.33 Hz, 1H).

Step G (R)-2-(1,3-dioxolan-2-yl)-N-(6-fluoro-4-methoxy-2,3-dihydro-1H-inden-1-yl)thieno[2,3-c]pyridin-7-amine

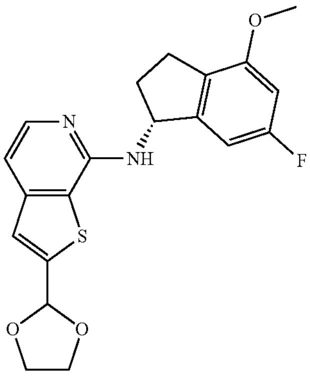 [SMILES: COc1cc(F)cc2c1CC[C@H]2Nc1nccc2cc(C3OCCO3)sc12]

A mixture of (R)-6-fluoro-4-methoxy-2,3-dihydro-1H-inden-1-amine (90 mg, 496.67 μmol), 7-chloro-2-(1,3-dioxolan-2-yl)thieno[2,3-c]pyridine (120.04 mg, 496.67 μmol), $Pd(OAc)_2$ (11.15 mg, 49.67 μmol), BINAP (61.85 mg, 99.33 μmol) and $Cs_2CO_3$ (485.47 mg, 1.49 mmol) in dioxane (5 mL) was degassed and purged with $N_2$ for 3 times, and then the mixture was stirred at 100° C. for 16 hrs under $N_2$ atmosphere. The reaction mixture was partitioned between water (20 mL) and EtOAc (20 mL*2). The organic phase was separated, washed with brine (30 mL), dried over $Na_2SO_4$, filtered and concentrated under reduced pressure to give a residue. The residue was purified by flash silica gel chromatography (Biotage®; 12 g SepaFlash® Silica Flash Column, Eluent of 0~50% Ethyl acetate/Petroleum ether gradient @18 mL/min) to give (R)-2-(1,3-dioxolan-2-yl)-N-(6-fluoro-4-methoxy-2,3-dihydro-1H-inden-1-yl)thieno[2,3-c]pyridin-7-amine (84 mg, 43.77% yield). LC-MS: m/z 387.1 $(M+H)^+$.

Step H (R)-7-((6-fluoro-4-methoxy-2,3-dihydro-1H-inden-1-yl)amino)thieno[2,3-c]pyridine-2-carbaldehyde

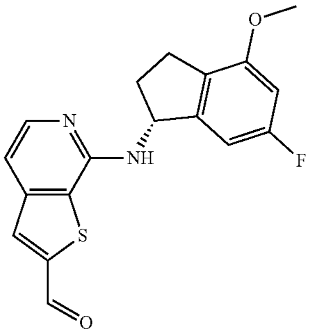 [SMILES: COc1cc(F)cc2c1CC[C@H]2Nc1nccc2cc(C=O)sc12]

To a solution of (R)-2-(1,3-dioxolan-2-yl)-N-(6-fluoro-4-methoxy-2,3-dihydro-1H-inden-1-yl)thieno[2,3-c]pyridin-7-amine (84 mg, 217.37 μmol) in THF (2 mL) was added aq. HCl (4 M, 2 mL). The mixture was stirred at 40° C. for 2 hrs. The solution was added saturated aqueous $NaHCO_3$ until pH=7-8. The mixture was extracted with EtOAc (20 mL*3). The organic layer was washed with brine (30 mL), dried over anhydrous of $Na_2SO_4$, filtered and concentrated in vacuum. Compound (R)-7-((6-fluoro-4-methoxy-2,3-dihydro-1H-inden-1-yl)amino)thieno[2,3-c]pyridine-2-carbaldehyde (72 mg, 96.74% yield) was obtained. LC-MS: m/z 343.0 $(M+H)^+$.

Step I 5-(4-(7-(((R)-6-fluoro-4-methoxy-2,3-dihydro-1H-inden-1-yl)amino)thieno[2,3-c]pyridin-2-yl)-2-(4-fluorophenethyl)-5-oxo-1,4,5,7,8,9-hexahydro-8,9a-methanopyrido[2,3-a]pyrrolizin-3-yl)-1,3,4-oxadiazol-2(3H)-one

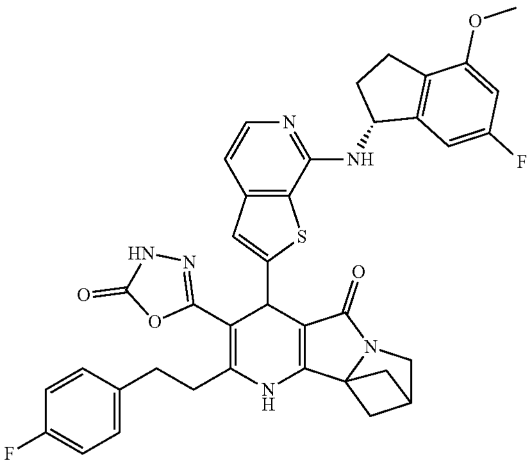 [SMILES: COc1cc(F)cc2c1CC[C@H]2Nc1nccc2cc(C3C4=C(NC(CCc5ccc(F)cc5)=C3c3n[nH]c(=O)o3)C35CC(CN3C4=O)C5)sc12]

A mixture of (R)-7-((6-fluoro-4-methoxy-2,3-dihydro-1H-inden-1-yl)amino)thieno[2,3-c]pyridine-2-carbaldehyde (62 mg, 181.08 μmol), potassium 5-oxo-1,2,3,5-tetrahydro-2,7a-methanopyrrolizin-7-olate (68.54 mg, 181.08 μmol), 5-(4-(4-fluorophenyl)-2-oxobutyl)-1,3,4-oxadiazol-2(3H)-one (45.31 mg, 181.08 μmol) and $NH_4OAc$ (27.92 mg, 362.16 μmol) in HOAc (3 mL) was degassed and purged with $N_2$ for 3 times, and then the mixture was stirred at 100° C. for 1 hr under $N_2$ atmosphere. The reaction mixture was concentrated under reduced pressure to remove HOAc. The residue was diluted with water (5 mL) and extracted with EtOAc (10 mL*2). The combined organic layers were washed with brine (10 mL), dried over $Na_2SO_4$, filtered and concentrated under reduced pressure to give a residue. The residue was purified by flash silica gel chromatography (Biotage®; 12 g SepaFlash® Silica Flash Column, Eluent of 0~100% Ethyl acetate/Petroleum ether gradient @18 mL/min) to give 5-(4-(7-(((R)-6-fluoro-4-methoxy-2,3-dihydro-1H-inden-1-yl)amino)thieno[2,3-c]pyridin-2-yl)-2-(4-fluorophenethyl)-5-oxo-1,4,5,7,8,9-hexahydro-8,9a-methanopyrido[2,3-a]pyrrolizin-3-yl)-1,3,4-oxadiazol-2(3H)-one (79 mg, 61.73% yield). LC-MS: m/z 707.3 $(M+H)^+$.

Step J (R)-5-(4-(7-((6-fluoro-4-methoxy-2,3-dihydro-1H-inden-1-yl)amino)thieno[2,3-c]pyridin-2-yl)-2-(4-fluorophenethyl)-5-oxo-5,7,8,9-tetrahydro-8,9a-methanopyrido[2,3-a]pyrrolizin-3-yl)-1,3,4-oxadiazol-2(3H)-one

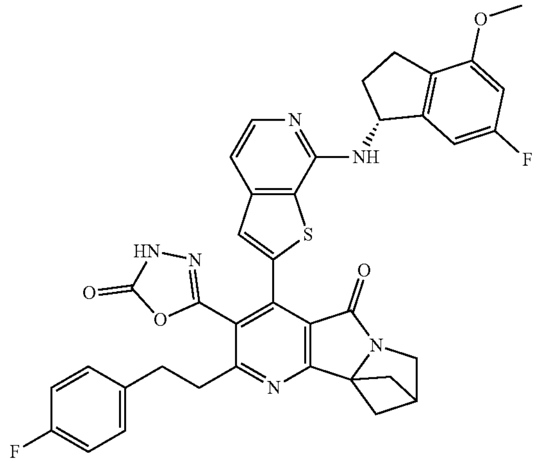

To a solution of 5-(4-(7-(((R)-6-fluoro-4-methoxy-2,3-dihydro-1H-inden-1-yl)amino)thieno[2,3-c]pyridin-2-yl)-2-(4-fluorophenethyl)-5-oxo-1,4,5,7,8,9-hexahydro-8,9a-methanopyrido[2,3-a]pyrrolizin-3-yl)-1,3,4-oxadiazol-2(3H)-one (69 mg, 97.63 μmol) in ACN (3 mL)/$H_2O$ (0.5 mL) was added CAN (53.52 mg, 97.63 μmol). The mixture was stirred at 25° C. for 1 hr. The reaction mixture was quenched by addition aqueous $NaHCO_3$ (5 mL) at 25° C., and extracted with EtOAc (5 mL*2). The combined organic layers were washed with brine (10 mL), dried over $Na_2SO_4$, filtered and concentrated under reduced pressure to give a residue. The residue was purified by prep-HPLC (column: Welch Xtimate C18 150*30 mm*5 um; mobile phase: [water(FA)-ACN]; gradient: 30%-60% B over 9 min) to give (R)-5-(4-(7-((6-fluoro-4-methoxy-2,3-dihydro-1H-inden-1-yl)amino)thieno[2,3-c]pyridin-2-yl)-2-(4-fluorophenethyl)-5-oxo-5,7,8,9-tetrahydro-8,9a-methanopyrido[2,3-a]pyrrolizin-3-yl)-1,3,4-oxadiazol-2(3H)-one (2.92 mg, 4.15% yield, 97.8% purity).

$^1H$ NMR (400 MHz, MeOD-$d_4$) δ ppm 7.96 (d, J=5.75 Hz, 1H), 7.44 (s, 1H), 7.13-7.20 (m, 3H), 6.94-7.02 (m, 2H), 6.62 (d, J=2.38 Hz, 1H), 6.59 (s, 1H), 5.82 (t, J=8.44 Hz, 1H), 4.61 (s, 2H), 3.84 (s, 3H), 3.69 (s, 2H), 3.26-3.30 (m, 3H), 3.08-3.16 (m, 2H), 2.95-3.04 (m, 1H), 2.79 (d, J=4.50 Hz, 2H), 2.65-2.77 (m, 2H), 2.01-2.07 (m, 1H), 1.82 (dd, J=4.38, 1.50 Hz, 2H). $^{19}F$ NMR (376 MHz, MeOD-$d_4$) δ ppm −115.74 (s, 1 F), −119.03 (s, 1 F). LC-MS: m/z 705.3 $(M+H)^+$.

(R)-5-(4-(7-((6,8-difluorochroman-4-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 295)

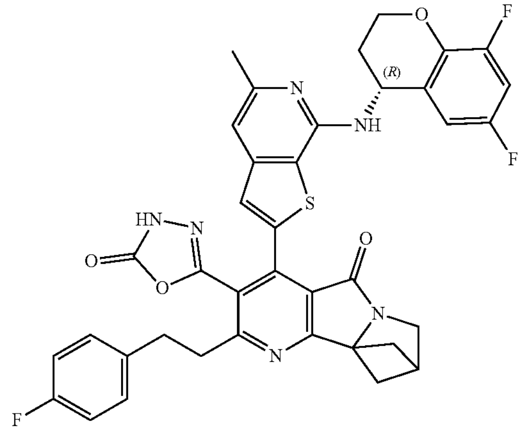

Compound 295 was synthesized using a similar procedure described in Example 20 by using the appropriate materials.

$^1H$ NMR (400 MHz, DMSO-$d_6$): δ 12.44-12.97 (brs, 0.53H), 7.31-7.34 (m, 2H), 7.19-7.23 (m, 2H), 7.14-7.17 (m, 1H), 7.07 (t, J=8.8 Hz, 2H), 6.96 (s, 1H), 6.89 (d, J=8.8 Hz, 1H), 5.61 (dd, J=6.0 Hz/J=19.6 Hz, 1H), 4.29-4.42 (m, 2H), 3.55 (s, 2H), 3.15-3.22 (s, 3H), 3.00-3.04 (m, 2H), 2.60-2.67 (m, 2H), 2.41 (m, 3H), 2.16-2.20 (m, 2H), 1.73 (d, J=3.6 Hz, 2H). $^{19}F$ NMR (377 MHz, DMSO-$d_6$): −117.04, −121.74, −132.93.

(S)-5-(2-(4-fluorophenethyl)-4-(5-methyl-7-((2,2,5-trifluoro-4-methoxy-2,3-dihydro-1H-inden-1-yl)amino)thieno[2,3-c]pyridin-2-yl)-5-oxo-8,9-dihydro-5H,7H-8,9a-methanopyrido[2,3-a]pyrrolizin-3-yl)-1,3,4-oxadiazol-2(3H)-one (Compound 296)

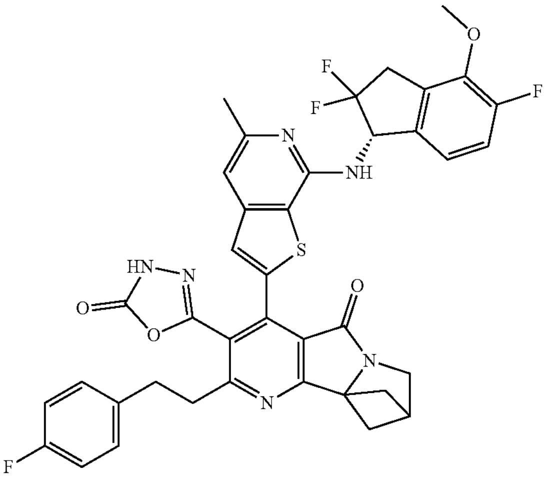 [SMILES: COc1c(F)ccc2c1CC(F)(F)[C@H]2Nc1nc(C)cc2cc(-c3c4c(nc(CCc5ccc(F)cc5)c3-c3n[nH]c(=O)o3)C35CC(CN3C4=O)C5)sc12]

Compound 296 was synthesized using a similar procedure described in Example 20 by using the appropriate materials. $^1$H NMR (400 MHz, DMSO-$d_6$): δ 12.78-12.64 (m, 1H), 7.42 (d, J=8.8 Hz, 1H), 7.35 (s, 1H), 7.23-7.15 (m, 3H), 7.07 (t, J=8.8 Hz, 2H), 7.04-6.99 (m, 2H), 6.27-6.19 (m, 1H), 3.91 (d, J=1.6 Hz, 3H), 3.62-3.58 (m, 1H), 3.56 (s, 2H), 3.30-3.28 (m, 1H), 3.22-3.17 (m, 3H), 3.08-3.01 (m, 2H), 2.68-2.62 (m, 2H), 2.40 (s, 3H), 1.77-1.71 (m, 2H). $^{19}$F NMR (377 MHz, DMSO-$d_6$): −106.16, −106.79, −117.01, −132.46.

(R)-5-(4-(7-((6,8-difluorochroman-4-yl)amino)-5-(difluoromethyl)thieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 297)

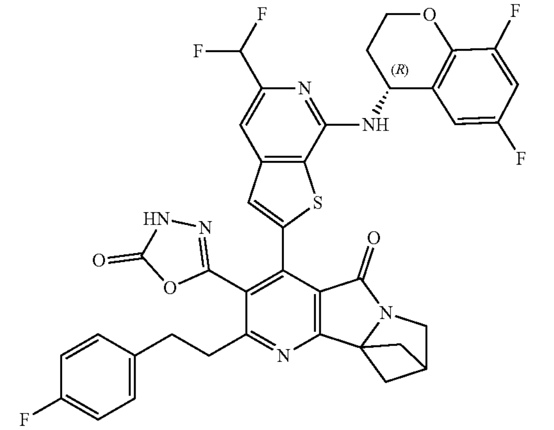

Compound 297 was synthesized using a similar procedure described in Example 21 by using the appropriate materials. (11.8 mg, 0.015 mmol, 7.69%)

$^1$H NMR (400 MHz, DMSO-d6): δ 12.72 (br s, 1H), 7.81 (d, J=7.6 Hz, 1H), 7.56 (s, 1H), 7.44 (s, 1H), 7.16-7.25 (m, 3H), 7.07 (t, J=8.8 Hz, 2H), 6.91-6.96 (m, 1H), 6.88 (t, J=15.2 Hz, 1H), 5.57 (q, J=6.8 Hz, 1H), 4.30-4.42 (m, 2H), 3.56 (s, 2H), 3.17-3.24 (m, 3H), 3.00-3.08 (m, 2H), 2.62-2.67 (m, 2H), 2.18-2.23 (m, 2H), 1.71-1.79 (m, 2H). $^{19}$F NMR (377 MHz, DMSO-d6): −114.68, −117.01, −121-62, −132.81. LC-MS: m/z 759.2 $(M+H)^+$.

(R)-5-(4-(7-((6-fluoro-4-methoxy-2,3-dihydro-1H-inden-1-yl)amino)-5-methylthieno[2,3-c]pyridin-2-yl)-2-(4-fluorophenethyl)-5-oxo-8,9-dihydro-5H,7H-8,9a-methanopyrido[2,3-a]pyrrolizin-3-yl)-1,3,4-oxadiazol-2(3H)-one (Compound 298)

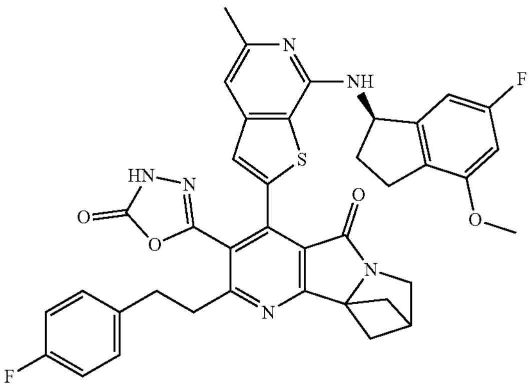 [SMILES: COc1cc(F)cc2c1CC[C@H]2Nc1nc(C)cc2cc(-c3c4c(nc(CCc5ccc(F)cc5)c3-c3n[nH]c(=O)o3)C35CC(CN3C4=O)C5)sc12]

Compound 298 was synthesized using a similar procedure described in Example 20 by using the appropriate materials. $^1$H NMR (400 MHz, DMSO-$d_6$): δ 12.69 (s, 1H), 7.32 (s, 1H), 7.17-7.23 (m, 3H), 7.05-7.09 (m, 2H), 6.93 (s, 1H), 6.72 (dd, J=2.0 Hz/J=11.6 Hz, 1H), 6.61 (dd, J=2.0 Hz/J=8.8 Hz, 1H), 5.87 (q, J=8.0 Hz, 1H), 3.80 (s, 3H), 3.56 (s, 2H), 3.30-3.32 (m, 1H), 3.17-3.21 (m, 3H), 3.01-3.05 (m, 2H), 2.86-2.93 (m, 1H), 2.64-2.68 (m, 3H), 2.41 (s, 3H), 1.96-2.06 (m, 1H), 1.75 (d, J=4.8 Hz, 2H). $^{19}$F NMR (377 MHz, DMSO-$d_6$): −113.77, −117.02. LC-MS: m/z 719.5 $(M+H)^+$.

5-((S)-4-(7-(((R)-5,6-difluoro-4-methoxy-2,3-dihydro-1H-inden-1-yl)amino)-5-methylthieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 299)

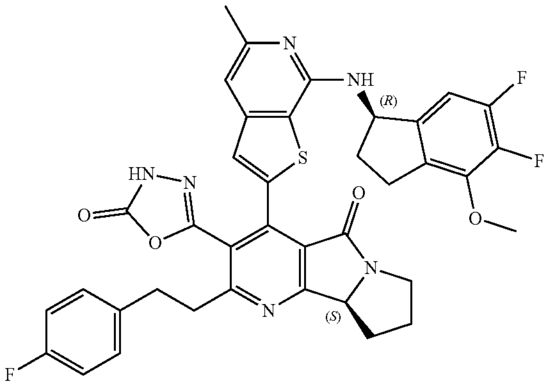

Compound 299 was synthesized using a similar procedure described in Example 20 by using the appropriate materials. (501.26 mg, 0.681 mmol, 52.46%)

$^1$H NMR (400 MHz, DMSO-d6): δ 12.70 (br s, 1H), 7.34 (s, 1H), 7.19-7.24 (m, 3H), 7.03-7.10 (m, 2H), 6.91-6.97 (m,

2H), 5.82 (q, J=8.0 Hz, 1H), 4.87 (dd, J=10.0 Hz, J=6.0 Hz, 1H), 3.95 (d, J=1.2 Hz, 3H), 3.50-3.59 (m, 1H), 3.26-3.29 (m, 1H), 3.16-3.22 (m, 2H), 2.96-3.12 (m, 3H), 2.79-2.90 (m, 1 H), 2.52-2.56 (m, 1H), 2.41 (s, 3H), 2.34-2.36 (m, 1H), 2.23-2.31 (m, 2H), 1.99-2.10 (m, 1H), 1.37-1.49 (m, 1H). $^{19}$F NMR (377 MHz, DMSO-d6): −117.02, −138.67, −158.73. LC-MS: m/z 723.2 (M+H)$^+$.

(R)-5-(4-(7-((5-fluoro-4-methoxy-2,3-dihydro-1H-inden-1-yl)amino)-5-methylthieno[2,3-c]pyridin-2-yl)-2-(3-fluorophenethyl)-5-oxo-8,9-dihydro-5H,7H-8,9a-methanopyrido[2,3-a]pyrrolizin-3-yl)-1,3,4-oxadiazol-2(3H)-one (Compound 300)

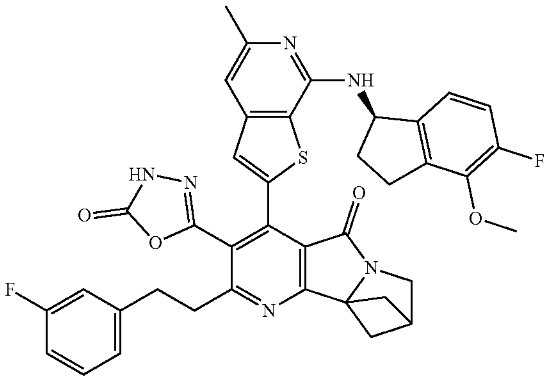 [SMILES: COc1c(F)ccc2c1CC[C@H]2Nc1nc(C)cc2cc(-c3c4c(nc(CCc5cccc(F)c5)c3-c3n[nH]c(=O)o3)C35CC(CN3C4=O)C5)sc12]

Compound 300 was synthesized using a similar procedure described in Example 20 by using the appropriate materials. (6.24 mg, 6.19%)

$^1$H NMR (400 MHz, DMSO-d$_6$): δ 12.70 (br s, 1H), 7.27-7.33 (m, 2H), 7.15 (d, J=8.4 Hz, 1H), 6.98-7.07 (m, 4H), 6.90-6.95 (m, 2H), 5.83-5.89 (m, 1H), 3.87 (d, J=1.2 Hz, 3H), 3.56 (s, 2H), 3.19-3.25 (m, 3H), 3.03-3.09 (m, 3H), 2.80-2.91 (m, 1H), 2.62-2.67 (m, 2H), 2.54-2.56 (m, 1H), 2.40 (s, 3H), 2.01-2.12 (m, 1H) 1.71-1.78 (m, 2H). $^{19}$F NMR (377 MHz, DMSO-d$_6$): δ −113.58, −135.42. LC-MS: m/z 719.3 (M+H)$^+$.

5-((S)-4-(7-(((1S,2R)-2,5-difluoro-4-methoxy-2,3-dihydro-1H-inden-1-yl)amino)-5-methylthieno[2,3-c]pyridin-2-yl)-2-(4-fluorophenethyl)-5-oxo-7,8,9,9a-tetrahydro-5H-pyrido[2,3-a]pyrrolizin-3-yl)-1,3,4-oxadiazol-2(3H)-one (Compound 301)

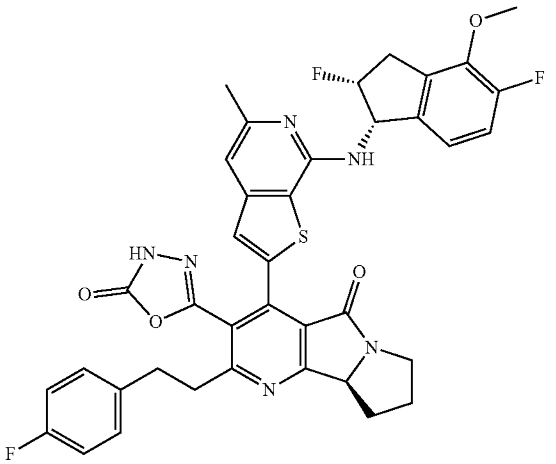 [SMILES: COc1c(F)ccc2c1C[C@@H](F)[C@H]2Nc1nc(C)cc2cc(-c3c4c(nc(CCc5ccc(F)cc5)c3-c3n[nH]c(=O)o3)[C@@H]3CCCN3C4=O)sc12]

Compound 301 was synthesized using a similar procedure described in Example 20 by using the appropriate materials. (651.68 mg, 67.46%)

$^1$H NMR (400 MHz, DMSO-d6): δ 12.66 (br s, 1H), 7.35 (s, 1H), 7.18-7.23 (m, 3H), 7.14 (dd, J=12.0 Hz, J=8.0 Hz, 1H), 7.05-7.09 (m, 2H), 6.95-7.02 (m, 2H), 5.86-5.99 (m, 1H), 5.46-5.65 (m, 1H), 4.87 (dd, J=10.0 Hz, J=6.0 Hz, 1H), 3.90 (s, 3H), 3.52-3.59 (m, 1H), 3.37-3.42 (m, 1H), 3.26-3.30 (m, 1H), 3.12-3.23 (m, 3H), 2.96-3.07 (m, 2H), 2.42 (s, 3H), 2.24-2.40 (m, 3H), 1.39-1.48 (m, 1H). $^{19}$F NMR (377 MHz, DMSO-d6): −117.02, −134.32, −191.67. LC-MS: m/z 725.3 (M+H)$^+$.

5-(7-cyclopropyl-4-(7-(((R)-5-fluoro-4-methoxy-2,3-dihydro-1H-inden-1-yl)amino)-5-methylthieno[2,3-c]pyridin-2-yl)-2-(4-fluorophenethyl)-5-oxo-6,7-dihydro-5H-pyrrolo[3,4-b]pyridin-3-yl)-1,3,4-oxadiazol-2(3H)-one (Compound 302)

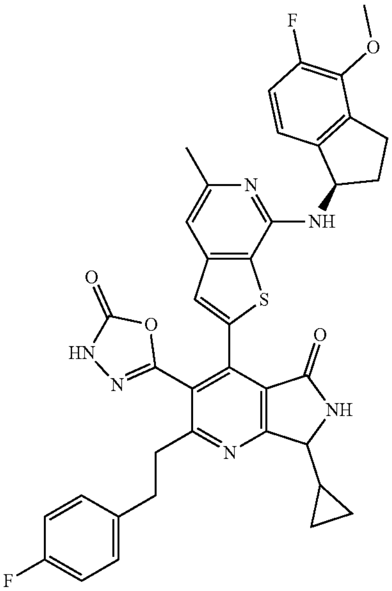 [SMILES: COc1c(F)ccc2c1CC[C@H]2Nc1nc(C)cc2cc(-c3c4c(nc(CCc5ccc(F)cc5)c3-c3n[nH]c(=O)o3)C(C3CC3)NC4=O)sc12]

Compound 302 was synthesized using a similar procedure described in Example 20 by using the appropriate materials. (8.10 mg, 32.14%)

$^1$H NMR (400 MHz, DMSO-d6): δ 9.00 (s, 1H), 7.30 (d, J=1.2 Hz, 1H), 7.20-7.24 (m, 2H), 7.14 (d, J=8.4 Hz, 1H), 7.04-7.08 (m, 2H), 6.93-7.02 (m, 2H), 6.92 (s, 1H), 5.83-5.89 (m, 1H), 4.42 (d, J=1.6 Hz, 1H), 3.87 (s, 3H), 3.19 (t, J=7.6 Hz, 2H), 3.01-3.10 (m, 3H), 2.81-2.89 (m, 1H), 2.53-2.55 (m, 1H), 2.40 (s, 3H), 2.02-2.12 (m, 1H), 1.15-1.24 (m, 1H), 0.57-0.67 (m, 2H), 0.36-0.44 (m, 1H), 0.26-0.35 (m, 1H). $^{19}$F NMR (377 MHz, DMSO-d6): −117.15, −135.45. LC-MS: m/z 707.3 (M+H)$^+$.

Example 42
5-((S)-2-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (Compound 303)
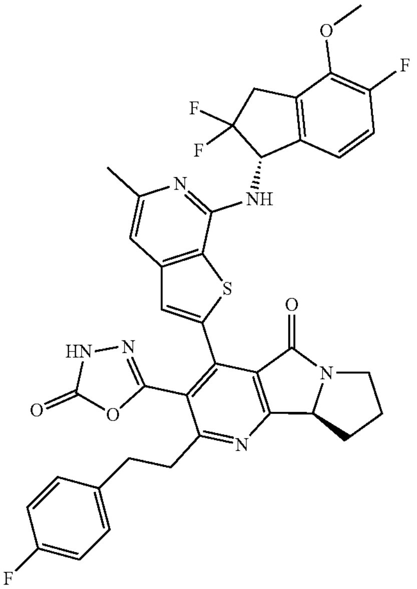
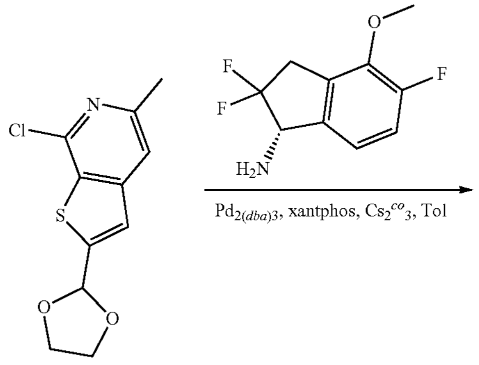
a
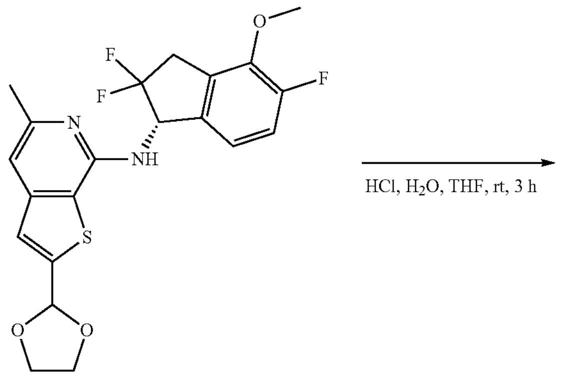
b -continued
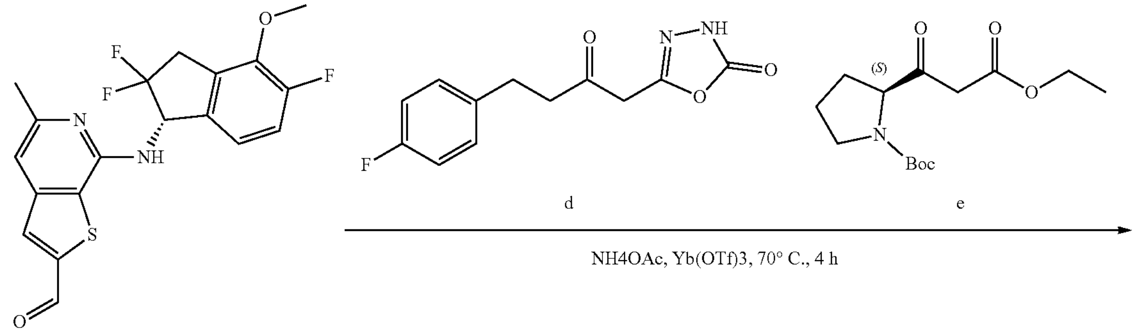
c
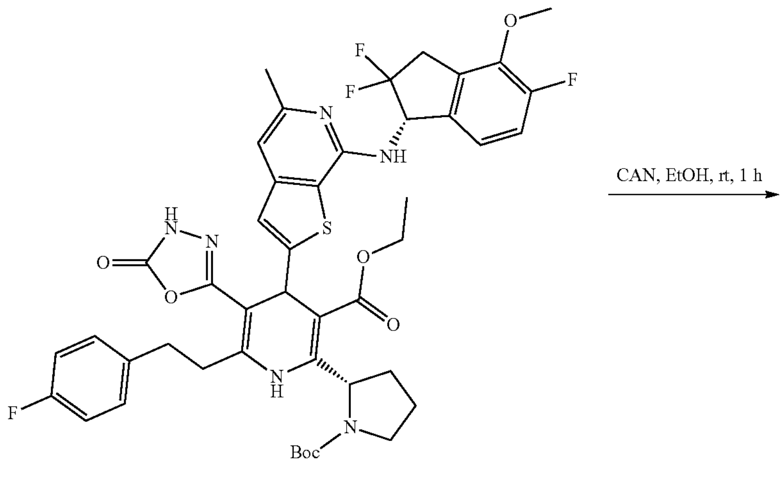
f
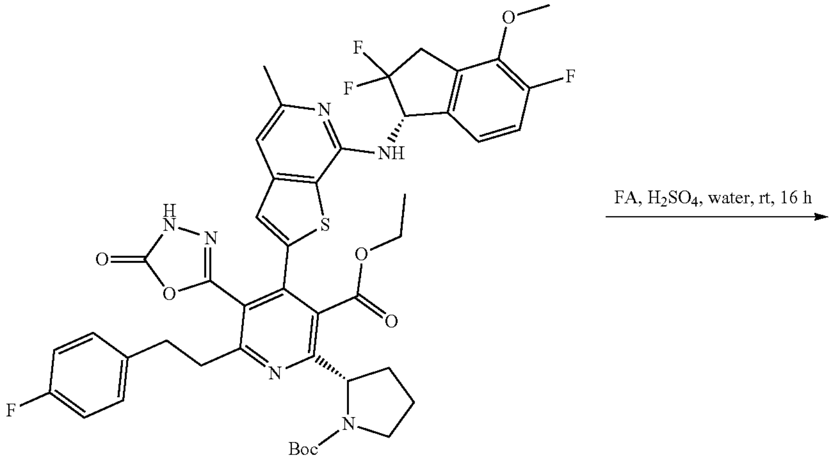
g -continued
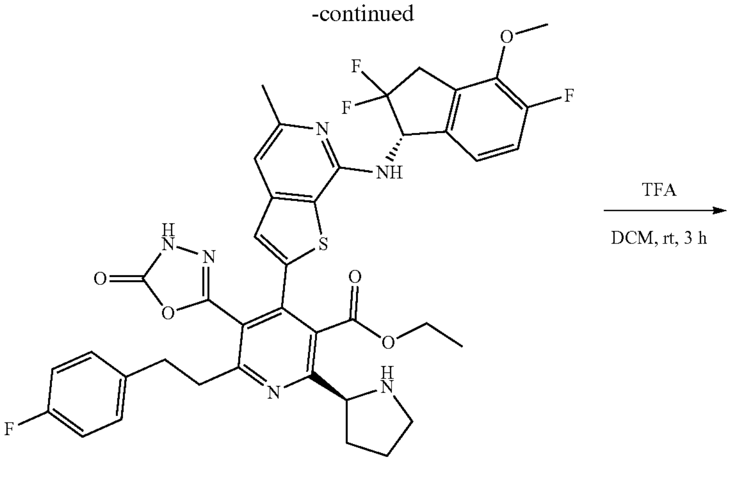
h
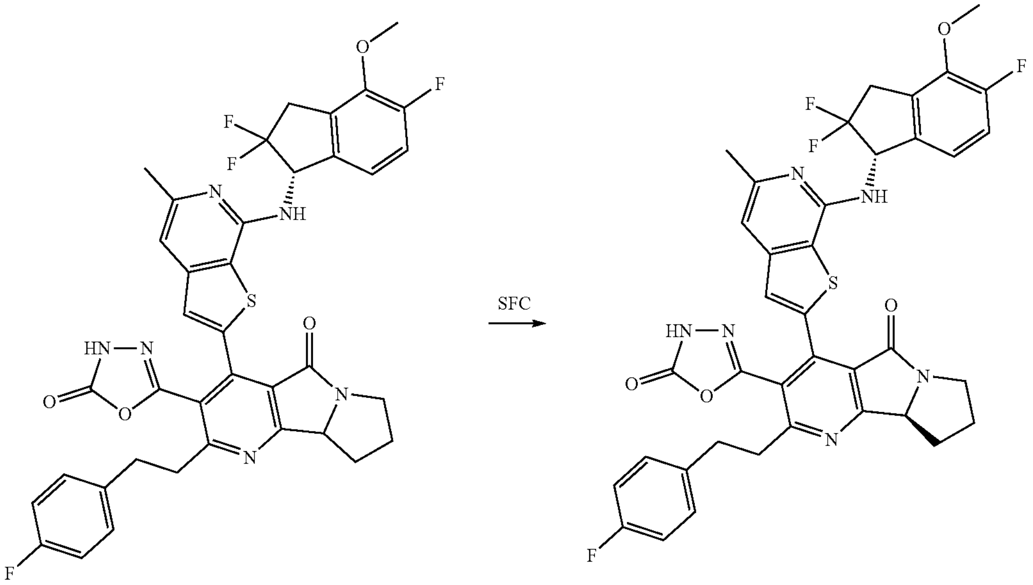
i Step A (S)-2-(1,3-dioxolan-2-yl)-5-methyl-N-(2,2,5-trifluoro-4-methoxy-2,3-dihydro-1H-inden-1-yl) thieno[2,3-c]pyridin-7-amine

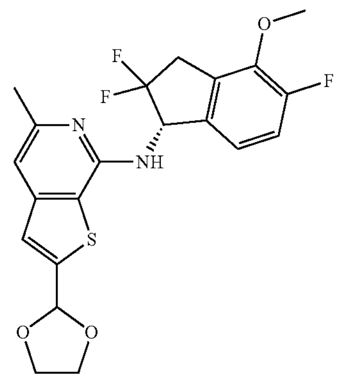 [SMILES: COc1c(F)ccc2c1CC(F)(F)[C@H]2Nc1nc(C)cc2cc(C3OCCO3)sc12]

To a solution of 7-chloro-2-(1,3-dioxolan-2-yl)-5-methylthieno[2,3-c]pyridine (2033.69 mg, 7.953 mmol) in Toluene (100.0 mL) was added (S)-2,2,5-trifluoro-4-methoxy-2,3-dihydro-1H-inden-1-amine (1727.31 mg, 7.953 mmol), $Pd_2(dba)_3$ (728.26 mg, 0.795 mmol), XANT PHOS (920.35 mg, 1.591 mmol), $Cs_2CO_3$ (10364.75 mg, 31.811 mmol), the mixture was stirred at 110° C. overnight under $N_2$. The mixture was diluted with EA (100 mL) and water (100 mL). The organic layer was separated, washed with brine (100 mL×2), dried over $Na_2SO_4$ and concentrated in vacuo. The residue was purified using silica gel column chromatography eluting with PE:EA=10:1. The residue was concentrated in vacuo to afford the title compound (S)-2-(1,3-dioxolan-2-yl)-5-methyl-N-(2,2,5-trifluoro-4-methoxy-2,3-dihydro-1H-inden-1-yl)thieno[2,3-c]pyridin-7-amine (2150 mg, 4.926 mmol, 61.94%). LC-MS: m/z 437.3 $(M+H)^+$.

Step B (S)-5-methyl-7-((2,2,5-trifluoro-4-methoxy-2,3-dihydro-1H-inden-1-yl)amino)thieno[2,3-c]pyridine-2-carbaldehyde

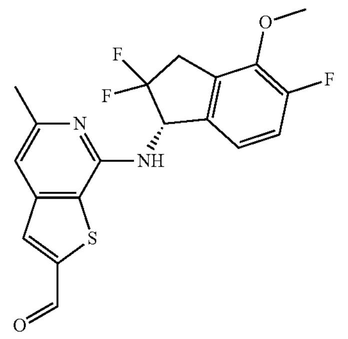 [SMILES: COc1c(F)ccc2c1CC(F)(F)[C@H]2Nc1nc(C)cc2cc(C=O)sc12]

To a solution of (S)-2-(1,3-dioxolan-2-yl)-5-methyl-N-(2,2,5-trifluoro-4-methoxy-2,3-dihydro-1H-inden-1-yl)thieno[2,3-c]pyridin-7-amine (2100 mg, 4.812 mmol) in THF (30.0 mL), $H_2O$ (30.0 mL) was added HCl in dioxane (30.0 mL, 6 mol/L in dioxane) at 0° C., the mixture was stirred at rt for 3 h under $N_2$. The mixture was diluted with EA (100 mL) and saturated $Na_2CO_3$ solution. The organic layer was separated, washed with saturated brine, dried over $Na_2SO_4$ and concentrated in vacuo to afford the title compound (S)-5-methyl-7-((2,2,5-trifluoro-4-methoxy-2,3-dihydro-1H-inden-1-yl)amino)thieno[2,3-c]pyridine-2-carbaldehyde (1850 mg, 4.715 mmol, 97.98%). LC-MS: m/z 393.0 $(M+H)^+$.

Step C ethyl 2-((S)-1-(tert-butoxycarbonyl)pyrrolidin-2-yl)-6-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-(5-oxo-4,5-dihydro-1,3,4-oxadiazol-2-yl)-1,4-dihydropyridine-3-carboxylate

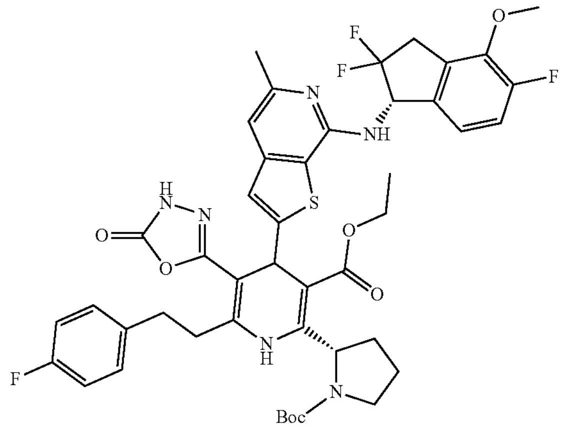

To a solution of (S)-5-methyl-7-((2,2,5-trifluoro-4-methoxy-2,3-dihydro-1H-inden-1-yl)amino)thieno[2,3-c]pyridine-2-carbaldehyde (400 mg, 1.019 mmol) in EtOH (8.0 mL) was added tert-butyl (S)-2-(3-ethoxy-3-oxopropanoyl)pyrrolidine-1-carboxylate (290.87 mg, 1.019 mmol), 5-(4-(4-fluorophenyl)-2-oxobutyl)-1,3,4-oxadiazol-2(3H)-one (255.08 mg, 1.019 mmol), $NH_4OAC$ (235.72 mg, 3.058 mmol), $Yb(OTf)_3$ (63.20 mg, 0.102 mmol) then the mixture was stirred at 70° C. overnight under $N_2$. The mixture was concentrated in vacuo to afford the title compound ethyl 2-((S)-1-(tert-butoxycarbonyl)pyrrolidin-2-yl)-6-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-(5-oxo-4,5-dihydro-1,3,4-oxadiazol-2-yl)-1,4-dihydropyridine-3-carboxylate (908 mg, 1.019 mmol, 99.98%). LC-MS: m/z 891.5 $(M+H)^+$.

Step D ethyl 2-((S)-1-(tert-butoxycarbonyl)pyrrolidin-2-yl)-6-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-(5-oxo-4,5-dihydro-1,3,4-oxadiazol-2-yl)nicotinate

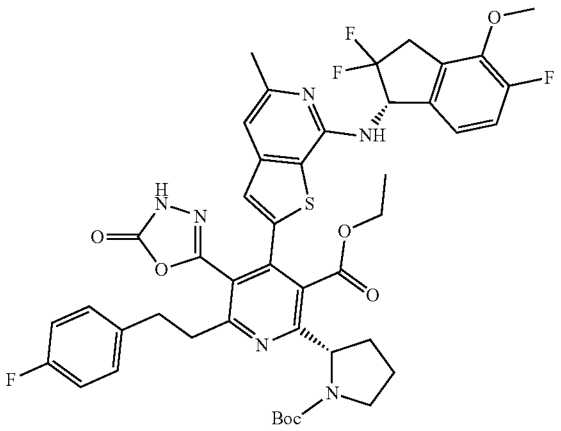 [SMILES: CCOC(=O)c1c([C@@H]2CCCN2C(=O)OC(C)(C)C)nc(CCc2ccc(F)cc2)c(-c2n[nH]c(=O)o2)c1-c1cc2cc(C)nc(N[C@H]3c4ccc(F)c(OC)c4CC3(F)F)c2s1]

To a solution of ethyl 2-((S)-1-(tert-butoxycarbonyl)pyrrolidin-2-yl)-6-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-(5-oxo-4,5-dihydro-1,3,4-oxadiazol-2-yl)-1,4-dihydropyridine-3-carboxylate (908 mg, 1.019 mmol) in EtOH (15.0 mL) was added CAN (1116.97 mg, 2.038 mmol), the mixture was stirred at rt for 1 h under $N_2$. The mixture was diluted with EA and saturated $NaHCO_3$ solution. The organic layer was separated, washed with brine, dried over $Na_2SO_4$ and concentrated in vacuo. The residue was filtered and purified using prep-HPLC (0.1% $NH_3 \cdot H_2O$ in the mixture of ACN and water) to afford the title compound ethyl 2-((S)-1-(tert-butoxycarbonyl)pyrrolidin-2-yl)-6-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-(5-oxo-4,5-dihydro-1,3,4-oxadiazol-2-yl)nicotinate (860 mg, 0.967 mmol, 94.93%). LC-MS: m/z 889.5 $(M+H)^+$.

Step E ethyl 6-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-(5-oxo-4,5-dihydro-1,3,4-oxadiazol-2-yl)-2-((S)-pyrrolidin-2-yl)nicotinate

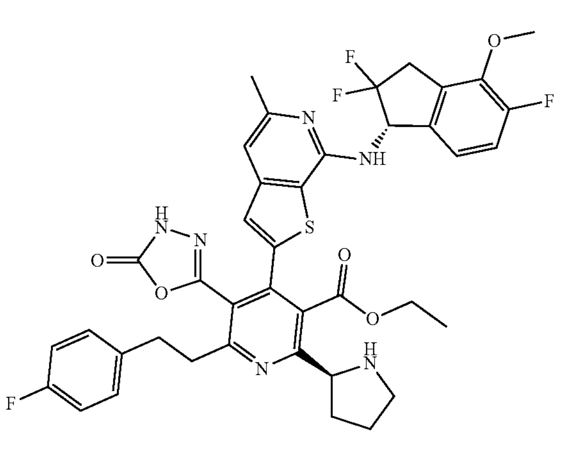 [SMILES: CCOC(=O)c1c([C@@H]2CCCN2)nc(CCc2ccc(F)cc2)c(-c2n[nH]c(=O)o2)c1-c1cc2cc(C)nc(N[C@H]3c4ccc(F)c(OC)c4CC3(F)F)c2s1]

To a solution of ethyl 2-((S)-1-(tert-butoxycarbonyl)pyrrolidin-2-yl)-6-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-(5-oxo-4,5-dihydro-1,3,4-oxadiazol-2-yl)nicotinate (800 mg, 0.900 mmol) in $H_2SO_4$ in FA (60.0 mL, 5.937 mmol) was added $H_2O$ (30.0 mL), the mixture was stirred at rt overnight under $N_2$. The mixture was diluted with EA and water. The organic layer was separated, washed with saturated brine, dried over $Na^2SO_4$ and concentrated in vacuo to afford the title compound ethyl 6-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-(5-oxo-4,5-dihydro-1,3,4-oxadiazol-2-yl)-2-((S)-pyrrolidin-2-yl)nicotinate (700 mg, 0.887 mmol, 98.61%). LC-MS: m/z 789.5 $(M+H)^+$.

Step F 5-(2-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one

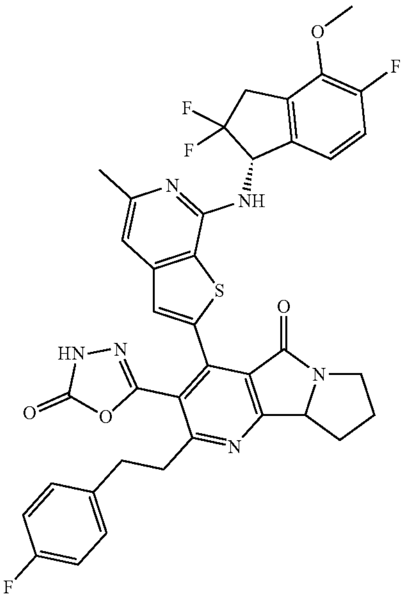 [SMILES: COc1c(F)ccc2c1CC(F)(F)[C@H]2Nc1nc(C)cc2cc(-c3c4c(nc(CCc5ccc(F)cc5)c3-c3n[nH]c(=O)o3)C3CCCN3C4=O)sc12]

To a solution of ethyl 6-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-(5-oxo-4,5-dihydro-1,3,4-oxadiazol-2-yl)-2-((S)-pyrrolidin-2-yl)nicotinate (640 mg, 0.811 mmol) in DCM (30.0 mL) was added TEA (3.382 mL, 24.330 mmol), the mixture was stirred at rt for 3 h under $N_2$. The mixture was diluted with EA and water. The organic layer was separated, washed with brine, dried over $Na_2SO_4$ and concentrated in vacuo. The residue was filtered and purified using prep-HPLC (0.10% $NH_3 \cdot H_2O$ in the mixture of ACN and water) to afford the title compound 5-(2-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (450.0 mg, 74.75%). LC-MS: m/z 743.2 $(M+H)^+$.

Step G 5-((S)-2-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one

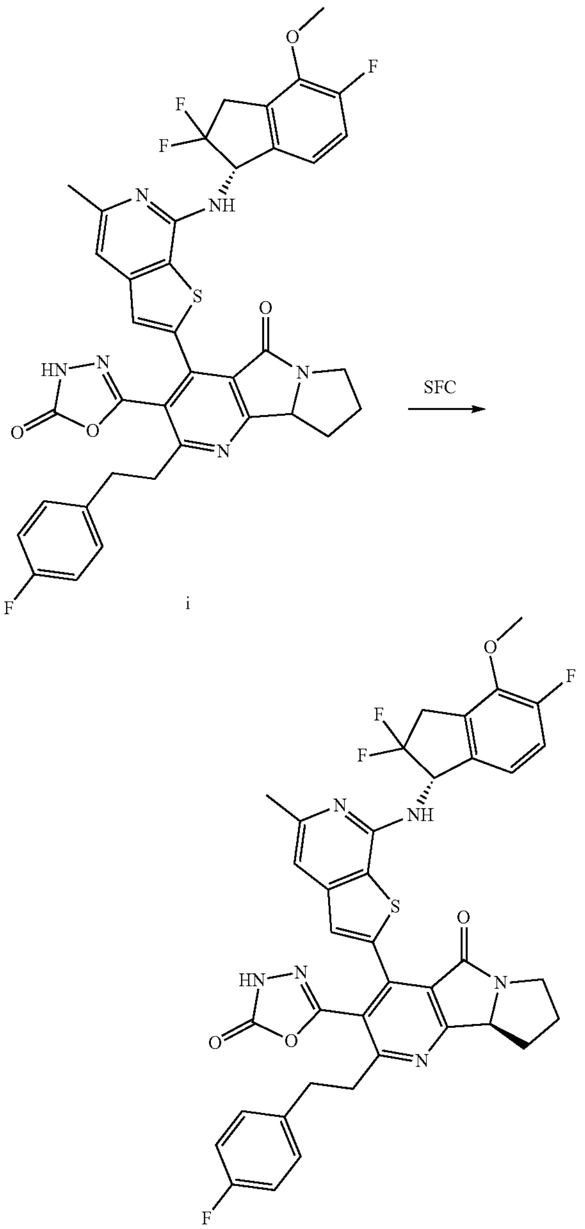

i

The product of 5-(2-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (450 mg) was separated directly by chiral SFC (column: DAICEL CHIRALCEL OJ (100 mm*3.0 mm, 3.0 um); mobile phase: [CO2-MeOH (0.1% DEA)]; B %: 80%%, isocratic elution mode) to give 5-((S)-2-(4-fluorophenethyl)-4-(5-methyl-7-(((S)-2,2,5-trifluoro-4-methoxy-2,3-dihydro-1H-inden-1-yl)amino)thieno[2,3-c]pyridin-2-yl)-5-oxo-7,8,9,9a-tetrahydro-5H-pyrido[2,3-a]pyrrolizin-3-yl)-1,3,4-oxadiazol-2(3H)-one (338.39 mg, yield: 75.19%). LC-MS: m/z 743.2 $(M+H)^+$.

$^1H$ NMR (400 MHz, DMSO-$d_6$): δ 12.70 (s, 1H), 7.45 (d, J=9.2 Hz, 1H), 7.36 (s, 1H), 7.22-7.16 (m, 3H), 7.06 (t, J=8.8 Hz, 2H), 7.06-6.99 (m, 2H), 6.28-6.16 (m, 1H), 4.89-4.85 (m, 1H), 3.91 (d, J=1.2 Hz, 3H), 3.61-3.51 (m, 3H), 3.30-3.26 (m, 2H), 3.19 (t, J=7.6 Hz, 2H), 3.11-2.96 (m, 2H), 2.40 (s, 3H), 2.36-2.28 (m, 1H), 2.27-2.21 (m, 2H), 1.48-1.37 (m, 1H). $^{19}F$ NMR (377 MHz, DMSO-$d_6$): −106.20, −106.81, −117.00, 132.42.

Biological Assay

Amylin Receptor cAMP Assay I

AMYRs are heterodimers of the class B calcitonin (CT) G-protein-coupled receptor (CTR) and receptor activity-modifying proteins (RAMPs). All three RAMPs can interact with the CTR and form AMY1, AMY2, AMY3 with RAMP1, RAMP2 and RAMP3, respectively. Like other class B1 GPCRs, the CT receptor family is canonically coupled to Gs-mediated cAMP production, and measurement of cAMP accumulation has been the primary assay used to determine peptide selectivity and potency.

To optimize functional activity directed toward Gαs coupling, COS-7 cells were stably transfected with human calcitonin receptor (CTR) and RAMP3, simultaneously. 100×concentration of compound working solutions were prepared (Agilent Technologies Bravo) with 4-fold serial dilution in 384-well Echo LDV plate (Labcyte, Cat #LP-0200). 100 nL/well 100×concentration of compound working solutions were moved to 384-well white low volume plate (Greiner, Cat #784075) using Labcyte ECHO550. 1×105 cells/mL COS-7/CTR or COS-7/AMY3 (HD Biosciences) cell suspensions prepared with assay buffer [DPBS containing 0.5 mM IBMX (Sigma, Cat #15879) and 0.1% BSA (GENVIEW, Cat #FA016-100g)], 10 μL cell suspensions were added to each well of previous generated assay plate which already contains 100 nL compound at 100× concentration using ThermoFisher Multidrop Combi (1000 cells/well). Seal the plate and incubate at 37° C. with 5% $CO_2$ for 30 min.

After incubation, the cAMP assay signal was generated using cAMP Hi-range Kit (Cisbio). 5 μL cAMP-d2 working solution was added to each well, followed by 5 μL Anti-cAMP antibody-cryptate working solution which was added to each well using ThermoFisher Multidrop Combi. The samples were then incubated at room temperature for 1 hour protected from light. the fluorescence was read at 665 and 615 nm with Reader PerkinElmer EnVision.

% Activity=100%×(mean RLU of test sample−mean RLU of vehicle control)/(mean RLU of MAX control−mean RLU of vehicle control))

Amylin Receptor cAMP Assay II

AMYRs are heterodimers of the class B calcitonin (CT) G-protein-coupled receptor (CTR) and receptor activity-modifying proteins (RAMPs). All three RAMPs can interact with the CTR and form AMY1, AMY2, AMY3 with RAMP1, RAMP2 and RAMP3, respectively. Like other class B1 GPCRs, the CT receptor family is canonically coupled to Gs-mediated cAMP production, and measurement of cAMP accumulation has been the primary assay used to determine peptide selectivity and potency.

To optimize functional activity directed toward Gαs coupling, COS-7 cells were stably transfected with human calcitonin receptor (CTR) and RAMP3, simultaneously. 100×concentration of compound working solutions were prepared with 4-fold serial dilution in 384-well Echo LDV plate (Labcyte, Cat #LP-0200-BC). 200 nL/well 100×concentration of compound working solutions were moved to 384-well white microplate (Perkin Elmer, Cat #6007680) using Labcyte ECHO550. 1×10$^5$ cells/mL COS-7/AMY3 cell suspensions prepared with assay buffer [HBSS containing 20 mM HEPES (Gibco, Cat #15630-080), 0.5 mM IBMX (Sigma, Cat #15879) and 0.1% Casein (Sigma, Cat #C4765)], 20 μL cell suspensions were added to each well of previous generated assay plate which already contains 200 nL compound at 100×concentration using ThermoFisher Multidrop Combi (2000 cells/well). Seal the plate and incubate at 37° C. with 5% $CO_2$ for 30 min.

After incubation, the cAMP assay signal was generated using cAMP dynamic 2 kit (Revvity, Cat #62AM4PEC). 10 μL cAMP-d2 working solution was added to each well, followed by 10 μL Anti-cAMP antibody-cryptate working solution which was added to each well using CERTUS FLEX LIQUID DISPENSER. The samples were then incubated at room temperature for 1 hour protected from light. the fluorescence was read at 665 and 615 nm with Reader PerkinElmer EnVision 2105.

% Activity=100−(mean RLU of test sample−mean RLU of positive control)/(mean RLU of vehicle control−mean RLU of positive control)×100

Calcitonin Receptor (CTR) cAMP Assay

The calcitonin receptor (CTR) belongs to the subfamily of GPCRs known as the secretin or 'B' family of GPCRs. Like other class B1 GPCRs, the CT receptor family is canonically coupled to Gs-mediated cAMP production, and measurement of cAMP accumulation has been the primary assay used to determine peptide selectivity and potency.

To optimize functional activity directed toward Gαs coupling, COS-7 cells were stably transfected with human calcitonin receptor (CTR) to create COS7-human CTR Clone #2 stable cell line. 100×concentration of compound working solutions were prepared with 4-fold serial dilution in 384-well Echo LDV plate (Labcyte, Cat #LP-0200-BC). 200 nL/well 100×concentration of compound working solutions were moved to 384-well white microplate (Perkin Elmer, Cat #6007680) using Labcyte ECHO550. 1×10$^5$ cells/mL COS7-human CTR Clone #2 cell suspensions prepared with assay buffer [HBSS containing 20 mM HEPES (Gibco, Cat #15630-080), 0.5 mM IBMX (Sigma, Cat #15879) and 0.1% Casein (Sigma, Cat #C4765)], 20 μL cell suspensions were added to each well of previous generated assay plate which already contains 200 nL compound at 100×concentration using ThermoFisher Multidrop Combi (2000 cells/well). Seal the plate and incubate at 37° C. with 5% $CO_2$ for 30 min.

After incubation, the cAMP assay signal was generated using cAMP dynamic 2 kit (Revvity, Cat #62AM4PEC). 10 μL cAMP-d2 working solution was added to each well, followed by 10 μL Anti-cAMP antibody-cryptate working solution which was added to each well using CERTUS FLEX LIQUID DISPENSER. The samples were then incubated at room temperature for 1 hour protected from light. the fluorescence was read at 665 and 615 nm with Reader PerkinElmer EnVision 2105.

% Activity=100−(mean RLU of test sample−mean RLU of positive control)/(mean RLU of vehicle control−mean RLU of positive control)×100

The activity of the tested compounds is provided in Table 3 below.

TABLE 3

| Compound No. | Amylin Receptor cAMP Stimulation Activity: $EC_{50}$ (nM) | Calcitonin Receptor cAMP Stimulation Activity: $EC_{50}$ (nM) |
|---|---|---|
| 101 | 101** | 12.9 |
| 102 | 12.2** | 0.800 |
| 103 | 273** | 21.5 |
| 104 | 25.5** | 0.926 |
| 107 | 34.4** | 9.03 |
| 108 | 121* | 2.42 |
| 111 | 401** | 205 |
| 113 | 1120** | 271 |
| 114 | 425** | 396 |
| 115 | 566** | 28.8 |
| 116 | 253** | 25.6 |
| 117 | 113** | 53.5 |
| 120 | 23.6** | 1.24 |
| 123 | 42.9** | 1.19 |
| 124 | 18.2** | 0.628 |
| 125 | 50.5** | 0.711 |
| 127 | 143** | 4.36 |
| 128 | 21.9** | 1.13 |
| 130 | 38.3** | 3.06 |
| 133 | 90.7** | 4.42 |
| 139 | 41.5** | 2.70 |
| 140 | 19.1** | 2.13 |
| 141 | 711** | 88.8 |
| 146 | 54.1** | 3.18 |
| 147 | 51.9** | 2.80 |
| 148 | 288** | 18.7 |
| 150 | 25.4** | 1.06 |
| 151 | 159** | 22 |
| 152 | 5100** | 513 |
| 153 | 16.6** | 2.58 |
| 154 | 648** | 52.8 |
| 155 | 33.5** | 1.21 |
| 156 | 55.4** | 2.48 |
| 157 | 115** | 7.42 |
| 158 | 12.8** | 1.19 |
| 159 | 28.7** | 1.17 |
| 160 | 12.2** | 0.724 |
| 161 | 35.8** | 1.82 |
| 162 | 3.71** | 0.157 |
| 163 | 11.2** | 0.588 |
| 164 | 39.9** | 4.28 |
| 165 | 6.73** | 0.539 |
| 166 | 1.38** | 0.0875 |
| 167 | 4.38** | 0.13 |
| 168 | 15.3** | 0.341 |
| 169 | 254** | 10.2 |
| 170 | 33.1** | 1.19 |
| 171 | 71.4** | 1.52 |
| 172 | 51.1** | 2.06 |
| 173 | 16.9** | 0.788 |
| 174 | 31.9** | 0.347 |
| 175 | 26.8** | 0.741 |
| 176 | 10.7** | 0.557 |
| 177 | 1810** | 39.4 |
| 178 | 203** | 3.19 |
| 179 | 34.2** | 1.25 |
| 180 | 12.7** | 0.559 |
| 181 | 3.5** | 0.105 |
| 182 | 52.9** | 7.85 |
| 183 | 4.23** | 0.143 |
| 184 | 3.59** | 0.247 |
| 185 | 231** | 15.2 |
| 186 | 37.2** | 0.682 |
| 187 | 0.608** | 0.0484 |
| 188 | 6.57** | 0.223 |
| 189 | 0.213** | 0.0262 |
| 190 | 0.184** | 0.00786 |
| 191 | 0.318** | 0.0127 |
| 192 | 0.8** | 0.00532 |
| 193 | 0.226** | 0.00749 |
| 194 | 1.96** | 0.229 |
| 195 | 0.0995** | 0.00616 |
| 196 | 0.196** | 0.00979 |

TABLE 3-continued

| Compound No. | Amylin Receptor cAMP Stimulation Activity: $EC_{50}$ (nM) | Calcitonin Receptor cAMP Stimulation Activity: $EC_{50}$ (nM) |
|---|---|---|
| 197 | 1790** | 58.9 |
| 198 | 1002** | 19.2 |
| 199 | 300.5** | 3.7 |
| 200 | 1310** | 8.61 |
| 201 | 1371** | 19.3 |
| 202 | 1749** | 66.2 |
| 203 | 528.8** | 4.69 |
| 204 | 265.6** | 5.06 |
| 205 | 342.1** | 5.7 |
| 206 | 1594** | 26.1 |
| 207 | 11.3** | 0.309 |
| 208 | 74.36** | 0.331 |
| 209 | 17.16** | 0.154 |
| 210 | 467.5** | 23 |
| 211 | 434** | 3.85 |
| 212 | 11701** | 526 |
| 213 | 53.08** | 0.786 |
| 214 | 129.3** | 1.92 |
| 215 | 7.23** | 0.406 |
| 216 | 1338** | 152 |
| 217 | 47.8** | 0.706 |
| 218 | 89.3** | 11.5 |
| 219 | 437.5** | 27.4 |
| 220 | 11351** | 20.5 |
| 221 | 864.5** | 15.5 |
| 222 | 511** | 12.8 |
| 223 | 757.5** | 27.6 |
| 224 | 50.7** | 0.702 |
| 225 | 14.6** | 0.836 |
| 226 | 14.2** | 1.08 |
| 227 | 33.3** | 1.67 |
| 228 | 3028** | 25.7 |
| 229 | 48.4** | 13.4 |
| 230 | 17.4** | 0.51 |
| 231 | 15346** | 171 |
| 232 | 11997** | 412 |
| 233 | 1817** | 36.3 |
| 234 | 48.1** | 1.83 |
| 235 | 18.1** | 0.236 |
| 236 | 127.9** | 177 |
| 237 | 18.5** | 0.591 |
| 238 | 75.7** | 5.12 |
| 239 | 23.4** | 0.975 |
| 240 | 182** | 8.9 |
| 241 | 33.5** | 1.72 |
| 242 | 18.4** | 0.668 |
| 243 | 11.2** | 1.18 |
| 244 | 22.7** | 1.16 |
| 245 | 19.1** | 0.469 |
| 246 | 6.78** | 0.219 |
| 247 | 2412** | 21.1 |
| 248 | 4201** | 102 |
| 249 | 62843** | 857 |
| 250 | 102** | 4.5 |
| 251 | 82.8** | 7.28 |
| 252 | 248** | 7.9 |
| 253 | 1.88** | 0.0708 |
| 254 | 0.707** | 0.0659 |
| 255 | 0.318** | 0.0127 |
| 256 | 12.8** | 0.33 |
| 257 | 10.2** | 0.696 |
| 258 | 1.91** | 0.171 |
| 259 | 1.52** | 0.152 |
| 260 | 1.24** | 0.0529 |
| 261 | 6.35** | 0.807 |
| 262 | 2.81** | 0.0963 |
| 263 | 0.629** | 0.0341 |
| 264 | 7.4** | 0.247 |
| 265 | 7.342** | 0.174 |
| 266 | 182.1** | 2.75 |
| 267 | 14.6** | 0.738 |
| 268 | 1.07** | 0.077 |
| 269 | 1.78** | 0.0975 |

TABLE 3-continued

| Compound No. | Amylin Receptor cAMP Stimulation Activity: $EC_{50}$ (nM) | Calcitonin Receptor cAMP Stimulation Activity: $EC_{50}$ (nM) |
|---|---|---|
| 270 | 1.6** | 0.148 |
| 271 | 3.13** | 0.178 |
| 272 | 1.45** | 0.0666 |
| 273 | 1.79** | 0.165 |
| 274 | 4.54** | 0.255 |
| 275 | 0.394** | 0.0262 |
| 276 | 1.57** | 0.0602 |
| 277 | 0.368** | 0.0207 |
| 278 | 0.517** | 0.0636 |
| 279 | 0.318** | 0.051 |
| 280 | 0.935** | 0.114 |
| 281 | 0.733** | 0.239 |
| 282 | 0.464** | 0.0464 |
| 283 | 1.571** | 0.0191 |
| 284 | 81.6** | 4.23 |
| 285 | 0.208** | 0.0136 |
| 286 | 0.175** | 0.00668 |
| 287 | 0.35** | 0.0178 |
| 288 | 1.59** | 0.0436 |
| 289 | 0.54** | 0.0645 |
| 290 | 1641** | 17.6 |
| 291 | 0.363** | 0.0138 |
| 292 | 298.4** | 7.36 |
| 293 | 2.68** | 0.0485 |
| 294 | 0.562** | 0.0435 |
| 295 | 1.21** | 0.0289 |
| 296 | 0.272** | 0.0164 |
| 297 | 1.07** | 0.0413 |
| 298 | 0.747** | 0.0212 |
| 299 | 0.363** | 0.0172 |
| 300 | 0.362** | 0.016 |
| 301 | 0.857** | 0.0551 |
| 302 | 3.97** | 0.134 |
| 303 | 0.695** | 0.0337 |

*Amylin Receptor CAMP Assay I

**Amylin Receptor CAMP Assay II

The invention claimed is:

1. A compound selected from the group consisting of:

189

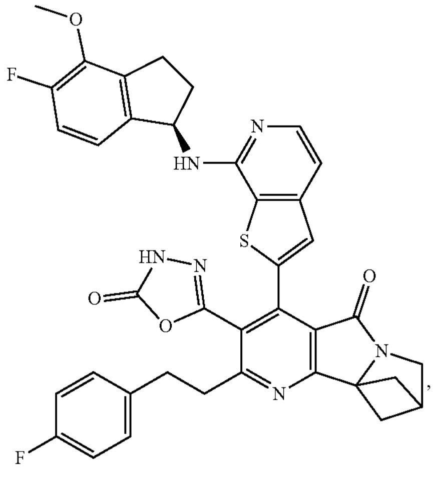
,

-continued
192
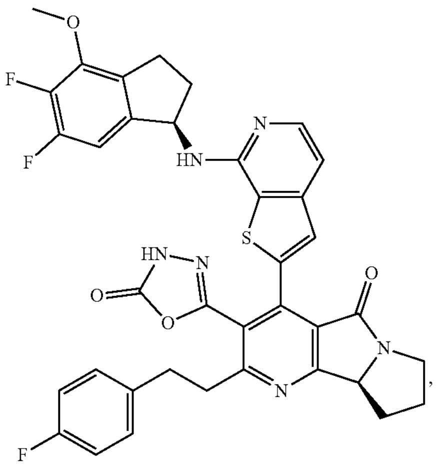
193
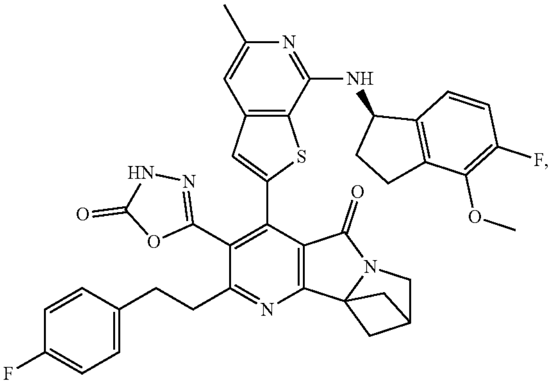
195
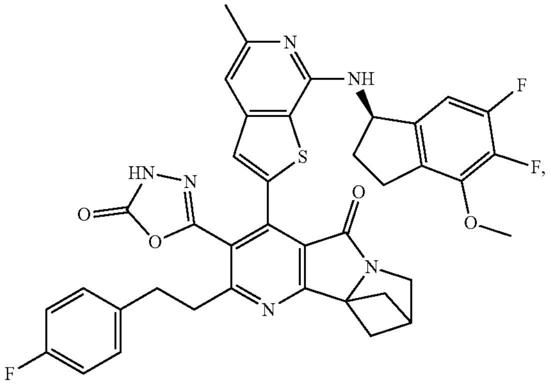
-continued
196
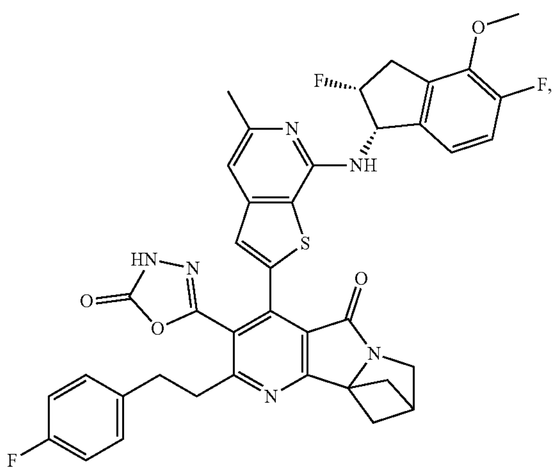
287
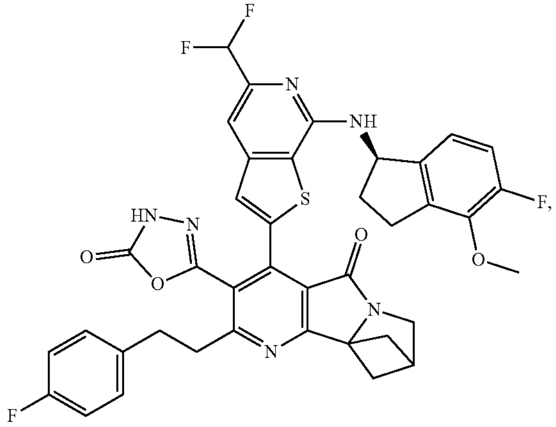
291
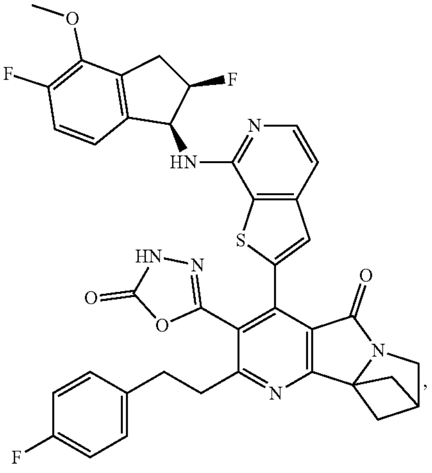

-continued
296
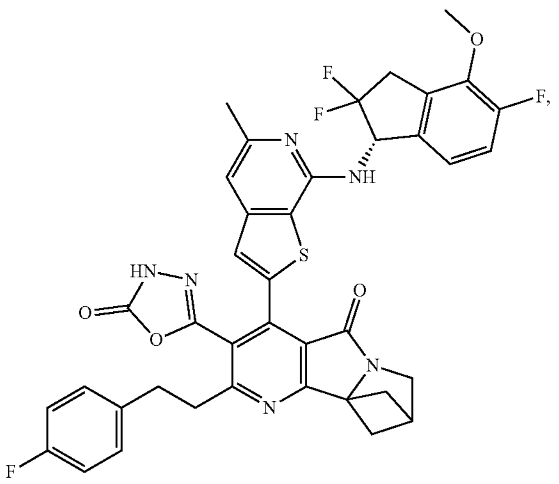
299
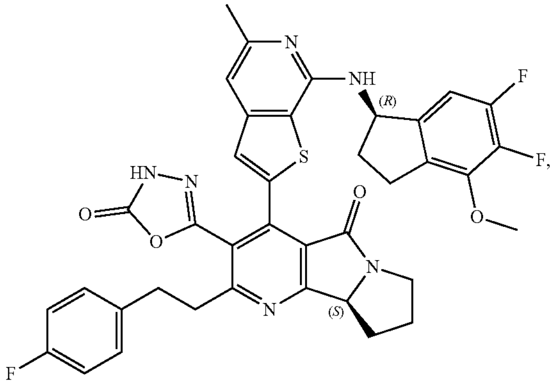
301
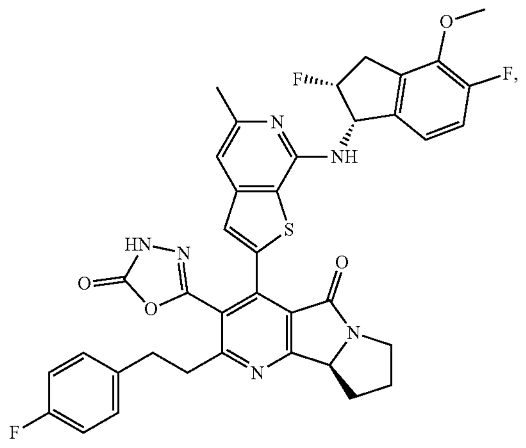
and
-continued
303
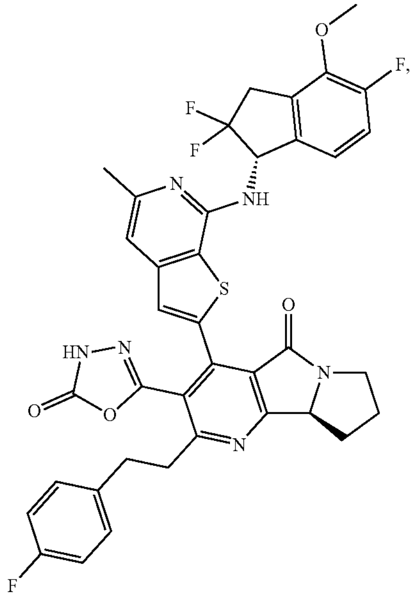
or a pharmaceutically acceptable salt thereof.
2. A pharmaceutical composition comprising a compound of claim 1, or a pharmaceutically acceptable salt thereof, and a pharmaceutically acceptable excipient.
3. The compound of claim 1, wherein the compound is selected from the group consisting of:
189
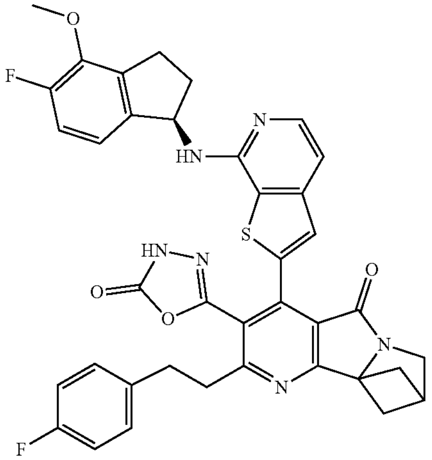
, -continued
192
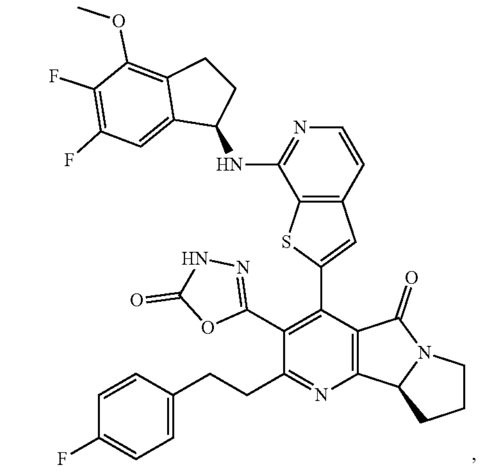
,
193
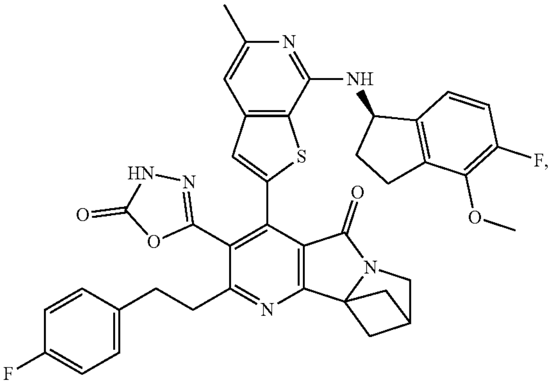
195
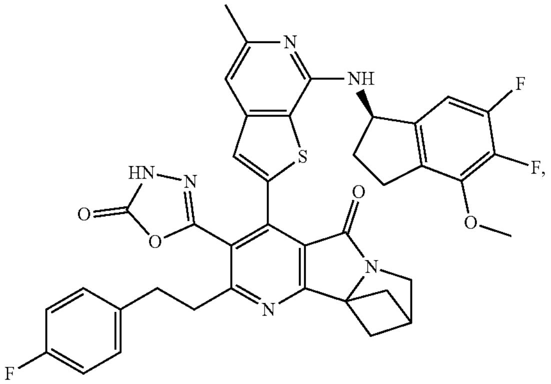
-continued
196
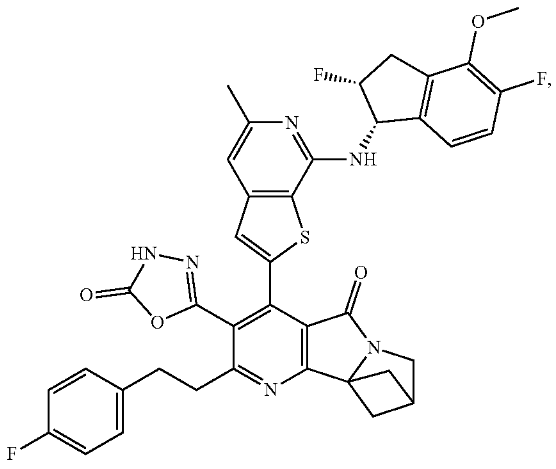
287
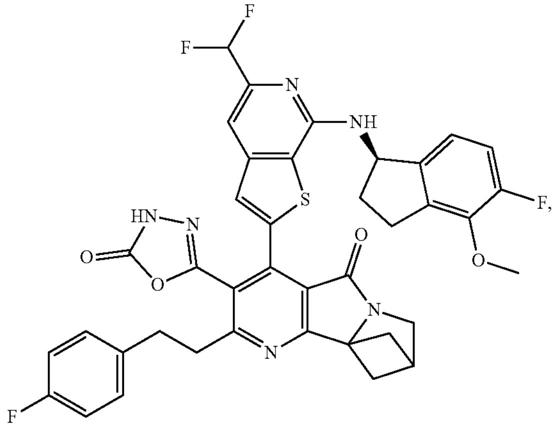
291
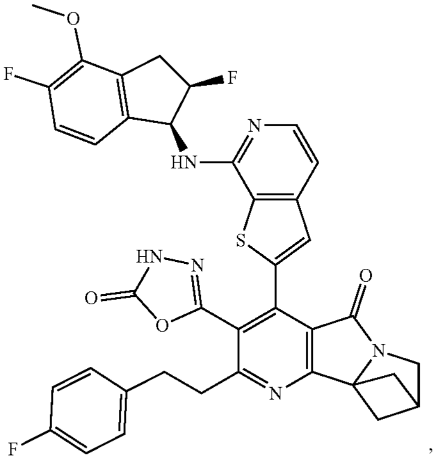
, -continued

296

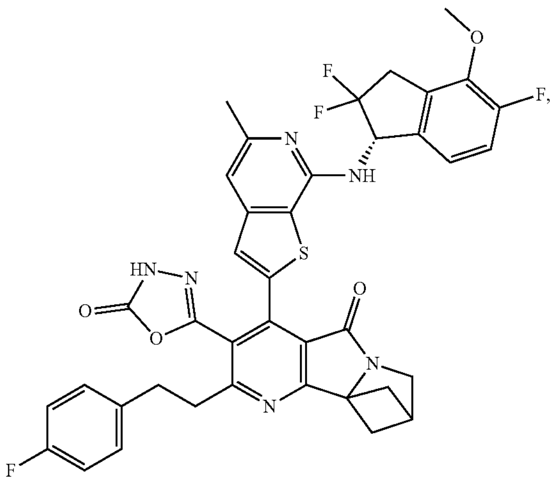

299

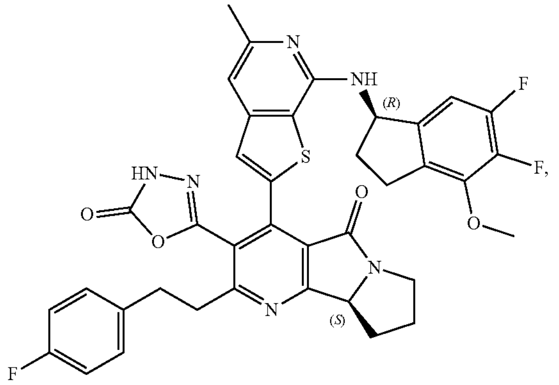

301

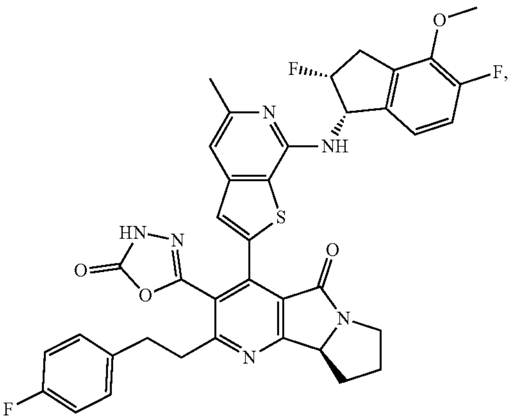

and

-continued

303

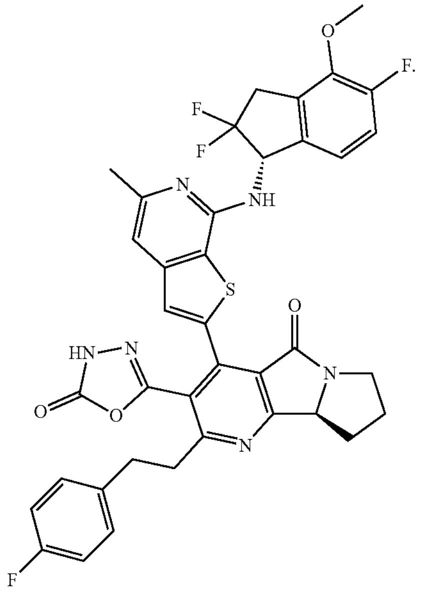

4. A pharmaceutical composition comprising a compound of claim 3, and a pharmaceutically acceptable excipient.

5. The compound of claim 1, wherein the compound is:

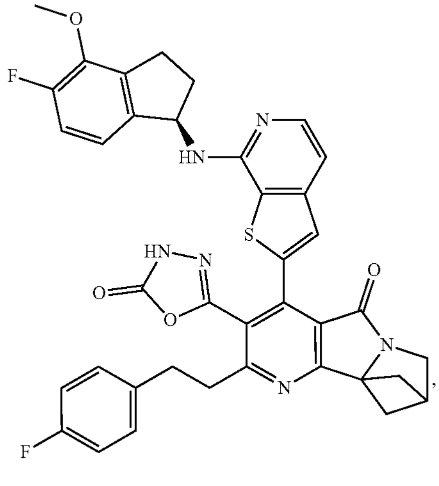 [SMILES: COc1c(F)ccc2c1CC[C@H]2Nc1nccc2cc(-c3c4c(nc(CCc5ccc(F)cc5)c3-c3n[nH]c(=O)o3)C35CC(CN3C4=O)C5)sc12]

, or a pharmaceutically acceptable salt thereof.

6. A pharmaceutical composition comprising a compound of claim 5, or a pharmaceutically acceptable salt thereof, and a pharmaceutically acceptable excipient.

7. The compound of claim 1, wherein the compound is:

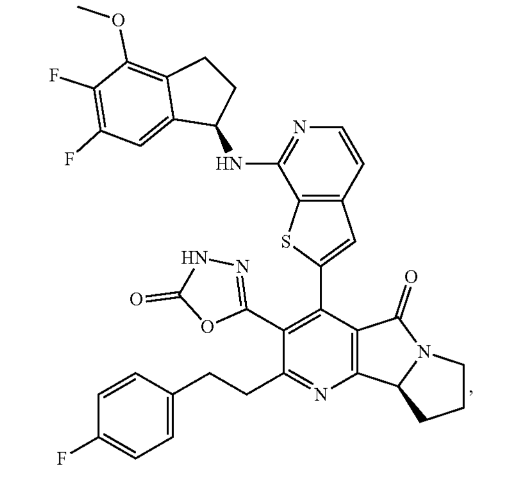 [SMILES: COc1c(F)c(F)cc2c1CC[C@H]2Nc1nccc2cc(-c3c4c(nc(CCc5ccc(F)cc5)c3-c3n[nH]c(=O)o3)[C@@H]3CCCN3C4=O)sc12]

or a pharmaceutically acceptable salt thereof.

8. A pharmaceutical composition comprising a compound of claim 7, or a pharmaceutically acceptable salt thereof, and a pharmaceutically acceptable excipient.

9. The compound of claim 1, wherein the compound is:

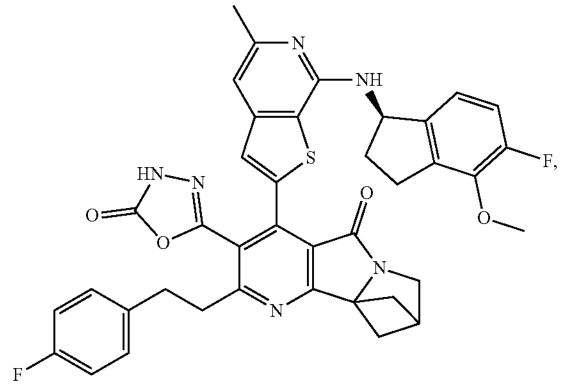 [SMILES: COc1c(F)ccc2c1CC[C@H]2Nc1nc(C)cc2cc(-c3c4c(nc(CCc5ccc(F)cc5)c3-c3n[nH]c(=O)o3)C35CC(CN3C4=O)C5)sc12]

or a pharmaceutically acceptable salt thereof.

10. A pharmaceutical composition comprising a compound of claim 9, or a pharmaceutically acceptable salt thereof, and a pharmaceutically acceptable excipient.

11. A compound which is:

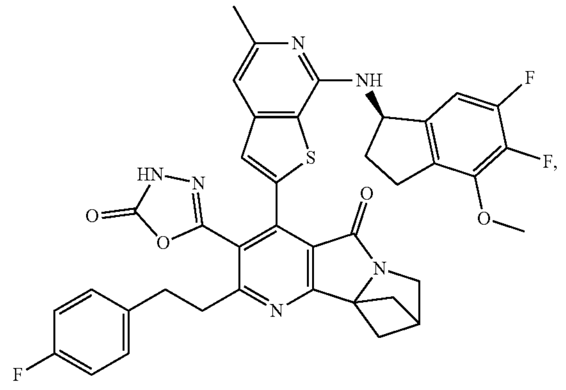 [SMILES: COc1c(F)c(F)cc2c1CC[C@H]2Nc1nc(C)cc2cc(-c3c4c(nc(CCc5ccc(F)cc5)c3-c3n[nH]c(=O)o3)C35CC(CN3C4=O)C5)sc12]

or a pharmaceutically acceptable salt thereof.

12. A pharmaceutical composition comprising a compound of claim 11, or a pharmaceutically acceptable salt thereof, and a pharmaceutically acceptable excipient.

13. A compound which is:

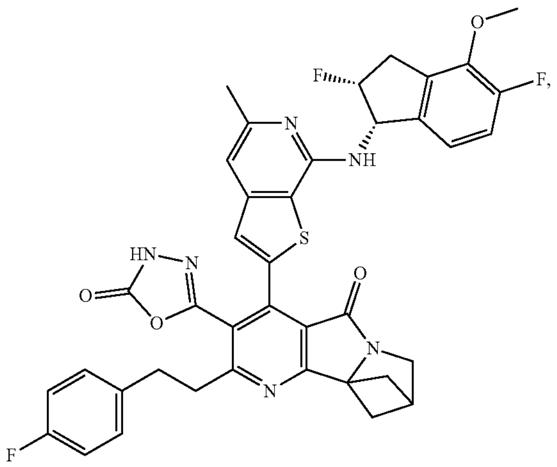 [SMILES: COc1c(F)ccc2c1C[C@@H](F)[C@H]2Nc1nc(C)cc2cc(-c3c4c(nc(CCc5ccc(F)cc5)c3-c3n[nH]c(=O)o3)C35CC(CN3C4=O)C5)sc12]

or a pharmaceutically acceptable salt thereof.

14. A pharmaceutical composition comprising a compound of claim 13, or a pharmaceutically acceptable salt thereof, and a pharmaceutically acceptable excipient.

15. The compound of claim 1, wherein the compound is:

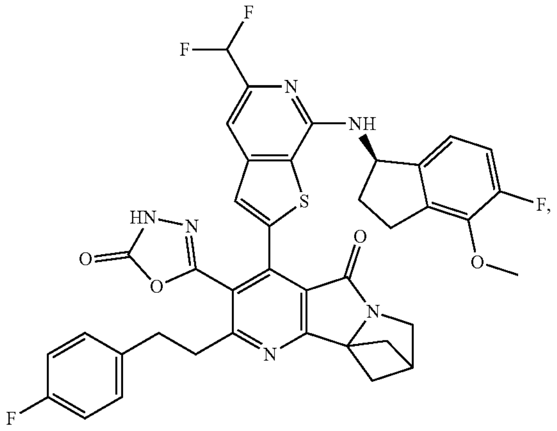 [SMILES: COc1c(F)ccc2c1CC[C@H]2Nc1nc(C(F)F)cc2cc(-c3c4c(nc(CCc5ccc(F)cc5)c3-c3n[nH]c(=O)o3)C35CC(CN3C4=O)C5)sc12]

or a pharmaceutically acceptable salt thereof.

16. A pharmaceutical composition comprising a compound of claim 15, or a pharmaceutically acceptable salt thereof, and a pharmaceutically acceptable excipient.

17. The compound of claim 1, wherein the compound is:

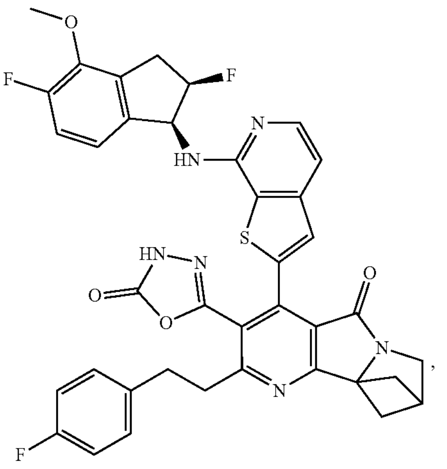 [SMILES: COc1c(F)ccc2c1C[C@@H](F)[C@H]2Nc1nccc2cc(-c3c4c(nc(CCc5ccc(F)cc5)c3-c3n[nH]c(=O)o3)C35CC(CN3C4=O)C5)sc12]

or a pharmaceutically acceptable salt thereof.

18. A pharmaceutical composition comprising a compound of claim 17, or a pharmaceutically acceptable salt thereof, and a pharmaceutically acceptable excipient.

19. The compound of claim 1, wherein the compound is:

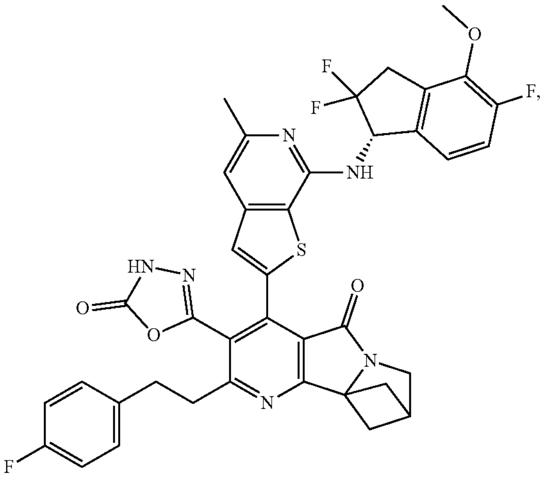 [SMILES: COc1c(F)ccc2c1CC(F)(F)[C@H]2Nc1nc(C)cc2cc(-c3c4c(nc(CCc5ccc(F)cc5)c3-c3n[nH]c(=O)o3)C35CC(CN3C4=O)C5)sc12]

or a pharmaceutically acceptable salt thereof.

20. A pharmaceutical composition comprising a compound of claim 19, or a pharmaceutically acceptable salt thereof, and a pharmaceutically acceptable excipient.

21. The compound of claim 1, wherein the compound is:

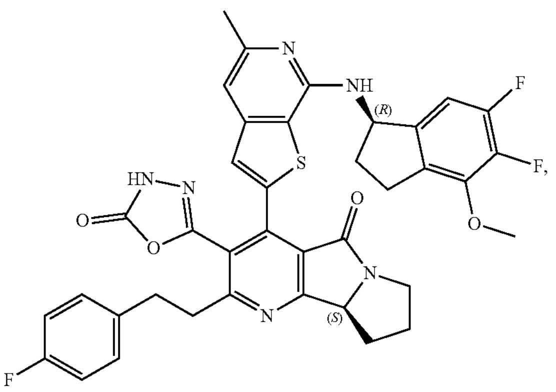

or a pharmaceutically acceptable salt thereof.

22. A pharmaceutical composition comprising a compound of claim 21, or a pharmaceutically acceptable salt thereof, and a pharmaceutically acceptable excipient.

23. The compound of claim 1, wherein the compound is:

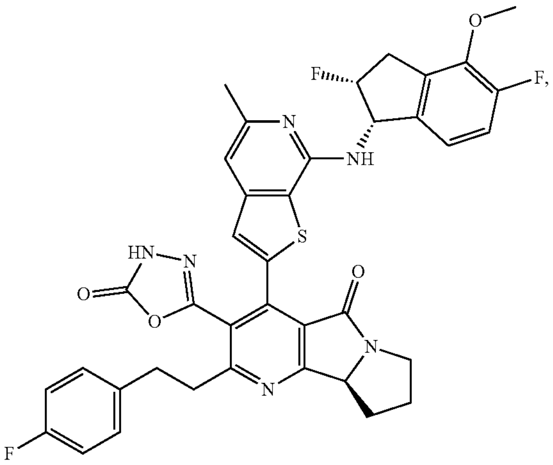 [SMILES: COc1c(F)ccc2c1C[C@@H](F)[C@H]2Nc1nc(C)cc2cc(-c3c4c(nc(CCc5ccc(F)cc5)c3-c3n[nH]c(=O)o3)[C@@H]3CCCN3C4=O)sc12]

or a pharmaceutically acceptable salt thereof.

24. A pharmaceutical composition comprising a compound of claim 23, or a pharmaceutically acceptable salt thereof, and a pharmaceutically acceptable excipient.

25. A compound which is:

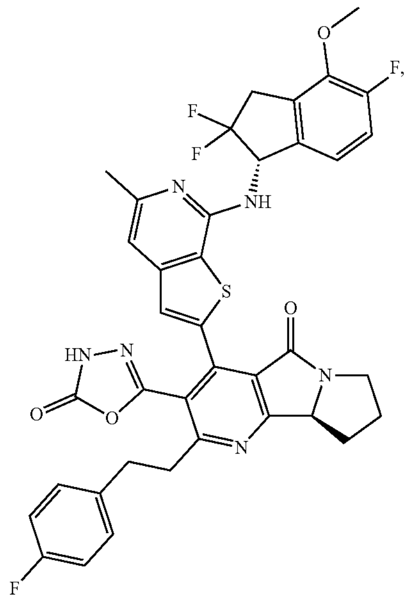 [SMILES: COc1c(F)ccc2c1CC(F)(F)[C@H]2Nc1nc(C)cc2cc(-c3c4c(nc(CCc5ccc(F)cc5)c3-c3n[nH]c(=O)o3)[C@@H]3CCCN3C4=O)sc12]

or a pharmaceutically acceptable salt thereof.

26. A pharmaceutical composition comprising a compound of claim 25, or a pharmaceutically acceptable salt thereof, and a pharmaceutically acceptable excipient.

* * * * *